US007259266B2

(12) United States Patent
Carter et al.

(10) Patent No.: US 7,259,266 B2
(45) Date of Patent: *Aug. 21, 2007

(54) BENZOPYRAN COMPOUNDS USEFUL FOR TREATING INFLAMMATORY CONDITIONS

(75) Inventors: Jeffry Carter, Chesterfield, MO (US); David Brown, Chesterfield, MO (US); Li Xing, Chesterfield, MO (US); Karl Aston, Pacific, MO (US); John Springer, O'Fallon, MO (US); Francis Koszyk, Prospect Heights, IL (US); Steven Kramer, Des Plaines, IL (US); Renee Huff, Park Ridge, IL (US); Yi Yu, Glenview, IL (US); Bruce Hamper, Kirkwood, MO (US); Subo Laio, Ballwin, MO (US); Angela Deprow, Cape Girardeau, MO (US); Teresa Fletcher, Kirkwood, MO (US); E. Ann Hallinan, Evanston, IL (US); James Kiefer, Chesterfield, MO (US); David Limburg, Wildwood, MO (US); Lijuan Wang, Wildwood, MO (US); Cindy Ludwig, St. Louis, MO (US); John McCall, Highland Park, IL (US); John Talley, Sommerville, MA (US)

(73) Assignee: Pharmacia Corporation, Chesterfield, MO (US)

( * ) Notice: Subject to any disclaimer, the term of this patent is extended or adjusted under 35 U.S.C. 154(b) by 487 days.

This patent is subject to a terminal disclaimer.

(21) Appl. No.: 10/801,429

(22) Filed: Mar. 16, 2004

(65) Prior Publication Data
US 2005/0148777 A1 Jul. 7, 2005

Related U.S. Application Data

(60) Provisional application No. 60/459,215, filed on Mar. 31, 2003.

(51) Int. Cl.
C07D 311/04 (2006.01)
(52) U.S. Cl. .................................................. 549/398
(58) Field of Classification Search ............. 514/394, 514/444, 453, 454, 456; 549/383, 387, 389, 549/404, 405, 398
See application file for complete search history.

(56) References Cited

U.S. PATENT DOCUMENTS

| 3,794,734 | A | 2/1974 | Cragoe, Jr. et al. | 424/330 |
| 6,034,256 | A | 3/2000 | Carter et al. | 549/456 |
| 6,077,850 | A | 6/2000 | Carter et al. | 514/311 |
| 6,271,253 | B1 | 8/2001 | Carter et al. | 514/432 |
| 7,138,411 | B2 * | 11/2006 | Carter et al. | 514/311 |
| 2003/0013793 | A1 * | 1/2003 | Wilson, III | 524/398 |
| 2003/0114418 | A1 * | 6/2003 | Pulaski et al. | 514/62 |

FOREIGN PATENT DOCUMENTS

| WO | WO98/47890 | * 10/1998 |
| WO | WO00/23433 | 4/2000 |
| WO | WO00/38716 | 7/2000 |
| WO | WO02/096516 | 12/2002 |

OTHER PUBLICATIONS

Alabaster, et al., *J. Med. Chem.*, 31(10), 2048-2056 (1988).
Casiraghi, et al., *J.C.S.Perkin I*, 318-321 (1978).
Gierse et al., *J. Biochem.*, 305, 479-484 (1995).
Heck, *Palladium Reagents in Organic Synthesis*, Academic Press (1985).
Leroy, et al., *J. Fluorine Chem.*, 40(1), 23-32 (1988).
Levai, et al., *Synthetic Commun.*, 22(12), 1735-1750 (1992).
Moshfegh, et al., *Helv. Chim. Acta.* 65(4), 1229-1232 (1982).
Newman, et al., M.W., *J. Org. Chem.*, 36(10), 1398-1401 (1971).
O'Reilly et al., *Baculovirus Expression Vectors: A Laboratory Manual* (1992).
Otterness, et al., Laboratory models for testing nonsteroidal anti-inflammatory drugs, *Non-steroidal Anti-inflammatory Drugs*, ed. by Lombardino, (1985).
Smith, *A Manual of Methods for Baculovirus Vectors and Insect Cell Cultures*, Texas Agric. Exp. Station Bull. 1555 (1987).
Suzuki, et al., *Chem. Pharm. Bull.*, 31(5), 1751-1753 (1983).
Turner, *J. Org. Chem.*, 48(20), 3401-3408 (1983).
Tyle, *Pharmaceutical Research*, 3(6), 318-326 (1986).
Winter, et al., *Proc. Soc. Exp. Biol. Med.*, 111, 544-547 (1962).
Xie, et al., *Synthetic Commun.*, 24(1), 53-58 (1994).

* cited by examiner

*Primary Examiner*—Celia Chang
(74) *Attorney, Agent, or Firm*—Julie M. Lappin

(57) ABSTRACT

The subject invention concerns methods and compounds that have utility in the treatment of a condition associated with cyclooxygenase-2 mediated disorders. Compounds of particular interest are benzopyrans and their analogs defined by formula 1

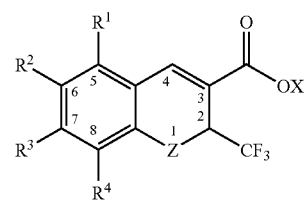

Wherein Z, X, $R^1$, $R^2$, $R^3$, and $R^4$ are as described in the specification.

1 Claim, No Drawings

BENZOPYRAN COMPOUNDS USEFUL FOR TREATING INFLAMMATORY CONDITIONS

This application claims priority to application No. 60/459,215, filed Mar. 31, 2003

FIELD

This invention is in the field of anti-inflammatory pharmaceutical agents and specifically relates to compounds, compositions and methods for treating cyclooxygenase-2 mediated disorders, such as inflammation and inflammation-related disorders.

BACKGROUND

Prostaglandins play a major role in the inflammation process and the inhibition of prostaglandin production, especially production of $PGG_2$, $PGH_2$ and $PGE_2$ has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

Description of the some benzopyran compounds useful for treating inflammatory conditions is provided in U.S. Pat. No.6,034,256. U.S. Pat. No.6,077,850 provides further description of benzopyran compounds useful in treating inflammatory conditions. Some further benzopyran compounds useful for treating inflammatory conditions are described in U.S. Pat. No. 6,271,253.

BRIEF DESCRIPTION

The novel benzopyran derivatives disclosed herein are safe and effective antiinflammatory agents. The substituted benzopyran derivatives disclosed herein preferably selectively inhibit cyclooxygenase-2 over cyclooxygenase-1.

Compounds of the current invention have not been described as antiinflammatory cyclooxygenase inhibitors.

The following description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Among its many embodiments the present invention provides a compound of

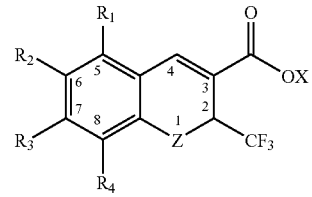

or a pharmaceutically acceptable salt thereof, wherein: X is selected from the group consisting of H, alkyl, and a pharmaceutically acceptable cation; Z is selected from the group consisting of O, S and NH; wherein $R^1$, $R^2$, $R^3$, and $R^4$ are each independently selected from the group consisting of H, alkenyl, alkoxy, alkoxyalkyl, alkoxycarbonylalkyl, alkyl, alkylamino, alkylcarbonyl, alkylheteroaryl, alkylsulfonylalkyl, alkylthio, alkynyl, aminocarbonylalkyl, aryl, arylalkenyl, arylalkoxy, arylalkyl, arylalkylamino, arylalkynyl, arylcarbonyl, aryloxy, cyano, dialkylamino, halo, haloalkoxy, haloalkyl, heteroaryl, heteroarylalkoxy, heteroarylcarbonyl, hydroxy and hydroxyalkyl; wherein each of aryl, wherever it occurs, is independently substituted with one to five substituents selected from the group consisting of alkyl, alkoxy, alkylamino, cyano, halo, haloalkyl, hydroxy, and nitro.

The present invention further provides a pharmaceutical composition comprising a compound of Formula 1 or a pharmaceutically acceptable salt thereof, wherein: X, Z, $R^1$, $R^2$, $R^3$, and $R^4$ are each independently as described above; and a pharmaceutically acceptable excipient.

The present invention further provides a method for the treatment or prevention of a COX-2 mediated disorder in a subject in need of such treatment or prevention, wherein the method comprises administering to the subject an amount of a compound of Formula 1 or a pharmaceutically acceptable salt thereof, wherein: X, Z, $R^1$, $R^2$, $R^3$, and $R^4$ are each independently as described above; and wherein the amount of the compound is effective for the treatment or prevention of the COX-2 mediated disorder.

DETAILED DESCRIPTION

Compounds of the present invention are useful for, but not limited to, the treatment of inflammation in a subject, and for treatment of other cyclooxygenase-2 mediated disorders, such as, as an analgesic in the treatment of pain and headaches, including migraine headaches, or as an antipyretic for the treatment of fever. For example, compounds of the invention are useful to treat arthritis, including but not limited to rheumatoid arthritis, spondyloarthropathies, gouty arthritis, osteoarthritis, systemic lupus erythematosus and juvenile arthritis. Such compounds of the invention will be useful in the treatment of asthma, bronchitis, menstrual cramps, preterm labor, tendonitis, bursitis, allergic neuritis, cytomegalovirus infectivity, apoptosis including HIV induced apoptosis, lumbago, liver disease including hepatitis, skin-related conditions such as psoriasis, eczema, acne, UV damage, burns and dermatitis. Compounds of the invention also will be useful to treat gastrointestinal conditions such as inflammatory bowel disease, Crohn's disease, gastritis, irritable bowel syndrome and ulcerative colitis. Compounds of the invention will be useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. The compounds will also be useful in the treatment of ophthalmic diseases, such as retinitis, conjunctivitis, retinopathies (including diabetic retinopathy), uveitis, ocular photophobia, conditions involving elevated intraocular pressure (including glaucoma), sarcoidosis, macular degeneration (including wet-type macular degeneration and dry-type degeneration), ocular neovascularization, retinal neovascularization (including neovascularization following injury or infection), comeal graft rejection, retrolental fibroplasias, post-opthalmic surgery inflammation (including cataract surgery, retinal detachment surgery, lens implantation surgery, corneal transplant surgery and refractive surgery), blepharitis, endophthalmitis, episcleritis, keratitis, keratoconjunctivitis, keratoconjunctivitis sicca, Mooren's ulcer, macular edema, intraoperative miosis, ocular pain, and of acute injury to the eye tissue. The compounds will also be useful in the treatment of pulmonary inflammation, such as that associated with viral infections and cystic fibrosis, and in bone reorption such as associated with osteoporosis.

The compounds will also be useful for the treatment of certain central nervous system disorders, such as cortical dementias including Alzheimer's disease, schizophrenia, neurodegeneration, and central nervous system damage resulting from stroke, ischemia and trauma. The term "treatment" includes partial or total inhibition of the dementia, including Alzheimer's disease, vascular dementia, multi-infarct dementia, pre-senile dementia, alcoholic dementia, and senile dementia.

The compounds of the invention are useful as anti-inflammatory agents, such as for the treatment of arthritis, with the additional benefit of having significantly less harmful side effects. These compounds will also be useful in the treatment of allergic rhinitis, respiratory distress syndrome, endotoxin shock syndrome, and liver disease. The compounds will also be useful in the treatment of pain, but not limited to postoperative pain, dental pain, muscular pain, and pain resulting from cancer.

The method above will be useful for, but not limited to, treating and preventing inflammation-related cardiovascular disorders in a subject. The method will be useful for treatment and prevention of vascular diseases, coronary artery disease, aneurysm, vascular rejection, arteriosclerosis, atherosclerosis including cardiac transplant atherosclerosis, myocardial infarction, embolism, stroke, thrombosis, including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

The compounds will be useful for, but not limited to, the treatment of angiogenesis-related disorders in a subject. According to the present invention, the compounds can be administered to a subject in need of angiogenesis inhibition. The method will be useful for treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including invantile hemaginomas, angiofibroma of the nasopharynx and avascular necrosis of bone; and disorders of the female reproductive system such as endometriosis.

Compounds of the invention will be useful for the prevention or treatment of benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body. Preferably, neoplasia is selected from gastrointestinal cancer, Barrett's esophagus, liver cancer, bladder cancer, pancreas cancer, ovary cancer, prostate cancer, cervical cancer, lung cancer, breast cancer and skin cancer, such as squamus cell and basal cell cancers. The compounds can also be used to treat the fibrosis which occurs with radiation therapy. The method can be used to treat subjects having adenomatous polyps, including those with familial adenomatous polyposis (FAP). Additionally, the method can be used to prevent polyps from forming in patients at risk of FAP. Furthermore the compounds of the present invention will be useful for treatment or prevention of side effects from oncology-related therapies such as radiation therapy or chemotherapy. For example the present compounds will be useful to alleviate diarrhea caused by chemotherapy with topoisomerases (such as irinotecan).

Besides being useful for human treatment, these compounds are also useful for veterinary treatment of companion animals, exotic animals and farm animals, including mammals, rodents, and the like. More preferred animals include horses, dogs, and cats.

Definitions

The term "prevention" includes either preventing the onset of clinically evident cardiovascular disorders altogether or preventing the onset of a preclinically evident stage of cardiovascular disorder in individuals. This includes prophylactic treatment of those at risk of developing a disease, such as a cardiovascular disorder, dementia or cancer, for example.

The phrase "therapeutically-effective" is intended to qualify the amount of each agent which will achieve the goal of improvement in disorder severity and the frequency of incidence over treatment of each agent by itself, while avoiding adverse side effects typically associated with alternative therapies.

The term "COX-2 selective" as used herein means the ability of a compound to inhibit COX-2 more than it inhibits COX-1 in an in vitro assay. The present invention includes compounds which are COX-2 selective. Preferably, the COX-2 selective compounds have an in vitro COX-2 $IC_{50}$ of less than about 0.5 micromolar. The COX-2 selective compounds preferably have a selectivity ratio of COX-2 inhibition over COX-1 inhibition of at least 2, preferably at least 5, more preferably at least 10, still more preferably at least 20, more preferably still at least 50 and yet more preferably at least 100. Even more preferably, the COX-2 selective compounds have a COX-1 $IC_{50}$ of greater than about 5 micromolar. Such preferred selectivity will indicate an ability to reduce the incidence of common NSAID-induced side effects.

The term "COX-1 selective" as used herein means the ability of a compound to inhibit COX-1 more than it inhibits COX-2 in an in vitro assay. The present invention also includes compounds which are COX-1 selective. Preferably, the COX-1 selective compounds have an in vitro COX-1 $IC_{50}$ of less than about 0.5 micromolar. The COX-1 selective compounds preferably have a selectivity ratio of COX-1 inhibition over COX-2 inhibition of at least 2, preferably at least 5, more preferably at least 10, still more preferably at least 20, more preferably still at least 50 and yet more preferably at least 100. Even more preferably, the COX-1 selective compounds have a COX-2 $IC_{50}$ of greater than about 5 micromolar. Such preferred selectivity will have usefulness, for example, in tissues in which COX-1 enzyme products produce a deleterious effect to the subject.

The terms "benzopyran" and "chromene" are used interchangeably.

"Alkyl", "alkenyl," and "alkynyl" unless otherwise noted are each straight chain or branched chain hydrocarbons of from one to twenty carbons for alkyl or two to twenty carbons for alkenyl and alkynyl in the present invention and therefore mean, for example, methyl, ethyl, propyl, butyl, pentyl or hexyl and ethenyl, propenyl, butenyl, pentenyl, or hexenyl and ethynyl, propynyl, butynyl, pentynyl, or hexynyl respectively and isomers thereof.

"Aryl" means a fully unsaturated mono- or multi-ring carbocyle, including, but not limited to, substituted or unsubstituted phenyl, naphthyl, or anthracenyl.

"Heterocycle" means a saturated or unsaturated mono- or multi-ring carbocycle wherein one or more carbon atoms can be replaced by N, S, P, or O. This includes, for example, the following structures:

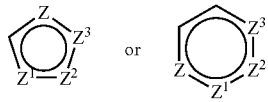

wherein Z, $Z^1$, $Z^2$ or $Z^3$ is C, S, P, O, or N, with the proviso that one of Z, $Z^1$, $Z^2$ or $Z^3$ is other than carbon, but is not O or S when attached to another Z atom by a double bond or when attached to another O or S atom. Furthermore, the optional substituents are understood to be attached to Z, $Z^1$, $Z^2$ or $Z^3$ only when each is C.

The term "heteroaryl" means a fully unsaturated heterocycle.

In either "heterocycle" or "heteroaryl," the point of attachment to the molecule of interest can be at the heteroatom or elsewhere within the ring.

The term "hydroxy" means a group having the structure —OH.

The term "halogen" or "halo" means a fluoro, chloro, bromo or iodo group.

The term "haloalkyl" means alkyl substituted with one or more halogens.

The term "cycloalkyl" means a mono- or multi-ringed carbocycle wherein each ring contains three to ten carbon atoms, and wherein any ring can contain one or more double or triple bonds. Examples include radicals such as cyclopropyl, cyclobutyl, cyclopentyl, cyclohexyl, cycloalkenyl, and cycloheptyl. The term "cycloalkyl" additionally encompasses spiro systems wherein the cycloalkyl ring has a carbon ring atom in common with the seven-membered heterocyclic ring of the benzothiepine.

The term "oxo" means a doubly bonded oxygen.

The term "cycloaklylidene" means a mono- or multi-ringed carbocycle wherein a carbon within the ring structure is doubly bonded to an atom which is not within the ring structures.

The term "nitro" means a group having the formula —$NO_2$.

The term "sulfo" means a sulfo group, —$SO_3$H, or its salts.

The term "thio" means a group having the formula —SH.

The term "sulfoalkyl" means an alkyl group to which a sulfonate group is bonded, wherein said alkyl is bonded to the molecule of interest.

The term "aminosulfony" means a group having the formula —$SO_2NH_2$.

The term "alkylthio" means a moiety containing an alkyl radical which is attached to an sulfer atom, such as a methylthio radical. The alkylthio moiety is bonded to the molecule of interest at the sulfer atom of the alkylthio.

The term "aryloxy" a moiety containing an aryl radical which is attached to an oxygen atom, such as a phenoxy radical. The aryloxy moiety is bonded to the molecule of interest at the oxygen atom of the aryloxy.

The term "alkenyloxy" a moiety containing an alkenyl radical which is attached to an oxygen atom, such as a 3-propenyloxy radical. The alkenyloxy moiety is bonded to the molecule of interest at the oxygen atom of the alkenyloxy.

The term "arylalkyl" means an aryl-substituted alkyl radical such as benzyl. The term "alkylarylalkyl" means an arylalkyl radical that is substituted on the aryl group with one or more alkyl groups.

The term "amino" means a group having the structure —$NH_2$. Optionally the amino group can be substituted for example with one, two or three groups such as alkyl, alkenyl, alkynyl, aryl, and the like.

The tern "cyano" means a group having the structure —CN or "H

The term "heterocyclylalkyl" means an alkyl radical that is substituted with one or more heterocycle groups.

The term "heteroarylalkyl" means an alkyl radical that is substituted with one or more heteroaryl groups.

The term "alkylheteroarylalkyl" means a heteroarylalkyl radical that is substituted with one or more alkyl groups.

The term "alkoxy" means a moiety containing an alkyl radical which is attached to an oxygen atom, such as a methoxy radical. The alkoxy moiety is bonded to the molecule of interest at the oxygen atom of the alkoxy. Examples of such radicals include methoxy, ethoxy, propoxy, isopropoxy, butoxy and tert-butoxy.

The term "carboxy" means the carboxy group, —$CO_2$H, or its salts.

The term "carbonyl", whether used alone or with other terms, such as "alkoxycarbonyl", means —(C═O)—.

The term "alkanoyl" means a —C(═O)H group, examples of such alkanoyl radicals include formyl, acetyl, propionyl, butyryl, isobutyryl, valeryl, isovaleryl, pivaloyl, hexanoyl, and radicals formed from succinic, glycolic, gluconic, lactic, malic, tartaric, citric, ascorbic, glucuronic, maleic, fumaric, pyruvic, mandelic, pantothenic, β-hydroxybutyric, galactaric and galacturonic acids.

The term "carboxyalkyl" means an alkyl radical that is substituted with one or more carboxy groups. Preferable carboxyalkyl radicals are "lower carboxyalkyl" radicals having one or more carboxy groups attached to an alkyl radical having one to six carbon atoms.

The term "carboxyheterocycle" means a heterocycle radical that is substituted with one or more carboxy groups.

The term "carboxyheteroaryl" means a heteroaryl radical that is substituted with one or more carboxy groups.

The term "carboalkoxyalkyl" means an alkyl radical that is substituted with one or more alkoxycarbonyl groups. Preferable carboalkoxyalkyl radicals are "lower carboalkoxyalkyl" radicals having one or more alkoxycarbonyl groups attached to an alkyl radical having one to six carbon atoms.

The term "carboxyalkylamino" means an amino radical that is mono- or di-substituted with carboxyalkyl. Preferably, the carboxyalkyl substituent is a "lower carboxyalkyl" radical wherein the carboxy group is attached to an alkyl radical having one to six carbon atoms.

When used in combination, for example "alkylaryl" or "arylalkyl," the individual terms listed above have the meaning indicated above.

Description

Among its many embodiments the present invention provides a compound of Formula 1

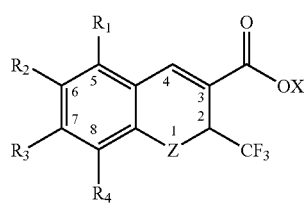

or a pharmaceutically acceptable salt thereof, wherein: X is selected from the group consisting of H, alkyl, and a pharmaceutically acceptable cation; Z is selected from the group consisting of O, S and NH; wherein $R^1$, $R^2$, $R^3$, and $R^4$ are each independently selected from the group consisting of H, alkenyl, alkoxy, alkoxyalkyl, alkoxycarbonylalkyl, alkyl, alkylamino, alkylcarbonyl, alkylheteroaryl, alkylsulfonylalkyl, alkylthio, alkynyl, aminocarbonylalkyl, aryl, arylalkenyl, arylalkoxy, arylalkyl, arylalkylamino, arylalkynyl, arylcarbonyl, aryloxy, cyano, dialkylamino, halo, haloalkoxy, haloalkyl, heteroaryl, heteroarylalkoxy, heteroarylcarbonyl, hydroxy and hydroxyalkyl; wherein each of aryl, wherever it occurs, is independently substituted with one to five substituents selected from the group consisting of alkyl, alkoxy, alkylamino, cyano, halo, haloalkyl, hydroxy, and nitro.

In one embodiment Z is O.

In one embodiment, $R^1$, $R^2$, $R^3$, and $R^4$ are each independently selected from the group consisting of H, $(C_2-C_{10})$-alkenyl, $(C_1-C_{10})$-alkoxy, $(C_1-C_{10})$-alkoxy-$(C_1-C_{10})$-alkyl, $(C_1-C_{10})$-alkoxycarbonyl-$(C_1-C_{10})$-alkyl, $(C_1-C_{10})$-alkyl, $(C_1-C_{10})$-alkylamino, $(C_1-C_{10})$-alkylcarbonyl, $(C_1-C_{10})$-alkylheteroaryl, $(C_1-C_{10})$-alkylsulfonyl-$(C_1-C_{10})$-alkyl, $(C_1-C_{10})$-alkylthio, $(C_2-C_{10})$-alkynyl, aminocarbonyl-$(C_1-C_{10})$-alkyl, aryl, aryl-$(C_2-C_{10})$-alkenyl, aryl-$(C_1-C_{10})$-alkoxy, aryl-$(C_1-C_{10})$-alkyl, aryl-$(C_1-C_{10})$-alkylamino, aryl-$(C_2-C_{10})$-alkynyl, arylcarbonyl, aryloxy, cyano, di-$(C_1-C_{10})$-alkylamino, halo, halo-$(C_1-C_{10})$-alkoxy, halo-$(C_1-C_{10})$-alkyl, heteroaryl, heteroaryl-$(C_1-C_{10})$-alkoxy, heteroarylcarbonyl, hydroxy and hydroxy-$(C_1-C_{10})$-alkyl; wherein each of aryl, wherever it occurs, is independently substituted with one to five substituents selected from the group consisting of $(C_1-C_{10})$-alkyl, $(C_1-C_{10})$-alkoxy, $(C_1-C_{10})$-alkylamino, cyano, halo, halo-$(C_1-C_{10})$-alkyl, hydroxy, and nitro.

In one embodiment, $R^1$, $R^2$, $R^3$, and $R^4$ are each independently selected from the group consisting of H, $(C_2-C_{10})$-alkenyl, $(C_1-C_{10})$-alkoxy, $(C_1-C_{10})$-alkyl, $(C_1-C_{10})$-alkylamino, $(C_1-C_{10})$-alkylcarbonyl, $(C_1-C_{10})$-alkylheteroaryl, $(C_1-C_{10})$-alkylsulfonyl-$(C_1-C_{10})$-alkyl, $(C_1-C_{10})$-alkylthio, $(C_2-C_{10})$-alkynyl, aryl, aryl-$(C_1-C_{10})$-alkyl, aryl-$(C_2-C_{10})$-alkynyl, arylcarbonyl, aryloxy, di-$(C_1-C_{10})$-alkylamino, halo, halo-$(C_1-C_{10})$-alkoxy, heteroaryl, and heteroaryl-$(C_1-C_{10})$-alkoxy; wherein each of aryl, wherever it occurs, is independently substituted with one to five substituents selected from the group consisting of $(C_1-C_{10})$-alkyl, $(C_1-C_{10})$-alkoxy, $(C_1-C_{10})$-alkylamino, cyano, halo, halo-$(C_1-C_{10})$-alkyl, hydroxy, and nitro.

In one embodiment, $R^1$, $R^2$, $R^3$, and $R^4$ are each independently selected from the group consisting of H, $(C_2-C_{10})$-alkenyl, $(C_1-C_{10})$-alkoxy, $(C_1-C_{10})$-alkyl, $(C_1-C_{10})$-alkylamino, $(C_1-C_{10})$-alkylsulfonyl-$(C_1-C_{10})$-alkyl, $(C_1-C_{10})$-alkylthio, $(C_2-C_{10})$-alkynyl, aryl, aryl-$(C_1-C_{10})$-alkyl, aryl-$(C_2-C_{10})$-alkynyl, arylcarbonyl, di-$(C_1-C_{10})$-alkylamino, halo, halo-$(C_1-C_{10})$-alkoxy, and heteroaryl; wherein each of aryl, wherever it occurs, is independently substituted with one to five substituents selected from the group consisting of $(C_1-C_{10})$-alkyl, $(C_1-C_{10})$-alkoxy, and halo.

In one embodiment, $R_1$, $R_2$, $R_3$, and $R^4$ are each independently selected from the group consisting of H, $(C_1-C_{10})$-alkoxy, $(C_1-C_{10})$-alkyl, $(C_1-C_{10})$-alkylthio, $(C_2-C_{10})$-alkynyl, aryl, aryl-$(C_1-C_{10})$-alkyl, aryl-$(C_2-C_{10})$-alkynyl, arylcarbonyl, halo, and halo-$(C_1-C_{10})$-alkoxy; wherein each of aryl, wherever it occurs, is independently substituted with one to five substituents selected from the group consisting of $(C_1-C_{10})$-alkyl and halo.

In one embodiment, $R^1$, $R^2$, $R^3$, and $R^4$ are each independently selected from the group consisting of H, $(C_1-C_8)$-alkoxy, $(C_1-C_8)$-alkyl, $(C_1-C_8)$-alkylsulfonyl-$(C_1-C_8)$-alkyl, $(C_1-C_8)$-alkylthio, $(C_2-C_8)$-alkynyl, aryl, aryl-$(C_1-C_8)$-alkyl, aryl-$(C_2-C_8)$-alkynyl, arylcarbonyl, halo, and halo-$(C_1-C_8)$-alkoxy; wherein each of aryl, wherever it occurs, is independently substituted with one to five substituents selected from the group consisting of $(C_1-C_8)$-alkyl and halo.

In one embodiment, $R^1$, $R^2$, $R^3$, and $R^4$ are each independently selected from the group consisting of H, $(C_1-C_5)$-alkoxy, $(C_1-C_5)$-alkyl, methylalkylsulfonyl-$(C_1-C_8)$-alkyl, $(C_1-C_5)$-alkylthio, $(C_2-C_5)$-alkynyl, aryl, aryl-$(C_1-C_5)$-alkyl, aryl-$(C_2-C_5)$-alkynyl, arylcarbonyl, halo, and halo-$(C_1-C_5)$-alkoxy; wherein each of aryl, wherever it occurs, is independently substituted with one to five substituents selected from the group consisting of $(C_1-C_5)$-alkyl and halo.

In one embodiment of the present invention the compound has an S-absolute configuration, an R-absolute configuration, or a mixture of S- and R-absolute configuration at the 2-carbon of Formula 1. In one embodiment the compound has an S-absolute configuration at the 2-carbon. Alternatively the compound has an R-absolute configuration at the 2-carbon. In another alternative the compound comprises a mixture of S- and R-absolute configuration at the 2-carbon. In a further embodiment the compound is racemic.

In another embodiment the present invention provides a compound of Formula 1 wherein X is H. Alternatively X can be a pharmaceutically acceptable cation. By way of non-limiting example X can be an ammonium cation, an alkylammonium cation, a dialkylammonium cation, a trialkylammonium cation, a tetraalkylammonium cation, an alkali metal cation, or an alkaline earth cation. The pharmaceutically acceptable cation can be an alkali metal cation. In one embodiment the alkali metal cation is selected from the group consisting of sodium and potassium. In another embodiment the alkali metal cation is sodium. Alternatively the alkali metal cation can be potassium.

In yet another embodiment the pharmaceutically acceptable cation is an alkaline earth metal cation. For example the alkaline earth metal cation can be calcium. In another example the alkaline earth metal cation is magnesium.

In one embodiment the compound is selected from the group consisting of:

(2R)-6-chloro-7-isobutyl-2-(trifluoromethyl)-2H-chromene-3-carboxylic acid;
6-chloro-7-isobutyl-2-(trifluoromethyl)-2H-chromene-3-carboxylic acid;
(2R)-7-benzyl-6-chloro-2-(trifluoromethyl)-2H-chromene-3-carboxylic acid;
7-benzyl-6-chloro-2-(trifluoromethyl)-2H-chromene-3-carboxylic acid;
7-butoxy-6-chloro-8-methyl-2-(trifluoromethyl)-2H-chromene-3-carboxylic acid;
7-benzyl-6-bromo-2-(trifluoromethyl)-2H-chromene-3-carboxylic acid;
7-butyl-6-chloro-2-(trifluoromethyl)-2H-chromene-3-carboxylic acid;
6,8-dichloro-7-(2-ethylbutoxy)-2-(trifluoromethyl)-2H-chromene-3-carboxylic acid;
6-chloro-8-methyl-7-propoxy-2-(trifluoromethyl)-2H-chromene-3-carboxylic acid;
6-chloro-7-(isobutylthio)-2-(trifluoromethyl)-2H-chromene-3-carboxylic acid;
6-chloro-7-(2-ethylbutoxy)-8-methyl-2-(trifluoromethyl)-2H-chromene-3-carboxylic acid;
6-chloro-7-(isopentyloxy)-8-methyl-2-(trifluoromethyl)-2H-chromene-3-carboxylic acid;
8-methyl-6-(trifluoromethoxy)-2-(trifluoromethyl)-2H-chromene-3-carboxylic acid;
6,8-dichloro-7-isobutoxy-2-(trifluoromethyl)-2H-chromene-3-carboxylic acid;
8-chloro-6-iodo-2-(trifluoromethyl)-2H-chromene-3-carboxylic acid;
7-benzyl-6-methyl-2-(trifluoromethyl)-2H-chromene-3-carboxylic acid;
7-(sec-butylthio)-6-chloro-2-(trifluoromethyl)-2H-chromene-3-carboxylic acid;
(2S)-6-ethyl-8-methyl-2-(trifluoromethyl)-2H-chromene-3-carboxylic acid;
6,8-dichloro-5-methyl-2-(trifluoromethyl)-2H-chromene-3-carboxylic acid;
6-chloro-8-(4-chloro-3-methylphenyl)-2-(trifluoromethyl)-2H-chromene-3-carboxylic acid;
8-ethyl-6-(trifluoromethoxy)-2-(trifluoromethyl)-2H-chromene-3-carboxylic acid;
(2S)-6-chloro-8-methyl-2-(trifluoromethyl)-2H-chromene-3-carboxylic acid;
(2S)-8-ethyl-6-(trifluoromethoxy)-2-(trifluoromethyl)-2H-chromene-3-carboxylic acid;
(2S)-6-chloro-5,7-dimethyl-2-(trifluoromethyl)-2H-chromene-3-carboxylic acid;
6-chloro-8-(4-methylphenyl)-2-(trifluoromethyl)-2H-chromene-3-carboxylic acid;
6-chloro-8-(3-fluoro4-methylphenyl)-2-(trifluoromethyl)-2H-chromene-3-carboxylic acid;
8-propyl-6-(trifluoromethoxy)-2-(trifluoromethyl)-2H-chromene-3-carboxylic acid;
5-bromo-6,7-dichloro-8-methoxy-2-(trifluoromethyl)-2H-chromene-3-carboxylic acid;
6-chloro-8-(4-ethylphenyl)-2-(trifluoromethyl)-2H-chromene-3-carboxylic acid;
7-benzoyl-6-chloro-2-(trifluoromethyl)-2H-chromene-3-carboxylic acid;
8-pent-1-ynyl-6-(trifluoromethoxy)-2-(trifluoromethyl)-2H-chromene-3-carboxylic acid;
6-bromo-5,7-dichloro-8-ethoxy-2-(trifluoromethyl)-2H-chromene-3-carboxylic acid;
(2S)-6-chloro-5-methyl-2-(trifluoromethyl)-2H-chromene-3-carboxylic acid;
6-chloro-7,8-dimethyl-2-(trifluoromethyl)-2H-chromene-3-carboxylic acid;
(2S)-6-ethyl-2-(trifluoromethyl)-2H-chromene-3-carboxylic acid;
6-chloro-7-(3,3-dimethylbutyl)-2-(trifluoromethyl)-2H-chromene-3-carboxylic acid;
6-chloro-8-(methylthio)-2-(trifluoromethyl)-2H-chromene-3-carboxylic acid;
6-chloro-7-propoxy-2-(trifluoromethyl)-2H-chromene-3-carboxylic acid;
6,7-dichloro-8-methoxy-5-methyl-2-(trifluoromethyl)-2H-chromene-3-carboxylic acid;
6-chloro-8-methyl-7-(neopentyloxy)-2-(trifluoromethyl)-2H-chromene-3-carboxylic acid;
6-chloro-5,7,8-trimethyl-2-(trifluoromethyl)-2H-chromene-3-carboxylic acid;
8-(phenylethynyl)-6-(trifluoromethoxy)-2-(trifluoromethyl)-2H-chromene-3-carboxylic acid;
6,8-dichloro-5,7-dimethyl-2-(trifluoromethyl)-2H-chromene-3-carboxylic acid;
5-chloro-6,8-dimethyl-2-(trifluoromethyl)-2H-chromene-3-carboxylic acid;
7-benzyl-5,6-dichloro-2-(trifluoromethyl)-2H-chromene-3-carboxylic acid;
6-chloro-5,7-dimethyl-2-(trifluoromethyl)-2H-chromene-3-carboxylic acid;
6,8-dimethyl-2-(trifluoromethyl)-2H-chromene-3-carboxylic acid;
6-ethyl-2-(trifluoromethyl)-2H-chromene-3-carboxylic acid; and
(2S)-6,8-dimethyl-2-(trifluoromethyl)-2H-chromene-3-carboxylic acid;

or their isomer and pharmaceutically acceptable salt thereof.

In one embodiment the compound is selected from the group consisting of:

(2R)-6-chloro-7-isobutyl-2-(trifluoromethyl)-2H-chromene-3-carboxylic acid;
6-chloro-7-isobutyl-2-(trifluoromethyl)-2H-chromene-3-carboxylic acid;
(2R)-7-benzyl-6-chloro-2-(trifluoromethyl)-2H-chromene-3-carboxylic acid;
7-benzyl-6-chloro-2-(trifluoromethyl)-2H-chromene-3-carboxylic acid;
7-butoxy-6-chloro-8-methyl-2-(trifluoromethyl)-2H-chromene-3-carboxylic acid;
7-benzyl-6-bromo-2-(trifluoromethyl)-2H-chromene-3-carboxylic acid;
7-butyl-6-chloro-2-(trifluoromethyl)-2H-chromene-3-carboxylic acid;
6,8-dichloro-7-(2-ethylbutoxy)-2-(trifluoromethyl)-2H-chromene-3-carboxylic acid;
6-chloro-8-methyl-7-propoxy-2-(trifluoromethyl)-2H-chromene-3-carboxylic acid;

6-chloro-7-(isobutylthio)-2-(trifluoromethyl)-2H-chromene-3-carboxylic acid;
6-chloro-7-(2-ethylbutoxy)-8-methyl-2-(trifluoromethyl)-2H-chromene-3-carboxylic acid;
6-chloro-7-(isopentyloxy)-8-methyl-2-(trifluoromethyl)-2H-chromene-3-carboxylic acid;
8-methyl-6-(trifluoromethoxy)-2-(trifluoromethyl)-2H-chromene-3-carboxylic acid;
6,8-dichloro-7-isobutoxy-2-(trifluoromethyl)-2H-chromene-3-carboxylic acid;
8-chloro-6-iodo-2-(trifluoromethyl)-2H-chromene-3-carboxylic acid;
7-benzyl-6-methyl-2-(trifluoromethyl)-2H-chromene-3-carboxylic acid;
7-(sec-butylthio)-6-chloro-2-(trifluoromethyl)-2H-chromene-3-carboxylic acid;
(2S)-6-ethyl-8-methyl-2-(trifluoromethyl)-2H-chromene-3-carboxylic acid;
6,8-dichloro-5-methyl-2-(trifluoromethyl)-2H-chromene-3-carboxylic acid;
6-chloro-8-(4-chloro-3-methylphenyl)-2-(trifluoromethyl)-2H-chromene-3-carboxylic acid;
8-ethyl-6-(trifluoromethoxy)-2-(trifluoromethyl)-2H-chromene-3-carboxylic acid;
(2S)-6-chloro-8-methyl-2-(trifluoromethyl)-2H-chromene-3-carboxylic acid;
(2S)-8-ethyl-6-(trifluoromethoxy)-2-(trifluoromethyl)-2H-chromene-3-carboxylic acid;
(2S)-6-chloro-5,7-dimethyl-2-(trifluoromethyl)-2H-chromene-3-carboxylic acid;
6-chloro-8-(4-methylphenyl)-2-(trifluoromethyl)-2H-chromene-3-carboxylic acid;
6-chloro-8-(3-fluoro-4-methylphenyl)-2-(trifluoromethyl)-2H-chromene-3-carboxylic acid;
8-propyl-6-(trifluoromethoxy)-2-(trifluoromethyl)-2H-chromene-3-carboxylic acid;
5-bromo-6,7-dichloro-8-methoxy-2-(trifluoromethyl)-2H-chromene-3-carboxylic acid;
6-chloro-8-(4-ethylphenyl)-2-(trifluoromethyl)-2H-chromene-3-carboxylic acid; and
(2S)-6,8-dimethyl-2-(trifluoromethyl)-2H-chromene-3-carboxylic acid;

or their isomer and pharmaceutically acceptable salt thereof.

In one embodiment the compound isselected from the group consisting of
7-benzoyl-6-chloro-2-(trifluoromethyl)-2H-chromene-3-carboxylic acid;
7-(pyridin-3-ylcarbonyl)-2-(trifluoromethyl)-2H-chromene-3-carboxylic acid trifluoroacetate;
7-(2-furyl)-2-(trifluoromethyl)-2H-chromene-3-carboxylic acid;
7-benzyl-5,6-dichloro-2-(trifluoromethyl)-2H-chromene-3-carboxylic acid;
7-benzyl-6-chloro-8-methyl-2-(trifluoromethyl)-2H-chromene-3-carboxylic acid;
7-benzyl-8-methyl-2-(trifluoromethyl)-2H-chromene-3-carboxylic acid;
(2S)-6-chloro-8-methyl-2-(trifluoromethyl)-2H-chromene-3-carboxylic acid;
(2R)-6-chloro-8-methyl-2-(trifluoromethyl)-2H-chromene-3-carboxylic acid;
8-chloro-6-ethoxy-2-(trifluoromethyl)-2H-chromene-3-carboxylic acid;
8-chloro-6-(2,2,2-trifluoroethoxy)-2-(trifluoromethyl)-2H-chromene-3-carboxylic acid;
6-(benzyloxy)-8-chloro-2-(trifluoromethyl)-2H-chromene-3-carboxylic acid;
8-chloro-6-(hexyloxy)-2-(trifluoromethyl)-2H-chromene-3-carboxylic acid;
8-chloro-6-propoxy-2-(trifluoromethyl)-2H-chromene-3-carboxylic acid;
(2R)-8-chloro-6-methoxy-2-(trifluoromethyl)-2H-chromene-3-carboxylic acid;
(2S)-8-chloro-6-methoxy-2-(trifluoromethyl)-2H-chromene-3-carboxylic acid;
5,8-dichloro-6-methoxy-2-(trifluoromethyl)-2H-chromene-3-carboxylic acid;
7,8-dichloro-6-methoxy-2-(trifluoromethyl)-2H-chromene-3-carboxylic acid;
6,8-dichloro-7-(2-ethylbutoxy)-2-(trifluoromethyl)-2H-chromene-3-carboxylic acid;
6,8-dichloro-7-(3,3-dimethylbutoxy)-2-(trifluoromethyl)-2H-chromene-3-carboxylic acid;
6,8-dichloro-7-isobutoxy-2-(trifluoromethyl)-2H-chromene-3-carboxylic acid;
7-(benzyloxy)-6,8-dichloro-2-(trifluoromethyl)-2H-chromene-3-carboxylic acid;
7-tert-butoxy-6,8-dichloro-2-(trifluoromethyl)-2H-chromene-3-carboxylic acid;
8-chloro-6-iodo-2-(trifluoromethyl)-2H-chromene-3-carboxylic acid;
6-chloro-5,7-dimethyl-2-(trifluoromethyl)-2H-chromene-3-carboxylic acid;
(2R)-6-chloro-5,7-dimethyl-2-(trifluoromethyl)-2H-chromene-3-carboxylic acid;
(2S)-6-chloro-5,7-dimethyl-2-(trifluoromethyl)-2H-chromene-3-carboxylic acid;
6-chloro-7,8-dimethyl-2-(trifluoromethyl)-2H-chromene-3-carboxylic acid;
6-chloro-5,7,8-trimethyl-2-(trifluoromethyl)-2H-chromene-3-carboxylic acid;
6-chloro-5,8-dimethyl-2-(trifluoromethyl)-2H-chromene-3-carboxylic acid;
7-tert-pentyl-2-(trifluoromethyl)-2H-chromene-3-carboxylic acid;
6-chloro-7-tert-pentyl-2-(trifluoromethyl)-2H-chromene-3-carboxylic acid;
7-(1,1-dimethylbutyl)-2-(trifluoromethyl)-2H-chromene-3-carboxylic acid;
6-chloro-7-(1,1-dimethylbutyl)-2-(trifluoromethyl)-2H-chromene-3-carboxylic acid;
7-tert-butyl-6-methoxy-2-(trifluoromethyl)-2H-chromene-3-carboxylic acid;
6-chloro-7-isopropenyl-2-(trifluoromethyl)-2H-chromene-3-carboxylic acid;
6-chloro-7-(2-methoxy-1,1-dimethylethyl)-2-(trifluoromethyl)-2H-chromene-3-carboxylic acid;
7-tert-butyl-5-chloro-6-methoxy-2-(trifluoromethyl)-2H-chromene-3-carboxylic acid;
7-tert-butyl-5,8-dichloro-6-methoxy-2-(trifluoromethyl)-2H-chromene-3-carboxylic acid;
6-chloro-7-(2-hydroxy-1,1-dimethylethyl)-2-(trifluoromethyl)-2H-1-benzopyran-3-carboxylic acid;
(2R)-6-chloro-7-(2-hydroxy-1,1-dimethylethyl)-2-(trifluoromethyl)-2H-chromene-3-carboxylic acid;
(2S)-6-chloro-7-(2-hydroxy-1,1-dimethylethyl)-2-(trifluoromethyl)-2H-chromene-3-carboxylic acid;
6,8-dichloro-5-methyl-2-(trifluoromethyl)-2H-chromene-3-carboxylic acid;
6,7-dimethoxy-2-(trifluoromethyl)-2H-chromene-3-carboxylic acid;

5,8-dichloro-6,7-dimethoxy-2-(trifluoromethyl)-2H-chromene-3-carboxylic acid;
5-chloro-6,7-dimethoxy-2-(trifluoromethyl)-2H-chromene-3-carboxylic acid;
8-chloro-6,7-dimethoxy-2-(trifluoromethyl)-2H-chromene-3-carboxylic acid;
6-chloro-5-methyl-2-(trifluoromethyl)-2H-chromene-3-carboxylic acid;
5-methyl-2-(trifluoromethyl)-2H-chromene-3-carboxylic acid;
(2S)-6-chloro-5-methyl-2-(trifluoromethyl)-2H-chromene-3-carboxylic acid;
(2R)-6-chloro-5-methyl-2-(trifluoromethyl)-2H-chromene-3-carboxylic acid;
6-chloro-7-(dipropylamino)-2-(trifluoromethyl)-2H-chromene-3-carboxylic acid;
6,8-dichloro-5,7-dimethyl-2-(trifluoromethyl)-2H-chromene-3-carboxylic acid;
5,7-dimethyl-2-(trifluoromethyl)-2H-chromene-3-carboxylic acid;
6-ethyl-8-methyl-2-(trifluoromethyl)-2H-chromene-3-carboxylic acid;
(2S)-6-ethyl-8-methyl-2-(trifluoromethyl)-2H-chromene-3-carboxylic acid;
(2R)-6-ethyl-8-methyl-2-(trifluoromethyl)-2H-chromene-3-carboxylic acid;
6-ethyl-7-methyl-2-(trifluoromethyl)-2H-chromene-3-carboxylic acid;
6-ethyl-8-propyl-2-(trifluoromethyl)-2H-chromene-3-carboxylic acid;
6-isopropyl-2-(trifluoromethyl)-2H-chromene-3-carboxylic acid;
6-isopropyl-7-methyl-2-(trifluoromethyl)-2H-chromene-3-carboxylic acid;
6-chloro-7-(ethoxymethyl)-2-(trifluoromethyl)-2H-chromene-3-carboxylic acid;
6-ethyl-8-methoxy-2-(trifluoromethyl)-2H-chromene-3-carboxylic acid;
8-tert-butyl-6-ethyl-2-(trifluoromethyl)-2H-chromene-3-carboxylic acid;
6,8-diethyl-2-(trifluoromethyl)-2H-chromene-3-carboxylic acid;
6-[3,5-bis(trifluoromethyl)phenyl]-2-(trifluoromethyl)-2H-chromene-3-carboxylic acid;
6-(4-methoxyphenyl)-2-(trifluoromethyl)-2H-chromene-3-carboxylic acid;
6-thien-3-yl-2-(trifluoromethyl)-2H-chromene-3-carboxylic acid;
6-(2-furyl)-2-(trifluoromethyl)-2H-chromene-3-carboxylic acid;
6-(4-methylthien-2-yl)-2-(trifluoromethyl)-2H-chromene-3-carboxylic acid;
6-(3-nitrophenyl)-2-(trifluoromethyl)-2H-chromene-3-carboxylic acid;
6-(1,3-benzodioxol-5-yl)-2-(trifluoromethyl)-2H-chromene-3-carboxylic acid;
6-(4-methylphenyl)-2-(trifluoromethyl)-2H-chromene-3-carboxylic acid;
6-pyridin-4-yl-2-(trifluoromethyl)-2H-chromene-3-carboxylic acid;
6-(3-isopropylphenyl)-2-(trifluoromethyl)-2H-chromene-3-carboxylic acid;
6-(2-naphthyl)-2-(trifluoromethyl)-2H-chromene-3-carboxylic acid;
6-pyridin-3-yl-2-(trifluoromethyl)-2H-chromene-3-carboxylic acid;
6-(1H-indol-6-yl)-2-(trifluoromethyl)-2H-chromene-3-carboxylic acid;
6-quinolin-8-yl-2-(trifluoromethyl)-2H-chromene-3-carboxylic acid;
6-(3,4-dimethoxyphenyl)-2-(trifluoromethyl)-2H-chromene-3-carboxylic acid;
2-(trifluoromethyl)-6-[4-(trifluoromethyl)phenyl]-2H-chromene-3-carboxylic acid;
2-(trifluoromethyl)-6-[3-(trifluoromethyl)phenyl]-2H-chromene-3-carboxylic acid;
8-chloro-6-phenyl-2-(trifluoromethyl)-2H-chromene-3-carboxylic acid;
8-chloro-6-(4-chlorophenyl)-2-(trifluoromethyl)-2H-chromene-3-carboxylic acid;
8-chloro-6-(2-chlorophenyl)-2-(trifluoromethyl)-2H-chromene-3-carboxylic acid;
8-chloro-6-(4-fluorophenyl)-2-(trifluoromethyl)-2H-chromene-3-carboxylic acid;
8-chloro-6-thien-3-yl-2-(trifluoromethyl)-2H-chromene-3-carboxylic acid;
8-chloro-6-(2-furyl)-2-(trifluoromethyl)-2H-chromene-3-carboxylic acid;
8-chloro-6-(3-nitrophenyl)-2-(trifluoromethyl)-2H-chromene-3-carboxylic acid;
6-(1,3-benzodioxol-5-yl)-8-chloro-2-(trifluoromethyl)-2H-chromene-3-carboxylic acid;
8-chloro-6-(4-methoxyphenyl)-2-(trifluoromethyl)-2H-chromene-3-carboxylic acid;
8-chloro-6-(4-methylphenyl)-2-(trifluoromethyl)-2H-chromene-3-carboxylic acid;
8-chloro-6-(3-isopropylphenyl)-2-(trifluoromethyl)-2H-chromene-3-carboxylic acid;
8-chloro-6-(2-naphthyl)-2-(trifluoromethyl)-2H-chromene-3-carboxylic acid;
8-chloro-6-pyridin-3-yl-2-(trifluoromethyl)-2H-chromene-3-carboxylic acid;
8-chloro-6-(H-indol-5-yl)-2-(trifluoromethyl)-2H-chromene-3-carboxylic acid;
8-chloro-6-quinolin-8-yl-2-(trifluoromethyl)-2H-chromene-3-carboxylic acid;
8-chloro-6-(3,4-dimethoxyphenyl)-2-(trifluoromethyl)-2H-chromene-3-carboxylic acid;
8-chloro-2-(trifluoromethyl)-6-[4-(trifluoromethyl)phenyl]-2H-chromene-3-carboxylic acid;
8-chloro-2-(trifluoromethyl)-6-[3-(trifluoromethyl)phenyl]-2H-chromene-3-carboxylic acid;
8-chloro-6-(3-furyl)-2-(trifluoromethyl)-2H-chromene-3-carboxylic acid;
8-chloro-6-(3-methoxyphenyl)-2-(trifluoromethyl)-2H-chromene-3-carboxylic acid;
8-chloro-6-ethyl-2-(trifluoromethyl)-2H-chromene-3-carboxylic acid;
6-butyl-2-(trifluoromethyl)-2H-chromene-3-carboxylic acid;
6-butyl-8-chloro-2-(trifluoromethyl)-2H-chromene-3-carboxylic acid;
8-chloro-6-ethynyl-2-(trifluoromethyl)-2H-chromene-3-carboxylic acid;
8-chloro-2-(trifluoromethyl)-6-vinyl-2H-chromene-3-carboxylic acid;
8-chloro-6-(phenylethynyl)-2-(trifluoromethyl)-2H-chromene-3-carboxylic acid;
8-chloro-6-cyano-2-(trifluoromethyl)-2H-chromene-3-carboxylic acid;
6-acetyl-8-chloro-2-(trifluoromethyl)-2H-chromene-3-carboxylic acid;

6-allyl-8-chloro-2-(trifluoromethyl)-2H-chromene-3-carboxylic acid;
8-chloro-6-prop-1-ynyl-2-(trifluoromethyl)-2H-chromene-3-carboxylic acid;
6-chloro-8-(3-methylbut-1-ynyl)-2-(trifluoromethyl)-2H-chromene-3-carboxylic acid;
6-chloro-8-prop-1-ynyl-2-(trifluoromethyl)-2H-chromene-3-carboxylic acid;
8-but-1-ynyl-6-chloro-2-(trifluoromethyl)-2H-chromene-3-carboxylic acid;
6-chloro-8-(4-fluorophenyl)-2-(trifluoromethyl)-2H-chromene-3-carboxylic acid;
6-chloro-8-(3-chloro-4-fluorophenyl)-2-(trifluoromethyl)-2H-chromene-3-carboxylic acid;
6-chloro-8-(3,5-dichlorophenyl)-2-(trifluoromethyl)-2H-chromene-3-carboxylic acid;
6-chloro-8-(3,4-dichlorophenyl)-2-(trifluoromethyl)-2H-chromene-3-carboxylic acid;
6-chloro-8-(3-fluorophenyl)-2-(trifluoromethyl)-2H-chromene-3-carboxylic acid;
6-chloro-8-(3-chlorophenyl)-2-(trifluoromethyl)-2H-chromene-3-carboxylic acid;
6-chloro-8-(2-methylphenyl)-2-(trifluoromethyl)-2H-chromene-3-carboxylic acid;
6-chloro-8-(3-methylphenyl)-2-(trifluoromethyl)-2H-chromene-3-carboxylic acid;
6-chloro-8-(4-methylphenyl)-2-(trifluoromethyl)-2H-chromene-3-carboxylic acid;
6-chloro-2-(trifluoromethyl)-8-[3-(trifluoromethyl)phenyl]-2H-chromene-3-carboxylic acid;
6-chloro-2-(trifluoromethyl)-8-[4-(trifluoromethyl)phenyl]-2H-chromene-3-carboxylic acid;
6-chloro-8-(4-ethoxyphenyl)-2-(trifluoromethyl)-2H-chromene-3-carboxylic acid;
6-chloro-8-(3-cyanophenyl)-2-(trifluoromethyl)-2H-chromene-3-carboxylic acid;
6-chloro-8-(3-ethoxyphenyl)-2-(trifluoromethyl)-2H-chromene-3-carboxylic acid;
6-chloro-8-(2-ethoxyphenyl)-2-(trifluoromethyl)-2H-chromene-3-carboxylic acid;
8-[3,5-bis(trifluoromethyl)phenyl]-6-chloro-2-(trifluoromethyl)-2H-chromene-3-carboxylic acid;
6-chloro-8-pyridin-4-yl-2-(trifluoromethyl)-2H-chromene-3-carboxylic acid;
6-chloro-2-(trifluoromethyl)-8-[2-(trifluoromethyl)phenyl]-2H-chromene-3-carboxylic acid;
6-chloro-8-(4-cyanophenyl)-2-(trifluoromethyl)-2H-chromene-3-carboxylic acid;
6-chloro-8-pyridin-3-yl-2-(trifluoromethyl)-2H-chromene-3-carboxylic acid;
6-chloro-8-(3,5-difluorophenyl)-2-(trifluoromethyl)-2H-chromene-3-carboxylic acid;
6-chloro-8-(3,5-dimethylphenyl)-2-(trifluoromethyl)-2H-chromene-3-carboxylic acid;
6-chloro-8-(3-isopropylphenyl)-2-(trifluoromethyl)-2H-chromene-3-carboxylic acid;
8-(4-tert-butylphenyl)-6-chloro-2-(trifluoromethyl)-2H-chromene-3-carboxylic acid;
6-chloro-8-(2,4-dimethylphenyl)-2-(trifluoromethyl)-2H-chromene-3-carboxylic acid;
6-chloro-8-(4-methyl-3-nitrophenyl)-2-(trifluoromethyl)-2H-chromene-3-carboxylic acid;
8-(4-butylphenyl)-6-chloro-2-(trifluoromethyl)-2H-chromene-3-carboxylic acid;
6-chloro-8-(5-chloro-2-methoxyphenyl)-2-(trifluoromethyl)-2H-chromene-3-carboxylic acid;
8-(4-acetylphenyl)-6-chloro-2-(trifluoromethyl)-2H-chromene-3-carboxylic acid;
6-chloro-8-(4-ethylphenyl)-2-(trifluoromethyl)-2H-chromene-3-carboxylic acid;
6-chloro-8-(3-fluoro-4-methylphenyl)-2-(trifluoromethyl)-2H-chromene-3-carboxylic acid;
6-chloro-8-(3,4-dimethylphenyl)-2-(trifluoromethyl)-2H-chromene-3-carboxylic acid;
6-chloro-8-(4-hydroxyphenyl)-2-(trifluoromethyl)-2H-chromene-3-carboxylic acid;
6-chloro-8-(4-chloro-3-methylphenyl)-2-(trifluoromethyl)-2H-chromene-3-carboxylic acid;
6-chloro-8-(4-fluoro-3-methylphenyl)-2-(trifluoromethyl)-2H-chromene-3-carboxylic acid;
6-chloro-2-(trifluoromethyl)-8-(3,4,5-trimethoxyphenyl)-2H-chromene-3-carboxylic acid;
6-chloro-8-(3-fluoro-4-methoxyphenyl)-2-(trifluoromethyl)-2H-chromene-3-carboxylic acid;
6-chloro-8-(4-methoxy-3-methylphenyl)-2-(trifluoromethyl)-2H-chromene-3-carboxylic acid;
6-chloro-8-(4-isobutylphenyl)-2-(trifluoromethyl)-2H-chromene-3-carboxylic acid;
6-chloro-8-(4-methoxy-3,5-dimethylphenyl)-2-(trifluoromethyl)-2H-chromene-3-carboxylic acid;
6-chloro-8-thien-3-yl-2-(trifluoromethyl)-2H-chromene-3-carboxylic acid;
6-chloro-8-(3-nitrophenyl)-2-(trifluoromethyl)-2H-chromene-3-carboxylic acid;
6-chloro-8-[4-(dimethylamino)phenyl]-2-(trifluoromethyl)-2H-chromene-3-carboxylic acid;
7-methoxy-6-phenyl-2-(trifluoromethyl)-2H-chromene-3-carboxylic acid;
7-methoxy-6-thien-3-yl-2-(trifluoromethyl)-2H-chromene-3-carboxylic acid;
7-methoxy-6-(4-methoxyphenyl)-2-(trifluoromethyl)-2H-chromene-3-carboxylic acid;
7-methoxy-2-(trifluoromethyl)-6-[4-(trifluoromethyl)phenyl]-2H-chromene-3-carboxylic acid;
7-methoxy-2-(trifluoromethyl)-6-[3-(trifluoromethyl)phenyl]-2H-chromene-3-carboxylic acid;
6-(3-furyl)-7-methoxy-2-(trifluoromethyl)-2H-chromene-3-carboxylic acid;
7-methoxy-6-(3-methoxyphenyl)-2-(trifluoromethyl)-2H-chromene-3-carboxylic acid;
6-(2-furyl)-7-methoxy-2-(trifluoromethyl)-2H-chromene-3-carboxylic acid;
7-methoxy-6-(3-nitrophenyl)-2-(trifluoromethyl)-2H-chromene-3-carboxylic acid;
6-(1,3-benzodioxol-5-yl)-7-methoxy-2-(trifluoromethyl)-2H-chromene-3-carboxylic acid;
7-methoxy-6-(4-methylphenyl)-2-(trifluoromethyl)-2H-chromene-3-carboxylic acid;
6-(3-isopropylphenyl)-7-methoxy-2-(trifluoromethyl)-2H-chromene-3-carboxylic acid;
7-methoxy-6-(2-naphthyl)-2-(trifluoromethyl)-2H-chromene-3-carboxylic acid;
7-methoxy-6-pyridin-3-yl-2-(trifluoromethyl)-2H-chromene-3-carboxylic acid;
6-(3,4-dimethoxyphenyl)-7-methoxy-2-(trifluoromethyl)-2H-chromene-3-carboxylic acid;
7-methoxy-6-quinolin-8-yl-2-(trifluoromethyl)-2H-chromene-3-carboxylic acid;
6-(4-chlorophenyl)-7-methoxy-2-(trifluoromethyl)-2H-chromene-3-carboxylic acid;
6-(2-chlorophenyl)-7-methoxy-2-(trifluoromethyl)-2H-chromene-3-carboxylic acid;

6-(4-fluorophenyl)-7-methoxy-2-(trifluoromethyl)-2H-chromene-3-carboxylic acid;
6-iodo-7-methoxy-2-(trifluoromethyl)-2H-chromene-3-carboxylic acid;
6-ethyl-7-methoxy-2-(trifluoromethyl)-2H-chromene-3-carboxylic acid;
7-methoxy-6-methyl-2-(trifluoromethyl)-2H-chromene-3-carboxylic acid;
7-methoxy-2-(trifluoromethyl)-6-vinyl-2H-chromene-3-carboxylic acid;
6-ethynyl-7-methoxy-2-(trifluoromethyl)-2H-chromene-3-carboxylic acid;
6-acetyl-7-methoxy-2-(trifluoromethyl)-2H-chromene-3-carboxylic acid;
7-methoxy-6-prop-1-ynyl-2-(trifluoromethyl)-2H-chromene-3-carboxylic acid;
7-ethoxy-6-ethyl-2-(trifluoromethyl)-2H-chromene-3-carboxylic acid;
6-ethyl-7-(pyridin-3-ylmethoxy)-2-(trifluoromethyl)-2H-chromene-3-carboxylic acid;
6-ethyl-7-(pyridin-4-ylmethoxy)-2-(trifluoromethyl)-2H-chromene-3-carboxylic acid;
6-ethyl-7-propoxy-2-(trifluoromethyl)-2H-chromene-3-carboxylic acid;
6-ethyl-7-(2-ethylbutoxy)-2-(trifluoromethyl)-2H-chromene-3-carboxylic acid;
8-iodo-7-methoxy-2-(trifluoromethyl)-2H-chromene-3-carboxylic acid;
8-chloro-6-ethyl-7-methoxy-2-(trifluoromethyl)-2H-chromene-3-carboxylic acid;
5,7-dichloro-6-ethoxy-2-(trifluoromethyl)-2H-chromene-3-carboxylic acid;
5,7-dichloro-6-methoxy-2-(trifluoromethyl)-2H-chromene-3-carboxylic acid;
5,7-dichloro-6-isopropoxy-2-(trifluoromethyl)-2H-chromene-3-carboxylic acid;
6-chloro-5-phenoxy-2-(trifluoromethyl)-2H-chromene-3-carboxylic acid;
sodium 8-chloro-6-ethynyl-2-(trifluoromethyl)-2H-chromene-3-carboxylate;
sodium 8-but-1-ynyl-6-chloro-2-(trifluoromethyl)-2H-chromene-3-carboxylate;
sodium 6-chloro-8-(3-fluoro-4-methylphenyl)-2-(trifluoromethyl)-2H-chromene-3-carboxylate;
sodium 6-chloro-8-(4-ethylphenyl)-2-(trifluoromethyl)-2H-chromene-3-carboxylate;
sodium 6-chloro-8-(4-chloro-3-methylphenyl)-2-(trifluoromethyl)-2H-chromene-3-carboxylate;
sodium 6-chloro-8-(4-methoxy-3-methylphenyl)-2-(trifluoromethyl)-2H-chromene-3-carboxylate;
sodium 6-ethyl-7-methoxy-2-(trifluoromethyl)-2H-chromene-3-carboxylate;
sodium 6-chloro-5-phenoxy-2-(trifluoromethyl)-2H-chromene-3-carboxylate;
5,7,8-trichloro-6-methoxy-2-(trifluoromethyl)-2H-chromene-3-carboxylic acid;
8-iodo-6-(trifluoromethoxy)-2-(trifluoromethyl)-2H-chromene-3-carboxylic acid;
8-methyl-6-(trifluoromethoxy)-2-(trifluoromethyl)-2H-chromene-3-carboxylic acid;
8-(phenylethynyl)-6-(trifluoromethoxy)-2-(trifluoromethyl)-2H-chromene-3-carboxylic acid;
8-prop-1-ynyl-6-(trifluoromethoxy)-2-(trifluoromethyl)-2H-chromene-3-carboxylic acid;
8-pent-1-ynyl-6-(trifluoromethoxy)-2-(trifluoromethyl)-2H-chromene-3-carboxylic acid;
8-ethynyl-6-(trifluoromethoxy)-2-(trifluoromethyl)-2H-chromene-3-carboxylic acid;
8-ethyl-6-(trifluoromethoxy)-2-(trifluoromethyl)-2H-chromene-3-carboxylic acid;
8-isobutyl-6-(trifluoromethoxy)-2-(trifluoromethyl)-2H-chromene-3-carboxylic acid;
8-propyl-6-(trifluoromethoxy)-2-(trifluoromethyl)-2H-chromene-3-carboxylic acid;
8-pentyl-6-(trifluoromethoxy)-2-(trifluoromethyl)-2H-chromene-3-carboxylic acid;
(2S)-8-ethyl-6-(trifluoromethoxy)-2-(trifluoromethyl)-2H-chromene-3-carboxylic acid;
(2R)-8-ethyl-6-(tri fluoromethoxy)-2-(trifluoromethyl)-2H-chromene-3-carboxylic acid;
(2S)-8-ethyl-6-(trifluoromethoxy)-2-(trifluoromethyl)-2H-chromene-3-carboxylic acid;
6-(trifluoromethoxy)-2-(trifluoromethyl)-8-vinyl-2H-chromene-3-carboxylic acid;
8-(2-phenylethyl)-6-(trifluoromethoxy)-2-(trifluoromethyl)-2H-chromene-3-carboxylic acid;
8-cyano-6-(trifluoromethoxy)-2-(trifluoromethyl)-2H-chromene-3-carboxylic acid;
8-but-1-ynyl-6-(trifluoromethoxy)-2-(trifluoromethyl)-2H-chromene-3-carboxylic acid;
8-butyl-6-(trifluoromethoxy)-2-(trifluoromethyl)-2H-chromene-3-carboxylic acid;
8-allyl-6-(trifluoromethoxy)-2-(trifluoromethyl)-2H-chromene-3-carboxylic acid;
6,8-dichloro-7-iodo-2-(trifluoromethyl)-2H-chromene-3-carboxylic acid;
5-chloro-8-propoxy-2-(trifluoromethyl)-2H-chromene-3-carboxylic acid;
5-chloro-8-(2-ethylbutoxy)-2-(trifluoromethyl)-2H-chromene-3-carboxylic acid;
8-(benzyloxy)-5-chloro-2-(trifluoromethyl)-2H-chromene-3-carboxylic acid;
5-chloro-8-methoxy-2-(trifluoromethyl)-2H-chromene-3-carboxylic acid;
5,6-dichloro-8-methoxy-2-(trifluoromethyl)-2H-chromene-3-carboxylic acid;
5,7-dichloro-8-propoxy-2-(trifluoromethyl)-2H-chromene-3-carboxylic acid;
5-bromo-8-methoxy-2-(trifluoromethyl)-2H-chromene-3-carboxylic acid;
5-bromo-8-ethoxy-2-(trifluoromethyl)-2H-chromene-3-carboxylic acid;
8-propoxy-2-(trifluoromethyl)-2H-chromene-3-carboxylic acid;
8-butoxy-2-(trifluoromethyl)-2H-chromene-3-carboxylic acid;
8-(benzyloxy)-2-(trifluoromethyl)-2H-chromene-3-carboxylic acid;
8-(3-furylmethoxy)-2-(trifluoromethyl)-2H-chromene-3-carboxylic acid;
6-bromo-8-ethoxy-2-(trifluoromethyl)-2H-chromene-3-carboxylic acid;
6-bromo-5,7-dichloro-8-ethoxy-2-(trifluoromethyl)-2H-chromene-3-carboxylic acid;
5,6,7-trichloro-8-propoxy-2-(trifluoromethyl)-2H-chromene-3-carboxylic acid;
8-butoxy-5,6,7-trichloro-2-(trifluoromethyl)-2H-chromene-3-carboxylic acid;
5,6,7-trichloro-8-ethoxy-2-(trifluoromethyl)-2H-chromene-3-carboxylic acid;
6,7-dichloro-8-methoxy-5-methyl-2-(trifluoromethyl)-2H-chromene-3-carboxylic acid;

6-chloro-7-propoxy-2-(trifluoromethyl)-2H-chromene-3-carboxylic acid;
6-chloro-7-(2-ethylbutoxy)-2-(trifluoromethyl)-2H-chromene-3-carboxylic acid;
6-chloro-7-(3,3-dimethylbutoxy)-2-(trifluoromethyl)-2H-chromene-3-carboxylic acid;
7-(benzyloxy)-6-chloro-2-(trifluoromethyl)-2H-chromene-3-carboxylic acid;
7-tert-butoxy-6-chloro-2-(trifluoromethyl)-2H-chromene-3-carboxylic acid;
6-chloro-7-methoxy-2-(trifluoromethyl)-2H-chromene-3-carboxylic acid;
5-bromo-6,7-dichloro-8-methoxy-2-(trifluoromethyl)-2H-chromene-3-carboxylic acid;
8-ethoxy-6-methyl-2-(trifluoromethyl)-2H-chromene-3-carboxylic acid;
6,8-dimethyl-2-(trifluoromethyl)-2H-chromene-3-carboxylic acid;
(2S)-6,8-dimethyl-2-(trifluoromethyl)-2H-chromene-3-carboxylic acid;
(2R)-6,8-dimethyl-2-(trifluoromethyl)-2H-chromene-3-carboxylic acid;
(2R)-6,8-dimethyl-2-(trifluoromethyl)-2H-chromene-3-carboxylic acid compound with (1S)-1-phenylethanamine (1:1);
(2R)-6,8-dimethyl-2-(trifluoromethyl)-2H-chromene-3-carboxylic acid compound with (1R)-1-phenylethanamine (1:1);
5-chloro-6,8-dimethyl-2-(trifluoromethyl)-2H-chromene-3-carboxylic acid;
6-ethyl-2-(trifluoromethyl)-2H-chromene-3-carboxylic acid;
(2S)-6-ethyl-2-(trifluoromethyl)-2H-chromene-3-carboxylic acid;
(2R)-6-ethyl-2-(trifluoromethyl)-2H-chromene-3-carboxylic acid;
6-(1,1-difluoroethyl)-2-(trifluoromethyl)-2H-chromene-3-carboxylic acid;
6-tert-butyl-8-chloro-2-(trifluoromethyl)-2H-chromene-3-carboxylic acid;
7-(1-phenylvinyl)-2-(trifluoromethyl)-2H-chromene-3-carboxylic acid;
7-(1-phenylethyl)-2-(trifluoromethyl)-2H-chromene-3-carboxylic acid;
6,8-dichloro-7-[isobutyl(methyl)amino]-2-(trifluoromethyl)-2H-chromene-3-carboxylic acid;
6,8-dichloro-7-(methylamino)-2-(trifluoromethyl)-2H-chromene-3-carboxylic acid;
6,8-dichloro-7-(isobutylamino)-2-(trifluoromethyl)-2H-chromene-3-carboxylic acid;
6-chloro-7-methoxy-8-methyl-2-(trifluoromethyl)-2H-chromene-3-carboxylic acid;
6-chloro-7-(2-ethylbutoxy)-8-methyl-2-(trifluoromethyl)-2H-chromene-3-carboxylic acid;
6-chloro-8-methyl-7-propoxy-2-(trifluoromethyl)-2H-chromene-3-carboxylic acid;
6-chloro-7-isobutoxy-8-methyl-2-(trifluoromethyl)-2H-chromene-3-carboxylic acid;
7-butoxy-6-chloro-8-methyl-2-(trifluoromethyl)-2H-chromene-3-carboxylic acid;
6-chloro-8-methyl-7-(neopentyloxy)-2H-chromene-3-carboxylic acid;
6-chloro-7-(isopentyloxy)-8-methyl-2-(trifluoromethyl)-2H-chromene-3-carboxylic acid;
sodium 6,8-dichloro-7-(2-ethylbutoxy)-2-(trifluoromethyl)-2H-chromene-3-carboxylate;
sodium 6-chloro-7-isobutyl-2-(trifluoromethyl)-2H-chromene-3-carboxylate;
sodium 8-ethoxy-6-methyl-2-(trifluoromethyl)-2H-chromene-3-carboxylate;
sodium 6-chloro-7-(2-ethylbutoxy)-8-methyl-2-(trifluoromethyl)-2H-chromene-3-carboxylate;
sodium (2S) 6-ethyl-2-(trifluoromethyl)-2H-chromene-3-carboxylate;
sodium (2R) 6-ethyl-2-(trifluoromethyl)-2H-chromene-3-carboxylate;
sodium 8-ethyl-6-(trifluoromethoxy)-2-(trifluoromethyl)-2H-chromene-3-carboxylate;
sodium (2S)-6,8-dimethyl-2-(trifluoromethyl)-2H-chromene-3-carboxylate;
Sodium 7-(sec-butylthio)-6-chloro-2-(trifluoromethyl)-2H-chromene-3-carboxylate;
sodium 2-(trifluoromethyl)-8-propyl-6-(trifluoromethoxy)-2H-chromene-3-carboxylate;
sodium (S)-8-ethyl-2-(trifluoromethyl)-6-(trifluoromethoxy)-2H-chromene-3-carboxylate;
sodium (2S)-8-chloro-6-methoxy-2-(trifluoromethyl)-2H-chromene-3-carboxylate;
sodium 6-chloro-7-(3,6-dihydropyridin-1(2H)-yl)-2-(trifluoromethyl)-2H-chromene-3-carboxylate;
sodium 2-(trifluoromethyl)-8-phenethyl-6-(trifluoromethoxy)-2H-chromene-3-carboxylate;
6-chloro-8-methyl-7-propoxy-2-(trifluoromethyl)-2H-chromene-3-carboxylic acid;
sodium 6-chloro-8-methyl-7-(neopentyloxy)-2-(trifluoromethyl)-2H-chromene-3-carboxylate;
sodium (2S)-6-chloro-8-methyl-2-(trifluoromethyl)-2H-chromene-3-carboxylate;
sodium 8-allyl-6-(trifluoromethoxy)-2-(trifluoromethyl)-2H-chromene-3-carboxylate;
7-benzyl-6-bromo-2-(trifluoromethyl)-2H-chromene-3-carboxylic acid;
7-benzyl-6-methyl-2-(trifluoromethyl)-2H-chromene-3-carboxylic acid;
7-benzyl-6-ethyl-2-(trifluoromethyl)-2H-chromene-3-carboxylic acid;
7-benzyl-6-propyl-2-(trifluoromethyl)-2H-chromene-3-carboxylic acid;
7-benzyl-6-butyl-2-(trifluoromethyl)-2H-chromene-3-carboxylic acid;
7,8-dimethoxy-2-(trifluoromethyl)-2H-chromene-3-carboxylic acid;
6-chloro-7,8-dimethoxy-2-(trifluoromethyl)-2H-chromene-3-carboxylic acid;
7-tert-butoxy-2-(trifluoromethyl)-2H-chromene-3-carboxylic acid;
7-methoxy-8-methyl-2-(trifluoromethyl)-2H-chromene-3-carboxylic acid;
7-(2-ethylbutoxy)-8-methyl-2-(trifluoromethyl)-2H-chromene-3-carboxylic acid;
7-(2-furylmethoxy)-2-(trifluoromethyl)-2H-chromene-3-carboxylic acid;
6-chloro-8-isopropyl-5-methyl-2-(trifluoromethyl)-2H-chromene-3-carboxylic acid;
6-chloro-7-(ethylthio)-2-(trifluoromethyl)-2H-chromene-3-carboxylic acid;
6-chloro-7-(isopentylthio)-2-(trifluoromethyl)-2H-chromene-3-carboxylic acid;
6-chloro-7-(propylthio)-2-(trifluoromethyl)-2H-chromene-3-carboxylic acid;
6-chloro-7-(isobutylthio)-2-(trifluoromethyl)-2H-chromene-3-carboxylic acid;

7-(butylthio)-6-chloro-2-(trifluoromethyl)-2H-chromene-3-carboxylic acid;
7-(sec-butylthio)-6-chloro-2-(trifluoromethyl)-2H-chromene-3-carboxylic acid;
6-chloro-7-[isobutyl(methyl)amino]-2-(trifluoromethyl)-2H-chromene-3-carboxylic acid;
6-chloro-7-(3,6-dihydropyridin-1 (2H)-yl)-2-(trifluoromethyl)-2H-chromene-3-carboxylic acid;
6-chloro-7-[ethyl(methyl)amino]-2-(trifluoromethyl)-2H-chromene-3-carboxylic acid;
7-[butyl(ethyl)amino]-6-chloro-2-(trifluoromethyl)-2H-chromene-3-carboxylic acid;
7-[benzyl(methyl)amino]-6-chloro-2-(trifluoromethyl)-2H-chromene-3-carboxylic acid;
7-(benzylamino)-6-chloro-2-(trifluoromethyl)-2H-chromene-3-carboxylic acid;
6-chloro-7-(diethylamino)-2-(trifluoromethyl)-2H-chromene-3-carboxylic acid;
7-butyl-6-chloro-2-(trifluoromethyl)-2H-chromene-3-carboxylic acid;
6-chloro-7-(3,3-dimethylbutyl)-2-(trifluoromethyl)-2H-chromene-3-carboxylic acid;
6-chloro-7-isobutyl-2-(trifluoromethyl)-2H-chromene-3-carboxylic acid;
(2R)-6-chloro-7-isobutyl-2-(trifluoromethyl)-2H-chromene-3-carboxylic acid;
(2S)-6-chloro-7-isobutyl-2-(trifluoromethyl)-2H-chromene-3-carboxylic acid;
6-chloro-7-isopropyl-2-(trifluoromethyl)-2H-chromene-3-carboxylic acid;
4,6-dichloro-7-isopropyl-2-(trifluoromethyl)-2H-chromene-3-carboxylic acid;
6-chloro-7-propyl-2-(trifluoromethyl)-2H-chromene-3-carboxylic acid;
7-benzyl-6-chloro-2-(trifluoromethyl)-2H-chromene-3-carboxylic acid;
(2R)-7-benzyl-6-chloro-2-(trifluoromethyl)-2H-chromene-3-carboxylic acid;
(2S)-7-benzyl-6-chloro-2-(trifluoromethyl)-2H-chromene-3-carboxylic acid;
(2R)-7-benzyl-6-chloro-2-(trifluoromethyl)-2H-chromene-3-carboxylic acid compound with (1R)-1-phenylethanamine (1:1);
6,8-Dibromo-2-(trifluoro-methyl)-1,2-dihydroquinoline-3-carboxylic acid;
8-Bromo-6-methyl-2-(trifluoromethyl)-1,2-dihydroquinoline-3-carboxylic acid;
6-chloro-8-methyl-2-(trifluoromethyl)-1,2-dihydroquinoline-3-carboxylic acid;
6-(4-fluorophenyl)-2-(trifluoromethyl)-1,2-dihydroquinoline-3-carboxylic acid;
6-chloro-7-(2-ethylphenoxy)-2-(trifluoromethyl)-2H-chromene-3-carboxylic acid;
6-chloro-7-(2-methoxyphenoxy)-2-(trifluoromethyl)-2H-chromene-3-carboxylic acid;
6-chloro-7-(2,3-dimethoxyphenoxy)-2-(trifluoromethyl)-2H-chromene-3-carboxylic acid;
6-chloro-7-(2,6-dimethoxyphenoxy)-2-(trifluoromethyl)-2H-chromene-3-carboxylic acid;
6-chloro-7-(2-propylphenoxy)-2-(trifluoromethyl)-2H-chromene-3-carboxylic acid;
7-(4-propylphenoxy)-2-(trifluoromethyl)-2H-chromene-3-carboxylic acid;
7-(2,5-dimethylphenoxy)-2-(trifluoromethyl)-2H-chromene-3-carboxylic acid;
7-(2-ethylphenoxy)-2-(trifluoromethyl)-2H-chromene-3-carboxylic acid;
7-(2-methoxyphenoxy)-2-(trifluoromethyl)-2H-chromene-3-carboxylic acid;
7-(2,3-dimethoxyphenoxy)-2-(trifluoromethyl)-2H-chromene-3-carboxylic acid;
7-(2,6-dimethoxyphenoxy)-2-(trifluoromethyl)-2H-chromene-3-carboxylic acid;
7-(2-propylphenoxy)-2-(trifluoromethyl)-2H-chromene-3-carboxylic acid;
7-(5-isopropyl-2-methylphenoxy)-2-(trifluoromethyl)-2H-chromene-3-carboxylic acid;
7-(4-chloro-2-methylphenoxy)-2-(trifluoromethyl)-2H-chromene-3-carboxylic acid;
7-(2,6-dimethylphenoxy)-2-(trifluoromethyl)-2H-chromene-3-carboxylic acid;
7-(mesityloxy)-2-(trifluoromethyl)-2H-chromene-3-carboxylic acid;
7-(2,4-dimethylphenoxy)-2-(trifluoromethyl)-2H-chromene-3-carboxylic acid;
7-(2-chloro-4-methylphenoxy)-2-(trifluoromethyl)-2H-chromene-3-carboxylic acid;
7-(2-bromo4-methylphenoxy)-2-(trifluoromethyl)-2H-chromene-3-carboxylic acid;
7-(4-ethylphenoxy)-2-(trifluoromethyl)-2H-chromene-3-carboxylic acid;
7-(2-fluorophenoxy)-2-(trifluoromethyl)-2H-chromene-3-carboxylic acid;
7-(2,5-difluorophenoxy)-2-(trifluoromethyl)-2H-chromene-3-carboxylic acid;
7-(2-fluoro-5-methylphenoxy)-2-(trifluoromethyl)-2H-chromene-3-carboxylic acid;
7-(4-methylphenoxy)-2-(trifluoromethyl)-2H-chromene-3-carboxylic acid;
7-(2-chloro4-methoxyphenoxy)-2-(trifluoromethyl)-2H-chromene-3-carboxylic acid;
7-(4-ethoxyphenoxy)-2-(trifluoromethyl)-2H-chromene-3-carboxylic acid;
7-(2,4-difluorophenoxy)-2-(trifluoromethyl)-2H-chromene-3-carboxylic acid;
7-(2-chloro-4,5-dimethylphenoxy)-2-(trifluoromethyl)-2H-chromene-3-carboxylic acid;
7-(4-fluoro-2-methylphenoxy)-2-(trifluoromethyl)-2H-chromene-3-carboxylic acid;
7-(2-bromo-5-fluorophenoxy)-2-(trifluoromethyl)-2H-chromene-3-carboxylic acid;
7-(2-bromo-4,5-difluorophenoxy)-2-(trifluoromethyl)-2H-chromene-3-carboxylic acid;
7-(2,4-dibromophenoxy)-2-(trifluoromethyl)-2H-chromene-3-carboxylic acid;
7-(4-bromo-2-chlorophenoxy)-2-(trifluoromethyl)-2H-chromene-3-carboxylic acid;
7-(2-bromo-4-fluorophenoxy)-2-(trifluoromethyl)-2H-chromene-3-carboxylic acid;
7-(2-chloro-4-fluorophenoxy)-2-(trifluoromethyl)-2H-chromene-3-carboxylic acid;
7-(4-iodo-2-methylphenoxy)-2-(trifluoromethyl)-2H-chromene-3-carboxylic acid;
7-(4-chloro-2-fluorophenoxy)-2-(trifluoromethyl)-2H-chromene-3-carboxylic acid;
7-(4-bromo-2-fluorophenoxy)-2-(trifluoromethyl)-2H-chromene-3-carboxylic acid;
7-(2-methoxy-4-methylphenoxy)-2-(trifluoromethyl)-2H-chromene-3-carboxylic acid;
7-(2-methylphenoxy)-2-(trifluoromethyl)-2H-chromene-3-carboxylic acid;
2-(trifluoromethyl)-7-(2,3,5-trimethylphenoxy)-2H-chromene-3-carboxylic acid;

7-(2,3-dimethylphenoxy)-2-(trifluoromethyl)-2H-chromene-3-carboxylic acid;
7-(3-methylphenoxy)-2-(trifluoromethyl)-2H-chromene-3-carboxylic acid;
7-(4-chlorophenoxy)-2-(trifluoromethyl)-2H-chromene-3-carboxylic acid;
7-(3-chlorophenoxy)-2-(trifluoromethyl)-2H-chromene-3-carboxylic acid;
5-fluoro-2-(trifluoromethyl)-2H-chromene-3-carboxylic acid;
5-(2,3-dimethylphenoxy)-2-(trifluoromethyl)-2H-chromene-3-carboxylic acid;
5-phenoxy-2-(trifluoromethyl)-2H-chromene-3-carboxylic acid;
5-(4-chloro-2-methylphenoxy)-2-(trifluoromethyl)-2H-chromene-3-carboxylic acid;
5-(2-methylphenoxy)-2-(trifluoromethyl)-2H-chromene-3-carboxylic acid;
5-(3-methylphenoxy)-2-(trifluoromethyl)-2H-chromene-3-carboxylic acid;
5-(2-chloro-4,5-dimethylphenoxy)-2-(trifluoromethyl)-2H-chromene-3-carboxylic acid;
5-(3-chlorophenoxy)-2-(trifluoromethyl)-2H-chromene-3-carboxylic acid;
5-(2,4-dimethylphenoxy)-2-(trifluoromethyl)-2H-chromene-3-carboxylic acid;
5-(2,5-dimethylphenoxy)-2-(trifluoromethyl)-2H-chromene-3-carboxylic acid;
5-(4-ethylphenoxy)-2-(trifluoromethyl)-2H-chromene-3-carboxylic acid;
5-(4-methylphenoxy)-2-(trifluoromethyl)-2H-chromene-3-carboxylic acid;
5-(4-fluorophenoxy)-2-(trifluoromethyl)-2H-chromene-3-carboxylic acid;
5-(4-chlorophenoxy)-2-(trifluoromethyl)-2H-chromene-3-carboxylic acid;
5-(3,4-dichlorophenoxy)-2-(trifluoromethyl)-2H-chromene-3-carboxylic acid;
5-(2-naphthyloxy)-2-(trifluoromethyl)-2H-chromene-3-carboxylic acid;
5-(1-naphthyloxy)-2-(trifluoromethyl)-2H-chromene-3-carboxylic acid;
5-(4-methoxyphenoxy)-2-(trifluoromethyl)-2H-chromene-3-carboxylic acid;
2-(trifluoromethyl)-5-(2,3,5-trimethylphenoxy)-2H-chromene-3-carboxylic acid;
5-(4-chloro-3,5-dimethylphenoxy)-2-(trifluoromethyl)-2H-chromene-3-carboxylic acid;
5-(2-methoxy-4-methylphenoxy)-2-(trifluoromethyl)-2H-chromene-3-carboxylic acid;
5-(2-fluorophenoxy)-2-(trifluoromethyl)-2H-chromene-3-carboxylic acid;
5-(2,6-dimethylphenoxy)-2-(trifluoromethyl)-2H-chromene-3-carboxylic acid;
5-(4-propylphenoxy)-2-(trifluoromethyl)-2H-chromene-3-carboxylic acid;
5-(2,5-difluorophenoxy)-2-(trifluoromethyl)-2H-chromene-3-carboxylic acid;
5-(2-chloro-4-methoxyphenoxy)-2-(trifluoromethyl)-2H-chromene-3-carboxylic acid;
5-(2-methoxyphenoxy)-2-(trifluoromethyl)-2H-chromene-3-carboxylic acid;
6,8-dichloro-5-fluoro-2-(trifluoromethyl)-2H-chromene-3-carboxylic acid;
6,8-dichloro-5-(2,3-dimethylphenoxy)-2-(trifluoromethyl)-2H-chromene-3-carboxylic acid;
6,8-dichloro-5-(3-methylphenoxy)-2-(trifluoromethyl)-2H-chromene-3-carboxylic acid;
6,8-dichloro-5-(4-chloro-2-methylphenoxy)-2-(trifluoromethyl)-2H-chromene-3-carboxylic acid;
6,8-dichloro-5-(2-chloro-4-methylphenoxy)-2-(trifluoromethyl)-2H-chromene-3-carboxylic acid;
6,8-dichloro-5-(4-chloro-2-fluorophenoxy)-2-(trifluoromethyl)-2H-chromene-3-carboxylic acid;
6,8-dichloro-5-(4-fluoro-2-methylphenoxy)-2-(trifluoromethyl)-2H-chromene-3-carboxylic acid;
6,8-dichloro-5-(2-methoxy-4-methylphenoxy)-2-(trifluoromethyl)-2H-chromene-3-carboxylic acid;
6,8-dichloro-5-(4-chlorophenoxy)-2-(trifluoromethyl)-2H-chromene-3-carboxylic acid;
6,8-dichloro-5-(2-chloro-4,5-dimethylphenoxy)-2-(trifluoromethyl)-2H-chromene-3-carboxylic acid;
6,8-dichloro-5-(2,4-dimethylphenoxy)-2-(trifluoromethyl)-2H-chromene-3-carboxylic acid;
6,8-dichloro-5-(2-fluoro-5-methylphenoxy)-2-(trifluoromethyl)-2H-chromene-3-carboxylic acid;
6,8-dichloro-5-(4-methylphenoxy)-2-(trifluoromethyl)-2H-chromene-3-carboxylic acid;
6,8-dichloro-5-(3-chlorophenoxy)-2-(trifluoromethyl)-2H-chromene-3-carboxylic acid;
6,8-dichloro-5-(2,5-dimethylphenoxy)-2-(trifluoromethyl)-2H-chromene-3-carboxylic acid;
6,8-dichloro-5-(4-ethoxyphenoxy)-2-(trifluoromethyl)-2H-chromene-3-carboxylic acid;
6,8-dichloro-5-(2-methylphenoxy)-2-(trifluoromethyl)-2H-chromene-3-carboxylic acid;
6,8-dichloro-5-(4-ethylphenoxy)-2-(trifluoromethyl)-2H-chromene-3-carboxylic acid;
6,8-dichloro-5-(2-chloro-4-methoxyphenoxy)-2-(trifluoromethyl)-2H-chromene-3-carboxylic acid;
6-chloro-5-(2,3-dimethylphenoxy)-2-(trifluoromethyl)-2H-chromene-3-carboxylic acid;
6-chloro-5-(3-methylphenoxy)-2-(trifluoromethyl)-2H-chromene-3-carboxylic acid;
6-chloro-5-(4-chloro-2-methylphenoxy)-2-(trifluoromethyl)-2H-chromene-3-carboxylic acid;
6-chloro-5-(2-chloro-4-methylphenoxy)-2-(trifluoromethyl)-2H-chromene-3-carboxylic acid;
6-chloro-5-(4-chloro-2-fluorophenoxy)-2-(trifluoromethyl)-2H-chromene-3-carboxylic acid;
6-chloro-5-(4-fluoro-2-methylphenoxy)-2-(trifluoromethyl)-2H-chromene-3-carboxylic acid;
6-chloro-5-(2-methoxy-4-methylphenoxy)-2-(trifluoromethyl)-2H-chromene-3-carboxylic acid;
6-chloro-5-(4-chlorophenoxy)-2-(trifluoromethyl)-2H-chromene-3-carboxylic acid;
6-chloro-5-(2-chloro4,5-dimethylphenoxy)-2-(trifluoromethyl)-2H-chromene-3-carboxylic acid;
6-chloro-5-(2,4-dimethylphenoxy)-2-(trifluoromethyl)-2H-chromene-3-carboxylic acid;
6-chloro-5-(2-fluoro-5-methylphenoxy)-2-(trifluoromethyl)-2H-chromene-3-carboxylic acid;
6-chloro-5-(4-methylphenoxy)-2-(trifluoromethyl)-2H-chromene-3-carboxylic acid;
6-chloro-5-(3-chlorophenoxy)-2-(trifluoromethyl)-2H-chromene-3-carboxylic acid;
6-chloro-5-(2,5-dimethylphenoxy)-2-(trifluoromethyl)-2H-chromene-3-carboxylic acid;
6-chloro-5-(4-ethoxyphenoxy)-2-(trifluoromethyl)-2H-chromene-3-carboxylic acid;
6-chloro-5-(2-methylphenoxy)-2-(trifluoromethyl)-2H-chromene-3-carboxylic acid;

6-chloro-5-(4-ethylphenoxy)-2-(trifluoromethyl)-2H-chromene-3-carboxylic acid;
6-chloro-5-(2-chloro-4-methoxyphenoxy)-2-(trifluoromethyl)-2H-chromene-3-carboxylic acid;
6-chloro-5-ethoxy-2-(trifluoromethyl)-2H-chromene-3-carboxylic acid;
6-chloro-5-(2-furyl)-2-(trifluoromethyl)-2H-chromene-3-carboxylic acid;
6-chloro-5-thien-3-yl-2-(trifluoromethyl)-2H-chromene-3-carboxylic acid;
6-chloro-5-(4-methylphenyl)-2-(trifluoromethyl)-2H-chromene-3-carboxylic acid;
6-chloro-5-(3-methylphenyl)-2-(trifluoromethyl)-2H-chromene-3-carboxylic acid;
6-chloro-5-(3-isopropylphenyl)-2-(trifluoromethyl)-2H-chromene-3-carboxylic acid;
6-chloro-5-phenyl-2-(trifluoromethyl)-2H-chromene-3-carboxylic acid;
6-chloro-5-ethyl-2-(trifluoromethyl)-2H-chromene-3-carboxylic acid;
6-chloro-5-fluoro-2-(trifluoromethyl)-2H-chromene-3-carboxylic acid;
6-chloro-5-iodo-2-(trifluoromethyl)-2H-chromene-3-carboxylic acid;
7-fluoro-6-methyl-2-(trifluoromethyl)-2H-chromene-3-carboxylic acid;
7-(4-chloro-2-methylphenoxy)-6-methyl-2-(trifluoromethyl)-2H-chromene-3-carboxylic acid;
6,7-dimethyl-2-(trifluoromethyl)-2H-chromene-3-carboxylic acid;
7-ethyl-6-methyl-2-(trifluoromethyl)-2H-chromene-3-carboxylic acid;
7-butyl-6-methyl-2-(trifluoromethyl)-2H-chromene-3-carboxylic acid;
7-(2,3-dimethylphenyl)-6-methyl-2-(trifluoromethyl)-2H-chromene-3-carboxylic acid;
7-isobutyl-6-methyl-2-(trifluoromethyl)-2H-chromene-3-carboxylic acid;
7-(4-ethylphenyl)-6-methyl-2-(trifluoromethyl)-2H-chromene-3-carboxylic acid;
7-(4-ethylphenoxy)-6-methyl-2-(trifluoromethyl)-2H-chromene-3-carboxylic acid;
7-(2-chloro-4-methoxyphenoxy)-6-methyl-2-(trifluoromethyl)-2H-chromene-3-carboxylic acid;
7-(4-fluoro-2-methylphenoxy)-6-methyl-2-(trifluoromethyl)-2H-chromene-3-carboxylic acid;
7-fluoro-8-methyl-2-(trifluoromethyl)-2H-chromene-3-carboxylic acid;
8-methyl-7-phenoxy-2-(trifluoromethyl)-2H-chromene-3-carboxylic acid;
7-(2,4-difluorophenoxy)-8-methyl-2-(trifluoromethyl)-2H-chromene-3-carboxylic acid;
7-(2,5-difluorophenoxy)-8-methyl-2-(trifluoromethyl)-2H-chromene-3-carboxylic acid;
7-(4-chlorophenoxy)-8-methyl-2-(trifluoromethyl)-2H-chromene-3-carboxylic acid;
7-(3-chlorophenoxy)-8-methyl-2-(trifluoromethyl)-2H-chromene-3-carboxylic acid;
7-(4-methoxyphenoxy)-8-methyl-2-(trifluoromethyl)-2H-chromene-3-carboxylic acid;
7-(2-chloro-4-methylphenoxy)-8-methyl-2-(trifluoromethyl)-2H-chromene-3-carboxylic acid;
8-methyl-7-(2-methylphenoxy)-2-(trifluoromethyl)-2H-chromene-3-carboxylic acid;
7-(4-ethylphenoxy)-8-methyl-2-(trifluoromethyl)-2H-chromene-3-carboxylic acid;
8-methyl-7-(4-methylphenoxy)-2-(trifluoromethyl)-2H-chromene-3-carboxylic acid;
7-(2,4-dimethylphenoxy)-8-methyl-2-(trifluoromethyl)-2H-chromene-3-carboxylic acid;
8-methyl-2-(trifluoromethyl)-7-(2,3,5-trimethylphenoxy)-2H-chromene-3-carboxylic acid;
7-(2,6-dimethylphenoxy)-8-methyl-2-(trifluoromethyl)-2H-chromene-3-carboxylic acid;
7-(mesityloxy)-8-methyl-2-(trifluoromethyl)-2H-chromene-3-carboxylic acid;
7-(3,4-dichlorophenoxy)-8-methyl-2-(trifluoromethyl)-2H-chromene-3-carboxylic acid;
7-(4-fluorophenoxy)-8-methyl-2-(trifluoromethyl)-2H-chromene-3-carboxylic acid;
7-(2-fluorophenoxy)-8-methyl-2-(trifluoromethyl)-2H-chromene-3-carboxylic acid;
8-methyl-7-(4-propylphenoxy)-2-(trifluoromethyl)-2H-chromene-3-carboxylic acid;
7-(2-methoxy4-methylphenoxy)-8-methyl-2-(trifluoromethyl)-2H-chromene-3-carboxylic acid;
7-(4-ethoxyphenoxy)-8-methyl-2-(trifluoromethyl)-2H-chromene-3-carboxylic acid;
7-(4-chloro-2-fluorophenoxy)-8-methyl-2-(trifluoromethyl)-2H-chromene-3-carboxylic acid;
7-(4-bromo-2-fluorophenoxy)-8-methyl-2-(trifluoromethyl)-2H-chromene-3-carboxylic acid;
7-(2-chloro-4,5-dimethylphenoxy)-8-methyl-2-(trifluoromethyl)-2H-chromene-3-carboxylic acid;
7-(2-chloro-4-fluorophenoxy)-8-methyl-2-(trifluoromethyl)-2H-chromene-3-carboxylic acid;
7-(2-fluoro-5-methylphenoxy)-8-methyl-2-(trifluoromethyl)-2H-chromene-3-carboxylic acid;
7-(2-bromo-5-fluorophenoxy)-8-methyl-2-(trifluoromethyl)-2H-chromene-3-carboxylic acid;
7-(4-chloro-2-methylphenoxy)-8-methyl-2-(trifluoromethyl)-2H-chromene-3-carboxylic acid;
8-methyl-7-(1-naphthyloxy)-2-(trifluoromethyl)-2H-chromene-3-carboxylic acid;
8-benzyl-6-chloro-2-(trifluoromethyl)-2H-chromene-3-carboxylic acid;
2R)-8-chloro-6-ethynyl-2-(trifluoromethyl)-2H-chromene-3-carboxylic acid;
(2S)-8-chloro-6-ethynyl-2-(trifluoromethyl)-2H-chromene-3-carboxylic acid;
(2R)-6-chloro-7-(4-ethylphenoxy)-2-(trifluoromethyl)-2H-chromene-3-carboxylic acid;
(2S)-6-chloro-7-(4-ethylphenoxy)-2-(trifluoromethyl)-2H-chromene-3-carboxylic acid;
(2R)-6-chloro-7-(4-chloro-2-methylphenoxy)-2-(trifluoromethyl)-2H-chromene-3-carboxylic acid;
(2S)-6-chloro-7-(4-chloro-2-methylphenoxy)-2-(trifluoromethyl)-2H-chromene-3-carboxylic acid;
(2R)-6-chloro-7-(2,4-dimethylphenoxy)-2-(trifluoromethyl)-2H-chromene-3-carboxylic acid;
(2S)-6-chloro-7-(2,4-dimethylphenoxy)-2-(trifluoromethyl)-2H-chromene-3-carboxylic acid;
(2S)-6-chloro-7-(3,5-dichloro-4-methylphenoxy)-2-(trifluoromethyl)-2H-chromene-3-carboxylic acid;
(2R)-6-chloro-7-(3,5-dichloro-4-methylphenoxy)-2-(trifluoromethyl)-2H-chromene-3-carboxylic acid;
(2R)-6-chloro-7-(2-chloro-4-methylphenoxy)-2-(trifluoromethyl)-2H-chromene-3-carboxylic acid;
(2S)-6-chloro-7-(2-chloro-4-methylphenoxy)-2-(trifluoromethyl)-2H-chromene-3-carboxylic acid;
(2R)-2-(trifluoromethyl)-7-(2,3,5-trimethylphenoxy)-2H-chromene-3-carboxylic acid;

(2S)-2-(trifluoromethyl)-7-(2,3,5-trimethylphenoxy)-2H-chromene-3-carboxylic acid;
(2R)-7-(2,5-dimethylphenoxy)-2-(trifluoromethyl)-2H-chromene-3-carboxylic acid;
(2S)-7-(2,5-dimethylphenoxy)-2-(trifluoromethyl)-2H-chromene-3-carboxylic acid;
(2R)-7-(2-methylphenoxy)-2-(trifluoromethyl)-2H-chromene-3-carboxylic acid;
(2S)-7-(2-methylphenoxy)-2-(trifluoromethyl)-2H-chromene-3-carboxylic acid;
(2R)-7-(4-chloro-2-methylphenoxy)-2-(trifluoromethyl)-2H-chromene-3-carboxylic acid;
(2S)-7-(4-chloro-2-methylphenoxy)-2-(trifluoromethyl)-2H-chromene-3-carboxylic acid;
(2R)-6-chloro-7-(2-chloro-4,5-dimethylphenoxy)-2-(trifluoromethyl)-2H-chromene-3-carboxylic acid;
(2S)-6-chloro-7-(2-chloro-4,5-dimethylphenoxy)-2-(trifluoromethyl)-2H-chromene-3-carboxylic acid;
(2R)-6-chloro-7-(4-methylphenoxy)-2-(trifluoromethyl)-2H-chromene-3-carboxylic acid;
(2S)-6-chloro-7-(4-methylphenoxy)-2-(trifluoromethyl)-2H-chromene-3-carboxylic acid;
(2R)-6-chloro-7-(2-methylphenoxy)-2-(trifluoromethyl)-2H-chromene-3-carboxylic acid;
(2S)-6-chloro-7-(2-methylphenoxy)-2-(trifluoromethyl)-2H-chromene-3-carboxylic acid;
(2R)-6-chloro-7-(2-chloro-4-methoxyphenoxy)-2-(trifluoromethyl)-2H-chromene-3-carboxylic acid;
(2S)-6-chloro-7-(2-chloro-4-methoxyphenoxy)-2-(trifluoromethyl)-2H-chromene-3-carboxylic acid;
(2R)-6-chloro-7-(4-fluoro-2-methylphenoxy)-2-(trifluoromethyl)-2H-chromene-3-carboxylic acid;
(2S)-6-chloro-7-(4-fluoro-2-methylphenoxy)-2-(trifluoromethyl)-2H-chromene-3-carboxylic acid;
(2R)-6-chloro-7-(2-methoxy-4-methylphenoxy)-2-(trifluoromethyl)-2H-chromene-3-carboxylic acid;
(2S)-6-chloro-7-(2-methoxy-4-methylphenoxy)-2-(trifluoromethyl)-2H-chromene-3-carboxylic acid;
(2S)-5-phenoxy-2-(trifluoromethyl)-2H-chromene-3-carboxylic acid;
(2R)-5-phenoxy-2-(trifluoromethyl)-2H-chromene-3-carboxylic acid;
(2R)-6-chloro-5-phenoxy-2-(trifluoromethyl)-2H-chromene-3-carboxylic acid;
(2S)-6-chloro-5-phenoxy-2-(trifluoromethyl)-2H-chromene-3-carboxylic acid;
(2R)-6-chloro-5-(3-chlorophenoxy)-2-(trifluoromethyl)-2H-chromene-3-carboxylic acid;
(2S)-6-chloro-5-(3-chlorophenoxy)-2-(trifluoromethyl)-2H-chromene-3-carboxylic acid;
5,7-dichloro-6-ethoxy-2-(trifluoromethyl)-2H-chromene-3-carboxylic acid;
5,7-dichloro-6-ethoxy-2-(trifluoromethyl)-2H-chromene-3-carboxylic acid;
5,7-dichloro-6-isopropoxy-2-(trifluoromethyl)-2H-chromene-3-carboxylic acid;
5,7-dichloro-6-isopropoxy-2-(trifluoromethyl)-2H-chromene-3-carboxylic acid;
(2S)-6-chloro-8-(4-methylphenyl)-2-(trifluoromethyl)-2H-chromene-3-carboxylic acid;
(2R)-6-chloro-8-(4-methylphenyl)-2-(trifluoromethyl)-2H-chromene-3-carboxylic acid;
(2S)-6-chloro-8-(3-fluoro-4-methylphenyl)-2-(trifluoromethyl)-2H-chromene-3-carboxylic acid;
(2R)-6-chloro-8-(3-fluoro-4-methylphenyl)-2-(trifluoromethyl)-2H-chromene-3-carboxylic acid;
(2S)-6-chloro-8-(4-ethylphenyl)-2-(trifluoromethyl)-2H-chromene-3-carboxylic acid;
(2R)-6-chloro-8-(4-ethylphenyl)-2-(trifluoromethyl)-2H-chromene-3-carboxylic acid;
(2S)-6-chloro-8-(4-methoxy-3-methylphenyl)-2-(trifluoromethyl)-2H-chromene-3-carboxylic acid;
(2R)-6-chloro-8-(4-methoxy-3-methylphenyl)-2-(trifluoromethyl)-2H-chromene-3-carboxylic acid;
sodium 7-(2,5-dimethylphenoxy)-2-(trifluoromethyl)-2H-chromene-3-carboxylate;
sodium 5-(4-chloro-2-methylphenoxy)-2-(trifluoromethyl)-2H-chromene-3-carboxylate;
sodium (2S)-5-phenoxy-2-(trifluoromethyl)-2H-chromene-3-carboxylate;
sodium (2S)-8-chloro-6-ethynyl-2-(trifluoromethyl)-2H-chromene-3-carboxylate;
sodium (2R)-7-(2,5-dimethylphenoxy)-2-(trifluoromethyl)-2H-chromene-3-carboxylate;
sodium (2R)-2-(trifluoromethyl)-7-(2,3,5-trimethylphenoxy)-2H-chromene-3-carboxylate;
sodium 7-(2-methylphenoxy)-2-(trifluoromethyl)-2H-chromene-3-carboxylate;
sodium 2-(trifluoromethyl)-7-(2,3,5-trimethylphenoxy)-2H-chromene-3-carboxylate;
sodium 6-chloro-7-(2-propylphenoxy)-2-(trifluoromethyl)-2H-chromene-3-carboxylate;
sodium 6-chloro-5-(3-chlorophenoxy)-2-(trifluoromethyl)-2H-chromene-3-carboxylate;
sodium 5-phenoxy-2-(trifluoromethyl)-2H-chromene-3-carboxylate;
sodium 5-(3-chlorophenoxy)-2-(trifluoromethyl)-2H-chromene-3-carboxylate;
sodium (2S)-8-but-1-ynyl-6-chloro-2-(trifluoromethyl)-2H-chromene-3-carboxylate;
sodium (2S)-6-chloro-8-(3-fluoro-4-methylphenyl)-2-(trifluoromethyl)-2H-chromene-3-carboxylate;
sodium (2S)-6-chloro-8-(4-ethylphenyl)-2-(trifluoromethyl)-2H-chromene-3-carboxylate;
sodium 7-(4-ethylphenoxy)-8-methyl-2-(trifluoromethyl)-2H-chromene-3-carboxylate;
(2R)-6,8-dichloro-7-isobutoxy-2-(trifluoromethyl)-2H-chromene-3-carboxylic acid;
(2S)-6,8-dichloro-7-isobutoxy-2-(trifluoromethyl)-2H-chromene-3-carboxylic acid;
6-chloro-7-{[isopropyl(methyl)amino]methyl}-2-(trifluoromethyl)-2H-chromene-3-carboxylic acid trifluoroacetate;
6-chloro-7-[(diisopropylamino)methyl]-2-(trifluoromethyl)-2H-chromene-3-carboxylic acid trifluoroacetate;
6-chloro-7-{[ethyl(methyl)amino]methyl}-2-(trifluoromethyl)-2H-chromene-3-carboxylic acid trifluoroacetate;
(2R)-6-chloro-8-methyl-7-(3-methylbutoxy)-2-(trifluoromethyl)-2H-chromene-3-carboxylic acid;
(2S)-6-chloro-8-methyl-7-(3-methylbutoxy)-2-(trifluoromethyl)-2H-chromene-3-carboxylic acid;
(2R)-6-chloro-7-(4-methylbenzyl)-2-(trifluoromethyl)-2H-chromene-3-carboxylic acid;
(2S)-6-chloro-7-(4-methylbenzyl)-2-(trifluoromethyl)-2H-chromene-3-carboxylic acid;
6-chloro-7-(4-cyanobenzyl)-2-(trifluoromethyl)-2H-chromene-3-carboxylic acid;
8-(hydroxymethyl)-6-methyl-2-(trifluoromethyl)-2H-chromene-3-carboxylic acid;
8-(methoxymethyl)-6-methyl-2-(trifluoromethyl)-2H-chromene-3-carboxylic acid;
8-(ethoxymethyl)-6-methyl-2-(trifluoromethyl)-2H-chromene-3-carboxylic acid;

6-methyl-2-(trifluoromethyl)-2H-chromene-3,8-dicarboxylic acid;
8-benzyl-6-methyl-2-(trifluoromethyl)-2H-chromene-3-carboxylic acid;
8-(1-hydroxyethyl)-6-methyl-2-(trifluoromethyl)-2H-chromene-3-carboxylic acid;
6-methyl-8-(2,2,2-trifluoroethyl)-2-(trifluoromethyl)-2H-chromene-3-carboxylic acid;
8-ethyl-6-methyl-2-(trifluoromethyl)-2H-chromene-3-carboxylic acid;
8-methoxy-6-methyl-2-(trifluoromethyl)-2H-chromene-3-carboxylic acid;
6-chloro-5-isopropyl-8-methyl-2-(trifluoromethyl)-2H-chromene-3-carboxylic acid
(2R)-6-chloro-8-isopropyl-5-methyl-2-(trifluoromethyl)-2H-chromene-3-carboxylic acid;
(2S)-6-chloro-8-isopropyl-5-methyl-2-(trifluoromethyl)-2H-chromene-3-carboxylic acid;
(2R)-6-chloro-7-(isobutylthio)-2-(trifluoromethyl)-2H-chromene-3-carboxylic acid;
(2S)-6-chloro-7-(isobutylthio)-2-(trifluoromethyl)-2H-chromene-3-carboxylic acid;
6-chloro-7-(propylamino)-2-(trifluoromethyl)-2H-chromene-3-carboxylic acid;
6-chloro-7-(isobutylamino)-2-(trifluoromethyl)-2H-chromene-3-carboxylic acid;
7-(butylamino)-6-chloro-2-(trifluoromethyl)-2H-chromene-3-carboxylic acid;
6-chloro-7-(isopentylamino)-2-(trifluoromethyl)-2H-chromene-3-carboxylic acid;
6-chloro-7-[(3,3-dimethylbutyl)amino]-2-(trifluoromethyl)-2H-chromene-3-carboxylic acid;
(2R)-6-chloro-7-[isobutyl(methyl)amino]-2-(trifluoromethyl)-2H-chromene-3-carboxylic acid;
(2S)-6-chloro-7-[isobutyl(methyl)amino]-2-(trifluoromethyl)-2H-chromene-3-carboxylic acid;
6-chloro-7-(neopentylamino)-2-(trifluoromethyl)-2H-chromene-3-carboxylic acid;
7-(sec-butylamino)-6-chloro-2-(trifluoromethyl)-2H-chromene-3-carboxylic acid;
7-benzyl-2-(trifluoromethyl)-2H-chromene-3-carboxylic acid;
7-(2-chlorobenzyl)-2-(trifluoromethyl)-2H-chromene-3-carboxylic acid;
7-(4-chlorobenzyl)-2-(trifluoromethyl)-2H-chromene-3-carboxylic acid;
7-(2,4-dimethylbenzyl)-2-(trifluoromethyl)-2H-chromene-3-carboxylic acid;
(2S)-7-butyl-6-chloro-2-(trifluoromethyl)-2H-chromene-3-carboxylic acid;
(2R)-7-butyl-6-chloro-2-(trifluoromethyl)-2H-chromene-3-carboxylic acid;
(2R)-6-chloro-7-(3,3-dimethylbutyl)-2-(trifluoromethyl)-2H-chromene-3-carboxylic acid;
(2S)-6-chloro-7-(3,3-dimethylbutyl)-2-(trifluoromethyl)-2H-chromene-3-carboxylic acid;
6-chloro-7-(3-methoxybenzyl)-2-(trifluoromethyl)-2H-chromene-3-carboxylic acid;
7-(3-hydroxybenzyl)-2-(trifluoromethyl)-2H-chromene-3-carboxylic acid;
6-chloro-7-(3-hydroxybenzyl)-2-(trifluoromethyl)-2H-chromene-3-carboxylic acid;
7-(5-bromo-3-chloro-2-methoxybenzyl)-6-chloro-2-(trifluoromethyl)-2H-chromene-3-carboxylic acid;
7-(5-bromo-2-methoxybenzyl)-2-(trifluoromethyl)-2H-chromene-3-carboxylic acid;
6-chloro-7-(3-chloro-2-methoxy-5-methylbenzyl)-2-(trifluoromethyl)-2H-chromene-3-carboxylic acid;
6-bromo-7-(2-bromobenzyl)-2-(trifluoromethyl)-2H-chromene-3-carboxylic acid;
6-chloro-7-(3-methylbutyl)-2-(trifluoromethyl)-2H-chromene-3-carboxylic acid;
7-(5-bromo-2-methoxybenzyl)-6-chloro-2-(trifluoromethyl)-2H-chromene-3-carboxylic acid;
6,8-dichloro-7-(propylamino)-2-(trifluoromethyl)-2H-chromene-3-carboxylic acid;
(2R)-7-benzyl-6-methyl-2-(trifluoromethyl)-2H-chromene-3-carboxylic acid;
(2S)-7-benzyl-6-methyl-2-(trifluoromethyl)-2H-chromene-3-carboxylic acid;
6-(benzyloxy)-7-bromo-2-(trifluoromethyl)-2H-chromene-3-carboxylic acid;
7-benzyl-6-(benzyloxy)-2-(trifluoromethyl)-2H-chromene-3-carboxylic acid;
7-benzyl-6-hydroxy-2-(trifluoromethyl)-2H-chromene-3-carboxylic acid;
6-methyl-7-(2-methylbenzyl)-2-(trifluoromethyl)-2H-chromene-3-carboxylic acid;
7-benzyl-6-methoxy-2-(trifluoromethyl)-2H-chromene-3-carboxylic acid;
7-benzyl-6-butoxy-2-(trifluoromethyl)-2H-chromene-3-carboxylic acid;
7-benzyl-6-(pentyloxy)-2-(trifluoromethyl)-2H-chromene-3-carboxylic acid;
7-benzyl-6-hexyl-2-(trifluoromethyl)-2H-chromene-3-carboxylic acid;
7-benzyl-6-pentyl-2-(trifluoromethyl)-2H-chromene-3-carboxylic acid;
7-benzyl-6-propoxy-2-(trifluoromethyl)-2H-chromene-3-carboxylic acid;
7-benzyl-6-ethoxy-2-(trifluoromethyl)-2H-chromene-3-carboxylic acid;
7-bromo-6-methoxy-2-(trifluoromethyl)-2H-chromene-3-carboxylic acid;
7-benzyl-6-(hexyloxy)-2-(trifluoromethyl)-2H-chromene-3-carboxylic acid;
7-(isobutylamino)-2-(trifluoromethyl)-2H-chromene-3-carboxylic acid;
7-(neopentylamino)-2-(trifluoromethyl)-2H-chromene-3-carboxylic acid;
7-[isobutyl(methyl)amino]-2-(trifluoromethyl)-2H-chromene-3-carboxylic acid;
6-bromo-8-methyl-2-(trifluoromethyl)-2H-chromene-3-carboxylic acid;
6-methoxy-8-methyl-2-(trifluoromethyl)-2H-chromene-3-carboxylic acid;
6-ethoxy-8-methyl-2-(trifluoromethyl)-2H-chromene-3-carboxylic acid;
7-[isobutyl(methyl)amino]-6-methyl-2-(trifluorbmethyl)-2H-chromene-3-carboxylic acid;
7-(isobutylamino)-6-methyl-2-(trifluoromethyl)-2H-chromene-3-carboxylic acid;
7-tert-butyl-6-methyl-2-(trifluoromethyl)-2H-chromene-3-carboxylic acid;
6,8-dimethoxy-2-(trifluoromethyl)-2H-chromene-3-carboxylic acid;
6-(hydroxymethyl)-8-methyl-2-(trifluoromethyl)-2H-chromene-3-carboxylic acid;
6,8-dichloro-5,7-dimethoxy-2-(trifluoromethyl)-2H-chromene-3-carboxylic acid;
6-chloro-5,7-dimethoxy-2-(trifluoromethyl)-2H-chromene-3-carboxylic acid;

6-chloro-7-methoxy-8-(methoxymethyl)-2-(trifluoromethyl)-2H-chromene-3-carboxylic acid;
8-benzyl-6-(trifluoromethoxy)-2-(trifluoromethyl)-2H-chromene-3-carboxylic acid;
8-acetyl-6-(trifluoromethoxy)-2-(trifluoromethyl)-2H-chromene-3-carboxylic acid;
8-phenyl-6-(trifluoromethoxy)-2-(trifluoromethyl)-2H-chromene-3-carboxylic acid;
(2R)-8-methyl-6-(trifluoromethoxy)-2-(trifluoromethyl)-2H-chromene-3-carboxylic acid;
(2S)-8-methyl-6-(trifluoromethoxy)-2-(trifluoromethyl)-2H-chromene-3-carboxylic acid;
(2R)-8-propyl-6-(trifluoromethoxy)-2-(trifluoromethyl)-2H-chromene-3-carboxylic acid;
(2S)-8-propyl-6-(trifluoromethoxy)-2-(trifluoromethyl)-2H-chromene-3-carboxylic acid;
8-(2-hydroxyethyl)-6-(trifluoromethoxy)-2-(trifluoromethyl)-2H-chromene-3-carboxylic acid;
8-(1-hydroxy-1-methylethyl)-6-(trifluoromethoxy)-2-(trifluoromethyl)-2H-chromene-3-carboxylic acid;
8-isopropyl-6-(trifluoromethoxy)-2-(trifluoromethyl)-2H-chromene-3-carboxylic acid;
8-hydroxy-6-(trifluoromethoxy)-2-(trifluoromethyl)-2H-chromene-3-carboxylic acid;
8-methoxy-6-(trifluoromethoxy)-2-(trifluoromethyl)-2H-chromene-3-carboxylic acid;
8-ethoxy-6-(trifluoromethoxy)-2-(trifluoromethyl)-2H-chromene-3-carboxylic acid;
6-chloro-8-methoxy-5-methyl-2-(trifluoromethyl)-2H-chromene-3-carboxylic acid;
sodium 6-(benzyloxy)-8-chloro-2-(trifluoromethyl)-2H-chromene-3-carboxylate;
sodium 8-methyl-6-(trifluoromethoxy)-2-(trifluoromethyl)-2H-chromene-3-carboxylate;
sodium (2R)-7-benzyl-6-chloro-2-(trifluoromethyl)-2H-chromene-3-carboxylate;
sodium 6-ethyl-2-(trifluoromethyl)-2H-chromene-3-carboxylate;
sodium 6-chloro-7-(2,4-dimethylbenzyl)-2-(trifluoromethyl)-2H-chromene-3-carboxylate;
sodium (2R)-8-ethyl-6-(trifluoromethoxy)-2-(trifluoromethyl)-2H-chromene-3-carboxylate;
sodium 6-chloro-7-(isobutylthio)-2-(trifluoromethyl)-2H-chromene-3-carboxylate;
sodium 6-chloro-7-(isobutylamino)-2-(trifluoromethyl)-2H-chromene-3-carboxylate;
sodium 8-acetyl-6-(trifluoromethoxy)-2-(trifluoromethyl)-2H-chromene-3-carboxylate;
sodium (2S)-8-methyl-6-(trifluoromethoxy)-2-(trifluoromethyl)-2H-chromene-3-carboxylate;
sodium (2R)-6-chloro-7-[isobutyl(methyl)amino]-2-(trifluoromethyl)-2H-chromene-3-carboxylate;
sodium (2R)-6-chloro-7-(3,3-dimethylbutyl)-2-(trifluoromethyl)-2H-chromene-3-carboxylate;
sodium (2S)-8-propyl-6-(trifluoromethoxy)-2-(trifluoromethyl)-2H-chromene-3-carboxylate;
sodium (2S)-6-chloro-8-isopropyl-5-methyl-2-(trifluoromethyl)-2H-chromene-3-carboxylate;
sodium (2R)-6-chloro-7-(4-methylbenzyl)-2-(trifluoromethyl)-2H-chromene-3-carboxylate;
sodium (2S)-6-chloro-8-methyl-7-(3-methylbutoxy)-2-(trifluoromethyl)-2H-chromene-3-carboxylate;
sodium 6-methyl-7-(2-methylbenzyl)-2-(trifluoromethyl)-2H-chromene-3-carboxylate;
sodium (2R)-6-chloro-7-(isobutylthio)-2-(trifluoromethyl)-2H-chromene-3-carboxylate;
sodium 5,8-dichloro-6,7-dimethoxy-2-(trifluoromethyl)-2H-chromene-3-carboxylate;
sodium 6-chloro-7-(4-chlorobenzyl)-2-(trifluoromethyl)-2H-chromene-3-carboxylate;
sodium 6-isopropyl-7-methyl-2-(trifluoromethyl)-2H-chromene-3-carboxylate;
sodium (2R)-6-chloro-7-isobutyl-2-(trifluoromethyl)-2H-chromene-3-carboxylate;
6-ethyl-8-propyl-2-(trifluoromethyl)-2H-chromene-3-carboxylic acid;
6,8-diethyl-2-(trifluoromethyl)-2H-chromene-3-carboxylic acid;
sodium 6,8-diethyl-2-(trifluoromethyl)-2H-chromene-3-carboxylate;
(2R)-6-chloro-7,8-dimethyl-2-(trifluoromethyl)-2H-chromene-3-carboxylic acid;
(2S)-6-chloro-7,8-dimethyl-2-(trifluoromethyl)-2H-chromene-3-carboxylic acid;
sodium (2S)-6-chloro-7,8-dimethyl-2-(trifluoromethyl)-2H-chromene-3-carboxylate;
5-chloro-6-ethyl-8-methyl-2-(trifluoromethyl)-2H-chromene-3-carboxylic acid;
6-chloro-7-(2-methylbenzyl)-2-(trifluoromethyl)-2H-chromene-3-carboxylic acid;
6-chloro-7-(2-methylbenzyl)-2-(trifluoromethyl)-2H-chromene-3-carboxylic acid;
6-chloro-7-(2-methylbenzyl)-2-(trifluoromethyl)-2H-chromene-3-carboxylic acid;
6-chloro-7-(2-methoxybenzyl)-2-(trifluoromethyl)-2H-chromene-3-carboxylic acid;
6-chloro-7-(ethoxymethyl)-5-methyl-2-(trifluoromethyl)-2H-chromene-3-carboxylic acid;
6-chloro-5-(hydroxymethyl)-7-methyl-2-(trifluoromethyl)-2H-chromene-3-carboxylic acid;
6-chloro-7-(hydroxymethyl)-5-methyl-2-(trifluoromethyl)-2H-chromene-3-carboxylic acid;
6-chloro-7-(3-fluoro-4-methylbenzyl)-2-(trifluoromethyl)-2H-chromene-3-carboxylic acid;
6-chloro-7-(2-ethylbenzyl)-2-(trifluoromethyl)-2H-chromene-3-carboxylic acid;
6-chloro-7-(2-ethylbenzyl)-2-(trifluoromethyl)-2H-chromene-3-carboxylic acid;
sodium 6-chloro-7-(2-methylbenzyl)-2-(trifluoromethyl)-2H-chromene-3-carboxylate;
6-ethyl-8-thien-3-yl-2-(trifluoromethyl)-2H-chromene-3-carboxylic acid;
(2R)-6,8-diethyl-2-(trifluoromethyl)-2H-chromene-3-carboxylic acid;
(2R)-6-ethyl-8-propyl-2-(trifluoromethyl)-2H-chromene-3-carboxylic acid;
sodium 6-chloro-7-(2-methoxybenzyl)-2-(trifluoromethyl)-2H-chromene-3-carboxylate;
6-(4-methylphenoxy)-2-(trifluoromethyl)-2H-chromene-3-carboxylic acid;
6-chloro-5-(ethoxymethyl)-7-methyl-2-(trifluoromethyl)-2H-chromene-3-carboxylic acid;
6-chloro-5,7-bis(ethoxymethyl)-2-(trifluoromethyl)-2H-chromene-3-carboxylic acid; and sodium (2R)-6,8-diethyl-2-(trifluoromethyl)-2H-chromene-3-carboxylate;

or their isomer and pharmaceutically acceptable salt thereof. The present invention further includes tautomers of the compounds described herein.

In another embodiment the present invention comprises a pharmaceutical composition comprising a therapeutically-effective amount of a compound of Formula 1 and a pharmaceutically-acceptable excipient. For example the excipient can comprise a carrier, an adjuvant or a diluent.

The present invention also comprises a method of treating cyclooxygenase-2 mediated disorders, such as inflammation, in a subject, the method comprising treating the subject having or susceptible to such disorder with a therapeutically-effective amount of a compound of Formula 1.

Also included in the family of compounds of Formula 1 are the stereoisomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active base and then separation of the mixture of diastereoisomers by crystallization, followed by liberation of the optically active bases from these salts. Examples of appropriate bases are brucine, strychnine, dehydroabietylamine, quinine, cinchonidine, ephedrine, alpha-methylbenzylamine, amphetamine, deoxyphedrine, chloramphenicol intermediate, 2-amino-1-butanol, and 1-(1-napthyl)ethylamine. A different process for separation of optical isomers involves the use of a chiral chromatography column optimally chosen to maximize the separation of the enantiomers. Still another available method involves synthesis of covalent diastereoisomeric molecules. The synthesized diastereoisomers can be separated by conventional means such as chromatography, distillation, crystallization or sublimation, and then hydrolyzed to deliver the enantiomerically pure compound. The optically active compounds of Formula 1 can likewise be obtained by utilizing optically active starting materials. These isomers may be in the form of a free acid, a free base, an ester or a salt. Additional methods for resolving optical isomers are known to those skilled in the art.

Also included in the family of compounds of Formula 1 are the protected acids thereof, such as the esters, hydroxyamino derivatives, amides and sulfonamides. Thus primary and secondary amines can be reacted with the chromene-3-carboxylic acids of Formula 1 to form amides which can be useful as prodrugs. Preferred amines heterocyclicamines, including optionally substituted aminothiazoles, optionally substituted amino-isoxazoles, and optionally substituted aminopyridines; aniline derivatives; sulfonamides; aminocarboxylic acids; and the like. Additionally, 1-acyldihydroquinolines can behave as prodrugs for the 1H-dihydroquinolines. The esters, hydroxyamino derivatives and sulfonamides can be prepared from the acids by methods known to one skilled in the art.

The compounds of the present invention can be administered for the prophylaxis and treatment of cyclooxygenase related (e.g. COX-1 related or COX-2 related) diseases or conditions by any means, preferably oral, that produce contact of these compounds with their site of action in the body. For the prophylaxis or treatment of the conditions referred to above, the compounds of the present invention can be used as the compound per se. Pharmaceutically acceptable salts are particularly suitable for medical applications because of their greater aqueous solubility relative to the parent compound. Such salts must clearly have a pharmaceutically acceptable anion or cation. Suitable pharmaceutically-acceptable acid addition salts of compounds of Formula 1 may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, .beta.-hydroxybutyric, salicyclic, galactaric and galacturonic acid. Suitable pharmaceutically-acceptable base addition salts of compounds of Formula 1 include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula 1.

Alternatively, pharmaceutically acceptable salts can comprise an anionic counterion, for example where the molecule contains a cationic functional group such as an ammonium group. The anions, of course, are also required to be pharmaceutically acceptable and are also selected from the above list.

The compounds of the present invention can be administered to the subject as the neat compound alone. Alternatively the compounds of the present invention can be presented with one or more pharmaceutically acceptable excipients in the form of a pharmaceutical composition. A useful excipient can be, for example, a carrier. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present, including other compounds of the present invention. The pharmaceutical compositions of the invention can be prepared by any of the well known techniques of pharmacy, consisting essentially of admixing the components.

These compounds can be administered by any conventional means available for use in conjunction with pharmaceuticals, either as individual therapeutic compounds or as a combination of therapeutic compounds.

The amount of compound which is required to achieve the desired biological effect will, of course, depend on a number of factors such as the specific compound chosen, the use for which it is intended, the mode of administration, and the clinical condition of the recipient.

In general, a daily dose can be in the range of from about 0.01 to about 100 mg/kg bodyweight/day, in another embodiment the range is from about 0.05 mg to about 50 mg/kg bodyweight/day, in another embodiment the range is from about 0.01 to about 20 mg/kg bodyweight/day. In yet another embodiment the range is from about 0.01 to about 10 mg/kg bodyweight/day. This total daily dose can be administered to the patient in a single dose, or in proportionate multiple subdoses. Subdoses can be administered 2 to 6 times per day. Doses can be in sustained release form effective to obtain desired results.

Orally administrable unit dose formulations, such as tablets or capsules, can contain, for example, from about 0.1 mg to about 1000.0 mg of the compound, in another embodiment about 1.0 mg to about 500 mg of compound, in another embodiment from about 2.0 mg to about 400.0 mg of compound, in another embodiment from about 2.0 mg to about 200.0 mg of compound, In another embodiment from about 2.0 mg to about 100.0 mg of compound, in another embodiment from about 2.0 mg to about 50.0 mg of compound. In the case of pharmaceutically acceptable salts, the weights indicated above refer to the weight of the ion derived from the salt.

Oral delivery of the compound of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

When administered intravenously, the daily dose can, for example, be in the range of from about 0.1 mg/kg body weight to about 20 mg/kg body weight, in another embodiment from about 0.25 mg/kg body weight to about 10 mg/kg body weight, in another embodiment from about 0.4 mg/kg body weight to about 5 mg/kg body weight. This dose can be conveniently administered as an infusion of from about 10 mg/kg body weight to about 2000 ng/kg body weight per minute. Infusion fluids suitable for this purpose can contain, for example, from about 0.1 ng to about 10 mg, in another embodiment from about 1 ng to about 200 mg per milliliter. Unit doses can contain, for example, from about 1 mg to about 200 g of the compound of the present invention. Thus, ampoules for injection can contain, for example, from about 1 mg to about 200 mg.

Pharmaceutical compositions according to the present invention include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular compound which is being used. In most cases, the preferred route of administration is oral.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.1 to 25%, advantageously 0.5 to 10% and particularly about 1.5% w/w.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or molding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Pharmaceutical compositions suitable for buccal (sublingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of the present invention. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of a compound disclosed herein.

Pharmaceutical compositions suitable for rectal administration are preferably presented as unit-dose suppositories. These can be prepared by admixing a compound of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain a compound of the present invention in an optionally buffered, aqueous solution, dissolved and/or dispersed in an adhesive, or dispersed in a polymer. A suitable concentration of the active compound is about 1% to 35%, in another embodiment about 3% to 15%. As one particular possibility, the compound can be delivered from the patch by electrotransport or iontophoresis, for example, as described in Pharmaceutical Research, 3(6), 318 (1986).

In any case, the amount of active ingredient that can be combined with carrier materials to produce a single dosage form to be administered will vary depending upon the host treated and the particular mode of administration.

The solid dosage forms for oral administration including capsules, tablets, pills, powders, and granules noted above comprise one or more compounds of the present invention admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutically acceptable carriers encompass all the foregoing and the like.

Treatment Regimen

The dosage regimen to prevent, give relief from, or ameliorate a disease condition with the compounds and/or compositions of the present invention is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular compound employed, whether a drug delivery system is utilized, and whether the compound is administered as part of a drug combination. Thus, the dosage regimen actually employed may vary widely and therefore deviate from the preferred dosage regimen set forth above.

Initial treatment of a patient suffering from a therapeutic condition can begin with the dosages indicated above. Treatment should generally be continued as necessary over a period of several weeks to several months or years until the disease condition has been controlled or eliminated. Patients undergoing treatment with the compounds or compositions disclosed herein can be routinely monitored by, for example, measuring serum cholesterol levels by any of the methods well known in the art, to determine the effectiveness of therapy. Continuous analysis of such data permits modification of the treatment regimen during therapy so that optimal effective amounts of compounds of the present invention are administered at any point in time, and so that the duration of treatment can be determined as well. In this way, the treatment regimen/dosing schedule can be rationally modified over the course of therapy so that the lowest amount of the compound of the present invention which exhibits satisfactory effectiveness is administered, and so that administration is continued only so long as is necessary to successfully treat the condition.

The administration of compounds of the present invention may be used alone or in conjunction with additional therapies known to those skilled in the art in the prevention or treatment of neoplasia. Alternatively, the compounds described herein may be used in conjunctive therapy. By way of example, the compounds may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases (MMP), SOD mimics or $alpha_v beta_3$ inhibitors may be used.

A first family of antineoplastic agents which may be used in combination with compounds of the present invention consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimeterxate, tyrosine kinase inhibitors, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, -SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A 10, anti-neoplaston A2, antineoplaston A3, antineoplaston A5, anti-neoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphirin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methyla-nilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, topoisomerase inhibitors (including irinotecan and topotecan ), Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in combination with compounds of the present invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The present compounds will also be useful in combination with radiation therapy for treatment of neoplasias including malignant tumors.

The present compounds may also be used in co-therapies, partially or completely, in addition to other antiinflammatories, such as together with steroids, NSAIDs, nitric oxide synthase inhibitors (NOS inhibitors, including iNOS inhibitors), kinase inhibitors (including IKK inhibitors and MK-2 inhibitors), p-38 inhibitors, TNF inhibitors, 5-lipoxygenase inhibitors, $LTB_4$ receptor antagonists and $LTA_4$ hydrolase inhibitors. Suitable LTA4 hydrolase inhibitors include RP-64966, (S,S)-3-amino-4-(4-benzyloxyphenyl)-2-hydroxybutyric acid benzyl ester (Scripps Res. Inst.), N-(2(R)-(cyclohexylmethyl)-3-(hydroxycarbamoyl)propionyl)-L-alanine (Searle), 7-(4-(4-ureidobenzyl)phenyl)heptanoic acid (Rhone-Poulenc Rorer), and 3-(3-(1E,3E-tetradecadienyl)-2-oxiranyl)benzoic acid lithium salt (Searle). Suitable $LTB_4$ receptor antagonists include, among others, ebselen, linazolast, ontazolast, Bayer Bay-x-1005, Ciba Geigy compound CGS-25019C, Leo Derunark compound ETH-615, Merck compound MAFP, Terumo compound TMK-688, Tanabe compound T-0757, Lilly compounds LY-213024, LY-210073, LY223982, LY233469, and LY255283, LY-293111, 264086 and 292728, ONO compounds ONO-LB457, ONO-4057, and ONO-LB-448, Shionogi compound S-2474, calcitrol, Lilly compounds Searle compounds SC-53228, SC-41930, SC-50605 and SC-51146, Warner Lambert compound BPC 15, SmithKline Beecham compound SB-209247 and SK&F compound SKF-104493. Preferably, the $LTB_4$ receptor antagonists are selected from calcitrol, ebselen, Bayer Bay-x-1005, Ciba Geigy compound CGS-25019C, Leo Denmark compound ETH-615, Lilly compound LY-293111, Ono compound ONO-4057, and Terumo compound TMK-688. Suitable 5-LO inhibitors include, among others, Abbott compounds A-76745, 78773 and ABT761, Bayer Bay-x-1005, Cytomed CMI-392, Eisai E-3040, Scotia Pharmaceutica EF-40, Fujirebio F-1322, Merckle ML-3000, Purdue Frederick PF-5901, 3M Pharmaceuticals R-840, rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast.

The present compounds may also be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. More preferred will be combinations with compounds selected from morphine, meperidine, codeine, pentazocine, buprenorphine, butorphanol, dezocine, meptazinol, hydrocodone, oxycodone, methadone, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirfentanil, amitriptyline, DuP63 1, Tramadol [(-) enantiomer], GP-531, acadesine, AKI-1, AKI-2, GP-1683, GP-3269,4030W92, tramadol racemate, Dynorphine A, E-2078, AXC3742, SNX-111, ADL2-1294, ICI-204448, CT-3, CP-99,994, and CP-99,994.

The present compounds will also be useful in therapeutic combination with lipid-lowering drugs including HMG Co-A reductase inhibitors (including pravastatin, simvastatin, lovastatin, ZD4522, atorvastatin, cerivastatin, and fluvastatin), bile acid sequestrants (including cholestyramine and cholestepol), nicotinic acis derivatives (including niacin), fibric acid deravitives (including clofibrate, gemfibrozil, fenofibrate, ciprofibrate and bezafibrate), MTP inhibitors, ACAT inhibitors, and CETP inhibitors.

The compounds will also be useful for the control of urinary conditions and other muscarinic receptor-related conditions in therapeutic combination with an anti-muscarinic agent such as tolterodine, tiotropium, ipratropium, pirenzepine, homatropine, scopolamine, and atropine.

The compounds will also be useful in therapeutic combination with a sex steroid for the treatment or prevention of menstrual cramps.

The compounds will also be useful alone or in combination with other therapeutic agents for the treatment or prevention of migraine headaches. Such combination therapies include caffeine, an ergot alkaloid (such as ergotamine or dihydroergotamine), a $5-HT_{1B/1D}$ receptor antagonist (such as sumatriptan), and a GABA-analog (such as gabopentin).

The compounds can be used in co-therapies, in place of other conventional antiinflammatories, in combination with one or more antihistamines, decongestants, diuretics, antitussive agents or with other agents previously known to be effective in combination with antiinflammatory agents.

General Synthetic Procedures

The compounds of the invention can be synthesized according to the following procedures of Schemes 1-16, wherein the R1-R6 substituents are as defined for Formulas I-II, above, except where further noted.

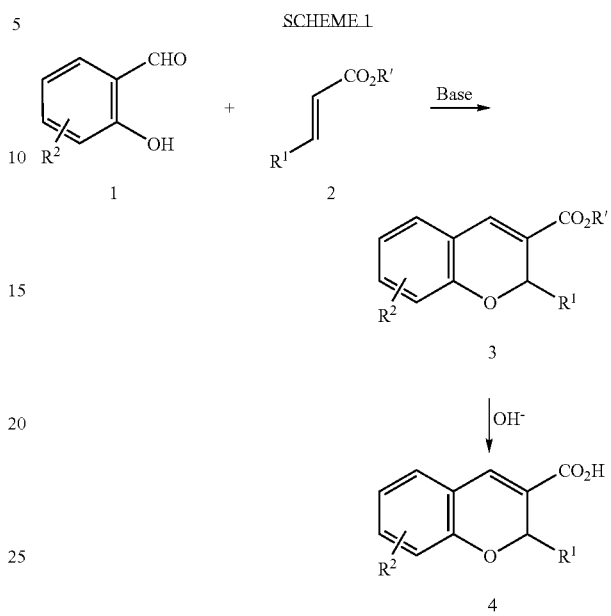

Synthetic Scheme 1 illustrates the general method for the preparation of a wide variety of substituted 2H-1-benzopyran derivatives 3 and 4. In step 1, a representative ortho-hydroxybenzaldehyde (salicylaldehyde) derivative 1 is condensed with an acrylate derivative 2 in the presence of base, such as potassium carbonate in a solvent such as dimethylformamide, to afford the desired 2H-1-benzopyran ester 3. Alternative base-solvent combinations for this condensation includes an organic base such as triethylamine, diazobicyclononane, with or without a solvent such as dimethyl sulfoxide. Mixtures of organic and inorganic base in various stoichiometry, with or without an added solvent, can also be used. In step 2 the ester is hydrolyzed to the corresponding acid, such as by treatment with aqueous base (sodium hydroxide) in a suitable solvents such as ethanol or THF-alcohol mixtures to afford after acidification the substituted 2H-1-benzopyran-3-carboxylic acid 4.

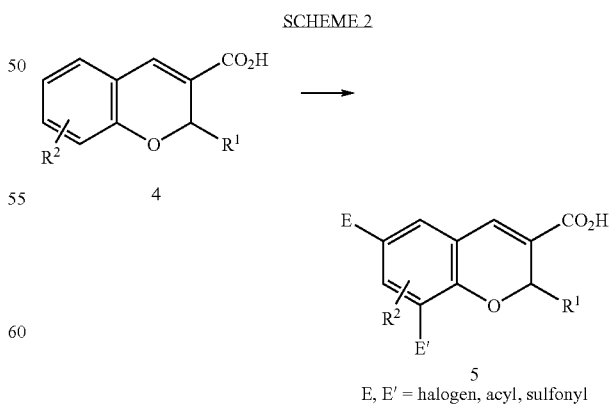

Synthetic Scheme 2 shows the general method for functionalizing selected 2H-1-benzopyrans. Treatment of the 2H-1-benzopyran carboxylic acid 4 or ester 3 with an electrophillic agent makes a 6-substituted 2H-1-benzopyran 5. A wide variety of electrophillic agents react selectively with 2H1-1-benzopyrans 4 in the 6-position to provide new analogs in high yield. Electrophillic reagents such as halogen (chlorine or bromine) give the 6-halo derivatives. Chlorosulfonic acid reacts to afford the 6-position sulfonyl chloride that can further be converted to a sulfonamide or sulfone. Friedel-Crafts acylation of 4 provides 6-acylated 2H-1-benzopyrans in good to excellent yield. A number of other electrophiles can be used to selectively react with these 2H-1-benzopyrans in a similar manner. A 6-position substituted 2H-1-benzopyran can react with an electrophilic reagent at the 8-position using similar chemistries to that described for electrophilic substitution of the 6-position. This yields an 2H-1-benzopyran which is substituted at both the 6 and 8 positions.

If $R^2$ is a moiety that activates aryls toward electrophilic substitution, this can occur on the benzopyran nucleus in the 5, 6, 7, or 8 positions. Thus a 6-methoxy substituent can direct electrophilic substitution to the 5 or 7-positions. Similar ortho/para directors at different positions about the benzopyran 5, 6, 7, or 8 positions can activate the ortho or para positions (relative to that substituent) towards substitution where possible.

allows substitution at position 4 of the 2H-1-benzopyran. In this case a commercially or synthetically available subtituted ortho-hydroxy acetophenone 6 is treated with two or more equivalents of a strong base such as lithium bis(trimethylsilyl)amide in a solvent such as tetrahydrofuran (THF), followed by reaction with diethyl carbonate to afford the beta-keto ester 7. Ester 7 is condensed with an acid chloride or anhydride in the presence of a base such as potassium carbonate in a solvent such as toluene with heat to afford 4-oxo-4H-1-benzopyran 8. Reduction of the olefin can be accomplished by a variety of agents including sodium borohydride ($NaBH_4$) in solvent mixtures such as ethanol and tetrahydrofuran (THF), or by use of triethylsilane in a solvent such as trifluoroacetic acid, or by catalytic reduction using palladium on charcoal and hydrogen gas in a solvent such as ethanol to yield the new beta-keto ester 9 (two tautomeric structures shown). Acylation of the oxygen of the ketone enolate in the presence of a base such as 2,6-di-tert-butyl-4-methylpyridine, an acylating agent such as trifluoromethanesulfonic anhydride, and using a solvent such as methylene chloride yields the enol-triflate 10. Triflate 10 can be reduced with reagents such as tri-n-butyltin hydride, lithium chloride and a palladium (0) catalyst such as tetrakis(triphenylphosphine)palladium (0) in a solvent such as tet-

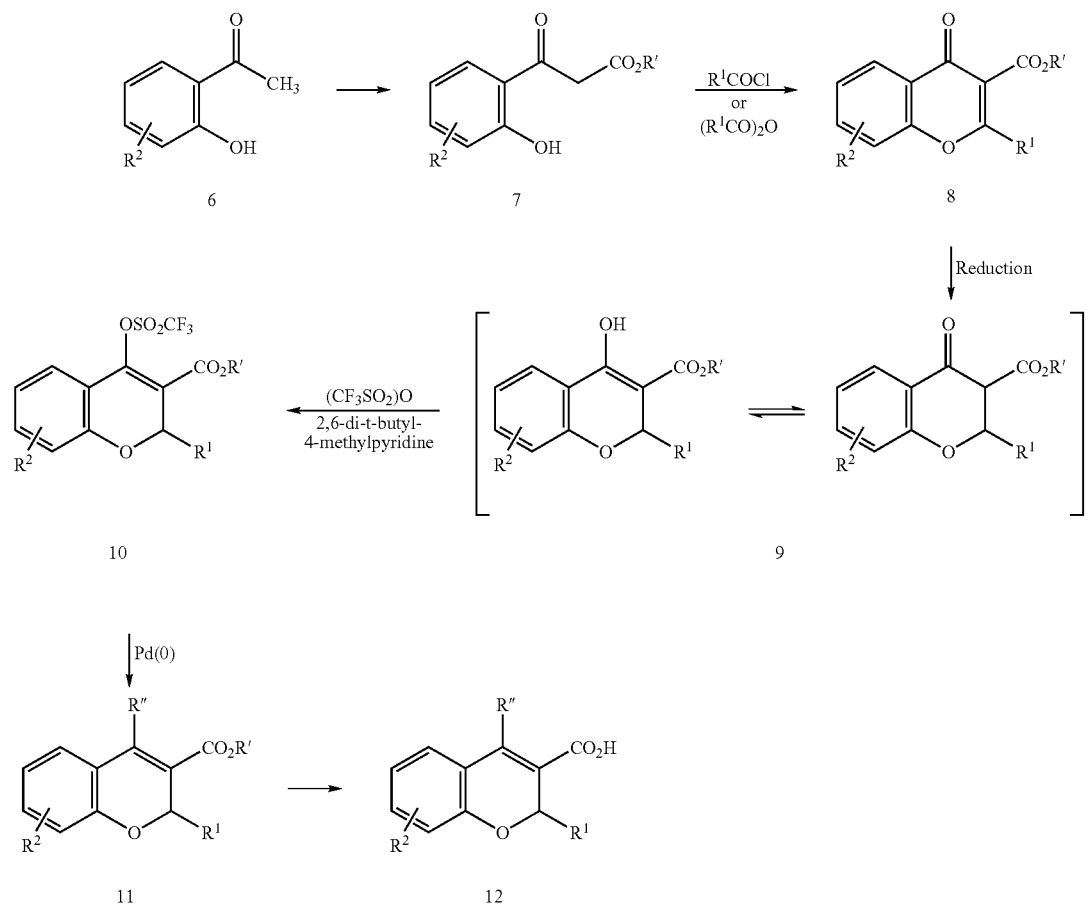

SCHEME 3

Synthetic Scheme 3 illustrates a second general synthesis of substituted 2H-1-benzopyran-3-carboxylic acids which rahydrofuran to yield 2H-1-benzopyran ester 11 where R" is hydrogen. The ester 11 can be saponified with a base such as 2.5 N sodium hydroxide in a mixed solvent such as tetrahydrofuran-ethanol-water (7:2:1) to yield the desired substituted 2H-1-benzopyran-3-carboxylic acid.

To incorporate a carbon fragment $R^3$ one can treat triflate 10 with reagents known to undergo "cross-coupling" chemistries such a tributylethyenyltin, lithium chloride and a palladium (0) catalyst such as tetrakis(triphenylphosphine) palladium (0) in a solvent such as tetrahydrofuran to yield 2H-1-benzopyran ester 11 where $R^3$ is a vinyl moiety. The ester 6 can be saponified with a base such as 2.5 N sodium hydroxide in a mixed solvent such as tetrahydrofuran-ethanol-water (7:2:1) to yield the desired 4-vinyl-2H-1-benzopyran-3-carboxylic acid (12, R"=$CH_2CH$—). Similarly triflate 10 can be converted under similar conditions using tri-n-butylphenyltin to 2H-1-benzopyran where $R^3$=phenyl and by hydrolysis of the ester converted to the carboxylic acid 12 where $R^3$=phenyl. Using a similar strategy, substituents which be incorporated as substitutent $R^3$ can be substituted olefins, substituted aromatics, substituted heteroaryl, acetylenes and substituted acetylenes.

If $R^1$=H in structure 8, treatment with $CF_3Si(CH_3)_3$ (or similar CF3 silyl reagent) accompanied by fluoride (F—) may provide structure 9 wherein $R^1$=$CF_3$.

SCHEME 4

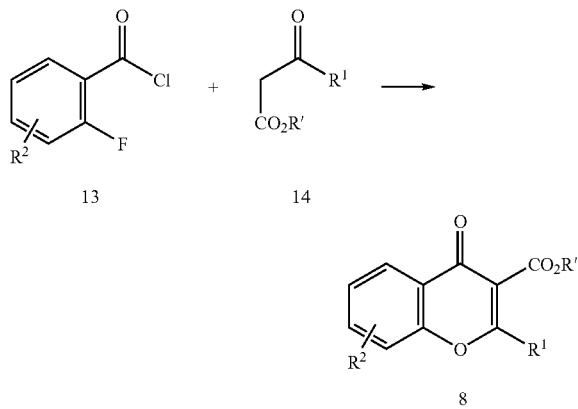

Synthetic Scheme 4 shows an alternative general procedure for the preparation of 4-oxo-4H-1-benzopyran 8. Treatment of an ortho-fluorobenzoyl chloride with an appropriately substituted beta-keto ester 14 with a base such as potassium carbonate in a solvent such as toluene provides 4-oxo-4H1-1-benzopyran 8. 4-Oxo-4H-1-benzopyran 8 can be converted to 2H-1-benzopyran 12 as described in Scheme 3.

SCHEME 5

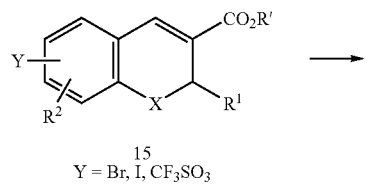

15
Y = Br, I, $CF_3SO_3$

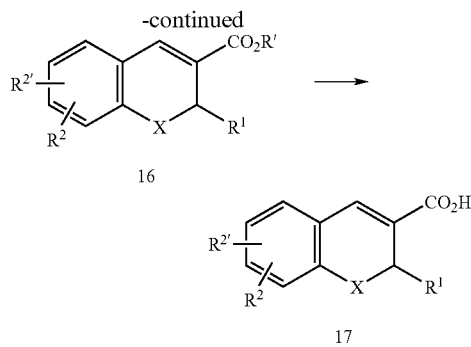

Synthetic Scheme 5 shows a general method for substitution of the aromatic ring of the 2H-1-benzopyran. This can be accomplished through organo-palladium mediated "cross-coupling" chemistryusing a palladium (0) catalyst to couple benzopyran 15 at position Y, where Y is iodide, bromide, chloride, boronic acids and esters, substituted boranes, zinc species, magnesium species or triflate, with an alkyl, acetylene, olefinic, nitrile (cyanide), or aryl coupling agent. Appropriate coupling agents can include functionalized alkyl, alkenyl, aryl groups substituted with boranes, boronic acids boronic esters, zinc, tin, copper or magnesium species. Palladium coupling strategies using alcohols, phenols, anilines, or amines to couple benzopyran 15 at position Y can also be performed. Futher, use of acid chlorides or appropriate coupling agents with carbon monoxide can yield the corresponding ketones. Some of these appropriate coupling agents can be generated in situ using the appropriate metals and reactive organic precursors. Substituted acetylenes, as the coupling agent will provide the corresponding substituted acetylene. Substituted aryl moieties can be incorporated using arylboronic acids or esters; nitrites can be incorporated by use of zinc (II) cyanide. The resulting ester 16 can be converted to carboxylic acid 17 as described in Scheme 1.

Another approach to substitution of the aryl moiety of the benzopyran 15 is to convert Y, where Y is iodide or bromide, to a perfluoroalkyl moiety. Exemplary of this transformation is the conversion of 15 (Y=iodide) to 16 ($R^{2'}$=pentafluoroethyl) using a potassium pentafluoropropionate and copper (I) iodide in hexamethylphosphoramide (HMPA). The resulting ester 16 can be converted to carboxylic acid 15 as described in Scheme 1.

A similar method adds substitution of the aromatic ring in dihydroquinoline-3-carboxylates. This can be accomplished through organopalladium couplings with aryl iodides, bromides, or triflates and various coupling agents (R. F. Heck, *Palladium Reagents in Organic Synthesis*. Academic Press 1985). When using a suitable palladium catalyst such as tetrakis(triphenyl-phospine)palladium (0) in this reaction, coupling agents such as alkynes provide disubstituted alkynes, phenyl boronic acids afford biphenyl compounds, and cyanides produce arylcyano compounds. A number of other palladium catalysts and coupling reagents could be used to selectively react with appropriately substituted dihydroquinoline-3-carboxylates in a similar manner.

SCHEME 6

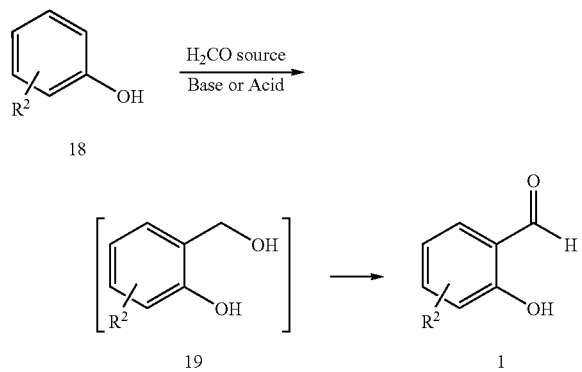

SCHEME 7

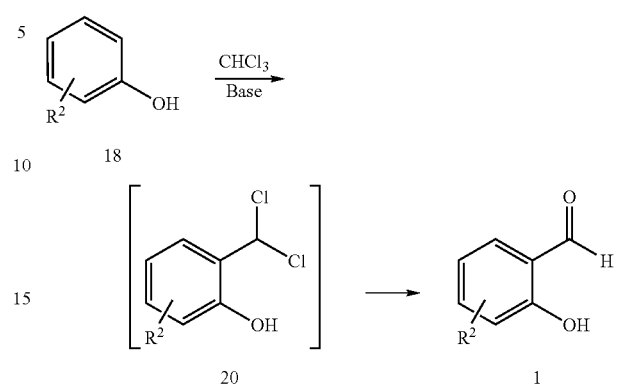

Synthetic Scheme 6 shows a general synthetic route for conversion of a commercially or synthetically available substituted phenol into a substituted salicylaldehyde. Several different methods which utilize formaldehyde or a chemically equivalent reagent are described in detail below.

Reaction of an appropriately substituted phenol 18 in basic media with formaldehyde (or chemical equivalent) will yield the corresponding salicylaldehyde 1. The intermediate, ortho-hydroxymethylphenol 19, will under appropriate reaction conditions be oxidized to the salicylaldehyde 1 in situ. The reaction commonly employs ethyl magnesium bromide or magnesium methoxide (one equivalent) as the base, toluene as the solvent, paraformaldehyde (two or more equivalents) as the source of formaldehyde, and employs hexamethylphoramide (HMPA) or N,N,N',N'-tetramethylethylenediamine (TMEDA). (See: Casiraghi, G. et al., J. C. S. Perkin I, 1978, 318-321.) A related method is the use of $MgCl_2$ and formaldehyde (or chemical equivalent) with the phenol 18 to produce the salicylaldehyde 1.

Alternatively an appropriately substituted phenol 18 may react with formaldehyde under aqueous basic conditions to form the substituted ortho-hydroxybenzyl alcohol 19 (See: a) J. Leroy and C. Wakselman, J. Fluorine Chem., 40, 23-32 (1988). b) A. A. Moshfegh, et al., Helv. Chim. Acta., 65, 1229-1232 (1982)). Commonly used bases include aqueous potassium hydroxide or sodium hydroxide. Formalin (38% formaldehyde in water) is commonly employed as the source of formaldehyde. The resulting ortho-hydroxybenzyl alcohol 19 can be converted to the salicylaldehyde 1 by an oxidizing agent such as manganese (IV) dioxide in a solvent such as methylene chloride or chloroform (See: R -G. Xie, et al., Synthetic Commun. 24, 53-58 (1994)).

An appropriately substituted phenol 18 can be treated under acidic conditions with hexamethylenetetramine (HMTA) to prepare the salicylaldehyde 1 (Duff Reaction; See: Y. Suzuki, and H. Takahashi, Chem. Pharm. Bull., 31, 1751-1753 (1983)). This reaction commonly employs acids such as acetic acid, boric acid, methanesulfonic acid, or trifluoromethanesulfonic acid. The source of formaldehyde commonly used is hexamethylenetetramine. A related procedure utilizes $MgCl_2$ (anhydrous) and paraformaldehyde and the appropriately substituted phenol 18 to prepare the salicylaldehyde 1.

Synthetic Scheme 7 shows the Reimer-Tiemann reaction in which an commercially or synthetically available appropriately substituted phenol 18 will under basic conditions react with chloroform to yield a substituted salicylaldehyde 1 (See: Cragoe, E. J.; Schultz, E. M., U.S. Pat. No. 3,794, 734, 1974).

SCHEME 8

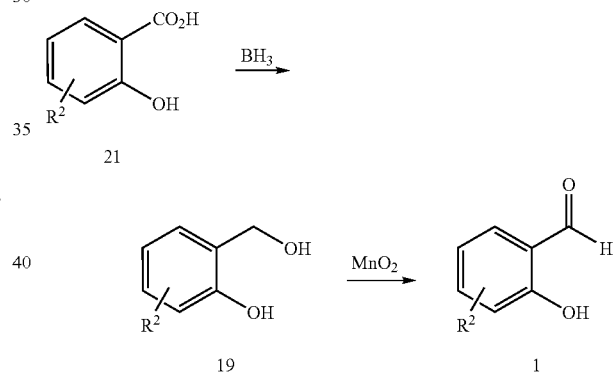

Synthetic Scheme 8 shows the conversion of a commercially or synthetically available appropriately substituted salicylic acid 21 to its respective salicylaldehyde 1 via an intermediate 2-hydroxybenzyl alcohol 19. Reduction of the salicylic acid 21 can be accomplished with a hydride reducing agent such as borane in a solvent such as tetrahydrofuran. Treatment of the intermediate 2-hydroxybenzyl alcohol 19 with an oxidizing agent such as manganese (IV) oxide in a solvent such as methylene chloride or chloroform provides salicylaldehyde 1.

SCHEME 9

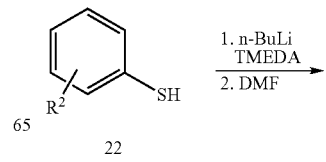

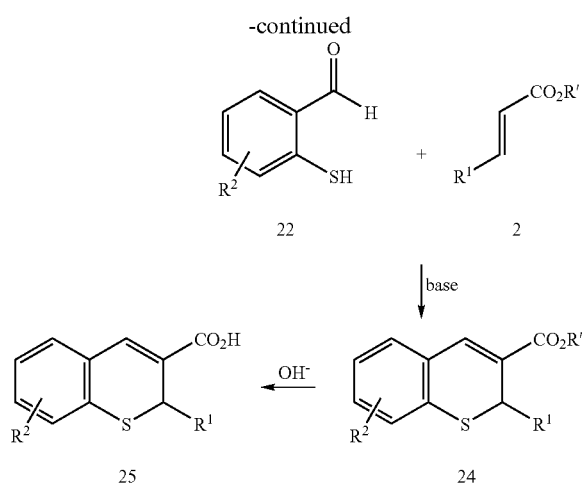

Synthetic Scheme 9 illustrates a general synthetic method for preparation of a wide variety of substituted 2-(trifluoromethyl)-2H-1-benzothiopyran-3-carboxylic acids (25). In step 1, an appropriately commercially or synthetically available substituted thiophenol 22 is ortho-metallated with a base such as n-butyllithium employing TMEDA (N,N,N', N'-tetramethylenediamine) followed by treatment with dimethylfonnamide to provide the 2-mercaptobenzaldehyde 23. Condensation of the 2-mercaptobenzaldehyde 23 with an acrylate 2 in the presence of base provides ester 24 which can be saponified in the presence of aqueous base to afford the substituted 2H-1-benzothiopyran-3-carboxylic acids 25.

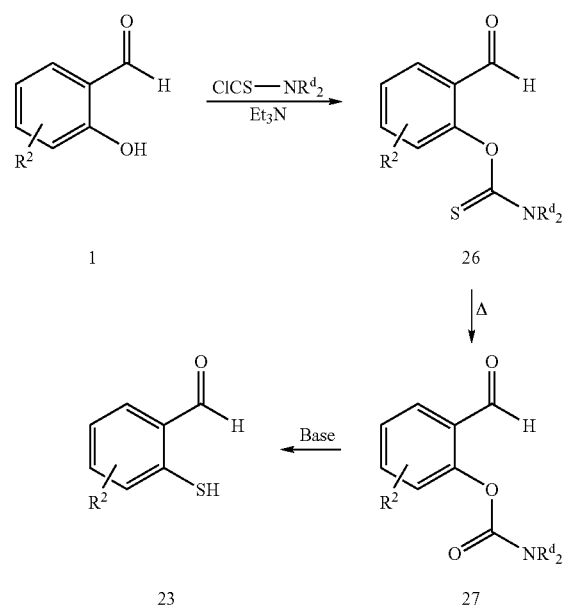

Synthetic Scheme 10 shows a method for preparing a substituted 2-mercaptobenzaldehyde from an appropriate commercially or synthetically available substituted salicylaldehyde. In step 1, the phenolic hydroxyl of salicylaldehyde 1 is converted to the corresponding O-aryl thiocarbamate 26 by acylation with an appropriately substituted thiocarbamoyl chloride such as N,N-dimethylthiocarbamoyl chloride in a solvent such as dimethylformamide using a base such as triethylamine. In Step 2, O-aryl thiocarbamate 26 rearranges to S-aryl thiocarbamate 27 when heated sufficiently such as to 200° C. using either no solvent or a solvent such as N,N-dimethylaniline (See: A. Levai, and P. Sebok, Synth. Commun., 22 1735-1750 (1992)). Hydrolysis of S-aryl thiocarbamate 27 with a base such as 2.5 N sodium hydroxide in a solvent mixture such as tetrahydrofuran and ethanol yields the substituted 2-mercaptobenzaldehyde 23 which can be converted to the substituted 2H-1-benzothiopyran-3-carboxylic acids 25 as described in Scheme 9.

SCHEME 11

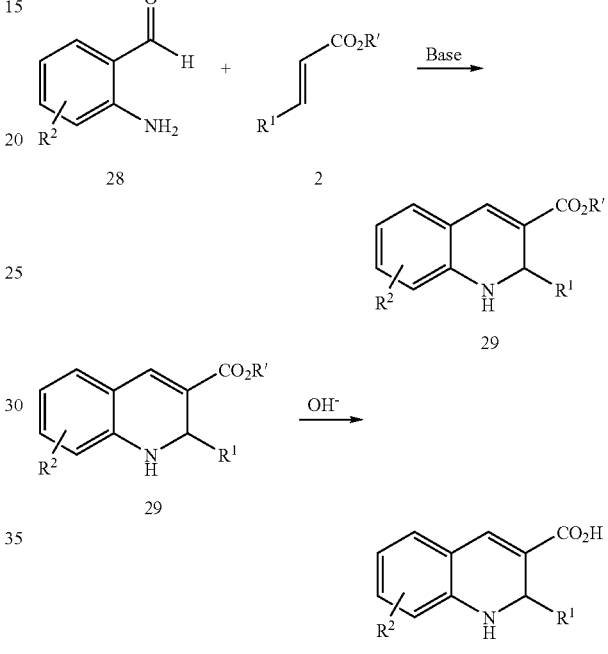

Synthetic Scheme 11 illustrates the general method for the preparation of a wide variety of dihydroquinoline-3-carboxylic acid derivatives 30. $R^2$ represents the aromatic substititution of commercially and synthetically available 2-aminobenzaldeydes 28. The 2-amino-benzaldehyde derivative 28, where $R^2$ represents various substitutions, is condensed with a acrylate derivative 2 in the presence of base such as potassium carbonate, triethylamine, or diazbicyclo[2.2.2]undec-7-ene in solvents such as dimethylformamide to afford the dihydroquinoline-3-carboxylate esters 29. The ester 29 can be saponified to the corresponding acid, such as by treatment with aqueous inorganic base such as 2.5 N sodium hydroxide in a suitable solvent such as ethanol to afford after acidification the desired dihydroquinoline-3-carboxylic acid 30.

SCHEME 12

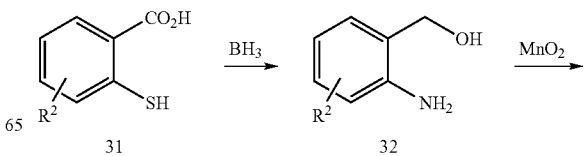

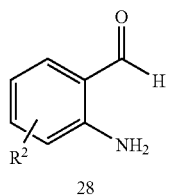

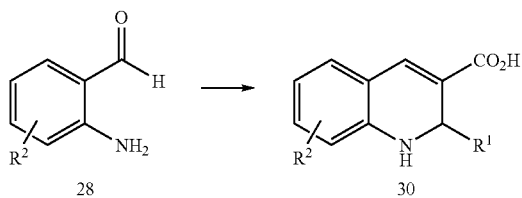

Synthetic Scheme 12 illustrates the preparation of dihydroquinoline-3-carboxylic acid 30 from 2-aminobenzoic acids 31. $R^2$ represents the aromatic substitution of commercially and synthetically available 2-aminobenzoic acids 31. Reduction of the representative 2-aminobenzoic acid 31 to the desired 2-aminobenzyl alcohol 32 was accomplished with a hydride reducing agent such as borane in a solvent such as tetrahydrofuran. Treatment of the desired 2-aminobenzyl alcohol 32 with an oxidizing agent such as manganese (IV) oxide in a solvent such as methylene chloride provides the representative 2-aminobenzaldehydes 28. (C. T. Alabaster, et al. *J. Med. Chem.* 31, 2048-2056 (1988)) The 2-aminobenzaldehydes were converted to the desired dihydroquinoline-3-carboxylic acid 30 as described in Scheme 11.

SCHEME 13

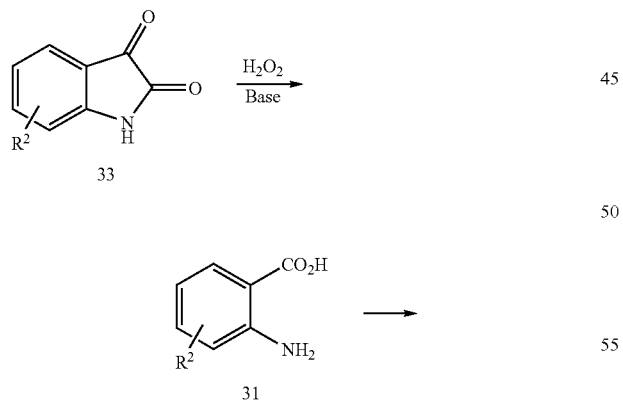

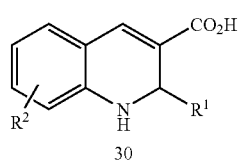

Synthetic Scheme 13 illustrates the general method for the preparation of a wide variety of dihydroquinoline-3-carboxylic acid derivatives 30 from isatins 33. $R^2$ represents the aromatic substitution of commercially and synthetically available isatins 33. A representative isatin 33 was treated with basic peroxide generated from hydrogen peroxide and a base such as sodium hydroxide to afford the desired representative 2-aminobenzoic acids 31 (M. S. Newman and M. W. Lougue, J. Org. Chem., 36,1398-1401 (1971)). The 2-aminobenzoic acids 31 are subsequently converted to the desired dihydroquinoline-3-carboxylic acid derivatives 30 as described in synthetic Scheme 12.

SCHEME 14

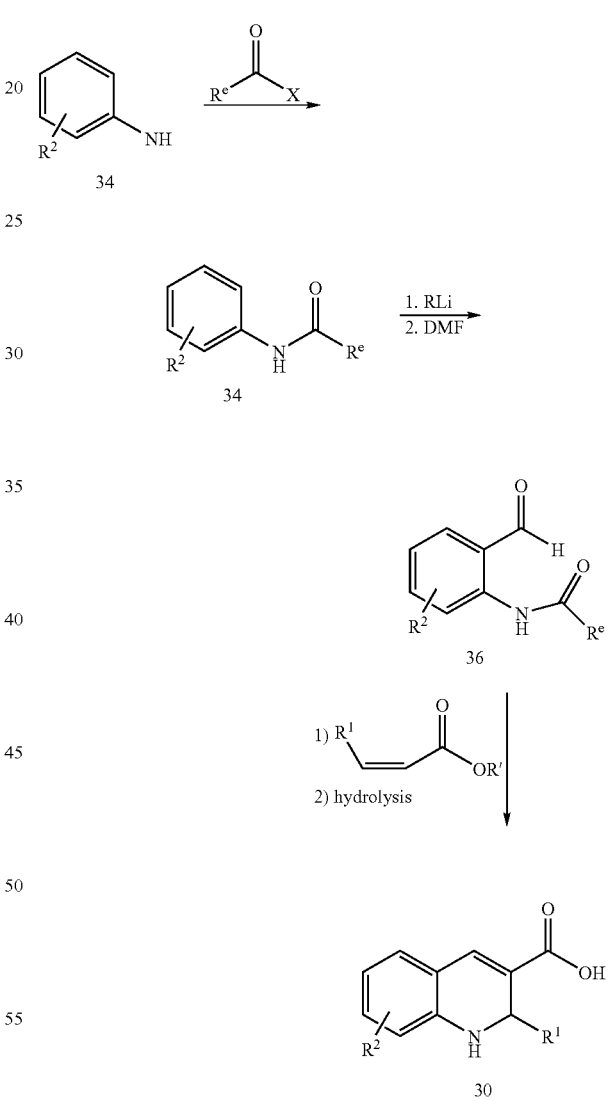

Synthetic Scheme 14 is another general method for the preparation of dihydroquinoline-3-carboxylic acid derivatives 30. In step 1, an appropriate commercially or synthetically available substituted aniline 34 can be treated with an acylating reagent such as pivaloyl chloride yielding an amide 35. The ortho-dianion of amide 35 is prepared by treating amide 35 with organo-lithium bases such as n-bu- 5tyllithium or tert-butyllithium in tetrahydrofuran at low temperature. The dianion is quenched with dimethylformamide to afford the acylated-2-amino-benzaldehydes 36. (J. Turner, *J. Org. Chem.*, 48, 3401-3408 (1983)) Reaction of these aldehydes in the presence of bases such as lithium hydride with a acrylate followed by work up with aqueous inorganic bases and hydrolysis, such as by treatment with aqueous base (sodium hydroxide) in a suitable solvent such as ethanol affords, after acidification, a dihydroquinoline-3-carboxylic acid 30.

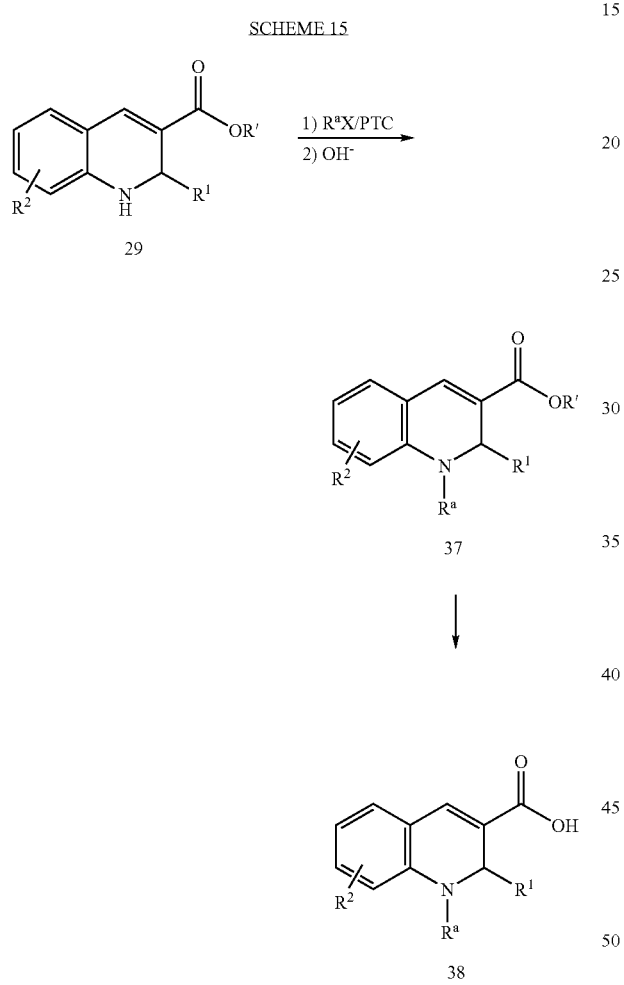

Synthetic Scheme 15 shows a general method for alkylation of the nitrogen of dihydroquinoline-3-carboxylate ester derivatives 29. The step involves treatment of dihydroquinoline-3-carboxylate ester derivatives 29 with alkyl halides such as iodoethane in the presence of phase transfer catalysts such a tetrabutylammonium iodide, and a base such as caustic (50% aqueous sodium hydroxide) in a solvent such as dichloromethane. These conditions afford the N-alkylated dihyrdoquinoline-3-carboxylate esters 37. Saponification of 37 with aqueous base provides N-alkylated-dihyroquinoline-3-carboxylic acid derivatives 38.

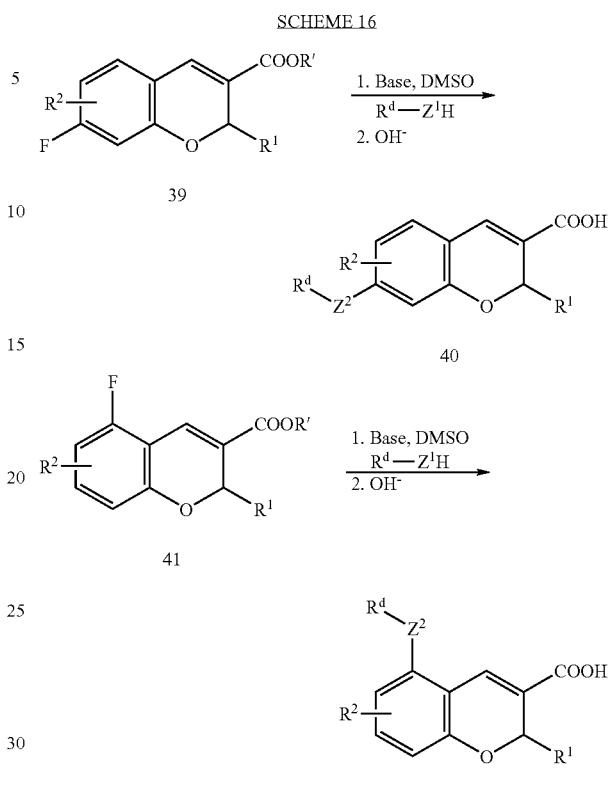

Synthetic Scheme 16 shows a general method for the preparation of a 5 or 7-ether ($Z^1$=O), thioether ($Z^1$=S), or amine ($Z^1$=NH or NR), substituted benzopyran-3-carboxylic ester. An appropriately substituted phenol, thiophenol, hydroxy-heterocycle, mercaptoheterocycle, alcohol, alkylthiol, amine (mono or di-substituted) can be condensed under basic conditions using a base such as potassium carbonate in a solvent such as dimethysulfoxide, at temperature above room temperature, such as 100° C., with an appropriately substituted 7-fluorobenzopyran derivative 30 to yield the corresponding ether or thioether. Hydrolysis of the ester with an aqueous base such as lithium hydroxide or sodium hydroxide in a solvent mixture such as tetrahydrofuran-ethanol-water yields acid 40. When appropriate, a thioether ($Z^2$=S) can be oxidized to the sulfoxide ($Z^2$=SO) or sulfone ($Z^2$=SO$_2$) with an oxidant such as OXONE® or m-CPBA either before or after ester hydrolysis. In this chemistry $R^d$ can include aryl, heteroaryl, heterocyclic, alicyclic, branched or linear aliphatic, branched or linear perfluoro-aliphatic moiety.

An alternative approach for preparing the salicylaldehyde precursors is shown in Scheme 17. An phenol 21 is O-alkylated with an appropriate protecting group (P) which may consist of any ortho-directing protecting group (DoM). Groups may include the methyl, methoxymethyl, methoxyethoxymethyl, tetrahydropyranyl (THP) or other ethers. These protected phenols can be C-deprotonated with a suitable base such as an alkyl lithium including butyllithium, or with lithium amides such as lithium diisopropylamide or lithium bis(trimethylsilyl)amide. This anion can be formylated directly with formylating agents such as DMF (dimethyl formamide). Workup and deprotection of the phenol provides the salicylaldehyde 1. Deprotection of the described phenol alkyl ethers can be accomplished under acidic conditions. Alternatively, the resulting ortho anion can be reacted with reactive electrophilic reagents ($R^e$). These may include alkyl halides, alkyl or aryl esters, alkyl or aryl aldehydes, silyl halides, or halogenating reagents. In appropriate cases, the resulting protected (additionally substituted) phenol can be deprotonated again and formylated by reaction with DMF or other formylating agent. Workup and deprotection of the phenol provides the substituted salicylaldehyde 44.

SCHEME 17

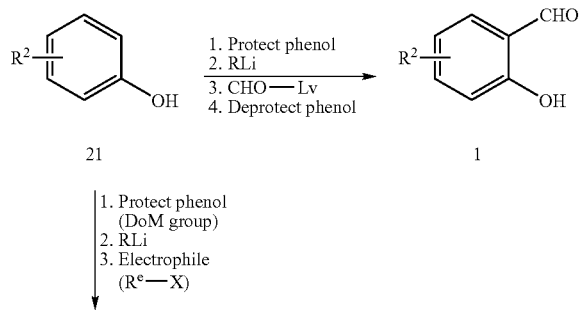

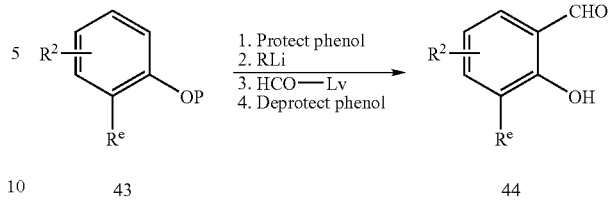

The aforementioned chemistries may be applicable to a solid-phase approach as shown in Scheme 18. An example of such a strategy is the covalent attachment of the carboxylic acid to a polymer (45). The attachment of the compound may be through an ester linkage, but is not limited to that functional group. The X funcitionality of the resin can be an alkyl halide, an alcohol, or other functional groups. Subsequent to this attachment, additional chemical transformations can be accomplished to replace substituents to form a differentially substituted product 46 or additional functionality added to form product 48. Respective cleavage of the product 46 and 48 yield the free carboxylic acids 47 and 49. This cleavage can be accomplished by a variety of conditions employing acidic, basic, lewis acids or lewis bases, nucleophiles, and solvolysis.

SCHEME 18

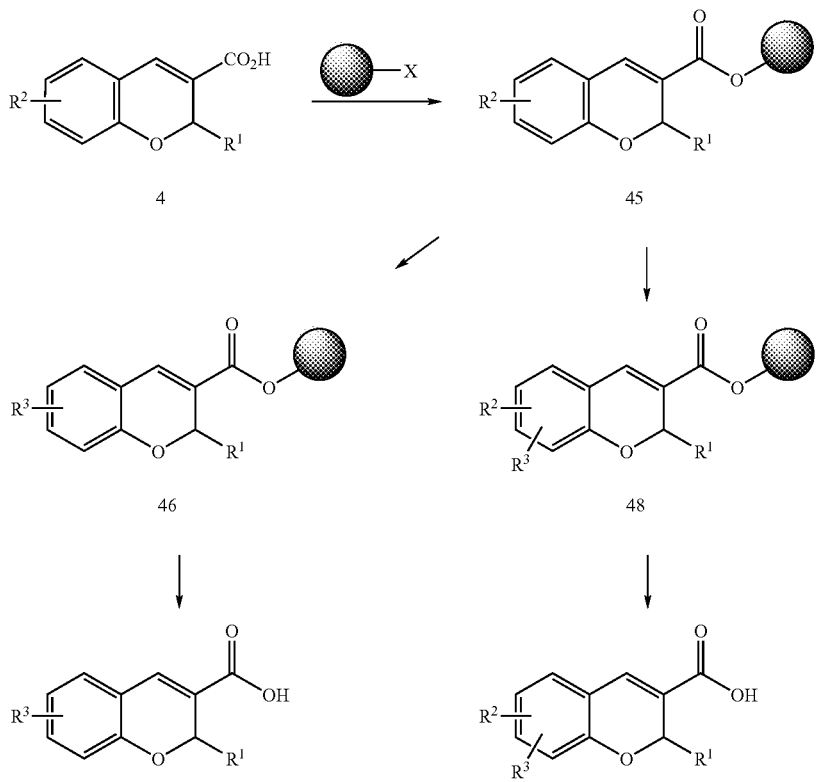

Detailed Preparative Method

The following abbreviations are used:
a—alpha
ACN—acetonitrile
$BBr_3$—boron tribromide
9-BBN-9-borabycyclo[3.3.1]nonane
$Br_2$—bromine
n-BuLi-n-butyllithium
$(BzO)_2$—benzoyl peroxide
Calc'd—calculated
$CH_2Cl_2$ or DCM—methylene chloride or dichloromethane
CD—circular dichroism
$CDCl_3$—deuterated chloroform
$CD_3OD$—deuterated methanol
$Cl_2$—chlorine gas
$CCl_4$—carbon tetrachloride
con., conc, concd, or conc'd—concentrated
CuI—copper (I) iodide
DMAP—N,N-dimethyl amino pyrodine
DME—ethylene glycol dimethyl ether
DMF—dimethylfonnamide
DMSO—dimethyl sulfoxide
DPPP-—1,3-bis-diphenyl phosphino propane
$Et_2O$ —diethyl ether
EtOAc—ethyl acetate
EtOH—ethanol
$Et_3SiH$—triethyl silane
ESHRMS—electron spray high resolution Mass
h—hour
HBr—hydrobromic acid
HCl—hydrochloric acid
HF—hydrogen fluoride
HMPA—hexamethyl phosphoric triamide
HMTA—hexamethylenetetraamine, methenamine
$H_2O$—water
HOAc—acetic acid
IPA—isopropanol
KCN—potassium cyanide
$K_2CO_3$—potassium carbonate
$KHSO_4$—potassium sulfate
$K_3PO_4$—potassium phosphate
LCMS—liquor chromatography Mass
LiOH—lithium hydroxide
MeOH—methanol
$MgSO_4$—magnesium sulfate
MTBE—methyl t-butyl ether
M+H—M+1
M−H—M−1
m/z—mass/charge
$NaBH_4$—sodium borohydride
NBS—N-bromosuccinimide
NaHCO3—sodium bicarbonate
$NH_4Cl$—ammonium chloride
$NH_4F$—ammonium fluoride
$NaN_3$—sodium azide
NaOH—sodium hydroxide
NaOD—deuterated sodium hydroxide
$Na_2SO_4$—sodium sulfate
OXONE—potassium peroxymonosulfate
$Pd(dba)_2$—bis (dibenzyllideneacetone)palladium
$PdCl_2(PPh_3)_2$—bis(triphenylphosphine)palladium (II) chloride
Pd (dppf)Cl $CH_2Cl_2$—[1,1'-bis(diphenylphosphino)ferrocene]chloropalladium complex with dichloromethane
$Pd(PPh_3)_4$—tetra-triphenylphosphine palladium
$[(t-Bu_3P)PdBr]_2$—palladium (I) tri-tert-butyl phosphine bromide dimer
$PPh_3$—triphenyl phosphine
$P_2O_5$—phosphorous pentoxide
psi—pounds per square inch
RPHPLC—reverse phase high pressure liquid chromatography
sat. or sat'd. or satd—saturated
TBAF—tetrabutylammonium fluoride
TEA—triethyl amine
TFA—trifluoroacetic acid
THF—tetrahydrofuran
$TiCl_4$—Tin (IV) chloride
TMAF—tetramethylammonium fluoride
TMEDA—tetrametylethylenediamine
$TMSCF_3$—trimethyl(trifluoromethyl)silane
Tfp—trifurylphosphine
µ—micro (for example, µL or µM)
Zn—zinc powder
$ZnCl_2$—zinc chloride In the following examples, NMR chemical shift values are represented in ppm shift upfield from TMS (δ).

In the following examples, the particular numbers assigned to each compound are of no significance, they are merely the numbers assigned by the inventors. Gaps in the sequence do not imply that any examples have not been disclosed.

EXAMPLE 1a

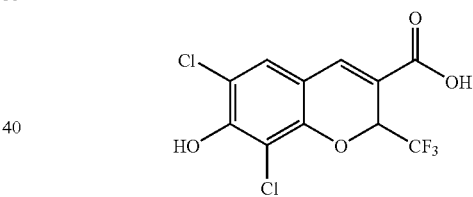

6,8-dichloro-7-hydroxy-2-(trifluoromethyl)-2H-chromene-3-carboxylic acid

Step 1. Preparation of ethyl 7-hydroxy-2-(trifluoromethyl)-2H-chromene-3-carboxylate A mixture of 2,4-dihydroxy benzaldehyde (20.0 g, 0.145 mole) and ethyl 4,4,4-trifluorocrotonate (36.58 g, 0.217 mole) was dissolved in anhydrous DMF (40 mL). The solution was warmed to 60° C., treated with anhydrous $K_2CO_3$ (40.0 g, 0.290 mole), and maintained at 80° C. for 48 h. The reaction was cooled to room temperature, diluted with 3N HCl, and extracted with ethyl acetate. The combined extracts were washed with brine, dried over anhydrous $MgSO_4$, filtered, and concentrated in vacuo to afford an oil. The oil was passed through the silica plug and the plug was washed with 20% EtOAc in hexane to give yellow solid (13.22 g, 31.6%): LCMS m/z 311.05 (M+Na). $^1$H NMR ($CDCl_3$/400 MHz) 7.67 (s, 1H), 7.09 (d, 1H, J=8.8 Hz), 6.46 (m, 2H), 5.67 (q, 1H, J=6 Hz), 4.29 (q, 2H, J=7.2 Hz), 1.33 (t, 3H, J=7.2 Hz).

Step 2. Preparation of ethyl 6,8-dichloro-7-hydroxy-2-(trifluoromethyl)-2H-chromene-3-carboxylate A solution of the ester from Step 1 (2.1 g, 7.29 mmole) in acetic acid (30 mL) was stirred at 10° C. The pre-prepared solution of $Cl_2$ (gas) in acetic acid (31 mL, 8.7 mmol) was added to above solution. The mixture was stirred for 2 hours. After $Cl_2$ (gas) was blown away, Zn powder (5 eq) was added to the mixture and the mixture was stirred for 10 min. The Zn salts were removed and the filtrate was evaporated to dryness. The residue was purified by normal phase silica chromatography eluting with 20% EtOAc in hexane to give white solid (0.22 g, 8%) as the di-chloro compound: LCMS m/z 356.95 (M+H). $^1$H NMR (CDCl$_3$/400 MHz) 7.60 (s, 1H), 7.16 (s, 1H), 5.80 (q, 1H, J=6.8 Hz), 4.30 (q, 2H, J=7.2 Hz), 1.33 (t, 3H, J=7.2 Hz).

Step 3. Preparation of 6-chloro-2-(trifluoromethyl)-2H-chromene-3-carboxylic acid A solution of the ester from Step 2 (0.20 g, 0.56 mmole) was dissolved in 3 mL mixture of MeOH/ACN/H$_2$O=1/1/1, treated with lithium hydroxide (81 mg, 3.36 mmole) and stirred at room temperature for 2 days. The reaction mixture was acidified with 1.0 N HCl to pH=1 and was extracted with EtOAc. The organic layer was washed with water, dried over anhydrous MgSO$_4$, and filtered. The filtrate was evaporated and dried in vacuo to afford the title compound as a yellow solid (0.11 g, 60%): ESHRMS m/z 326.9438 (M−H, $C_{11}H_4O_4F_3Cl_2$, Calc'd 326.9433). $^1$H NMR (acetone-d$_6$/400 MHz) 7.82 (s, 1H), 7.46(s, 1H), 6.00 (q, 1H, J=7.0 Hz).

EXAMPLE 1b

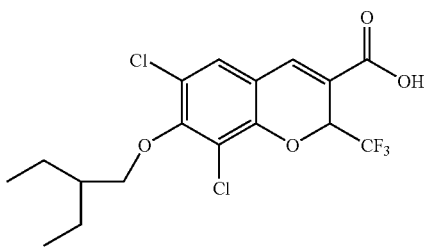

6,8-dichloro-7-(2-ethylbutoxy)-2-(trifluoromethyl)-2H-chromene-3-carboxylic acid

Step 1. Preparation of ethyl 7-(2-ethylbutoxy)-2-(trifluoromethyl)-2H-chromene-3-carboxylate The polymer bound PPh$_3$ was suspended in THF for 15 min. Ethyl 7-hydroxy-2-(trifluoromethyl)-2H-chromene-3-carboxylate from Example 1a, Step 1 (2.0 g, 6.94 mmole) and 2-ethyl-1-butanol (1.3 mL, 10.35 mmole) were added to above slurry and the mixture was stirred at r.t. for 15 min. Ethyl azodicarboxylate (1.6 mL, 10.35 mmole) was added to above mixture dropwise and the mixture was stirred at room temperature overnight. LCMS indicated product formation and that there was a trace amount of starting material present. The polymer was filtered off through celite pad and the pad was washed with ether. The filtrate was concentrated and the product mixture was suspended in hexane. The suspension was filtered and the filtrate was evaporated and dried in vacuo to afford yellow oil, (2.37 g, 92%): LCMS m/z 394.95 (M+Na). This ester was of suitable purity to use without further purification.

Step 2. Preparation of ethyl 6,8-dichloro-7-(2-ethylbutoxy)-2-(trifluoromethyl)-2H-chromene-3-carboxylate Sodium acetate (1.0 g, 12.1mmole) was added to a solution of the ester from Step 1 (1.2 g, 3.2 mmole) in acetic acid (40 mL). $Cl_2$ (gas) was bubbled into the above solution until a precipitate was seen. The mixture was stirred for 2 hours. After $Cl_2$ (gas) was blown away, Zn powder(5 eq) was added to the mixture and stirred for 30 min. The Zn salts were removed by filtration and the filtrate was evaporated to dry. The residue was purified by flash chromatography with 10% ethyl acetate in hexane to give a clear oil (0.77 g, 49%) containing a mixture of the di-chloro compound (84%) and a mono-chloro (16%)compound by NMR. This ester mixture was of suitable purity to use without further purification.

Step 3. Preparation of 6,8-dichloro-7-(2-ethylbutoxy)-2-(trifluoromethyl)-2H-chromene-3-carboxylic acid The ester from Step 2 (0.75 g, 1.70 mmole) was dissolved in 4 mL methanol and 4 mL THF. Sodium hydroxide (2.5 N) (1.6 mL, 4 mmole) was added to above solution and the solution was stirred at room temperature for 5 hour. The reaction mixture was acidified with 1.5 N HCl to pH=1. The compound was extracted with EtOAc. The organic layer was washed with water and dried over anhydrous MgSO$_4$ and filtered. The filtrate was evaporated and dried in vacuo to afford a crude yellow solid (0.6 g, 85%). This solid was purified by RPHPLC to give the title compound as a white solid (0.16 g, 28.4%): ESHRMS m/z411.0343 (M−H, $C_{17}H_{16}O_4F_3Cl_2$, Calc'd 411.0372). $^1$H NMR (acetone-d$_6$/400 MHz) 7.89(s, 1H),7.62(s, 1H),5.98(q, 1H, J=7.0 Hz), 4.01 (d, 1H, J=5.6 Hz), 1.71 (m, 1H), 1.61 (m, 2H), 1.53 (m, 2H), 0.971 (t, 6H, J=7.2 Hz).

EXAMPLE 1c

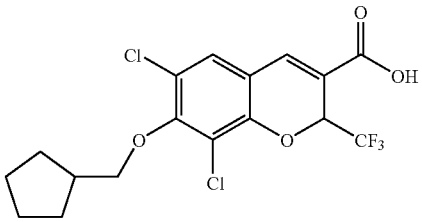

6,8-dichloro-7-(cyclopentylmethoxy)-2-(trifluoromethyl)-2H-chromene-3-carboxylic acid The 6,8-dichloro-7-(cyclopentylmethoxy)-2-(trifluoromethyl)-2H-chromene-3-carboxylic acid was prepared by a procedure similar to the method described in Example 1b using ethyl 7-hydroxy-2-(trifluoromethyl)-2H-chromene-3-carboxylate from Example 1a, Step 1 as the starting material: ESHRMS m/z 409.0187 (M−H, $C_{17}H_{14}O_4F_3Cl_2$, Calc'd 409.0216). $^1$H NMR (acetone-d$_{6b}$/400 MHz) 7.87 (s, 1H), 7.60 (s, 1H), 5.98 (q, 1H, J=7.0 Hz), 3.96 (d, 1H, J=5.6 Hz), 2.45 (m, 1H), 1.85 (m, 2H), 1. (m, 2H), 1.84 (m, 3H), 1.57 (m, 3H).

EXAMPLE 1d

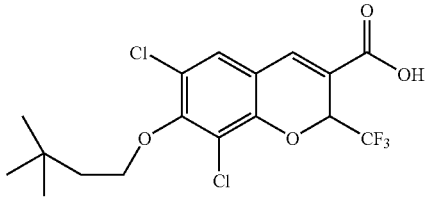

6,8-dichloro-7-(3,3-di methylbutoxy)-2-(trifluoromethyl)-2H-chromene-3-carboxylic acid The 6,8-dichloro-7-(3,3-dimethylbutoxy)-2-(trifluoromethyl)-2H-chromene-3-carboxylic acid was prepared by a procedure similar to the method described in Example 1b using ethyl 7-hydroxy-2-(trifluoromethyl)-2H-chromene-3-carboxylate from Example 1a, Step 1 as the starting material: ESHRMS m/z 411.0414 (M–H, $C_{17}H_{16}O_4F_3Cl_2$, Calc'd 411.0372). $^1$H NMR (acetone-$d_6$/400 MHz) 7.92 (s, 1H), 7.66 (s, 1H), 6.13 (q, 1H, J=7.0 Hz), 4.19 (t, 1H, J=5.6 Hz), 1.89 (t, 2H), 1.05 (s, 9H).

EXAMPLE 1e

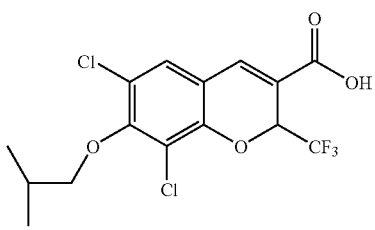

6,8-dichloro-7-isobutoxy-2-(trifluoromethyl)-2H-chromene-3-carboxylic acid

The 6,8-dichloro-7-isobutoxy-2-(trifluoromethyl)-2H-chromene-3-carboxylic acid was prepared by a procedure similar to the method described in Example 1-b using ethyl 7-hydroxy-2-(trifluoromethyl)-2H-chromene-3-carboxylate from Example 1a, Step 1 as the starting material: ESHRMS m/z 383.0016 (M–H, $C_{15}H_{12}O_4F_3Cl_2$, Calc'd 383.0059). $^1$H NMR (acetone-$d_6$/400 MHz) 7.87 (s, 1H), 7.60 (s, 1H), 5.97 (q, 1H, J=7.2 Hz), 3.86 (d, 1H, J=6.4 Hz), 2.15 (m, 1H), 1.07 (d, 6H, J=6.4 Hz).

EXAMPLE 1f

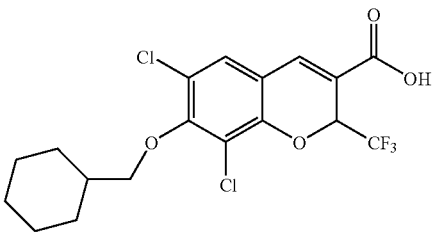

6,8-dichloro-7-(cyclohexylmethoxy)-2-(trifluoromethyl)-2H-chromene-3-carboxylic acid The 6,8-dichloro-7-(cyclohexylmethoxy)-2-(trifluoromethyl)-2H-chromene-3-carboxylic acid was prepared by a procedure similar to the method described in Example 1b using ethyl 7-hydroxy-2-(trifluoromethyl)-2H-chromene-3-carboxylate from Example 1a, Step 1 as the starting material: ESHRMS m/z 423.0324 (M–H, $C_{18}H_{16}O_4F_3Cl_2$, Calc'd 423.0372). $^1$H NMR (acetone-$d_6$/400 MHz) 7.89 (s, 1H), 7.61 (s, 1H), 5.98 (q, 1H, J=7.0 Hz), 3.88 (d, 2H, J=5.6 Hz), 1.77 (m, 3H), 1.68 (m, 3H), 1.29 (m, 2H), 1.22 (m, 3H).

EXAMPLE 1g

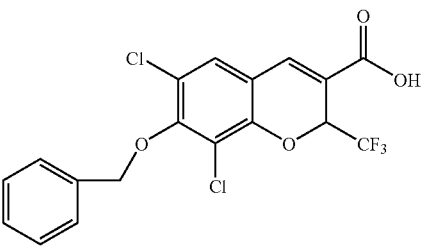

7-(benzyloxy)-6,8-dichloro-2-(trifluoromethyl)-2H-chromene-3-carboxylic acid

The 7-(benzyloxy)-6,8-dichloro-2-(trifluoromethyl)-2H-chromene-3-carboxylic acid was prepared by a procedure similar to the method described in Example 1b using ethyl 7-hydroxy-2-(trifluoromethyl)-2H-chromene-3-carboxylate from Example 1a, Step 1 as the starting material: ESHRMS m/z 416.9899 (M–H, $C_{18}H_{10}O_4F_3Cl_2$, Calc'd 416.9903). $^1$H NMR (acetone-$d_6$/400 MHz) 7.90 (s, 1H), 7.64 (s, 1H), 7.57 (m, 2H), 7.40 (m, 3H), 5.99 (q, 1H, J=7.0 Hz), 5.14 (s, 2H).

EXAMPLE 1h

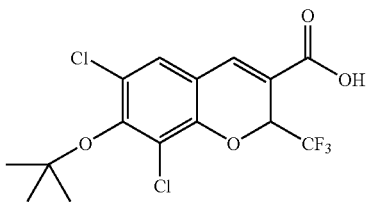

7-tert-butoxy-6,8-dichloro-2-(trifluoromethyl)-2H-chromene-3-carboxylic acid

Step 1. Preparation of ethyl 7-tert-butoxy-2-(trifluoromethyl)-2H-chromene-3-carboxylate Ethyl 7-hydroxy-2-(trifluoromethyl)-2H-chromene-3-carboxylate from Example 1a, Step 1 (2.0 g, 6.94 mmole) was treated with t-butyl trichloroacetaimidate in cyclohexane at room temperature. After addition of a catalytic amount of boron trifluoride etherate (139 uL), the mixture (orange solid precipitated) was stirred at room temperature overnight. Solid sodium bicarbonate (2.33 g, 27.76 mmole) was added into the mixture. The mixture was passed through the silica plug and was washed with 6% ethyl acetate in hexane. The filtrate containing the product was evaporated to give yellow oil (1.34 g, 56%) having >90% purity: LCMS m/z 367.00 (M+Na). $^1$H NMR (CDCl$_3$/400 MHz) 7.70 (s, 1H), 7.12 (m, 1H), 6.63 (s, 1H), 6.61 (m, 1H), 5.68 (q, 1H, J=7.2 Hz), 4.30 (q, 2H, J=7.2 Hz), 1.33 (t, 3H, J=7.2 Hz). This ester was of suitable purity to use without further purification.

Step 2. Preparation of ethyl 7-tert-butoxy-6,8-dichloro-2-(trifluoromethyl)-2H-chromene-3-carboxylate Sodium acetate (0.71 g, 8.72 mmole) was added to a solution of the ester from Step 1 (0.60 g, 1.74 mmole) in acetic acid (30 mL). Cl$_2$ (gas) was bubbled into the above solution until a precipitate formed. The mixture was stirred for 2 hours. After Cl$_2$ (gas) was blown away, Zn powder (5 eq) was added to the mixture and stirred for 15 min. The Zn salts were removed by filtration and the filtrate was evaporated to dryness. The residue was purified by Biotage silica chromatography with 10% ethyl acetate in hexane to give clear oil (0.12 g) as a mixture of mono and di-chloro products, some of which possessed no tert-butyl group.

Step 3. Preparation of 7-tert-butoxy-6,8-dichloro-2-(trifluoromethyl)-2H-chromene-3-carboxylic acid The mono and di-chloro ester from Step 2 (0.11 g, 0.28 mmole) was dissolved in 0.75 mL methanol and 0.75 mL THF. Sodium hydroxide (2.5 N) (0.3 mL, 0.75 mmole) was added to above solution and stirred at room temperature overnight. The reaction mixture was acidified with 1.5 N HCl to pH =2. The compound was extracted out with EtOAc. The organic layer was washed with water and dried over anhydrous MgSO$_4$. The filtrate was evaporated and dried in vacuo to afford a yellow solid. The mixture was purified by RPHPLC to give the desired 6,8-dichloro product as awhite solid (29 mg, ca. 28 % yield). ESHRMS m/z383.0082 (M−H, C$_{15}$H$_{26}$O$_4$F$_3$Cl$_2$, Calc'd 383.0059). $^1$H NMR (acetone-d$_6$/400 MHz) 7.88 (s, 1H), 7.60 (s, 1H), 5.97 (q, 1H, J=6.8 Hz), 1.51 (s, 9H). In addition the 6-monochloro product was obtained as a white solid 29 mg (ca. 28% yield):

EXAMPLE 2a

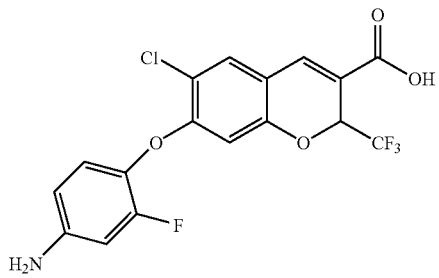

7-(4-amino-2-fluorophenoxy)-6-chloro-2-(trifluoromethyl)-2H-chromene-3-carboxylic acid Step 1. Preparation of ethyl 7-(2-fluoro-4-nitrophenoxy)-2-(trifluoromethyl)-2H-chromene-3-carboxylate Ethyl 7-hydroxy-2-(trifluoromethyl)-2H-chromene-3-carboxylate from Example 1a, Step 1 (0.50 g, 1.73 mmole), 1,2-difluoro-4-nitrobenzene (0.30 g, 1.91 mmole), and cesium carbonate (0.62 g, 1.91 mmole) were mixed in DMF (2 mL). Copper (I) trifluoromethanesulfonate benzene complex (5 mg) was added to above mixture. The mixture was heated to 90° C. for 6 hour. LCMS indicated product formation and there was no starting material present. The reaction was quenched with sodium bicarbonate (sat.) and extracted with ethyl acetate. The organic layer was washed with brine and dried over anhydrous MgSO$_4$. The filtrate was evaporated and dried in vacuo to afford a brown oil, which was purified by Biotage silica chromatography with 20% ethyl acetate in hexane to provide a light yellow oil (0.62 g, 84%): LCMS m/z 449.65 (M+Na). $^1$NMR (CDCl$_3$/400 MHz) 8.05 (m, 2H), 7.70 (s, 1H), 7.24 (m, 1H), 7.17 (dd, 1H, J=8.8, 8 Hz), 6.66 (m, 1H), 6 65 (s, 1H), 5.69 (q, 1H, J=6.8 Hz), 4.30 (q, 2H, J=7.2 Hz), 1.33 (t, 3H, J=7.2 Hz).

Step 2. Preparation of ethyl 7-(4-amino-2-fluorophenoxy)-6-chloro-2-(trifluoromethyl)-2H-chromene-3-carboxylate A solution of the ester from Step 1 (0.5 g, 1.17 mmole) in acetic acid was stirred at 10° C. The pre-prepared solution of Cl$_2$ (gas) in acetic acid (10 mL, 4.0 mmole was added to the above solution. The mixture was stirred for 2 hour. After Cl$_2$ (gas) was blown away, Zn powder (5 eq) was added to the mixture and stirred for 30 min. The Zn salts were removed by filtration and the filtrate was evaporated to dryness. The residue was purified by normal phase silica chromatography with 20% ethyl acetate in hexane to give the ester as a yellow oil, which solidified upon standing (0.43 g, 85%): LCMS m/z 431.75 (M+H). $^1$NMR (CDCl$_3$/400 MHz) 7.61 (s, 1H), 7.27 (s, 1H), 6.95 (dd, 1H, J=8.4 Hz), 6.50 (dd, 1H, J=12, 2.4 Hz ), 6.42 (m, 1H), 5.61 (q, 1H, J=6.8 Hz), 4.30 (q, 2H, J=7.2 Hz), 1.33 (t, 3H, J=7.2 Hz).

Step 3. Preparation of 7-(4-amino-2-fluorophenoxy)-6-chloro-2-(trifluoromethyl)-2H-chromene-3-carboxylic acid The ester from Step 2 (0.10 g, 0.23 mmole) was dissolved in 0.5 mL methanol and 0.5 mL THF. Sodium hydroxide (2.5

N) (0.2 mL, 0.46 mmole) was added to above solution and stirred at room temperature for overnight. The reaction mixture was acidified with 0.5 N HCl. The compound was extracted out with EtOAc. The organic layer was washed with water and dried over anhydrous $MgSO_4$. The filtrate was evaporated and dried in vacuo to afford the title compound as a yellow solid (0.07 g, 75%): LCMS m/z 402.85 (M+H). $^1$H NMR (acetone-$d_6$/400 MHz) 7.89 (s, 1H), 7.73 (s, 1H), 7.67 (dd, 1H, J=10.8, 2.4 Hz), 7.53 (dd, 1H, J=10, 1.6 Hz), 7.47 (m, 1H), 5.81 (q, 1H, J=7.0 Hz).

EXAMPLE 2b

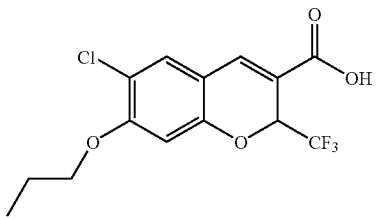

6-chloro-7-propoxy-2-(trifluoromethyl)-2H-chromene-3-carboxylic acid

Step 1. Preparation of ethyl 7-propoxy-2-(trifluoromethyl)-2H-chromene-3-carboxylate The ethyl 7-propoxy-2-(trifluoromethyl)-2H-chromene-3-carboxylate was prepared by a procedure similar to the method described in Example 1b, Step 1 using ethyl 7-hydroxy-2-(trifluoromethyl)-2H-chromene-3-carboxylate from Example 1a, Step 1 as the starting material. LCMS m/z 331.05 (M+H). This ester was of suitable purity to use without further purification.

Step 2. Preparation of ethyl 6-chloro-7-propoxy-2-(trifluoromethyl)-2H-chromene-3-carboxylate The ester from Step 1 (0.4 g, 1.2 mmole) in acetic acid (10 mL) was treated with $Cl_2$ (gas) in HOAc solution (Preprepared 0.5 M) (7.3 ml, 3.6 mmole). The mixture was stirred for 3 hours. After $Cl_2$ (gas) was blown away, Zn powder (3 eq) was added to the mixture and stirred for 30 min. The Zn salts were removed by filtration and the filtrate was evaporated to dryness. The residue was purified by flash chromatography with 10% ethyl acetate in hexane to give clear oil (0.33 g, 69%). This ester was of suitable purity to use without further purification.

Step 3. Preparation of 6-chloro-7-propoxy-2-(trifluoromethyl)-2H-chromene-3-carboxylic acid The 6-chloro-7-propoxy-2-(trifluoromethyl)-2H-chromene-3-carboxylic acid was prepared by a procedure similar to the method described in Example 2a, step 3: ESHRMS m/z335.0334 (M−H, $C_{14}H_{11}O_4F_3Cl$, Calc'd 335.0292). $^1$H NMR (acetone-$d_6$/400 MHz) 7.81 (s, 1H), 7.51 (s, 1H), 6.78 (s, 1H), 5.80 (q, 1H, J=7.0 Hz), 4.10 (m, 2H), 1.85 (m, 2H), 1.05 (q, 3H, J=7.0 Hz).

EXAMPLE 2c

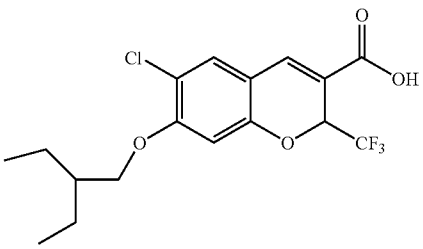

6-chloro-7-(2-ethylbutoxy)-2-(trifluoromethyl)-2H-chromene-3-carboxylic acid

The 6-chloro-7-(2-ethylbutoxy)-2-(trifluoromethyl)-2H-chromene-3-carboxylic acid was prepared by a procedure similar to the method described in Example 1b using ethyl 7-hydroxy-2-(trifluoromethyl)-2H-chromene-3-carboxylate from Example 1a, Step 1 as the starting material: ESHRMS m/z 423.0585 (M−H+2Na, $C_{17}H_{17}O_4F_3ClNa_2$, Calc'd 423.0557). $^1$H NMR (acetone-$d_6$/400 MHz) 7.83 (s, 1H), 7.53 (s, 1H), 6.84 (s, 1H), 5.79 (q, 1H, J=7.2 Hz), 4.08 (m, 2H), 1.72 (m, 1H), 1.53 (m, 4H), 0.95 (t, 6H, J=6.8 Hz).

EXAMPLE 2d

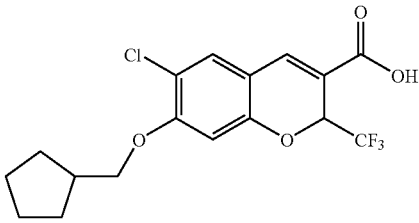

6-chloro-7-(cyclopentylmethoxy)-2-(trifluoromethyl)-2H-chromene-3-carboxylic acid The 6-chloro-7-(cyclopentylmethoxy)-2-(trifluoromethyl)-2H-chromene-3-carboxylic acid was prepared by a procedure similar to the method described in Example 1c using ethyl 7-hydroxy-2-(trifluoromethyl)-2H-chromene-3-carboxylate from Example 1a, (q, 1H, J=7.2 Hz), 4.08 (d, 2H, J=6.8 Hz), 2.42(m, 1H), 1.67 (m, 2H), (m, 2H), 1.47(m, 2H).

EXAMPLE 2e

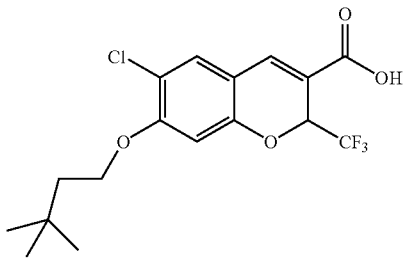

6-chloro-7-(3,3-dimethylbutoxy)-2-(trifluoromethyl)-2H-chromene-3-carboxylic acid The 6-chloro-7-(3,3-dimethylbutoxy)-2-(trifluoromethyl)-2H-chromene-3-carboxylic acid was prepared by a procedure similar to the method described in Example 1d using ethyl 7-hydroxy-2-(trifluoromethyl)-2H-chromene-3-carboxylate from Example 1a, Step 1 as the starting material: ESHRMS m/z 377.0750 (M–H, $C_{17}H_{17}O_4F_3Cl$, Calc'd 377.0762). $^1$H NMR(acetone-$d_6$/400 MHz) 7.87 (s, 1H), 7.59 (s, 1H), 6.92 (s, 1H), 5.88 (q, 1H, J=7.0 Hz), 4.24 (t, 1H, J=5.6 Hz), 4.30 (m, 2H), 1.89 (t, 2H), 1.05 (s, 9H).

EXAMPLE 2f

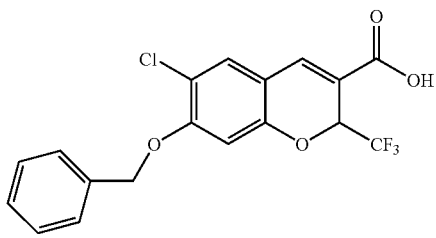

7-(benzyloxy)-6-chloro-2-(trifluoromethyl)-2H-chromene-3-carboxylic acid

The 7-(benzyloxy)-6-chloro-2- (trifluoromethyl)-2H-chromene-3-carboxylic acid was prepared by a procedure similar to the method described in Example 1g using ethyl 7-hydroxy-2-(trifluoromethyl)-2H-chromene-3-carboxylate from Example 1a, Step 1 as the starting material: ESHRMS m/z383.0277 (M–H, $C_{18}H_{11}O_4F_3Cl$, Calc'd 383.0292). $^1$H NMR (acetone-$d_6$/400 MHz) 7.89 (s, 1H), 7.62 (s, 1H), 7.58 (m, 2H), 7.46 (m, 3H), 6.98 (s, 1H), 5.87 (q, 1H, J=7.0 Hz), 5.37 (s, 2H).

EXAMPLE 2g

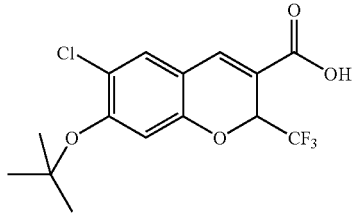

7-tert-butoxy-6-chloro-2-(trifluoromethyl)-2H-chromene-3-carboxylic acid

The 7-tert-butoxy-6-chloro-2-(trifluoromethyl)-2H-chromene-3-carboxylic acid was prepared by a procedure similar to the method described in Example 1h using ethyl 7-hydroxy-2-(trifluoromethyl)-2H-chromene-3-carboxylate from Example 1a, Step 1 as the starting material: ESHRMS m/z 349.0480 (M–H, $C_{15}H_{13}O_4F_3Cl$, Calc'd 349.0449). $^1$H NMR (acetone-$d_6$/400 MHz) 7.84 (s, 1H), 7.56 (s, 1H), 6.89 (s, 1H), 5.80 (q, 1H, J=6.8 Hz), 1.46 (s, 9H).

EXAMPLE 2h

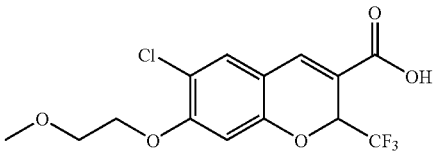

6-chloro-7-(2-methoxyethoxy)-2-(trifluoromethyl)-2H-chromene-3-carboxylic acid

Step 1. Preparation of ethyl 7-(2-methoxyethoxy)-2-(trifluoromethyl)-2H-chromene-3-carboxylate The methyl 7-(2-methoxyethoxy)-2-(trifluoromethyl)-2H-chromene-3-carboxylate was prepared by a procedure similar to the method described in Example 1b, Step 1 using ethyl 7-hydroxy-2-(trifluoromethyl)-2H-chromene-3-carboxylate from Example 1a, Step 1 as the starting material. The residue was purified by flash chromatography (silica gel with 10-30% ethyl acetate in hexane to give clear oil (2.0 g, 83%): LCMS m/z 333.10 (M+H). This ester was of suitable purity to use without further purification.

Step 2. Preparation of ethyl 6-chloro-7-(2-methoxyethoxy)-2-(trifluoromethyl)-2H-chromene-3-carboxylate The ester from step 1 (1.0 g, 3.0 mmole) in acetic acid (100 mL) was treated with $Cl_2$ (gas) in HOAc solution (Pre-prepared 0.5 M) (8.0 ml, 4.0 mmol). The mixture was stirred for 18 hours. After $Cl_2$ (gas) was blown away, Zn powder (3 eq) was added to the mixture and stirred for 30 min. The Zn salts were removed and the filtrate was evaporated to dryness. The residue was purified by flash chromatography (silica gel) with 10-15% ethyl acetate in hexane to give a white solid (0.82 g, 75%): LCMS m/z 367.00 (M+H). This ester was of suitable purity to use without further purification.

Step 3. Preparation of 6-chloro-7-(2-methoxyethoxy)-2-(trifluoromethyl)-2H-chromene-3-carboxylic acid The 6-chloro-7-(2-methoxyethoxy)-2-(trifluoromethyl)-2H-chromene-3-carboxylic acid was prepared by a procedure similar to the method described in Example 2a, Step 3: ESHRMS m/z 351.0280 (M−H, $C_{14}H_{11}O_5F_3Cl$, Calc'd 351.0242). $^1$H NMR ($CDCl_3$/300 MHz) 7.73 (s, 1H), 7.25 (s, 1H), 6.60 (s, 1H), 5.65 (q, 1H, J=7.0 Hz), 4.20 (m, 2H), 3.82 (m, 2H), 3.48 (s, 3H).

EXAMPLE 2i

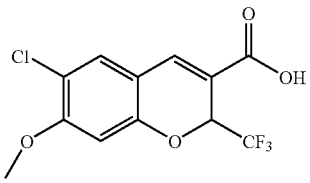

6-chloro-7-methoxy-2-(trifluoromethyl)-2H-chromene-3-carboxylic acid

Step 1. Preparation of ethyl 7-methoxy-2-(trifluoromethyl)-2H-chromene-3-carboxylate A mixture of 2-hydroxy-4-methoxybenzaldehyde (50.1 g, 329 mmole), ethyl 444-trifluorocrotonate (58.7 mL, 394 mmole) and $K_2CO_3$ (49.9 g, 0.361 mmole) in DMF (155 mL) was stirred 80° C. under a $N_2$ atmosphere for 2 h. $H_2O$ was added and the mixture was extracted with EtOAc. The crude product was purified by filtration through a plug of silica gel and recrystallized to give the product as a yellow crystalline solid: EIHRMS m/z 302.0748 (M+, $C_{14}H_{13}ClF_3O_4$, Calc'd 302.0766).

Step 2. Preparation of ethyl 6-chloro-7-methoxy-2-(trifluoromethyl)-2H-chromene-3-carboxylate To a solution of the ester prepared as in Step 1 (5.04 g, 16.7 mmole) in glacial acetic acid was added slowly $Cl_2$ gas for 3 minutes. After standing for 8 minutes, powdered zinc (2.25 g, 34.4 mmole) was added with the mixture becoming slightly warm. The mixture was stirred until GCMS shows that polychlorinated byproducts were removed. $H_2O$ was added and the mixture was extracted with EtOAc. The extract was washed with aqueous $NaHCO_3$, $H_2O$, aqueous $NH_4Cl$, dried and concentrated in vacuo. The crude product was purified by silica chromatography (9:1 hexanes:EtOAc) to give the product as an impure mixture that was carried on without further purification: EIHRMS m/z 336.0376 (M+, $C_{14}H_{12}ClF_3O_4$, Calc'd 336.0376).

Step 3. Preparation of 6-chloro-7-methoxy-2-(trifluoromethyl)-2H-chromene-3-carboxylic acid The ester from Step 2 (4 g, 12 mmole) was dissolved in a mixture of $THF:MeOH:H_2O$ and $LiOH.H_2O$ (4 g, 95 mmole) was added and the mixture was stirred for 2 h at room temperature and then concentrated in vacuo. The mixture was acidified with 10% HCl and extracted with EtOAc. The EtOAc layer was washed twice with $H_2O$, aqueous $NH_4Cl$ solution, dried over $Na_2SO_4$ concentrated in vacuo and to give 1.3 g (36% yield) of the product: $^1$H NMR ($CDCl_3$/300 MHz) 7.48 (s, 1), 7.09 (s, 1H), 6.47 (s, 1H), 5.56 (q, 1H, J=6.9 Hz), 3.79 (s, 3H); ESHRMS m/z 307.0012 (M−H, $C_{12}H_7ClF_3O_4$, Calc'd 306.9985).

EXAMPLE 3a

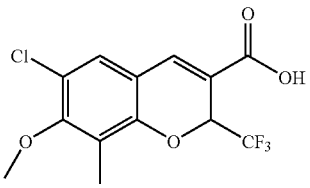

6-chloro-7-methoxy-8-methyl-2-(trifluoromethyl)-2H-chromene-3-carboxylic acid

Step 1. Preparation of 2-hydroxy-4-methoxy-3-methylbenzaldehyde

A mixture of 2,4-dimethoxy 3-methyl benzaldehyde (3.75 g, 20.8 mmole) and beryllium chloride (5.0 g, 62.5 mmole) in anhydrous toluene (50 mL) was heated to reflux for 3.5 hour. The solvent was evaporated under reduced pressure to yield an orange residue, which was treated with 2 N HCl. The compound was extracted with methylene chloride and the organic layer was dried over anhydrous $MgSO_4$. The filtrate was evaporated and dried in vacuo to give an orange solid (3.4 g, 99%): LCMS m/z 168.05 (M+H). $^1$H NMR ($CDCl_3$/300 MHz) 11.45 (s, 1H), 9.72 (s, 1H), 7.37 (d, 1H, J=8.7 Hz), 6.57 (d, 1H, J=8.7 Hz), 3.92 (s, 3H), 2.10 (s, 3H).

Step 2. Preparation of ethyl 7-methoxy-8-methyl-2-(trifluoromethyl)-2H-chromene-3-carboxylate A mixture of benzaldehyde from Step 1 (3.0 g, 18.07 mmole) and ethyl 4,4,4-trifluorocrotonate (4.5 g, 27.11 mmole) was dissolved in anhydrous DMF (20 mL), warmed to 60° C. and treated with anhydrous $K_2CO_3$ (4.99 g, 36.14 mmole). The solution was maintained at 90° C. for 24 hours. LCMS analysis indicated that the reaction was complete. After the reaction was cooled to room temperature, the solution was extracted with ethyl acetate. The combined extracts were washed with brine, dried over anhydrous $MgSO_4$, filtered and concentrated in vacuo to afford brown solid, that was dissolved in MeOH (40 mL) and was precipitated upon adding 13 mL water. The suspension was filtered and dried on vacuum yielding a light brown solid: (4.37 g, 76.6%): LCMS m/z339.10 (M+Na). $^1$H NMR ($CDCl_3$/400 MHz) 7.68 (s, 1H), 7.03(d, 1H, J=8.7 Hz), 6.50 (d, 1H, J=8.7 Hz), 5.70 (q, 1H, J=6 Hz), 4.29 (q, 2H, J=7.2 Hz), 3.84 (s, 3H), 2.09(s, 3H), 1.33 (t, 3H, J=7.2 Hz).

Step 3. Preparation of ethyl 6-chloro-7-methoxy-8-methyl-2-(trifluoromethyl)-2H-chromene-3-carboxylate Sodium acetate (0.65 g, 7.9 mmole) was added to a solution of the ester from Step 2 (0.50 g, 1.58 mmole) in acetic acid (30 mL). Cl$_2$ (gas) was bubbled into the above solution until a precipitate was noted. The mixture was stirred for 0.5 hour. After Cl$_2$ (gas) was blown away, Zn powder (5 eq) was added to the mixture and stirred for 30 min. The Zn salts were removed by filtration and the filtrate was evaporated to dryness to give a brown oil (0.54 g, 97%): $^1$H NMR (CDCl$_3$/300 MHz) 7.64 (s, 1H), 7.13(s, 1H), 5.75 (q, 1H, J=6 Hz), 4.33 (q, 2H, J=7.2 Hz), 3.86 (s, 3H), 2.22(s, 3H), 1.37 (t, 3H, J=7.2 Hz).

Step 4. Preparation of 6-chloro-7-methoxy-8-methyl-2-(trifluoromethyl)-2H-chromene-3-carboxylic acid The ester from Step 3 (0.50 g, 1.43 mmole) was dissolved in 3.5 mL methanol and 4 mL THF. Sodium hydroxide (2.5 N) (1.7 mL, 4.28 mmole) was added to above solution and stirred at room temperature overnight. The reaction mixture was acidified with 1.5 N HCl. The compound was extracted with EtOAc. The organic layer was washed with water, dried over anhydrous MgSO$_4$, and filtered. The filtrate was evaporated and dried in vacuo to afford a light brown solid (0.4 g, 87%), which contained about 20% of the 6-mono-Cl compound. The mixture was purified by RPHPLC to give the title compound as a white solid (0.16 g, 28.4%): ESHRMS m/z321.0129 (M–H, C$_{13}$H$_9$O$_4$F$_3$Cl, Calc'd 321.0136). $^1$H NMR (acetone-d$_6$/400 MHz) 7.83 (s, 1H), 7.43 (s, 1H), 5.85 (q, 1H, J=7.0 Hz), 3.83 (s, 3H), 2.18 (s, 3H).

EXAMPLE 3b

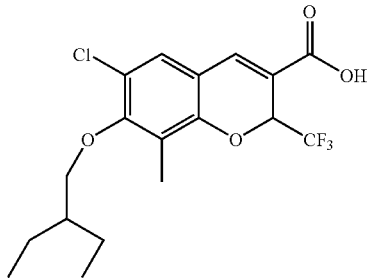

6-chloro-7-(2-ethylbutoxy)-8-methyl-2-(trifluoromethyl)-2H-chromene-3-carboxylic acid

Step 1. Preparation of methyl 7-hydroxy-8-methyl-2-(trifluoromethyl)-2H-chromene-3-carboxylate The ethyl 7-methoxy-8-methyl-2-(trifluoromethyl)-2H-chromene-3-carboxylate from Example 3a, Step 2 (3.0 g, 9.49 mmole) was dissolved in methylene chloride (120 mL). The solution was chilled to −78° C. and BBr$_3$ (94.9 mL, 1 M solution in CH$_2$Cl$_2$) was added slowly to the above solution. The reaction was slowly warmed to room temperature and stirred overnight. The reaction was cooled to −78° C. and MeOH (30 mL) added in. After the solution was stirred at room temperature for 2 h, the reaction was evaporated to dryness to give a brownish solid having ca.90% purity. The crude product was further purified by passing through a silica plug to give a yellow solid (2.7 g, 80%): LCMS m/z 311.05 (M+Na). $^1$H NMR (acetone-d$_6$/400 MHz) 9.11 (s, 1H), 7.75 (s, 1H), 7.11(d, 1H, J=8.4 Hz), 6.59 (d, 1H, J=8.4 Hz), 5.78 (q, 1H, J=6 Hz), 3.79 (s, 3H), 2.09(s, 3H).

Step 2. Preparation of methyl 7-(2-ethylbutoxy)-8-methyl-2-(trifluoromethyl)-2H-chromene-3-carboxylate Polymer bound PPh$_3$ was suspended in THF for 15 min. Methyl 7-hydroxy-8-methyl-2-(trifluoromethyl)-2H-chromene-3-carboxylate from Step 1 (1.5 g, 5.21 mmole) and 2-ethyl butanol (0.96 mL, 7.81 mmole) were added to the above slurry and stirred for 15 min. Ethyl azodicarboxylate (1.23 mL, 7.81 mmole) was added to above mixture dropwise and the mixture was stirred at room temperature overnight. LCMS indicated product formation and that there was no starting material present. The polymer was filtered off through celite pad and the pad was washed with ether. The filtrate was concentrated and the product mixture was suspended in hexane. The undissolved solid was removed by filtration and the filtrate was evaporated and dried in vacuo to afford yellow solid, (1.76 g, 98%): LCMS m/z395.15 (M+Na). $^1$H NMR (CDCl$_3$/400 MHz) 7.68 (s, 1H), 7.00 (d, 1H, J=8.4 Hz), 6.48 (d, 1H, J=8.4 Hz), 5.68 (q, 1H, J=7.2 Hz), 3.89 (m, 2H), 3.82 (s, 3H), 2.09 (s, 3H), 1.72 (m, 1H), 1.53 (m, 4H), 0.95 (m, 6H). This ester was of suitable purity to use without further purification.

Step 3. Preparation of methyl 6-chloro-7-(2-ethylbutoxy)-8-methyl-2-(trifluoromethyl)-2H-chromene-3-carboxylate Sodium acetate (2.1 g, 25.8 mmole) was added to a solution of the ester from Step 2 (1.2 g, 3.22 mmole) in acetic acid (100 mL). Cl$_2$ (gas) was bubbling to the above solution until see the precipitate. The mixture was stirred for. 1 hour. After Cl$_2$ (gas) was blown away, Zn (5 eq) was added to the mixture and stirred for 30 min. Zn salt was removed and the filtrate was evaporated to dryness. The residue was purified by Biotage silica chromatography with 10% ethyl acetate in hexane to give a clear oil (0.60 g, 49%): LCMS m/z407.15(M+H). $^1$H NMR (CDCl$_3$/400 MHz) 7.63 (s, 1H), 7.08 (s, 1H), 5.70 (q, 1H, J=7.2 Hz), 3.84 (s, 3H), 3.80 (m, 2H), 2.17 (s, 3H), 1.68 (m, 1H), 1.53 (m, 4H), 0.95 (m, 6H).

Step 4. Preparation of 6-chloro-7-(2-ethylbutoxy)-8-methyl-2-(trifluoromethyl)-2H-chromene-3-carboxylic acid The ester from Step 3 (0.55 g, 1.35 mmole) was dissolved in 3.5 mL methanol and 3.5 mL THF. Sodium hydroxide (2.5 N) (1.6 mL, 4 mmole) was added to above solution and stirred at room temperature overnight. The reaction mixture was acidified with 1.5 N HCl. The compound was extracted with EtOAc. The organic layer was washed with water and dried over anhydrous MgSO$_4$. The filtrate was evaporated and dried in vacuo, after recrystalization with EtOH and water to afford a yellow solid (0.31 g, 59%): ESHRMS m/z391.0884 (M–H, C$_{18}$H$_{19}$O$_4$F$_3$Cl, Calc'd 391.0918). $^1$H NMR (acetone-d$_6$/400 MHz) 7.84 (s, 1H), 7.45 (s, 1H), 5.88 (q, 1H, J=7.0 Hz), 3.92 (m, 2H), 2.17 (s, 3H), 1.71 (m, 1H), 1.61 (m, 2H), 1.53 (m, 2H), 0.971 (t, 6H, J=7.2 Hz).

EXAMPLE 3c

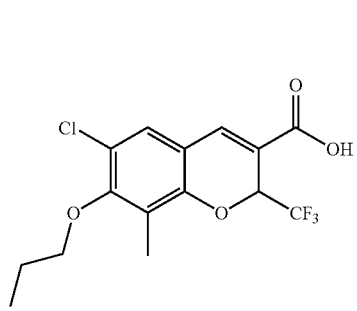

6-chloro-8-methyl-7-propoxy-2-(trifluoromethyl)-
2H-chromene-3-carboxylic acid

The 6-chloro-8-methyl-7-propoxy-2-(trifluoromethyl)-2H-chromene-3-carboxylic acid was prepared by the procedure similar to the method described in Example 3b: ESHRMS m/z 349.0447 (M–H, $C_{15}H_{13}O_4F_3Cl$ Calc'd 349.0449). $^1$H NMR (acetone-$d_6$/300 MHz) 7.85 (s, 1H), 7.45 (s, 1H), 5.88 (q,1H, J=7.0 Hz),3.92 (m, 2H), 2.21 (s,3H), 1.84 (m, 2H), 1.07 (t, 6H, J=7.2 Hz).

EXAMPLE 3d

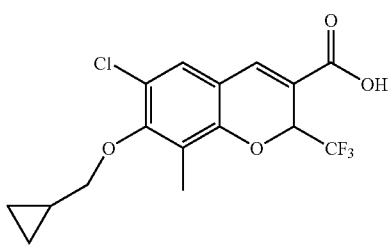

6-chloro-7-(cyclopropylmethoxy)-8-methyl-2-(trifluoromethyl)-2H-chromene-3-carboxylic acid The 6-chloro-7-(cyclopropylmethoxy)-8-methyl-2-(trifluoromethyl)-2H-chromene-3-carboxylic acid was prepared by the procedure similar to the method described in Example 3b. ESHRMS m/z361.0455 (M–H, $C_{16}H_{13}O_4F_3Cl$, Calc'd 361.0449). $^1$H NMR (acetone-$d_6$/300 MHz) 7.84 (s, 1H), 7.45 (s, 1H), 5.88 (q, 1H, J=7.0 Hz), 3.86 (m, 2H), 2.21 (s, 3H), 1.31 (m, 1H), 0.59 (m, 2H), 0.35 (m, 2H).

EXAMPLE 3e

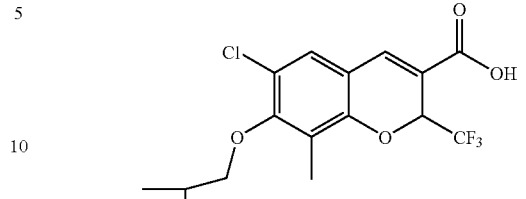

6-chloro-7-isobutoxy-8-methyl-2-(trifluoromethyl)-
2H-chromene-3-carboxylic acid The 6-chloro-7-isobutoxy-8-methyl-2-(trifluoromethyl)-2H-chromene-3-carboxylic acid was prepared by the procedure similar to the method described in Example 3b: ESHRMS m/z363.0636 (M–H, $C_{16}H_{15}O_4F_3Cl$, Calc'd 363.0605). $^1$H NMR (acetone-$d_6$/300 MHz) 7.84 (s, 1H), 7.45 (s, 1H), 5.88 (q, 1H, J=7.0 Hz), 3.75 (m, 2H), 2.21 (s, 3H), 2.13 (m, 1H), 1.08 (d, 6H, J=6.9 Hz).

EXAMPLE 3f

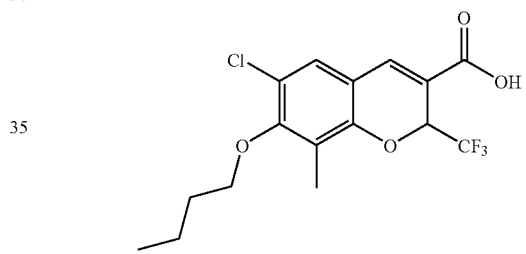

7-butoxy-6-chloro-8-methyl-2-(trifluoromethyl)-2H-
chromene-3-carboxylic acid

The 7-butoxy-6-chloro-8-methyl-2-(trifluoromethyl)-2H-chromene-3-carboxylic acid was prepared by the procedure similar to the method described in Example 3b: ESHRMS m/z363.0631 (M–H, $C_{16}H_{15}O_4F_3Cl$, Calc'd 363.0605). $^1$H NMR (acetone-$d_6$/300 MHz) 7.84 (s, 1H), 7.45 (s, 1H), 5.88 (q, 1H, J=7.0 Hz), 3.75 (m, 2H), 2.21 (s, 3H), 1.86 (m, 2H), 1.58 (m, 2H), 0.98 (t, 3H, J=7.2 Hz).

EXAMPLE 3g

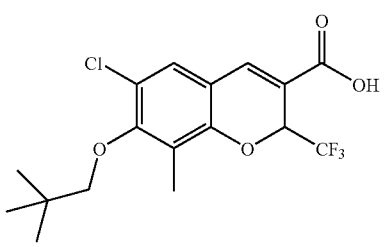

6-chloro-8-methyl-7-(neopentyloxy)-2-(trifluoromethyl)-2H-chromene-3-carboxylic acid The 6-chloro-8-methyl-7-(neopentyloxy)-2-(trifluoromethyl)-2H-chromene-3-carboxylic acid was prepared by the procedure similar to the method described in Example 3b: ESHRMS m/z 377.0758 (M–H, $C_{17}H_{17}O_4F_3Cl$, Calc'd 377.0762). $^1$H NMR (acetone-$d_6$/300 MHz) 7.84 (s, 1H), 7.45 (s, 1H), 5.88 (q, 1H, J=7.0 Hz), 3.65(d, 1H, J=8.3 Hz), 3.61 (d, 1H, J=8.3 Hz), 2.21 (s, 3H), 1.12 (s, 9H).

EXAMPLE 3h

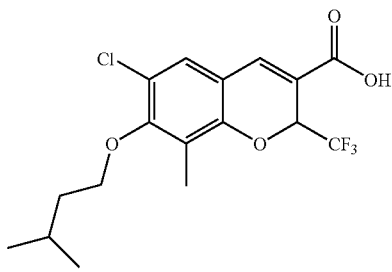

6-chloro-7-(isopentyloxy)-8-methyl-2-(trifluoromethyl)-2H-chromene-3-carboxylic acid The 6-chloro-7-(isopentyloxy)-8-methyl-2-(trifluoromethyl)-2H-chromene-3-carboxylic acid was prepared by the procedure similar to the method described in Example 3b: ESHRMS m/z 377.0765 (M–H, $C_{17}H_{17}O_4F_3Cl$, Calc'd 377.0762). $^1$H NMR (acetone-$d_6$/300 MHz) 7.84 (s, 1H), 7.45 (s, 1H), 5.88 (q, 1H, J=7.0 Hz), 3.62 (t, 2H, J=6.6 Hz), 2.21 (s, 3H), 1.96 (m, 1H), 1.75 (m, 2H), 1.12 (s, 6H, J=6.3 Hz).

EXAMPLE 3i

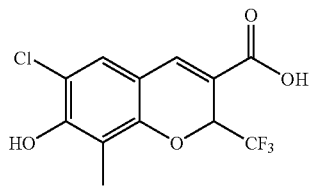

6-chloro-7-hydroxy-8-methyl-2-(trifluoromethyl)-2H-chromene-3-carboxylic acid

The 6-chloro-7-hydroxy-8-methyl-2-(trifluoromethyl)-2H-chromene-3-carboxylic acid was prepared by the procedure similar to the method described in Example 3b: ESHRMS m/z 306.9996 (M–H, $C_{12}H_7O_4F_3Cl$, Calc'd 306.9979). $^1$H NMR (acetone-$d_6$/300 MHz) 7.84 (s, 1H), 7.45 (s, 1H), 5.88 (q, 1H, J=7.0 Hz), 2.21 (s, 3H).

EXAMPLE 4a

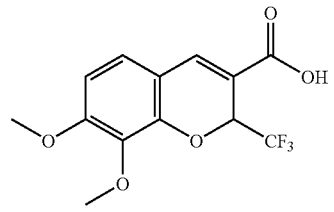

7,8-dimethoxy-2-(trifluoromethyl)-2H-chromene-3-carboxylic acid

Step 1. Preparation of ethyl 7,8-dimethoxy-2-(trifluoromethyl)-2H-chromene-3-carboxlate To a solution of 3,4-dimethoxysalicylaldehyde (5 g, 27 mmole) in DMF (50 mL) was added, potassium carbonate (3.79 g, 27.5 mmole) and ethyl 4,4,4-trifluorocrotonate (5.08 g, 30 mmole). The mixture was heated to 65° C. for 4 h. The reaction was cooled to room temperature, poured into $H_2O$ (150 mL), and extracted with ethyl acetate (2×150 mL). The combined organic phases were washed with aqueous $NaHCO_3$ solution (2×50 mL), aqueous 3 N HCl solution (2×50 mL), and brine (2×50 mL), dried over $Na_2SO_4$, filtered, and concentrated in vacuo producing the ethyl ester (6.3 g, 70%) as an amber oil. This ester was of suitable purity to use without further purification: 1HNMR (DMSO-$d_6$/400 MHz) 7.86 (s, 1H), 7.23 (d, 1H, J=8.6 Hz), 6.75 (d, 1H, J=8.6 Hz), 5.95 (q, 1H, J=7.1 Hz), 4.23 (m, 2H, J=3.4 Hz), 3.81 (s, 3H), 3.67 (s, 3H), 1.24 (t, 3H, J=7.1 Hz).

Step 2. 7,8-dimethoxy-2-(trifluoromethyl)-2H-chromene-3-carboxylic acid

To the ester (Step 1) was added THF(7):EtOH(2):$H_2O$ (1) followed by LiOH (1.5 eq) and heated to 40° C. for 4 h. The reaction was cooled to room temperature, concentrated in vacuo, acidified with HCl to pH 1, filtered solid and subjected solid to preparative reverse phase chromatography to produce the title compound (350 mg, 99%): ESHRMS m/z 303.0435 (M–H, $C_{13}H_{10}F_3O_5$, Calc'd 303.0475). $^1$H NMR (DMSO-$d_6$/400 MHz) 13.23 (s, 1H), 7.86 (s, 1H), 7.23 (d, 1H, J=8.6 Hz), 6.75 (d, 1H, J=8.6 Hz), 5.95 (q, 1H, J=7.1 Hz), 3.81 (s, 3H), 3.67 (s, 3H), 1.24.

EXAMPLE 4b

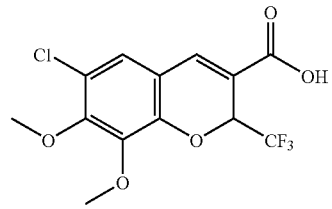

6-chloro-7,8-dimethoxy-2-(trifluoromethyl)-2H-chromene-3-carboxylic acid

Step 1. Preparation of ethyl 6-chloro-7,8-dimethoxy-2-(trifluoromethyl)-2H-chromene-3-carboxylate The ester Example 4a, Step 1 (365 mg, 1 mmole) was dissolved in acetic acid (25 mL). Chlorine gas was bubbled through this solution for 15 min. The solution was allowed to stand at room temperature for 30 minutes. The reaction was cooled to room temperature, poured into $H_2O$ (150 mL), and extracted with ethyl acetate (2×150 mL). The combined organic phases were washed with aqueous $NaHCO_3$ solution (2×50 mL), aqueous 3N HCl solution (2×50 mL), and brine (2×50 mL), dried over $Na_2SO_4$, filtered and concentrated in vacuo producing the ethyl ester (385 mg, 95%) as an amber oil. This ester was of suitable purity to use without further purification: ESLRMS m/z 367 (M+H).

Step 2. 7,8-dimethoxy-2-(trifluoromethyl)-2H-chromene-3-carboxylic

The ester (Step 1) was hydrolyzed to form the carboxylic acid via a method similar to that described in Example 4a, Step 2. (317 mg, 99%): ESHRMS m/z 337.0037 (M–H, $C_{13}H_9ClF_3O_5$, Calc'd 337.0055). $^1$HNMR (DMSO-$d_6$/400 MHz) 13.33 (brs, 1H), 7.79 (s, 1H), 7.44 (s, 1H), 6.00 (q, 1H, J=7.1 Hz), 3.80 (s, 3H), 3.70 (s, 3H).

EXAMPLE 5a

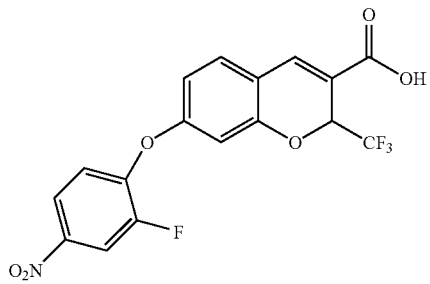

7-(2-fluoro-4-nitrophenoxy)-2-(trifluoromethyl)-2H-chromene-3-carboxylic acid

The 7-(2-fluoro-4-nitrophenoxy)-2-(trifluoromethyl)-2H-chromene-3-carboxylic acid was prepared by hydrolysis of ethyl 7-(2-fluoro-4-nitrophenoxy)-2-(trifluoromethyl)-2H-chromene-3-carboxylate from Example 2a, Step 1 using the procedure similar to the method described in Example 2a, Step 3: ESHRMS m/z 398.0242 (M–H, $C_{17}H_8F_4O_6N$, Calc'd 398.0282). $^1$H NMR (acetone-$d_6$/400 MHz) 8.20 (m, 1H), 8.16 (m, 1H), 7.89 (s, 1H), 7.45 (m, 1H), 7.31 (m, 1H), 6.81 (m, 2H), 5.69 (q, 1H, J=6.8 Hz).

EXAMPLE 5b

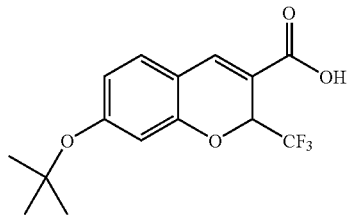

7-tert-butoxy-2-(trifluoromethyl)-2H-chromene-3-carboxylic acid

The 7-tert-butoxy-2-(trifluoromethyl)-2H-chromene-3-carboxylic acid as prepared by hydrolysis of ethyl 7-tert-butoxy-2-(trifluoromethyl)-2H-chromene-3-carboxylate from Example 1h, Step 1 using the procedure similar to the method described in Example 1h, Step 3): ESHRMS m/z315.0840 (M–H,$C_{15}H_{14}O_4F_3$, Calc'd 315.0839). $^1$H NMR (acetone-$d_6$/400 MHz) 7.84 (s, 1H), 7.35 (d, 1H, J=8.4 Hz), 7.35 (dd, 1H, J=8.4, 2.4 Hz), 6.62 (d, J=2 1H), 5.75 (q, 1H, J=6.8 Hz), 1.39 (s, 9H).

EXAMPLE 5c

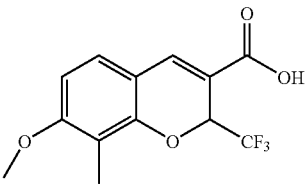

7-methoxy-8-methyl-2-(trifluoromethyl)-2H-chromene-3-carboxylic acid

The 7-methoxy-8-methyl-2-(trifluoromethyl)-2H-chromene-3-carboxylic acid was prepared by hydrolysis of ethyl 7-methoxy-8-methyl-2-(trifluoromethyl)-2H-chromene-3-carboxylate from Example 3a, Step 2 using procedure similar to the method described in Example 1h, Step 3: ESHRMS m/z287.0502 (M–H, $C_{13}H_{10}O_4F_3$, Calc'd 287.0526). $^1$H NMR (acetone-$d_6$/300 MHz) 7.82 (s, 1H), 7.29 (d, 1H, J=8.4 Hz), 6.72 (d, 1H, J=8.4 Hz), 5.80 (q, 1H, J=6.8 Hz), 3.90 (s, 3H), 2.08 (s, 3H).

EXAMPLE 5d

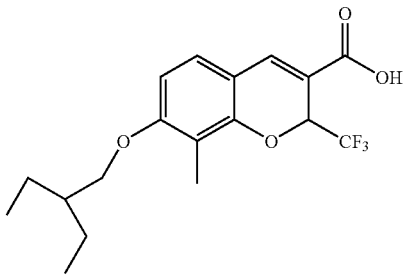

7-(2-ethylbutoxy)-8-methyl-2-(trifluoromethyl)-2H-chromene-3-carboxylic acid The 7-(2-ethylbutoxy)-8-methyl-2-(trifluoromethyl)-2H-chromene-3-carboxylic acid was prepared by hydrolysis of methyl 7-(2-ethylbutoxy)-8-methyl-2-(trifluoromethyl)-2H-chromene-3-carboxylate from Example 3b, Step 2 using the procedure similar to the method described in Example 1h, Step 3: ESHRMS m/z 357.1325 (M–H, $C_{18}H_{20}O_4F_3$, Calc'd 357.1308). $^1$H NMR (acetone-$d_6$/400 MHz) 7.81 (s, 1H), 7.26 (d, 1H, J=8.4Hz), 6.71 (d, 1H, J=8.4 Hz), 5.80 (q, 1H, J=6.8 Hz), 3.99 (m, 2H), 2.09 (s, 3H), 1.07 (m, 1H), 1.51 (m, 4H), 0.94 (t, 6H, J=6.8 Hz).

EXAMPLE 5e

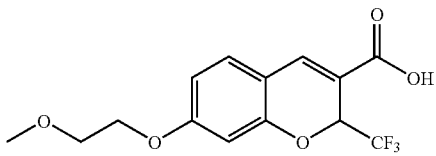

7-(2-methoxyethoxy)-2-(trifluoromethyl)-2H-chromene-3-carboxylic acid

Step 1. Preparation of ethyl 7-(2-methoxyethoxy)-2-(trifluoromethyl)-2H-chromene-3-carboxylate The ethyl 7-(2-methoxyethoxy)-2-(trifluoromethyl)-2H-chromene-3-carboxylate was prepared by a procedure similar to the method described in Example 1b, Step 1 using ethyl 7-hydroxy-2-(trifluoromethyl)-2H-chromene-3-carboxylate from Example 1a, Step 1 as the starting material. The residue was purified by flash chromatography (silica gel) with 10-30% ethyl acetate in hexane to give clear oil (2.0 g, 83%): LCMS m/z 333.1(M+H). This ester was of suitable purity to use without further purification.

Step 2. Preparation of 7-(2-methoxyethoxy)-2-(trifluoromethyl)-2H-chromene-3-carboxylic acid The 7-(2-methoxyethoxy)-2-(trifluoromethyl)-2H-chromene-3-carboxylic acid was prepared by a procedure similar to the method described in Example 2a, Step 3: ESHRMS m/z 317.0648 (M–H, $C_{14}H_{12}F_3O_5$, Calc'd 317.0631). $^1$H NMR (CDCl$_3$/400 MHz) 7.78 (s, 1H), 7.14 (d, 1H, J=8.4 Hz), 6.52 (m, 2H), 5.63 (q, 1H, J=7.0 Hz), 4.12 (m, 2H), 3.74 (m, 2H), 3.44 (s, 3H).

EXAMPLE 5f

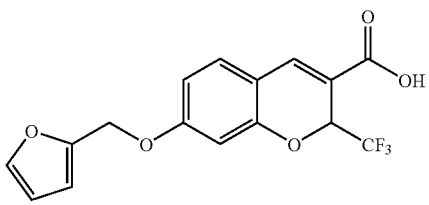

7-(2-furylmethoxy)-2-(trifluoromethyl)-2H-chromene-3-carboxylic acid

The 7-(2-furylmethoxy)-2-(trifluoromethyl)-2H-chromene-3-carboxylic acid was prepared by the procedure similar to the method described in Example 5e: ESHRMS m/z 339.0461 (M–H, $C_{16}H_{10}F_3O_5$, Calc'd 339.0475). $^1$H NMR (CDCl$_3$/300 MHz) 7.82 (s, 1H), 7.45 (s, 1H), 7.14 (d, 1H, J=8.4 Hz), 6.64 (m, 2H), 6.42 (m, 2H), 5.65 (q, 1H, J=7.0 Hz), 5.02 (m, 2H).

EXAMPLE 5g

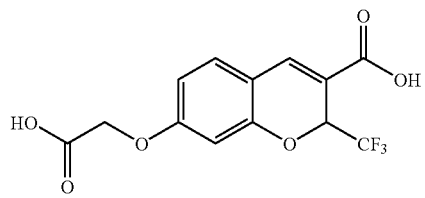

7-(carboxymethoxy)-2-(trifluoromethyl)-2H-chromene-3-carboxylic acid

The 7-(carboxymethoxy)-2-(trifluoromethyl)-2H-chromene-3-carboxylic acid was prepared by the procedure similar to the method described in Example 5e: ESHRMS m/z 7.0247 (M–H, $C_{13}H_8F_3O_6$, Calc'd 317.0267)31. $^1$H NMR (DMSO/300 MHz) 13.05 (brs, 2H), 7.79 (s, 1H), 7.39 (d, 1H, J=8.4 Hz), 6.60 (m, 2H), 5.84 (q, 1H, J=7.0 Hz), 4.73 (s, 2H).

EXAMPLE 6

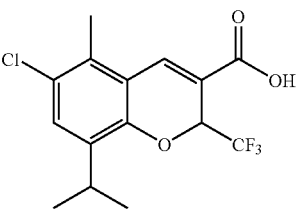

6-chloro-8-isopropyl-5-methyl-2-(trifluoromethyl)-2H-chromene-3-carboxylic acid

Step 1. Preparation of 3-chloro-6-hydroxy-5-isopropyl-2-methylbenzaldehyde

To a solution of 4-chloro-2-isopropyl-5-methylphenol (5.00 g, 27.08 mmole) in anhydrous acetonitrile (150 mL) was added $MgCl_2$ (3.87 g, 40.61 mmole), TEA (10.28 mL, 101.55 mmole) and paraformaldehyde (5.48 g, 182.79 mmole), and the resulting mixture was refluxed under a dry $N_2$ atmosphere for 18 hrs. The mixture was then cooled, acidified with 2.4 N HCl and extracted with EtOAc (2×250 ml). The combined extracts were washed with brine (100 ml), dried over $MgSO_4$, filtered and concentrated in vacuo to give dark orange oil which was subjected to flash chromatography (silica gel) and eluted with 25% hexane/ $CH_2Cl_2$ to yield 5.8 g (99% yield) of the product as a pale yellow oil. GCMS m/z 212.0 (M+). This ester was of suitable purity to use without further purification.

Step 2. Preparation of ethyl 6-chloro-8-isopropyl-5-methyl-2-(trifluoromethyl)-2H-chromene-3-carboxylate A mixture of 3-chloro-6-hydroxy-5-isopropyl-2-methylbenzaldehyde prepared as in Step 1 (5.21 g, 24.56 mmole), $K_2CO_3$ (6.78 g, 49.12 mmole) and ethyl 4,4,4-trifluocrotonate (6.19 g, 36.84 mmole) in anhydrous DMF (30.0 mL) was heated to 90° C. under a dry $N_2$ atmosphere for 18 hrs. The mixture was then cooled, poured into 1.2 N HCl (100 ml) and extracted with EtOAc (2×100 mL). The combined extracts were washed with brine (100 mL), dried over $MgSO_4$, filtered and concentrated in vacuo to give a dark orange oil which was subject to flash chromatography (silica gel) and eluted with 50% hexane/$CH_2Cl_2$ to yield 3.94 g (44%) of the product as an orange oil: GCMS m/z 362.0 (M+). $^1$H NMR ($CDCl_3$/400 MHz) 7.98 (s, 1H), 7.26 (s, 1H), 5.75 (q, 1H, J=7.0 Hz), 4.36 (m, 2H), 3.28 (m, 1H), 2.45 (s, 3H), 1.39 (m, 3H), 1.23 (m, 6H).

Step 3. Preparation of 6-chloro-8-isopropyl-5-methyl-2-(trifluoromethyl)-2H-chromene-3-carboxylic acid The 6-chloro-8-isopropyl-5-methyl-2-(trifluoromethyl)-2H-chromene-3-carboxylic acid was prepared by a procedure similar to the method described in Example 2a, Step 3: ESHRMS m/z 333.0538 (M−H, $C_{15}H_{13}O_3F_3Cl$, Calc'd 333.0500). $^1$H NMR ($CDCl_3$/400 MHz) 8.08 (s, 1H), 7.34 (s, 1H), 5.87 (q, 1H, J=7.0 Hz), 3.28 (m, 1H), 2.46 (s, 3H), 1.22 (m, 6H).

EXAMPLE 7a

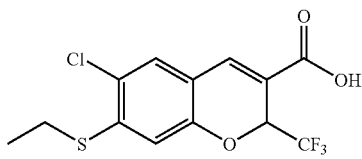

6-chloro-7-(ethylthio)-2-(trifluoromethyl)-2H-chromene-3-carboxylic acid

Step 1. Preparation of 5-chloro-4-fluoro-2-hydroxybenzaldehyde

To 4-chloro-3-fluorophenol (25 g, 171 mmole) was added the methanesulfonic acid (130 mL) and the mixture was stirred at r.t. An ice-water bath was used to bring the temperature of the stirred mixture to 10° C. Methenamine (47.8 g, 341 mmole) was added portionwise in 3 gm scoops to allow the solid to dissolve and keep the temperature below 40° C. Addition was complete after 90 minutes.—CAUTION: If the addition is carried out too fast, the solid will react exothermically with the acid and decompose. The mixture was heated to 100° C. At 70° C., a change in the reaction mixture color was noticed and a solid formed. Once the temperature of 100° C. was reached, the heating manifold was removed and the mixture allowed to cool to r.t. The reaction mixture was poured into 1 L of ice water and extracted 3×w/$CH_2Cl_2$. The combined extracts were filtered through a silica plug (4.5×9 cm), washed with additional $CH_2Cl_2$ and concd to give a crude yellow solid. Kugelrohr distillation (100 millitorr, 60° C.) gave 18.06 g (60.6%) of a white solid: $^1$H NMR shows >95% purity: $^1$H NMR ($CDCl_3$) 6.79 (d, 1H, J=10.3 Hz), 7.62 (d, 1H, J=7.9 Hz), 9.80 (s, 1H), 11.23 (d, 1H, J=1.5 Hz).

Step 2. Preparation of ethyl 6-chloro-7-fluoro-2-(trifluoromethyl)-2H-chromene-3-carboxylate To the aldehyde (17.46 g, 100 mmole) from Step 1 in DMF (25 mL) was added $K_2CO_3$ (15.2 g, 110 mmole). The mixture was stirred, heated to 70° C. and treated with ethyl trifluorocrotonate (22.4 mL, 150 mmole). After 2 h, the mixture was heated to 95° C. After a total of 4 h, an additional 16 mL of crotonate was added and the mixture allowed to stir for 4 h at 95° C. and an additional 12 h at r.t. The reaction was complete by LCMS. This mixture was treated with 300 mL of 1N HCl and extracted 4× with $CH_2Cl_2$. The combined extracts were filtered through silica (4.5×6 cm) and the silica plug washed with additional $CH_2Cl_2$. The extracts were concd, the crude solid triturated with cold methanol, the solid collected and air dried to afford 19.1 g of a tan solid. The mother liquors were concd, dissolved in $CH_2Cl_2$ and filtered through a new silica plug following the same approach as above to give a second crop of 4.1 g of solid. The mother liquors were diluted with $H_2O$ and the solid collected to give a third crop of 3.16 g of solid. Total yield was 26.36 g (81.2%). The first and second crop were >95% by $^1$H NMR. The third crop was >90% pure: $^1$HNMR ($CDCl_3$) 1.35 (t, 3H, J=7.1 Hz), 4.33 (m, 2H), 5.71 (q, 1H, J=6.7 Hz), 6.82 (d, 1H, J=9.4 Hz), 7.28 (d, 1H, 7.9 Hz), 7.63 (s, 1H). $^{19}$FNMR (CDCl3) −78.9 (d, 3F, J=6.7 Hz), −106.7 (t, 1F, J=8.7 Hz). $^{13}$CNMR (CDCl3) 14.2, 61.7, 70.9 (q, C2, J=33.3 Hz), 105.5 (d, C8,J=25.5 Hz), 114.9 (d, J=18.7 Hz), 116.4, 117.1, 123.1 (q,CF3,J=287.2 Hz), 130.4 (d, J=1.5 Hz), 134.9 (d, J=1.9 Hz), 152.9 (d, J=11.4 Hz), 160.1 (d, C7, J=255.2 Hz), 163.4 (C=O)

Step 3. Preparation of ethyl 6-chloro-7-(ethylthio)-2-(trifluoromethyl)-2H-chromene-3-carboxylate A mixture of ethyl 6-chloro-7-fluoro-2-(trifluoromethyl)-2H-chromene-3-carboxylate (Step2) (0.5 g, 1.54 mmole) and ethanethiol (0.1 g, 1.54 mmole) was dissolved in anhydrous DMF (5 mL), warmed to 90° C. and treated with K₂CO₃ (0.25 g, 1.84 mmole). The solution was maintained at 90° C. for 48 hrs, cooled to room temperature, filtered through celite and condensed to a viscous oil. The oil was purified by flash chromatography (silica gel) with 10-40% ethyl acetate in hexane to give light yellow solid (0.24 g, 43%): GCMS 366.00 (M+). $^1$H NMR (CDCl$_3$/400 MHz) 7.60 (s, 1H), 7.27 (s, 1H), 6.77 (s, 1H), 5.67 (q, 1H, J=7.0 Hz), 4.29 (m, 2H), 2.96 (m, 2H), 1.40 (m, 3H), 1.35 (m, 3H).

Step 4. Preparation of 6-chloro-7-(ethylthio)-2-(trifluoromethyl)-2H-chromene-3-carboxylic acid The 6-chloro-7-(ethylthio)-2-(trifluoromethyl)-2H-chromene-3-carboxylic acid was prepared by a procedure similar to the method described in Example 1h, step 3: ESHRMS m/z 336.9886 (M−H, C$_{13}$H$_9$O$_3$F$_3$ClS, Calc'd 336.9908). $^1$H NMR (acetone-d$_6$/300 MHz) 7.86 (s, 1H), 7.54 (s, 1H), 6.98 (s, 1H), 5.84 (q, 1H, J=7.0 Hz), 3.12 (q, 2H, J=7.2 Hz), 1.39 (t, 3H, J=7.2 Hz).

EXAMPLE 7b

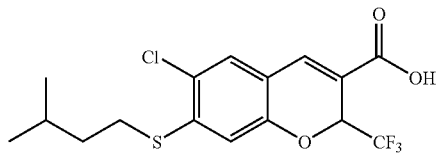

6-chloro-7-(isopentylthio)-2-(trifluoromethyl)-2H-chromene-3-carboxylic acid

The 6-chloro-7-(isopentylthio)-2-(trifluoromethyl)-2H-chromene-3-carboxylic acid was prepared by the procedure similar to the method described in Example 7a. ESHRMS m/z 379.0420 (M−H, C$_{16}$H$_{15}$F$_3$O$_3$ClS, Calc'd 379.0377). $^1$H NMR (acetone-d$_6$/400 MHz) 7.85 (s, 1H), 7.52 (s, 1H), 6.99 (s, 1H), 5.82 (q, 1H, J=7.0 Hz), 3.10 (t, 2H, J=8.0 Hz), 1.84 (m, 1H), 1.64 (m, 2H), 1.59 (m, 3H), 0.93 (m, 3H).

EXAMPLE 7c

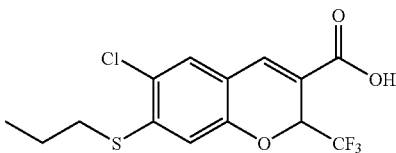

6-chloro-7-(propylthio)-2-(trifluoromethyl)-2H-chromene-3-carboxylic acid

The 6-chloro-7-(propylthio)-2-(trifluoromethyl)-2H-chromene-3-carboxylic acid was prepared by the procedure similar to the method described in Example 7a. ESHRMS m/z 351.0076 (M−H, C$_{14}$H$_{11}$F$_3$O$_3$ClS, Calc'd 351.0064). $^1$H NMR (acetone-d$_6$/400 MHz) 7.86 (s, 1H), 7.54 (s, 1H), 6.99 (s, 1H), 5.83 (q, 1H, J=7.0 Hz), 3.09 (t, 2H, J=8.0 Hz), 1.76 (m, 2H), 1.12 (m, 3H).

EXAMPLE 7d

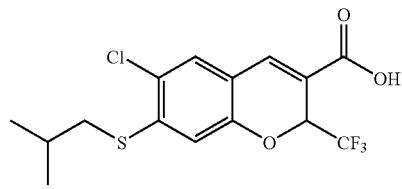

6-chloro-7-(isobutylthio)-2-(trifluoromethyl)-2H-chromene-3-carboxylic acid

The 6-chloro-7-(isobutylthio)-2-(trifluoromethyl)-2H-chromene-3-carboxylic acid was prepared by the procedure similar to the method described in Example 7a. LCMS 367.10 (M+H). $^1$H NMR (acetone-d$_6$/300 MHz) 7.86 (s, 1H), 7.54 (s, 1H), 6.99 (s, 1H), 5.83 (q, 1H, J=7.0 Hz), 2.99 (m, 2H), 1.99 (m, 1H), 1.10 (m, 6H).

EXAMPLE 7e

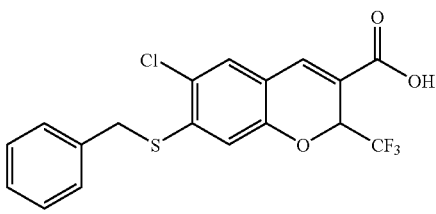

7-(benzylthio)-6-chloro-2-(trifluoromethyl)-2H-chromene-3-carboxylic acid

The 7-(benzylthio)-6-chloro-2-(trifluoromethyl)-2H-chromene-3-carboxylic acid was prepared by the procedure similar to the method described in Example 7a. ESHRMS m/z 399.0036 (M−H, C$_{18}$H$_{11}$F$_3$O$_3$ClS, Calc'd 399.0064). $^1$H NMR (acetone-d$_6$/300 MHz) 7.86 (s, 1H), 7.54 (m, 3H), 7.32 (m, 3H), 7.08 (s, 1H), 5.83 (q, 1H, J=7.0 Hz), 4.40 (s, 2H).

EXAMPLE 7f

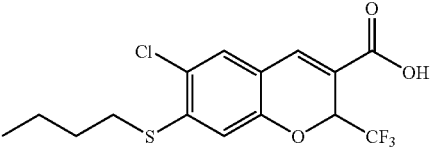

7-(butylthio)-6-chloro-2-(trifluoromethyl)-2H-chromene-3-carboxylic acid

The 7-(butylthio)-6-chloro-2-(trifluoromethyl)-2H-chromene-3-carboxylic acid was prepared by the procedure similar to the method described in Example 7a. ESHRMS m/z 365.0208 (M–H, $C_{15}H_{13}F_3O_3ClS$, Calc'd 365.0221). $^1$H NMR (acetone-$d_6$/300 MHz) 7.85 (s, 1H), 7.53 (s, 1H), 6.98 (s, 1H), 5.82 (q, 1H, J=7.0 Hz), 3.10 (m, 2H), 1.72 (m, 2H), 1.53 (m, 2H), 0.96 (m, 3H).

EXAMPLE 7g

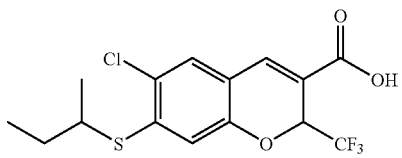

7-(sec-butylthio)-6-chloro-2-(trifluoromethyl)-2H-chromene-3-carboxylic acid

The 7-(sec-butylthio)-6-chloro-2-(trifluoromethyl)-2H-chromene-3-carboxylic acid was prepared by the procedure similar to the method described in Example 7a. ESHRMS m/z 365.0226 (M–H, $C_{15}H_{13}F_3O_3ClS$, Calc'd 365.0221). $^1$H NMR (acetone-$d_6$/300 MHz) 7.86 (s, 1H), 7.54 (s, 1H), 7.04 (s, 1H), 5.82 (q, 1H, J=7.0 Hz), 3.57 (m, 1H), 1.72 (m, 2H), 1.37 (m, 3H), 1.05 (m, 3H).

EXAMPLE 8a

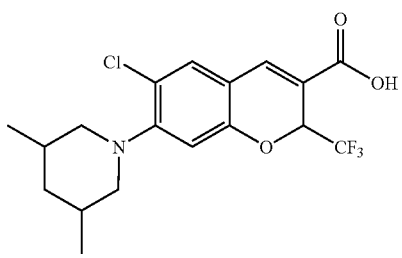

6-chloro-7-(3,5-dimethylpiperidin-1-yl)-2-(trifluoromethyl)-2H-chromene-3-carboxylic acid Step 1. Preparation of ethyl 6-chloro-7-(3,5-dimethylpiperidin-1-yl)-2-(trifluoromethyl)-2H-chromene-3-carboxylate A mixture of ethyl 6-chloro-7-fluoro-2-(trifluoromethyl)-2H-chromene-3-carboxylate (from Example 7a, Step 2) (0.5 g, 1.54 mmole) and 3,5-dimethylpiperidine (0.17 g, 1.54 mmole) was dissolved in anhydrous DMF (5 mL), warmed to 90° C. and treated with $K_2CO_3$ (0.25 g, 1.84 mmole). The solution was maintained at 90° C. for 48 hrs, cooled to room temperature, filtered through celite and condensed to a viscous oil. The oil was purified by Biotage silica chromatography with 30% methylene chloride in hexane to give light yellow oil (0.6 g, 93%). GCMS m/z 417.00 (M+). $^1$H NMR (CDCl$_3$/300 MHz) 7.61 (s, 1H), 7.18 (s, 1H), 6.60 (s, 1H), 5.67 (q, 1H, J=7.0 Hz), 4.67 (m, 2H), 3.40 (m, 2H), 2.18 (m, 2H), 1.86 (m, 2H), 1.31 (m, 3H), 1.04 (m, 3H), 0.90 (m, 6H), 0.68 (m, 1H).

Step 2. Preparation of 6-chloro-7-(3,5-dimethylpiperidin-1-yl)-2-(trifluoromethyl)-2H-chromene-3-carboxylic acid The 6-chloro-7-(3,5-dimethylpiperidin-1-yl)-2-(trifluoromethyl)-2H-chromene-3-carboxylic acid was prepared by a procedure similar to the method described in Example 2a, Step 3. ESHRMS m/z 390.1048 (M+H, $C_{18}H_{20}O_3F_3ClN$, Calc'd 390.1078). $^1$H NMR (acetone-$d_6$/400 MHz) 7.80 (s, 1H), 7.47 (s, 1H), 6.71 (s, 1H), 5.78 (q, 1H, J=7.0 Hz), 3.38 (m, 2H), 2.27 (m, 2H), 1.84 (m, 2H), 1.04 (m, 1H), 0.92 (m, 6H), 0.76 (m, 1H).

EXAMPLE 8b

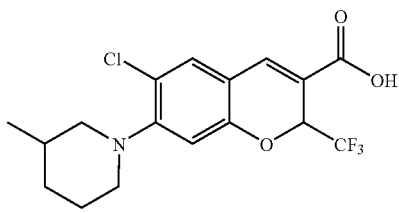

6chloro-7-(3-methylpiperidin-1-yl)-2-(trifluoromethyl)-2H-chromene-3-carboxylic acid The 6-chloro-7-(3-methylpiperidin-1-yl)-2-(trifluoromethyl)-2H-chromene-3-carboxylic acid was prepared by the procedure similar to the method described in Example 8a. ESHRMS m/z 376.0931 (M+H, $C_{17}H_{18}F_3O_3ClN$ Calc'd 376.0922). $^1$H NMR (acetone-$d_6$/400 MHz) 7.82 (s, 1H), 7.48 (s, 1H), 6.71 (s, 1H), 5.78 (q, 1H, J=7.0 Hz), 3.41 (m,2H), 2.38 (m, 1H), 1.75 (m, 5H), 1.10 (m, 1H), 0.93 (m, 3H).

EXAMPLE 8c

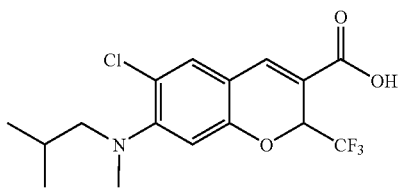

6-chloro-7-[isobutyl(methyl)amino]-2-(trifluoromethyl)-2H-chromene-3-carboxylic acid The 6-chloro-7-[isobutyl(methyl)amino]-2-(trifluoromethyl)-2H-chromene-3-carboxylic acid was prepared by the procedure similar to the method described in Example 8a. ESHRMS m/z 364.0897 (M+H, $C_{16}H_{18}F_3O_3ClN$ Calc'd 364.0922). $^1$H NMR (acetone-$d_6$/400 MHz) 7.81 (s, 1H), 7.46 (s, 1H), 6.76 (s, 1H), 5.78 (q, 1H, J=7.0 Hz), 3.04 (m, 2H), 2.95 (s, 3H), 1.96 (m, 1H), 0.96 (m, 6H).

EXAMPLE 8d

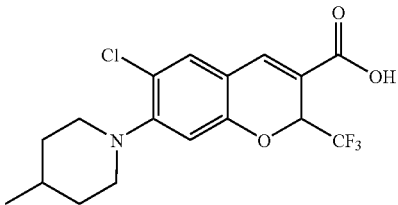

6-chloro-7-(4-methylpiperidin-1-yl)-2-(trifluoromethyl)-2H-chromene-3-carboxylic acid The 6-chloro-7-(4-methylpiperidin-1-yl)-2-(trifluoromethyl)-2H-chromene-3-carboxylic acid was prepared by the procedure similar to the method described in Example 8a. ESHRMS m/z 376.0924 (M+H, $C_{17}H_{18}F_3O_3ClN$, Calc'd 376.0922). $^1$H NMR (acetone-$d_6$/300 MHz) 7.81 (s, 1H), 7.48 (s, 1H), 6.72 (s, 1H), 5.79 (q, 1H, J=7.0 Hz), 3.48 (m, 2H), 2.72 (m, 2H), 1.75 (m, 2H), 1.58 (m, 1H), 1.38 (m, 2H), 0.98 (m, 3H).

EXAMPLE 8e

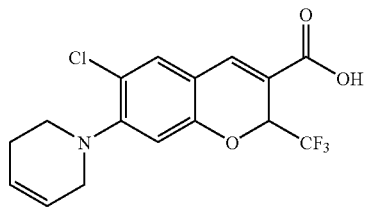

6-chloro-7-(3,6-dihydropyridin-1(2H)-yl)-2-(trifluoromethyl)-2H-chromene-3-carboxylic acid The 6-chloro-7-(3,6-dihydropyridin-1(2H)-yl)-2-(trifluoromethyl)-2H-chromene-3-carboxylic acid was prepared by the procedure similar to the method described in Example 8a. ESHRMS m/z 360.0592 (M+H, $C_{16}H_{14}F_3O_3ClN$, Calc'd 360.0609). $^1$H NMR (acetone-$d_6$/400 MHz) 7.81 (s, 1H), 7.49 (s, 1H), 6.74 (s, 1H), 5.79 (m, 3H), 3.68 (m, 2H), 3.39 (m, 1H), 3.22 (m, 1H), 2.30 (m, 2H).

EXAMPLE 8f

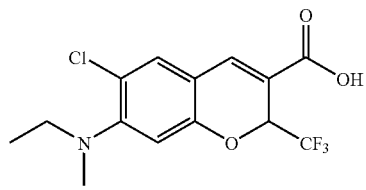

6-chloro-7-[ethyl(methyl)amino]-2-(trifluoromethyl)-2H-chromene-3-carboxylic acid The 6-chloro-7-[ethyl(methyl)amino]-2-(trifluoromethyl)-2H-chromene-3-carboxylic acid was prepared by the procedure similar to the method described in Example 8a. ESHRMS m/z 336.0574 (M+H, $C_{14}H_{14}F_3O_3ClN$, Calc'd 336.0609). $^1$H NMR (acetone-$d_6$/400 MHz) 7.81 (s, 1H), 7.46 (s, 1H), 6.71 (s, 1H), 5.77 (q, 1H, J=7.0 Hz), 3.21 (m, 2H), 2.84 (s, 3H), 0.96 (m, 3H).

EXAMPLE 8g

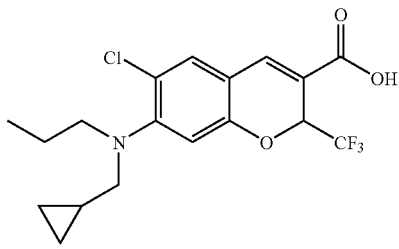

6-chloro-7-[(cyclopropylmethyl)(propyl)amino]-2-(trifluoromethyl)-2H-chromene-3-carboxylic acid The 6-chloro-7-[(cyclopropylmethyl)(propyl)amino]-2-(trifluoromethyl)-2H-chromene-3-carboxylic acid was prepared by the procedure similar to the method described in Example 8a. ESHRMS m/z 390.1040(M+H, $C_{18}H_{20}F_3O_3ClN$, Calc'd 390.1078). $^1$H NMR (acetone-$d_6$/300 MHz) 7.83 (s, 1H), 7.48 (s, 1H), 6.84 (s, 1H), 5.79 (q, 1H, J=7.0 Hz), 3.33 (m, 2H), 3.11 (m, 2H), 1.53 (m, 2H), 1.00 (m, 1H), 0.90 (m, 3H), 0.45, (m, 2H), 0.10 (m, 2H).

EXAMPLE 8h

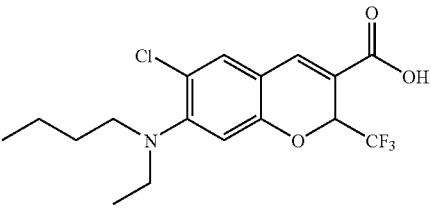

7-[butyl(ethyl)amino]-6-chloro-2-(trifluoromethyl)-2H-chromene-3-carboxylic acid The 7-[butyl(ethyl)amino]-6-chloro-2-(trifluoromethyl)-2H-chromene-3-carboxylic acid was prepared by the procedure similar to the method described in Example 8a. ESHRMS m/z 378.1058 (M+H, $C_{17}H_{20}F_3O_3ClN$, Calc'd 378.1078). $^1$H NMR (acetone-$d_6$/300 MHz) 7.83 (s, 1H), 7.49 (s, 1H), 6.79 (s, 1H), 5.79 (q, 1H, J=7.0 Hz), 3.24 (m, 4H), 1.51 (m, 2H), 1.31 (m, 2H), 1.10 (m, 3H), 0.91 (m, 3H).

EXAMPLE 8i

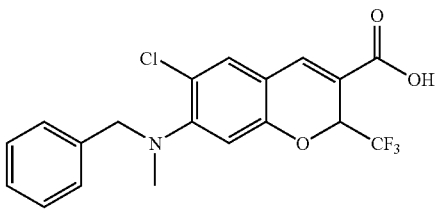

7-[benzyl(methyl)amino]-6-chloro-2-(trifluoromethyl)-2H-chromene-3-carboxylic acid The 7-[benzyl(methyl)amino]-6-chloro-2-(trifluoromethyl)-2H-chromene-3-carboxylic acid was prepared by the procedure similar to the method described in Example 8a. ESHRMS m/z 398.0788 (M+H, $C_{19}H_{16}F_3O_3ClN$, Calc'd 398.0765). $^1$H NMR (acetone-$d_6$/300 MHz) 7.84 (s, 1H), 7.53 (s, 1H), 7.36 (m, 5H), 6.77 (s, 1H), 5.79 (q, 1H, J=7.0 Hz), 4.36 (m, 2H), 2.77 (s, 3H).

EXAMPLE 8j

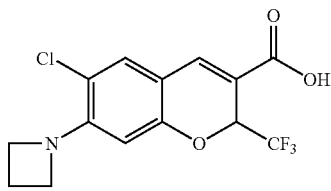

7-azetidin-1-yl-6-chloro-2-(trifluoromethyl)-2H-chromene-3-carboxylic acid

The 7-azetidin-1-yl-6-chloro-2-(trifluoromethyl)-2H-chromene-3-carboxylic acid was prepared by the procedure similar to the method described in Example 8a. ESHRMS m/z 334.0441 (M+H, $C_{14}H_{12}F_3O_3ClN$, Calc'd 334.0452). $^1$H NMR (acetone-$d_6$/300 MHz) 7.75 (s, 1H), 7.28 (s, 1H), 6.09 (s, 1H), 5.72 (q, 1H, J=7.0 Hz), 4.23 (m, 4H), 2.35 (m, 2H).

EXAMPLE 8k

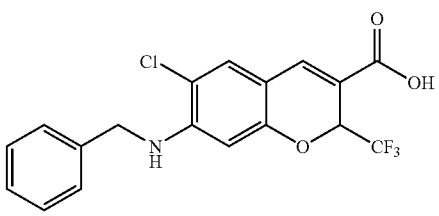

7-(benzylamino)-6-chloro-2-(trifluoromethyl)-2H-chromene-3-carboxylic acid

The 7-(benzylamino)-6-chloro-2-(trifluoromethyl)-2H-chromene-3-carboxylic acid was prepared by the procedure similar to the method described in Example 8a. ESHRMS m/z 384.0583 (M+H, $C_{18}H_{14}F_3O_3ClN$, Calc'd 384.0609). $^1$H NMR (acetone-$d_6$/400 MHz) 7.73 (s, 1H), 7.40 (m, 6H), 6.28 (s, 1H), 5.66 (q, 1H, J=7.0 Hz), 4.58 (m, 2H).

EXAMPLE 8l

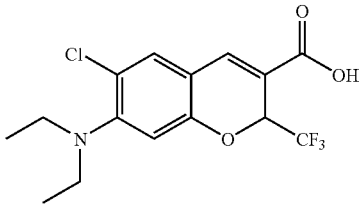

6-chloro-7-(diethylamino)-2-(trifluoromethyl)-2H-chromene-3-carboxylic acid

Step 1. Preparation of ethyl 7-(diethylamino)-2-(trifluoromethyl)-2H-chromene-3-carboxylate The ethyl 7-(diethylamino)-2-(trifluoromethyl)-2H-chromene-3-carboxylate was prepared by a procedure similar to the method described in Example 1a, Step 1. GCMS m/z 343.0 (M+). This ester was of suitable purity to use without further purification.

Step 2. Preparation of ethyl 6-chloro-7-(diethylamino)-2-(trifluoromethyl)-2H-chromene-3-carboxylate The ethyl 6-chloro-7-(diethylamino)-2-(trifluoromethyl)-2H-chromene-3-carboxylate was prepared by a procedure similar to the method described in Example 1h, Step 2. GCMS m/z 377.0 (M+). $^1$H NMR (CDCl$_3$/400 MHz) 7.59 (s, 1H), 7.17 (s, 1H), 6.59 (s, 1H), 5.65 (q, 1H, J=7.0 Hz), 4.28 (m, 2H), 3.19 (m, 4H), 1.32 (m, 3H), 1.09 (m, 6H). This ester was of suitable purity to use without further purification.

Step 3. Preparation of 6-chloro-7-(diethylamino)-2-(trifluoromethyl)-2H-chromene-3-carboxylic acid The 6-chloro-7-(diethylamino)-2-(trifluoromethyl)-2H-chromene-3-carboxylic acid was prepared by a procedure similar to the method described in Example 2a, Step 3. ESHRMS m/z 350.0774 (M+H, $C_{15}H_{16}O_3F_3ClN$, Calc'd 350.0765). $^1$H NMR (CDCl$_3$/400 MHz) 7.73 (s, 1H), 7.20 (s, 1H), 6.59 (s, 1H), 5.63 (q, 1H, J=7.0 Hz), 3.23 (m, 4H), 1.10 (m, 6H).

EXAMPLE 9a

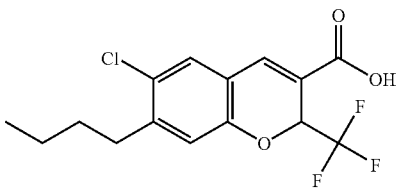

7-butyl-6-chloro-2-(trifluoromethyl)-2H-chromene-3-carboxylic acid

Step 1. Preparation of 2-hydroxy4-iodobenzaldehyde

To a chilled solution of commercially available 2-iodophenol (30 g, 136 mmole) in ACN was added $MgCl_2$ (19.5 g, 204 mmole) portion-wise while maintaining the temperature below 10° C., followed by paraformaldehyde (28.6 g, 954 mmole) and TEA (76 mL, 545 mmole) producing a 15° C. exotherm. The solution was heated to 72° C. for 2 h. The reaction was cooled to room temperature and poured into Saturated aqueous Ammonium Chloride (500 mL), extracted with ethyl acetate (2×150 mL). The combined organic phases were washed with aqueous $NaHCO_3$ solution (2×150 mL), aqueous 1N HCl solution (2×150 mL), and brine (2×150 mL), dried over $Na_2SO_4$, filtered and concentrated in vacuo. The crude material was subjected to flash chromatography (Silica, 5% Ethyl acetate/Hexane). Desired fractions were collected and combined, removed solvent in vacuo producing the ethyl ester (27 g, 79%) as a yellow solid. This salicylaldehyde was of suitable purity to use without further purification. $^1$HNMR (DMSO-$d_6$/400 MHz) 10.95 (s, 1H), 10.19 (s, 1H), 7.33 (m, 3H), 4.31 (m, 1H).

Step 2. Preparation of ethyl 7-iodo-2-(trifluoromethyl)-2H-chromene-3-carboxylate The aldehyde from Step 1 (25 g, 114 mmole) was condensed in a method similar to that described in Example 4a, Step 1. (15 g, 52%). This ester was of suitable purity to use without further purification: ESHRMS m/z 361.1040 (M−H, $C_{13}H_9IF_3O_3$, Calc'd 361.1046).

Step 3. Preparation of ethyl 7-butyl-2-(trifluoromethyl)-2H-chromene-3-carboxylate 1-Butene was bubbled through 9-BBN in THF (6.53 mL, 6.5 mmole) for 15 minutes, resulting solution stirred at room temperature overnight. To this solution was added the ester (Step 2), (2.0 g, 5 mmole) dissolved into THF (25 mL), Pd(dppf)Cl $CH_2Cl_2$ (0.133 g, 5 mole %), $K3PO_{4(aq)}$ (3.5 mL, 7.1 mmole). The reaction was heated to 60° C. for 4 h. The reaction was cooled to room temperature, poured into $H_2O$ (150 mL), and extracted with ethyl acetate (2×150 mL). The combined organic phases were washed with aqueous $NaHCO_3$ solution (2×50 mL), aqueous 3N HCl solution (2×50 mL), and brine (2×50 mL), dried over $Na_2SO_4$, filtered and concentrated in vacuo. The crude material was subjected to flash chromatography (Silica, 2% Ethyl acetate/Hexane). Desired fractions were collected and combined, removed solvent in vacuo producing the ethyl ester (600 mg, 56%) as an amber oil. This ester was of suitable purity to use without further purification. ESLRMS m/z 329 (M+H).

Step 4. Preparation of ethyl 7-butyl-6-chloro-2-(trifluoromethyl)-2H-chromene-3-carboxylate The ester from Step 1 was chlorinated via a method similar to that described in Example 4b, Step 1 (91%). This ester was of suitable purity to use without further purification. $^1$HNMR (DMSO-$d_6$/400 MHz), 7.88 (s, 1H), 7.60 (s, 1H), 7.02 (s, 1H), 5.92 (q, 1H, J=7.1 Hz), 2.62 (m, 2H), 1.49 (m, 2H), 1.25 (m, 2H), 0.866 (t, 3H, J=7.3 Hz).

Step 5. Preparation of 7-butyl-6-chloro-2-(trifluoromethyl)-2H-chromene-3-carboxylic acid The ester (Step 4) was hydrolyzed to form the title carboxylic acid via a method similar to that described in Example 4a, Step 2, (99%). ESHRMS m/z 333.0497 (M−H, $C_{15}H_{13}ClF_3O_3$, Calc'd 333.0500). $^1$HNMR (DMSO-$d_6$/400 MHz), 13.13 (s, 1H), 7.79 (s, 1H), 7.56 (s, 1H), 7.00 (s, 1H), 5.89 (q, 1H, J=7.1 Hz), 2.62 (t, 2H, J=7.5 Hz), 1.50 (m, 2H), 1.30 (m, 2H), 0.860 (t, 3H, J=7.3 Hz).

EXAMPLE 9b

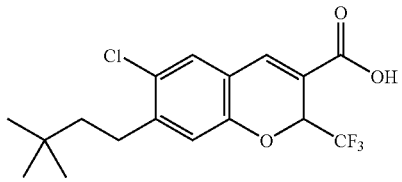

6-chloro-7-(3,3-dimethylbutyl)-2-(trifluoromethyl)-2H-chromene-3-carboxylic acid

Step 1. Preparation of ethyl 7-(3,3-dimethylbutyl)-2-(trifluoromethyl)-2H-chromene-3-carboxylate Neohexene was added to a solution of 9-BBN in THF (6.53 mL, 6.5 mmole) resulting solution stirred at room temperature overnight. To this solution was added the ester Example 9a, Step 2 (2.0 g, 5 mmole) dissolved into THF (25 mL), Pd(dppf)Cl. $CH_2Cl_2$ (0.133 g, 5 mole %), $K_3PO_{4(aq)}$ (3.5 mL, 7.1 mmole). The reaction was heated to 60° C. for 4 hours. The reaction workup and purification was conducted according to Example 9a, Step 1 producing the ethyl ester (720 mg, 62%) as an amber oil. This ester was of suitable purity to use without further purification. ESLRMS m/z 357 (M+H).

Step 2. Preparation of ethyl 6-chloro-7-(3,3-dimethylbutyl)-2-(trifluoromethyl)-2H-chromene-3-carboxylate The ester (Step 1) was chlorinated via a method similar to that described in Example 4b, Step 1 (87%). This ester was of suitable purity to use without further purification. ESLRMS m/z 376 (M+H).

Step 3. Preparation of 6-chloro-7-(3,3-dimethylbutyl)-2-(trifluoromethyl)-2H-chromene-3-carboxylic acid The ester (Step 2) was hydrolyzed to form the carboxylic acid via a method similar to that described in Example 4a, Step 2 (99%). ESHRMS m/z 361.0801 (M−H, $C_{17}H_{17}ClF_3O_3$, Calc'd 361.0813). $^1$HNMR (DMSO-$d_6$/400 MHz) 13.23 (brs, 1H), 7.80 (s, 1H), 7.55 (s, 1H), 7.01 (s, 1H), 5.89 (q, 1H, J=7.1 Hz), 3.30 (m, 2H), 2.56-2.60 (m, 2H), 1.31-1.37 (m, 2H), 0.91 (s, 9H).

EXAMPLE 9c

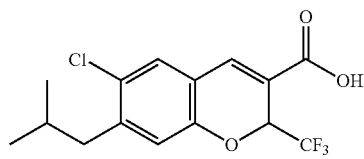

6-chloro-7-isobutyl-2-(trifluoromethyl)-2H-chromene-3-carboxylic acid

Step 1. Preparation of ethyl 7-isobutyl-2-(trifluoromethyl)-2H-chromene-3-carboxylate This compound was prepared and purified via a method similar to that described in Example 9a, Step 3 with the appropriate substitution of isobutylene producing the ethyl ester (720 mg, 58%) as an amber oil. This ester was of suitable purity to use without further purification. EILRMS m/z 328 (M+).

Step 2. Preparation of ethyl 6-chloro-7-isobutyl-2-(trifluoromethyl)-2H-chromene-3-carboxylate The ester (Step 1) was chlorinated via a method similar to that described in Example 4b, Step 1 (92%). This ester was of suitable purity to use without further purification. ESLRMS m/z 363 (M+H). $^1$HNMR (DMSO-$d_6$/400 MHz) 7.88 (s, 1H), 7.61 (s, 1H), 5.96 (q, 1H, J=7.1 Hz), 4.18-4.27 (m, 2H), 2.51-2.53 (d, 2H, J=7.2 Hz), 1.84-1.91 (m, 2H), 1.240 (t, 1H, J=7.1 Hz), 0.842 (m, 6H).

Step 3. Preparation of 6-chloro-7-isobutyl-2-(trifluoromethyl)-2H-chromene-3-carboxylic acid The ester (Step 2) was hydrolyzed to form the carboxylic acid via a method similar to that described in Example 4a, Step 2 (99%). ESHRMS m/z 333.0496 (M−H, $C_{15}H_{13}ClF_3O_3$, Calc'd 333.0500). $^1$HNMR (DMSO-$d_6$/400 MHz) 13.31 (brs, 1H), 7.81 (s, 1H), 7.5 (s, 1H), 6.97 (s, 1H), 5.89 (q, 1H, J=7.1 Hz), 2.51 (d, 2H, J=6.7 Hz), 1.85-1.89 (m, 1H), 0.843 (m, 6H).

EXAMPLE 9d

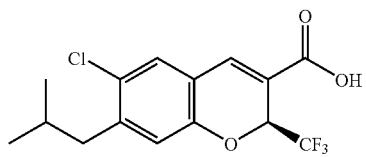

(2S)-6-chloro-7-isobutyl-2-(trifluoromethyl)-2H-chromene-3-carboxylic acid

A racemic mixture of the compound prepared in Example 9c, Step 3 was resolved by chiral chromatography using a Chiralcel OJ column eluting with EtOH/heptane/TFA=5/95/0.1 and detecting at 254 nm as peak I with retention time 6.60 min. ESHRMS m/z 333.0496 (M−H, $C_{15}H_{13}ClF_3O_3$, Calc'd 333.0500). $^1$HNMR (DMSO-$d_6$/400 MHz) 13.31 (brs, 1H), 7.81 (s, 1H), 7.5 (s, 1H), 6.97 (s, 1H), 5.89 (q, 1H, J=7.1 Hz), 2.51 (d, 2H, J=6.7 Hz), 1.85-1.89 (m, 1H), 0.843 (m, 6H).

EXAMPLE 9e

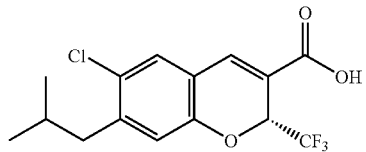

(2R)-6-chloro-7-isobutyl-2-(trifluoromethyl)-2H-chromene-3-carboxylic acid

A racemic mixture of the compound prepared in Example 9c, Step 3 was resolved by chiral separation using Chiralcel OJ column eluting with EtOH/Heptane/TFA=5/95/0.1 and detecting at 254 nm as peak 2 with retention time 9.77 min. ESHRMS m/z 333.0496 (M−H, $C_{15}H_{13}ClF_3O_3$, Calc'd 333.0500). $^1$HNMR (DMSO-$d_6$/400 MHz) 13.31 (brs, 1H), 7.81 (s, 1H), 7.5 (s, 1H), 6.97 (s, 1H), 5.89 (q, 1H, J=7.1 Hz), 2.51 (d, 2H, J=6.7 Hz), 1.85-1.89 (m, 1H), 0.843 (m, 6H).

EXAMPLE 9f

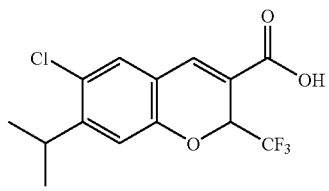

6-chloro-7-isopropyl-2-(trifluoromethyl)-2H-chromene-3-carboxylic acid

Step 1. Preparation of 2-hydroxy-4-isopropylbenzaldehyde

To a chilled solution of commercially available 3-isopropyphenol (5 g, 36.7 mmole) in ACN was added $MgCl_2$ (5.24 g, 55 mmole) portion-wise while maintaining the temperature below 10° C., followed by paraformaldehyde (7.72 g, 257 mmole) and TEA (20.47 mL, 146 mmole) producing a 15° C. exotherm. The solution was heated to 72° C. for 2 h. The reaction was cooled to room temperature and poured into Saturated aqueous Ammonium Chloride (200 mL), extracted with ethyl acetate (2×50 mL). The combined organic phases were washed with aqueous $NaHCO_3$ solution (2×50 mL), aqueous 1N HCl solution (2×50 mL), and brine (2×50 mL), dried over $Na_2SO_4$, filtered and concentrated in vacuo. The crude material was subjected to flash chromatography (Silica, 5% Ethyl acetate/Hexane). Desired fractions were collected and combined, removed solvent in vacuo producing the ethyl ester (4.6 g, 76%) as a yellow solid. This salicylaldehyde was of suitable purity to use without further purification: EILRMS m/z 164 (M+).

Step 2. Preparation of ethyl 7-isopropyl-2-(trifluoromethyl)-2H-chromene-3-carboxylate This salicylaldehyde (Step 1) was condensed with Ethyl-4,4,4-triflurocrotonate via a similar method to that of Example 4a, Step 1 producing the ethyl ester (8.21 g, 84%) as yellow solid. This ester was of suitable purity to use without further purification: ESLRMS m/z 315 (M+H).

Step 3. Preparation of ethyl 6-chloro-7-isopropyl-2-(trifluoromethyl)-2H-chromene-3-carboxylate The ester (Step 2) was chlorinated via a method similar to that described in Example 4b, Step 1 (82%). This ester was of suitable purity to use without further purification: ESLRMS m/z 349 (M+H).

Step 4. Preparation of (2R)-6-chloro-7-isobutIyl-2-(trifluoromethyl)-2H-chromene-3-carboxylic acid The ester (Step 3) was hydrolyzed to form the carboxylic acid via a method similar to that described in Example 4a, Step 2 (99%): ESHRMS m/z 319.0309 (M−H, $C_{14}H_{11}ClF_3O_3$, Calc'd 319.0343). $^1$HNMR (DMSO-$d_6$/400 MHz) 13.26 (brs, 1H), 7.81 (s, 1H), 7.57 (s, 1H), 7.01 (s, 1H), 5.90 (q, 1H, J=7.1 Hz), 3.29 (m, 1H), 1.14-1.17 (m, 6H).

EXAMPLE 9g

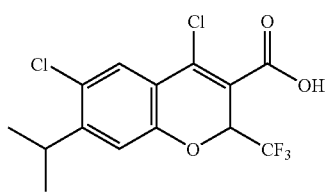

4,6-dichloro-7-isopropyl-2-(trifluoromethyl)-2H-chromene-3-carboxylic acid

Step 1. Preparation of ethyl 4,6-dichloro-7-isopropyl-2-(trifluoromethyl)-2H-chromene-3-carboxylate The ester (Example 9f, Step 3) was chlorinated via a method similar to that described in Example 4b, Step 1 (29%). This ester was of suitable purity to use without further purification: ESLCMS m/z 383 (M+H).

Step 2. Preparation of 4,6-dichloro-7-isopropyl-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 352.9934 (M−H, $C_{14}H_{10}Cl_2F_3O_3$, Calc'd 352.9954). $^1$HNMR (DMSO-$d_6$/400 MHz) 14.1 (brs, 1H), 7.64 (s, 1H), 7.11 (s, 1H), 6.15 (q, 1H, J=7.1 Hz), 3.27 (m, 1H), 1.175 (m, 6H).

EXAMPLE 9h

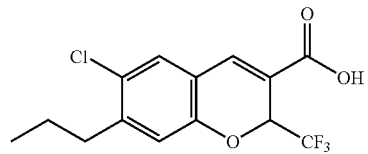

6-chloro-7-propyl-2-(trifluoromethyl)-2H-chromene-3-carboxylic acid

Step 1. Preparation of ethyl 7-propyl-2-(trifluoromethyl)-2H-chromene-3-carboxylate This compound was prepared and purified via a method similar to that described in Example 9a, Step 3 with the appropriate substitution of propene producing the ethyl ester (1.24 g, 78%) as an amber oil. This ester was of suitable purity to use without further purification: ESLRMS m/z 315 (M+H).

Step 2. Preparation of ethyl 6-chloro-7-propyl-2-(trifluoromethyl)-2H-chromene-3-carboxylate The ester (Step 1) was chlorinated via a method similar to that described in Example 4b, Step 1. This ester was of suitable purity to use without further purification: ESLRMS m/z 349 (M+H).

Step 3. Preparation of 6-chloro-7-propyl-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 319.0326 (M−H, $C_{14}H_{11}ClF_3O_3$, Calc'd 319.0343). $^1$HNMR (DMSO-$d_6$/400 MHz) 13.35 (brs, 1H), 7.80 (s, 1H), 7.56 (s, 1H), 7.00 (s, 1H), 5.89 (q, 1H, J=7.1 Hz), 2.59 (m, 2H), 1.52 (m, 2H), 0.873 (m, 3H).

EXAMPLE 9i

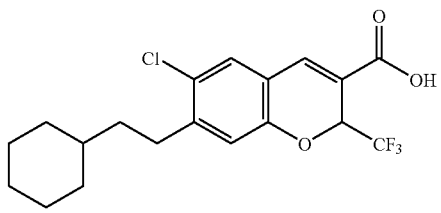

6-chloro-7-(2-cyclohexylethyl)-2-(trifluoromethyl)-2H-chromene-3-carboxylic acid

Step 1. Preparation of ethyl 7-(2-cyclohexylethyl)-2-(trifluoromethyl)-2H-chromene-3-carboxylate This compound was prepared and purified via a method similar to that described in Example 9b, Step 1 with the appropriate substitution of propene producing the ethyl ester (1.21 g, 63%) as a tan solid. This ester was of suitable purity to use without further purification: ESLRMS m/z 383 (M+H).

Step 2. Preparation of ethyl 6-chloro-7-(2-cyclohexylethyl)-2-(trifluoromethyl)-2H-chromene-3-carboxylate The ester (Step 1) was chlorinated via a method similar to that described in Example 4b, Step 1 (85%). This ester was of suitable purity to use without further purification: ESLRMS m/z 417 (M+H).

Step 3. Preparation of 6-chloro-7-(2-cyclohexylethyl)-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 387.0969 (M−H, $C_{19}H_{19}ClF_3O_3$, Calc'd 387.0996). $^1$HNMR (DMSO-$d_6$/400 MHz) 13.20 (brs 1H), 7.77 (s, 1H), 7.54 (s, 1H), 6.98 (s, 1H), 5.88 (q, 1H, J=7.1 Hz), 2.61 (m, 2H), 1.55-1.70 (m, 5H), 1.38 (m, 2H), 1.09-1.20 (m, 4H), 0.860-0.917 (m, 2H).

EXAMPLE 9j

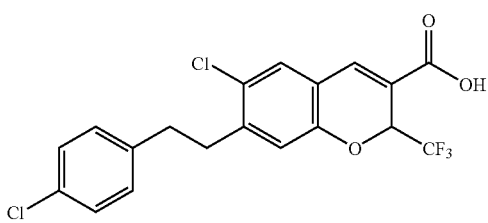

6-chloro-7-[2-(4-chlorophenyl)ethyl]-2-(trifluoromethyl)-2H-chromene-3-carboxylic acid

Step 1. Preparation of ethyl 7-[2-(4-chlorophenyl)ethyl]-2-(trifluoromethyl)-2H-chromene-3-carboxylate This compound was prepared and purified via a method similar to that described in Example 9b, Step 1 with the appropriate substitution ofp-chlorostyrene producing the ethyl ester (1.15 g, 55%) as a yellow solid. This ester was of suitable purity to use without further purification: ESLRMS m/z 397 (M+H).

Step 2. Preparation of ethyl 6-chloro-7-[2-(4-chlorophenyl)ethyl]-2-(trifluoromethyl)-2H-chromene-3-carboxylate The ester (Step 1) was chlorinated via a method similar to that described in Example 4b, Step 1 (82%). This ester was of suitable purity to use without further purification: ESLRMS m/z 431 (M+H).

Step 3. Preparation of 6-chloro-7-[2-(4-chlorophenyl)ethyl]-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 415.0110 (M−H, $C_{19}H_{12}Cl_2F_3O_3$, Calc'd 415.0098). HNMR (DMSO-$d_6$/400 MHz) 13.25 (brs, 1H), 7.82 (s, 1H), 7.61 (s, 1H), 7.33 (d, 2H, J=8.3), 7.20 (d, 2H, J=8.3 Hz), 7.03 (s, 1H), 5.91 (q, 1H, J=7.1 Hz), 4.00 (s, 2H).

EXAMPLE 9k

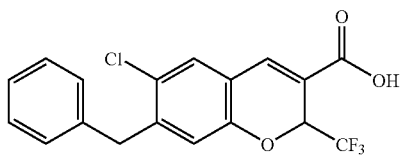

7-benzyl-6-chloro-2-(trifluoromethyl)-2H-chromene-3-carboxylic acid

Step 1. Preparation of ethyl 7-benzyl-2-(trifluoromethyl)-2H-chromene-3-carboxylate To a solution of β-benzyl 9-BBN (20 mL, 10 mmole) in THF (20 mL) was added the ester Example 9a, Step 3 dissolved into THF (25 mL), Pd (dppf)Cl CH$_2$Cl$_2$ (0.133 g, 5 mole %), K$_3$PO$_4$(aq)(3.5 mL, 7.1 mmole). The reaction was heated to 60° C. for 4 h. The reaction workup and purification was conducted according to Example 9a, Step 1 producing the ethyl ester (1.4 g, 76%) as a pale yellow solid. This ester was of suitable purity to use without further purification: ESLRMS m/z 363 (M+H).

Step 2. Preparation of ethyl 7-benzyl-6-chloro-2-(trifluoromethyl)-2H-chromene-3-carboxylate The ester (Step 1) was chlorinated via a method similar to that described in Example 4b, Step 1 (80%). This ester was of suitable purity to use without further purification: ESLRMS m/z 397 (M+H).

Step 3. Preparation of 7-benzyl-6-chloro-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 367.0343 (M–H, $C_{18}H_{11}ClF_3O_3$, Calc'd 367.0329). $^1$HNMR (DMSO-$d_6$/400 MHz) 13.34 (brs, 1H), 7.81 (s, 1H), 7.61 (s, 1H), 7.25-7.29 (m, 2H), 7.17-7.19 (m, 3H), 6.99 (s, 1H), 5.89 (q, 1H, J=7.1 Hz), 4.00 (s, 2H).

EXAMPLE 9l

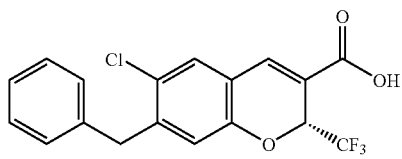

(2R)-7-benzyl-6-chloro-2-(trifluoromethyl)-2H-chromene-3-carboxylic acid

A racemic mixture of the compound prepared in Example 9k, Step 3 was chirally resolved using the same protocol as for Example 9d, Step 1 as peak 2 with retention time 5.76 min: ESHRMS m/z 367.0343 (M–H, $C_{20}H_{11}ClF_3O_3$, Calc'd 367.0329). $^1$HNMR (DMSO-$d_6$/400 MHz) 13.34 (brs, 1H), 7.81 (s, 1H), 7.61 (s, 1H), 7.25-7.29 (m, 2H), 7.17-7.19 (m, 3H), 6.99 (s, 1H), 5.89 (q, 1H, J=7.1 Hz), 4.00 (s, 2H). $[\alpha]^{25}_{589}$=+2.0 in MeOH.

EXAMPLE 9m

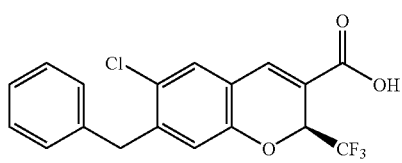

(2S)-7-benzyl-6-chloro-2-(trifluoromethyl)-2H-chromene-3-carboxylic acid

A racemic mixture of the compound prepared in Example 9k, Step 3 was chirally resolved using the same protocol as for Example 9d, Step 1 as peak 1 with retention time 4.27 min: ESHRMS m/z 367.0343 (M–H, $C_{18}H_{11}ClF_3O_3$, Calc'd 367.0329). $^1$HNMR (DMSO-$d_6$/400 MHz) 13.34 (brs, 1H), 7.81 (s, 1H), 7.61 (s, 1H), 7.25-7.29 (m, 2H), 7.17-7.19 (m, 3H), 6.99 (s, 1H), 5.89 (q, 1H, J=7.1 Hz), 4.00 (s, 2H). $[\alpha]^{25}_{589}$=–1.4 degrees (in MeOH).

EXAMPLE 9n

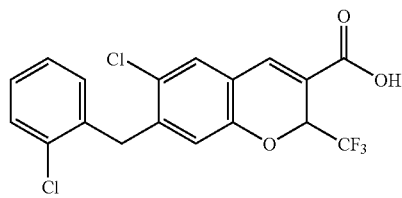

6-chloro-7-(2-chlorobenzyl)-2-(trifluoromethyl)-2H-chromene-3-carboxylic acid

Step 1. Preparation of ethyl 7-(2-chlorobenzyl)-2-(trifluoromethyl)-2H-chromene-3-carboxylate To a solution of the ester Example 9a, step 2 (2.0 g, 5 mmole) dissolved into THF (25 mL) was added Pd(dba)$_2$ (58 mg, 2 mole %), tfp (47 mg, 4 mole %) followed by the syringe addition of 2-chlorobenzylzinc chloride. The reaction was heated to 65° C. for 6 h. The reaction workup and purification was conducted according to Example 9a, Step 1 producing the ethyl ester (1.4 g, 70%) as a yellow solid. This ester was of suitable purity to use without further purification: ESLRMS m/z 397 (M+H).

Step 2. Preparation of ethyl 6-chloro-7-(2-chlorobenzyl)-2-(trifluoromethyl)-2H-chromene-3-carboxylate The ester (Step 1) was chlorinated via a method similar to that described in Example 4b, Step 1 (78%). This ester was of suitable purity to use without further purification: ESLRMS m/z 431 (M+H). $^1$HNMR (DMSO-$d_6$/400 MHz) 1.98 (brs, 1H), 7.91 (s, 1H), 7.70 (s, 1 H), 7.47 (m, 1H), 7.29 (m, 2H), 7.11 (m, 1H), 6.68 (s, !H), 5.95 (q, 1H, J=7.1 Hz), 4.23 (m, 2H), 4.11 (d, 2H, J=6.3 Hz), 1.24 (t, 3H, J=7.1 Hz).

Step 3. Preparation of 6-chloro-7-(2-chlorobenzyl)-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 400.9984 (M–H, $C_{18}H_{10}Cl_2F_3O_3$, Calc'd 400.9954). $^1$HNMR (DMSO-$d_6$/400 MHz) 13.34 (brs, 1H), 7.79 (s, 1H), 7.64 (s, 1H), 7.27 (m, 2H), 7.11 (m, 1H), 6.66 (s, 1H), 5.88 (q, 1H, J=7.1 Hz), 4.1 (d, 2H, J=6.3 Hz).

EXAMPLE 9o

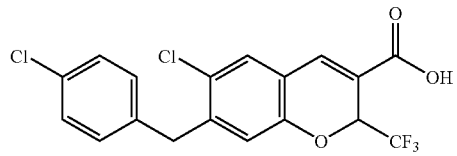

6-chloro-7-(4-chlorobenzyl)-2-(trifluoromethyl)-2H-chromene-3-carboxylic acid

Step 1. Preparation of ethyl 7-(4-chlorobenzyl)-2-(trifluoromethyl)-2H-chromene-3-carboxylate This compound was prepared and purified via a method similar to that described in Example 9n, Step 1 with the appropriate substitution of 4-chlorobenzylzinc chloride producing the ethyl ester (1.4 g, 70%) as a yellow solid. This ester was of suitable purity to use without further purification: ESLRMS m/z 397 (M+H).

Step 2. Preparation of ethyl 6-chloro-7-(4-chlorobenzyl)-2-(trifluoromethyl)-2H-chromene-3-carboxylate The ester (Step 1) was chlorinated via a method similar to that described in Example 4b, Step 1 (81%). This ester was of suitable purity to use without further purification: EILRMS m/z 430 (M+).

Step 3. Preparation of 6-chloro-7-(4-chlorobenzyl)-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 400.9993 (M−H, $C_{18}H_{10}Cl_2F_3O_3$, Calc'd 400.9954). $^1$HNMR (DMSO-$d_6$/400 MHz) 13.21 (brs, 1H), 7.82 (s, 1H), 7.61 (s, 1H), 7.33 (d, 2H, J=8.3 Hz), 7.20 (d, 2H, J=8.3 Hz), 7.03 (s, 1H), 5.91 (q, 1H, J=7.1 Hz), 4.00 (s, 2H).

EXAMPLE 9p

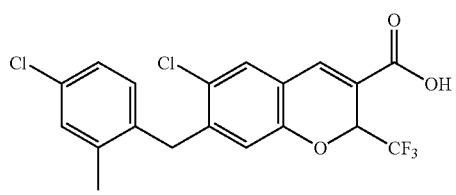

6-chloro-7-(4-chloro-2-methylbenzyl)-2-(trifluoromethyl)-2H-chromene-3-carboxylic acid Step 1. Preparation of (4-chloro-2-methylphenyl)(3-methoxyphenyl)methanone To a chilled stirred solution of 3-methoxybenzoyl chloride (5.0 g, 29.3 mmole) in acetone/water (3:1) was added 4-chloro-2-methylphenylboronic acid (5.0 g, 29.3 mmole) followed by PdCl$_2$ (0.259 g, 5 mole %) and sodium carbonate (23.87 mL, 47 mmole). The solution was allowed to stir at room temperature overnight. The reaction workup and purification was conducted according to Example 9a, Step 1 producing the title compound (5.8 g, 76%). This ester was of suitable purity to use without further purification: ESLRMS m/z 261.1 (M+H).

Step 2. Preparation of 3-(4-chloro-2-methylbenzyl)phenyl methyl ether

To a solution of the methyl ether, Step 1 (5.8 g, 22 mmole), in dichloromethane (15 mL) was added triethylsilane (14.2 mL, 88.9 mmole) followed by the addition of TFA (25.36 mL, 222 mmole). The solution was allowed to stir at room temperature overnight. The reaction was quenched into saturated HN$_4$Cl (aq), and extracted with dichloromethane (2×150 mL). The combined organic phases were washed with aqueous NaHCO$_3$ solution (2×50 mL), aqueous 3N HCl solution (2×50 mL), and brine (2×50 mL), dried over Na2SO$_4$, filtered, and concentrated in vacuo. The crude material was subjected to flash chromatography (Silica, 5% Ethyl acetate/Hexane). Desired fractions were collected and combined, removed solvent in vacuo producing the title compound (4.5 g, 82%) as a clear oil. This methyl ether was of suitable purity to use without further purification: ESLRMS m/z 247.1 (M+H).

Step 3. Preparation of 3-(4-chloro-2-methylbenzyl)phenol

To a chilled (−20° C.) stirred solution of the methyl ether, step 2 (3.01 g, 12 mmole) was added BBr$_3$ 1M in CH$_2$Cl$_2$ (121.99 mL, 121 mmole). The resulting solution was allowed to warm to room temperature and stir overnight. The reaction is cooled (−20° C.) and methanol was added via syringe. Solvent was removed in vacuo and the crude material was subjected to flash chromatography (Silica, 10% Ethyl acetate/Hexane). Desired fractions were collected and combined, removed solvent in vacuo producing the title compound (2.18 g, 77%) as a clear oil. This methyl ether was of suitable purity to use without further purification: EILRMS m/z 232 (M+).

Step 4. Preparation of 4-(4-chloro-2-methylbenzyl)-2-hydroxybenzaldehyde

The phenol (Step 3) was formylated via a method similar to that described in Example 9f, Step1: ESLRMS m/z 261.1 (M+H)

Step 5. Preparation of ethyl 7-(4-chloro-2-methylbenzyl)-2-(trifluoromethyl)-2H-chromene-3-carboxylate The aldehyde (Step 4) was condensed via a method similar to that described in Example 4a, Step 1. This aldehyde was of suitable purity to use without further purification: ESHRMS m/z 409.0862 (M−H, $C_{19}H_{13}ClF_3O_3$, Calc'd 409.0813).

Step 6. Preparation of ethyl 6-chloro-7-(4-chloro-2-methylbenzyl)-2-(trifluoromethyl)-2H-chromene-3-carboxylate The ester (Step 5) was chlorinated via a method similar to that described in Example 4b, Step 1 (68%). This ester was of suitable purity to use without further purification: ESLRMS m/z 445.2 (M+H).

Step 7. Preparation of 6-chloro-7-(4-chloro-2-methylbenzyl)-2-(trifluoromethyl)-2H-chromene-3-carboxylic acid The ester (Step 6) was hydrolyzed to form the carboxylic acid via a method similar to that described in Example 4a, Step 2 (99%): ESHRMS m/z 415.0119 (M−H, $C_{19}H_{12}Cl_2F_3O_3$, Calc'd 415.0110). $^1$HNMR (DMSO-$d_6$/400 MHz) 13.35 (brs, 1H), 7.81 (s, 1H), 7.65 (s, 1H), 7.27 (s, 1H), 7.17 (d, 1H, J=10.4 Hz), 6.9 (d, 1H, J=10.4 Hz), 6.65 (s, 1H), 5.88 (q, 1H, J=7.1 Hz), 3.96 (m, 2H), 2.17 (s, 3H).

EXAMPLE 9q

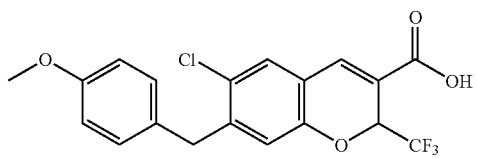

6-chloro-7-(4-methoxybenzyl)-2-(trifluoromethyl)-2H-chromene-3-carboxylic acid

Step 1. Preparation of ethyl 7-(4-methoxybenzyl)-2-(trifluoromethyl)-2H-chromene-3-carboxylate This compound was prepared and purified via a method similar to that described in Example 9n, Step 1 with the appropriate substitution of 4-chloro-2-methylbenzylzinc chloride producing the ethyl ester (2.95 g, 81%) as a yellow solid. This ester was of suitable purity to use without further purification: ESLRMS m/z 393.2 (M+H).

Step 2. Preparation of ethyl 6-chloro-7-(4-methoxybenzyl)-2-(trifluoromethyl)-2H-chromene-3-carboxylate The ester (Step 1) was chlorinated via a method similar to that described in Example 4b, Step 1 (62%). This ester was of suitable purity to use without further purification: ESLRMS m/z 427 (M+H).

Step 3. Preparation of 6-chloro-7-(4-methoxybenzyl)-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 397.0452 (M−H, $C_{19}H_{13}ClF_3O_4$, Calc'd 397.0449). $^1$HNMR (DMSO-$d_6$/400 MHz) 13.16 (brs, 1H), 7.78 (s, 1H), 7.35 (d, 1H, J=7.6 Hz), 7.29 (s, 1H), 7.15 (d, 1H, J=8.3 Hz), 7.03 (d, 1H, J=8.3 Hz), 6.89 (m, 2H), 5.83 (q, 1H, J=7.1 Hz), 3.83 (s, 2H), 3.67 (s, 3H).

EXAMPLE 9r

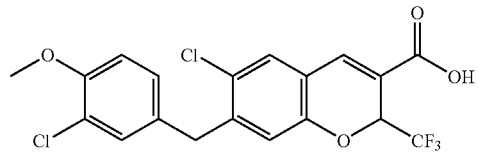

6-chloro-7-(3-chloro-4-methoxybenzyl)-2-(trifluoromethyl)-2H-chromene-3-carboxylic acid Step 1. Preparation of ethyl 6-chloro-7-(3-chloro-4-methoxybenzyl)-2-(trifluoromethyl)-2H-chromene-3-carboxylate The ester (Example 9q, Step 2) was chlorinated via a method similar to that described in Example 4b, Step 1 (23%). This ester was of suitable purity to use without further purification: ESLRMS m/z 461 (M+H).

Step 2. Preparation of 6-chloro-7-(3-chloro-4-methoxybenzyl)-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 431.0079 (M−H, $C_{19}H_{12}Cl_2F_3O_4$, Calc'd 431.0059). '$HNMR (DMSO-$d_6$/400 MHz) 13.32 (brs, 1H), 7.81 (s, 1H), 7.61 (s, 1H), 7.39 (s, 1H), 7.24 (d, 1H, J=2.0 Hz), 7.12 (d, 1H, J=2.0 Hz), 7.10 (d, 1H, J=2.0 Hz), 7.04 (t, 1H, J=8.0 Hz), 5.86 (q, 1H, J=7.1 Hz), 3.94 (s, 2H), 3.78 (s, 3H).

EXAMPLE 9s

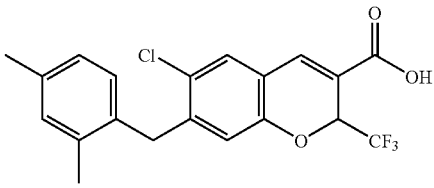

6-chloro-7-(2,4-dimethylbenzyl)-2-(trifluoromethyl)-2H-chromene-3-carboxylic acid Step 1. Preparation of (2,4-dimethylphenyl)(3-methoxyphenyl)methanone The title compound was coupled via a similar method to that described in Example 9p, Step 1 (89%). This ketone was of suitable purity to use without further purification: ESLRMS m/z 241 (M+H).

Step 2. Preparation of 3-(2,4-dimethylbenzyl)phenyl methyl ether

The ketone (Step 1) was reduced via a method similar to that described in Example 9p, Step 2 (92%). This methyl ether was of suitable purity to use without further purification: EILRMS m/z 226 (M+).

Step 3. Preparation of 3-(2,4-dimethylbenzyl)phenol

The methyl ether (Step 1) was deprotected via a method similar to that described in Example 9p, Step 3 (98%). This phenol was of suitable purity to use without further purification: EILRMS m/z 212 (M+).

Step 4. Preparation of 4-(2,4-dimethylbenzyl)-2-hydroxybenzaldehyde

The phenol (Step 3) was formylated via a method similar to that described in Example 9f, Step 1 (78%). This aldehyde was of suitable purity to use without further purification: ESLRMS m/z 241 (M+H).

Step 5. Preparation of ethyl 7-(2,4-dimethylbenzyl)-2-(trifluoromethyl)-2H-chromene-3-carboxylate The aldehyde (Step 4) was condensed via a method similar to that described in Example 4a, Step 1. This aldehyde was of suitable purity to use without further purification: ESLRMS m/z 391 (M+H).

Step 6. Preparation of ethyl 6-chloro-7-(2,4-dimethylbenzyl)-3 8a-dihydro-2H-chromene-3-carboxlate The ester (Step 5) was chlorinated via a method similar to that described in Example 4b, Step 1 (83%). This ester was of suitable purity to use without further purification: ESLRMS m/z 425 (M+H).

Step 7. Preparation of 6-chloro-7-(2,4-dimethylbenzyl)-2-(trifluoromethyl)-2H-chromene-3-carboxylic acid The ester (Step 6) was hydrolyzed to form the carboxylic acid via a method similar to that described in Example 4a, Step 2 (99%): ESHRMS m/z 395.0676 (M−H, $C_{20}H_{15}ClF_3O_3$, Calc'd 395.0656). $^1$HNMR (DMSO-$d_6$/400 MHz) 13.25 (s, 1H), 7.81 (s, 1H), 7.64 (s, 1H), 7.00 (s, 1H), 6.92 (d, 1H, J=8.0 Hz), 6.81 (d, 1H, J=7.7 Hz), 6.53 (s, 1H), 5.86 (q, 1H, J=7.1 Hz), 3.91 (s, 2H), 2.22 (s, 3H), 2.10 (s, 3H).

EXAMPLE 9t

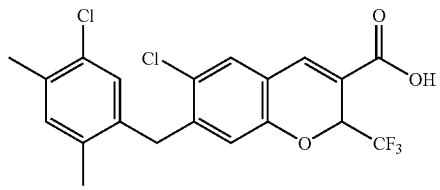

6-chloro-7-(5-chloro-2,4-dimethylbenzyl)-2-(trifluoromethyl)-2H-chromene-3-carboxylic acid Step 1. Preparation of ethyl 6-chloro-7-(5-chloro-2,4-dimethylbenzyl)-2-(trifluoromethyl) 2H-chromene-3-carboxylate The ester (Example 9s, Step 4) was chlorinated via a method similar to that described in Example 4b, Step 1 (18%). This ester was of suitable purity to use without further purification: ESLRMS m/z 459 (M+H).

Step 2. Preparation of 6-chloro-7-(5-chloro-2,4-dimethylbenzyl)-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 429.0290 (M−H, $C_{20}H_{14}Cl_2F_3O_3$, Calc'd 429.0267). $^1$HNMR (DMSO-$d_6$/400 MHz), 13.25 (s, 1H), 7.82 (s, 1H), 7.66 (s, 1H), 7.17 (s, 1H), 6.91 (s, 1H), 6.64 (s, 1H), 5.89 (q, 1H, J=7.1 Hz), 3.93 (s, 2H), 2.23 (s, 3H), 2.10 (s, 3H).

EXAMPLE 9u

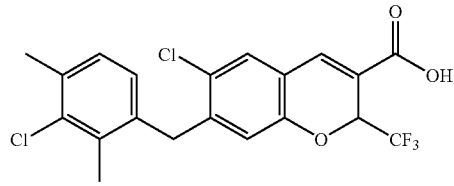

6-chloro-7-(3-chloro-2,4-dimethylbenzyl)-2-(trifluoromethyl)-2H-chromene-3-carboxylic acid Step 1. Preparation of ethyl 6-chloro-7-(3-chloro-2.4-dimethylbenzyl)-2-(trifluoromethyl)-2H-chromene-3-carboxylate The ester (Example 9s, Step 4) was chlorinated via a method similar to that described in Example 4b, Step 1 (23%). This ester was of suitable purity to use without further purification: ESLRMS m/z 459 (M+H).

Step 2. Preparation of 6-chloro-7-(3-chloro-2,4-dimethylbenzyl)-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 429.0259 (M−H, $C_{20}H_{14}Cl_2F_3O_3$, Calc'd 429.0267). '$HNMR (DMSO-$d_6$/400 MHz) 13.39 (sbrs, 1H), 7.82 (s, 1H), 7.66 (s, 1H), 7.17 (s, 1H), 6.91 (s, 1H), 6.94 (s, 1H), 5.88 (q, 1H, J=7.1 Hz), 3.98 (s, 2H), 2.23 (s, 1H), 2.10 (s, 1H).

EXAMPLE 9v

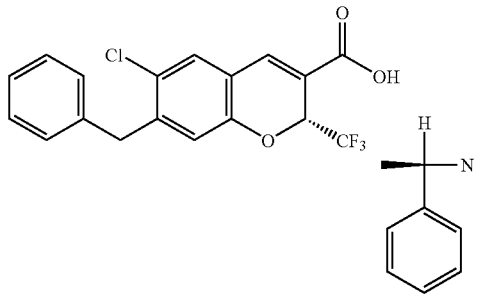

(2R)-7-benzyl-6-chloro-2-(trifluoromethyl)-2H-chromene-3-carboxylic acid compound with (1R)-1-phenylethanamine (1:1)

(2R)-7-benzyl-6-chloro-2-(trifluoromethyl)-2H-chromene-3-carboxylic acid from Example 91 (50 mg, 0.135 mmole) was dissolved into 1% Ethyl Acetate/Hexane (2 mL). (R)-(+)-α-methylbenzylamine (0.017 mL, 0.135 mmole) was added and the solution was allowed to stand at room temperature for 1 week until crystals appeared. Absolute configuration was determined by small molecule x-ray diffraction.

EXAMPLE 9w

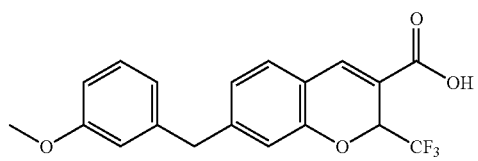

7-(3-methoxybenzyl)-2-(trifluoromethyl)-2H-chromene-3-carboxylic acid

Step 1. Preparation of ethyl 7-(3-methoxybenzyl)-2-(trifluoromethyl)-2H-chromene-3-carboxylate This compound was prepared and purified via a method similar to that described in Example 9n, Step 1 with the appropriate substitution of 3-methoxybenzylzinc chloride producing the ethyl ester (2.95 g, 81%) as a yellow solid. This ester was of suitable purity to use without further purification: ESLRMS m/z 393 (M+H).

Step 2. Preparation of 7-(3-methoxybenzyl)-2-(trifluoromethyl)-2H-chromene-3-carboxylic acid The ester (Step 2) was hydrolyzed to form the carboxylic acid via a method similar to that described in Example 4a, Step 2 (99%): ESHRMS m/z 363.0827 (M−H, $C_{19}H_{14}F_3O_4$, Calc'd 363.0839). $^1$HNMR (DMSO-$d_6$/400 MHz) 13.17 (brs, 1H), 7.78 (s, 1H), 7.35 (d, 1H, J=7.7 Hz), 7.17 (t, 1H, J=7.9 Hz), 6.89 (m, 2H), 6.74 (m, 3H), (q, 1H, J=7.1 Hz), 3.86 (s, 2H), 3.68 (s, 3H).

EXAMPLE 9x

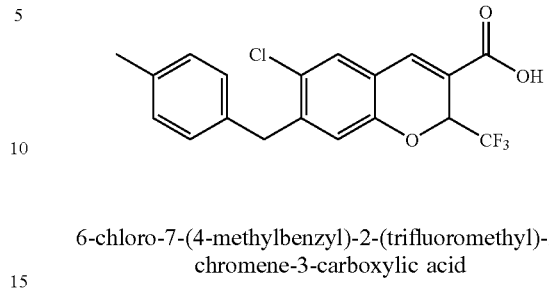

6-chloro-7-(4-methylbenzyl)-2-(trifluoromethyl)-2H-chromene-3-carboxylic acid

Step 1. Preparation of ethyl 7-(4-methylbenzoyl)-2-(trifluoromethyl)-2H-chromene-3-carboxylate The ethyl 7-iodo-2-(trifluoromethyl)-2H-chromene-3-carboxylate from Example 9a, Step 2 (3.0 g, 7.53 mmol), 4-methylphenylboronic acid (1.11 g, 8.26 mmol), $K_2CO_3$ (3.12 g, 22.59 mmol), and $PdCl_2(PPh_3)_2$ (159 mg, 0.225 mmol) were mixed in dioxane (30 mL) in a sterling bomb. Carbon monoxide was bubbling to 40 psi. The reaction was heated to 80° C. for 5 h. After filtration, the reaction was quenched with NH4Cl and extracted with EtOAc. The organic layer was washed and dried over $MgSO_4$. The filtrate was evaporated and dried in vacuo to afford yellow solid (1.2 g, 41%): LCMS m/z 391.10 (M+H). $^1$H NMR (CDCl$_3$/400 MHz) 7.75 (s, 1H), 7.69 (d, 2H, J=8.0 Hz), 7.39(d, 1H, J=8.0 Hz), 7.36 (s, 1H), 7.31 (d, 1H, J=8.0 Hz), 7.28 (d, 2H, J=8.0 Hz), 7.25(s, 1H), 5.78 (q, 1H, J=6 Hz), 4.33 (m, 2H), 2.43(s, 3H), 1.35 (t, 3H, J=7.2 Hz).

Step 2. Preparation of ethyl 7-(4-methylbenzyl)-2-(trifluoromethyl)-2H-chromene-3-carboxylate The ester from Step 1 was dissolved in TFA (18 mL). Et$_3$SiH was added dropwise at room temperature. The reaction was stirred at room temperature overnight. The reaction was quenched with NaHCO$_3$ and extracted with ether. The organic layer was dried over MgSO$_4$. The filtrate was concentracted to give yellow oil, which was purified by Biotage with 3-5% EtOAc in hexane to give clear oil quantity: LCMS m/z 377.15 (M+H). $^1$H NMR (CDCl$_3$/400 MHz) 7.68 (s, 1H), 7.08 (m, 4H), 6.79 (d, 1H, J=6.4 Hz), 5.68 (q, 1H, J=7.2 Hz), 4.29 (m, 2H), 3.89 (s, 2H), 2.31 (s, 3H), 1.35 (t, 3H, J=7.2 Hz).

Step 3. Preparation of ethyl 6-chloro-7-(4-methylbenzyl)-2-(trifluoromethyl)-2H-chromene-3-carboxylate Sodium acetate (1.03 g, 12.6 mmol) was added to a solution of the ester from Step 2 (0.95 g, 2.53 mmole) in acetic acid (30 mL). Cl$_2$ (gas) was bubbling to the above solution until see the precipitate. The mixture was stirred for 2 hour. After Cl$_2$ (gas) was blowed away, Zn (5 eq) was added to the mixture and stirred for 30 min. Zn salt was removed and the filtrate was evaporated to give yellow oil (1.0 g, 97%): LCMS for mono-Cl$C_{21}H_{18}O_3F_3$Cl, 409.10 (M+H) and for di-Cl$C_{121}H_{17}O_3F_3Cl_2$, (M+H)443.05. This ester was of suitable purity to use without further purification.

Step 4. Preparation of 6-chloro-7-(4-methylbenzyl)-2-(trifluoromethyl)-2H-chromene-3-carboxylic acid The ester from Step 3 (1.0 g, 2.44 mmole) was dissolved in 4.0 mL methanol and 4.0 mL THF. Sodium hydroxide (2.5 N) (2.4 mL, 6.1 mmole) was added to above solution and stirred at 50° C. for 6 h. The crude was purified by RPHPLC with 60% ACN in water to afford a offwhite solid (0.324 g, 35%): ESHRMS m/z 391.0474 (M−H, $C_{19}H_{13}O_3F_3Cl$, Calc'd 381.0500). $^1$H NMR (acetone-$d_6$/400 MHz) 7.87 (s, 1H), 7.56 (s, 1H), 7.13 (m 4H), 6.91 (s, 1H), 5.80 (q, 1H, J=7.0 Hz), 4.07 (d, 1H, J=14.7 Hz), 4.01 (d, 1H, J=14.7 Hz), 2.27 (s, 3H).

EXAMPLE 9y

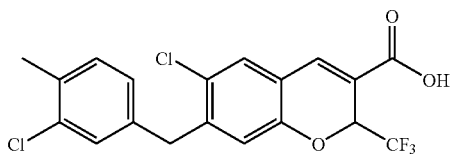

6-chloro-7-(3-chloro-4-methylbenzyl)-2-(trifluoromethyl)-2H-chromene-3-carboxylic acid The 6-chloro-7-(3-chloro-4-methylbenzyl)-2-(trifluoromethyl)-2H-chromene-3-carboxylic acid as prepared by same procedure as Example 9p, Step 4: ESHRMS m/z 415.0087 (M−H, $C_{19}H_{12}O_3F_3Cl_2$, Calc'd 415.0110). $^1$H NMR (acetone-$d_6$/400 MHz) 7.87 (s, 1H), 7.57 (s, 1H), 7.28 (m 2H), 7.13 (m, 1H), 6.99 (s, 1H), 5.83 (q, 1H, J=7.0 Hz), 4.08 (m, 2H), 2.30 (s, 3H).

EXAMPLE 9z

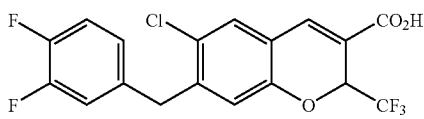

6-chloro-7-(3,4-difluorobenzyl)-2-(trifluoromethyl)-2H-chromene-3-carboxylic acid Step 1. Preparation of ethyl 7-(3,4-difluorobenzyl)-2-(trifluoromethyl)-2H-chromene-3-carboxylate A solution of Pd(dba)$_2$ (57.5 mg, 0.100 mmole) and tfp (46.7 mg, 0.201 mmole) in anhydrous THF (10.0 mL) was stirred at room temperature for 20 minutes and then cooled to 0° C. Ethyl 7-iodo-2-(trifluoromethyl)-2H-chromene-3-carboxylate prepared as in Example 9a, Step 2 (2.00 g, 5.02 mmole) was added as a solid, followed by a solution of 3,4-difluorobenzyl zinc bromide in anhydrous THF (20.0 mL-0.5 M, 0.100 mmole) added dropwise over 5 minutes. The mixture was stirred at 0° C. for 0.5 h, then at room temperature for 24 h and was then poured into sat. NH$_4$Cl (100 mL) and extracted with EtOAc (2×200 mL). The combined extracts were washed with brine (50 mL), dried over MgSO$_4$, filtered and concentrated in vacuo to give 3.45 g of an orange oil. The crude product was purified by silica chromatography (92.5:7.5 hexanes:EtOAc) to give 1.81 g (91 % yield) of the product as a yellow oil: EIHRMS m/z 398.0955 (M+, $C_{20}H_{15}F_5O_3$, Calc'd 398.0941).

Step 2. Preparation of ethyl 6-chloro-7-(3,4-difluorobenzyl)-2-(trifluoromethyl)-2H-chromene-3-carboxylate To a solution of the ester prepared as in Step 1 (0.920 g, 2.31 mmole) in glacial acetic acid (50 mL) was added Cl$_2$ gas for 1 minute. After standing for 25 minutes at room temperature, the solvent was removed in vacuo and the residue was redissolved in glacial acetic acid (50 mL). Powdered zinc (0.250 g, 3.82 mmole) was added and the mixture was stirred for 20 minutes. The solid was removed by filtration and the filtrate was concentrated in vacuo to give a crystalline solid. The crude product was purified by recrystallization from EtOAc-hexanes to give 0.95 g (95% yield) of the product as colorless needles: EIHRMS m/z 432.0573 (M+, $C_{20}H_{14}ClF_5O_3$, Calc'd 432.0552).

Step 3. Preparation of 6-chloro-7-(3,4-difluorobenzyl)-2-(trifluoromethyl)-2H-chromene-3-carboxylic acid To a solution of the ester prepared as in Step 2 (0.84 g, 1.94 mmole) in a 7:2:1 THF:EtOH:H$_2$O mixture (10 mL) was added LiOH.H$_2$O (0.122 g, 2.91 mmole). The mixture was stirred at 50° C. for 75 minutes and the solvent was removed in vacuo. The residue was redissolved in H$_2$O, filtered and acidified with 1 N HCl. The resulting solid was filtered, washed with H$_2$O and dried in vacuo to give 763 mg (97% yield) of the product as an off-white solid: $^1$H NMR (dmso-$d_6$/300 MHz) 13.40 (brs, 1H), 7.80 (s, 1H), 7.62 (s, 1H), 7.24-7.39 (m, 2H), 7.00-7.05 (m, 2H), 5.92 (q, 1H, J=7.3 Hz), 4.01 (s, 2H); ESHRMS m/z 403.0140 (M−H, $C_{18}H_9ClF_5O_3$, Calc'd 403.0155).

EXAMPLE 9aa

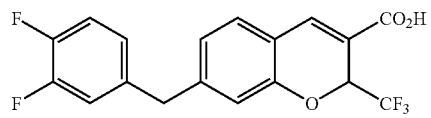

7-(3,4-difluorobenzyl)-2-(trifluoromethyl)-2H-chromene-3-carboxylic acid

The 7-(3,4-difluorobenzyl)-2-(trifluoromethyl)-2H-chromene-3-carboxylic acid was prepared by the method similar to that described in Example 9z, Step 3 to give the product as a yellow solid using the ester from Example 9z, Step 1 as a starting material: $^1$H NMR (dmso-$d_6$/300 MHz) 13.18 (brs, 1H), 7.28-7.80 (m, 3H), 7.06-7.10 (m, 1H), 6.91-6.93 (m, 2H), 5.85 (q, 1H, J=7.3 Hz), 3.91 (s, 1H); ESHRMS m/z 369.0545 (M−H, $C_{18}H_{10}F_5O_3$, Calc'd 369.0516).

EXAMPLE 9bb

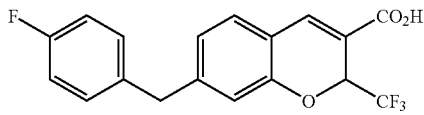

7-(4-fluorobenzyl)-2-(trifluoromethyl)-2H-chromene-3-carboxylic acid

Step 1. Preparation of ethyl 7-(4-difluorobenzyl)-2-(trifluoromethyl)-2H-chromene-3-carboxylate A solution of Pd(dba)$_2$ (53.7 mg, 0.0934 mmole) and tfp (43.3 mg, 0.187 mmole) in anhydrous THF (8.0 mL) was stirred at room temperature for 5 minutes and then cooled to 0° C. Ethyl 7-iodo-2-(trifluoromethyl)-2H-chromene-3-carboxylate prepared as in Example 9a, Step 2 (1.86 g, 4.67 mmole) was added as a solution in anhydrous THF (7.0 mL), followed by a solution of 4-difluorobenzyl zinc chloride in anhydrous THF (14.0 mL-0.5 M, 0.700 mmole). The mixture allowed to warm room temperature. After stirring for 17.5 h, additional 4-difluorobenzyl zinc chloride (10.0 mL-0.5 M/THF, 0.500 mmole) was added at room temperature and stirring was continued for 45 minutes. Additional 4-difluorobenzyl zinc chloride (5.0 mL-0.5 M/THF, 0.250 mmole) was added at room temperature and stirring was continued until disappearance of starting material. The mixture was then poured into sat. NH$_4$Cl (100 mL) and extracted with EtOAc (2×200 mL). The combined extracts were washed with brine (50 mL), dried over MgSO$_4$, filtered and concentrated in vacuo to give 2.41 g of a red-brown oil. The crude product was purified by silica chromatography (9:1 hexanes:EtOAc) to give 1.58 g (89% yield) of the product as a yellow oil: E1HRMS m/z 380.0999 (M+, C$_{20}$H$_{16}$F$_4$O$_3$, Calc'd 380.1036).

Step 2. Preparation of 7-(4-difluorobenzyl)-2-(trifluoromethyl)-2H-chromene-3-carboxylic acid The ester prepared in Step 1 was hydrolyzed via a method similar to that described in Example 9x, Step 3 to give the product as a white crystalline solid: $^1$H NMR (dmso-d$_6$/300 MHz) 13.18 (brs, 1H), 7.80 (s, 1H), 7.37 (d, 1H, J=7.7 Hz), 7.24-7.29 (m, 2H), 7.07-7.14 (m, 2H), 6.88-6.91 (m, 2H), 5.85 (q, 1H, J=7.3 Hz), 3.91 (s, 1H); ESHRMS m/z 351.0623 (M-H, C$_{18}$H$_{11}$F$_4$O$_3$, Calc'd 351.0639).

EXAMPLE 10

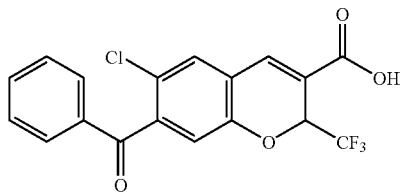

7-benzoyl-6-chloro-2-(trifluoromethyl)-2H-chromene-3-carboxylic acid

Step 1. Preparation of 7-benzoyl-6-chloro-2-(trifluoromethyl)-2H-chromene-3-carboxylic acid The acid (100 mg, 0.271 mmole) Example 9K, Step 3 was dissolved into Acetic Acid (glacial) (10 mL). Chromic Anhydride$_{(s)}$ (5 eq) was added. The reaction was heated to 90° C. for 1 h. the reaction was cooled to 0° C. and diluted with water (100 mL), extracted with Ethyl Acetate (2×50 mL), combined and washed the organic layer with brine (2×25 mL) followed by NaHCO$_3$ (2×50 mL). The organic was dried over Na$_2$SO$_4$, filtered and concentrated in vacuo. The solid was subjected to reverse phase chromatography eluting with ACN/water (gradient 5 to 95 ACN). Collected and combined desired fractions, concentrated in vacuo producing the benzyl ketone (22 mg, 21%): ESHRMS m/z 381.0138 (M-H, C$_{18}$H$_9$ClF$_3$O$_4$, Calc'd 381.0136).

EXAMPLE 11

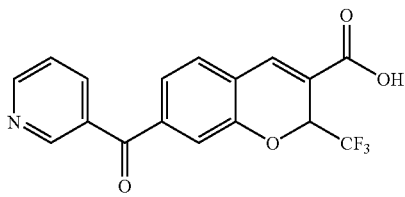

7-(pyridin-3-ylcarbonyl)-2-(trifluoromethyl)-2H-chromene-3-carboxylic acid

Step 1. Preparation of ethyl 7-(pyridin-3-ylcarbonyl)-2-(trifluoromethyl)-2H-chromene-3-carboxylate The ethyl 7-iodo-2-(trifluoromethyl)-2H-chromene-3-carboxylate from Example 9a, Step 2 (1.0 g, 2.51 mmol), pyridin-3-ylboronic acid (0.34g, 2.76 mmol), K$_2$CO$_3$ (1.04 g, 7.53 mmol), and PdCl$_2$(PPh$_3$)$_2$ (53 mg, 0.075 mmol) were mixed in dioxane (10 mL) in a sterling bomb. The reactor was charged withcarbon monoxide (40 psi). The reaction was heated to 80° C. for 6 h then room temperature overnight. After filtration, the reaction was quenched with NH$_4$Cl and extracted with EtOAc. The organic layer was washed and dried over MgSO$_4$. The filtrate was evaporated and dried in vacuo to afford crude which was purified by RPHPLC with 50 to 95% ACN in water to give yellow solid (39 mg, 4%): LCMS m/z 378.10 (M+H). $^1$H NMR (CDCl$_3$/400 MHz) 9.08 (s, 1H), 8.97 (d, 1H, J=5.2 Hz), 8.48 (d, 1H, J=8.0 Hz), 7.81 (dd, 1H, J=7.6, 5.2 Hz), 7.75 (s, 1H), 7.40 (m, 3H), 5.76 (q, 1H, J=6 Hz), 4.34 (m, 2H), 1.36 (t, 3H, J=7.2 Hz).

Step 2. Preparation of 7-(pyridin-3-ylcarbonyl)-2-(trifluoromethyl)-2H-chromene-3-carboxylic acid The ester from Step 1 (38 mg, 0.08 mmole) was dissolved in 0.5 mL methanol and 0.5 mL THF. Sodium hydroxide (2.5 N) (0.2 mL, 0.5 mmole) was added to above solution and stirred at 50° C. for 4 h. The crude was purified by RPHPLC with 45% ACN in water to afford a white solid (15 mg, 41%):

LCMS m/z 350.05 (M+H). $^1$H NMR (DMSO-$d_6$/400 MHz) 8.87 (s, 1H), 8.83 (d, 1H, J=6.8 Hz), 8.11 (d, 1H, J=10.4 Hz), 7.94 (s,1H), 7.69 (d, 1H, J=14 Hz), 7.60 (m, 1H), 7.42 (d, 1H, J=10.4 Hz), 7.34 (s, 1H), 6.03 (q, 1H, J=9.6 Hz).

EXAMPLE 12

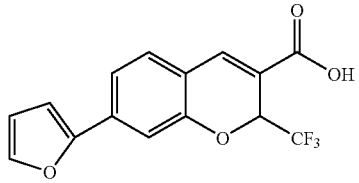

7-(2-furyl)-2-(trifluoromethyl)-2H-chromene-3-carboxylic acid

Step 1. Preparation of ethyl 7-(2-furyl)-2-(trifluoromethyl)-2H-chromene-3-carboxylate The ethyl 7-iodo-2-(trifluoromethyl)-2H-chromene-3-carboxylate from Example 9a, Step 2 (2.0 g, 5.02 mmol), 2-furylboronic acid (0.62 g, 5.52 mmol), $K_2CO_3$ (2.08 g, 15.06 mmol), and $PdCl_2(PPh_3)_2$ (106 mg, 0.15 mmol) were mixed in dioxane (20 mL) in a sterling bomb. Carbon monoxide was bubbling to 40 psi. The reaction was heated to 80° C. for 12 h. After filtration, the reaction was quenched with $NH_4Cl$ and extracted with EtOAc. The organic layer was washed and dried over $MgSO_4$. The filtrate was evaporated and dried in vacuo to afford crude which was purified Biotage Chromatography with 10 to 20% ethyl acetate in hexane to give yellow solid (350 mg, 21%): LCMS m/z 339.05 (M+H). $^1$H NMR (CDCl$_3$/300 MHz) 7.74 (s, 1H), 7.51 (s, 1H), 8.97 (m, 3H), 6.76 (d, 1H, J=3.3 Hz), 6.51 (m, 1H), 5.73 (q, 1H, J=6.9 Hz), 4.34 (m,2H), 1.36 (t, 3H, J=7.2 Hz).

Step 2. Preparation of 7-(pyridin-3-ylcarbonyl)-2-(trifluoromethyl)-2H-chromene-3-carboxylic acid The ester from Step 1 (340 mg, 1.0 mmole) was dissolved in 2.5 mL methanol and 2.5 mL THF. Sodium hydroxide (2.5 N) (1.0 mL, 2.5 mmole) was added to above solution and stirred at 50° C. for 4 h. The crude was purified by RPHPLC with 45% ACN in water to afford a white solid (293 mg, 95%): ESHRMS m/z 309.0320 (M−H, $C_{15}H_8O_4F_3N$, Calc'd 309.0369). $^1$H NMR (DMSO-$d_6$/400 MHz) 7.88 (s, 1H), 7.69 (d, 1H, J=1.6 Hz), 7.50 (d, 1H, J=8.0 Hz), 7.44 (dd, 1H, J=8.0, 1.3 Hz), 7.34 (s, 1H), 7.05 (d, 1H, J=2.4 Hz), 6.59 (m, 1H), 7.34 (s, 1H), 5.82 (q, 1H, J=7.2 Hz).

EXAMPLE 13

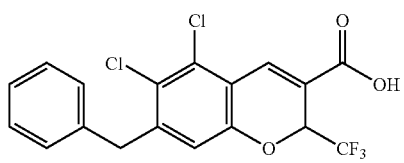

7-benzyl-5,6-dichloro-2-(trifluoromethyl)-2H-chromene-3-carboxylic acid

Step 1. Preparation of ethyl 7-benzyl-5,6-dichloro-2-(trifluoromethyl)-2H-chromene-3-carboxylate The ester (Example 9k, Step 2) was chlorinated via a method similar to that described in Example 4b, Step 1 (18%). This ester was of suitable purity to use without further purification. ESLRMS m/z 431 (M+H).

Step 2. Preparation of 7-benzyl-5.6-dichloro-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 400.9947 (M−H, $C_{18}H_{10}Cl_2F_3O_3$, Calc'd 400.9954). $^1$HNMR (DMSO-$d_6$/400 MHz) 13.12 (brs, 1H), 7.67 (s, 1H), 7.25 (m, 2H), 7.18 (m, 3H), 7.09 (s, 1H), 6.14 (q, 1H, J=7.1 Hz), 4.04 (s, 2H).

EXAMPLE 14a

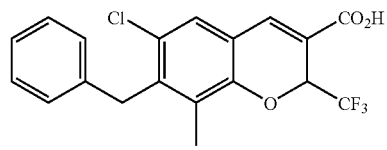

7-benzyl-6-chloro-8-methyl-2-(trifluoromethyl)-2H-chromene-3-carboxylic acid

Step 1. Preparation of 3-benzoyl-2-methylphenyl acetate

A mixture of 3-(chlorocarbonyl)-2-methylphenyl acetate (10.0 g, 47.0 mmole), $PdCl_2$ (83.4 mg, 0.470 mmole), $Na_2CO_3$ (8.13 g, 76.7 mmole) and phenyl boronic acid (6.02 g, 49.4 mmole) in a 3:1 acetone:$H_2O$ mixture (300 mL) was stirred at room temperature for 5 days. The acetone was removed in vacuo and the aqueous mixture was extracted with EtOAc (2×200 mL). The combined extracts were washed with brine (100 mL), dried over $MgSO_4$, filtered and concentrated in vacuo to give 7.68 g (64% yield) of the product as a white crystalline solid: E1HRMS m/z 254.0939 (M+, $C_{16}H_{14}O_3$, Calc'd 254.0943).

Step 2. Preparation of (3-hydroxy-2-methylphenyl)(phenyl)methanone

A mixture of 3-benzoyl-2-methylphenyl acetate prepared as in Step 1 (6.85 g, 26.9 mmole) and KOH (15.0 g, 267 mmole) in $H_2O$ (100 mL) was stirred at room temperature for 18 h. The aqueous mixture was then washed with ethyl ether (3×200 mL), cooled to 0° C. and acidified with con. HCl. The resulting solid was filtered, washed with $H_2O$ and dried in vacuo to give 0.99 g (17% yield) of the product as an off-white crystalline solid: EIHRMS m/z 212.0829 (M+, $C_{14}H_{12}O_2$, Calc'd 212.0837).

Step 3. Preparation of 3-benzyl-2-methylphenol

A solution of (3-hydroxy-2-methylphenyl)(phenyl)methanone prepared as in Step 2 (1.60 g, 7.54 mmole) in anhydrous $CH_2Cl_2$ (70 mL) was cooled to 0° C. Triethylsilane (32.5 mL, 203 mmole) and TFA (52.3 mL, 679 mmole) were added in portions at 0° C. over a period of 3 days with the mixture brought back to reflux after each addition. After 3 days, the mixture was cooled, poured into sat. $NH_4Cl$ (200 mL) and extracted with $CH_2Cl_2$ (3×200 mL). The combined extracts were washed with $H_2O$ (200 mL), brine (100 mL), dried over $MgSO_4$, filtered and concentrated in vacuo to give a yellow oil. The crude product was purified by silica chromatography (95:5 hexanes:EtOAc) to give 1.19 g (80% yield) of the product as a pale yellow oil: EIHRMS m/z 198.1072 (M+, $C_{14}H_{14}O$, Calc'd 198.1045).

Step 4. Preparation of 4-benzyl-2-hydroxy-3-methylbenzaldehyde

To a solution of 3-benzyl-2-methylphenol prepared as in Step 3 (1.06 g, 5.36 mmole) in anhydrous acetonitrile (25 mL) were added $MgCl_2$ (0.776 g, 8.04 mmole), TEA (2.80 mL, 20.1 mmole) and paraformaldehyde (1.09 g, 36.2 mmole), and the resulting mixture was refluxed under a dry $N_2$ atmosphere for 3 h. The mixture was then cooled, acidified with 1 N HCl and extracted with EtOAc (2×100 ml). The combined extracts were washed with brine (100 ml), dried over $MgSO_4$, filtered and concentrated in vacuo to give 1.10 g (91% yield) of the product as a pale yellow oil: EIHRMS m/z 226.1008 (M+, $C_{15}H_{14}O_2$, Calc'd 226.0994).

Step 5. Preparation of ethyl 7-benzyl-8-methyl-2-(trifluoromethyl)-2H-chromene-3-carboxylate A mixture of 4-benzyl-2-hydroxy-3-methylbenzaldehyde prepared as in Step 4 (1.07 g, 4.73 mmole), $K_2CO_3$ (0.654 g, 4.73 mmole) and ethyl 444-trifluocrotonate (484 uL, 5.67 mmole) in anhydrous DMF (5.0 mL) was heated to 85° C. under a dry $N_2$ atmosphere for 2.75 h. The mixture was then cooled, poured into 1N HCl (100 ml) and extracted with EtOAc (2×100 mL). The combined extracts were washed with brine (100 mL), dried over $MgSO_4$, filtered and concentrated in vacuo to give 1.86 g of a yellow oil. The crude product was purified by silica chromatography (95:5 hexanes:EtOAc) to give 1.04 g (59% yield) of the product as a light yellow oil: EIHRMS m/z 376.1310 (M+, $C_{21}H_{19}F_3O_3$, Calc'd 376.1286).

Step 6. Preparation of ethyl 7-benzyl-8-methyl-2-(trifluoromethyl)-2H-chromene-3-carboxylate The ester prepared in Step 5 was chlorinated via a method similar to that described in Example 9z, Step 2 to give the product as a pale yellow crystalline solid: EIHRMS m/z 410.0928 (M+, $C_{15}H_{14}O_2$, Calc'd 410.0897).

Step 7. Preparation of 7-benzyl-6-chloro-8-methyl-2-(trifluoromethyl)-2H-chromene-3-carboxylic acid The ester prepared in Step 6 was hydrolyzed via a method similar to that described in Example 9z, Step 3 to give the crude product a white solid. Purification by recrystallization from IPA-EtOH-$CH_2Cl_2$-hexanes gave the product as a pale yellow solid: ESHRMS m/z 381.0545 (M−H, $C_{19}H_{13}ClF_3O_3$, Calc'd 381.0500). $^1H$ NMR (dmso-$d_6$/300 MHz) 13.35 (brs, 1H), 7.84 (s, 1H), 7.57 (s, 1H), 7.14-7.28 (m, 3H), 7.02-7.04 (m, 2 H), 5.96 (q, 1H, J=7.3 Hz), 4.17 (m, 2H), 2.10 (s, 3H).

EXAMPLE 14b

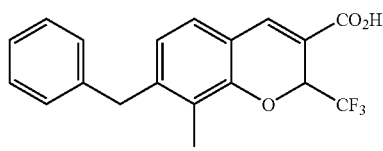

7-benzyl-8-methyl-2-(trifluoromethyl)-2H-chromene-3-carboxylic acid

Ethyl 7-benzyl-8-methyl-2-(trifluoromethyl)-2H-chromene-3-carboxylate prepared as in Example 14a, Step 5 was hydrolyzed via a method similar to that described in Example 18a, Step 2 to give the product as an off-white solid: ESHRMS m/z 347.0879 (M−H, $C_{19}H_{14}F_3O_3$, Calc'd 347.0890). $^1H$ NMR (dmso-$d_6$/300 MHz) 13.15 (brs, 1H), 7.80 (s, 1H), 7.10-7.29 (m, 6H), 6.85 (d, 1H, J=7.7 Hz), 5.89 (q, 1H, J=7.3 Hz), 3.97 (s, 2H), 2.07 (s, 3H).

EXAMPLE 16

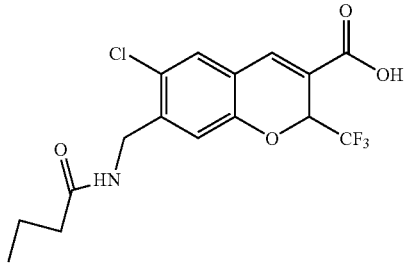

7-[(butyrylamino)methyl]-6-chloro-2-(trifluoromethyl)-2H-chromene-3-carboxylic acid

Step 1. Preparation of ethyl 7-methyl-2-(trifluoromethyl)-2H-chromene-3-carboxylate A mixture of 2-hydroxy 4-methyl benzaldehyde (50.0 g, 0.367 mole) and ethyl 4,4,4-trifluorocrotonate (308.8 g, 1.84 mole) was dissolved in anhydrous DMF (10 mL) and $Et_3N$ (20 mL) warmed to 60° C. and treated with anhydrous $K_2CO_3$ (81 g, 0.58 mole). The solution was maintained at 90° C. for 2 hours, LCMS indicated 60% converting. Additional $Et_3N$ (10 mL) was added to the mixture and the reaction was heated for another 2 hr. The reaction was cooled to room temperature, and diluted with water. The solution was extracted with ethyl acetate. The combined extracts were washed with brine, dried over anhydrous $MgSO_4$, filtered and concentrated in vacuo to afford a brown oil, solidify upon standing. The crystalline solid was collected and washed with hexane and dried to give 40.2 g off white crystalline solid. The mother liquor was concentrated to give crude, which was recrystalized from EtOH and water to give 48.5 g offwhite solid (totally yield 84%): LCMS m/z 287.15 (M+H). $^1$H NMR (CDCl$_3$/300 MHz) 7.70 (s, 1H), 7.11 (d, 1H, J=8.1 Hz), 6.80 (m, 2H), 5.67 (q, 1H, J=6 Hz), 4.29 (in, 2H), 1.33 (t, 3H, J=7.2 Hz).

Step 2. Preparation of ethyl 6-chloro-7-methyl-2-(trifluoromethyl)-2H-chromene-3-carboxylate The ethyl 6-chloro-7-methyl-2-(trifluoromethyl)-2H-chromene-3-carboxylate was prepared by the procedure similar to that described in Example 1a, Step 2. After recrystalization in EtOH to give white crystalline compound (3.6 g, 80%): LCMS m/z 321.25 (M+H). $^1$H NMR (CDCl$_3$/400 MHz) 7.62 (s, 1H), 7.18 (s, 1H), 6.85 (s, 1H), 5.67 (q, 1H, J=6.8 Hz), 4.30 (q, 2H, J=7.2 Hz), 1.33 (t, 3H, J=7.2 Hz).

Step 3. Preparation of ethyl 7-(bromomethyl)-6-chloro-2-(trifluoromethyl)-2H-chromene-3-carboxylate The ester from Step 2 (2.0 g, 6.24 mmole) was dissolved in CCl$_4$ (10 mL) and the solution was heated. NBS and (BzO)$_2$ were added to the above warm solution and the reaction was heated to reflux overnight. The reaction was cooled down and solid was filtered off. The filtrate was washed with NaHCO$_3$ and brine. The organic layer was dried over anhydrous MgSO$_4$ and evaporated to dry. The crude compound was purified by flash chromatography with 10% EtOAc in hexane to give white solid (2.11 g, 85%): LCMS m/z 397.05 (M+H). $^1$H NMR (acetone-d$_6$/400 MHz) 7.62 (s, 1H), 7.25 (s, 1H), 7.06 (s, 1H), 5.66 (q, 1H, J=7.0 Hz), 4.47 (m, 2H), 4.31 (m, 2H), 1.34 (m, 3H).

Step 4. Preparation of ethyl 7-(azidomethyl)-6-chloro-2-(trifluoromethyl)-2H-chromene-3-carboxylate The ester from step 3 (2.2 g, 5.5 mmole) and sodium azide (1.79 g, 27.5 mmole) were dissolved in DMF (15 mL). The mixture was heated at 50° C. under nitrogen for overnight. The solid was filtered off and washed with EtOAc. The organic layer was washed with water and dried over MgSO$_4$. After concentrated the ester was of suitable purity to use without further purification.

Step 5. Preparation of ethyl 7-(aminomethyl)-6-chloro-2-(trifluoromethyl)-2H-chromene-3-carboxylate The ester from Step 4 (0.93 g, 2.57 mmole) was dissolved in EtOH (30 mL). 10% Pd-C (0.11 g, 11% weight) was added to the solution after flushing nitrogen. The mixture was stirred at hydrogen sphere for overnight. Pd was filtered off the filtrate was concentrated to give yellow oil (0.9 g, 100%): LCMS m/z 336.05 (M+H). This ester was of suitable purity to use without further purification.

Step 6. Preparation of ethyl 7-[(butyrlamino)methyl]-6-chloro-2-(trifluoromethyl)-2H-chromene-3-carboxylate The amine from step 4 (0.9 g, 2.68 mmole) was dissolved in DMF (10 mL) at r.t., the butyryl chloride (0.39 mL, 3.76 mmole) was added to above solution. After Et$_3$N (0.52 mL, 7.08 mmol) was added to the solution, it was stirred at r.t. overnight. The reaction was quenched with NH$_4$Cl and the compound was extracted with EtOAc. The organic layer was washed with brine and dried over MgSO$_4$. The crude compound was purified by Biotage silica flash chromatography using 20 to 30% EtOAc in hexane to give yellow solid (0.70 g, 64.5%): LCMS m/z 406.10(M+H). $^1$H NMR (acetone-d$_6$/300 MHz) 7.62 (s, 1H), 7.25 (s, 1H), 6.98 (s, 1H), 5.83 (bs, 1H), 5.68 (q, 1H, J=6.6 Hz), 4.47 (m, 2H), 4.31 (m, 2H), 2.20 (m, 2H), 1.68 (m, 2H), 1.32 (m, 3H), 0.97 (m, 3H).

Step 7. Preparation of 7-[(butyrylamino)methyl]-6-chloro-2-(trifluoromethyl)-2H-chromene-3-carboxylic acid The 7-[(butyrylamino)methyl]-6-chloro-2-(trifluoromethyl)-2H-chromene-3-carboxylic acid was prepared by the procedure similar to the method described in Example 1a, Step 3: ESHRMS m/z 376.0598 (M−H, C$_{16}$H$_{14}$F$_3$O$_4$ClN, Calc'd 376.0558). $^1$H NMR (acetone-d$_6$/300 MHz) 7.85 (s, 1H), 7.66 (bs, 1H), 7.53 (s, 1H), 7.04 (s, 1H), 5.84 (q, 1H, J=7.0 Hz), 4.45 (m, 2H), 2.28 (t, 2H, J=7.3 Hz) 1.67 (m, 2H), 0.931(t, 3H, J=7.3 Hz).

EXAMPLE 17a

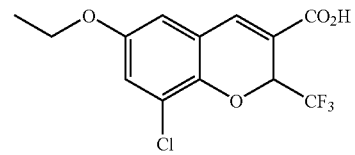

8-chloro-6-ethoxy-2-(trifluoromethyl)-2H-chromene-3-carboxylic acid

Step 1. Preparation of 3-chloro-2-hydroxy-5-methoxybenzaldehyde

To a solution of 2-chloro-4-methoxyphenol (25.0 g, 158 mmole) in anhydrous acetonitrile (625 mL) under a dry N$_2$ atmosphere was added MgCl$_2$ (22.5 g, 236 mmole) and TEA (82.3 mL, 591 mmole). The mixture warmed slightly as the MgCl$_2$ was added. Paraformaldehyde (32.0 g, 1.06 mmiole) was then added, the mixture was refluxed for 4.5 h and allowed to stand at room temperature overnight. Additional paraformaldehyde (14.2 g, 474 mmole) was added and reflux was resumed. After 4 h, the mixture was cooled, additional paraformaldehyde (32.0 g, 1.06 mmole) was added and reflux was resumed for another 2.25 h. The mixture was then cooled to room temperature, acidified with 1 N HCl and extracted with ethyl ether (4×500 mL). The combined extracts were washed with brine (250 mL), dried over MgSO$_4$, filtered and concentrated in vacuo to give 30.3 g of a yellow crystalline solid. Recrystallization from iso-propanol-H$_2$O gave 11.9 g (41% yield) of the product as a yellow crystalline solid: $^1$H NMR (dmso-d$_6$/300MHz) 10.47 (brs, 1H, 10.11 (s, 1H), 7.36 (d, 1H, J=3.0 Hz), 7.19 (d, 1H, J=3.0 Hz), 3.73 (s, 3H).

Step 2. Preparation of ethyl 8-chloro-6-methoxy-2-(trifluoromethyl)-2H-chromene-3-carboxylate A mixture of 3-chloro-2-hydroxy-5-methoxybenzaldehyde prepared as in Step 1 (9.00 g, 48.2 mmole), K$_2$CO$_3$ (6.67 g, 48.2 mmole) and ethyl 4,4,4-trifluorocrotonate (8.65 mL, 57.9 mmole) in anhydrous DMF (20 mL) under a dry $N_2$ atmosphere was stirred at room temperature for 30 minutes and was then heated to 85° C. for 3 h. Additional ethyl 444-trifluorocrotonate (3.00 mL, 20.1 mmole) was then added and the mixture was stirred at 85° C. overnight. The mixture was then cooled and poured into 1 N HCl (200 mL). Following extraction with EtOAc (3×200 mL), the combined extracts were washed with 0.25 N NaOH until the washes were basic, brine, dried over $MgSO_4$, filtered and concentrated in vacuo. The crude product was purified by crystallization from ethanol to give 11.0 g (68% yield) of the product as a yellow crystalline solid: $^1$H NMR (dmso-$d_6$/300 MHz) 7.92 (s, 1H), 7.18 (d, 1H, J=2.8 Hz), 7.13 (d, 1H, J=2.8 Hz), 6.05 (q, 1H, J=7.3 Hz), 4.21-4.29 (m, 2H), 3.73 (s, 3H), 1.26 (t, 3H, J=7.1 Hz).

Step 3. Preparation of ethyl 8-chloro-6-hydroxy-2-(trifluoromethyl)-2H-chromene-3-carboxylate A solution of ethyl 8-chloro-6-methoxy-2-(trifluoromethyl)-2H-chromene-3-carboxylate prepared as in Step 2 (1.41 g, 4.19 mmole) in anhydrous $CH_2Cl_2$ (80 mL) was cooled to −78° C. and a solution of $BBr_3$ in $CH_2C_2$ (42 mL-1.0 M, 42.0 mmole) was added dropwise under a dry $N_2$ atmosphere. The dry ice bath was removed and the mixture was allowed to warm to room temperature. After 3 h, the mixture was cooled to −78° C. and quenched by the addition of anhydrous MeOH (20 mL). The solvent was removed in vacuo and the residue extracted with EtOAc (200 mL). The extract was washed with brine, dried over $MgSO_4$, filtered and concentrated in vacuo to give a light brown solid. Purification by silica chromatography (98:2 $CH_2Cl_2$—MeOH gave 1.10 g (82% yield) of the product a as dark yellow solid: EIHRMS m/z 322.0215 (M+, $C_{13}H_{n10}ClF_3O_4$, Calc'd 322.0220). $^1$H NMR (dmso-$d_6$/300 MHz) 9.79 (s, 1H), 7.89 (s, 1H), 6.78-6.91 (m, 2H), 5.99 (q, 1H, J=7.3 Hz), 4.17-4.32 (m, 2H), 1.26 (t, 3H, J=7.05 Hz);

Step 4. Preparation of ethyl 8-chloro-6-ethoxy-2-(trifluoromethyl)-2H-chromene-3-carboxylate To a solution of ethyl 8-chloro-6-hydroxy-2-(trifluoromethyl)-2H-chromene-3-carboxylate prepared as in Step 3 (0.500 g, 1.55 mmole) in anhydrous DMF (5.0 mL) under a dry $N_2$ atmosphere was added KI (26 mg, 0.155 mmole), $K_2CO_3$ (0.643 g, 4.65 mmole) and ethyl iodide (272 uL, 4.65 mmole). After stirring overnight at room temperature, the mixture was poured into $H_2O$ (150 mL), saturated with solid NaCl and extracted with EtOAc (200 mL). The extract was then washed with brine (2×200 mL), dried over $MgSO_4$, filtered and concentrated in vacuo to give a quantitative yield of the product as a tan solid: EIHRMS m/z 350.0564 (M+, $C_{15}H_{14}ClF_3O_4$, Calc'd 350.0533). $^1$H NMR (dmso-$d_6$/300 MHz) 7.93 (s, 1H), 7.18 (d, 1H, J=3.0 Hz), 7.13 (d, 1H, J=2.8 Hz), 6.06 (q, 1H, J=7.3 Hz), 4.23-4.31 (m, 2H), 4.01 (q, 2H, 7.0 Hz), 1.29 (q, 6H, J=7.0 Hz).

Step 5. Preparation of 8-chloro-6-ethoxy-2-(trifluoromethyl)-2H-chromene-3-carboxylic acid To a solution of the ester from Step 4 (250 mg, 0.713 mmole) in a 7:2:1 THF:EtOH:$H_2O$ mixture (10 mL) was added LiOH.$H_2O$ (44.9 mg, 1.07 mmole). The mixture was stirred room temperature for 15 minutes and then at 50° C. for 75 minutes. After standing at room temperature for 2.75 days, the solvent was removed in vacuo. The residue was redissolved in $H_2O$ (20 mL) and washed with ethyl ether (20 mL). The aqueous layer was concentrated to a volume of 5 mL and acidified with 1 N HCl. The resulting solid was filtered, washed with $H_2O$ and dried in vacuo to give 216 mg (94% yield) of the product as a yellow crystalline solid: ESHRMS m/z 321.0135 (M−H, $C_{13}H_9ClF_3O_4$, Calc'd 321.0136). $^1$H NMR (dmso-$d_6$/300 MHz) 13.45 (brs, 1H), 7.88 (s, 1H), 7.13-7.16 (m, 2H), 6.02 (q, 1H, J=7.3 Hz), 4.03 (q, 2H, J=6.9 Hz), 1.32 (t, 3H, J=6.9 Hz).

EXAMPLE 17b

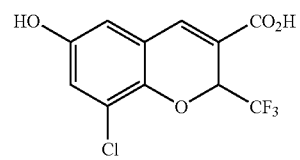

8-chloro-6-hydroxy-2-(trifluoromethyl)-2H-chromene-3-carboxylic acid

The ester from Example 17a, Step 3 was hydrolyzed via a method similar to that described in Example 17a, Step 5 to give the product as a yellow crystalline solid: ESHRMS m/z 292.9848 (M−H, $C_{11}H_5ClF_3O_4$, Calc'd 292.9823). $^1$H NMR (dmso-$d_6$/300 MHz) 13.40 (brs, 1H), 9.80 (s, 1H), 7.86 (s, 1H), 6.90-6.92 (m, 2H), 5.97 (q, 1H, J=7.2 Hz).

EXAMPLE 17c

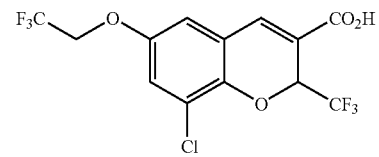

8-chloro-6-(2,2,2-trifluoroethoxy)-2-(trifluoromethyl)-2H-chromene-3-carboxylic acid Step 1. Preparation of ethyl 8-chloro-6-(2,2,2-trifluoroethoxy)-2-(trifluoromethyl)-2H-chromene-3-carboxylate To a solution of ethyl 8-chloro-6-hydroxy-2-(trifluoromethyl)-2H-chromene-3-carboxylate prepared as in Example 17a, Step 3 (0.500 g, 1.55 mmole) in anhydrous DMF (5.0 mL) under a dry $N_2$ atmosphere was added KI (26 mg, 0.155 mmole), $K_2CO_3$ (0.321 g, 2.33 mmole) and 2,2,2-trifluoroethyl iodide (0.458 mL, 4.65 mmole) and the mixture was stirred at room temperature for 1 h, and then at 40° C. for 1 h. Additional $K_2CO_3$ (0.647 g, 4.65 mmole) and 2,2,2-trifluoroethyl iodide (0.458 mL, 4.65 mmole) were added to the mixture and the temperature was raised to 50° C. overnight. Additional 2,2,2-trifluoroethyl iodide (0.458 mL (4.65 mmole) was added and the temperature was raised to 85° C. for 18.5 h. The mixture was then poured into sat. $NaHCO_3$ (100 mL) and extracted with EtOAc (2×200 mL). The combined extracts were then washed with brine (2×200 mL), dried over $MgSO_4$, filtered and concentrated in vacuo to give a brown oil. Purification of the crude product by silica chromatography (6:1 hexanes:EtOAc) gave 0.237 g (41% yield) of the product as a light yellow crystalline solid: EIHRMS m/z 404.0246 (M+, $C_{15}H_{11}ClF_6O_4$, Calc'd 404.0250).

Step 2. Preparation of 8-chloro-6-(2,2,2-trifluoroethoxy)-2-(trifluoromethyl)-2H-chromene-3-carboxylic acid The ester from Step 1 was hydrolyzed via a method similar to that described in Example 9z, Step 3 to give the product as a yellow crystalline solid: ESHRMS m/z 374.9855 (M−H, $C_{13}H_6ClF_6O_4$, Calc'd 374.9853). $^1$H NMR (dmso-$d_6$/300 MHz) 13.54 (brs, 1H), 7.88 (s, 1H), 7.37 (d, 1H, J=2.7 Hz), 7.32 (d, 1H, J=2.8 Hz), 6.09 (q, 1H, J=7.1 Hz), 4.81 (q, 2H, J=8.9 Hz).

EXAMPLE 17d

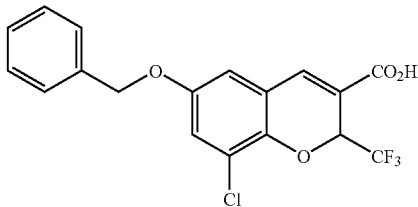

6-(benzyloxy)-8-chloro-2-(trifluoromethyl)-2H-chromene-3-carboxylic acid

Step 1. Preparation of ethyl 6-(benzyloxy)-8-chloro-2-(trifluoromethyl)-2H-chromene-3-carboxylate To a solution of ethyl 8-chloro-6-hydroxy-2-(trifluoromethyl)-2H-chromene-3-carboxylate prepared as in Example 17a, Step 3 (1.00 g, 3.10 mmole) in anhydrous DMF (10.0 mL) was added KI (51.5 mg, (0.310 mmole), $K_2CO_3$ (1.29 g, 9.30 mmole) and benzyl bromide (1.11 ml, 9.30 mmole). The suspension was stirred at room temperature for 2 h and poured into $H_2O$ (150 mL) and extracted with EtOAc (3×100 mL). The combined extracts were washed with brine (2×100 mL), dried over $MgSO_4$ and concentrated in vacuo to give a yellow oil. Purification by silica chromatography (6:1 hexanes:EtOAc) gave 1.12 g (87.5% yield) of the product as a yellow crystalline solid: EIHRMS m/z 412.0689 (M+, $C_{20}H_{16}ClF_3O_4$, Calc'd 412.0680).

Step 2. 6-(benzyloxy)-8-chloro-2-(trifluoromethyl)-2H-chromene-3-carboxylic acid The ester from Step 1 was hydrolyzed via a method similar to that described in Example 9z, Step 3 to give the crude product as a tacky solid. Brine was added and the mixture was extracted with EtOAc (20 mL). The EtOAc solution was dried over $MgSO_4$, filtered and concentrated in vacuo to give the product as a yellow crystalline solid in quantitative yield: ESHRMS m/z 383.0311 (M−H, $C_{18}H_{11}ClF_3O_4$, Calc'd 383.0292). $^1$H NMR (dmso-$d_6$/300 MHz) 13.49 (brs, 1H), 7.90 (s, 1H), 7.34-7.50 (m, 5H), 7.27 (s, 2H), 6.05 (q, 1H, J=7.2 Hz), 5.12 (s, 2H).

EXAMPLE 17e

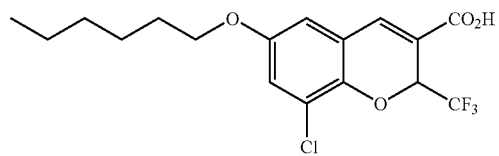

8-chloro-6-(hexyloxy)-2-(trifluoromethyl)-2H-chromene-3-carboxylic acid

Step 1. Preparation of ethyl 8-chloro-6-(hexyloxy)-2-(trifluoromethyl)-2H-chromene-3-carboxylate The ester was prepared via a method similar to that described in Example 17d, Step 1. The crude product was purified by silica chromatography (6:1 hexanes:EtOAc) to give the product as a yellow oil: EIHRMS m/z 404.1147 (M+, $C_{19}H_{22}ClF_3O_4$, Calc'd 404.1159).

Step 2. Preparation of 8-chloro-6-(hexyloxy)-2-(trifluoromethyl)-2H-chromene-3-carboxylic acid The ester from Step 1 was hydrolyzed via a method similar to that described in Example 9z, Step 3 to give the product as a yellow solid: ESHRMS m/z 377.0771 (M−H, $C_{17}H_{17}ClF_3O_4$, Calc'd 377.0762). $^1$H NMR (dmso-$d_6$, 300 MHz) 13.47 (brs, 1H), 7.89 (s, 1H), 7.15-7.18 (m, 2H), 6.04 (q, 1H, J=7.25 Hz), 3.98 (t, 2H, J=6.2 Hz), 1.69-1.74 (m, 2H), 1.32-1.43 (m, 6H), 0.89-0.91 (m, 3H).

EXAMPLE 17f

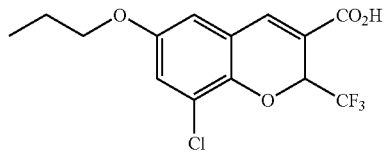

8-chloro-6-propoxy-2-(trifluoromethyl)-2H-chromene-3-carboxylic acid

Step 1. Preparation of ethyl 8-chloro-6-propoxy-2-(trifluoromethyl)-2H-chromene-3-carboxylate The ester was prepared via a method similar to that described in Example 17d, Step 1. The crude product was recrystallized from EtOAc-hexanes to give the product as a tan solid: EIHRMS m/z 364.0711 (M+, $C_{16}H_{16}ClF_3O_4$, Calc'd 364.0689).

Step 2. Preparation of 8-chloro-6-propoxy-2-(trifluoromethyl)-2H-chromene-3-carboxylic acid The ester from Step 1 was hydrolyzed at 70° C. via a method similar to that described in Example 9z, Step 3 to give the product as a yellow solid: ESHRMS m/z 335.0263 (M−H, $C_{14}H_{11}ClF_3O_4$, Calc'd 335.0292). $^1$H NMR (dmso-$d_6$, 300 MHz) 13.48 (brs, 1H), 7.90 (s, 1H), 7.16-7.18 (m, 2H), 6.04 (q, 1 H, J=7.3 Hz), 3.95 (t, 2H, J=6.4 Hz), 1.71-1.78 (m, 2H), 1.00 (t, 3H, J=7.3 Hz).

EXAMPLE 17g

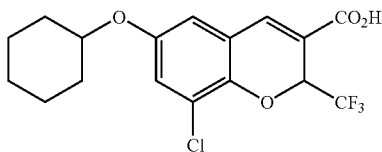

8-chloro-6-(cyclohexyloxy)-2-(trifluoromethyl)-2H-chromene-3-carboxylic acid

Step 1. Preparation of ethyl 8-chloro-6-(cyclohexyloxy)-2-(trifluoromethyl)-2H-chromene-3-carboxylate To a solution of ethyl 8-chloro-6-hydroxy-2-(trifluoromethyl)-2H-chromene-3-carboxylate prepared as in Example 17a, Step 3 (1.00 g, 3.10 mmole) in anhydrous DMF (10.0 mL) was added KI (51.5 mg, (0.310 mmole), $K_2CO_3$ (1.29 g, 9.30 mmole) and cyclohexyl iodide (1.20 mL, 9.30 mmole). The suspension was heated at 50° C. for 17 h and then the temperature was slowly raised to 80° C. and stirred overnight. Additional cyclohexyl iodide (1.20 mL, 9.30 mmole) was added and the temperature was maintained at 100-120° C. for 3 days. The mixture was then cooled and poured into $H_2O$ (200 mL), which was saturated with solid NaCl. Following extraction with EtOAc (2×100 mL), the combined extracts were washed with brine (3×100 mL) and concentrated in vacuo. Purification by silica chromatography (6:1 hexanes:EtOAc) gave 45 mg (3.5% yield) of the product: EIHRMS m/z 404.0999 (M+, $C_{19}H_{20}ClF_3O_4$, Calc'd 404.1002).

Step 2. Preparation of 8-chloro-6-(cyclohexyloxy)-2-(trifluoromethyl)-2H-chromene-3-carboxylic acid The ester from Step 1 was hydrolyzed via a method similar to that described in Example 9z, Step 3 to give the product as a yellow crystalline solid: ESHRMS m/z 375.0642 (M−H, $C_{17}H_{15}ClF_3O_4$, Calc'd 375.0605). $^1$H NMR (dmso-$d_6$, 300 MHz) 13.39 (brs, 1H), 7.84 (s, 1H), 7.15 (d, 1H, J=2.8 Hz), 7.10 (d, 1H, J=2.8Hz), 5.98 (q, 1H, J=7.3 Hz), 4.20-4.35 (m, 1H), 1.14-1.87 (m, 10H).

EXAMPLE 17h

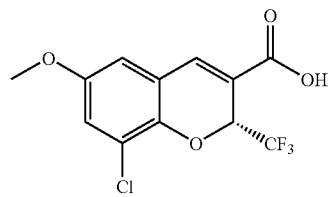

(2R)-8-chloro-6-methoxy-2-(trifluoromethyl)-2H-chromene-3-carboxylic acid

The (2R)-8-chloro-6-methoxy-2-(trifluoromethyl)-2H-chromene-3-carboxylic acid was resolved by chiral separation of racemic 8-chloro-6-methoxy-2-(trifluoromethyl)-2H-chromene-3-carboxylic acid from U.S. Pat. No. 6,271,253 B1, Example 40 using ChiralPak AD column eluting with EtOH/heptane/TFA=5/95/0.1 and detecting at 254 nm as peak 1 with retention time 8.55 min: ESHRMS m/z 306.9953 (M−H, $C_{12}H_8F_3O_4Cl$, Calc'd 306.9979). $^1$H NMR (acetone-$d_6$/400 MHz) 7.87 (s, 1H), 7.08 (m, 2H), 5.87 (q, 1H, J=7.0 Hz), 3.82 (s, 3H).

EXAMPLE 17i

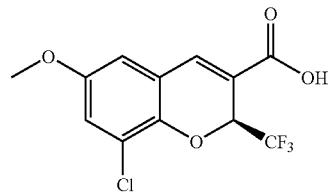

(2S)-8-chloro-6-methoxy-2-(trifluoromethyl)-2H-chromene-3-carboxylic acid

The (2S)-8-chloro-6-methoxy-2-(trifluoromethyl)-2H-chromene-3-carboxylic acid was resolved by chiral separation of racemic 8-chloro-6-methoxy-2-(trifluoromethyl)-2H-chromene-3-carboxylic acid from U.S. Pat. No. 6,271,253 B1, Example 40 using ChiralPak AD column eluting with EtOH/heptane/TFA=5/95/0.1 and detecting at 254 nm as peak 2 with retention time 10.58 min: ESHRMS m/z 306.9963 (M−H, $C_{12}H_7F_3O_4Cl$, Calc'd 306.9979). $^1$H NMR (acetone-$d_6$/400 MHz) 7.87 (s, 1H), 7.08 (m,2H), 5.87 (q,1H, J=7.0 Hz), 3.82 (s, 3H).

EXAMPLE 18a

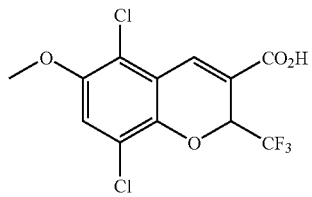

5,8-dichloro-6-methoxy-2-(trifluoromethyl)-2H-chromene-3-carboxylic acid

Step 1. Preparation of ethyl 5,8-dichloro-6-methoxy-2-(trifluoromethyl)-2H-chromene-3-carboxylate To a solution of ethyl 8-chloro-6-methoxy-2-(trifluoromethyl)-2H-chromene-3-carboxylate prepared as in U.S. Pat. No. 6,271,253 B1 Example 40 (2.32 g, 6.89 mmole) in glacial acetic acid (100 mL) was added $Cl_2$ gas for 0.5 minutes. After standing for 20 min, the solvent was removed in vacuo and the remaining acetic acid was azeotroped with hexanes to give a crystalline solid containing a mixture of regioisomers. The crude product was purified by recrystallization from ethyl acetate-hexanes to give 189 mg (7.4% yield) of the product as colorless needles: EIHRMS m/z 369.9986 (M+, $C_{14}H_{11}C_2lF_3O_4$, Calc'd 369.9986).

Step 2. Preparation of 5,8-dichloro-6-methoxy-2-(trifluoromethyl)-2H-chromene-3-carboxylic acid To a solution of the ester from Step 1 (0.174 g, 0.469 mmole) in a 7:2:1 THF:EtOH:H$_2$O mixture (10 mL) was added LiOH.H$_2$O (29.5 mg (0.704 mmole). The mixture was stirred at room temperature overnight and the solvent was removed in vacuo. The residue was redissolved in H$_2$O, filtered (0.45 □ PTFE) and acidified with 1 N HCl. The resulting solid was filtered, washed with H$_2$O and dried in vacuo to give 134 mg (83% yield) of the product as an yellow solid: ESHRMS m/z 340.9607 (M–H, $C_{12}H_6C_{12}F_3O_4$, Calc'd 340.9590). $^1$H NMR (dmso-d$_6$, 300 MHz) 13.70 (brs, 1H), 7.90 (s, 1H), 7.41 (s, 1H), 6.10 (q, 1H, J=7.1 Hz), 3.86 (s, 3H).

EXAMPLE 19

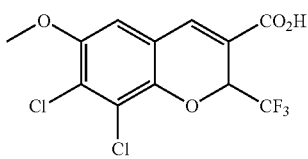

7,8-dichloro-6-methoxy-2-(trifluoromethyl)-2H-chromene-3-carboxylic acid

Step 1. Preparation of ethyl 7,8-dichloro-6-methoxy-2-(trifluoromethyl)-2H-chromene-3-carboxylate The ester was prepared as described in Example 18a, Step 1 and purified by recrystallizion from EtOAc-hexanes, followed by silica chromatography (3:1 hexanes:EtOAc) to give the 0.292 g (11% yield) of the product as a yellow crystalline solid: EIHRMS m/z 369.9986 (M+, $C_{14}H_{11}C_2lF_3O_4$, Calc'd 369.9986).

Step 2. Preparation of 7,8-dichloro-6-methoxy-2-(trifluoromethyl)-2H-chromene-3-carboxylic acid The ester from Step 1 was hydrolyzed via a method similar to that described in Example 18a, Step 2 to give the product as a pale yellow solid: ESHRMS m/z 340.9567 (M–H, $C_{12}H_6Cl_2F_3O_4$, Calc'd 340.9590). $^1$NMR (dmso-d$_6$, 300 MHz) 13.45 (brs, 1H), 7.89 (s, 1H), 7.42 (s, 1H), 6.07 (q, 1H, J=7.1 Hz), 3.87 (s, 3H);

EXAMPLE 20a

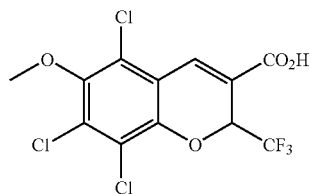

5,7,8-trichloro-6-methoxy-2-(trifluoromethyl)-2H-chromene-3-carboxylic acid

Step 1. Preparation of ethyl 5,7,8-trichloro-6-methoxy-2-(trifluoromethyl)-2H-chromene-3-carboxylate A solution of ethyl 8-chloro-6-methoxy-2-(trifluoromethyl)-2H-chromene-3-carboxylate prepared as in U.S. Pat. No. 6,271,253 B1 Example 40 (0.500 g, 1.49 mmole) in glacial acetic acid (25 mL) was saturated with Cl$_2$ gas. After standing overnight at room temperature, the solvent was removed in vacuo and the remaining acetic acid was azeotroped with hexanes. The crude product was purified by silica chromatography (9:1 ethyl acetate:hexanes), followed by crystallization from hexanes to give 0.244 g (41% yield) of the product as colorless needles: EIHRMS m/z 403.9564 (M+, $C_{14}H_{10}Cl_3F_3O_4$, Calc'd 403.9597).

Step 2. Preparation of 5,7,8-trichloro-6-methoxy-2-(trifluoromethyl)-2H-chromene-3-carboxylic acid The ester from Step 1 was hydrolyzed via a method similar to that described in Example 17a, Step 5 to give the product as a white crystalline solid: ESHRMS m/z 374.9178 (M–H, $C_{12}H_5F_3O_4Cl_3$, Calc'd 374.9200). $^1$H NMR (dmso-d$_6$, 300 MHz) 13.86 (brs, 1H), 7.90 (s, 1H), 6.28 (q, 1H, J=7.1 Hz) 3.86 (s, 3H).

EXAMPLE 21a

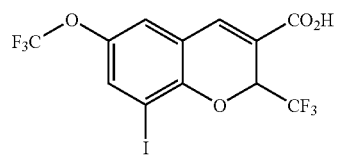

8-iodo-6-(trifluoromethoxy)-2-(trifluoromethyl)-2H-chromene-3-carboxylic acid

Step 1. Preparation of 2-hydroxy-3-iodo-5-(trifluoromethoxy)benzaldehyde

A mixture of 2-hydroxy-5-(trifluoromethoxy)benzaldehyde (5.09 g, 24.7 mmole) and N-iodosuccinimide (13.9 g, 61.8 mmole) in anhydrous DMF (50 mL) was stirred at room temperature for 2 days under a dry N$_2$ atmosphere. The solvent was removed in vacuo and the residue was dissolved in EtOAc (200 mL), washed with 0.5 N HCl (200 mL), H$_2$O (200 mL), aqueous sodium thiosulfate (100 mL), brine (100 mL), dried over MgSO$_4$, filtered and concentrated in vacuo to give a yellow solid. Purification by sublimation under vacuum at 85° C. gave 7.97 g (97% yield) of the product as a white solid: EIHRMS m/z 331.9159 (M+, C$_8$H$_8$F$_3$O$_4$, Calc'd 331.9157).

Step 2. Preparation of ethyl 8-iodo-6-(trifluoromethoxy)-2-(trifluoromethyl)-2H-chromene-3-carboxylate A mixture of 2-hydroxy-3-iodo-5-(trifluoromethoxy)benzaldehyde prepared as in step 1 (60.0 g, 181 mmole), ethyl 4,4,4-trifluocrotonate (108 mL, 723 mmole) and TEA (50.4 mL, 361 mmole) was heated to 85° C. for 66 h. The mixture was concentrated in vacuo and the product was crystallized from EtOH-H$_2$O to give 78.0 g (90% yield) of the product as light yellow needles: $^1$H NMR (dmso-d$_6$, 300 MHz) 7.95 (s, 1H), 7.86 (d, 1H, J=2.4 Hz), 7.70 (d, 1H, J=1.8 Hz), 6.17 (q, 1H, J=7.0 Hz), 4.18-4.34 (m, 2H), 1.26 (t, 3H, J=7.0 Hz).

Step 3. Preparation of 8-iodo-6-(trifluoromethoxy)-2-(trifluoromethyl)-2H-chromene-3-carboxylic acid The ester from Step 2 was hydrolyzed at 60° C. via a method similar to that described in Example 17d, Step 2 to give the product as a light yellow crystalline solid: ESHRMS m/z 452.9012 (M−H, C$_{12}$H$_4$F$_6$O$_4$, Calc'd 452.9053). $^1$H NMR (dmso-d$_6$, 300 MHz) 13.51 (brs, 1H), 7.87 (s, 1H), 7.84(1, 1H, J=2.2Hz), 7.76 (d, 1H, J=1.8Hz), 6.10 (q, 1H, J=7.1 Hz).

EXAMPLE 21b

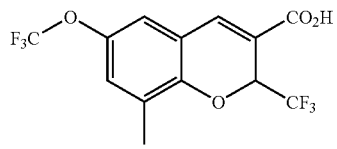

8-methyl-6-(trifluoromethoxy)-2-(trifluoromethyl)-2H-chromene-3-carboxylic acid

Step 1. Preparation of ethyl 8-methyl-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (0.500 g, 1.04 mmole), trimethylboroxine (145 uL, 1.04 mmole), PdCl$_2$(dppf)$_2$·CH$_2$Cl$_2$ (0.084 mg, 0.104 mmole) and Cs$_2$CO$_3$ (1.01 g, 3.11 mmole) in 10% aqueous dioxane (2.5 mL) was heated to 110° C. under a dry N$_2$ atmosphere for 6 h. The mixture was poured into EtOAc (100 mL), washed with brine (2×50 mL), dried over MgSO$_4$, filtered and concentrated in vacuo to give an oily yellow solid. Purification by silica chromatography (9:1 hexanes:EtOAc) gave 0.320 g (83% yield) of the product as a yellow crystalline solid: EIHRMS m/z 370.0650 (M+, C$_{15}$H$_2$F$_6$O$_4$, 370.0640).

Step 2. Preparation of 8-methyl-6-(trifluoromethoxy)-2-(trifluoromethyl)-2H-chromene-3-carboxylic acid The ester from Step 1 was hydrolyzed via a method similar to that described in Example 9z, Step 3 to give the product as a white solid: ESHRMS m/z 341.0268 (M−H, C$_{13}$H$_7$F$_6$O$_4$, Calc'd 341.0243). $^1$H NMR (dmso-d$_6$, 300 MHz) 13.40 (brs, 1H), 7.87 (s, 1H), 7.43 (s, 1H), 7.31 (s, 1H), 5.99 (q, 1H, J=7.3 Hz), 2.20 (s, 3H).

EXAMPLE 21c

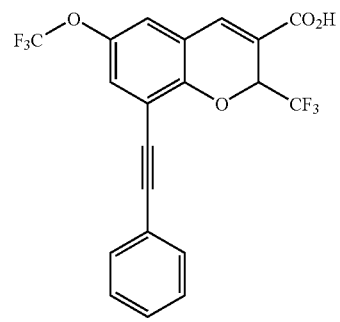

8-(phenylethynyl)-6-(trifluoromethoxy)-2-(trifluoromethyl)-2H-chromene-3-carboxylic acid

Step 1. Preparation of ethyl 8-(phenylethynyl)-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (1.00 g, 2.07 mmole), phenylacetylene (0.455 mL, 4.15 mmole), CuI (39.5 mg, 0.207 mmole), PdCl$_2$(dppf)$_2$·CH$_2$Cl$_2$ (169 mg, 0.207 mmole) and TEA (0.867 mL, 6.22 mmole) in anhydrous toluene (10 mL) was stirred at room temperature for 18.5 h. The mixture was then poured into brine (100 mL) and extracted with EtOAc. The EtOAc layer was separated, dried over MgSO$_4$, filtered and concentrated in vacuo. The residue was purified by silica chromatography (9:1 hexanes:EtOAc) to give 0.802 g (85% yield) of the product as a yellow crystalline solid: EIHRMS m/z 456.0781 (M+, C$_{14}$H$_{14}$F$_6$O$_4$, Calc'd 456.0796).

Step 2. Preparation of 8-(phenylethynyl)-6-(trifluoromethoxy)-2-(trifluoromethyl)-2H-chromene-3-carboxylic acid The ester from Step 1 was hydrolyzed via a method similar to that described in Example 18a, Step 2 to give the product as a yellow solid: ESHRMS m/z 427.0375 (M−H, C$_{20}$H$_9$F$_6$O$_4$, Calc'd 427.0400). $^1$H NMR (dmso-d$_6$, 300 MHz) 13.53 (brs, 1H), 7.92 (s, 1H), 7.44-7.87 (m, 7H), 6.15 (q, 1H, J=7.1 Hz).

EXAMPLE 21d

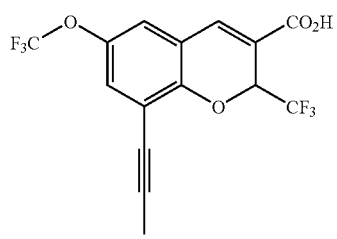

8-prop-1-ynyl-6-(trifluoromethoxy)-2-(trifluoromethyl)-2H-chromene-3-carboxylic acid

Step 1. Preparation of ethyl 8-prop-1-ynyl-6-(trifluoromethoxy)-2-(trifluoromethyl)-2H-chromene-3-carboxylate To a Parr bottle containing a mixture of ethyl 8-iodo-6-(trifluoromethoxy)-2-(trifluoromethyl)-2H-chromene-3-carboxylate prepared as in Example 21 a, Step 2 (0.500 g, 1.04 mmole), CuI (20 mg, 0.104 mmole), PdCl$_2$(dppf)$_2$.CH$_2$Cl$_2$ (84.5 mg, 0.104 mmole) and TEA (434 uL, 3.11 mmole) in anhydrous toluene (10 mL) was added at −78° C. propyne (2 ml) and the bottle was sealed. After stirring for 23 h at room temperature, an additional propyne (5 ml) was added and the mixture was stirred an additional 23 h at room temperature. Additional PdCl$_2$(dppf)$_2$.CH$_2$Cl$_2$ (120 mg, 0.147 mmole) was added and the mixture was stirred at room temperature for an additional 24 h. The mixture was then poured into brine (100 mL) and extracted with EtOAc (200 mL). The EtOAc layer was separated, dried over MgSO$_4$, filtered and concentrated in vacuo. The residue was purified by silica chromatography (9:1 hexanes:EtOAc) to give 0.363 g (89% yield) of the product as a yellow crystalline solid: EIHRMS m/z 394.0644 (M+, C$_{17}$H$_{12}$F$_6$O$_4$, Calc'd 394.0640).

Step 2. Preparation of 8-prop-1-ynyl-6-(trifluoromethoxy)-2-(trifluoromethyl)-2H-chromene-3-carboxylic acid The ester from Step 1 was hydrolyzed via a method similar to that described in Example 17d, Step 2 to give a quantitative yield of the product as a tan crystalline solid: ESHRMS m/z 365.0275 (M−H, C$_{15}$H$_7$F$_6$O$_4$, Calc'd 365.0243). $^1$H NMR (dmso-d$_6$, 300 MHz) 13.49 (brs, 1H), 7.88 (s, 1H), 7.59 (s, 1H), 7.42 (d, 1H, J=2.2 Hz), 6.09 (q, 1H, J=7.2 Hz), 2.08 (s, 3H).

EXAMPLE 21e

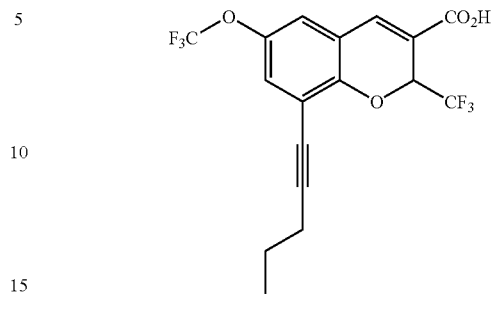

8-pent-1-ynyl-6-(trifluoromethoxy)-2-(trifluoromethyl)-2H-chromene-3-carboxylic acid

Step 1. Preparation of ethyl 8-pent-1-ynyl-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (0.500 g, 1.04 mmole), 1-pentyne (0.205 mL, 2.08 mmole), CuI (20 mg, 0.104 mmole), PdCl$_2$(dppf)$_2$.CH$_2$Cl$_2$ (84.5 mg, 0.104 mmole) and TEA (0.434 mL, 3.11 mmole) in anhydrous toluene (5 mL) was stirred at room temperature for 23 h. Additional 1-pentyne (2.0 ml, 20.3 mmole) was then added and the mixture was stirred an additional 24 h. Additional PdCl$_2$(dppf)$_2$.CH$_2$Cl$_2$ (120 mg, 0.147 mmole) was then added and the mixture was stirred an additional 24 h. The mixture was then poured into brine (100 mL) and extracted with EtOAc (200 mL). The EtOAc layer was separated, dried over MgSO$_4$, filtered and concentrated in vacuo. The residue was purified by silica chromatography (9:1 hexanes:EtOAc) to give 0.41 g (93% yield) of the product as a yellow crystalline solid: EIHRMS m/z 422.0946 (M+, C$_{19}$H$_{16}$F$_6$O$_4$, Calc'd 422.0953).

Step 2. Preparation of 8-pent-1-ynyl-6-(trifluoromethoxy)-2-(trifluoromethyl)-2H-chromene-3-carboxylic acid The ester from Step 1 was hydrolyzed via a method similar to that described in Example 17d, Step 2 to give the product: ESHRMS m/z 393.0566 (M−H, C$_{17}$H$_{11}$F$_6$O$_4$, Calc'd 393.0556). $^1$H NMR (dmso-d$_6$, 300 MHz) 13.48 (brs, 1H), 7.88 (s, 1H), 7.59 (d, 1H, J−2.2 Hz), 7.41 (d, 1H, J=2.4 Hz), 6.06 (q, 1H, J=7.0 Hz), 2.43 (1, 2H, J=6.9 Hz), 1.48-1.90 (m, 2H), 0.99 (t, 3H, J=7.5 Hz).

EXAMPLE 21f

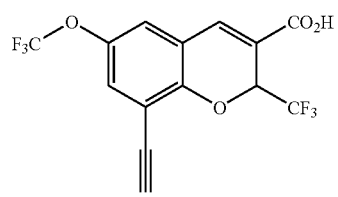

8-ethynyl-6-(trifluoromethoxy)-2-(trifluoromethyl)-2H-chromene-3-carboxylic acid

Step 1. Preparation of ethyl 6-(trifluoromethoxy)-2-(trifluoromethyl)-8-[(trimethylsilyl)ethynl]-2H-chromene-3-carboxylate A mixture of ethyl 8-iodo-6-(trifluoromethoxy)-2-(trifluoromethyl)-2H-chromene-3-carboxylate prepared as in Example 21 a, Step 2 (25.0 g, 51.9 mmole), ethynyl(trimethyl)silane (36.6 mL, 256 mmole), CuI (0.988 g, 5.19 mmole), Pd(PPh$_3$)$_4$ (5.99 g, 5.19 mmole) and TEA (21.7 mL, 156 mmole), and in anhydrous toluene (200 mL) was stirred at room temperature for 2 days. Additional CuI (0.99 g, 5.19 mmole) was added and stirring was continued for another 1day. Again, additional CuI (2.0 g, 10.5 mmole) was added and stirring was continued for another 3 days. The mixture was then poured into brine (500 mL) and extracted with EtOAc (500 mL). The EtOAc layer was separated, dried over MgSO$_4$ and filtered through a plug of silica gel (95:5 hexanes:EtOAc) to give 24 g of the product (quantitative yield) as a tan solid: EIHRMS m/z 452.0853 (M+, C$_{19}$H$_{18}$F$_6$O$_4$Si, Calc'd 452.0879).

Step 2. Preparation of ethyl 8-ethynyl-6-(trifluoromethoxy)-2-(trifluoromethyl)-2H-chromene-3-carboxylate To a solution of ethyl 6-(trifluoromethoxy)-2-(trifluoromethyl)-8-[(trimethylsilyl)ethynyl]-2H-chromene-3-carboxylate prepared as in Step 1 (22.8 g, 50.3 mmole) in anhydrous CH$_2$Cl$_2$ (200 mL) was added a solution of TBAF (62.9 mL-1.0 M in THF), 62.9 mmole) under a dry N$_2$ atmosphere. The mixture was stirred for 10 minutes and then poured into sat. NH$_4$Cl (200 mL) and extracted with EtOAc (500 mL). The EtOAc extract was washed with brine (100 mL), dried over MgSO$_4$, filtered and concentrated in vacuo to give 40 g of a dark brown oil. The crude product was purified by silica chromatography (98:2 hexanes:CH$_2$Cl$_2$) to give 13.9 g (73% yield) of the product as a yellow crystalline solid: EIHRMS m/z 380.0505 (M+, C$_{16}$H$_{10}$F$_6$O$_4$, Calc'd 380.0483).

Step 3. Preparation of 8-ethynyl-6-(trifluoromethoxy)-2-(trifluoromethyl)-2H-chromene-3-carboxylic acid The ester from Step 2 was hydrolyzed via a method similar to that described in Example 17d, Step 2 to give the product as yellow oil: ESHRMS m/z 351.0110 (M–H, C$_{14}$H$_5$F$_6$O$_4$, Calc'd 351.0087). $^1$H NMR (dmso-d$_6$, 300 MHz) 13.52 (brs, 1H), 7.90 (s, 1H), 7.68 (s, 1H), 7.54 (s, 1H, J=2.6 Hz), 6.11 (q, 1H, J=7.1 Hz),4.57 (s, 1H).

EXAMPLE 21g

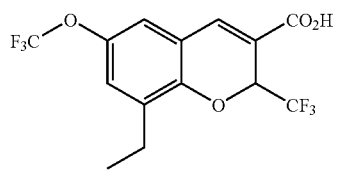

8-ethyl-6-(trifluoromethoxy)-2-(trifluoromethyl)-2H-chromene-3-carboxylic acid

Step 1. Preparation of ethyl 8-ethyl-6-(trifluoromethoxy)-2-(trifluoromethyl)-2H-chromene-3-carboxylate A mixture of ethyl 8-ethynyl-6-(trifluoromethoxy)-2-(trifluoromethyl)-2H-chromene-3-carboxylate prepared as in Example 21f, Step 2 (12.2 g, 32.0 mmole) and 10% Pd/C (1.22 g) in absolute EtOH (250 mL) was hydrogenated at 30 psi for 3 h. The catalyst was then removed by filtration and the solution concentrated in vacuo to give the product in assumed quantitative yield as an off-white solid. The solid was carried on without further purification: EIHRMS m/z 384.0759 (M+, C$_{16}$H$_{14}$F$_6$O$_4$, Calc'd 384.0796).

Step 2. Preparation of 8-ethyl-6-(trifluoromethoxy)-2-(trifluoromethyl)-2H-chromene-3-carboxylic acid The ester from Step 1 was hydrolyzed via a method similar to that described in Example 17d, Step 2 to give the product as a light yellow crystalline solid: ESHRMS m/z 355.0389 (M–H, C$_{14}$H$_9$F$_6$O$_4$, Calc'd 355.0400). $^1$H NMR (dmso-d$_6$, 300 MHz) 13.39 (brs, 1H), 7.88 (s,1H), 7.44 (d, 1H, J=2.2 Hz), 7.28 (d, 1H, J=2.4 Hz), 6.00 (q, 1H, J=7.3 Hz), 2.54-2.68 (m, 2H), 1.12 (t, 3H, J=7.5 Hz).

EXAMPLE 21h

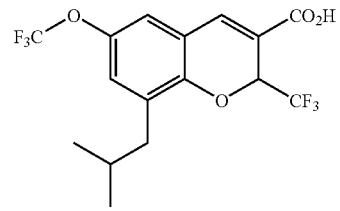

8-isobutyl-6-(trifluoromethoxy)-2-(trifluoromethyl)-2H-chromene-3-carboxylic acid

Step 1. Preparation of ethyl 8-isobutyl-6-(trifluoromethoxy)-2-(trifluoromethyl)-2H-chromene-3-carboxylate Isobutylene was bubbled into a solution of 9-BBN (3.32 mL-0.5 M in THF, 1.66 mmole) at 0° C. for 15 minutes and the mixture was stirred for 15 minutes, maintaining the temperature at 0° C. Isobutylene was again bubbled into the solution for 15 min and the mixture was stirred for 1 h at room temperature. To the mixture was added ethyl 8-iodo-6-(trifluoromethoxy)-2-(trifluoromethyl)-2H-chromene-3-carboxylate prepared as in Example 21a, Step 2 (0.400 g, 0.830 mmole) as a solution in anhydrous THF (3.0 mL), PdCl$_2$(dppf)$_2$.CH$_2$Cl$_2$ (33.9 mg, 0.0415 mmole) and a K$_3$PO$_4$ solution (0.934 mL-2.0M, 1.87 mmole). The resulting mixture was stirred at room temperature for 45 minutes, poured into sat. NaHCO$_3$ (100 mL) and extracted with EtOAc (100 mL). The EtOAc solution was washed with 1N HCl (100 mL), brine (50 mL), dried over MgSO$_4$ and concentrated in vacuo. Purification by silica chromatography (9:1 hexanes:EtOAc) followed by reverse phase chromatography (acetonitrile:0.5% TFA-H$_2$O) gave 110 mg (32% yield) of the product as a white crystalline solid: EIHRMS m/z 411.1109 (M+, $C_{18}H_{18}F_6O_4$, Calc'd 411.1140).

Step 2. Preparation of 8-isobutyl-6-(trifluoromethoxy)-2-(trifluoromethyl)-2H-chromene-3-carboxylic acid The ester from Step 1 was hydrolyzed via a method similar to that described in Example 17d, Step 2 to give the product as a yellow crystalline solid: ESHRMS m/z 383.0710 (M−H, $C_{16}H_{13}F_6O_4$, Calc'd 383.0713). $^1$H NMR (dmso-$d_6$, 300 MHz) 13.37 (brs, 1H), 7.88 (s, 1H), 7.45 (d, 1H, J=2.4 Hz), 7.24 (d, 1H, J=2.4 Hz), 5.98 (q, 1H, J=7.1 Hz), 2.36-2.58 (m, 2H), 1.84-1.93 (m, 1H), 0.85 (d, 3H, J=3.2 Hz), 0.83 (d, 3H, J=3.0 Hz).

EXAMPLE 21i

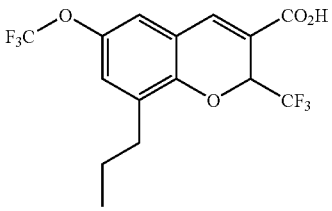

8-propyl-6-(trifluoromethoxy)-2-(trifluoromethyl)-2H-chromene-3-carboxylic acid

To a Paar bottle was added 8-prop-1-ynyl-6-(trifluoromethoxy)-2-(trifluoromethyl)-2H-chromene-3-carboxylic acid prepared as in Example 21 d, Step 2 (150 mg, 0.409 mmole), 10% Pd/C (75 mg) and absolute EtOH (10 mL). The mixture was hydrogenated at 30 psi for 2 h. The catalyst was filtered, the solvent was removed in vacuo and the resulting oily solid triturated with hexanes to give 76 mg (50% yield) of the product as an off-white solid: ESHRMS m/z 369.0559 (M−H, $C_{15}H_{11}F_6O_4$, Calc'd 369.0556). $^1$H NMR (dmso-$d_6$, 300 MHz) 13.38 (brs, 1H), 7.87 (s, 1H), 7.43 (s, 1H), 7.26 (s, 1H), 5.99 (q, 1H, J=7.3 Hz), 2.51-2.66 (m, 2H), 1.48-1.60 (m, 2H), 0.86 (t, 3H, J=7.3 Hz).

EXAMPLE 21j

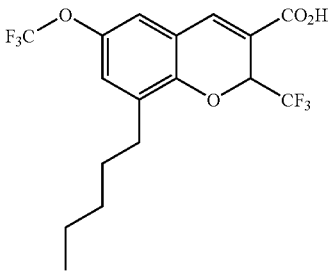

8-pentyl-6-(trifluoromethoxy)-2-(trifluoromethyl)-2H-chromene-3-carboxylic acid

8-Pent-1-ynyl-6-(trifluoromethoxy)-2-(trifluoromethyl)-2H-chromene-3-carboxylic acid prepared as in Example 21e, Step 2 was hydrogenated as described in Example 21i, Step 1. Purification by reverse phase chromatography (acetonitrile:0.5% TFA-$H_2O$) gave the product as a brown oil: ESHRMS m/z 397.0846 (M−H, $C_{17}H_{15}F_6O_4$, Calc'd 397.0869). $^1$H NMR (dmso-$d_6$, 300 MHz) 13.39 (brs, 1H), 7.87 (s, 1H), 7.42 (d, 1H, J=2.2 Hz), 7.25 (s, 1H, J=2.4 Hz), 5.98 (q, 1H, J=7.3 Hz), 2.46-2.65 (m, 2H), 1.47-1.57 (m, 2H), 1.21-1.33 (m, 4H), 0.83 (t, 3H, J=6.8 Hz).

EXAMPLE 21k

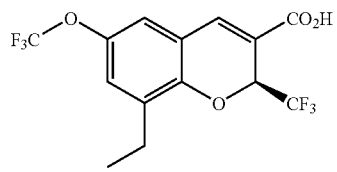

(2S)-8-ethyl-6-(trifluoromethoxy)-2-(trifluoromethyl)-2H-chromene-3-carboxylic acid Racemic 8-ethyl-6-(trifluoromethoxy)-2-(trifluoromethyl)-2H-chromene-3-carboxylic acid prepared as in Example 21g, Step 2 (10.1 g) was resolved by chiral separation using a Chiralcel OJ column eluting with EtOH/heptane/TFA=5/95/0.1 and detecting at 254 nm as peak 1 with retention time 5.03 min to give 4.65 g (46% yield) the product as an off-white solid: ESLRMS m/z 357.1 (M+H, $C_{14}H_{11}F_6O_4$, Calc'd 357.1). $^1$H NMR (dmso-$d_6$, 400 MHz) 13.39 (brs, 1H), 7.87 (s, 1H), 7.43 (d, 1H, J=2.4 Hz), 7.27 (d, 1H, J=2.7 Hz), 5.99 (q, 1H, J=7.3 Hz), 2.50-2.67 (m, 2H), 1.11 (t, 3H, J=7.5 Hz).

EXAMPLE 21l

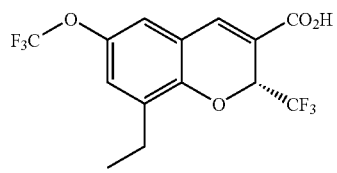

(2R)-8-ethyl-6-(trifluoromethoxy)-2-(trifluoromethyl)-2H-chromene-3-carboxylic acid Racemic 8-ethyl-6-(trifluoromethoxy)-2-(trifluoromethyl)-2H-chromene-3-carboxylic acid prepared as in Example 21g, Step 2 (10.1 g) was resolved by chiral separation using Chiralcel OJ column eluting with EtOH/heptane/TFA=5/95/0.1 and detecting at 254 nm as peak 2 with retention time 5.55 min to give 4.41 g (44% yield) of the product as a light yellow solid: ESLRMS m/z 357.2 (M+H, $C_{14}H_{11}F_6O_4$, Calc'd 357.1). $^1$H NMR (dmso-$d_6$, 300 MHz) 13.39 (brs, 1H), 7.88 (s, 1H), 7.44 (d, 1H, J=2.2 Hz), 7.27 (d, 1H, J=2.4 Hz), 6.00 (q, 1H, J=7.3 Hz), 2.54-2.67 (m, 2H), 1.12 (t, 3H, J=7.5 Hz).

EXAMPLE 21m

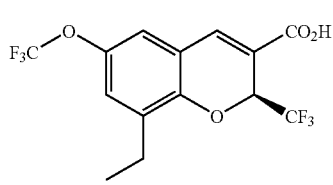 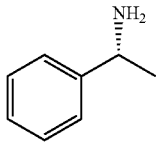

(2S)-8-ethyl-6-(trifluoromethoxy)-2-(trifluoromethyl)-2H-chromene-3-carboxylic acid compound with (1R)-1-phenylethanamine (S)-8-ethyl-6-(trifluoromethoxy)-2-(trifluoromethyl)-2H-chromene-3-carboxylic acid prepared as in Example 21k (17.8 mg, 0.0500 mmole) and (1R)-1-phenylethanamine (12.7 uL, 0.0500 mmole) were added to a few drops of isopropanol. Heptane (0.30 mL) was then added and the solvent was allowed to slowly evaporate from the loosely capped vial. Crystals had formed in the solution after standing at room temperature for 1 day. X-ray crystal structure analysis confirmed the title compound to be the (S)-enantiomer.

EXAMPLE 21n

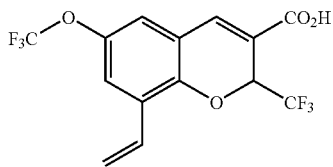

6-(trifluoromethoxy)-2-(trifluoromethyl)-8-vinyl-2H-chromene-3-carboxylic acid

Step 1. Preparation of ethyl 6-(trifluoromethoxy)-2-(trifluoromethyl)-8-vinyl-2H-chromene-3-carboxylate To a mixture of ethyl 8-iodo-6-(trifluoromethoxy)-2-(trifluoromethyl)-2H-chromene-3-carboxylate prepared as in Example 21a, Step 2 (1.00 g, 2.07 mmole) and Pd(PPh$_3$)$_4$ (0.239 g, 0.207 mmole) in anhydrous toluene (50 mL) under a dry N$_2$ atmosphere was added tributylvinyltin (0.665 mL, 2.28 mmole). The mixture was refluxed for 3 h and stirred at r.t for 18 h. After refluxing for and additional 21 h, sat. NH$_4$F solution (50 mL) was added, the mixture was stirred for 30 minutes and extracted with EtOAc (200 mL). The extract was washed with brine (50 mL), dried over MgSO$_4$, filtered and concentrated in vacuo. Purification by silica chromatography (95:5 hexanes:EtOAc) gave 0.510 g (64% yield) of the product as a crystalline solid: EIHRMS m/z 382.0620 (M+, C$_{16}$H$_{12}$F$_6$O$_4$, Calc'd 382.0640).

Step 2. Preparation of 6-(trifluoromethoxy)-2-(trifluoromethyl)-8-vinyl-2H-chromene-3-carboxylic acid The ester from Step 1 was hydrolyzed via a method similar to that described in Example 17d, Step 2 to give the product as a yellow crystalline solid: ESHRMS m/z 353.0246 (M–H, C$_{14}$H$_7$F$_3$O$_3$, Calc'd 353.0243). $^1$H NMR (dmso-d$_6$, 300 MHz) 13.45 (brs, 1H), 7.89 (s, 1H), 7.63 (d, 1H, J=2.7 Hz), 7.54 (2, 1H), 6.84 (dd, 1H, J=11.3, 18.0 Hz), 6.04 (q, 1H, J=7.0 Hz), 6.03 (d, 1H, J=17.2 Hz), 5.47 (d, 1H, J=11.7 Hz).

EXAMPLE 21o

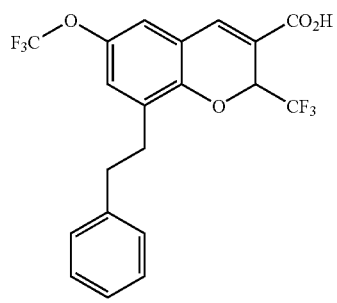

8-(2-phenylethyl)-6-(trifluoromethoxy)-2-(trifluoromethyl)-2H-chromene-3-carboxylic acid 8-(Phenylethynyl)-6-(trifluoromethoxy)-2-(trifluoromethyl)-2H-chromene-3-carboxylic acid prepared as in Example 21 c, step 2 was hydrogenated via a method similar to that described in Example 21j to give the product as a light tan crystalline solid: ESHRMS m/z 431.0698 (M–H, C$_{20}$H$_{13}$F$_6$O$_4$, Calc'd 431.0713). $^1$H NMR (dmso-d$_6$, 300 MHz) 13.41 (brs, 1H), 7.89 (s, 1H), 7.44 (d, 1H, J=2.4 Hz), 7.23-7.28 (m,2H), 7.14-7.18 (m, 4H), 6.04 (q, 1H, J=7.3 Hz), 2.80-2.96 (m, 4H).

EXAMPLE 21p

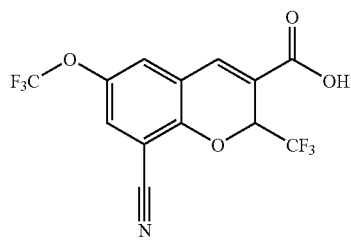

8-cyano-6-(trifluoromethoxy)-2-(trifluoromethyl)-2H-chromene-3-carboxylic acid

Step 1. Preparation of ethyl 8-cyano-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (2.00 g, 4.15 mmole), CuI (158 mg, 0.830 mmole), KCN (1.08 g, 16.6 mmole) and Pd(PPh$_3$)$_4$ (480 mg, 0.415 mmole) in anhydrous THF (5.0 mL) were refluxed under a dry N$_2$ atmosphere for 2.5 days. The mixture was then poured into brine (100 mL), extracted with EtOAc (100 mL), dried over MgSO$_4$ and concentrated in vacuo. Purification by silica chromatography followed by crystallization from EtOAc-hexanes gave 1.30 g (82% yield) of the product a yellow crystalline solid: EIHRMS m/z 399.0812 (M+NH$_4$, C$_{15}$H$_9$NO$_4$F$_6$NH$_4$, Calc'd 399.0774).

Step 2. Preparation of 8-cyano-6-(trifluoromethoxy)-2-(trifluoromethyl)-2H-chromene-3-carboxylic acid The ester from Step 1 was hydrolyzed via a method similar to that described in Example 18a, Step 2 to give the crude product as an off-white solid: $^1$H NMR (dmso-d$_6$, 300 MHz) 13.69 (brs, 1H), 8.05 (d, 1H, J=2.2 Hz), 7.99 (d, 1H, J=2.0 Hz), 6.29 (q, 1H, J=7.0 Hz), 4.16 (q, 1H, J=7.3 Hz), 1.56 (d, 3H, J=7.3 Hz); ESHRMS m/z 352.0048 (M−H, C$_{13}$H$_4$F$_6$O$_4$, Calc'd 352.0039).

EXAMPLE 21q

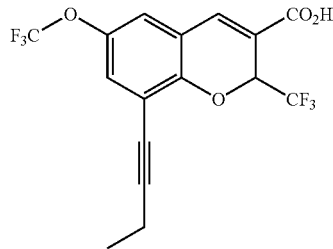

8-but-1-ynyl-6-(trifluoromethoxy)-2-(trifluoromethyl)-2H-chromene-3-carboxylic acid Step 1. Preparation of ethyl 8-but-1-ynyl-6-(trifluoromethoxy)-2-(trifluoromethyl)-2H-chromene-3-carboxylate To a Parr bottle containing a mixture of ethyl 8-iodo-6-(trifluoromethoxy)-2-(trifluoromethyl)-2H-chromene-3-carboxylate prepared as in Example 21 a, Step 2 (1.00 g, 2.07 mmole), CuI (39 mg, 0.207 mmole), PdCl$_2$(dppf)$_2$.CH$_2$Cl$_2$ (167 mg, 0.0.207 mmole) and TEA (867 uL, 6.22 mmole) in anhydrous toluene (10 mL) was added at −78° C. 1-butyne (5 ml) and the bottle was sealed. After stirring for overnight at room temperature, additional CuI (390 mg, 2.07 mmole) and PdCl$_2$(dppf)$_2$.CH$_2$Cl$_2$ (1.67 g, 2.07 mmole) were added and the vessel was resealed. After stirring for 2.5 days, the mixture was cooled to −78° C. and additional CuI (200 mg, 1.05 mmole) and PdCl$_2$(dppf)$_2$.CH$_2$Cl$_2$ (0.500 g, 0.613 mmole), anhydrous toluene (10 mL) and 1-butyne (5 ml) were added and the vessel was resealed. After stirring at room temperature for 4 days, additional CuI (390 mg, 2.07 mmole) and PdCl$_2$(dppf)$_2$.CH$_2$Cl$_2$ (0.500 g, 0.613 mmole) were added and the vessel was resealed and stirred at room temperature overnight. The mixture was then poured into brine (100 mL) and extracted with EtOAc (200 mL). The extract was dried over MgSO$_4$, filtered and concentrated in vacuo. Purification by silica chromatography (95:5 EtOAc: hexanes) gave the product as a crystalline solid: EIHRMS m/z 408.0773 (M+, C$_{18}$H]$_4$F$_6$O$_4$, Calc'd 408.0796).

Step 2. Preparation of 8-but-1-ynyl-6-(trifluoromethoxy)-2-(trifluoromethyl)-2H-chromene-3-carboxylic acid The ester from Step 1 was hydrolyzed via a method similar to that described in Example 17d, Step 2 to give the crude product as an yellow solid: $^1$H NMR (dmso-d$_6$, 300 MHz) 13.48 (brs, 1H), 7.89 (s, 1H), 7.60 (d, 1H, J=2.2 Hz), 7.41 (d, 1H, J=2.4 Hz), 6.08 (q, 1H, J=7.0 Hz), 2.45 (q, 2H, J=7.5 Hz), 1.16 (t, 3H, J=7.5 Hz); ESHRMS m/z 379.0389 (M−H, C$_{16}$H$_9$F$_6$O$_4$, Calc'd 379.0400).

EXAMPLE 21r

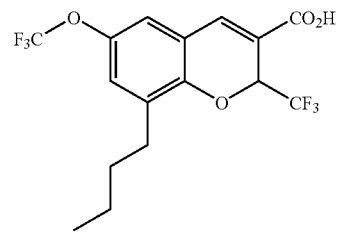

8-butyl-6-(trifluoromethoxy)-2-(trifluoromethyl)-2H-chromene-3-carboxylic acid

Step 1. Preparation of ethyl 8-butyl-6-(trifluoromethoxy)-2-(trifluoromethyl)-2H-chromene-3-carboxylate A mixture of ethyl 8-but-1-ynyl-6-(trifluoromethoxy)-2-(trifluoromethyl)-2H-chromene-3-carboxylate prepared as in Example 21q, Step 1 (450 mg, 1.10 mmole) and 10% Pd/C (45 mg) in absolute ethanol was hydrogenated at 30 psi for 1.5 h. The catalyst was removed by filtration and the solvent was removed in vacuo to give 310 mg (68% yield) of the product as a yellow crystalline solid: EIHRMS m/z 412.1099 (M+, C$_{18}$H$_{18}$F$_6$O$_4$, Calc'd 412.1109).

Step 2. Preparation of 8-butyl-6-(trifluoromethoxy)-2-(trifluoromethyl)-2H-chromene-3-carboxylic acid The ester from Step 1 was hydrolyzed via a method similar to that described in Example 17d, Step 2 to give the crude product as an yellow solid: $^1$H NMR (dmso-d$_6$, 300 MHz) 13.39 (brs, 1H), 7.88 (s, 1H), 7.43 (d, 1H, J=2.3 Hz), 7.26 (d, 1H, J=2.4 Hz), 5.99 (q, 1H, J=7.3 Hz), 2.49-2.68 (m, 2H), 1.45-1.55 (m, 2H), 1.21-1.33 (m, 2H), 0.86 (t, 3H, J=7.5 Hz); ESHRMS m/z 383.0742 (M−H, C$_{16}$H$_{13}$F$_6$O$_4$, Calc'd 383.0713).

EXAMPLE 21s

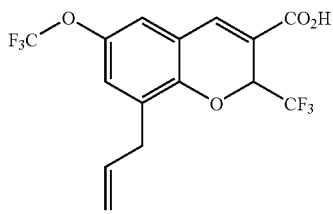

8-allyl-6-(trifluoromethoxy)-2-(trifluoromethyl)-2H-chromene-3-carboxylic acid

Step 1. Preparation of ethyl 8-allyl-6-(trifluoromethoxy)-2-(trifluoromethyl)-2H-chromene-3-carboxylate To a mixture of ethyl 8-iodo-6-(trifluoromethoxy)-2-(trifluoromethyl)-2H-chromene-3-carboxylate prepared as in Example 21a, Step 2 (1.00 g, 2.07 mmole) and Pd(PPh$_3$)$_4$ (0.239 g, 0.207 mmole) in anhydrous toluene (50 mL) under a dry N$_2$ atmosphere was added tributylallyltin (0.707 mL, 2.28 mmole). The mixture was refluxed for 16 h and 20% NH$_4$F solution (50 mL) was added. The mixture was stirred for 1 h and extracted with EtOAc (200 mL). The extract was washed with brine (100 mL), dried over Na$_2$SO$_4$, filtered and concentrated in vacuo. Purification by silica chromatography (9:1 hexanes:EtOAc) gave 0.770 g (94% yield) of the product as a yellow oil: EIHRMS m/z 396.0769 (M+, C$_{17}$H$_{14}$F$_6$O$_4$, Calc'd 396.0796).

Step 2. Preparation of 8-allyl-6-(trifluoromethoxy)-2-(trifluoromethyl)-2H-chromene-3-carboxylic acid The ester from Step 1 was hydrolyzed via a method similar to that described in Example 9x, Step 3 to give the product as a yellow crystalline solid. Purification by reverse phase chromatography (acetonitrile:0.5% TFA-H$_2$O) gave 439.mg (68% yield) of the product as an off-white solid: $^1$H NMR (dmso-d$_6$, 300 MHz) 13.43 (brs, 1H), 7.90 (s, 1H), 7.50 (s, 1H), 7.27 (s, 1H), 5.86-6.05 (m, 2H), 5.02-5.08 (m, 2H), 3.29-3.45 (m, 2H); ESHRMS m/z 367.0437 (M–H, C$_{15}$H$_9$F$_6$O$_3$, Calc'd 367.0400).

EXAMPLE 21t

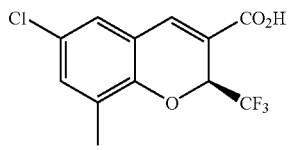

(2S)-6-chloro-8-methyl-2-(trifluoromethyl)-2H-chromene-3-carboxylic acid

Racemic 6-chloro-8-methyl-2-(trifluoromethyl)-2H-chromene-3-carboxylic acid prepared as in U.S. Pat. No. 6,271,253 B1 Example 38 (10.0 g) was resolved by chiral separation using a Chiralcel OJ column eluting with EtOH/heptane/TFA=5/95/0.1 and detecting at 254 nm as peak 1 with retention time 6.05 min to give 4.94 g (49% yield) the product as a solid. X-ray crystal structure analysis confirmed the title compound to be the (S)-enantiomer: $^1$H NMR (dmso-d$_6$, 300 MHz) 13.36 (brs, 1H), 7.82 (s, 1H), 7.44 (d, 1H, J=2.7 Hz), 7.33 (d, 1H, J=2.0 Hz), 5.95 (q, 1H, J=7.3 Hz), 2.16 (s, 3H); ESLRMS m/z 293 (M+H, C$_{12}$H$_9$ClF$_3$O$_3$, Calc'd 293).

EXAMPLE 21u

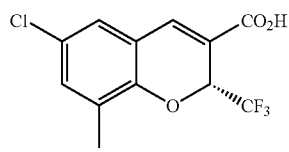

(2R)-6-chloro-8-methyl-2-(trifluoromethyl)-2H-chromene-3-carboxylic acid

Racemic 6-chloro-8-methyl-2-(trifluoromethyl)-2H-chromene-3-carboxylic acid prepared as in U.S. Pat. No. 6,271,253 B1 Example 38 (10.0 g) was resolved by chiral separation using a Chiralcel OJ column eluting with EtOH/heptane/TFA=5/95/0.1 and detecting at 254 nm as peak 2 with retention time 7.68 min to give 3.99 g (40% yield) the product as a solid: ESLRMS m/z 293 (M+H, C$_{12}$H$_9$F$_3$O$_3$, Calc'd 293).

EXAMPLE 22

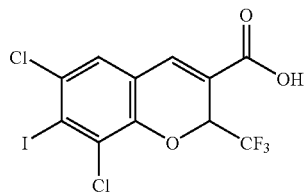

6,8-dichloro-7-iodo-2-(trifluoromethyl)-2H-chromene-3-carboxylic acid

Step 1. Preparation of 2-hydroxy-4-iodobenzaldehyde

The commercially available 3-iodophenol was formylated via a method similar to that described in Example 9f; Stepi: $^1$HNMR (DMSO-d$_6$/300 MHz) 10.95 (s, 1H), 10.19 (s, 1H), 7.33 (m, 3H), 4.31 (m, 1H).

Step 2. Preparation of ethyl 6.8-dichloro-7-iodo-2-(trifluoromethyl)-2H-chromene-3-carboxylate The salicylaldehyde (Step 1) (6.05 g, 24.4 mmole) was chlorinated via a method similar to that described in Example 4b, Step 1 (3.91 g, 51%). This ester was of suitable purity to use without fuirther purification. $^1$HNMR (CDCl$_3$/300 MHz) 11.55 (s, 1H), 9.84 (s, 1H), 7.6 (s, 1H).

Step 3. Preparation of ethyl 7-iodo-2-(trifluoromethyl)-2H-chromene-3-carboxylate The ester (Step 2)(3.85 g, 12.1 mmole) was condensed via a method similar to that described in Example 4a, Step 1. (2.83 g, 50%) This ester was of suitable purity to use without further purification: $^1$HNMR (CDCl$_3$/300 MHz) 7.64 (s, 1H), 7.30 (d, 1H, J=9.2 Hz), 5.83 (q, 1H, J=7.1 Hz), 4.32-4.40 (m, 2H), 1.36-1.57 (m, 3H).

Step 4. Preparation of 6,8-dichloro-7-iodo-2-(trifluoromethyl)-2H-chromene-3-carboxylic acid The ester (Step 3) was hydrolyzed to form the carboxylic acid via a method similar to that described in Example 4a, Step 2 (99%): 1HNMR (CDCl$_3$-d$_6$/300 MHz) 7.95 (s, 1H), 7.78 (s, 1 H), 6.05(q, 1H, J=7.1 Hz).

EXAMPLE 23a

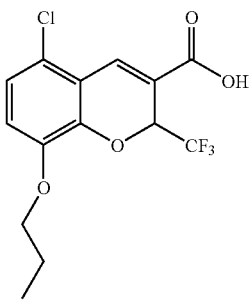

5-chloro-8-propoxy-2-(trifluoromethyl)-2H-chromene-3-carboxylic acid

Step 1. Preparation of ethyl 8-hydroxy-2-(trifluoromethyl)-2H-chromene-3-carboxylate The ethyl 8-hydroxy-2-(trifluoromethyl)-2H-chromene-3-carboxylate was prepared by the procedure similar to that described in Example 1a, Step 1 by using 2,3-dihydroxy benzaldehyde as starting materials: LCMS m/z 289.15 (M+H). $^1$H NMR (CDCl$_3$/400 MHz) 7.72 (s, 1H), 6.98 (dd, 1H, J=1.6, 8.0 Hz), 6.88 (m, 1H), 6.79 (dd, 1H, J=1.6, 7.6 Hz), 5.76 (q, 1H, J=6 Hz), 4.29 (m, 2H), 1.33 (t, 3H, J=7.2 Hz).

Step 1. Preparation of 5-chloro-8-propoxy-2-(trifluoromethyl)-2H-chromene-3-carboxylic acid The 5-chloro-8-propoxy-2-(trifluoromethyl)-2H-chromene-3-carboxylic acid was prepared by the procedure similar to the method described in Example 2b using ethyl 8-hydroxy-2-(trifluoromethyl)-2H-chromene-3-carboxylate Step 1 as starting material: ESHRMS m/z 335.0253 (M–H, C$_{14}$H$_{104}$F$_3$, Calc'd 335.0292). $^1$H NMR (acetone-d$_6$/400 MHz) 8.02 (s, 1H), 7.14 (d, 1H, J=8.8 Hz), 7.10 (d, 1H, J=8.8 Hz), 5.90 (q, 1H, J=7.0 Hz), 4.03 (m, 2H), 1.78(m, 2H), 1.07(t, 3H, J=7.2 Hz).

EXAMPLE 23b

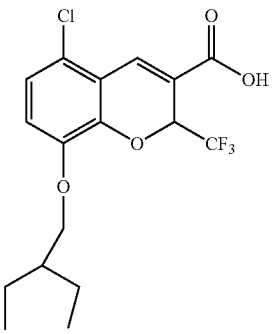

5-chloro-8-(2-ethylbutoxy)-2-(trifluoromethyl)-2H-chromene-3-carboxylic acid

The 5-chloro-8-(2-ethylbutoxy)-2-(trifluoromethyl)-2H-chromene-3-carboxylic acid was prepared by the procedure similar to the method described in Example 23a: ESHRMS m/z 377.0761 (M–H, C$_{17}$H$_{17}$O$_4$F$_3$Cl, Calc'd 377.0762). $^1$H NMR (acetone-d$_6$/400 MHz) 8.02 (s, 1H), 7.14 (d, 1H, J=8.8 Hz), 7.10 (d, 1H, J=8.8 Hz), 5.90 (q, 1H, J=7.0 Hz), 4.03 (m, 2H), 1.66 (m, 1H), 1.49 (m, 4H), 0.93 (t, 6H, J=7.2 Hz).

EXAMPLE 23c

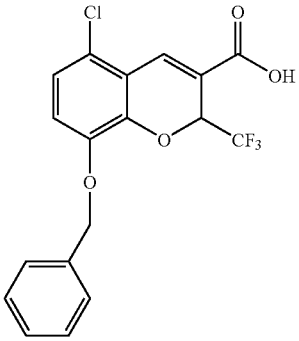

8-(benzyloxy)-5-chloro-2-(trifluoromethyl)-2H-chromene-3-carboxylic acid

The 8-(benzyloxy)-5-chloro-2-(trifluoromethyl)-2H-chromene-3-carboxylic acid was prepared by the procedure similar to the method described in Example 23a: ESHRMS m/z 383.0326 (M–H, C$_{18}$H$_{11}$O$_4$F$_3$Cl, Calc'd 383.0303). $^1$H NMR (CDCl$_3$/300 MHz) 8.17 (s, 1H), 7.34 (m, 5H), 6.92 (d, 1H, J=8.8 Hz), 6.92 (d, 1H, J=8.8 Hz), 5.79 (q, 1H, J=7.0 Hz), 5.16 (d, 1H, J=12 Hz), 5.14 (d, 1H, J=12 Hz).

EXAMPLE 23d

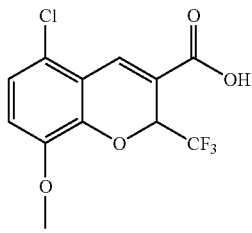

5-chloro-8-methoxy-2-(trifluoromethyl)-2H-chromene-3-carboxylic acid

Step 1. Preparation of ethyl 8-methoxy-2-(trifluoromethyl)-2H-chromene-3-carboxylate The 2-hydroxy-3-methoxybenzaldehyde (3.05 g, 20mmol) was dissolved in DMSO (9 mL). TEA (4.09 g, 40 mmol) and ethyl 4,4,4-trifluorocrotonate (6.93 g, 40 mmol) were added to above solution. The reaction was heated to 70° C. and monitored by TLC and GCMS until done. The reaction was quenched with 10% HCl. The compound was extracted with EtOAc and washed with water and NH$_4$Cl. The organic was dried over MgSO$_4$. After concentrated, the crude compound was purified by flash column with 20% EtOAc in hexane. This ester was of suitable purity to use without further purification.

Step 2. Preparation of 5-chloro-8-methoxy-2-(trifluoromethyl)-2H-chromene-3-carboxylic acid The 5-chloro-8-methoxy-2-(trifluoromethyl)-2H-chromene-3-carboxylic acid was prepared by the procedure similar to the method described in Example 2b, Step 2, 3: ESHRMS m/z 307.0006 (M−H, C$_{12}$H$_7$O$_4$F$_3$Cl, Calc'd 306.9979). $^1$H NMR (CDCl$_3$/300 MHz) 8.17 (s, 1H), 7.02 (d, 1H, J=8.7 Hz), 6.91 (d, 1H, J=8.7 Hz), 5.77 (q, 1H, J=7.0 Hz), 3.89 (s, 3H). Anal. Calc'd for C$_{12}$H$_8$ClF$_3$O$_4$. C, 46.70; H, 2.61. Found: C, 46.40; H, 2.71.

EXAMPLE 23e

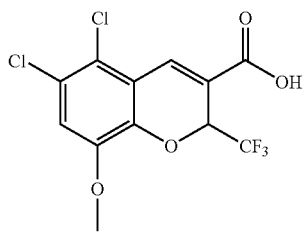

5,6-dichloro-8-methoxy-2-(trifluoromethyl)-2H-chromene-3-carboxylic acid

The 5,6-dichloro-8-methoxy-2-(trifluoromethyl)-2H-chromene-3-carboxylic acid was prepared by the procedure similar to the method described in Example 1b, Step 2, 3 using ethyl 8-methoxy-2-(trifluoromethyl)-2H-chromene-3-carboxylate Example 23d, Step 1 as starting material: ESHRMS m/z 340.9600 (M−H, C$_{12}$H$_6$O$_4$F$_3$C$_2$, Calc'd 340.9590). $^1$H NMR (CDCl$_3$/300 MHz) 7.93 (s, 1H), 6.92 (s, 1H), 5.67 (q, 1H, J=7.0 Hz), 3.78 (s, 3H).

EXAMPLE 23f

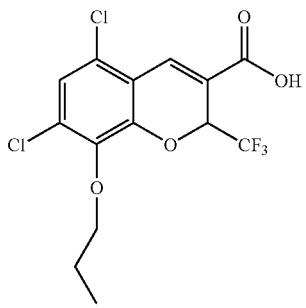

5,7-dichloro-8-propoxy-2-(trifluoromethyl)-2H-chromene-3-carboxylic acid

The 5,7-dichloro-8-propoxy-2-(trifluoromethyl)-2H-chromene-3-carboxylic acid acid was prepared by the procedure similar to the method described in Example 2b using ethyl 8-hydroxy-2-(trifluoromethyl)-2H-chromene-3-carboxylate from Example 23a, Step 1 as starting material: ESHRMS m/z 368.9950 (M−H, C$_{14}$H$_{10}$O$_4$F$_3$Cl$_2$, Calc'd 368.9903). $^1$H NMR (acetone-d$_6$/ 400 MHz) 8.02 (s, 1H), 7.30 (s,1H), 5.90 (q, 1H, J=7.0 Hz), 4.03 (m, 2H), 1.78 (m, 2H), 1.07(t, 3H, J=7.2 Hz).

EXAMPLE 24a

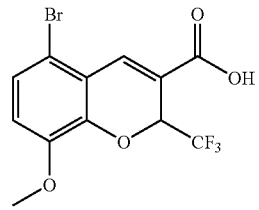

5-bromo-8-methoxy-2-(trifluoromethyl)-2H-chromene-3-carboxylic acid

Step 1. Preparation of ethyl 5-bromo-8-methoxy-2-(trifluoromethyl)-2H-chromene-3-carboxylate The ethyl 5-bromo-8-methoxy-2-(trifluoromethyl)-2H-chromene-3-carboxylate was prepared by a procedure similar to the method described in Example 23d, Step 1: $^1$H NMR (CDCl$_3$/300 MHz) 7.98 (s, 1H), 7.18 (d, 1H, J=8.7 Hz), 6.83 (d, 1H, J=8.7 Hz), 5.78 (q, 1H, J=7.0 Hz), 4.39 (m, 2H), 1.37 (m, 3H).

Step 2. Preparation of 5-bromo-8-methoxy-2-(trifluoromethyl)-2H-chromene-3-carboxylic acid The 5-bromo-8-methoxy-2-(trifluoromethyl)-2H-chromene-3-carboxylic acid was prepared by a procedure similar to the method described in Example 2a, Step 3. ESHRMS m/z 350.9495 (M–H, $C_{12}H_8O_4F_3Br$, Calc'd 350.9474). $^1$H NMR (CDCl$_3$/300 MHz) 7.85 (s, 1H), 7.05 (d, 1H, J=8.8 Hz), 6.71 (d, 1H, J=8.8 Hz), 5.65 (q, 1H, J=7.0 Hz), 3.75 (s, 3H).

EXAMPLE 24b

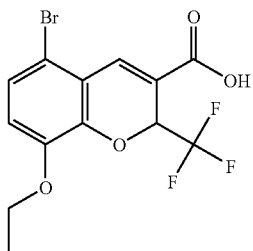

5-bromo-8-ethoxy-2-(trifluoromethyl)-2H-chromene-3-carboxylic acid

Step 1. Preparation of ethyl 5-bromo-8-ethoxy-2-(trifluoromethyl)-2H-chromene-3-carboxylate The ester (Example 28d, step 2) was brominated via a similar method to that described in Example 41, step 1 (76%) EIHRMS m/z 394.0028 (M–H, $C_{15}H_{14}ClF_3O_4$, Calc'd 393.9979).

Step 2. Preparation of 5-bromo-8-ethoxy-2-(trifluoromethyl)-2H-chromene-3-carboxylic acid The ester (Step 1) was hydrolyzed to form the carboxylic acid via a method similar to that described in Example 4a, Step 2, (99%). $^1$HNMR (CDCl$_3$-d$_6$/400 MHz), 8.13 (s, 1H), 7.16 (d, 1H, J=8.6 Hz), 6.86 (d, 1H, J=8.6 Hz), 5.77 (q, 1H, J=7.1 Hz), 4.07-4.14 (m, 2H), 1.41-1.46 (m, 3H)

EXAMPLE 25a

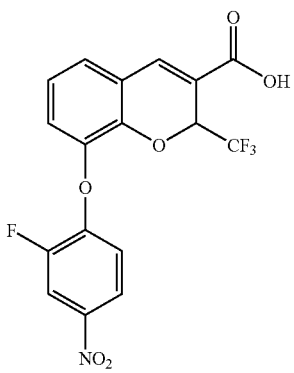

8-(2-fluoro-4-nitrophenoxy)-2-(trifluoromethyl)-2H-chromene-3-carboxylic acid

The 8-(2-fluoro-4-nitrophenoxy)-2-(trifluoromethyl)-2H-chromene-3-carboxylic acid was prepared by the procedure similar to that described in Example 5a using ethyl 8-hydroxy-2-(trifluoromethyl)-2H-chromene-3-carboxylate from Example 23a, Step 1 as starting material: ESHRMS m/z 398.0264 (M–H, $C_{17}H_8O_6F_4N$, Calc'd 398.0282). $^1$H NMR (acetone-d$_6$/400 MHz) 7.85 (dd, 1H, J=10.8, 2.8 Hz), 8.07 (m, 1H), 7.96 (s, 1H), 7.50 (dd, 1H, J=8.0, 1.6 Hz), 7.40 (dd, 1H, J=8.0, 1.6 Hz), 7.21 (t, 1H, J=8.0), 7.02 (t, 1H, J=8.0 Hz) 5.84 (q, 1 H, J=7.0 Hz).

EXAMPLE 25b

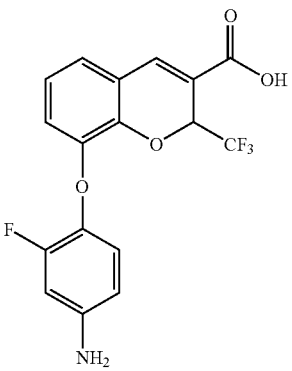

8-(4-amino-2-tluorophenoxy)-2-(trifluoromethyl)-2H-chromene-3-carboxylic acid

The 8-(4-amino-2-fluorophenoxy)-2-(trifluoromethyl)-2H-chromene-3-carboxylic acid was prepared by the procedure similar to the method described in Example 2a using ethyl 8-hydroxy-2-(trifluoromethyl)-2H-chromene-3-carboxylate from Example 23a, Step 1 as starting material: ESHRMS m/z 368.0560 (M–H, $C_{17}H_{10}O_4F_4N$, Calc'd 368.0540). $^1$H NMR (acetone-d$_6$/400 MHz) 7.98 (s, 1H), 7.37 (m, 1H), 7.25 (m, 1H), 7.14 (m, 1H), 7.05 (m, 2H), 6.87 (m, 1H), 6.62 (m, 1H), 5.84 (q, 1H, J=7.0 Hz).

EXAMPLE 25c

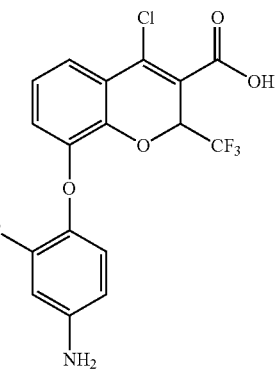

8-(4-amino-2-fluorophenoxy)-4-chloro-2-(trifluoromethyl)-2H-chromene-3-carboxylic acid The 8-(4-amino-2-fluorophenoxy)-4-chloro-2-(trifluoromethyl)-2H-chromene-3-carboxylic acid (TFA salt) was prepared by the procedure similar to the method described in Example 2a using ethyl 8-hydroxy-2-(trifluoromethyl)-2H-chromene-3-carboxylate from Example 23a, Step 1 as starting material: ESHRMS m/z 402.0158 (M−H, $C_{17}H_9O_4F_4NCl$, Calc'd 402.0151). $^1$H NMR (acetone-$d_6$/400 MHz) 7.75 (dd, 1H, J=8.0, 1.0 Hz), 7.59 (dd, 1H, J=10.6, 2.3 Hz), 7.39 (dd, 1H, J=8.3, 1.5), 7.37 (m, 1H), 7.25 (m, 1H), 7.10 (m, 1H), 5.98 (q, 1H, J=7.0 Hz).

EXAMPLE 25d

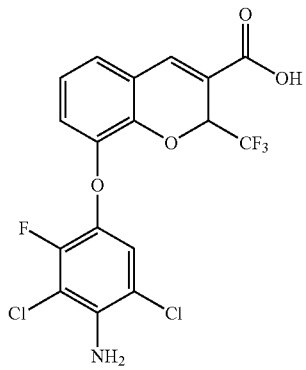

8-(4-amino-3,5-dichloro-2-fuorophenoxy)-2-(trifluoromethyl)-2H-chromene-3-carboxylic acid The 8-(4-amino-3,5-dichloro-2-fluorophenoxy)-2-(trifluoromethyl)-2H-chromene-3-carboxylic acid was prepared by chlorination of 8-(4-amino-2-fluorophenoxy)-1-(trifluoromethyl)-2H-chromene-3-carboxylic acid from Example 25b using the procedure similar to the method described in Example 2a, Step 2: ESHRMS m/z 436.9560 (M−H, $C_{17}H_7O_5F_4Cl_2$, Calc'd 436.9601). $^1$H NMR (acetone-$d_6$/300 MHz) 7.93 (s, 1H), 7.35 (dd, 1H, J=7.2, 1.2 Hz), 7.21 (dd, 1H, J=8.1, 1.5 Hz), 7.08 (m, 2H), 7.05 (m, 2H), 5.84 (q, 1H, J=7.0 Hz).

EXAMPLE 25e

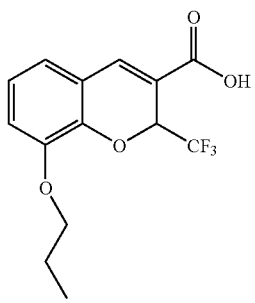

8-propoxy-2-(trifluoromethyl)-2H-chromene-3-carboxylic acid

The 8-propoxy-2-(trifluoromethyl)-2H-chromene-3-carboxylic acid was prepared by the procedure similar to the method described in Example 5e using ethyl 8-hydroxy-2-(trifluoromethyl)-2H-chromene-3-carboxylate from Example 23a, Step 1 as starting material: ESHRMS m/z 301.0691 (M−H, $C_{14}H_{12}O_4F_3$, Calc'd 301.0682). $^1$H NMR (CDCl$_3$/300 MHz) 7.89 (s, 1H), 6.98 (m, 3H), 5.80 (q, 1H5 J=7.0 Hz), 4.05 (m, 2H), 1.88 (m, 2H), 1.08 (t, 3H, J=7.4 Hz).

EXAMPLE 25f

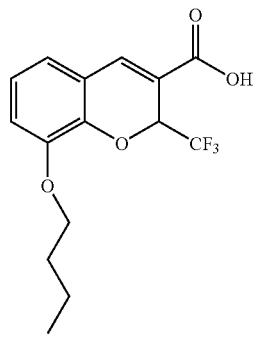

8-butoxy-2-(trifluoromethyl)-2H-chromene-3-carboxylic acid

The 8-butoxy-2-(trifluoromethyl)-2H-chromene-3-carboxylic acid was prepared by the procedure similar to the method described in Example 5e using ethyl 8-hydroxy-2-(trifluoromethyl)-2H-chromene-3-carboxylate from Example 23a, Step 1 as starting material: ESHRMS m/z 315.0815 (M−H, $C_{15}H_{14}O_4F_3$, Calc'd 368.0540). $^1$HNMR (CDCl$_3$/300 MHz) 7.85 (s, 1H), 6.98 (m, 3H), 5.76 (q, 1H, J=7.0 Hz), 4.06 (m, 2H), 1.82 (m, 2H), 1.50 (m, 2H), 0.97 (t, 3H, J=7.4 Hz).

EXAMPLE 25g

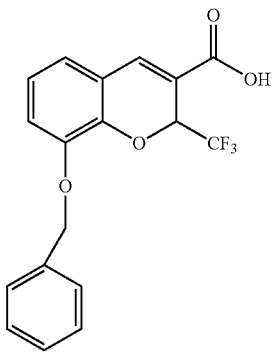

8-(benzyloxy)-2-(trifluoromethyl)-2H-chromene-3-carboxylic acid

The 8-(benzyloxy)-2-(trifluoromethyl)-2H-chromene-3-carboxylic acid was prepared by the procedure similar to the method described in Example 5e using ethyl 8-hydroxy-2-(trifluoromethyl)-2H-chromene-3-carboxylate from Example 23a, Step 1 as starting material: ESHRMS m/z 349.0710 (M–H, $C_{18}H_{12}O_4F_3$, Calc'd 349.0682). $^1$H NMR (CDCl$_3$/300 MHz) 7.86 (s, 1H), 7.34 (m, 5H), 7.00 (m, 1H), 6.89 (m, 1H), 5.80 (q, 1H, J=7.0 Hz), 5.22 (d, 1H, J=12.3 Hz), 5.19 (d, 1H, J=12.3 Hz).

EXAMPLE 25h

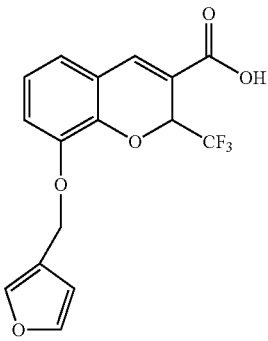

8-(3-furylmethoxy)-2-(trifluoromethyl)-2H-chromene-3-carboxylic acid

The 8-(3-furylmethoxy)-2-(trifluoromethyl)-2H-chromene-3-carboxylic acid was prepared by the procedure similar to the method described in Example 5e using ethyl 8-hydroxy-2-(trifluoromethyl)-2H-chromene-3-carboxylate from Example 23a, Step 1 as starting material: ESHRMS m/z 339.0510 (M–H, $C_{16}H_{10}O_5F_3$, Calc'd 339.0457). $^1$H NMR (CDCl$_3$/300 MHz) 7.85(s, 1H), 7.47 (s, 1H), 7.41 (m, 1H), 7.02 (m, 1H), 6.90(m, 2H), 6.48 (s, 1H), 5.84 (q, 1H, J=7.0 Hz), 5.07 (q, 1H, J=11.7 Hz), 5.01(q, 1H, J=11.7 Hz).

EXAMPLE 26

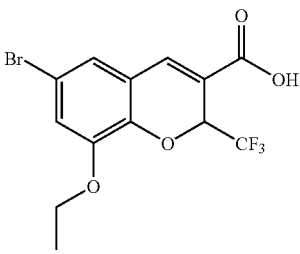

6-bromo-8-ethoxy-2-(trifluoromethyl)-2H-chromene-3-carboxylic acid

Step 1. Preparation of 5-bromo-3-ethoxy-2-hydroxybenzaldehyde

Bromine (2.95 g, 15.95 mmol) was added to a stirring solution of 3-ethoxy-2-hydroxybenzaldehyde (5.30 g, 31.9 mmol), which was dissolved in 30% HBr/HOAc The solution was stirred for 1.5 hrs at r.t. The reaction was quenched with H$_2$O and extracted with ethyl acetate. The organic layer was washed with sat. ammonium chloride and dried over anhydrous sodium sulfate. Upon filtration the filtrate was concentrated in vacuo and purified by flash chromatography (silica gel) and eluted with 5% EtOAc/hexanes to yield 1.56 g (20%) of the title compound as a colorless oil: ESHRMS m/z 242.9657 (M–H, $C_9H_9O_3Br$, Calc'd 242.9662).

Step 2. Preparation of ethyl 6-bromo-8-ethoxy-2-(trifluoromethyl)-2H-chromene-3-carboxylate The ethyl 6-bromo-8-ethoxy-2-(trifluoromethyl)-2H-chromene-3-carboxylate was prepared by a procedure similar to the method described in Example 23d, Step 1 using aldehyde from Step 1 as starting material: GCMS m/z 394.0 (M+). $^1$H NMR (CDCl$_3$/400 MHz) 7.63 (s, 1H), 7.06 (s, 1H), 6.99 (s, 1H), 5.78 (q, 1H, J=7.0 Hz), 4.34 (m, 2H), 4.11 (m, 2H), 1.45 (m, 3H), 1.37 (m, 3H).

Step 3. Preparation of 6-bromo-8-ethoxy-2-(trifluoromethyl)-2H-chromene-3-carboxylic acid The 6-bromo-8-ethoxy-2-(trifluoromethyl)-2H-chromene-3-carboxylic acid was prepared by a procedure similar to the method described in Example 2a, Step 3: ESHRMS m/z 364.9637 (M–H, $C_{13}H_9O_4F_3Br$, Calc'd 364.9631). $^1$H NMR (CDCl$_3$/400 MHz) 7.74 (s, 1H), 7.07 (s, 1H), 7.00 (s, 1H), 5.74 (q, 1H, J=7.0 Hz), 4.10 (m, 2H, J=7.0 Hz), 1.43 (q, 3H, J=7.0 Hz).

EXAMPLE 27

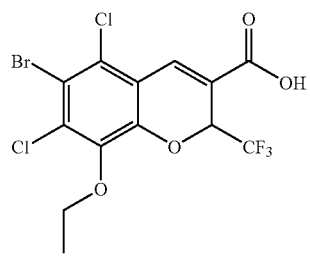

6-bromo-5,7-dichloro-8-ethoxy-2-(trifluoromethyl)-2H-chromene-3-carboxylic

Step 1. Preparation of ethyl 6-bromo-5,7-dichloro-8-ethoxy-2-(trifluoromethyl)-2H-chromene-3-carboxylate The ethyl 6-bromo-5,7-dichloro-8-ethoxy-2-(trifluoromethyl)-2H-chromene-3-carboxylate was prepared by a procedure similar to the method described in Example 1h, Step 2 using ethyl 6-bromo-8-ethoxy-2-(trifluoromethyl)-2H-chromene-3-carboxylate from Example 26, Step 2 as starting material: GCMS m/z 464.0 (M+). $^1$H NMR (CDCl$_3$/400 MHz) 8.03 (s, 1H), 5.80 (q, 1H, J=7.0 Hz), 4.34 (m, 2H), 4.10 (m, 2H), 1.42 (m, 3H), 1.37 (m, 3H).

Step 2. Preparation of 6-bromo-5,7-dichloro-8-ethoxy-2-(trifluoromethyl)-2H-chromene-3-carboxylic acid The 6-bromo-5,7-dichloro-8-ethoxy-2-(trifluoromethyl)-2H-chromene-3-carboxylic acid was prepared by a procedure similar to the method described in Example 2a, Step 3: ESHRMS m/z 432.8829 (M–H, $C_{13}H_7O_4F_3BrCl_2$, Calc'd 432.8851). ¹H NMR (CDCl₃/400 MHz) 8.18 (s, 1H), 5.78 (q, 1H, J=7.0 Hz), 4.12 (m, 2H), 1.43 (m, 3H).

EXAMPLE 28a

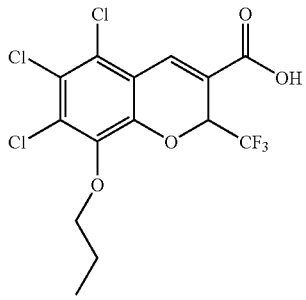

5,6,7-trichloro-8-propoxy-2-(trifluoromethyl)-2H-chromene-3-carboxylic acid

The 5,6,7-trichloro-8-propoxy-2-(trifluoromethyl)-2H-chromene-3-carboxylic acid was prepared by the procedure similar to the method described in Example 2b using ethyl 8-hydroxy-2-(trifluoromethyl)-2H-chromene-3-carboxylate from Example 23a, Step 1 as starting material: ESHRMS m/z 402.9490 (M–H, C₄H₉O₄F₃Cl₃,Calc'd 402.9513). ¹H NMR (CDCl₃/300 MHz) 8.19 (s, 1H), 5.79 (q, 1H, J=7.0 Hz), 4.02 (m, 2H), 1.83 (m, 2H), 1.07 (t, 3H, J=7.2 Hz).

EXAMPLE 28b

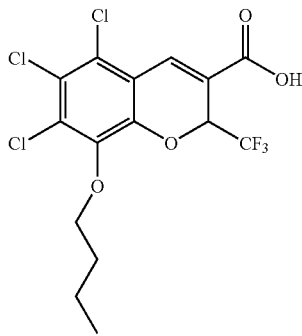

8-butoxy-5,6,7-trichloro-2-(trifluoromethyl)-2H-chromene-3-carboxylic acid

The 8-butoxy-5,6,7-trichloro-2-(trifluoromethyl)-2H-chromene-3-carboxylic acid was prepared by the procedure similar to the method described in Example 2b using ethyl 8-hydroxy-2-(trifluoromethyl)-2H-chromene-3-carboxylate from Example 23a, Step 1 as starting material: ESHRMS m/z 416.9670 (M–H, C₁₅H₁₁O₄F₃Cl₃,Calc'd 416.9649). ¹H NMR (acetone-d₆/400 MHz) 8.04 (s, 1H), 6.06 (q, 1H, J=6.8 Hz), 4.10 (m, 2H), 1.83(m, 2H), 1.54 (m, 2H), 0.96 (t, 3H, J=7.6 Hz).

EXAMPLE 28d

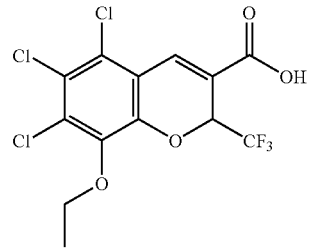

5,6,7-trichloro-8-ethoxy-2-(trifluoromethyl)-2H-chromene-3-carboxylic acid

Step 1. Preparation of ethyl 8-ethoxy-2-(trifluoromethyl)-2H-chromene-3-carboxylate The commercially available 3-ethoxysalicylaldehyde (15 g, 90.26 mmole) was condensed in a method similar to that described in Example 4a, Step 1. (18 g, 64%) This ester was of suitable purity to use without further purification: EIHRMS m/z 316.0887 (M–H, C₁₅H₁₅ClF₃O₄, Calc'd 316.0922).

Step 2. Preparation of ethyl 5,6,7-trichloro-8-ethoxy-2-(trifluoromethyl)-2H-chromene-3-carboxylate The ester (Step 1) was chlorinated via a method similar to that described in Example 4b, Step 1 (98%). This ester was of suitable purity to use without further purification. EIHRMS m/z 417.9753 (M–H, C₁₅H₁₂Cl₃F₃O₄, Calc'd 417.9785). Step 3. Preparation of 5,6,7-trichloro-8-ethoxy-2-(trifluoromethyl)-2H-chromene-3-carboxylic acid The ester (Step 3) was hydrolyzed to form the carboxylic acid via a method similar to that described in Example 4a, Step 2. (99%): ESHRMS m/z 388.9384 (M–H, C₁₃H₇Cl₃F₃O₄, Calc'd 388.9357). ¹HNMR (DMSO-d₆/400 MHz), 13.89 (brs, 1H), 7.84 (s, 1H), 6.20 (q, 1H, J=7.1 Hz), 4.07-4.14 (m, 2H), 1.41-1.46 (m, 3H).

EXAMPLE 29

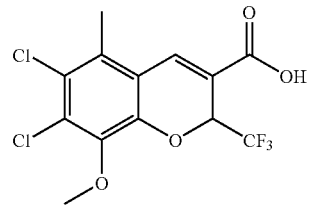

6,7-dichloro-8-methoxy-5-methyl-2-(trifluoromethyl)-2H-chromene-3-carboxylic acid Step 1. Preparation of ethyl 5-bromo-8-methoxy-2-(trifluoromethyl)-2H-chromene-3-carboxylate The ethyl 5-bromo-8-methoxy-2-(trifluoromethyl)-2H-chromene-3-carboxylate was prepared by a procedure similar to the method described in Example 24a, Step 1: $^1$H NMR (CDCl$_3$/300 MHz) 7.98 (s, 1H), 7.18 (d, 1H, J=8.7 Hz), 6.83 (d, 1H, J=8.7 Hz), 5.78 (q, 1H, J=7.0 Hz), 4.39 (m, 2H), 1.37 (m, 3H).

Step 2. Preparation of ethyl 5-bromo-6,7-dichloro-8-methoxy-2-(trifluoromethyl)-2H-chromene-3-carboxylate The ethyl 5-bromo-8-methoxy-2-(trifluoromethyl)-2H-chromene-3-carboxylate was prepared by a procedure similar to the method described in Example 1h, Step 2: $^1$H NMR (CD$_3$OD/300 MHz) 8.02 (s, 1H), 7.25 (s, 1H), 5.80 (q, 1H, J=7.0 Hz), 4.34 (m, 2H), 3.91 (s, 3H), 1.37 (m, 3H).

Step 3. Preparation of ethyl 6,7-dichloro-8-methoxy-5-methyl-2-(trifluoromethyl)-2H-chromene-3-carboxylate Pd(PPh$_3$)$_4$ (0.13 g, 0.85 mmol), K$_2$CO$_3$ (0.34 g, 0.85 mmol) and trimethylboroxine (0.14 g, 0.85 mmol) was added to a stirring solution of ethyl 5-bromo-6,7-dichloro-8-methoxy-2-(trifluoromethyl)-2H-chromene-3-carboxylate (0.38 g, 0.85 mmol) dissolved in 1,4-dioxane and heated to reflux for 24 hrs. Allowed to cool to R.T., filtered through celite and washed with EtOAc. The resulting solution was condensed in vacuo and purified by flash chromatography (silica gel) and eluted with 10% EtOAc/ hexanes to yield 0.18 g (56%) of the title compound as an amorphous solid: GCMS m/z 384.0 (M+). $^1$H NMR (CDCl$_3$/300 MHz) 7.92 (s, 1H), 5.80 (q, 1H, J=7.0 Hz), 4.35 (m, 2H), 3.89 (s, 3H), 2.47 (s, 3H), 1.36 (m, 3H).

Step 4. Preparation of 6,7-dichloro-8-methoxy-5-methyl-2-(trifluoromethyl)-2H-chromene-3-carboxylic acid The 6,7-dichloro-8-methoxy-5-methyl-2-(trifluoromethyl)-2H-chromene-3-carboxylic acid was prepared by a procedure similar to the method described in Example 2a, Step 3: ESHRMS m/z 354.9782 (M−H, C$_{13}$H$_8$O$_4$F$_3$Cl$_2$, Calc'd 354.9746). $^1$H NMR (CDCl$_3$/300 MHz) 8.08 (s, 1H), 5.78 (q, 1H, J=7.0 Hz), 3.90 (s, 3H), 2.49 (s, 3H).

EXAMPLE 30

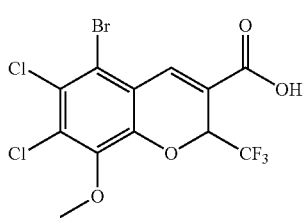

5-bromo-6,7-dichloro-8-methoxy-2-(trifluoromethyl)-2H-chormene-3-carboxylic acid

Step 1. Preparation of ethyl 5-bromo-8-methoxy-2-(trifluoromethyl)-2H-chromene-3-carboxylate The ethyl 5-bromo-8-methoxy-2-(trifluoromethyl)-2H-chromene-3-carboxylate was prepared by a procedure similar to the method described in Example 1a, Step 1: $^1$H NMR (CDCl$_3$/300 MHz) 7.98 (s, 1H), 7.18 (d, 1H, J=8.7 Hz), 6.83 (d, 1H, J=8.7 Hz), 5.78 (q, 1H, J=7.0 Hz), 4.39 (m, 2H), 1.37 (m, 3H).

Step 2. Preparation of ethyl 5-bromo-6,7-dichloro-8-methoxy-2-(trifluoromethyl)-2H-chromene-3-carboxylate The ethyl 5-bromo-8-methoxy-2-(trifluoromethyl)-2H-chromene-3-carboxylate was prepared by a procedure similar to the method described in Example 1h, Step 2: $^1$H NMR (CD$_3$OD/300 MHz) 8.02 (s, 1H), 7.25 (s, 1H), 5.80 (q, 1H, J=7.0 Hz), 4.34 (m, 2H), 3.91 (s, 3H), 1.37 (m, 3H).

Step 3. Preparation of 5-bromo-6,7-dichloro-8-methoxy-2-(trifluoromethyl)-2H-chromene-3-carboxylic acid The 5-bromo-6,7-dichloro-8-methoxy-2-(trifluoromethyl)-2H-chromene-3-carboxylic acid was prepared by a procedure similar to the method described in Example 2a, Step 3: ESHRMS m/z 420.8657 (M−H, C$_{12}$H$_5$O$_4$F$_3$Cl$_2$Br, Calc'd 420.8672). $^1$H NMR (CDCl$_3$/300 MHz) 7.87 (s, 1H), 5.67 (q, 1H, J=7.0 Hz), 3.77 (s, 3H).

EXAMPLE 31

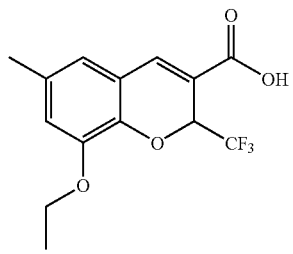

8-ethoxy-6-methyl-2-(trifluoromethyl)-2H-chromene-3-carboxylic acid

Step 1. Preparation of ethyl 6-bromo-8-ethoxy-2-(trifluoromethyl)-2H-chromene-3-carboxylate The ethyl 6-bromo-8-ethoxy-2-(trifluoromethyl)-2H-chromene-3-carboxylate was prepared by a procedure similar to the method described in Example 26, Step 2: GCMS m/z 394.0 (M+). $^1$H NMR (CDCl$_3$/400 MHz) 7.63 (s, 1H), 7.06 (s, 1H), 6.99 (s, 1H), 5.78 (q, 1H, J=7.0 Hz), 4.34 (m, 2H), 4.11 (m, 2H), 1.45 (m, 3H), 1.37 (m, 3H).

Step 2. Preparation of ethyl 8-ethoxy-5-methyl-2-(trifluoromethyl)-2H-chromene-3-carboxylate The ethyl 8-ethoxy-5-methyl-2-(trifluoromethyl)-2H-chromene-3-carboxylate was prepared by a procedure similar to the method described in Example 29, Step 3: $^1$H NMR (CDCl$_3$/300 MHz) 7.66 (s, 1H), 6.78 (s, 1H), 6.65 (s, 1H), 5.74 (q, 1H, J=7.0 Hz), 4.31 (m, 2H), 4.11 (m, 2H), 2.27 (s, 3H), 1.42 (m, 3H), 1.34 (m, 3H).

Step 3. Preparation of 8-ethoxy-6-methyl-2-(trifluoromethyl)-2H-chromene-3-carboxylic acid The 8-ethoxy-6-methyl-2-(trifluoromethyl)-2H-chromene-3-carboxylic acid was prepared by a procedure similar to the method described in Example 2a, Step 3. ESHRMS m/z 301.0667 (M–H, $C_{14}H_{12}O_4F_3$, Calc'd 301.0682): $^1$H NMR (CDCl$_3$/300 MHz) 7.80 (s, 1H), 6.81 (s, 1H), 6.68 (s, 1H), 5.73 (q, 1H, J=7.0 Hz), 4.11 (m, 2H), 2.28 (s,3H), 1.43 (m, 3H).

EXAMPLE 32a

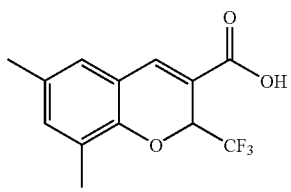

6,8-dimethyl-2-(trifluoromethyl)-2H-chromene-3-carboxylic acid

Step 1. Preparation of 2-hydroxy-3 5-dimethylbenzaldehyde

To a solution of 2,4-dimethylphenol (24.9 g, 204 mmole) in anhydrous toluene (75 mL) at 0° C. was added HMPA (35 mL) and then a solution of ethylmagnesium bromide (61 mL-3 M in ethyl ether, 0.183 mmole), keeping the temperature <10° C. Then paraformaldehyde (13 g, 0.43 mole) was added and the cooling was removed. The ethyl ether was removed by distillation and the mixture was refluxed. The mixture was quenched with 10% HCl and EtOAc was added. The EtOAc solution was washed twice with H$_2$O, twice with aqueous NH$_4$Cl, dried over Na$_2$SO$_4$ and concentrated in vacuo. Purification by silica chromatography (98:2 hexanes: EtOAc) gave 17.9 g (59% yield) of the product as a yellow oil: ESHRMS m/z 147.0619 (M–H, $C_9H_9O_2$, Calc'd 147.0603).

Step 2. Preparation of ethyl 6,8-dimethyl-2-(trifluoromethyl)-2H-chromene-3-carboxylate A mixture of 2-hydroxy-3,5-dimethylbenzaldehyde prepared as in Step 1 (6.16 g, 0.411 mole), ethyl 444-trifluorocrotonate (13.4 g, 0.970 mole) and TEA (8.3 g, 0.82 mole) in DMSO (10 mL) was heated at 90° C. A slow reaction rate was seen by GCMS. K$_2$CO$_3$ was then added and when the reaction was mostly complete, 10% HCl was added, followed by EtOAc. The layers were separated and the EtOAc layer was washed twice with H$_2$O, twice with aqueous NH$_4$Cl, dried over Na$_2$SO$_4$, filtered and concentrated in vacuo to give an orange oil. The crude product was purified by silica chromatography (9:1 hexanes:EtOAc) to give 5.47 g (44% yield) of the product: EIHRMS m/z 300.0938 (M+, $C_{15}H_{15}F_3O_3$, Calc'd 300.0973).

Step 3. Preparation of 6,8-dimethyl-2-(trifluoromethyl)-2H-chromene-3-carboxylic acid The ester from Step 2 was hydrolyzed via a method similar to that described in Example 17d, Step 2 to give the product: $^1$H NMR (CDCl$_3$/400 MHz) 7.79 (s, 1H), 7.01 (s, 1H), 6.88 (s, 1H), 5.68 (q, 1H, J=6.9 Hz), 2.24 (s, 3H), 2.20 (s, 3H); ESHRMS m/z 271.0575 (M–H, $C_{13}H_{10}F_3O_3$, Calc'd 271.0582).

EXAMPLE 32b

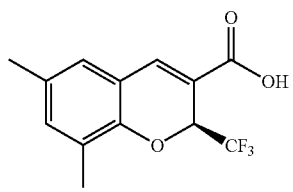

(2S)-6,8-dimethyl-2-(trifluoromethyl)-2H-chromene-3-carboxylic acid

The (2S)-6,8-dimethyl-2-(trifluoromethyl)-2H-chromene-3-carboxylic acid was resolved by chiral separation of racemic 6,8-dimethyl-2-(trifluoromethyl)-2H-chromene-3-carboxylic acid from Example 32a using Chiralcel OJ column eluting with EtOH/heptane/TFA=5/95/0.1 and detecting at 254 nm as peak 2 with retention time 6.36 min: $^1$H NMR (acetone-d$_6$/300 MHz) 7.81 (s, 1H), 7.09 (s, 2H), 5.80 (q, 1H, J=7.2 Hz), 2.25 (s, 3H), 2.21 (s, 1H). $[a]^{25}_{589}$=+3.2 degrees (MeOH) and $[a]^{25}_{436}$=+37.8 degrees (MeOH).

EXAMPLE 32c

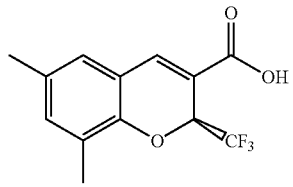

(2R)-6,8-dimethyl-2-(trifluoromethyl)-2H-chromene-3-carboxylic acid

The (2R)-6,8-dimethyl-2-(trifluoromethyl)-2H-chromene-3-carboxylic acid was resolved by chiral separation of racemic 6,8-dimethyl-2-(trifluoromethyl)-2H-chromene-3-carboxylic acid from Example 32a using Chiralcel OJ column eluting with EtOH/heptane/TFA=5/95/0.1 and detecting at 254 nm as peak 1 with retention time 4.38 min: $^1$H NMR (acetone-d$_6$/300 MHz) 7.81 (s, 1H), 7.09 (s, 2H), 5.80 (q, 1H, J=7.2 Hz), 2.25 (s, 3H), 2.21 (s, 1H). $[a]^{25}_{589}$=−7.6 degrees(MeOH) and $[a]^{25}_{436}$=−40.4 degrees (MeOH).

EXAMPLE 32d

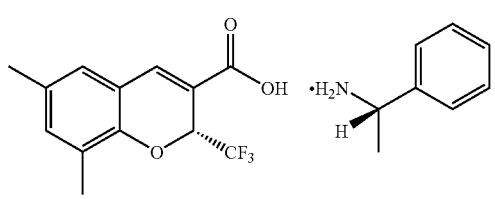

(2R)-6,8-dimethyl-2-(trifluoromethyl)-2H-chromene-3-carboxylic acid compound with (1S)-1-phenylethanamine (1:1)

The (2R)-6,8-dimethyl-2-(trifluoromethyl)-2H-chromene-3-carboxylic acid from Example 32c (138.5 mg, 0.51 mmole) was dissolved into Ethyl Acetate (2 mL) and IPA (2mL). (S)-(+)-ox-methylbenzylamine (61.6 mg, 0.51 mmol) was added into the solution. Hexane (12 mL) was added to above solution while it was stirring. The solution was standing without cover until crystals appeared. The absolute configuration of the complex was determined by small molecule x-ray diffraction: $^1$H NMR (acetone-$d_6$/400 MHz) 7.76 (s, 1H), 7.39 (d, 2H, J=7.2 Hz), 7.27 (t, 2H, J=7.2 Hz), 7.17 (t, 1H, J=6.8 Hz), 7.06 (s, 2H), 5.80 (q, 1H, J=7.2 Hz), 2.23 (s, 3H), 2.19 (s, 1H).

EXAMPLE 32e

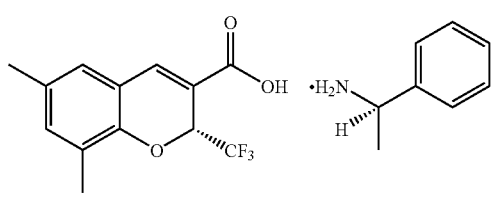

(2R)-6,8-dimethyl-2-(trifluoromethyl)-2H-chromene-3-carboxylic acid compound with (1R)-1-phenylethanamine (1:1)

The (2R)-6,8-dimethyl-2-(trifluoromethyl)-2H-chromene-3-carboxylic acid compound with (1R)-1-phenylethanamine (1:1) was prepared by the procedure similar to the method described in Example 32d: $^1$H NMR (acetone-d6/400 MHz) 7.76 (s, 1H), 7.39 (d, 2H, J=7.2 Hz), 7.27 (t, 2H, J=7.2 Hz), 7.17 (t, 1H, J=6.8 Hz), 7.06 (s, 2H), 5.80 (q, 1H, J=7.2 Hz), 2.23 (s, 3H), 2.19 (s, 1H).

EXAMPLE 32f

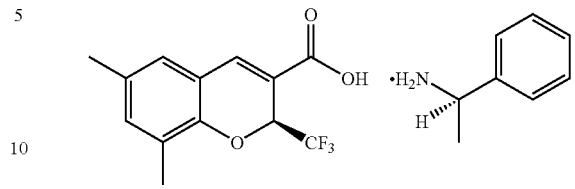

(2S)-6,8-dimethyl-2-(trifluoromethyl)-2H-chromene-3-carboxylic acid compound with (1R)-1-phenylethanamine (1:1)

The (2S)-6,8-dimethyl-2-(trifluoromethyl)-2H-chromene-3-carboxylic acid compound with (1R)-1-phenylethanamine (1:1) was prepared by the procedure similar to the method described in Example 32d: $^1$H NMR (acetone-$d_6$/400 MHz) 7.76 (s, 1H), 7.39 (d, 2H, J=7.2 Hz), 7.27 (t, 2H, J=7.2 Hz), 7.17 (t, 1H, J=6.8 Hz), 7.06 (s, 2H), 5.80 (q, 1H, J=7.2 Hz), 2.23 (s, 3H), 2.19 (s, 1H).

EXAMPLE 33

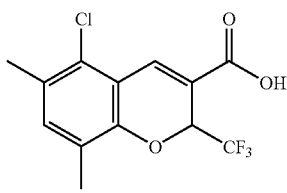

5-chloro-6,8-dimethyl-2-(trifluoromethyl)-2H-chromene-3-carboxylic acid

Step 1. Preparation of ethyl 5-chloro-6,8-dimethyl-2-(trifluoromethyl)-2H-chromene-3-carboxulate The ester (Example 32a, Step 2) was chlorinated via a method similar to that described in Example 4b, Step 1 (91%). This ester was of suitable purity to use without further purification: $^1$HNMR (Chloroform-$d_6$/400 MHz), 8.09 (s, 1H), 7.02 (s, 1H), 5.71 (q, 1H, J=7.1 Hz), 4.28-4.35 (m, 2H), 2.27 (s 3H), 2.17 (s, 3H), 1.33-1.37 (m, 3H).

Step 2. Preparation of 5-chloro-6,8-dimethyl-2-(trifluoromethyl)-2H-chromene-3-carboxylic acid The ester (Step 1) was hydrolyzed to form the carboxylic acid via a method similar to that described in Example 4a, Step 2. (132 mg, 99%): ESHRMS m/z 305.0171 (M−H, $C_{13}H_9ClF_3O_3$, Calc'd 305.0187). $^1$HNMR (Chloroform-$d_6$/400 MHz) 7.86 (s, 1H), 6.83 (s, 1H), 5.49(q, 1H, J=7.1 Hz), 2.06 (s, 3H), 1.96 (s, 3H).

EXAMPLE 34a

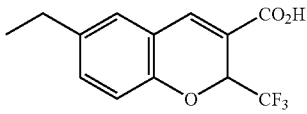

6-ethyl-2-(trifluoromethyl)-2H-chromene-3-carboxylic acid

Step 1. Preparation of ethyl 2-(trifluoromethyl)-2H-I-benzopyran-3-carboxcylate

A three-neck flask fitted with overhead mechanical stirrer, condenser, thermocouple/heating mantle, and nitrogen inlet was charged with salicylaldebyde (56.03 g, 4581.81 mmole) and DMF (200 mL). With stirring, $K_2CO_3$ (63.41 g, 458.81 mmol) was added yielding a yellow suspension. Ethyl 4,4,4-trifluorocrotonate was added with warming. Initially the temperature rose to 106° C., and then was maintained with heating at 90° C. for 20 h. The reaction was allowed to cool to RT, was diluted with water, and was transferred to a separatory funnel. This mixture was extracted with $Et_2O$ and the organic phases combined. The ethereal phase was washed with water, saturated $NaHCO_3$, brine and dried over $MgSO_4$, filtered and concentrated to yield a clear, brown oil: bp 116° C., ~2 mm. HNMR (acetone-$d_6$/300 MHz) 7.89 (s, 1H), 7.52-7.38 (m, 2H), 7.09 (dt, 1 J=1.0, 7.7 Hz), 7.03 (d, 1H, J=8.3 Hz), 5.84 (q, 1H, J=7.3 Hz), 4.39-4.23 (m, 2H), 1.33 (t, 3H, J=7.0 Hz). GCMS m/z 272 (M+).

Step 2: Preparation of ethyl 6-acetyl-2-(trifluoromethyl)-2H-chromene-3-carboxylate A 500 mL three neck round bottom flask was fitted with stir bar, thermocouple and heating mantle, condenser, and nitrogen inlet and charged with dichloromethane (150 mL), ethyl 2-trifluoromethyl-2H-chromene-3-carboxylate (14.94 g, 54.882 mmole), and $AlCl_3$ (18.29 g, 137.21 mmole). With stirring, the reaction was chilled to 0° C. followed by addition of acetyl chloride (5.85 mL, 6.46 g, 82.32 mmole). The reaction was stirred at RT for three days and then at reflux for six days. The reaction was poured over ice and was extracted with dichloromethane. The organic phase was dried over $MgSO_4$, filtered and concentrated in vacuo to yield a solid. This solid was triturated with hexanes to provide a slurry. Vacuum filtration of the slurry yielded the title compound as a white solid. (11.78 g, 68.3%): mp 101-103° C. $^1$H NMR (acetone-$d_6$/300 MHz) 8.14(s, 1H), 8.04 (d d, 1H, J=8.7, 2.2 Hz), 7.98(s, 1H), 7.13 (d, 1H, J=8.6 Hz), 5.95 (q, 1H, J=6.8 Hz), 4.38-4.23 (m, 2 H), 2.57(s, 3H), 1.33(t, 3H, J=7.0 Hz). GCMS m/z 314 (M+).

Step 3: Preparation of ethyl 6-ethyl-2-(trifluoromethyl)-2H-chromene-3-carboxylate A 50 mL single-neck round bottom flask was charged with ethyl 6-acetyl-2-(trifluoromethyl)-2H-chromene-3-carboxylate (1.465 g, 4.662 mmole), dichloromethane (4 mL), and triethyl silane (1.71 mL, 1.25 g, 10.72 mmole) and stirred at RT overnight. The crude reaction was poured into water and extracted several times with dichloromethane. The combined organics were washed with water, then with aqueous 10% sodium carbonate solution, dried over $MgSO_4$, filtered and concentrated in vacuo to yield a colorless oil. This oil was purified by silica chromatography (9 hexane: 1 ethyl acetate) yielding the title compound as a clear, colorless oil (1.25 g, 89%): $^1$H NMR (acetone-$d_6$/300 MHz) 7.84 (s, 1H), 7.30 (d, 1H, J=2.0 Hz), 7.26 (dd, 1H, J=8.3, 2.0 Hz), 6.93 (d, 1H, J=8.3 Hz), 5.79 (q, 1H, J=7.3 Hz), 4.37-4.24 (m, 2H), 2.60 (q, 2H, J=7.6 Hz), 1.32 (t, 3H, J=7.3 Hz), 1.20 (t, 3H, J=7.6 Hz). GCMS m/z 300 (M+).

Step 4: Preparation of 6-ethyl-2-(trifluoromethyl)-2H-chromene-3-carboxylic acid A 15 mL single-neck round bottom flask was charged with ethyl 6-ethyl-2-(trifluoromethyl)-2H-chromene-3-carboxylate (0.238 g, 0.932 mmole), THF:EtOH:$H_2O$ (7:2:1 by volume, 3 mL), and aqueous NaOH (0.41 mL of 2.5 N aq solution, 1.026 mmole). The reaction was stirred at RT under nitrogen for 3 days and was concentrated in vacuo (high vacuum) to yield a semi-solid. The semi-solid was dissolved in $H_2O$, washed with diethyl ether, and sparged with nitrogen with gentle warming. The resulting organic solvent-free aqueous phase was acidified with concentrated HCl with stirring providing a slurry. The slurry was vacuum filtered yielding a white solid. The solid was dried on high vacuum yielding the title compound as a white powder (0.178 g, 70%): mp 145-149° C. LCMS m/z 273.15 (M+H). HRMS m/z 271.0600 (M−H, $C_{13}H_{10}F_3O$, Cald'd 271.0577). $^1$H NMR (acetone-$d_6$/300 MHz) 7.86 (s, 1H), 7.30 (d, 1H, J=2.0 Hz), 7.27 (d, 1H, J=8.3 Hz), 6.94 (d, 1H, J=8.3 Hz), 5.77 (q, 1H, J=7.0 Hz), 2.61 (q, 2H, J=7.5 Hz), 1.21 (t, 3H, J=7.5 Hz).

EXAMPLE 34b

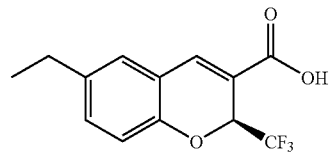

(2S)-6-ethyl-2-(trifluoromethyl)-2H-chromene-3-carboxylic acid

The (2S) 6-ethyl-2-(trifluoromethyl)-2H-chromene-3-carboxylic acid was resolved by chiral separation of racemic 6-ethyl-2-(trifluoromethyl)-2H-chromene-3-carboxylic acid from Example 34a using Chiralcel OJ column eluting with EtOH/heptane/TFA=5/95/0.1 and detecting at 254 nm as peak 2 with retention time 6.50 min: $^1$H NMR (acetone-$d_6$/400 MHz) 7.84 (s, 1H), 7.29 (d, 1H, J=2.0 Hz), 7.24 (dd, 1H, J=8.4, 2.4 Hz), 6.92(d, 1H, J=8.4 Hz), 5.90 (q, 1H, J=7.0 Hz), 2.59 (q, 2H, J=7.6 Hz), 1.19 (t, 3H, J=7.6 Hz). $[□]^{25}_{589}$=+32.3 in MeOH and $[□]^{25}_{436}$=+146.5 in MeOH.

EXAMPLE 34c

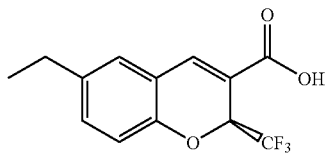

(2R)-6-ethyl-2-(trifluoromethyl)-2H-chromene-3-carboxylic acid

The (2R) 6-ethyl-2-(trifluoromethyl)-2H-chromene-3-carboxylic acid was resolved by chiral separation of racemic 6-ethyl-2-(trifluoromethyl)-2H-chromene-3-carboxylic acid from Example 34a using Chiralcel OJ column eluting with EtOH/heptane/TFA=5/95/0.1 and detecting at 254 nm as peak with retention time 5.16 min: $^1$H NMR (acetone-$d_6$/400 MHz) 7.84 (s, 1H), 7.29 (d, 1H, J=2.0 Hz), 7.24 (dd, 1H, J=8.4, 2.4 Hz), 6.92(d, 1H, J=8.4 Hz), 5.90 (q, 1H, J=7.0 Hz), 2.59 (q, 2H, J=7.6 Hz), 1.19 (t, 3H, J=7.6 Hz). $[a]^{25}_{589}=-33.9$ degrees(MeOH) and $[a]^{25}_{436}=-134.9$ degrees (MeOH).

EXAMPLE 34d

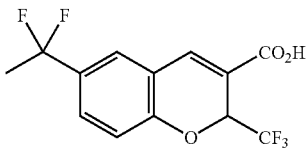

6-(1,1-difluoroethyl)-2-(trifluoromethyl)-2H-chromene-3-carboxylic acid

Step 1. Preparation of ethyl 6-(1,1-difluoroethyl)-2-(trifluoromethyl)-2H-chromene-3-carboxylate A 15 mL three-neck round bottom flask fitted with nitrogen inlet, thermocouple/heating mantle, and stoppers was charged with ethyl 6-acetyl-2-(trifluoromethyl)-2H-chromen-3-carboxylate from Example 34a, Step 2 (0.997 g, 3.173 mmole) and deoxofluor™ (2 mL, 2.4 g, 10.8 mmole) and stirred at 65° C. for 24 h, then at 75° C. for 5 h. The reaction was cooled to RT, was diluted with ethyl acetate, and was washed with water. The resulting ethyl acetate phase was washed with 2N HCl solution, water, and 10% sodium carbonate solution, brine, and dried over MgSO$_4$. The resulting suspension was filtered and the solution concentrated in vacuo yielding a brown oil. This oil was purified by silica chromatography (hexanes: ethyl acetate; 9:1) yielding the title product as an oily, white crystalline solid (0.410 g, 38%): mp 48-51° C. $^1$H NMR (acetone-$d_6$/300 MHz) 7.95 (s, 1H), 7.72 (s, 1H), 7.61 (d, 1H, J=8.5 Hz), 7.13 (d, 1H, J=8.5 Hz), 5.91 (q, 1H, J=7.1Hz), 4.41-4.2 (m, 2H), 1.96 (t,3H, J=18.4 Hz), 1.33 (t, 1H, J=7.1 Hz). GCMS m/z 336 (M+).

Step 2: Preparation of 6-(1,1-difluoroethyl)-2-(trifluoromethyl)-2H-chromene-3-carboxylic acid A 500 mL round bottom flask was charged with ethyl 6-(1,1-difluoroethyl)-2-(trifluoromethyl)-2H-chromene-3-carboxylate from Step 1 (0.385 g, 1.145 mmole), THF: EtOH: H$_2$O (7:2:1 volume ratio, 3 ml), and aqueous NaOH (0.55 mL, 1.374 mmole) and stirred at r.t. for two days. The reaction was concentrated in vacuo yielding a semi-solid. The semi-solid was dissolved in water washed with diethyl ether, and the resulting aqueous phase sparged with nitrogen with warming. The resulting organic solvent-free aqueous phase was acidified with concentrated HCl solution (to pH 1) yielding a gummy solid. This mixture was extracted with ethyl acetate. The combined organics were dried over MgSO$_4$, filtered, diluted with isooctane, and concentrated in vacuo yielding an oil. Upon standing, the oil formed a white crystalline powder (0.159 g, 45%): mp 156-158° C. (w/decomp). LCMS m/z 309 (M+H). HRMS m/z 307.0408 (M–H, $C_{13}H_8F_5O_3$, Calc'd 307.0388). $^1$H NMR (acetone-$d_6$/300 MHz) 12.2-11.2 (br s, ~0.5H (1H exch), 7.97 (s, 1H), 7.72 (s, 1H), 7.61(d d, 1H, J=8.5, 2.2 Hz), 7.13 (d, 1H, J=8.7 Hz), 5.89 (q, 1H, J=7.0 Hz), 1.97 (t, 3H, J=18.3 Hz).

EXAMPLE 34e

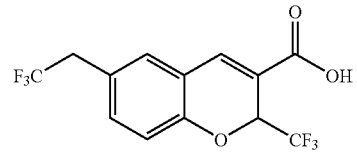

6-(2,2,2-trifluoroethyl)-2-(trifluoromethyl)-2H-chromene-3-carboxylic acid

Step 1. Preparation of ethyl 6-formyl-2-(trifluoromethyl)-2H-1-benzopyran-3-carboxylate A 50 mL round bottom flask was charged with 5-formyl-salicylaldehyde (3.21 g, 21.39 mmol), ethyl 4,4,4-trifluorocrotonate (3.50 mL, 3.96 g, 23.53 mmol), dimethylformamide (15 mL) and potassium carbonate (2.95 g, 21.39 mmol) and heated to 60° C. for 12 hours. Additional ethyl 4,4,4-trifluorocrotonate (3.50 mL, 3.96 g, 23.53 mmol) was added and the reaction heated for 16 hours at 75° C. After cooling to room temperature, the reaction was partitioned between H$_2$O and diethyl ether. The organic phase was washed with saturated NaHCO$_3$ solution, KHSO$_4$ solution (0.25 M), brine, treated with decolorizing carbon (warming gently). The resulting black suspension was dried over MgSO$_4$, vacuum filtered through diatomaceous earth, and concentrated in vacuo yielding an orange crystalline mass. This material was recrystallized from hot hexanes yielding the ester (1.51 g, 24%) as orange crystals: mp 84.3-86.2° C. $^1$H NMR (acetone-$d_6$/300 MHz) 9.96 (s, 1H), 8.06 (d, 1H, J=2 Hz), 8.02 (s, 1H), 7.99 (dd, 1H, J=8.5, 2.0 Hz), 7.24 (d, 1H, J=8.5 Hz), 5.99 (q, 1H, J=7.1 Hz), 4.43-4.25 (m, 2H), 1.34 (t, 3H, J=7.3 Hz). FABLRMS m/z 301 (M+H). EIHRMS m/z 300.0605 (M+, Calc'd 300.0609). Anal. Calc'd for $C_{14}H_{11}F_3O_4$: C, 56.01; H, 3.69. Found: C, 56.11; H, 3.73.

Step 2. Preparation of ethyl 6-(1-hydroxy-2,2,2-trifluoroethyl)-2-(trifluoromethylh-2H-1-benzopyran-3-carboxylate The aldehyde from Step 1 (0.89 g, 3.0 mmol) was cooled to 0° C. and treated with a 0.5 M solution of trimethyl (trifluoromethyl)silane (8.4 mL, 4.2 mmol) and four drops of a 1.0M solution of tetrabutylammonium fluoride was added. The reaction was allowed to warm to room temperature and stirred for 21.1 hours. The reaction was quenched with 3 N HCl, extracted with ethyl acetate, washed with water, brine, dried over $MgSO_4$, and concentrated in vacuo to give a brown oil (1.02 g). This oil was purified by flash chromatography over silica gel, eluting with 10% ethyl acetate/hexanes to afford a brown oil (0.77 g, 58%): $^1$H NMR ($CDCl_3$/300 MHz) 7.72 (d, 1H, J=3.4 Hz), 7.34 (m, 2H), 6.99 (d, 1H, J=8.5 Hz), 5.71 (q, 1H, J=6.8 Hz), 4.83 (q, 1H, J=6.4 Hz), 4.33 (m, 2H), 1.35 (t, 3H, J=7.1 Hz), 0.11 (s, 9H). FABLRMS m/z 443 (M+H).

Step 3. Preparation of ethyl 6-12,2,2-trifluoro-1-[(1H-imidazol-1-ylcarbonothioyl)oxylethyl]-2-(trifluoromethyl)-2H-chromene-3-carboxylate The alcohol from Step 2 (1 g, 2.7 mmol) was dissolved in $CH_2Cl_2$. The thiocarbonydiimidazole (0.72 g, 4.05 mmol) was added to above solution, followed by DMAP (105 mg, 0.86 mmol). The mixture was stirred at r.t. for 2 h. tHe mixture was passed through the silic plug and plug was washed with 15% to 30% EtOAc in hexane to give lightly yellow oil (2.5 g, 59%). LCMS m/z 481.05 (M+H). $^1$H NMR ($CDCl_3$/400 MHz) 8.37 (s, 1H), 7.72 (d, 1H, J=6.4 Hz), 7.65 (s, 1H), 7.45 (m, 1H), 7.34 (m, 1H), 7.08 (s, 1H), 7.04 (d, 1H, J=8.4 Hz), 6.66 (m, 1H), 5.71 (q, 1 H, J=6.8 Hz), 4.33 (m, 2H), 1.35 (t, 3H, J=7.1 Hz).

Step 4. Preparation of ethyl 6-(2,2.2-trifluoroethyl)-2-(trifluoromethyl)-2H-chromene-3-carboxylate The ester from Step 3 (2.4 g, 5 mmol) was dissolved in toluene (15 mL). The $Et_3SiH$ (30 mL, 0.18 mol) was added to above solution. The mixture was heated to reflux. The benzoyl peroxide (1.21 g, 5 mmol) in toluene (15 mL) was added in 4 portions at 15 min intervals. The mixture was heated to reflux for 2 h. The mixture was passed through silic plug and plug was washed with 10% to 20% EtOAc in hexane to give lightly yellow oil. This ester was of suitable purity to use without further purification.

Step 5. Preparation of 6-(2,2,2-trifluoroethyl)-2-(trifluoromethyl)-2H-chromene-3-carboxylic acid The 6-(2,2,2-trifluoroethyl)-2-(trifluoromethyl)-2H-chromene-3-carboxylic acid was prepared by the procedure similar to the method described in Example 1 a, Step 3. ESHRMS m/z 325.0294 (M–H, $C_{13}H_7F_6O_3$, Calc'd 325.0251). $^1$H NMR (acetone-$d_6$/400 MHz) 7.88 (s, 1H), 7.47 (s, 1H), 7.41 (d, 1H, J=5.6 Hz), 7.04 (d, 1H, J=8.4 Hz), 5.84 (q, 1H, J=7.0 Hz), 3.54 (t, 2H, J=11.2 Hz).

EXAMPLE 35

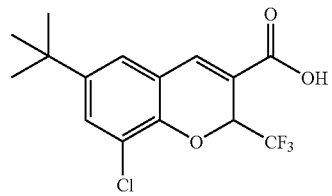

6-tert-butyl-8-chloro-2-(trifluoromethyl)-2H-chromene-3-carboxylic acid

Step 1. Preparation of 5-tert-butyl-3-chloro-2-hydroxybenzaldehyde

The 5-tert-butyl-3-chloro-2-hydroxybenzaldehydert-butyl-3-chloro-2-hydroxybenzaldehyde was prepared by the procedure similar to the method described in Example 1a, Step 2 using 5-tert-butyl-2-hydroxybenzaldehyde as starting material. This aldehyde was of suitable purity to use without further purification.

Step 2. Preparation of ethyl 6-tert-butyl-8-chloro-2-(trifluoromethyl)-2H-chromene-3-carboxylate The ethyl 6-tert-butyl-8-chloro-2-(trifluoromethyl)-2H-chromene-3-carboxylate was prepared by the procedure similar to the method described in Example 1a, Step 1 using 5-tert-butyl-3-chloro-2-hydroxybenzaldehyde from Step 1 as starting material. This ester was of suitable purity to use without further purification.

Step 3. Preparation of 6-tert-butyl-8-chloro-2-(trifluoromethyl)-2H-chromene-3-carboxylic acid The 6-tert-butyl-8-chloro-2-(trifluoromethyl)-2H-chromene-3-carboxylic acid was prepared prepared by the procedure similar to the method described in Example 1a, Step 3, using ethyl 6-tert-butyl-8-chloro-2-(trifluoromethyl)-2H-chromene-3-carboxylate from Step 2 as starting material. ESHRMS m/z 333.0485 (M–H, $C_{15}H_{13}O_3F_3Cl$, Calc'd 333.0500). $^1$H NMR (acetone-$d_6$/300 MHz) 7.93 (s, 1H), 7.52 (m, 2H), 5.90 (q, 1H, J=7.0 Hz), 1.33 (s, 9H).

EXAMPLE 36

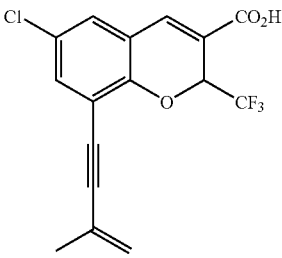

6-chloro-8-(3-methylbut-3-en-1-ynyl)-2-(trifluoromethyl)-2H-chromene-3-carboxylic Step 1. Preparation of ethyl 6-chloro-8-(3-methyl-but-3-en-1-ynyl)-2-(trifluoromethyl)-2H-chromene-3-carboxylate To a solution of ethyl 6-chloro-8-iodo-2-(trifluoromethyl)-2H-chromene-3-carboxylate prepared as in U.S. Pat. No. 6,271,253 B1 Example 73, Step 2 (0.342 g, 0.790 mmole) in degassed anhydrous toluene was added Pd(PPh$_3$)$_4$ (54 mg, 0.47 mmole), CuI (15 mg, 0.079 mmole), TEA (0.275 mg, 2.72 mmole) and 2-methylbut-1-en-3-yne (0.247 g, 3.74 mmole) and the mixture was stirred under a N$_2$ atmosphere. After the reaction was determined to be complete by GCMS, H$_2$O and EtOAc were added and the layers were separated. The EtOAc layer was washed with 10% HCl, twice with H$_2$O, twice with aqueous NH$_4$Cl, dried over Na$_2$SO$_4$ and concentrated in vacuo. Purification of the crude product by silica chromatography (95:5 hexanes:EtOAc) gave 155 mg (53% yield) of the product as a white crystalline solid: $^1$H NMR (CDCl$_3$/300 MHz) 7.62 (s, 1H), 7.37 (d, 1H, J=2.4 Hz), 7.14 (d, 1H, J=2.4 Hz), 5.80 (q, 1H, J=6.6 Hz), 5.44 (m, 1H), 5.35-5.36 (m, 1H), 4.31-4.34 (m, 2H), 1.99 (s, 3H), 1.36 (t, 3H, J=7.1 Hz).

Step 2. Preparation of 6-chloro-8-(3-methylbut-3-en-1-ynyl)-2-(trifluoromethyl)-2H-chromene-3-carboxylic acid The ester from step 1 (96.4 mg, 0.260 mmole) was hydrolyzed via a method similar to that described in Example 17d, Step 2 and crystallized from hot hexanes to give the product: $^1$H NMR (CDCl$_3$/400 MHz 7.76 (s, 1H), 7.41 (d, 1H, J=2.4 Hz), 7.19 (d, 1H, J=2.4 Hz), 5.79 (q, 1H, J=6.6 Hz), 2.00 (s, 3H); ESHRMS m/z 341.0197 (M–H, C$_{16}$H$_9$ClF$_3$O$_3$, Calc'd 341.0187).

EXAMPLE 37a

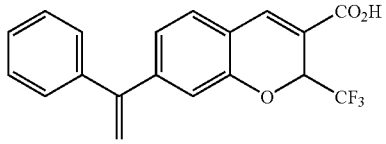

7-(1-phenylvinyl)-2-(trifluoromethyl)-2H-chromene-3-carboxylic acid

Step 1. Preparation of phenyl(3-{[2-(trimethylsilyl)ethoxy]methoxy}phenyl)methanone To a solution of (3-hydroxyphenyl)(phenyl)methanone (30.0 g, 151 mmole) in anhydrous THF (300 mL) at 0° C. was slowly added a solution of potassium-t-butoxide (200 mL-1 M in THF, 0.200 mmole), followed by a slow addition of [2-(chloromethoxy)ethyl](trimethyl)silane (32.1 mL, 182 mmole). After stirring the mixture for 2 h, the solvent was removed in vacuo and the residue redissolved in a mixture of H$_2$O (200 mL) and EtOAc (200 mL). The aqueous layer was further extracted with EtOAc (2×100 mL). The combined extracts were washed with H$_2$O (200 mL), 0.1 N HCl (500 mL), brine (100 mL), dried over MgSO$_4$, filtered and concentrated in vacuo to give an orange oil. The crude product was redissolved in hexanes and filtered through a silica-gel plug to give the product as an impure pale yellow oil which is carried on without further purification: ESHRMS m/z 329.1586 (M+H, C$_{19}$H$_{25}$O$_3$Si, Calc'd 329.1567).

Step 2. Preparation of 3-(1-phenylvinyl)phenol

To a solution of TiCl$_4$ (4.01 mL, 36.5 mmole) in anhydrous CH$_2$Cl$_2$ (100 mL) under a dry N$_2$ atmosphere was added a solution of trimethylaluminum (36.5 mL-2.0 M in toluene, 73.0 mmole) at 0° C. The mixture was stirred for 30 minutes, cooled to –40 to –50° C. and a solution of phenyl (3-{[2-(trimethylsilyl)ethoxy]methoxy]phenyl)}methanone (13.33 g-75 wt. %, 30.4 mmole) in anhydrous CH$_2$Cl$_2$ (20 mL) was added and the mixture was allowed to warm to room temperature while stirring overnight. The mixture was then cooled to 0° C. and H$_2$O was added dropwise. Following acidification to pH 1 with 1N HCl, the mixture was extracted with EtOAc (2×300 mL). The combined extracts were washed with brine (100 mL), dried over MgSO$_4$, filtered and concentrated in vacuo to give 4.22 g (71% yield) of the product as a yellow oil: EIHRMS m/z 196.0894 (M+, C$_{14}$H$_{12}$O, Calc'd 196.0888).

Step 3. Preparation of 2-hydroxy-4-(1-phenylvinyl)benzaldehyde

A mixture of the phenol from step 2 (4.15 g, 21.1 mmole), MgCl$_2$ (3.02 g, 31.7 mmole), TEA (11.1 mL, 79.3 mmole) and paraformaldehyde (4.29 g, 143 mmole) in anhydrous acetonitrile (100 mL) was refluxed for 17 h. Additional MgCl$_2$ (1.5 g, 15.8 mmole), TEA (5.6 mL, 40 mmole) and paraformaldehyde (2.23 g, 74 mmole) were then added and reflux was continued for 2 h. The mixture was then cooled, acidified with 1N HCl and extracted with EtOAc (2×200 mL). The combined extracts were washed with brine (100 mL), dried over MgSO$_4$, filtered and concentrated in vacuo. The crude product was purified by filtration through a silica-gel plug (9:1 hexanes:EtOAc) to give 4.28 g (91% yield) of the product as a yellow oil: EIHRMS m/z 224.0837 (M+, C$_{15}$H$_{12}$O$_2$, Calc'd 224.0837).

Step 4. Preparation of ethyl 7-(1-phenylvinyl)-2-(trifluoromethyl)-2H-chromene-3-carboxylate A mixture of 2-hydroxy-4-(1-phenylvinyl)benzaldehyde prepared as in Step 3 (4.17 g, 18.6 mmole), K$_2$CO$_3$ (2.57 g, 18.6 mmole) and ethyl 444-trifluocrotonate (3.34 mL, 22.3 mmole) in anhydrous DMF (20 mL) was heated to 85° C. under a dry N$_2$ atmosphere for 16.5 h. The mixture was then cooled, poured into 1N HCl (100 ml) and extracted with EtOAc (2×100 mL). The combined extracts were washed with brine (50 mL), dried over MgSO$_4$ and concentrated in vacuo. The crude product was purified by silica chromatography (3:1 CH$_2$Cl$_2$:hexanes) to give 2.33 g (33% yield) of the product as a light yellow oil: EIHRMS m/z 374.1120 (M+, C$_{21}$H$_{17}$F$_3$O$_3$, Calc'd 374.1130).

Step 5. Preparation of 7-(1-phenylvinyl)-2-(trifluoromethyl)-2H-chromene-3-carboxylic acid The ester from Step 4 was hydrolyzed via a method similar to that described in Example 18a, Step 2 to give the product as a white crystalline solid: $^1$H NMR (dmso-d$_6$, 300 MHz) 13.26 (brs, 1H), 7.87 (s, 1H), 7.46 (d, 11H, J=2.9 Hz), 7.34-7.40 (m, 3H), 7.25-7.28 (m, 2H), 6.96 (dd, 1H, J=1.6, 7.9 Hz), 6.89 (s, 1H), 5.99 (q, 1H, J=7.3 Hz), 5.63 (s, 1H), 5.51 (s, 1H); ESHRMS m/z 345.0722 (M−H, $C_{19}H_{12}F_3O_3$, Calc'd 345.0733).

EXAMPLE 37b

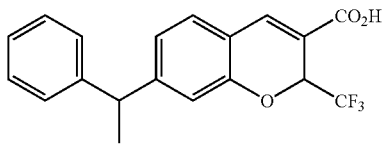

7-(1-phenylethyl)-2-(trifluoromethyl)-2H-chromene-3-carboxylic acid

Step 1. Preparation of ethyl 7-(1-phenylethyl)-2-(trifluoromethyl)-2H-chromene-3-carboxylate A mixture of ethyl 7-(1-phenylvinyl)-2-(trifluoromethyl)-2H-chromene-3-carboxylate prepared as in Example 50a, step 4 (2.13 g, 5.69 mmole) and 10% Pd/C (150 mg) in absolute EtOH (30 mL) was hydrogenated at 30 psi for 3 h. The catalyst was removed by filtration and the filtrate was concentrated in vacuo. Purification of the crude product by silica chromatography (92.5 hexanes:EtOAc) gave 1.62 g (75% yield) of the product as a colorless oil: EIHRMS m/z 376.1279 (M+, $C_{21}H_{19}F_3O_3$, Calc'd 376.1286).

Step 2. Preparation of 7-(1-phenylethyl)-2-(trifluoromethyl)-2H-chromene-3-carboxylic acid The ester from Step 1 was hydrolyzed via a method similar to that described in Example 18a, Step 2 to give the crude product as a solid. Purification by reverse phase chromatography (acetonitrile:0.5% TFA-H$_2$O) gave the product as an off-white crystalline solid: $^1$H NMR (dmso-d$_6$, 300 MHz) 13.20 (brs, 1H), 7.81 (s, 1H),.7.36-7.40 (m, 1H), 7.28-7.30 (m, 4H), 7.16-7.23 (m, 1H), 6.92-7.00 (m, 2H), 5.87 (q, 1H, J=7.3 Hz), 4.16 (q, 1H, J=7.3 Hz), 1.56 (d, 3H, J=7.3 Hz); ESHRMS m/z 347.0864 (M−H, $C_{19}H_{14}F_3O_3$, Calc'd 347.0890).

EXAMPLE 38a

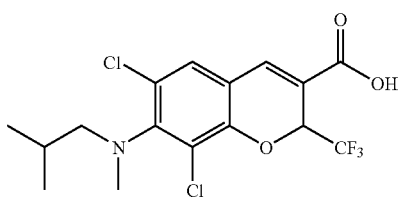

6,8-dichloro-7-[isobutyl(methyl)amino]-2-(trifluoromethyl)-2H-chromene-3-carboxylic acid Step 1. Preparation of ethyl 6-chloro-7-[isobutyl (methyl)aminol-2-(trifluoromethyl)-2H-chromene-3-carboxylate The ethyl 6-chloro-7-[isobutyl(methyl)amino]-2-(trifluoromethyl)-2H-chromene-3-carboxylate was prepared by the procedure similar to the method described in Example 8a, Step 1. GCMS m/z 391.0 (M+). $^1$H NMR (acetone-d$_6$/400 MHz) 7.61 (s, 1H), 7.19 (s, 1H), 6.60 (s, 1H), 5.66 (q, 1H, J=7.0 Hz), 4.30 (m, 2H), 2.96 (m, 2H), 2.93 (s, 3H), 1.96 (m, 1H), 1.33 (m, 3H), 0.96 (m, 6H).

Step 2. Preparation of ethyl 6,8-dichloro-7-risobutyl (methyl)aminol-2-(trifluoromethyl)-2H-chromene-3-carboxylate The ethyl 6,8-dichloro-7-[isobutyl(methyl)amino]-2-(trifluoromethyl)-2H-chromene-3-carboxylate was prepared by the procedure similar to the method described in Example 1a, Step 2. GCMS m/z 425.0 (M+). $^1$H NMR (CDCl$_3$/400 MHz) 7.57 (s, 1H), 7.06 (s, 1H), 5.78 (q, 1H, J=7.0 Hz), 4.28 (m, 2H), 3.38 (m, 2H), 3.21 (s, 3H), 1.85 (m, 1H), 1.32 (m, 3H), 0.96 (m, 6H).

Step 3. 6,8-dichloro-7-fisobulyl(methylamino]-2-(trifluoromethyl)-2H-chromene-3-carboxylic acid The 6,8-dichloro-7-[isobutyl(methyl)amino]-2-(trifluoromethyl)-2H-chromene-3-carboxylic acid was prepared by a procedure similar to the method described in Example 8a, step 2. ESHRMS m/z 396.0371 (M+H, $C_{16}H_7O_3F_3Cl_2N$, Calc'd 396.0376). $^1$H NMR (acetone-d$_6$/400 MHz) 7.86 (s, 11H), 7.53 (s, 11H), 5.78 (q, 1H, J=7.0 Hz), 3.02 (m, 2H), 2.86 (m, 3H), 1.82 (m, 1H), 0.90 (m, 6H).

EXAMPLE 38b

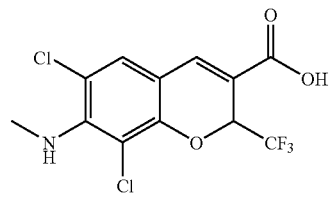

6,8-dichloro-7-(methylamino)-2-(trifluoromethyl)-2H-chromene-3-carboxylic acid

Step 1. Preparation of ethyl 6-chloro-7-[isobutyl (methyl)amino]-2-(trifluoromethyl)-2H-chromene-3-carboxylate The ethyl 6-chloro-7-[isobutyl(methyl)amino]-2-(trifluoromethyl)-2H-chromene-3-carboxylate was prepared by the procedure similar to the method described in Example 8a, Step 1. GCMS m/z 391.0 (M+). $^1$H NMR (acetone-d$_6$/400 MHz) 7.61 (s, 1H), 7.19 (s, 1H), 6.60 (s, 1H), 5.66 (q, 1H, J=7.0 Hz), 4.30 (m, 2H), 2.96 (m, 2H), 2.93 (s, 3H), 1.96 (m, 1H), 1.33 (m, 3H), 0.96 (m, 6H).

Step 2. Preparation of ethyl 6,8-dichloro-7-(methylamino)-2-(trifluoromethyl)-2H-chromene-3-carboxylate The ethyl 6,8-dichloro-7-(methylamino)-2-(trifluoromethyl)-2H-chromene-3-carboxylate was prepared by the procedure similar to the method described in Example 1b, Step 2. GCMS m/z 425.0 (M+). $^1$H NMR (CDCl$_3$/400 MHz) 7.57 (s, 1H), 7.06 (s, 1H), 5.78 (q, 1H, J=7.0 Hz), 4.28 (m, 2H), 3.21 (s, 3H), 1.32 (m, 3H).

Step 3. 6,8-dichloro-7-(methylamino)-2-(trifluoromethyl)-2H-chromene-3-carboxylic acid The 6,8-dichloro-7-(methylamino)-2-(trifluoromethyl)-2H-chromene-3-carboxylic acid was prepared by a procedure similar to the method described in Example 8a, Step 2. ESHRMS m/z 339.9777 (M+H, $C_{12}H_9O_3F_3Cl_2N$, Calc'd 339.9750). $^1H$ NMR (acetone-$d_6$/400 MHz) 7.80 (s, 1H), 7.41 (s, 1H), 5.89 (q, 1H, J=7.0 Hz), 3.25 (m, 3H).

EXAMPLE 38c

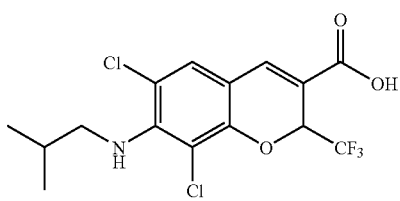

6,8-dichloro-7-(isobutylamino)-2-(trifluoromethyl)-2H-chromene-3-carboxylic acid The 6,8-dichloro-7-(isobutylamino)-2-(trifluoromethyl)-2H-chromene-3-carboxylic acid was prepared by a procedure similar to the method described in Example 38b. ESHRMS m/z 382.0242(M+H, $C_{15}H_{15}O_3F_3Cl_2N$, Calc'd 382.0219). $^1H$ NMR (acetone-$d_6$/400 MHz) 7.82 (s, 1H), 7.45 (s, 1H), 5.91 (q, 1H, J=7.0 Hz), 3.45 (m, 2H), 1.86 (m, 1H), 0.95 (m, 6H).

EXAMPLE 39a

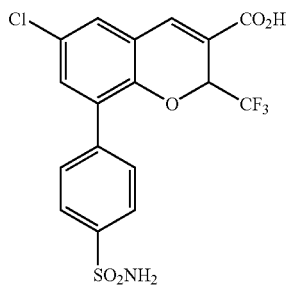

8-[4-(aminosulfonyl)phenyl]-6-chloro-2-(trifluoromethyl)-2H-chromene-3-carboxylic acid Chlorosulfonic acid (5 mL) was cooled to −20° C. and 6-chloro-8-phenyl-2-(trifluoromethyl)-2H-chromene-3-carboxylic acid prepared as in U.S. Pat. No. 6,271,253 B1 Example 129, Step 2 (61.7 mg, 0.174 mmole) was added as a solid. The bright orange mixture was then added dropwise to a cold ammonium hydroxide solution, EtOAc was added and the mixture was stirred for 1 h. The EtOAc layer was separated, washed with $H_2O$, aqueous $NH_4Cl$, dried over $Na_2SO_4$, concentrated in vacuo and triturated with hexanes to give the product: $^1H$ NMR ($CD_3OD$/400 MHz) 7.95 (d, 2H, J=8.6 Hz), 7.81 (s, 1H), 7.66 (d, 2H, J=8.6 Hz), 7.46 (d, 1H, J=2.6 Hz), 7.42 (d, 1H, J=2.6 Hz), 5.80 (q, 1H, J=7.0 Hz); ESHRMS m/z 431.9945 (M−H, $C_{17}H_{10}ClF_3NO_5S$, Calc'd 431.9915).

EXAMPLE 39b

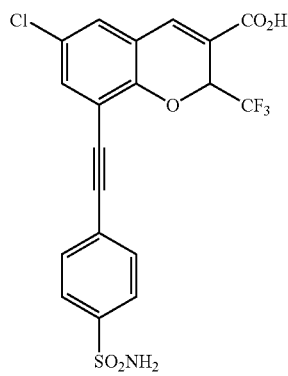

8-{[4-(aminosulfonyl)phenyl]ethynyl}-6-chloro-2-(trifluoromethyl)-2H-chromene-3-carboxylic acid

Step 1. Preparation of 4-[(trimethylsilyl)ethynyl]benzenesulfonamide

To a solution of 4-bromobenzenesulfonamide (4.51 g, 19.1 mmole) in toluene (900 mL) at 75° C. was added ethynyl(trimethyl)silane (4 g, 40 mmole), Pd(PPh$_3$)$_4$ (1.3 g, 1.1 mmole), CuI (0.46 g, 2.42 mmole) and TEA (5.7 g, 56 mmole) and the mixture was allowed to cool to room temperature while stirring. Additional Pd(PPh$_3$)$_4$ (1 g, 0.9 mmole) was added and the mixture was stirred at room temperature. After 5 days, ethyl ether was added and the mixture was washed with 10% HCl, $H_2O$, sat. aqueous $NH_4Cl$, dried over $Na_2SO_4$ and concentrated in vacuo to give 2.93 g (61% yield) of the product: ESHRMS m/z 271.0935 (M+NH$_4$, $C_{11}H_{15}NO_2SSiNH_4$, Calc'd 271.0937).

Step 2. Preparation of 4-ethynylbenzenesulfonamide

To a solution of 4-[(trimethylsilyl)ethynyl]benzenesulfonamide prepared as in Step 1 (1.69 g, 3.13 mmole) in anhydrous THF under a $N_2$ atmosphere was added TBAF (10 mL-1.0 M in THF, 10 mmole) and the resulting mixture was stirred at room temperature. When silica TLC (1:1 hexanes:EtOAc) indicated the reaction was complete, 10% HCl and EtOAc were added. The EtOAc layer was separated, washed twice with $H_2O$, aqueous $NH_4Cl$, dried over $Na_2SO_4$ and concentrated in vacuo to give 0.748 g (62% yield) of the product: ESHRMS m/z 199.0506 (M+NH$_4$, $C_8H_7NO_2SNH_4$, Calc'd 199.0541).

Step 3. Preparation of ethyl 8-{[4-(aminosulfonyl)phenyl]ethynyl}-6-chloro-2-(trifluoromethyl)-2H-chromene-3-carboxylate Ethyl 6-chloro-8-iodo-2-(trifluoromethyl)-2H-chromene-3-carboxylate prepared as in U.S. Pat. No. 6,271,253 B1 Example 73, Step 2 was reacted with 4-ethynylbenzene sulfonamide prepared as in Step 2 via a method similar to that described in Example 21f, Step 1 to give the product: ESHRMS m/z 503.0686 (M+NH$_4$, $C_{21}H_{15}ClF_3O_5SNH_4$, Calc'd 503.0655).

Step 4. Preparation of 8-{[4-(aminosulfonyl)phenyl]ethynyl}-6-chloro-2-(trifluoromethyl)-2H-chromene-3-carboxylic acid The ester from Step 3 was hydrolyzed via a method similar to that described in Example 17d, Step 2 to give the product: $^1$H NMR (CD$_3$OD/400 MHz) 7.88 (d, 2H, J=8.6 Hz), 7.64 (d, 2H, J=8.6 Hz), 7.45 (s, 1H), 7.39 (d, 1H, J=2.4 Hz), 7.26 (d, 1H, J=2.6 Hz), 5.98 (q, 1H, J=7.0 Hz); ESHRMS m/z 455.9885 (M−H, C$_{19}$H$_{10}$ClF$_3$NO$_5$S, Calc'd 455.9915).

EXAMPLE 40a

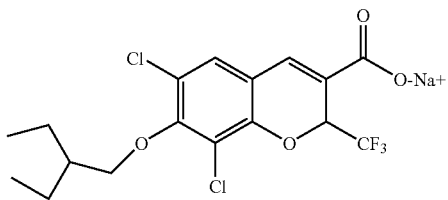

sodium 6,8-dichloro-7-(2-ethylbutoxy)-2-(trifuoromethyl)-2H-chromene-3-carboxylate The 6,8-dichloro-7-(2-ethylbutoxy)-2-(trifluoromethyl)-2H-chromene-3-carboxylic acid from Example 1b was dissolved in a minimum amount of EtOH. NaOH (0.5016 N from Aldrich) (1 equivalent relative to the free acid) was added dropwise to the above solution via a Burette. The solvent was removed in vacuo and the resulting solid was redissolved in water. The solvent was removed in vacuo and the residue dried under high vacuum to produce the sodium salt. $^1$H NMR (acetone-d$_6$/400 MHz) 7.58 (s, 1H), 7.10 (s, 1H), 6.20 (q, 1H, J=7.0 Hz), 3.95 (m, 2H), 1.65 (m, 1H), 1.51 (m, 4H), 0.971 (m, 6H).

EXAMPLE 40b

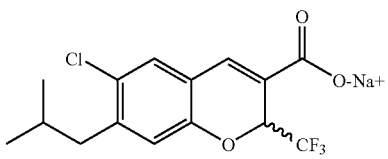

sodium 6-chloro-7-isobutyl-2-(trifluoromethyl)-2H-chromene-3-carboxylate

NaOH (0.5006 N) was added to a stirred solution of the acid (Example 9c, Step 3) in 10 mL EtOH (abs). The resulting solution stirred at room temperature for 1 h. The solvent was removed in vacuo producing the sodium salt (99%). $^1$HNMR (DMSO-d$_6$/400 MHz) 7.81 (s, 1H), 7.5 (s, 1H), 6.97 (s, 11H), 5.89 (q, 1H, J=7.1 Hz), 2.51 (d, 2H, J=6.7 Hz), 1.85-1.89 (m, 1H), 0.843 (m, 6H).

EXAMPLE 40c

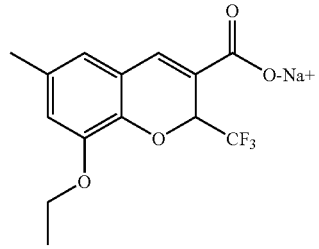

sodium 8-ethoxy-6-methyl-2-(trifluoromethyl)-2H-chromene-3-carboxylate

The sodium 8-ethoxy-6-methyl-2-(trifluoromethyl)-2H-chromene-3-carboxylate was prepared by the procedure similar to that described in Example 40a using the carboxylic acid from Example 31. H NMR (D$_2$O/300 MHz) 7.26 (s, 1H), 6.83 (d, 1H, J=1.2 Hz), 6.68 (d, 1H, J=1.2 Hz), 5.67 (q, 1H, J=7.2 Hz), 4.02 (q, 2H, J=6.9 Hz), 2.13 (s, 3H), 1.24 (t, 3H, J=7.0 Hz).

EXAMPLE 40d

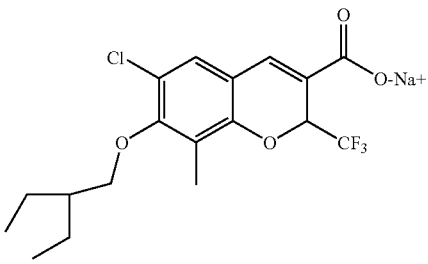

sodium 6-chloro-7-(2-ethylbutoxy)-8-methyl-2-(trifluoromethyl)-2H-chromene-3-carboxylate The sodium 6-chloro-7-(2-ethylbutoxy)-8-methyl-2-(trifluoromethyl)-2H-chromene-3-carboxylate was prepared by the procedure similar to that described in Example 40a using the carboxylic acid from Example 3b. $^1$H NMR (acetone-d$_6$/300 MHz) 7.54 (s, 1H), 7.01 (s, 1H), 6.18 (q, 1H, J=7.0 Hz), 3.78 (m, 2H), 2.07 (s, 3H), 1.61 (m, 5H), 1.51 (m, 4H), 0.971 (m, 6H).

EXAMPLE 40e

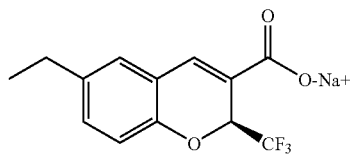

sodium (2S) 6-ethyl-2-(trifluoromethyl)-2H-chromene-3-carboxylate

The sodium (2S) 6-ethyl-2-(trifluoromethyl)-2H-chromene-3-carboxylate was prepared by the procedure similar to that described in Example 40a using the carboxylic acid from Example 34b. ¹H NMR (acetone-$d_6$/400 MHz) 7.54 (s, 1H), 6.99 (dd, 1H, J=8.0, 2.0 Hz), 6.94 (d, 1H, J=1.6 Hz), 6.73(d, 1H, J=8.4 Hz), 5.95 (q, 1H, J=7.0 Hz), 2.46 (q, 2H, J=7.6 Hz), 1.10 (t, 3H, J=7.6 Hz).

EXAMPLE 40f

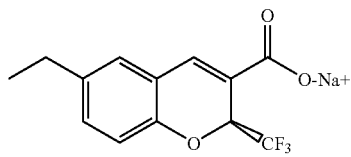

sodium (2R) 6-ethyl-2-(trifluoromethyl)-2H-chromene-3-carboxylate

The sodium (2R) 6-ethyl-2-(trifluoromethyl)-2H-chromene-3-carboxylate was prepared by the procedure similar to that described in Example 40a using the carboxylic acid from Example 34c. ¹H NMR (acetone-$d_6$/400 MHz) 7.54 (s, 1H), 6.99 (dd, 1H, J=8.0, 2.0 Hz), 6.94 (d, 1H, J=1.6 Hz), 6.73(d, 1H, J=8.4 Hz), 5.95 (q, 1H, J=7.0 Hz), 2.46 (q, 2H, J=7.6 Hz), 1.10 (t, 3H, J=7.6 Hz).

EXAMPLE 40g

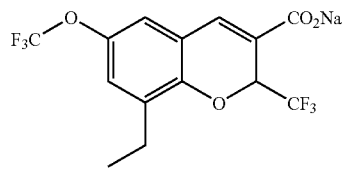

8-ethyl-6-(trifluoromethoxy)-2-(trifluoromethyl)-2H-chromene-3-carboxylate

To a solution of the carboxylic acid prepared as in Example 21g, Step 2 (85 mg, 0.239 mmole) in EtOH was added aqueous NaOH (0.4756 mL of 0.5017 N solution, 0.239 mmole). The solvent was removed in vacuo to give 81.5 mg (90% yield) of the product as an off-white crystalline solid: ESLRMS m/z 357.1 (M+H, $C_{14}H_{10}F_6O_4$, Calc'd 357.1).

EXAMPLE 40h

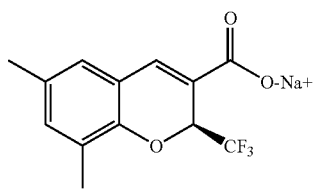

sodium (2S)-6,8-dimethyl-2-(trifluoromethyl)-2H-chromene-3-carboxylate

The sodium (2S)-6,8-dimethyl-2-(trifluoromethyl)-2H-chromene-3-carboxylate was prepared by the procedure similar to that described in Example 40a using the carboxylic acid from Example 32b. ¹H NMR ($D_2O$/300 MHz) 7.18 (s, 1H), 6.87 (s, 1H), 6.78 (s, 1H), 5.60(q, 1H, J=7.5 Hz), 2.07 (s, 3H), 2.03 (s, 3H).

EXAMPLE 40i

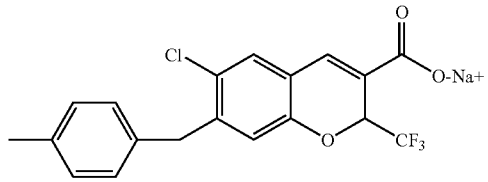

sodium 6-chloro-7-(4-methylbenzyl)-2-(trifluoromethyl)-2H-chromene-3-carboxylate The sodium 6-chloro-7-(4-methylbenzyl)-2-(trifluoromethyl)-2H-chromene-3-carboxylate was prepared by the procedure similar to that described in Example 40a using the carboxylic acid from Example 9x as starting material: ¹H NMR ($D_2O$/300 MHz) 7.09 (s, 1H), 6.88 (s, 1H), 6.66 (m, 4H), 6.36 (s, 1H), 5.53 (q, 1H, J=6.3 Hz), 3.47 (q, 2H, J=14 Hz), 1.87 (s, 3H).

EXAMPLE 40j

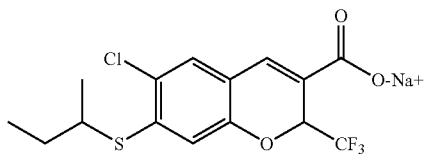

Sodium 7-(sec-butylthio)-6-chloro-2-(trifluoromethyl)-2H-chromene-3-carboxylate

Sodium 7-(sec-butylthio)-6-chloro-2-(trifluoromethyl)-2H-chromene-3-carboxylate was prepared from 7-(sec-butylthio)-6-chloro-2-(trifluoromethyl)-2H-chromene-3-carboxylic acid (Example 7g) using the procedure similar to the method described in Example 40a: ESHRMS m/z 365.0221 (M−H, $C_{15}H_{14}F_3O_3ClS$, Calc'd 365.0222). ¹H NMR ($CD_3OD$/400 MHz) 7.34 (s, 1H), 7.25 (s, 1H), 6.90 (s, 1H), 5.82 (q, 1H, J=7.0 Hz), 3.36 (m, 1H), 1.65 (m, 2H), 1.30 (m, 3H), 1.03 (m, 3H).

EXAMPLE 40k

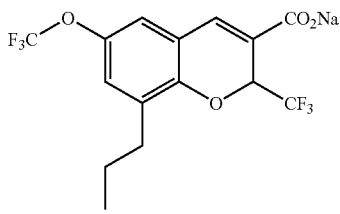

sodium 8-propyl-6-(trifluoromethoxy)-2-(trifluoromethyl)-2H-chromene-3-carboxylate The sodium 8-propyl-6-(trifluoromethoxy)-2-(trifluoromethyl)-2H-chromene-3-carboxylate was prepared via a method similar to that described in Example 40g using the carboxylic acid from Example 21i to give the product as an off-white solid: ESLRMS m/z 371.0 (M+H, $C_{15}H_{12}F_6O_4$, Calc'd 371.1).

EXAMPLE 40l

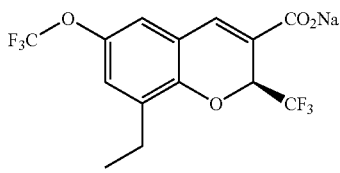

sodium (2S)-8-ethyl-6-(trifluoromethoxy)-2-(trifluoromethyl)-2H-chromene-3-carboxylate The sodium (2S)-8-ethyl-6-(trifluoromethoxy)-2-(trifluoromethyl)-2H-chromene-3-carboxylate was prepared via a method similar to that described in Example 40g using the carboxylic acid from Example 21k to give the product as a white solid: ESLRMS m/z 357.1 (M+H, $C_{14}H_{10}F_6O_4$, Calc'd 357.1).

EXAMPLE 40m

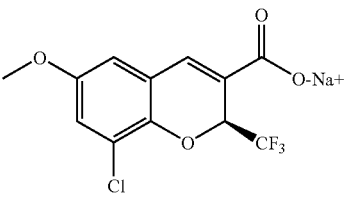

sodium (2S)-8-chloro-6-methoxy-2-(trifluoromethyl)-2H-chromene-3-carboxylate

Sodium (2S)-8-chloro-6-methoxy-2-(trifluoromethyl)-2H-chromene-3-carboxylate was prepared from (2S)-8-chloro-6-methoxy-2-(trifluoromethyl)-2H-chromene-3-carboxylic acid (Example 17i) using the procedure similar to the method described in Example 40a: ESHRMS m/z 307.0004 (M−H, $C_{12}H_7F_3O_4Cl$, Calc'd 306.9979). $^1$H NMR ($D_2O$/300 MHz) 7.16 (s, 1H), 6.83 (s, 1H), 6.68 (s, 1H), 5.66 (q, 1H, J=7.0 Hz), 3.64 (s, 3H).

EXAMPLE 40n

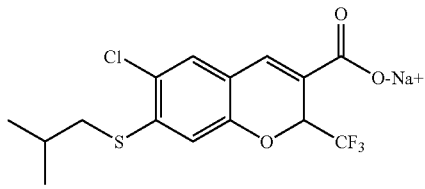

sodium 6-chloro-7-(isobutylthio)-2-(trifluoromethyl)-2H-chromene-3-carboxylate

Sodium 6-chloro-7-(isobutylthio)-2-(trifluoromethyl)-2H-chromene-3-carboxylate was prepared from 6-chloro-7-(isobutylthio)-2-(trifluoromethyl)-2H-chromene-3-carboxylic acid (Example 7d) using the procedure similar to the method described in Example 40a: $^1$H NMR ($CD_3OD$/300 MHz) 7.33 (s, 1H), 7.22 (s, 1H), 6.82 (s, 1H), 5.79 (q, 1H, J=7.0 Hz), 2.83 (m, 2H), 1.94 (m, 1H), 0.84 (m, 6H).

EXAMPLE 40o

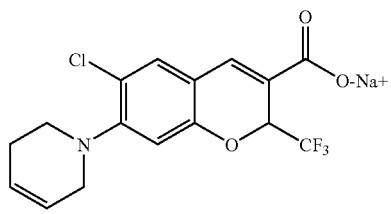

sodium 6-chloro-7-(3,6-dihydropyridin-1(2H)-yl)-2-(trifluoromethyl)-2H-chromene-3-carboxylate Sodium 6-chloro-7-(3,6-dihydropyridin-1(2H)-yl)-2-(trifluoromethyl)-2H-chromene-3-carboxylate was prepared from 6-chloro-7-(3,6-dihydropyridin-1 (2H)-yl)-2-(trifluoromethyl)-2H-chromene-3-carboxylic acid (Example 8e) using the procedure similar to the method described in Example 40a $^1$H NMR ($D_2O$/400 MHz) 7.18 (m, 2H), 6.69 (s, 1H), 5.68 (m, 3H), 3.36 (m, 2H), 3.04 (m, 2H), 2.13 (m, 2H).

EXAMPLE 40p

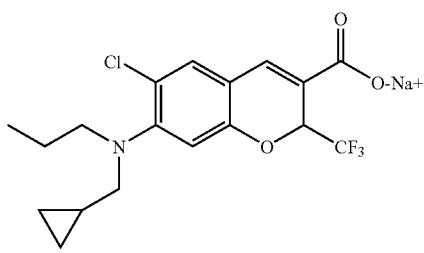

sodium 6-chloro-7-[(cyclopropylmethyl)(propyl)amino]-2-(trifluoromethyl)-2H-chromene-3-carboxylate Sodium 6-chloro-7-[(cyclopropylmethyl)(propyl)amino]-2-(trifluoromethyl)-2H-chromene-3-carboxylate was prepared from 6-chloro-7-[(cyclopropylmethyl) (propyl) amino]-2-(trifluoromethyl)-2H-chromene-3-carboxylic acid (Example 8g) using a procedure similar to the method described in Example 40a: ESHRMS m/z 390.1066 (M+H, $C_{18}H_{19}F_3O_3ClN$, Calc'd 390.1078). $^1$H NMR ($CD_3OD$/300 MHz) 7.38 (s, 1H), 7.19 (s, 1H), 6.70 (s, 1H), 5.73 (q, 1H, J=7.0 Hz), 3.18 (m, 2H), 2.97 (m, 2H), 1.47 (m, 2H), 1.00 (m, 4H), 0.45, (m, 2H), 0.10 (m, 2H).

EXAMPLE 40q

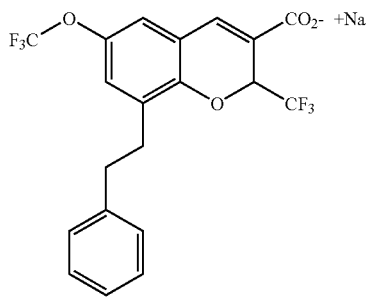

sodium 8-(2-phenylethyl)-6-(trifluoromethoxy)-2-(trifluoromethyl)-2H-chromene-3-carboxylate To a solution of the carboxylic acid prepared as in Example 21o (43.2 mg, 0.0999 mmole) in EtOH (1.0 mL) was added aqueous NaOH (199.6 uL-0.5006 N, 0.0999 mmole). The solvent was removed in vacuo, the residue redissolved in $H_2O$ and lyophilized to give 40.3 mg (89% yield) of the product as a solid: ESLRMS m/z 433.3 (M+H, $C_{20}H_{14}F_6O_4$, Calc'd 433.1).

EXAMPLE 40r

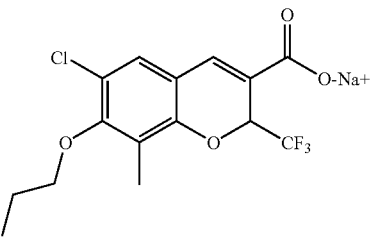

sodium 6-chloro-8-methyl-7-propoxy-2-(trifluoromethyl)-2H-chromene-3-carboxylate The sodium 6-chloro-8-methyl-7-propoxy-2-(trifluoromethyl)-2H-chromene-3-carboxylate was prepared by the procedure similar to that described in Example 40a using the carboxylic acid from Example 3c. $^1$H NMR ($D_2O$/400 MHz) 7.12 (s, 1H), 6.98 (s, 1H), 5.63 (1H, J=7.2 Hz), 3.70 (m, 2H), 1.94 (s, 3H), 1.65 (m, 2H), 0.86 (t, 3H, J=7.6 Hz).

EXAMPLE 40s

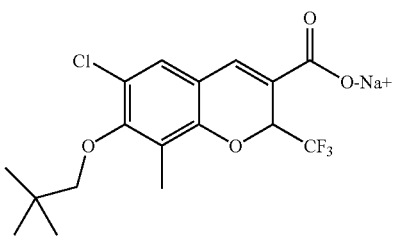

sodium 6-chloro-8-methyl-7-(neopentyloxy)-2-(trifluoromethyl)-2H-chromene-3-carboxylate The sodium 6-chloro-8-methyl-7-(neopentyloxy)-2-(trifluoromethyl)-2H-chromene-3-carboxylatewas prepared by the procedure similar to that described in Example 40a using the carboxylic acid from Example 3g. $^1$H NMR ($D_2O$/400 MHz) 7.11 (s, 1H), 6.89 (s, 1H), 5.60 (q, 1H, J=7.2 Hz), 3.27 (s, 2H), 1.88(s, 3H), 0.83 (s, 9H).

EXAMPLE 40t

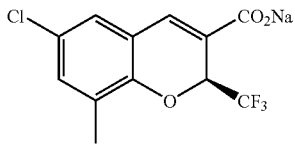

sodium (2S)-6-chloro-8-methyl-2-(trifluoromethyl)-2H-chromene-3-carboxylate

The sodium (2S)-6-chloro-8-methyl-2-(trifluoromethyl)-2H-chromene-3-carboxylate was prepared via a method similar to that described in Example 40g using carboxylic acid from Example 21t as starting material to give the product as a pale yellow solid: ESLRMS m/z 293.0 (M+H, $C_{12}H_9F_3O_3$, Calc'd 293.0).

EXAMPLE 40v

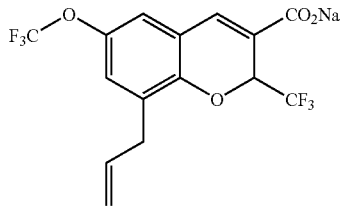

sodium 8-allyl-6-(trifluoromethoxy)-2-(trifluoromethyl)-2H-chromene-3-carboxylate The sodium 8-allyl-6-(trifluoromethoxy)-2-(trifluoromethyl)-2H-chromene-3-carboxylatewas prepared via a method similar to that described in Example 40g using carboxylic acid from Example 21s, Step 2 as starting material to give the product as an off-white solid: ESLRMS m/z 369.4 (M+H, $C_{15}H_{11}F_6O_4$, Calc'd 369.1).

EXAMPLE 41

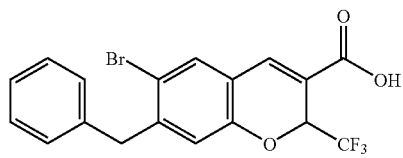

7-benzyl-6-bromo-2-(trifluoromethyl)-2H-chromene-3-carboxylic acid

Step 1. Preparation of ethyl 7-benzyl-6-bromo-2-(trifluoromethyl)-2H-chromene-3-carboxylate The ester (Example 9k, step 1) was dissolved in acetic acid (glacial) (20 mL), $Br_2$ was added and the solution stirred at room temperature for 1h. The reaction was concentrated in vacuo. Water (50 mL) was added to the residue then the reaction was extracted with ethyl acetate (2×50 mL). The organic layers were combined and washed with brine (2×50 mL), dried over $Na_2SO_4$, filtered and concentrated in vacuo producing the Bromo ester (93%). ESLRMS m/z 441 (M+H).

Step 2. Preparation of 7-benzyl-6-bromo-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 410.9841 (M−H, $C_{18}H$, $BrF_3O_3$, Calc'd 410.9838). $^1$HNMR (DMSO-$d_6$/400 MHz) 13.34 (brs, 1H), 7.91 (s, 1H), 7.71 (s, 1H), 7.42-7.54 (m, 2H), 7.28-7.39 (m, 3H), 6.99 (s, 1H), 5.89 (q, 1H, J=7.1 Hz), 4.00 (s, 2H).

EXAMPLE 42a

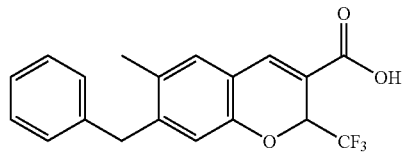

7-benzyl-6-methyl-2-(trifluoromethyl)-2H-chromene-3-carboxylic acid

Step 1. Preparation of ethyl 7-benzyl-6-methyl-2-(trifluoromethyl)-2H-chromene-3-carboxylate The ester (Example 41, Step 1) (1.0 g, 2.2 mmole) was added to a stirred solution of DMF (15 mL). Trimethylboroxane (0.316 mL, 2.2 mmole) was added along with Pd(PPh$_3$)$_4$ (0.261 g, 10 mole %) followed by $K_2CO_3$. the solution was heated to 100° C. for 8 h. The solution was poured into water (50 mL), extracted with Ethyl Acetate (2×50 mL), the organic layers were combined and washed with 1N HCl (2×50 mL) followed by brine (2×50 mL). The organic layer was dried over $Na_2SO_4$, filtered and concentrated in vacuo to produce the ester (67%). ESLRMS m/z 377 (M+H).

Step 2. Preparation of 7-benzyl-6-methyl-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 347.0896 (M−H, $C_{19}H_{14}F_3O_3$, Calc'd 347.0890). $^1$HNMR (DMSO-$d_6$/400 MHz) 13.19 (brs, 1H), 7.74 (s, 1H), 7.11-7.27 (m, 6H), 6.74 (q, 1H, J=7.1 Hz), 3.91 (s, 2H), 2.11 (s, 3H).

EXAMPLE 42b

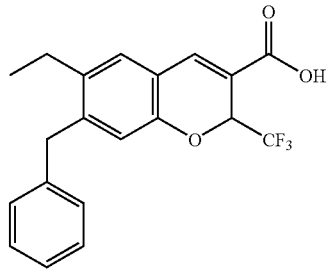

7-benzyl-6-ethyl-2-(trifluoromethyl)-2H-chromene-3-carboxylic acid

Step 1. Preparation of ethyl 7-benzyl-6-ethyl-2-(trifluoromethyl)-2H-chromene-3-carboxylate The ester (Example 41, Step 1) (1.0 g, 2.2 mmole) was added to a stirred solution of THF (20 mL) containing triethylborane, (4.53 mL, 4.5 mmole). Pd(dppf)Cl$_2$.CH2Cl2 (0.092 g, 5 mole %), followed by K3PO4(aq), 2M (2.49 mL, 4.9 mmole). The solution was heated to 70° C. for 4 h. The solution was poured into water (50 mL), extracted with Ethyl Acetate (2×50 ML), the organic layers were combined and washed with 1N HCl (2×50 mL) followed by brine (2×50 mL). The organic layer was dried over $Na_2SO_4$, filtered and concentrated in vacuo. Subjected the crude material to flash chromatography (Silica, 5% Ethyl Acetate/Hexane, collected and combined desired fractions, concentrated in vacuo to produce the ester (325 mg, 37%). This ester was of suitable purity to use without further purification. ESLRMS m/z 391 (M+H).

Step 2. Preparation of 7-benzyl-6-ethyl-2-(trifluoromethyl)-2H-chromene-3-carboxylic acid The ester (Step 1) was hydrolyzed to form the carboxylic acid via a method similar to that described in Example 4a, Step 2. ESHRMS m/z 361.1056 (M–H, $C_{20}H_{16}F_3O_3$, Calc'd 361.1046). $^1$HNMR (DMSO-$d_6$/400 MHz) 13.18 (brs, 1H), 7.79 (s, 1H), 7.10-7.28 (m, 6H), 6.73 (s, 1H), 5.79 (q, 1H, J=7.1 Hz), 3.94 (s, 2H), 2.61 (m, 2H), 1.03 (t, 3H, J=7.1 Hz).

EXAMPLE 42c

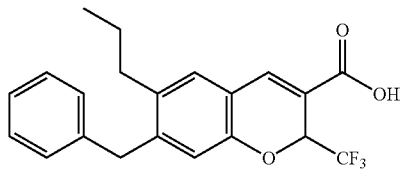

7-benzyl-6-propyl-2-(trifluoromethyl)-2H-chromene-3-carboxylic acid

Step 1. Preparation of ethyl 7-benzyl-6-propyl-2-(trifluoromethyl)-2H-chromene-3-carboxylate This compound was prepared and purified via a method similar to that described in Example 9a, Step 3 with the appropriate substitution of propene, producing the ester (425 mg, 45%). This ester was of suitable purity to use without further purification. ESLRMS m/z 405 (M+H).

Step 2. Preparation of 7-benzal-6-propyl-2-(trifluoromethyl)-2H-chromene-3-carboxylic acid The ester (Step 1) was hydrolyzed to form the carboxylic acid via a method similar to that described in Example 4a, Step 2 (99%): ESHRMS m/z 375.1195 (M–H, $C_{21}H_{18}F_3O_3$, Calc'd 375.1203). $^1$HNMR (DMSO-$d_6$/400 MHz) 13.15 (brs, 1H), 7.77 (s, 1H), 7.10-7.28 (m, 6H), 6.72 (s, 1H), 5.79 (q, 1H, J=7.1 Hz), 3.94 (s, 2H), 2.38-2.44 (m, 2H), 1.32-1.44 (m, 2H), 0.835 (t, 3H, J=7.2 Hz).

EXAMPLE 42d

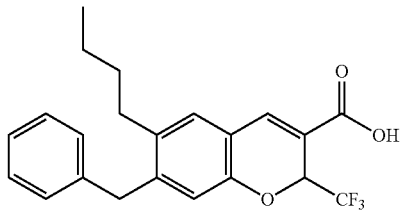

7-benzyl-6-butyl-2-(trifluoromethyl)-2H-chromene-3-carboxylic acid

Step 1. Preparation of ethyl 7-benzyl-6-butyl-2-(trifluoromethyl)-2H-chromene-3-carboxylate This compound was prepared and purified via a method similar to that described in Example 42b, Step 1, with the appropriate substitution of tributylborane producing the ester (423 mg, 45%). ESLRMS m/z 419 (M+H).

Step 2. Preparation of 7-benzyl-6-bulyl-2-(trifluoromethyl)-2H-chromene-3-carboxylic acid The ester (Step 1) was hydrolyzed to form the carboxylic acid via a method similar to that described in Example 4a, Step 2: ESHRMS m/z 389.1372 (M–H, $C_{22}H_{20}F_3O_3$, Calc'd 389.1359). $^1$HNMR (DMSO-$d_6$/400 MHz) 13.14 (s, 1H), 7.77 (s, 1H), 7.09-7.28 (m, 6H), 6.73 (s, 1H), 5.80 (q, 1H, J=7.1 Hz), 3.94 (s, 2H), 2.61 (t, 2H, J=7.0 Hz), 1.20-1.29 (m, 2H), 1.30-1.37 (m, 2H), 0.810 (t, 3H, J=7.1 Hz).

EXAMPLE 44

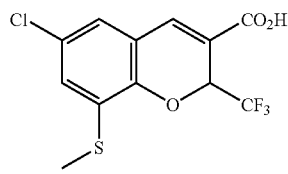

6-chloro-8-(methylthio)-2-(trifluoromethyl)-2H-chromene-3-carboxylic acid

Step 1. Preparation of ethyl 6-chloro-2-(trifluoromethyl)-2H-chromene-3-carboxylate 5-Chlorosalicylaldehyde (20.02 g, 0.128 mole) and ethyl 4,4,4-trifluorocrotonate (23.68 g, 0.14 mole) were dissolved in anhydrous DMF, warmed to 60° C. and treated with anhydrous $K_2CO_3$ (17.75 g, 0.128 mole). The solution was maintained at 60° C. for 20 hours, cooled to room temperature, and diluted with water. The solution was extracted with ethyl acetate. The combined extracts were washed with brine, dried over anhydrous $MgSO_4$, filtered and concentrated in vacuo to afford 54.32 g of an oil. The oil was dissolved in 250 mL of methanol and 100 mL of water, whereupon a white solid formed that was isolated by filtration. The resulting solid was washed with water and dried in vacuo, to afford the ester as a yellow solid (24.31 g, 62%): mp 62-64° C. $^1$H NMR (CDCl$_3$/90 MHz) 7.64 (s, 1H), 7.30-7.21 (m, 2H), 6.96 (d, 1H, J=Hz), 5.70 (q, 1H, J=Hz), 4.30 (q, 2H, J=7.2 Hz), 1.35 (t, 31H, J=7.2 Hz).

Step 2. Preparation of ethyl 6-chloro-8-(chlorosulfonyl)-2-(trifluoromethyl)-2H-chromene-3-carboxylate To ice-chilled, stirred chlorosulfonic acid (15 mL) was added ethyl 6-chloro-2-(trifluoromethyl)-2H-I-benzopyran-3-carboxylate ethyl 6-chloro-2-(trifluoromethyl)-2H-1-benzopyran-3-carboxylate (Step 1, 2.0 g, 6.5 mmol) portion wise and allowed to warm to r.t and stir for 60 h. The resulting dark brown homogeneous solution was added drop-wise to stirred ice/water (200 mL) forming a suspension. The resulting precipitate was collected by vacuum filtration. This product was purified by silica chromatography. The resulting mixture was dissolved in ethyl acetate, washed with NaHCO$_3$ solution and brine, dried over MgSO$_4$, filtered and concentrated in vacuo yielding the title compound as a solid. This solid was of sufficient purity to use in the subsequent step.

Step 3. Preparation of ethyl 6-chloro-8-(methylthio)-2-(trifluoromethyl)-2H-chromene-3-carboxylate To benzene (solvent) was added ethyl 6-chloro-8-(chlorosulfonyl)-2-(trifluoromethyl)-2H-chromene-3-carboxylate (Step 2, 0.68 g, 1.68 mmol), iodine (0.11 g, 0.84 mmol), and triphenyl phosphine (4.41 g, 16.8 mmol) amd the resulting mixture heated to reflux for 4 h and allowed to cool to RT and stand for 48 h. To this crude reaction was added Et$_3$N (0.58 mL, 0.424 g, 4.20 mmol) and methyl iodide (0.06 mL, 0.13 g, 0.92 mmol). After extractive workup and silica chromatography the title compound was obtained as a yellow, crystalline mass (0.215 g, 36%). $^1$HNMR (CDCl$_3$-d$_6$/300 MHz) 7.59 (s, 1H), 7.07 (d, J=2.4 Hz, 1H), 6.98 (d, J=2.4 Hz, 1H), 5.78 (q, 1H, J=6.8 Hz), 4.20-4.40 (m, 3H), 2.42 (s, 3H), 1.33 (t, 3H, J=7.3 Hz).

Step 4. Preparation of 6-chloro-8-(methylthio)-2-(trifluoromethyl)-2H-chromene-3-carboxylic acid To a stirred solution of ethyl 6-chloro-8-(methylthio)-2-(trifluoromethyl)-2H-chromene-3-carboxylate (Step 3, 0.203 g, 0.575 mmol) in THF:EtOH:H$_2$O (7:2:1, 5 mL), was added aqueous sodium hydroxide (0.63 mmol, 0.25 mL of 2.5 N soln.) and allowed to stir for two days. The resulting clear, yellow solution was concentrated in vacuo, was diluted with water (35 mL), and was acidified with concentrated HCl resulting in formation of a yellow suspension. Vacuum filtration of the suspension yielded the title compound as a yellow powder (0.132 g, 71%). $^1$HNMR (acetone-d$_6$/300 MHz) 7.87 (s, 1H), 7.34 (d, J=2.2 Hz, 1H), 7.25 (d, J=2.2 Hz, 1H), 5.93 (q, 1H, J=7.05 Hz), 2.53 (s, 3H). LRMS m/z 323 (M−H); ESHRMS m/z 322.9782 (M−H, C$_{12}$H$_7$F$_3$O$_3$ClS, Calc'd 322.9757). Anal. Calc'd for C$_{12}$H$_8$F$_3$O$_3$ClS: C, 44.39; H, 2.48. Found: C, 44.63; H, 2.52.)

EXAMPLE 45

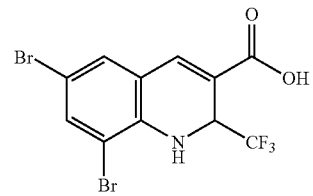

6,8-dibromo-2-(trifluoromethyl)-1,2-dihydryoquinoline-3-carboxylic acid

Step 1. Preparation of ethyl 6,8-dibromo-2-(trifluoromethyl)-1,2-dihydroquinoline-3-carboxylate The 2-amino-3,5-dibromobenzaldehyde (6.50 g, 23.3 mmol), triethylamine (6.96 g, 69.9 mmol) and ethyl 4,4,4-trifluorocrotonate (7.85 g, 46.6 mmol) were mixed in dimethylsulfoxide (12.0 mL) at 90° C. for 48 h. The solution was cooled to room temperature and the solution poured into ethyl acetate (100 mL). The solution was extracted with saturated aqueous ammonium chloride (2×100 mL), dried over sodium sulfate, filtered, and concentrated in vacuo. The ethyl 6,8-dibromo-2-(trifluoromethyl)-1,2-dihydroquinoline-3-carboxylate (4.3 g, 10.0 mmol) was isolated as a yellow solid by flash silica chromatography (43% yield): MS m/z 428 (M−H, calcd 428).

Step 2. Preparation of 6,8-dibromo-2-(trifluoromethyl)-1,2-dihydroquinoline-3-carboxylic acid Ethyl 6,8-dibromo-2-(trifluoromethyl)-1,2-dihydroquinoline-3-carboxylate (732.0 mg, 1.70 mmol) was suspended in methanol-tetrahydrofuran-water (5 mL, 7:2:1). Lithium hydroxide (214 mg, 5.108 mmol) was added and the mixture was gently heated to reflux for two hours. The reaction was cooled to room temperature and 1 N aqueous hydrochloric acid added until pH=1. The organic solvent was removed in vauco to afford a suspension of a crude yellow solid. Diethyl ether (50 mL) was added, and the solution was washed with water (2×50 mL), saturated ammonium chloride (2×50 mL), dried over sodium sulfate and filtered. The filtrate was concentrated in vacuo to yield 6,8-dibromo-2-(trifluoromethyl)-1,2-dihydroquinoline-3-carboxylic acid (633.0 mg, 1.52 mmol) as a yellow solid (89% yield): $^1$H NMR (CD$_3$OD$_3$, 300 MHz)7.07 (s, 1H), 7.57 (d, 1H, J=2.0 Hz), 7.39 (d, 1H, J=2.0 Hz), 5.26 (m, 1H). Anal. Calcd for C$_{11}$H$_6$Br$_2$F$_3$NO$_3$: C, 32.95; H, 1.51; N, 3.49. Found: C, 32.88; H, 1.51; N, 3.46.

EXAMPLE 46

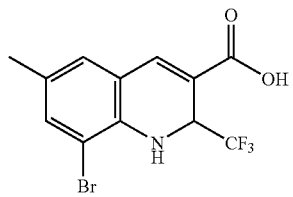

8-Bromo-6-methyl-2-(trifluoromethyl)-1,2-dihydroquinoline-3-carboxylic acid

Step 1. Preparation of (2-amino-3-bromo-5-methylphenyl)methanol

The 2-amino-3-bromo-5-methylbenzoic acid (20.0 g, 86.0 mmol) was dissolved in tetrahydrofuran (200 ml) and cooled to 0° C. A solution of borane dimethylsulfide complex (15.6 mL, 156.0 mmol) was dissolved in tetrahydrofuran (40 mL) and added dropwise. The solution was kept at 0° C. for an additional 30 minutes, warmed to room temperature for 2 h and finally refluxed for 16 h. The solution was cooled to room temperature and methanol (10 mL) added slowly to control the gas evolution. The solution was stirred for 30 minutes at room temperature and 1 N hydrochloric acid added. The solution was stirred for 3 h and solvent removed to a volume of about 100 mL. Water (200 mL) was added and the solution extracted with diethylether (200 mL). The aqueous layer was collected, adjusted to pH=12 with 1N sodium hydroxide which formed a solid in the solution. The solid was collected, dissolved in ethyl acetate (100 mL), dried over sodium sulfate and solvent removed at reduced pressure. The (2-amino-3-bromo-5-methylphenyl)methanol (9.5 g, 43.9 mmol) was obtained as a off white solid. (51% yield): HRMS m/z 216.0047; calcd for M+H 216.0024.

Step 2: Preparation of 2-amino-3-bromo-5-methylbenzaldehyde

The (2-amino-3-bromo-5-methylphenyl)methanol (7.80 g, 36.1 mmol) was dissolved in tetrahydrofuran (20 mL). Dichloromethane (50 mL) was added along with activated carbon (16.3 g). Manganese dioxide (9.4 g, 108 mmol) was added and the solution stirred at 40° C. for 16 h. The solution was cooled to room temperature and vacuum filtered through a celite. The solvent was removed at reduced pressure and the 2-amino-3-bromo-5-methylbenzaldehyde (6.10 g, 28.5 mmol) obtained by recrystallization from diethyl ether/hexanes (1:10, 100 mL) (78% yield): Melting point 99.6-101.2° C. $^1$H NMR (300 MHz, CDCL$_3$) 9.77 (s, 1H), 7.46 (s, 1H), 7.26 (s, 1H), 6.48 (bs, 2H), 2.76 (s, 3H). HRMS m/z 213.9902; calcd for M+H 213.9962.

Step 3: Preparation of ethyl 8-bromo-6-methyl-2-(trifluoromethyl)-1,2-dihydroquinoline-3-carboxylate The 2-amino-3-bromo-5-methylbenzaldehyde (5.60 g, 26.2 mmol), diazbicyclo[2.2.2]-undec-7-ene (9.2 g, 61.3 mmol), and ethyl 4,4,4-trifluorocrotonate (10.9 g, 65.4 mmol) were mixed in 1,3-dimethyl-3,4,5,6-tetrahydro-2 (1H)-pyrimidinone(12.0 mL) at 60° C. for 8 h. The solution was cooled to room temperature and poured into ethyl acetate-hexanes (1:1, 100 mL). The solution was extracted with 2.5 N aqueous hydrochloric acid (2×50 mL), saturated aqueous ammonium chloride (2×50 mL), dried over sodium sulfate, filtered, and concentrated in vacuo. The resulting dark yellow oil was taken up in hexanes (30 mL) and yellow powder crystals formed upon standing. The ethyl 8-bromo-6-methyl-2-(trifluoromethyl)-1,2-dihydroquinoline-3-carboxylate (7.2 g, 19.9 mmol) was collected by vacuum filtration. (75% yield). mp 122.2-123.6° C. HRMS m/z 364.0142; calcd for M+H 364.0155.

Step 4: Preparation of 8-bromo-6-methyl-2-(trifluoromethyl)-1,2-dihydroquinoline-3-carboxylic acid Ethyl 8-bromo-6-methyl-2-(trifluoromethyl)-1,2-dihydroquinoline-3-carboxylate (1.8 g, 4.95 mmol) was suspended in methanol-tetrahydrofuran-water (20 mL, 7:2:1). Lithium hydroxide (414 mg, 9.88 mmol) was added and the mixture was gently heated to reflux for two hours. The reaction was cooled to room temperature and 1 N aqueous hydrochloric acid added until pH=1. The organic solvent was removed in vauco to afford a suspension of a crude yellow solid. Diethyl ether (50 mL) was added, and the solution was washed with water (2×50 mL), saturated ammonium sulfate (2×50 mL), dried over sodium sulfate and filtered. The filtrate was concentrated in vacuo to yield 8-bromo-6-methyl-2-(trifluoromethyl)-1,2-dihydroquinoline-3-carboxylic acid (1.3 g, 4.05 mmol) as a yellow solid (82% yield). $^1$H NMR (300 MHz, CDCL$_3$) 7.78 (s, 1H), 7.82 (s, 1H), 6.59 (s, 1H), 5.20 (m, 2H), 5.13 (bs, 1H), 2.34 (s, 1H). HRMS m/z 334.9763; (M+, $C_{12}H_9BrF_3NO_2$ calcd 334.9769).

EXAMPLE 47

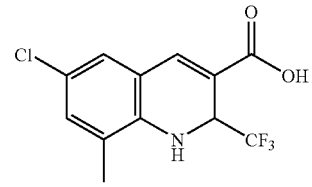

6-chloro-8-methyl-2-(trifluoromethyl)-1,2-dihydroquinoline-3-carboxylic acid

Step 1: Preparation of 2-amino-5-chloro-3-methylbenzoic acid

The 5-chloro-7-methyl-1H-indole-2,3-dione (25.0 g, 0.13 mol), potassium hydroxide (8.4 g, 0.15 mmol) and 30% hydrogen peroxide (21.6 g, 0.18 mol) were mixed together in methanol (300 mL) at 0° C. for 2 h followed by 16 h at room temperature. The solution was poured into ethyl acetate (500 mL) and extracted with I N hydrochloric acid (3×200 mL) followed by brine (1×50 mL). The solution was dried over sodium sulfate and solvent removed at reduced pressure. The 2-amino-5-chloro-3-methylbenzoic acid (18.0 g, 0.10 mmol) was isolated as a yellow solid (75% yield). HRMS m/z 185.0238; calcd 185.0244.

Step 2: Preparation of (2-amino-5-chloro-3-methylphenyl)methanol

The 2-amino-5-chloro-3-methylbenzoic acid (15.6 g, 84.3 mmol) was dissolved in tetrahydrofuran (200 ml) and cooled to 0° C. A solution of borane dimethylsulfide complex (16.8 mL, 16.8 mmol) was dissolved in tetrahydrofuran (40 mL) and added dropwise. The solution was kept at 0° C. for an additional 30 minutes and warmed to room temperature for 2 h and finally refluxed for 16 h. The solution was cooled to room temperature and methanol (10 mL) added slowly to control the gas evolution. The solution was stirred for 30 minutes at room temperature and 1 N hydrochloric acid added. The solution was stirred for 3 h and solvent removed to a volume of about 100 mL. Water (200 mL) was added and the solution extracted with diethylether (200 mL). The aqueous layer was collected, adjusted to pH=12 with 1N sodium hydroxide which formed a solid in the solution. The solid was collected, dissolved in ethyl acetate (100 mL), dried over sodium sulfate and solvent removed at reduced pressure. (2-Amino-5-chloro-3-methylphenyl)methanol (10.8 g, 63.1 mmol) was obtained as a light yellow solid (75% yield). HRMS m/z 172.0544; calcd for M+H 172.0524.

Step 3: Prepration of 2-amino-5-chloro-3-methylbenzaldehyde

The (2-amino-5-chloro-3-methylphenyl)methanol (10.8 g, 63.1 mmol) was dissolved in tetrahydrofuran (20 mL). Dichloromethane (50 mL) was added along with activated carbon (16.3 g). Activated manganese dioxide (16.8 g, 189 mmol) was added and the solution stirred at 40° C. for 16 h. The solution was cooled to room temperature and vacuum filtered through a celite. The solvent was removed at reduced pressure and the 2-amino-5-chloro-3-methylbenzaldehyde (7.90 g, 46.0 mmol) obtained by recrystallization from diethyl ether/hexanes (1:10, 100 mL). HRMS m/z 169.0280; calcd 169.0294.

Step 4: Preparation of ethyl 6-chloro-8-methyl-2-(trifluoromethyl)-1,2-dihydroquinoline-3-carboxylate The 2-amino-5-chloro-3-methylbenzaldehyde (5.60 g, 33.1 mmol), diazbicyclo[2.2.2]-undec-7-ene (12.1 g, 82.0 mmol), and ethyl 4,4,4-trifluorocrotonate (13.9 g, 82.7 mmol) were mixed in 1,3-dimethyl-3,4,5,6-tetrahydro-2 (1H)-pyrimidinone(12.0 mL) at 60° C. for 8 h. The solution was cooled to room temperature and the solution poured into ethyl acetate-hexanes (1:1, 100 mL). The solution was extracted with 2.5 N aqueous hydrochloric acid (2×50 mL), saturated aqueous ammonium chloride (2×50 mL), dried over sodium sulfate, filtered, and concentrated in vacuo. The resulting dark yellow oil was taken up in hexanes (30 mL) and yellow powder crystals formed upon standing. The ethyl 6-chloro-8-methyl-2-(trifluoromethyl)-1,2-dihydroquinoline-3-carboxylate (6.6 g, 20.7 mmol) was collected by vacuum filtration (60% yield). mp 154-155° C. HRMS m/z 216.0047; calcd for M+H 216.0024.

Step 5: Preparation of 6-chloro-8-methyl-2-(trifluoro-methyl)-1,2-dihydroquinoline-3-carboxylic acid Ethyl 6-chloro-8-methyl-2-(trifluoromethyl)-1,2-dihydroquinoline-3-carboxylate (4.5, 0.51 mmol) was suspended in methanol-tetrahydrofuran-water (50 mL, 7:2:1). Lithium hydroxide (1.70 g, 42.3 mmol) was added, and the mixture was gently heated to reflux for two hours. The reaction was cooled to room temperature and 1 N aqueous hydrochloric acid added until pH=1. The organic solvent was removed in vauco to afford a suspension of a crude yellow solid. Diethyl ether (200 mL) was added, and the solution was washed with water (2×200 mL), saturated ammonium sulfate (2×200 mL), dried over sodium sulfate and filtered. The filtrate was concentrated in vacuo to yield 6-chloro-8-methyl-2-(trifluoromethyl)-1,2-dihydroquinoline-3-carboxylic acid (3.8 g, 13.4 mmol) as a yellow solid (95% yield). (CDCl₃, 300 MHz) 7.56 (s, 1H), 6.93 (s, 1H), 6.90 (s, 1H), 5.11 (q, 1H, J=7.2 Hz), 4.78 (bs, 1H), 2.08 (s, 3H). HRMS m/z 291.0286 (M+, $C_{12}H_9ClF_3NO_2$, calcd 291.0274).

EXAMPLE 48

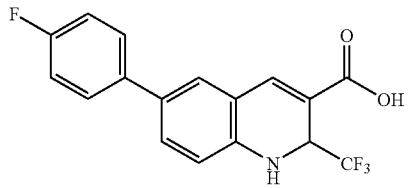

6-(4-fluorophenyl)-2-(trifluoromethyl)-1,2-dihydro-quinoline-3-carboxylic acid

Step 1: Preparation of ethyl 6-iodo-1,2-dihydro-2-(trifluoromethyl)-3-guinolinecarboxylate The 5-iodo-2-aminobenzaldehyde was prepared from the commercially available 5-iodo-2-aminobenzoic acid utilizing a previously described literature procedure (Alabaster, C. J. Med. Chem, 1988, 10, 2048-2056). The 5-iodo-2-aminobenzaldehyde (24.0 g, 96.7 mmol), diazbi-cyclo [2.2.2]-undec-7-ene (32.2 g, 212.0 mmol), and ethyl 4,4,4-trifluorocrotonate (35.7 g, 212.0 mmol) were mixed in 1,3-dimethyl-3,4,5,6-tetrahydro-2(1H)-pyrimidinone (48 mL) at 60° C. for 8 h. The solution was cooled to room temperature and the solution poured into ethyl acetate-hexanes (1:1, 500 mL). The solution was extracted with 2.5 N aqueous hydrochloric acid (2×200 mL), saturated aqueous ammonium chloride (2×200 mL), dried over sodium sulfate, filtered, and concentrated in vacuo. The resulting dark yellow oil was taken up in hexanes (100 mL) and yellow powder crystals formed upon standing. The ethyl 6-iodo-1, 2-dihydro-2-(trifluoromethyl)-3-quinolinecarboxylate (19.3 g, 48.8 mmol) was collected by vacuum filtration (50% yield). mp 137-138° C. ¹H NMR (CDCl₃, 300 MHz) 7.62 (s, 1H), 7.36-7.48 (m, 2H), 6.43 (d, J=8.2 Hz), 5.36 (brs, 1H), 5.11 (q, 1H, J=7.1 Hz), 4.25 4.35 (m, 2H), 1.34 (t, 3H, J=7.0 Hz). HRMS m/z 395.9716; Calcd for M−H, 395.9708.

Step 2: Preparation of ethyl 6-(4-fluorophenyl)-2-(trifluoromethyl)-1,2-dihydroquinoline-3-carboxylate The ethyl 6-(4-fluorophenyl)-2-(trifluoromethyl)-1,2-dihydroquinoline-3-carboxylate (700 mg, 1.76 mmol), para-flourophenyl boronic acid (257 mg, 1.85 mmol), palladium II acetate, (3.48 mg, 0.015 mmol), triphenylphosphine (12.2 mg, 0.045 mmol) and sodium bicarbonate (222 mg, 2.11 mmol) was refluxed in n-propanol/water (5.0 mL of 9:1) for 1 H. The solution was poured into ethyl acetate (50 mL), extracted with water (2×25 mL), 1 N hydrochloric acid (2×25 mL), and saturated aqueous ammonium chloride (2×25 mL). The organic layer was dried over sodium sulfate, solvent removed at reduced pressure, and the ester isolated by flash silica chromatography (0-25% ethyl acetate in hexanes). The ethyl 6-(4-fluorophenyl)-2-(trifluoromethyl)-1,2-dihydroquinoline-3-carboxylate (243 mg, 0.66 mmol) was triturated from hexanes as a yellow solid (26% yield). HRMS m/z 364.0989; Calcd for M−H 394.0960.

Step 3: 6-(4-fluorophenyl)-2-(trifluoromethyl)-l2-dihydroquinoline-3-carboxylic acid Ethyl 6-(4-fluorophenyl)-2-(trifluoromethyl)-1,2-dihydroquinoline-3-carboxylate (189 mg, 0.51 mmol) was suspended in methanol-tetrahydrofuran-water (10 mL, 7:2:1). Lithium hydroxide (42 mg, 0.1.53 mmol) was added, and the mixture was gently heated to reflux for two hours. The reaction was cooled to room temperature and 1 N aqueous hydrochloric acid added until pH=1. The organic solvent was removed in vauco to afford a suspension of a crude yellow solid. Diethyl ether (20 mL) was added, and the solution was washed with water (2×20 mL), saturated ammonium sulfate (2×20 mL), dried over sodium sulfate and filtered. The filtrate was concentrated in vacuo to yield 6-(4-fluorophenyl)-2-(trifluoromethyl)-1,2-dihydroquinoline-3-carboxylic acid (152 mg, 0.45 mmol) as a yellow solid (88% yield). $^1$H NMR (CD$_3$OD$_3$, 300 MHz) 7.81 (s, 1H), 7.40-7.56 (m, 4H), 7.10 (t, 1H, J=9.1 Hz), 6.78 (d, 1H, J=8.3 Mz), 5.12 (m, 1H). HRMS m/z 337.0732; calcd 337.0726.

EXAMPLE 100

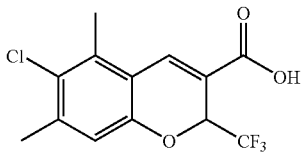

6-chloro-5,7-dimethyl-2-(triflururomethyl)-2H-chromene-3-carboxylic acid

Step 1: Preparation of 3-chloro-6-hydroxy-2,4-dimethylbenzaldehyde

To a solution of 4-chloro-3,5-dimethyl-phenol (10.0 g, 63.9 mmol) in 400 mL CH$_3$CN was added MgCl$_2$ (9.12 g, 95.8 mmol), TEA (23.9 g, 32.9 mL, 236 mmol), and (CH$_2$O)$_n$ (13.4 g, 304 mmol). The reaction was heated at reflux for 4 h. After cooling to room temperature, 2 N HCl was added until the reaction was pH 3. The aqueous layer was extracted two times with 300 mL of Et$_2$O. The organic layer was filtered and the filtrate was washed one time with saturated brine, followed by drying over MgSO$_4$, and concentrated under vacuum. Crude desired (12.6 g) was isolated. Under flash chromatography conditions, 6.9 g (59%) of pure compound was isolated.

Step 2: Preparation of ethyl 6-chloro-5,7-dimethyl-2-(trifluoromethyl)-2H-chromene-3-carboxylate To a solution of 3-chloro-6-hydroxy-2,4-dimethylbenzaldehyde (6.9 g, 37.4 mmol) in 80 mL of DMF was added dried finely powdered K$_2$CO$_3$ (11.36 g, 82.2 mmol). With mechanical stirring, the reaction was heated to 65° C. To the suspension was added dropwise ethyl trifluorocrotonate (7.54 g, 44.9 mmol). The stirring reaction was heated at 90° C. for 1.5 h. K$_2$CO$_3$ was filtered from the cooled reaction. From the reaction under vacuum, DMF was removed. The resulting residue was dissolved in 400 mL EtOAc. The organic solution was washed with 100 mL 1 M KHSO$_4$, 70 mL of satd. KHCO$_3$, 100 mL brine, followed by drying over MgSO$_4$, and concentrating under vacuum. The crude desired product (13.8 g) of was isolated. After employing flash chromatography conditions, pure compound (9.8 g, 78%) of was isolated and its structure confirmed by NMR and LC-MS.

Step 3: Preparation of 6-chloro-5,7-dimethyl-2-(trifluoromethyl)-2H-chromene-3-carboxylic acid To a suspension of ethyl 6-chloro-5,7-dimethyl-2-(trifluoromethyl)-2H-chromene-3-carboxylate (4.00 g, 11.9 mmol) in 40 mL of EtOH was added a solution of NaOH (1.2 g, 30 mmol) in 18 mL of H$_2$O. The reaction was heated at reflux for 1.5 h. Once cooled, the reaction was neutralized with 2 N HCl. The product that precipitated from solution was filtered and washed with H$_2$O. After drying in the vacuum oven at 50° C., a pale yellow solid, 6-chloro-5,7-dimethyl-2-(trifluoromethyl)-2H-chromene-3-carboxylic acid, (3.46 g, 95%) was isolated.

$^1$H NMR (MeOH-d$_4$) 7.93 (s, 1H), 6.76 (s, 1H), 5.65 (q, 1H, J=7.15 Hz), 2.39 (s, 3H), 2.31 (s, 3H). DSC 203.59° C.

EXAMPLE 101

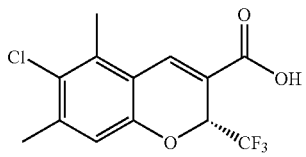

(2R)-6-chloro-5,7-dimethyl-2-(trifluoromethyl)-2H-chromene-3-carboxylic acid (2R)-6-chloro-5,7-dimethyl-2-(trifluoromethyl)-2H-chromene-3-carboxylic acid Isomers of 6-chloro-5,7-dimethyl-2-(trifluoromethyl)-2H-chromene-3-carboxylic acid were separated by chiral chromatography using Chiralcel AS or AD. (2R)-6-chloro-5,7-dimethyl-2-(trifluoromethyl)-2H-chromene-3-carboxylic acid had a negative specific rotation. Chiral HPLC analysis on Chirobiotic T (MeOH/H$_2$O/HOAc/TEA) gave a retention time of 6.03 min for (2R)-6-chloro-5,7-dimethyl-2-(trifluoromethyl)-2H-chromene-3-carboxylic acid.

EXAMPLE 102

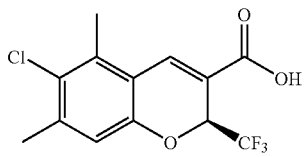

(2S)-6-chloro-5,7-dimethyl-2-(trifluoromethyl)-2H-chromene-3-carboxylic acid

Isolation of (2S)-6-chloro-5,7-dimethyl-2-(trifluoromethyl)-2H-chromene-3-carboxylic acid See Example 101. (2S)-6-chloro-5,7-dimethyl-2-(trifluoromethyl)-2H-chromene-3-carboxylic acid had a positive specific rotation. Chiral HPLC analysis on Chirobiotic T (MeOH/H$_2$O/HOAc/TEA) gave a retention time of 8.02 min for (2S)-6-chloro-5,7-dimethyl-2-(trifluoromethyl)-2H-chromene-3-carboxylic acid.

EXAMPLE 103

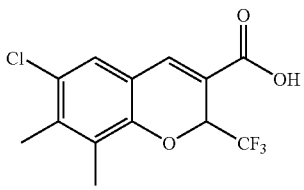

6-chloro-7,8-dimethyl-2-(trifluoromethyl)-2H-chromene-3-carboxylic acid

Step 1: Preparation of 2-hydroxy-3,4-dimethylbenzaldehyde

2-Hydroxy-3,4-dimethylbenzaldehyde was prepared in the same manner as described in Example 100 Step 1 except the starting material was 2,3-dimethylphenol.

Step 2: Preparation of ethyl 7,8-dimethyl-2-(trifluoromethyl)-2H-chromene-3-carboxylate Ethyl 7,8-dimethyl-2-(trifluoromethyl)-2H-chromene-3-carboxylate was prepared in the same manner as Example 100 Step 2 except the starting material was 6-hydroxy-2,4-dimethylbenzaldehyde.

Step 3: Preparation of ethyl 6-chloro-7,8-dimethyl-2-(trifluoromethyl)-2H-chromene-3-carboxylate To a solution of ethyl 7,8-dimethyl-2-(trifluoromethyl)-2H-chromene-3-carboxylat (4.0 g, 13.3 mmol) in 75 mL HOAc was added Cl$_2$ until the solvent was saturated as indicated by the greenish chlorine cloud above the solvent. After 2 h, the reaction was flushed with N$_2$ and subsequently treated with excess Zn dust for 1.5 h. The reaction mixture was decanted from the Zn and concentrated under vacuum. The resulting residue was dissolved in 300 mL of EtOAc and washed with 100 mL 1 M KHSO$_4$ and 100 mL brine. The organic layer was dried over MgSO$_4$, filtered and concentrated under vacuum. The yield of ethyl 6-chloro-7,8-dimethyl-2-(trifluoromethyl)-2H-chromene-3-carboxylate was 5.2 g.

Step 4: Preparation of 6-chloro-7,8-dimethyl-2-(trifluoromethyl)-2H-chromene-3-carboxylic acid 6-Chloro-7,8-dimethyl-2-(trifluoromethyl)-2H-chromene-3-carboxylic acid was prepared in the same manner as Example 100 Step 3 only the starting material was ethyl 6-chloro-7,8-dimethyl-2-(trifluoromethyl)-2H-chromene-3-carboxylate. $^1$H NMR (MeOH-d$_4$) 7.68 (s, 1H), 7.20 (s, 1H), 5.78 (q, 1H, J=7.08 Hz), 2.36 (s, 3H), 2.23 (s, 3H). DSC 216.32° C.

EXAMPLE 104

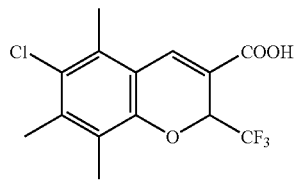

6-chloro-5,7,8-trimethyl-2-(trifluoromethyl)-2H-chromene-3-carboxylic) acid

Step 1: Preparation of 6-hydroxy-2,4,5-trimethylbenzaldehyde

To a solution of 2,3,5-trimethylphenol (11.2 g, 82.0 mmoles) in 400 mL of acetonitrile was added paraformaldehyde (17.2 g, 574 mmoles), anhydrous MgCl$_2$ (11.7 g, 123 mmoles), and TEA (43 mL 31 g, 308 mmoles). The mixture was refluxed for 6 h with stirring. After cooling, the mixture was partially concentrated, water added, and the mixture acidified with dilute aqueous HCl. The mixture was extracted with three times with Et$_2$O, the combined organic extracts washed with brine, dried over Na$_2$SO$_4$, filtered, and concentrated. Chromatography of the residue over silica gel using DCM as eluent gave 6-hydroxy-2,4,5-trimethylbenzaldehyde, 8.8 g, as an oil.

Step 2: Preparation of ethyl 5,7,8-trimethyl-2-(trifluoromethyl)-2H-chromene-3-carboxylate To a solution of 6-hydroxy-2,4,5-trimethylbenzaldehyde (2.77 g, 17.1 mmoles) in 50 mL of dry DMF was added anhydrous K$_2$CO$_3$ (5.19 g, 37.6 mmoles), and ethyl 4,4,4-trifluorocrotonate (3.16 g, 18.8 mmoles). The mixture was stirred rapidly under a drying tube at 100° C. for 3 h. After cooling, the mixture was diluted with DMF, filtered, and evaporated. Chromatography of the residue over silica gel using DCM as eluent gave ethyl 5,7,8-trimethyl-2-(trifluoromethyl)-2H-chromene-3-carboxylate, 3.75 g, as an oil.

Step 3: Preparation of ethyl 6-chloro-5,7,8-trimethyl-2-(trifluoromethyl)-2H-chromene-3-carboxylate Into a solution of ethyl 5,7,8-trimethyl-2-(trifluoromethyl)-2H-chromene-3-carboxylate in 50 mL of HOAc was bubbled a stream of Cl$_2$ gas until a persistent appearance of Cl$_2$ was visible above the solution. The mixture was stirred for 1 h, after which N$_2$ gas was bubbled through to expel excess Cl$_2$. Zn dust (731 mg, 11.2 mg-atm) was added, the mixture was stirred for 30 min, and evaporated. Chromatography of the residue over silica gel using DCM as eluent gave ethyl 6-chloro-5,7,8-trimethyl-2-(trifluoromethyl)-2H-chromene-3-carboxylate, 3.01 g, as an oil.

Step 4: Preparation of 6-chloro-5,7,8-trimethyl-2-(trifluoromethyl)-2H-chromene-3-carboxylic) acid A solution of 3.01 g (8.62 mmoles) of ethyl 6-chloro-5,7,8-trimethyl-2-(trifluoromethyl)-2H-chromene-3-carboxylate was treated in a similar manner found in Example 100 Step 3. This afforded 6-chloro-5,7,8-trimethyl-2-(trifluoromethyl)-2H-chromene-3-carboxylic) acid, 2.52 g, as a white solid. $^1$H NMR (acetone-$d_6$) 8.07 (s, 1H), 5.85 (q, 1H, J=7.2 Hz), 2.50 (s, 3H), 2.40 (s, 3H), 2,24 (s, 3H).

EXAMPLE 105

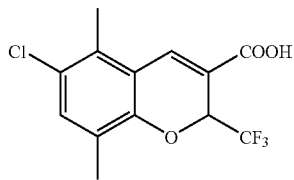

6-chloro-5,8-dimethyl-2-(trifluoromethyl)-2H-chromene-3-carboxylic acid

Step 1: Preparation of 6-hydroxy-2,5-dimethylbenzaldehyde

6-Hydroxy-2,5-dimethylbenzaldehyde was prepared by the method of Example 104 Step 1 except that 2,5-dimethylphenol was used as the starting phenol.

Step 2: Preparation of ethyl 5,8-dimethyl-2-(trifluoromethyl)-2H-chromene-3-carboxylate Ethyl 5,8-dimethyl-2-(trifluoromethyl)-2H-chromene-3-carboxylate was prepared by the method of Example 104 Step 2 except that 6-hydroxy-2,5-dimethylbenzaldehyde was used in place of 6-hydroxy-2,4,5-trimethylbenzaldehyde.

Step 3: Preparation of ethyl 6-chloro-5,8-dimethyl-2-(trifluoromethyl)-2H-chromene-3-carboxylate Ethyl 6-chloro-5,8-dimethyl-2-(trifluoromethyl)-2H-chromene-3-carboxylate was prepared by the method of Example 104 Step 3 except that ethyl 5,8-dimethyl-2-(trifluoromethyl)-2H-chromene-3-carboxylate was used in place of ethyl 6-chloro-5,7,8-trimethyl-2-(trifluoromethyl)-2H-chromene-3-carboxylate.

Step 4: Preparation of 6-chloro-5,8-dimethyl-2-(trifluoromethyl)-2H-chromene-3-carboxylic acid 6-Chloro-5,8-dimethyl-2-(trifluoromethyl)-2H-chromene-3-carboxylic acid was obtained as a very pale, yellowish solid by the method of Example 104 Step 4 except that ethyl 6-chloro-5,8-dimethyl-2-(trifluoromethyl)-2H-chromene-3-carboxylate was used in place of ethyl 6-chloro-5,7,8-trimethyl-2-(trifluoromethyl)-2H-chromene-3-carboxylate. $^1$H NMR (acetone-$d_6$) 8.06 (s, 1H), 7.34 (s, 1H), 5.87 (q, 1H, J=7.2 Hz), 2.48 (s, 3H), 2.23 (s, 3H).

EXAMPLE 106

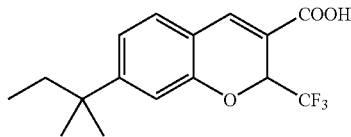

7-tert-pentyl-2-(trifluoromethyl)-2H-chromene-3-carboxylic acid

Step 1: Preparation of 2-(3-methoxyphenyl)-2-methylpropanenitrile

To 190 mL of DMSO was added 55 mL of 50% aqueous NaOH, forming a stirrable pasty mass. A solution of 3-methoxyphenylacetonitrile (25.0 g, 270 mmoles) in 25 mL of DMSO was added slowly with stirring. After a few minutes, 32 mL of iodomethane was added, producing an exotherm. A further portion of iodomethane was added, stirring continued until the mixture cooled, and the mixture was kept at room temperature. Ice was added, and the mixture extracted with several portions of $Et_2O$. The combined organic extracts were washed twice with water, once with brine, dried over $Na_2SO_4$, filtered, and evaporated to give the title compound, 27.7 g, as an oil.

Step 2: Preparation of 2-(3-methoxyphenyl)-2-methylpropanal

To a ice cold stirred solution of 2-(3-methoxyphenyl)-2-methylpropanenitrile (27.7 g, 158 mmoles) in 250 mL of THF was added dropwise diisobutylaluminum hydride in heptane (202 mL, 1.0M solution). The mixture was allowed to warm to room temperature overnight. After cooling, a solution of concentrated $H_2SO_4$ (21.5 mL) in 85 mL of water was cautiously added in small portions. The resulting mixture was partitioned between $Et_2O$ and water, the aqueous layer further extracted, and the combined organic extracts dried over $Na_2SO_4$, filtered, and evaporated to give 2-(3-methoxyphenyl)-2-methylpropanal, 21.7 g, as an oil.

Step 3: Preparation of 1-(1,1-dimethylprop-2-enyl)-3-methoxybenzene

A solution of sodium dimsylate was prepared by dissolving hexane washed 60% NaH (4.89 g, 122 mmoles) in mineral oil in 120 mL of DMSO with heating to 60° C. To 40 mL of this solution added methyltriphenylphosphonium bromide (14.5 g, 40.7 mmoles) of as a solid, forming a thick paste. A solution of 2-(3-methoxyphenyl)-2-methylpropanal (5.00 g, 28.1 mmoles) in 6 mL of DMSO was added, and the mixture stirred overnight. The mixture was partitioned between $Et_2O$ and water, and the aqueous layer further extracted with $Et_2O$. The combined organic extracts were washed with water and brine, dried over $Na_2SO_4$, filtered, and evaporated. Chromatography of the residue over silica gel using DCM as eluent gave 1-(1,1-dimethylprop-2-enyl)-3-methoxybenzene, 4.25 g, as an oil.

Step 4: Preparation of 1-methoxy-3-tert-pentylbenzene

Hydrogenation of 1-(1,1-dimethylprop-2-enyl)-3-methoxybenzene using 5% palladium on carbon in ethanol under 5 psi of hydrogen gas gave 1-methoxy-3-tert-pentylbenzene, 3.27 g.

Step 5: Preparation of 3-tert-pentylphenol

To a solution of 1-methoxy-3-tert-pentylbenzene (3.22 g, 18.1 mmoles) in 100 mL of DCM stirring in −78° C. bath was added dropwise 2.14 mL (5.68 g) of $BBr_3$. The mixture was stirred while warming to room temperature. After 3 h, ice was added, and the organic layer separated, dried over $Na_2SO_4$, filtered and evaporated affording 3-tert-pentylphenol, 2.77 g, as an oil.

Step 6: Preparation of 2-hydroxy-4-tert-penlylbenzaldehyde

2-Hydroxy-4-tert-pentylbenzaldehyde was prepared by the method of Example 104 Step 1 except that 3-tert-pentylphenol was used in place of 2,3,5-trimethylphenol.

Step 7: Preparation of ethyl 7-tert-pentyl-2-(trifluoromethyl)-2H-chromene-3-carboxylate Ethyl 7-tert-pentyl-2-(trifluoromethyl)-2H-chromene-3-carboxylate was prepared by the method of Example 104 Step 2 except that 2-hydroxy-4-tert-pentylbenzaldehyde was used in place of 6-hydroxy-2,4,5-trimethylbenzaldehyde.

Step 8: Preparation of 7-tert-pentyl-2-(trifluoromethyl)-2H-chromene-3-carboxylic acid 7-tert-Pentyl-2-(trifluoromethyl)-2H-chromene-3-carboxylic acid was prepared by the method of Example 104 Step 3 except that ethyl 7-tert-pentyl-2-(trifluoromethyl)-2H-chromene-3-carboxylate was used in place of ethyl 5,7,8-trimethyl-2-(trifluoromethyl)-2H-chromene-3-carboxylate. $^1H$ NMR (acetone-$d_6$) 7.98 (s, 1 H), 7.41 (d, 1H, J=8.0 Hz), 7.11 (dd, J=8.0 Hz, J=1.8Hz), 7.01 (d, J=1.8Hz), 5.80 (q, 1H, J=7.2 Hz), 1.68 (q, 2H, J=5.5Hz), 1.30 (s, 6H), 0.69 (t, 3H, J=5.5 Hz).

EXAMPLE 107

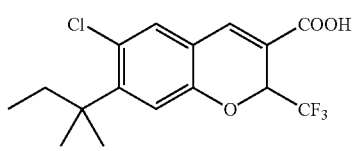

6-chloro-7-tert-pentyl-2-(trifluoromethyl)-2H-chromene-3-carboxylic acid

Step 1: Preparation of ethyl 6-chloro-7-tert-pentyl-2-(trifluoromethyl)-2H-chromene-3-carboxylate Ethyl 6-chloro-7-tert-pentyl-2-(trifluoromethyl)-2H-chromene-3-carboxylate was prepared by the method of Example 104 Step 3 except that ethyl 7-tert-pentyl-2-(trifluoromethyl)-2H-chromene-3-carboxylate was used in place of ethyl 5,7,8-trimethyl-2-(trifluoromethyl)-2H-chromene-3-carboxylate.

Step 2: Preparation of 6-chloro-7-tert-pentyl-2-(trifluoromethyl)-2H-chromene-3-carboxylic acid 6-Chloro-7-tert-pentyl-2-(trifluoromethyl)-2H-chromene-3-carboxylic acid was prepared by the method of Example 104 Step 4 except that ethyl 6-chldro-7-tert-pentyl-2-(trifluoromethyl)-2H-chromene-3-carboxylate was used in place of ethyl 6-chloro-5,7,8-trimethyl-2-(trifluoromethyl)-2H-chromene-3-carboxylate. $^1H$ NMR ($CDCl_3$) 7.76 (s, 1H), 7.23 (s, 1H), 7.02 (s, 1H), 5.67 (q, 1H, J=7.2 Hz), 2.00 (m, 1H), 1.94 (m, 1H), 1.42 (s, 3H), 1.41 (S, 3h), 0.66 (t, 3H, J=7.5 Hz).

EXAMPLE 108

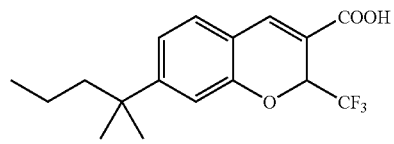

7-(1,1-dimethylbutyl)-2-(trifluoromethyl)-2H-chromene-3-carboxylic acid

Step 1: Preparation of 3-r(2Z)-1,1-dimethylbut-2-enyl]phenyl methyl ether

3-[1,1-dimethylbut-2-enyl]phenyl methyl ether was prepared by the method of Example 106 Step 3 except that ethyltriphenylphosphonium bromide was used in place of methyltriphenylphosphonium bromide.

Step 2: 3-(1,1-dimethylbutyl)phenyl methyl ether 3-(1,1-Dimethylbutyl)phenyl methyl ether was prepared by the method of Example 106 Step 4 except that 3-[1,1-dimethylbut-2-enyl]phenyl methyl ether was used in place of 1-(1,1-dimethylprop-2-enyl)-3-methoxybenzene.

Step 3: Preparation of 3-(1,1-dimethylbutyl)phenol 3-(1,1-Dimethylbutyl)phenol was prepared by the method of Example 106 Step 5 except that 3-(1,1-dimethylbutyl)phenyl methyl ether was used in place of 1-methoxy-3-tert-pentylbenzene.

Step 4: Preparation of 4-(1,1-dimethylbutyl)-2-hydroxybenzaldehyde

The title benzaldehyde was prepared by the method of Example 106 Step 6 except that 3-(1,1-dimethylbutyl)phenol was used in place of 3-tert-pentylphenol.

Step 5: Preparation of ethyl 7-(1,1-dimethylbutyl)-2-(trifluoromethyl)-2H-chromene-3-carboxylate Ethyl 7-(1,1-dimethylbutyl)-2-(trifluoromethyl)-2H-chromene-3-carboxylate was prepared by the method of Example 106 Step 7 except that 4-(1,1-dimethylbutyl)-2-hydroxybenzaldehyde was used in place of 2-hydroxy-4-tert-pentylbenzaldehyde.

Step 6: Preparation of 7-(1,1-dimethylbutyl)-2-(trifluoromethyl)-2H-chromene-3-carboxylic acid 7-(1,1-Dimethylbutyl)-2-(trifluoromethyl)-2H-chromene-3-carboxylic acid was prepared by the method of Example 106 Step 8 except that ethyl 7-(1,1-dimethylbutyl)-2-(trifluoromethyl)-2H-chromene-3-carboxylate was used in place of ethyl 7-tert-pentyl-2-(trifluoromethyl)-2H-chromene-3-carboxylate. $^1$H NMR (acetone-$d_6$) 7.85 (s, 1H), 7.39 (2H, J=8 Hz), 7.06 (dd, J=8 Hz, J=1.8 Hz), 7.00 (d, 1H, J=1.8 Hz), 5.79 (q, 1H, J=7.2 Hz), 1.61 (m, 2H), 1.30 (s, 6H), 1.08 (m, 2H), 0.83 (t, 3H, J=5.5 Hz).

EXAMPLE 109

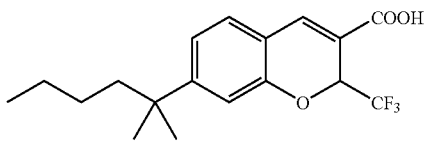

7-(1,1-dimethylpentyl)-2-(trifluoromethyl)-2H-chromene-3-carboxylic acid

Step 1: Preparation of 1-[(2Z)-1,1-dimethylpent-2-enyl]-3-methoxybenzene

The title compound was prepared by the method of Example 106 Step 3 except that propyltriphenylphosphonium bromide was used in place of methyltriphenylphosphonium bromide.

Step 2: Preparation of 1-(1,1-dimethylpentyl)-3-methoxybenzene

The title compound was prepared by the method of Example 106 Step 4 except that 1-[(2Z)-1,1-dimethylpent-2-enyl]-3-methoxybenzene was used in place of 1-(1,1-dimethylprop-2-enyl)-3-methoxybenzene.

Step 3: Preparation of 3-(1,1-dimethylpentyl)phenol 3-(1,1-Dimethylpentyl)phenol was prepared by the method of Example 106 Step 5 except that 1-(1,1-dimethylpentyl)-3-methoxybenzene was used in place of 1-methoxy-3-tert-pentylbenzene.

Step 4: Preparation of 4-(1,1-dimethylpentyl)-2-hydroxybenzaldehyde 4-(1,1-Dimethylpentyl)-2-hydroxybenzaldehyde was prepared by the method of Example 106 Step 6 except that 3-(1,1-dimethylpentyl)phenol was used in place of 3-tert-pentylphenol.

Step 5: Preparation of ethyl 7-(1,1-dimethylpentyl)-2-(trifluoromethyl)-2H-chromene-3-carboxlate Ethyl 7-(1,1-dimethylpentyl)-2-(trifluoromethyl)-2H-chromene-3-carboxylate was prepared by the method of Example 106 Step 7 except that 4-(1,1-dimethylpentyl)-2-hydroxybenzaldehyde was used in place of 2-hydroxy-4-tert-pentylbenzaldehyde.

Step 6: Preparation of 7-(1,1-dimethylpentyl)-2-(trifluoromethyl)-2H-chromene-3-carboxylic acid 7-(1,1-Dimethylpentyl)-2-(trifluoromethyl)-2H-chromene-3-carboxylic acid was prepared by the method of Example 106 Step 8 except that ethyl 7-(1,1-dimethylpentyl)-2-(trifluoromethyl)-2H-chromene-3-carboxylate was used in place of ethyl 7-tert-pentyl-2-(trifluoromethyl)-2H-chromene-3-carboxylate. $^1$H NMR (acetone-$d_6$) 7.88 (s, 1H), 7.40 (d, 1H, J=8 Hz), 7.11 (dd, J=8 Hz, J=1.8 Hz), 7.01 (d, 1H, J=1.8 Hz), 5.80 (q, 1H, J=7.2 Hz), 1.65 (m, 2H), 1.31 (s, 6H), 1.23 (m, 2H), 1.07 (m, 2H), 0.83 (t, J=5.5 Hz). LCMS m/z=343.2 (M+H)

EXAMPLE 110

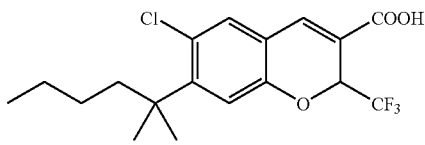

6-chloro-7-(1,1-dimethylpentyl)-2-(trifluoromethyl)-2H-chromene-3-carboxylic acid Step 1: Preparation of ethyl 6-chloro-7-(1,1-dimethylpentyl)-2-(trifluoromethyl)-2H-chromene-3-carboxylate Ethyl 6-chloro-7-(1,1-dimethylpentyl)-2-(trifluoromethyl)-2H-chromene-3-carboxylate was prepared by the method of Example 104 Step 3 except that ethyl 7-(1,1-dimethylpentyl)-2-(trifluoromethyl)-2H-chromene-3-carboxylate was used in place of ethyl 5,7,8-trimethyl-2-(trifluoromethyl)-2H-chromene-3-carboxylate.

Step 2: Preparation of 6-chloro-7-(1,1-dimethylpentyl)-2-(trifluoromethyl)-2H-chromene-3-carboxylic acid 6-Chloro-7-(1,1-dimethylpentyl)-2-(trifluoromethyl)-2H-chromene-3-carboxylic acid was prepared by the method of Example 104 Step 4 except that ethyl 6-chloro-7-(1,1-dimethylpentyl)-2-(trifluoromethyl)-2H-chromene-3-carboxylate was used in place of ethyl 6-chloro-5,7,8-trimethyl-2-(trifluoromethyl)-2H-chromene-3-carboxylate. $^1$H NMR (acetone-$d_6$) 7.87 (s, 1H), 7.51 (s, 1H), 7.07 (s, 1H), 5.84 (q, 1H, J=7.2 Hz), 1.95 (m, 2H), 1.46 (s, 6H), 1.25 (m, 2H), 1.02 (m, 2H), 0.83 (t, 3H, J=5.5 Hz).

EXAMPLE 111

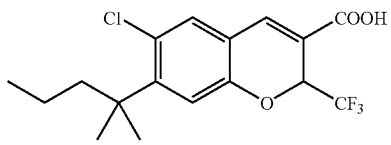

6-chloro-7-(1,1-dimethylbutyl)-2-(trifluoromethyl)-2H-chromene-3-carboxylic acid Step Preparation of 1 ethyl 6-chloro-7-(1,1-dimethylbutyl)-2-(trifluoromethyl)-2H-chromene-3-carboxylate Ethyl 6-chloro-7-(1,1-dimethylbutyl)-2-(trifluoromethyl)-2H-chromene-3-carboxylate was prepared by the method of Example 104 Step 3 except that ethyl 7-(1,1-dimethylbutyl)-2-(trifluoromethyl)-2H-chromene-3-carboxylate was used in place of ethyl 5,7,8-trimethyl-2-(trifluoromethyl)-2H-chromene-3-carboxylate.

Step 2: Preparation of 6-chloro-7-(1,1-dimethylbutyl)-2-(trifluoromethyl)-2H-chromene-3-carboxylic acid 6-Chloro-7-(1,1-dimethylbutyl)-2-(trifluoromethyl)-2H-chromene-3-carboxylic acid was prepared by the method of Example 104 Step 4 except that ethyl 6-chloro-7-(1,1-dimethylbutyl)-2-(trifluoromethyl)-2H-chromene-3-carboxylate was used in place of ethyl 6-chloro-5,7,8-trimethyl-2-(trifluoromethyl)-2H-chromene-3-carboxylate. $^1$H NMR (acetone-d$_6$) 7.83 (s, 1H), 7.47 (s, 1H), 7.03 (s, 1H), 5.80 (q, 1H, J=7.2 Hz), 1.92 (m, 2H), 1.41 (s, 6H), 0.99 (m, 2H), 0.80 (t, 3H, J=5.5 Hz).

EXAMPLE 112

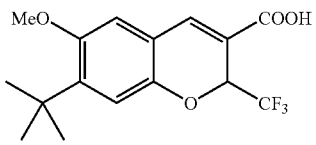

7-tert-butyl-6-methoxy-2-(trifluoromethyl)-2H-chromene-3-carboxylic acid

Step 1: Preparation of 4-tert-butyl-2-hydroxy-5-methoxybenzaldehyde 4-t-Butyl-2-hydroxy-5-methoxybenzaldehyde was prepared by the method of Example 104 Step 1 except that 3-t-butyl-4-methoxyphenol was used in place of 2,3,5-trimethylphenol.

Step 2: Preparation of ethyl 7-tert-butyl-6-methoxy-2-(trifluoromethyl)-2H-chromene-3-carboxylate Ethyl 7-tert-butyl-6-methoxy-2-(trifluoromethyl)-2H-chromene-3-carboxylate was prepared by the method of Example 104 Step 2 except that 4-tert-butyl-2-hydroxy-5-methoxybenzaldehyde was used in place of 6-hydroxy-2,4,5-trimethylbenzaldehyde.

Step 3: Preparation of 7-tert-butyl-6-methoxy-2-(trifluoromethyl)-2H-chromene-3-carboxylic acid 7-t-Butyl-6-methoxy-2-(trifluoromethyl)-2H-chromene-3-carboxylic acid was prepared by the method of Example 104 Step 4 except that ethyl 7-tert-butyl-6-methoxy-2-(trifluoromethyl)-2H-chromene-3-carboxylate was used in place of ethyl 6-chloro-5,7,8-trimethyl-2-(trifluoromethyl)-2H-chromene-3-carboxylate.

EXAMPLE 113

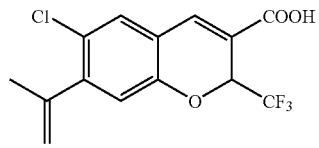

6-chloro-7-isopropenyl-2-(trifluoromethyl)-2H-chromene-3-carboxylic acid

Step 1: Preparation of 2-(3-hydroxyphenyl)-2-methylpropanal

To a solution of 2-(3-methoxyphenyl)-2-methylpropanal (20.0 g, 112 mmoles) in 90 mL of N-methylpyrrolidinone was added thiophenol (11.5 mL, 112 mmoles) and anhydrous K$_2$CO$_3$ (1.55 g, 11.2 mmoles). The mixture was stirred at 210-215 ° C. for 3 h. After cooling, the mixture was partitioned between Et$_2$O and 5% aqueous NaOH. The aqueous layer was acidified with dilute HCl and extracted with DCM. The combined organic extracts were dried over Na$_2$SO$_4$, filtered, and evaporated. Chromatography of the residue using 25% EtOAc—hexane as eluent gave the title compound, 10.3 g, as a pale yellow oil.

Step 2: Preparation of 4-(1,1-dimethyl-2-oxoethyl)-2-hydroxybenzaldehyde 4-(1,1-Dimethyl-2-oxoethyl)-2-hydroxybenzaldehyde was prepared by the method of Example 104 Step 1 except that 2-(3-hydroxyphenyl)-2-methylpropanal was used in place of 2,3,5-trimethylphenol.

Step 3: Preparation of ethyl 7-(1,1-dimethyl-2-oxoethyl)-2-(trifluoromethyl)-2H-chromene-3-carboxylate Ethyl 7-(1,1-dimethyl-2-oxoethyl)-2-(trifluoromethyl)-2H-chromene-3-carboxylate was prepared by the method of Example 104 Step 2 except that 4-(1,1-dimethyl-2-oxoethyl)-2-hydroxybenzaldehyde was used in place of 6-hydroxy-2,4,5-trimethylbenzaldehyde.

Step 4: Preparation of ethyl 6-chloro-7-isopropenyl-2-(trifluoromethyl)-2H-chromene-3-carboxylate The title compound was prepared by the method of Example 104 Step 3 except that ethyl 7-(1,1-dimethyl-2- oxoethyl)-2-(trifluoromethyl)-2H-chromene-3-carboxylate was used in place of ethyl 5,7,8-trimethyl-2-(trifluoromethyl)-2H-chromene-3-carboxylate.

Step 5: Preparation of 6-chloro-7-isopropenyl-2-(trifluoromethyl)-2H-chromene-3-carboxylic acid The title compound was prepared by the method of Example 104 Step 4 except that ethyl 6-chloro-7-isopropenyl-2-(trifluoromethyl)-2H-chromene-3-carboxylate was used in place of ethyl 6-chloro-5,7,8-trimethyl-2-(trifluoromethyl)-2H-chromene-3-carboxylate. $^1$H NMR (acetone-$d_6$) 7.82 (s, 1H), 7.50 (s, 1H), 6.87 (s, 1H), 5.78 (q, 1H, J=7.2 Hz), 5.23 (br s, 1H), 4.94 (br s, 1H), 2.02 (br s, 3H).

EXAMPLE 114

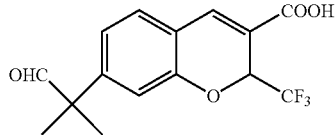

7-(1,1-dimethyl-2-oxoethyl)-2-(trifluoromethyl)-2H-chromene-3-carboxylic acid

Step 1: 7-(1,1-dimethyl-2-oxoethyl)-2-(trifluoromethyl)-2H-chromene-3-carboxylic acid 7-(1,1-Dimethyl-2-oxoethyl)-2-(trifluoromethyl)-2H-chromene-3-carboxylic acid
was prepared by the method of Example 104 step 4 except that ethyl 7-(1,1-dimethyl-2-oxoethyl)-2-(trifluoromethyl)-2H-chromene-3-carboxylate was used in place of ethyl 6-chloro-5,7,8-trimethyl-2-(trifluoromethyl)-2H-chromene-3-carboxylate. $^1$H NMR (CDCl$_3$). 9.50 (s, 1H), 7.83 (s, 1H), 7.25 (d, 1H, J=8.0 Hz), 6.94 (br s, 1H), 6.91 (dd, J=8.0 Hz, J=7.2 Hz), 5.70 (q, 1H, J=7.2 Hz), 1.46 (s, 6H).

EXAMPLE 115

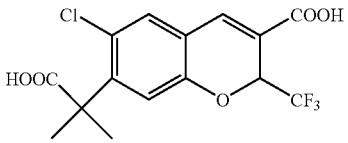

7-(1-carboxy-1-methylethyl)-6-chloro-2-(trifluoromethyl)-2H-chromene-3-carboxylic acid Step 1: Preparation of 2-[3-(ethoxycarbonyl)-2-(trifluoromethyl)-2H-chromen-7-yl]-2-methylpropanoic acid To a solution of ethyl 7-(1,1-dimethyl-2-oxoethyl)-2-(trifluoromethyl)-2H-chromene-3-carboxylate (500 mg, 1.46 mmoles) in 20 mL of dioxane was added a solution of 80% NaClO$_2$ (727 mg, (582 mg), 6.43 mmoles) in 5 mL of water. The resulting mixture was stirred in an oil bath at 90° C. for 1.5 h, and cooled. The mixture was partitioned between DCM and water, further extracted, and the combined organic extracts dried over Na$_2$SO$_4$, filtered, and evaporated. Chromatography of the residue over silica gel using 30% EtOAc—hexane—1% HOAc as eluent gave the title compound, 400 mg, as an oil.

Step 2: Preparation of 7-(1-carboxy-1-methylethyl)-6-chloro-2-(trifluoromethyl)-2H-chromene-3-carboxylic acid Cl$_2$ gas was bubbled through a solution of the title product of Example 115 Step 1 (400 mg, 1.12 mmoles) in 20 mL of HOAc while protecting the mixture from light. After 3 min, the mixture was stirred for 30 min, N$_2$ bubbled through briefly, Zn dust (500 mg, 7.6 mg-atrn) added, and the mixture stirred for 30 min. After chromatography of the residue over silica gel using 30% EtOAc—hexane—1% HOAc as eluent, the appropriate fractions were combined and evaporated to give a mixture of chlorinated product and starting material. The residue was retreated as described above, and following chromatography, there was obtained an 85:15 mixture of product and starting material, 241 mg, which was used as is for the next step.

A solution of 241 mg (0.613 mmol) of the above mixture in 15 mL of ethanol was treated with a solution of 366 mg of 50% aqueous NaOH in 3 mL of water. The mixture was brought to reflux and cooled. Following acidification to pH 1 with dilute aqueous HCl, the mixture was partially concentrated producing a pure white solid, which was isolated by filtration, washed, and dried to give a 85:15 mixture of chlorinated and unchlorinated diacids, which were used as is for the next step.

The acid above (85:15) was dissolved in 10 mL of HOAc, and Cl$_2$ gas bubbled through. The resulting mixture was stirred for 5 h, and N$_2$ bubbled through briefly. Zn dust (200 mg, 3.1 mg-atm) was added, the mixture stirred for 1 h, and concentrated. Chromatography of the residue using 1% HOAc—EtOAc as eluent gave the title compound, 125 mg, as a white crystalline solid. $^1$H NMR (CDCl$_3$) 7.76 (s, 1H), 7.07 (s, 1H), 5.69 (q, 1H, J=7.2 Hz), 1.66 (s, 6H).

EXAMPLE 116

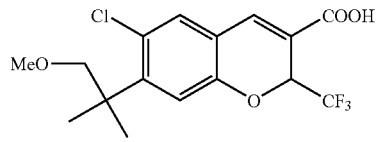

6-chloro-7-(2-methoxy-1,1-dimethylethyl)-2-(trifluoromethyl)-2H-chromene-3-carboxylic acid Step 1: Preparation of ethyl 7-(2-hydroxy-1,1-dimethylethyl)-2-(trifluoromethyl)-2H-chromene-3-carboxylate To a solution of ethyl 7-(1,1-dimethyl-2-oxoethyl)-2-(trifluoromethyl)-2H-chromene-3-carboxylate (6.90 g, 20.2 mmoles) in 200 mL of MeOH stirring in an ice bath, was added portionwise NaBH$_4$ (763 mg, 20.2 mmoles) as a solid. After 25 min, HOAc was cautiously added, and the solution concentrated. The residue was partitioned between DCM and water, and the organic extract dried over Na$_2$SO$_4$, filtered, and evaporated. Chromatography of the residue over silica gel using a gradient of 0-10% EtOAc—DCM as eluent gave the title compound, 5.4 g, as a very pale yellow oil.

Step 2: Preparation of ethyl 6-chloro-7-(2-hydroxy-1,1-dimethylethyl)-2-(trifluoromethyl)-2H-chromene-3-carboxylate A single treatment of ethyl 7-(2-hydroxy-1,1-dimethylethyl)-2-(trifluoromethyl)-2H-chromene-3-carboxylate (5.4 g 16 mmoles) with Cl$_2$ was performed as described in Example 115 Step 2. Chromatography of the residue using a gradient of 0-10% EtOAc—DCM as eluent gave the title compound, 3.7 g, as a nearly colorless oil.

Step 3: Preparation of ethyl 6-chloro-7-(2-methoxy-1,1-dimethylethyl)-2-(trifluoromethyl)-2H-chromene-3-carboxylate To a solution of ethyl 6-chloro-7-(2-hydroxy-1,1-dimethylethyl)-2-(trifluoromethyl)-2H-chromene-3-carboxylate (205 mg, 0.584 mmole) in 8 mL of dry DMF was added 86 mg of 60% NaH, and 0.5 mL of iodomethane. The mixture was stirred overnight at room temperature. Water was added, the mixture extracted with DCM, the combined organic extracts dried over Na$_2$SO$_4$, filtered, and evaporated. Chromatography of the residue over silica gel using DCM as eluent gave the title compound, 49 mg, as an oil.

Step 4: Preparation of 6-chloro-7-(2-methoxy-1,1-dimethylethyl)-2-(trifluoromethyl)-2H-chromene-3-carboxylic acid The title compound was prepared by the method of Example 104 Step 4 except that ethyl 6-chloro-7-(2-methoxy-1,1-dimethylethyl)-2-(trifluoromethyl)-2H-chromene-3-carboxylate was used in place of ethyl 6-chloro-5,7,8-trimethyl-2-(trifluoromethyl)-2H-chromene-3-carboxylate. $^1$H NMR (CDCl$_3$) 7.64 (s, 1H), 7.20 (s, 1H), 7.05 (s. 1H), 5.64 (q, 1H, J=7.2 Hz), 3.97 (d, 1H, J=9 Hz), 3.56 (d, 1H, J=9 Hz), 3.35 (s, 3H), 1.47 (s, 3H), 1.46 (s, 3H).

EXAMPLE 117

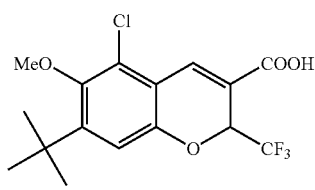

117-1

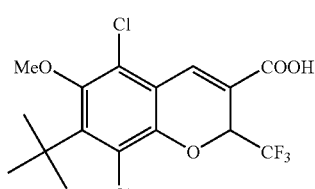

117-2

7-tert-butyl-5-chloro-6-methoxy-2-(trifluoromethyl)-2H-chromene-3-carboxylic acid and 7-tert-butyl-5,8-dichloro-6-methoxy-2-(trifluoromethyl)-2H-chromene-3-carboxylic acid Step 1: Preparation of ethyl 7-tert-butyl-5-chloro-6-methoxy-2-(trifluoromethyl)-2H-chromene-3-carboxylate and ethyl 7-tert-butyl-5,8-dichloro-6-methoxM-2-(trifluoromethyl)-2H-chromene-3-carboxylate A single chlorination on ethyl 7-tert-butyl-6-methoxy-2-(trifluoromethyl)-2H-chromene-3-carboxylate (500 mg, 1.40 mmoles) was performed as described in Example 115. Chromatography of the residue over silica gel using 25% EtOAc—hexane gave a mixture of monochloro and dichloro products, which were used as is for the next reaction.

Step 2: Preparation of 7-tert-butyl-5-chloro-6-methoxy-2-(trifluoromethyl)-2H-chromene-3-carboxylic acid and 7-tert-butyl-5.8-dichloro-6-methoxy-2-(trifluoromethyl)-2H-chromene-3-carboxylic acid A mixture of ethyl 7-tert-butyl-5-chloro-6-methoxy-2-(trifluoromethyl)-2H-chromene-3-carboxylate and ethyl 7-tert-butyl-5,8-dichloro-6-methoxy-2-(trifluoromethyl)-2H-chromene-3-carboxylate (330 mg) was hydrolyzed as described in Example 104 Step 4. Radial chromatography of the residue over silica gel using 40% EtOAc—hexane—1% HOAc as eluent gave the title compounds as white solids.

Isomer 117-1: (7-tert-butyl-5-chloro-6-methoxy-2-(trifluoromethyl)-2H-chromene-3-carboxylic acid):16 mg; $^1$H NMR (acetone-d$_6$) 8.02 (s, 1H), 6.94 (s, 1H), 5.80 (q, 1H, J=7.2 Hz), 3.89 (s, 3H), 1.37 (s, 9H). LCMS m/z=365 (M+H)

Isomer 117-2: (7-tert-butyl-5,8-dichloro-6-methoxy-2-(trifluoromethyl)-2H-chromene-3-carboxylic acid): 18 mg; $^1$H NMR (acetone-d$_6$) 8.07 (s, 1H), 6.02 (q, 1H, J=7.2 Hz), 3.78 (s, 3H), 1.66 (s, 9H). LCMS m/z=399, 400, 401 (M, M+H, M+2H)

EXAMPLE 118

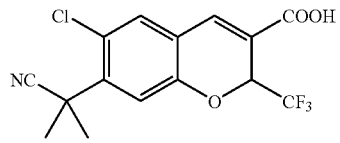

6-chloro-7-(1-cyano-1-methylethyl)-2-(trifluoromethyl)-2H-chromene-3-carboxylic acid Step 1: Preparation of 2-(3-hydroxyphenyl)-2-methylpropanenitrile A mixture of the title product of Example 106 Step 1 (520 mg, 2.97 mmoles) and pyridinium hydrochloride (2 g, 17.3 mmol) was stirred in an oil bath at 200-220 ° C. under a drying tube and so maintained for 3 h. After cooling, the mixture was partitioned between DCM and water, further extracted, and the combined organic extracts dried over Na$_2$SO$_4$, filtered, and evaporated to give the title compound, 416 mg, as a brownish oil.

Step 2: Preparation of 2-(4-formyl-3-hydroxyphenyl)-2-methylpropanenitrile

The title benzaldehyde was prepared by the method of Example 104 Step 1 except that the phenol of Example 118 Step 1 was used in place of 2,3,5-trimethylphenol.

Step 3: Preparation of ethyl 7-(1-cyano-1-methylethyl)-2-(trifluoromethyl)-2H-chromene-3-carboxylate The title benzopyran was prepared by the method of Example 104 Step 2 except that the title product of Example 118 Step 2 was used in place of the title product of Example 104a.

Step 4: Preparation of ethyl 6-chloro-7-(1-cyano-1-methylethyl)-2-(trifluoromethyl)-2H-chromene-3-carboxcylate The title product of Example 118 Step 3 was treated a single time in the manner described in Example 115 Step 2. Chromatography of the residue over silica gel using DCM as eluent gave a 3:1 mixture of the title compound and starting material, which was used as is for the next reaction.

Step 5: Preparation of 6-chloro-7-(1-cyano-1-methylethyl)-2-(trifluoromethyvl-2H-chromene-3-carboxylic acid The mixture described in Example 118 Step 4 (111 mg) and 127 mg of 50% aqueous NaOH in 0.5 mL of water in 8 mL of MeOH was stirred at room temperature for 4 h. The mixture was acidified with aqueous HCl and extracted twice with DCM. The combined organic extracts were dried over $Na_2SO_4$, filtered, and evaporated. The residue was dissolved in hexane—EtOAc and allowed to crystallize. The title compound, 44 mg, was isolated by filtration as a pure white crystalline solid. $^1H$ NMR ($CDCl_3$) 7.77 (s, 1H), 7.35 (s, 1H), 7.13 (s, 1H), 5.71 (q, 1H, J=7.2 Hz), 1.87 (s, 6H). LCMS m/z=346.0 (M+H).

EXAMPLE 119

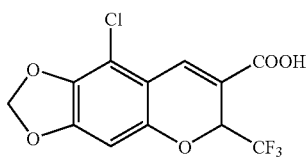

9-chloro-6-(trifluoromethyl)-6H-[1,3]dioxolo[4,5-g]chromene-7-carboxylic acid

Step 1: Preparation of 6-hydroxy-1,3-benzodioxole-5-carbaldehyde

The title compound was prepared by the method of Example 104 Step 1 except that sesamol was used in place of 2,3,5-trimethylphenol.

Step 2: Preparation of ethyl 6-(trifluoromethyl)-6H-[1,3]dioxolo[4,5-g]chromene-7-carboxylate The title benzopyran was prepared by the method of Example 104 Step 2 except that the title benzaldehyde of Example 119 Step 1 was used in place of the title benzaldehyde of Example 104 Step 1.

Step 3: Preparation of ethyl 9-chloro-6-(trifluoromethyl)-6H-[1,3]dioxolo[4,5-g]chromene-7-carboxylate To a solution of ethyl 6-(trifluoromethyl)-6H-[1,3]dioxolo[4,5-g]chromene-7-carboxylate (500 mg, 1.58 mmoles) in 6 mL of TFA was added a solution of $Cl_2$ 6 mL, 0.28M) in TFA. After 30 min, another 6 mL of $Cl_2$ solution was added and stirring continued. Zn dust (1.00 g, 15.3 mg-atm) was added, and stirred overnight. After concentration, the residue was chromatographed over silica gel using 20% EtOAc—hexane as eluent to give the title compound, 460 mg, as a yellow solid.

Step 4: Preparation of 9-chloro-6-(trifluoromethyl)-6H-[1,3dioxolo[4,5-g]chromene-7-carboxylic acid The title compound was prepared by the method of Example 104 Step 4 except that the title product of Example 119 Step 3 was used in place of Example 104 Step 3. The title compound was a yellow solid. $^1H$ NMR (acetone-$d_6$) 7.98 (s, 1H), 6.73 (s, 1H), 6.24 (s, 2H), 6.02 (q, 1H, J=7.2 Hz). LCMS m/z=323.0, 325.0 (M+H, M+2H)).

EXAMPLE 120

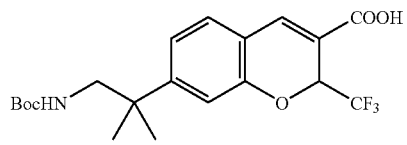

7-{2-[(tert-butoxycarbonyl)amino]-1,1-dimethylethyl}-2-(trifluoromethyl)-2H-chromene-3-carboxylic acid Step 1: Preparation of 3-(2-amino-1-dimethylethyl)phenol The title product of Example 118 Step 1 (19.9 g, 121 mmoles) was reduced using $PtO_2$ as catalyst in HOAc for 24 h under 60 psi of hydrogen at room temperature. After filtration, the solution was concentrated, and the title compound used as is for the next reaction.

Step 2: Preparation of tert-butyl 2-(3-hydroxyphenyl)-2-methylpropylcarbamate

To a mixture of the title product of Example 120 Step 1 (approximately 121 mmoles), $NaHCO_3$ (37 g, 440 mmol) in 250 mL of EtOAc, and 250 mL of water was added di-tert-butyl dicarbonate (33 g, 151 mmoles). The mixture was stirred rapidly for 3 days. The organic layer was separated, dried over $Na_2SO_4$, filtered, and evaporated to give the title compound, 36 g, as a brown oil.

Step 3: Preparation of tert-butyl 2-(4-formyl-3-hydroxyphenyl)-2-methylpropylcarbamate The title benzaldehyde was prepared by the method of Example 104 Step 1 except that the title product of Example 120 Step 2 was used in place of 2,3,5-trimethylphenol.

Step 4: Preparation of ethyl 7-{2-[(tert-butoxycarbonyl)amino]-1,1-dimethylethyl}-2-(trifluoromethyl)-2H-chromene-3-carboxylate The title benzopyran was prepared by the method of Example 104 Step 2 except that the title product of Example 120 Step 3 was used in place of the title product of Example 104 Step 2.

Step 5: Preparation of 7-{2-[(tert-butoxycarbonyl)amino]-1,1-dimethylethyl}-2-(trifluoromethyl)-2H-chromene-3-carboxylic acid The title compound was prepared by the method of Example 104 Step 4 except that the title product of Example 120 Step 4 was used in place of the title product of Example 104 Step 3. $^1$H NMR (CDCl$_3$-DMSO-d$_6$) 7.69 (s, 1H), 7.18 (d, 1H, J=8.0 Hz), 6.99 (d, 1H, J=8.0 Hz), 6.95 (br s, 11H), 5.72 (q, 1H, J=7.2 Hz), 4.67 (t, 1H, J=6.0 Hz), 3.28 (d, 2H, J=6.0 Hz), 1.39 (s, 9H), 1.29 (s, 6H). LCMS m/z=360, 361 (M+H, M+2H)

EXAMPLE 121

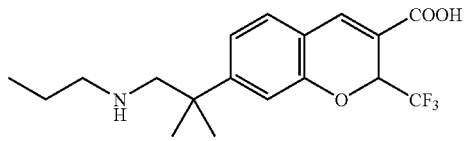

7-1,1-dimethyl-2-(propylamino)ethyl]-2-(trifluoromethyl)-2H-chromene-3-carboxylic acid hydrochloride

Step 1: Preparation of ethyl 7-[1,1-dimethyl-2-(propylamino)ethyl]-2-(trifluoromethyl)-2H-chromene-3-carboxylate To a solution of the title product of Example 113 Step 3 (198 mg, 0.579 mmole) in 8 mL of MeOH and 1 mL of HOAc was added n-propylamine (68 mg, 1.2 mmoles), 0.9 mL of 1 M sodium cyanoborohydride in THF, and 1 g of activated 4 Å molecular sieves. The resulting mixture was stirred overnight at room temperature. The mixture was diluted with MeOH, filtered through Celite, concentrated, azeotropically distilled with toluene. Chromatography of the residue over silica gel using 10% MeOH—DCM gave the title compound, 220 mg, as a colorless oil.

Step 2: Preparation of 7-[1,1-dimethyl-2-(propylamino)ethyl]-2-(trifluoromethyl)-2H-chromene-3-carboxylic acid To a solution of the title product of Example 121 Step 1 (88 mg, 0.23 mmole) in 5 mL of MeOH was added a solution of 243 mg of 50% aqueous NaOH in 1 mL of water. The mixture was refluxed for 1 h, cooled, and acidified to pH 1. The reaction was concentrated, and the remaining solvent lyophilized. The resulting white solid was triturated with water, the solid isolated by filtration, washed with water, and dried affording the title compound, 23 mg, as a white solid. $^1$H NMR (DMSO-d$_6$) 7.74 (s, 1H), 7.42 (d, 1H, J=8 Hz), 7.12 (dd, 1H, J=8 Hz, J=1.6 Hz), 7.10 (br s, 1H), 5.88 (q, 1H, J=7.2 Hz), 3.13 (dd, 2H, J=13 Hz, J=6 Hz), 2.73 (dd, 2H, J=8 Hz), J=8 Hz), 1.58 (m, 2H), 1.36 (s, 3H), 1.34 (s, 3H), 0.83 (t, 3H, J=8 Hz).

EXAMPLE 122

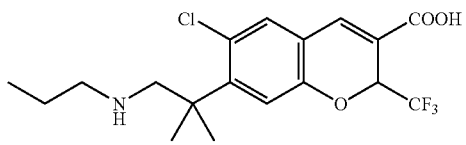

6-chloro-7-1,1-dimethyl-2-(propylamino)ethyl]-2-(trifluoromethyl)-2H-chromene-3-carboxylic acid hydrochloride

Step 1: Preparation of ethyl 6-chloro-7-[1,1-dimethyl-2-(propylamino)ethyl]-2-(trifluoromethyl)-2H-chromene-3-carboxylate The title compound was prepared by the method of Example 104 Step 3 except that the title product of Example 121 Step 1 was used in place of the title product of Example 104 Step 2.

Step 2: Preparation of 6-chloro-7-[1,1-dimethyl-2-(propylamino)ethyl]-2-(trifluoromethyl)-2H-chromene-3-carboxylic acid hydrochloride The title compound was prepared by the method of Example 121 Step 2 except that the title product of Example 122 Step 1 was used in place of the title product of Example 121 Step 1. $^1$H NMR (DMSO-d$_6$) 7.68 (s, 1H), 7.56 (s, 1H), 7.01 (s, 1H), 5.92 (q, 1H, J=7.2 Hz), 2.78 (m, 2H), 2.51 (m, 2H), 1.58 (m, 2H), 1.50 (s, 6H), 0.84 (t, 3H, J=5.5 Hz). LCMS m/z=392.0, 394.0 (M+H).

EXAMPLE 123

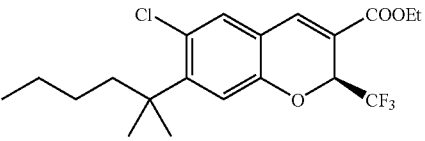

Ethyl (2S)-6-chloro-7-(1,1-dimethylpentyl)-2-(trifluoromethyl)-2H-chromene-3-carboxylate Step 1: Preparation of ethyl (2S)-6-chloro-7-(1,1-dimethylpentyl)-2-(trifluoromethyl)-2H-chromene-3-carboxylate The title product of Example 110 Step 1 was separated into its S and R enantiomers by chiral preparative chromatography on a Chiral Pak AD column using 2:98 isopropanol—heptane as eluent, to give the title compounds of Examples 123 and 124.

EXAMPLE 124

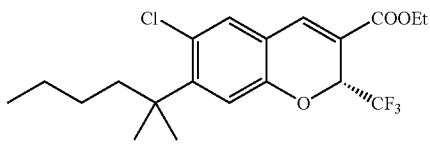

Ethyl (2R)-6-chloro-7-(1,1-dimethylpentyl)-2-(trifluoromethyl)-2H-chromene-3-carboxylate See Example 123.

EXAMPLE 125

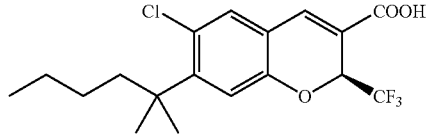

(2S)-6-chloro-7-(1,1-dimethylpentyl)-2-(trifluoromethyl)-2H-chromene-3-carboxylic acid Step 1: Preparation of (2S)-6-chloro-7-(1,1-dimethylpentyl)-2-(trifluoromethyl)-2H-chromene-3-carboxylic acid To a solution of the title compound of Example 123 (123 mg, 0.304 mmoles) in 8 mL of MeOH was added a solution of 163mg of 50% aqueous NaOH in 1.5 mL of water. After stirring for 4 h, the mixture was acidified with dilute aqueous HCl and extracted with DCM. The combined organic extracts were dried over $Na_2SO_4$, filtered, and evaporated to give the title compound, 99 mg, as a pale yellow solid. $^1H$ NMR ($CDCl_3$) 7.76 (s, 1H), 7.22 (s, 1H), 7.01 (s, 1H), 5.67 (q, 1H, J=7.2 Hz), 1.99 (m, 1H), 1.87 (m, 1H), 1.43 (s, 3H), 1.42 (s, 3H), 1.25 (m, 2H), 0.98 (m, 2H), 0.83 (t, 3H, J=7.0 Hz).

EXAMPLE 126

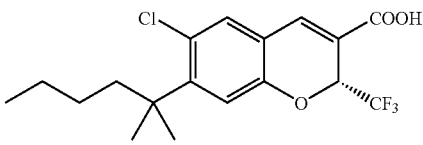

(2R)-6-chloro-7-(1,1-dimethylpentyl)-2-(trifluoromethyl)-2H-chromene-3-carboxylic acid Step 1: Preparation of (2R)-6-chloro-7-(1,1-dimethylpentyl)-2-(trifluoromethyl)-2H-chromene-3-carboxylic acid The title product was prepared by the method of Example 125 Step 1 except that the title compound of Example 124 was used in place of the title product of Example 123. $^1H$ NMR ($CDCl_3$) 7.76 (s, 1H), 7.22 (s, 1H), 7.01 (s, 1H), 5.67 (q, 1H, J=7.2 Hz), 1.99 (m, 1H), 1.87 (m, 1H), 1.43 (s, 3H), 1.42 (s, 3H), 1.25 (m, 2H), 0.98 (m, 2H), 0.83 (t, 3H, J=7.0 Hz).

EXAMPLE 127

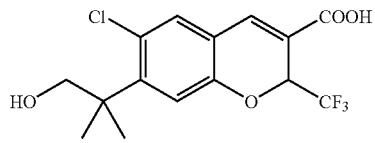

6-chloro-7-(2-hydroxy-1,1-dimethylethyl)-2-(trifluoromethyl)-2H-chromene-3-carboxylic acid Step 1: Preparation of 6-chloro-7-(2-hydroxy-1,1-dimethylethyl)-2-(trifluoromethyl)-2H-chromene-3-carboxylic acid The title compound was prepared as a racemic mixture by the method of Example 104 Step 4 except that the title product of Example 116 Step 2 was used in place of the title product of Example 104 Step 3.

EXAMPLE 128

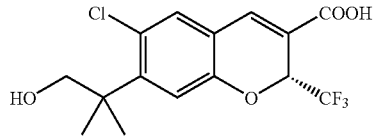

(2R)-6-chloro-7-(2-hydroxy-1,1-dimethylethyl)-2-(trifluoromethyl)-2H-chromene-3-carboxylic acid Step 1: Preparation of (2R)-6-chloro-7-(2-hydroxy-1,1-dimethylethyl)-2-(trifluoromethyl)-2H-chromene-3-carboxylic acid The title product of Example 127 was separated into its enantiomers by chiral preparative chromatography on a ChiralPak AD column using 20:80:0.1 isopropanol—heptane—TFA as eluent. The title product Example 128 was obtained as a single isomer. $^1$H NMR (CDCl$_3$) 7.61 (s, 1H), 7.23 (s, 1H), 7.09 (s, 1H), 5.66 (q, 1H, J=7.2Hz), 4.23 (d, 1H, J=11 Hz), 3.87 (d, 1H, J=11 Hz), 1.48 (s, 3H), 1.47 (s, 3H).

EXAMPLE 129

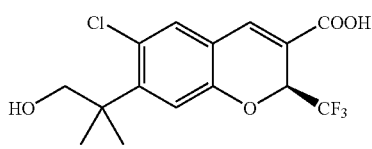

(2S)-6-chloro-7-(2-hydroxy-1,1-dimethylethyl)-2-(trifluoromethyl)-2H-chromene-3-carboxylic acid Step 1: Preparation of (2S)-6-chloro-7-(2-hydroxy-1,1-dimethylethyl)-2-(trifluoromethyl)-2H-chromene-3-carboxylic acid From the chiral chromatography was obtained a mixture of hydroxy compound and trifluoroacetate ester. To a solution of 113 mg of the mixture in 5 mL of MeOH was added 0.5 mL of triethylamine, and the resulting mixture was stirred overnight at room temperature. After concentration, the mixture was taken up in DCM, washed with aqueous HCl, dried over Na$_2$SO$_4$, filtered, and evaporated to give the title compound, 59 mg, as an off-white solid. $^1$H NMR (CDC$_3$) 7.61 (s, 1H), 7.23 (s, 1H), 7.09 (s, 1H), 5.66 (q, 1H, J=7.2 Hz), 4.23 (d, 1H, J=11 Hz), 3.87 (d, 1H, J=11 Hz), 1.48 (s, 3H), 1.47 (s, 3H).

EXAMPLE 130

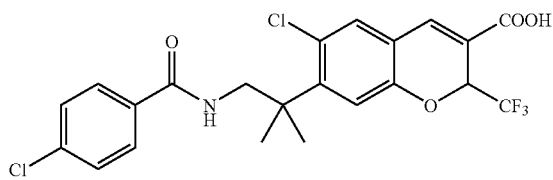

6-chloro-7-{2-[(4-chlorobenzoyl)amino]-1,1-dimethylethyl}-2-(trifluoromethyl)-2H-chromene-3-carboxylic acid Step 1: Preparation of ethyl 6-chloro-7-{2-[amino]-1,1-dimethylethyl}-2-(trifluoromethyl)-2H-chromene-3-carboxylate hydrochloride Into a solution of the title product of Example 120 Step 4 (3.47 g, 7.83 mmoles) in 50 mL of HOAc was bubbled Cl$_2$ gas. After 4 h, N$_2$ gas was bubbled through, Zn dust (2.1 g, 32.1 mg-atm) was added, and the mixture stirred for 1 h. The mixture was concentrated, and the residue chromatographed over silica gel using 10% MeOH—DCM as eluent to give the title compound, 3.61 g, as a white foam.

Step 2: Preparation of ethyl 6-chloro-7-{2-[(4-chlorobenzoyl)amino]-1,1-dimethylethyl}-2-(trifluoromethyl)-2H-chromene-3-carboxylate To a solution of the title product of Example 130 Step 1 (150 mg, 0.397 mmole) in 5 mL of pyridine was added a solution of 4-chlorobenzoyl chloride (90 mg, 0.51 mmole) in 1 mL of DCM. The mixture was stirred for 2 h, and 750 mg of Tris amine resin was added. After stirring overnight, the mixture was filtered and concentrated to give the title compound, which was used as is for the next step.

Step 3: Preparation of 6-chloro-7-{2-[(4-chlorobenzoyl)amino]-1,1-dimethylethyl}-2-(trifluoromethyl)-2H-chromene-3-carboxylic acid The title product of Example 130 Step 2 was dissolved in 5 mL of MeOH, and a solution of 244 mg of 50% aqueous NaOH in 1 mL of water was added. After stirring for 2 h, the mixture was acidified, extracted with DCM, the combined organic extracts dried over Na$_2$SO$_4$, filtered, and evaporated. Chromatography of the residue over silica gel using 25% EtOAc—heptane—1% HOAc gave the title compound, 65 mg, as a pure white crystalline solid. $^1$H NMR (DMSO-d$_6$) 8.34 (t, 1H, J=4.6 Hz), 7.86 (s, 1H), 7.72 (d, 2H, J=8.8 Hz), 7.60 (s, 1H), 7.48 (d, 2H, J=8.8Hz), 7.03 (s, 1H), 5.93 (q, 1H, J=7.2 Hz), 3.78 (m, 2H), 1.44 (s, 6H). LCMS m/z=488.0.

EXAMPLE 131

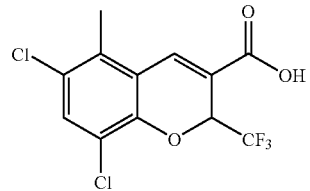

6,8-Dichloro-5-methyl-2-(trifluoromethyl)-2H-chromene-3-carboxylic acid

Step 1: Preparation of 3-chloro-2-hydroxy-6-methylbenzaldehyde

3-Chloro-6-methylsalicylaldehyde (0.96 g, 5.6 mmol) was prepared from 2-chloro-5-methylphenol (2.85 g, 20 mmol) by the method of Example 100 Step 1. The product structure was consistent with both $^1$H and $^{13}$C NMR analyses.

Step 2: Preparation of ethyl 8-chloro-5-methyl-2-(trifluoromethyl)-2H-chromene-3-carboxylate Ethyl 8-chloro-5-methyl-2-(trifluoromethyl)-2H-chromene-3-carboxylate (0.47 g, 1.46 mmol) was prepared from salicylaldehyde Example 131 Step 1 (0.86 g, 5 mmol)

by the method of Example 100 Step 2. The product structure was consistent with both ¹H and ¹⁹F NMR analyses.

Step 3: Preparation of ethyl 6,8-dichloro-5-methyl-2-(trifluoromethyl)-2H-chromene-3-carboxylate Cl₂ gas was bubbled through a solution of monochloroester Example 131 Step 2 (0.47 g, 1.46 mmol) in 10 mL HOAc for approximately 12 minutes until a persistent green-yellow color was observed, stirred at room temperature for 1 h. This mixture was treated with several portions of Zn dust until Zn persisted in the reaction for more than 10 minutes. The mixture was stirred at room temperature overnight. The unreacted Zn was filtered and the solids washed with EtOAc, The filtrate was concentrated in vacuo, azeotropically reconcentrated with heptane, leaving 0.63 g of off-white (crude) solids which were consistent with the desired dichloro ester according to ¹H, ¹⁹F and ¹³C NMR analyses.

Step 4: Preparation of 6,8-dichloro-5-methyl-2-(trifluoromethyl)-2H-chromene-3-carboxylic acid The title product of Example 131 Step 4 (0.12 g, 0.37 mmol) was prepared from ethyl 6,8-dichloro-5-methyl-2-(trifluoromethyl)-2H-chromene-3-carboxylate (0.61 g, 1.46 mmol) by the method of Example 100 Step 3.
¹H NMR (MeOH-d₄) 8.00 (s, 1H), 7.50 (s, 1H), 5.88 (q, 1H, J=7.1 Hz), 2.45 (s, 3H), ¹⁹F NMR (MeOH-d₄) −78.49.

EXAMPLE 132

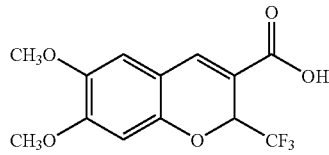

6,7-Dimethoxy-2-(trifluoromethyl)-2H-chromene-3-carboxylic acid

Step 1: Preparation of 2-hydroxy-4,5-dimethoxylbenzaldehyde

2-Hydroxy-4,5-dimethoxylbenzaldehyde (5.72 g, 31.8 mmol) was prepared from 3,4-dimethoxyphenol (7.71 g, 50 mmol) by the method of Example 100 Step 3. The product structure was consistent with both ¹H and ¹³C NMR analyses.

Step 2: Preparation of ethyl 6,7-dimethoxy-2-(trifluoromethyl)-2H-chromene-3-carboxylate Ethyl 6,7-dimethoxy-2-(trifluoromethyl)-2H-chromene-3-carboxylate (8.32 g, 25.0 mmol) was prepared from 2-hydroxy-4,5-dimethoxylbenzaldehyde (5.50 g, 30.2 mmol) by the method of Example 100 Step 2. The product structure was consistent with both ¹H and ¹⁹F NMR analyses.

Step 3: Preparation of 6,7-Dimethoxy-2-(trifluoromethyl)-2H-chromene-3-carboxylic acid The title compound (1.73 g, 5.7 mmol) was prepared from ester Example 132 Step 2 (2.0 g, 6 mmol) by the method of Example 100 Step 3. ¹H NMR (MeOH-d₄) 7.74 (s, 1H), 6.87 (s, 1H), 6.63 (s, 1H), 5.67 (q, 1H, J=7.0 Hz), 3.88 (s, 3H), 8.83 (s, 3H), ¹⁹F NMR (MeOH-d₄) −78.34.

EXAMPLE 133

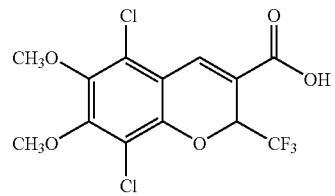

5,8-dichloro-6,7-dimethoxy-2-(trifluoromethyl)-2H-chromene-3-carboxylic acid

Step 1: Preparation of ethyl 5,8-dichloro-6,7-dimethoxU-2-(trifluoromethyl)-2H-chromene-3-carboxylate Ethyl 5,8-dichloro-6,7-dimethoxy-2-(trifluoromethyl)-2H-chromene-3-carboxylate (0.48 g, 1.19 mmol) was prepared from ethyl 6,7-dimethoxy-2-(trifluoromethyl)-2H-chromene-3-carboxylate (2.0 g, 6 mmol) by the method of Example 131 Step 3, followed by chromatographic purification. The product structure was consistent with ¹H, ¹⁹F and ¹³C NMR analyses.

Step 2: Preparation of 5,8-dichloro-6,7-dimethoxy-2-(trifluoromethyl)-2H-chromene-3-carboxylic acid 5,8-Dichloro-6,7-dimethoxy-2-(trifluoromethyl)-2H-chromene-3-carboxylic acid (0.36 g, 0.95 mmol) was prepared from ethyl 5,8-dichloro-6,7-dimethoxy-2-(trifluoromethyl)-2H-chromene-3-carboxylate (0.48 g, 1.2 mmol) by the method of Example 100 Step 3.
¹H NMR (MeOH-d₄) 8.00 (s, 1H), 5.90 (q, 1H, J=7.1 Hz), 3.99 (s, 3H), 3.87 (s, 3H). ¹⁹F NMR (MeOH-d₄) −78.55.

EXAMPLE 134

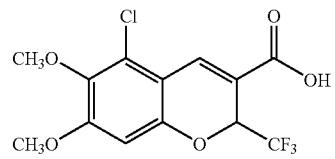

(5-chloro-6,7-dimethoxy-2-(trifluoromethyl)-2H-chromene-3-carboxylic acid

Step 1: Preparation of ethyl 5-chloro-6,7-dimethoxy-2-(trifluoromethyl)-2H-chromene-3-carboxylate and ethyl 8-chloro-6,7-dimethoxy-2-(trifluoromethyl)-2H-chromene-3-carboxylate Ethyl 6,7-dimethoxy-2-(tfifluoromethyl)-2H-chromene-3-carboxylate (0.67 g, 2 mmol) was dissolved in 4 mL TFA and cooled to 0° C., subsequently treated with a total of 13 mL of a saturated solution of $Cl_2$ in TFA (0.28 M). After stirring for 15 min at 0° C., at room temperature for an additional 45 min, Zn dust was added slowly in several portions until solids persisted for 10 minutes. The mixture was stirred overnight. This mixture was filtered, concentrated in vacuo, diluted with MTBE, washed twice with dilute brine, followed by saturated brine, and dried. After stripping the solvent, the residue was chromatographed yielding ethyl 5-chloro-6,7-dimethoxy-2-(trifluoromethyl)-2H-chromene-3-carboxylate (0.35 g, 1.03 mmol) and ethyl 8-chloro-6,7-dimethoxy-2-(trifluoromethyl)-2H-chromene-3-carboxylate (0.09 g, 0.26 mmol). The product structures were both consistent with $^1H$, $^{19}F$ and $^{13}C$ NMR analyses.

Step 2: Preparation of 5-chloro-6,7-dimethoxy-2-(trifluoromethyl)-2H-chromene-3-carboxylic acid Chloro-6,7-dimethoxy-2-(trifluoromethyl)-2H-chromene-3-carboxylic acid (0.24 g, 0.71 mmol) was prepared from the 5-chloroester of Example 134 Step 1 (0.30 g, 0.82 mmol) by the method of Example 100 Step 3.

$^1H$ NMR (CDCl3) 8.03 (s, 1H), 6.53 (s, 1H), 5.68 (q, 1H, J=6.9 Hz), 3.91 (s, 3H), 3.82 (s, 3H) $^{19}F$ NMR (CDCl3) −77.24. M+1, 2: 339, 340

EXAMPLE 135

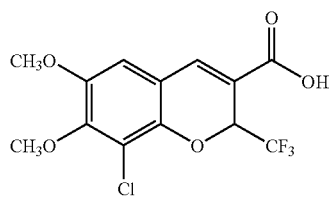

8-chloro-6,7-dimethoxy-2-(trifluoromethyl)-2H-chromene-3-carboxylic acid

Step 1: Preparation of 8-chloro-6,7-dimethoxy-2-(trifluoromethyl)-2H-chromene-3-carboxylic acid The title chromene (0.08 g, 0.24 mmol) was prepared from the 8-chloroester of Example 134 Step 1 (0.09 g, 0.27 mmol) by the method of Example 100 Step 3. $^1H$ NMR (CDCl$_3$) 7.69 (s, 1H), 6.73 (s, 1H), 5.76 (q, 1H, J=6.8 Hz), 3.93 (s, 3H), 3.86 (s, 3H) $^{19}F$ NMR (CDCl$_3$) −77.32. LCMS m/z=339, 340

EXAMPLE 136

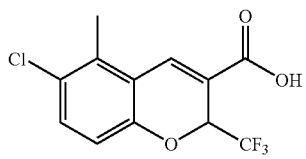

6-chloro-5-methyl-2-(trifluoromethyl)-2H-chromene-3-carboxylic acid

Step 1: Preparation of 2-hydroxy-6-methylbenzaldehyde

2-Hydroxy-6-methylbenzaldehyde was prepared by the method of Noguchi, Satoshi et al, *Biosci. Biotechnol. Biochem.* 1997, 61 1546-1547.

Step 2: Preparation of ethyl 5-methyl-2-(trifluoromethyl)-2H-chromene-3-carboxvlate Ethyl 5-methyl-2-(trifluoromethyl)-2H-chromene-3-carboxylate (1.28 g, 4.47 mmol) was prepared from the benzaldehyde of Example 136 Step 1 (1.56 g, 6.9 mmol) by the method of Example 100 Step 2. The product structure was consistent with both $^1H$ and $^{19}F$ NMR analyses.

Step 3: ethyl 6-chloro-5-methyl-2-(trifluoromethyl)-2H-chromene-3-carboxylate

Ethyl 6-chloro-5-methyl-2-(trifluoromethyl)-2H-chromene-3-carboxylate (0.94 g, 2.9 mmol) was prepared from ethyl 5-methyl-2-(trifluoromethyl)-2H-chromene-3-carboxylate (1.26 g, 4.4 mmol) by the method of Example 103 Step 3. The product structure was consistent with $^1H$, $^{19}F$ and $^{13}C$ NMR analyses.

Step 4: 6-chloro-5-methyl-2-(trifluoromethyl)-2H-chromene-3-carboxylic acid

6-Chloro5-methyl-2-(trifluoromethyl)-2H-chromene-3-carboxylic acid was prepared from ethyl 6-chloro-5-methyl-2-(trifluoromethyl)-2H-chromene-3-carboxylate (0.60 g, 1.9 mmol) by the method of Example 100 Step 3.

$^1H$ NMR (MeOH-d$_4$) 8.02 (s, 1H), 7.37 (d, 1H J=8.6 Hz), 6.85 (d, 1H J=8.6 Hz) 5.74 (q, 1H, J=7.1 Hz), 2.43 (s, 3H). $^{19}F$ NMR (MeOH-d$_4$) −78.36.

EXAMPLE 137

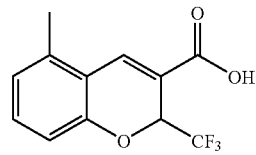

5-methyl-2-(trifluoromethyl)-2H-chromene-3-carboxylic acid

Step 1: Preparation of 5-methyl-2-(trifluoromethyl)-2H-chromene-3-carboxylic acid The title compound was prepared from the ester described in Example 136 Step 2 by the method of Example 100 Step 3. $^1H$ NMR (MeOH-d$_4$) 7.74 (s, 1H), 7.12 (t, 1H J=7.9 Hz), 6.82 (d, 1H J=7.6 Hz), 6.75 (d, 1H J=8.1 Hz), 5.80 (q, 1H, J=7.4 Hz), 2.41 (s, 3H).

EXAMPLE 138

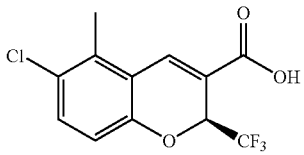

(2S)-6-chloro-5-methyl-2-(trifluoromethyl)-2H-chromene-3-carboxylic acid

Step 1: Chiral Separation of ethyl 6-chloro-5-methyl-2-(trifluoromethyl)-2H-chromene-3-carboxylate The ester isomers of Example 136 Step 3 were separated by chiral chromatography using Chiralpak AD support. Chiral GC analysis on Restek Rt-BDEX_sm column (30 m, ID 0.32 mm, Film 0.25 μm), temperature program: 175 to 215° C. @ 2.5° C./min—He carrier gas gave the following retention times: $1^{st}$ isomer—7.19 min, $2^{nd}$ isomer—7.35 min.

Step 2: Preparation of (2S)-6-chloro-5-methyl-2-(trifluoromethyl)-2H-chromene-3-carboxylic acid The first isomer of Example 138 Step 1 (0.10 g, 0.32 mmol) was converted to the corresponding acid (0.09 g, 0.31 mmol) by the method of Example 100 Step 3. Example 138 Step 2 had positive specific rotation. Chiral HPLC analysis on Chirobiotic T (MeOH/$H_2O$/HOAc/TEA) gave a retention time of 5.76 min.

$^1$H NMR (CDCl$_3$) 8.11 (s, 1H), 7.33 (d, 1H J=8.6 Hz), 6.83 (d, 1H J=8.6 Hz ), 5.65 (q, 1H, J=7.1 Hz), 2.47 (s, 3H). $^{19}$F NMR (CDCl$_3$) −76.83.

EXAMPLE 139

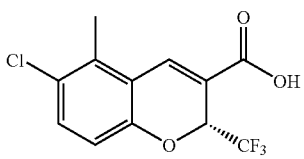

(2R)-6-chloro-5-methyl-2-(trifluoromethyl)-2H-chromene-3-carboxylic acid

Step 1: Preparation of (2R)-6-chloro-5-methyl-2-(trifluoromethyl)-2H-chromene-3-carboxylic acid The second isomer of Example 138 Step 1 (1.03 g, 3.2 mmol) was converted to its corresponding acid (0.89 g, 3.04 mmol) by the method of Example 100 Step 3. Example 139 had a negative specific rotation. Chiral HPLC analysis on Chirobiotic T (MeOH/$H_2O$/HOAc/TEA) gave a retention time of 5.33 min.

$^1$H NMR (CDCl$_3$) 8.11 (s, 1H), 7.33 (d, 1H J=8.6 Hz), 6.83 (d, 1H J=8.6 Hz), 5.65 (q, 1H, J=7.1 Hz), 2.47 (s, 3H). $^{19}$F NMR (CDCl$_3$) −76.82.

EXAMPLE 140

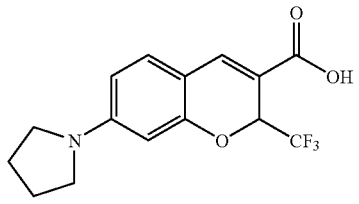

7-pyrrolidin-1-yl-2-(trifluoromethyl)-2H-chromene-3-carboxylic acid

Step 1: Preparation of ethyl 7-pyrrolidin-1-yl-2-(trifluoromethyl)-2H-chromene-3-carboxylate Ethyl 7-iodo-2-(trifluoromethyl)-2H-chromene-3-carboxylate (0.40 g, 1.0 mmol), was dissolved in 3 mL toluene, followed by the addition of Pd(OAc)$_2$ (23 mg), P(t-Bu)$_3$, 10 wt % in hexane (0.21 g), Cs$_2$CO$_3$ (0.56 g, 1.7 mmol) and pyrrolidine (0.10 g, 1.4 mmol), in a sealed tube flushed with argon, and stirred vigorously while heating to 75° C. for 21 hours. The reaction was cooled, filtered, and stripped, leaving a dark red-orange oil, which was purified by flash chromatography, which gave ethyl 7-pyrrolidin-1-yl-2-(trifluoromethyl)-2H-chromene-3-carboxylate (0.27 g, 0.79 mmol) as a yellow solid. The product structure was consistent with $^1$H, $^{19}$F and $^{13}$C NMR analyses.

Step 2: Preparation of 7-pyrrolidin-1-yl-2-(trifluoromethyl)-2H-chromene-3-carboxylic acid 7-Pyrrolidin-1-yl-2-(trifluoromethyl)-2H-chromene-3-carboxylic acid was prepared from ester Example 138 Step 1 (0.21 g, 0.60 mmol) by the method of Example 100 Step 3.

$^1$H NMR (MeOH-d$_4$) 7.68 (s, 1H), 7.1 (d, 1H J=8.2 Hz), 6.22 (dd, 1H J=8.2, 2.1 Hz), 6.11 (d, 1H J=2.1 Hz), 5.61 (q, 1H, J=7.2 Hz), 3.31 (m, 4H), 2.01 (m, 4H). $^{19}$F NMR (MeOH-d$_4$) −78.66.

EXAMPLE 141

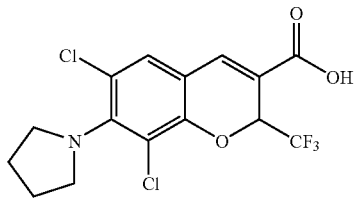

6,8-dichloro-7-pyrrolidin-1-yl-2-(trifluoromethyl)-2H-chromene-3-carboxylic acid Step 1: Preparation of ethyl 6-chloro-7-pyrrolidin-1-yl-2-(trifluoromethyl)-2H-chromene-3-carboxylate and ethyl 6,8-dichloro-7-pyrrolidin-1-yl-2-(trifluoromethyl)-2H-chromene-3-carboxylate The ester of Example 140 Step 1 (0.35 g, 1.0 mmol) was treated with Cl$_2$ following the method of Example 103 Step 3, after which chromatographic separation gave both the faster eluting 6,8-dichloro ester (0.11 g, 0.27 mmol) as well as the 6-chloro ester derivative (0.14 g, 0.37 mmol). The product structures were both consistent with $^1$H, $^{19}$F and $^{13}$C NMR analyses.

Step 2: Preparation of 6,8-dichloro-7-pyrrolidin-1-yl-2-(trifluoromethyl)-2H-chromene-3-carboxylic acid The 6,8-dichloro ester of Example 141 Step 1 (0.10 g, 0.25 mmol) was converted to 6,8-dichloro-7-pyrrolidin-1-yl-2-(trifluoromethyl)-2H-chromene-3-carboxylic acid (0.09 g, 0.24 mmol) by the method of Example 100 Step 3.

$^1$H NMR (CDCl$_3$) 7.64 (s, 1H), 7.15 (s, 1H), 5.78 (q, 1H, J=7.0 Hz), 3.33-3.68 (m,4H), 1.95-1.99 (m, 4H), $^{19}$F NMR (CDCl$_3$) −73.35. LCMS m/z=383, 384 (M+H, M+2H).

EXAMPLE 142

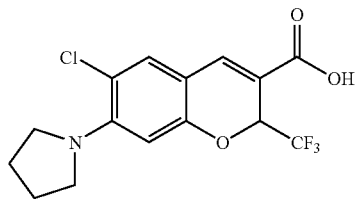

6-chloro-7-pyrrolidin-1-yl-2-(trifluoromethyl)-2H-chromene-3-carboxylic acid

Step 1: Preparation of 6-chloro-7-pyrrolidin-1-yl-2-(trifluoromethyl)-2H-chromene-3-carboxylic acid The 6-chloro ester of Example 141 Step 2 (0.13 g, 0.35 mmol) was converted to 6-chloro-7-pyrrolidin-1-yl-2-(trifluoromethyl)-2H-chromene-3-carboxylic acid (0.11 g, 0.32 mmol) by the method of Example 100 Step 3.

$^1$H NMR (MeOH-d$_4$) 7.66 (s, 1H), 7.22 (s, 1H), 6.42 (s, 1H), 5.68 (q, 1H, J=7.1 Hz), 3.58 (m, 4H), 1.99 (m, 4H), $^{19}$F NMR (MeOH-d4) −78.60. LCMS m/z=348,349 (M+H, M+2H).

EXAMPLE 143

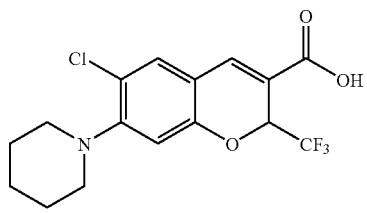

6-chloro-7-piperidin-1-yl-2-(trifluoromethyl)-2H-chromene-3-carboxylic acid

Step 1: Preparation of ethyl 7-piperidin-1-yl-2-(trifluoromethyl)-2H-chromene-3-carboxylate Ethyl 7-iodo-2-(trifluoromethyl)-2H-chromene-3-carboxylate (0.60 g, 1.5 mmol) was converted to ethyl 7-piperidin-1-yl-2-(trifluoromethyl)-2H-chromene-3-carboxylate (0.38 g, 1.06 mmol) by the method of Example 138 Step 1. The product structure was consistent with $^1$H, $^{19}$F and $^{13}$C NMR analyses.

Step 2: Preparation of ethyl 6-chloro-7-piperidin-1-yl-2-(trifluoromethyl)-2H-chromene-3-carboxlate The ester of Example 143 Step 1 (0.38 g, 1.06 mmol) was treated with Cl$_2$ following the method of Example 103 Step 3 to give ethyl 6-chloro-7-piperidin-1-yl-2-(trifluoromethyl)-2H-chromene-3-carboxylate (0.16 g, 0.41 mmol). The product structure was consistent with $^1$H, $^{19}$F and $^{13}$C NMR analyses.

Step 3: Preparation of 6-chloro-7-piperidin-I-yl-2-(trifluoromethyl)-2H-chromene-3-carboxylic acid The 6-chloro ester of Example 143 Step 2 (0.16 g, 0.41 mmol) was converted to 6-chloro-7-piperidin-1-yl-2-(trifluoromethyl)-2H-chromene-3-carboxylic acid (0.13 g, 0.36 mmol) by the method of Example 100 Step 3.

$^1$H NMR (CDCl$_3$) 7.74 (s, 1H), 7.21 (s, 1H), 6.61 (s, 1H), 5.65 (q, 1H, J=6.9 Hz), 3.10-3.16 (m, 2H), 3.00-3.05 (m, 2H), 1.71-1.76 (m, 4H), 1.59-1.64 (m, 2H), $^{19}$F NMR (CDCl$_3$) −77.14. LCMS m/z=362,363 (M+H, M+2H).

EXAMPLE 144

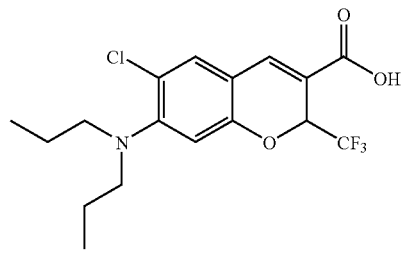

6-chloro-7-(dipropylamino)-1-yl-2-(trifluoromethyl)-2H-chromene-3-carboxylic acid Step 1: Preparation of ethyl 7-(dipropylamino)-1-yl-2-(trifluoromethyl)-2H-chromene-3-carboxylate Ethyl 7-iodo-2-(trifluoromethyl)-2H-chromene-3-carboxylate (0.60 g, 1.5 mmol) was converted to ethyl 7-(dipropylamino)-1-yl-2-(trifluoromethyl)-2H-chromene-3-carboxylate (0.38 g, 1.06 mmol) by the method of Example 140 Step 1. The product structure was consistent with $^1$H, $^{19}$F and $^{13}$C NMR analyses.

Step 2: Preparation of ethyl 6-chloro-7-(dipropylamino)-1-yl-2-(trifluoromethyl)-2H-chromene-3-carboxylate Ethyl 7-(dipropylamino)-1-yl-2-(trifluoromethyl)-2H-chromene-3-carboxylate (0.38 g, 1.06 mmol) was treated with Cl$_2$ following the method of Example 131 Step 3 to give ethyl 6-chloro-7-(dipropylamino)-1-yl-2-(trifluoromethyl)-2H-chromene-3-carboxylate (0.16 g, 0.41 mmol). The product structure was consistent with $^1$H, $^{19}$F and $^{13}$C NMR analyses.

Step 3: Preparation of 6-chloro-7-(dipropylamino)-1-yl-2-(trifluoromethyl)-2H-chromene-3-carboxylic acid Ethyl 6-chloro-7-(dipropylamino)-1-yl-2-(trifluoromethyl)-2H-chromene-3-carboxylate (0.16 g, 0.40 mmol) was converted to 6-chloro-7-(dipropylamino)-1-yl-2-(trifluoromethyl)-2H-chromene-3-carboxylic acid (0.13 g, 0.35 mmol) by the method of Example 100 Step 3.

$^1$H NMR (CDCl$_3$) 7.74 (s, 1H), 7.20 (s, 1H), 6.60 (s, 1H), 5.65 (q, 1H, J=6.9 Hz), 3.11-3.19 (m, 4H), 1.25-1.58 (m, 4H), 0.85-0.89 (m, 6H) $^{19}$F NMR (CDCl$_3$) −77.08. LCMS m/z=378, 379(M+H,M+2H):

EXAMPLE 145

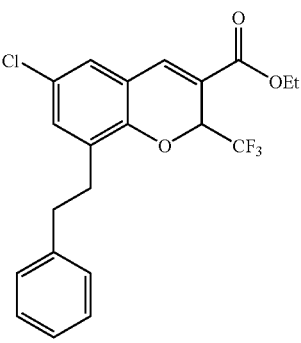

6-chloro-8-(2-phenylethyl)-2-(trifluoromethyl)-2H-chromene-3-carboxylic acid

Step 1: Preparation of ethyl 6-chloro-8-(2-phenylethyl)-2-(trifluoromethyl)-2H-chromene-3-carboxylate Ethyl 6-chloro-8-(2-phenylethynyl)-2-(trifluoromethyl)-2H-chromene-3-carboxylate (0.30 g, 0.74 mmol) was dissolved in ethanol, mixed with Pt$_2$O catalyst and reduced under a hydrogen atmosphere at 20 psi for 4 h at room temperature. The mixture was filtered, stripped and purified by flash chromatography on silica gel, giving ethyl 6-chloro-8-(2-phenylethyl)-2-(trifluoromethyl)-2H-chromene-3-carboxylate (0.21 g, 0.51 mmol). The product structure was consistent with $^1$H, $^{19}$F and $^{13}$C NMR analyses.

Step 2: 6-chloro-8-(2-phenylethyl)-2-(trifluoromethyl)-2H-chromene-3-carboxylic acid The 6-chloro ester of Example 145 Step 1 (0.20 g, 0.49 mmol) was converted to 6-chloro-8-(2-phenylethyl)-2-(trifluoromethyl)-2H-chromene-3-carboxylic acid (0.16 g, 0.42 mmol) by the method of Example 100 Step 3.

$^1$H NMR (CDCl$_3$) 7.17-7.32 (m, 5H), 7.11 (d, 1H, J=2.5 Hz), 7.08 (d, 1H, J=2.5 Hz) 5.76 (q, 1H, J=6.8 Hz), 2.83-2.97 (m, 4H). $^{19}$F NMR (CDCl$_3$) −76.97. LCMS m/z=384, 385 (M+H,M+2H).

EXAMPLE 146

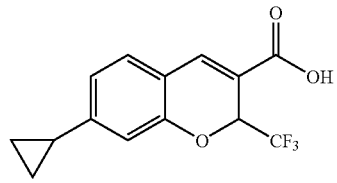

7-cyclopropyl-2-(trifluoromethyl)-2H-chromene-3-carboxylic acid

Step 1: Preparation of 7-iodo-2-(trifluoromethyl)-2H-chromene-3-carboxylic acid To a suspension of ethyl 7-iodo-2-(trifluoromethyl)-2H-chromene-3-carboxylate (1.50 g, 3.9 mmol) in 5 mL EtOH was added NaOH (0.46 g, 11.6 mmol) in 2.5 mL of H$_2$O. After heating for 1.5 h, reaction solvent was removed under vacuum. The resulting sodium salt was used immediately.

Step 2: Preparation of 7-cyclopropyl-2-(trifluoromethyl)-2H-chromene-3-carboxylic acid To a suspension of (9-BBN)$_2$ (1.96 g, 8.7 mmol) in 10 mL THF was added propargyl bromide (0.53 g, 4.4 mmol). After heating for 2 h and cooling to room temperature, NaOH (0.52 g, 13 mmol) in 4.3 mL of H$_2$O was added and the reaction was stirred for 1 h. In a separate flask under argon was added the title product of Example 146 Step 1 in 5 mL of THF and Pd(PPh$_3$)$_4$. The reaction from the original flask was transferred to the second flask via cannula. After refluxing for 18 h and cooling to room temperature, 25 mL of H$_2$O was added. The organic solvent was removed from the reaction under vacuum. The aqueous layer was extracted three times with 70 mL EtOAc. The combined organic extractions were washed one time with 50 mL of 1 N HCl and one time with 50 mL of saturated brine. Following drying over MgSO$_4$ and concentrating under vacuum, the product was purified by flash column chromatography and reverse phase chromatography on YMC ODS-AQ in MeOH/H$_2$O to yield desired product (0.40 g, 40%).

EXAMPLE 147

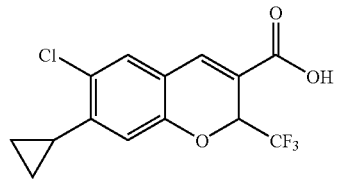

6-chloro-7-cyclopropyl-2-(trifluoromethyl)-2H-chromene-3-carboxylic acid

Step 1: Preparation of 6-chloro-7-cyclopropyl-2-(trifluoromethyl)-2H-chromene-3-carboxylic acid To a solution of the product of Example 146 Step 2 (0.28 g, 1.0 mmol) in 5 mL HOAc was added Cl$_2$ in HOAc (3.0 mL, ~1.5 mmol). After 0.75 h, the reaction was treated with Zn dust for 1.5 h. The reaction mixture was decanted from the Zn and concentrated under vacuum. The resulting residue was triturated with H₂O, filtered, and washed with H₂O. The yield of 6-chloro-7-cyclopropyl-2-(trifluoromethyl)-2H-chromene-3-carboxylic acid was 0.26 g (82%) after drying overnight in a vacuum oven at 50° C.

$^1$H NMR (MeOH-d$_4$) 7.74 (s, 1H), 6.57 (s, 1H), 5.73 (q, 1H, J=7.06 Hz), 2.21 (dd, 2H, J=2.0, 8.5 Hz), 0.75 (m, 2H).

EXAMPLE 148

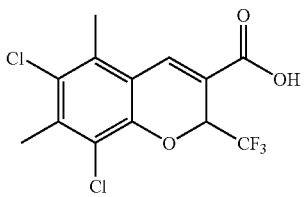

6,8-dichloro-5,7-dimethyl-2-(trifluoromethyl)-2H-chromene-3-carboxylic acid

Step 1: Preparation of 2-hydroxy-4,6-dimethylbenzaldehyde

The title product of Example 148 Step 1 was prepared in the same manner as described in Example 100 Step 1 starting with 3,5-dimethyl-phenol.

Step 2: Preparation of ethyl 5,7-dimethyl-2-(trifluoromethyl)-2H-chromene-3-carboxylate The title product of Example 148 Step 2 was prepared in the same manner as described in Example 100 Step 2 starting with the title product of Example 148 Step 1.

Step 3: Preparation of ethyl 6,8-dichloro-5,7-dimethyl-2-(trifluoromethyl)-2H-chromene-3-carboxylate The title product of Example 148 Step 3 was prepared in the same manner as described in Example 103 Step 3 starting with ethyl 5,7-dimethyl-2-(trifluoromethyl)-2H-chromene-3-carboxylate.

Step 4: Preparation of 6,8-dichloro-5,7-dimethyl-2-(trifluoromethyl)-2H-chromene-3-carboxylic acid 6,8-Dichloro-5,7-dimethyl-2-(trifluoromethyl)-2H-chromene-3-carboxylic acid was prepared in the same manner as described in Example 100 Step 3 starting with ethyl 6,8-dichloro-5,7-dimethyl-2-(trifluoromethyl)-2H-chromene-3-carboxylate. $^1$H NMR (MeOH-d$_4$) 7.93 (s, 1H), 5.81 (q, 1H, J=6.98 Hz), 2.49 (s, 3H), 2.43 (s, 3H)

EXAMPLE 149

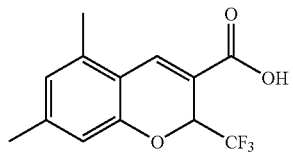

5,7-dimethyl-2-(trifluoromethyl)-2H-chromene-3-carboxylic acid

Step 1: Preparation of 5,7-dimethyl-2-(trifluoromethyl)-2H-chromene-3-carboxylic acid 5,7-Dimethyl-2-(trifluoromethyl)-2H-chromene-3-carboxylic acid was prepared in the same manner as described in Example 100 Step 3 starting with ethyl 5,7-dimethyl-2-(trifluoromethyl)-2H-chromene-3-carboxylate. $^1$H NMR (MeOH-d$_4$) 7.95 (s, 1H), 6.72 (bs, 1H), 6.65 (s, 1H), 5.67 (q, 1H, J=7.18 Hz), 2.39 (s, 3H), 2.31 (s, 3H)

EXAMPLE 150

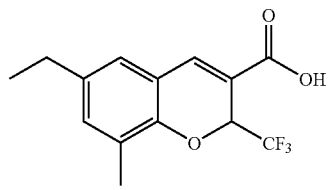

6-ethyl-8-methyl-2-(trifluoromethyl)-2H-chromene-3-carboxylic acid

Step 1: Preparation of 4-ethyl-2-methylphenol

A mixture of 3-methyl-4-hydroxyacetophenone (12.0 g, 79.9 mmol), 20% Pd(OH)₂/C in HOAc was subjected to hydrogenation conditions at 25° C. under 60 psi. After 16 h, the catalyst was removed from the reaction by filtration. The filtrate was concentrated. The product was dried under high vacuum for 18 h to give a clear oil (10.1 g, 93%).

Step 2: Preparation of 5-ethyl-2-hydroxy-3-methylbenzaldehyde

To a solution of the phenol of Example 150 Step 1 (5.0 g, 36.7 mmol) in 200 mL CH₃CN, was added MgCl₂ (5.25 g, 55.1 mmol), TEA (13.9 g, 19.2 mL, 137.6 mmol), and (CHO)N (8.3 g, 280 mmol). The reaction was heated at reflux for 3 h. After cooling, the reaction was diluted with EtOAc (500 mL) and acidified with aqueous 2N HCl until the reaction was pH 4. The reaction was diluted with 300 mL H₂O. The organic layer was washed with H₂O, with brine, dried over MgSO₄, and concentrated. The residue was purified by flash chromatography (on SiO₂, hexane/EtOAc=94/6) to give 3.2 g (53%) of the desired product as a clear oil.

Step 3: Preparation of ethyl 6-ethyl-8-methyl-2-(trifluoromethyl)-2H-chromene-3-carboxylate To a mixture of the benzaldehde of Example 150 Step 2 (1.8 g, 11.0 mmol) and finely powdered $K_2CO_3$ (3.34 g, 24.2 mmol) in DMF (20 mL), was added ethyl 4,4,4-trifluorocrotonate (2.2 g, 13.2 mmol). The reaction was heated to 85° C. After 2 h, the reaction was cooled to 25° C., and diluted with EtOAc (200 mL) and $H_2O$ (200 mL). The organic layer was the washed with saturated $NaHCO_3$ (150 mL), $H_2O$ (100 mL), brine (150 mL), dried over $MgSO_4$, filtered, and concentrated under reduced pressure to give a brown residue. The residue was dried under high vacuum to give 2.7 g (78%) of a brown crystalline solid.

Step 4: Preparation of 6-ethyl-8-methyl-2-(trifluoromethyl)-2H-chromene-3-carboxylic acid To a solution of ethyl 6-ethyl-8-methyl-2-(trifluoromethyl)-2H-chromene-3-carboxylate (2.6 g, 8.3 mmol) in EtOH (90 mL), was added 1N NaOH (24.8 mL, 24.8 mmol). The reaction was stirred at 25° C. for 18 h. The ethanol was removed from the reaction under reduced pressure. The residue was acidified with 2N HCl. The product was extracted into EtOAc (300 mL) then washed with brine (100 mL), dried over $MgSO_4$, filtered, and concentrated. The crude product was dissolved in 20 mL EtOAc and then diluted with 150 mL hexane. The resulting solution was chilled at 0° C. for 30 min. The product, which precipitated from the solution, was collected by filtration. The desired product was isolated as an off-white solid in quantities of 1.6 g (68%). $^1$H NMR (DMSO-$d_6$) 1.15 (t, 3H, J=7.56 Hz), 2.16 (s, 3H), 2.51 (q, 2H, J=7.6 Hz), 5.89 (q, 1H, J=7.4 Hz), 7.11 (d, 1H, J=2.1 Hz), 7.14 (d, 1H, J=2.1 Hz), 7.79 (s, 1H).

EXAMPLE 151

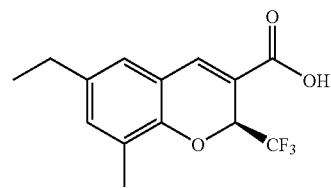

(2S)-6-ethyl-8-methyl-2-(trifluoromethyl)-2H-chromene-3-carboxylic acid

Step 1: Preparation of (+)-6-ethyl-8-methyl-2-(trifluoromethyl)-2H-chromene-3-carboxylic acid Products (isomers) of Example 150 Step 4 were separated by chiral chromatography on a ChiralPak AD column using iPrOH/heptane/TFA(5/95/0.1) as the mobile phase. The product of Example 151 Step 1 had a retention time of 5.58 min and a positive specific rotation. $^1$H NMR (DMSO-$d_6$) 1.15 (t, 3H, J=7.56 Hz), 2.16 (s, 3H), 2.51 (q, 2H, J=7.6 Hz), 5.89 (q, 1H, J=7.4 Hz), 7.11 (d, 1H, J=2.1 Hz), 7.14 (d, 1H, J=2.1 Hz), 7.79 (s, 1H).

EXAMPLE 152

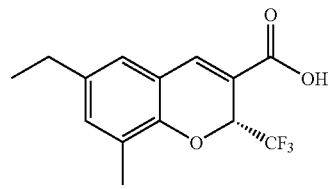

(2R)-6-ethyl-8-methyl-2-(trifluoromethyl)-2H-chromene-3-carboxylic acid

Step 1: Preparation of (−)-6-ethyl-8-methyl-2-(trifluoromethyl)-2H-chromene-3-carboxylic acid See Example 151 Step 1. Example 152 had a retention time of 4.58 min and a negative specific rotation. $^1$H NMR (DMSO-$d_6$) 1.15 (t, 3H, J=7.56 Hz), 2.16 (s, 3H), 2.51 (q, 2H, J=7.6 Hz), 5.89 (q, 1H, J=7.4 Hz), 7.11 (d, 1H, J=2.1 Hz), 7.14 (d, 1H, J=2.1 Hz), 7.79 (s, 1H).

EXAMPLE 153

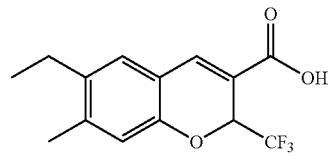

6-ethyl-7-methyl-2-(trifluoromethyl)-2H-chromene-3-carboxylic acid

Step 1: Preparation of 6-ethyl-7-methyl-2-(trifluoromethyl)-2H-chromene-3-carboxylic acid 6-Ethyl-7-methyl-2-(trifluoromethyl)-2H-chromene-3-carboxylic acid was synthesized in the same manner described using the procedures of Example 150 using 2-methyl-4-hydroxyacetophenone as the starting material. $^1$H NMR (DMSO-$d_6$) 1.14 (t, 3H, J=7.5 Hz), 2.25 (s, 3H), 2.51 (q, 2H, J=7.5 Hz), 5.83 (dd, 1H, J=7.4 Hz), 6.84 (s, 1H), 7.24 (s, 1H), 7.80 (s, 1H).

EXAMPLE 154

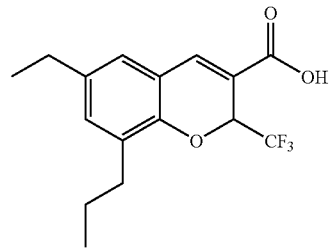

6-ethyl-8-propyl-2-(trifluoromethyl)-2H-chromene-3-carboxylic acid

6-Ethyl-8-propyl-2-(trifluoromethyl)-2H-chromene-3-carboxylic acid was synthesized in the same manner described using the procedures of Example 150 using 3'-allyl-4'-hydroxyacetophenone as the starting material. $^1$H NMR (MeOH-d$_4$) 0.93 (t, 3H, J=7.3 Hz), 1.20 (t, 3H, J=7.6 Hz), 1.60 (hextet, 2H, J=7.5 Hz), 2.45-2.65 (m, 4H), 5.73 (q, 1H, J=7.2 Hz). 6.96 (d, 1H, J=2.1 Hz), 7.03 (d, 1H, J=2.1 Hz). 7.73 (s, 1H).

EXAMPLE 155

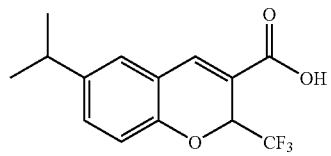

6-isopropyl-2-(trifluoromethyl)-2H-chromene-3-carboxylic acid

Step 1: Preparation of 2-hydroxy-5-isopropylbenzaldehyde

The formylation reaction was carried out in the same manner described in Example 150 Step 2 using 4-isopropylphenol (5.0 g, 36.7 mmol). The clean product, which is a golden oil, was isolated in quantities of 5.2 g (86%).

Step 2: Preparation of ethyl 6-isopropyl-2-(trifluoromethyl)-2H-chromene-3-carboxylate The cyclization reaction was carried out in the same manner described in Example 150 Step 3 using the product of Example 155 Step 1 (3.0 g, 18.3 mmol). The crude product was purified by flash chromatography (hexane/EtOAc=9/1) to give a clean product in quantities of 4.54 g (79%).

Step 3: Preparation of 6-isopropyl-2-(trifluoromethyl)-2H-chromene-3-carboxylic acid The product of Example 155 Step 2 (2.1 g, 6.7 mmol) was converted to the acid according to procedure of Example 150 Step 4. The product, which is an off-white solid, was isolated in quantities of 1.6 g (68%). $^1$H NMR (DMSO-d$_6$) 1.17 (s, 3H), 1.19 (s, 3H), 2.79-2.88 (m, 1H), 5.86 (q, 1H, J=7.3 Hz), 6.94 (d, 2H, J=8.4 Hz), 7.25 (dd, 1H, J=6.3 Hz, J=2.2Hz), 7.37 (d, 1H, J=2.2), 7.83 (s, 1H).

EXAMPLE 156

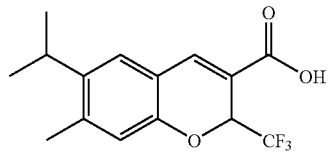

6-isopropyl-7-methyl-2-(trifluoromethyl)-2H-chromene-3-carboxylic acid

Step 1: Preparation of 6-isopropyl-7-methyl-2-(trifluoromethyl)-2H-chromene-3-carboxylic acid 6-Isopropyl-7-methyl-2-(trifluoromethyl)-2H-chromene-3-carboxylic acid was synthesized in the same manner using the procedures described in Example 155 starting with 4-isopropyl-3-methylphenol. $^1$H NMR (DMSO-d$_6$) 1.14 (s, 3H), 1.16 (s, 3H), 2.26 (s, 1H), 2.95-3.06 (m, 1H), 5.81 (q, 1H, J=7.5 Hz), 6.76 (s, 1H), 7.24 (s, 1H), 7.58 (s, 1H).

EXAMPLE 157

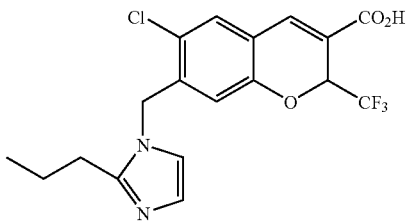

6-chloro-7-[(2-propyl-1H-imidazol-1-yl)methyl]-2-(trifluoromethyl)-2H-chromene-3-carboxylic acid hydrochloride Step 1: Preparation of 5-chloro-2-hydroxy-4-methylbenzaldehyde 4-chloro-3-methylphenol (10.0 g, 70.1 mmol) was converted to the aldehyde using the procedure described in Example 150 Step 2. The desired product as a pale yellow solid was isolated in quantities of 8.8 g (74%).

Step 2: Preparation of ethyl 6-chloro-7-methyl-2-(trifluoromethyl)-2H-chromene-3-carboxylate The product of Example 157 step 1 (8.9 g, 52.2 mmol) was converted to the chromene using the procedure of Example 150 Step 3. The desired product as a yellow solid which was isolated in quantities of 9.9 g (59%).

Step 3: Preparation of ethyl 7-(bromomethyl)-6-chloro-2-(trifluoromethyl)-2H-chromene-3-carboxylate To a mixture of the product of Example 157 Step 2 (4.0 g, 12.5 mmol), N-bromosuccinimide (2.3 g, 13.1 mmol), and 21 mL benzene, was added benzoyl peroxide (145 mg. 0.6 mmol). The reaction was heated to 84° C. After 5 h, the reaction was cooled to 25° C. and stored overnight. Solid was removed from the reaction by filtration, and washed with 4 mL benzene. To the filtrate, was added N-bromosuccinimide (1.0 g, 5.7 mmol) and benzoyl peroxide (145 mg, 0.6 mmol). The reaction was heated to 84° C. After 2.5 h, the reaction was cooled to 25° C. The solid was removed from the reaction by filtration and the filtrate was concentrated. The residue was purified by flash chromatography (toluene/EtOAc=9/1) to give 3.9 g a yellow solid of reasonably pure material, which was used without further purification.

Step 4: Preparation of ethyl 6-chloro-7-[(2-propyl]-1H-imidazol-1-yl)methyl]-2-(trifluoromethyl)-2H-chromene-3-carboxylate A solution of 2-propylimidazole (76 mg, 0.69 mmol) in 1 mL DME was added to a mixture NaH (32 mg, 0.81 mol, 60% dispersion in mineral oil) at 0° C. under argon. After 20 min, a solution of the product of Example 157 Step 3 (250 mg, 0.62 mol) in 2 mL DME was added at 0° C. The reaction was warmed to 25° C. After 1.5 h, the reaction was filtered through a pad of Celite (1"), and washed with EtOAc (20 mL). The filtrate was concentrated to give a pale brown oil in 0.21 g (80%).

Step 5: Preparation of 6-chloro-7-[(2-propyl-1H-imidazol-1-yl)methyl]-2-(trifluoromethyl)-2H-chromene-3-carboxylic acid The product of Example 157 Step 4 (0.21 g, 0.5 mmol) was converted to the acid according to procedure of Example 150 Step 4. The clean product was obtained by purifying the crude product by HPLC (column: Delta Pak 300×50mm I.D., C 18, 15 μM) using a $H_2O-CH_3CN$ gradient (conditions:$CH_3CN-H_2O$ 10-50% in 30 min). The yield of an off-white solid was 66 mg (30%). $^1$H NMR (MeOH-$d_4$) 0.99 (t, 3H, J=7.41 Hz), 1.73 (hextet, 2H, J=7.8 Hz), 3.00 (t, 2H, J=7.8 Hz), 5.51 (s, 2H), 5.83 (q, 1H, J=7.0 Hz), 6.86 (s, 1H), 7.46 (d, 1H, J=2.1 Hz), 7.54 (d, 1H, J=2.1 Hz), 7.81 (s, 1H), 7.89 (s, 1H).

EXAMPLE 158

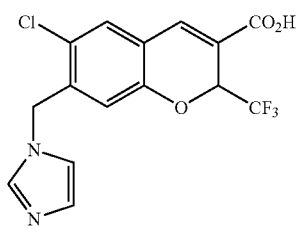

6-chloro-7-(1H-imidazol-1-ylmethyl)-2-(trifluoromethyl)-2H-chromene-3-carboxylic acid hydrochloride 6-Chloro-7-[(2-methyl-1H-imidazol-1-yl)methyl]-2-(trifluoromethyl)-2H-chromene-3-carboxylic acid trifluoroacetate hydrochloride was synthesized using the procedures described in Example 157 using imidazole as the starting amine. 158: $^1$H NMR (MeOH-$d_4$) 5.44-5.52 (m, 2H), 5.76 (q, 1H, J=6.94 Hz), 7.02 (s, 1H), 7.53 (s, 1H), 7.56 (s, iH), 7.73 (s, 1H), 9.00 (s, 1H).

EXAMPLE 159

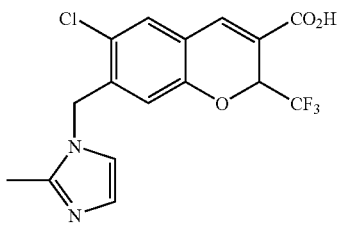

6-chloro-7-[(2-methyl-1H-imidazol-1-yl)methyl]-2-(trifluoromethyl)-2H-chromene-3-carboxylic acid trifluoroacetate hydrochloride 6-Chloro-7-[(2-methyl-1H-imidazol-1-yl)methyl]-2-(trifluoromethyl)-2H-chromene-3-carboxylic acid trifluoroacetate hydrochloride was synthesized using the procedures described in Example 157 using 2-methylimidazole as the starting amine. $^1$H NMR (MeOH-$d_4$) 2.66 (s, 3H), 5.41-5.51 (m, 2H), 5.83 (q, 1H, J=7.0 Hz), 6.90 (s, 1H), 7.42 (d, 1H, J=2.2 Hz), 7.49 (d, 1H, J=2.2 Hz), 7.59 (s, 1H), 7.81 (s, 1H).

EXAMPLE 160

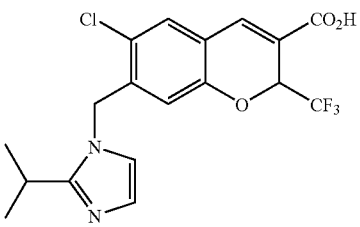

6-chloro-7-[(2-isopropyl-1H-imidazol-1-yl)methyl]-2-(trifluoromethyl)-2H-chromene-3-carboxylic acid hydrochloride 6-Chloro-7-[(2-isopropyl-1H-imidazol-1-yl)methyl]-2-(trifluoromethyl)-2H-chromene-3-carboxylic acid hydrochloride was synthesized using the procedures described in Example 157 using 2-isopropylimidazole as the starting amine. $^1$H NMR (MeOH-$d_4$) 1.35 (s, 3H), 1.37 (s, 3H), 3.45-3.54 (m, 1H), 5.54 (s, 2H), 5.83 (q, 1H, J=7.0 Hz), 6.82 (s, 1H), 7.44 (d, 1H, J=2.1 Hz), 7.55 (d, 1H, J=2.1 Hz), 7.59 (s, 1H), 7.80 (s, 1H).

EXAMPLE 161

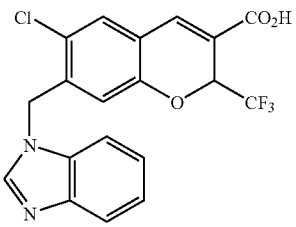

7-(1H-benzimidazol-1-ylmethyl)-6-chloro-2-(trifluoromethyl)-2H-chromene-3-carboxylic acid hydrochloride 7-(1H-benzimidazol-1-ylmethyl)-6-chloro-2-(trifluoromethyl)-2H-chromene-3-carboxylic acid hydrochloride was synthesized using the procedures described in Example 157 starting with benzimidazole.

$^1$H NMR (DMSO-$d_6$) 5.80 (s, 2H), 5.98 (q, 1H, J=7.1 Hz), 7.05 (s, 1H), 7.55-7.59 (m, 2H), 7.77-7.80 (m, 2H), 7.88-7.90 (m, 2H).

EXAMPLE 162a and −162b

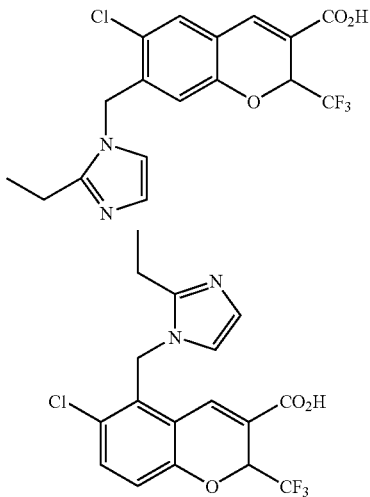

6-chloro-7-[(2-ethyl-1H-imidazol-1-yl)methyl]-2-(trifluoromethyl)-2H-chromene-3-carboxylic acid hydrochloride and 6-chloro-5-[(2-ethyl-1H-imidazol-1-yl)methyl]-2-(trifluoromethyl)-2H-chromene-3-carboxylic acid hydrochloride

Step 1: Preparation of 5-chloro-2-hydroxy-4-methylbenzaldehyde and 5-chloro-2-hydroxy-6-methylbenzaldehyde 4-chloro-3-methylphenol (10.0 g, 70.1 mmol) was converted to the aldehydes using the procedure of Example 150 Step 2. Impurities were removed by flash chromatography (hexane/EtOAc=9/1). A mixture of regioisomeric aldehydes was obtained in a 94:6 ratio and found to be a pale yellow solid which was isolated in quantities of 8.8 g (74%).

Step 2: Preparation of ethyl 6-chloro-7-methyl-2-(trifluoromethyl)-2H-chromene-3-carboxylate and ethyl 6-chloro-5-methyl-2-(trifluoromethyl)-2H-chromene-3-carboxylate The products of Example 162 Step 1 (8.9 g, 52.2 mmol) were converted to the chromenes using the procedure of Example 150 Step 3. The crude products were purified by flash chromatography (heptane/EtOAc=8/2) to give the mixture of chromenes as a yellow solid in quantities of 9.9 g (59%).

Step 3: Preparation of ethyl 7-(bromomethyl)-6-chloro-2-(trifluoromethyl)-2H-chromene-3-carboxylate and ethyl 5-(bromomethyl)-6-chloro-2-(trifluoromethyl)-2H-chromene-3-carboxylate The products of Example 162 Step 2 (4.0 g, 12.5 mmol) were converted to the bromides using the procedure of Example 157 Step 3. The residue was purified by flash chromatography (toluene/EtOAc=9/1) to give the mixture of products as a yellow solid (3.9 g, 78%).

Step 4: Preparation of ethyl 6-chloro-7-[(2-ethyl-1H-imidazol-1-yl)methyl]-2-(trifluoromethyl)-2H-chromene-3-carboxylylate and ethyl 6-chloro-5-[(2-ethyl-1H-imidazol-1-yl)methyl]-2-(trifluoromethyl)-2H-chromene-3-carboxylate The products of Example 162 Step 3 (300 mg, 0.75 mmol) were converted to the 2-ethyl-imidazoles using the procedure of Example 157 Step 4. The product was a pale brown oil (320 mg, 70%).

Step 5: Preparation of 6-chloro-7-[(2-ethyl-1H-imidazol-1-yl)methyl]-2-(trifluoromethyl)-2H-chromene-3-carboxylylic acid hydrochloride and 6-chloro-5-[(2-ethyl-1H-imidazol-1-yl)methyl]-2-(trifluoromethyl)-2H-chromene-3-carboxylic acid hydrochloride The products of Example 162 Step 4 were converted to their acids according to procedure of Example 150 Step 4. The clean products were obtained by purifying the crude product by reverse phase HPLC (column: Delta Pak 300×50 mm I.D., C 18, 15 μM) using a $H_2O$—$CH_3CN$ gradient (conditions:$CH_3CN$—$H_2O$ 10-50% in 30 min). The product, 162-1, was isolated as a pale yellow solid in quantities of 100 mg. The product, 162-2, was isolated as a pale yellow solid in quantities of 15 mg.

162-1 $^1$H NMR (MeOH-$d_4$) 1.37 (t, 2H, J=7.4 Hz), 3.08 (q, 2H, J=7.6 Hz), 5.48-5.56 (m, 2H), 5.88 (q, 1H, J=7.0 Hz), 6.90 (s, 1H), 7.47 (d, 1H, J=2.1 Hz), 7.55 (d, 1H, J=2.1 Hz), 7.62 (s, 1H), 7.85 (s, 1H). 162-2 $^1$H NMR (MeOH-$d_4$) 1.44 (t, 2H, J=7.5 Hz), 3.17 (q, 2H, J=7.7 Hz), 5.68-5.74 (m, 2H), 5.89 (q, 1H, J=7.0 Hz), 6.98 (d, 1H, J=2.1 Hz)), 7.22 (d, 1H, J=8.8 Hz), 7.45 (d, 1H, J=2.1 Hz), 7.59 (d, 1H, J=8.8 Hz), 8.05 (s, 1H).

EXAMPLE 163a and –163b

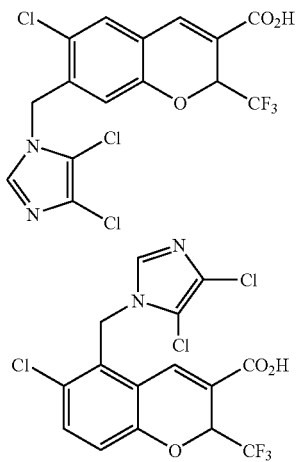

6-chloro-7-[(4,5-dichloro-1H-imidazol-1-yl)methyl]-
2-(trifluoromethyl)-2H-chromene-3-carboxylic acid
hydrochloride and 6-chloro-5-[(4,5-dichloro-1H-imidazol-1-yl)methyl]-
2-(trifluoromethyl)-2H-chromene-3-carboxylic acid Step 1: Preparation of 6-chloro-7-[(4,5-dichloro-
1H-imidazol-1-yl)methyl]-2-(trifluoromethyl)-2H-
chromene-3-carboxylic acid hydrochloride and
6-chloro-5-[(4,5-dichloro-1H-imidazol-1-yl)methyl]-
2-(trifluoromethyl)-2H-chromene-3-carboxylic acid
hydrochloride 6-Chloro-7-[(4,5-dichloro-1H-imidazol-1-yl)methyl]-2-
(trifluoromethyl)-2H-chromene-3-carboxylic acid hydrochloride and 6-chloro-5-[(4,5-dichloro-1H-imidazol-1-yl)
methyl]-2-(trifluoromethyl)-2H-chromene-3-carboxylic
acid hydrochloride were synthesized in the same manner
described in Example 162 and using 4,5-dichloroimidazole
in the alkylation reaction.

163-1 $^1$H NMR (DMSO-d$_6$) 5.27-5.37 (m, 2H), 5.97 (q, 1H, J=7.2 Hz), 6.55 (s, 1H), 7.75 (s, 1H), 7.87 (s, 1H), 7.93 (s, 1H).

163-2 $^1$H NMR (DMSO- d$_6$) 5.47-5.56 (m, 2H), 5.85 (q, 1H, J=7.0 Hz), 7.16 (d, 1H, J=8.83 Hz), 7.40 (s, 1H), 7.55 (d, 1H, J=8.8 Hz), 8.07 (s, 1H).

EXAMPLE 164

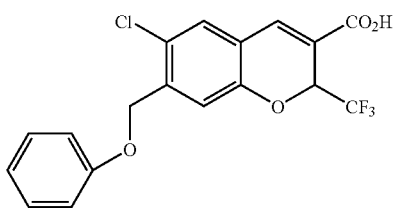

6-chloro-7-(phenoxymethyl)-2-(trifluoromethyl)-2H-
chromene-3-carboxylic acid

Step 1: Preparation of ethyl 6-chloro-7-(phenoxym-
ethyl)-2-(trifluoromethyl)-2H-chromene-3-carboxy-
late A solution of phenol (117 mg, 0.69 mmol) in 1 mL DMF was added to a mixture of NaH (30 mg, 0.75 mmol) in 1 mL DMF at 0° C. under argon. After 30 min, a solution of ethyl 7-(bromomethyl)-6-chloro-2-(trifluoromethyl)-2H-chromene-3-carboxylate (250 mg, 0.62 mmol) in 2 mL DMF described in Example 157 Step 3 was added dropwise. The reaction was warmed to 25° C. After 18 h, the reaction was filtered through a pad of Celite (1") and washed with EtOAc (20 mL). The filtrate was concentrated to give a pale yellow solid in 230 mg.

Step 2: Preparation of 6-chloro-7-(phenoxymethyl)-
2-(trifluoromethyl)-2H-chromene-3-carboxylic acid The product of Example 164 Step 1 (0.22 g, 0.53 mmol) was converted to the acid according to procedure of Example 150 Step 4, and purified by reverse phase HPLC (column: Delta Pak 300×50 mm I.D., C18, 15 µM), using CH$_3$CN—H$_2$O gradient 10-50% in 30 min to give a pale yellow solid in 80 mg (40%).

$^1$H NMR (DMSO-d$_6$) 5.12 (s, 2H), 5.98 (q, 1H, J=7.3 Hz), 6.98 (t, 1H, J=7.4 Hz), 7.04 (d, 2H, J=7.8 Hz), 7.26 (s, 1H), 7.32(dt, 2H, J=2.0 Hz, J=7.4 Hz), 7.72 (s, 1H), 7.89 (s, 1H).

EXAMPLE 165

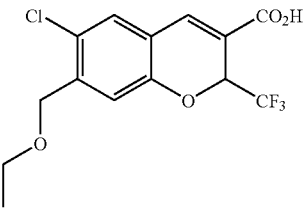

6-chloro-7-(ethoxymethyl)-2-(trifluoromethyl)-2H-
chromene-3-carboxylic acid

Step 1: Preparation of ethyl 6-chloro-7-(ethoxym-
ethyl)-2-(trifluoromethyl)-2H-chromene-3-carboxy-
late A solution of pyrrole (55 mg, 0.75 mmol) in 1.5 mL DME was added to a mixture of NaH (38 mg, 0.83 mmol) in I mL DME at 0° C. under argon. The mixture was stirred at 0° C. for 10 min and then warmed to 25° C. After 30 min, a solution of ethyl 7-(bromomethyl)-6-chloro-2-(trifluoromethyl)-2H-chromene-3-carboxylate (300 mg, 0.75 mmol), from Example 162 Step 3, was dissolved in 2.5 mL DME was added dropwise. After 3 h, the reaction was filtered through a pad of Celite (1") and washed with EtOAc (10 mL). The filtrate was concentrated to give a brown oil in 350 mg (100%).

Step 2: Preparation of 6-chloro-7-(ethoxymethyl)-2-(trifluoromethyl)-2H-chromene-3-carboxylic acid The product of Example 165a (350 mg, 0.75mmol) was converted to the acid according to procedure of 150d, and purified by reverse phase HPLC (column: Delta Pak 300×50 mm I.D., C18, 15 μM), using $CH_3CN$—$H_2O$ gradient 10-50% in 30 min to give the titled product as a pale brown solid in 60 mg. $^1$H NMR (MeOH-$d_4$) 1.27 (t, 3H, J=7.0 Hz), 3.63 (q, 2H, J=7.0 Hz), 4.54 (s, 1H), 5.78 (q, 1H, J=7.0 Hz), 7.12 (s, 1 H), 7.39 (s, 1H), 7.77 (s, 1H).

EXAMPLE 166

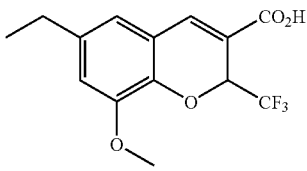

6-ethyl-8-methoxy-2-(trifluoromethyl-2H-chromene-3-carboxylic acid

Step 1: Preparation of 2-(4-ethyl-2-methoxyphenoxy)tetrahydro-2H-pyran

Ethyl guiacol (10 g, 65 mmol) was dissolved in 100 mL of EtOAc and to this solution was added 8.9 mL of 3,4-dihydro-2H-pyran (97.5 mmol, 8.2 g) followed by a catalytic amount of a 4.0 M solution of HCl/dioxane. The reaction was stirred at 25° C. overnight. The following day the solution was washed with aqueous 1N NaOH and evaporated to dryness. The crude mixture was redissolved in ether then stirred with aqueous 1N NaOH for a short period of time, stopped and allowed to stand overnight. The two phases were separated and the organic layer was washed with $H_2O$ and brine. The resulting solution was dried ($Na_2SO_4$). The solution was filtered and evaporated to dryness to provide 9.9 g of colorless oil (64%). This material was used as is without further purification.

Step 2: Preparation of 5-ethyl-3-methoxy-2-(tetrahydro-2H-pyran-2-yloxy)benzaldehyde To a solution, cooled to −78 ° C., of the product from Example 166 Step 1 (1.0 g, 4.2 mmol) in 7.0 mL of hexane, and 0.70 mL of TMEDA (4.6 mmol, 543.2 mg) was added n-BuLi (2.9 mL, 1.6 M in hexane). After the addition, the reaction was warmed to 25° C. After 5 hours, DMF (0.5 mL) in 3 mL of hexane was added. The reaction was quenched with $H_2O$ and the resulting solution was washed with $H_2O$. The organic extracts were dried over $MgSO_4$, filtered, and evaporated to give 1.1 g of golden oil (100%), which was reasonably pure as judged by $^1$H NMR, and used as is without further purification.

Step 3: Preparation of 5-ethyl-2-hydroxy-3-methoxybenzaldehyde

The title product from Example 166 Step 2 (1.1 g, 4.1 mmol ) was dissolved in 10 mL of $CH_3OH$ and to this solution was added 10 mL of 2N HCl. The reaction was stirred at 25° C. overnight. The reaction was diluted with 25 mL of EtOAc and washed with an aqueous solution of saturated $NaHCO_3$. The organic extracts were dried over $MgSO_4$, filtered and concentrated under reduced pressure to give 660 mg (85%) of a very clean product as judged by $^1$H NMR and used as is without further purification.

Step 4: Preparation of ethyl 6-ethyl-8-methoxy-2-(trifluoromethyl)-2H-chromene-3-carboxylate To the product from Example 166 Step 3 (410 mg, 2.27 mmol) dissolved in 4.1 mL of anhydrous DMF was added anhydrous $K_2CO_3$ (658.8 mg, 4.76 mmol) and 80 mg of powdered 4 Å molecular sieves followed by the addition of ethyl 4,4,4-trifluorocrotonate (450.5 mg, 0.40 mL, 2.68 mmol). The reaction was heated to 80-85° C. for 2 h. Another portion of ethyl 4,4,4-trifluorocrotonate (0.17 mL) was added and the resulting solution was heated overnight. The following day the reaction was diluted with EtOAc (200 mL) and $H_2O$ (200 mL). More EtOAc was added till the layers could be distinguished. The organic extracts were washed with an aqueous solution of saturated $NaHCO_3$ (50 mL), $H_2O$ (100 mL) and brine (50 mL), dried over $MgSO_4$, filtered, and evaporated under reduced pressure to give a dark brown oil which was purified by flash chromatography (25% EtOAc/hexane) to give 450 mg (38%) of desired product which crystallized upon standing.

Step 5: Preparation of 6-ethyl-8-methoxy-2-(trifluoromethyl)-2H-chromene-3-carboxylic acid The ester from Example 166 Step 4 (167.1 mg, 0.50 mmol) was converted to the acid according the procedure of Example 150 Step 4 to give 137 mg (90%) of 6-ethyl-8-methoxy-2-(trifluoromethyl)-2H-chromene-3-carboxylic acid, a yellow solid. $^1$H NMR (MeOH-$d_4$) 7.75 (s, 1H), 6.94 (d, 1H, J=1.8 Hz), 6.79 (d, 1H, J=1.9 Hz), 5.77 (q, 1H, J=7.1 Hz), 3.87 (s, 3H), 2.61 (q, 2H, J=7.6 Hz), 1.25 (t, 3H, J=7.6 Hz).

EXAMPLE 167a and −167b

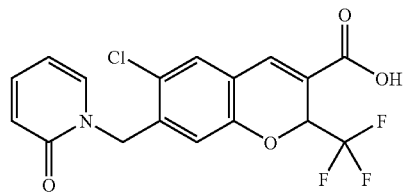

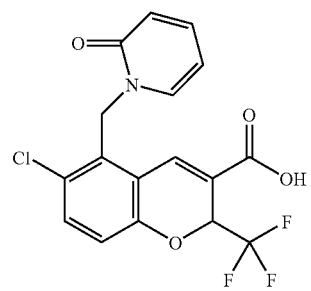

6-chloro-7-1(2-oxopyridin-1(2H)-yl) methyl]-2-(trifluoromethyl)-2H-chromene-3-carboxylic acid and 6-chloro-5-[(2-oxopyridin-1(2H)-yl) methyl]-2-(trifluoromethyl)-2H-chromene-3-carboxylic acid Step 1: Preparation of ethyl 6-chloro-7-[(2-oxopyridin-1(2H)-yl) methyl]-2-(trifluoromethyl)-2H-chromene-3-carboxylate and ethyl 6-chloro-5-[(2-oxopyridin-1(2H)-yl) methyl]-2-(trifluoromethyl)-2H-chromene-3-carboxylate The reaction was carried out in the same manner described in Example 157 Step 4 using 2-hydroxypyridine (140.3 mg, 1.4 mmol) and the bromide from Example 157 Step 3 (592.3 mg, 1.4 mmol). The crude product mixture was purified by flash chromatography (10/90-50/50 toluene-EtOAc) to give 209 mg (35%) of yellow oil.

Step 2: Preparation of 6-chloro-7-[(2-oxopyridin-1(2H)-yl) methyl]-2-(trifluoromethyl)-2H-chromene-3-carboxylic acid and 6-chloro-5-[(2-oxopyridin-1(2H)-yl) methyl]-2-(trifluoromethyl)-2H-chromene-3-carboxylic acid The ester from Example 167 Step 1 was converted to acid according to the procedure of Example 150 Step 4. The crude product was purified by reverse phase HPLC (column: Delta Pak 300×50 mm I.D., C18, 15 μM), using a H$_2$O—CH$_3$CN gradient 90/10-50/50 over 30 min, to give two products 167-1 and -2. $^1$H NMR 167-1: (DMSO-d$_6$) 7.90 (s, 1H), 7.75 (d,d, 1H, J=6.8 Hz, 1.9Hz) 7.72 (s, 1H), 7.52 (d,d,d, 1H, J=9.1 Hz, 7.4 Hz, 2.2 Hz), 6.47 (d, 1H, J=9.2 Hz), 6.38 (s, 1H), 6.32 (t,d, 1H, J=6.6 Hz, 1.3 Hz), 5.94 (q, 1H, J=7.2 Hz), 5.16 (d, 1H, J=15.9 Hz), 5.10 (d, 1H, J=16.0 Hz). 167-2 (DMSO-d$_6$) 8.16 (s, 1H), 7.54 (d, 1H, J=8.8 Hz), 7.39 (d,d,d, 1H, J=9.0 Hz, 6.7 Hz, 2.0 Hz), 7.33 (d,d, 1H, J=6.8 Hz, 1.7 Hz), 7.15 (d, 1H, J=8.8 Hz), 6.39 (d, 1H, J=8.8 Hz), 6.19 (t,d, 1H, J=6.6 Hz, 1.3 Hz) 5.95 (q, 1H, J=7.2 Hz) 5.39 (d, 1H, J=15.0 Hz) 5.24 (d, 1H, J=15.0 Hz).

EXAMPLEs 168a and −168b

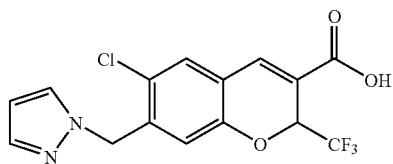

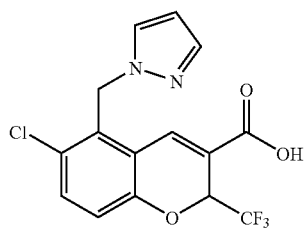

6-chloro-7-(1H-pyrazol-1-ylmethyl)-2-(trifluoromethyl)-2H-chromene-3-carboxylic acid and 6-chloro-5-(1H-pyrazol-1-ylmethyl)-2-(trifluoromethyl)-2H-chromene-3-carboxylic acid Step 1: Preparation 6-chloro-7-(1H-pyrazol-1-ylmethyl)-2-(trifluoromethyl)-2H-chromene-3-carboxylic acid and 6-chloro-5-(1H-pyrazol-1-ylmethyl)-2-(trifluoromethyl)-2H-chromene-3-carboxylic acid The reaction was carried out in the same manner described in Example 157 step 4 using pyrazole (76.0 mg, 1.11 mmol) and the bromide (592.3 mg, 1.4 mmol) from Example 157 Step 3. The crude product, an oil, was purified by flash chromatography (90/10 toluene-EtOAc) to give 144 mg (33%) of the desired material.

Step 2: Preparation of 6-chloro-7-(1H-p:razol-1-ylmethyl)-2-(trifluoromethyl)-2H-chromene-3-carboxylic acid and 6-chloro-5-(1H-pyrazol-1-ylmethyl)-2-(trifluoromethyl)-2H-chromene-3-carboxylic acid The ester (106 mg) of Example 168 Step 1 was converted to the acid according to the procedure of Example 166 Step 5 to give two products 168-1 and 168-2.

$^1$H NMR (MeOH-d$_4$) 7.79 (2H), 7.62 (d, 1H, J=1.7 Hz), 7.49 (s, 1H), 6.42 (t, 1H, J=2.1 Hz), 6.36 (s, 1H), 5.77 (q, 1H, J=7.0 Hz), 5.52 (d, 1H, J=16.8 Hz), 5.46 (d, 1H, J=16.8 Hz).

$^1$H NMR (MeOH-d$_4$) 8.22 (s, 1H), 7.56 (d, 1H, J=2.0 Hz), 7.51-7.48 (3H), 7.07 (d,d, 1H, J=8.2 Hz, 0.6 Hz), 6.30 (t, 1H, J=2.1 Hz), 5.80 (q, 1H, J=7.1 Hz), 5.66 (d, 1H, J=15.3 Hz), 5.63 (d, 1H,J=15.2 Hz).

EXAMPLE 169

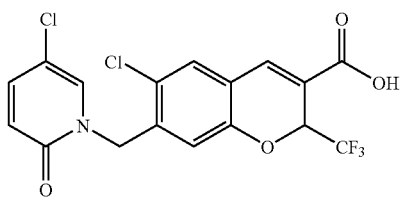

6-chloro-7-[(5-chloro-2-oxopyridin-1(2H)-yl) methyl]-2-(trifluoromethyl)-2H-chromene-3-carboxylic acid Step 1: Preparation of ethyl 6-chloro-7-[(5-chloro-2-oxopyridin-1(2H)-yl) methyl]-2-(trifluoromethyl)-2H-chromene-3-carboxylate The formation of the ester was performed according to the procedure outlined in Example 157 Step 4 starting with 97 mg of 5-chloro-2-pyridinol, 20.7 mg of sodium hydride (60% dispersion in mineral oil) and 300 mg of the bromide from Example 157 Step 3. The compound was purified on the FlashMaster® chromatography system eluting with 25% EA/hexane then 50% EA/hexane to give 128 mg (38%) of the desired compound.

Step 2: Preparation of 6-chloro-7-[(5-chloro-2-oxopyridin-1(2H)-yl) methyl]-2-(trifluoromethyl)-2H-chromene-3-carboxylic acid The ester of Example 169 Step 1 was converted to the acid according to procedure of Example 150 to give 75 mg (60%) of the desired acid, 169. $^1$H NMR (DMSO-$d_6$) 8.05 (d, 1H, J=2.8 Hz), 7.87 (s, 1H), 7.72 (s, 1H), 7.59 (d,d, 1H, J=9.7 Hz, 2.9 Hz), 6.53 (d, 1H, J=9.8 Hz), 6.47 (s, 1H), 5.95 (q, 1H, J=7.2 Hz), 5.12 (d, 1H, J=16.0 Hz), 5.07 (d, 1H, J=16.2 Hz).

EXAMPLE 170

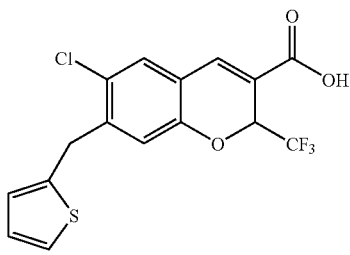

6-chloro-7-(thien-2-ylmethyl)-2-(trifluoromethyl)-2H-chromene-3-carboxylic acid

Step 1: Preparation of ethyl 6-chloro-7-formyl-2-(trifluoromethyl)-2H-chromene-3-carboxylate A crude preparation of the bromide (1.6 g, 4.0 mmol) from Example 157c was dissolved in 9 mL of anhydrous DMSO and to this solution was added solid NaHCO$_3$ (383.4 mg, 4.5 mmol). The solution was heated to 100° C. for 1.5 h. The reaction was removed from the heat and allowed to stand at 25° C. overnight. The next day the reaction was poured into 300 mL of brine and washed with 3×200 mL of EtOAc. The organic extracts were washed with brine, dried over MgSO$_4$, and filtered to give a brown solid which was purified by flash chromatography (97/3 toluene-EtOAc). All fractions containing desired product were collected to give a yellow solid. The solid was washed with hexane to give 382 mg of the desired product.

Step 2: Preparation of ethyl 6-chloro-7-[hydroxy (thien-2-yl)methyl]-2-(trifluoromethyl)-2H-chromene-3-carboxylate The title product from Example 170 Step 1 (100 mg, 0.31 mmol) was dissolved in 1.0 mL of Et$_2$O and cooled to −30° C. To this solution was added 0.31 mL thiophene-2-yl magnesium bromide solution (1.0 M in THF). After 10 minutes, the reaction mixture was pipetted over ice and diluted with ether and a dilute solution of H$_2$SO$_4$. The organic extracts were washed with a saturated solution of NaHCO$_3$, dried over MgSO$_4$, filtered, and evaporated under reduced pressure to dryness to provide 112 mg of a yellow oil. This oil was used as is without further purification.

Step 3: Preparation of ethyl 6-chloro-7-(thien-2-ylmethyl)-2-(trifluoromethyl)-2H-chromene-3-carboxylate The crude oil from Example 170 Step 2 was dissolved in 1 mL of DCM. To this solution was added triethylsilane (41 µL, 0.26 mmol) and 20 µL of TFA and stirred at 25° C. After 24 h, the solution was stirred vigorously with solid NaHCO$_3$ and H$_2$O, which quenched the reaction. Stirring was stopped after 5 min, and the solution was allowed to separate into layers. The reaction mixture stood in this state for one day prior to workup. The organic layer was dried over MgSO$_4$, filtered, and evaporated under reduced pressure to give an orange oil. The crude product was purified by flash chromatography to give reasonably pure compound.

Step 4: Preparation of 6-chloro-7-(thien-2-ylmethyl)-2-(trifluoromethyl)-2H-chromene-3-carboxylic acid The ester obtained from Example 170 Step 3 was converted to the acid according to the procedure of Example 150 Step 4. The product (20 mg) contained a major impurity amounting to 14%, which was determined to be the 7-methyl-6-chlorochromene, which can be removed by reverse phase HPLC (column: Delta Pak 300×50 mm I.D. C18, 15 µM) using a H$_2$O—CH$_3$CN gradient (conditions: 90/10-50/50 over 30 minutes) which gave pure product. $^1$H NMR (MeOH-$d_4$) 7.54 (s, 1H), 7.14 (s, 1H), 7.07 (d, 1H, J=4.3 Hz), 6.76-6.73 (3H), 5.55 (q, 1H, J=6.9 Hz), 4.15 (d, 1H, J=16.7 Hz), 4.05 (d, 1H, J=16.1 Hz).

EXAMPLE 171

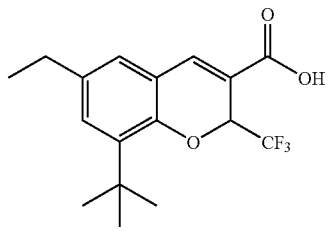

8-tert-butyl-6-ethyl-2-(trifluoromethyl)-2H-chromene-3-carboxylic acid 8-tert-butyl-6-ethyl-2-(trifluoromethyl)-2H-chromene-3-carboxylic acid hydrochloride was synthesized by the same procedures described in Example 155 using 2-tert-butyl-4-ethylphenol as the starting material. $^1$H NMR (DMSO-$d_6$) 1.16 (t, 3H, J=7.6 Hz), 1.34 (s, 9H), 2.54 (q, 2H, J=7.6 Hz), 5.96 (q, 1H, J=7.4 Hz), 7.17 (d, 1H, J=2.2 Hz), 7.18 (d, 1H, J=2.0 Hz), 7.78 (s, 1H).

EXAMPLE 172

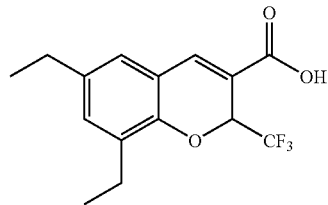

6,8-diethyl-2-(trifluoromethyl)-2H-chromene-3-carboxylic acid 6,8-diethyl-2-(trifluoromethyl)-2H-chromene-3-carboxylic acid was synthesized using procedures described in Example 150 with 5-ethyl-2-hydroxyacetophenone as the stating material. $^1$H NMR (DMSO-d$_6$) 1.20 (t, 3 H, J=7.5 Hz), 1.22 (t, 3H, J=7.6 Hz), 2.54-2.66 (m, 4H), 5.70 (q, 1H, J=7.0 Hz), 6.92 (d, 1H, J=2.1 Hz), 7.06 (d, 1H, J=2.1), 7.84 (s, 1H).

EXAMPLE 173

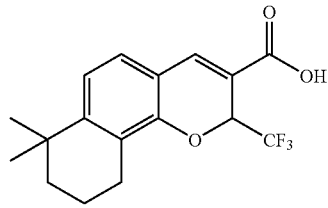

7,7-dimethyl-2-(trifluoromethyl)-7,8,9,10-tetrahydro-2H-benzo [h] chromene-3-carboxylic acid The title compound of Example 173 was prepared using procedures described in Example 100 starting with 5,5-dimethyl-5,6,7,8-tetrahydronaphthalen-1-ol. $^1$H NMR (MeOH-d$_4$) 7.75 (s, 1H), 7.10 (q, 2H, J=8.1 Hz), 5.77 (q, 1H, J=7.2 Hz), 2.66 (m, 2H), 1.82 (m, 2H), 1.68 (m, 2H), 1.31 (s, 3H), 1.30 (s, 3H).

EXAMPLE 174

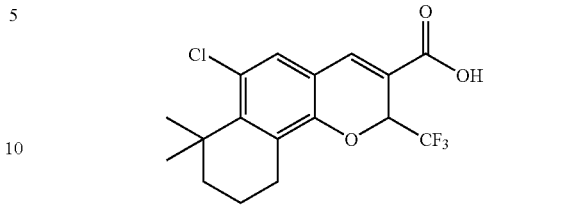

6-chloro-7,7-dimethyl-2-(trifluoromethyl)-7,8,9,10-tetrahydro-2H-benzo [h]chromene-3-carboxylic acid The title compound of Example 174 was prepared in the same manner as described in Example 103 Steps 3 and 4 except the starting material was ethyl 7,7-dimethyl-2-(trifluoromethyl)-7,8,9,10-tetrahydro-2H-benzo[h]chromene-3-carboxylate, an intermediate in the preparation of the title compound of Example 173. $^1$H NMR (MeOH-d$_4$) 7.63 (s, 1H), 7.13 (s, 1H), 5.72 (q, 1H, J=7.1 Hz), 2.61 (m, 2H), 1.67 (m, 2H), 1.62 (m, 2H), 1.44 (s, 3H), 1.43 (s, 3H).

EXAMPLE 175

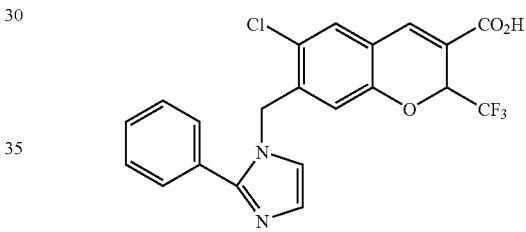

6-chloro-7-[(2-phenyl-1H-imidazol-1-yl)methyl]-2-(trifluoromethyl)-2H-chromene-3-carboxylic acid hydrochloride 6-chloro-7-[(2-phenyl-1H-imidazol-1-yl)methyl]-2-(trifluoromethyl)-2H-chromene-3-carboxylic acid hydrochloride was synthesized using the procedures described in Example 157 using 2-phenylimidazole: $^1$H NMR (DMSO-d$_6$) 5.47-5.56 (m, 2H), 5.98 (q, 1H, J=7.2 Hz), 6.84 (s, 1H), 7.60-7.71 (m, 6H), 7.83-7.87 (m, 3H).

TABLE 1

| Example Number | Formula | Theory | Found |
| --- | --- | --- | --- |
| Example 100 | C$_{13}$H$_{10}$ClF$_3$O$_3$•0.15 H$_2$O | C, 50.47, H, 3.29 | C, 50.25, H, 3.12 |
| Example 101 | C$_{13}$H$_{10}$ClF$_3$O$_3$ | C, 50.92, H, 3.29 | C, 50.85, H, 3.40 |
| Example 102 | C$_{13}$H$_{10}$ClF$_3$O$_3$ | C, 50.92, H, 3.29 | C, 50.92, H, 3.29 |
| Example 103 | C$_{13}$H$_{10}$ClF$_3$O$_3$ | C, 50.92, H, 3.29, Cl, 11.56 | C, 50.81, H, 3.10, Cl, 11.86 |
| Example 104 | C$_{14}$H$_{12}$ClF$_3$O$_3$ | C, 52.43, H, 3.77 | C, 52.59, H, 3.80 |

TABLE 1-continued

| Example Number | Formula | Theory | Found |
|---|---|---|---|
| Example 105 | $C_{13}H_{10}ClF_3O_3$ | C, 50.92, H, 3.29 | C, 50.85, H, 3.20 |
| Example 106 | $C_{16}H_{17}F_3O_3$ | C, 61.14, H, 5.45 | C, 61.11, H, 5.45 |
| Example 107 | $C_{16}H_{16}ClF_3O_3$ | C, 55.10, H, 4.62 | C, 55.05, H, 4.64 |
| Example 108 | $C_{17}H_{19}F_3O_3$ | C, 62.19, H, 5.83 | C, 62.11, H, 5.68 |
| Example 110 | $C_{18}H_{20}ClF_3O_3$ | C, 57.38, H, 5.35. | C, 57.44, H, 5.12. |
| Example 111 | $C_{17}H_{18}ClF_3O_3 \cdot 0.25\ H_2O$ | C, 55.59, H, 4.94 | C, 55.20, H, 4.86 |
| Example 112 | $C_{16}H_{17}ClF_3O_4$ | C, 58.16, H, 5.19 | C, 58.06, H, 4.93 |
| Example 114 | $C_{15}H_{13}F_3O_4 \cdot 0.25\ H_2O$ | C, 56.52, H, 4.11 | C, 56.40, H, 4.68 |
| Example 115 | $C_{15}H_{12}ClF_3O_5 \cdot 2\ H_2O$ | C, 44.96, H, 3.94 | C, 44.96, H, 3.02 |
| Example 116 | $C_{16}H_{16}ClF_3O_4$ | C, 52.69, H, 4.42 | C, 52.31, H, 4.68 |
| Example 121 | $C_{18}H_{22}F_3NO_4 \cdot HCl$ | C, 54.90, H, 5.89, N, 3.56 | C, 54.61, H, 6.49, N, 3.20 |
| Example 125 | $C_{18}H_{20}ClF_3O_3$ | C, 57.38, H, 5.35 | C, 56.98, H, 5.62 |
| Example 126 | $C_{18}H_{20}ClF_3O_3 \cdot 0.25\ H_2O$ | C, 56.70, H, 5.29 | C, 56.63, H, 5.49 |
| Example 128 | $C_{15}H_{14}ClF_3O_4 \cdot 0.125\ H_2O$ | C, 51.04, H, 4.00 | C, 50.64, H, 4.40 |
| Example 129 | $C_{15}H_{14}ClF_3O_4 \cdot 0.75\ H_2O$ | C, 49.46, H, 3.87 | C, 49.46, H, 4.32 |
| Example 132 | $C_{13}H_{11}F_3O_5$ | C 51.33%, H 3.64% | C 51.11%, H 3.63% |
| Example 133 | $C_{13}H_9Cl_2F_3O_5$ | C 41.85%, H 2.43%, Cl 19.00% | C 41.92%, H 2.34%, Cl 18.96% |
| Example 136 | $C_{12}H_8ClF_3O_3$ | C 49.25%, H 2.76%, Cl 12.11% | C 48.91%, H 2.61%, Cl 11.94% |
| Example 138 | $C_{12}H_8ClF_3O_3 \cdot 0.3\ H_2O.$ | C 48.36%, H 2.91% | C 48.38%, H 2.99% |
| Example 139 | $C_{12}H_8ClF_3O_3$ | C 49.25%, H 2.76%, Cl 12.11% | C 49.03%, H 2.99%, Cl 12.44% |
| Example 140 | $C_{15}H_{14}F_3NO_3$ | C 57.51%, H 4.50%, N 4.47% | C 57.47%, H 4.70%, N 4.39% |
| Example 146 | $C_{14}H_{11}IF_3O_3 \cdot 0.25\ H_2O$ | C, 58.24 H, 4.01 | C, 58.55 H, 4.08 |
| Example 147 | $C_{14}H_{10}ClF_3O_3 \cdot 0.25\ H_2O$ | C, 52.03 H, 3.27 | C, 51.32 H, 3.47 |
| Example 148 | $C_{13}H_9Cl_2F_3O_3$ | C, 45.77; H, 2.66; Cl, 20.79. | C, 45.95; H, 2.53; Cl, 20.27. |
| Example 149 | $C_{13}H_{11}F_3O_3$ | C, 57.36%, H, 4.07% | C, 57.23%, H, 3.95% |
| Example 150 | $C_{14}H_{13}O_3F_3$ | C, 58.74; H, 4.58. | C, 58.75; H, 4.45. |
| Example 153 | $C_{14}H_{13}O_3F_3$ | C, 58.74; H, 4.58. | C, 58.50; H, 4.62. |
| Example 154 | $C_{16}H_{17}O_3F_3$ | C, 61.14; H, 5.45. | C, 61.09; H, 5.61. |
| Example 155 | $C_{14}H_{13}O_3F_3$ | C, 58.74; H, 4.58. | C, 58.65; H, 4.88. |
| Example 156 | $C_{15}H_{15}O_3F_3 \cdot 1.1\ H_2O$ | C, 56.28; H, 5.42. | C, 56.13; H, 5.07. |
| Example 157 | $C_{18}H_{16}N_2O_3ClF_3 \cdot HCl.$ | C, 48.45; H, 4.07; N, 6.28. | C, 48.18; H, 4.19; N, 6.19. |
| Example 158 | $C_{15}H_{10}N_2O_3ClF_3 \cdot 1.0\ HCl.$ | C, 45.59; H, 2.81; N, 7.81. | C, 45.39; H, 2.95; N, 6.98. |
| Example 159 | $C_{16}H_{12}N_2O_3ClF_3 \cdot 1.5\ HCl \cdot 0.5\ CF_3COOH$ | C, 42.15; H, 2.91; N, 5.78. | C, 42.36; H, 2.95; N, 5.34. |

TABLE 1-continued

| Example Number | Formula | Theory | Found |
|---|---|---|---|
| Example 160 | $C_{18}H_{16}N_2O_3ClF_3$•HCl.1.5 $H_2O$ | C, 46.57; H, 4.34; N, 6.03. | C, 46.87; H, 4.49; N, 6.19. |
| Example 161 | $C_{19}H_{12}N_2O_3ClF_3$•1.5 HCl | C, 49.24; H, 2.94; N, 6.04. | C, 49.34; H, 3.32; N, 5.87. |
| Example 162-1 | $C_{17}H_{14}N_2O_3ClF_3$•1.5 HCl•0.25 $H_2O$ | C, 45.79; H, 3.62; N, 6.28. | C, 45.90; H, 4.05; N, 6.32 |
| Example 162-2 | $C_{17}H_{14}N_2O_3ClF_3$•1.75 HCl | C, 45.32; H, 3.52; N, 6.22. | C, 45.11; H, 3.81; N, 6.19. |
| Example 163-1 | $C_{15}H_8N_2O_3ClF_3$•0.25 HCl | C, 41.26; H, 1.90; N, 6.41. | C, 41.40; H, 2.03; N, 6.32. |
| Example 163-2 | $C_{15}H_8N_2O_3ClF_3$•$H_2O$ | C, 40.43; H, 2.26; N, 6.29. | C, 40.99; H, 2.76; N, 5.96. |
| Example 164 | $C_{18}H_{12}O_4ClF_3$ | C, 56.19; H, 3.14. | C, 55.96; H, 3.23. |
| Example 165 | $C_{14}H_{12}O_4ClF_3$•0.2 $H_2O$ | C, 49.41; H, 3.67. | C, 49.11; H, 3.74. |
| Example 166 | $C_{14}H_{13}O_4F_3$ | C, 55.63; H, 4.34. | C, 55.60; H, 4.79. |
| Example 167-1 | $C_{17}H_{11}NO_4ClF_3$•0.5 $H_2O$ | C, 51.94; H, 3.03; N, 3.48. | C, 51.73; H, 3.06; N, 3.55. |
| Example 167-2 | $C_{17}H_{11}NO_4ClF_3$•0.5 $H_2O$•0.5 TFA | C, 47.86; H, 2.79; N, 3.10. | C, 47.69; H, 2.75; N, 3.08. |
| Example 168-1 | $C_{15}H_{10}N_2O_3ClF_3$•0.5 HCl•0.6 TFA | C, 40.38; H, 2.53; N, 5.81. | C, 40.05; H, 2.30; N, 6.00. |
| Example 168-2 | $C_{15}H_{10}N_2O_3ClF_3$•1.5 HCl | C, 43.58; H, 2.80; N, 6.78. | C, 43.34; H, 2.78; N, 7.58. |
| Example 169 | $C_{17}H_{10}NO_4Cl_2F_3$•0.2 $H_2O$ | C, 48.31; H, 2.61; N, 3.24 | C, 48.39; H, 2.56; N, 3.12 |
| Example 170 | $C_{16}H_{10}O_3ClF_3S$•0.9 $H_2O$ | C, 49.15; H, 3.04. | C, 49.13; H, 2.79. |
| Example 171 | $C_{17}H_{19}O_3F_3$ | C, 62.19; H, 5.83. | C, 62.08; H, 6.06. |
| Example 172 | $C_{15}H_{15}O_3F_3$ | C, 60.00; H, 5.04. | C, 59.82; H, 5.20. |
| Example 173 | $C_{17}H_{17}O_3F_3$ | C, 62.57; H, 5.25. | C, 62.56; H, 5.50. |
| Example 174 | $C_{17}H_{16}ClO_3F_3$ | C, 56.60; H, 4.47, Cl, 9.83. | C, 56.50; H, 4.39, Cl, 10.07 |
| Example 175 | $C_{12}H_{14}N_2O_3ClF_3$•HCl | C, 52.52; H, 3.36; N, 5.83. | C, 52.24; H, 3.72; N, 5.63 |

Parallel chemistry General: Analytical LCMS reverse phase chromatography was carried out using a C18 column 2.1 mm i.d.×30 mm and a linear gradient of 5% acetonitrile in 0.1% TFA/water to 95% acetonitrile in 0.1% TFA/water over 4.5 min. at a flow rate of 1 mL/min. The eluant composition was held at 95% acetonitrile in 0.1% TFA/water from 4.5 min to 5 min. The LCMS was equipped with a diode array detector, a mass spectral detector (MSD) and an evaporative light scattering detector. A flow splitter was attached after the UV diode array detector to allow flow to a mass spectral detector (MSD) and the ELS. The mass spectra were obtained using an Agilent MSD in electrospray positive mode. Preparative reverse phase chromatography was carried out using a C 18 column 41.4 mm i.d. of 50 mm, 100 mm or 300 mm length.

Compounds prepared by parallel synthesis methods are recorded in the appropriate tables and characterized by determination of purity, confirmation of molecular weight, analytical HPLC retention time (LC, min) and gravimetric determination of yield. The HPLC retention time was determined using analytical LCMS reverse phase analysis and represents the time obtained for the compound having the desired molecular ion. The retention time is based on the observed time in the UV chromatogram. The molecular ion listed in the table is the baseline (100%) peak, unless otherwise noted. Purity of the compounds prepared by parallel synthesis was determined by detection of the peak of the desired molecular ion and integration of the corresponding peak detected either by UV at 254 nm or by ELS. Purity is described as percent and is a ratio of the area of the desired peak over the total area of all peaks in the chromatogram. The percent yield is based on gravimetric determination of the final product after suitable purification.

Parallel Synthesis of a Compound Library with 6 and 8-Position Substitutions

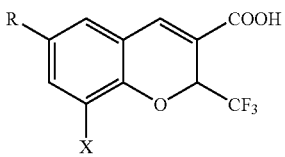

X = H or Cl
R = as described

Preparation of Intermediates and Examples 201-261

Preparation of Ethyl 6-iodo-2-(trifluoromethyl)-2H-chromene-3-carboxylate

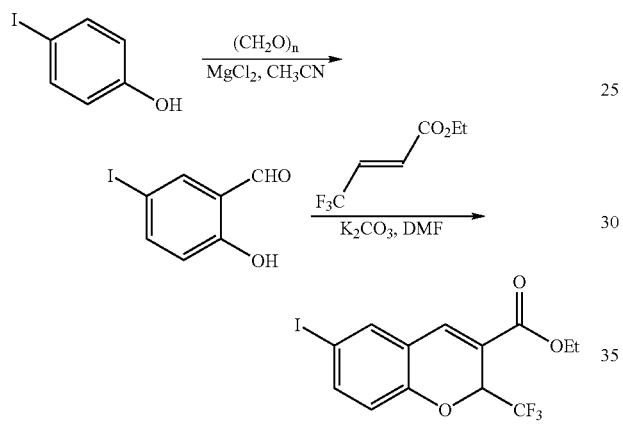

Step 1. Preparation of 2-hydroxy-5-iodobenzaldehyde

To the mixture of 20 g (91 mmol) of 4-iodophenol and 25.1 g (264 mmol) anhydrous magnesium dichloride in 455 mL of anhydrous acetonitrile was added triethylamine and paraformaldehyde. The mixture was heated to reflux for 4 h, allowed to cool to rt and treated with 500 mL of 5% HCl. The solution was extracted three times with EtOAc. The combined organic extracts were washed with brine (3×) and dried over anhydrous magnesium sulfate. The dried organic solution was evaporated to afford an oil, which was purified by silica gel chromatography with EtOAc/hexane (2:8). Concentration of the desired fractions afforded 15 g (66%) of a yellow solid, which was used directly in the next step without further purification.

Step 2. Preparation of Ethyl 6-iodo-2-(trifluoromethyl)-2H-chromene-3-carboxylate To a solution of 6.0 g (24 mmol) of 2-hydroxy-5-iodobenzaldehyde and 5 mL (33.3 mmol) of ethyl 4,4,4-trifluorocrotonate in 20 mL of dry DMF at 60° C. was added potassium carbonate in one portion. The mixture was stirred at 60° C. overnight. After cooling to room temperature, the solid was filtered and washed with EtOAc. The combined filtrates were diluted by addition with 300 mL EtOAc and washed with brine. The organic phase was dried over anhydrous magnesium sulfate and evaporated to afford an oil, which was further purified silica gel chromatography with EtOAc/hexane (1:9). Concentration of the desired fractions afforded 4.7 g (49%) of a light yellow solid: $^1$H NMR(CDCl$_3$/300 MHz) 7.65-7.55 (m, 3H), 6.78 (d, J=8.4Hz, 1H), 5.72 (q, J=6.6 Hz, 1H), 4.34(m, 2H), 1.37(t, J=6.9 Hz, 3H). MS (ES+) 398.9 (M+H, 100).

Preparation of Ethyl 8-chloro-6-iodo-2-(trifluoromethyl)-2H-chromene-3-carboxylate

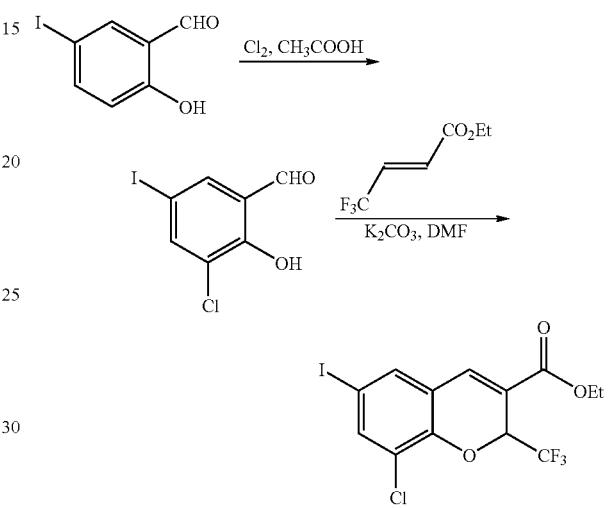

Step 1. Preparation of 3-chloro-2-hydroxy-5-iodobenzaldehyde

To 24 g (96.8 mmole) of 5-iodosalicylaldehyde in 320 mL of acetic acid was added an excess of gaseous chlorine. After addition of about 10 g of Cl$_2$, a white solid appeared in the solution. The mixture was heated to 70° C. and allowed to stir for 3 h. The heated solution was homogeneous and remained so after cooling to rt. The mixture was added to 1200 mL of water and allowed to stir for 1 h. The resultant solid was collected by filtration, washed with water, filtered and allowed to air dry to afford 27.3 g of a yellow solid. The solid was recrystallized by dissolving the material in 250 mL of hot methanol and adding 80 mL of H$_2$O. After standing overnight, the crystalline solid was collected and air-dried to afford 20.3 g (74.2%) of a yellow solid. The product contained a minor impurity (approx. 9% by $^1$H NMR) and was used in the next step without further purification: $^1$H NMR (CDCl$_3$/400 MHz) 7.78 (d, 1H, J=2.1 Hz), 7.88 (d, 1H, J=1.8 Hz), 9.83 (s, 1H), 11.40 (s, 1H); $^{13}$C NMR (CDCl$_3$/100 MHz) 79.5, 122.8, 123.7, 140.3, 144.4, 156.9, 194.8; MS (ESI+) 283 (M+1, 100); HRMS (EI) m/z calcd for (C$_7$H$_4$O$_2$ICl) 281.8945, found 281.8899.

Step 2. Preparation of ethyl 8-chloro-6-iodo-2-(trifluoromethyl)-2H-chromene-3-carboxylate To 18 g (63.7 mmole) of 3-chloro-2-hydroxy-5-iodobenzaldehyde in 16 mL of DMF was added 14.3 mL (16.1 g, 95.6 mmole) of ethyl trifluorocrotonate and 9.69 g (70 mmole) of K$_2$CO$_3$. The mixture was heated to 100° C. for 2 h. The mixture was allowed to cool, treated with 300 mLs of H₂O and extracted three times with Et₂O. The combined extracts were washed with water and filtered through a silica plug (4.5×6 cm). The silica was washed with methylene chloride and combined filtrates concd to give 10.39 g of a yellow solid. Recystalization in hexanes gave 6.64 g (24.1%) of a crystalline, yellow solid: ¹H NMR (CDCl₃/400 MHz) 1.35 (t, 3H, J=7.1 Hz), 4.33 (m, 2H), 5.81 (q, 1H, J=6.6 Hz), 7.44 (d, 1H, J=2.0 Hz), 7.62 (s, 1H), 7.66 (d, 1H, J=2.0 Hz); ¹⁹F NMR (CDCl₃/400 MHz) −79.0 (d, 3F, J=6.8 Hz); ¹³C NMR (CDCl₃/100 MHz) 13.1, 60.8, 70.4 (q, J=33.7 Hz), 82.6 (C-I), 117.7, 121.2, 121.8, 121.9 (q, J=287.2 Hz), 133.6, 134.9, 139.9, 147.9, 162.0; MS (ESI+) 433 (M+1, 100); HRMS (EI) m/z calcd for (C₁₃H₉O₃IClF₃) 431.9237, found 431.9221.

Preparation of Ethyl 6-Bromo-8-chloro-2-(trifluoromethyl)-2H-chromene-3-carboxylate The ethyl 6-bromo-8-chloro-2-(trifluoromethyl)-2H-chromene-3-carboxylate was prepared from 5-bromo-3-chloro-2-hydroxybenzaldehyde in an analogous manner to step 2, preparation of ethyl 8-chloro-6-iodo-2-(trifluoromethyl)-2H-chromene-3-carboxylate.

EXAMPLE 201

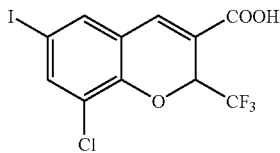

8-Chloro-6-iodo-2-(trifluoromethyl)-2H-chromene-3-carboxylic acid

To 180 mg (0.42 mmole) of ethyl 8-chloro-6-iodo-2-(trifluoromethyl)-2H-chromene-3-carboxylate was added 100 mgs of LiOH—H₂O and 5 mL of a solvent mixture of THF/MeOH/H₂O (7:2:1). The mixture was heated to reflux for 30 min. and allowed to cool to rt. After standing overnight, the mixture was concd in vacuo, treated with 20 mL 1N HCl and allowed to stir. The mixture was extracted three times with Et₂O, the combined extracts dried and concd in vacuo to give 150 mgs (88.3%) of an off-white solid: ¹H NMR (CDCl₃/d⁶-acetone/400 MHz) 5.86 (q, 1H, J=6.7 Hz), 7.60 (s, 1H), 7.70 (s, 1H), 7.75 (s, 1H); ¹⁹F NMR (CDCl₃/d⁶-acetone/400 MHz) −79.2 (d, 3F, J=6.8 Hz); MS(ESI+) 405 (M+1, 100, one Cl pattern); HRMS (ES-) m/z calcd for (C₁₁H₄O₃IClF₃) 402.8840, found 402.8850.

Preparation of 6-Aryl-2-(trifluoromethyl)-2H-chromene-3-carboxylic acids

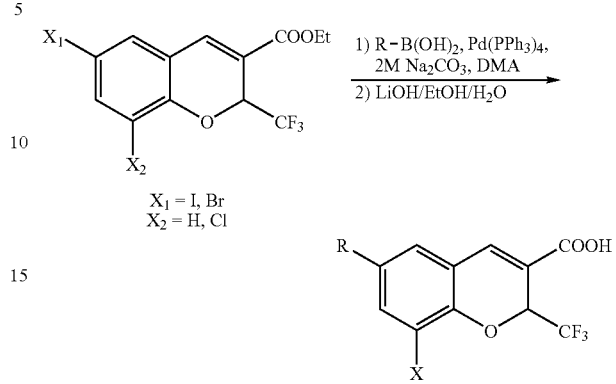

X₁ = I, Br
X₂ = H, Cl

EXAMPLE 202

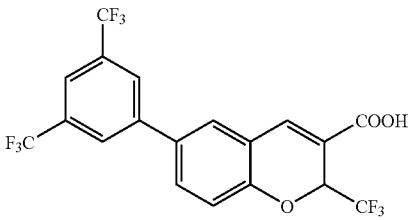

6-[3,5-bis(trifluoromethyl)phenyl]-2-(trifluoromethyl)-2H-chromene-3-carboxylic acid Step 1. Preparation of Ethyl 6-[3,5-bis(trifluoromethyl)phenyl]-2-(trifluoromethyl)-2H-chromene-3-carboxylate To the solution of 0.3 g (0.75 mmol) of ethyl 6-iodo-2-(trifluoromethyl)-2H-chromene-3-carboxylate in 10 mL of dimethylacetylamide under nitrogen atmosphere was added 87 mg (0.0075 mmol) of tetrakistriphenylphosphine, 0.29 g (1.13 mmol) 3,5-ditrifluoromethylphenylboric acid, and 1.0 mL of 2.0 M aqueous sodium carbonate solution. The mixture was bubbled with nitrogen gas for two min. and subsequently heated to 95° C. overnight. After cooling to room temperature, 50 mL of 4:1 EtOAc/MeOH mixture was added. To the resulting mixture was added 50 mL of brine. The product was extracted with ethyl acetate three times. The combined organic phases were washed with brine and dried over anhydrous magnesium sulfate. After removing the volatiles, the residue was purified on a silica gel column with EtOAc/hexane (1:9) to afford 0.20 g (56%) of a light grey solid: ¹H NMR (CDCl₃/400 MHz) 7.94(s, 2H), 7.83(s, 1H), 7.80(s, 1H), 7.55(dd, J=2.4 Hz, 8.4 Hz, 1H), 7.46(s, J=2.4 Hz, 1H), 7.31(s, 1H), 7.10(d, J=8.4 Hz, 1H), 5.75(q, J=6.4 Hz, 1H), 4.32(m, 2H), 1.35(t, J=7.2 Hz). MS (ES+) 485.0(M+1, 100). HRMS (EI) m/z calcd for (C₂₁H₁₃F₉O₃) 484.0721, found 484.0687.

Step 2. Preparation of 6-[3,5-bis(trifluoromethyl)phenyl]-2-(trifluoromethyl)-2H-chromene-3-carboxylic acid To the solution of 150 mg (0.31 mmol) of ethyl 6-[3,5-bis(trifluoromethyl)phenyl]-2-(trifluoromethyl)-2H-chromene-3-carboxylate in 5 mL of tetrahydrofliran was added a solution of 51 mg (1.24 mmol) of lithium hydroxide (LiOH.2H$_2$O) in 5 mL of water. The resulting mixture was heated to reflux for one hr. After cooling to room temperature, the volatiles were removed. The residue was diluted with water, then acidified at 0° C. with dilute hydrochloric acid to pH=1.5. The product was then extracted with ethyl ether. The combined organic extracts were dried over anhydrous magnesium sulfate. Evaporation of the dried organic solution afforded 0.13 g (92%) of a light yellow solid: $^1$H NMR (CDCl$_3$/400 MHz) 7.89(s, 2H), 7.78(s, 1H), 7.77(s, 1H), 7.51(dd, J=2.4 Hz, 8.4 Hz, 1H), 7.41(d, J=2.4Hz, 1 H), 7.06(d, J=8.4 Hz, 1H), 5.69(m, 1H). MS (ES+) 457.0(M+1, 100).

Preparation of 6-Aryl-2-(trifluoromethyl)-2H-chromene-3-carboxylic acids by a Parallel Method

EXAMPLE 203

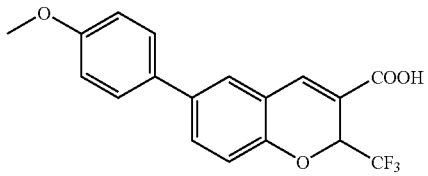

6-(4-methoxyphenyl)-2-(trifluoromethyl)-2H-chromene-3-carboxylic acid

Step 1. Preparation of ethyl 6-(4-methoxyphenyl)-2-(trifluoromethyl)-2H-chromene-3-carboxylate All reactions were carried out in an aluminum reactor block equipped with a condensor, inert atmosphere and space for 24 vessels (Prep Reactor, J-Kem, St. Louis, Mo.). A solution of 0.20 g (0.5 mmol) of ethyl 6-iodo-2-(trifluoromethyl)-2H-chromene-3-carboxylate in 3 mL of anhydrous dimethylacetamide was prepared in a 50 mL glass centrifuge tube equipped with a septum screw cap. The solution was degassed by bubbling nitrogen through the mixture for 10 min. The solution was treated with 0.11 mL (0.75 mmol) of 4-methoxybenzeneboronic acid, 58 mg (0.1 eq, 0.05 mmol) of tetrakis(triphenylphosphine)-palladium (0) and 2.0 mL of degassed 2M aqueous Na$_2$CO$_3$ (4.0 eq, 2.0 mmol). The solution was flushed with nitrogen, capped, heated to 95° C for 16 hours in an aluminum reactor block equipped with a condenser and kept under nitrogen atmosphere. After cooling to room temperature, brine was added and the mixture extracted 4 times with ethyl acetate. The organic layer was dried over sodium sulfate, filtered and dried under a stream of nitrogen. The product was used in the next step without further purification.

Step 2. Preparation of 6-(4-methoxyphenyl)-2-(trifluoromethyl)-2H-chromene-3-carboxylic acid The product of step 1 was dissolved in a mixture of 5 mL of ethanol and 1 mL of THF. A solution of 165 mg of lithium hydroxide monohydrate in 6 mL of water was prepared and added to the solution of the ester. The vessel was capped and heated to 80° C. for 1 hour. After cooling to room temperature, the mixture was concd using a nitrogen stream. The basic solution was acidified with 3N HCl to pH=2 and extracted 4 times with ethyl acetate. The organic layers were combined, dried over sodium sulfate, filtered and concd. The sample was purified by reverse phase chromatography system to afford 63.2 mg (36%) of a yellow solid: $^1$H NMR (CDCl$_3$, CD$_3$OD/400 MHz) 3.78 (s, 3H), 5.64 (q, 1H, J=6.8 Hz), 6.89(d, 2H, J=8.8 Hz), 6.95 (d, 1H, J=8.8 Hz), 7.32 (s, 1H), 7.40-7.44 (m, 3H), 7.72 (s, 1H); MS (ES+) 351 (M+1, 100); LC-MS purity 100% (UV and ELSD); HRMS (ES−) m/z calcd for (M−1; C$_{18}$H$_{12}$O$_4$F$_3$) 349.0682, found 349.0678.

Preparation of 6-Aryl-2-(trifluoromethyl)-2H-chromene-3-carboxylic Acids by a Parallel Method The following Examples in table 2 were prepared as previously described for 6-(4-methoxyphenyl)-2-(trifluoromethyl)-2H-chromene-3-carboxylic acid using parallel synthesis apparatus and either ethyl 6-iodo-2-(trifluoromethyl)-2H-chromene-3-carboxylate or ethyl 8-chloro-6-bromo-2-(trifluoromethyl)-2H-chromene-3-carboxylate as the starting material.

TABLE 2

Yield, Purity and Mass Spectral Data for 6-Aryl-2-(trifluoromethyl)-2H-chromene-3-carboxylic Acids Prepared by Parallel Synthesis Methods.[1]

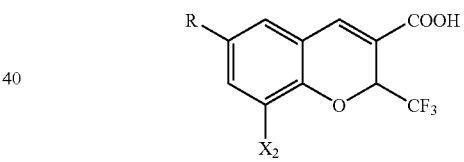

| Example | LC (ret. Time) | MS (ES+) | % Purity | % Yield |
|---|---|---|---|---|
| X2 = H | | | | |
| 204 | 3.004 | 327 | 99 | 33 |
| 205 | 2.849 | 311 | 99 | 39 |
| 206 | 1.838 | 336 | 95 | 48 |
| 207 | 3.213 | 341 | 97 | 43 |
| 208 | 3.039 | 365 | 99 | 44 |
| 209 | 2.971 | 365 | 99 | 37 |
| 203 | 3.024 | 351 | 99 | 36 |
| 210 | 3.273 | 335 | 99 | 36 |
| 211 | 1.537 | 322 | 95 | 19 |
| 212 | 3.554 | 363 | 97 | 35 |
| 213 | 2.657 | 352 | 97 | 39 |
| 214 | 3.431 | 371 | 95 | 46 |
| 215 | 3.241 | 366 | 95 | 46 |
| 216 | 1.470 | 322 | 99 | 29 |
| 217 | 2.776 | 360 | 95 | 57 |
| 218 | 2.114 | 372 | 99 | 43 |
| 219 | 2.786 | 381 | 95 | 43 |
| 220 | 2.745 | 383 | 95 | 23 |
| 221 | 3.379 | 389 | 95 | 38 |
| 222 | 3.368 | 389 | 95 | 32 |
| X2 = Cl | | | | |
| 223 | 3.278 | 355 | 99 | 65 |
| 224 | 3.502 | 390 | 99 | 41 |

TABLE 2-continued

Yield, Purity and Mass Spectral Data for 6-Aryl-2-(trifluoromethyl)-2H-chromene-3-carboxylic Acids Prepared by Parallel Synthesis Methods.[1]

| Example | LC (ret. Time) | MS (ES+) | % Purity | % Yield |
|---|---|---|---|---|
| 225 | 3.353 | 390 | 100 | 42 |
| 226 | 3.272 | 373 | 100 | 67 |
| 227 | 3.129 | 361 | 99 | 66 |
| 228 | 3.059 | 345 | 97 | 73 |
| 229 | 2.119 | 370 | 95 | 53 |
| 230 | 3.138 | 400 | 95 | 52 |
| 231 | 3.132 | 399 | 88 | 62 |
| 232 | 3.208 | 385 | 100 | 75 |
| 233 | 3.448 | 369 | 99 | 74 |
| 234 | 3.734 | 397 | 100 | 74 |
| 235 | 2.928 | 386 | 100 | 35 |
| 236 | 3.593 | 405 | 100 | 53 |
| 237 | 3.437 | 401 | 95 | 77 |
| 238 | 1.840 | 356 | 95 | 10 |
| 239 | 2.996 | 394 | 95 | 53 |
| 240 | 2.502 | 406 | 100 | 7 |
| 241 | 3.007 | 415 | 100 | 37 |
| 242 | 2.740 | 417 | 95 | 44 |
| 243 | 3.651 | 423 | 100 | 75 |
| 244 | 3.523 | 423 | 100 | 77 |
| 245 | 2.983 | 345 | 98 | 75 |
| 246 | 3.256 | 385 | 95 | 77 |

[1]See General Experimental section for description of recorded data. LC indicates the chromatographic retention time in min. % Purity was determined by UV at 254 nm.

EXAMPLE 232

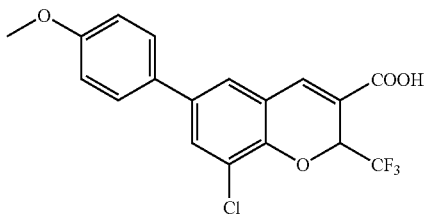

8-Chloro-6-(4-methoxyphenyl)-2-(trifluoromethyl)-2H-chromene-3-carboxylic acid

The sample obtained from the parallel synthesis method was purified by reverse phase chromatography system to afford 150.6 mg (75%) of a yellow solid: $^1$H NMR (CDCl$_3$, CD$_3$OD/300 MHz) 3.87 (s, 3H), 5.85 (q, 1H, J=6.3 Hz), 7.0 (d, 1H, J=8.1 Hz), 7.36 (s, 1H), 7.48 (d, 2H, J=8.7 Hz), 7.58 (s, 1H), 7.82 (s, 1H); MS (ES+) 385 (M+1, 100)

Preparation of 6-Alkyl-2-(trifluoromethyl)-2H-chromene-3-carboxylic Acids

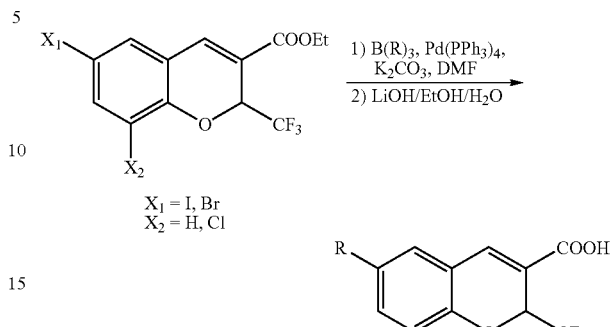

$X_1$ = I, Br
$X_2$ = H, Cl

EXAMPLE 247

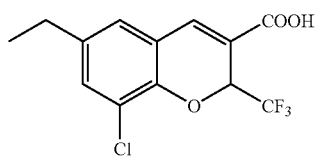

8-Chloro-6-ethyl-2-(trifluoromethyl)-2H-chromene-3-carboxylic acid

Step 1. Preparation of ethyl 8-chloro-6-ethyl-2-(trifluoromethyl)-2H-chromene-3-carboxylate To a solution of 500 mg (1.16 mmol) ethyl 8-chloro-6-iodo-2-(trifluoromethyl)-2H-chromene-3-carboxylate in 3 mL of anhydrous DMF was added 0.481 g (3.48 mmol, 3.0 eq.) of potassium carbonate, 0.134 g (0.116 mmol, 0.1 eq.) of tetrakis(triphenylphosphine)-palladium(0) and 1.74 mL (1.74 mmol, 1.5 eq.) of 1M triethylborane in THF. The vessel was heated to 110° C. for 5 hours under a nitrogen atmosphere. After cooling to room temperature, the mixture was treated with water and extracted with ethyl acetate. The organic layer was washed 4 times with water and 2 times with brine, dried over sodium sulfate, filtered and concd in vacuo. The product was carried to the next step without further purification.

Step 2. Preparation of 8-chloro-6-ethyl-2-(trifluoromethyl)-2H-chromene-3-carboxylic acid The ester obtained from step 1 was dissolved in 5 mL ethanol and 1 mL of THF. A solution of 165 mg lithium hydroxide monohydrate in 6 mL of water was prepared and added to the ester solution. The vessel was capped and heated to 80° C. for 1 hour. After cooling to room temperature, the ethanol and tetrahydrofuran were removed using a nitrogen stream. The basic solution was then acidified with 3N HCl until the pH=2 then extracted 4 times with ethyl acetate. The organic layers were combined, dried over sodium sulfate, filtered and solvent removed. The sample was purified by reverse phase chromatography system to afford 153 mg (70%) of a light brown solid: ¹H NMR (CDCl₃, CD₃O D/400 MHz) 1.22 (t, 3H, J=7.6 Hz), 2.58 (q, 2H, J=7.6 Hz), 5.78 (q, 1H, J=6.8 Hz), 6.97 (s, 1H), 7.21 (s, 1H), 7.70 (s, 1H); MS (ES+) 307 (M+1, 50); LC-MS purity 95% at 3.026 min. (UV), 100% (ELSD); HRMS (ES−) m/z calcd for (M−1; C₁₃H₉O₃ClF₃) 305.0187, found 305.0210.

EXAMPLE 248

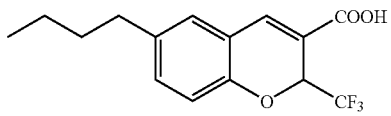

6-Butyl-2-(trifluoromethyl)-2H-chromene-3-carboxylic acid

Using the method described for 8-chloro-6-ethyl-2-(trifluoromethyl)-2H-chromene-3-carboxylic acid, a brown solid (10.2 mg, 12%) was obtained: 1H NMR (CDCl₃, CD₃OD/400 MHz) 0.85 (t, 3H, J=7.2 Hz), 1.26 (m, 2H), 1.49 (m, 2H), 2.47 (t, 2H, J=7.6 Hz), 5.58 (m, 1H), 6.80 (d, 1H, J=8 Hz), 6.95 (s, 1H), 7.05 (d, 1H, J=8 Hz), 7.65 (s, 1H); MS (ES+) 301 (M+1, 100); LC-MS purity 100% (ELSD), 95% (UV) at 3.263 min.

EXAMPLE 249

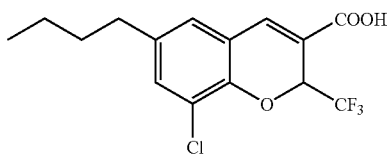

6-Butyl-8-chloro-2-(trifluoromethyl)-2H-chromene-3-carboxylic acid

Using the method described for 8-chloro-6-ethyl-2-(trifluoromethyl)-2H-chromene-3-carboxylic acid, a tan solid (232.9 mg, 50%) was obtained: ¹H NMR (CDCl₃, CD₃OD/ 300 MHz) 0.93 (t, 3H, J=7.2 Hz), 1.37 (m, 2H), 1.59 (m, 2H), 2.53 (t, 2H, J=7.8 Hz ), 5.29 (q, 1H, J=6.9 Hz), 6.95 (d, 1H, J=2.1 Hz), 7.19 (d, 1H, J=1.8 Hz), 7.71 (s, 1H); MS (ES+) 335 (M+1, 100); LC-MS purity 95% at 3.430 min. (UV), 100% (ELSD); HRMS (ES−) m/z calcd for (M−1; C₁₅H₁₃O₃ClF₃) 333.0500, found 333.0491.

Preparation of 6-Substituted-2-(trifluoromethyl)-2H-chromene-3-carboxylic Acids

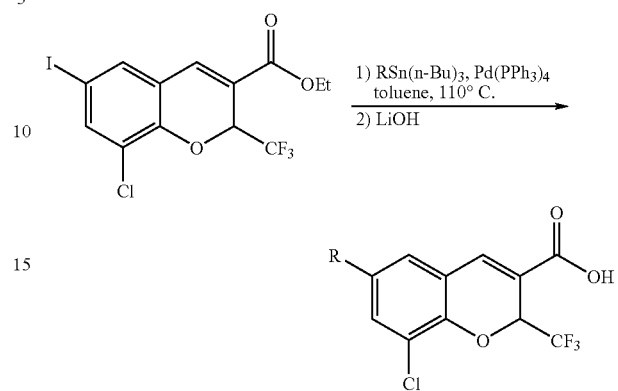

EXAMPLE 250

8-Chloro-6-ethynyl-2-(trifluoromethyl)-2H-chromene-3-carboxylic acid

Step 1. Preparation of ethyl 8-chloro-6-ethynyl-2-(trifluoromethyl)-2H-chromene-3-carboxylate To 0.86 g (2.0 mmole) of ethyl 8-chloro-6-iodo-2-(trifluoromethyl)-2H-chromene-3-carboxylate was added 46 mg (0.040 mmole) tetrakis(triphenylphosphine)palladium(0), 6 mLs degassed toluene and 0.64 mL (0.69 g, 2.2 mmole) tributyl(ethynyl)tin. The stirred mixture was heated to reflux for 3 h. After allowing the reaction to cool, the mixture was washed with 20% aq. ammonium fluoride and the aqueous layer extracted three times with diethyl ether. The combined extracts were filtered through silica, the silica washed with diethyl ether and the organic fractions concd in vacuo. Chromatographic purification (70 g silica, 5% ethyl acetate/ hexanes) afforded a solid which was triturated with hexanes to give 0.50 g (75.6%) of a crystalline solid: ¹H NMR (d⁶-acetone/400 MHz) 1.32 (t, 3H, J=7.1 Hz), 3.73 (s,1H), 4.32 (m, 2H), 6.04 (q, 1H, J=6.9 Hz), 7.60 (m, 2H), 7.90 (s, 1H); ¹⁹F NMR (d⁶-acetone/400 MHz) −79.6 (d, 3F, J=6.8 Hz); MS(ESI+) 331 (M+1, 100, one Cl pattern).

Step 2. Preparation of 8-chloro-6-ethynyl-2-(trifluoromethyl)-2H-chromene-3-carboxylic acid To 450 mg (1.36 mmole) of ethyl 8-chloro-6-iodo-2-(trifluoromethyl)-2H-chromene-3-carboxylate was added 9 mL of a solvent mixture of THF/MeOH (7:2) followed by 172 mgs of LiOH—H₂O in 1 mL of H₂O. The mixture was stirred for 30 min at rt. The mixture was concd, treated with 10 mL of water and acidified with conc. HCl (approx. 0.4 mL). The producted oiled out of solution and was extracted three times with diethyl ether. Combined extracts were dried and concd to afford 0.32 g of a crude yellow solid. Chromatography (C18, Gilson 10×4 cm, 7 injections of 50 mgs each) afforded 0.18 g (43.7%) of a white solid: $^1$H NMR (d$^6$-acetone/400 MHz) 3.74 (s, 1H), 6.03 (q, 1H, 6.8 Hz), 7.61 (m, 2H), 7.92 (s, 1H); $^{13}$C NMR (d6-acetone/400 MHz) 72.0 (q, J=33.2 Hz), 80.0, 81.6, 118.3, 119.6, 121.7, 121.8 (q, J=0.7 Hz), 124.2 (q, J=286.6 Hz), 132.5, 136.1, 136.7, 149.9, 164.6; $^{19}$F NMR (d$^6$-acetone/400 MHz) −79.6 (d, 3F, J=6.5 Hz); MS (ES+) 303 (M+1, 27), 291 (65), 289 (51), 235 (100), 233 (79); MS(ES−) 301 (M−1, 100), 303 (35); HRMS (EI−) m/z calcd for (C$_{13}$H$_5$O$_3$ClF$_3$) 300.9874, found 300.9837.

Preparation of 8-Chloro-6-substituted-2-(trifluoromethyl)-2H-chromene-3-carboxylic Acids by a Parallel Method The following Examples in table 3 were prepared as previously described for ethyl 8-chloro-6-ethynyl-2-(trifluoromethyl)-2H-chromene-3-carboxylate using parallel synthesis apparatus with each reaction carried out on 1.0 mmole scale.

TABLE 3

Yield, Purity and Mass Spectral Data for 8-Chloro-6-substitued-2-(trifluoromethyl)-2H-chromene-3-carboxylic Acids Prepared by Parallel Synthesis Methods.[1]

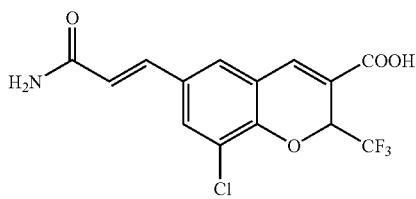

| Example | LC (ret. Time) | MS (ES+) | % Purity | % Yield |
|---|---|---|---|---|
| 251 | 3.54 | 305 | 98.7 | 23 |
| 252 | 4.20 | 379 | >99 | 13.4 |
| 253 | 2.91 | 304 | 77.4 | — |
| 254 | 3.09 | 321 | >99 | 12.4 |
| 255 | 3.69/3.77[2] | 319 | >99 | 3.1 |
| 256 | 3.65 | 317 | >99 | 28.9 |

[1]See General Experimental section for description of recorded data. LC indicates the chromatographic retention time in min. % Purity was determined by ELS.
[2]A 1:1 mixture of E and Z isomers (as determined by H NMR and LCMS) was obtained in a combined yield of 3.1%.

Preparation of 6-Substituted-2-(trifluoromethyl)-2H-chromene-3-carboxylic Acids

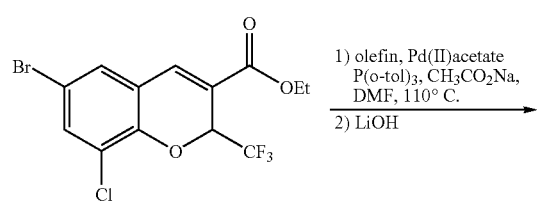

1) olefin, Pd(II)acetate P(o-tol)$_3$, CH$_3$CO$_2$Na, DMF, 110° C.
2) LiOH

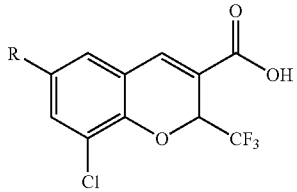

EXAMPLE 257

6-1(1E)-3-amino-3-oxoprop-1enyl]-8-chloro-2-(trifluoromethyl)-2H-chromene-3-carboxylic acid Step 1. Preparation of ethyl 6-[(1E)-3-amino-3-oxoprop-1-enyl]-8-chloro-2-(trifluoromethyl)-2H-chromene-3-carboxylate To the mixture of 0.4 g (1.0 mmol) of ethyl 6-Bromo-8-Chloro-2-(trifluoromethyl)-2H-chromene-3-carboxylate, 45 mg (0.2 mmol) of palladium acetate, 122 mg (0.4 mmol) of tri-o-tolylphosphine, 451 mg (5.5 mmol) of sodium acetate under nitrogen atmosphere was added 6 mL of anhydrous dimethylformamide, followed by addition of 107 mg (1.5 mmol) of acrylamide. The resulting mixture was shaken at 110° C. for 85 hrs. LC-MS indicated that the reaction was done. To the reaction was added 50 mL of ethylacetate. The resulting organic solution was washed with brine and dried over anhydrous magnesium sulfate. After removing the volatiles, the residue was purified by reverse phase chromatography to afford 0.23 g off-white solid, which was carried on to the next step.

Step 2. Preparation of 6-[(1E)-3-amino-3-oxoprop-1-enyl]-8-chloro-2-(trifluoromethyl)-2H-chromene-3-carboxylic acid The product of step 1 was dissolved in 3 mL of THF and treated with a solution of 0.13 g (2.55 mmol) lithium hydroxide hydrate in 3 mL of water. The mixture was treated with 3 mL of ethanol and heated to 80° C. for two hrs. The volatiles were removed, the residue was acidified at 0° C. to pH=1.0 with dilute hydrochloric acid. The product was extracted with ethyl acetate, washed with brine and dried over anhydrous magnesium sulfate. Concentration of the organic fraction afforded 0.169 g (48.6%) of an off-white solid: $^1$H NMR(DMSO/300 MHz) 7.87(s, 1H), 7.70(d, J=2.1 HZ, 1H), 7.55(d, J=2.1 Hz, 1H), 7.48(d, J=15.9 Hz, 1H), 6.63(d, J=15.9 Hz, 1H), 5.96(q, J=6.6 Hz, 1H). MS (ESI+) 348.0 (M+1, 100). MS(ES−) 346.0(M−1, 100). HRMS (ES−) m/z calcd for (M−H; C$_{14}$H$_8$ClF$_3$NO$_4$): 346.0088, found 346.0078.

EXAMPLE 258

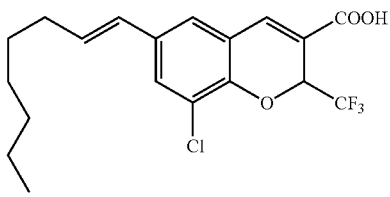

8-chloro-6-[(1E)-oct-1-enyl]-2-(trifluoromethyl)-2H-chromene-3-carboxylic acid

Preparation of 8-chloro-6-[(1E)-oct-1-enyl]-2-(trifluoromethyl)-2H-chromene-3-carboxylic acid This Example was prepared using the method for the preparation of 6-[(1E)-3-amino-3-oxoprop-1-enyl]-8-chloro-2-(trifluoromethyl)-2H-chromene-3-carboxylic acid. Yellow solid, 55mg, yield=14.1%, purity=100%. $^1$H NMR (CDCl$_3$/300 MHz) 7.70(s, 1H), 7.26(d, J=1.8 Hz, 1H), 6.98(s, J=1.8 Hz, 1H), 6.16-5.98 (m, 2H), 5.65 (q, J=6.6 Hz, 1H,), 2.06(m, 2H), 1.34-1.16(m, 8H), 0.76(m, 3H). MS (ESI+) 389.1 (M+1, 100). MS(ES−) 387.1 (m−1, 100). HRMS (ES$^-$) m/z calcd for (M−H; C$_{19}$H$_{19}$ClF$_3$O$_3$): 387.0969, found 387.0963.

EXAMPLE 259

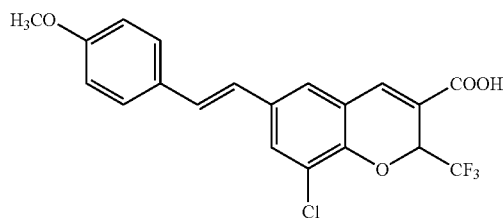

8-chloro-6-[(E)-2-(4-methoxyphenyl)ethenyl]-2-(trifluoromethyl)-2H-chromene-3-carboxylic acid Preparation of 8-chloro-6-[(E)-2-(4-methoxyphenyl)ethenyl]-2-(trifluoromethyl)-2H-chromene-3-carboxylic acid This Example was prepared using the method for the preparation of 6-[(1E)-3-amino-3-oxoprop-1-enyl]-8-chloro-2-(trifluoromethyl)-2H-chromene-3-carboxylic acid. Yellow solid, 140 mg, yield=34.1%, purity=100%, $^1$H NMR (CDCl$_3$/300 MHz) 7.73 (s, 1H), 7.49(s, 1H), 7.42-7.40(m, 2H), 7.23(s, 1H), 6.98-6.77(m,4H), 5.79(q, J=6.6 Hz, 1H), 3.82(s, 3H). MS (ESI+) 411.0(M+1, 100). MS(ES−) 409.0 (M−1), HRMS (ES$^-$) m/z calcd for (M−H; C$_{20}$H$_{13}$ClF$_3$O$_4$): 409.0449, found 409.0428.

EXAMPLE 260

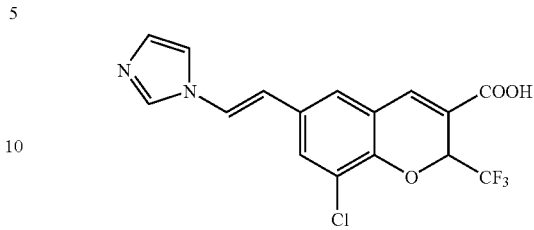

8-chloro-6-[(E)-2-(1H-imidazol-1-yl)ethenyl]-2-(trifluoromethyl)-2H-chromene-3-carboxylic acid Preparation of 8-chloro-6-[(E)-2-(1H-imidazol-1-yl)ethenyl]-2-(trifluoromethyl)-2H-chromene-3-carboxylic acid This Example was prepared using the method for the preparation of of 6-[(1E)-3-amino-3-oxoprop-1-enyl]-8-chloro-2-(trifluoromethyl)-2H-chromene-3-carboxylic acid. White solid, 130 mg, yield=35%, purity=94%. $^1$H NMR (CD$_3$OD/300 MHz) 8.84(s, 1H), 7.61(s, 2H), 7.52-7.22(m, 4H), 7.21(s, 1H), 6.93(d, J=14.7 Hz 1H), 5.70(q, J=6.6 Hz, 1H). MS (ESI+) 371.0(M+1, 100).

EXAMPLE 261

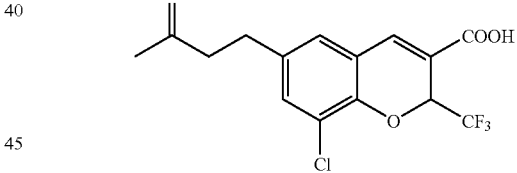

8-chloro-6-(3-oxo-butanyl)-2-(trifluoromethyl)-2H-chromene-3-carboxylic acid

Preparation of 8-chloro-6-(3-oxo-butanyl)-2-(trifluoromethyl)-2H-chromene-3-carboxylic acid This Example was prepared using the method for the preparation of of 6-[(1E)-3-amino-3-oxoprop-1-enyl]-8-chloro-2-(trifluoromethyl)-2H-chromene-3-carboxylic acid. Off-white solid, 130 mg, yield=37.3%, purity=95%.

$^1$H NMR (CDCl$_3$/300 MHz) 7.84(s, 1H), 7.28(s, 1H), 7.05(s, 1H), 5.81(q, J=6.6 Hz,1H), 2.83(m,4H), 2.20(s, 3H). MS (ESI+) 291.0 (M−58, 100),371.0 (M+23, 52), 349.0 (M+1, 40). MS(ES−) 347.0 (M−1, 100). HRMS (ES−) m/z calcd for (M−H; C$_{15}$H$_{11}$ClF$_3$O$_4$): 347.0292, found 347.0296.

Parallel Synthesis of a Compound Library with 6 and 8-Position Substitutions

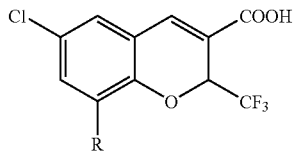

R = as described

Preparation of Intermediates and Examples 262-356

Preparation of 6-Chloro-8-alkynyl-2-(trifluoromethyl)-2H-chromene-3-carboxylic Acids by Sonagashira Couplings

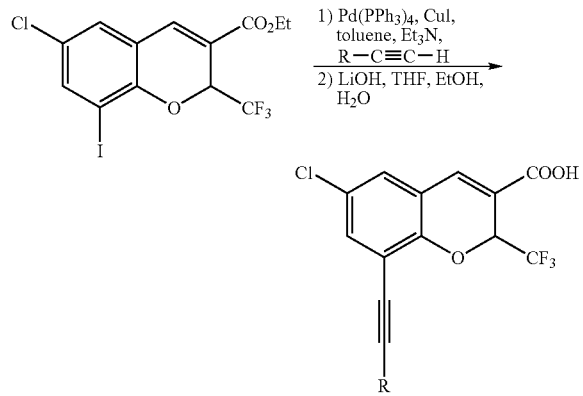

EXAMPLE 262

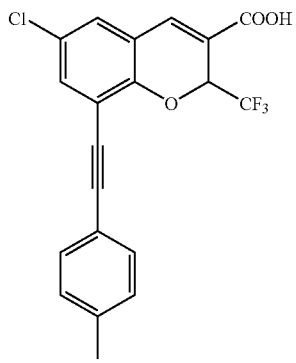

6-Chloro-8-[(4-methylphenyl)ethynyl]-2-(trifluoromethyl)-2H-chromene-3-carboxylic Acid Step 1. Preparation of ethyl-6-chloro-8-[(4-methylphenil)ethynyl]-2-(trifluoromethyl)-2H-chromene-3-carboxylate To 0.150 g (0.347 mmole) of ethyl-6-chloro-8-iodo-2-(trifluoromethyl)-2H-chromene-3-carboxylate was added 20 mg (0.017 mmole) tetrakis(triphenylphosphine)palladium (0), 6.6 mg (0.035 mmole) copper (I) iodide, 3 mL degassed toluene, 0.15 mL (1.041 mmole) degassed TEA, and 0.066 mL (0.521 mmole) 4-ethynyl toluene. The mixture was stirred overnight at room temperature. The mixture was concd and the resulting oil was filtered through silica. The silica was washed with hexanes, ethyl acetate, and dichloromethane and clean fractions were combined to afford 0.114 g of a crystalline solid: MS (ES+) 421 (M+1, 100).

Step 2. Preparation of 6-chloro-8-[(4-methylphenl) ethynyl]-2-(trifluoromethyl)-2H-chromene-3-carboxylic acid To 0.114 g (0.271 mmole) of ethyl-6-chloro-8-[(4-methylphenyl)ethynyl]-2-(trifluoromethyl)-2H-chromene-3-carboxylate was added 1.5 mL of a solvent mixture of THF/EtOH/$H_2O$ (7:2:1) followed by 22 mg (0.524 mmole) of LiOH—$H_2O$. The mixture was stirred overnight at room temperature. The mixture was concd, treated with 2 mL of water and acidified with 0.5N HCl. The product precipitated out of solution and was washed three times with water. The resulting solid was dried to afford 0.103 g (76% 2-step yield)) of a crude green solid: $^1$H NMR ($d^6$-DMF/400 MHz) 2.36 (s, 3H), 6.11 (q, 1H, J=7.2 Hz), 7.30 (d, 2H, J=8.4 Hz), 7.48 (d, 2H, J=8.0 Hz), 7.66 (d, 1H, J=2.4 Hz), 7.74 (d, 1H, J=2.4 Hz), 7.98 (s, 1H); MS (ES+) 393 (M+1, 100); HRMS (ES-) m/z calcd for ($C_{20}H_{12}O_3ClF_3$) 391.0343, found 391.0294.

Preparation of 6-Chloro-8-alkynyl-2-(trifluoromethyl)-2H-chromene-3-carboxylic Acids by a Parallel Method The following Examples in table 4 were prepared as previously described for 6-Chloro-8-[(4-methylphenyl)ethynyl]-2-(trifluoromethyl)-2H-chromene-3-carboxylic acid using parallel synthesis apparatus and were purified as needed by filtration, extraction, or reverse phase chromatography.

Table 4: Yield, Purity and Mass Spectral Data for 6-Chloro-8-alkynyl-2-(trofluoromethyl)-2H-chromene-3-carboxylic Acids prepared by Parallel Synthesis Methods.[1]

TABLE 4

| Example | LC (min) | MS (ES+) | HRMS | % Purity | % Yield |
|---------|----------|----------|------|----------|---------|
| 262 | 4.160 | 393 | 391.0294 | 100 | 76 |
| 263 | 2.832 | 347 | 345.0132 | 100 | 50 |
| 264 | 3.323 | 387 | 385.0454 | 100 | 23 |
| 265 | 2.260 | 360 | 360.0645[2] | 97 | 43 |
| 266 | 2.242 | 346 | 346.0496[2] | 100 | 25 |
| 267 | 2.597 | 388 | 371.0666[7] | 100 | 38 |
| 268 | 3.110 | 394 | 412.0590[3] | 100 | 16 |
| 269 | 3.956 | 409 | 407.0303 | 100 | 66 |
| 270 | 2.725 | 333 | 330.9957 | 99 | 67 |
| 271 | 2.133 | 332 | 332.0324[2] | 73[6] | 72 |

TABLE 4-continued

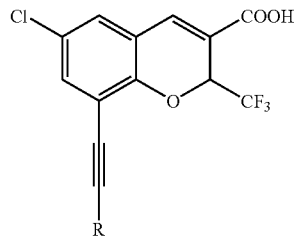

| Example | LC (min) | MS (ES+) | HRMS | % Purity | % Yield |
|---|---|---|---|---|---|
| 272 | 3.419 | 395 | 393.0154 | 97 | 38 |
| 273 | 2.970 | 361 | 359.0311 | 98 | 70 |
| 274 | 3.266 | 347 | 345.0139 | 99 | 25 |
| 275 | 2.732 | 347 | 344.9741 | >95 | 17 |
| 276 | 2.541[4] | 345 | 343.0314 | 100 | 70 |
| 277 | 2.960[4] | 393 | 391.0338 | 100 | 40 |
| 278 | 3.094[4] | 447 | 445.0100 | 100 | 54 |
| 279 | 1.585[4] | 394 | 394.0438[2] | 100 | 53 |
| 280 | 3.195[4] | 385 | 383.0675 | 100 | 66 |
| 281 | 2.784[4] | 407 | 405.0526 | 100 | 76 |
| 282 | 2.476[4] | 409 | 407.0296 | 100 | 72 |
| 283 | 1.764[4] | 373 | 371.0281 | 100 | 8 |
| 284 | 1.671[4] | 380 | 380.0291[2] | 96 | 50 |
| 285 | 2.721[4] | 397 | 395.0100 | 100 | 43 |
| 286 | 2.840[4] | 413 | 410.9804 | 100 | 58 |
| 287 | 3.138[4] | 475 | 474.9208 | 100 | 22 |
| 288 | 1.936[4] | 411 | 411.0736 | 100 | 13 |
| 289 | 1.862[4] | 370 | 387.0688[5] | 100 | 24 |

[1]See General Experimental section for description of recorded data. LC indicates the chromatographic retention time in min. HRMS indicates the observed molecular ion (M − H) by high-resolution mass spectrometry in electrospray negative mode. % Purity was determined by ELS detection.
[2]Electrospray positive mode, M + 1 ion.
[3]Electrospray positive mode, M + H + H$_2$O ion.
[4]HPLC retention time determined with a linear gradient from 40% acetonitrile in 0.1% TFA/water at time = 0 min to 95% acetonitrile at 4.5 min.
[5]Electrospray positive mode, M + NH$_4$ ion.
[6]Purity of 100% by UV at 254 nm.
[7]Electrospray positive mode, M-NH$_3$ ion.

EXAMPLE 290

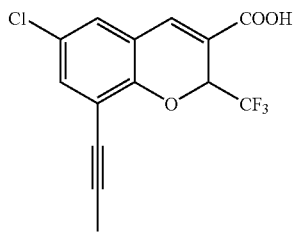

6-Chloro-8-prop-1-ynyl-2-(trifluoromethyl)-2H-chromene-3-carboxylic acid

Step 1. Preparation of ethyl-6-chloro-8-prop-1-ynyl-2-(trifluoromethyl)-2H-chromene-3-carboxylate A mixture of 0.50 g (1.160 mmole) of ethyl-6-chloro-8-iodo-2-(trifluoromethyl)-2H-chromene-3-carboxylate, 67 mg (0.058 mmole) tatrakis(triphenylphosphine)palladium (0), 22 mg (0.116 mmole) copper (I) iodide, 10 mL degassed toluene and 0.484 mL (3.48 mmole) degassed TEA was cooled to −78° C. and treated with an excess of condensed gaseous propyne. The mixture was stirred for thirty minutes at −78° C. and allowed to warm to room temperature. The mixture was then stirred overnight. The reaction mixture was concd and the resulting oil was filtered through silica. The silica was washed with hexanes and dichloromethane and clean fractions were combined to afford 0.320 g (80%) of a crystalline solid: 1H NMR (CDCl$_3$/400 MHz) 1.33 (t, 3H, J=7.2 Hz), 2.09 (s, 3H), 4.27-4.35 (m, 2H), 5.77 (q, 1H, J=6.8 Hz), 7.10 (d, 1H J=2.4 Hz), 7.31 (d, 1H, J=2.4 Hz), 7.59 (s, 1H); MS (ES+) 345 (M+1, 100).

Step 2. Preparation of 6-chloro-8-prop-1-ynyl-2-(trifluoromethyl)-2H-chromene-3-carboxylic acid To 0.320 g (1.01 mmole) of ethyl-6-chloro-8-prop-1-ynyl-2-(trifluoromethyl)-2H-chromene-3-carboxylate was added 5 mL of a solvent mixture of THF/EtOH/H$_2$O (7:2:1) followed by 64 mg (1.52 mmole) of LiOH-H$_2$0. The mixture was stirred at 60° C. for two hours. The mixture was concd, treated with water and acidified with 0.5N HCl. The product precipitated out of solution and was washed three times with water. The resulting solid was dried to afford 0.050 g (16%) of a brown solid: 1H NMR (CDCl$_3$/400 MHz) 1.83 (s,3H), 5.77 (q, 1H, J=6.8 Hz), 6.89 (d, 1H, J=2.4 Hz), 7.03 (d, 1H, J=2.4 Hz), 7.35 (s, 1H); MS (ES−) 315 (M−1, 100). HRMS (ES−) m/z calcd for (C$_{14}$H$_8$O$_3$ClF$_3$) 315.0030, found 315.0048.

EXAMPLE 285

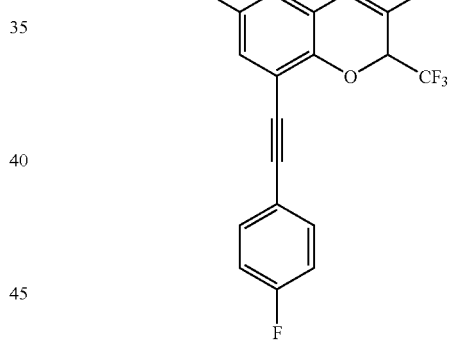

6-Chloro-8-[(4-fluorophenyl)ethynyl]-2-(trifluoromethyl)-2H-chromene-3-carboxylic acid Step 1. Preparation of ethyl-6-chloro-8-[(4-fluorophenyl)ethyl]-2-(trifluoromethyl)-2H-chromene-3-carboxylate To 0.350 g (0.809 mmole) of ethyl-6-chloro-8-iodo-2-(trifluoromethyl)-2H-chromene-3-carboxylate was added 47 mg (0.040 mmole) tetrakis(triphenylphosphine)palladium (0), 15 mg (0.081 mmole) copper (I) iodide, 5mL degassed toluene, 0.338 mL (2.43 mmole) degassed TEA, and 0.139 mL (1.21 mmole)1-ethynyl-4-fluorobenzene. The mixture was stirred overnight at room temperature. The mixture was concd and the resulting oil was purified using reverse phase chromatography to afford a crystalline solid. MS (ES+) 425 (M+1, 100).

Step 2. Preparation of 6-chloro-8-[(4-fluorophenyl)ethynyl]-2-(trifluoromethyl)-2H-chromene-3-carboxylic acid To 0.344 g (0.809 mmole) of ethyl-6-chloro-8-[(4-fluorophenyl)ethynl]-2-(trifluoromethyl)-2H-chromene-3-carboxylate was added 5.0 mL of a solvent mixture of THF/EtOH/$H_2O$ (7:2:1) followed by 51 mg (1.21 mmole) of LiOH—$H_2O$. The mixture was stirred at 60° C. for two hours. The mixture was concd, diluted with water, and acidified with 0.5N HCl. The crude material was purified using reverse phase chromatography to afford 0.138 g of a yellow crystalline solid (43% 2-step yield): $^1$H NMR (d-DMF/400 MHz) 6.11 (q,1H, J=7.2 Hz), 7.31-7.36 (m, 2H),7.64-7.69 (m, 3H), 7.75 (d, 1H, J=2.4 Hz), 7.98 (s, 1H); MS (ES−) 395 (M−1, 100); HRMS (ES−) m/z calcd for ($C_{19}H_9O_3ClF_4$) 395.0093, found 395.0100.

EXAMPLE 291

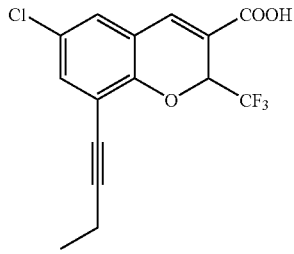

8-But-1-ynyl-6-chloro-2-(trifluoromethyl)-2H-chromene-3-carboxylic acid

Step 1. Preparation of ethyl-8-but-1-ynyl-6-chloro-2-(trifluoromethyl)-2H-chromene-3-carboxylate A mixture of 1.00 g (2.31 mmole) of ethyl-6-chloro-8-iodo-2-(trifluoromethyl)-2H-chromene-3-carboxylate, 134 mg (0.116 mmole) tetrakis(triphenylphosphine)palladium (O), 44 mg (0.231 mmole) copper (I) iodide, 20 mL degassed toluene and 0.965 mL (6.94 mmole) degassed TEA was cooled to −78° C. and treated with an excess of condensed gaseous 1-butyne. The mixture was stirred for thirty minutes at −78° C. and allowed to warm to room temperature and stirred overnight. The reaction mixture was concd and the resulting oil was purified using reverse phase chromatography to afford 0.768 g (93%) of a crystalline solid: $^1$H NMR (CDCl$_3$/400 MHz) 1.24 (t, 3H, J=7.2 Hz), 1.34 (t, 3H, J=7.2 Hz), 2.45 (q, 2H, J=7.6 Hz), 4.27-4.35 (m, 2H), 5.78 (q, 1H, J=6.8 Hz), 7.10 (d, 1H, J=2.4 Hz), 7.32 (d, 1H, J=2.4 Hz), 7.59 (s, 1H); MS (ES+) 359 (M+1, 100).

Step 2. Preparation of 8-but-1-ynyl-6-chloro-2-(trifluoromethyl)-2H-chromene-3-carboxylic acid To 0.768 g (2.14 mmole) of ethyl-8-but-1-ynyl-6-chloro-2-(trifluoromethyl)-2H-chromene-3- carboxylate was added 11 mL of a solvent mixture of THF/EtOH/$H_2O$ (7:2: 1) followed by 135 mg (3.22 mmole) of LiOH—$H_2O$. The mixture was stirred at 60° C. for two hours. The mixture was concd, treated with water, and acidified with 0.5N HCl. The crude solid was purified by reverse phase chromatography to afford 0.575 g (81%) of a yellow crystalline solid: $^1$H NMR (CDCl$_3$/400 MHz) 1.24 (t, 3H, J=7.2 Hz), 2.46 (q, 2H, J=7.6 Hz), 5.74 (q, 1H J=6.8 Hz), 7.16 (d, 1H, J=2.8 Hz), 7.39 (d, 1H, J=2.4 Hz), 7.81 (s, 1H); MS (ES+) 331 (M+1, 100); HRMS (ES−) m/z calcd for ($C_{15}H_{10}O_3ClF_3$) 329.0187, found 329.0202.

EXAMPLE 292

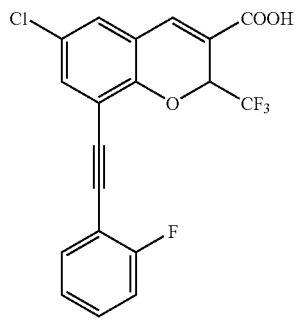

6-Chloro-8-[(2-fluorophenyl)ethynyl]-2-(trifluoromethyl)-2H-chromene-3-Carboxylic acid

Step 1. Preparation of ethyl-6-chloro-8-[(2-fluorophenyl)ethynyl]-2-(trifluoromethyl)-2H-chromene-3-carboxylate To 0.502 g (1.161 mmole) of ethyl-6-chloro-8-iodo-2-(trifluoromethyl)-2H-chromene-3-carboxylate was added 67 mg (0.060 mmole) tetrakis(triphenylphosphine)palladium (0), 22 mg (0.116 mmole) copper (I) iodide, 10 mL degassed toluene, 0.484 mL (3.48 mmole) degassed TEA, and 0.199 mL (1.74 mmole) 2-fluorophenylacetylene. The mixture was stirred overnight at room temperature. The mixture was concd and the resulting oil was purified using reverse phase chromatography to afford 0.440 g (89%) of a crystalline solid: $^1$H NMR (CDCl$_3$/400 MHz) 1.35 (t, 3H, J=6.8 Hz), 4.26-4.38 (m, 2H), 5.83 (q, 1H, J=6.8 Hz), 7.08-7.15 (m, 2H), 7.18 (d, 1H J=2.4 Hz), 7.31-7.37 (m, 1H), 7.45 (d, 1H, J=2.4 Hz), 7.49-7.53 (m, 1H), 7.63 (s, 1H); (ES+) 425 (M+1, 100).

Step 2. Preparation of 6-chloro-8-[(2-fluorophenyl)ethynyll-2-(trifluoromethyl)-2H-chromene-3-carboxylic acid To 0.387 g (0.911 mmole) of ethyl-6-chloro-8-[(2-fluorophenyl)ethynyl]-2-(trifluoromethyl)-2H-chromene-3-carboxylate was added 5.0 mL of a solvent mixture of THF/EtOH/$H_2O$ (7:2:1) followed by 57 mg (1.37 mmole) of LiOH—$H_2O$. The mixture was stirred at 60° C. for two hours. The mixture was concd, diluted with water and acidified with 0.5N HCl. The crude material was purified using reverse phase chromatography to afford 0.289 g (80%) of a yellow crystalline solid: $^1$H NMR (CDCl$_3$/400 MHz) 5.80 (q, 1H, J=6.4 Hz), 7.09-7.16 (m, 2H), 7.24 (d, 1H, J=2.4 Hz), 7.32-7.38 (m, 1H), 7.50-7.54 (m, 2H), 7.83 (s, 1H); MS (ES+) 397 (M+1, 100); HRMS (ES−) m/z calcd for ($C_{19}H_9O_3ClF_4$) 395.0093, found 395.0094.

EXAMPLE 293

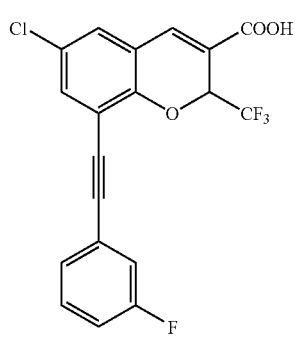

6-Chloro-8-[(3-fluorophenyl)ethynyl]-2-(trifluoromethyl)-2H-chromene-3-carboxylic acid Step 1. Preparation of ethyl-6-Chloro-8-[(3-fluorophenyl)ethynyl]-2-(trifluoromethyl)-2H-chromene-3-carboxylate To 0.502 g (1.161 mmole) of ethyl-6-chloro-8-iodo-2-(trifluoromethyl)-2H-chromene-3-carboxylate was added 67 mg (0.060 mmole) tetrakis(triphenylphosphine)palladium (0), 22 mg (0.116 mmole) copper (I) iodide, 10 mL degassed toluene, 0.484 mL (3.48 mmole) degassed TEA, and 0.199 mL (1.74 mmole) 3-fluorophenylacetylene. The mixture was stirred overnight at room temperature. The mixture was concd and the resulting oil was purified using reverse phase chromatography to afford 0.440 g (89%) of a crystalline solid: $^1$H NMR (CDCl$_3$/400 MHz) 1.35 (t,3H, J=6.8 Hz), 4.28-4.37 (m, 2H), 5.83 (q, 1H, J=6.8 Hz), 7.04-7.09 (m, 1H), 7.18 (d, 1H, J=2.4 Hz), 7.20-7.23 (m, 1H), 7.30-7.33 (m, 2H), 7.44 (d, 1H, J=2.8 Hz), 7.63 (s, 1H); MS (ES+) 425 (M+1, 100).

Step 2. Preparation of 6-chloro-8-[(3-fluorophenyl)ethynyl]-2-(trifluoromethyl)-2H-chromene-3-carboxylic acid To 0.440 g (1.036 mmole) of ethyl-6-Chloro-8-[(3-fluorophenyl)ethynyl]-2-(trifluoromethyl)-2H-chromene-3-carboxylate was added 5.2 mL of a solvent mixture of THF/EtOH/H$_2$O (7:2:1) followed by 65 mg (1.55 mmole) of LiOH—H$_2$O. The mixture was stirred at 60° C. for two hours. The mixture was concd, diluted with water and acidified with 0.5N HCl. The crude material was purified using reverse phase chromatography to afford 0.387 g (94%) of a yellow crystalline solid: $^1$H NMR (CDCl$_3$/400 MHz) 5.79 (q, 1H, J=6.4 Hz), 7.04-7.09 (m, 1H), 7.21-7.23 (m, 2H), 7.31-7.33 (m, 2H), 7.50 (d, 1H, J=2.4 Hz), 7.84 (s, 1H); MS (ES+) 397 (M+1, 100); HRMS (ES−) m/z calcd for (C$_{19}$H$_9$O$_3$ClF$_4$) 395.0093, found 395.0092.

EXAMPLE 294

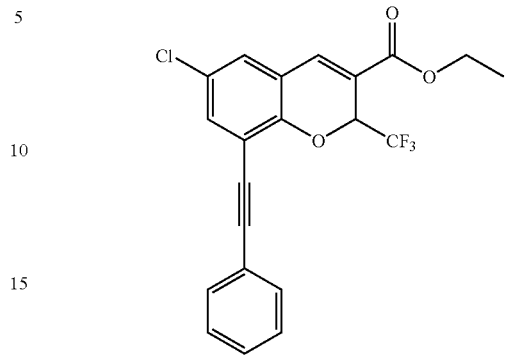

Ethyl 6-Chloro-8-(phenylethynyl)-2-(trifluoromethyl)-2H-chromene-3-carboxylate

To 2.000 g (4.624 mmole) of ethyl-6-chloro-8-iodo-2-(trifluoromethyl)-2H-chromene-3-carboxylate was added 267 mg (0.231 mmole) tetrakis(triphenylphosphine)palladium(0), 88 mg (0.462 mmole) copper (I) iodide, 40 mL degassed toluene, 1.930 mL (13.87 mmole) degassed TEA, and 0.762 mL (6.94 mmole) phenylacetylene. The mixture was stirred overnight at room temperature. The mixture was concd and the resulting oil was purified using reverse phase chromatography to afford 1.648 g (88%) of a yellow crystalline solid: $^1$H NMR (CDCl$_3$/400 MHz) 1.35 (t, 3H, J=7.2 Hz), 4.27-4.39 (m, 2H), 5.83 (q, 1H, J=6.4 Hz), 7.17 (d, 1H, J=2.4 Hz), 7.34-7.37 (m, 3H), 7.45 (d, 1H, J=2.4 Hz), 7.51-7.55 (m, 2H), 7.63 (s, 1H); MS (ES+) 407 (M+1, 100); MS (EI) 406 (M+, 39), 337 (100), 309 (45).

EXAMPLE 295

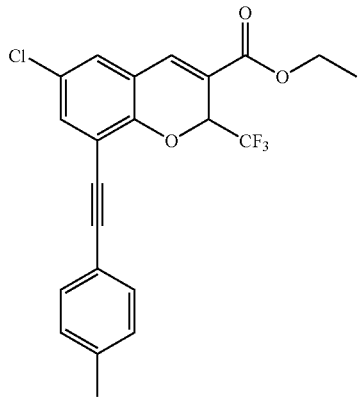

Ethyl 6-chloro-8-1(4-methylphenyl)ethynyl]-2-(trifluoromethyl)-2H-chromene-3-carboxylate To 2.000 g (4.624 mmole) of ethyl-6-chloro-8-iodo-2-(trifluoromethyl)-2H-chromene-3-carboxylate was added 267 mg (0.231 mmole) tetrakis(triphenylphosphine)palladium(0), 88 mg (0.462 mmole) copper (I) iodide, 40 mL degassed toluene, 1.930 mL (13.87 mmole) degassed TEA, and 0.880 mL (6.94 mmole) 4-ethnyltoluene. The mixture was stirred overnight at room temperature. The mixture was concd and the resulting oil was purified using reverse phase chromatography to afford 1.193 g (61%) of a yellow crystalline solid: $^1$H NMR (CDCl$_3$/400 MHz) 1.35 (t, 3H, J=7.2 Hz), 2.36 (s, 3H), 4.28-4.37 (m, 2H), 5.82 (q, 1H, J=6.8 Hz), 7.14-7.17 (m, 3H), 7.41-7.43 (m, 3H), 7.62 (s, 1H); MS (ES+) 421 (M+1, 100); MS (El) 420 (M+, 42), 351 (100), 323 (49).

EXAMPLE 296

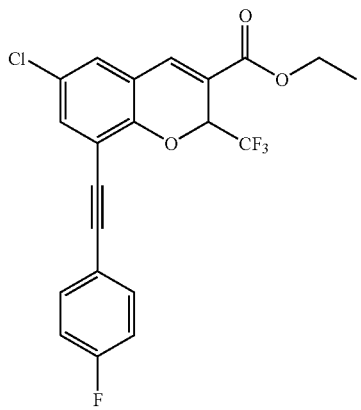

Ethyl 6-chloro-8-[(4-fluorophenyl)ethynyl]-2-(trifluoromethyl)-2H-chromene-3-carboxylate To 2.000 g (4.624 mmole) of ethyl-6-chloro-8-iodo-2-(trifluoromethyl)-2H-chromene-3-carboxylate was added 267 mg (0.231 mmole) tetrakis(triphenylphosphine)palladium(0), 88 mg (0.462 mmole) copper (I) iodide, 40 mL degassed toluene, 1.930 mL (13.87 mmole) degassed TEA, and 0.833 g (6.94 mmole) 1-ethnyl-4-fluorobenzene. The mixture was stirred overnight at room temperature. The mixture was concd and the resulting oil was purified using reverse phase chromatography to afford 1.804 g (92%) of a tan crystalline solid: $^1$H NMR (CDCl$_3$/400 MHz) 1.35 (t, 3H, J=7.2 Hz), 4.274.39 (m, 2H), 5.82 (q, 1H, J=6.8 Hz), 7.02-7.08 (m, 2H), 7.17 (d, 1H, J=2.4 Hz), 7.43 (d, 1H, J=2.4 Hz), 7.49-7.53 (m, 2H), 7.63 (s, 1H); MS (ES+) 425 (M+1, 100); MS (EI) 424 (M+, 34), 355 (100), 327 (55).

EXAMPLE 297

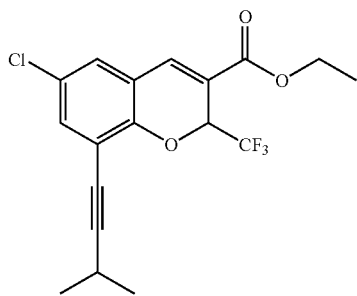

Ethyl 6-chloro-8-(3-methylbut-1-ynyl)-2-(trifluoromethyl)-2H-chromene-3-carboxylate To 2.000 g (4.624 mmole) of ethyl-6-chloro-8-iodo-2-(trifluoromethyl)-2H-chromene-3-carboxylate was added 267 mg (0.231 mmole) tetrakis(triphenylphospine)palladium(0), 88 mg (0.462 mmole) copper (I) iodide, 40 mL degassed toluene, 1.930 mL (13.87 mmole) degassed TEA, and 0.473 g (6.94 mmole) 3-methyl-1-butyne. The mixtures was stirred overnight at room temperature. The mixture was concd and the resulting oil was purified using reverse phase chromatography to afford 1.573 g (91%) of a yellow crystalline solid: $^1$H NMR (CDCl$_3$/400 MHz) 1.26 (d, 6H, J=6.8 Hz), 1.34 (t, 3H, J=7.2 Hz), 2.80 (septet, 1H, J=6.8 Hz), 4.27-4.35 (m, 2H), 5.78 (q, 1H, J=6.8 Hz), 7.09 (d, J=2.4 Hz), 7.31 (d, 1H, J=2.4 Hz), 7.59 (s, 1H); MS (ES+) 373 (M+1, 100): MS (EI) 372 (M+, 22), 303 (100), 275 (35).

Preparation of Wang resin 6-chloro-8-iodo-2-(trifluoromethyl)-2H-chromene-3-carboxylate

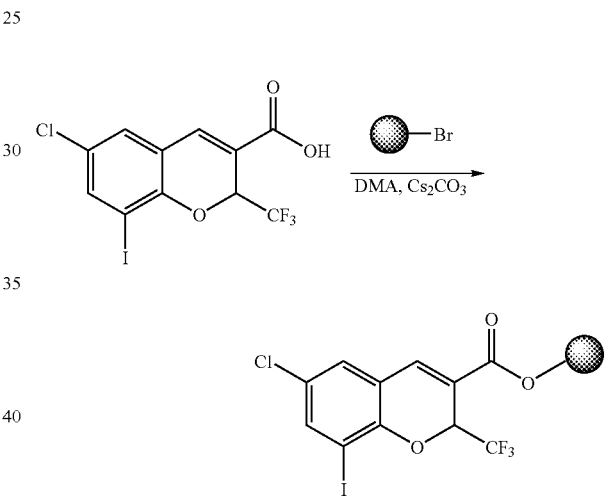

To a slurry of 53 g (63.6 mmole) of bromo-Wang resin (4-(Bromomethyl)phenoxymethylpolystyrene, NovaBiochem cat # 01-64-0186, 1.20 meq/g) in 1 L of anhydrous dimethylacetamide was added 31.1 g (95.5 mmole) of cesium carbonate and 38.62 g (95.5 mmole) of 6-chloro-8-iodo-2-(trifluoromethyl)-2H-chromene-3-carboxylic acid. The slurry was allowed to stir at rt overnight. The mixture was filtered and the resin washed three times each with DMF, MeOH and CH$_2$Cl$_2$. The collected resin was air dried to afford 73.75 g of a yellow-white resin. Resin loading was determined by direct cleavage NMR by treatment of 73.4 mg of resin with 1.00 mL of a 5.85 M solution of hexamethyldisiloxane in CDCl$_3$/TFA (1:1). After 1 h, the filtrate was collected and the resin washed three times with a minimal amount of CDCl$_3$. The combined filtrates were analyzed by NMR to provide loading and analysis of the resin: Direct Cleavage $^1$H NMR loading=1.071 meq/g; $^1$H NMR (CDCl$_3$+TFA/400 MHz) 5.79 (q, 1H, J=6.6 Hz), 7.27 (d, 1H, J=2.2 Hz), 7.81 (m, 2H).

Preparation of 6-Chloro-8-aryl-2-(trifluoromethyl)-2H-chromene-3-carboxylic Acids by Suzuki Couplings

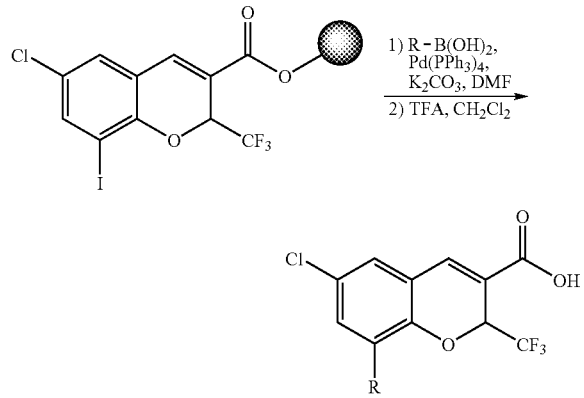

EXAMPLE 298

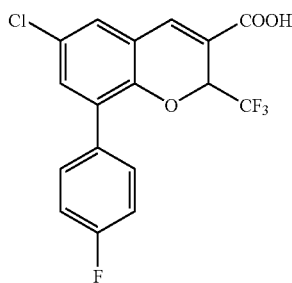

6-Chloro-8-(4-fluorophenyl)-2-(trifluoromethyl)-2H-chromene-3-carboxylic acid

Preparation of 6-chloro-8-(4-fluorophenyl)-2-(trifluoromethyl)-2H-chromene-3-carboxylic acid. To 0.400 g (0.428 mmole) of Wang resin 6-chloro-8-iodo-2-(trifluoromethyl)-2H-chromene-3-carboxylate was added 50 mg (0.043 mmole) tetrakis(triphenylphosphine)palladium(0), 0.180 g (1.285 mmole) 4-fluorophenylboronic acid, 0.857 mL $K_2CO_3$ (2M soln degassed), and 4 mL degassed DMF. The reaction mixture was heated to 100° C. for 18 hr. The reaction mixture was transferred and washed as follows: DMF (×5), $H_2O$ (×5), MeOH (×5), and $CH_2Cl_2$ (×5). The resin was treated with 2 mL (TFA:$CH_2CL_2$, 1:1) for 30 minutes. The filtrate was collected and treatment was repeated. The resin was washed with $CH_2Cl_2$ (×2) and all filtrates were combined and concd. The resulting oil was purified using reverse phase chromatography to afford 0.055 g (34%) of a yellow crystalline solid: $^1$H NMR (CDCl$_3$/400 MHz) 5.66 (q, 1H, J=6.8 Hz), 7.10-7.15 (m, 2H), 7.26 (d, 1H, J=2.4 Hz), 7.37 (d, 1H, J=2.4 Hz), 7.42-7.47 (m, 2H), 7.90 (s, 1H); MS (ES+) 373 (M+1, 100); HRMS (ES−) m/z calcd for ($C_{17}H_9O_3ClF_4$) 371.0093, found 371.0067.

Preparation of 6-Chloro-8-aryl-2-(trifluoromethyl)-2H-chromene-3-carboxylic Acids by a Parallel Method The following Examples in table 5 were prepared as previously described for 6-chloro-8-(4-fluorophenyl)-2-(trifluoromethyl)-2H-chromene-3-carboxylic acid using parallel synthesis apparatus and were purified as needed by reverse phase chromatography.

Table 5: Yield, Purity and Mass Spectral Data for 6-Chloro-8-aryl-2-(trifluoromethyl)-2H-chromene-3-carboxylic Acids Prepared by Parallel Synthesis Methods.

TABLE 5

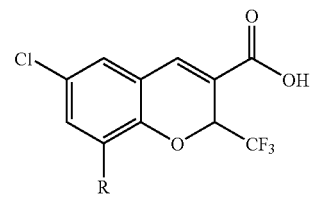

| Example | LC (min) | MS (ES+) | HRMS | % Purity | % Yield |
|---|---|---|---|---|---|
| 298 | 2.391 | 373 | 371.0067 | 100 | 34 |
| 299 | 2.705 | 407 | 404.9710 | 100 | 25 |
| 300 | 3.055 | 423 | 420.9372 | 100 | 44 |
| 301 | 2.960 | 423 | 420.9399 | 100 | 38 |
| 302 | 2.389 | 373 | 371.0084 | 100 | 34 |
| 303 | 2.631 | 389 | 386.9831 | 100 | 37 |
| 304 | 2.478 | 369 | 367.0361 | 100 | 36 |
| 305 | 2.594 | 369 | 367.0321 | 100 | 38 |
| 306 | 2.604 | 369 | 367.0303 | 100 | 33 |
| 307 | 2.674 | 423 | 421.0025 | 100 | 40 |
| 308 | 2.742 | 423 | 421.0016 | 100 | 43 |
| 309 | 2.582 | 399 | 397.0485 | 100 | 18 |
| 310 | 2.809 | 439 | 437.0014 | 100 | 37 |
| 311 | 2.070 | 380 | 378.0154 | 100 | 24 |
| 312 | 2.051 | 383 | 381.0119 | 100 | 14 |
| 313 | 2.585 | 399 | 397.0439 | 100 | 4 |
| 314 | 3.355[2] | 399 | 397.0470 | 100 | 11 |
| 315 | 2.040 | 383 | 381.0160 | 100 | 15 |
| 316 | 3.059 | 491 | 489.0095 | 100 | 32 |
| 317 | 2.168[2] | 356 | 354.0106 | 100 | 6 |
| 318 | 2.448 | 423 | 421.0026 | 100 | 11 |
| 319 | 2.860 | 415 | — | 100 | 22 |
| 320 | 2.389 | 401 | 399.0082 | 100 | 19 |
| 321 | 2.100 | 380 | 378.0138 | 100 | 23 |
| 322 | 1.215 | 356 | 354.0174 | 100 | 18 |
| 323 | 2.501 | 391 | 388.9970 | 100 | 39 |
| 324 | 1.718 | 399 | 397.0072 | 99 | 3 |
| 325 | 2.860 | 383 | 381.0519 | 100 | 28 |
| 326 | 3.030 | 397 | 395.0640 | 100 | 15 |
| 327 | 3.239 | 411 | 409.0766 | 100 | 38 |
| 328 | 3.582[2] | 383 | 381.0549 | 100 | 38 |
| 329 | 3.329[2] | 414 | 412.0220 | 100 | 43 |
| 330 | 3.808 | 431 | 429.0453 | 100 | 36 |
| 331 | 4.055[2] | 411 | 409.0775 | 100 | 41 |
| 332 | 3.382 | 419 | 416.9866 | 100 | 20 |
| 333 | 3.006[2] | 397 | 395.0312 | 100 | 34 |
| 334 | 3.661[2] | 383 | 381.0509 | 100 | 42 |
| 335 | 3.519 | 387 | 385.0288 | 100 | 38 |
| 336 | 2.327[2] | 384 | 384.0643[3] | 100 | 20 |
| 337 | 3.210[2] | 413 | 411.0242 | 100 | 18 |
| 338 | 3.619[2] | 383 | 381.0498 | 100 | 40 |
| 339 | 2.529[2] | 428 | 428.0497[3] | 100 | 13 |
| 340 | 2.640[2] | 385 | 383.0324 | 100 | 17 |
| 341 | 1.295 | 384 | 384.0643[3] | 92 | 5 |
| 342 | 1.755[2] | 371 | 369.0152 | 100 | 4 |
| 343 | 2.461 | 439 | 437.0397 | 100 | 22 |
| 344 | 2.007[2] | 394 | 392.0304 | 100 | 1 |
| 345 | 3.083[2] | 413 | 411.0199 | 100 | 30 |
| 346 | 3.903[2] | 403 | 400.9926 | 100 | 39 |
| 347 | 2.858[2] | 425 | 423.0201 | 100 | 9 |
| 348 | 2.656[2] | 399 | 397.0095 | 100 | 4 |

TABLE 5-continued

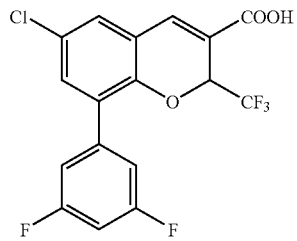

| Example | LC (min) | MS (ES+) | HRMS | % Purity | % Yield |
|---|---|---|---|---|---|
| 349 | 3.643[2] | 387 | 382.0242 | 100 | 31 |
| 350 | 3.099[2] | 445 | 443.0473 | 100 | 4 |
| 351 | 2.609[2] | 412 | 412.0553[3] | 100 | 12 |
| 352 | 3.799[2] | 439 | 436.9999 | 100 | 4 |
| 353 | 2.824[2] | 427 | 425.0346 | 100 | 5 |
| 354 | 3.069[2] | 397 | 395.0280 | 100 | 11 |
| 355 | 3.322[2] | 403 | — | 100 | 27 |
| 356 | 3.623[2] | 399 | 397.0442 | 99 | 58 |
| 357 | 4.229[2] | 411 | 409.0797 | 100 | 35 |
| 358 | 2.670[2] | 448 | 465.0491[4] | 100 | 13 |
| 359 | 3.495[2] | 427 | 425.0360 | 100 | 33 |
| 360 | 2.590[2] | 412 | 425.0588 | 100 | 18 |
| 361 | 3.971[2] | 447 | 445.0463 | 100 | 18 |
| 362 | 3.671[2] | 413 | 411.0573 | 100 | 23 |
| 363 | 1.895[2] | 370 | 368.0321 | 100 | 15 |
| 364 | 3.268[2] | 361 | 358.9743 | 100 | 3 |
| 365 | 3.260[2] | 400 | 398.0000 | 100 | 39 |
| 366 | 1.942[2] | 370 | 370.0462[3] | 100 | 25 |
| 367 | 2.493[2] | 398 | 398.0803[3] | 100 | 34 |
| 368 | 3.553[2] | 427 | 425.0385 | 100 | 30 |
| 369 | 2.488[2] | 428 | 428.0530[3] | 100 | 16 |

[1]See General Experimental section for description of recorded data. LC indicates the chromatographic retention time determined with a linear gradient from 40% acetonitrile in 0.1% TFA/water at time = 0 min to 95% acetonitrile at 4.5 min. HRMS indicates the observed molecular ion (M-H) by high-resolution mass spectrometry in electrospray negative mode. % Purity was determined by ELS detection.
[2]LC indicates the chromatographic retention time determined with a linear gradient from 5% acetonitrile in 0.1% TFA/water at time = 0 min to 95% acetonitrile at 4.5 min.
[3]Electrospray positive mode, M + 1 ion.
[4]Electrospray positive mode, M + $NH_4$ ion.

EXAMPLE 319

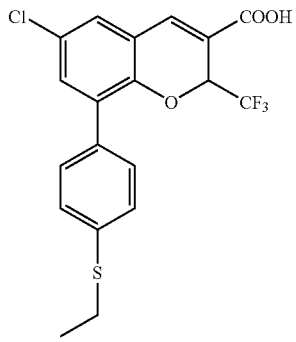

6-Chloro-8-[4-(ethylthio)phenyl]-2-(trifluoromethyl)-2H-chromene-3-carboxylic acid Preparation of 6-chloro-8-[4-(ethylthio)phenyl]-2-(trifluoromethyl)-2H-chromene-3-carboxylic acid. The sample obtained from the parallel synthesis method was purified using reverse phase chromatography to afford 0.039 g (22%) of a yellow crystalline solid: $^1$H NMR (CDCl$_3$/400 MHz) 1.36 (t, 3H, J=7.2 Hz), 3.00 (q, 2H, J=7.2 Hz), 5.68 (q, 1H, J=6.8 Hz), 7.22 (d, 1H, J=2.4 Hz), 7.34-7.41 (m, 5H), 7.81 (s, 1H); MS (ES+) 415 (M+1, 100).

EXAMPLE 323

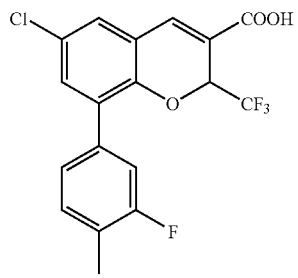

6-Chloro-8-(3,5-difluorophenyl)-2-(trifluoromethyl)-2H-chromene-3-carboxylic acid Preparation of 6-chloro-8-(3,5-difluorophenyl)-2-(trifluoromethyl)-2H-chromene-3-carboxylic acid. The sample obtained from the parallel synthesis method was purified using reverse phase chromatography to afford 0.066 g (39%) of a yellow crystalline solid: $^1$H NMR (CDCl$_3$/400 MHz) 5.69 (q, 1H, J=6.8 Hz), 6.82-6.87 (m, 1H), 6.99-7.05 (m, 2H), 7.31 (d, 1H, J=2.4 Hz), 7.38 (d, 1H, J=2.8 Hz), 7.91 (s, 1H); MS (ES−) 389 (M−1, 100); HRMS (ES−) m/z calcd for ($C_{17}H_8O_3ClF_5$) 388.9998, found 388.9970.

EXAMPLE 335

6-Chloro-8-(3-fluoro4-methylphenyl)-2-(trifluoromethyl)-2H-chromene-3-carboxylic acid Preparation of 6-Chloro-8-(3-fluoro4-methylphenyl)-2-(trifluoromethyl)-2H-chromene-3-carboxylic acid. The sample obtained from the parallel synthesis method (0.536 mmol scale) was purified using reverse phase chromatography to afford 0.079 g (38%) of a yellow crystalline solid: $^1$H NMR (CDCl$_3$/400 MHz) 2.32 (d, 3H, J=1.6 Hz), 5.66 (q, 1H, J=6.8 Hz), 7.13-7.16 (m, 2H), 7.25-7.27 (m, 2H), 7.37 (d, 1H, J=2.4 Hz), 7.89 (s, 1H); MS (ES+) 387 (M+1, 100); HRMS (ES−) m/z calcd for ($C_{18}H_{11}O_3ClF_4$) 385.0249, found 385.0288.

EXAMPLE 334

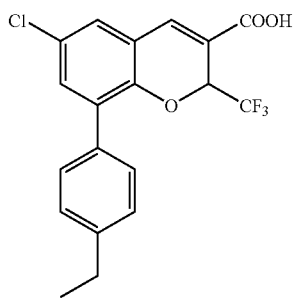

6-Chloro-8-(4-ethylphenyl)-2-(trifluoromethyl)-2H-chromene-3-carboxylic acid

Preparation of 6-chloro-8-(4-ethylphenyl)-2-(trifluoromethyl)-2H-chromene-3-carboxylic acid. The sample obtained from the parallel synthesis method (0.536 mmole scale) was purified using reverse phase chromatography to afford 0.087 g (42%) of a yellow crystalline solid: $^1$H NMR (CDCl$_3$/400 MHz) 1.28 (t, 3H, J=7.6 Hz), 2.70 (q,2H, J=7.6 Hz), 5.68 (q, 1H, J=6.8 Hz), 7.21. (d, 1H, J=2.8 Hz), 7.27-7.29 (m,2H), 7.36 (d, 1H, J=2.4 Hz), 7.39-7.41 (m, 2H), 7.82 (s, 1H); MS (ES+) 383 (M+1, 100); HRMS (ES−) m/z calcd for (C$_{19}$H$_{14}$O$_3$ClF$_3$) 381.0500, found 381.0509.

EXAMPLE 346

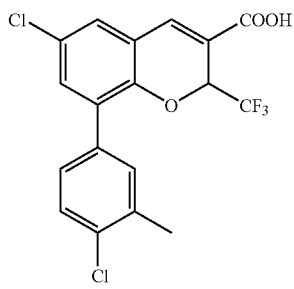

6-Chloro-8-(4-chloro-3-methylphenyl)-2-(trifluoromethyl)-2H-chromene-3-carboxylic acid Preparation of 6-chloro-8-(4-chloro-3-methylphenyl)-2-(trifluoromethyl)-2H-chromene-3-carboxylic acid. The sample obtained from the parallel synthesis method (0.536 mmole scale) was purified using reverse phase chromatography to afford 0.085 g (39%) of a yellow crystalline solid: $^1$H NMR (CD$_3$OD/400 MHz) 2.36 (s, 3H), 5.73 (q, 1H, J=6.8 Hz), 7.21-7.23 (m, 1H), 7.28-7.29 (m, 1H), 7.32-7.35 (m, 3H), 7.75 (s, 1H); MS (ES−) 401 (M−1, 100); HRMS (ES−) m/z calcd for (C$_{18}$H$_{11}$O$_3$Cl$_2$F$_3$) 400.9954, found 400.9926.

EXAMPLE 356

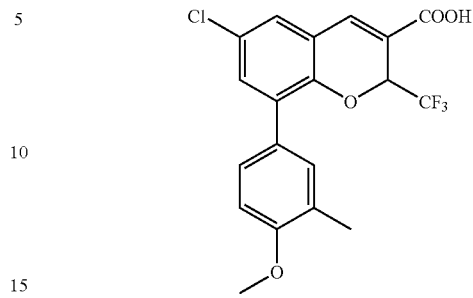

6-Chloro-8-(4-methoxy-3-methylphenyl)-2-(trifluoromethyl)-2H-chromene-3-carboxylic acid Preparation of 6-chloro-8-(4-methoxy-3-methylphenyl)-2-(trifluoromethyl)-2H-chromene-3-carboxylic acid. The sample obtained from the parallel synthesis method (0.536 mmole scale) was purified using reverse phase chromatography to afford 0.124 g (58%) of a yellow crystalline solid: $^1$H NMR (CD$_3$OD/400 MHz) 2.20 (s, 3H), 3.84 (s, 3H), 5.74 (q, 1H, J=6.8 Hz), 6.92 (d, 1H, J=8.0 Hz), 7.25-7.29 (m, 4H), 7.76 (s, 1H); MS (ES+) 399 (M+1, 100); HRMS (ES−) m/z calcd for (C$_{19}$H$_{14}$O$_4$ClF$_3$) 397.0449, found 397.0442.

Parallel Synthesis of a Compound Library with 6 and 7-Position Substitutions

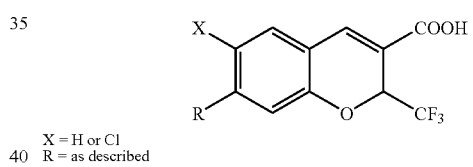

X = H or Cl
R = as described

Preparation of Intermediates and Synthesis of Examples 370-483

Preparation of Ethyl 6-Chloro-7-fluoro-2-(trifluoromethyl)-2H-chromene-3-carboxylate

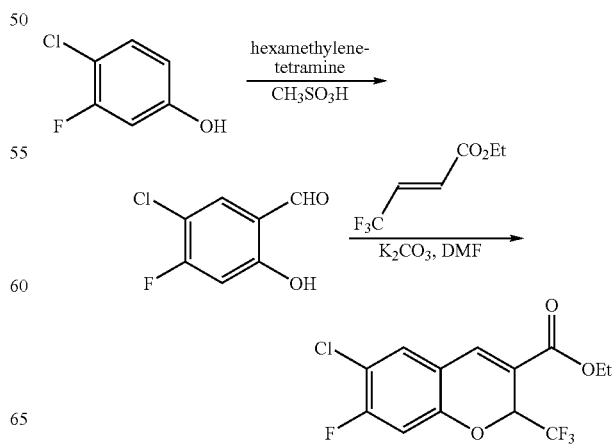

Step 1. Preparation of 5-chloro-4-fluoro-2-hydroxybenzaldehyde

To the 4-chloro-3-fluorophenol (25 g, 171 mmole) was added methanesulfonic acid (130 mL) and the mixture was stirred at rt. An ice-water bath was used to bring the temperature of the stirred mixture to 10° C. Methenamine (47.8 g, 341 mmole) was added portionwise in 3 gm scoops to allow the solid to dissolve and keep the temperature below 40° C. Addition was complete after 90 minutes.—CAUTION: If the addition is carried out too fast, the solid will react exothermically with the acid and decompose. The mixture was heated to 100° C. At 70° C., a change in the reaction mixture color was noticed and a solid formed. Once the temperature of 100° C. was reached, the heating manifold was removed and the mixture allowed to cool to rt. The reaction mixture was poured into IL of ice water and extracted 3 times with $CH_2Cl_2$. The combined extracts were filtered through a silica plug (4.5×9 cm), washed with additional $CH_2Cl_2$ and concd to give a crude yellow solid. Kugelrohr distillation (100 mtorr, 60° C.) gave 18.06 g (60.6%) of a white solid: $^1$H NMR ($CDCl_3$) 6.79 (d, 1H, J=10.3 Hz), 7.62 (d, 1H, J=7.9 Hz), 9.80 (s, 1H), 11.23 (d, 1H, J=1.5 Hz).

Step 2. Preparation of ethyl 6-chloro-7-fluoro-2-(trifluoromethyl)-2H-chromene-3-carboxulate To the aldehyde (17.46 g, 100 mmole) from Step 1 in 25 mL of DMF was added $K_2CO_3$ (15.2 g, 110 mmole). The mixture was stirred, heated to 70° C. and treated with ethyl trifluorocrotonate (22.4 mL, 150 mmole). After 2 h, the mixture was heated to 95° C. After a total of 4 h, an additional 16 mL of ethyl trifluorocrotonate was added and the mixture allowed to stir for 4 h at 95° C. and an additional 12 h at rt. The reaction was complete by LCMS. This mixture was treated with 300 mL of 1N HCl and extracted 4 times with $CH_2Cl_2$. The combined extracts were filtered through silica (4.5×6 cm) and the silica plug washed with additional $CH_2Cl_2$. The extracts were concd, the crude solid triturated with cold methanol, the solid collected and air dried to afford 19.1 g of a tan solid. The mother liquors were concd, dissolved in $CH_2Cl_2$ and filtered through a new silica plug following the same approach as above to give a second crop of 4.1 g of solid. The mother liquors were diluted with $H_2O$ and the solid collected to give a third crop of 3.16 g of solid. Total yield was 26.36 g (81.2%). The first and second crop were >95% by $^1$H NMR. The third crop was >90% pure: $^1$HNMR ($CDCl_3$) 1.35 (t, 3H, J=7.1 Hz), 4.33 (m, 2H), 5.71 (q, 1H, J=6.7 Hz), 6.82 (d, 1H, J=9.4 Hz), 7.28 (d, 1H, 7.9 Hz), 7.63 (s, 1H). $^{19}$FNMR (CDCl3) −78.9 (d, 3F, J=6.7 Hz), −106.7 (t, 1F, J=8.7 Hz). $^{13}$CNMR (CDCl3) 14.2, 61.7, 70.9 (q, C2, J=33.3 Hz), 105.5 (d, C8, J=25.5 Hz), 114.9 (d, J=18.7 Hz), 116.4, 117.1, 123.1 (q, CF3, J=287.2 Hz), 130.4 (d, J=1.5 Hz), 134.9 (d, J=1.9 Hz), 152.9 (d, J=11.4 Hz), 160.1 (d, C7, J=255.2 Hz), 163.4 (C=O); MS(ES+) 325 (M+1, 100).

Preparation of 6-Chloro-7-aryloxy-2-(trifluoromethyl)-2H-chromene-3-carboxylic Acids

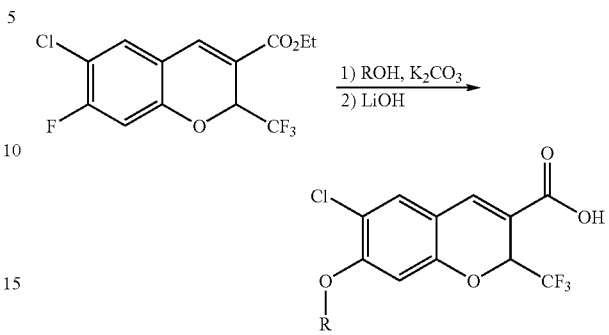

EXAMPLE 370

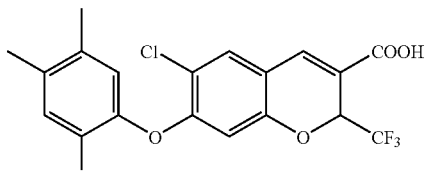

6-Chloro-7-(2-chloro-4,5-dimethylphenoxy)-2-(trifluoromethyl)-2H-chromene-3-carboxylic acid

Step 1. Preparation of ethyl 6-chloro-7-(2-chloro-4,5-dimethylphenoxy)-2-(trifluoromethyl)-2H-chromene-3-carboxylate To 325 mg (1.0 mmole) of ethyl 6-chloro-7-fluoro-2-(trifluoromethyl)-2H-chromene-3-carboxylate in 2.5 mL of DMF was added 172 mg (1.1 mmole) of 2-chloro-4,5-dimethylphenol and 193.5 mg (1.4 mmole) of potassium carbonate. The suspension was prepared in a capped vial and placed in an aluminum heating block equipped with a shaker. The aluminum block was heated to 110° C. for 16 h. After allowing the vial to cool, the mixture was treated with 10 mL of water and 2 mL of diethyl ether. The organic layer was removed and the aqueous layer extracted two times with diethyl ether. Combined organic extracts were filtered through 5 g of silica and the silica washed with 10 mL of diethyl ether. The filtrates were concentrated under a stream of $N_2$ to afford an off-white solid, which was used in the next step without further purification: $^1$H NMR ($CDCl_3$/300 MHz) 1.36 (t, 3H, J=7.2 Hz), 2.25, (s, 3H), 2.27 (s, 3H), 4.32 (m, 2H), 5.66 (q, 1H, J=6.8 Hz), 6.27 (s, 1H), 6.93 (2, 1H), 7.25 (s, 1H), 7.33 (s, 1H), 7.66 (s, 1H); $^{19}$F NMR ($CDCl_3$/300 MHz) −78.9 (d, 3F, J=6.2 Hz).

Step 2. Preparation of 6-Chloro-7-(2-chloro-4,5-dimethylphenoxy)-2-(trifluoromethyl)-2H-chromene-3-carboxylic acid To the concd product of step 1 in a suitable vial was added 400 mg (mmole) of lithium hydroxide monohydrate, 1 mL of water, 2 mL of methanol and 7 mL of THF. The vial was capped, in an aluminum heating block and the block heated to 100° C. for 30 min. After allowing the vial to cool to rt, the mixture was treated with 5 mL of 1N HCl and 2 mL of diethyl ether. The organic layer was removed and the aqueous layer extracted two times with diethyl ether. Combined organic extracts were concd by evaporation of solvent under a stream of $N_2$ followed by conc in vacuo to afford 150 mg (34.6%) of a yellow solid: $^1$H NMR (CDCl$_3$/300 MHz) 2.26 (s, 3H), 5.64 (q, 1H, J=6.8 Hz), 6.27 (s, 1H), 6.94 (s, 1H), 7.26 (s, 1H), 7.3H (s, 1H), 11.28 (hs, 1H); MS (ES−) 431 (M−1, 100); HRMS (ES−) m/z calcd for (M−H; $C_{19}H_{12}Cl_2F_3O_4$) 431.0059, found 431.0048.

Preparation of 6-Chloro-7-aryloxy-2-(trifluoromethyl)-2H-chromene-3-carboxylic Acids by a Parallel Method The following Examples in Table 6 were prepared as previously described for 6-chloro-7-(2-chloro-4,5-dimethylphenoxy)-2-(trifluoromethyl)-2H-chromene-3-carboxylic acid using parallel synthesis apparatus with each reaction carried out on either 1.0 or 0.5 mmole scale. Products were purified as needed by reverse phase chromatography (C 18 column, 40 mm i.d.×100 mm, gradient CH$_3$CN/0.1% TFA in H$_2$O).

TABLE 6

Yield, Purity, Mass Spectral Data and HPLC Retention Time for 6-Chloro-7-aryloxy-2-(trifluoromethyl)-2H-chromene-3-carboxylic Acids Prepared by Parallel Synthesis Methods[1]

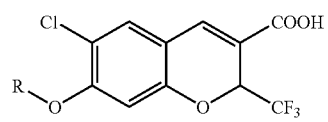

| Example | LC (ret. Time) | MS (ES+) | % Purity | % Yield |
|---|---|---|---|---|
| 370 | 4.304 | 433 | 95 | 34.6 |
| 371 | 3.581 | 399 | 89 | 76.1 |
| 372 | 3.377 | 417 | 99 | 79.1 |
| 373 | 3.636 | 419 | 99 | 78.0 |
| 374 | 3.793 | 453 | 99 | 79.1 |
| 375 | 3.704 | 413 | 83 | 71.7 |
| 376 | 3.555 | 399 | 95 | 82.5 |
| 377 | 3.38 | 385 | 99 | 80.2 |
| 378 | 3.587 | 399 | 94 | 77.2 |
| 379 | 3.363 | 385 | 99 | 68.8 |
| 380 | 2.295 | 414 | 94 | 68.7 |
| 381 | 3.888 | 445 | 99 | 40.3 |
| 382 | 3.837 | 425 | 94 | 82.1 |
| 383 | 3.768 | 413 | 91 | 81.9 |
| 384 | 3.748 | 453[2] | 85 | 62.2 |
| 385 | 3.712 | 413 | 94 | 70.1 |
| 386 | 3.736 | 413 | 94 | 82.6 |
| 387 | 3.829 | 427 | 94 | 75.9 |
| 388 | 3.525 | 463[3] | 99 | 76.9 |
| 389 | 3.868 | 427 | 96 | 85.1 |
| 390 | 3.666 | 411 | 96 | 76.3 |
| 391 | 3.111 | 389 | 99 | 67.0 |
| 392 | 3.347 | 385 | 94 | 70.5 |
| 393 | 2.216 | 436 | 99 | 13.1 |
| 394 | 2.996 | 406 | 91 | 49.8 |
| 395 | 3.305 | 415 | 99 | 68.3 |
| 396 | 2.801 | 386 | 93 | 45.8 |
| 397 | 1.895 | 386 | 99 | 48.7 |
| 398 | 3.812 | 443 | 99 | 68.6 |
| 399 | 3.151 | 389 | 97 | 60.6 |
| 400 | 2.964 | 415 | 99 | 64.3 |
| 401 | 3.024 | 389 | 99 | 62.1 |
| 402 | 2.811 | 431 | 99 | 63.0 |
| 403 | 3.669 | 477 | 99 | 58.6 |
| 404 | 3.227 | 435 | 99 | 61.1 |
| 405 | 3.376 | 403 | 99 | 69.9 |
| 406 | 3.558 | 451 | 97 | 54.6 |
| 407 | 3.825 | 433 | 92 | 72.5 |
| 408 | 3.631 | 419 | 95 | 66.7 |
| 409 | 3.345 | 403 | 95 | 68.3 |
| 410 | 2.717 | 450[3] | 99 | 52.4 |
| 411 | 3.099 | 407 | 99 | 67.9 |
| 412 | 3.893 | 433 | 99 | 70.4 |
| 413 | 3.501 | 439 | 99 | 62.2 |
| 414 | 3.956 | 605[2] | 99 | 67.8 |
| 415 | 3.691 | 527[4] | 93 | 71.1 |
| 416 | 3.25 | 449[3] | 99 | 61.3 |
| 417 | 3.809 | 475 | 99 | 53.6 |
| 418 | 3.651 | 439 | 99 | 64.3 |
| 419 | 3.71 | 499[3] | 99 | 59.5 |
| 420 | 3.328 | 467[3] | 99 | 70.2 |
| 421 | 3.317 | 467[3] | 99 | 53.9 |
| 422 | 3.317 | 485[3] | 91 | 74.6 |
| 423 | 3.587 | 453[2] | 99 | 0.0 |
| 424 | 2.78 | 426 | 99 | 0.0 |
| 425 | 3.069 | 430 | 99 | 0.0 |
| 426 | 3.893 | 422 | 77 | 2.7 |
| 427 | 3.878 | 436 | 74 | 1.7 |
| 428 | 3.506 | 512 | 95 | 7.4 |
| 429 | 3.319 | 421 | 91 | 2.0 |
| 430 | 2.838 | 406 | 89 | 17.3 |
| 431 | 3.312 | 450[3] | 95 | 16.0 |
| 432 | 3.836 | 490 | 92 | 4.8 |
| 433 | 3.33 | 423 | 99 | 36.9 |
| 434 | 3.993 | 427 | 99 | 21.6 |
| 435 | 3.885 | 413 | 99 | 27.2 |
| 436 | 3.516 | 473 | 74 | 27.0 |
| 437 | 3.469 | 423 | 99 | 33.6 |
| 438 | 3.136 | 407 | 99 | 41.7 |
| 439 | 3.445 | 457 | 99 | 40.7 |
| 440 | 3.334 | 403 | 99 | 34.5 |
| 441 | 3.651 | 399 | 99 | 28.5 |
| 442 | 3.674 | 419 | 99 | 23.6 |
| 443 | 3.582 | 467[3] | 99 | 37.7 |
| 444 | 3.433 | 403 | 99 | 36.1 |
| 445 | 3.74 | 473 | 99 | 18.4 |
| 446 | 3.858 | 461 | 99 | 31.5 |
| 447 | 3.957 | 481 | 99 | 28.7 |
| 448 | 3.151 | 429[5] | 99 | 33.6 |
| 449 | 3.88 | 511 | 99 | 31.5 |
| 450 | 3.739 | 483[6] | 99 | 38.6 |
| 451 | 3.837 | 413 | 99 | 21.1 |
| 452 | 3.981 | 463[3] | 99 | 38.3 |
| 453 | 3.778 | 419 | 99 | 35.1 |
| 454 | 3.86 | 399 | 99 | 31.7 |
| 455 | 4.379 | 489 | 99 | 37.9 |
| 456 | 4.308 | 481 | 99 | 33.0 |
| 457 | 4.37 | 439 | 99 | 30.5 |
| 458 | 3.817 | 441 | 99 | 27.8 |
| 459 | 4.056 | 413 | 99 | 38.1 |
| 460 | 3.54 | 415 | 99 | 26.8 |
| 461 | 2.815 | 415 | 99 | 37.4 |
| 462 | 4.267 | 427 | 99 | 26.9 |
| 463 | 4.379 | 441 | 99 | 33.7 |
| 464 | 3.772 | 441 | 99 | 31.7 |
| 465 | 2.97 | 449 | 99 | 31.1 |

TABLE 6-continued

Yield, Purity, Mass Spectral Data and HPLC Retention Time for 6-Chloro-7-aryloxy-2-(trifluoromethyl)-2H-chromene-3-carboxylic Acids Prepared by Parallel Synthesis Methods[1]

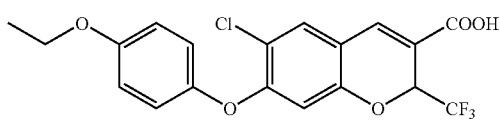

| Example | LC (ret. Time) | MS (ES+) | % Purity | % Yield |
| --- | --- | --- | --- | --- |
| 466 | 3.606 | 449[3] | 99 | 40.8 |
| 467 | 3.151 | 383[7] | 99 | 41.7 |
| 468 | 2.516 | 383[8] | 99 | 29.6 |

[1]See General Experimental section for description of recorded data. % Purity was determined by UV at 254 nm.
[2]Listed ion is the M + 1 of a $Cl_3$ cluster; (M + 1, 100; M + 3, 97).
[3]Listed ion is the M + 1 of a ClBr cluster; (M + 1, 77; M + 3, 100).
[4]Listed ion is the M + 1 of a $ClBr_2$ cluster; (M + 1, 44; M + 3, 100).
[5]429 (M + 1, 65), 397 (100).
[6]Listed ion is the M + 1 of a $Cl_2Br$ cluster; (M + 1, 61; M + 3, 100).
[7]383 (M-$OCH_3$, 100), detailed characterization obtained by ES-, $^1$H NMR and HRMS (see below).
[8]383 (M-OH, 100), detailed characterization obtained by ES-, 1$^1$H NMR and HRMS (see below).

EXAMPLE 395

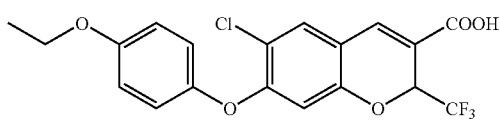

6-Chloro-7-(4-ethoxyphenoxy)-2-(trifluoromethyl)-2H-chromene-3-carboxylic acid

The sample obtained from the parallel synthesis method (table 2) was concd to afford 141.8 mg (68.3%) of an off-white solid: $^1$H NMR (d$^6$-acetone/400 MHz) 1.37 (t, 3H, J=7.0 Hz), 4.06 (q, 2H, J=7.0 Hz), 5.77 (q, 1H, J=7.1 Hz), 6.38 (s, 1H), 7.01 (d, 2H, J=6.8 Hz), 7.09 (d, 2H, J=6.8 Hz), 7.64 (s, 1H), 7.85 (s, 1H); $^{19}$F NMR (d$^6$-acetone/400 MHz) −79.4 (d, 3F, J=7.7 Hz); $^{13}$CNMR (d$^6$-acetone/100 MHz) 15.0, 64.4, 71.5 (q, J=32.7 Hz), 105.3, 115.5, 116.6, 117.5, 122.2, 124.5(q, J=287.1 Hz), 131.6, 136.1, 148.8, 153.7, 157.5, 158.6, 163.3; MS (ES−) 413 (M−1, 100); HRMS (ES−) m/z calcd for ($C_{19}H_{13}ClF_3O_5$) 413.0398, found 413.0396.

EXAMPLE 432

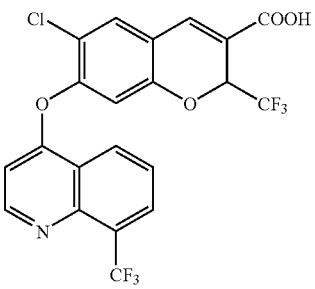

6-Chloro-2-(trifluoromethyl)-7-{ [8-(trifluoromethyl)quinolin-4-yl] oxy}-2H-chromene-3-carboxylic acid The sample obtained from the parallel synthesis method (table 2) was concd to afford 11.7 mg (4.8%) of an off-white solid: $^1$H NMR (d$^6$-acetone/400 MHz) 5.93 (q, 1H, J=7.0 Hz), 6.86 (d, 1H, J=5.1 Hz), 7.24 (s, 1 H), 7.82 (m, 2H), 7.98 (d, 1H, J=7.4 Hz), 8.25 (d, 1H, J=7.2 Hz), 8.65 (d, 1H, J=8.5 Hz), 8.88 (d, 1H, J=5.1 Hz); $^{19}$F NMR (d$^6$-acetone/400 MHz) −60.9 (s, 3F), −79.3 (d, 3F, J=7.7 Hz); MS (ES−) 488 (M+1, 100); HRMS (ES−) m/z calcd for ($C_{21}H_9ClF_6NO_4$) 488.0119, found 488.0112.

EXAMPLE 443

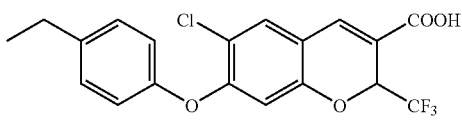

6-Chloro-7-(4-ethylphenoxy)-2-(trifluoromethyl)-2H-chromene-3-carboxylic acid

The sample obtained from the parallel synthesis method (table 2) was concd to afford 56.8 mg (28.5%) of an off-white solid: $^1$H NMR (d$^6$-acetone/400 MHz) 1.22 (t, 3H, J=7.6 Hz), 2.66 (q, 2H, J=7.6 Hz), 5.78 (q, 1H, J=7.1 Hz), 6.45 (s, 1H), 7.04 (d, 2H, J=8.4 Hz), 7.31 (d, 2H, J=8.5 Hz), 7.67 (s, 1H), 7.88,(s, 1H); MS (ES−) 397 (M−1, 100); HRMS (ES−) m/z calcd for ($C_{19}H_{13}ClF_3O_4$) 397.0449, found 397.0484.

EXAMPLE 444

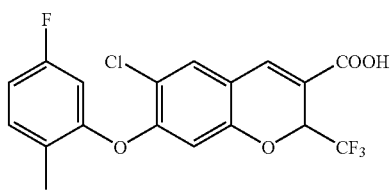

6-Chloro-7-(5-fluoro-2-methylphenoxy)-2-(trifluoromethyl)-2H-chromene-3-carboxylic acid The sample obtained from the parallel synthesis method (table 2) was concd to afford 72.7 mg (36.1%) of an off-white solid: $^1$H NMR (d$^6$-acetone/300 MHz) 2.22 (s, 3H), 5.85 (q, 1H, J=7.0 Hz), 6.53 (s, 1H), 6.88 (dd, 1H), 7.02 (dt, 1H), 7.43 (t, 1H), 7.75 (s, 1H), 7.94 (s,1H); MS (ES−) 401 (M−1, 100); HRMS (ES−) m/z calcd for (M−1; $C_{18}H_{10}ClF_4O_4$) 401.0198, found 401.0187.

EXAMPLE 454

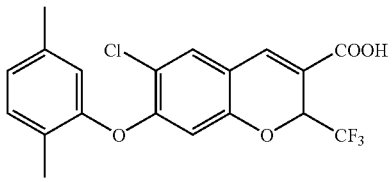

6-Chloro-7-(2,5-dimethylpbenoxy)-2-(trifluoromethyl)-2H-chromene-3-carboxylic acid The sample obtained from the parallel synthesis method (table 2) was concd to afford 63.2 mg (31.7%) of an off-white solid: $^1$H NMR (CD$_3$OD/300 MHz) 2.13 (s, 3H), 2.35 (s, 3H), 5.73 (q, 1H, J=7.0 Hz), 6.18 (s, 1H), 6.83 (s, 1H), 7.05 (d, 1H, J=7.8 Hz), 7.24 (d, 1H, J=7.7 Hz), 7.54 (s, 1H), 7.79 (s, 1H); MS (ES−) 397 (M−1, 100); HRMS (ES−) m/z calcd for ($C_{19}H_{13}ClF_3O_4$) 397.0449, found 397.0419.

EXAMPLE 467

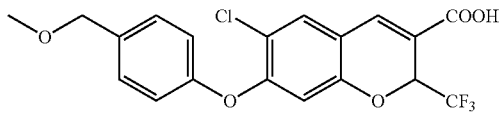

6-Chloro-7-[4-(methoxymethyl)phenoxy]-2-(trifluoromethyl)-2H-chromene-3-carboxylic acid The sample obtained from the parallel synthesis method (table 2) was concd to afford 86.3 mg (41.7%) of an off-white solid: $^1$H NMR (d$^6$-acetone/300 MHz) 3.39 (s, 3H), 4.49 (s, 2H), 5.84 (q, 1H, J=7.0 Hz), 6.57 (s, 1H), 7.14 (d, 2H, J=6.6 Hz), 7.48 (d, 2H, J=8.6 Hz), 7.72 (s, 1H), 7.93 (s, 1H); MS (ES−) 413 (M−1, 100); HRMS (ES−) m/z calcd for (M−1; $C_{19}H_{13}ClF_3O_5$) 413.0398, found 413.0443.

EXAMPLE 468

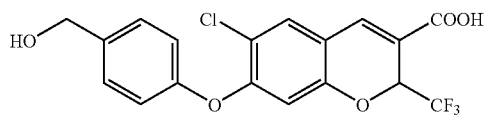

6-Chloro-7-14-(hydroxymethyl)phenoxyl-2-(trifluoromethyl)-2H-chromene-3-carboxylic acid The sample obtained from the parallel synthesis method (table 2) was concd to afford 59.2 mg (29.6%) of an off-white solid: $^1$H NMR (d$^6$-acetone/300 MHz) 2.67 (s, 1H), 4.71 (s, 2H), 5.83 (q, 1H, J=7.0 Hz), 6.52 (s, 1H), 7.13 (d, 2H, J=6.6 Hz), 7.51 (d, 2H, J=8.6 Hz), 7.72 (s, 1H), 7.92 (s, 1H); MS (ES−) 399 (M−1, 100); HRMS (ES−) m/z calcd for (M−1; $C_{18}H_{11}ClF_3O_5$) 399.0242, found 399.0267.

EXAMPLE 469

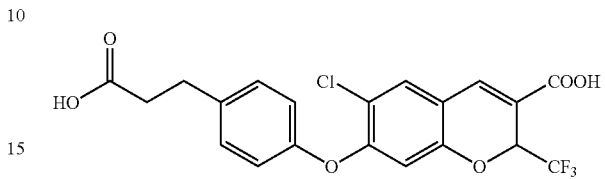

7-[4-(2-Carboxyethyl)phenoxy]-6-chloro-2-(trifluoromethyl)-2H-chromene-3-carboxylic acid Using the two step parallel synthesis route from ethyl 6-chloro-7-fluoro-2-(trifluoromethyl)-2H-chromene-3-carboxylate and methyl 3-(4-hydroxyphenyl)propionate, a mixture of two components was obtained. The two products were separated by reverse phase chromatography (C18, 4 cm i.d.×10 cm, 5% to 95% gradient CH$_3$CN/H$_2$O/0.1%TFA). The less retained component (analytical LC retention time=3.40 min, ELS purity >99%) was concd in vacuo to afford 61.1 mg (27.6%) of a white solid: $^1$H NMR (d$^6$-acetone/400 MHz) 2.59 (t, 2H, J=7.6 Hz), 2.92 (t, 2H, J=7.6 Hz), 5.78 (q, 1H, J=7.1 Hz), 7.04 (d, 2H, J=8.6 Hz), 7.36 (d, 2H, J=8.6 Hz), 7.66 (s, 1H), 7.82 (s, 1H); $^{19}$F NMR (d$^6$-acetone/100 MHz) −79.2 (d, 3F, J=6.8 Hz); MS(ES+) 443 (75%, M+1), 465 (100%, M+Na); MS(ES−) 441 (M−1, 100); HRMS (ES−) m/z calcd for (M−1; $C_{20}H_{13}O_6ClF_3$) 441.0347, found 441.0347.

EXAMPLE 470

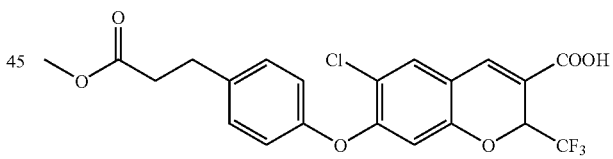

6-Chloro-7-14-(3-methoxy-3-oxopropyl)phenoxyl-2-(trifluoromethyl)-2H-chromene-3-carboxylic acid Using the two step parallel synthesis route from ethyl 6-chloro-7-fluoro-2-(trifluoromethyl)-2H-chromene-3-carboxylate and methyl 3-(4-hydroxyphenyl)propionate, a mixture of two components was obtained. The two products were separated by reverse phase chromatography (C18, 4 cm i.d.×10 cm, 5% to 95% gradient CH$_3$CN/H$_2$O/0.1%TFA). The more retained component (analytical LC retention time=3.83 min, ELS purity >99%) was concd in vacuo to afford 66.0 mg (29.0%) of a white solid: $^1$H NMR (d$^6$-acetone/400 MHz) 2.64 (t, 2H, J=7.6 Hz), 2.94 (t, 2H, J=7.6 Hz), 3.82 (s, 3H), 5.80 (q, 1H, J=7.0 Hz), 7.04 (d, 2H, J=8.6 Hz), 7.36 (d, 2H, J=8.6 Hz), 7.67 (s, 1H), 7.86 (s, 1H); $^{19}$F NMR (d$^6$-acetone/100 MHz) −79.5 (d, 3F, J=7.7 Hz); MS (ES+) 457 (M+1, 100); MS(ES−) 455 (M−1, 100); HRMS (ES−) m/z calcd for (M−1; $C_{21}H_{16}O_6ClF_3$) 455.0504, found 455.0490.

EXAMPLE 471

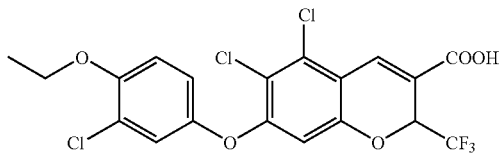

5,6-Dichloro-7-(3-chloro-4-ethoxyphenoxy)-2-(trifluoromethyl)-2H-chromene-3-carboxylic acid To 135 mg (0.32 mmole) of 6-chloro-7-(4-ethoxyphenoxy)-2-(trifluoromethyl)-2H-chromene-3-carboxylic acid in 3 mLs of glac. acetic acid was added excess (approx. 1 g) of gaseous chlorine. After stirring overnight, the mixture was added to 20 mL of water. The reaction mixture was extracted three times w/Et$_2$O, dried and concd. Preparative reverse phase chromatography afforded 38 mg (24%) an off-white solid: $^1$H NMR (d$^6$-acetone/400 MHz) 1.41 (t, 3H, J=7.0 Hz), 4.15 (q, 2H, J=7.0 Hz), 5.44 (q, 1H, J=6.6 Hz), 6.50 (s, 1H), 7.05 (dd, 1H, J=3.0 Hz, J=8.9 Hz), 7.17 (d, 1H, J=9.0 Hz, 7.21 (d, 1H, J=2.8 Hz), 7.66 (s, 1H); $^{13}$C NMR (d$^6$-acetone/100 MHz) 14.9, 65.8, 77.7 (q, J=31.5 Hz), 106.6, 115.5, 117.1, 118.3, 120.1, 122.5, 123.3 (q, J=283.6 Hz), 124.0, 131.6, 149.4, 151.6, 152.8, 155.7, 164.4; MS (ES+) 483 (M+1, 100); HRMS (ES−) m/z calcd for ($C_{19}H_{13}O_6Cl_3F_3$) 498.9724, found 498.9712 (M−H+H$_2$O).

Preparation of Ethyl 6-chloro-7-(2-chloro-4-bromophenoxy)-2-(trifluoromethyl)-2H-chromene-3-carboxylate

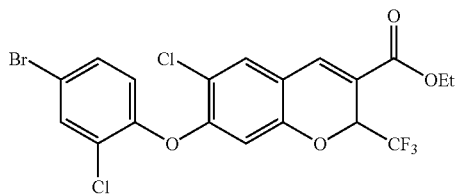

To the mixture of 1.5 g (4.61 mmol) of ethyl 6-chloro-7-fluoro-2-(trifluoromethyl)-2H-chromene-3-carboxylate, 1.04 g (6.44mmol) of 2-chloro-4-bromophenol, and 0.89 g (8.76 mmol) potassium carbonate was added 10 mL of anhydrous DMF. The resulting mixture was heated to 110° C. for five hrs. After cooling to room temperature the reaction was treated with 150 mL of ethyl acetate. The organic phase was washed with saturated sodium bicarbonate three times and brine three times and dried over anhydrous magnesium sulfate. After removing the volatiles, the residue was purified on a silica gel column with EtOAc/hexane (1:9) to afford 1.8 g (76.3%) of a light yellow solid: $^1$H NMR (CDCl$_3$/400MHz) 7.69(s, 1H), 7.68(s, 1H), 7.47 (dd,1H, J=2.4 Hz, 8.7 Hz), 7.37 (s, 1H), 7.00 (d, J=8.7 Hz, 1H), 6.38(s, 1H), 5.70(q, 1H, J=6.6 Hz), 4.35 (m, 2H), 1.38(t, 3H, J=7.2 Hz). MS (ESI+) 511 (M+1, 60), 513 (M+3, 100); HRMS (EI) m/z calcd for ($C_{19}H_{12}BrCl_2F_3O_4$) 509.9248, found 509.9274.

Preparation of Ethyl 6-chloro-7-(2-fluoro-4-bromophenoxy)-2-(trifluoromethyl)-2H-chromene-3-carboxylate

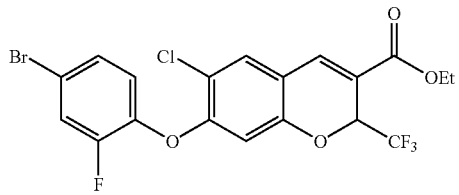

Following the general procedure for ethyl 6-chloro-7-aryloxy-2-(trifluoromethyl)-2H-chromene-3-carboxylates, an 79% yield of the desired compound was obtained as a yellow solid: $^1$H NMR (CDCl$_3$/400 MHz) 7.63 (s, 1H), 7.39 (dd, J=2.4 Hz, 10 Hz, 1H), 7.32-7.29 (m, 2H), 7.00 (t, J=8.4 Hz, 1H), 6.38 (s, 1H), 5.65 (q, J=6.8 Hz, 1H), 4.30 (m, 2H), 1.33 (t, J=7.2 Hz, 3H); LC-MS(ES+) 496.9 (+2, 100), 494.9 (M+1, 73); HRMS (EI+) m/z calcd for ($C_{19}H_{12}ClBrF_4O_4$) 493.9544, found 493.9551.

Preparation of Ethyl 6-chloro-7-(2-methyl-4-iodophenoxy)-2-(trifluoromethyl)-2H-chromene-3-carboxylate

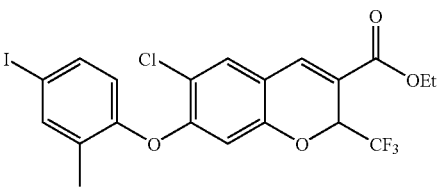

Following the general procedure for ethyl 6-chloro-7-aryloxy-2-(trifluoromethyl)-2H-chromene-3-carboxylates, an 56% yield of the desired compound was obtained as a light yellow solid: $^1$H NMR (CDCl$_3$/400 MHz) 7.63 (s, 1H), 7.61 (d, J=1.2 Hz, 1H), 7.52 (dd, J=1.6 Hz, 8.8 Hz, 1H), 7.30 (s, 1H), 6.68(d, J=8.4 Hz, 1H), 6.28 (s, 1H), 5.63 (q, J=7.2 Hz, 1H), 4.30 (m, 2H), 2.15 (s, 3H), 1.33(t, J=7.2 Hz, 3H); LC-MS(ES+) 538.9 (M+1, 100). HRMS (EI) m/z calcd for ($C_{20}H_{15}ClF_3IO_4$) 537.9656, found 537.9634.

Preparation of Ethyl 6-chloro-7-(2,5-difluoro4-bromophenoxy)-2-(trifluoromethyl)-2H-chromene-3-carboxylate

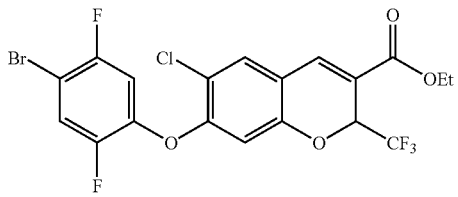

Following the general procedure for ethyl 6-chloro-7-aryloxy-2-(trifluoromethyl)-2H-chromene-3-carboxylates, an 56% yield of the desired compound was obtained as a light yellow solid: $^1$H NMR (CDCl$_3$/300 MHz) 7.63(s, 1H), 7.44(dd, J=9.6 Hz, J=6.2 Hz, 1H), 7.32(s, 1H), 6.88(dd, J=8 Hz, J=6.8Hz, 1H), 6.47(s, 1H), 5.66(q, J=6.4 Hz, 1H), 4.31(m, 1H), 1.34(t, J=6.8 Hz, 3H).

Preparation of 6-Chloro-7-(substituted)phenyloxy-2-(trifluoromethyl)-2H-chromene-3-carboxylic Acids by Palladium Coupling Reactions

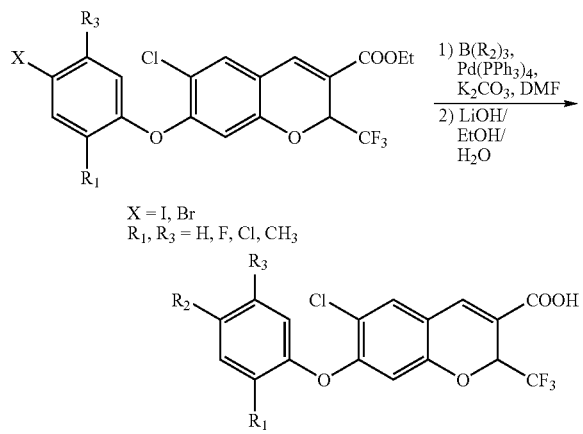

X = I, Br
R$_1$, R$_3$ = H, F, Cl, CH$_3$

EXAMPLE 472

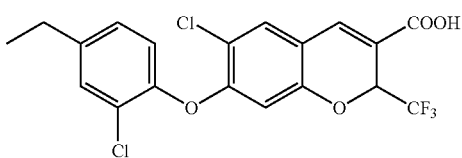

6-Chloro-7-(2-chloro-4-ethylphenoxy)-2-(trifluoromethyl)-2H-chromene-3-carboxylic acid Step 1 Preparation of ethyl 6-chloro-7-(2-chloro-4-ethylphenoxy)-2-(trifluoromethyl)-2H-chromene-3-carboxylate To the mixture of 0.3g (0.59 mmol, 1.0 eqv) of ethyl 6-chloro-7-(2-chloro-4-bromophenoxy)-2-(trifluoromethyl)-2H-chromene-3-carboxylate, 0.32 g (2.3 mmol) of potassium carbonate, 68 mg (0.059 mmol ) of tetrakistriphenyl-phosphinepalladium (0), and 2.5 mL of anhydrous DMF under nitrogen was added 0.83 mL (0.83 mmol, 1.0 M in THF) of triethylborane. The mixture was heated to 110° C. and shaken for five hrs. LC-MS indicated that the reaction was completed. After cooling to room temperature, the reaction was added to 50 mL of ethyl acetate. The resulting organic phase was washed with brine three times, and dried over anhydrous magnesium sulfate. After removing the volatiles, the residue was purified on silica gel column with 1:9 EtOAc/hexane to afford 0.23 g (84.7%) of a light yellow solid. The product was used directly in the next step.

Step 2. Preparation of 6-chloro-7-(2-chloro-4-ethylphenoxy)-2-(trifluoromethyl)-2H-chromene-3-carboxylic acid The isolated light yellow solid (230 mg, 0.5 mmol) was dissolved in 3 mL of tetrhydrofuran. To the resulting solution was added a solution of 104 mg (2.5 mmol) of lithium hydroxide (LiOH.2H$_2$O) in 3 mL of water, followed by addition of 3 mL of ethanol. The resulting solution was heated at 80° C. for one hr. LC-MS indicated that the reaction was complete. The volatiles were removed, the aqueous residue was diluted with water, and then acidified at 0° C. to pH=1.0 with dilute hydrochloric acid. The product were extracted with ethyl acetate, and dried over anhydrous magnesium sulfate. After removing the volatiles, the residue was purified by reverse phase HPLC to afford 90 mg (41%) of a light yellow solid: $^1$H NMR (CDCl$_3$/300 MHz) 7.83(s, 1H), 7.40 (s, 1H), 7.37(s, 1H), 7.19(d, J=8.1 Hz, 1H), 7.10(d, J=8.1 Hz, 1H), 6.32(s, 1H), 5.65(m, 1H), 2.71(q, J=7.5 Hz, 2H), 1.31 (t, J=7.5 Hz, 3H). MS(ES+) 433.0(M+1, 100). MS(ES−) 431.0(M−1, 100). HRMS (ES−) m/z calcd for (M−H; C$_{19}$H$_{12}$Cl$_2$F$_3$O$_4$):431.0059, found: 431.0022.

Preparation of 6-Chloro-7-(substituted)phenyloxy-2-(trifluoromethyl)-2H-chromene-3-carboxylic Acids by a Parallel Method The following Examples in Table 7 were prepared as previously described for 6-chloro-6-(2-chloro-4-ethylphenoxy)-2-(trifluoromethyl)-2H-chromene-3-carboxylic acid using a parallel synthesis apparatus.

TABLE 7

Yield, Purity and Mass Spectral Data for 6-Chloro-7-(substituted)phenyloxy-2-(trifluoromethyl)-2H-chromene-3-carboxylic Acids Prepared by Parallel Synthesis Methods.[1]

| Example | LC | MS (ES+) | % Purity | % Yield |
|---|---|---|---|---|
| 473 | 3.375 | 403 | 100 | 64 |
| 474 | 3.553 | 417 | 98 | 28 |
| 475 | 3.420 | 421 | 95 | 56 |
| 476 | 4.173 | 441 | 95 | 8 |
| 477 | 3.783 | 413 | 100 | 49 |

[1] See General Experimental section for description of recorded data. LC indicates the chromatographic retention time in min. % Purity was determined by UV detection at 254 nm.

EXAMPLE 474

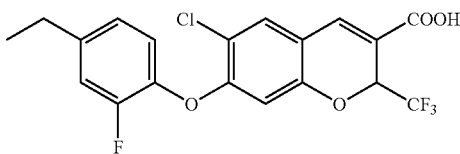

6-Chloro-7-(4-ethyl-2-fluorophenoxy)-2-(trifluoromethyl)-2H-chromene-3-carboxylic acid The product was prepared using the general parallel synthesis method described for 6-chloro-7-(2-chloro-4-ethylphenoxy)-2-(trifluoromethyl)-2H-chromene-3-carboxylic acid. The sample was purified with the Gilson reverse phase chromatography system to afford 18.7 mg (28%) of a light yellow solid: $^1$H NMR (CDCl$_3$, CD$_3$OD/300 MHz) 1.16 (t, 3H, J=7.5 Hz), 2.57 (q, 2H, J=7.5 Hz), 5.46 (m, 1H), 6.24 (s, 1H), 6.93 (m, 2H), 7.22 (d, 1H, J=1.5 Hz), 7.30 (s, 1H), 7.56 (s, 1H); MS (ES+) 417 (M+1, 100); LC-MS purity 99% at 3.553 min. (UV), 100% ELSD; HRMS (ES–) m/z calcd for (M–1; C$_{19}$H$_{12}$O$_4$ClF$_4$) 415.0355, found 415.0376.

EXAMPLE 477

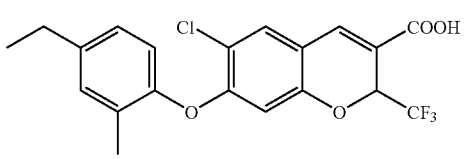

6-Chloro-7-(4-ethyl-2-methylphenoxy)-2-(trifluoromethyl)-2H-chromene-3-carboxylic acid The product was prepared using the general parallel synthesis method described for 6-chloro-7-(2-chloro-4-ethylphenoxy)-2-(trifluoromethyl)-2H-chromene-3-carboxylic acid. Purification by reverse phase chromatography afforded 67.5 mg (49%) of a light yellow solid: $^1$H NMR (CDCl$_3$, CD$_3$OD/400 MHz) 1.26 (t, 3H, J=7.6 Hz), 2.15 (s, 1H), 2.65(q, 2H, J=7.6 Hz), 5.62 (q, 1H, J=3.2 Hz), 6.25 (s, 1H), 6.91 (d, 1H, J=8.4 Hz), 7.07 (d, 1H, J=8 Hz), 7.19 (s, 1H), 7.35 (s, 1H), 7.67 (s, 1H); MS (ES+) 413 (M+1, 100); LC-MS purity 100% at 3.779 min. (UV and ELSD); HRMS (ES–) m/z calcd for (M–1; C$_{20}$H$_{15}$ClF$_3$O$_4$) 411.0605, found 411.0584.

Preparation of 6-Chloro-7-(substituted)phenyloxy-2-(trifluoromethyl)-2H-chromene-3-carboxylic Acids by Stille Reactions

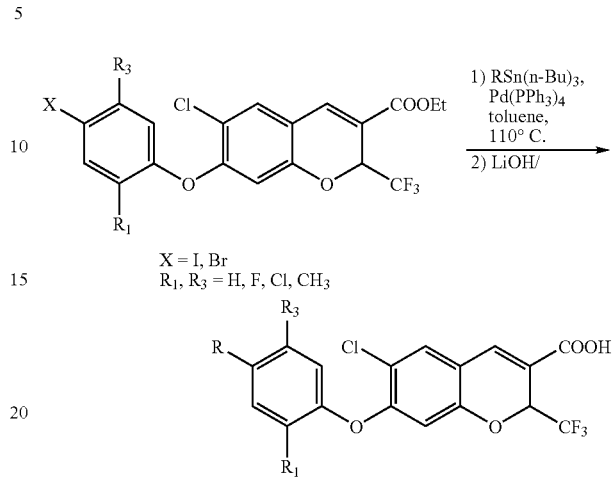

X = I, Br
R$_1$, R$_3$ = H, F, Cl, CH$_3$

EXAMPLE 478

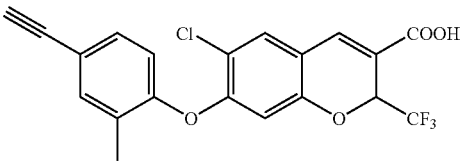

6-Chloro-7-(4-ethynyl-2-methylphenoxy)-2-(trifluoromethyl)-2H-chromene-3-carboxylic acid Step 1. Preparation of ethyl 6-chloro-7-(4-ethynyl-2-methylphenoxy)-2-(trifluoromethyl)-2H-chromene-3-carboxylate To a solution of 0.28 g (0.52 mmol) of ethyl 6-chloro-7-(2-methyl-4-iodophenoxy)-2-(trifluoromethyl)-2H-chromene-3-carboxylate and 12 mg (0.0104 mmol) of tetrakistriphenylphosphine-palladium in 3.5 mL of anhydrous toluene was added 168 uL (0.586 mmol) of tributyl(ethynyl) tin. The resulting solution was heated to 110° C. and shaken for three hrs. LC-MS indicated that the reaction was complete. After cooling to room temperature, the reaction was quenched with addition of 20% aqueous ammonium fluoride. The product was extracted with ethyl acetate. The organic phase was separated and washed with brine, dried over anhydrous magnesium sulfate. After removing the volatiles, the residues were purified by silica gel chromatography with EtOAc/hexane (1:9). The product was carried on to the next step.

Step 2. Preparation of 6-chloro-7-(4-ethynyl-2-methylphenoxy)-2-(trifluoromethyl)-2H-chromene-3-carboxylic acid The product of step 1 (230 mg, 0.53 mmol) was dissolved in 3 ml of tetrahydrofuran. To the resulting solution was added a solution of lithium hydroxide (111 mg, 2.6 mmol)

in 3 mL of water, followed by addition of 3 mL of ethanol. The resulting solution was heated to 80° C. for one hr, LC-MS indicated that the reaction was complete. The volatiles were removed. The residue was diluted with water, and acidified at 0° C. with dilute hydrochloric acid to pH=1.0. The product was extracted with ethyl acetate, and dried over anhydrous magnesium sulfate. After removing the volatiles, the crude product was purified by reverse phase HPLC. The product was obtained 70 mg (28.8%) of a light yellow solid: $^1$H NMR (CDCl$_3$/300 MHz) 7.82 (s, 1H), 7.48(s, 1H), 7.42-7.40(m, 2H), 6.93(d, J=8.1 Hz, 1H), 6.36(s, 1H), 5.66 (q, J=6.9 Hz, 1H), 3.11(s, 1H), 2.23(s, 3H). MS (ESI+) 409.0(M+1, 100). MS(ES−) 407.0(M−H, 100). HRMS (ES−) m/z calcd for (M−H; C$_{20}$H$_{11}$ClF$_3$O$_4$): 407.0292, found: 407.0317

EXAMPLE 479

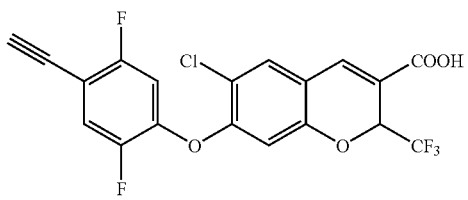

6-Chloro-7-(4-ethynyl-2,5-difluorophenoxy)-2-(trifluoromethyl)-2H-chromene-3-carboxylic acid Using the general method described for 6-chloro-7-(4-ethynyl-2-methylphenoxy)-2-(trifluoromethyl)-2H-chromene-3-carboxylic acid, the product was obtained in 35.8% yield as a light yellow solid: $^1$H NMR(CD$_3$OD/300 MHz) 7.70(s, 1H), 7.37-7.32(m, 2H), 6.80(t, J=8.4 Hz, 1H), 6.56(s, 1H), 5.69(q, J=6.3 Hz, 1H), 3.38(s, 1H); MS (ES+) 430.9 (M+1, 100); HRMS (ES−) m/z calcd for (M−1: C$_{19}$H$_7$ClF$_5$O$_4$) 428.9948, found 428.9902.

EXAMPLE 480

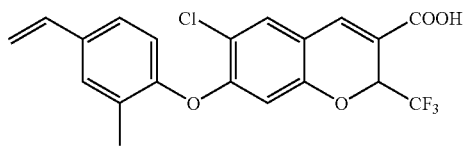

6-Chloro-7-(2-methyl-4-vinylphenoxy)-2-(trifluoromethyl)-2H-chromene-3-carboxylic acid Using the general method described for 6-chloro-7-(4-ethynyl-2-methylphenoxy)-2-(trifluoromethyl)-2H-chromene-3-carboxylic acid, the product was obtained as 161.7 mg (31%) of a light yellow solid: $^1$H NMR (CD$_3$OD/300 MHz) 2.21 (s, 3H),5.27 (d, 1H, J=11.1 Hz), 5.77 (m, 2H), 6.28 (s, 1H), 6.77 (dd, 1H, J=11.1 Hz, 17.7 Hz), 6.94 (d, 1H, J=8.4 Hz), 7.38 (dd, 1H, J=0.9 Hz, 8.1 Hz), 7.45 (s, 1H), 7.56 (s, 1H), 7.80 (s, 1H); MS(ES+) 411 (M+1, 100); LC-MS purity 100% at 3.605 min. (UV and ELSD); HRMS (ES−) m/z calcd for (M−1; C$_{20}$H$_{13}$O$_4$ClF$_3$) 409.0449, found 409.0447.

EXAMPLE 481

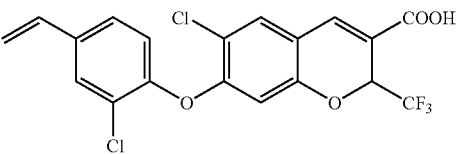

6-Chloro-7-(2-chloro4-vinylphenoxy)-2-(trifluoromethyl)-2H-chromene-3-carboxylic acid Using the general method described for 6-chloro-7-(4-ethynyl-2-methylphenoxy)-2-(trifluoromethyl)-2H-chromene-3-carboxylic acid, the product was obtained as 157.5 mg (27%) of a light yellow solid: $^1$H NMR(CD$_3$OD/300 MHz) 5.35 (d, 1H, J=10.8 Hz), 5.74 (q, 1H, J=6.9 Hz), 5.84 (d, 1H, J=17.7 Hz), 6.33 (s, 1H), 6.75 (dd, 1H, J=11.1 Hz, 17.7 Hz), 7.10 (d, 1H, J=8.4 Hz), 7.46 (dd, 1H, J=2.1 Hz, 6.3 Hz), 7.54 (s, 1H), 7.65 (d, 1H, J=2.1 Hz), 7.79 (s, 1H); MS (ES+) 432 (M+1, 100); LC-MS purity 100% at 3.539 min. (UV and ELSD); HRMS (ES−) m/z calcd for (M−1; C$_{19}$H$_{10}$O$_4$Cl$_2$F$_3$) 428.9903, found 428.9895.

EXAMPLE 480

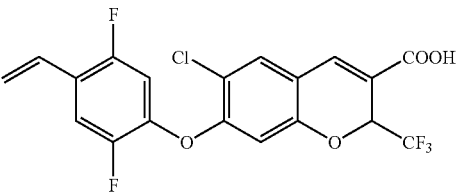

6-Chloro-7-(2,5-difluoro-4-vinylphenoxy)-2-(trifluoromethyl)-2H-chromene-3-carboxylic acid Using the general method described for 6-chloro-7-(4-ethynyl-2-methylphenoxy)-2-(trifluoromethyl)-2H-chromene-3-carboxylic acid, the product was obtained as 190.5 mg (37%) of a light yellow solid: $^1$H NMR (CD$_3$OD/300 MHz) 5.48 (d, 1H, J=11.1 Hz), 5.81 (m, 1H), 5.94 (d, 1H, J=17.7 Hz), 6.65 (s, 1H), 6.89 (dd, 1H, J=5.7 Hz, 9 Hz), 7.13 (dd, 1H, J=7.2 Hz, 9 Hz), 7.61 (s, 1H), 7.71 (dd, 1H, J=6.3 Hz, 9.9 Hz), 7.83 (s, 1H); MS (ES+) 433 (M+1, 100); LC-MS purity 100% at 3.493 min. (UV and ELSD); HRMS (ES−) m/z calcd for (M−1; C$_{19}$H$_9$O$_4$ClF$_5$) 431.0104, found 431.0099.

EXAMPLE 483

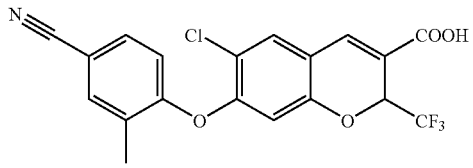

6-Chloro-7-(4-cyano-2-methylphenoxy)-2-(trifluoromethyl)-2H-chromene-3-carboxylic acid Preparation of 6-chloro-7-(4-cyano-2-methylphenoxy)-2-(trifluoromethyl)-2H-chromene-3-carboxylic acid A solution of 0.34 g (0.63 mmol) of Ethyl 6-chloro-7-(2-methyl-4-iodophenoxy)-2-(trifluoromethyl)-2H-chromene-3-carboxylate and 68 mg (0.76 mmol) of copper (I) cyanide in 4 mL of anhydrous dimethylformamide was stirred to 130° C. overnight. LC-MS indicated that the reaction was completed. After cooling to room temperature, the reaction was dumped into 100 mL of ethyl acetate. The organic solution was then washed with 30% aqueous ethylenediamine solution three times to remove cupper, then washed with with brine, and dried over anhydrous magnesium sulfate. After removing the volatiles, the residue was purified on silica gel column with 1:9 EtOAc/hexane. The obtained compound (0.14 g, 0.32 mmol) was dissolved in 3 mL of tetrahydrofuran. To the resulting solution was added a solution of 67.2 mg (1.6 mmol) of lithium hydroxide (LiOH.2H$_2$O) in 3 mL of water, followed by addition of 3 mL of ethanol. The resulting solution was heated to 50° C. for one hr, then at rt for one hr. The volatiles were removed. The residue was diluted with water, and acidified at 0° C. with dilute hydrochloric acid to pH=1, and the product was extracted with ethyl acetate. The combined organic extracts were washed with birne, and dried over anhydrous magnesium sulfate. After removing the volatiles, the residue was purified on reverse phase HPLC. The product was obtained as white solid, 70 mg, purity=100%, yield=27%. $^1$H NMR (CDCl$_3$/CD$_3$OD/300 MHz) 7.66(s, 1H), 7.56(d, 1H), 7.46 (dd, J=1.5, 8.4 Hz, 1H), 7.34(s, 1H), 6.80(d, J=8.4 Hz, 1H), 6.51(s, 1H), 5.66(q, J=6.9 Hz, 1H), 2.31(s, 3H); MS (ES+) 410 (M+1, 100); HRMS (ES−) m/z calcd for (M−1; C$_{19}$H$_{10}$ClF$_3$NO$_4$) 408.0245, found 408.0227.

Preparation of 6-Substituted-7-methoxy-2-(trifluoromethyl)-2H-chromene-3-carboxylic Acids

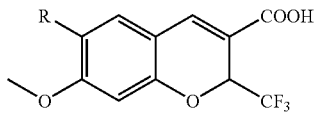

R = as described

Synthesis of Intermediates and Examples 484-515

Preparation of Ethyl 6-iodo-7-methoxy-2-(trifluoromethyl)-2H-chromene-3-carboxylate

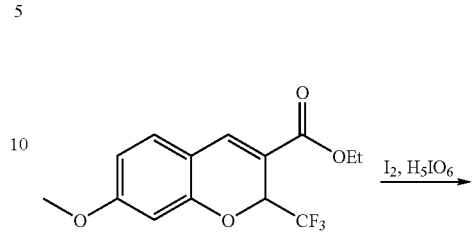

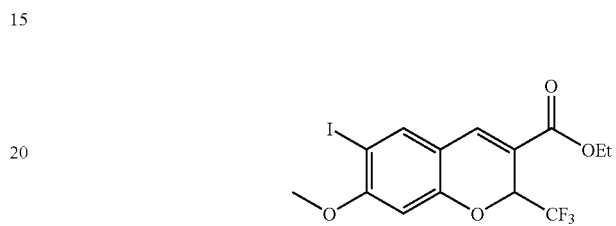

To a solution of 8 g (26.5 mmol) of ethyl 7-methoxy-2-(trifluoromethyl)-2H-chromene-3-carboxylate in 60 mL of ethanol was added 2.8 g (11.2 mmol) of iodine, followed by addition of a solution of 9.0 g (39.5 mmol) of periodic acid in 25 mL of water. The resulting solution was heated to 70° C. for five hrs. After cooling to room temperature, the volatiles were removed, the residue was dissolved in ethyl acetate, and the organic phase washed with saturated aqueous sodium sulfite and satr' brine. The resultant solution was dried over anhydrous magnesium sulfate and the volatiles were removed. The residue was purified by silica gel chromatography with hexane/ethyl acetate mixture to afford 9.8 g (70%) of a light yellow solid: $^1$H NMR (CDCl$_3$/300 MHz) 7.62(s, 1H), 7.60(s, 1H), 6.49(s, 1H), 5.69(q, J=6.9 Hz, 1H), 4.30(m, 2H), 3.89(s, 3H), 1.34(t, J=7.2 Hz, 3H). MS (ESI+) 428.9(M+1, 100). HRMS (EI) m/z calcd for (C$_{14}$H$_{12}$F$_3$O$_4$) 427.9732, found 427.9741.

Preparation of 7-Methoxy-6-substituted-2-(trifluoromethyl)-2H-chromene-carboxylic Acids by Suzuki Couplings

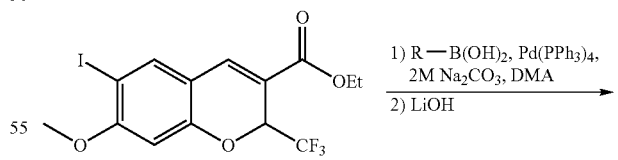

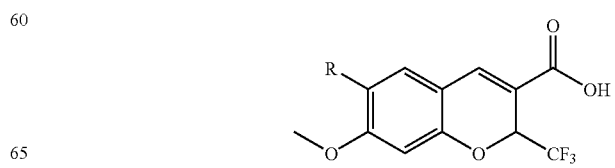

EXAMPLE 484

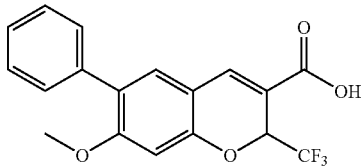

7-Methoxy-6-phenyl-2-(trifluoromethyl)-2H-chromene-3-carboxylic acid

Step 1. Preparation of ethyl 7-methoxy-6-phenyl-2-(trifluoromethyl)-2H-chromene-3-carboxylate A solution of 0.20 g (0.47 mmol) of ethyl 6-iodo-7-methoxy-2-(trifluoromethyl)-2H-chromene-3-carboxylate in 3 mL of anhydrous DMA was prepared and bubbled with nitrogen for 10 min. The solution was treated with 86 mg (0.70 mmol) phenylboronic acid, 54 mg of tetrakis(triphenylphosphine)-palladium(0) (0.1 eq, 0.0467 mmol) and 1.2 mL of 2M aqueous, degassed $Na_2CO_3$ (4.8 eq, 2.24 mmol). The solution was flushed with nitrogen, capped, heated to 95° C. for 16 hours. After cooling to room temperature, brine was added and the mixture extracted 4 times with ethyl acetate. The organic layer was dried over sodium sulfate, filtered and concd under a stream of nitrogen. The product was of sufficient purity to be used directly in the next step.

Step 2. Preparation of 7-methoxM–6-phenyl-2-(trifluoromethyl)-2H-chromene-3-carboxylic acid The ester obtained from step 1 was hydrolyzed to acid by dissolving the sample in 5 mL of ethanol and 1 mL of tetrahydrofuran. A solution of 165 mg of Lithium hydroxide in 6 mL of water was prepared and added to the organic solution. The vessel was capped and heated to 80° C. for 1 hour. After cooling to room temperature, the solution was concd using a nitrogen stream. The basic solution was acidified with 3N HCl until the pH=2 and extracted 4 times with ethyl acetate. The organic layers were combined, dried over sodium sulfate, filtered and solvent removed. The sample was purified using reverse phase chromatography to afford 107.8 mg (66%) of a light yellow solid: $^1$H NMR ($CDCl_3$, $CD_3OD$/300 MHz) 3.77 (s, 3H), 5.61-5.68 (m, 1H), 6.56 (s, 1H), 7.09 (s, 1H), 7.24-7.39 (m, 5H), 7.68 (s, 1H); MS (ES+) 351 (M+1, 100) LC-MS purity 100% at 2.978 min. (UV and ELSD); HRMS (ES–) m/z calcd for (M–1; $C_{18}H_{12}O_4F_3$) 349.0682, found 349.0663.

Preparation of 7-Methoxy-6-substituted-2-(trifluoromethyl)-2H-chromene-3-carboxylic Acids by a Parallel Method The following Examples in table 8 were prepared as previously described for 7-methoxy-6-phenyl-2-(trifluoromethyl)-2H-chromene-3-carboxylic acid using parallel synthesis apparatus.

TABLE 8

Yield, Purity and Mass Spectral Data for 7-Methoxy-6-substituted-2-(trifluoromethyl)-2H-chromene-3-carboxylic Acids Prepared by Parallel Synthesis Methods.[1]

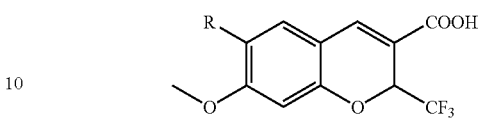

| Example | LC | MS (ES+) | % Purity | % Yield |
|---|---|---|---|---|
| 485 | 2.968 | 357 | 99 | 89 |
| 486 | 2.959 | 381 | 99 | 67 |
| 487 | 2.568 | 382 | 99 | 48 |
| 488 | 3.198 | 397 | 98 | 72 |
| 489 | 3.361 | 419 | 98 | 101 |
| 490 | 3.325 | 419 | 98 | 90 |
| 491 | 2.818 | 341 | 98 | 77 |
| 492 | 2.957 | 381 | 98 | 39 |
| 493 | 2.890 | 341 | 95 | 63 |
| 494 | 1.855 | 366 | 98 | 25 |
| 495 | 2.974 | 396 | 95 | 86 |
| 496 | 2.891 | 395 | 95 | 33 |
| 497 | 3.116 | 365 | 100 | 63 |
| 498 | 3.469 | 393 | 99 | 72 |
| 499 | 3.323 | 401 | 95 | 59 |
| 500 | 1.639 | 352 | 95 | 90 |
| 501 | 2.725 | 411 | 95 | 17 |
| 502 | 2.393 | 413 | 100 | 49 |
| 503 | 2.428 | 381 | 99 | 43 |
| 504 | 1.930 | 402 | 100 | 20 |
| 484 | 2.978 | 351 | 100 | 66 |
| 505 | 3.262 | 385 | 96 | 59 |
| 506 | 3.025 | 385 | 95 | 48 |
| 507 | 3.027 | 369 | 100 | 73 |

[1]See General Experimental section for description of recorded data. LC indicates the chromatographic retention time in min. % Purity was determined by UV detection at 254 nm.

EXAMPLE 508

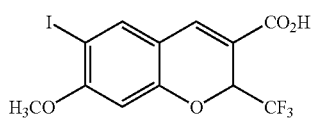

6-Iodo-7-methoxy-2-(trifluoromethyl)-2H-chromene-3-carboxylic acid

To the solution of 3.0 g (7.0 mmol) of ethyl 6-iodo-7-methoxy-2-(trifluoromethyl)-2H-chromene-3-carboxylate in 50 mL of tetrahydrofuran was added a solution of 1.2 g (28 mmol) of lithium hydroxide hydrate in 55 mL of water. The resulting solution was heated to reflux for four hr. The volatiles were removed. The residue was diluted with water. The resulting solution was acidified at 0° .C with dilute hydrochloric acid to pH=1.5. The product was extracted with ethyl acetate. The organic phase was dried over anhydrous magnesium sulfate, filtered and concd to afford 2.5 g (81%) of a light yellow solid: $^1$H NMR ($CDCl_3$/400 MHz) 7.56(s, 1H), 7.52(s, 1H), 6.42(s, 1H), 5.60(q, J=6.8 Hz, 1H), 3.81 (s, 3H). MS (ESI+) 400.9 (M+1, 100). MS(ES–) 398.9(M–H, 100). HRMS (ES–) m/z calcd for ($C_{12}H_7F_3O_4$) M–H: 398.9336, found 398.9359.

Preparation of 6-Substituted-7-methoxy-2-(trifluoromethyl)-2H-chromene-3-carboxylic Acids

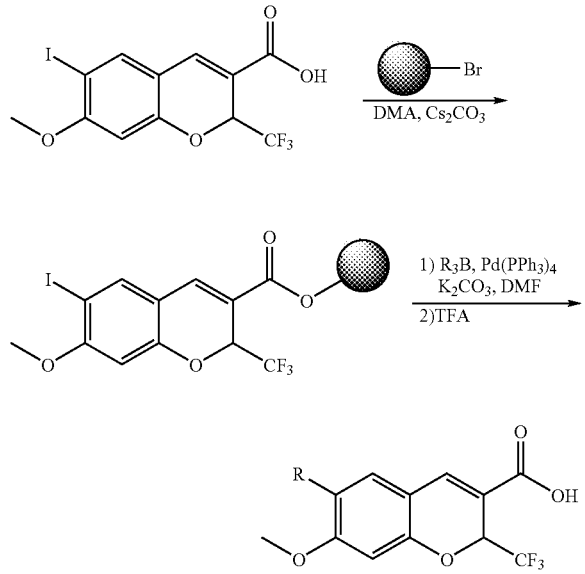

EXAMPLE 509

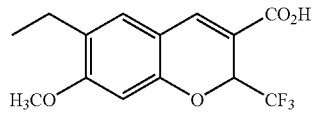

6-Ethyl-7-methoxy-2-(trifluoromethyl)-2H-chromene-3-carboxylic acid

Step 1. Preparation of Wang resin 6-iodo-7-methoxy-2-(trifluoromethyl)-2H-chromene-3-carboxylate To the mixture of 208 mg (0.64 mmol) of cesium carbonate and 516 mg (1.28 mmol) of 6-iodo-7-methoxy-2-(trifluoromethyl)-2H-chromene-3-carboxylic acid was added 5 mL of methanol. After stirring for 30 min, the mixture turned into a clear light yellow solution, with bubbling observed during the interim. The solution was concd and the residue dried in vacuo for three hrs to afford the cesium salt. Bromo-Wang resin (4-(Bromomethyl)phenoxymethylpolystyrene, NovaBiochem cat # 01-64-0186, 1.20 meq/g) was washed successively with $CH_2Cl_2$ and anhydrous DMF, filtered and treated with a solution of the cesium salt in 2 mL of DMF. The resulting resin slurry was heated to 60° C. and shaken for two hr. After cooling to room temperature, the excess reagents were drained, the resin was washed three times each with $DMF/H_2O$ (1:1), DMF, DCM and anhydrous DMF. The loading of resin was determined by $^1H$ NMR (HMDS as internal standard) to be 0.40 mmol/g. The resin was used directly in the next step.

Step 2. Preparation of 6-ethyl-7-methoxy-2-(trifluoromethyl)-2H-chromene-3-carboxylic acid To the resin from step 1 was added 343 mg (2.48 mmol) of potassium carbonate, 78 mg (0.067 mmol) of tetrakistriphenylphosphinopalladium(0), 2 mL of anhydrous DMF, and 1.92 mL (1.0 M in THF, 1.92 mmol) of triethylborane. The mixture was shaken at 110° C. for 15 h. After cooling to room temperature, 3 mL of water was added. The reactor was shaken five min and the excess reagents and solvents were drained. The resin was washed five times with DMF/water (1:1), five times with DMF, and three times with DCM. The resin was treated with 95% TFA/DCM (2×5 mL) for 45 min. The filtrates were collected and resin was washed with DCM. Combined filtrates were concd and purified by silica chromatography (ethyl acetate/hexanes; 3:7) to afford 52 mg (81%) of a light yellow solid: $^1H$ NMR ($CDCl_3$/400 MHz) 7.83(s, 1H), 7.00(s, 1H), 6.50(s, 1H), 5.66(q, J=6.8 Hz, 1H), 3.86(s, 3H), 2.55(q, J=7.6Hz, 2H, ), 1.17(t, J=7.6 Hz, 3H). MS (ESI+) 303.1 (M+1, 100). MS(SE−) 301.1 (M−H, 100). HRMS (ES⁻) m/z calcd for ($C_{14}H_{12}F_3O_4$) M−H: 301.0682, found 301.0649.

EXAMPLE 510

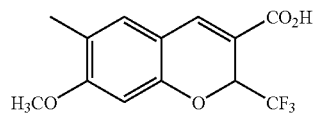

6-Methyl-7-methoxy-2-(trifluoromethyl)-2H-chromene-3-carboxylic acid

This compound was prepared using the same procedure for preparation of 6-ethyl-7-methoxy-2-(trifluoromethyl)-2H-chromene-3-carboxylic acid. Light yellow solid, 48 mg, yield=65%, purity =95%. $^1H$ NMR($CDCl_3$/400 MHz) 7.80 (s, 1H), 7.00(s, 1H), 6.49 (s, 1H ), 5.65(q, J=6.8 Hz, 1H ), 3.86(s, 3H ), 2.13(s, 3H ). MS (ES+) 289 (M+1, 100); LC-MS (ES−) 287 (M−H, 100); HRMS (ES−) m/z calcd for (M−1; $C_{13}H_{11}F_3O_4$) 287.0458, found 287.0450.

Preparation of 7-Methoxy-2-(trifluoromethyl)-6-substituted-2H-chromene-3-carboxylic Acids by Stille Coupling

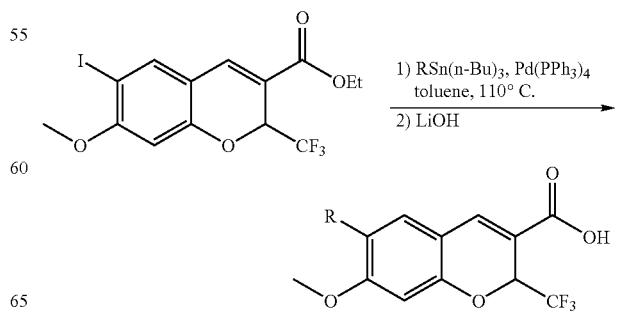

EXAMPLE 511

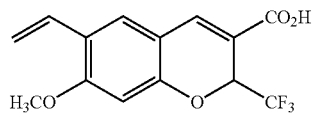

7-methoxy-2-(trifluoromethyl)-6-vinyl-2H-chromene-3-carboxylic acid

Step 1. Preparation of ethyl 7-methoxy-2-(trifluoromethyl)-6-vinyl-2H-chromene-3-carboxylate To a solution of 0.3 g (0.7 mmol) ethyl 6-iodo-7-methoxy-2-(trifluoromethyl)-2H-chromene-3-carboxylate and 16 mg (0.0139 mmol) tetrakis(triphenyl-phosphine)-palladium(0) in 4.2 mL of anhydrous toluene under nitrogen atmosphere was added 228 uL (0.785 mmol) tributyl(vinyl)tin. The resulting solution was heated to 115° C. for three h. To the cooled reaction mixture was added 20 ml of 20% ammonium fluoride. After stirring for 15 min, the product was extracted three times with ethyl acetate. The combined organic extracts were washed twice with 20% ammonium fluoride, washed with brine and dried over anhydrous magnesium sulfate. The crude product was purified by silica chromatography with EtOAc/hexane (1:9) and used directly in the next step.

Step 2. Preparation of 7-methoxy-2-(trifluoromethyl)-6-vinyl-2H-chromene-3-carboxylic acid The isolated intermediate from step 1 (150 mg, 0.46 mmol) was dissolved in 3 mL of THF. To the resulting solution was added a solution of lithium hydroxide (2.3 mmol.) in 3 mL of water. To the resulting mixture was added 3 mL of ethanol. The resulting solution was heated to 80° C. for three h. The mixture was concd in vacuo and the residue acidified to pH=1.0 with dilute aqueous hydrochloric acid. The product was extracted with ethyl acetate. The combined organic extracts were washed with brine and dried over anhydrous magnesium sulfate. The solution was concd in vacuo to afford 110 mg (52%) of the final product: $^1$H NMR (CDCl$_3$/300 MHz) 7.80(s, 1H), 7.48(s, 1H), 6.98-6.88(dd, J=17.7 Hz, 11.2 Hz, 1H), 6.66(s, 1H), 5.80-5.69(m, 2H), 5.20(d, J=11.4 Hz, 1H), 3.90(s, 3H). MS (ESI+) 301.1 (M+1, 100). MS(ES−) 299.1 (M−H, 100). HRMS (ES$^−$) m/z calcd for (C$_{14}$H$_{10}$F$_3$O$_4$) M−H: 299.0526, found 299.0500.

EXAMPLE 512

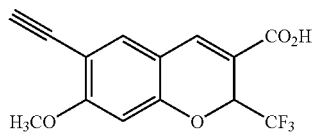

6-ethynyl-7-methoxy-2-(trifluoromethyl)-2H-chromene-3-carboxylic acid

This Example was obtained using the general method for preparation of 7-methoxy-2-(trifluoromethyl)-6-vinyl-2H-chromene-3-carboxylic acid and gave 93 mg (44.6%) of a light yellow solid: $^1$H NMR(CD$_3$OD/300 MHz) 7.77(s, 1H), 7.44(s, 1H), 6.71(s, 1H), 5.80(q, J=6.9 Hz, 1H), 3.92(s, 3H), 3.58(s, 1H). MS (ESI+) 299.1(M+1, 100).

EXAMPLE 513

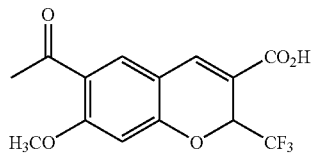

6-acetyl-7-methoxy-2-(trifluoromethyl)-2H-chromene-3-carboxylic acid

This Example was prepared using the same procedure for preparation of 7-methoxy-2-(trifluoromethyl)-6-vinyl-2H-chromene-3-carboxylic acid and afforded 40 mg (62.9%) of a yellow solid: $^1$H NMR (CDCl$_3$/300 MHz) 7.62(s, 1H ), 7.61(s, 1H), 6.49(s, 1H), 5.61(q, J=6.6 Hz, 1H), 3.84(s, 3H), 2.46(s, 3H). MS (ESI+) 317.0(M+1, 100).

EXAMPLE 514

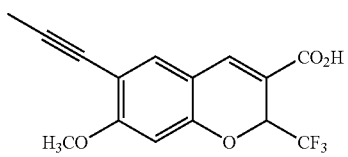

7-methoxy-6-prop-1-ynyl-2-(trifluoromethyl)-2H-chromene-3-carboxylic acid

This Example was prepared using the same procedure for preparation of 7-methoxy-2-(trifluoromethyl)-6-vinyl-2H-chromene-3-carboxylic acid and afforded 50 mg (22.9%) of a yellow solid: $^1$H NMR (CDCl$_3$/300 MHz) 7.69(s, 1H), 7.26(s, 1H), 6.53(s, 1H ), 5.68(q, J=6.9 Hz, 1H), 3.92(s, 3H ), 2.11(s, 3H). MS (ESI+) 313.0 (M+1, 100).

EXAMPLE 515

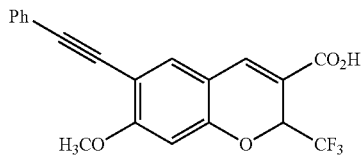

7-methoxy-6-(phenylethynyl)-2-(trifluoromethyl)-2H-chromene-3-carboxylic acid

This Example was prepared using the same procedure for preparation of 7-methoxy-2-(trifluoromethyl)-6-vinyl-2H-chromene-3-carboxylic acid and gave 56 mg (21.4%) of a yellow solid: $^1$H NMR (CDCl$_3$/300 MHz) 7.73(s, 1H), 7.57-7.54(m, 2H), 7.39-7.29(m, 4H), 6.58(s, 1H ), 5.73(q, J=6.9 Hz, 1H), 3.96(s, 3H). MS (ESI+) 749.1 (2M+1, 100), 375.1 (M+1, 88). MS(ES–) 373.1 (M–H, 100). HRMS (ES$^-$) m/z calcd for (M–H; C$_{20}$H$_{12}$F$_3$O$_4$): 373.0682, found 373.0701.

Preparation of 6-Substituted-7-substitutedoxy-2-(trifluoromethyl)-2H-chromene-3-carboxylic Acids

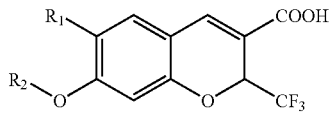

R$_1$, R$_2$ = as described

Synthesis of Intermediates and Examples 516-526

EXAMPLE 516

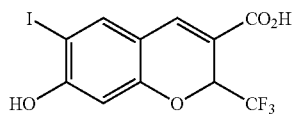

7-hydroxy-6-iodo-2-(trifluoromethyl)-2H-chromene-3-carboxylic acid

This Example was prepared using the same procedure as described in the preparation of 6-ethyl-7-hydroxy-2-(trifluoromethyl)-2H-chromene-3-carboxylic acid. Starting with ethyl 6-iodo-7-methoxy-2-(trifluoromethyl)-2H-chromene-3-carboxylate gave 2.2 g (81%) of a yellow solid: $^1$H NMR (CD$_3$OD/400 MHz) 7.69(s, 1H), 7.63(s, 1H), 6.45(s, 1H), 5.69(q, J=6.8 Hz, 1H). MS (ES–) 386.9(M+H, 100).

Preparation of 6-Ethyl-7-hydroxy-2-(trifluoromethyl)-2H-chromene-3-carboxylic Acid

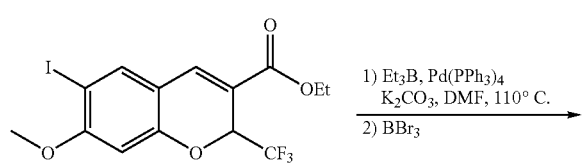

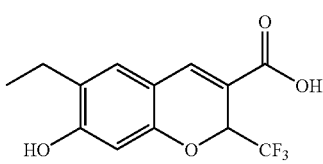

EXAMPLE 517

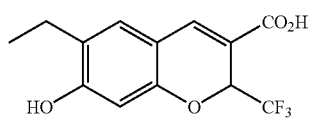

6-Ethyl-7-hydroxy-2-(trifluoromethyl)-2H-chromene-3-carboxylic acid

Step 1. Preparation of ethyl 6-ethyl-7-methoxU-2-(trifluoromethyl)-2H-chromene-3-carboxylate To a mixture of 13.2 g (30.9 mmol) of ethyl 6-iodo-7-methoxy-2-(trifluoromethyl)-2H-chromene-3-carboxylate, 3.6 g (3.1 mmol) of tetrakis(triphenylphosphine)-palladium (0) and 12.8 g (93 mmol) of potassium carbonate in 83 mL of anhydrous DMF was added 43.3 mL (1.0 M/THF, 43.3 mmol) triethylboran. The resulting mixture was heated to 110° C. (oil bath) and stirred for seven h. After cooling to room temperature, the reaction was added to 700 mL of ethyl acetate. The organic phase was then washed with brine and dried over anhydrous magnesium sulfate. After removing the volatiles, the residue was purified by silica chromatography with ethyl acetate/hexane to afford 6.9 g (68%) of a light yellow solid: $^1$H NMR(CDCl$_3$/400 MHz) 7.68(s, 1H), 6.96(s, 1H), 6.48(s, 1H), 5.67(q, 1H), 4.30(m, 2H), 3.03(s, 3H), 2.53(q, J=7.6 Hz, 2H), 1.33(t, J=6.8 Hz, 3H), 1.15(t, J=7.6 HZ, 3H). MS (ESI+) 331.1 (M+1, 100). HRMS (EI) m/z calcd for (C$_{16}$H$_{17}$F$_3$O$_4$) 330.1079, found 330.1063.

Step 2. Preparation of ethyl 6-ethyl-7-hydroxy-2-(trifluoromethyl)-2H-chromene-3-carboxylate To a solution of 6.8 g (20.6 mmol) of ethyl 6-ethyl-7-methoxy-2-(trifluoromethyl)-2H-chromene-3-carboxylate in 30 mL of anhydrous DCM at –78° C. in dry ice/acetone bath was added dropwise a solution of 206 ml (1.0 M in DCM, 206 mmol) of boron tribromide. After finishing addition, the dry ice/acetone bath was removed. The reaction was stirred at room temperature overnight. The reaction was cooled back to –78° C. in dry ice/acetone bath and treated dropwise with 250 mL of methanol. The reaction was allowed to warm to room temperature and subsequently concd in vacuo. The residue was purified by silica chromatography with EtOAc/hexane (2:8). The collected fractions were concd and used directly in step 3.

Step 3. Preparation of 6-ethyl-7-hydroxy-2-(trifluoromethyl)-2H-chromene-3-carboxylic acid To the product of step 2 was added 80 mL of ethanol, followed by addition of a solution of 3.5 g (83 mmol) of lithium hydroxide hydrate in 80 mL of water. The resulting solution was heated to reflux for three h. The mixture was concd, the residue treated with 50 mL of water and the resulting solution acidified to pH=1.0 with dilute hydrochloric acid. The product was extracted with ethyl acetate. The combined organic extracts were washed with brine and dried over anhydrous magnesium sulfate. After removing the volatiles, the residue was further purified by silica chromatography with 1% HOAc in EtOAc/hexane (2:8) to afford 5.6 g (94%) of a green-yellow solid: $^1$H NMR (CDCl$_3$/400

MHz) 7.80(s, 1H), 7.01(s, 1H), 6.43(s, 1H), 5.62(q, J=6.8Hz, 1H), 2.56(q, J=7.6 Hz, 2H), 1.26(t, J=7.6 Hz, 3H). MS (ESI+) 289.1(M+1, 100). MS(ES−) 287.1(M−H, 100). HRMS (ES−) m/z calcd for (M−H; $C_{13}H_{10}F_3O_4$): 287.0526, found 287.0504.

Preparation of Wang Resin 6-Ethyl-7-hydroxy-2-(trifluoromethyl)-2H-chromene-3-carboxylate

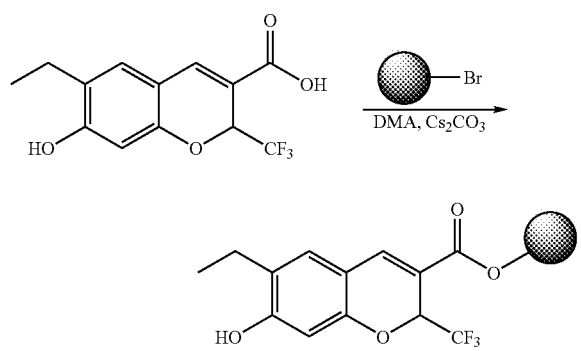

Commercially available 4-(bromomethyl)phenoxymethyl polystyrene (13 g, NovaBiochem, #01-64-0186, 100-200 mesh, 1.20 mmol/g) was swollen in anhydrous DMF for 1.5 h. The resin was washed with anhydrous twice with DMF and subsequently treated with 180 mL of anhydrous DMF, 4 g (13.9 mmol) of 6-ethyl-7-hydroxy-2-(trifluoromethyl)-2H-chromene-3-carboxylic acid and 7.6 g (23.1 mmol) of cesium carbonate. The resin was stirred with an overhead stirrer for 2 hours at room temperature. The slurry was filtered and the resin retreated with 4.0 g of acid and 7.6 g of cesium carbonate. After stirring for 18 h at rt, the resin was filtered and washed three times each with 50% DMF/$H_2O$, DMF, MeOH and DCM. A small portion (approx. 100 mgs) of resin was cleaved by treatment with 50% TFA/DCM for 30 min. The resin was washed with twice with DCM and the collected filtrates concd in vacuo to afford the released 6-ethyl-7-hydroxy-2-(trifluoromethyl)-2H-chromene-3-carboxylic acid: $^1$H NMR (CDCl$_3$,TFA/400 MHz) 1.23 (t, 3H, J=7.6), 2.58 (q, 2H, J=7.6 Hz), 5.61 (q, 1H, J=6.8 Hz), 6.49 (s, 1H), 7.07 (s, 1H), 7.92 (s, 1H); LC-MS purity 84% (UV), 95% (ELSD).

Preparation of 7-Alkoxy-6-ethyl-2-(trifluoromethyl)-2H-chromene-3-carboxylic Acids

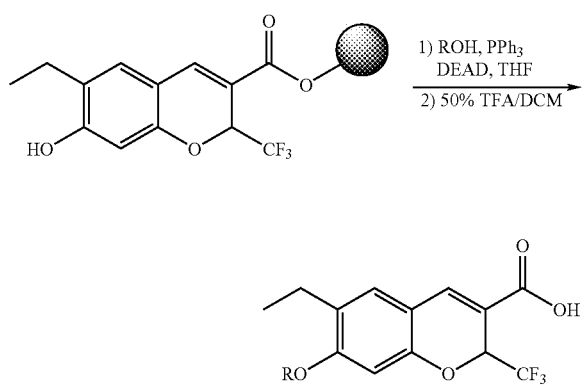

EXAMPLE 518

7-Ethoxy-6-ethyl-2-(trifluoromethyl)-2H-chromene-3-carboxylic acid

A slurry of 100 mg (0.096 mmol) of Wang resin 6-ethyl-7-hydroxy-2-(trifluoromethyl)-2H-chromene-3-carboxylate in DCM was prepared in a solid phase reaction polypropylene tube and allowed to stand for 2 hours. The resin was filtered, washed twice with anhydrous THF and subsequently treated with 1 mL THF, 126 mg (0.483 mmol, 5 eq.) of PPh$_3$, 28 uL (0.483 mmol, 5 eq.) of ethanol and 77 uL (0.483 mmol, 5 eq.) of DEAD. The resin was then shaken at room temperature under nitrogen overnight. After 28 hours, the resin was drained and washed four times each with THF, DMF, MeOH and DCM. The resin (approx. 100 mgs) was cleaved by treatment with 50% TFA/DCM for 30 min. The resin was washed 3 times with DCM, the collected filtrates filtered through silica and the filtrates concentrated in vacuo to yield 24.8 mg (26%) of a yellow solid: 1H NMR (d$^6$-acetone/300 MHz) 1.20 (t, 3H, J=7.5 Hz), 1.46 (t, 3H, J=6.9 Hz), 2.60 (q, 2H, J=7.8 Hz), 4.16-4.20 (m, 2H), 5.78 (q, 1H, J=7.2 Hz), 6.64 (s, 1H), 7.24 (s, 1H), 7.84 (s, 1H); MS (ES+) 317 (M+1, 100) LC-MS purity 72% (UV) at 3.163 min., 100% (ELSD); HRMS (ES−) m/z calcd for (M−1; $C_{15}H_{14}O_4F_3$) 315.0839, found 315.0832.

Preparation of 7-Alkoxy-6-ethyl-2-(trifluoromethyl)-2H-chromene-3-carboxylic Acids by a Parallel Method The following Examples in table 9 were prepared as previously described for 7-ethoxy-6-ethyl-2-(trifluoromethyl)-2H-chromene-3-carboxylic acid using parallel synthesis apparatus.

TABLE 9

Yield, Purity and Mass Spectral Data for 7-Alkoxy-6-ethyl-2-(trifluoromethyl)-2H-chromene-3j-carboxylic Acids Prepared by Parallel Syntesis Methods.[1]

| Example | LC | MS (ES+) | % Purity | % Yield |
| --- | --- | --- | --- | --- |
| 519 | 3.849 | 371 | 95 | 8.5 |
| 520 | 3.656 | 357 | 95 | 3.4 |
| 521 | 1.961 | 380 | 95 | 6.5 |
| 522 | 1.879 | 380 | 95 | 15 |
| 518 | 3.163 | 317 | 72 | 26 |
| 523 | 3.389 | 331 | 94 | 7.9 |

[1]See General Experimental section for description of recorded data. LC indicates the chromatographic retention time in min. % Purity was determined by UV detection at 254 nm.

EXAMPLE 524

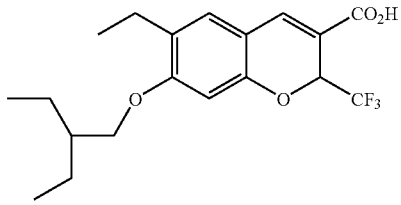

6-ethyl-7-(2-ethylbutoxy)-2-(trifluoromethyl)-2H-chromene-3-carboxylic acid

The product was obtained following the method described for 7-ethoxy-6-ethyl-2-(trifluoromethyl)-2H-chromene-3-carboxylic acid. The crude product was purified by silica chromatography with 1% TFA in ethyl acetate/hexanes (2:8) to afford 60 mg (24.2%) of a light yellow solid: $^1$H NMR (CDCl$_3$/400 MHz) 7.83(s, 1H), 7.00(s, 1H), 6.50(s, 1H), 5.66(q, J=6.8 Hz, 1H), 3.93-3.85(m, 2H), 2.58-2.53(m, 2H), 1.69(m, 1H), 1.54-1.43(m, 4H), 1.19-1.15(m, 3H), 0.97-0.93 (m, 6H). MS(ES+) 373.1(M+1, 100).

EXAMPLE 525

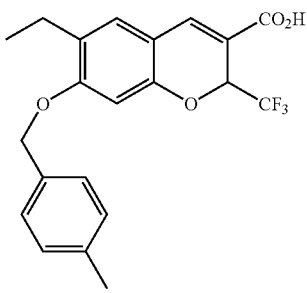

6-Ethyl-7-[(4-methylbenzyl)oxy]-2-(trifluoromethyl)-2H-chromene-3-carboxylic acid The product was obtained following the method described for 7-ethoxy-6-ethyl-2-(trifluoromethyl)-2H-chromene-3-carboxylic acid. Concentration of the filtrates afforded 13 mg light yellow solid: $^1$H NMR(CDCl$_3$/400 MHz) 7.83(s, 1H), 7.25(s, 1H), 7.14-7.09(m, 4H), 6.95(s, 1H), 5.70(q, J=7.2 Hz, 1H), 4.00(m, 2H), 2.51(q, J=7.6 Hz, 2H), 2.30(s, 3H), 1.19(t, J=7.2 Hz, 3H). MS(ES+) 393.1 (M+1, 100).

Preparation of 6-Ethyl-7-{12-(methylthio)pyrimidin4-yl}oxyl-2-(trifluoromethyl)-2H-chromene-3-carboxylic acid

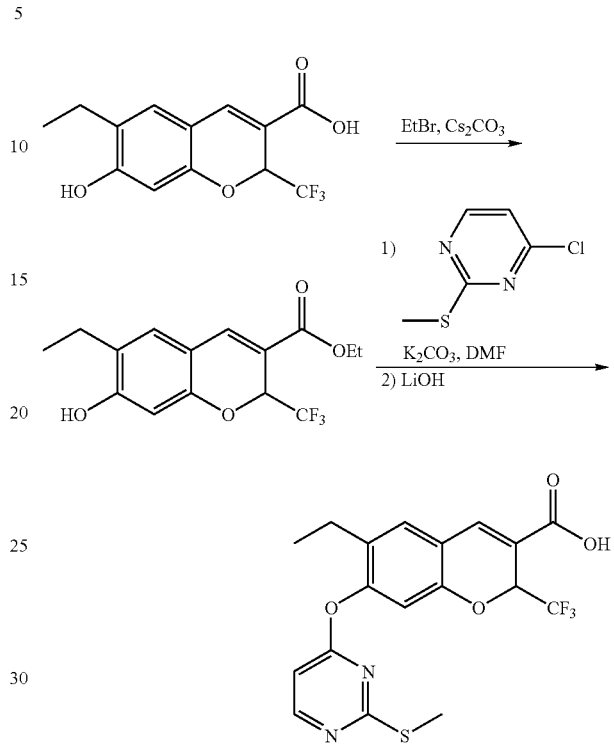

EXAMPLE 526

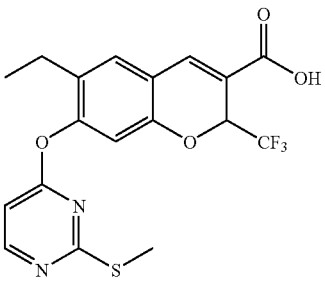

6-Ethyl-7-{[2-(methylthio)pyrimidin-4-yl]oxy}-2-(trifluoromethyl)-2H-chromene-3-carboxylic acid Step 1. Preparation of Ethyl 6-ethyl-7-hydroxy-2-(trifluoromethyl)-2H-chromene-3-carboxylate To a solution of 0.3 g (1.04 mmol) of 6-ethyl-7-hydroxy-2-(trifluoromethyl)-2H-chromene-3-carboxylic acid in 5 mL of anhydrous dimethylformamide was added 255 mg (0.78 mmol) of cesium carbonate in one portion, followed by addition of 103 uL (1.7 mmol) of ethyl bromide. The reaction was stirred at room temperature overnight. The reaction was added to 100 mL of ethyl acetate. The organic phase was washed with brine three times, and dried over anhydrous magnesium sulfate. After removing the volatiles, the residue was purified by silica chromatography with EtOAc/hexane (3:7) to afford 0.21 g (67%) of a light yellow solid: $^1$H NMR (CDCl$_3$/400 MHz) 7.68(s, 1H), 7.00(s, 1H), 6.42(s, 1H), 5.63 (q, J=7.2 Hz, 1H), 5.38(s, 1H), 4.28(m, 2H), 2.54(q, J=7.2 Hz, 2H), 1.31(t, J=7.2 Hz, 3H), 1.20(t, J=7.6 Hz, 3H), MS (ESI+) 317 (M+1, 100).

Step 2. Preparation of Ethyl 6-ethyl-7-{[2-(methylthio)pyrimidin-4-yl]oxy}-2-(trifluoromethyl)-2H-chromene-3-carboxylate To the mixture of 172 mg (0.54 mmol) of Ethyl 6-ethyl-7-hydroxy-2-(trifluoromethyl)-2H-chromene-3-carboxylate and 320 mg (1.95 mmol) of potassium carbonate in 3 mL of anhydrous dimethylformmamide was added 270 uL (2.3 mmol) of 4-chloro-2-methylthiopyrimidine. The mixture was heated at 130° C. for half an hour. After cooling to room temperature, the reaction was dumped into 50 mL of brine, the product was extracted with ethyl acetate. The combined organic phases were washed with brine, and dried over anhydrous magnesium sulfate. After removing the volatiles, the residue was purified by silica chromatography with 1:9 EtOAc/Hexane (1:9) to afford 102 mg (43%) of a yellow solid: $^1$H NMR (CDCl$_3$/400 MHz) 8.35(d, 5.2 Hz, 1H), 7.72(s, 1H), 7.13(s, 1H), 6.74(s, 1H), 6.54(d, J=5.6 Hz, 1H), 5.66(q, J=6.8 Hz, 1H), 4.30(m, 2H), 2.45(q, J=7.6 Hz, 2H), 2.27(s, 3H), 1.33(t, J=7.2 Hz, 3H), 1.12(t, J=7.6 Hz, 3H); MS (ESI+) 441 (M+1, 100).

Step 3. Preparation of 6-ethyl-7-{[2-(methylthio)pyrimidin-4-yl]oxy}-2-(trifluoromethyl)-2H-chromene-3-carboxylic acid To the solution of 100 mg (0.23 mmol) intermediate isolated from step 2 in 1.5 mL of tetrahydrofuran was added a solution of 48 mg (1.2 mmol) lithium hydroxide in 2.5 mL of water, followed by addition of 2.5 mL of ethanol. The reaction was then heated to reflux for one h. After cooling to room temperature, the volatiles were removed, the residue was diluted with water, then acidified at 0° C. with dilute hydrochloric acid to pH=1.0. The product was extracted with ethyl ether. The combined organic phases were washed with brine, dried over anhydrous magnesium sulfate and concd in vacuo to afford 50 mg (53%) of a yellow solid: $^1$H NMR (CDCl$_3$/400 MHz) 8.40(d, J=6 Hz, 1H), 7.85(s, 1H), 7.17(s, 1H), 6.78(s, 1H, 6.58(d, J=5.6 Hz, 1H), 5.66(q, J=7.2 Hz, 1H), 2.48(q, J=7.2 Hz, 2H), 2.29(s, 3H), 1.14(t, J=7.6 Hz, 3H); MS (ES+) 413 (M+1, 100), HRMS (EI) m/z calcd for (C$_{18}$H$_{16}$F$_3$N$_2$O$_4$S) 413.0777, found 413.0768.

Preparation of 8-Iodo-7-methoxy-2-(trifluoromethyl)-2H-chromene-3-carboxylic Acid

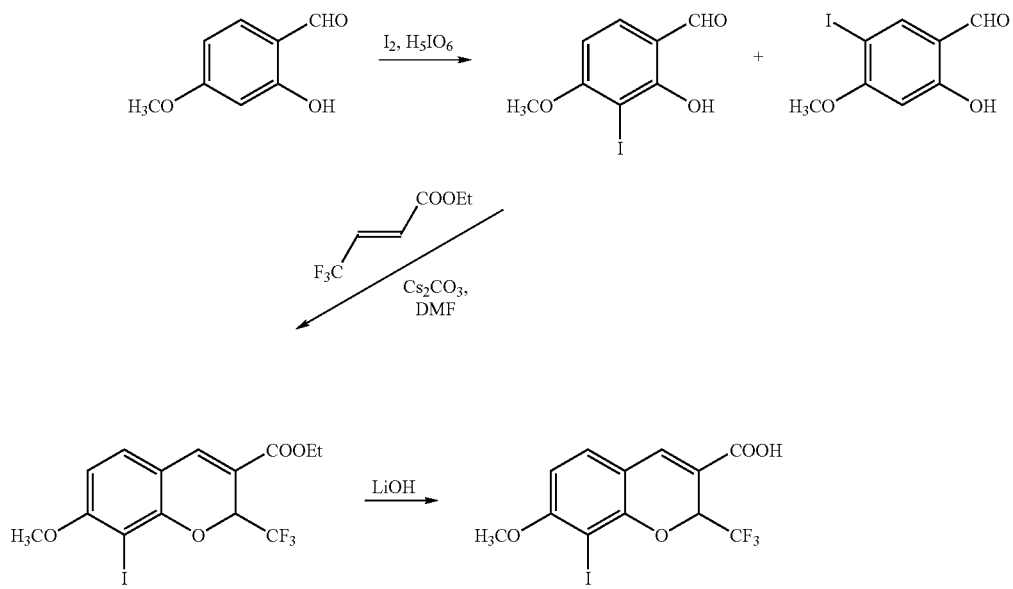

EXAMPLE 527

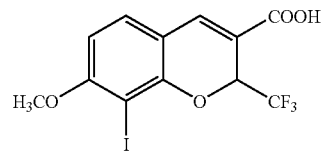

8-Iodo-7-methoxy-2-(trifluoromethyl)-2H-chromene-3-carboxylic acid

Step 1. Preparation of 2-hydroxy-3-iodo-4-methoxybenzaldehyde

To a solution of 4.0 g (26.3 mmol) of 2-hydroxyl-4-methoxybenzaldehyde in 30 mL of ethanol was added 1.87 g (7.4 mmol) of iodine, followed by addition of a solution of 6 g (26.3 mmol) of periodic acid in 10 mL of water. The resulting dark yellow solution was heated to 68° C. for two h. After cooling to room temperature, the reaction was added to 300 mL of ethyl acetate. The resulting organic solution was washed with saturated aqueous solution of sodium sulfite, washed with brine and dried over anhydrous magnesium sulfate. After removing the volatiles, the crude products were purified by silica chromatography to afford 1.8 g (49%) of a light yellow solid: $^1$H NMR(CDCl$_3$/400 MHz,) 12.18(s, 1H), 9.63(s, 1H), 7.53(d, J=8.4 Hz, 1H), 6.56(d, J=8.4 Hz, 1H), 3.99(s, 3H). $^{13}$C NMR (CDCl$_3$/400 MHz) 194.2, 165.3, 163.0, 136.3, 116.1, 103.6, 57.2. MS (ESI+) 278.9(M+1, 100).

Step 2. Preparation of ethyl 8-iodo-7-methoxy-2-(trifluoromethyl)-2H-chromene-3-carboxylate To the mixture of 1.5 g (5.4 mmol) of 2-hydroxy-3-iodo-4-methoxybenzaldehyde, 3.1 mL (20.6 mmol) of ethyl trifluoromethylcrotonate, and 4.2 g(12.9 mmol) of cesium carbonate was added 8 mL of anhydrous N,N-dimethylformamide. The mixture was heated to 90° C. overnight. After cooling to room temperature, to the reaction was added 150 mL of ethyl acetate. The organic solution was filtered, washed with brine and dried over anhydrous magnesium sulfate. After removing the volatiles, the residue was purified by silica chromatography with ethyl acetate/hexane (2:8) to give 0.3 g (14%) a light yellow solid: $^1$H NMR (CDCl$_3$/400 MHz) 7.65(s, 1H), 7.17(d, J=8.4 Hz, 1H), 6.50(d, J=8.4 Hz, 1H), 5.80(q, J=6.8 Hz,1H), 4.30(m, 2H), 3.92(s, 3H), 1.33(t, J=7.6 Hz, 3H). MS (ESI+) 429.0(M+1, 100). HRMS (EI+) m/z calcd for (C$_{14}$H$_{12}$F$_3$O$_4$) 427.9732, found 427.9715.

Step 3. Preparation of 8-iodo-7-methoxy-2-(trifluoromethyl)-2H-chromene-3-carboxylic acid To the solution of 0.4 g (0.93 mmol) of ethyl 8-iodo-7-methoxy-2-(trifluoromethyl)-2H-chromene-3-carboxylate in 8 mL of tetrahydrofuran was added a solution of 155 mg (3.7 mmol) of lithium hydroxide hydrate (LiOH—H$_2$O) in 15 mL of water. The resulting solution was heated to reflux for one h. After cooling to room temperature, the volatiles were removed, the residue was acidified at 0° C. to pH=1.5 with dilute hydrochloric acid. The product was extracted with ethyl ether. The combined organic extracts were washed with brine, dried over anhydrous magnesium sulfate and concd in vacuo to afford 0.30 g (81%) of a light yellow solid: $^1$H NMR (CDCl$_3$/400 MHz) 7.67(s, 1H), 7.18(d, J=8.4 Hz, 1H), 6.51(d, J=8.4 Hz, 1H), 5.78(q, J=6.8 Hz, 1H), 3.92(s, 3H). MS (ESI+) 400.9 (M+1, 100). MS(ES−) 398.9 (M−H, 100). HRMS (ES−) m/z calcd for (M−H; C$_{12}$H$_7$F$_3$O$_4$): 398.9336, found 398.9368.

Chlorination and Derivitization of 6-Ethyl-7-hydroxy-2-(trifluoromethyl)-2H-chromene-3-carboxylic Acid

EXAMPLES 528-531

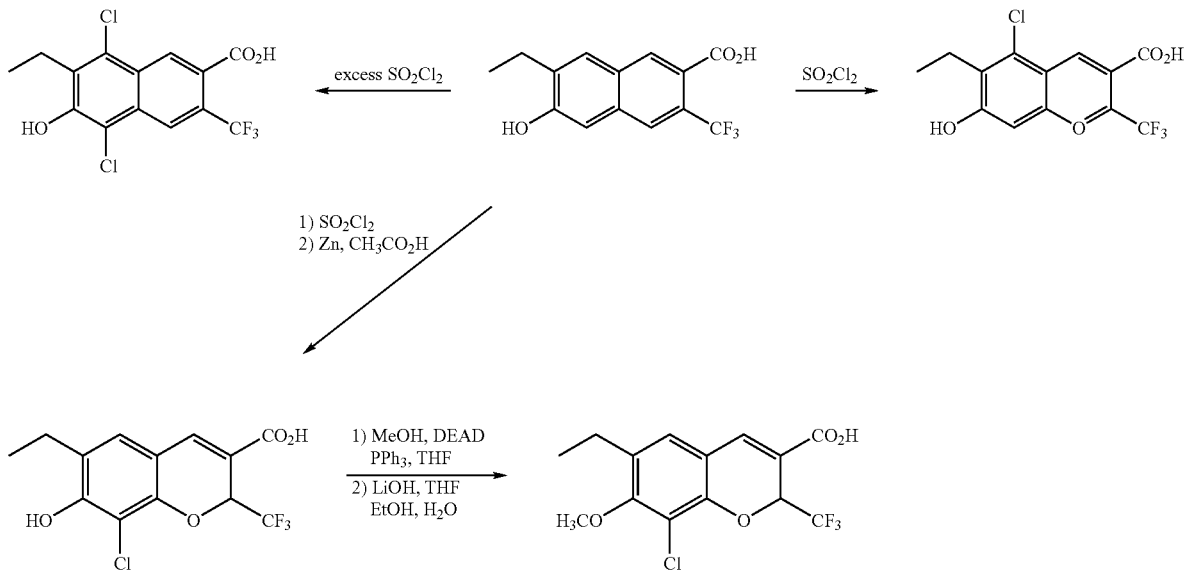

EXAMPLE 528

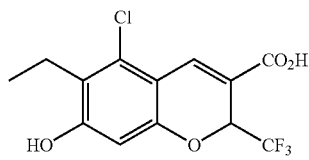

5-Chloro-6-ethyl-7-hydroxy-2-(trifluoromethyl)-2H-chromene-3-carboxylic acid

To a mixture of 100 mg (0.35 mmol) of 6-ethyl-7-hydroxy-2-(trifluoromethyl)-2H-chromene-3-carboxylic acid in 5 mL of anhydrous dichloromethane was added dropwise a solution of 0.42 mL (1.0 M in dichloromethane, 0.42 mmol) sulfuryl chloride. The resulting solution was stirred at room temperature for one hour. The sample was concd and the residue purified on a silica gel column with ethyl acetate:hexane: acetic acid to give 60 mg (52%) of a light yellow solid: $^1$H NMR(CDCl$_3$/400 MHz) 7.71(s, 1H), 6.71(s, 1H), 5.99(s, 1H), 5.65(q, J=6.0 Hz, 1H), 2.38(m, 1H), 2.06(m, 1H), 0.84(t, J=7.6 Hz, 3H); MS (ESI+) 323.0

(M+1, 100); LCMS (ES–) 321 (M–H, 100); HRMS (ES–) m/z calcd for (M–1; $C_{13}H_9ClF_3O_4$) 321.0136, found 321.0118.

EXAMPLE 529

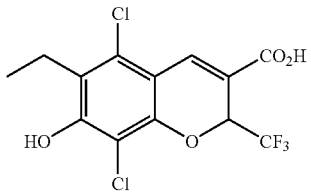

5,8-Dichloro-6-ethyl-7-hydroxy-2-(trifluoromethyl)-2H-chromene-3-carboxylic acid To a suspension of 1.5 g (5.2 mmol) of 6-ethyl-7-hydroxy-2-(trifluoromethyl)-2H-chromene-3-carboxylic acid in 45 mL of anhydrous dichloromethane was added dropwise a solution of 1.0 M sulfuryl chloride (22.75 mmol, 4.4 eqv). The resulting suspension was stirred at room temperature for 12 h; the reaction turned into a clear yellow solution. The sample was concd and the residue dissolved in ethyl acetate, washed with brine and dried over anhydrous magnesium sulfate. Silica chromatography with ethyl acetate:hexane: acetic acid as the eluant afforded 0.12 g (21.5%) of a white solid: $^1$H NMR (CDCl$_3$/400 MHz) 7.72(s, 1H), 6.68(s, 1H), 5.79(q, J=5.6 Hz, 1H), 2.42(m, 1H), 2.11(m, 1H), 0.85(t, J=7.6 Hz, 3H). MS (ESI+) 357.0 (M+1, 100). MS(ES–) 355.0 (M–H, 100). HRMS (ES–) m/z calcd for ($C_{13}H_8Cl_2F_3O_4$) M–H: 354.9746, found: 354.9724.

EXAMPLE 530

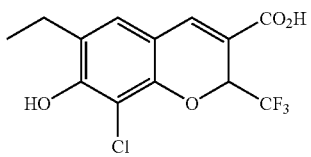

8-Chloro-6-ethyl-7-hydroxy-2-(trifluoromethyl)-2H-chromene-3-carboxylic acid

To a mixture of 1.0 g (3.4 mmol) of 6-ethyl-7-hydroxy-2-(trifluoromethyl)-2H-chromene-3-carboxylic acid in anhydrous dichloromethane (30 mL) was added 4.2 mL (1.0 M in DCM, 22 mmol) sulfuryl chloride dropwise. The resulting mixture was stirred at room temperature for 24 h. The sample was concd and the residue dissolved in 30 mL of acetic acid, followed by addition of 0.5 g granular Zn. The mixture was stirred at room temperature for 3 h, filtered and the filtrate evaporated. The residue was purified by chromatography to afford 0.20 g (18%) of a white solid: $^1$H NMR(CDCl$_3$/400 MHz) 7.79 (s, 1H), 7.26 (s, 1H), 5.77 (q, J=6.8 Hz, 1H), 2.63(q, J=7.6 Hz, 2H), 1.21(t, J=7.6 Hz, 3H). MS (ESI+) 323.0 (M+1, 100).

EXAMPLE 531

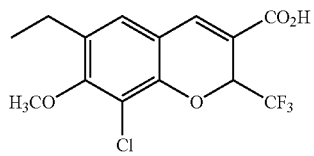

8-Chloro-6-ethyl-7-methoxy-2-(trifluoromethyl)-2H-chromene-3-carboxylic acid

Step 1. Preparation of methyl 8-chloro-6-ethyl-7-methoxy-2-(trifluoromethyl)-2H-chromene-3-carboxylate To a solution of 0.16 g (0.5 mmol) of 8-chloro-6-ethyl-7-hydroxy-2-(trifluoromethyl)-2H-chromene-3-carboxylic acid and 49 uL (2.4 mmol) of methanol in 3 mL of anhydrous tetrahydrofuran was added 0.31 g (1.2 mmol) of triphenylphosphine and 474 uL (1.2 mmol) of diethylazadicarboxylate. The resulting yellow solution was stirred at room temperature for one h. The volatiles were removed and the residue purified on a silica gel column with ethyl acetate/hexane to afford 162 mg (92.4%) of a white solid: $^1$H NMR (CDCl$_3$/300 MHz) 7.66 (s, 1H), 6.96 (s, 1H), 5.76 (q, J=6.6 Hz, 1H), 3.86 (s, 3H), 3.84 (s, 3H), 2.60 (q, J=7.5 Hz, 2H), 1. 19(t, J=7.8 Hz, 3H). MS (ES+) 35 1.0 (M+1, 100).

Step 2. 8-Chloro-6-ethyl-7-methoxy-2-(trifluoromethyl)-2H-chromene-3-carboxylic acid To a solution of 0.14 g(0.4 mmol) of methyl 8-chloro-6-ethyl-7-methoxy-2-(trifluoromethyl)-2H-chromene-3-carboxylate in 5 mL of tetrahydrofuran was added a solution of 82 mg (1.95 mmol ) lithium hydroxide in 8 mL of water, followed by addition of 3 mL of ethanol. The resulting solution was heated to reflux for two h. The mixture was concd in vacuo. The residue was diluted with water and acidified to pH=1.0 with dilute hydrochloric acid. The product was extracted with ethyl acetate and the combinced organic extracts dried over anhydrous magnesium sulfate. Concentration in vacuo afforded 86 mg (64%) of a the product as white solid: $^1$H NMR (CDCl$_3$/400 MHz) 7.80(s, 1H ), 7.01(s, 1H ), 5.77(q, J=6.8 Hz, 1H), 3.89(s, 3H), 2.62(q, J=7.6 Hz, 2H), 1.21(t, J=7.2 Hz, 3H). MS (ESI+) 337.0 (M+1, 100). MS(ES–) 335.0 (M–H, 100), HRMS (ES–) m/z calcd for ($C_{14}H_{11}ClF_3O_4$) M–H: 335.0292, found 335.0297.

Preparation of 6,8-Dichloro-7-substitutedoxy-2-(trifluoromethyl)-2H-chromene-3-carboxylic Acids

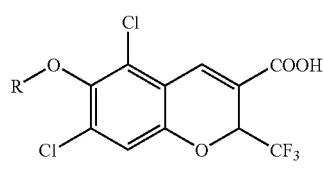

R = as described

Synthesis of Intermediates and Examples 532-535

Preparation of Ethyl 5,7-Dichloro-6-hydroxy-2-(trifluoromethyl)-2H-chromene-3-carboxylate

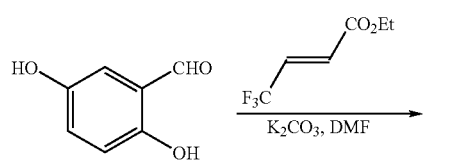

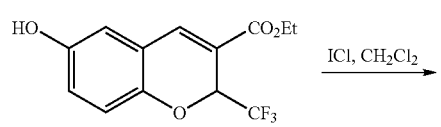

Preparation of 5,7-Dichloro-6-alkoxy-2-(trifluoromethyl)-2H-chromene-3-carboxylic Acids

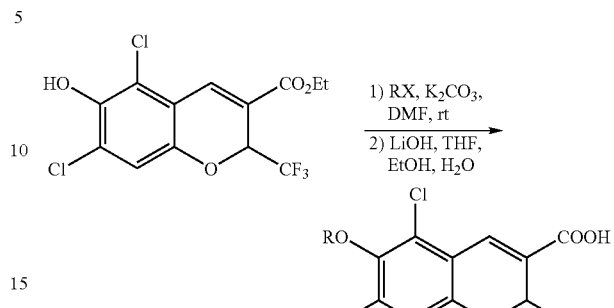

EXAMPLE 532

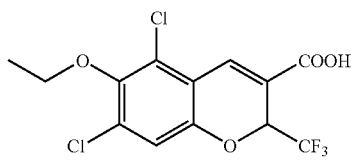

5,7-Dichloro-6-ethoxy-2-(trifluoromethyl)-2H-chromene-3-carboxylic acid

Step 1 Preparation of ethyl 6-hydroxy-2-(trifluoromethyl)-2H-chromene-3-carboxylate A mixture of 10 g (72.5 mmol) of 2,4-dihydroxybenzaldehyde, 15.3 mL (101.4 mmol) of ethyl 4-triflouromethyl-crotonate, and 20 g (145 mmol) of potassium carbonate in 25 mL of anhydrous dimethylformmamide was heated to 90° C. for three h. After cooling to room temperature, the reaction was added to 500 mL of ethyl acetate. The organic phase was washed with brine three times, dried over anhydrous magnesium sulfate and concd in vacuo. Silica chromatography with EtOAc/hexane (3:7) gave 19.0 g (98%) of a yellow solid: $^1$H NMR (CDCl$_3$/400 MHz) 7.63 (s, 1H), 6.85(d, J=8.8 Hz, 1H), 6.79(dd, J=8.8 Hz, 2.8 Hz, 1H), 6.70(d, J=2.8 Hz, 1H), 5.63(q, J=6.8 Hz, 1H), 4.31(m, 2H), 1.34(t, J=7.2 Hz, 3H). MS (ESI+) 289.1 (M+1, 100).

Step 2 Preparation of ethyl 5,7-dichloro-6-hydroxy-2-(trifluoromethyl)-2H-chromene-3-carboxylate To a solution of 1.0 g (3.5 mmol) of ethyl 6-hydroxy-2-(trifluoromethyl)-2H-chromene-3-carboxylate in 10 mL of anhydrous dichloromethane was added a solution of 1.5 mL (30 mmol) of iodomonochloride in 5 mL anhydrous dichloromethane. The resulting brown solution was stirred at room temperature for one hour. The reaction was added to 50 mL of ethyl acetate. The organic solution was washed with sat. sodium sulfite solution three times, washed with brine three times and dried over anhydrous magnesium sulfate. Concentration in vacuo afforded 0.8 g (64%) of a yellow solid: $^1$H NMR (CDC$_3$/300 MHz) 8.00 (s, 1H), 7.01(s, 1H), 5.81(s, 1H), 5.70(q, J=6.6 Hz, 1H), 4.38(m, 2H), 1.40(t, J=7.2 Hz, 3H); MS (ESI+) 357.0 (M+1, 100).

Step 1. Preparation of ethyl 5,7-dichloro-6-ethoxy-2-(trifluoromethyl)-2H-chromene-3-carboxlate To a solution of 0.10 g (0.28 mmol) ethyl 5,7-dichloro-6-hydroxy-2-(trifluoromethyl)-2H-chromene-3-carboxylate in 2 mL of anh. DMF was added 77 mg (0.56 mmol) of potassium carbonate and 23 uL (0.31 mmol) ethyl bromide.

The resulting solution was stirred at room temperature for 18 hours. The solution was poured into ethyl acetate and washed with brine 3 times. The organic layer was dried over sodium sulfate, filtered and concd in vacuo. The crude ester was used directly in the next step without further purification.

Step 2. Preparation of 5,7-dichloro-6-ethoxy-2-(trifluoromethyl)-2H-chromene-3-carboxylic acid The product of step 1 was dissolved in 5 mL THF and 1 mL ethanol. A solution of 61 mg of lithium hydroxide monohydrate in 6 mL of water was added to the organic solution. The vessel was capped and heated to 80° C. for 1 hour. After cooling to room temperature, the sample was concd using a nitrogen stream. The basic solution was then acidified with 3N HCl until the pH=2 and extracted 4 times with ethyl acetate. The organic layers were combined, dried over sodium sulfate, filtered and solvent removed. The sample was purified by reverse phase chromatography to afford 72.6 mg (70%) of a brown solid: $^1$H NMR (CDCl$_3$, CD$_3$OD/300 MHz) 1.46 (t, 3H, J=6.6 Hz), 4.08 (q, 2H, J=7.2 Hz), 5.71 (q, 2H, J=6.9 Hz), 7.01 (s, 1H), 8.08 (s, 1H); MS (ES+) 357 (M+1, 100), 359 (M+3, 68); LC-MS purity 100% at 3.166 min. (UV and ELSD); HRMS (ES−) m/z calcd for (M−1; C$_{13}$H$_8$O$_4$Cl$_2$F$_3$) 354.9746, found 354.9744.

EXAMPLE 533

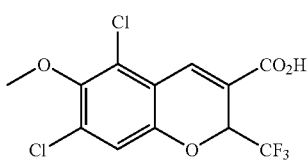

5,7-dichloro-6-methoxy-2-(trifluoromethyl)-2H-chromene-3-carboxylic acid

The compound was prepared using the method developed for 5,7-dichloro-6-ethoxy-2-(trifluoromethyl)-2H-chromene-3-carboxylic acid. After removing the volatiles, the residue was purified by reverse phase HPLC to afford 60 mg (41%) of a white solid: $^1$H NMR (CDCl$_3$/300 MHz) 8.19(s, 1H), 7.06(s, 1H), 5.71(q, J=6.9 Hz, 1H), 3.92(s, 3H). MS (ESI+) 343.0.0 (M+1, 100).

EXAMPLE 534

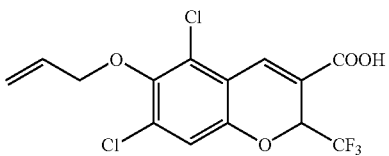

6-(Allyloxy)-5,7-dichloro-2-(trifluoromethyl)-2H-chromene-3-carboxylic acid

The compound was prepared using the method developed for 5,7-dichloro-6-ethoxy-2-(trifluoromethyl)-2H-chromene-3-carboxylic acid. After removing the volatiles, the residue was purified by reverse phase HPLC to afford 79.6 mg (73%) of an ivory solid: $^1$H NMR (CDCl$_3$, CD$_3$OD/300 MHz) 4.46 (d, 2H, J=6 Hz), 5.24 (dd, 1H, J=0.9 Hz, 10.2 Hz), 5.37 (dd, 1H, J=1.5 Hz, 17.1 Hz), 5.63 (q, 1H, J=6.6 Hz), 6.02-6.07 (m, 1H), 6.94 (s, 1H), 7.97 (s, 1H); MS (ES+) 369 (M+1, 100), 371 (M+3, 64); LC-MS purity 95% at 3.212 min. (UV), 100% (ELSD); HRMS (ES−) m/z calcd for (M−1; C$_{14}$H$_8$O$_4$Cl$_2$F$_3$) 366.9746, found 366.9753.

EXAMPLE 535

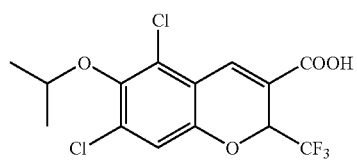

5,7-Dichloro-6-isopropoxy-2-(trifluoromethyl)-2H-chromene-3-carboxylic acid

The compound was prepared using the method developed for 5,7-dichloro-6-ethoxy-2-(trifluoromethyl)-2H-chromene-3-carboxylic acid. After removing the volatiles, the residue was purified by reverse phase HPLC to afford 67.2 mg (70%) of an ivory solid: $^1$H NMR (CDCl$_3$, CD$_3$OD/300 MHz) 1.37 (m, 6H), 4.55 (m, 1H), 5.69(m,1H), 7.00 (s, 1H), 8.05 (s, 1H); MS (ES+) 371 (M+l, 100), 373 (M+3, 65); LC-MS purity 100% at 3.321 min. (UV and ELSD); HRMS (ES−) m/z calcd for (M−1; C$_{14}$H$_{10}$O$_4$Cl$_2$F$_3$) 368.9903, found 386.9929.

Preparation of 6-Chloro-5-phenoxy-2-(trifluoromethyl)-2H-chromene-3-carboxylic acid

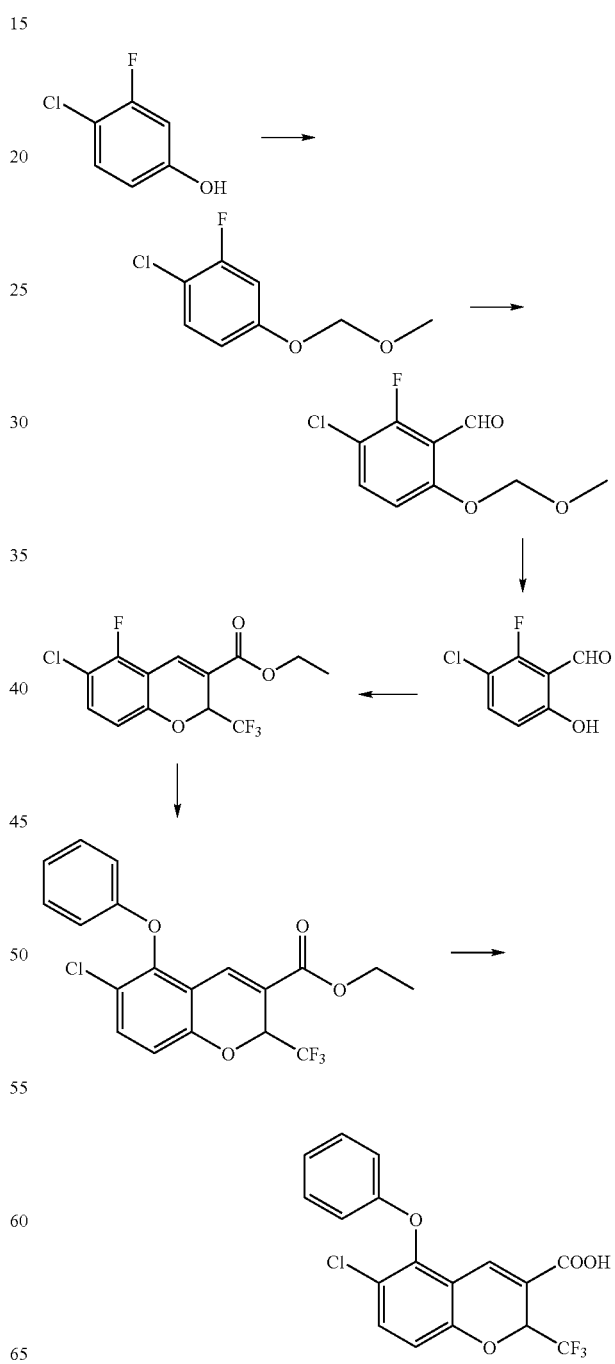

EXAMPLE 536

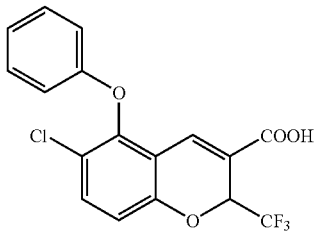

6-Chloro-5-phenoxy-2-(trifluoromethyl)-2H-chromene-3-carboxylic acid

Step 1. Preparation of 1-chloro-2-fluoro(methoxymethoxy)benzene

A solution of 51.3 g (350 mmole) of 3-fluoro-4-chlorophenol in 700 mL of $CH_2Cl_2$ under $N_2$ was prepared and cooled to 5° C. The stirred mixture was treated with 35.3 mL (37.5 g, 465 mmole) of chloromethyl methyl ether. The reactor was equipped with a thermocouple and an addition funnel. To the stirred mixture was added dropwise 61 mL of DIEA (45.2 g, 350 mmole) such that the temperature did not exceed 10° C. After 30 min, an additional 30 mL of DIEA was added dropwise. After a total of 1 h, an additional 30 mL of DIEA was added. The mixture was allowed to stand overnight. The solution was washed with 900 mL of 1N HCl and the aqueous layer extracted three times with $Et_2O$. Combined extracts were dried with Mg2SO4, carefully concd and distilled in vacuo 78-81° C. @ 9 torr to afford 62.5 g (93.7%) of a clear, colorless liquid: $^1$H NMR (CDCl$_3$/400 MHz) 3.46 (s, 3H), 5.13 (s, 2H), 6.77 (ddd, J=1H, 8.9 Hz, 2.8 Hz, 1.3 Hz), 6.87 (dd, 1H, J=10.7 Hz, 2.8 Hz), 7.26 (t, 1H, J=8.7 Hz); $^{19}$F NMR (CDCl$_3$/400 MHz) -113.5 (t, 1F, J=9.7 Hz); $^{13}$C NMR (CDCl$_3$/100 MHz) 56.1, 94.6, 105.2 (d, J=24.2 Hz), 112.8 (d, J=3.4 Hz), 130.5 (d, J=1.1 Hz), 156.9 (d, J=9.7 Hz), 158.3 (d, J=248.1 Hz); MS (EI+) 190 (M+, 12), 129 (8), 117 (8), 45 (100); HRMS (EI) m/z calcd for ($C_8H_8O_2ClF$) 190.0197, found 190.0175.

Step 2. Preparation of 3-chloro-2-fluoro-6-(methoxymethoxy)benzaldehyde

A solution of 4.39 mL (3.38 g, 29.1 mmole) of TMEDA in 40 mL of THF was cooled to -78° C. and subsequently treated with 22.4 mL (29.1 rnmole) of 1.3 M sec-butyllithium in cyclohexane. After allowing the mixture to stir for 15 min, the solution was treated with 3.7 g (19.4 mmole) of 1-chloro-2-fluoro(methoxymethoxy)benzene and allowed to stir for 30 min. The reaction mixture was subsequently treated with 2.25 mL (29.1 mmole) of DMF, the ice bath removed and the reaction allowed to stir for 30 min. The reaction was treated with 4.0 mL of AcOH followed by 100 mL of $H_2O$. The mixture was extracted three times with $Et_2O$, the combined extracts were washed with brine, dried and concd to afford 4.26 g (100%) of a clear, yellow oil which solidified on standing: mp 44-49° C.; $^1$H NMR (CDCl$_3$/400 MHz) 3.52 (s, 3H), 5.29 (s, 2H), 7.01 (dd, 1H, J=9.0 Hz, 1.5 Hz), 7.51 (dd, J=1H, 9.0 Hz, 8.0 Hz), 10.42 (d, 1H, J=1.3 Hz); $^{19}$F NMR (CDCl$_3$/400 MHz) -116.5 (d, 1F, J=8.7 Hz); $^{13}$C NMR(CDClhd 3/100 MHz) 56.7, 95.2, 111.5 (d, J=4.5 Hz), 114.7 (d, J=17.7 Hz), 115.8 (d, J=9.0 Hz), 135.7 (d, J=2.3 Hz), 157.9 (d, J=264.6 Hz), 158.2 (d, J=4.4 Hz), 186.3 (d, J=2.1 Hz); MS (ESI+) 187 (M-OCH3, 100).

Step 3. Preparation of 3-chloro-2-fluoro-6-hydroxybenzaldehyde

To 3.25 g (14.9 mmole) of 3-chloro-2-fluoro-6-(methoxymethoxy)benzaldehyde was added 30 mL of THF, 30 mL of 2-propanol, 15 mL of $H_2O$ and 15 mL of conc. HCl. The mixture was allowed to stir overnight and concd in vacuo to give an aqueous slurry. The slurry was extracted three times with $Et_2O$, washed with brine, concd to give 2.56 g of a yellow solid. The sample was dissolved in 40 mLs hot methanol, treated with 40 mLs water and allowed to cool. Filtration and air drying afforded 1.22 g (35.8%) of a yellow, crystalline solid: mp 78-79° C.; $^1$H NMR (CDCl$_3$/400 MHz) 6.76 (d, 1H, J=9.1 Hz), 7.51 (t, 1H, J=8.7 Hz), 10.27 (s, 1H), 11.39 (s, 1H); $^{19}$F NMR (CDCl$_3$/400 MHz) -123.5 (d, 1F, J=6.8 Hz); $^{13}$C NMR (CDCl$_3$/100 MHz) 110.6(d, J=17.0 Hz), 111.1 (d, J=11.1 Hz), 114.6 (d, J=4.4 Hz), 138.4 (d, J=2.7 Hz), 159.6 (d, J=260.2 Hz), 161.3 (d, J=2.9 Hz), 191.7 (d, J=9.0 Hz); MS(EI) 174 (M, 100), 176 (M+2, 30). Anal. Calc'd for $C_7H_4ClFO_2$: C, 48.16; H, 2.31. Found: C, 48.34; H, 2.45.

Step 4. Preparation of ethyl 6-chloro-5-fluoro-2-(trifluoromethyl)-2H-chromene-3-carboxylate To 1.1 g (6.7 mmole) of 3-chloro-2-fluoro-6-hydroxybenzaldehyde in 2 mL DMF was added 1.0 g (7.2 mmole) of potassium carbonate and 3A molecular sieves. The stirred mixture was heated to 70° C. and treated with 1.5 mL (1.69 g, 10.0 mmole) of ethyl 4,4,4-trifluorocrotonate. After lh the mixture was treated with an additional 1.5 mL of ethyl 4,4,4-trifluorocrotonate and allowed to react overnight. To the cooled mixture was added 1N HCl, the mixture extracted three times with methylene chloride and the combined organic fractions dried and concd. The resultant oil was dissolved in ether, washed three times with water and concd to give an oil. Chromatographic purification (silica, 5-10% EtOAc/hex) gave 0.76 g (35%) of a clear, yellow oil: $^1$H NMR (CDCl$_3$/400 MHz) 1.37 (t, 3H, J=7.2 Hz), 4.34 (m, 2H), 5.72 (q, 1H, J=6.8 Hz), 6.77 (d, 1H, J=8.8 Hz), 7.32 (t, 1H, J=8.5 Hz), 7.92 (s, 1H); $^{19}$F NMR (CDCl$_3$/400 MHz) -78.7 (d, 3F, J=6.8 Hz), -119.6 (d, 1F, J=7.7 Hz); $^{13}$C NMR (CDCl$_3$/100 MHz) 14.2, 61.9, 70.8 (q, J=33.4 Hz), 110.0 (d, J=18.1 Hz), 112.6 (d, J=4.0 Hz), 114.4 (d, J=17.3 Hz), 118.2 (J=2.3 Hz), 123.2 (q, J=287.3 Hz), 129.2 (d, J=4.6 Hz), 133.2 (d, J=1.3 Hz), 152.2 (d, J=4.4 Hz), 154.9 (d, J=256.4 Hz), 163.3; MS (ESI+) 325 (M+l, 100); MS (EI) 324 (M+, 21), 255 (100), 227 (83); HRMS (EI) m/z calcd for ($C_{13}H_9O_3ClF_4$) 324.0176, found 324.0171.

Step 5. Preparation of ethyl 6-chloro-5-phenoxy-2-(trifluoromethyl)-2H-chromene-3-carboxylate To 162.3 g (0.5 mmole) of ethyl 6-chloro-5-fluoro-2-(trifluoromethyl)-2H-chromene-3-carboxylate was added 75 mg (0.80 mmole) of phenol and 120 mg (0.87 mmole) of potassium carbonate in 1.5 mL DMF. The mixture was heated to 110° C. and allowed to stir overnight. After cooling, the mixture was diluted with water and extracted three times with diethyl ether. The combined organic fractions were washed with water, dried and concd to give a crude oil. Preparative reverse phase chromatography (C 18, 4.0 cm×25 cm column, gradient 50%-100% CH3CN) afforded 50 mg (25.1%) of a clear, colorless oil: $^1$H NMR (CDCl$_3$/400 MHz) 1.28 (t, 3H, J=7.1 Hz), 4.26 (m, 2H), 5.70 (q, 1H, J=6.7 Hz), 6.82 (d, 2H, J=7.9 Hz), 6.87 (d, 1H, J=8.7 Hz), 7.06 (t, 1H, J=7.4 Hz), 7.31 (t, 2H, J=8.1 Hz), 7.38 (d, 1H, J=8.9 Hz), 7.79 (s, 1H); $^{19}$F NMR (CDCl$_3$/400 MHz) −78.7 (d, 3F, 6.8 Hz); MS (ESI+) 399 (M+1, 100); MS (EI) 398 (M+, 50), 329 (100), 283 (79), 231 (32); HRMS (EI) m/z calcd for (C$_{19}$H$_{14}$O$_4$ClF$_3$) 398.0533, found 398.0538.

Step 6. Preparation of 6-chloro-5-phenoxy-2-(trifluoromethyl)-2H-chromene-3-carboxylic acid To the sample obtained from Step 5 was added 3.5 mL of THF, 1 mL of methanol and 0.5 mL of a solution of 100 mg of LiOH—H$_2$O in H$_2$O. The mixture was stirred and heated to 100° C. for 30 min. After stirring at rt overnight, the mixture was diluted with 1N HCl and extracted three times with Et2O. Combined extracts were dried and concd in vacuo to afford 49.5 mgs (quant.) of a yellow solid: $^1$H NMR (d$^6$-acetone/400 MHz) 5.89 (q, 1H, J=7.0 Hz), 6.88 (d, 2H, J=7.8 Hz), 7.06-7.12 (m, 2H), 7.37 (t, 2H, J=8.1 Hz), 7.61 (d, 1H, J=9.0 Hz), 7.77 (s, 1H); $^{19}$F NMR (d$^6$-acetone/400 MHz) −79.3 (d, 3F, J=6.7 Hz); $^{13}$C NMR (d$^6$-acetone/100 MHz) 71.2 (q, J=33.0 Hz), 115.1, 115.8, 116.6 (q, J=1.1 Hz), 119.3 (q, J=0.8 Hz), 122.0, 123.8, 124.5 (q, J=286.9 Hz), 130.9, 131.2, 134.7, 148.7, 153.6, 158.8, 164.4; MS (ES+) 283 (M+1, 100); MS (ES−) 369 (M−H, 100); HRMS (ES−) m/z calcd for (C$_{17}$H$_9$O$_4$ClF$_3$) 369.0136, found 369.0159.

General Procedure for Formation of Sodium Salts

EXAMPLE 537

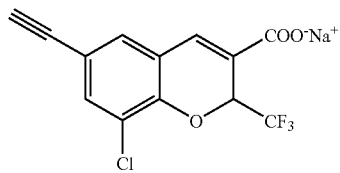

Sodium 8-chloro-6-ethynyl-2-(trifluoromethyl)-2H-chromene-3-carboxylate

A solution of 56.5 mg (0.187 mmole) of 8-chloro-6-ethynyl-2-(trifluoromethyl)-2H-chromene-3-carboxylic acid in 1.5 mL of ethanol was treated with 1.85 mL of 0.1008N NaOH. The resultant mixture was lyophilized to provide 59 mg (quant.) of an off-white solid: $^1$H NMR (CD$_3$OD/400 MHz) 5.97 (q, 1H, J=7.0 Hz), 7.31 (d, 1H, J=1.7 Hz), 7.39 (s, 1 H), 7.41 (d, 1H, J=1.9 Hz), the acetylenic proton exchanges under the basic conditions; MS (ES+) 303 (M+l, 100).

EXAMPLE 538

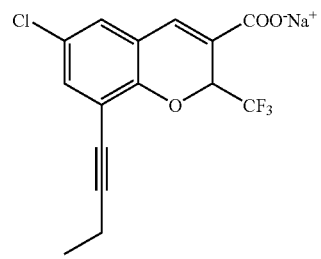

Sodium 8-but-1-ynyl-6-chloro-2-(trifluoromethyl)-2H-chromene-3- carboxylate

A solution of 75.8 mg (0.229 mmole) of 8-but-1-ynyl-6-chloro-2-(trifluoromethyl)-2H-chromene-3-carboxylic acid in 2.0 mL of ethanol was treated with 2.274 mL of 0.1008N NaOH. The resultant mixture was lyophilized to provide a quantitative yield of a yellow solid: $^1$H NMR (CD$_3$OD/400 MHz) 1.22 (t, 3H, J=7.6 Hz), 2.44 (q, 2H, J=7.6 Hz), 5.88 (q, 1H J=7.2 Hz), 7.17-7.19 (m, 2H), 7.32 (s, 1H).

EXAMPLE 539

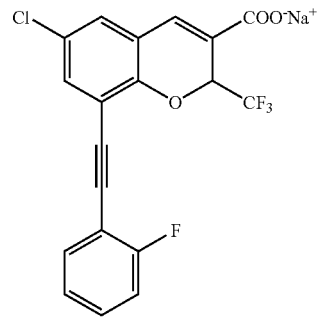

Sodium 6-chloro-8-[(2-fluorophenyl)ethynyl]-2-(trifluoromethyl)-2H-chromene-3-Carboxylate A solution of 84.3 mg (0.213 mmole) of 6-chloro-8-[(2-fluorophenyl)ethynyl]-2-(trifluoromethyl)-2H-chromene-3-carboxylic acid in 2.0 mL of ethanol was treated with 2.108 mL of 0.1008N NaOH. The resultant mixture was lyophilized to provide a quantitative yield of a yellow solid: $^1$H NMR (CD$_3$OD/400 MHz) 5.97 (q, 1H, J=7.2 Hz), 7.14-7.20 (m, 2H), 7.28-7.30 (m, 1H), 7.36-7.42 (m, 3H), 7.51-7.54 (m, 1H).

EXAMPLE 540

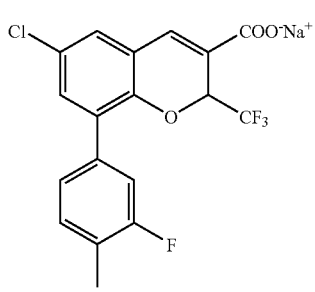

Sodium 6-chloro-8-(3-fluoro4-methylphenyl)-2-(trifluoromethyl)-2H-chromene-3-carboxylate A solution of 52.0 mg (0.135 mmole) of 6-chloro-8-(3-fluoro-4-methylphenyl)-2-(trifluoromethyl)-2H-chromene-3-carboxylic acid in 2.0 mL of ethanol was treated with 1.334 mL of 0.1008N NaOH. The resultant mixture was lyophilized to provide a quantitative yield of a yellow solid: $^1$H NMR (CD$_3$OD/400 MHz) 2.29 (d, 3H, J=1.6 Hz), 5.84 (q, 1H, J=7.2 Hz), 7.17-7.20 (m, 2H), 7.24-7.29 (m, 3H), 7.40 (s, 1H).

EXAMPLE 541

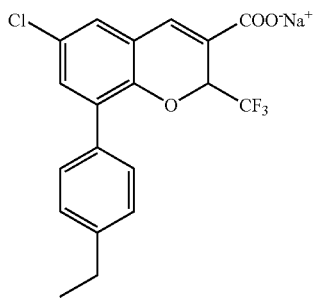

Sodium 6-Chloro-8-(4-ethylphenyl)-2-(trifluoromethyl)-2H-chromene-3-carboxylate

A solution of 6-chloro-8-(4-ethylphenyl)-2-(trifluoromethyl)-2H-chromene-3-carboxylic acid 51.9 mg (0.136 mmole) in 2.0 mL of ethanol was treated with 1.345 mL of 0.1008N NaOH. The resultant mixture was lyophilized to provide a quantitative yield of a yellow solid: $^1$H NMR (CD$_3$OD/400 MHz) 1.25 (t, 3H, J=7.6 Hz), 2.67 (q, 2H, J=7.6 Hz), 5.82 (q, 1H, J=7.2 Hz), 7.21-7.25 (m, 4H), 7.38-7.40 (m, 3H).

EXAMPLE 542

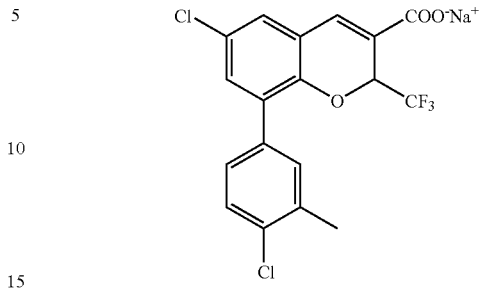

Sodium 6-Chloro-8-(4-chloro-3-methylphenyl)-2-(trifluoromethyl)-2H-chromene-3-carboxylate A solution of 6-chloro-8-(4-chloro-3-methylphenyl)-2-(trifluoromethyl)-2H-chromene-3-carboxylic acid 31.5 mg (0.078 mmole) in 2.0 mL of ethanol was treated with 0.775 mL of 0.1008N NaOH. The resultant mixture was lyophilized to provide a quantitative yield of a yellow solid: $^1$H NMR (CD$_3$OD/400 MHz) 2.39 (s, 3H), 5.77 (q, 1H, J=6.8 Hz), 7.25-7.28 (m, 1H), 7.34 (d, 1H, J=2.4 Hz), 7.37-7.40 (m, 3H), 7.79 (s, 1H).

EXAMPLE 543

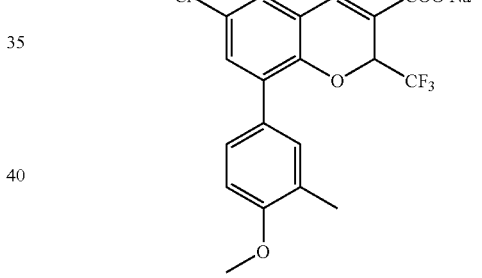

Sodium 6-Chloro-8-(4-methoxy-3-methylphenyl)-2-(trifluoromethyl)-2H-chromene-3-carboxylate A solution of 6-chloro-8-(4-methoxy-3-methylphenyl)-2-(trifluoromethyl)-2H-chromene-3-carboxylic acid 46.6 mg (0.117 mmole) in 2.0 mL of ethanol was treated with 1.160 mL of 0.1008N NaOH. The resultant mixture was lyophilized to provide a quantitative yield of a yellow solid: $^1$H NMR (CD$_3$OD/400 MHz) 2.20 (s, 3H), 3.85 (s, 3H), 5.77 (q, 1H, J=6.8 Hz), 6.93 (d, 1H, J=8.0 Hz), 7.26-7.32 (m, 4H), 7.78 (s, 1H).

EXAMPLE 544

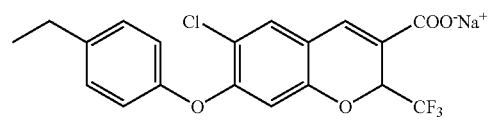

Sodium 6-chloro-7-(4-ethylphenoxy)-2-(trifluoromethyl)-2H-chromene-3-carboxylate A solution of 47.6 mg (0.119 mmole) of 6-chloro-7-(4-ethylphenoxy)-2-(trifluoromethyl)-2H-chromene-3-carboxylic acid in 1.5 mL of ethanol was treated with 1.18 mL of 0.1008N NaOH. The resultant mixture was lyophilized to provide 51 mg (quant.) of an off-white solid: $^1$H NMR (CD$_3$OD/400 MHz) 1.25 (t, 3H, J=7.7 Hz), 2. 68 (q, 2H, J=7.7 Hz), 5.79 (q, 1H, J=7.2 Hz), 6.92 (d, 2H, J=8.6 Hz), 7.25 (d, 2H, J=8.6 Hz), 7.37 (m, 2H); MS (ES+) 399 (M+1, 100).

EXAMPLE 545

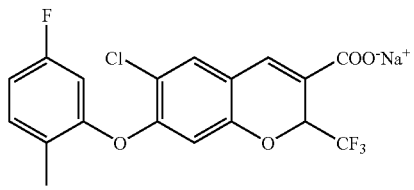

Sodium 6-chloro-7-(5-fluoro-2-methylphenoxy)-2-(trifluoromethyl)-2H-chromene-3-carboxylate Following the general procedure for sodium salt formation, an off-white solid was obtained: $^1$H NMR (CD$_3$OD/300 MHz) 2.22 (s, 3H), 5.85 (q, 1H, J=7.2 Hz), 6.38 (s, 1H), 6.64 (dd, 1H), 6.92 (m, 1H), 7.34 (m, 1H), 7.42 (s, 1H), 7.45 (s,1H).

EXAMPLE 546

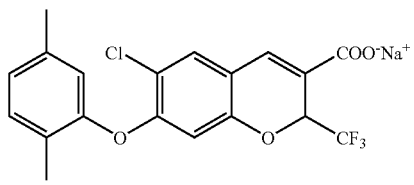

Sodium 6-chloro-7-(2,5-dimethylphenoxy)-2-(trifluoromethyl)-2H-chromene-3-carboxylate Following the general procedure for Example 545, an off-white solid was obtained: $^1$H NMR (CD$_3$OD/300 MHz) 2.15 (s, 3H), 2.34 (s, 3H), 5.81 (q, 1H, J=7.2 Hz), 6.18 (s, 1H), 6.79 (s, 1H), 7.02 (d, 1H, J=7.6 Hz), 7.22 (d, 1H, J=7.8 Hz), 7.40 (s, 2H).

EXAMPLE 547

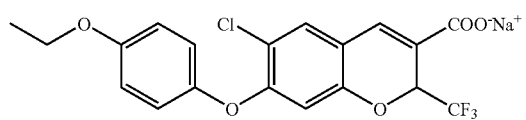

Sodium 6-chloro-7-(4-ethoxyphenoxy)-2-(trifluoromethyl)-2H-chromene-3-carboxylate Following the general procedure for Example 545, an off-white solid was obtained: $^1$H NMR (CD$_3$OD/300 MHz) 1.43 (t, 3H, J=6.9 Hz), 4.08 (q, 2H, J=7.0 Hz), 5.81(q, 1H, J=7.1 Hz), 6.32 (q, 1H), 7.00 (s, 4H), 7.39 (s, 1H), 7.40 (s, 1H).

EXAMPLE 548

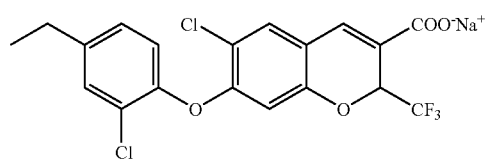

Sodium 6-chloro-7-(2-chloro-4-ethylphenoxy)-2-(trifluoromethyl)-2H-chromene-3-carboxylate Following the general procedure for sodium salt formation, an off-white solid was obtained. LC-MS (ES−) 431 (M−H, 100). HRMS (ES−) m/z calcd for (M−1; C$_{19}$H$_{12}$Cl$_2$F$_3$O$_4$) 431.0059, found 431.0025.

EXAMPLE 549

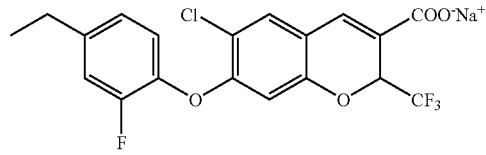

Sodium 6-chloro-7-(2-fluoro-4-ethylphenoxy)-2-(trifluoromethyl)-2H-chromene-3-carboxylate Following the general procedure for sodium salt formation, an ivory solid was obtained: $^1$H NMR (CD$_3$OD/300 MHz) 1.45 (t, 3H, J=5.7 Hz), 2.90 (q, 2H, J=5.4 Hz), 5.90 (q, 1H, J=4.8 Hz), 6.46 (s, 1H), 7.29 (d, 2H, J=3.9 Hz), 7.36 (d, 1H, J=9 Hz), 7.70 (s, 1H), 7.94 (s, 1H); MS (ES+) 417 (M+1, 100); LC-MS purity 99% at 3.515 min. (UV), 100% ELSD.

EXAMPLE 550

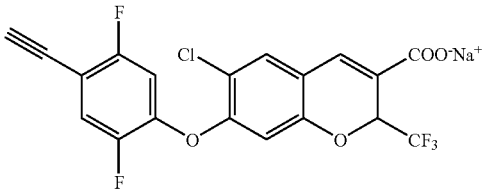

Sodium 6-chloro-7-(4-ethynyl-2,5-difluorophenoxy)-2-(trifluoromethyl)-2H-chromene-3-carboxylate Following the general procedure for sodium salt formation, a light yellow solid was obtained: $^1$H NMR(CD$_3$OD/ 300MHz) 7.49-7.44(m, 3H), 6.85(dd, J=6.6 Hz, 9.5 Hz, 1H), 6.68(s, 1H ), 5.89(q, J=7.2 Hz, 1H), the acetylenic proton exchanges under the basic conditions.

EXAMPLE 551

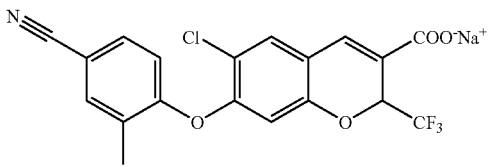

Sodium 6-chloro-7-(4-cyano-2-methylphenoxy)-2-(trifluoro-methyl)-2H-chromene-3-carboxylate Following the general procedure for sodium salt formation, a light yellow solid was obtained: $^1$H NMR (CD$_3$OD/ 300 MHz) 7.71 (s, 1H), 7.59-7.56(dd, J=2.1 Hz, 8.4 Hz, 1H), 7.49(s, 1H), 7.45(s, 1H), 6.83(d, J=8.4 Hz, 1H), 6.68(s, 1H), 5.99(d, J=7.2 Hz, 1H), 2.39(s, 3H).

EXAMPLE 552

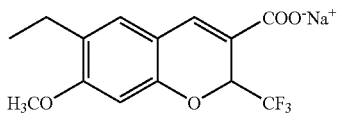

Sodium 6-Ethyl-7-methoxy-2-(trifluoromethyl)-2H-chromene-3-carboxylate

To the solution of 0.785 g (2.51 mm) of 6-ethyl-7-methoxy-2-(trifluoromethyl)-2H-chromene-3-carboxylic acid in 20 mL of ethanol was added 24.9 mL of 0.1008 N aqueous solution of sodium hydroxide. The resulting solution was stirred at room temperature for half an hour. The volatiles were removed. The residue was dissolved in 20 mL of water. The resulting solution was frozen and lyophilized to give a light yellow solid. LC-MS (ES−) 301 (M−H, 100). HRMS (ES−) m/z calcd for (M−1; C$_{14}$H$_{12}$F$_3$O$_4$) 301.0790, found 301.0810.

EXAMPLE 553

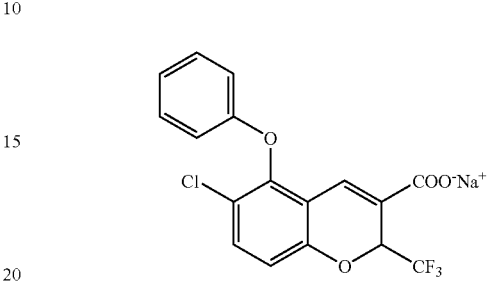

Sodium 6-Chloro-5-phenoxy-2-(trifluoromethyl)-2H-chromene-3-carboxylate

A solution of 110 mg (0.297 mmole) of 6-chloro-5-phenoxy-2-(trifluoromethyl)-2H-chromene-3-carboxylic acid in 3.0 mL of ethanol was treated with 2.94 mL of 0.1008N NaOH. The resultant mixture was lyophilized to provide 116 mg (quant.) of an off-white solid: $^1$H NMR (CD$_3$OD/400 MHz) 5.90 (q, 1H, J=7.2 Hz), 6.81 (d, 2H, J=8.3 Hz), 6.93 (d, 1H, J=8.9 Hz) 7.05 (t, 1H, J=7.5 Hz), 7.32 (t, 2H, J=8.6 Hz), 7.42 (d, 1H, J=8.9 H), 7.56 (s, 1H); MS (ES+) 371 (M+1, 100).

EXAMPLE 601a

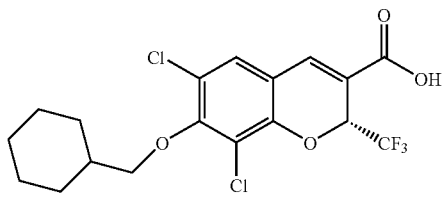

(2R) 6,8-dichloro-7-(cyclohexylmethoxy)-2-(trifluoromethyl)-2H-chromene-3-carboxylic acid A racemic mixture of the compound prepared in Example I f was resolved by chiral separation using Chiralpak AD column eluting with iPA/heptane/TFA=5/95/0.1 and detecting at 254 nm to give a R-enantiomer as peak 1 with retention time 3.29 min: ESHRMS m/z 423.0344 (M−H, C$_{18}$H$_{16}$O$_4$F$_3$Cl$_2$, Calc'd 423.0372). $^1$H NMR (acetone-d$_6$/ 400 MHz) 7.89 (s, 1H), 7.61 (s, 1H), 5.98 (q, 1H, J=7.0 Hz),3.88 (d, 2H, J=5.6 Hz), 1.77 (m, 3H), 1.68 (m, 3H), 1.29 (m, 2H), 1.22 (m, 3H). " $^9$F NMR (d$_6$-benzene; 6 eq of (R)-(+)-1-(1-naphthyl)ethylamine/400MHz) −78.14 (d, 3F, J=7.8 Hz, S-enantiomer), −78.26 (d, 3F, J=7.5 Hz, R-enantiomer).

EXAMPLE 601b

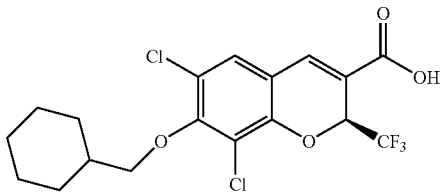

(2S) 6,8-dichloro-7-(cyclohexylmethoxy)-2-(trifluoromethyl)-2H-chromene-3-carboxylic acid A racemic mixture of the compound prepared in Example 1f was resolved by chiral separation using Chiralpak AD column eluting with iPA/heptane/TFA=5/95/0.1 and detecting at 254 nm to give a S-enantiomer as peak 2 with retention time 6.56 min: ESHRMS m/z 423.0392 (M–H, $C_{18}H_{16}O_4F_3Cl_2$, Calc'd 423.0372). $^1$H NMR (acetone-$d_6$/400 MHz) 7.89 (s, 1H), 7.61 (s, 1H), 5.98 (q, 1H, J=7.0 Hz), 3.88 (d, 2H, J=5.6 Hz), 1.77 (m, 3H), 1.68 (m, 3H), 1.29 (m, 2H), 1.22 (m, 3H). $^{19}$F NMR ($d_6$-benzene; 6 eq of (R)-(+)-1-(1-naphthyl)ethylamine/400 MHz)−78.14 (d, 3F, J=7.8 Hz, S-enantiomer), −78.26 (d, 3F, J=7.5 Hz, R-enantiomer).

EXAMPLE 601c

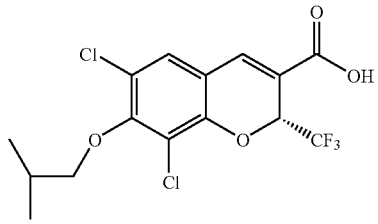

(2R) 6,8-dichloro-7-isobutoxy-2-(trifluoromethyl)-2H-chromene-3-carboxylic acid

A racemic mixture of the compound prepared in Example 1e was resolved by chiral separation using Chiralpak AD column eluting with iPA/heptane/TFA=10/90/0.1 and detecting at 254 nm to give a R-enantiomer as peak 1 with retention time 3.99 min: ESHRMS m/z 383.0016 (M–H, $C_{15}H_{12}O_4F_3Cl_2$, Calc'd 383.0059). $^1$H NMR (acetone-$d_6$/400 MHz) 7.87 (s, 1H), 7.60 (s, 1H), 5.97 (q, 1H, J=7.2 Hz), 3.86 (d, 1H, J=6.4 Hz), 2.15 (m, 1H), 1.07 (d, 6H, J=6.4 Hz). $^{19}$F NMR ($d_6$-benzene; 6 eq of (R)-(+)-1-(1-naphthyl) ethylamine/400 MHz) 78.17 (d, 3F, J=7.2 Hz, S-enantiomer,), −78.30 (d, 3F, J=7.2 Hz, R-enantiomer).

EXAMPLE 601d

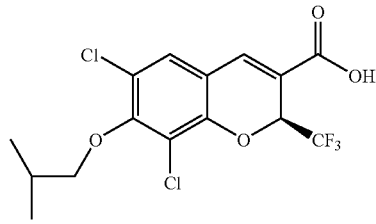

(2S) 6,8-dichloro-7-isobutoxy-2-(trifluoromethyl)-2H-chromene-3-carboxylic acid

A racemic mixture of the compound prepared in Example 1e was resolved by chiral separation using Chiralpak AD column eluting with iPA/heptane/TFA=10/90/0.1 and detecting at 254 nm to give a S-enantiomer as peak 2 with retention time 4.80 min: ESHRMS m/z 383.0016 (M–H, $C_{15}H_{12}O_4F_3Cl_2$, Calc'd 383.0059). $^1$H NMR (acetone-$d_6$/400 MHz) 7.87 (s, 1H), 7.60 (s, 1H), 5.97 (q, 1H, J=7.2 Hz), 3.86 (d, 1H, J=6.4 Hz), 2.15 (m, 1H), 1.07 (d, 6H, J=6.4 Hz). $^{19}$F NMR ($d_6$-benzene; 6 eq of (R)-(+)-1-(1-naphthyl)ethylamine/400 MHz) −78.17 (d, 3F, J=7.2 Hz, S-enantiomer,), −78.30 (d, 3F, J=7.2 Hz, R-enantiomer).

EXAMPLE 602a

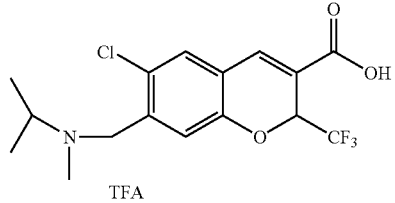

6-chloro-7-{[isopropyl(methyl)aminol methyl]-2-(trifluoromethyl)-2H-chromene-3-carboxylic acid trifluoroacetate Step 1. Preparation of ethyl 6-chloro-7-{[isopropyl(methyl)amino]methyl}-2-(trifluoromethyl)-2H-chromene-3-carboxylate The ethyl 7-(bromomethyl)-6-chloro-2-(trifluoromethyl)-2H-chromene-3-carboxylate from Example 16, Step 3 (01597/1 PR) (1.0 g, 2.5 mmol) was dissolved in DMF (5 mL). The solution was cooled at ice bath under nitrogen and the isopropyl(methyl)-amine (0.26 mL, 2.5 mmole) was added into the solution followed by addition of potassium carbonate (0.345 g, 2.5 mmol). After the mixture was stirred at r.t for 3 hr, LCMS indicated that the product was formed. The reaction was quenched with water and extracted with EtOAc. The organic layer was washed with brine and dried over MgSO$_4$ and filtered. The filtrate was concentrated to afford the crude product. The ester was of suitable purity to use without further purification.

Step 2. Preparation of 6-chloro-7-{[isopropyl(methyl)amino]methyl}-2-(trifluoromethyl)-2H-chromene-3-carboxylic acid A solution of the ester from Step 1 was dissolved in 10 mL mixture of MeOH/THF=1/1, treated with sodium hydroxide (2.5 N, 2.5 mL), and stirred at room temperature overnight. The reaction mixture was acidified with 1.0 N HCl to pH=1. The compound was extracted with EtOAc. The organic layer was washed with water and dried over anhydrous MgSO$_4$. The filtrate was concentrated and purified by RPHPLC with 40% to 95% ACN in water with 0.05% TFA to give 0.5 g an off white solid (2 steps 57% yield): ESHRMS m/z 364.0922 (M+H, C$_{16}$H$_{18}$O$_3$F$_3$NCl, Calc'd 364.0959). $^1$H NMR (acetone-d$_6$/400 MHz) 7.82 (s, 1H), 7.67 (s, 1H), 7.54 (s, 1H), 5.82 (q, 1H, J=6.8 Hz), 4.56 (s, 2H), 3.85 (m, 1H), 2.86 (s, 3H), 1.50 (d, 6H, J=6.8 Hz).

EXAMPLE 602b

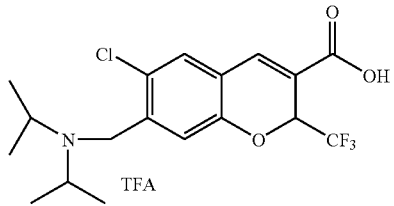

6-chloro-7-(diisopropylamino)methyl]-2-(trifluoromethyl)-2H-chromene-3-carboxylic acid trifluoroacetate The 6-chloro-7-[(diisopropylamino)methyl]-2-(trifluoromethyl)-2H-chromene-3-carboxylic acid trifluoroacetate was prepared as a white foam (2 steps yield 37%) by a procedure similar to the method described in Example 602a: ESHRMS m/z 392.1266 (M+H, C$_{18}$H$_{22}$O$_3$F$_3$ClN, Calc'd 392.1235). $^1$H NMR (acetone-d$_6$/400 MHz) 7.89 (s, 1H), 7.72 (s, 1H), 7.51 (s, 1H), 5.88 (q, 1H, J=7.0 Hz), 4.71 (s, 2H), 4.10 (m, 2H), 1.57 (d, 12H, J=6.4 Hz).

EXAMPLE 602c

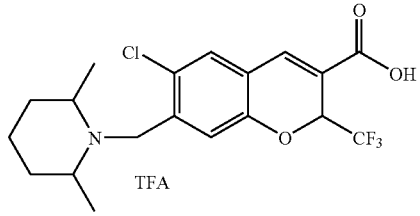

6-chloro-7-[(2,6-dimethylpiperidin-1-yl)methyl]-2-(trifluoromethyl)-2H-chromene-3-carboxylic acid trifluoroacetate The 6-chloro-7-[(2,6-dimethylpiperidin-1-yl)methyl]-2-(trifluoromethyl)-2H-chromene-3-carboxylic acid trifluoroacetate was prepared as a yellow foam (2 steps yield 38%) by a procedure similar to the method described in Example 602a: ESHRMS m/z 404.1242 (M+H, C$_{19}$H$_{22}$O$_3$F$_3$CN, Calc'di44.1235). $^1$H NMR(acetone-d$_6$/400 MHz)7.88 (s, 1H), 7.71 (d, 1H, J=4.0 Hz), 7.50 (d, 1H, J=13 Hz), 5.87 (q, 1H, J=7.0 Hz), 4.62 (d, 2H, J=13 Hz), 3.5 (m, 2H), 2.86 (m, 2H), 2.4 (m, 1H), 1.8 (m, 2H), 1.6 (m, 1H), 0.96 (m, 6H).

EXAMPLE 602d

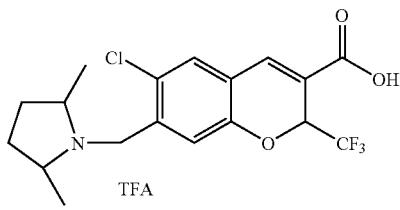

6-chloro-7-[(2,5-dimethylpyrrolidin-1-yl)methyl]-2-(trifluoromethyl)-2H-chromene-3-carboxylic acid trifluoroacetate The 6-chloro-7-[(2,5-dimethylpyrrolidin-1-yl)methyl]-2-(trifluoromethyl)-2H-chromene-3-carboxylic acid trifluoroacetate was prepared as a yellow oil (2 steps yield 23.6%) by a procedure similar to the method described in Example 602a: ESHRMS m/z 390.1085 (M+H, C$_{18}$H$_{20}$O$_3$F$_3$ClN, Calc'd 390.1078). $^1$H NMR (acetone-d$_6$/400 MHz) 7.89 (m, 1H), 7.71 (m, 2H), 5.88 (q, 1H, J=7.0 Hz), 4.72 (s, 2H), 3.91 (m, 2H), 2.40 (m, 2H), 1.9 (m, 2H), 1.40 (m, 6H).

EXAMPLE 602e

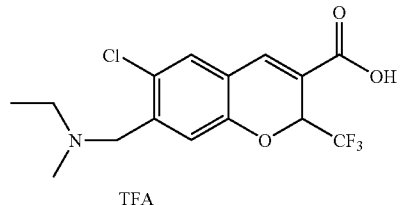

6-chloro-7-{[ethyl(methyl)amino]methyl}-2-(trifluoromethyl)-2H-chromene-3-carboxylic acid trifluoroacetate The 6-chloro-7-{[ethyl (methyl)amino]methyl}-2-(trifluoromethyl)-2H-chromene-3-carboxylic acid trifluoroacetate was prepared as an offwhite foam (2 steps yield 18%) by a procedure similar to the method described in Example 602a: ESHRMS m/z 350.0792 (M+H, C$_{15}$H$_{16}$O$_3$F$_3$ClN, Calc'd 350.0765). $^1$H NMR (acetone-d$_6$/400 MHz) 7.59 (s, 1H), 7.34 (s, 1H), 7.07 (s, 1H), 5.66 (q, 1H, J=6.8 Hz), 4.35 (m, 1H), 4.10 (m, 1H), 3.16 (m, 2H), 2.66 (s, 3H), 1.22 (m, 3H, J=6.8 Hz).

EXAMPLE 603a

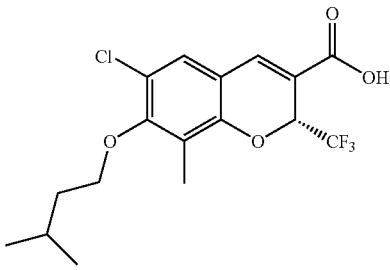

(2R) 6-chloro-7-(isopentyloxy)-8-methyl-2-(trifluoromethyl)-2H-chromene-3-carboxylic acid A racemic mixture of the compound prepared in Example 3h was resolved by chiral separation using Chiralpak AD-spring column eluting with iPA/heptane/TFA=5/95/0.1 and detecting at 254 nm to give a R-enantiomer as peak 1 with retention time 4.74 min: ESHRMS m/z 377.0777 (M−H, $C_{17}H_{17}O_4F_3Cl$, Calc'd 377.0762). $^1$H NMR (acetone-$d_6$/300 MHz) 7.84 (s, 1H), 7.45 (s, 1H), 5.88 (q, 1H, J=7.0 Hz), 3.62 (t, 2H, J=6.6 Hz), 2.21 (s, 3H), 1.96 (m, 1H), 1.75 (m, 2H), 1.12 (s, 6H, J=6.3 Hz). $^{19}$F NMR ($d_6$-benzene; 6 eq of(R)-(+)-1-(1-naphthyl)ethylamine/300 MHz) −78.20 (d, 3F, J=7.8 Hz, S-enantiomer,), −78.35 (d, 3F, J=7.5 Hz, R-enantiomer).

EXAMPLE 603b

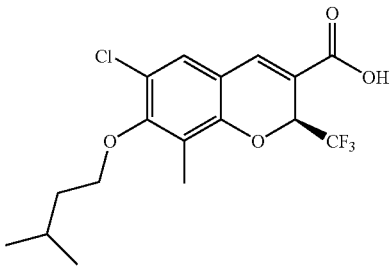

(2S) 6-chloro-7-(isopentyloxy)-8-methyl-2-(trifluoromethyl)-2H-chromene-3-carboxylic acid A racemic mixture of the compound prepared in Example 3h was resolved by chiral separation using Chiralpak AD-spring column eluting with iPA/heptane/TFA=5/95/0.1 and detecting at 254 nm to give a S-enantiomer as peak 2 with retention time 6.61 min: ESHRMS m/z 377.0765 (M−H, $C_{17}H_{17}O_4F_3Cl$, Calc'd 377.0762). $^1$H NMR (acetone-$d_6$/300 MHz) 7.84 (s, 1H), 7.45 (s, 1H), 5.88 (q, 1H, J=7.0 Hz), 3.62 (t, 2H, J=6.6 Hz), 2.21 (s, 3H), 1.96 (m, 1H), 1.75 (m, 2H), 1.12 (s, 6H, J=6.3 Hz). $^{19}$F NMR ($d_6$-benzene; 6 eq of (R)-(+)-1-(1-naphthyl)ethylamine/300 MHz) −78.20 (d, 3F, J=7.8 Hz, S-enantiomer,), −78.35 (d, 3F, J=7.5 Hz, R-enantiomer).

EXAMPLE 604a

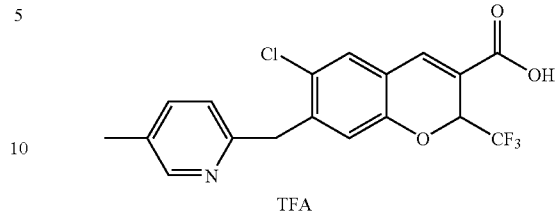

6-chloro-7-[(5-methylpyridin-2-yl)methyl]-2-(trifluoromethyl)-2H-chromene-3-carboxylic acid trifluoroacetate Step 1. Preparation of ethyl 6-chloro-7-[(5-methylpyridin-2-yl)methyl]-2-(trifluoromethyl)-2H-chromene-3-carboxylate The bromo (5-methylpyridin-2-yl)magnesium (10.4 mL, 2.6 mmole) was diluted by 5 mL THF under nitrogen and the solution was cooled to −78° C. ZnCl$_2$ (340 mg, 2.5 mmole) was added to above solution and the mixture was stirred for 0.5 hr. The ethyl 7-(bromomethyl)-6-chloro-2-(trifluoromethyl)-2H-chromene-3-carboxylate from Example 16, Step 3 (01597/1 PR) (1.0 g, 2.5 mmol) was added to above mixture and followed by PdCl$_2$(PPh$_3$)$_2$ (18 mg, 0.025 mmole). The mixture was warmed to room temperature and heated to 50° C. for 3 hr. LCMS indicated that the product was formed around 15%. The solid was filtered off and the filtrate was concentrated to give a crude mixture, which was purified by RPHPLC eluted with 10 to 95% ACN in water with 0.05% TFA to afford 150 mg the desired product as a brown oil (yield 15%), which had suitable purity to use without further purification.

Step 2. Preparation of 6-chloro-7-[(5-methylpyridin-2-yl)methyl]-2-(trifluoromethyl)-2H-chromene-3-carboxylic acid trifluoroacetate The 6-chloro-7-[(5-methylpyridin-2-yl)methyl]-2-(trifluoromethyl)-2H-chromene-3-carboxylic acid trifluoroacetate was prepared as a brown oil (yield 29%) by a procedure similar to the method described in Example 602a, Step 2: ESHRMS m/z 384.0608 (M+H, $C_{18}H_{14}O_3F_3ClN$, Calc'd 384.0609). $^1$H NMR (acetone-$d_6$/400 MHz) 8.73 (m, 1H), 8.27 (dd, 1H, J=8.4, 1.6 Hz), 7.88 (s, 1H), 7.63 (d, 1H, J=8.5 Hz), 7.63 (s, 1H), 7.20 (s, 1H), 5.84 (q, 1H, J=7.2 Hz), 4.58 (d, 2H, J=3.2 Hz), 2.53 (s, 3H).

EXAMPLE 604b

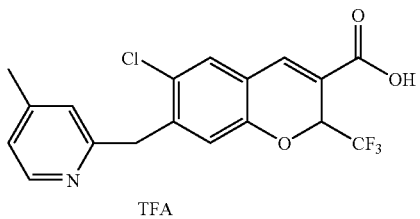

6-chloro-7-[(4-methylpyridin-2-yl)methyl]-2-(trifluoromethyl)-2H-chromene-3-carboxylic acid trifluoroacetate Step 1. Preparation of ethyl 6-chloro-7-[(4-methylpyridin-2-yl)methyl]-2-(trifluoromethyl)-2H-chromene-3-carboxylate The bromo (4-methylpyridin-2-yl)magnesium (10.4 mL, 2.6 mmole) was diluted by 5 mL THF and the solution was cooled to −78° C. $ZnCl_2$ (340 mg, 2.5 mmole) was added to above solution and the mixture was slowly warmed to r.t and heated to 50 OC for 3 hrs. The mixture was cooled to −78° C. again and ethyl 7-(bromomethyl)-6-chloro-2-(trifluoromethyl)-2H-chromene-3-carboxylate from Example 16, Step 3 (1.0 g, 2.5 mmol) was added to above mixture and followed by $PdCl_2(PPh_3)_2$ (18 mg, 0.025 mmole). The mixture was warmed to 50° C. for 3 hrs. LCMS indicated that around 40% product was formed. The reaction was quenched with 1 N HCl and extracted with EtOAc. The organic layer was washed with brine and dried over $MgSO_4$. The filtrate was concentrated to afford the crude product, which was purified by RPHPLC eluted with 10 to 95% ACN in water with 0.05% TFA to give 50 mg the desired product as a brown oil (yield 5%), which had suitable purity to use without further purification.

Step 2. Preparation of 6-chloro-7-[(4-methylpyridin-2-yl)methyl]-2-(trifluoromethyl)-2H-chromene-3-carboxylic acid trifluoroacetate The 6-chloro-7-[(5-methylpyridin-2-yl)methyl]-2-(trifluoromethyl)-2H-chromene-3-carboxylic acid trifluoroacetate was prepared as a white solid (yield 45%) by a procedure similar to the method described in Example 604a, Step 2: ESHRMS m/z 384.0628 (M+H, $C_{18}H_{14}O_3F_3ClN$, Calc'd 384.0609).

EXAMPLE 604c

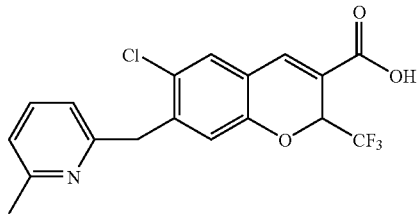

TFA 6-chloro-7-[(6-methylpyridin-2-yl)methyl]-2-(trifluoromethyl)-2H-chromene-3-carboxylic acid trifluoroacetate The 6-chloro-7-[(6-methylpyridin-2-yl)methyl]-2-(trifluoromethyl)-2H-chromene-3-carboxylic acid trifluoroacetate was prepared as a yellow solid (2 steps yield 4.2%) by a procedure similar to the method described in Example 604b: ESHRMS m/z 384.0628 (M+H, $C_{18}H_{14}O_3F_3ClN$, Calc'd 384.0609). $^1$H NMR (acetone-$d_6$/300 MHz) 8.11 (t, 1H, J=7.0 Hz), 7.88 (s, 1H), 7.62 (s, 1H), 7.55 (d, 1H, J=7.0 Hz), 7.33 (d, 1H, J=7.0 Hz), 7.15 (s, 1 H), 5.84 (q, 1H, J=7.2 Hz), 4.53 (d, 2H, J=3.2 Hz), 2.73 (s, 3H).

EXAMPLE 604d

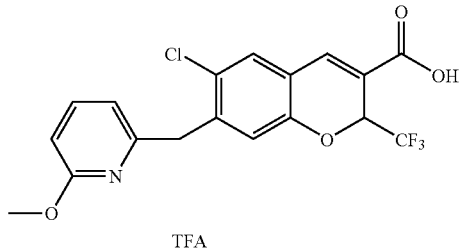

TFA 6-chloro-7-[(5-methoxypyridin-2-yl)methyl]-2-(trifluoromethyl)-2H-chromene-3-carboxylic acid trifluoroacetate The 6-chloro-7-[(5-methoxypyridin-2-yl)methyl]-2-(trifluoromethyl)-2H-chromene-3-carboxylic acid trifluoroacetate prepared as a yellow solid (2 steps yield 5.3%) by a procedure similar to the method described in Example 604b: ESHRMS m/z 400.0565 (M+H, $C_{18}H_{14}O_6F_3ClN$, Calc'd 400.0558). $^1$H NMR (acetone-$d_6$/400 MHz) 7.87 (s, 1H), 7.60 (t, 1H, J=7.2 Hz), 7.55 (s, 1H), 7.08 (s, 1H), 6.82 (d, 1H, J=7.2 Hz), 6.60 (d, 1H, J=7.2 Hz), 5.81 (q, 1H, J=7.2 Hz), 4.15 (s, 2H), 3.80 (s, 3H).

EXAMPLE 604e

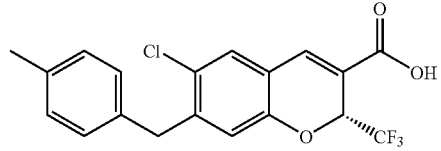

(2R) 6-chloro-7-(4-methylbenzyl)-2-(trifluoromethyl)-2H-chromene-3-carboxylic acid A racemic mixture of the compound prepared in Example 9x was resolved by chiral separation using Chiralpak AD column eluting with iPA/heptane/TFA=20/80/0.1 and detecting at 254 nm give a R-enantiomer as peak 1 with retention time 4.90 min: ESHRMS m/z 381.0536 (M−H, $C_{19}H_{13}O_3F_3Cl$, Calc'd 381.0500). $^1$H NMR (acetone-$d_6$/400 MHz) 7.87 (s, 1H), 7.56 (s, 1H), 7.13 (m 4H), 6.91 (s, 1H), 5.80 (q, 1H, J=7.0 Hz), 4.07 (d, 1H, J=14.7 Hz), 4.01 (d, 1H, J=14.7 Hz), 2.27 (s, 3H). $^{19}$FNMR($d_6$-benzene; 6 eq of(R)-(+)-1-(1-naphthyl)ethylamine/300 MHz) −78.20 (d, 3F, J=7.5 Hz, S-enantiomer), −78.35 (d, 3F, J=7.5 Hz, R-enantiomer).

EXAMPLE 604f

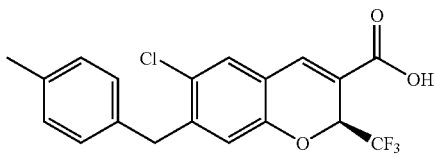

(2S) 6-chloro-7-(4-methylbenzyl)-2-(trifluoromethyl)-2H-chromene-3-carboxylic acid A racemic mixture of the compound prepared in Example 9x was resolved by chiral separation using Chiralpak AD column eluting with iPA/heptane/TFA=20/80/0.1 and detecting at 254 nm give a S-enantiomer as peak 2 with retention time 6.61 min: ESHRMS m/z 381.0540 (M−H, $C_{19}H_{13}O_3F_3Cl$, Calc'd 381.0500). $^1$H NMR (acetone-$d_6$/400 MHz) 7.87 (s, 1H), 7.56 (s, 1H), 7.13 (m 4H), 6.91 (s, 1H), 5.80 (q, 1H, J=7.0 Hz), 4.07 (d, 1H, J=14.7 Hz), 4.01 (d, 1H, J=14.7 Hz), 2.27 (s, 3H). $^{19}$F NMR ($d_6$-benzene; 6 eq of(R)-(+)-1-(1-naphthyl)ethylamine/300 MHz) −78.20 (d, 3F, J=7.5 Hz, S-enantiomer), −78.35 (d, 3F, J=7.5 Hz, R-enantiomer).

EXAMPLE 604g

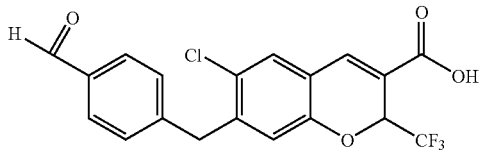

6-chloro-7-(4-formylbenzyl)-2-(trifluoromethyl)-2H-chromene-3-carboxylic acid

Step 1. Preparation of ethyl 6-chloro-7-(4-formyl-benzal)-2-(trifluoromethyl)-2H-chromene-3-carboxylate The ethyl 7-(bromomethyl)-6-chloro-2-(trifluoromethyl)-2H-chromene-3-carboxylate from Example 16, Step 3 (2.0 g, 5.0 mmol) and Pd(PPh$_3$)$_4$ (174 mg, 0.15 mmole) were mixed in DME (50 mL) and the mixture was heated at 50° C. for 10 min. The solution of 4-formylphenylboronic acid (1.12 g, 7.5 mmole) in EtOH/DME (1:1, 4 mL) was added to above mixture and followed by adding 2 M Na$_2$CO$_3$ (5 mL, 10 mmole). The mixture then was heated to 90° C. for overnight. The reaction was quenched with water and extracted with EtOAc. The organic layer was washed with brine and dried over MgSO$_4$ and filtered. The filtrate was concentrated to afford the crude product, which was purified by Biotage chromatography eluted with 5 to 10% EtOAc in hexane to give 1 g the desired product as a yellow solid (47%), which had suitable purity to use without fuirther purification.

Step 2. Preparation of 6-chloro-7-(4-formylbenzyl)-2-(trifluoromethyl)-2H-chromene-3-carboxylic acid The 6-chloro-7-(4-formylbenzyl)-2-(trifluoromethyl)-2H-chromene-3-carboxylic acid was prepared as a white solid (44% yield) by a procedure similar to the method described in Example 2a, Step 2: ESHRMS m/z 395.0327 (M−H, $C_{19}H_{11}O_4F_3Cl$, Calc'd 395.0292). $^1$H NMR (acetone-$d_6$/400 MHz) 10.00 (s, 1H), 7.88 (s, 1H), 7.87 (d,2H, J=7.6 Hz), 7.59 (s, 1H), 7.48 (d, 2H, J=7.6 Hz), 7.04 (s, 1H), 5.82 (q, 1H, J=7.2 Hz), 4.23 (d, 2H, J=4.4 Hz).

EXAMPLE 604h

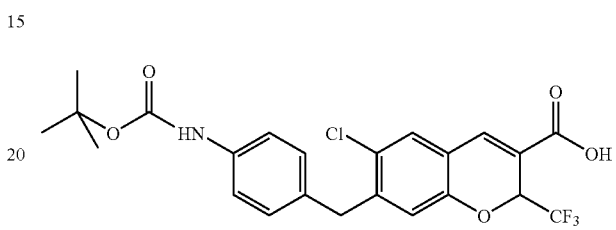

7-{4-[(tert-butoxycarbonyl)amino]benzyl}-6-chloro-2-(trifluoromethyl)-2H-chromene-3-carboxylic acid The 7-{4-[(tert-butoxycarbonyl)amino]benzyl}-6-chloro-2-(trifluoromethyl)-2H-chromene-3-carboxylic acid was prepared as a yellow solid (Step 1 yield 76% and Step 2 yield 54%) by a procedure similar to the method described in Example 604h: $^1$H NMR (acetone-$d_6$/400 MHz) 8.34 (bs, 1H), 7.87 (s, 1H), 7.56 (s, 1H), 7.50 (d, 1H, J=8.4 Hz), 7.17 (d, 1H, J=8.4 Hz), 6.61 (s, 1H), 5.80 (q, 1H, J=7.2 Hz), 4.04 (m, 2H), 1.46 (s, 9H).

EXAMPLE 604i

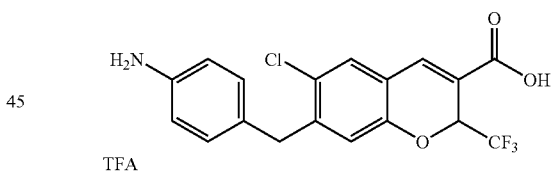

7-(4-aminobenzyl)-6-chloro-2-(trifluoromethyl)-2H-chromene-3-carboxylic acid trifluoroacetate The 7-{4-[(tert-butoxycarbonyl)amino]benzyl}-6-chloro-2-(trifluoromethyl)-2H-chromene-3-carboxylic acid (300 mg, 0.62 mmole) was stirred in 3 mL dioxane and 0.62 mL HCl (4M) in dioxane for 6 hrs. $^1$HNMR indicated that the reaction mixture was 1:1 ratio of starting material:product. Additional 0.3 mL 12 N HCl in 2 mL water was added to above mixture. After the mixture was stirred for overnight, 0.3 mL 12 N HCl was added. After another overnight stirring, the solution of 3 mL 12 N HCl in 3 mL MeOH and 3 mL water was added to above mixture and the mixture was stirred for 6 hrs. The mixture was purified by RPHPLC elute with 20 to 65% ACN in water with 0.1% TFA to give the desired product as a white solid with >95% purity: ESHRMS m/z 384.0594 (M+H, $C_{18}H_{14}O_3F_3ClN$, Calc'd 384.0609). ¹H NMR (acetone-$d_6$/400 MHz) 7.87 (s, 1H), 7.58(s, 1H), 7.39 (d, 1H, J=8.4 Hz), 7.22 (d, 1H, J=8.4 Hz), 6.02 (s, 1H), 5.82 (q, 1H, J=7.2 Hz), 4.15 (m, 2H).

EXAMPLE 604j

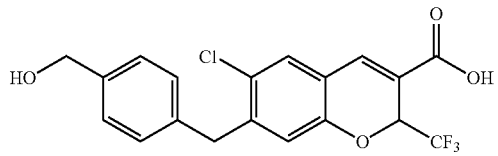

6-chloro-7-[4-(hydroxymethyl)benzyl]-2-(trifluoromethyl)-2H-chromene-3-carboxylic acid The 6-chloro-7-(4-formylbenzyl)-2-(trifluoromethyl)-2H-chromene-3-carboxylic acid (Example 604 g) (210 mg, 0.49 mmole) was dissolved in MeOH:THF (1:1) (3 mL). NaBH$_4$ (20 mg, 0.49 mmole) was added to the above solution portionwise. After stiring for 15 min, the reaction was finished. The reaction was quenched with (sat.) NH$_4$Cl, the organic layer was extracted with EtOAc and dried over MgSO$_4$ and filtered. The filtrate was concentrated to give the title compound as an oil, which solidify upon standing as a white solid 200 mg (95% yield): ESHRMS m/z 397.0457 (M−H, $C_{19}H_{13}O_4F_3Cl$, Calc'd 397.0449). ¹H NMR (acetone-$d_6$/400 MHz) 7.87 (s, 1H), 7.57 (s, 1H), 7.31 (d, 2H, J=8.2 Hz), 7.22 (d, 2H, J=8.2 Hz), 6.92 (s, 1H), 5.80 (q, 1H, J=7.2 Hz), 4.59 (s, 2H), 4.09 (d, 2H, J=4.3 Hz).

EXAMPLE 604k

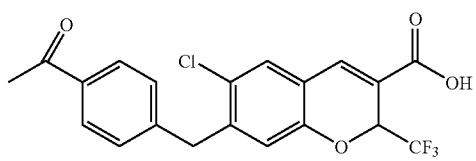

7-(4-acetylbenzyl)-6-chloro-2-(trifluoromethyl)-2H-chromene-3-carboxylic acid

The 7-(4-acetylbenzyl)-6-chloro-2-(trifluoromethyl)-2H-chromene-3-carboxylic acid was prepared as a white solid (2 steps yield 40%) by a procedure similar to the method described in Example 604h: ESHRMS m/z 409.0432 (M−H, $C_{20}H_{13}O_4F_3Cl$, Calc'd 409.0449). ¹H NMR (acetone-$d_6$/400 MHz) 7.93 (d, 2H, J=8.4 Hz), 7.88 (s, 1H), 7.59 (s, 1H), 7.39 (d, 2H, J=8.4 Hz), 7.01 (s, 1H),5.83(q, 1H, J=7.2 Hz), 4.19 (d, 2H, J=3.6 Hz), 2.55 (s, 3H).

EXAMPLE 604l

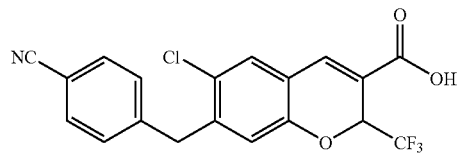

6-chloro-7-(4-cyanobenzyl)-2-(trifluoromethyl)-2H-chromene-3-carboxylic acid

The 6-chloro-7-(4-cyanobenzyl)-2-(trifluoromethyl)-2H-chromene-3-carboxylic acid was prepared as an offwhite solid (Step 1 yield 49%, Step 2 yield 99%) by a procedure similar to the method described in Example 604h: ESHRMS m/z 392.0289 (M−H, $C_{19}H_{10}O_3F_3ClN$, Calc'd 392.0296). ¹H NMR (acetone-$d_6$/400 MHz) 7.88 (s,1H), 7.72 (d, 2H, J=8.0 Hz), 7.59 (s, 1H), 7.47 (d, 2H, J=8.0 Hz), 7.06 (s, 1H), 5.83 (q, 1H, J=7.2 Hz), 4.22 (d, 2H, J=3.6 Hz).

EXAMPLE 604m

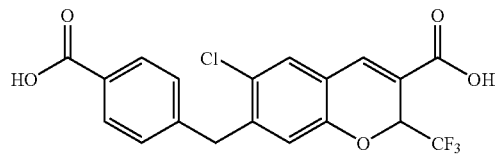

7-(4-carboxybenzyl)-6-chloro-2-(trifluoromethyl)-2H-chromene-3-carboxylic acid

The 7-(4-carboxybenzyl)-6-chloro-2-(trifluoromethyl)-2H-chromene-3-carboxylic acid was prepared as a white solid (2 steps yield 6%) by a procedure similar to the method described in Example 604h: ESHRMS m/z 411.0207 (M−H, $C_{19}H_{11}O_5F_3Cl$, Calc'd 411.0242). ¹H NMR (acetone-$d_6$/400 MHz) 7.98 (d, 2H, J=8.4 Hz), 7.87 (s, 1H), 7.56 (s, 1H), 7.39 (d, 2H, J=8.4 Hz), 7.01 (s, 1H), 5.81(q, 1H, J=7.2 Hz), 4.20 (d, 2H, J=3.6 Hz).

EXAMPLE 604n

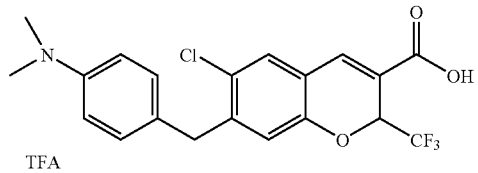

6-chloro-7-[14-(dimethylamino)benzyl]-2-(trifluoromethyl)-2H-chromene-3-carboxylic acid trifluoroacetate The 6-chloro-7-[4-(dimethylamino)benzyl]-2-(trifluoromethyl)-2H-chromene-3-carboxylic acid trifluoroacetate was prepared as a yellow oil (2 steps yield 6.5%) by a procedure similar to the method described in Example 604h: ESHRMS m/z 412.0948 (M+H, $C_{20}H_{18}O_3F_3ClN$, Calc'd 412.0922). $^1$H NMR (acetone-$d_6$/400 MHz) 7.86 (s, 1H), 7.56 (s, 1H), 7.27 (m, 4H), 6.95 (s, 1H), 5.81(q, 1H, J=7.2 Hz), 4.07 (m, 2H), 3.11 (s, 6H).

EXAMPLE 604o

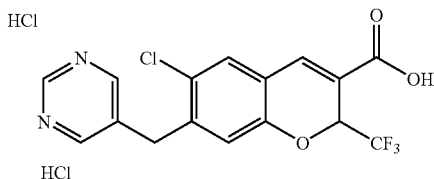

6-chloro-7-(pyrimidin-5-ylmethyl)-2-(trifuoromethyl)-2H-chromene-3-carboxylic acid dihydrochloride The 6-chloro-7-(pyrimidin-5-ylmethyl)-2-(trifluoromethyl)-2H-chromene-3-carboxylic acid dihydrochloride was prepared as a yellow semi-solid (2 steps yield 13.1%) by a procedure similar to the method described in Example 604h: ESHRMS m/z 371.0438 (M+H, $C_{16}H_{11}O_3F_3ClN_2$, Calc'd 371.0405). $^1$H NMR (acetone-$d_6$/400 MHz) 9.02 (s, 1H), 8.71 (s, 1H), 7.88 (s, 1H), 7.60 (s, 1H), 7.15 (s, 1H), 5.84 (q, 1H, J=7.2 Hz),4.18 (d, 2H, J=2.4 Hz).

EXAMPLE 604p

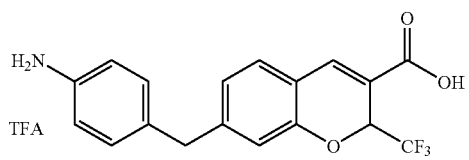

7-(4-aminobenzyl)-2-(trifluoromethyl)-2H-chromene-3-carboxylic acid trifluoroacetate Step 1. Preparation of ethyl 7-{4-[(tert-butoxycarbonyl)amino]benzyl}-2-(trifluoromethyl)-2H-chromene-3-carboxylate The ester from Example 604h, Step 1 (100 mg, 0.195mmol) was dissolved in THF. 1% Pd/CaCO$_3$ was added to above solution and the mixture was hydrogenated at 25 psi and 25° C. for 3 hrs. LCMS indicated that there were >94% desired product and <6% overreduction product. The solid was filtered off and the filtrate was concentrated to give an offwhite solid, which had suitable purity to use without further purification.

Step 2. Preparation of 7-(4-aminobenzyl)-2-(trifluoromethyl)-2H-chromene-3-carboxylic acid trifluoroacetate The ester from Step 1 was dissolved in 0.3 mL HCl in THF/H$_2$O=1/1. The mixture was stirred at r.t for 2 days. Additional 2 mL TFA was added to above solution and the solution was stirred for 2 days. LCMS indicated that there was less than 10% product. The mixture was heated at 50° C. for 4 hrs. After purification, the combined deBoc-ester was redissolved in THF/MeOH=2/1 and NaOH (2.5 N, 2.5 eq). The mixture was stirred at r.t overnight. The mixture was purified by RPHPLC to give the title compound as an amorphous solid: ESHRMS m/z 350.0994 (M+H, $C_{18}H_{15}O_3F_3N$, Calc'd 350.0999). $^1$H NMR (acetone-$d_6$/300 MHz) 7.38 (m, 3H), 7.11 (d, 1H, J=8.4 Hz), 7.00 (d, 1H, J=8.1 Hz), 6.93 (s, 1H), 6.71 (d, 1H, J=8.1 Hz), 5.78 (q, 1H, J=7.2 Hz), 4.04 (s, 2H).

EXAMPLE 604q

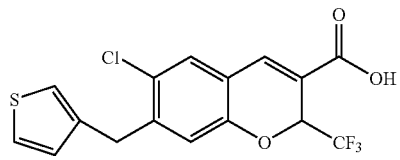

6-chloro-7-(thien-3-ylmethyl)-2-(trifuoromethyl)-2H-chromene-3-carboxylic acid

Step 1. Preparation of ethyl 6-chloro-7-(thien-3-ylmethyl)-2-(trifluoromethyl)-2H-chromene-3-carboxylate The ethyl 7-(bromomethyl)-6-chloro-2-(trifluoromethyl)-2H-chromene-3-carboxylate from Example 16, Step 3 (2.0 g, 5.0 mmole) was dissolved in DME (10.8 mL). The thien-3-ylboronic acid (127.96 mg, 5.0 mmole) was added to above solution and followed by addition of Pd(PPh$_3$)$_4$ (40 mg). After addition of 2M Na$_2$CO$_3$ (5.0 mL), the reaction was heated to 60-70° C. The color of the reaction changed from yellow to red and back to yellow. The solution was heated to reflux for 2 hrs. Additional 107 mg of thien-3-ylboronic acid and Pd(PPh$_3$)$_4$ (8 mg) were added to above mixture. After 2 hsr, the reaction was diluted with 5 ml of water and extracted with EtOAc. The organic layer was washed with NaHCO$_3$ (sat.) and dried over MgSO$_4$ and filtered. The filtrate was concentrated to afford the title ester. The ester (dark oil) was purified by chromatography eluted with 5 to 10% EtOAc in Hexane to give 620 mg, which had suitable purity to use without further purification.

Step 2. Preparation of 6-chloro-7-(thien-3-ylmethyl)-2-(trifluoromethyl)-2H-chromene-3-carboxylic acid The 6-chloro-7-(thien-3-ylmethyl)-2-(trifluoromethyl)-2H-chromene-3-carboxylic acid was prepared by a procedure similar to the method described in Example 2a, Step 2: $^1$H NMR (acetone-$d_6$/400 MHz) 7.88 (s, 1H), 7.42 (s, 1H), 7.39 (m, 1H), 7.09 (m, 1H), 6.98 (m, 1H), 6.85 (s, 1H), 5.78 (q, 1H, J=7.2 Hz), 4.09 00 (d, 2H, J=4.4 Hz).

EXAMPLE 605a

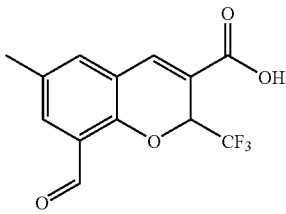

8-formyl-6-methyl-2-(trifluoromethyl)-2H-chromene-3-carboxylic acid

Step 1. Preparation of ethyl 8-formyl-6-methyl-2-(trifluoromethyl)-2H-chromene-3-carboxylate A mixture of 2-hydroxy-5-methyl-1,3-benzenedicarboxaldehyde (5.0 g, 30.46 mmole), $K_2CO_3$ (8.41 g, 60.92 mmole) and ethyl 4,4,4-trifluorocrotonate (7.68 g, 45.69 mmole) in anhydrous DMF (40.0 mL) was heated to 80° C. under a dry $N_2$ atmosphere for 18 hrs. The mixture was then cooled, poured into 1.2 N HCl (100 mL) and extracted with EtOAc (2×100 mL). The combined extracts were washed with brine (100 mL), dried over $MgSO_4$, filtered and concentrated in vacuo to give a dark red oil which was subject to flash chromatography (silica gel) and eluted with 50% $CH_2Cl_2$/hexane to give a light yellow solid (2.2 g, 23%): GCMS m/z 314.0 (M+). $^1$H NMR (CDCl$_3$/400 MHz) 10.42 (s, 1H), 7.70 (s, 1H), 7.65 (s, 1H), 7.26 (s, 1H), 5.80 (q, 1H, J=7.0 Hz), 4.33 (m, 2H), 2.32 (s, 3H), 1.35 (m, 3H).

Step 2. Preparation of 8-formyl-6-methyl-2-(trifluoromethyl)-2H-chromene-3-carboxylic acid The 8-formyl-6-methyl-2-(trifluoromethyl)-2H-chromene-3-carboxylic acid was prepared by a procedure similar to the method described in Example 602a, Step 2: LCMS m/z 287.3, 309.2 (M+H, M+23). $^1$H NMR (acetone-d$_6$/400 MHz) 10.42 (s, 1H), 7.91 (s, 1H), 7.62 (s, 1H), 5.98 (q, 1H, J=7.0 Hz), 2.35 (s, 3H).

EXAMPLE 605b

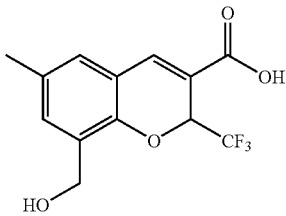

8-(hydroxymethyl)-6-methyl-2-(trifluoromethyl)-2H-chromene-3-carboxylic acid

Step 1. Preparation of ethyl 8-(hydroxymethyl)-6-methyl-2-(trifluoromethyl)-2H-chromene-3-carboxylate The ethyl 8-formyl-6-methyl-2-(trifluoromethyl)-2H-chromene-3-carboxylate from Example 605a, Step 1 (0.32 g, 1.02 mmole) was dissolved in a mixture of THF (1.5 mL) and ethanol (1.5 mL) and the solution was chilled to 0° C. (ice bath). Sodium borohydride (0.04 g, 1.02 mmole) was added portionwise to the above solution and the mixture was allowed to stir for 1 hour. The reaction was quenched with 0.5N HCl (5 mL) and extracted with $CH_2Cl_2$ (2×10 mL). The combined extracts were washed with brine (20 mL), dried over $MgSO_4$, filtered and concentrated in vacuo to give a yellow oil (0.3 g, 93%): GCMS m/z 316.0 (M+). $^1$H NMR (CDCl$_3$/400 MHz) 7.78 (s, 1H), 7.11 (s, 1H), 6.96 (s, 1H), 5.71 (q, 1H, J=7.0 Hz), 4.67 (m, 2H), 4.30 (m, 2H), 2.27 (s, 3H), 1.33 (m, 3H).

Step 2. Preparation of 8-(hydroxymethyl)-6-methyl-2-(trifluoromethyl)-2H-chromene-3-carboxylic acid The 8-(hydroxymethyl)-6-methyl-2-(trifluoromethyl)-2H-chromene-3-carboxylic acid was prepared by a procedure similar to the method described in Example 602a, Step 2: ESHRMS m/z 287.0520 (M−H, $C_{13}H_{10}O_4F_3$, Calc'd 287.0526). $^1$H NMR (DMSO-d$_6$/400 MHz) 7.77 (s, 1H), 7.26 (s, 1H), 7.14 (s, 1H), 5.84 (q, 1H, J=7.0 Hz), 5.18 (brs, 1H), 4.46 (s, 2H), 2.23 (s, 3H).

EXAMPLE 605c

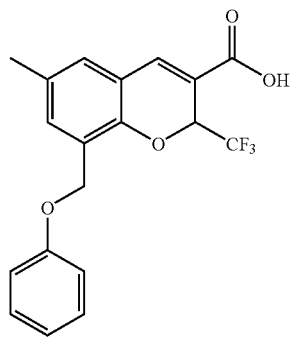

6-methyl-8-(phenoxymethyl)-2-(trifluoromethyl)-2H-chromene-3-carboxylic acid

Step 1. Preparation of ethyl 6-methyl-8-(phenoxymethyl)-2-(trifluoromethyl)-2H-chromene-3-carboxylate The polymer bound triphenylphosphine (1.2 g, 3.6 mmole) was suspended in anhydrous THF (10 mL) and the mixture was allowed to stir for 15 minutes. The ethyl 8-(hydroxymethyl)-6-methyl-2-(trifluoromethyl)-2H-chromene-3-carboxylate prepared as in Example 605b, Step 1 (0.38 g, 1.20 mmole), phenol (0.17 g, 1.80 mmole) and DEAD (0.31 g, 1.80 mmole) were added to above mixture, which was allowed to stir for 18 hours. The resulting mixture was filtered through a plug of celite and condensed in vacuo to give an off-white solid (0.47 g, 98%). No further purification was performed. GCMS m/z 392.0 (M+).

Step 2. Preparation of 6-methyl-8-(phenoxymethyl)-2-(trifluoromethyl)-2H-chromene-3-carboxylic acid The 6-methyl-8-(phenoxymethyl)-2-(trifluoromethyl)-2H-chromene-3-carboxylic acid was prepared by a procedure similar to the method described in Example 602a, Step 2: ESHRMS m/z 363.0831 (M−H, $C_{19}H_{14}O_4F_3$, Calc'd 363.0839). ¹H NMR (acetone-d₆/400 MHz) 7.88 (s, 1H), 7.30 (s, 1H), 7.26 (m, 4H), 6.97 (m, 3H), 5.86 (q, 1H, J=7.0 Hz), 5.12 (s, 2H), 2.30 (s, 3H).

EXAMPLE 605d

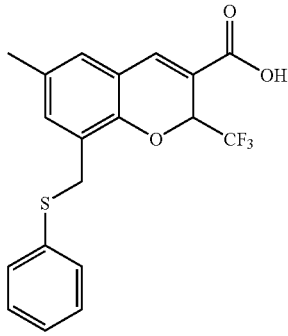

6-methyl-8-[(phenylthio)methyl]-2-(trifluoromethyl)-2H-chromene-3-carboxylic acid Step 1. Preparation of ethyl 6-methyl-8-[(phenylthio)methyl]-2-(trifluoromethyl)-2H-chromene-3-carboxylate The polymer bound triphenylphosphine (1.2 g, 3.6 mmole) was suspended in anhydrous THF (10 mL) and the mixture was allowed to stir for 15 minutes. The ethyl 8-(hydroxymethyl)-6-methyl-2-(trifluoromethyl)-2H-chromene-3-carboxylate prepared as in Example 605b, Step 1 (0.38 g, 1.20 mmole), benzenethiol (0.20 g, 1.80 mmole) and DEAD (0.31 g, 1.80 mmole) were added to above mixture, which was allowed to stir for 18 hours. The resulting mixture was filtered through a plug of celite and condensed in vacuo to give a yellow oil (0.49 g, 98%). No further purification was performed. GCMS m/z 408.0 (M+).

Step 2. Preparation of 6-methyl-8-(phenoxygnethyl)-2-(trifluoromethyl)-2H-chromene-3-carboxylic acid The 6-methyl-8-(phenoxymethyl)-2-(trifluoromethyl)-2H-chromene-3-carboxylic acid was prepared by a procedure similar to the method described in Example 602a, Step 2: ESHRMS m/z 379.0585 (M–H, C₁₉H₁₄O₃F₃S, Calc'd 379.0610). ¹H NMR (CDCl₃/400 MHz) 7.82 (s, 1H), 7.29 (m, 5H), 7.20 (s, 1H), 6.95 (s, 1H), 5.72 (q, 1H, J=7.0 Hz), 4.11 (s, 2H), 2.21 (s, 3H).

EXAMPLE 605e

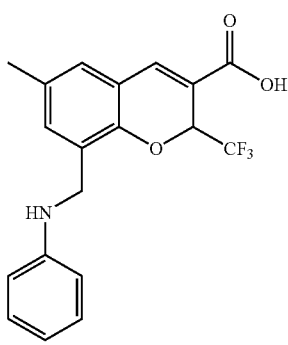

8-(anilinomethyl)-6-methyl-2-(trifluoromethyl)-2H-chromene-3-carboxylic acid

Step 2 1. Preparation of ethyl 8-(iodomethyl)-6-methyl-2-(trifluoromethyl)-2H-chromene-3-carboxylate The suspension, of polymer bound triphenylphosphine (0.29 g, 0. 88 mmole), in anhydrous CH₂Cl₂ (5 mL) was cooled to 0° C. (ice bath) and stirred for 15 minutes. The ethyl 8-(hydroxymethyl)-6-methyl-2-(trifluoromethyl)-2H-chromene-3-carboxylate prepared as in Example 605b, Step 1 (0.20 g, 0.63 mmole), imidazole (0.06 g, 0.88 mmole) and iodine (0.19 g, 0.76 mmole) were added to above suspension, which was allowed to stir for 15 minutes at 0° C. The mixture was warmed to room temperature and stirred for an additional 3 hours. The resulting mixture was filtered through a plug of celite and condensed in vacuo to give an oil. The oil was purified by flash chromatography (silica gel) with 50% methylene chloride in hexane to give a light yellow oil (0.14 g, 79%): GCMS m/z 426.00 (M+). ¹H NMR (CDCl₃/400 MHz) 7.64 (s, 1H), 7.11 (s, 1H), 6.94 (s, 1H), 5.79 (q, 1H, J=7.0 Hz), 4.44 (m, 2H), 4.31 (m, 2H), 2.24 (s, 3H), 1.33 (m, 3H).

Step 2. Preparation of ethyl 8-(anilinomethyl)-6-methyl-2-(trifluoromethyl)-2H-chromene-3-carboxylate A mixture of ethyl 8-(iodomethyl)-6-methyl-2-(trifluoromethyl)-2H-chromene-3-carboxylate (0.14 g, 0.32 mmole) and aniline (0.03 mL, 0.32 mmole) was dissolved in anhydrous DMF (2 mL), the solution was warmed to 90° C. and treated with K₂CO₃ (0.05 g, 0.39 mmole). The reaction was maintained at 90° C. for 24 hrs, cooled to room temperature, filtered through celite. The filtrate was condensed to give an oil. The oil was purified by flash chromatography (silica gel) with 70% methylene chloride in hexane to give a light yellow oil (0.11 g, 88%): GCMS m/z 391.00 (M+). ¹H NMR (CDCl₃/400 MHz) 7.70 (s, 1H), 7.19 (m, 3H), 6.94 (s, 1H), 6.74 (m, 11H), 6.65 (m, 2H), 5.77 (q, 1H, J=7.0 Hz), 4.33 (m, 4H), 4.18 (brs, 1H), 2.25 (s, 3H), 1.36 (m, 3H).

Step 3. Preparation of 8-(anilinomethyl)-6-methyl-2-(trifluoromethyl)-2H-chromene-3-carboxylic acid The 8-(anilinomethyl)-6-methyl-2-(trifluoromethyl)-2H-chromene-3-carboxylic acid was prepared by a procedure similar to the method described in Example 602a, Step 2: ESHRMS m/z 362.0989 (M–H, C₁₉H₁₅O₃F₃N, Calc'd 362.0999). ¹H NMR (acetone-d₆/400 MHz) 7.74 (s, 1H), 7.28 (s, 1H), 7.15 (s, 1H), 7.07 (m, 2H), 6.62 (m, 2H), 6.58 (m, 1H), 5.87 (q, 1H, J=7.0 Hz), 4.35 (m, 2H), 2.21 (s, 3H).

EXAMPLE 605f

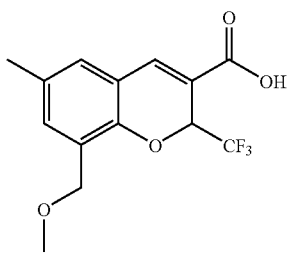

8-(methoxymethyl)-6-methyl-2-(trifluoromethyl)-2H-chromene-3-carboxylic acid

Step 1. Preparation of ethyl 8-(methoxymethyl)-6-methyl-2-(trifluoromethyl)-2H-chromene-3-carboxylate The ethyl 8-(iodomethyl)-6-methyl-2-(trifluoromethyl)-2H-chromene-3-carboxylate prepared as in Example 605e, Step 2 (0.2 g, 0.47 mmole) was dissolved in methanol (5 mL) and then the solution was cooled to 0° C. (ice bath). Sodium methoxide (0.32 mL, 1.41 mmole) was added dropwise to above solution, which was stirred for 2 hours at 0° C. The solution was warmed to room temperature and stirred for an additional 2 hours. The reaction was condensed in vacuo to give a yellow oil (0.15 g, 98%). No further purification was performed: GCMS m/z 330.00 (M+).

Step 2. Preparation of 8-(methoxymethyl)-6-methyl-2-(trifluoromethyl)-2H-chromene-3-carboxylic acid The 8-(methoxymethyl)-6-methyl-2-(trifluoromethyl)-2H-chromene-3-carboxylic acid was prepared by a procedure similar to the method described in Example 602a, Step 2: ESHRMS m/z 301.0664 (M–H, $C_{14}H_{12}O_4F_3$, Calc'd 301.0682). $^1$H NMR (acetone-$d_6$/400 MHz) 7.83 (s, 1H), 7.27 (s, 1H), 7.19 (s, 1H), 5.80 (q, 1H, J=7.0 Hz), 4.45 (m, 2H), 3.36 (s, 3H), 2.29 (s, 3H).

EXAMPLE 605g

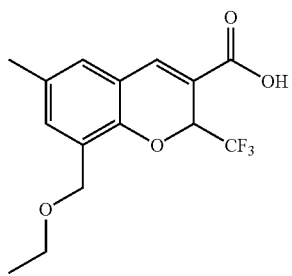

8-(ethoxymethyl)-6-methyl-2-(trifluoromethyl)-2H-chromene-3-carboxylic acid

Step 1. Preparation of ethyl 8-(ethoxymethyl)-6-methyl-2-(trifluoromethyl)-2H-chromene-3-carboxylate The ethyl 8-(iodomethyl)-6-methyl-2-(trifluoromethyl)-2H-chromene-3-carboxylate prepared as in Example 605e, Step 2 (0.2 g, 0.47 mmole) was dissolved in methanol (5 mL) and the solution was cooled to 0° C. (ice bath). Sodium ethoxide (0.10 g, 1.41 mmole) was added dropwise to the above solution, which was stirred for 2 hours at 0° C. The solution was warmed to room temperature and stirred for an additional 2 hours. The reaction was condensed in vacuo to give a yellow oil (0.16 g, 98%). No further purification was performed: GCMS m/z 344.00 (M+).

Step 2. Preparation of 8-(ethoxymethyl)-6-methyl-2-(trifluoromethyl)-2H-chromene-3-carboxylic acid The 8-(ethoxymethyl)-6-methyl-2-(trifluoromethyl)-2H-chromene-3-carboxylic acid was prepared by a procedure similar to the method described in Example 602a, Step 2: ESHRMS m/z 315.0852 (M–H, $C_{15}H_{14}O_4F_3$, Calc'd 315.0839). $^1$H NMR (acetone-$d_6$/400 MHz) 7.82 (s,1H), 7.29 (s, 1H), 7.18 (s, 1H), 5.79 (q, 1H, J=7.0 Hz),4.49 (m,2H), 3.53 (m, 2H), 2.24 (s, 3H), 1.18 (s, 3H).

EXAMPLE 605h

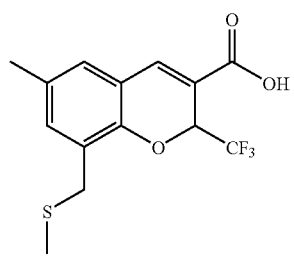

6-methyl-8-[(methylthio)methyl]-2-(trifluoromethyl)-2H-chromene-3-carboxylic acid Step 1. Preparation of ethyl 6-methyl-8-[(methylthio)methyl]-2-(trifluoromethyl)-2H-chromene-3-carboxylate The ethyl 8-(iodomethyl)-6-methyl-2-(trifluoromethyl)-2H-chromene-3-carboxylate prepared as in Example 605e, Step 2 (0.2 g, 0.47 mmole) was dissolved in methanol (4 mL) and cooled to 0° C. (ice bath). Sodium thiomethoxide (0.04 g, 0.52 mmole) was added dropwise and stirred for 2 hours at 0° C. The solution was warmed to room temperature and stirred for an additional 2 hours. The reaction was condensed in vacuo to give a yellow oil (0.16 g, 98%). No further purification was performed: GCMS m/z 346.00 (M+).

Step 2. Preparation of 8-(ethoxymethyl)-6-methyl-2-(trifluoromethyl)-2H-chromene-3-carboxylic acid The 8-(ethoxymethyl)-6-methyl-2-(trifluoromethyl)-2H-chromene-3-carboxylic acid was prepared by a procedure similar to the method described in Example 602a, Step 2: ESHRMS m/z 317.0466 (M–H, $C_{14}H_{12}O_3F_3S$, Calc'd 317.0454). $^1$H NMR (acetone-$d_6$/400 MHz) 7.82 (s, 1H), 7.22 (s, 1H), 7.17 (s, 1H),5.82 (q, 1H, J=7.0 Hz),3.68 (s, 3H), 2.27 (s, 3H).

EXAMPLE 605i

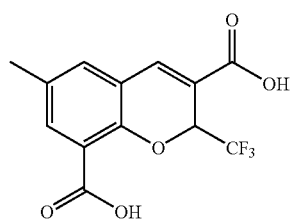

6-methyl-2-(trifluoromethyl)-2H-chromene-3,8-dicarboxylic acid

Step 1. Preparation of diethyl 6-methyl-2-(trifluoromethyl)-2H-chromene-3,8-dicarboxylate A mixture of ethyl 3-formyl-2-hydroxy-5-methylbenzoate (6.18 g, 29.69 mmole), $K_2CO_3$ (8.19 g, 59.38 mmole), triethylamine (1.99 g, 118.75 mmole), and ethyl 4,4,4-trifluorocrotonate (19.95 g, 118.75 mmole) in anhydrous DMSO (40.0 mL) was heated to 90° C. under a dry $N_2$ atmosphere for 5 hrs. The mixture was then cooled and allowed to stir at room temperature for 15 hours. The reaction was poured into 1.2 N HCl (100 mL) and extracted with EtOAc (2×100 mL). The combined extracts were washed with brine (100 mL), dried over $MgSO_4$, filtered and concentrated in vacuo to give a dark red oil which was subject to flash chromatography (silica gel) and eluted with 100% $CH_2Cl_2$ to give a light orange solid (4.5 g, 42%): $^1$H NMR (acetone-$d_6$/400 MHz) 7.84 (s, 1H), 7.61 (s, 1H), 7.46 (s, 1H), 5.86 (q, 1H, J=7.0 Hz), 4.30 (m, 4H), 2.31 (s, 3H), 1.33 (m, 6H).

Step 2. Preparation of 6-methyl-2-(trifluoromethyl)-2H-chromene-3,8-dicarboxylic acid The 6-methyl-2-(trifluoromethyl)-2H-chromene-3,8-dicarboxylic acid was prepared by a procedure similar to the method described in Example 602a, Step 2: ESHRMS m/z 301.0329 (M–H, $C_{13}H_8O_5F_3$, Calc'd 301.0318). $^1$H NMR (acetone-$d_6$/300 MHz) 7.87 (s, 1H), 7.71 (s,1H), 7.48 (s, 1H), 5.87 (q, 1H, J=7.0 Hz), 2.34 (s,3H).

EXAMPLE 605j

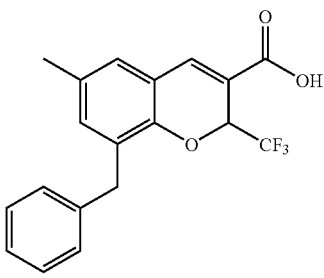

8-(hydroxymethyl)-6-methyl-2-(trifluoromethyl)-2H-chromene-3-carboxylic acid

Step 1. Preparation of ethyl 8-[hydroxy(phenyl)methl]-6-methyl-2-(trifluoromethyl)-2H-chromene-3-carboxylate The ethyl 8-formyl-6-methyl-2-(trifluoromethyl)-2H-chromene-3-carboxylate prepared as in Example 605a, Step 1 (0.45 g, 1.43 mmole) was dissolved in anhydrous THF (5 mL) and the solution was cooled to −78° C. (dry ice/acetone). Phenylmagnesium bromide (1.58 mL, 1.58 mmole) was added to the above solution dropwise, which was allowed to stir for 4 hours. The reaction was quenched with saturated ammonium chloride (20 mL) and extracted with EtOAc (2×20 mL). The combined extracts were washed with brine (20 mL), dried over $MgSO_4$, filtered and concentrated in vacuo to give an orange oil. The oil was purified by flash chromatography (silica gel) with 100% $CH_2Cl_2$ to give a light yellow oil (0.3g, 54%): GCMS m/z 392.0 (M+). $^1$H NMR (CDCl$_3$/400 MHz) 7.62 (s, 1H), 7.32 (m, 6H), 6.95 (s, 1H), 6.10 (s, 1H), 5.68 (q, 1H, J=7.0 Hz), 4.28 (m, 2H), 2.28 (s, 3H), 1.32 (m, 3H).

Step 2. Preparation of ethyl 8-benzyl-6-methyl-2-(trifluoromethyl)-2H-chromene-3-carboxylate The ethyl 8-[hydroxy(phenyl)methyl]-6-methyl-2-(trifluoromethyl)-2H-chromene-3-carboxylate (0.28 g, 0.70 mmole) was dissolved in trifluoroacetic acid (5 mL). Triethylsilane (0.24 g, 2.10 mmole) was added dropwise to above solution, which was allowed to stir for 18 hours. The reaction was quenched with saturated sodium bicarbonate (15 mL) and extracted with EtOAc (2×20 mL). The combined extracts were washed with brine (20 mL), dried over $MgSO_4$, filtered and concentrated in vacuo to give a yellow oil, which solidified upon standing (0.3 g, 98%): GCMS m/z 376.0 (M+). $^1$H NMR (CDCl$_3$/400 MHz) 7.67 (s, 1H), 7.25 (m, 3H), 7.20 (m, 2H), 6.93 (s, 1H), 6.89 (s, 1H), 5.70 (q, 1H, J=7.0 Hz), 4.29 (m, 2H), 3.94 (m, 2H), 2.22 (s, 3H), 1.32 (m, 3H).

Step 3. Preparation of 8-(hydroxymethyl)-6-methyl-2-(trifluoromethyl)-2H-chromene-3-carboxylic acid The 8-(hydroxymethyl)-6-methyl-2-(trifluoromethyl)-2H-chromene-3-carboxylic acid was prepared by a procedure similar to the method described in Example 602a, Step 2: ESHRMS m/z 347.0859 (M–H, $C_{19}H_{14}O_3F_3$, Calc'd 347.0890). $^1$H NMR (CDCl$_3$/300 MHz) 7.79 (s, 1H), 7.28 (m, 3H), 7.24 (m, 2H), 6.97 (s, I1H), 6.92 (s, 1H), 5.68 (q, 1H, J=7.0 Hz), 3.94 (m, 2H), 2.23 (s, 3H).

EXAMPLE 605k

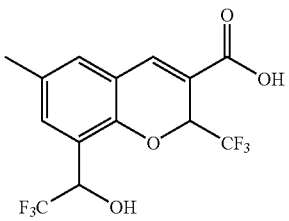

6-methyl-8-(2,2,2-trifluoro-l-hydroxyethyl)-2-(trifluoromethyl)-2H-chromene-3-carboxylic acid Step 1. Preparation of ethyl 6-methyl-8-(2,2,2-trifluoro-I-hydroxyethyl)-2-(trifluoro-methyl)-2H-chromene-3-carboxylate The aldehyde from Example 605a, Step 1 (2.0 g, 6.37 mmol) in THF (20 mL) was cooled to 0° C. and treated with 98% trimethyl(trifluoromethyl)silane (1.18 g, 8.28 mmol) and 15 mg tetramethylammonium fluoride. The reaction was allowed to warm to room temperature and stirred for overnight. The HF (48%, 0.24 mL) was added to the reaction and the reaction was stirred for 6 hours. After LCMS indicated that there was no starting material in the reaction, the reaction was quenched with water, extracted with ethyl acetate, washed with water, brine, dried over MgSO$_4$, and concentrated in vacuo to give a yellow semisolid (2.84 g), which had suitable purity to use without further purification.

Step 2. Preparation of 6-methyl-8-(2,2,2-trifluoro-1-hydroxyethyl)-2-(trifluoromethyl)-2H-chromene-3-carboxylic acid The 6-methyl-8-(2,2,2-trifluoro-1-hydroxyethyl)-2-(trifluoromethyl)-2H-chromene-3-carboxylic acid was prepared as a yellow solid (78% yield) by a procedure similar to the method described in Example 2a, Step 2: ESHRMS m/z 355.0393 (M–H, C$_{14}$H$_9$O$_4$F$_6$, Calc'd 355.0400). $^1$H NMR (acetone-d$_6$/400 MHz) 7.87 (s, 1H), 7.53 (s, 1H), 7.33 (s, 1H), 5.86 (q, 1H, J=7.2 Hz), 5.55 (m, 1H), 2.31 (s, 3H).

EXAMPLE 605l

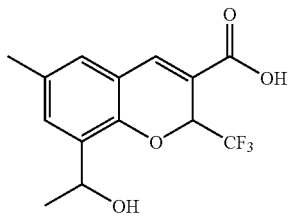

8-(1-hydroxyethyl)-6-methyl-2-(trifluoromethyl)-2H-chromene-3-carboxylic acid

Step 1. Preparation of ethyl 8-(1-hydroxyethyl)-6-methyl-2-(trifluoromethyl)-2H-chromene-3-carboxylate The ethyl 8-formyl-6-methyl-2-(trifluoromethyl)-2H-chromene-3-carboxylate prepared as in Example 605a, Step 1 (1.00 g, 3.18 mmole) was dissolved in anhydrous THF (10 mL) and the solution was cooled to –78° C. (dry ice/acetone). Methylmagnesium bromide (1.16 mL, 3.50 mmole) was added dropwise to the above solution, which was allowed to stir for 2 hours. The reaction was quenched with saturated ammonium chloride (20 mL) and extracted with EtOAc (2×20 mL). The combined extracts were washed with brine (20 mL), dried over MgSO$_4$, filtered and concentrated in vacuo to give a yellow oil. The oil was purified by flash chromatography (silica gel) with 10% MeOH/ CH$_2$Cl$_2$ to give a light yellow oil (0.3g, 54%): GCMS m/z 330.0 (M+). $^1$H NMR (CDCl$_3$/400 MHz) 7.67 (s, 1H), 7.26 (s, 1H), 6.94 (s, 1H), 5.68 (q, 1H, J=7.0 Hz), 5.11 (m, 1H), 4.30 (m, 2H), 2.28 (s, 3H), 1.47 (m, 3H), 1.34 (m, 3H).

Step 2. Preparation of 8-(1-hydroxyethyl)-6-methyl-2-(trifluoromethyl)-2H-chromene-3-carboxylic acid The 8-(1-hydroxyethyl)-6-methyl-2-(trifluoromethyl)-2H-chromene-3-carboxylic acid was prepared by a procedure similar to the method described in Example 602a, Step 2: ESHRMS m/z 301.0681 (M–H, C$_{14}$H$_{12}$O$_4$F$_3$, Calc'd 301.0682). $^1$H NMR (acetone-d$_6$/400 MHz) 7.82 (s, 1H), 7.45 (s, 1H), 7.12 (s, 1H), 5.80 (q, 1H, J=7.0 Hz), 5.12 (m, 1H), 3.94 (m, 2H), 2.29 (s, 3H) 1.35 (m, 3H).

EXAMPLE 605m

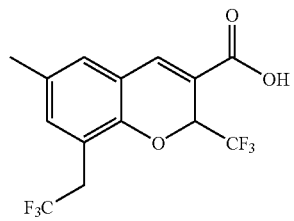

6-methyl-8-(2,2,2-trifluoroethyl)-2-(trifluoromethyl)-2H-chromene-3-carboxylic acid Step 1. Preparation of ethyl 6-methyl-8-{2,2,2-trifluoro-1-[(1H-imidazol-1-ylcarbonothioyl)oxy]ethyl}-2-(trifluoromethyl)-2H-chromene-3-carboxylate The alcohol from Example 605k, Step 1 (2.20 g, 5.73 mmol) was dissolved in CH$_2$Cl$_2$ (40 mL). The thiocarbonyldiimidazole (1.70 g, 8.59 mmol) was added to above solution, followed by DMAP (89.6 mg, 0.73 mmol). The mixture was stirred at r.t. overnight. Additional thiocarbonydiimidazole (0.2 g, 0.11 mmol) was added to above solution and the reaction was stirred at r.t for 4 hours. The mixture was passed through the silic plug and plug was washed with 30% EtOAc in hexane to give a lightly yellow oil (2.16 g, 76%): LCMS m/z 495.05 (M+H), which had suitable purity to use without further purification.

Step 2. Preparation of ethyl 6-methyl-8-(2,2,2-trifluoroethyl)-2-(trifluoromethyl)-2H-chromene-3-carboxylate The ester from Step 1 (2.1 g, 4.25 mmol) was dissolved in toluene (15 mL). The Et$_3$SiH (30 mL, 0.18 mol) was added to above solution. The mixture was heated to reflux. The benzoyl peroxide (1.03 g, 4.25 mmol) in toluene (15 mL) was added in 4 portions at 15 min intervals. The mixture was heated to reflux for 2 hours and stirred at r.t overnight. The mixture was passed through silic plug and plug was washed with 5% to 10% EtOAc in hexane to give crude product: LCMS m/z 369.15 (M+H). This ester was of suitable purity to use without further purification.

Step 2. Preparation of 6-methyl-8-(2,2,2-trifluoro-1-hydroxyethyl)-2-(trifluoromethyl)-2H-chromene-3-carboxylic acid The 6-methyl-8-(2,2,2-trifluoro-1-hydroxyethyl)-2-(trifluoromethyl)-2H-chromene-3-carboxylic acid was prepared as offwhite solid by a procedure similar to the method described in Example 2a, Step 2: ESHRMS m/z 339.0467 (M–H, C$_{14}$H$_9$O$_3$F$_6$, Calc'd 339.0450). $^1$H NMR (acetone-d$_6$/400 MHz) 7.86 (s, 1H), 7.30 (s, 1H), 7.28 (s, 1H), 5.88 (q, 1H, J=7.2 Hz), 3.59 (m, 2H), 2.31 (s, 3H).

EXAMPLE 605n

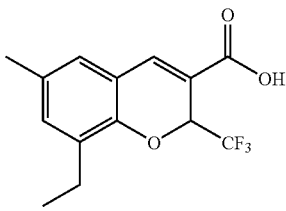

8-ethyl-6-methyl-2-(trifluoromethyl)-2H-chromene-3-carboxylic acid

Step 1. Preparation of ethyl 8-ethyl-6-methyl-2-(trifluoromethyl)-2H-chromene-3-carboxylate The ethyl 8-(1-hydroxyethyl)-6-methyl-2-(trifluoromethyl)-2H-chromene-3-carboxylate prepared as in Example 605l, Step 1 (0.30 g, 0.91 mmole) was dissolved in trifluoroacetic acid (5 mL). Triethylsilane (0.32 g, 2.73 mmole) was added dropwise to the above solution, which was allowed to stir for 18 hours. The reaction was quenched with saturated sodium bicarbonate (15 mL) and extracted with Et$_2$O (2×20 mL). The combined extracts were washed with brine (20 mL), dried over MgSO$_4$, and filtered. The filtrate was concentrated in vacuo to give a yellow oil which solidified upon standing (0.28 g, 98%): GCMS m/z 314.0 (M+). $^1$H NMR (CDCl$_3$/400 MHz) 7.66 (s, 1H), 6.98 (s, 1H), 6.85 (s, 1H), 5.70 (q, 1H, J=7.0 Hz), 4.30 (m, 2H), 2.61 (m, 2H), 2.25 (s, 3H), 1.32 (m, 3H), 1.15 (m, 3H).

Step 2. Preparation of 8-ethyl-6-methyl-2-(trifluoromethyl)-2H-chromene-3-carboxylic acid The 8-ethyl-6-methyl-2-(trifluoromethyl)-2H-chromene-3-carboxylic acid was prepared by a procedure similar to the method described in Example 602a, Step 2: ESHRMS m/z 285.0752 (M–H, C$_{14}$H$_{12}$O$_3$F$_3$, Calc'd 285.0733). $^1$H NMR (CDCl$_3$/300 MHz) 7.82 (s, 1H), 7.02 (s, 1H), 6.89 (s, 1H), 5.68 (q, 1H, J=7.0 Hz), 2.64 (m, 2H), 2.26 (s, 3H), 1.18 (m, 3H).

EXAMPLE 605o

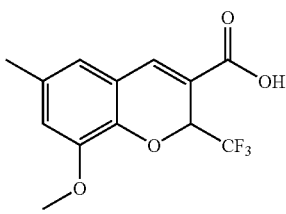

8-methoxy-6-methyl-2-(trifluoromethyl)-2H-chromene-3-carboxylic acid

Step 1. Preparation of 5-bromo-2-hydroxy-3-methoxybenzaldehyde

The solution of 2-hydroxy-3-methoxybenzaldehyde (10.0 g, 65.79 mmole) in acetic acid (50 mL) was cooled to 0° C. (ice bath). Bromine (12.55 g, 78.95 mmole) was added dropwise to above solution, which was allowed to stir for 2 hours. The reaction was warmed to room temperature and diluted with water (100 mL). A light brown precipitate was formed. The solid was filtered and washed with water (50 mL). The filtrate was dried on high vacuum to give a light brown solid (12.2 g, 80.0%): GCMS m/z 231.0 (M+). $^1$H NMR (CDCl$_3$/400 MHz) 10.97 (s, 1H), 9.82 (s, 1H), 7.29 (s, 1H), 7.15 (s, 1H), 3.89 (m, 3H).

Step 2. Preparation of ethyl 6-bromo-8-methoxy-2-(trifluoromethyl)-2H-chromene-3-carboxulate A mixture of 5-bromo-2-hydroxy-3-methoxybenzaldehyde (3.44 g, 14.89 mmole), K$_2$CO$_3$ (4.10 g, 29.78 mmole), triethylamine (6.02 g, 59.57 mmole), and ethyl 4,4,4-trifluorocrotonate (10.00 g, 59.57 mmole) in anhydrous DMSO (5.0 mL) was heated to 90° C. under a dry N$_2$ atmosphere for 18 hrs. The contents were poured into 2.4 N HCl (50 ml) and extracted with EtOAc (2×100 mL). The combined extracts were washed with brine (100 mL), dried over MgSO$_4$, filtered and concentrated in vacuo to give a dark yellow oil which was subject to flash chromatography (silica gel) and eluted with 10% EtOAc/hexanes to give a light yellow oil which solidified upon standing (3.5 g, 63%): GCMS m/z 380.0 (M+). $^1$H NMR (CDCl$_3$/400 MHz) 7.59 (s, 1H), 7.02 (s, 1H), 6.97 (s, 1H), 5.73 (q, 1H, J=7.0 Hz), 4.29 (m, 2H), 3.86 (s, 3H), 1.32 (m, 3H).

Step 3. Preparation of ethyl 8-methoxy-6-methyl-2-(trifluoromethyl)-2H-chromene-3-carboxylate A mixture of ethyl 6-bromo-8-methoxy-2-(trifluoromethyl)-2H-chromene-3-carboxylate (0.40 g, 1.05 mmole), trimethylboroxine (0.33 g, 2.63 mmole), Pd(PPh$_3$)$_4$ (0.13 g, 0.11 mmole) and K$_2$CO$_3$ (0.58 g, 4.20 mmole) in anhydrous DMF (5.0 mL) was heated to 90° C. under a dry N$_2$ atmosphere for 18 hrs. The contents were poured into 2.4 N HCl (20 ml) and extracted with EtOAc (2×20 mL). The combined extracts were washed with brine (20 mL), dried over MgSO$_4$, filtered and concentrated in vacuo to give a yellow oil which was subject to flash chromatography (silica gel) and eluted with 10% EtOAc/ hexanes to give a light yellow oil (0.23 g, 70%): GCMS m/z 316.0 (M+). $^1$H NMR (CDCl$_3$/400 MHz) 7.64 (s, 1H), 6.74 (s, 1H), 6.63 (s, 1H), 5.70 (q, 1H, J=7.0 Hz), 4.28 (m, 2H), 3.85 (s, 3H), 2.26 (s, 3H), 1.32 (m, 3H).

Step 4. Preparation of 8-methoxy-6-methyl-2-(trifluoromethyl)-2H-chromene-3-carboxylic acid The 8-methoxy-6-methyl-2-(trifluoromethyl)-2H-chromene-3-carboxylic acid was prepared by a procedure similar to the method described in Example 602a, Step 2: ESHRMS m/z 287.0546 (M–H, C$_{13}$H$_{10}$O$_4$F$_3$, Calc'd 287.0526). $^1$H NMR (CDCl$_3$/300 MHz) 7.82 (s, 1H), 7.02 (s, 1H), 6.89 (s, 1H), 5.68 (q, 1H, J=7.0 Hz), 2.64 (m, 2H), 2.26 (s, 3H), 1.18 (m, 3H).

EXAMPLE 606a

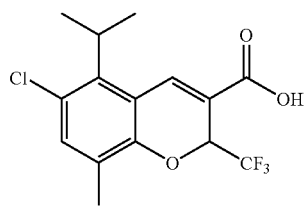

6-chloro-5-isopropyl-8-methyl-2-(trifluoromethyl)-2H-chromene-3-carboxylic acid

Step 1. Preparation of 3-chloro-6-hydroxy-2-isopropyl-5-methylbenzaldehyde

The 4-chloro-5-isopropyl-2-methylphenol (5.0 g, 27.08 mmole) and magnesium chloride (3.87 g, 40.61 mmole) were mixed in acetonitrile (150 mL) and the mixture was cooled to 0° C. (ice bath). Triethylamine (10.28 g, 101.55 mmole) followed by para-formaldehyde (5.48 g, 182.79 mmole) were added to above mixture, which was stirred at 0° C. for 1 hour. The mixture was warmed to room temperature and then heated to 90° C. for 1 week. The contents were poured into water (100 mL) and extracted with EtOAc (2×100 mL). The combined extracts were washed with brine (50 mL), dried over MgSO$_4$, filtered and concentrated in vacuo to give an off-white solid which was subject to flash chromatography (silica gel) and eluted with 100% CH$_2$Cl$_2$ to give an off-white solid (1.83 g, 32%): GCMS m/z 212.0 (M+).

Step 2. Preparation of ethyl 6-chloro-5-isopropyl-8-methyl-2-(trifluoromethyl)-2H-chromene-3-carboxylate A mixture of 3-chloro-6-hydroxy-2-isopropyl-5-methyl-benzaldehyde (1.83 g, 8.6 mmole), K$_2$CO$_3$ (2.38 g, 17.3 mmole) and ethyl 4,4,4-trifluorocrotonate (2.17 g, 12.9 mmole) in anhydrous DMF (10.0 mL) was heated to 90° C. under a dry N$_2$ atmosphere for 18 hrs. The mixture was then cooled, poured into 0.5 N HCl (50 ml) and extracted with EtOAc (2×50 mL). The combined extracts were washed with brine (50 mL), dried over MgSO$_4$, filtered and concentrated in vacuo to give a dark oil which was subject to flash chromatography (silica gel) and eluted with 50% CH$_2$Cl$_2$/hexanes to give a yellow oil (2.1 g, 68%): GCMS m/z 362.0 (M+). $^1$H NMR (CDCl$_3$/400 MHz) 8.07 (s, 1H), 7.02 (s, 1H), 5.64 (q, 1H, J=7.0 Hz), 4.23 (m, 2H), 3.39 (s, 3H), 3.23 (m, 1H), 1.26 (m, 3H), 1.12 (m, 6H).

Step 3. Preparation of 6-chloro-5-isopropyl-8-methyl-2-(trifluoromethyl)-2H-chromene-3-carboxylic acid The 6-chloro-5-isopropyl-8-methyl-2-(trifluoromethyl)-2H-chromene-3-carboxylic acid was prepared by a procedure similar to the method described in Example 602a, Step 2: ESHRMS m/z 333.0501 (M−H, C$_{15}$H$_{13}$O$_3$F$_3$Cl, Calc'd 333.0500). $^1$H NMR (acetone-d$_6$/400 MHz) 8.20 (s, 1H), 7.31 (s, 2H), 5.84 (q, 1H, J=7.0 Hz), 3.73 (s, 1H), 2.20 (s, 3H), 1.41 (m, 6H).

EXAMPLE 606b

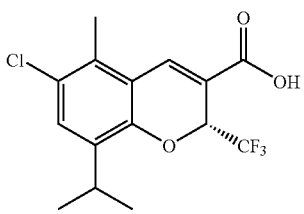

(2R)-6-chloro-8-isopropyl-5-methyl-2-(trifluoromethyl)-2H-chromene-3-carboxylic acid A racemic mixture of the compound prepared in Example 6 was resolved by chiral chromatography using a Kromasil 10CHI-DMB column eluting with 20% MTBE in heptane with 0.2% acetic acid and detecting at 280nm to give R-enantiomer as peak 1 with retention time 7.95 minutes: $^1$H NMR (acetone-d$_6$/400 MHz) 7.54 (s, 1 H), 7.12 (s, 1H), 5.64 (q, 1H, J=7.0 Hz), 3.08 (m, 1H), 2.22 (s, 3H), 1.01 (m, 6H). $^{19}$F NMR (benzene-d6/ 400 MHz; 6eq. of (R)-(+)-(1-naphthyl)ethylamine) −77.95 (d, 3F, J=10.4 Hz, S-enantiomer), −78.00 (d, 3F, J=10.4 Hz, R-enantiomer).

EXAMPLE 606c

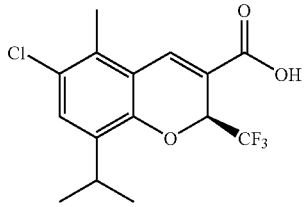

(2S)-6-chloro-8-isopropyl-5-methyl-2-(trifluoromethyl)-2H-chromene-3-carboxylic acid A racemic mixture of the compound prepared in Example 6 was resolved by chiral chromatography using a Kromasil 10CHI-DMB column eluting with 20% MTBE in heptane with 0.2% acetic acid and detecting at 280nm to give S-enantiomer as peak 2 with retention time 10.26 minutes: $^1$H NMR (acetone-d$_6$/400 MHz) 7.54 (s, 1H), 7.12 (s, 1H), 5.64 (q, 1H, J=7.0 Hz), 3.08 (m, 1H), 2.22 (s, 3H), 1.01 (m, 6H). $^{19}$F NMR (benzene-d$_6$/400 MHz; 6eq. of (R)-(+)-(1-naphthyl)ethylamine) −77.95 (d, 3F, J=10.4 Hz, S-enantiomer), −78.00 (d, 3F, J=10.4 Hz, R-enantiomer).

EXAMPLE 607a

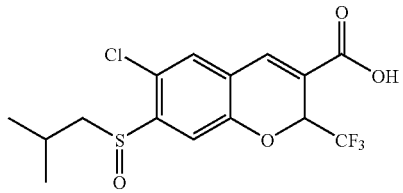

6-chloro-7-(isobutylsulfinyl)-2-(trifluoromethyl)-2H-chromene-3-carboxylic acid

Step 1. Preparation of ethyl 6-chloro-7-(isobutylsulfinyl)-2-(trifluoromethyl)-2H-chromene-3-carboxylate The Ethyl 6-chloro-7-(isobutylthio)-2-(trifluoromethyl)-2H-chromene-3-carboxylate (Example 7d) (0.47 g, 1.19 mmole) was dissolved in a mixture of acetone (10 mL) and water (10 mL) and cooled to 0° C. (ice bath). The reaction was treated with oxone (0.73 g, 1.19 mmole) and stirred at 0° C. for 10 minutes followed by warming to room temperature for 4 hours. The reaction mixture was diluted with water (20 mL) and extracted with EtOAc (2×50 mL). The combined extracts were washed with brine (50 mL), dried over MgSO$_4$, filtered and concentrated in vacuo to give a yellow solid which was subject to HPLC (reverse phase) and eluted with 50-95% ACN/water with 0.05% TFA to give a yellow solid (0.4 g, 82%): LCMS m/z 411.0 (M+H). $^1$H NMR (CDCl$_3$/400 MHz) 7.65 (s, 1H), 7.54 (s, 1H), 7.24 (s, 1H), 5.73 (q, 1H, J=7.0 Hz), 4.30 (m, 2H), 2.90 (m, 1H), 2.70 (m, 1H), 2.38 (m, 1H), 1.33 (m, 3H), 1.20 (m, 3H), 1.07 (m, 3H).

Step 2. Preparation of 6-chloro-7-(isobutylsulfinyl)-2-(trifluoromethyl)-2H-chromene-3-carboxylic acid The 6-chloro-7-(isobutylsulfinyl)-2-(trifluoromethyl)-2H-chromene-3-carboxylic acid was prepared by a procedure similar to the method described in Example 602a, Step 2: ESHRMS m/z 381.0142 (M−H, C$_{15}$H$_{13}$O$_4$F$_3$ClS, Calc'd 381.0170). $^1$H NMR (acetone-d$_6$/400 MHz) 7.95 (s, 1H), 7.69 (s, 1H), 7.44 (s, 1H), 5.94 (q, 1H, J=7.0 Hz), 2.98 (m, 1H), 2.64 (m, 1H), 2.27 (m, 1H), 1.18 (m, 3H), 1.06 (m, 3H).

EXAMPLE 607b

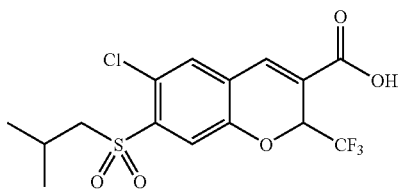

6-chloro-7-(isobutylsulfonyl)-2-(trifluoromethyl)-2H-chromene-3-carboxylic acid

Step 1. Preparation of ethyl 6-chloro-7-(isobutylsulfonyl)-2-(trifluoromethyl)-2H-chromene-3-carboxylate The ethyl 6-chloro-7-(isobutylthio)-2-(trifluoromethyl)-2H-chromene-3-carboxylate (Example 7d, Step 2) (0.44 g, 1.12 mmole) was dissolved in a mixture of acetone (5 mL) and water (5 mL) and cooled to 0° C. (ice bath). The reaction was treated with oxone (2.06 g, 3.35 mmole) and stirred at 0° C. for 10 minutes followed by warming to room temperature for 18 hours. The reaction mixture was diluted with water (20 mL) and extracted with EtOAc (2×50 mL). The combined extracts were washed with brine (50 mL), dried over MgSO$_4$, filtered and concentrated in vacuo to give a yellow solid as a mixture of oxidized products. The mixture was not further purified and carried forward to the next Step: GCMS m/z 426.0 (M+).

Step 2. Preparation of 6-chloro-7-(isobutylsulfonyl)-2-(trifluoromethyl)-2H-chromene-3-carboxylic acid The 6-chloro-7-(isobutylsulfonyl)-2-(trifluoromethyl)-2H-chromene-3-carboxylic acid was prepared by a procedure similar to the method described in Example 602a, Step 2: ESHRMS m/z 397.0092 (M−H, C$_{15}$H$_{13}$O$_5$F$_3$ClS, Calc'd 397.0119). $^1$H NMR (acetone-d$_6$/400 MHz) 7.97 (s, 1H), 7.85 (s, 1H), 7.65 (s, 1H), 5.98 (q, 1H, J=7.0 Hz), 3.41 (m, 2H), 2.21 (m, 1H), 1.06 (m, 6H).

EXAMPLE 607c

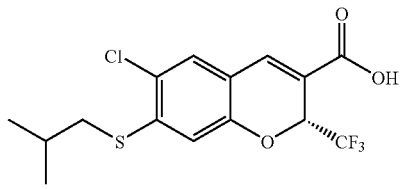

(2R)-6-chloro-7-(isobutylthio)-2-(trifluoromethyl)-2H-chromene-3-carboxylic acid A racemic mixture of the compound prepared in Example 7d was resolved by chiral chromatography using a Daicel Chiral Pak AD column eluting with 30% ethanol in heptane and detecting at 244 nm to give R-enantiomer as peak 1 with retention time 6.86 minutes: ESHRMS m/z 365.0270 (M−H, C$_{15}$H$_{13}$F$_3$O$_3$ClS, Calc'd 365.0226). $^1$H NMR (acetone-d$_6$/400 MHz) 7.20 (s, 1H), 7.16 (s, 1H), 6.74 (s, 1H), 5.65 (q, 1H, J=7.0 Hz), 2.72 (m, 2H), 1.78 (m, 1H), 0.90 (m, 6H). $^{19}$F NMR (benzene-d$_6$/400 MHz; 6eq. of (R)-(+)-(1-naphthyl)ethylamine) −77.81 (d, 3F, J=7.2 Hz, S-enantiomer), −78.01 (d, 3F, J=8.4 Hz, R-enantiomer).

EXAMPLE 607d

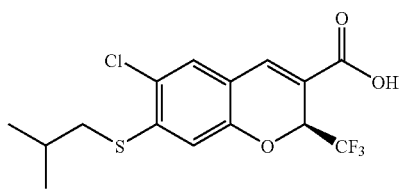

(2S)-6-chloro-7-(isobutylthio)-2-(trifluoromethyl)-2H-chromene-3-carboxylic acid A racemic mixture of the compound prepared in Example 7d was resolved by chiral chromatography using a Daicel Chiral Pak AD column eluting with 30% ethanol in heptane and detecting at 244 rnn to give S-enantiomer as peak 2 with retention time 8.76 minutes: ESHRMS m/z 365.0255 (M−H, C$_{15}$H$_{13}$F$_3$O$_3$ClS, Calc'd 365.0226). $^1$H NMR (acetone-d$_6$/400 MHz) 7.20 (s, 1H), 7.16 (s, 1H), 6.74 (s, 1H), 5.65 (q, 1H, J=7.0 Hz), 2.72 (m, 2H), 1.78 (m, 1H), 0.90 (m, 6H). $^{19}$F NMR (benzene-d$_6$/400 MHz; 6 eq. of (R)-(+)-(1-naphthyl)ethylamine) −77.81 (d, 3F, J=7.2 Hz, S-enantiomer), −78.01 (d, 3F, J=8.4 Hz, R-enantiomer).

EXAMPLE 608a

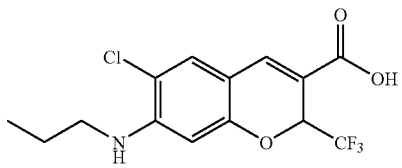

6-chloro-7-(propylamino)-2-(trifluoromethyl)-2H-chromene-3-carboxylic acid

Step 1. Preparation of ethyl 6-chloro-7-(propylamino)-2-(trifluoromethyl)-2H-chromene-3-carboxylate A mixture of ethyl 6-chloro-7-fluoro-2-(trifluoromethyl)-2H-chromene-3-carboxylate (Example 7a, Step 2) (0.5 g, 1.54 mmole) and propylamine (0.13 mL, 1.54 mmole) was dissolved in anhydrous DMF (5 mL), which was warmed to 90° C. and treated with $K_2CO_3$ (0.25 g, 1.84 mmole). The mixture was maintained at 90° C. for 24 hrs, cooled to room temperature, filtered through celite and condensed to a viscous oil. The oil was purified by flash chromatography (silica gel) with 40% methylene chloride in hexane to give a light yellow oil (0.44 g, 79%): GCMS m/z 363.00 (M+). $^1$H NMR (CDCl$_3$/400 MHz) 7.57 (s, 1H), 7.08 (s, 1H), 6.23 (s, 1H), 5.63 (q, 1H, J=7.0 Hz), 4.73 (brs, 1H), 4.26 (m, 2H), 3.14 (m, 2H), 1.66 (m, 2H), 1.31 (m, 3H), 1.01 (m, 3H).

Step 2. Preparation of 6-chloro-7-(propylamino)-2-(trifluoromethyl)-2H-chromene-3-carboxylic acid The 6-chloro-7-(propylamino)-2-(trifluoromethyl)-2H-chromene-3-carboxylic acid was prepared by a procedure similar to the method described in Example 602a, Step 2: ESHRMS m/z 334.0488 (M–H, $C_{14}H_{12}O_3F_3ClN$, Calc'd 334.0452). $^1$H NMR (acetone-d$_6$/400 MHz) 7.74 (s, 1H), 7.35 (s, 1H), 6.37 (s, 1H), 5.71 (q, 1H, J=7.0 Hz), 3.27 (m, 2H), 1.68 (m, 2H), 0.98 (m, 3H).

EXAMPLE 608b

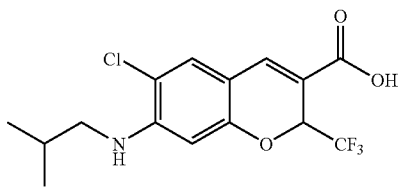

6-chloro-7-(isobutylamino)-2-(trifluoromethyl)-2H-chromene-3-carboxylic acid

Step 1. Preparation of ethyl 6-chloro-7-(isobutylamino)-2-(trifluoromethyl)-2H-chromene-3-carboxylate A mixture of ethyl 6-chloro-7-fluoro-2-(trifluoromethyl)-2H-chromene-3-carboxylate (Example 7a, Step 2) (0.5 g, 1.54 mmole) and isobutylamine (0.15 mL, 1.54 mmole) was dissolved in anhydrous DMF (5 mL), which was warmed to 90° C. and treated with $K_2CO_3$ (0.25 g, 1.84 mmole). The mixture was maintained at 90° C. for 24 hrs, cooled to room temperature, filtered through celite and condensed to a viscous oil. The oil was purified by flash chromatography (silica gel) with 40% methylene chloride in hexane to give a light yellow oil (0.44 g, 76%): GCMS m/z 377.00 (M+). $^1$H NMR (CDCl$_3$/400 MHz) 7.57 (s, 1H), 7.09 (s, 1H), 6.30 (s, 1H), 5.63 (q, 1H, J=7.0 Hz), 4.27 (m, 2H), 3.00 (m, 2H), 1.95 (m, 1H), 1.31 (m, 3H), 1.00 (m, 6H).

Step 2. Preparation of 6-chloro-7-(isobutylamino)-2-(trifluoromethyl)-2H-chromene-3-carboxylic acid The 6-chloro-7-(isobutylamino)-2-(trifluoromethyl)-2H-chromene-3-carboxylic acid was prepared by a procedure similar to the method described in Example 602a, Step 2: ESHRMS m/z 348.0604 (M–H, $C_{15}H_{14}O_3F_3ClN$, Calc'd 348.0609). $^1$H NMR (acetone-d$_6$/400 MHz) 7.74 (s, 1H), 7.35 (s, 1H), 6.37 (s, 1H), 5.71 (q, 1H, J=7.0 Hz), 3.31 (m, 2H), 2.00 (m, 1H), 0.98 (m, 6H).

EXAMPLE 608c

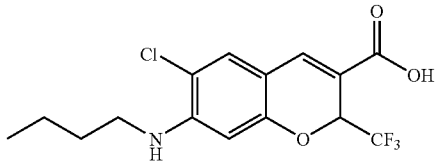

6-chloro-7-(butylamino)-2-(trifluoromethyl)-2H-chromene-3-carboxylic acid

Step 1. Preparation of ethyl 6-chloro-7-(butylamino)-2-(trifluoromethyl)-2H-chromene-3-carboxylate A mixture of ethyl 6-chloro-7-fluoro-2-(trifluoromethyl)-2H-chromene-3-carboxylate (Example 7a, Step 2) (0.5 g, 1.54 mmole) and butylamine (0.15 mL, 1.54 mmole) was dissolved in anhydrous DMF (5 mL), warmed to 90° C. and treated with $K_2CO_3$ (0.25 g, 1.84 mmole). The solution was maintained at 90° C. for 24 hrs, cooled to room temperature, filtered through celite and condensed to a viscous oil. The oil was purified by flash chromatography (silica gel) with 40% methylene chloride in hexane to give a light yellow oil (0.46g, 79%): GCMS m/z 377.00 (M+). $^1$H NMR (CDCl$_3$/400 MHz) 7.58 (s, 1H), 7.08 (s, 1H), 6.23 (s, 1H), 5.63 (q, 1H, J=7.0 Hz), 4.70 (brs, 1H), 4.27 (m, 2H), 3.17 (m, 2H), 1.63 (m, 2H), 1.43 (m, 2H), 1.31 (m, 3H), 0.98 (m, 3H).

Step 2. Preparation of 6-chloro-7-(butylamino)-2-(trifluoromethyl)-2H-chromene-3-carboxylic acid The 6-chloro-7-(butylamino)-2-(trifluoromethyl)-2H-chromene-3-carboxylic acid was prepared by a procedure similar to the method described in Example 602a, Step 2: ESHRMS m/z 348.0599 (M–H, $C_{15}H_{14}O_3F_3ClN$, Calc'd 348.0609). $^1$H NMR (acetone-d$_6$/400 MHz) 7.74 (s, 1H), 7.35 (s, 1H), 6.37 (s,1H), 5.71 (q, 1H, J=7.0 Hz), 3.30 (m, 2H), 1.66 (m, 2H), 1.44 (m, 2H), 0.95 (m, 3H).

EXAMPLE 608d

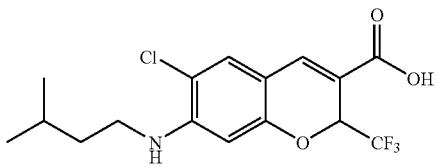

6-chloro-7-(isopentylamino)-2-(trifluoromethyl)-2H-chromene-3-carboxylic acid

Step 1. Preparation of ethyl 6-chloro-7-(isopentylamino)-2-(trifluoromethyl)-2H-chromene-3-carboxylate A mixture of ethyl 6-chloro-7-fluoro-2-(trifluoromethyl)-2H-chromene-3-carboxylate (Example 7a, Step 2) (0.5 g, 1.54 mmole) and isopentylamine (0.18 mL, 1.54 mmole) was dissolved in anhydrous DMF (5 mL), warmed to 90° C. and treated with $K_2CO_3$ (0.25 g, 1.84 mmole). The mixture was maintained at 90° C. for 24 hrs, cooled to room temperature, filtered through celite and condensed to a viscous oil. The oil was purified by flash chromatography (silica gel) with 40% methylene chloride in hexane to give light yellow solid (0.49 g, 82%): GCMS m/z 393.00 (M+). $^1$H NMR (CDCl$_3$/400 MHz) 7.58 (s, 1H), 7.09 (s, 1H), 6.31 (s, 1H), 5.64 (q, 1H, J=7.0 Hz), 4.27 (m, 2H), 3.19 (m, 2H), 1.71 (m, 1H), 1.57 (m, 2H), 1.31 (m, 3H), 0.96 (m, 6H).

Step 2. Preparation of 6-chloro-7-(isopentylamino)-2-(trifluoromethyl)-2H-chromene-3-carboxylic acid The 6-chloro-7-(isopentylamino)-2-(trifluoromethyl)-2H-chromene-3-carboxylic acid was prepared by a procedure similar to the method described in Example 602a, Step 2: ESHRMS m/z 362.0732 (M−H, $C_{16}H_{16}O_3F_3ClN$, Calc'd 362.0765). $^1$H NMR (acetone-d$_6$/400 MHz) 7.74 (s, 1H), 7.35 (s, 1H), 6.37 (s, 1H), 5.71 (q, 1H, J=7.0 Hz), 3.32 (m, 2H), 1.75 (m, 1H), 1.58 (m, 2H), 0.96 (m, 6H).

EXAMPLE 608e

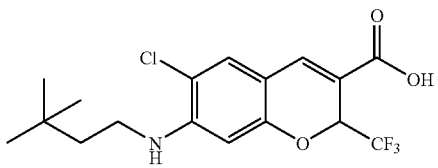

6-chloro-7-[(3,3-dimethylbutyl)aminol-2-(trifluoromethyl)-2H-chromene-3-carboxylic acid

Step 1. Preparation of ethyl 6-chloro-7-[(3,3-dimethylbutyl)amino]-2-(trifluoromethyl)-2H-chromene-3-carboxylate A mixture of ethyl 6-chloro-7-fluoro-2-(trifluoromethyl)-2H-chromene-3-carboxylate (Example 7a, Step 2) (0.5 g, 1.54 mmole) and 3,3-dimethylbutylamine (0.21 mL, 1.54 mmole) was dissolved in anhydrous DMF (5 mL), warmed to 90° C. and treated with $K_2CO_3$ (0.25 g, 1.84 mmole). The mixture was maintained at 90° C. for 24 hrs, cooled to room temperature, filtered through celite and condensed to a viscous oil. The oil was purified by flash chromatography (silica gel) with 40% methylene chloride in hexane to give light yellow solid (0.54 g, 87%): GCMS ml/z 405.00 (M+). $^1$H NMR (CDCl$_3$/400 MHz) 7.58 (s, 1H), 7.08 (s, 1H), 6.22 (s, 1H), 5.64 (q, 1H, J=7.0 Hz), 4.26 (m, 2H), 3.16 (m, 2H), 1.57 (m, 2H), 1.33 (m, 3H), 0.98 (s, 9H).

Step 2. Preparation of 6-chloro-7-[(3,3-dimethylbutyl)aminol-2-(trifluoromethyl)-2H-chromene-3-carboxylic acid The 6-chloro-7-[(3,3-dimethylbutyl)amino]-2-(trifluoromethyl)-2H-chromene-3-carboxylic acid was prepared by a procedure similar to the method described in Example 602a, Step 2: ESHRMS m/z 376.0885 (M−H, $C_{17}H_{18}O_3F_3ClN$, Calc'd 376.0922). $^1$H NMR (acetone-d$_6$/400 MHz) 7.74 (s, 1H), 7.35 (s, 1H), 6.37 (s, 1H), 5.71 (q, 1H, J=7.0 Hz), 3.32 (m, 2H), 1.61 (m, 2H), 0.99 (s, 9H).

EXAMPLE 608f

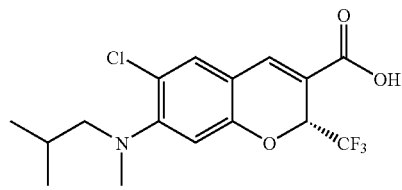

(2R)-6-chloro-7-[isobutyl(methyl)amino]-2-(trifluoromethyl)-2H-chromene-3-carboxylic acid A racemic mixture of the compound prepared in Example 8c, 01598/1 PR, was resolved by chiral chromatography using a ChiralPak AD column eluting with 10% isopropanol in heptane with 0.1% TFA and detecting at 280 nm to give R-enantiomer as peak 1 with retention time 4.44 minutes: ESHRMS m/z 364.0944 (M+H, $C_{16}H_{18}F_3O_4ClN$, Calc'd 364.0922). $^1$H NMR (acetone-d$_6$/400 MHz) 7.21 (s, 1H), 7.12 (s, 1H), 6.62 (s, 1H), 5.61 (q, 1H, J=7.0 Hz), 2.67 (m, 2H), 2.52 (s, 3H), 1.71 (m, 1H), 0.68 (m, 6H). $^{19}$F NMR (benzene-d$_6$/400 MHz; 6 eq. of (R)-(+)-(1-naphthyl)ethylamine) −77.86 (d, 3F, J=8.4 Hz, S-enantiomer), −78.05 (d, 3F, J=7.2 Hz, R-enantiomer).

EXAMPLE 608g

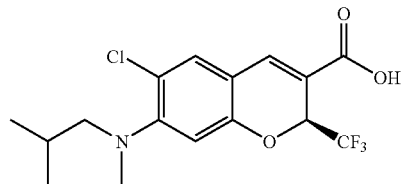

(2S)-6-chloro-7-[isobutyl(methyl)amino]-2-(trifluoromethyl)-2H-chromene-3-carboxylic acid A racemic mixture of the compound prepared in Example 8c was resolved by chiral chromatography using a ChiralPak AD column eluting with 10% isopropanol in heptane with 0.1% TFA and detecting at 280 nm to give S-enantiomer as peak 2 with retention time 9.24 minutes: ESHRMS m/z 364.0927 (M+H, $C_{16}H_{18}F_3O_4ClN$, Calc'd 364.0922). $^1$H NMR (acetone-$d_6$/400 MHz) 7.21 (s, 1H), 7.12 (s, 1H), 6.62 (s, 1H), 5.61 (q, 1H, J=7.0 Hz), 2.67 (m, 2H), 2.52 (s, 3H), 1.71 (m, 1H), 0.68 (m, 6H). $^{19}$F NMR (benzene-$d_6$/400 MHz; 6 eq. of (R)-(+)-(1-naphthyl)ethylamine) −77.86 (d, 3F, J=8.4 Hz, S-enantiomer), −78.05 (d, 3F, J=7.2 Hz, R-enantiomer).

EXAMPLE 608h

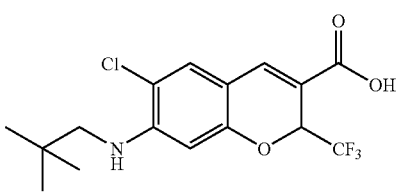

6-chloro-7-(neopentylamino)-2-(trifluoromethyl)-2H-chromene-3-carboxylic acid

Step 1. Preparation of ethyl 6-chloro-7-(neopentylamino)-2-(trifluoromethyl)-2H-chromene-3-carboxylate A mixture of ethyl 6-chloro-7-fluoro-2-(trifluoromethyl)-2H-chromene-3-carboxylate (Example 7a, Step 2) (0.5 g, 1.54 mmole) and 3,3-dimethylbutylamine (0.13 g, 1.54 mmole) was dissolved in anhydrous DMF (5 mL), warmed to 90° C. and treated with $K_2CO_3$ (0.25 g, 1.84 mmole). The mixture was maintained at 90° C. for 24 hrs, cooled to room temperature, filtered through celite and condensed to a viscous oil (0.6g, 98%). No further purification was performed: GCMS m/z 391.00 (M+).

Step 2. Preparation of 6-chloro-7-(neopentylamino)-2-(trifluoromethyl)-2H-chromene-3-carboxylic acid The 6-chloro-7-(neopentylamino)-2-(trifluoromethyl)-2H-chromene-3-carboxylic acid was prepared by a procedure similar to the method described in Example 602a, Step 2: ESHRMS m/z 362.0728 (M−H, $C_{16}H_{16}O_3F_3ClN$, Calc'd 362.0765). $^1$H NMR (CDCl$_3$/400 MHz) 7.71 (s, 1H), 7.13 (s, 1H), 6.28 (s, 1H), 5.62 (q, 1H, J=7.0 Hz), 2.98(m, 2H), 1.03 (s, 9H).

EXAMPLE 608i

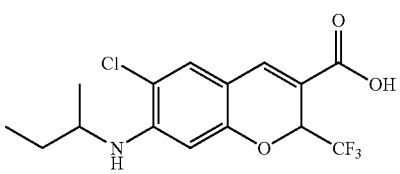

6-chloro-7-(sec-butylamino)-2-(trifluoromethyl)-2H-chromene-3-carboxylic acid

Step 1. Preparation of ethyl 6-chloro-7-(sec-butylamino)-2-(trifluoromethyl)-2H-chromene-3-carboxylate A mixture of ethyl 6-chloro-7-fluoro-2-(trifluoromethyl)-2H-chromene-3-carboxylate (Example 7a, Step 2) (0.5 g, 1.54 mmole) and 3,3-dimethylbutylamine (0.11 g, 1.54 mmole) was dissolved in anhydrous DMF (5 mL), warmed to 90° C. and treated with $K_2CO_3$ (0.25 g, 1.84 mmole). The mixture was maintained at 90° C. for 24 hrs, cooled to room temperature, filtered through celite and condensed to a viscous oil (0.58 g, 98%). No further purification was performed: GCMS m/z 377.00 (M+).

Step 2. Preparation of 6-chloro-7-(sec-butylamino)-2-(trifluoromethyl)-2H-chromene-3-carboxylic acid The 6-chloro-7-(sec-butylamino)-2-(trifluoromethyl)-2H-chromene-3-carboxylic acid was prepared by a procedure similar to the method described in Example 602a, Step 2: ESHRMS m/z 348.0624 (M−H, $C_{15}H_{14}O_3F_3ClN$, Calc'd 348.0609). $^1$H NMR (CDCl$_3$/400 MHz) 7.73 (s, 1H), 7.12 (s, 1H), 6.25 (s, 1H), 5.62 (q, 1H, J=7.0 Hz), 3.48 (m, 1H), 1.62 (m, 2H), 1.26 (m, 3H), 1.00 (m, 3H).

EXAMPLE 609a

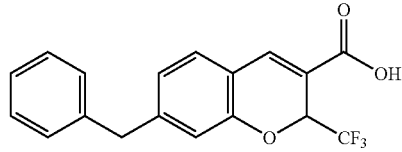

7-benzyl-2-(trifluoromethyl)-2H-chromene-3-carboxylic acid

The ester from Example 9k, Step 1 was added THF(7): EtOH(2): $H_2O$(1) followed by LiOH (1.5 eq) and heated to 40° C. for 4 h. The reaction was cooled to room temperature, concentrated in vacuo. Acidified with HCl conc to pH 1, filtered solid and subjected solid to preparative reverse phase chromatography to produce the title compound (95%): ESHRMS m/z 333.0751 (M−H, $C_{18}H_{12}O_3F_3$ Calc'd 333.0733). $^1$HNMR (DMSO-$d_6$/400 MHz), 13.13 (brs, 1H), 7.76 (s, 1H), 7.33 (d, 1H, J=7.5 Hz), 7.13-7.26 (m, 5H), 6.84-6.88 (m, 2H), 5.81 (q, 1H, J=7.1 Hz), 3.27 (s, 2H).

EXAMPLE 609b

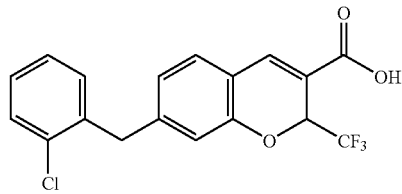

7-(2-chlorobenzyl)-2-(trifluoromethyl)-2H-chromene-3-carboxylic acid

The ester from Example 9n, Step 1 was hydrolyzed and purified to form the carboxylic acid using the same protocol as described in Example 609d (99%): ESHRMS m/z 367.0323 (M–H, $C_{18}H_{11}ClF_3O_3$ Calc'd 367.0343). $^1$HNMR (DMSO-$d_6$/400 MHz) 13.16 (brs, 1H), 7.78 (s, 1H), 7.23-7.43 (m, 5H), 6.83-6.85 (m, 1H), 6.80 (s, 1H), 5.83 (q, 1H, J=7.1 Hz), 4.04 (s, 2H).

EXAMPLE 609c

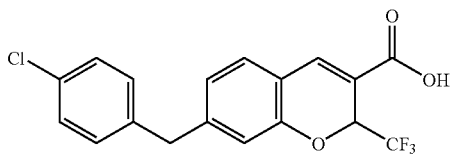

7-(4-chlorobenzyl)-2-(trifluoromethyl)-2H-chromene-3-carboxylic acid

The ester from Example 9o, Step 1 was hydrolyzed and purified to form the carboxylic acid using the same protocol as described in Example 609d (99%): ESHRMS m/z 367.0368 (M–H, $C_{18}H_{11}ClF_3O_3$ Calc'd 367.0343). $^1$HNMR (DMSO-$d_6$/400 MHz) 13.15 (brs, 1H), 7.76 (s, 1H), 7.29-7.40 (m, 3H), 7.21-7.24 (m, 2H), 6.87 (m, 2H), 5.82 (q, 1H, J=7.1 Hz), 3.88 (s, 2H).

EXAMPLE 609d

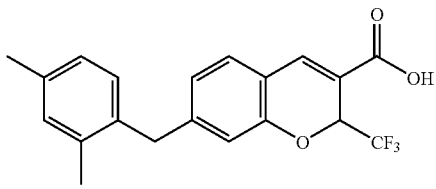

7-(2,4-dimethylbenzyl)-2-(trifluoromethyl)-2H-chromene-3-carboxylic acid

The ester from Example 9s, Step 5 was added THF(7):EtOH(2):H$_2$O(1) followed by LiOH (1.5 eq) and heated to 40° C. for 4 h. The reaction was cooled to room temperature, concentrated in vacuo. Acidified with HCl conc to pH 1, filtered solid and subjected solid to preparative reverse phase chromatography to produce the title compound (93%): ESHRMS m/z 361.1062 (M–H, $C_{20}H_{16}O_3F_3$ Calc'd 361.1046). $^1$HNMR (DMSO-$d_6$/400 MHz), 13.19 (s, 1H), 7.77 (s, 1H), 7.33 (d, 1H, J=7.6 Hz), 7.00 (m, 3H), 6.77 (d, 1H, J=7.7 Hz), 6.70 (s, 1H), 5.82 (q, 1H, J=7.1 Hz), 3.87 (s, 2H), 2.2 (s, 3H), 2.10 (s, 3H).

EXAMPLE 609e

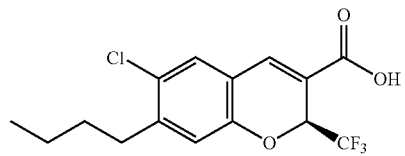

(2S)-7-butyl-6-chloro-2-(trifluoromethyl)-2H-chromene-3-carboxylic acid

A racemic mixture of the compound prepared in Example 9a, Step 5 was resolved by chiral separation using Chiralpak AD-spring column eluting with iPA/heptane/TFA=5/95/0.1 and detecting at 254 nm to give a S-enantiomer as peak 2 with retention time 7.83 min. ESHRMS m/z 333.0519 (M–H, $C_{15}H_{13}ClF_3O_3$ Calc'd 333.0500). $^1$HNMR (DMSO-$d_6$/400 MHz), 13.13 (s, 1H), 7.79 (s, 1H), 7.56 (s, 1H), 7.00 (s, 1H), 5.89 (q, 1H, J=7.1 Hz), 2.62 (t, 2H, J=7.5 Hz), 1.50 (m, 2H), 1.30 (m, 2H), 0.860 (t, 3H, J=7.3 Hz): $^{19}$FNMR (d6-benzene; 6 eq of (R)-(+)-1-(1-naphthyl)ethylamine) d −77.82 (d, 3F, J=6.8 Hz, R-enantiomer), −77.78 (d, 3F, J=6.8 Hz, S-enantiomer).

EXAMPLE 609f

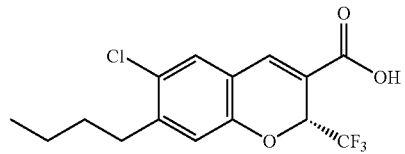

(2R)-7-butyl-6-chloro-2-(trifluoromethyl)-2H-chromene-3-carboxylic acid

A racemic mixture of the compound prepared in Example 9a, Step 5 was chirally resolved using the same protocol as for Example 609e, Step 1, R-enantiomer was identified as peak 1 with retention time 5.38 min: ESHRMS m/z 333.0489 (M–H, $C_{15}H_{13}ClF_3O_3$ Calc'd 333.0500). $^1$HNMR (DMSO-$d_6$/400 MHz), 13.13 (s, 1H), 7.79 (s, 1H), 7.56 (s, 1H), 7.00 (s, 1H), 5.89 (q, 1H, J=7.1 Hz), 2.62 (t, 2H, J=7.5 Hz), 1.50 (m, 2H), 1.30 (m, 2H), 0.860 (t, 3H, J=7.3 Hz). $^{19}$FNMR (d$^6$-benzene; 6 eq of (R)-(+)-1-(1-naphthyl)ethylamine) d −77.82 (d, 3F, J=6.8 Hz, R-enantiomer), −77.78 (d, 3F, J=6.8 Hz, S-enantiomer).

EXAMPLE 609g

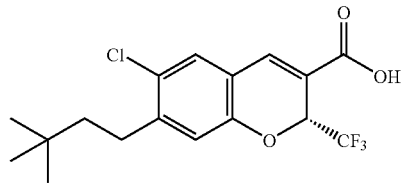

(2R)-6-chloro-7-(3,3-dimethylbutyl)-2-(trifluoromethyl)-2H-chromene-3-carboxylic acid A racemic mixture of the compound prepared in Example 9b, Step 3 was chirally resolved using the same protocol as for Example 609e, Step 1, R-enantiomer was identified as peak 1 with retention time 4.26 min: ESHRMS m/z 361.0797 (M–H, $C_{17}H_{17}ClF_3O_3$ Calc'd 361.0813). $^1$HNMR (DMSO-$d_6$/400 MHz) 13.23 (brs, 1H), 7.80 (s, 1H), 7.55 (s, 1H), 7.01 (s, 1H), 5.89 (q, 1H, J=7.1 Hz), 3.30 (m, 2H), 2.56-2.60 (m, 2H), 1.31-1.37 (m, 2H), 0.91 (s, 9H). $^{19}$FNMR (d6-benzene; 6 eq of (R)-(+)-1-(1-naphthyl)ethylamine) d–77.80 (d, 3F, J=6.8 Hz, R-enantiomer), –77.77 (d, 3F, J=6.8 Hz, S-enantiomer).

EXAMPLE 609h

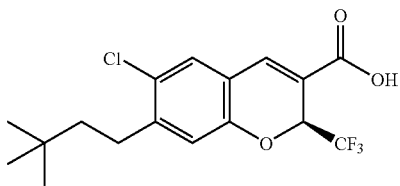

(2S)-6-chloro-7-(3,3-dimethylbutyl)-2-(trifluoromethyl)-2H-chromene-3-carboxylic acid A racemic mixture of the compound prepared in Example 9b, Step 3 was chirally resolved using the same protocol as for Example 609e, Step 1, S-enantiomer was identified as peak 2 with retention time 10.35 min: ESHRMS m/z 361.0848 (M–H, $C_{17}H_{17}ClF_3O_3$ Calc'd 361.0813). $^1$HNMR (DMSO-$d_6$/400 MHz) 13.23 (brs, 1H, 7.80 (s, 1H), 7.55 (s, 1H), 7.01 (s, 1H), 5.89 (q, 1H, J=7.1 Hz), 3.30 (m, 2H), 2.56-2.60 (m, 2H), 1.31-1.37 (m, 2H), 0.91 (s, 9H). $^{19}$FNMR (d6-benzene; 6 eq of (R)-(+)-1-(1-naphthyl)ethylamine) d–77.80 (d, 3F, J=6.8 Hz, R-enantiomer), –77.77 (d, 3F, J=6.8 Hz, S-enantiomer).

EXAMPLE 609i

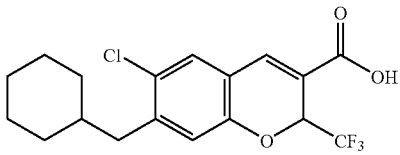

6-chloro-7-(cyclohexylmethyl)-2-(trifluoromethyl)-2H-chromene-3-carboxylic acid

Step 1. Preparation of ethyl 7-(cyclohexylmethyl)-2-(trifluoromethyl)-2H-chromene-3-carboxylate To a solution of the ester from Example 9a, Step 2 (3.0 g, 7.53 mmole) dissolved into THF (25 mL) was added Pd(dba)$_2$ (138 mg, 2 mole %), tfp (69 mg, 4 mole %) followed by the syringe addition of cyclohexylmethylzinc chloride (30 mL, 15 mmole). The reaction was heated to 65° C. for 6 hrs. The reaction was cooled to room temperature and poured into saturated aqueous ammonium chloride (200 mL), extracted with ethyl acetate (2×50 mL). The combined organic phases were washed with aqueous NaHCO$_3$ solution (2×50 mL), aqueous 1N HCl solution (2×50 mL), and brine (2×50 mL), dried over Na$_2$SO$_4$, filtered and concentrated in vacuo. The crude material was subjected to flash chromatography (Silica, 5% ethyl acetate/hexane). Desired fractions were collected and combined, removed solvent in vacuo producing the ethyl ester (2.10 g, 75%). This ester was of suitable purity to use without further purification: ESLRMS m/z 369.2 (M+H).

Step 2. Preparation of ethyl 6-chloro-7-(cyclohexylmethyl)-2-(trifluoromethyl)-2H-chromene-3-carboxylate The ester (Step 1) was chlorinated via a method similar to that described in Example 609m, Step 1 (85%). This ester was of suitable purity to use without further purification. ESLRMS m/z 403.1 (M+H).

Step 3. Preparation of 6-chloro-7-(cyclohexylmethyl)-2-(trifluoromethyl)-2H-chromene-3-carboxylic acid The ester (Step 2) was hydrolyzed and purified using the same protocol as described in Example 609d (99%): ESHRMS m/z 373.0832 (M–H, $C_{18}H_{17}ClF_3O_3$ Calc'd 373.0813). $^1$HNMR (DMSO-$d_6$/400 MHz), 13.28 (brs, 1H), 7.79 (s, 1H), 7.54 (s, 1H), 6.93 (s, 1H), 5.89 (q, 1H, J=7.1 Hz), 2.48-2.54 (m, 2H), 1.50-1.58 (m, 6H), 1.02-1.11 (m, 3H), 0.91-0.97 (m, 2H).

EXAMPLE 609j

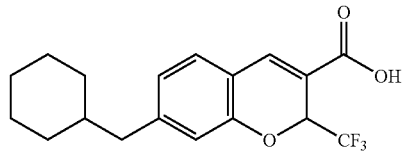

7-(cyclohexylmethyl)-2-(trifluoromethyl)-2H-chromene-3-carboxylic acid

The ester from Example 609i (Step 1) was hydrolyzed and purified using the same protocol as described in Example 609d (99%): ESHRMS m/z 339.1227 (M–H, $C_{18}H_{18}O_3F_3$ Calc'd 339.1203). $^1$HNMR (DMSO-$d_6$/400 MHz), 13.13 (s, 1H), 7.79 (s, 1H), 7.33 (d, 1H, J=7.7 Hz), 6.78-6.83 (m, 2H), 5.83 (q, 1H, J=7.1 Hz), 2.49 (m, 2H), 1.32-1.61 (m, 5H), 1.05-1.20 (m, 4H), 0.84-0.91 (m, 2H).

EXAMPLE 609k

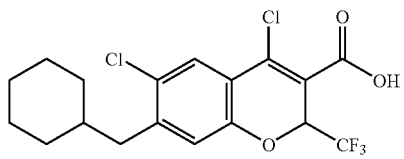

4,6-dichloro-7-(cyclohexylmethyl)-2-(trifluoromethyl)-2H-chromene-3-carboxylic acid Step 1. Preparation of ethyl 4,6-dichloro-7-(cyclohexylmethyl)-2-(trifluoromethyl)-2H-chromene-3-carboxylate The ester from Example 609i (Step 2) was further chlorinated following the same chlorination procedure as in Example 609m, Step 1 (34%). This ester was of suitable purity to use without further purification. ESLRMS m/z 437.1 (M+H).

Step 2. Preparation of 4,6-dichloro-7-(cyclohexylmethyl)-2-(trifluoromethyl)-2H-chromene-3-carboxylic acid The ester (Step 1) was hydrolyzed and purified using the same protocol as described in Example 609d (99%): ESHRMS m/z 407.0396 (M–H, $C_{18}H_{16}Cl_2F_3O_3$ Calc'd 407.0923). $^1$HNMR (DMSO-$d_6$/400 MHz), 13.13 (brs, 1H), 7.62 (s, 1H), 7.05 (s, 1H), 6.10 (q, 1H, J=7.1 Hz), 2.50-2.61 (m, 2H), 1.50-1.59 (m, 7H), 1.07-1.11 (m, 4H).

EXAMPLE 609l

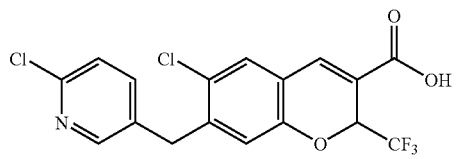

6-chloro-7-[(6-chloropyridin-3-yl)methyl]-2-(trifluoromethyl)-2H-chromene-3-carboxylic acid Step 1. Preparation of ethyl 7-[(6-chloropyridin-3-yl)methyl]-2-(trifluoromethyl)-2H-chromene-3-carboxylate The ethyl 7-[(6-chloropyridin-3-yl)methyl]-2-(trifluoromethyl)-2H-chromene-3-carboxylate was prepared and purified via a method similar to that described in Example 609i, Step 1 with the appropriate substitution of 2-chloro-5-methylpyridinezinc bromide (85%). ESLRMS m/z 398.1 (M+H).

Step 2. Preparation of ethyl 6-chloro-7-[(6-chloropyridin-3-yl)methyl]-2-(trifluoromethyl)-2H-chromene-3-carboxylate The ester (Step 1) was chlorinated using the same protocol as described in Example 609m, Step 1 (93%). This ester was of suitable purity to use without further purification: ESLRMS m/z 432.0 (M+H).

Step 3. Preparation of 6-chloro-7-[(6-chloropyridin-3-yl)methyl]-2-(trifluoromethyl)-2H-chromene-3-carboxylic acid The ester (Step 2) was hydrolyzed and purified using the same protocol as described in Example 609d (99%): ESHRMS m/z 401.9936 (M–H, $C_{17}H_9Cl_2O_3F_3N$ Calc'd 401.9906). $^1$HNMR (DMSO-$d_6$/400 MHz), 13.13 (s, 1H), 8.29 (d, 1H, J=2.1 Hz), 7.81 (s, 1H), 7.62-7.65 (m, 2H), 7.43 (d, 1H, J=8.1 Hz), 7.12 (s, 1H), 5.89 (q, 1H, J=7.1 Hz), 4.04 (s, 2H).

EXAMPLE 609m

6-chloro-7-(3-methoxybenzyl)-2-(trifluoromethyl)-2H-chromene-3-carboxylic acid

Step 1. Preparation of ethyl 6-chloro-7-(3-methoxybenzyl)-2-(trifluoromethyl)-2H-chromene-3-carboxylate The ester from Example 9w (Step 1) (1.00 g, 234 mmole) was dissolved into acetic acid (25 mL). Chlorine gas was bubbled through this solution for 15 min. The solution was allowed to stand at room temperature for 30 minutes. The reaction was cooled to room temperature, poured into $H_2O$ (150 mL), and extracted with ethyl acetate (2×150 mL). The combined organic phases were washed with aqueous $NaHCO_3$ solution (2×50 mL), aqueous 3N HCl solution (2×50 mL), and brine (2×50 mL), dried over $Na_2SO_4$, filtered and concentrated in vacuo producing 7-(2-chloro-3-methoxybenzyl)-2-(trifluoromethyl)-2H-chromene-3-carboxylic acid (42%), 7-(4-chloro-3-methoxybenzyl)-2-(trifluoromethyl)-2H-chromene-3-carboxylic acid (35%) and the title compound (158 mg, 17%) as an amber oil. This ester was of suitable purity to use without further purification: ESLRMS m/z 427.0 (M+H).

Step 2. Preparation of 6-chloro-7-(3-methoxybenzal)-2-(trifluoromethyl)-2H-chromene-3-carboxylic acid The ester (Step 1) was hydrolyzed and purified to form the carboxylic acid using the same protocol as described in Example 609d (99%): ESHRMS m/z 397.0460 (M–H, $C_{19}H_{13}ClF_3O_4$ Calc'd 397.0449). $^1$HNMR (DMSO-$d_6$/400 MHz) 13.16 (brs, 1H), 7.79 (s, 1H), 7.6 (s, 1H), 7.17-7.21 (m, 1H), 6.98 (s, 1H), 6.73-6.76 (m, 3H), 5.89 (q, 1H, J=7.1 Hz), 3.97 (s, 2H), 3.68 (s, 3H).

EXAMPLE 609n

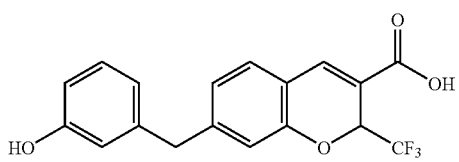

7-(3-hydroxybenzyl)-2-(trifluoromethyl)-2H-chromene-3-carboxylic acid

Step 1. Preparation of methyl 7-(3-hydroxybenzyl)-2-(trifluoromethyl)-2H-chromene-3-carboxylate To a chilled (−20° C.) stirred solution of the ester Example 9w (Step 1) (152 mg, 0.500 mmole) was added $BBr_3$ 1M in $CH_2Cl_2$ (1.60 mL, 1.67 mmole). The resulting solution was allowed to warm to room temperature and stir overnight. The reaction was cooled (−20° C.) and methanol was added via syringe. Solvent was removed in vacuo and the crude material was subjected to preparative reverse phase chromatography to produce the title compound (146 mg, 83%): ESLRMS m/z 365.0 (M+H).

Step 2. Preparation of 7-(3-hydroxybenzyl)-2-(trifluoromethyl)-2H-chromene-3-carboxylic acid The ester (step 1) was hydrolyzed and purified using the same method as described in 609d (97%): ESHRMS m/z 349.0683 (M−H, $C_{18}H_{12}F_3O_4$ Calc'd 349.0682). $^1$HNMR (DMSO-$d_6$/400 MHz) 13.16 (brs, 1H), 9.27 (brs, 1H), 7.78 (s, 1H), 7.35 (d, 1H, J=7.6 Hz), 7.04 (t, 1H, J=7.6 Hz), 6.84-6.88 (m, 2H), 6.55-6.63 (m, 3H), 5.83 (q, 1H, J=7.1 Hz), 3.80 (s, 2H).

EXAMPLE 609o

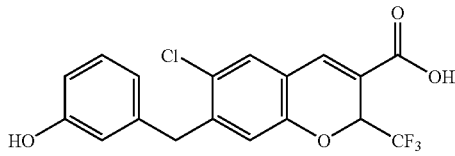

6-chloro-7-(3-hydroxybenzyl)-2-(trifluoromethyl)-2H-chromene-3-carboxylic acid

Step 1. Preparation of methyl 6-chloro-7-(3-hydroxybenzyl)-2-(trifluoromethyl)-2H-chromene-3-carboxylate The acid from Example 609m, Step 2 was subjected to the same protocol as described in 609n, Step 1 (77%): ESLRMS m/z 399.1 (M+H)

Step 2. 6-chloro-7-(3-hydroxybenzyl)-2-(trifluoromethyl)-2H-chromene-3-carboxylic acid The ester (Step 1) was hydrolyzed and purified using the same method as described in 609d (99%): ESHRMS m/z 383.0321 (M−H, $C_{18}H_{11}ClF_3O_4$ Calc'd 383.0292). $^1$HNMR (DMSO-$d_6$/400 MHz) 13.16 (brs, 1H), 9.29 (brs, 1H), 7.80 (s, 1H), 7.60 (s, 1H), 7.05 (t, 1H, J=7.7 Hz), 6.96 (s, 1H), 6.54-6.61 (m, 3H), 5.89 (q, 1H, J=7.1 Hz), 3.91 (s, 2H).

EXAMPLE 609p

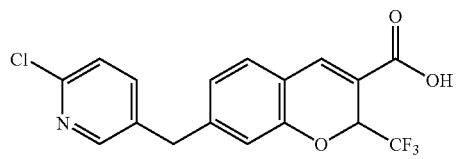

7-[(6-chloropyridin-3-yl)methyl]-2-(trifluoromethyl)-2H-chromene-3-carboxylic acid The ester in Example 6091 (Step 1) was hydrolyzed and purified using the same protocol as described in Example 609d (99%): ESHRMS m/z 368.0302 (M−H, $C_{17}H_{10}ClF_3NO_3$ Calc'd 368.0296). $^1$HNMR (DMSO-$d_6$/400 MHz), 13.16 (brs, 1H), 8.83 (d, 1H, J=2.2 Hz), 7.79 (s, 1H), 7.69-7.79 (m, 1H), 7.37-7.42 (m, 2H), 6.91-6.93 (m, 2H), 5.89 (q, 1H, J=7.1 Hz), 3.94 (m, 2H).

EXAMPLE 609r

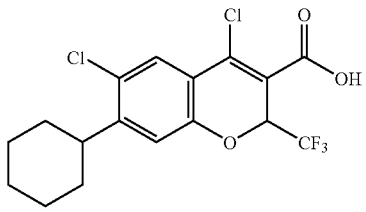

4,6-dichloro-7-cyclohexyl-2-(trifluoromethyl)-2H-chromene-3-carboxylic acid

Step 1. Preparation of ethyl 7-cyclohexyl-2-(trifluoromethyl)-2H-chromene-3-carboxylate The ethyl 7-cyclohexyl-2-(trifluoromethyl)-2H-chromene-3-carboxylate was prepared and purified via a method similar to that described in Example 609i, Step 1 with the appropriate substitution of cyclohexylzinc bromide (67%): ESLRMS m/z 355.1 (M+H).

Step 2 Preparation of ethyl 4,6-dichloro-7-cyclohexyl-2-(trifluoromethyl)-2H-chromene-3-carboxylate The ester (Step 1) was chlorinated using the same protocol as described in Example 609m, Step 1 (91%). This ester was of suitable purity to use without further purification: ESLRMS m/z 423.0 (M+H).

Step 3. Preparation of 4,6-dichloro-7-cyclohexyl-2-(trifluoromethyl)-2H-chromene-3-carboxylic acid The ester (Step 2) was hydrolyzed and purified using the same protocol as described in Example 609d (99%): ESHRMS m/z 393.0258 (M–H, $C_{17}H_{14}Cl_2F_3O_3$ Calc'd 393.0267). $^1$HNMR (DMSO-$d_6$/400 MHz), 13.13 (brs, 1H), 7.63 (s, 1H), 7.07 (s, 1H), 6.10 (q, 1H, J=7.1 Hz), 2.85 (m, 1H), 1.65-1.78 (m, 4H), 1.20-1.43 (m, 6H).

EXAMPLE 609s

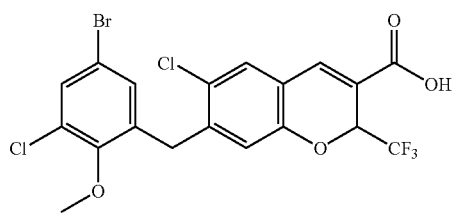

7-(5-bromo-3-chloro-2-methoxybenzyl)-6-chloro-2-(trifluoromethyl)-2H-chromene-3-carboxylic acid

Step 1. Preparation of ethyl 7-(5-bromo-2-methoxybenzyl)-2-(trifluoromethyl)-2H-chromene-3-carboxylate The ethyl 7-(5-bromo-2-methoxybenzyl)-2-(trifluoromethyl)-2H-chromene-3-carboxylate was prepared and purified using a method similar to that described in Example 609i, Step 1 with the appropriate substitution of 2-methoxy-5-bromobenzylzinc bromide (71%): ESLRMS m/z 471.0 (M+H).

Step 2. Preparation of ethyl 7-(5-bromo-3-chloro-2-methoxybenzyl)-6-chloro-2-(trifluoromethyl)-2H-chromene-3-carboxylate The ester (Step 1) was chlorinated using the same protocol as described in Example 609m, Step 1 (83%). This ester was of suitable purity to use without further purification: ESLRMS m/z 538.9 (M+H).

Step 3. Preparation of 7-(5-bromo-3-chloro-2-methoxybenzyl)-6-chloro-2-(trifluoromethyl)-2H-chromene-3-carboxylic acid The ester (Step 2) was hydrolyzed and purified using the same protocol as described in Example 609d (93%): ESHRMS m/z 508.9182 (M–H, $C_{19}H_{14}Cl_2F_3O_4$ Calc'd 508.9164). $^1$HNMR (DMSO-$d_6$/400 MHz), 13.16 (brs, 1H), 7.84 (s, 1H), 7.64-7.65 (m, 2H), 7.13 (m, 2H), 6.88 (m, 1H), 5.89 (q, 1H, J=7.1 Hz), 4.04 (m, 2H), 3.66 (s, 3H).

EXAMPLE 609t

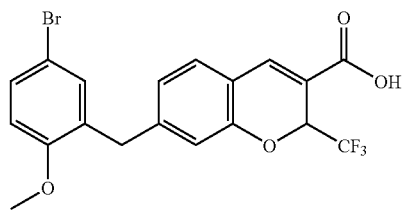

7-(5-bromo-2-methoxybenzyl)-2-(trifluoromethyl)-2H-chromene-3-carboxylic acid

This ester from Example 609s, Step 1 was hydrolyzed and purified using the same protocol as described in Example 609d (91%): ESHRMS m/z 440.9972 (M–H, $C_{19}H_3BrF_3O_4$ Calc'd 440.9944). $^1$HNMR (DMSO-$d_6$/400 MHz), 13.13 (brs, 1H), 7.78 (s, 1H), 7.31-7.36 (m, 3H), 6.82-6.93 (m, 3H), 5.89 (q, 1H, J=7.1 Hz), 3.84 (s, 2H), 3.73 (s, 3H).

EXAMPLE 609u

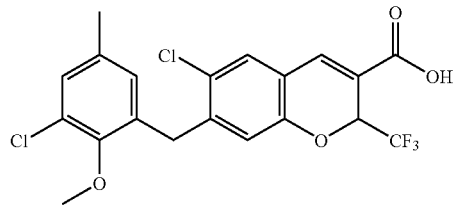

6-chloro-7-(3-chloro-2-methoxy-5-methylbenzyl)-2-(trifluoromethyl)-2H-chromene-3-carboxylic acid

Step 1. Preparation of ethyl 6-chloro-7-(3-chloro-2-methoxy-5-methylbenzml)-2-(trifluoromethyl)-2H-chromene-3-carboxylate The ester from Example 609s, Step 2 was subjected to the same protocol as described in 61 If, Step 1 (87%). The ester was of suitable purity to use in the next Step: ESLRMS m/z 475.0 (M+H).

Step 2. Preparation of 6-chloro-7-(3-chloro-2-methoxy-5-methylbenzyl)-2-(trifluoromethyl)-2H-chromene-3-carboxylic acid The ester (Step 1) was hydrolyzed and purified using the same protocol as described in Example 609d (92%): ESHRMS m/z 445.0246 (M–H, $C_{20}H_{14}Cl_2F_3O_4$ Calc'd 445.0216). $^1$HNMR (DMSO-$d_6$/400 MHz), 13.13 (brs, 1H), 7.83 (s, 1H), 7.64 (s, 1H), 7.18 (d, 1H, J=2 Hz), 6.78 (m, 2H), 5.89 (q, 1H, J=7.1 Hz), 3.60 (s, 2H), 2.17 (m, 3H).

EXAMPLE 609v

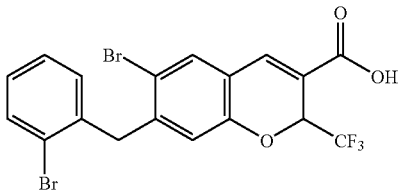

6-bromo-7-(2-bromobenzyl)-2-(trifluoromethyl)-2H-chromene-3-carboxylic acid

Step 1. Preparation of ethyl 7-(2-bromobenzyl)-2-(trifluoromethyl)-2H-chromene-3-carboxylate This compound was prepared and purified using a method similar to that described in Example 609i, Step 1 with the appropriate substitution of 2-bromobenzylzinc bromide producing the ester (87%): ESLRMS m/z 441.0 (M+H).

Step 2. Preparation of ethyl 6-bromo-7-(2-bromobenzyl)-2-(trifluoromethyl)-2H-chromene-3-carboxylate The ester (Step 1) was dissolved in acetic acid (glacial) (20 mL), $Br_2$ was added and the solution stirred at room temperature for 1 h. The reaction was concentrated in vacuo. Water (50 mL) was added to the residue then the reaction was extracted with Ethyl Acetate (2×50 mL). The organic layers were combined and washed with brine (2×50 mL), dried over $Na_2SO_4$, filtered and concentrated in vacuo producing the Bromo ester (88%). This ester was of suitable purity to use without further purification. ESLRMS m/z 518.9 (M+H).

Step 3. Preparation of 6-bromo-7-(2-bromobenzyl)-2-(trifluoromethyl)-2H-chromene-3-carboxylic acid The ester (Step 2) was hydrolyzed and purified using the same protocol as described in Example 609d (93%): ESHRMS m/z 488.9010 (M–H, $C_{18}H_{10}Br_2F_3O_3$ Calc'd 488.8943). $^1$HNMR (DMSO-$d_6$/400 MHz), 13.13 (brs, 1H), 7.81 (s, 1H), 7.63-7.65 (m, 1H), 7.05-7.33 (m, 4H), 6.60 (s, 1H), 5.89 (q, 1H, J=7.1 Hz), 4.08 (s, 2H).

EXAMPLE 609w

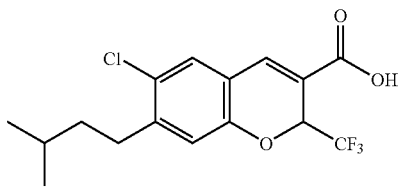

6-chloro-7-(3-methylbutyl)-2-(trifluoromethyl)-2H-chromene-3-carboxylic acid

Step 1. Preparation of ethyl 7-(3-methylbutyl)-2-(trifluoromethyl)-2H-chromene-3-carboxylate The ester from Example 9a, Step 2 was coupled and using a similar protocol as described in Example 611d, Step 1 using the appropriate substitution of 3-methylbut-1-ene (77%): ESLRMS m/z 343.1 (M+H).

Step 2. Preparation of ethyl 6-chloro-7-(3-methylbutyl)-2-(trifluoromethyl)-2H-chromene-3-carboxylate The ester (Step 1) was chlorinated using the same protocol as described in Example 609m, Step 1 (91%). This ester was of suitable purity to use without further purification: ESLRMS m/z 377.1 (M+H).

Step 3. Preparation of 6-chloro-7-(3-methylbutyl)-2-(trifluoromethyl)-2H-chromene-3-carboxylic acid The ester (Step 2) was hydrolyzed and purified using the same protocol as described in Example 609d (95%): ESHRMS m/z 347.0685 (M–H, $C_{16}H_{15}ClF_3O_3$ Calc'd 347.0656). $^1$HNMR (DMSO-$d_6$/400 MHz), 13.13 (brs, 1H), 7.81 (s, 1H), 7.56 (s, 1H), 7.00 (s, 1H), 5.89 (q, 1H, J=7.1 Hz), 2.47-2.64 (m, 2H), 1.52-1.54 (m, 2H), 1.37-1.41 (m, 3H), 0.87-0.89 (m, 6H). 7.00 (s, 1 H), 5.89 (q, 1H, J=7.1 Hz), 2.47-2.64 (m, 2H), 1.52-1.54 (m, 2H), 1.37-1.41 (m, 3H), 0.87-0.89 (m, 6H).

EXAMPLE 609x

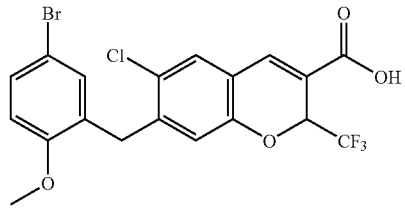

7-(5-bromo-2-methoxybenzyl)-6-c hlo ro-2-(trifluor methyl)-2H-chromene-3-carboxylic acid Step 1. Preparation of ethyl 6-chloro-7-iodo-2-(trifluoromethyl)-2H-chromene-3-carboxylate The ester from Example 9a, Step 2 was chlorinated using the same protocol as described in Example 609m, Step 1 (81%). This ester was of suitable purity to use without further purification: ESLRMS m/z 432.9 (M+H).

Step 2. Preparation of ethyl 7-(5-bromo-2-methoxyberzyl)-6-chloro-2-(trifluoromethyl)-2H-chromene-3-carboxylate The ester (Step 1) was coupled and purified via a method similar to that described in Example 609i, Step 1 with the appropriate substitution of 2-chloro-5-methylpyridinezinc bromide (89%): ESLRMS m/z 504.9 (M+H).

Step 3. Preparation of 7-(5-bromo-2-methoxybenzal)-6-chloro-2-(trifluoromethyl)-2H-chromene-3-carboxylic acid The ester (Step 2) was hydrolyzed and purified using the same protocol as described in Example 609d (96%): ESHRMS m/z 474.9587 (M–H, $C_{19}H_{12}BrClF_3O_4$ Calc'd 474.9554). $^1$HNMR (DMSO-$d_6$/400 MHz), 13.13 (brs, 1H), 7.83 (s, 1H), 7.40 (m, 1H), 7.08 (d, 1H, J=2.4 Hz), 6.96 (d, 1H, J=8.7 Hz), 6.76 (s, 1H), 5.89 (q, 1H, J=7.1 Hz), 3.93 (m, 2H), 3.73 (s, 3H).

EXAMPLE 610

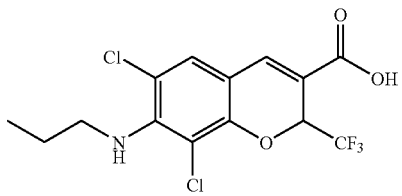

6,8-dichloro-7-(propylamino)-2-(trifluoromethyl)-2H-chromene-3-carboxylic acid

Step 1. Preparation of ethyl 6,8-dichloro-7-(propylamino)-2-(trifluoromethyl)-2H-chromene-3-carboxylate The ethyl 6-chloro-7-[(cyclopropylmethyl)(propyl)amino]-2-(trifluoromethyl)-2H-chromene-3-carboxylate (Example 8g) (0.45 g, 1.07 mmole) was dissolved in acetic acid (50 mL). Sodium acetate (0.7 g, 8.56 mmole) was added and let dissolve. Chlorine gas was bubbled through the solution for 3 minutes until a white precipitate began to form. The solution was stirred for an additional 3 hours. Zinc powder (0.35 g, 5.35 mmole) was added and the solution was stirred for 30 minutes. The reaction was filtered through a plug of celite and condensed to a yellow suspension. The suspension was partitioned between ether and water. The organic phase was washed with brine, dried over $MgSO_4$, filtered and concentrated in vacuo to give a yellow oil (0.4 g, 94%).

No further purification was performed: GCMS m/z 398.00 (M+).

Step 2. Preparation 6,8-dichloro-7-(propylamino)-2-(trifluoromethyl)-2H-chromene-3-carboxylic acid The 6,8-dichloro-7-(propylamino)-2-(trifluoromethyl)-2H-chromene-3-carboxylic acid was prepared by a procedure similar to the method described in Example 602a, Step 2: ESHRMS m/z 368.0064 (M–H, $C_{14}H_{11}O_3F_3Cl_2N$, Calc'd 368.0063). $^1H$ NMR (acetone-$d_6$/400 MHz) 7.80 (s, 1H), 7.43 (s, 1H), 5.90 (q, 1H, J=7.0 Hz), 3.57 (m, 2H), 1.61 (m, 2H), 0.93 (m, 3H).

EXAMPLE 611a

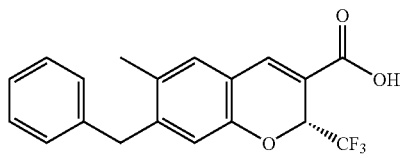

(2R)-7-benzyl-6-methyl-2-(trifluoromethyl)-2H-chromene-3-carboxylic acid

A racemic mixture of the compound prepared in Example 42a, Step 2 was chirally resolved using the same protocol as for Example 609e, Step 1, R-enantiomer was identified as peak 1 with retention time 5.45 min: ESHRMS m/z 347.0875 (M–H, $C_{19}H_{14}F_3O_3$ Calc'd 347.0890). $^1HNMR$ (DMSO-$d_6$/400 MHz) 13.19 (brs, 1H), 7.74 (s, 1H), 7.11-7.27 (m, 6H), 6.74 (q, 1H, J=7.1 Hz), 3.91 (s, 2H), 2.11 (s, 3H). R-isomer: $^{19}FNMR$ ($d^6$-benzene; 6 eq of (R)-(+)-1-(1-naphthyl)ethylamine) d –77.76 (d, 3F, J=6.8 Hz, R-enantiomer), –77.74 (d, 3F, J=6.8 Hz, S-enantiomer).

EXAMPLE 611b

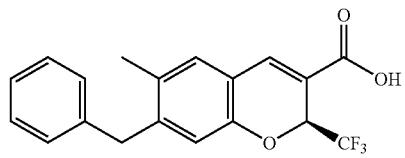

(2S)-7-benzyl-6-methyl-2-(trifluoromethyl)-2H-chromene-3-carboxylic acid

A racemic mixture of the compound prepared in Example 42a, Step 2 was chirally resolved using the same protocol as for Example 609e, Step 1, identified as peak 2 with retention time 10.00 min. ESHRMS m/z 347.0894 (M–H, $C_{19}H_{14}F_3O_3$ Calc'd 347.0890). $^1HNMR$ (DMSO-$d_6$/400 MHz) 13.19 (brs, 1H), 7.74 (s, 1H), 7.11-7.27 (m, 7H), 6.74 (q, 1H, J=7.1 Hz), 3.91 (s, 2H), 2.11 (s, 3H). S-isomer: $^{19}F$ NMR (d6-benzene; 6 eq of (R)-(+)-1-(1-naphthyl)ethylamine) d –77.76 (d, 3F, J=6.8 Hz, R-enantiomer), –77.74 (d, 3F, J=6.8 Hz, S-enantiomer).

EXAMPLE 611c

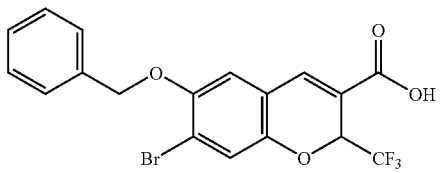

6-(benzyloxy)-7-bromo-2-(trifluoromethyl)-2H-chromene-3-carboxylic acid

Step 1. Preparation of 4-(benzyloxy)-3-bromophenol

To a mixture of MeOH (50 mL) and $K_2CO_3$ (49.36 g, 357 mmole) at r.t was dripped commercially available 2-bromobenzene-1,4-diol (15 g, 79 mmole) in MeOH (25 mL), followed by the syringe addition of benzyl bromide (14.93 g, 10.38 mL). The resulting mixture was refluxed for 8 hours. The reaction was cooled to RT and poured into saturated aqueous ammonium chloride (500 mL) and extracted with ethyl acetate (2×150). The combined organic phases were washed with aqueous $NaHCO_3$ solution (2×150 mL), aqueous 1N HCl solution (2×150 mL), and brine (2×150 mL), dried over $Na_2SO_4$, filtered and concentrated in vacuo. The crude material was subjected to flash chromatography (Silica, 10% Ethyl acetate/Hexane). ESLRMS m/z 280.9 (M+H).

Step 2. Preparation of 5-(benzyloxy)-4-bromo-2-hydroxybenzaldehyde

To a chilled solution of phenol (Step 1) (4.7 g, 16.8 mmole) in ACN was added MgCl$_2$ (1.92 g, 20 mmole) portion-wise while maintaining the temperature below 10° C., followed by paraformaldehyde (2.52 g, 84 mmole) and TEA (9.5 mL, 67 mmole) producing a 15° C. exotherm. The mixture was heated to 72° C. for 2 hrs. The reaction was cooled to room temperature and poured into saturated aqueous ammonium chloride (500 mL), extracted with ethyl acetate (2×150 mL). The combined organic phases were washed with aqueous NaHCO$_3$ solution (2×150 mL), aqueous 1N HCl solution (2×150 mL), and brine (2×150 mL), dried over Na$_2$SO$_4$, filtered and concentrated in vacuo. The crude material was subjected to flash chromatography (Silica, 5% ethyl acetate/hexane). ESLRMS m/z 306.9 (M+H).

Step 3. Preparation of ethyl 6-(benzyloxy)-7-bromo-2-(trifluoromethyl)-2H-chromene-3-carboxylate To a solution of aldehyde (Step 2) (1.80 g, 5.86 mmole) in DMF (50 mL) was added, potassium carbonate (1.21 g, 8.79 mmole) and ethyl 4,4,4-trifluorocrotonate (1.97 g, 11.7 mmole). The mixture was heated to 65° C. for 4 hrs. The reaction was cooled to room temperature, poured into H$_2$O (150 mL), and extracted with ethyl acetate (2×150 mL). The combined organic phases were washed with aqueous NaHCO$_3$ solution (2×50 mL), aqueous 3 N HCl solution (2×50 mL), and brine (2×50 mL), dried over Na$_2$SO$_4$, filtered, and concentrated in vacuo producing the ethyl ester (2.4 g, 89%). ESLRMS m/z 457.0 (M+H).

Step 4. Preparation of 6-(benzaloxy)-7-bromo-2-(trifluoromethyl)-2H-chromene-3-carboxylic acid The ester (Step 3) was hydrolyzed and purified using the same method as described in 609d (99%). ESHRMS m/z 426.9835 (M–H, C$_{18}$H$_{11}$BrF$_3$O$_4$ Calc'd 426.9787). $^1$HNMR (DMSO-d$_6$/400 MHz), 13.13 (s, 1H), 7.79 (s, 1H), 7.32–7.46 (m, 7H), 5.89 (q, 1H, J=7.1 Hz), 5.11 (s, 2H).

EXAMPLE 611d

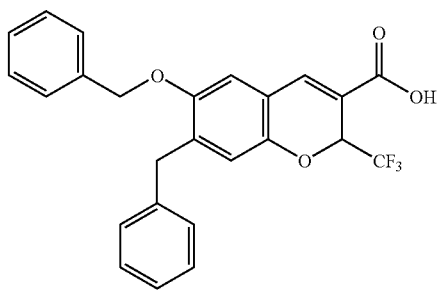

7-benzyl-6-(benzyloxy)-2-(trifluoromethyl)-2H-chromene-3-carboxylic acid

Step 1. Preparation of ethyl 7-benzyl-6-(benzyloxy)-2-(trifluoromethyl)-2H-chromene-3-carboxylate To a solution of β-benzyl 9-BBN (11.58 mL, 5.78 mmole) in THF (20 mL) was added the ester from Example 611c, Step 3 (1.32 mL, 2.89 mmole) dissolved into THF (25 mL), and the resulting solution stirred at room temperature for 15 min. To this solution was added the Pd(dppf)Cl.CH$_2$Cl$_2$ (0.118 g, 5 mole %)m and K$_3$PO$_{4(aq)}$ (3.18 mL, 6.36 mmole). The reaction was heated to 60° C. for 4 hrs. The reaction was cooled to room temperature, poured into H$_2$O (150 mL), and extracted with ethyl acetate (2×150 mL). The combined organic phases were washed with aqueous NaHCO$_3$ solution (2×50 mL), aqueous 3N HCl solution (2×50 mL), and brine (2×50 mL), dried over Na$_2$SO$_4$, filtered and concentrated in vacuo. The crude material was subjected to flash chromatography (Silica, 2% ethyl acetate/hexane). Desired fractions were collected and combined, removed solvent in vacuo producing the ethyl ester (1.22 g, 90%). ESLRMS m/z 469.1 (M+H).

Step 2. Preparation of 7-benzyl-6-(benzyloxy)-2-(trifluoromethyl)-2H-chromene-3-carboxylic acid The ester (Step 1) was hydrolyzed and purified using the same protocol as described in Example 609d (99%). ESLRMS m/z 439.1127 (M–H, C$_{25}$H$_{18}$F$_3$O$_4$,Calc'd 439.1152). $^1$HNMR (DMSO-d$_6$/400 MHz), 13.13 (s, 1H), 7.76 (s, 1H), 7.14–7.35 (m, 11H), 6.82 (s, 1H), 5.80 (q, 1H, J=7.1 Hz), 5.03 (s, 2H), 3.8 (m, 2H).

EXAMPLE 611e

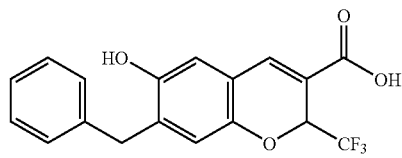

7-benzyl-6-hydroxy-2-(trifluoromethyl)-2H-chromene-3-carboxylic acid

Step 1. Preparation of methyl 7-benzyl-6-hydroxy-2-(trifluoromethyl)-2H-chromene-3-carboxylate The ester from Example 61 Id (Step 1) was deprotected using the same protocol as described in Example 609n (98%). ESLRMS m/z 365.0 M+H

Step 2. Preparation of 7-benzal-6-hydroxy-2-(trifluoromethyl)-2H-chromene-3-carboxylic acid The ester (Step 1) was hydrolyzed and purified using the same protocol as described in Example 609d (99%). ESHRMS m/z 349.0641 (M–H, C$_{18}$H$_{12}$F$_3$O$_4$ Calc'd 349.0682). $^1$HNMR (DMSO-d$_6$/400 MHz) 13.16 (brs, 1H), 9.41 (s, 1H), 7.73 (s, 1H),

EXAMPLE 611f

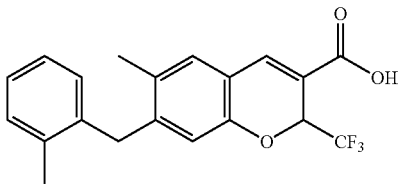

6-methyl-7-(2-methylbenzyl)-2-(trifluoromethyl)-2H-chromene-3-carboxylic acid

Step 1. Preparation of ethyl 6-methyl-7-(2-methylbenzyl)-2-(trifluoromethyl)-2H-chromene-3-carboxylate The ester from Example 609v, Step 2 (1.0 g, 1.92 mmole) was added to a stirred solution of DMF (15 mL). Trimethylboroxane (0.672 mL, 4.80 mmole) was added along with Pd(PPh$_3$)$_4$ (0.222 g, 10 mole %) followed by K$_2$CO$_3$. the solution was heated to 100° C. for 8 h. The solution was poured into water (50 mL), extracted with Ethyl Acetate (2×50 mL), the organic layers were combined and washed with 1N HCl (2×50 mL) followed by brine (2×50 mL). The organic layer was dried over Na$_2$SO$_4$, filtered and concentrated in vacuo to produce the ester (90%). The ester was used as is in the next step. ESLRMS m/z 391.1 (M+H).

Step 2. Preparation of 6-methyl-7-(2-methylbenzyl)-2-(trifluoromethyl)-2H-chromene-3-carboxylic acid The ester (Step 1) was hydrolyzed and purified using the same protocol as described in Example 609d (94%). ESHRMS m/z 361.1074 (M−H, C$_{20}$H$_{16}$F$_3$O$_3$ Calc'd 361.1046). $^1$HNMR (DMSO-d$_6$/400 MHz), 13.13 (brs, 1H), 7.74 (s, 1H), 7.24 (s, 1H), 7.06-7.17 (m, 3H), 6.85 (d, 1H, J=7.7 Hz), 6.37 (s, 1H), 5.74 (q, 1H, J=7.1 Hz), 3.85 (s, 2H), 2.45 (s, 3H), 2.12 (s, 3H).

EXAMPLE 611g

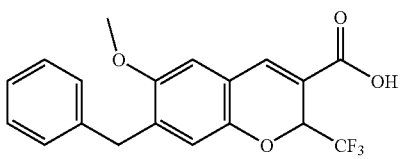

7-benzyl-6-methoxy-2-(trifluoromethyl)-2H-chromene-3-carboxylic acid

Step 1. Preparation of methyl 7-benzyl-6-methoxy-2-(trifluoromethyl)-2H-chromene-3-carboxylate Iodomethane (106 mg, 0.684 mmole), was dripped into a stirred solution of DMF (5mL) containing the acid from 611e, Step 2 (80 mg, 0.228 mmole) and K$_2$CO$_3$ (0.0946 mg, 0.68 mmole). The mixture was heated to reflux for 8 hours. The reaction was cooled to room temperature and poured into 3N HCl (50 mL) extracted with ethyl acetate. The combined organic phases were washed with brine (2×150 mL), dried over Na$_2$SO$_4$, filtered and concentrated in vacuo. The crude material was subjected to flash chromatography (Silica, 5% ethyl acetate/hexane). This compound was of suitable purity to use without further purification. ESLRMS 379.1 (M+H).

Step 2. Preparation of 7-benzyl-6-methoxy-2-(trifluoromethyl)-2H-chromene-3-carboxylic acid The ester (Step 1) was hydrolyzed and purified using the same protocol as described in Example 609d (99%). ESHRMS m/z 363.0857(M−H, C$_{19}$H$_{14}$F$_3$O$_4$ Calc'd 363.0839). $^1$HNMR (DMSO-d$_6$/400 MHz), 13.13 (brs, 1H), 7.78 (s, 1H), 7.11-7.26 (m, 6H), 6.75 (s, 1H), 5.89 (q, 1H, J=7.1 Hz), 3.90 (s, 2H), 3.70 (s, 3H).

EXAMPLE 611h

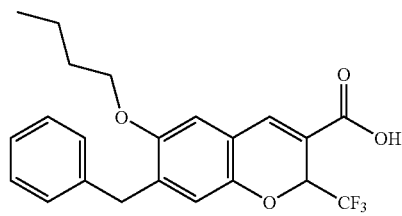

7-benzyl-6-butoxy-2-(trifluoromethyl)-2H-chromene-3-carboxylic acid

Step 1. Preparation of butyl 7-benzyl-6-butoxy-2-(trifluoromethyl)-2H-chromene-3-carboxylate The acid from Example 61 le, Step 2 was subjected to a similar protocol as described in Example 611g, Step 1 with the appropriate substitution 1-iodobutane of ESLRMS 463.2 (M+H)

Step 2. Preparation of 7-benzyl-6-(butoxy)-2-(trifluoromethyl)-2H-chromene-3-carboxylic acid The ester (Step 1) was hydrolyzed and purified using the same protocol as described in Example 609d (92%). ESHRMS m/z 405.1329 (M−H, C$_{22}$H$_{20}$F$_3$O$_4$Calc'd 405.1308). $^1$HNMR (DMSO-d$_6$/400 MHz), 13.13 (brs, 1H), 7.77 (s, 1H), 7.16-7.25 (m, 5H), 7.08 (s, 1H), 6.80 (s, 1H), 5.89 (q, 1H, J=7.1 Hz), 3.89 (m, 2H), 1.62-1.66 (m, 2H), 1.33-1.38 (m, 2H), 0.87 (t, 3H, J=7.1 Hz).

EXAMPLE 611i

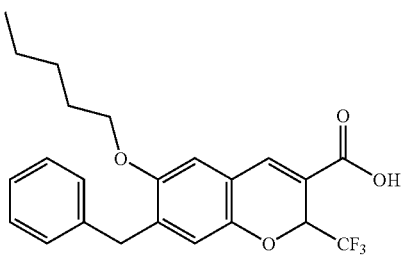

7-benzyl-6-(pentyloxy)-2-(trifluoromethyl)-2H-chromene-3-carboxylic acid

Step 1. Preparation of pentyl 7-benzyl-6-(pentyloxy)-2-(trifluoromethyl)-2H-chromene-3-carboxylate The acid from Example 61 le, Step 2 was subjected to a similar protocol as described in Example 61 lg, StepI with the appropriate substitution 1-iodopentane. (95%) ESLRMS 491.2 (M+H)

Step 2. Preparation of 7-benzyl-6-(pentyloxy)-2-(trifluoromethyl)-2H-chromene-3-carboxylic acid The ester (Step 1) was hydrolyzed and purified using the same protocol as described in Example 609d (91%). ESHRMS m/z 419.1501 (M−H, $C_{23}H_{22}F_3O_4$ Calc'd 419.1465). $^1$HNMR (DMSO-$d_6$/400 MHz), 13.13 (brs, 1H), 7.77 (s, 1H), 7.15-7.23 (m, 5H), 7.07 (s, 1H), 6.80 (s, 1H), 5.89 (q, 1H, J=7.1 Hz), 3.88 (m, 2H), 3.85 (m, 2H), 1.66 (brs, 2H), 1.29-1.30 (m, 4H), 0.84 (t, 3H, J=4 Hz).

EXAMPLE 611j

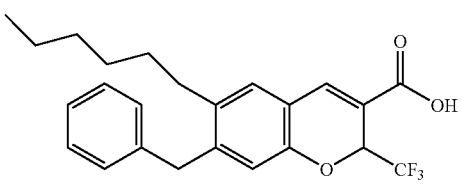

7-benzyl-6-hexyl-2-(trifluoromethyl)-2H-chromene-3-carboxylic acid

Step 1. Preparation of ethyl 7-benzMl-6-hexyl-2-(trifluoromethyl)-2H-chromene-3-carboxylate The ester from Example 41, Step 1 was coupled and purified using a similar protocol as described in Example 611d, Step 1 using the appropriate substitution of 1-hexene producing the ester (71%). ESLRMS m/z 447.2 (M+H).

Step 2. Preparation of 7-benzyl-6-hexyl-2-(trifluoromethyl)-2H-chromene-3-carboxylic acid The ester (Step 1) was hydrolyzed and purified using the same protocol as described in Example 609d (94%). ESHRMS m/z 417.1638 (M−H, $C_{24}H_{24}F_3O_3$ Calc'd 417.1672). $^1$HNMR (DMSO-$d_6$/400 MHz), 13.13 (brs, 1H), 7.77 (s, 1H), 7.09-7.27 (m, 5H), 6.73 (s, 1H), 5.89 (q, 1H, J=7.1 Hz), 3.93 (s, 2H), 2.41 (s, 2H), 1.32-1.37 (m, 2H), 1.18-1.23 (m, 6H), 0.80 (t, 3H, J=6 Hz).

EXAMPLE 611k

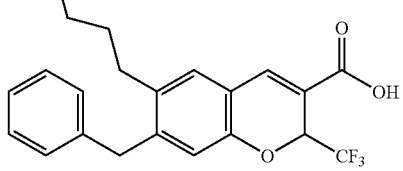

7-benzyl-6-pentyl-2-(trifluoromethyl)-2H-chromene-3-carboxylic acid

Step 1. Preparation of ethyl 7-benzyl-6-pentyl-2-(trifluoromethyl)-2H-chromene-3-carboxylate The ester from Example 41, Stepl was coupled and purified using a similar protocol as described in Example 611d, Step 1 using the appropriate substitution of 1-pentene (87%). ESLRMS m/z 432.1 (M+H).

Step 2. Preparation of 7-benzyl-6-pentyl-2-(trifluoromethyl)-2H-chromene-3-carboxylic acid The ester (Step 1) was hydrolyzed and purified using the same protocol as described in Example 609d (94%). ESHRMS m/z 403.1512 (M−H, $C_{23}H_{22}F_3O_3$ Calc'd 403.1516). $^1$HNMR (DMSO-$d_6$/400 MHz), 13.13 (brs, 1H), 7.77 (s, 1H), 7.09-7.28 (m, 6H), 6.73 (s, 1H), 5.89 (q, 1H, J=7.1 Hz), 3.94 (s, 2H), 2.41 (m, 2H), 1.32-1.36 (m, 2H), 1.18-1.22 (m, 4H), 0.77-0.81 (m, 3H).

EXAMPLE 611l

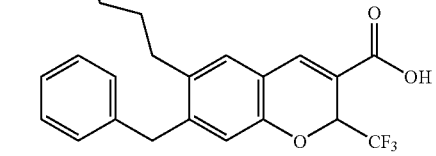

7-benzyl-6-(4-cyanobutyl)-2-(trifluoromethyl)-2H-chromene-3-carboxylic acid

Step 1. Preparation of ethyl 7-benzyl-6-(4-cyanobutyl)-2-(trifluoromethyl)-2H-chromene-3-carboxylate The ester from Example 41, Step 1 was coupled and purified using a similar protocol as described in Example 611d, Step 1 using the appropriate substitution of pent-4-enenitrile (51%). ESLRMS m/z 443.1 (M+H).

Step 2. Preparation of 7-benzyl-6-(4-cyanobutll)-2-(trifluoromethyl)-2H-chromene-3-carboxylic acid The ester (Step 1) was hydrolyzed and purified using the same protocol as described in Example 609d (96%). ESHRMS m/z 414.1311 (M–H, $C_{23}H_{19}F_3NO_3$ Calc'd 414.1312). $^1$HNMR (DMSO-$d_6$/400 MHz), 13.13 (brs, 1H), 7.78 (s, 1H), 7.25-7.28 (m, 3H), 7.17-7.19 (d, 1H, J=7.3 Hz), 7.12 (d, 2H, J=7.1 Hz), 5.89 (q, 1H, J=7.1 Hz), 3.94 (s, 2H), 2.42 (m, 2H), 1.51 (brs, 4H).

EXAMPLE 611m

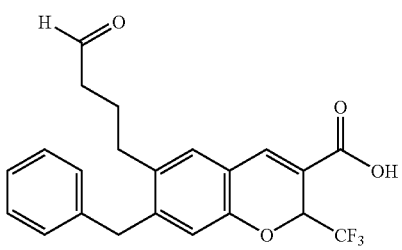

7-benzyl-6-(4-oxobutyl)-2-(trifluoromethyl)-2H-chromene-3-carboxylic acid

Step 1. Preparation of ethyl 7-benzyl-6-(4-oxobutyl)-2-(trifluoromethyl)-2H-chromene-3-carboxylate The ester from Example 41, Step 1 was coupled and purified using a similar protocol as described in Example 611d, Step 1 using the appropriate substitution of 4,4-diethoxybut-1-ene (62%). ESLRMS m/z 433.1 (M+H).

Step 2. Preparation of 7-benzyl-6-(4-oxobutyl)-2-(trifluoromethyl)-2H-chromene-3-carboxylic acid The ester (Step 1) was hydrolyzed and purified using the same protocol as described in Example 609d (91%). ESHRMS m/z 403.1190 (M–H, $C_{22}H_{18}F_3O_4$ Calc'd 403.1152). $^1$HNMR (DMSO-$d_6$/400 MHz), 13.13 (brs, 1H), 9.59 (s, 1H), 7.78 (s, 1H), 7.24-7.28 (m, 3H), 7.10-7.18 (m, 3H), 6.73 (s, 1H), 5.89 (q, 1H, J=7.1 Hz), 3.96 (s, 2H), 3.23-3.28 (m, 2H), 2.29-2.43 (m, 2H), 1.63-1.67 (m, 2H).

EXAMPLE 611n

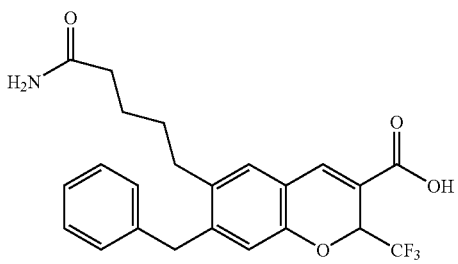

6-(5-amino-5-oxopentyl)-7-benzyl-2-(trifluoromethyl)-2H-chromene-3-carboxylic acid The acid from example 611l, Step 2 (500 mg, 1.12 mmole) was added to a solution of KOH (0.189 g, 3.30 mL) in t-BuOH (20 mL). The solution was refluxed for 24 hours. The reaction was cooled to room temperature and poured into 3N HCl aqueous, (25 mL), extracted with ethyl acetate (2×25 mL). The combined organic phases were washed with aqueous brine (2×50 mL), dried over $Na_2SO_4$, filtered and concentrated in vacuo. The crude material was subjected solid to preparative reverse phase chromatography to produce the title compound (99%). ESHRMS m/z 432.1423 (M–H, $C_{23}H_{21}F_3NO_4$ Calc'd 432.1455). $^1$HNMR (DMSO-$d_6$/400 MHz), 13.13 (brs, 1H), 7.75 (s, 1H), 7.22-7.27 (m, 3H), 7.08-7.16 (m, 3H), 6.69 (s, 1H), 6.62 (brs, 2H), 5.80 (q, 1H, J=7.1 Hz), 3.91 (s, 2H), 2.70 (m, 2H), 1.95-1.99 (m, 2H), 1.35-1.46 (m, 4H).

EXAMPLE 611o

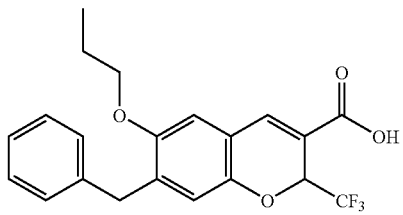

7-benzyl-6-propoxy-2-(trifluoromethyl)-2H-chromene-3-carboxylic acid

Step 1. Preparation of propyl 7-benzyl-6-propoxy-2-(trifluoromethyl)-2H-chromene-3-carboxylate The acid from Example 611e, Step 2 was subjected to a similar protocol as described in Example 611g, Step 1 with the appropriate substitution 1-iodopropane. (98%) ESLRMS 435.1 (M+H).

Step 2. Preparation of 7-benzyl-6-propoxy-2-(trifluoromethyl)-2H-chromene-3-carboxylic acid The ester (Step 1) was hydrolyzed and purified using the same protocol as described in Example 609d (97%). ESHRMS m/z 391.1135 (M–H, $C_{21}H_{18}F_3O_4$ Calc'd 391.1152). $^1$HNMR (DMSO-$d_6$/400 MHz), 13.13 (s, 1H), 7.76 (s, 1H), 7.12-7.26 (m, 5H), 7.07 (s, 1H), 6.80 (s, 1H), 5.76 (q, 1H, J=7.1 Hz), 3.83 (m, 4H), 1.67 (m, 2H). 0.91 (m, 3H).

EXAMPLE 611p

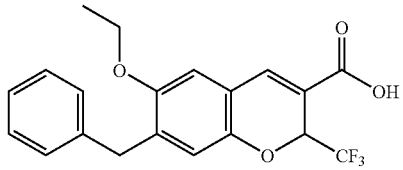

7-benzyl-6-ethoxy-2-(trifluoromethyl)-2H-chromene-3-carboxylic acid

Step 1. Preparation of ethyl 7-benzyl-6-ethoxy-2-(trifluoromethyl)-2H-chromene-3-carboxylate The acid from Example 611e, Step 2 was subjected to a similar protocol as described in Example 611g, Step 1 with the appropriate substitution 1-iodoethane. (97%) ESLRMS 407.1 (M+H).

Step 2. Preparation of 7-benzyl-6-ethoxy-2-(trifluoromethyl)-2H-chromene-3-carboxylic acid The ester (Step 1) was hydrolyzed and purified using the same protocol as described in Example 609d (99%). ESHRMS m/z 377.1033 (M–H, $C_{20}H_{16}F_3O_4$ Calc'd 377.0995). $^1$HNMR (DMSO-$d_6$/400 MHz), 13.13 (brs, 1H), 7.75 (s, 1H), 7.12-7.26 (m, 5H), 7.07 (s, 1H), 5.76 (q, 1H, J=7.1 Hz), 3.97 (m, 2H), 3.88 (m, 2H), 1.30 (m, 3H).

EXAMPLE 611q

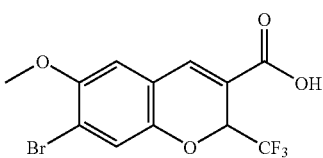

7-bromo-6-methoxy-2-(trifluoromethyl)-2H-chromene-3-carboxylic acid

Step 1. Preparation of methyl 7-bromo-6-hydroxy-2-(trifluoromethyl)-2H-chromene-3-carboxylate The ester from Example 611c (Step 3) was deprotected using the same protocol as described in Example 609n (95%). ESLRMS m/z 352.9 (M+H).

Step 2. Preparation of methyl 7-bromo-6-methoxy-2-(trifluorometh l)-2H-chromene-3-carboxulate The ester (Step 1) was subjected to a similar protocol as described in Example 611g, Step 1 with the appropriate substitution 1-iodomethane. (92%) ESLRMS 366.9 (M+H)

Step 3. Preparation of 7-bromo-6-methoxy-2-(trifluoromethyl)-2H-chromene-3-carboxylic acid The ester (Step 2) was hydrolyzed and purified using the same protocol as described in Example 609d (96%). ESHRMS m/z 350.9449 (M–H, $C_{12}H_7BrF_3O_4$ Calc'd 350.9474). $^1$HNMR (DMSO-$d_6$/400 MHz), 13.13 (brs, 1H), 7.82 (s, 1H), 7.50 (s, 1H), 7.29 (s, 1H), 5.89 (q, 1H, J=7.1 Hz), 2.46 (t, 3H, J=30 Hz).

EXAMPLE 611r

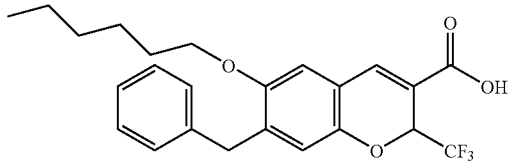

7-benzyl-6-(hexyloxy)-2-(trifluoromethyl)-2H-chromene-3-carboxylic acid

Step 1. Preparation of hexyl 7-benzyl-6-(hexyloxy)-2-(trifluoromethyl)-2H-chromene-3-carboxylate The acid from Example 611e, Step 2 was subjected to a similar protocol as described in Example 611g, Step 1 with the appropriate substitution 1-iodohexane. (95%) ESLRMS 519.2 (M+H)

Step 2. Preparation of 7-benzyl-6-(hexyloxy)-2-(trifluoromethyl)-2H-chromene-3-carboxylic acid The ester (Step 1) was hydrolyzed and purified using the same protocol as described in Example 609d (92%). ESHRMS m/z 433.1630 (M–H, $C_{24}H_{24}F_3O_4$ Calc'd 433.1621). $^1$HNMR (DMSO-$d_6$/400 MHz), 13.13 (brs, 1H), 7.77 (s, 1H), 7.11-7.24 (m, 5H), 5.89 (q, 1H, J=7.1 Hz), 3.80 (m, 2H), 3.79 (m, 2H), 1.61-1.68 (m, 2H), 1.20-1.33 (m, 4H), 0.84 (t, 3H, J=7 Hz).

EXAMPLE 612a

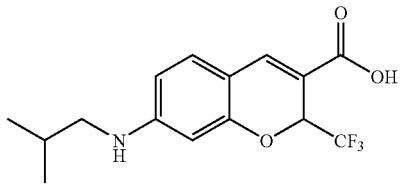

7-(isobutylamino)-2-(trifluoromethyl)-2H-chromene-3-carboxylic acid

Step 1. Preparation of 2-hydroxy-4-fluorobenzaldehyde

To the mixture of 3-fluorophenol (10 mL, 102 mmole), anhydrous magnesium chloride (28.2 g, 744.6 mmole) in 500 mL of anhydrous acetonitrile was added anhydrous triethylamine (67 mL, 382.5 mmole) and paraformaldehyde (22.3 g, 744.6 mmole). The mixture was then heated to reflux for five hours. After cooling to r.t, 500 mL of 5% aqueous hydrochloric acid was added. The product was extracted with ethyl acetate. The combined organic extracts were washed with 5% hydrochloric acid (×3), brine, and dried over anhydrous magnesium sulfate. After removing the volatiles, the residue was a light pink solid. 11 g, yield 72%. M.P: 67.5-69.0° C. ESHRMS m/z 139.0211(M–H, $C_7H_4FO_2$ calc'd 139.0201). $^1$H NMR (CDCl$_3$/300 MHz)

11.40 (s, 1H), 9.86 (s, 1H), 7.62-7.57 (m, 1H ), 6.79-6.67 (m, 2H). $^{3}$C (CDCl$_{3}$/300 MH) 195.4, 168.3 (d, J=258 Hz), 164.4 (d, J=14.9 Hz), 136.3 (d, J=12.6 Hz), 118.2 (d, J=2.0 Hz), 108.5 (d, J=23.3 Hz), 104.9 (d, J=24.4 Hz). $^{19}$F (CDCl$_{3}$/400 MHz) −97.9 (m).

Step 2. Preparation of ethyl 7-fluoro-2-(trifluoromethyl)-2H-chromene-3-carboxylate The mixture of 2-hydroxy-4-fluorobenzaldehyde (10 g, 71.4 mmole), ethyl 4,4,4-trifluorocrotonate (15 mL, 100 mmole), and anhydrous potassium carbonate (14.8 g, 107.1 mmole) in 40 ml dry dimethylformamide was heated to 90° C. for five hours. LC-MS indicated that the reaction was done. After cooling to room temperature, to the reaction was added 500 mL of ethyl acetate. The organic phase was washed with brine (×3), and was then dried over anhydrous magnesium sulfate. After removing the solvent, the residue was purified on silica gel column with 1:18 EtOAc:hexane. It gave 12.5 g (60%) of a light yellow oil. LCMS(ES+) 291.0(M+1, 100), EIHRMS m/z 290.0586 (M−H, C$_{13}$H$_{9}$F$_{4}$O$_{3}$ calc'd 290.0566). $^{1}$H NMR (CDCl$_{3}$/300 MHz) 7.73(s, 1H), 7.30-7.22(m, 1H), 6.79-6.73(m, 2H), 5.76(q, 1H, J=6.9 Hz), 4.38(m, 2H), 1.37(t, 3H, J=7.2 Hz). $^{13}$C (CDCl$_{3}$/300MH) 167.2, 164.0, 163.9, 155.0(d, J=13.0 Hz), 136.3 (d, J=1.28 Hz), 131.0(d, J=10.4 Hz), 123.5 (q, J=287.5 Hz), 115.0 (dd, J=2.4, 7.3 Hz), 110 (d, J=22.5 Hz), 104.4(d, J=26.0 Hz), 71.0(q, J=33.2 Hz), 61.7 (d, J=10.4 Hz), 14.4. $^{19}$F(CDCl$_{3}$/300 MHz) −79.0(d, J=6.5 Hz), −104.8 m).

Step 3. Preparation of ethyl 7-(isobutylamino)-2-(trifluoromethyl)-2H-chromene-3-carboxylate A mixture of ethyl 7-fluoro-2-(trifluoromethyl)-2H-chromene-3-carboxylate (0.45 g, 1.54 mmole) and isobutylamine (0.11 g, 1.54 mmole) was dissolved in anhydrous DMF (5 mL), warmed to 90° C. and treated with K$_{2}$CO$_{3}$ (0.25 g, 1.84 mmole). The mixture was maintained at 90° C. for 24 hrs, cooled to room temperature, filtered through celite and condensed to a viscous oil (0.53g, 98%). No further purification was performed. LCMS m/z 344.00 (M+H).

Step 4. Preparation of 7-(isobutylamino)-2-(trifluoromethyl)-2H-chromene-3-carboxylic acid The ethyl 7-(isobutylamino)-2-(trifluoromethyl)-2H-chromene-3-carboxylate (0.53 g, 1.54 mmole) was dissolved in a mixture of THF (5.0 mL) and ethanol (5.0 mL). 2.5N sodium hydroxide (1.54 mL) was added and the reaction was heated to 55° C. (oil bath) for 3 hours. The reaction was cooled to room temperature and stirred for 18 hours. The solution was condensed in vacuo to give a yellow oil. The oil was redissolved in water (20 mL), acidified with 2.4 N HCl to pH around 1 and extracted with EtOAc (2×20 mL). The combined extracts were washed with brine (20 mL), dried over MgSO$_{4}$, filtered and concentrated in vacuo to give a yellow oil which was subject to prep HPLC (reverse phase) and eluted with 50-95% ACN/ water with 0.05% TFA to give a yellow solid (0.1 g, 21%). ESHRMS m/z 314.1023 (M−H, C$_{15}$H$_{15}$O$_{3}$F$_{3}$N, Calc'd 314.0999). $^{1}$H NMR (CDCl$_{3}$/400 MHz) 7.78 (s, 1H), 7.01 (s, 1H), 6.24 (s, 2H), 5.60 (q, 1H, J=7.0 Hz), 2.97 (m, 2H), 1.91 (m, 1H), 0.98 (m, 6H).

EXAMPLE 612b

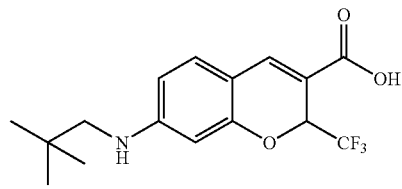

7-(neopentylamino)-2-(trifluoromethyl)-2H-chromene-3-carboxylic acid

Step 1. Preparation of ethyl 7-(neopentylamino)-2-(trifluoromethyl)-2H-chromene-3-carboxylate A mixture of ethyl 7-fluoro-2-(trifluoromethyl)-2H-chromene-3-carboxylate (Example 612a, Step 2) (0.45 g, 1.54 mmole) and 3,3-dimethylbutylamine (0.13 g, 1.54 mmole) was dissolved in anhydrous DMF (5 mL), warmed to 90° C. and treated with K$_{2}$CO$_{3}$ (0.25 g, 1.84 mmole). The mixture was maintained at 90° C. for 24 hrs, cooled to room temperature, filtered through celite and condensed to a viscous oil (0.55g, 98%). No further purification was performed. LCMS m/z 358.00 (M+H).

Step 2. Preparation of 7-(neopentylamino)-2-(trifluoromethyl)-2H-chromene-3-carboxylic acid The 7-(neopentylamino)-2-(trifluoromethyl)-2H-chromene-3-carboxylic acid was prepared by a procedure similar to the method described in Example 612a, Step 2. ESHRMS m/z 328.1121 (M−H, C$_{16}$H$_{17}$O$_{3}$F$_{3}$N, Calc'd 328.1155). $^{1}$H NMR (CDCl$_{3}$/400 MHz) 7.71 (s, 1H), 6.99 (s, 1H), 6.28 (s, 1H), 5.60 (q, 1H, J=7.0 Hz), 2.93 (m, 2H), 0.98 (s, 9H).

EXAMPLE 612c

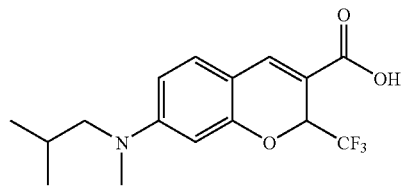

7-[isobutyl(methyl)amino]-2-(trifluoromethyl)-2H-chromene-3-carboxylic acid

Step 1. Preparation of ethyl 7-[isobutyl(methyl)amino]-2-(trifluoromethyl)-2H-chromene-3-carboxylate A mixture of ethyl 7-fluoro-2-(trifluoromethyl)-2H-chromene-3-carboxylate (Example 612a, Step 2) (0.45 g, 1.54 mmole) and 3,3-dimethylbutylamine (0.13 g, 1.54 mmole) was dissolved in anhydrous DMF (5 mL), warmed to 90° C. and treated with K$_{2}$CO$_{3}$ (0.25 g, 1.84 mmole). The mixture was maintained at 90° C. for 24 hrs, cooled to room temperature, filtered through celite and condensed to a viscous oil (0.55g, 98%). No further purification was performed. LCMS m/z 358.00 (M+H).

Step 2. Preparation of 7-[isobutyl(methyl)amino]-2-(trifluoromethyl)-2H-chromene-3-carboxylic acid The 7-[isobutyl(methyl)amino]-2-(trifluoromethyl)-2H-chromene-3-carboxylic acid was prepared by a procedure similar to the method described in Example 612a, Step 2. ESHRMS m/z 328.1112 (M−H, $C_{16}H_{17}O_3F_3N$, Calc'd 328.1155). $^1$H NMR (CDCl$_3$/400 MHz) 7.78 (s, 1H), 7.03 (s, 1H), 6.29 (m, 1H), 6.23 (s, 1H), 5.62 (q, 1H, J=7.0 Hz), 3.17 (m, 2H), 3.03 (s, 3H), 2.05 (m, 1H), 0.93 (s, 6H).

EXAMPLE 613a

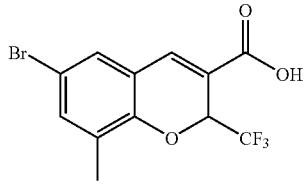

6-bromo-8-methyl-2-(trifluoromethyl)-2H-chromene-3-carboxylic acid

Step 1. Preparation of 5-bromo-2-hydroxy-3-methylbenzaldehyde

The solution of 2-Hydroxy-3-methylbenzaldehyde (1.0 g, 7.35 mmole) in acetic acid (6 mL) was cooled to 0° C. (ice bath). Bromine (1.36 g, 8.52 mmole) was added dropwise and allowed to stir for 2 hours. The reaction was warmed to room temperature and diluted with water (100 mL) yielding a light orange precipitate. The solid was filtered and washed with water (10 mL). Dried on high vacuum to give a light brown solid (1.4 g, 88.6%). $^1$H NMR (CDCl$_3$/400 MHz) 11.16 (s, 1H), 9.79 (s, 1H), 7.48 (s, 1H), 7.46 (s, 1H), 2.23 (s, 3H).

Step 2. Preparation of ethyl 6-bromo-8-methyl-2-(trifluoromethyl)-2H-chromene-3-carboxylate A mixture of 5-bromo-2-hydroxy-3-methoxybenzaldehyde (1.40 g, 6.51 mmole), K$_2$CO$_3$ (1.80 g, 13.02 mmole), triethylamine (2.63 g, 26.05 mmole), and ethyl 4,4,4-trifluorocrotonate (4.38 g, 26.05 mmole) in anhydrous DMSO (5.0 mL) was heated to 90 ° C. under a dry N$_2$ atmosphere for 18 hrs. The contents were poured into 2.4 N HCl (50 ml) and extracted with EtOAc (2×100 mL). The combined extracts were washed with brine (100 mL), dried over MgSO$_4$, filtered and concentrated in vacuo to give a dark yellow oil which was subject to flash chromatography (silica gel) and eluted with 10% EtOAc in hexanes to give a yellow solid (1.6 g, 68%). GCMS m/z 364.0 (M+). $^1$H NMR (CDCl$_3$/400 MHz) 7.59 (s, 1H), 7.27 (s, 1H), 7.16 (s, 1H), 5.70 (q, 1H, J=7.0 Hz), 4.29 (m, 2H), 2.19 (s, 3H), 1.32 (m, 3H).

Step 3. Preparation of 6-bromo-8-methyl-2-(trifluoromethyl)-2H-chromene-3-carboxylic acid The 6-bromo-8-methyl-2-(trifluoromethyl)-2H-chromene-3-carboxylic acid was prepared by a procedure similar to the method described in Example 602a, Step 2. ESHRMS m/z 334.9526 (M−H, $C_{12}H_7O_3F_3Br$, Calc'd 334.9525). $^1$H NMR (CDCl$_3$/400 MHz) 7.75 (s, 1H), 7.32 (s, 1H), 7.22 (s, 1H), 5.70 (q, 1H, J=7.0 Hz), 2.27 (s, 3H).

EXAMPLE 613b

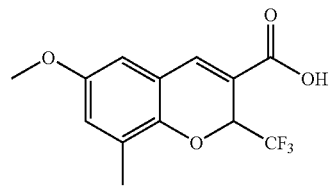

6-methoxy-8-methyl-2-(trifluoromethyl)-2H-chromene-3-carboxylic acid

Step 1. Preparation of ethyl 8-methyl-6-(4,4,5,5-tetramethyl-1,3,2-dioxaborolan-2-yl)-2-(trifluoromethyl)-2H-chromene-3-carboxylate The tricyclohexylphosphine (0.08 g, 0.28 mmole) and Pd(dba)$_2$ (0.07 g, 0.12 mmole) suspended in anhydrous dioxane (20 mL) was stirred for 15 minutes resulting in a red colored solution. Ethyl 6-bromo-8-methyl-2-(trifluoromethyl)-2H-chromene-3-carboxylate prepared as in Example 613a, Step 2 (1.43 g, 3.92 mmole), potassium acetate (0.58 g, 5.88 mmole), and bis (pinacolato)diboron (1.09 g, 4.31 mmole) was added and the resulting mixture was heated to 80° C. (oil bath) for 18 hours. The contents were poured into water (20 ml) and extracted with EtOAc (2×40 mL). The combined extracts were washed with brine (20 mL), dried over MgSO$_4$, filtered and concentrated in vacuo to give a dark green oil (1.62 g, 98%). No further purification was performed. GCMS m/z 412.0 (M+). LCMS m/z 413.0 (M+H).

Step 2. Preparation of ethyl 6-hydroxy-8-methyl-2-(trifluoromethyl)-2H-chromene-3-carboxylate The ethyl 8-methoxy-6-(4,4,5,5-tetramethyl-1,3,2-dioxaborolan-2-yl)-2-(trifluoromethyl)-2H-chromene-3-carboxylate (1.62 g, 3.92 mmole) was dissolved in THF (25 mL) and cooled to 0° C. (ice bath). Hydrogen peroxide (0.67 g, 5.88 mmole) followed by 2.5 N sodium hydroxide (1.57 mL) was added dropwise and the resulting solution was stirred for 3 hours. The contents were poured into water (40 mL) and acidified using 2.4 N HCl to pH around 1 and extracted with EtOAc (2×40 mL). The combined extracts were washed with brine (20 mL), dried over MgSO$_4$, filtered and concentrated in vacuo to give a yellow oil which was subject to flash chromatography (silica gel) and eluted with 0-100% EtOAc/hexanes to give yellow solid (0.84 g, 71%). GCMS m/z 302.0 (M+). LCMS m/z 303.0 (M+H). $^1$H NMR (CDCl$_3$/400 MHz) 7.59 (s, 1H), 6.60 (s, 1H), 6.51 (s, 1H), 5.64 (q, 1H, J=7.0 Hz), 4.28 (m, 2H), 2.17 (s, 3H), 1.31 (m, 3H).

Step 3. Preparation of ethyl 6-methoxy-8-methyl-2-(trifluoromethyl)-2H-chromene-3-carboxylate The ethyl 6-hydroxy-8-methyl-2-(trifluoromethyl)-2H-chromene-3-carboxylate (0.2 g, 0.66 mmole) and $K_2CO_3$ (0.48 g, 3.44 mmole) was suspended in acetone (7.5 mL). Iodomethane (0.93 g, 6.60 mmole) was added and heated to 55° C. for 3 hrs. The contents were filtered through a plug of celite and washed with acetone. The solution was concentrated in vacuo to give a yellow solid (0.22 g, 98%). GCMS m/z 316.0 (M+). LCMS m/z 317.0 (M+H). $^1$H NMR ($CDCl_3$/400 MHz) 7.64 (s, 1H), 6.72 (s, 1H), 6.55 (s, 1H), 5.65 (q, 1H, J=7.0 Hz), 4.28 (m, 2H), 3.73 (s, 3H), 2.20 (s, 3H), 1.32 (m, 3H).

Step 4. Preparation of 6-methoxy-8-methyl-2-(trifluoromethyl)-2H-chromene-3-carboxylic acid The 6-methoxy-8-methyl-2-(trifluoromethyl)-2H-chromene-3-carboxylic acid was prepared by a procedure similar to the method described in Example 602a, Step 2. ESHRMS m/z 287.0529 (M–H, $C_{13}H_{10}O_4F_3$, Calc'd 287.0526). $^1$H NMR ($CDCl_3$/300 MHz) 7.78 (s, 1H), 6.76 (s, 1H), 6.58 (s, 1H), 5.64 (q, 1H, J=7.0 Hz), 3.74 (s, 3H), 2.21 (s, 3H).

EXAMPLE 613c

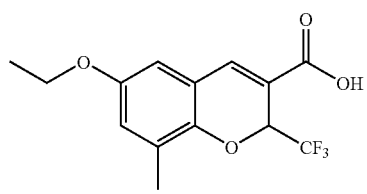

6-ethoxy-8-methyl-2-(trifluoromethyl)-2H-chromene-3-carboxylic acid

Step 1. Preparation of ethyl 6-ethoxy-8-methyl-2-(trifluoromethyl)-2H-chromene-3-carboxylate The ethyl 6-hydroxy-8-methyl-2-(trifluoromethyl)-2H-chromene-3-carboxylate prepared as in Example 613b, Step 2 (0.2 g, 0.66 mmole) and $K_2CO_3$ (0.48 g, 3.44 mmole) was suspended in acetone (7.5 mL). Iodoethane (1.03 g, 6.60 mmole) was added and heated to 55° C. for 3 hrs. The contents were filtered through a plug of celite and washed with acetone. The solution was concentrated in vacuo to give an orange solid (0.22 g, 98%). GCMS m/z 330.0 (M+). LCMS m/z 331.0 (M+H). $^1$H NMR ($CDCl_3$/400 MHz) 7.62 (s, 1H), 6.71 (s, 1H), 6.55 (s, 1H), 5.65 (q, 1H, J=7.0 Hz), 4.28 (m, 2H), 3.93 (m, 2H), 2.19 (s, 3H), 1.33 (m, 6H).

Step 2. Preparation of 6-ethoxy-8-methyl-2-(trifluoromethyl)-2H-chromene-3-carboxylic acid The 6-ethoxy-8-methyl-2-(trifluoromethyl)-2H-chromene-3-carboxylic acid was prepared by a procedure similar to the method described in Example 602a, Step 2. ESHRMS m/z 301.0706 (M–H, $C_{14}H_{12}O_4F_3$, Calc'd 301.0682). $^1$H NMR ($CDCl_3$/300 MHz) 7.78 (s, 1H), 6.76 (s, 1H), 6.56 (s, 1H), 5.63 (q, 1H, J=7.0 Hz), 3.94 (m, 2H), 2.21 (s, 3H) 1.36 (m, 3H).

EXAMPLE 614a

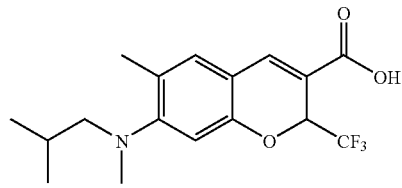

7-[isobutyl(methyl)amino]-6-methyl-2-(trifluoromethyl)-2H-chromene-3-carboxylic acid

Step 1. Preparation of ethyl 7-[isobutyl(methyl)amino]-6-methyl-2-(trifluoromethyl)-2H-chromene-3-carboxylate A mixture of ethyl 6-chloro-7-[isobutyl(methyl)amino]-2-(trifluoromethyl)-2H-chromene-3-carboxylate prepared as in Example 8c (0.50 g, 1.28 mmole), trimethylboroxine (0.38 g, 2.75 mmole), [(tBu$_3$P)PdBr]$_2$ (0.01 g), and $Cs_2CO_3$ (0.75 g, 2.31 mmole) in anhydrous diglyme (10.0 mL) was heated to 115° C. under a dry $N_2$ atmosphere for 18 hrs. The contents were poured into water (40 ml) and extracted with EtOAc (2×40 mL). The combined extracts were washed with brine (20 mL), dried over $MgSO_4$, filtered and concentrated in vacuo to give a yellow oil which was subject to HPLC (reverse phase) and eluted with 50-85% ACN/water with 0.05% TFA to give yellow solid (0.21 g, 45%). No further purification was performed. GCMS m/z 371.0 (M+). LCMS m/z 372.0 (M+H).

Step 2. Preparation of 7-risobutyl(methyl)amino]-6-methyl-2-(trifluoromethyl)-2H-chromene-3-carboxylic acid The 7-[isobutyl(methyl)amino]-6-methyl-2-(trifluoromethyl)-2H-chromene-3-carboxylic acid was prepared by a procedure similar to the method described in Example 602a, Step 2. ESHRMS m/z 342.1333 (M–H, $C_{17}H_{19}O_3F_3N$, Calc'd 342.1312). $^1$H NMR ($CDCl_3$/300 MHz) 7.79 (s, 1H), 7.02 (s, 1H), 6.67 (s, 1H), 5.62 (q, 1H, J=7.0 Hz), 2.95 (m, 2H), 2.85 (s, 3H), 2.29 (m, 3H) 1.85 (m, 1H), 0.89 (m, 6H).

EXAMPLE 614b

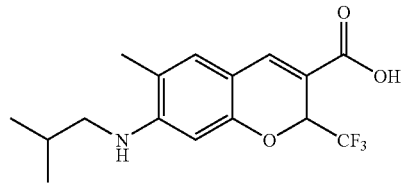

7-(isobutylamino)-6-methyl-2-(trifluoromethyl)-2H-chromene-3-carboxylic acid

Step 1. Preparation of ethyl 7-(isobutylamino)-6-methyl-2-(trifluoromethyl)-2H-chromene-3-carboxylate A mixture of ethyl 6-chloro-7-(isobutylamino)-2-(trifluoromethyl)-2H-chromene-3-carboxylate prepared as in Example 608b, Step 1 (2.10 g, 5.57 mmole), trimethylboroxine (1.58 mL, 12.66 mmole), [(tBu$_3$P)PdBr]$_2$ (0.04 g), and Cs$_2$CO$_3$ (3.17 g, 9.74 mmole) in anhydrous diglyme (10.0 mL) was heated to 115° C. under a dry N$_2$ atmosphere for 18 hrs. The contents were poured into water (40 ml) and extracted with EtOAc (2×40 mL). The combined extracts were washed with brine (20 mL), dried over MgSO$_4$, filtered and concentrated in vacuo to give an orange oil which was subject to flash chromatography (silica gel) and eluted with 0-15% EtOAc/hexanes to give yellow oil (0.5 g, 25%). No further purification was performed. GCMS m/z 357.0 (M+). LCMS m/z 358.0 (M+H).

Step 2. Preparation of 7-(isobutylamino)-6-methyl-2-(trifluoromethyl)-2H-chromene-3-carboxylic acid The 7-(isobutylamino)-6-methyl-2-(trifluoromethyl)-2H-chromene-3-carboxylic acid was prepared by a procedure similar to the method described in Example 602a, Step 2. ESHRMS m/z 330.1310 (M+H, C$_{16}$H$_{19}$O$_3$F$_3$N, Calc'd 330.1312). $^1$H NMR (CDCl$_3$/300 MHz) 7.72 (s, 1H), 6.87 (s, 1H), 6.23 (s, 1H), 5.58 (q, 1H, J=7.0 Hz), 2.99 (m, 2H), 2.06 (m, 3H) 1.95 (m, 1H), 0.98 (m, 6H).

EXAMPLE 615

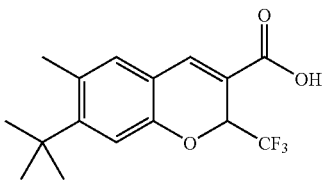

7-tert-butyl-6-methyl-2-(trifluoromethyl)-2H-chromene-3-carboxylic acid

Step 1. Preparation of ethyl 7-tert-butyl-6-methyl-2-(trifluoromethyl)-2H-chromene-3-carboxylate The ethyl 7-tert-butyl-6-chloro-2-(trifluoromethyl)-2H-chromene-3-carboxylate from Example 8, Step 2 (1 g, 2.75 mmole) was dissolved in diglyme (20 mL). Cs$_2$CO$_3$ (1.5 g, 3.07 mmole), trimethylboroxaine (0.75 mL, 5.36 mmole), and [(t-Bu$_3$P)PdBr]$_2$ (20 mg) were added to above solution. The mixture was heated to 115° C. for 15 hrs under nitrogen. LCMS indicated that there was 50% conversion. The reaction was cooled down and the water was added to quench the reaction. The product was extracted with EtOAc and washed with water. The crude mixture was purified by RPHPLC to give the desired product 360 mg as an oil (38% yield), which had suitable purity to use without further purification.

Step2. Preparation of 7-tert-butyl-6-methyl-2-(trifluoromethyl)-2H-chromene-3-carboxylic acid The 7-tert-butyl-6-methyl-2-(trifluoromethyl)-2H-chromene-3-carboxylic acid was prepared as a yellow solid (93%) by a procedure similar to the method described in Example 2a, Step 2: ESHRMS m/z 313.1056 (M−H, C$_{16}$H$_{16}$O$_3$F$_3$,Calc'd 313.1046). $^1$H NMR (acetone-d$_6$/400 MHz) 7.78 (s, 1H), 7.17 (s, 1H), 6.98 (s, 1H), 5.74 (q, 1H, J=7.2 Hz), 2.47 (s, 3H), 1.38 (s, 9H).

EXAMPLE 616

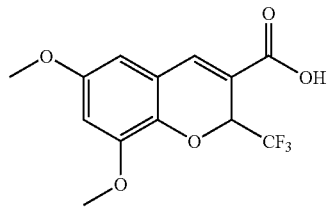

6,8-dimethoxy-2-(trifluoromethyl)-2H-chromene-3-carboxylic acid

Step 1. Preparation of ethyl 8-methoxy-6-(4,4,5,5-tetramethyl-1,3,2-dioxaborolan-2-yl)-2-(trifluoromethyl)-2H-chromene-3-carboxylate The tricyclohexylphosphine (0.01 g, 0.04 mmole) and Pd (dba) (0.01 g, 0.02 mmole) suspended in anhydrous dioxane (3 mL) was stirred for 15 minutes resulting in a red colored solution. Ethyl 6-bromo-8-methoxy-2-(trifluoromethyl)-2H-chromene-3-carboxylate prepared as in Example 605o, Step 2 (0.2 g, 0.52 mmole), potassium acetate (0.78 g, 0.78 mmole), and bis (pinacolato)diboron (0.15 g, 0.57 mmole) was added and the resulting mixture was heated to 80° C. (oil bath) for 18 hours. The contents were poured into water (10 ml) and extracted with EtOAc (2×20 mL). The combined extracts were washed with brine (20 mL), dried over MgSO$_4$, filtered and concentrated in vacuo to give a dark green oil (0.21 g, 95%). No further purification was performed. GCMS m/z 428.0 (M+). LCMS m/z 429.0 (M+H).

Step 2. Preparation of ethyl 6-hydroxy-8-methoxy-2-(trifluoromethyl)-2H-chromene-3-carboxylate The ethyl 8-methoxy-6-(4,4,5,5-tetramethyl-1,3,2-dioxaborolan-2-yl)-2-(trifluoromethyl)-2H-chromene-3-carboxylate (0.21 g, 0.49 mmole) was dissolved in THF (3 mL) and cooled to 0° C. (ice bath). Hydrogen peroxide (0.25 g, 0.074 mmole) followed by 2.5N sodium hydroxide (0.20 mL) was added dropwise and the resulting solution was stirred for 3 hours. The contents were poured into water (20 mL) and acidified using 2.4 N HCl to pH around 1 and extracted with EtOAc (2×20 mL). The combined extracts were washed with brine (20 mL), dried over MgSO$_4$, filtered and concentrated in vacuo to give a yellow oil which was subject to flash chromatography (silica gel) and eluted with 0-35% EtOAc/ hexanes to give yellow solid (0.1 g, 65%). LCMS m/z 319.0 (M+H). $^1$H NMR (CDCl$_3$/400 MHz) 7.58 (s, 1H), 6.50 (s, 1H), 6.29 (s, 1H), 5.66 (q, 1H, J=7.0 Hz), 4.29 (m, 2H), 3.86 (s, 3H), 1.32 (m, 3H).

Step 3. Preparation of ethyl 6,8-dimethoxy-2-(trifluoromethyl)-2H-chromene-3-carboxylate The ethyl 6-hydroxy-8-methoxy-2-(trifluoromethyl)-2H-chromene-3-carboxylate (0.1 g, 0.31 mmole) and K$_2$CO$_3$ (0.23 g, 1.64 mmole) was suspended in acetone (5.0 mL). Iodomethane (0.44 g, 3.1 mmole) was added and heated to 55 ° C. for 3 hrs. The contents were filtered through a plug of celite and washed with acetone. The solution was concentrated in vacuo to give a yellow solid (0.05 g, 50%). GCMS m/z 332.0 (M+). LCMS m/z 333.0 (M+H). $^1$H NMR (CDCl$_3$/400 MHz) 7.64 (s, 1H), 6.54 (s, 1H), 6.32 (s, 1H), 5.68 (q, 1H, J=7.0 Hz), 4.28 (m, 2H), 3.85 (s, 3H), 3.75 (s, 3H), 1.32 (m, 3H).

Step 4. Preparation of 6,8-dimethoxy-2-(trifluoromethyl)-2H-chromene-3-carboxylic acid The 6,8-dimethoxy-2-(trifluoromethyl)-2H-chromene-3-carboxylic acid was prepared by a procedure similar to the method described in Example 602a, Step 2. ESHRMS m/z 303.0448 (M–H, C$_{13}$H$_{10}$O$_5$F$_3$,Calc'd 303.0475). $^1$H NMR (CDCl$_3$/300 MHz) 7.77 (s, 1H), 6.57 (s, 1H), 6.34 (s, 1H), 5.68 (q, 1H, J=7.0 Hz), 3.86 (s, 3H), 3.76 (s, 3H).

EXAMPLE 617

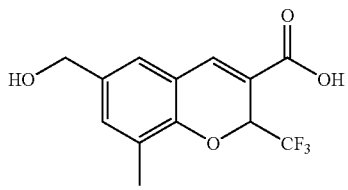

6-(hydroxymethyl)-8-methyl-2-(trifluoromethyl)-2H-chromene-3-carboxylic acid

Step 1. Preparation of 4-hydroxy-5-methylisophthalaldehyde

The 4-hydroxy-3-methylbenzaldehyde (7.0 g, 51.41 mmole) and magnesium chloride (7.3 g, 77.12 mmole) were mixed in acetonitrile (100 mL) and cooled to 0° C. (ice bath). Triethylamine (19.51 g, 192.79 mmole) followed by para-formaldehyde (10.41 g, 347 mmole) were added to above mixture, which was stirred for 1 hour. The mixture was warmed to room temperature and then heated to 90° C. for 18 hours. The contents were poured into water (100 mL) and extracted with EtOAc (2 X 100 mL). The combined extracts were washed with brine (50 mL), dried over MgSO$_4$, filtered and concentrated in vacuo to give an off-white solid which was subject to flash chromatography (silica gel) and eluted with 100% CH$_2$Cl$_2$ to give an off-white solid (2.2 g, 26%). GCMS m/z 164.0 (M+). $^1$H NMR (CDCl$_3$/400 MHz) 11.82 (s, 1H), 9.96 (s, 1H), 9.89 (s, 1H), 7.96 (s, 1H), 7.92 (s, 1H), 2.32 (s, 3H).

Step 2. Preparation of ethyl 6-formyl-8-methyl-2-(trifluoromethyl)-2H-chromene-3-carboxylate A mixture of 4-hydroxy-5-methylisophthalaldehyde (2.2 g, 13.41 mmole), K$_2$CO$_3$ (3.70 g, 26.82 mmole), triethylamine (5.42 g, 53.66 mmole) and ethyl 4,4,4-trifluocrotonate (9.01 g, 53.66 mmole) in anhydrous DMSO (5.0 mL) was heated to 90° C. under a dry N$_2$ atmosphere for 18 hrs. The mixture was then cooled, poured into 1.2 N HCl (50 ml) and extracted with EtOAc (2×50 mL). The combined extracts were washed with brine (50 mL), dried over MgSO$_4$, filtered and concentrated in vacuo to give a yellow oil which was subject to flash chromatography (silica gel) and eluted with 80% CH$_2$Cl$_2$/hexanes to give a yellow solid (1.9 g, 45%). GCMS m/z 314.0 (M+). $^1$H NMR (CDCl$_3$/400 MHz) 9.85 (s, 1H), 7.75 (s, 1H), 7.66 (s, 1H), 7.61 (s, 1H), 5.82 (q, 1H, J=7.0 Hz), 4.33 (m, 2H), 2.31 (s, 3H), 1.32 (m, 3H).

Step 3. Preparation of ethyl 6-(hydroxymethyl)-8-methyl-2-(trifluoromethyl)-2H-chromene-3-carboxylate The solution of ethyl 6-formyl-8-methyl-2-(trifluoromethyl)-2H-chromene-3-carboxylate (1.9 g, 6.05 mmole) dissolved in a mixture of THF (10 mL) and ethanol (10 mL) was cooled to 0° C. (ice bath). Sodium borohydride (0.11 g, 3.00 mmole) was added to above solution portionwise over 30 minutes. The mixture was poured into 1.2 N HCl (10 ml) and extracted with EtOAc (2×20 mL). The combined extracts were washed with brine (20 mL), dried over MgSO$_4$, filtered and concentrated in vacuo to give a yellow oil (1.9 g, 98%). No further purification was performed. GCMS m/z 316.0 (M+).

Step 4. Preparation of 6-(hydroxymethyl)-8-methyl-2-(trifluoromethyl)-2H-chromene-3-carboxylic acid The 6-(hydroxymethyl)-8-methyl-2-(trifluoromethyl)-2H-chromene-3-carboxylic acid was prepared by a procedure similar to the method described in Example 602a, Step 2. LCMS m/z 289.0 (M+H). Anal. Calcd. for C$_{13}$H$_{11}$O$_4$F$_3$: C, 54.2; H, 3.8; F, 19.8. Found: C, 54.0; H, 4.1; F, 19.7. $^1$H NMR (acetone-d$_6$/400 MHz) 7.86 (s, 1H), 7.26 (s, 2H), 5.83 (q, 1H, J=7.0 Hz), 4.55 (s, 2H), 2.24 (s, 3H).

EXAMPLE 618

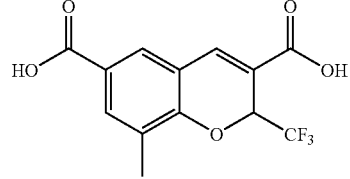

8-methyl-2-(trifluoromethyl)-2H-chromene-3,6-dicarboxylic acid

Step 1. Preparation of 3-formyl-4-hydroxy-5-methylbenzoic acid

The 4-hydroxy-3-methylbenzoic acid (10.1 g, 66.38 mmole) was suspended in methanesulfonic acid (50 mL) and cooled to 0° C. (ice bath). Hexamethylenetetramine (18.6 g, 132.75 mmole) was added portionwise over 1 hour. The reaction was warmed to room temperature followed by heating to 90° C. (oil bath) for 5 hours. The reaction was allowed to cool to room temperature and stired for 18 hours. The contents were poured into water (100 mL) and extracted with EtOAc (2×100 mL). The combined extracts were washed with brine (50 mL), dried over MgSO$_4$, filtered and concentrated in vacuo to give an off-white solid (9.0 g, 75%). $^1$H NMR (DMSO/400 MHz) 12.84 (brs, 1H), 11.40 (s, 1H), 10.09 (s, 1H), 8.20 (s, 1H), 7.98 (s, 1H), 2.21 (s, 3H).

Step 2. Preparation of 3-(ethoxycarbonyl)-8-methyl-2-(trifluoromethyl)-2H-chromene-6-carboxylic acid A mixture of 3-formyl-4-hydroxy-5-methylbenzoic acid (8.8 g, 48.89 mmole), K$_2$CO$_3$ (13.49 g, 97.78 mmole), triethylamine (19.79 g, 195.56 mmole), and ethyl 4,4,4- trifluorocrotonate (32.85 g, 195.56 mmole) in anhydrous DMSO (20.0 mL) was heated to 90° C. under a dry $N_2$ atmosphere for 18 hrs. The mixture was then cooled, poured into 2.0 N HCl (100 ml), and extracted with EtOAc (2×100 mL). The combined extracts were washed with brine (100 mL), dried over $MgSO_4$, filtered, and concentrated in vacuo to give an oily solid. Redissolved in acetone to givea white precipitat, which was filtered and dried on high vacuum (7.2 g, 51%). GCMS m/z 330.0 (M+). $^1$H NMR (DMSO/400 MHz) 12.99 (s, 1H), 8.11 (s, 1H), 8.06 (s, 1H), 7.94 (s, 1H), 6.19 (q, 1H, J=7.0 Hz), 4.35 (m, 2H), 2.31 (s, 3H), 1.36 (m, 3H).

Step 3. Preparation of 8-methyl-2-(trifluoromethyl)-2H-chromene-3,6-dicarboxylic acid The 8-methyl-2-(trifluoromethyl)-2H-chromene-3,6-dicarboxylic acid was prepared by a procedure similar to the method described in Example 602a, Step 2. ESHRMS m/z 301.0328 (M–H, $C_{13}H_8O_5F_3$, Calc'd 301.0318). $^1$H NMR (DMSO/400 MHz) 7.92 (s, 1H), 7.91 (s, 1H), 7.81 (s, 1H), 6.02 (q, 1H, J=7.0 Hz), 2.20 (s, 3H).

EXAMPLE 619a

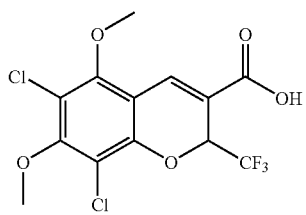

6,8-dichloro-5,7-dimethoxy-2-(trifluoromethyl)-2H-chromene-3-carboxylic acid

The solution of the 5,7-dimethoxy-2-(trifluoromethyl)-2H-chromene-3-carboxylic acid from Example 34 (WO 00/23433) (150 mg, 0.49 mmole) in acetic acid (1.0 mL) was stirred at 10° C. The pre-prepared solution of $Cl_2$ (gas) in acetic acid (1.1 mL, 0.64 mmol) was added to above solution. The mixture was stirred for 2 hours. After $Cl_2$ (gas) was blown away, Zn powder (5 eq) was added to the mixture and the mixture was stirred for 30 min. Zn salts were removed by filtration and the filtrate was evaporated to dryness. The residue was purified by RPHPLC and eluted with 30 to 85% ACN in water with 0.05% TFA. The 2nd peak fractions were combined to give the desired compound 45 mg (24.6%) as di-chloro compound: LCMS m/z 372.95 (M+H) at 5.878 min. ESHRMS m/z 370.9743 (M–H, $C_{13}H_8O_5F_3Cl_2$, Calc'd 370.9695). $^1$H NMR (CDCl$_3$/400 MHz) 7.93 (s, 1H), 6.00 (q, 1H, J=6.8 Hz), 3.97 (s, 3H), 3.94 (s, 3H).

EXAMPLE 619b

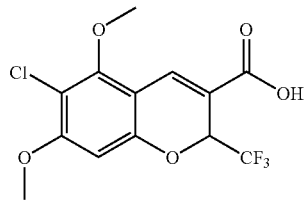

6-chloro-5,7-dimethoxy-2-(trifluoromethyl)-2H-chromene-3-carboxylic acid

The solution of the 5,7-dimethoxy-2-(trifluoromethyl)-2H-chromene-3-carboxylic acid from Example 34 (WO 00/23433) (150 mg, 0.49 mmole) in acetic acid (1.0 mL) was stirred at 10° C. The pre-prepared solution of $Cl_2$ (gas) in acetic acid (1.1 mL, 0.64 mmol) was added to above solution. The mixture was stirred for 2 hours. After $Cl_2$ (gas) was blown away, Zn powder (5 eq) was added to the mixture and the mixture was stirred for 30 min. Zn salts were removed by filtration and the filtrate was evaporated to dryness. The residue was purified by RPHPLC and eluted with 30 to 85% ACN in water with 0.05% TFA. The Ist peak fractions were combined to give the desired compound 28.6 mg (17.2%) as mono-chloro compound: LCMS m/z 339.05 (M+H) at 5.474 min. ESHRMS m/z 337.0112 (M–H, $C_{13}H_9O_5F_3Cl$, Calc'd 337.0085). $^1$H NMR (CDCl$_3$/400 MHz) 7.90 (s, 1H), 6.67 (s, 1H), 5.82 (q, 1H, J=6.8 Hz), 3.97 (s, 3H), 3.94 (s, 3H).

EXAMPLE 620

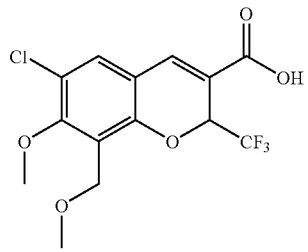

6-chloro-7-methoxy-8-(methoxymethyl)-2-(trifluoromethyl)-2H-chromene-3-carboxylic acid Step 1. Preparation of ethyl 8-(bromomethyl)-6-chloro-7-methoxy-2-(trifluoromethyl)-2H-chromene-3-carboxylate The ethyl 6-chloro-7-methoxy-8-methyl-2-(trifluoromethyl)-2H-chromene-3-carboxylate from Example 3a, Step 3 (3.3 g, 9.4 mmole) was dissolved in $CCl_4$ (30 mL) and the solution was heated to 60° C. NBS (1.84 g, 10.3 mmole) and $Bzo_2O$ (100 mg) were added to the above warm solution and the reaction was heated to reflux overnight. Additional NBS (1.84 g, 10.3 mmole) and $Bzo_2O$ (100 mg) were added to the above warm solution and the reaction was heated for 2 hrs. LCMS indicated that >95% product was formed. The reaction was cooled down and solid was filtered off. The filtrate was washed with NaHCO$_3$ and brine. The organic layer was dried over anhydrous MgSO$_4$ and evaporated to dry. The crude compound was used as crude ($^1$H NMR indicated that the ratio of starting material/product is 40/60).

Step2. Preparation of methyl 6-chloro-7-methoxy-8-(methoxymethyl)-2-(trifluoromethyl)-2H-chromene-3-carboxylate The crude 8-(bromomethyl) chromene ester (4.1g, 9.5 mmole) was dissolved in MeOH (40 mL). NaOMe (25%) (6.15 g, 28.5 mmole) was added to the above solution. The reaction was stirred at room temperature for 3 hrs. LCMS indicated that there were four new major peaks formation and there was no starting material present. The mixtrure was purified by Biotage chromatography to give 0.49 g title compound as a yellow oil (2 steps yield 14%). LCMS m/z 389.05 (M+Na).

Step3. Preparation of 6-chloro-7-methoxy-8-(methoxymethyl)-2-(trifluoromethyl)-2H-chromene-3-carboxylic acid The 6-chloro-7-methoxy-8-(methoxymethyl)-2-(trifluoromethyl)-2H-chromene-3-carboxylic acid was prepared as a yellow solid (yield 64%) by a procedure similar to the method described in Example 602a, Step 2: ESHRMS m/z 351.0254 (M–H, C$_{14}$H$_{11}$O$_5$F$_3$Cl, Calc'd 351.0242). $^1$H NMR (acetone-d$_6$/400 MHz) 7.87 (s, 1H), 7.61 (s, 1H), 5.89 (q, 1H, J=7.2 Hz), 4.49 (d, 2H, J=2.8 Hz), 3.91 (s, 3H), 3.34 (s, 3H).

EXAMPLE 621a

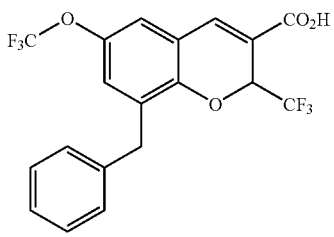

8-benzyl-6-(trifluoromethoxy)-2-(trifluoromethyl)-2H-chromene-3-carboxylic acid

Step 1. Preparation of ethyl 8-benzyl-6-(trifluoromethoxy)-2-(trifluoromethyl)-2H-chromene-3-carboxylate To a mixture of []-benzyl 9-BBN (4.12 mL-0.5 M in THF, 2.06 mmole) and Pd(dppf)ClCH$_2$Cl$_2$ (58.8 mg, 0.0721 mmole) in anhydrous THF (6 mL) at room temperature was added 8-iodo-6-(trifluoromethoxy)-2-(trifluoromethyl)-2H-chromene-3-carboxylate prepared as in Example 21a, Step 2 (01597/1 PR) (500 mg, 1.03 mmole) followed by aqueous K$_3$PO$_4$ (1.16 mL-2.0 M, 2.32 mmole). The resulting mixture became black within 30 seconds and was refluxed for 1.5 hrs. The mixture was then poured into aqueous HCl solution (100 mL-1.0 N), extracted with EtOAc (200 mL). The layers were separated and the EtOAc layer was washed with brine (100 mL), dried over MgSO$_4$, filtered, and concentrated in vacuo to give a brown oil. Purification by silica chromatography (9:1 hexanes:EtOAc) gave the impure product in assumed quantitative yield as a yellow crystalline solid: EIHRMS m/z 446.0933 (M+, C$_{21}$H$_{16}$F$_6$O$_4$, Calc'd 446.0953).

Step 2. Preparation of 8-benzyl-6-(trifluoromethoxy)-2-(trifluoromethyl)-2H-chromene-3-carboxylic acid To a solution of the ester prepared as in Step 1 (480 mg, 1.08 mmole) in a 7:2:1 THF:EtOH:H$_2$O mixture (10 mL) was added LiOH—H$_2$O (67.7 mg, 1.61 mmole). The mixture was stirred at room temperature overnight. The solvent was removed in vacuo and the residue was redissolved in H$_2$O, acidified with 1 N HCl and extracted with EtOAc (200 mL). The EtOAc extract was dried over MgSO$_4$, filtered and concentrated in vacuo to give 440 mg of crude product. Purification by reverse phase chromatography (acetonitrile:H$_2$O with 0.05% TFA) gave 327 mg (73% yield) of the product as a pale yellow crystalline solid: EIHRMS m/z 418.0618 (M+, C$_{19}$H$_{12}$F$_6$O$_4$, Calc'd 418.0640). $^1$H NMR (dmso-d$_6$/300 MHz) 13.40 (brs, 1H), 7.86 (s, 1H), 7.46 (s, 1H), 7.27-7.13 (m, 6H), 5.98 (q, J=7.3 Hz, 1H), 3.93 (s, 2H).

EXAMPLE 621b

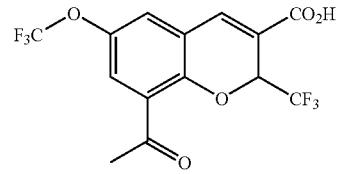

8-acetyl-6-(trifluoromethoxy)-2-(trifluoromethyl)-2H-chromene-3-carboxylic acid

A mixture of ethyl 8-iodo-6-(trifluoromethoxy)-2-(trifluoromethyl)-2H-chromene-3-carboxylate prepared as in Example 21a, Step 2 (2.41 g, 5.00 mmole), n-buytylvinyl ether (3.22 mL, 25.0 mmole), Pd(OAc)$_2$ (33.4 mg, 0.150 mmole), DPPP (136 mg, 0.330 mmole) and K$_2$CO$_3$ (0.830 g, 6.00 mmole), in a mixture of DMF (12.5 mL) and H$_2$O (1.5 mL) was stirred at 100° C. for 17 hrs. After the mixture was cooled to room temperature, 1N HCl (20 mL) was then added and the mixture was stirred for 30 minutes and then was extracted with EtOAc (2×200 mL). The extracts were combined and washed with H$_2$O (200 mL), brine (100 mL), dried over MgSO$_4$, and filtered. The solvent was removed in vacuo to give the crude product as a dark brown oil. Purification by silica chromatography (20% EtOAc in hexanes with 1% HOAc) gave 0.940 g (47% yield) of the product as a tan crystalline solid: EIHRMS m/z 370.0258 (M+, C$_{14}$H$_8$F$_6$O$_5$, Calc'd 370.0276). $^1$H NMR (dmso-d$_6$/300 MHz) 13.59 (brs, 1H), 7.95 (s, 1H), 7.85 (d, 1H, J=2.8 Hz), 7.58 (dd, 1H, J=4.0, 2.2 Hz), 6.19 (q, 1H, J=7.0 Hz), 2.58 (s, 3H).

EXAMPLE 621c

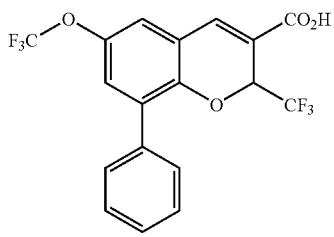

8-phenyl-6-(trifuoromethoxy)-2-(trifluoromethyl)-2H-chromene-3-carboxylic acid

Step 1. Preparation of ethyl 8-phenyl-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (0.500 g, 1.04 mmole), phenylboronic acid (133 mg, 1.09 mmole), Pd(OAc)$_2$ (7.00 mg, 0.031 mmole), triphenyl phosphine (24.4 mg, 0.093 mmole), and NaHCO$_3$ (132 mg, 1.25 mmole) in toluene (25 mL) and H$_2$O (5 mL) was stirred at room temperature for 21 hrs and was then refluxed for 1 h. Pd(PPh$_3$)$_4$ (120 mg, 0.104 mmole) was added and the mixture was refluxed for 1.5 hrs. LCMS indicated that the product was increased slightly. Additional Pd(PPh$_3$)$_4$ (120 mg, 0.104 mmole), NaHCO$_3$ (132 mg, 1.25 mmole) and phenylboronic acid (133 mg, 1.09 mmole) and EtOH (10 mL) to above mixture and the mixture was refluxed overnight. After cooling, the mixture was then poured into brine (100 mL) and extracted with EtOAc (100 mL). The EtOAc layer was separated, dried over MgSO$_4$ and filtered. The crude product was purified by silica chromatography (0-10% EtOAc—hexanes) to give 336 mg (85%, yield) of the product as an off-white solid: EIHRMS m/z 432.0807 (M+, C$_{20}$H$_{14}$F$_6$O$_4$, Calc'd 432.0796).

Step 2. Preparation of 8-phenyl-6-(trifluoromethoxy)-2-(trifluoromethyl)-2H-chromene-3-carboxylic acid To a solution of the ester prepared as in Step 1 (327 mg, 0.756 mmole) in a 7:2:1 THF:EtOH:H$_2$O mixture (10 mL) was added LiOH—H$_2$O (47.6 mg, 1.13 mmole). The mixture was stirred at room temperature for 17 hrs. The solvent was removed in vacuo and the residue was redissolved in H$_2$O, filtered and acidified with 1 N HCl. The resulting crystalline solid was filtered, washed with H$_2$O and dried in vacuo to give 292 mg (95% yield) of the product as a white solid: EIHRMS m/z 404.0506 (M+, C$_{18}$H$_{10}$F$_6$O$_4$, Calc'd 404.0483). $^1$H NMR (dmso-d$_6$/300 MHz) 13.48 (brs, 1H), 7.94 (s, 1H), 7.64 (d, 1H, J=2.2 Hz), 7.50-7.38 (m, 6H), 5.98 (q, 1H, J=7.3 Hz).

EXAMPLE 621d

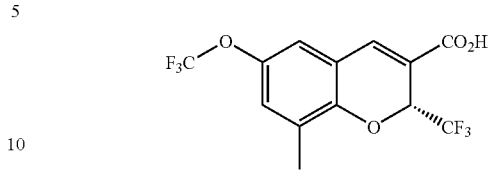

(2R)-8-methyl-6-(trifluoromethoxy)-2-(trifluoromethyl)-2H-chromene-3-carboxylic acid The racemic 8-methyl-6-(trifluoromethoxy)-2-(trifluoromethyl)-2H-chromene-3-carboxylic acid prepared as in Example 21b, Step 2 (130 mg) was resolved by chiral separation using a Chiral Pak AD column eluting with IPA/heptane/TFA (5/95/0.1) and detecting at 230 nm as peak 1 with retention time 3.28 minutes to give 59 mg (47% yield) the product as R-enantiomer: EIHRMS m/z 342.0356 (M+, C$_{13}$H$_8$F$_6$O$_4$, Calc'd 342.0327); $^1$H NMR (dmso-d$_6$, 400 MHz) 13.42 (brs, 1H), 7.85 (s, 1H), 7.42 (m, 1H), 7.31 (m, 1H), 5.99 (q, 1H, J=7.3 Hz), 2.20 (s,3H). $^{19}$F NMR (d6-benzene; 6 eq of(R)-(+)-1-(1-naphthyl)ethylamine) −58.33 (s, 3F), −78.23 (d, 3F, J=7.2 Hz, R-enantiomer), −58.34 (s, 3F), −78.21 (d, 3F, J=7.2 Hz, S-enantiomer).

EXAMPLE 621e

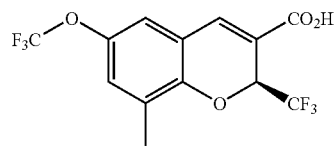

(2S)-8-methyl-6-(trifluoromethoxy)-2-(trifluoromethyl)-2H-chromene-3-carboxylic acid The racemic 8-methyl-6-(trifluoromethoxy)-2-(trifluoromethyl)-2H-chromene-3-carboxylic acid prepared as in Example 21b, Step 2 (130 mg) was resolved by chiral separation using a Chiral Pak AD column eluting with IPA/heptane/TFA (5/95/0.1) and detecting at 230 nm as peak 2 with retention time 3.97 minutes to give 57.1 mg (45% yield) the product as S-enantiomer: EIHRMS m/z 342.0315 (M+, C$_{13}$H$_8$F$_6$O$_4$, Calc'd 342.0327); $^1$H NMR (dmso-d$_6$, 400 MHz) 13.41 (brs, 1H), 7.86 (s, 1H), 7.42 (m, 1H), 7.31 (m, 1H), 5.99 (q, J=7.3 Hz,1H), 2.20 (s, 3H). $^{19}$F NMR (d6-benzene; 6 eq of(R)-(+)-1-(1-naphthyl)ethylamine) −58.33 (s, 3F), −78.23 (d, 3F, J=7.2 Hz, R-enantiomer), −58.34 (s, 3F), −78.21 (d, 3F, J=7.2 Hz, S-enantiomer).

EXAMPLE 621f

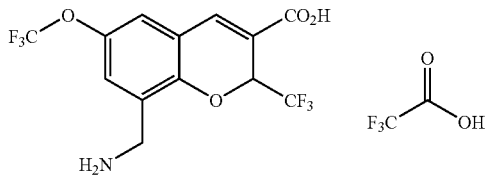

8-(aminomethyl)-6-(trifuoromethoxy)-2-(trifluoromethyl)-2H-chromene-3-carboxylic acid trifluoroacetate A mixture of 8-cyano-6-(trifluoromethoxy)-2-(trifluoromethyl)-2H-chromene-3-carboxylic acid prepared as in Example 21p, Step 2 (445 mg, 1.26 mmole) and 10% Pd/C (100 mg) in glacial acetic acid (20 mL) was hydrogenated at 20 psi for 1 h and the pressure released. After standing overnight, the catalyst filtrated and the solvent was removed in vacuo. Purification by reverse phase chromatography (acetonitrile: $H_2O$ with 0.05% TFA) to gave 200 mg (57% yield) of the product: ESHRMS m/z 358.0510 (M+H, $C_{13}H_{10}F_6O_4$, Calc'd 358.0509); $^1H$ NMR (dmso-$d_6$/300 MHz) 13.8 (brs, 1H), 8.29 (brs, 3H), 7.96 (s, 1H), 7.70 (s, 1H), 7.57 (s, 1H), 6.08 (q, 1H, J=7.1 Hz), 4.11 (dd, 2H, J=17.7, 5.84 Hz).

EXAMPLE 621g

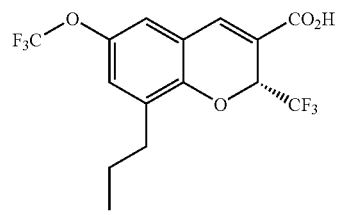

(2R)-8-propyl-6-(trifluoromethoxy)-2-(trifluoromethyl)-2H-chromene-3-carboxylic acid The racemic 8-propyl-6-(trifluoromethoxy)-2-(trifluoromethyl)-2H-chromene-3-carboxylic acid prepared as in Example 21i (1.56 g) was resolved by chiral separation using a Chiral Pak AD column eluting with IPA/heptane/TFA (2/98/0.1) and detecting at 280 nm as peak 1 with retention time 6.10minutes to give 658 mg (42% yield) the product as a light yellow solid as R-enantiomer: ESHRMS m/z 369.0562 (M−H, $C_{15}H_{11}F_6O_4$, Calc'd 369.0567); $^1H$ NMR (dmso-$d_6$, 300 MHz) 13.33 (brs, 1H), 7.87 (s, 1H), 7.44 (d, 1H, J=2.2 Hz), 7.26 (d, 1H, J=2.4 Hz), 5.99 (q, 1H, J=7.3 Hz), 2.65-2.47 (m, 2H), 1.60-1.48 (m, 2H), 0.86 (t, 3H, J=7.3 Hz). $^{19}F$ NMR (d6-benzene; 6 eq of(R)-(+)-1-(1-naphthyl)ethylamine) −58.33 (s, 3F), −77.98 (d, 3F, J=7.2 Hz, R-enantiomer), −58.35 (s, 3F), −77.96 (d, 3F, J=7.2 Hz, S-enantiomer).

EXAMPLE 621h

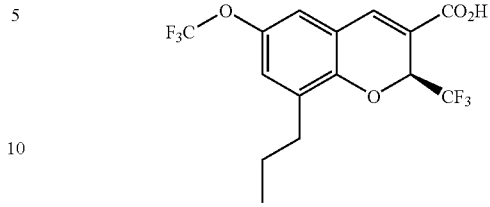

(2S)-8-propyl-6-(trifluoromethoxy)-2-(trifluoromethyl)-2H-chromene-3-carboxylic acid The racemic 8-propyl-6-(trifluoromethoxy)-2-(trifluoromethyl)-2H-chromene-3-carboxylic acid prepared as in Example 21i (1.56 g) was resolved by chiral separation using a Chiral Pak AD column eluting with IPA/heptane/TFA (2/98/0.1) and detecting at 280 nm as peak 2 with retention time 7.15 minutes to give 735 mg (47% yield) the product as a light yellow solid as S-enantiomer: ESHRMS m/z 369.0549 (M−H, $C_{15}H_{12}F_6O_4$, Calc'd 369.0567); $^1H$ NMR (dmso-$d_6$, 300 MHz) 13.35 (brs, 1H), 7.87 (s, 1H), 7.44 (d, 1H, J=2.2 Hz), 7.26 (d, 1H, J=2.4 Hz), 5.99 (q, 1H, J=7.3 Hz), 2.65-2.47 (m, 2H), 1.60-1.48 (m, 2H), 0.86 (t, 3H, J=7.3 Hz). $^{19}F$ NMR (d6-benzene; 6 eq of(R)-(+)-1-(1-naphthyl)ethylamine) −58.33 (s, 3F), −77.98 (d, 3F, J=7.2 Hz, R-enantiomer), −58.35 (s, 3F), −77.96 (d, 3F, J=7.2 Hz, S-enantiomer).

EXAMPLE 621i

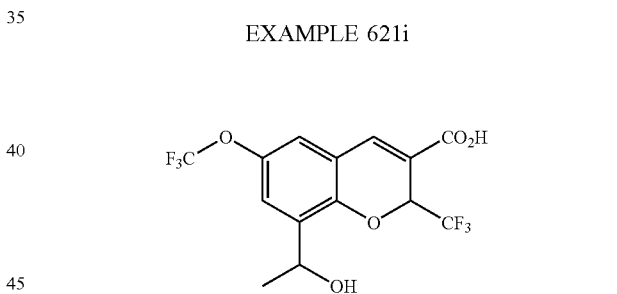

8-(1-hydroxyethyl)-6-(trifluoromethoxy)-2-(trifluoromethyl)-2H-chromene-3-carboxylic acid To a solution of 8-acetyl-6-(trifluoromethoxy)-2-(trifluoromethyl)-2H-chromene-3-carboxylic acid prepared as in Example 62 1b (0.980 g, 2.65 mmole) in a mixture of THF (25 mL) and absolute EtOH (25 mL) at 0° C. was added $NaBH_4$ (0.100 g, 2.65 mmole) in portions under a $N_2$ atmosphere. The ice bath was removed after 15 minutes and the mixture was stirred at room temperature for 2.75 hrs. The mixture was then poured into ice water (100 mL), which was then saturated with NaCl and extracted with EtOAc (2×200 mL). The extracts were combined, washed with brine, dried over $MgSO_4$, filtered and concentrated in vacuo to give the crude product as a pale yellow solid. Purification by silica chromatography (0% to 25% EtOAc:hexanes gradient) gave the crude product, which was further purified by crystallization from acetonitrile to give 516 mg (52% yield) of the product as an off-white crystalline solid: ESHRMS m/z 371.0378 (M–H, $C_{14}H_9F_6O_5$, Calc'd 371.0354); $^1$H NMR (dmso-$d_6$, 300 MHz) 13.42 (brs, 1H), 7.89 (s, 1H), 7.93 (d, 1H, J=2.6 Hz), 7.42 (s, 1H), 6.42 (q, 1H, J=7.3 Hz), 5.41 (m, 1H), 4.96 (d, 1H, J=3.4 Hz), 1.29 (d, 3H, J=6.2 Hz).

EXAMPLE 621j

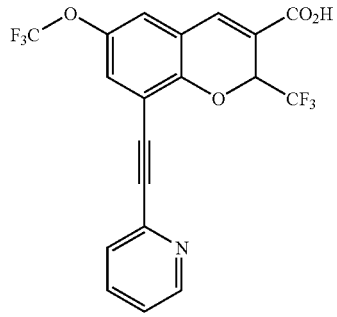

8-(pyridin-2-ylethynyl)-6-(trifluoromethoxy)-2-(trifluoromethyl)-2H-chromene-3-carboxylic acid Step 1. Preparation of ethyl 8-(pyridin-2-ylethynyl)-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (1.00 g, 2.07 mmole), 2-pyridylacetylene (419 uL, 4.15 mmole), CuI (39 mg, 0.207 mmole), $PdCl_2(dppf)_2$-$CH_2Cl_2$ (169 mg, 0.207 mmole) and TEA (0.866 mL, 6.21 mmole) in anhydrous toluene (10 mL) was stirred at room temperature for 5 days under a $N_2$ atmosphere. The mixture was then diluted with hexanes and purified by silica chromatography (0% to 75% EtOAc: hexanes gradient) to give 0.73 g (77% yield) the title product as a pale yellow crystalline solid: ESHRMS m/z 458.0849 (M+H, $C_{21}H_{14}F_6NO_4$, Calc'd 458.0822).

Step 2. Preparation of 8-(pyridin-2-ylethynyl)-6-(trifluoromethoxy)-2-(trifluoromethyl)-2H-chromene-3-carboxylic acid The ester from Step 1 was hydrolyzed via a method similar to that described in Example 621c, Step 2 using HOAc in the acidification step to give the product as a pale yellow solid: ESHRMS m/z 430.0507 (M+H, $C_9H_{10}F_6NO_4$, Calc'd 430.0509); $^1$H NMR (dmso-$d_6$, 300 MHz) 13.55 (brs, 1H), 8.62 (d, 1H, J=4.2 Hz), 7.93 (s, 1H), 7.90-7.84 (m, 1H), 7.73-7.62 (m, 3H), 7.47-7.42 (m, 1H), 6.18 (q, 1H, J=7.1 Hz).

EXAMPLE 621k

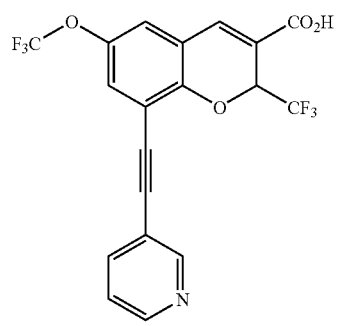

8-(pyridin-3-ylethynyl)-6-(trifluoromethoxy)-2-(trifuoromethyl)-2H-chromene-3-carboxylic acid Step 1. Preparation of ethyl 8-(pyridin-3-ylethynyl)-6-(trifluoromethoxy)-2-(trifluoromethyl)-2H-chromene-3-carboxcylate A mixture of ethyl 8-iodo-6-(trifluoromethoxy)-2-(trifluoromethyl)-2H-chromene-3-carboxylate prepared as in Example 21a, Step 2 (1.00 g, 2.07 mmole), 3-pyridylacetylene (419 uL, 4.15 mmole), CuI (39 mg, 0.207 mmole), $PdCl_2(dppf)_2$-$CH_2Cl_2$ (169 mg, 0.207 mmole) and TEA (0.866 mL, 6.21 mmole) in anhydrous toluene (10 mL) was stirred at room temperature for 5 days under a $N_2$ atmosphere. The mixture was then diluted with hexanes and purified by silica chromatography (0% to 75% EtOAc: hexanes gradient) to give 0.68 g (72% yield) of the product as a pale yellow crystalline solid: ESHRMS m/z 458.0827 (M+H, $C_{21}H_{14}F_6NO_4$, Calc'd 458.0822).

Step 2. Preparation of 8-(pyridin-3-ylethynyl)-6-(trifluoromethoxy)-2-(trifluoromethyl)-2H-chromene-3-carboxylic acid The ester from Step 1 was hydrolyzed via a method similar to that described in Example 621c, Step 2 using HOAc in the acidification step to give the product as a pale yellow solid: ESHRMS m/z 430.0527 (M+H, $C_{19}H_{10}F_6NO_4$, Calc'd 430.0509); $^1$H NMR (dmso-$d_6$, 300 MHz) 13.57 (brs, 1H), 8.73 (d, 1H, J=1.2 Hz), 8.62 (dd, 1H, J=4.8, 1.4 Hz), 7.97-7.93 (m, 2H), 7.72 (m, 1H), 7.67 (m, 1H), 7.49 (dd, 1H, J=7.9, 5.0 Hz), 6.17 (q, 1H, J=7.0 Hz).

EXAMPLE 621l

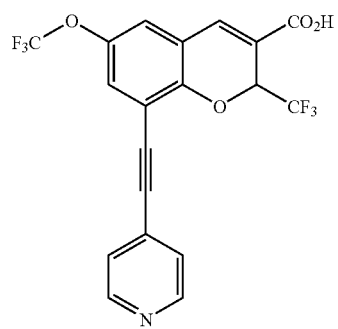

8-(pyridin-4-ylethynyl)-6-(trifluoromethoxy)-2-(trifluoromethyl)-2H-chromene-3-carboxylic acid Step 1. Preparation of ethyl 8-(pyridin-4-vlethynyl)-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (1.00 g, 2.07 mmole), 4-pyridylacetylene (419 uL, 4.15 mmole), CuI (39 mg, 0.207 mmole), PdCl$_2$(dppf)$_2$-CH$_2$Cl$_2$ (169 mg, 0.207 mmole) and TEA (0.866 mL, 6.21 mmole) in anhydrous toluene (10 mL) was stirred at room temperature for 5 days under a N$_2$ atmosphere. The mixture was then diluted with hexanes and purified by silica chromatography (0% to 75% EtOAc:hexanes gradient) to give 0.34 g (36% yield) of the product as a pale yellow crystalline solid: ESHRMS m/z 458.0822 (M+H, C$_{21}$H$_{14}$F$_6$NO$_4$, Calc'd 458.0822).

Step 2. Preparation of 8-(pyridin-4-vlethynyl)-6-(trifluoromethoxy)-2-(trifluoromethyl)-2H-chromene-3-carboxylic acid The ester from Step 1 was hydrolyzed via a method similar to that described in Example 621c, Step 2 using HOAc in the acidification step to give the product as a pale yellow solid: ESHRMS m/z 430.0531 (M+H, C$_{19}$H$_{10}$F$_6$NO$_4$, Calc'd 430.0509); $^1$H NMR (dmso-d$_6$, 300 MHz) 14.5 (brs, 1H), 8.64 (d, 2H, J=5.7 Hz), 7.58-7.48 (m, 5H), 6.08 (q, 1H, J=7.3 Hz).

EXAMPLE 621m

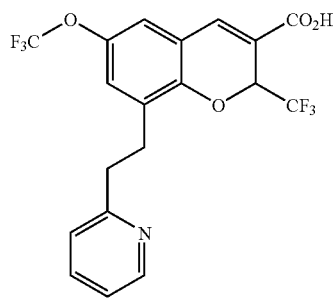

8-(2-pyridi n-2-ylethyl)-6-(trifl uoro methoxy)-2-(trifl uoro methyl)-2H-c hro men e-3-carboxylic acid A mixture of 8-(pyridin-2-ylethynyl)-6-(trifluoromethoxy)-2-(trifluoromethyl)-2H-chromene-3-carboxylic acid prepared as in Example 621j, Step 2 (684 mg, 1.59 mmole) and 10% Pd/C (100 mg) in glacial HOAc (20 mL) was hydrogenated at 20 psi for 2.5 h. The catalyst was filtrated, the solvent was removed in vacuo and the remaining HOAc was removed by azeotroping with hexanes to give the crude product as a tan solid. The solid was triturated with acetonitrile to give 362 mg (53% yield) of the product as an off-white solid: ESHRMS m/z 434.0834 (M+H, C$_{19}$H$_{14}$F$_6$NO$_4$, Calc'd 434.0822); $^1$H NMR (dmso-d$_6$/300 MHz) 13.43 (brs, 1H), 8.50 (d, 1H, J=4.8 Hz), 7.90 (s, 1H), 7.67 (t, 1H, J=7.7 Hz), 7.46 (s, 1H), 7.26-7.17 (m, 3H), 6.06 (q, 1H, J=7.3 Hz), 3.32-3.01 (m, 4H).

EXAMPLE 621n

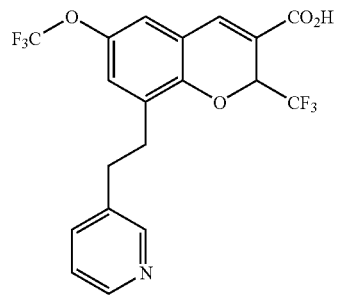

8-(3-pyridin-2-ylethyl)-6-(trifluoromethoxy)-2-(trifluoromethyl)-2H-chromene-3-carboxylic acid A mixture of 8-(pyridin-3-ylethynyl)-6-(trifluoromethoxy)-2-(trifluoromethyl)-2H-chromene-3-carboxylic acid prepared as in Example 621k, Step 2 (455 mg, 1.06 mmole) and 10% Pd/C (100 mg) in glacial HOAc (20 mL) was hydrogenated at 20 psi for 3.5 h. Additional 10% Pd/C (200 mg) was added and the mixture was hydrogenated at 20 psi for 1 h. The catalyst was then filtered, the solvent was removed in vacuo and the remaining HOAc was removed by azeotroping with hexanes to give the crude product as a solid. Suspended the solid in MeOH and added acetonitrile. Stirred the suspension, filtered the solid, washed with acetonitrile and dried in vacuo to give 308 mg (68% yield) of the product as an off-white solid: ESHRMS m/z 434.0835 (M+H, C$_{19}$H$_{14}$F$_6$NO$_4$, Calc'd 434.0822); $^1$H NMR (dmso-d$_6$/300 MHz) 13.40 (brs, 1H), 8.38-8.34 (m, 2H), 7.88 (s, 1H), 7.55 (d, 1H, J=7.7 Hz), 7.45 (d, 2H, J=2.2 Hz), 7.29-7.25 (m, 1H), 7.16 (d, 1H, J=2.2 Hz), 6.04 (q, 1H, J=7.3 Hz), 2.96-2.85 (m, 4H).

EXAMPLE 621o

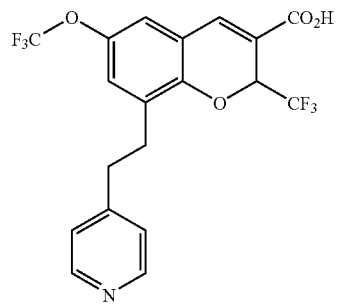

8-(4-pyridin-2-ylethyl)-6-(trifluoromethoxy)-2-(trifluoromethyl)-2H-chromene-3-carboxylic acid A mixture of 8-(pyridin4-ylethynyl)-6-(trifluoromethoxy)-2-(trifluoromethyl)-2H-chromene-3-carboxylic acid prepared as in Example 621l, Step 2 (241 mg, 0.562 mmole) and 10% Pd/C (500 mg) in glacial HOAc (10 mL) was hydrogenated at 20 psi for 8.5 hrs. Additional 10% Pd/C (200 mg) was added and the mixture was hydrogenated at 20 psi for 1 h. Additional 10% Pd/C (100 mg) was added and the mixture was hydrogenated at 20 psi for 23 hrs. Additional 10% Pd/C (200 mg) was added and the mixture was hydrogenated at 20 psi for 1 h. The catalyst was then filtered, the solvent was removed in vacuo and the remaining HOAc was removed by azeotroping with hexanes to give the crude product as a yellow oil. Purification by reverse phase chromatography (acetonitrile:0.05% TFA-H$_2$O) gave 82 mg (34% yield) of the product as a tan foam: ESHRMS m/z 434.0844 (M+H, $C_{19}H_{14}F_6NO_4$, Calc'd 434.0822); $^1$H NMR (dmso-d$_6$/300 MHz) 13.48 (brs, 1H), 8.71 (s, 2H), 7.92 (s, 1H), 7.66 (d, J=4.8 Hz, 2H), 7.50 (s, 1H), 7.28 (s, 1H), 6.06 (q, 1H, J=7.3 Hz), 3.18-2.99 (m, 4H).

EXAMPLE 621p

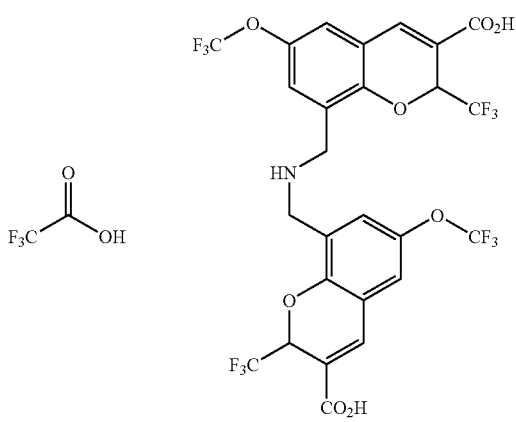

8-[({2-[3-carboxy-6-(trifluoromethoxy)-2-(trifluoromethyl)-2H-chromen-8-yl]ethyl}amino)methyl]-6-(trifluoromethoxy)-2-(trifluoromethyl)-2H-chromene-3-carboxylic acid trifluoroacetate A mixture of 8-cyano-6-(trifluoromethoxy)-2-(trifluoromethyl)-2H-chromene-3-carboxylic acid prepared as in Example 21p, Step 2 (445 mg, 1.26 mmole) and 10% Pd/C (100 mg) in glacial acetic acid (20 mL) was hydrogenated at 20 psi for 1 h and the pressure released. After standing overnight, the catalyst filtered and the solvent was removed in vacuo. Purification by reverse phase chromatography (acetonitrile:0.5% TFA-H$_2$O) gave 140 mg (32% yield) of the product: ESHRMS m/z 698.0694 (M+H, $C_{26}H_{16}Fl_2NO_8$, Calc'd 698.0679); $^1$H NMR (dmso-d$_6$/300 MHz) 13.6 (brs, 1H), 13.1 (brs, 1H), 9.39 (brs, 2H), 9.39 (brs, 2H), 7.95-7.93 (m, 2H), 7.72-7.70 (m, 2H), 7.63-7.59 (m, 2H), 6.00-5.91 (m, 2H), 4.29-4.17 (m, 4H).

EXAMPLE 621q

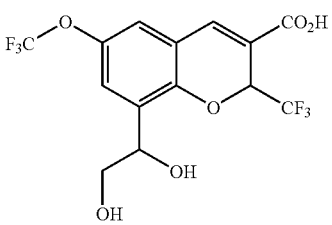

8-(1,2-dihydroxyethyl)-6-(trifluoromethoxy)-2-(trifluoromethyl)-2H-chromene-3-carboxylic acid Step 1. Preparation of ethyl 8-(1,2-dihydroxyethyl)-6-(trifluoromethoxy)-2-(trifluoromethyl)-2H-chromene-3-carboxylate To a solution of ethyl 6-(trifluoromethoxy)-2-(trifluoromethyl)-8-vinyl-2H-chromene-3-carboxylate prepared as in Example 21n, Step 1 (2.00 g, 5.23 mmole) in a mixture of acetone (40 mL) and H$_2$O (6 mL) was added 4-methylmorpholine-N-oxide (1.23 g, 10.5 mmole) followed by OsSO$_4$ (0.655 mL-2.5 wtO in isobutanol, 0.0523 mmole) and the resulting mixture was stirred at room temperature for 5 hrs. A solution of Na$_2$SO$_3$ (3.55 g, 20.4 mmole) in H$_2$O (10 mL) was then added and the mixture was extracted with EtOAc (2×200 mL). The combined extracts were washed with brine, dried over MgSO$_4$, filtered and concentrated in vacuo. Crystallization from EtOAc-hexanes gave 0.510 g (27% yield) of product A as a crystalline solid: ESHRMS m/z 415.0616 (M–H, $C_{16}H_{13}F_6O_6$, Calc'd 415.0592). Concentration of the filtrate in vacuo and purificaton of the resulting by silica chromatography (0%-75% EtOAc-hexanes gradient) gave 1.51 g (69% yield) of product B as a colorless solid: ESHRMS m/z 415.0616 (M–H, $C_{16}H_{13}F_6O_6$, Calc'd 415.0592). Product A and B were different ratio of the diasteroisomers.

Step 2. Preparation of 8-(1,2-dihydroxyethyl)-6-(trifluoromethoxy)-2-(trifluoromethyl)-2H-chromene-3-carboxylic acid The ester from Step 1 product B was hydrolyzed at 50° C. for 1 h via a method similar to that described in Example 621a, Step 2 to give the product (7:3 mixture of diastereomers) as an off-white solid: ESHRMS m/z 387.0259 (M–H, $C_{14}H_9F_6O_6$, Calc'd 387.0303); $^1$H NMR (dmso-d$_6$, 300 MHz) 13.40 (brs, 1H), 7.89 (s, 1H), 7.49 (d, 1H, J=2.7 Hz)), 7.40 (s, 1H), 5.98 (q, 1H, J=7.3 Hz), 5.56 (brs, 0.7 Hz), 5.48 (brs, 0.3 H), 4.85 (brs, 1.4 H), 4.79 (brs, 0.6 H), 3.56-3.48 (m, 1H), 3.31-3.26 (m, 1H).

EXAMPLE 621r

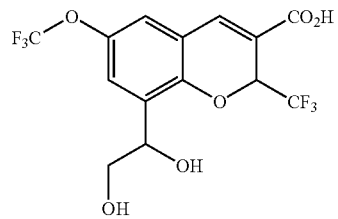

8-(1,2-dihydroxyethyl)-6-(trifluoromethoxy)-2-(trifluoromethyl)-2H-chromene-3-carboxylic acid The ester from Example 621q, Step 1 product A was hydrolyzed at 50° C. for 1 h via a method similar to that described in Example 621 a, Step 2 to give the product (1:9 mixture of diastereomers) as an off-white solid: ESHRMS m/z 387.0281 (M–H, $C_{14}H_9F_6O_6$, Calc'd 387.0303); $^1$H NMR (dmso-d$_6$, 300 MHz) 13.41 (brs, 1H), 7.89 (s, 1H), 7.48 (d, 1H, J=2.6 Hz)), 7.39 (d, 1H, J=2.0 Hz), 6.01 (q, 1H, J=7.3 Hz), 5.55 (brs, 0.1 H), 5.48 (brs, 0.9 H), 4.84 (brs, 2 H), 3.57-3.53 (m, 1H), 3.31-3.25 (m, 1H).

EXAMPLE 621s

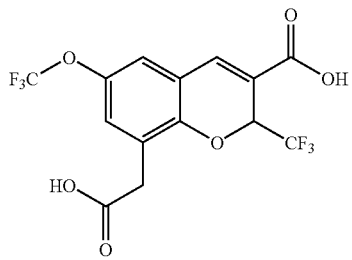

8-(carboxymethyl)-6-(trifluoromethoxy)-2-(trifluoromethyl)-2H-chromene-3-carboxylic acid

Step 1. Preparation of tributyl(ethoxyethynyl)stannane

A solution of n-butyllithium (18.7 mL-1.6 M in hexanes, 30.0 mmole) was added to anhydrous ethyl ether (20 mL) and the resulting mixture was then cooled to −30 to −40° C. A solution of ethoxy acetylene (5.00 g-40% in hexanes, 28.5 mmole) in ethyl ether (10 mL) was then added dropwise over 10 minutes. The resulting suspension was allowed to warm to room temperature, tributyltin chloride (9.29 g, 28.5 mmole) was added dropwise over 10 minutes and the mixture was stirred for 2 hrs. The mixture was filtered through a celite pad, washed with ethyl ether and concentrated in vacuo to give an assumed quantitative yield of the crude product as a red oil: $^1$H NMR (dmso-$d_6$/300 MHz) 4.04 (q, 2H, J=7.05 Hz), 1.54-1.44 (m, 6H), 1.34-1.21 (m, 12H), 0.96-0.78 (m, 15H).

Step 2. Preparation of ethyl 8-(ethoxyethvnyl)-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (01597/1 PR) (10.6 g, 21.9 mmole), crude tributyl(ethoxyethynyl)stannane prepared as in Step 1 (10.4 g, 28.5 mmole assumed), triethylammonium chloride (3.63 g, 21.9 mmole) and Pd (PPh$_3$)$_2$ (0.769 g, 1.10 mmole) in DMF (140 mL) was stirred at room temperature overnight. The mixture was hen diluted with H$_2$O and extracted with ethyl ether (2×200 mL). The combined extracts were washed with brine, dried over MgSO$_4$, filtered and concentrated in vacuo. Purification by silica chromatography (5%-6.5% EtOAc:hexanes gradient) gave 4.06 g (44% yield) of the product as a yellow crystalline solid: $^1$H NMR (dmso-$d_6$/300 MHz) 7.95 (s, 1H), 7.55 (d, 1H, J=2.0 Hz), 7.37 (d, 1H, J=2.2 Hz), 6.11 (q, 1H, J=7.3 Hz), 4.32-4.20 (m, 4H), 1.39 (t, 3H, J=7.1 Hz), 1.26 (t, 3H, J=7.2 Hz).

Step 3. Preparation of ethyl 8-(2-ethoxy-2-oxoethyl)-6-(trifluoromethoxy)-2-(trifluoromethyl)-2H-chromene-3-carboxylate A solution of ethyl 8-(ethoxyethynyl)-6-(trifluoromethoxy)-2-(trifluoromethyl)-2H-chromene-3-carboxylate prepared as in Step 2 (1.73 g, 4.08 mmole) in a mixture of acetone (32 mL) and H$_2$O (8 mL) was treated with H$_2$SO$_4$ (0.800 g, 8.15 mmole) and the resulting mixture was stiffed at room temperature for 2.5 hrs. Saturated NaHCO$_3$ (200 mL) and then solid K$_2$CO$_3$ were then added and the product was extracted with EtOAc (300 mL). The EtOAc solution was washed with brine, dried over MgSO$_4$, filtered and concentrated in vacuo. The crude product was purified by silica chromatography (0%-15% EtOAc-hexanes gradient) to give 1.47 g (82% yield) of the product as a yellow crystalline solid: EIHRMS m/z 442.0880 (M+, C$_{18}$H$_{16}$F$_6$O$_6$, Calc'd 442.0851).

Step 4. Preparation of 8-(carboxymethyl)-6-(trifluoromethoxy)-2-(trifluoromethyl)-2H-chromene-3-carboxylic acid The ester from Step 1 was hydrolyzed via a method similar to that described in Example 621a, Step 2 to give the product as a pale yellow solid: ESHRMS m/z 385.0143 (M–H, C$_{14}$H$_7$F$_6$O$_6$, Calc'd 385.0152); $^1$H NMR (dmso-$d_6$, 300 MHz) 13.3 (brs, 1H), 12.6 (brs, 1H), 7.90 (s, 1H), 7.53 (d, 1H, J=2.4 Hz), 7.38 (d, 1H, J=2.2 Hz), 5.98 (q, I1H, J=7.2 Hz), 3.67-3.55 (m, 2H).

EXAMPLE 621t

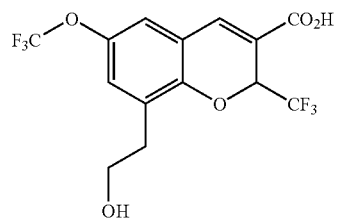

8-(2-hydroxyethyl)-6-(trifluoromethoxy)-2-(trifluoromethyl)-2H-chromene-3-carboxylic acid

Step 1. Preparation of 8-(ethoxvethvnyl)-6-(trifluoromethoxy)-2-(trifluoromethyl)-2H-chromene-3-carboxylic acid The ester from Example 21 s, Step 2 was hydrolyzed via a method similar to that described in Example 621 a, Step 2 using HOAc in the acidification step to give the product as a yellow solid: ESLRMS m/z 397.0 (M+H, C$_{16}$H$_{10}$F$_6$O$_5$, Calc'd 396.0).

Step 2. Preparation of 8-(2-ethoxy-2-oxoethyl)-6-(trifluoromethoxy)-2-(trifluoromethyl)-2H-chromene-3-carboxylic acid To a solution of the crude product from Step 1 (2.13 g) in a mixture of acetone (80 mL) and H$_2$O (10 mL) was added H$_2$SO$_4$ (0.250 g, 2.55 mmole) and the resulting mixture was stirred at room temperature for 2.5 hrs. Brine (200 mL) was added and the mixture was extracted with EtOAc (2×100 mL). The combined extracts were washed with brine, dried over MgSO$_4$, filtered and concentrated in vacuo to give 2.10 g of the crude product as a yellow oil: ESLRMS m/z 414.0 (M+H, C$_{16}$H$_{12}$F$_6$O$_6$, Calc'd 415.0).

Step 3. Preparation of 8-(2-hydroxyethyl)-6-(trifluoromethoxy)-2-(trifluoromethyl)-2H-chromene-3-carboxylic acid To a solution of crude ethyl 8-(2-ethoxy-2-oxoethyl)-6-(trifluoromethoxy)-2-(trifluoromethyl)-2H-chromene-3-carboxylate prepared as in Example 621s, Step 2. (2.10 g) in 1:1 THF-ethanol (100 mL) was added NaBH$_4$ (3.00 g, 79.3 mmole) and the mixture was stirred at room temperature for 1h. Additional NaBH$_4$ (3.00 g, 79.3 mmole) was then added and the mixture was stirred for 4 hrs. Additional NaBH$_4$ (3.00 g, 79.3 mmole) was then added and the mixture was stirred for 3hrs. H$_2$O (50 mL) was added and the mixture was stirred for 30 minutes. Brine (100 mL) was added; the mixture was acidified with 1N HCl and extracted with EtOAc (2×200 mL). The combined extracts were washed with brine (100 mL), dried over MgSO$_4$, filtered and concentrated in vacuo. The crude product was purified by silica chromatography (25% EtOAc/1% HOAc in hexanes to 100% EtOAc/1% HOAc in hexanes) to give an off-white crystalline solid. Recrystallization from EtOAc-hexanes gave 427 mg (23% yield) of the product as an off-white crystalline solid: ESHRMS m/z 371.0334 (M−H, C$_{14}$H$_9$F$_6$O$_5$, Calc'd 371.0354); $^1$H NMR (dmso-d$_6$/300 MHz) 13.40 (brs, 1H), 7.88 (s, 1H), 7.45 (d, 1H, J=2.2 Hz), 7.28 (d, 1H, J=2.4 Hz), 5.99 (q, 1H, J=7.3 Hz), 4.70 (s, 1H), 3.57 (s, 2H), 2.77-2.71 (m, 2H).

EXAMPLE 621u

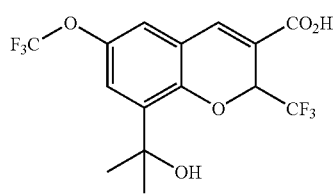

8-(1-hydroxy-1-methylethyl)-6-(trifluoromethoxy)-2-(trifluoromethyl)-2H-chromene-3-carboxylic acid

Step 1. Preparation of ethyl 8-acetyl-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (9.64 g, 20.0 mmole), n-buytylvinyl ether (12.9 mL, 100 mmole), Pd(OAc)$_2$ (135 mg, 0.600 mmole), DPPP (544 mg, 1.32 mmole) and K$_2$CO$_3$ (3.32 g, 24.0 mmole), in a mixture of DMF (50 mL) and H$_2$O (6 mL) was stirred at 100° C. for 46 hrs. After the mixture was cooled to room temperature, 1N HCl (100 mL) was then added and the mixture was extracted with EtOAc (2×200 mL). The extracts were combined and washed with H$_2$O (200 mL), brine (100 mL), dried over MgSO$_4$ and filtered. The solvent was removed in vacuo and the crude product was purified by silica chromatography (20% EtOAc in hexanes with 1% HOAc) to give 2.12 g (29% yield) of 8-acetyl-6-(trifluoromethoxy)-2-(trifluoromethyl)-2H-chromene-3-carboxylic acid prepared as in Example 21b as well as 1.44 g (18% yield) of the title compound as a yellow crystalline solid: ESHRMS m/z 399.0654 (M+H, C$_{16}$H$_{13}$F$_6$O$_5$, Calc'd 399.0662).

Step 2. Preparation of ethyl 8-(1-hydroxy-1-methylethyl)-6-(trifluoromethoxy-2-(trifluoromethyl)-2H-chromene-3-carboxylate To a solution of ethyl 8-acetyl-6-(trifluoromethoxy)-2-(trifluoromethyl)-2H-chromene-3-carboxylate prepared as in Step 1 (1.35 g, 3.39 mmole) in anhydrous THF (40 mL) at −78° C. under a dry N$_2$ atmosphere was added methylmagnesium bromide (1.30 mL-3.0 M in ether ether, 3.90 mmole) dropwise over 5 minutes. The mixture was stirred at −78° C. for 2 h, was then allowed to warrn to room temperature over 1 h and was then quenched with saturated NH$_4$Cl (20 mL). After stirring overnight, brine (100 mL) was added and the mixture was extracted with EtOAc (2×200 mL). The combined extracts were washed with brine (50 mL), dried over MgSO$_4$, filtered and concentrated in vacuo to give a yellow oil. The crude product was purified by silica chromatography (0%-20% EtOAc in hexanes) to give 700 mg (50% yield) of the product as a yellow crystalline solid: EIHRMS m/z 414.0895 (M−H, C$_{17}$H$_{16}$F$_6$O$_5$, Calc'd 414.0902).

Step 3. Preparation of 8-(1-hydroxy-1-methylethyl)-6-(trifluoromethoxy)-2-(trifluoromethyl)-2H-chromene-3-carboxylic acid The ester from Step 2 was hydrolyzed via a method similar to that described in Example 621c, Step 2 to give the product as an off-white solid: ESHRMS m/z 385.0498 (M−H, C$_{15}$H$_{11}$F$_6$O$_5$, Calc'd 385.0511); $^1$H NMR (dmso-d$_6$, 300 MHz) 13.40 (brs, 1H), 7.87 (s, 1H), 7.58 (d, 1H), J=2.6 Hz), 7.47 (d, 1H, J=2.6 Hz), 6.05 (q, 1H, J=7.3 Hz), 5.39 (s, 1H), 1.50 (s, 3H), 1.46 (s, 3H).

EXAMPLE 621v

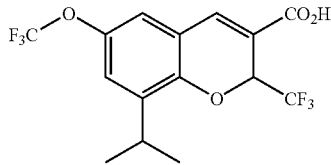

8-isopropyl-6-(trifluoromethoxy)-2-(trifluoromethyl)-2H-chromene-3-carboxylic acid To a solution of 8-(1-hydroxy--methylethyl)-6-(trifluoromethoxy)-2-(trifluoromethyl)-2H-chromene-3-carboxylic acid prepared as in Example 621 u, Step 3 (200 mg, 0.518 mmole) in anhydrous CH$_2$Cl$_2$ (10 mL) was added triethylsilane (414 uL, 2.59 mmole) and the mixture was stirred for 5 minutes. TFA (400 uL, 5.18 mmole) was then added and the mixture was stirred at room temperature for 20 hrs. Additional triethylsilane (8.18 mL, 51.8 mmole) was then added, the mixture was stirred for 2 hrs and additional TFA (4.00 mL, 51.8 mmole) was added and the mixture was stirred at room temperature for 6 days. The mixture was concentrated in vacuo and the crude product was purified by reverse phase chromatography (acetonitrile: 0.05% TFA-H$_2$O) to give 150 mg (78% yield) of the product as a white crystalline solid: ESHRMS m/z 369.0526 (M−H, C$_{15}$H$_{11}$F$_6$O$_4$, Calc'd 369.0562); $^1$H NMR (dmso-d$_6$/300 MHz) 13.39 (brs, 1H), 7.87 (s, 1H), 7.44 (d, 1H, J=1.8 Hz), 7.27 (d, 1H, J=2.6 Hz), 6.01 (q, 1H, J=7.3 Hz), 3.24-3.17 (m, 1H), 1.18 (d, 3H, J=7.0 Hz), 1.16 (d, 3H, J=6.9 Hz).

EXAMPLE 621w

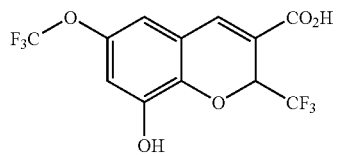

8-hydroxy-6-(trifluoromethoxy)-2-(trifluoromethyl)-2H-chromene-3-carboxylic acid Step 1. Preparation of ethyl 8-(4,4,5,5-tetramethyl-1,3,2-dioxaborolan-2-yl)-6-(trifluoromethoxy)-2-(trifluoromethyl)-2H-chromene-3-carboxylate A mixture of ethyl 8-iodo-6-(trifluoromethoxy)-2-(trifluoromethyl)-2H-chromene-3-carboxylate prepared as in Example 21a, Step 2 (2.01 g, 4.16 mmole), pinicolborane (1.81 mL, 12.5 mmole), Pd(dppf)ClCH$_2$Cl$_2$ (170 mg, 0.208 mmole) and TEA (2.32 mL, 16.6 mmole) in anhydrous dioxane (10.0 mL) was heated to 80° C. for 2 days. Additional pinicolborane (1.81 mL, 12.5 mmole) and Pd(dppf)Cl CH$_2$Cl$_2$ (170 mg, 0.208 mmole) was added and the mixture was heated as before for 20 hrs. The mixture was poured into brine (100 mL) and extracted with EtOAc (200 mL). The extract was dried over MgSO$_4$, filtered and concentrated in vacuo. The crude product was purified by silica chromatography (0%-60% EtOAc in hexanes) to give 1.18 g (59% yield) of the product as a yellow oil: $^1$H NMR (dmso-d$_6$/300 MHz) 7.95 (s, 1H), 7.73 (d, 1H, J=2.6 Hz), 7.42 (d, 1H, J=2.2 Hz), 6.00 (q, 1H, J=7.3 Hz), 4.29-4.19 (m, 2H), 1.27-1.23 (m, 15H).

Step 2. Preparation of ethyl 8-hydroxy-6-(trifluoromethoxy)-2-(trifluoromethyl)-2H-chromene-3-carboxylate To a solution of ethyl 8-(4,4,5,5-tetramethyl-1,3,2-dioxaborolan-2-yl)-6-(trifluoromethoxy)-2-(trifluoromethyl)-2H-chromene-3-carboxylate prepared as in Step 1 (600 mg, 1.24 mmole) in THF (20. mL) was added 30% H$_2$O$_2$ (192uL, 1.86 mmole) and aqueous NaOH (500 uL-2.5 N, 1.25 mmole) at 0° C. and the mixture was allowed to warm to room temperature. After stirring for 3.5 hrs, the mixture was acidified with 1N HCl, brine (50 mL) was added and the mixture was extracted with EtOAc (200 mL). The extract was dried over MgSO$_4$, filtered and concentrated in vacuo to give a yellow crystalline solid. The crude product was purified by silica chromatography (0%-25% EtOAc in hexanes) to give 422 mg (91% yield) of the product as an off-white solid: EIHRMS m/z 372.0421 (M+, C$_{14}$H$_{10}$F$_6$O$_5$, Calc'd 372.0432).

Step 3. Preparation of 8-hydroxy-6-(trifluoromethoxy)-2-(trifluoromethyl)-2H-chromene-3-carboxylic acid The ester from Step 2 was hydrolyzed via a method similar to that described in Example 621c, Step 2 to give the product as an off-white solid: ESHRMS m/z 343.0047 (M−H, C$_{12}$H$_5$F$_6$O$_5$, Calc'd 343.0036); $^1$H NMR (dmso-d$_6$, 300 MHz) 13.39 (brs, 1H), 10.33 (brs, 1H), 7.80 (s, 1H), 7.02 (d, 1H, J=1.8 Hz), 6.84 (d, 1H, J=2.0 Hz), 5.90 (q, 1H, J=7.3 Hz).

EXAMPLE 621x

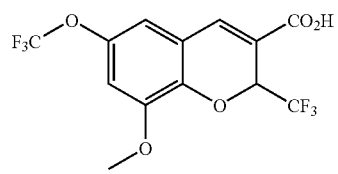

8-methoxy-6-(trifluoromethoxy)-2-(trifluoromethyl)-2H-chromene-3-carboxylic acid Step 1. Preparation of ethyl 8-methoxy-6-(trifluoromethoxy)-2-(trifluoromethyl)-2H-chromene-3-carboxylate A mixture of ethyl 8-hydroxy-6-(trifluoromethoxy)-2-(trifluoromethyl)-2H-chromene-3-carboxylate prepared as in Example 621w, Step 2 (165 mg, 0.442 mmole), iodomethane (82.8 uL, 1.33 mmole), KI (7.34 mg, 0.0442 mmole), K$_2$CO$_3$ (184 mg, 1.33 mmole) in anhydrous DMF (5.0 mL) was stirred at room temperature for 17 hrs. The mixture was then poured into brine (100 mL) and extracted with EtOAc (2×100 mL). The combined extracts were washed with brine, dried over MgSO$_4$, filtered and concentrated in vacuo to give a tan solid. The crude product was purified by silica chromatography (0%-25% EtOAc in hexanes) to give an assumed quantitative yield of the product as an off-white crystalline solid: EIHRMS m/z 386.0593 (M+, C$_{15}$H$_{12}$F$_6$O$_5$, Calc'd 386.0589).

Step 2. Preparation of 8-methoxy-6-(trifluoromethoxy)-2-(trifluoromethyl)-2H-chromene-3-carboxylic acid The ester from Step 1 was hydrolyzed via a method similar to that described in Example 621c, Step 2 to give the product as an off-white solid: ESHRMS m/z 397.0217 (M−H, C$_{13}$H$_7$F$_6$O$_5$, Calc'd 357.0192). $^1$H NMR (dmso-d$_6$, 300 MHz) 13.53 (brs, 1H), 7.88 (s, 1H), 7.18 (s, 7H), 7.15 (d, 1H, J=2.2 Hz), 5.98 (q, 1 H, J=7.3 Hz), 3.83 (s, 3H).

EXAMPLE 621y

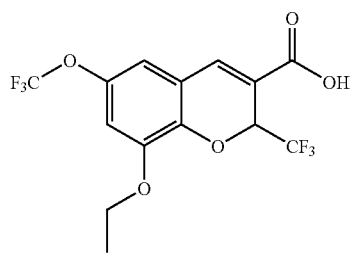

8-ethoxy-6-(trifluoromethoxy)-2-(trifluoromethyl)-2H-chromene-3-carboxylic acid

Step 1. Preparation of ethyl 8-ethoxy-6-(trifluoromethoxy)-2-(trifluoromethyl)-2H-chromene-3-carboxylate The title compound was prepared via a method similar to that in Example 621x, Step 1 which gave the product as an off-white solid: EIHRMS m/z 400.0723 (M+, $C_{16}H_{14}F_6O_5$, Calc'd 400.0745).

Step 2. Preparation of 8-ethoxy-6-(trifluoromethoxy)-2-(trifluoromethyl)-2H-chromene-3-carboxylic acid The ester from Step 1 was hydrolyzed via a method similar to that described in Example 621c, Step 2 to give the product as an off-white solid: ESHRMS m/z 371.0306 (M−H, $C_{14}H_9F_6O_5$, Calc'd 371.0349); $^1$H NMR (dmso-$d_6$, 300 MHz) 13.41 (brs, 1H), 7.85 (s, 1H), 7.17 (s, 1H). 7.13 (d, 1H, J=2.4 Hz), 6.00 (q, 1H, J=7.3 Hz), 4.17-4.02 (m, 2H), 1.30 (t,3H, J=7.1 Hz).

EXAMPLE 622

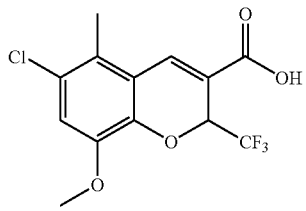

6-chloro-8-methoxy-5-methyl-2-(trifluoromethyl)-2H-chromene-3-carboxylic acid

Step 1. Preparation of ethyl 8-methoxy-5-methyl-2-(trifluoromethyl)-2H-chromene-3-carboxylate The ethyl 5-bromo-8-methoxy-2-(trifluoromethyl)-2H-chromene-3-carboxylate from Example 24 a, Step 1 (2.3 g, 6.037 mmole), trimethylboroxine (0.84 mL, 6.04 mmole), $PdCl_2(dppf)_2 \cdot CH_2Cl_2$ (0.487 g, 0.604 mmole), and $Cs_2CO_3$ (5.9 g, 18.11 mmole) were mixed in dioxane with 10% water (15 mL). The mixture was heated to 110° C. for 6 hrs and r.t overnight. The mixture was diluted with EtOAc, the organic layer was washed with water and dried over $MgSO_4$. The filtrate was concentrated and purified by Biotage chromatography with 5% EtOAc in hexane to give 1.41 g a yellow solid (74%): LCMS m/z 317.15 (M+H) at 6.225 min.

Step 2. Preparation of ethyl 6-chloro-8-methoxy-5-methyl-2-(trifluoromethyl)-2H-chromene-3-carboxylate The ethyl 6-chloro-8-methoxy-5-methyl-2-(trifluoromethyl)-2H-chromene-3-carboxylate was prepared as a yellow oil (100%) by a procedure similar to the method described in Example 619b, Step 1, which has suitable purity to use without further purification.

Step 3. Preparation of 6-chloro-8-methoxy-5-methyl-2-(trifluoromethyl)-2H-chromene-3-carboxylic acid The 6-chloro-8-methoxy-5-methyl-2-(trifluoromethyl)-2H-chromene-3-carboxylic acid was prepared as white solid (yield 20.5%) by a procedure similar to the method described in Example 602a, Step 2: ESHRMS m/z 321.0163 (M−H, $C_{13}H_9O_4F_3Cl$, Calc'd 321.0136). $^1$H NMR (acetone-$d_6$/400 MHz) 8.01 (s, 1H), 7.16 (s, 1H), 5.83 (q, 1H, J=7.2 Hz), 3.88 (s, 3H), 2.42 (s, 3H).

EXAMPLE 623a

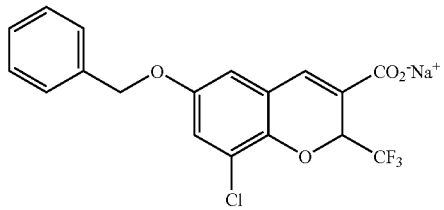

sodium 6-(benzyloxy)-8-chloro-2-(trifluoromethyl)-2H-chromene-3-carboxylate

To a solution of the carboxylic acid prepared as in Example 17d, Step 2 (332.8 mg, 0.8650 mmole) in EtOH (10 mL) was added aqueous NaOH (1.728 mL-0.5006 N, 0.8650 mmole). The solvent was removed in vacuo and the resulting solid was redissolved in water and filtered to remove haziness. The solvent was removed in vacuo and the resulting solid was dried in high vacuum to give 293 mg (86% yield) of the product as a yellow crystalline solid: $^1$H NMR (dmso-$d_6$/300 MHz) 7.44-7.29 (m, 5H), 7.20 s, 1H), 6.99 (s, 2H), 5.91 (q, J=7.5 Hz, 1H), 5.04 (s, 2H).

EXAMPLE 623b

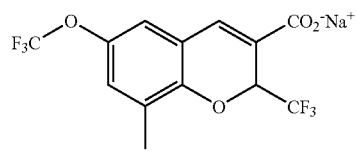

sodium 8-methyl-6-(trifluoromethoxy)-2-(trifluoromethyl)-2H-chromene-3-carboxylate Sodium 8-methyl-6-(trifluoromethoxy)-2-(trifluoromethyl)-2H-chromene-3-carboxylate was prepared via a method similar to that described in Example 623a using the carboxylic acid from Example 21b, Step 2 to give the product as an off-white solid: $^1$H NMR (dmso-$d_6$/300 MHz) 7.23 (s, 1H), 7.17 (m, 1H), 7.09 (m, 1H), 5.93 (q, J=7.5 Hz, 1H), 2.16 (s, 31H).

EXAMPLE 623c

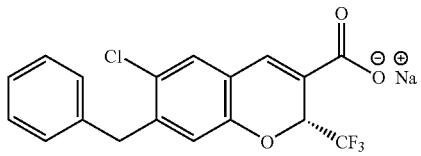

sodium (2R)-7-benzyl-6-chloro-2-(trifluoromethyl)-2H-chromene-3-carboxylate

The (2R)-7-benzyl-6-chloro-2-(trifluoromethyl)-2H-chromene-3-carboxylic acid from Example 91 was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-$d_6$/400 MHz) 7.81 (s, 1H), 7.61 (s, 1H), 7.25-7.29 (m, 2H), 7.17-7.19 (m, 3H), 6.99 (s, 1H), 5.89 (q, 1H, J=7.1 Hz), 4.00 (s, 2H).

EXAMPLE 623d

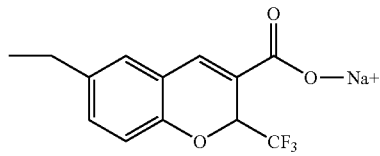

sodium 6-ethyl-2-(trifluoromethyl)-2H-chromene-3-carboxylate

The sodium 6-ethyl-2-(trifluoromethyl)-2H-chromene-3-carboxylate was prepared by the procedure similar to that described in Example 623a using the carboxylic acid from Example 34a. $^1$H NMR (DMSO-$d_6$/300 MHz) 7.21 (s, 1H), 7.08 (d, 1H, J=1.6 Hz), 7.00 (dd, 1H, J=8.1, 1.6 Hz), 6.79 (d, 1H, J=8.1 Hz), 5.83 (q, 1H, J=7.2 Hz), 2.51 (q, 2H, J=7.5 Hz), 1.14 (t, 3H, J=7.5 Hz).

EXAMPLE 623e

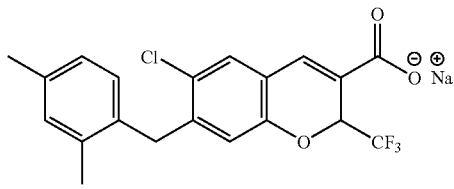

sodium 6-chloro-7-(2,4-dimethylbenzyl)-2-(trifluoromethyl)-2H-chromene-3-carboxylate The 6-chloro-7-(2,4-dimethylbenzyl)-2-(trifluoromethyl)-2H-chromene-3-carboxylic acid from Example 9s, Step 7 was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-$d_6$/400 MHz) 7.81 (s, 1H), 7.64 (s, 1H), 7.00 (s, 1H), 6.92 (d, 1H, J=8.0 Hz), 6.81 (d, 1H, J=7.7 Hz), 6.53 (s, 1H), 5.86 (q, 1H, J=7.1 Hz), 3.91 (s, 2H), 2.22 (s, 3H), 2.10 (s, 3H).

EXAMPLE 623f

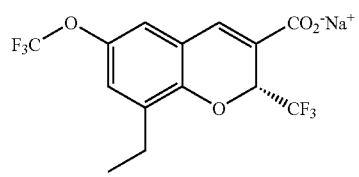

sodium (2R)-8-ethyl-6-(trifluoromethoxy)-2-(trifluoromethyl)-2H-chromene-3-carboxylate The sodium (2R)-8-ethyl-6-(trifluoromethoxy)-2-(trifluoromethyl)-2H-chromene-3-carboxylate was prepared via a method similar to that described in Example 623a using the carboxylic acid from Example 211 to give the product as an off-white solid: $^1$H NMR (dmso-$d_6$/300 MHz) 7.25 (s, 1H), 7.18 (m, 1H), 7.07 (m, 1H), 5.94 (q, J=7.6 Hz, 1H), 2.68-2.51 (m, 2H), 1.11 (t, J=7.3 Hz).

EXAMPLE 623g

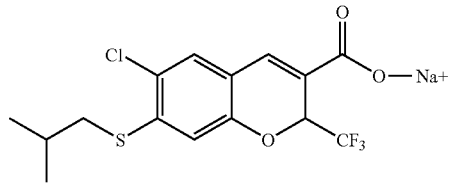

sodium 6-chloro-7-(isobutylthio)-2-(trifluoromethyl)-2H-chromene-3-carboxylate

The sodium 6-chloro-7-(isobutylthio)-2-(trifluoromethyl)-2H-chromene-3-carboxylate was prepared by the procedure similar to that described in Example 623a using the carboxylic acid from Example 7d, CASE 01598/1PR. $^1$H NMR (D$_2$O/400 MHz) 7.12 (s, 1H), 7.00 (s, 1H), 6.62 (s, 1H), 5.61 (q, 1H, J=7.0 Hz), 3.08 (m, 2H), 2.63 (m, 1H), 0.97 (m, 6H).

EXAMPLE 623h

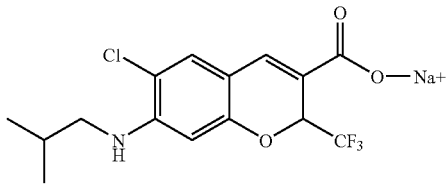

sodium 6-chloro-7-(isobutylamino)-2-(trifluoromethyl)-2H-chromene-3-carboxylate

The sodium 6-chloro-7-(isobutylamino)-2-(trifluoromethyl)-2H-chromene-3-carboxylate was prepared by the procedure similar to that described in Example 623a using the carboxylic acid from Example 608b. $^1$H NMR (D$_2$O/400 MHz) 7.20 (s, 1H), 7.09 (s, 1H), 6.25 (s, 1H), 5.60 (q, 1H, J=7.0 Hz), 2.86 (m, 2H), 1.78 (m, 1H), 0.80 (m, 6H).

EXAMPLE 623i

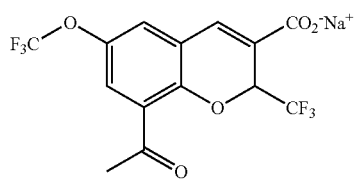

sodium 8-acetyl-6-(trifluoromethoxy)-2-(trifluoromethyl)-2H-chromene-3-carboxylate The sodium 8-acetyl-6-(trifluoromethoxy)-2-(trifluoromethyl)-2H-chromene-3-carboxylate was prepared via a method similar to that described in Example 623a using the carboxylic acid from Example 621b to give the product as a tan solid: $^1$H NMR (dmso-d$_6$/300 MHz) 7.65 (d, 1H, J=2.8 Hz), 7.41 (d, 1H, J=2.2 Hz), 7.37 (s, 1H), 6.10 (q, 1H, J=7.5 Hz), 2.57 (s, 3H).

EXAMPLE 623j

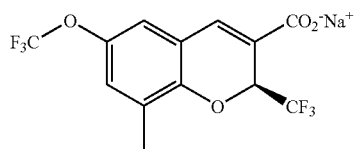

sodium (2S)-8-methyl-6-(trifluoromethoxy)-2-(trifluoromethyl)-2H-chromene-3-carboxylic acid The sodium (2S)-8-methyl-6-(trifluoromethoxy)-2-(trifluoromethyl)-2H-chromene-3-carboxylic acid was prepared via a method similar to that described in Example 623a using the carboxylic acid from Example 621e to give the product as an off-white solid: ESLRMS m/z 343.0 (M+H, C$_{13}$H$_9$F$_6$O$_4$, Calc'd 343.0).

EXAMPLE 623k

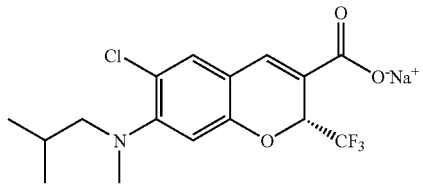

sodium (2R)-6-chloro-7-[isobutyl(methyl)amino]-2-(trifluoromethyl)-2H-chromene-3-carboxylate The sodium (2R)-6-chloro-7-[isobutyl(methyl)amino]-2-(trifluoromethyl)-2H-chromene-3-carboxylate was prepared by the procedure similar to that described in Example 623a using the carboxylic acid from Example 608f. $^1$H NMR (D$_2$O/400 MHz) 7.21 (s, 1H), 7.12 (s, 1H), 6.62 (s, 1H), 5.61 (q, 1H, J=7.0 Hz), 2.67 (m, 2H), 2.52 (s, 3H), 1.71 (m, 1H), 0.68 (m, 6H).

EXAMPLE 623l

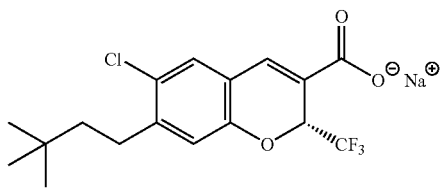

sodium (2R)-6-chloro-7-(3,3-dimethylbutyl)-2-(trifluoromethyl)-2H-chromene-3-carboxylate The (2R)-6-chloro-7-(3,3-dimethylbutyl)-2-(trifluoromethyl)-2H-chromene-3-carboxylic acid from Example 609g was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-d$_6$/400 MHz) 7.80 (s, 1H), 7.55 (s, 1H), 7.01 (s, 1H), 5.89 (q, 1H, J=7.1 Hz), 3.30 (m, 2H), 2.56-2.60 (m, 2H), 1.31-1.37 (m, 2H), 0.91 (s, 9H).

EXAMPLE 623m

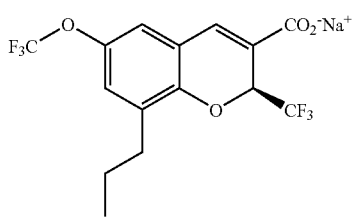

sodium (2S)-8-propyl-6-(trifluoromethoxy)-2-(trifluoromethyl)-2H-chromene-3-carboxylate The sodium (2S)-8-propyl-6-(trifluoromethoxy)-2-(trifluoromethyl)-2H-chromene-3-carboxylate was prepared via a method similar to that described in Example 623a using the carboxylic acid from Example 621h to give the product as an off-white solid: $^1$H NMR (dmso-d$_6$/300 MHz) 7.26 (s, 1H), 7.20 (s, 1H), 7.06 (s, 1H), 5.95 (q, 1H, J=7.5 Hz), 2.79-2.44 (m, 2H), 1.59-1.49 (m, 2H), 0.87 (t, 3H, J=7.3 Hz).

EXAMPLE 623n

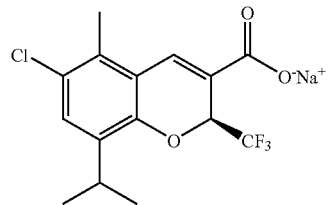

sodium (2S)-6-chloro-8-isopropyl-5-methyl-2-(trifluoromethyl)-2H-chromene-3-carboxylate The sodium (2S)-6-chloro-8-isopropyl-5-methyl-2-(trifluoromethyl)-2H-chromene-3-carboxylate was prepared by the procedure similar to that described in Example 623a using the carboxylic acid from Example 606c. $^1$H NMR (D$_2$O/400 MHz) 7.54 (s, 1H), 7.12 (s, 1H), 5.64 (q, 1H, J=7.0 Hz), 3.08 (m, 1H), 2.22 (s, 3H), 1.01 (m, 6H).

EXAMPLE 623o

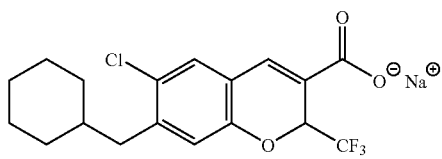

sodium 6-chloro-7-(cyclohexylmethyl)-2-(trifluoromethyl)-2H-chromene-3-carboxylate The 6-chloro-7-(cyclohexylmethyl)-2-(trifluoromethyl)-2H-chromene-3-carboxylic acid from Example 609i was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-d$_6$/400 MHz) 7.79 (s, 1H), 7.54 (s, 1H), 6.93 (s, 1H), 5.89 (q, 1H, J=7.1 Hz), 2.48-2.54 (m, 2H), 1.50-1.58 (m, 6H), 1.02-1.11 (m, 3H), 0.91-0.097 (m, 2H).

EXAMPLE 623p

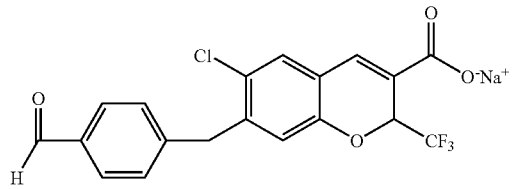

sodium 6-chloro-7-(4-formylbenzyl)-2-(trifluoromethyl)-2H-chromene-3-carboxylate The sodium 6-chloro-7-(4-formylbenzyl)-2-(trifluoromethyl)-2H-chromene-3-carboxylate was prepared by the procedure similar to that described in Example 623a using the carboxylic acid from Example 604g. $^1$H NMR (acetone-d$_6$/400 MHz) 10.00 (s, 1H), 7.84 (d, 2H, J=8.1 Hz), 7.58 (s, 1H), 7.42 (d, 2H, J=8.1 Hz), 7.18 (s, 1H), 6.76 (s, 1H), 6.00 (q, 1H, J=7.2 Hz), 4.08 (m, 2H, J=5.7 Hz).

EXAMPLE 623q

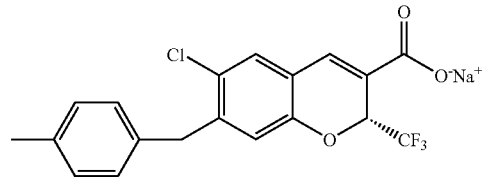

sodium (2R)-6-chloro-7-(4-methylbenzyl)-2-(trifluoromethyl)-2H-chromene-3-carboxylate The sodium (2R)-6-chloro-7-(4-methylbenzyl)-2-(trifluoromethyl)-2H-chromene-3-carboxylate was prepared by the procedure similar to that described in Example 623a using the carboxylic acid from Example 604e. $^1$H NMR (acetone-d$_6$/400 MHz) 7.42 (s, 1H), 7.18 (s, 1H), 7.08 (m, 4H), 6.69 (s, 1H), 5.91 (q, 1H, J=7.6 Hz), 3.96 (m, 2H), 2.25 (s, 3H).

EXAMPLE 623r

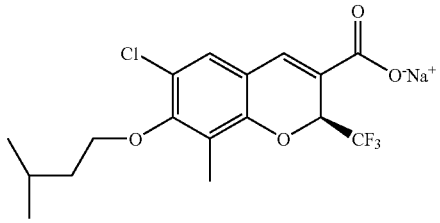

sodium (2S)-6-chloro-8-methyl-7-(3-methylbutoxy)-2-(trilluoromethyl)-2H-chromene-3-carboxylate The sodium (2S)-6-chloro-8-methyl-7-(3-methylbutoxy)-2-(trifluoromethyl)-2H-chromene-3-carboxylate was prepared by the procedure similar to that described in Example 623a using the carboxylic acid from Example 603b. $^1$H NMR (acetone-$d_6$/400 MHz) 7.51 (s, 1H), 6.96 (s, 1H), 6.06 (q, 1H, J=7.2 Hz), 3.85 (m, 2H), 1.89 (m, 1H), 1.62 (m, 2H), 0.95 (d, 6H, J=6.4 Hz).

EXAMPLE 623s

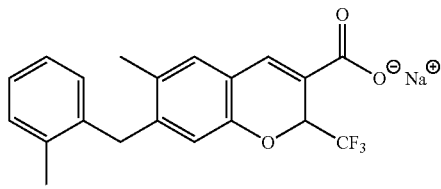

sodium 6-methyl-7-(2-methylbenzyl)-2-(trifluoromethyl)-2H-chromene-3-carboxylate The 6-methyl-7-(2-methylbenzyl)-2-(trifluoromethyl)-2H-chromene-3-carboxylic acid from Example 611f, Step 3 was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-$d_6$/400 MHz), 7.74 (s, 1H), 7.24 (s, 1H), 7.06-7.17 (m, 3H), 6.85 (d, 1H, J=7.7 Hz), 6.37 (s, 1H), 5.74 (q, 1H, J=7.1 Hz), 3.85 (s, 2H), 2.45 (s, 3H), 2.12 (s, 3H).

EXAMPLE 623t

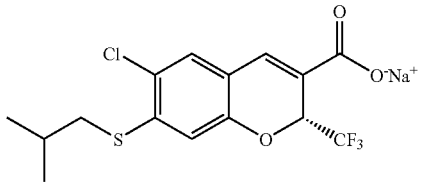

sodium (2R)-6-chloro-7-(isobutylthio)-2-(trifluoromethyl)-2H-chromene-3-carboxylate The sodium (2R)-6-chloro-7-(isobutylthio)-2-(trifluoromethyl)-2H-chromene-3-carboxylate was prepared by the procedure similar to that described in Example 623a using the carboxylic acid from Example 607c. $^1$H NMR (D$_2$O/400 MHz) 7.20 (s, 1H), 7.16 (s, 1H), 6.74 (s, 1H), 5.65 (q, 1H, J=7.0 Hz), 2.72 (m, 2H), 1.78 (m, 1H), 0.90 (m, 6H).

EXAMPLE 623u

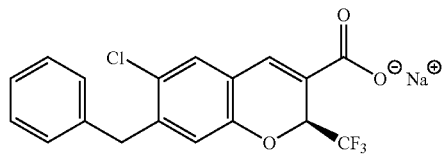

sodium (2S)-7-benzyl-6-chloro-2-(trifluoromethyl)-2H-chromene-3-carboxylate

The (2S)-7-benzyl-6-chloro-2-(trifluoromethyl)-2H-chromene-3-carboxylic acid from Example 9m was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-$d_6$/400 MHz) 7.81 (s, 1H), 7.61 (s, 1H), 7.25-7.29 (m, 2H), 7.17-7.19 (m, 3H), 6.99 (s, 1H), 5.89 (q, 1H, J=7.1 Hz), 4.00 (s, 2H).

EXAMPLE 623v

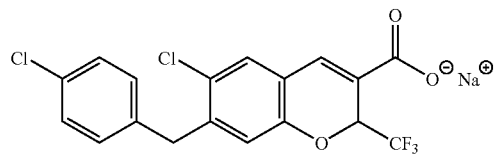

sodium 6-chloro-7-(4-chlorobenzyl)-2-(trifluoromethyl)-2H-chromene-3-carboxylate The 6-chloro-7-(4-chlorobenzyl)-2-(trifluoromethyl)-2H-chromene-3-carboxylic.

acid from Example 9o, Step 3 was dissolved in minimum amount of EtOH. NaOH (0.5016 N from Aldrich) (I eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-$d_6$/400 MHz) 7.82 (s, 1H), 7.61 (s, 1H), 7.33 (d, 2H, J=8.3 Hz), 7.20 (d, 2H, J=8.3 Hz), 7.03 (s, 1H), 5.91 (q, 1H, J=7.1 Hz), 4.00 (s, 2H).

EXAMPLE 623w

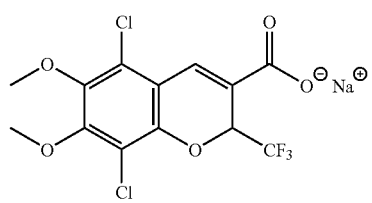

sodium 5,8-dichloro-6,7-dimethoxy-2-(trifluoromethyl)-2H-chromene-3-carboxylate The 5,8-dichloro-6,7-dimethoxy-2-(trifluoromethyl)-2H-chromene-3-carboxylic acid from Example 133, Step 2 was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (Methanol-$d_4$/400 MHz) 8.00 (s, 1H), 5.90 (q, 1H, J=7.1 Hz), 3.99 (s, 3H), 3.78 (s, 3H).

EXAMPLE 623x

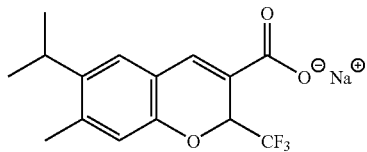

sodium 6-isopropyl-7-methyl-2-(trifluoromethyl)-2H-chromene-3-carboxylate

The (2S)-7-benzyl-6-chloro-2-(trifluoromethyl)-2H-chromene-3-carboxylic acid from Example 156 was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-$d_6$/400 MHz) 7.58 (s, 1H), 7.24 (s, 1H), 6.76 (s, 1H), 5.81 (q, 1H, J=7.5 Hz), 2.95-3.06 (m, 1H), 2.26 (s, 1H), 1.16 (s, 3H), 1.14 (s, 3H).

EXAMPLE 623z

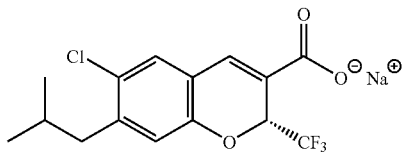

sodium (2R)-6-chloro-7-isobutyl-2-(trifluoromethyl)-2H-chromene-3-carboxylate The (2R)-6-chloro-7-isobutyl-2-(trifluoromethyl)-2H-chromene-3-carboxylic acid from Example 9e was dissolved in minimum amount of EtOH. NaOH (0.5016 N from Aldrich) (1 eq of free acid) was dropwise added to above solution through Burett. Solvent was removed in vacuo and the resulting solid was redissolved in water. The solvent was removed in vacuo and dried in high vacuo to produce the sodium salt. $^1$HNMR (DMSO-$d_6$/400 MHz) 7.81 (s, 1H), 7.5 (s, 1H), 6.97 (s, 1H), 5.89 (q, 1H, J=7.1 Hz), 2.51 (d, 2H, J=6.7 Hz), 1.85-1.89 (m, 1H), 0.843 (m, 6H).

Preparation of 6-Chloro-7-aryloxy-2-(trifluoromethyl)-2H-chromene-3-carboxylic Acids General Method for Preparation of 6-Chloro-7-aryloxy-2-(trifluoromethyl)-2H-chromene-3-carboxylic Acids by Parallel Synthesis

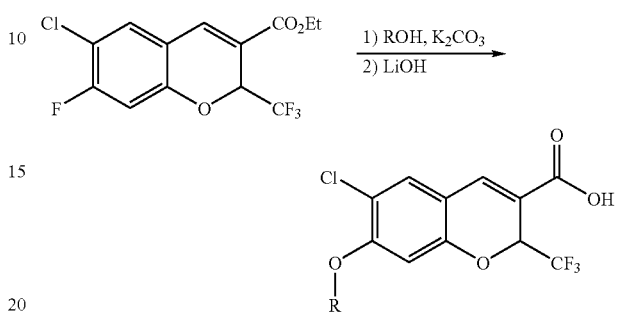

Step 1. Preparation of ethyl 6-chloro-7-(2-chloro-4,5-dimethylphenoxy)-2-(trifluoromethyl-2H-chromene-3-carboxylate To 325 mg (1.0 mmole) of ethyl 6-chloro-7-fluoro-2-(trifluoromethyl)-2H-chromene-3-carboxylate in 2.5 mL of DMF was added 172 mg (1.1 mmole) of 2-chloro-4,5-dimethylphenol and 193.5 mg (1.4 mmole) of potassium carbonate. The suspension was prepared in a capped vial and placed in an aluminum heating block equipped with a magnetic stirring. The aluminum block was heated to 100° C. for 16 hrs. After allowing the vial to cool, the mixture was treated with 10 mL of water and 2 mL of diethyl ether. The organic layer was removed and the aqueous layer was extracted two times with diethyl ether. Combined organic extracts were filtered through 5 g of silica and the silica was washed with 10 mL of diethyl ether. The filtrates were concentrated under a stream of $N_2$ to afford an off-white solid, which was used in the next step without further purification: 1H NMR (CDCl$_3$/300 MHz) 1.36 (t, 3H, J=7.2 Hz), 2.25, (s, 3H), 2.27 (s, 3H), 4.32 (m, 2H), 5.66 (q, 1H, J=6.8 Hz), 6.27 (s, 1H), 6.93 (2, 11H), 7.25 (s, 1H), 7.33 (s, 1H), 7.66 (s, 1H); $^{19}$F NMR (CDCl$_3$/300 MHz) –78.9 (d, 3F, J=6.2 Hz).

Step 2. Preparation of 6-Chloro-7-(2-chloro-4,5-dimetbylphenoxy)-2-(trifluoromethyl)-2H-chromene-3-carboxylic acid To the product of step 1 in a suitable vial was added 400 mg of lithium hydroxide monohydrate, 1 mL of water, 2 mL of methanol and 7 mL of THF. The vial was capped, in an aluminum heating block and the block was heated to 100° C. for 30 min. After allowing the vial to cool to rt, the mixture was treated with 5 mL of 1N HCl and 2 mL of diethyl layer. The organic layer was removed and the aqueous layer was extracted two times with diethyl ether. Combined organic extracts were concentrated by evaporation of solvent under a stream of $N_2$ followed by drying in vacuo to afford 150 mg (34.6%) of a yellow solid: $^1$H NMR (CDCl$_3$/300 MHz) 2.26 (s, 3H), 5.64 (q, 1H, J=6.8 Hz), 6.27 (s, 1H), 6.94 (s, 1H), 7.26 (s, 1H), 7.3H (s, 1H), 11.28 (hs, 1H); MS (ES–) 431 (M–1, 100); HRMS (ES–) m/z calcd for (M–H; C$_{19}$H$_{12}$Cl$_2$F$_3$O$_4$) 431.0059, found 431.0048.

Preparation of 6-Chloro-7-aryloxy-2-(trifluoromethyl)-2H-chromene-3-carboxylic Acids by a Parallel Method The following examples in Table 10 were prepared by the general method using parallel synthesis apparatus with each reaction carried out on 0.5 mmole scale. Products were purified as needed by reverse phase chromatography (C18 column, 40 mm i.d.×100 mm, gradient $CH_3CN/0.1\%$ TFA in $H_2O$).

TABLE 10

Yield, Purity and Mass Spectral Data for 6-Chloro-7-aryloxy-2-(trifluoromethyl)-2H-chromene-3-carboxylic acids prepared by Parallel Synthesis Methods.[1]

| Example # | LC (min) | MS (ES+) | HRMS | % Purity | % Yield |
|---|---|---|---|---|---|
| 700 | 3.248 | 429 | 427.0191 | 99 | 24 |
| 701 | 3.976 | 399 | 397.0449 | 99 | 24 |
| 702 | 3.499 | 401 | 399.0242 | 99 | 29 |
| 703 | 3.533 | 431 | 429.0347 | 99 | 27 |
| 704 | 3.491 | 413 | 411.0242 | 99 | 23 |
| 705 | 3.367 | 431 | 429.0347 | 99 | 22 |
| 706 | 3.545 | 477[2] | 476.9169[3] | 99 | 6 |
| 707 | 4.15 | 413 | 411.0605 | 99 | 23 |
| 708 | 3.302 | 399 | 397.0085 | 99 | 22 |
| 709 | 3.432 | 443 | 441.0347 | 99 | 30 |

[1]See General Experimental section for description of recorded data. LC indicates the chromatographic retention time in min. HRMS indicates the observed molecular ion (M-H) by high resolution mass spectometry in electrospray negative mode. % Purity was determined by ELS detection.
[2]Listed ion is the M + 1 of a ClBr cluster; (M + 1, 77; M + 3, 100).
[3]Electrospray negative mode, (M + 2 - 1) ion.

Preparation of 7-aryloxy-2-(trifluoromethyl)-2H-chromene-3-carboxylic Acids

Preparation of ethyl 7-fluoro-2-(trifluoromethyl)-2H-chromene-3-carboxylate

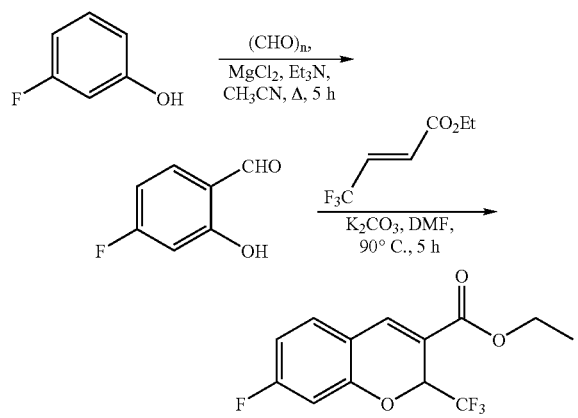

Step 1. Preparation of 2-hydroxy-4-Fluorobenzaldehyde

To the mixture of 3-fluorophenol (10 mL, 102 mmol), anhydrous magnesium chloride (28.2g, 744.6 mmol) in 500 mL of anhydrous acetonitrile was added anhydrous triethylamine (67 mL, 382.5 mmol) and paraformaldehyde (22.3g, 744.6 mmol). The mixture was then heated to reflux for five hrs. After cooling to room temperature, 500 mL of 5% aqueous hydrochloric acid was added. The product was extracted with ethyl acetate. The combined organic extracts were washed three times with 5% hydrochloric acid, brine, and dried over anhydrous magnesium sulfate. After removing the volatiles, the product was obtained as a light pink solid; 11 g, yield=72%. A small fraction was further purified on silica gel column with EtOAc/hexane mixture for further analytical characterization, it gave a white solid. M.P.=67.5-69.0° C. $^1$H NMR ($CDCl_3$/300 MHz) 11.40(s, 1H), 9.86(s, 1H), 7.62-7.57(m, 1H ), 6.79-6.67(m, 2H). $^{13}$C($CDCl_3$/300MH) 195.4, 168.3(d, J=258 Hz), 164.4(d, J=14.9 Hz), 136.3(d, J=12.6 Hz), 118.2(d, J=2.0 Hz), 108.5(d, J=23.3 Hz), 104.9(d, J=24.4 Hz). $^{19}$F ($CDCl_3$/400 MHz) -97.9(m). LC-MS couldn't observe the desired peak. HRMS (ES-) m/z calcd for ($C_7H_5FO_2$) 139.0201 (M-H), found 139.0211 (M-H).

Step 2. Preparation of ethyl 7-fluoro-2-(trifluoromethyl)-2H-chromene-3-carboxylate A mixture of 2-hydroxy-4-fluorobenzaldehyde (log, 71.4 mmol), ethyl 4,4,4-trifluorocrotonate (15 mL, 100 mmol), and anhydrous potassium carbonate (14.8 g, 107.1 mmol) in 40 ml dry dimethylformamide was heated to 90° C. for five hours. LC-MS indicated that the reaction was done. After cooling to room temperature, to the reaction was added 500 mL of ethyl acetate. The organic phase was washed with brine (×3), and was then dried over anhydrous magnesium sulfate. After removing the solvent, the residue was purified on silica gel column with 1:18 EtOAc/hexane. It gave 12.5 g (60%) product as a light yellow oil. $^1$H NMR ($CDCl_3$/300 MHz) 7.73(s, 1H), 7.30-7.22(m, 1H), 6.79-6.73(m, 2H), 5.76(q, J=6.9 Hz, 1H), 4.38(m, 2H), 1.37(t, J=7.2 Hz, 3H). $^{13}$C($CDCl_3$/300 MH) 167.2, 164.0, 163.9, 155.0(d, J=13.0 Hz), 136.3(d, J=1.28 Hz), 131.0(d, J=10.4 Hz), 123.5(q, J=287.5 Hz), 115.9(dd, J=2.4, 7.3 Hz), 110.2(d, J=22.5 Hz), 104.4(d, J=26.0 Hz), 71.0(q, J=33.2 Hz), 61.7(d, J=10.4 Hz), 14.4. $^{19}$F($CDCl_3$/300 MHz) -79.0(d, J=6.5 Hz), -104.8(m). LC-MS(ES+) 291.0(M+1, 100), HRMS (EI+) m/z calcd for ($C_{13}H_{10}F_4O_3$) 290.0566(M+), found 290.0586.

EXAMPLE 713

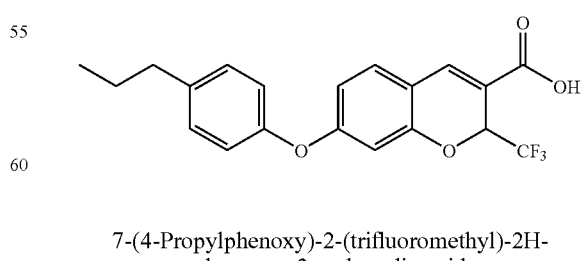

7-(4-Propylphenoxy)-2-(trifluoromethyl)-2H-chromene-3-carboxylic acid

To the mixture of ethyl 7-fluoro-2-(trifluoromethyl)-2H-chromene-3-carboxylate (0.29 g, 1.0 mmol) and potassium carbonate (0.21g, 1.4 mmol) was added 4-propylphenol (0.153 mL, 1.1 mmol) and 3 mL of dry DMF. The resulting mixture was heated at 110° C. for 15 hrs. LC-MS indicated that the reaction was done. To the reaction was added 15 mL of EtOAc. The resulting organic phase was washed with brine, and the volatiles were removed. To the residue was added 3 mL of THF, and a solution of lithium hydroxide hydrate (105 mg, 2.5 mmol) in 3 mL of water. Then to the resulting mixture was added 3 mL of ethanol. The resulting solution was heated at 80° C. for 5 hrs. LC-MS indicated that the reaction was completed. The volatiles were removed, the residue was diluted with water, and acidified at 0° C. with dilute HCl to pH=1.0, the product was extracted with ethyl acetate, and dried over anhydrous magnesium sulfate. After removing the volatiles, it gave a light yellow oil. The residue was purified on reverse phase HPLC. The product was obtained as a light yellow solid, 80 mg (21%). M.P.=143.5-146.5° C. $^1$H(CDCl$_3$/300 Mhz) 7.80(s, 1H), 7.18-7.13(m, 3H), 6.96(d, J=8.4 Hz, 2H), 6.59-6.52(m, 2H), 5.62(q, 1H, J=6.9 Hz), 2.57(t, 2H, J=6.9 Hz,), 1.67-1.57(m, 2H), 0.93(t, J=7.2 Hz, 3H). $^{13}$C NMR(CDCl$_3$/300 MHz)169.5, 163.6, 155.5, 153.0, 139.7(d, J=13.0 Hz), 131.4, 130.2(d, J=5.3 Hz), 123.7(q, J=287.6 Hz), 120.6, 119.8, 113.7, 112.8, 112.0, 105.0, 70.7(q, J=33.5 Hz), 73.6, 24.9, 14.1. $^{19}$F(CDCl$_3$/300 MHz) −78.96(d, J=6.9 Hz). LC-MS(EI+) 379.1 (M+1, 100). HRMS (EI+) m/z calcd for (C$_{20}$H$_{17}$F$_3$O$_4$) 378.1079(M$^+$), found 378.1061.

General Method for the Preparation of 7-aryloxy-2-(trifluoromethyl)-2H-chromene-3-carboxylic acids by a Parallel Synthesis Method

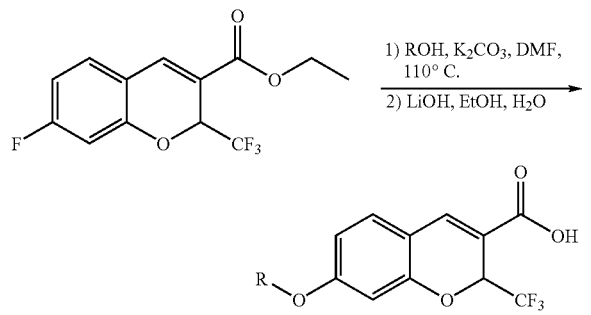

EXAMPLE 714

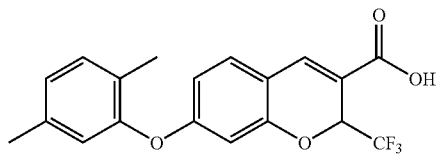

7-(2,5-Dimethylphenoxy)-2-(trifluoromethyl)-2H-chromene-3-carboxylic acid

Step 1. Preparation of ethyl 7-(2,5-dimethylphenoxy)-2-(trifluoromethyl)-2H-chromene-3-carboxylate To 0.200 g (0.689 mmole) of ethyl 7-fluoro-2-(trifluoromethyl)-2H-chromene-3-carboxylate in 2.5 mL of DMF was added 0.118 g (0.946 mmole) of 2,5-dimethyl phenol to the vessel followed by 0.131 g (0.946 mmole) of potassium carbonate. The suspension was prepared in a capped vial and placed in a J-KEM heating block equipped with shaker, condenser and nitrogen atmosphere. The block was heated to 110° C. for 20hrs. For work up, 10 mL of H$_2$O and 5 mL of ether was added to the mixture. The organic layer was separated and then the aqueous was extracted 3 times with ether. The product was then run through a pre-packed silica gel plug (20 mL, 5 g capacity) and the silica column washed with 4×5 mL aliquots of ether. Concentration of the solution afforded the product with was used directly in the next step without further purification.

Step 2. Preparation of 7-(2,5-Dimethylphenoxy)-2-(trifluoromethyl)-2H-chromene-3-carboxylic acid The product of Step 1 was dissolved in 4 mL of EtOH and 2 mL of THF. A solution of 0.116 g of LiOH in 4 mL of water was prepared and added to the organic solution. The reaction was capped and heated to 90° C. for 1 hour. After cooling to r.t, 6 mL of 1 N HCl and 3 mL of ether were added. The organic layer was separated and the aqueous was extracted twice with diethyl ether. The ether layers were concd under a stream of nitrogen and purified by reverse phase chromatography to afford 116 mg (46%) of a light yellow solid: $^1$H NMR (CD$_3$OD/400 MHz) 2.08 (s, 3H), 2.29 (s, 3H), 5.69 (q, 1H, J=6.8 Hz), 6.35 (d, 1H, J=2.0 Hz), 6.47 (dd, 1H, J=2 Hz, 8.0 Hz), 6.80 (s, 1H), 6.98 (d, 1H, J=7.6 Hz), 7.16 (d, 1H, J=8.0 Hz), 7.24 (d, 1H, J=8.4 Hz), 7.74 (s, 1H); MS (ES+) 365 (M+1, 100); LC-MS purity >95% (UV and ELSD) at 3.432 min. on UV spectra; HRMS (ES−) m/z calcd for (M−1; C$_{19}$H$_{14}$O$_4$F$_3$) 364.0922, found 364.0904.

Preparation of 7-aryloxy-2-(trifluoromethyl)-2H-chromene-3-carboxylic acids by Parallel Synthesis Method The following examples in Table 11 were prepared by the general method using parallel synthesis apparatus with each reaction carried out on 0.5 mmole scale. Products were purified as needed by reverse phase chromatography (C18 column, 40 mm i.d.×100 mm, gradient CH$_3$CN/0.1% TFA in H$_2$O).

TABLE 11

Yield, purity and Mass Spectral Data for 7-aryloxy-2-(trifluoromethyl)-2H-chromene-3-carboxylic acids prepared by Parallel Synthesis Methods.[1]

| Example # | LC (min) | MS (ES+) | HRMS | % Purity | % Yield |
|---|---|---|---|---|---|
| 715 | 3.07 | 395 | 393.058 | 99 | 11 |
| 716 | 3.806 | 365 | 363.0839 | 99 | 18 |
| 717 | 3.317 | 367 | 365.0631 | 99 | 29 |
| 718 | 3.298 | 397 | 395.0737 | 99 | 29 |
| 719 | 3.301 | 379 | 377.0631 | 99 | 16 |
| 720 | 3.175 | 397 | 395.0737 | 99 | 12 |
| 721 | 3.982 | 379 | 377.0995 | 99 | 23 |
| 722 | 3.117 | 365 | 363.0447 | 99 | 24 |
| 723 | 4.166 | 393 | 391.1152 | 99 | 23 |
| 724 | 3.301 | 409 | 407.0737 | 99 | 5 |
| 725 | 3.492 | 385 | 384.0389[2] | 94 | 27 |
| 726 | 3.379 | 365 | 364.0900[2] | >95 | 11 |
| 727 | 3.603 | 379 | 378.1073[2] | >95 | 10 |

TABLE 11-continued

Yield, purity and Mass Spectral Data for 7-aryloxy-2-(trifluoromethyl)-2H-chromene-3-carboxylic acids prepared by Parallel Synthesis Methods.[1]

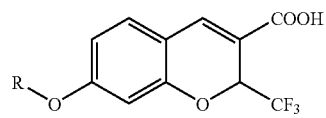

| Example # | LC (min) | MS (ES+) | HRMS | % Purity | % Yield |
|---|---|---|---|---|---|
| 728 | 3.245 | 383 | 382.0469[2] | >95 | 23 |
| 729 | 2.898 | 372 | 371.0150[2] | >95 | 4 |
| 730 | 3.638 | 365 | 364.0932[2] | >95 | 16 |
| 732 | 3.601 | 429 | 427.9857[2] | >95 | 25 |
| 733 | 3.656 | 365 | 364.0936[2] | >95 | 24 |
| 734 | 3.195 | 355 | 354.0520[2] | >95 | 37 |
| 735 | 3.245 | 373 | 372.0403[2] | >95 | 30 |
| 736 | 3.407 | 369 | 368.0667[2] | >95 | 16 |
| 737 | 3.145 | 372 | 371.0184[2] | >95 | 4 |
| 738 | 3.005 | 362 | 361.0559[2] | >95 | 4 |
| 740 | 3.447 | 351 | 350.0764[2] | >95 | 30 |
| 741 | 3.354 | 401 | 400.0294[2] | >95 | 26 |
| 742 | 3.401 | 381 | 380.0864[2] | >95 | 28 |
| 743 | 3.257 | 373 | 372.0401[2] | >95 | 38 |
| 744 | 3.542 | 399 | 397.0454 | >95 | 48 |
| 745 | 3.272 | 369 | 367.0568 | >95 | 44 |
| 746 | 3.269 | 433 | 430.9536 | >95 | 33 |
| 747 | 3.343 | 453[3] | 448.9442 | >95 | 31 |
| 748 | 3.582 | 495[3] | 490.8746 | >95 | 20 |
| 749 | 3.542 | 451[3] | 446.9279 | >95 | 24 |
| 750 | 3.389 | 385 | 383.0273 | >95 | 41 |
| 751 | 3.282 | 433[3] | 430.9543 | >95 | 22 |
| 752 | 3.241 | 389 | 387.0036 | >95 | 53 |
| 753 | 3.209 | 456 | 454.0491 | >95 | 5 |
| 754 | 3.663 | 477 | 474.9635 | >95 | 29 |
| 755 | 3.316 | 389 | 387.0067 | >95 | 52 |
| 756 | 3.374 | 433 | 430.9570 | >95 | 43 |
| 757 | 1.732 | 352 | 350.0617 | >95 | 26 |
| 758 | 3.151 | 381 | 379.0775 | >95 | 37 |
| 759 | 3.254 | 351 | 349.0640 | >95 | 46 |
| 760 | 3.610 | 379 | 377.0983 | >95 | 34 |
| 761 | 3.414 | 365 | 363.0821 | >95 | 40 |
| 762 | 3.282 | 351 | 349.0682 | >95 | 37 |
| 763 | 3.337 | 371 | 369.0131 | >95 | 10 |
| 764 | 3.831 | 371 | 369.0152 | >95 | 47 |

[1]See General Experimental section for description of recorded data. LC indicates the chromatographic retention time in min. HRMS indicates the observed molecular ion (M-H) by high-resolution mass spectrometry in electrospray negative mode. % Purity was determined by ELS detection.

[2]HRMS molecular ion electron impact (EI) mode.

[2]MS (M + 3) ion.

Preparation of 7-Arylthio-2-(trifluoromethyl)-2H-chromene-3-carboxylic acids

General Method for the Preparation of 7-arylthiooxy-2-(trifluoromethyl)-2H-Chromene-3-Carboxylic Acids by a Parallel Synthesis Method

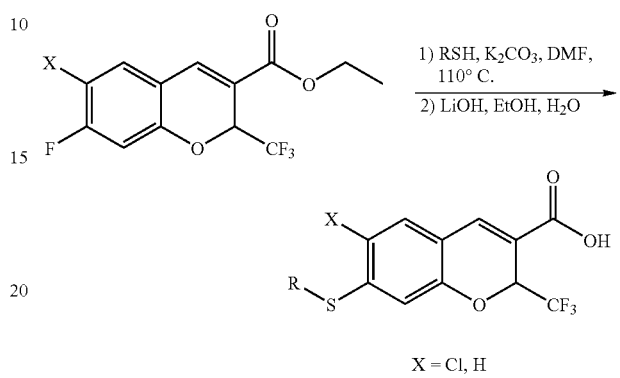

X = Cl, H

Step 1. Preparation of ethyl 7-arylthiooxy-2-(trifluoromethyl)-2H-chromene-3-carboxylate To 0.5 mmole of either ethyl 7-fluoro-2-(trifluoromethyl)-2H-chromene-3-carboxylate or ethyl 6-chloro-7-fluoro-2-(trifluoromethyl)-2H-chromene-3-carboxylate in 1.2 mL of DMF were added 0.55 mmole of thiol (RSH) and 97 mg (0.7 mmole) of potassium carbonate. The suspension was prepared in a capped vial and placed in an aluminum heating block equipped with a magnetic stirrer. The aluminum block was heated to 110° C. for 16 hrs. After allowing the vial to cool, the mixture was treated with 5 mL of water and 2 mL of diethyl ether. The organic layer was removed and the aqueous layer extracted two times with diethyl ether. Combined organic extracts were filtered through 5 g of silica and the silica washed with 10 mL of diethyl ether. The filtrates were concentrated under a stream of $N_2$ to afford an off-white solid, which was used in the next step without further purification.

Step 2. Preparation of 7-arylthiooxy-2-(trifluoromethyl)-2H-chromene-3-carboxylic acid To the concd product of step 1 in a suitable vial was added 200 mg of lithium hydroxide monohydrate, 1 mL of water, 2 mL of methanol and 7 mL of THF. The vial was capped, placed in an aluminum heating block and the block heated to 100° C. for 30 min. After allowing the vial to cool to r.t., the mixture was treated with 5 mL of 1N HCl and 2 mL of diethyl ether. The organic layer was removed and the aqueous layer extracted two times with diethyl ether. Combined organic extracts were concd by evaporation of solvent under a stream of $N_2$ followed by conc in vacuo. Products were purified as needed by reverse phase chromatography (C18 column, 40 mm i.d.×100 mm, gradient $CH_3CN$/0.1% TFA in $H_2O$).

Preparation of 7-Arylthiooxy-2-(trifluoromethyl)-2H-chromene-3-carboxvlic Acids by Parallel Synthesis Method The following examples in Table 12 were prepared by the general method and parallel synthesis apparatus with each reaction carried out on 0.5 mmole scale.

TABLE 12

Yield, Purity and Mass Spectral Data for 7-arylthiooxy-2-(trifluoromethyl)-2H-chromene-3-carboxylic acids prepared by Parallel Synthesis Methods.[1]

X = H, Cl

| Example # | LC (min) | MS (ES+) | HRMS | % Purity | % Yield |
|---|---|---|---|---|---|
| 765 | 3.896 | 387 | 385.2445 | 99 | 33 |
| 766 | 3.842 | 367 | 365.0493 | 99 | 26 |
| 767 | 3.619 | 383 | 381.0433 | 99 | 21 |
| 768 | 3.819 | 367 | 365.0479 | 99 | 28 |
| 769 | 3.886 | 387 | 385.2445 | 99 | 32 |
| 770 | 3.63 | 353 | 351.0325 | 99 | 42 |
| 771 | 4.044 | 401 | 399.0079 | 99 | 27 |
| 772 | 4.038 | 401 | 399.0047 | 99 | 43 |
| 773 | 4.069 | 421 | 418.9551 | 99 | 41 |

[1]See General Experimental section for description of recorded data. LC indicates the chromatographic retention time in min. HRMS indicates the observed molecular ion (M-H) by high-resolution mass spectrometry in electrospray negative mode. % Purity was determined by ELS detection.

Preparation of 5-aryloxy-2-(trifluoromethyl)-2H-chromene-3-carboxylic acids

Preparation of ethyl 5-Phenoxy-2-(trifluoromethyl)-2H-chromene-3-carboxylate

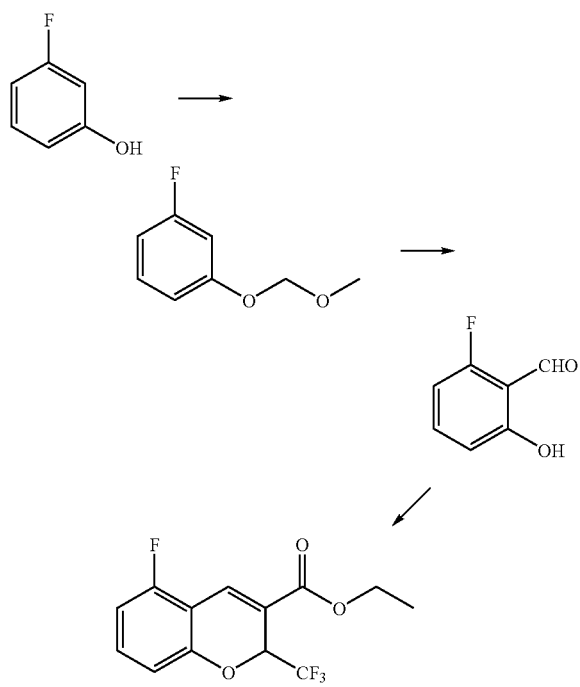

Step 1. Preparation of 1-fluoro-3-(methoxymethoxy)benzene

A solution of 22.4 g (200 mmole) of 3-fluorophenol in 400 mL of $CH_2Cl_2$ under $N_2$ was prepared and cooled to 5° C. The stirred mixture was treated with 23.1 g (267 mmole) of chloromethyl methyl ether. The reactor was equipped with a thermocouple and an addition funnel. To the stirred mixture was added dropwise 34.8 mL of DIEA (25.8 g, 200 mmole) such that the temperature did not exceed 10° C. After 30 min, an additional 18 mL of DIEA was added dropwise. After a total of 1 h, an additional 18 mL of DIEA was added. The mixture was allowed to stand overnight. The solution was washed with 500 mL of 1N HCl and the aqueous layer extracted two times with $CH_2Cl_2$. Combined extracts were dried with $Mg_2SO_4$, carefully concd and distilled in vacuo 61-68° C. @ 15 torr to afford 28.7 g (75.3%) of a clear, colorless liquid: (lit. bp 25-26° C. @ 0.6 torr); $^1H$ NMR ($CDCl_3$/400 MHz) 3.46 (s, 3H), 5.14 (s, 2H), 6.70 (tdd, 1H, J=8.3 Hz, J=2.4 Hz, 0.8 Hz), 6.75-6.82 (m, 2H), 7.21 (q, 1H, J=7.7 Hz); $^{19}F$ NMR ($CDCl_3$/400 MHz) -112.0 (m, 1F); 1$^{13}C$ NMR ($CDCl_3$/100 MHz) 56.1, 94.5, 104.1 (d, J=25.0 Hz), 108.6 (d, J=21.3 Hz), 111.9 (d, J=2.9 Hz), 130.2 (d, J=9.9 Hz), 158.6 (d, J=11.0 Hz), 163.5 (d, J=245.3 Hz).

Anal. Calc'd for $C_8H_9FO_2$: C, 61.53; H, 5.81. Found: C, 61.62; H, 5.87.

Literature ref: E. Marzi, F. Mongin, A. Spitaleri, M. Schlosser, Eur. J. Org. Chem. 2001, 2911-2915.

Step 2. Preparation of 2-fluoro-6-hydroxybenzaldehyde

A solution of 22.6 mL (17.4 g, 150 mmole) of TMEDA in 200 mL of THF was cooled to -78° C. and treated with 115.4 mL of 1.3 M sec-butyllithium in cyclohexane. After allowing the mixture to stir for 15 min, the solution was treated with 17.1 g (110 mmole) of 1-fluoro-3-(methoxymethoxy)benzene and allowed to stir for 30 min. The reaction mixture was subsequently treated with 12 mL of DMF, the ice bath removed and the reaction allowed to stir for 1 h. The mixture was added to a solution of 20 mL of acetic acid in 500 mL water. After the solution reached r.t the mixture was extracted three times with diethylether and the combined extracts washed with brine, dried and concd to afford 23.1 g of a crude oil. The oil was dissolved in 150 mL of THF and treated with 150 mL of 2-propanol and 75 mL of water. To the stirred solution was added 75 mL of conc HCl dropwise and the mixture allowed to stir overnight. The mixture was concd by distillation with a short column of the volatile solvents at atmospheric pressure to give an aqueous slurry of the product. This slurry was filtered and the collected solid washed with water. The solid was air dried for 2 h to give 8.89 g (58%) of an off white solid: mp 36.0-37.5° C. (lit. mp 37.5-38.0° C.); $^1H$ NMR ($CDCl_3$/400 MHz) 6.61 (ddd, 1H, J=0.8 Hz, J=8.3 Hz, J=9.0 Hz), 6.74 (d, 1H, J=8.5 Hz), 7.44 (dt, 1H, J=6.4 Hz, J=8.3 Hz), 10.25 (s, 1H), 11.45 (s, 1H); $^{19}F$ NMR ($CDCl_3$/400 MHz) -122.3 (dd, 1F, J=6.8 Hz, J=10.6 Hz); $^{13}C$ NMR ($CDCl_3$/100 MHz) 106.0 (d, CH, J=20.2 Hz), 110.7 (d, J=11.4 Hz) 113.8 (d, CH, J=3.8 Hz), 138.5 (d, CH, J=12.2 Hz), 163.1 (d, J=3.6 Hz), 164.9 (d, J=258.9 Hz), 192.4 (d, J=9.5 Hz).

Lit. Reference: Krause, G. H., et. Al., Z. Naturforsch B. Anorg. Chem. Org. Chem. Biochem. Biophy. Biol. 27 (1972) 663-674.

Step 3. Preparation of ethyl 5-fluoro-2-(trifluoromethyl)-2H-chromene-3-carboxylate A mixture of 8.7 g (62 mmole) of 2-fluoro-6-hydroxybenzaldehyde, 18.6 mL (20.9 g, 124 mmole) of ethyl trifluorocrotonate and 17.3 mL (12.6 g, 124 mmole) of triethylamine was heated to reflux. After 3 hrs an additional 18.6 mL of ethyl trifluorocrotonate and 2 g of potassium carbonate was added and the mixture heated for 3 days. The mixture was allowed to cool, concd in vacuo, diluted with 1N HCl and extracted three times with diethyl ether. The combined extracts were washed with 1N HCl, brine, dried and concd to afford a dark oil. Kugelrohr distillation (0.2 torr, 50° C.) afforded 11.2 g (62%) of a white solid: mp 45.5-47.0° C.; $^1$H NMR (CDCl$_3$/400 MHz) 1.33 (t, 3H, J=7.1 Hz), 4.30 (m, 2H), 5.68 (q, 1H, J=6.8 Hz), 6.70 (t, 1H, J=9.0 Hz), 6.76 (d, 1H, J=8.3 Hz), 7.24 (q, 1H, J=7.2 Hz), 7.92 (s, 1H); $^{19}$F NMR (CDCl$_3$/ 400 MHz) −78.9 (d, 3F, J=7.7 Hz), −118.9 (m, 1F); $^{13}$C NMR (CDCl$_3$/100 MHz) 14.2, 61.6, 70.7 (q, J=33.2 Hz), 108.7 (d, J=18.7 Hz), 109.2 (d, CH, J=20.6 Hz), 111.9 (d, CH, J=3.2 Hz), 117.0, 123.3 (q, J=287.5 Hz), 129.9 (d, CH, J=5.0 Hz), 133.2 (d, CH, J=10.3 Hz), 153.9, 158.5, 162.3 (d, J=253.5 Hz); MS(ES+) 291 (M+1, 100); MS(EI) 290 (M+, 13), 245 (18), 221 (100), 193 (99); HRMS (EI) m/z calcd for (C$_{13}$H$_{10}$O$_3$F$_4$) 290.0566, found 290.0589.

EXAMPLE 774

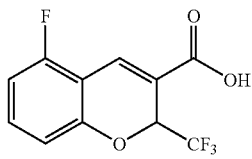

5-fluoro-2-(trifluoromethyl)-2H-chromene-3-carboxylic acid

To a solution of 290 mg (1.0 mmole) of ethyl 5-fluoro-2-(trifluoromethyl)-2H-chromene-3-carboxylate in 7 mLs of THF and 2 mL of methanol was added a solution of 85 mg of lithium hydroxide monohydate in 1.0 mL of water. The mixture was heated to reflux for 30 min and allowed to cool to rt. After stirring overnight, the mixture was treated with 75 mL of 1N HCl and extracted three times with diethyl ether. The combined extracts were washed with brine, dried and concd in vacuo to afford 210 g (80%) of a white solid: $^1$H NMR (d6-acetone/400 MHz) 5.86 (q, 1H, J=7.1 Hz), 6.88 (m, 2H), 7.44 (q, 1H, J=6.7 Hz), 7.93 (s, 1H); $^{19}$F NMR (d6-acetone/400 MHz) −120.9 (t, 1F, J=7.7 Hz), −79.4 (d, 3F, J=7.7 Hz); MS (ES+) 263 (M+l, 100); MS (ES−) 261 (M−1, 100); HRMS (ES−) m/z calcd for (C$_{11}$H$_6$F$_4$O$_3$) 261.0175, found 261.0193.

General Method for Preparation of 5-aryloxy-2-(trifluoromethyl)-2H-chromene-3-carboxylic Acids by Parallel Synthesis

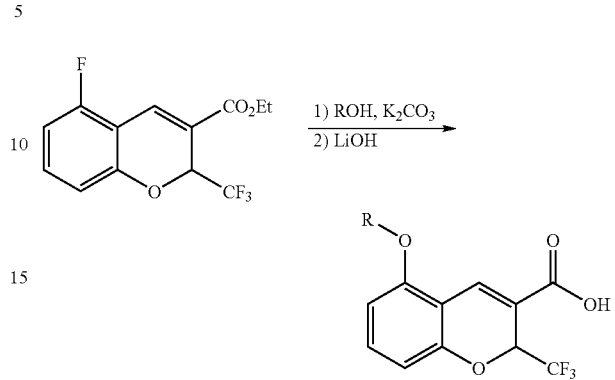

Step 1. Preparation of ethyl 5-aryloxy-2-(trifluoromethyl)-2H-chromene-3-carboxylate To 0.5 mmole of ethyl 5-fluoro-2-(trifluoromethyl)-2H-chromene-3-carboxylate in 1.2 mL of DMF was added 0.55 mmole of phenol (ROH) and 97 mg (0.7 mmole) of potassium carbonate. The suspension was prepared in a capped vial and placed in an aluminum heating block equipped with a magnetic stirrer. The aluminum block was heated to 110° C. for 16 hrs. After allowing the vial to cool, the mixture was treated with 5 mL of water and 2 mL of diethyl ether. The organic layer was removed and the aqueous layer extracted two times with diethyl ether. Combined organic extracts were filtered through 5 g of silica and the silica washed with 10 mL of diethyl ether. The filtrates were concentrated under a stream of N$_2$ to afford an off-white solid, which was used in the next step without further purification.

Step 2. Preparation of 5-aryloxv-2-(trifluoromethyl)-2H-chromene-3-carboxylic acid To the concd product of step 1 in a suitable vial was added 200 mg of lithium hydroxide monohydrate, 1 mL of water, 2 mL of methanol and 7 mL of THF. The vial was capped, placed in an aluminum heating block and the block heated to 100° C. for 30 min. After allowing the vial to cool to rt, the mixture was treated with 5 mL of 1N HCl and 2 mL of diethyl ether. The organic layer was removed and the aqueous layer extracted two times with diethyl ether. Combined organic extracts were concd by evaporation of solvent under a stream of N$_2$ followed by conc in vacuo. Products were purified as needed by reverse phase chromatography (C18 column, 40 mm i.d.×100 mm, gradient CH$_3$CN/0.1% TFA in H$_2$O).

Preparation of 5-aryloxy-2-(trifluoromethyl)-2H-chromene-3-carboxylic acids by a Parallel Method The following examples in Table 13 were prepared by the general method using parallel synthesis apparatus with each reaction carried out on either 1.0 or 0.5 mmole scale.

TABLE 13

Yield, Purity and Mass Spectral Data for 5-aryloxy-2-(trifluoromethyl)-2H-chromene-3-carboxylic Acids Prepared by Parallel Synthesis Methods.[1]

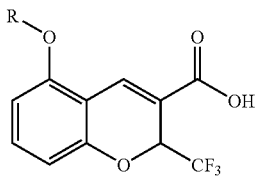

| Example # | LC (min) | MS (ES+) | HRMS | % Purity | % Yield |
|---|---|---|---|---|---|
| 775 | 3.181 | 365 | 363.0839 | 99 | 14.99 |
| 776 | 3.446 | 337 | 335.0526 | 99 | 24.27 |
| 777 | 3.851 | 385 | 383.0292 | 82 | 27.81 |
| 778 | 3.619 | 351 | 349.0682 | 99 | 19.53 |
| 779 | 3.654 | 383 | 381.0403 | 99 | 24.11 |
| 780 | 3.664 | 351 | 349.0682 | 99 | 20.78 |
| 781 | 3.95 | 399 | 397.0449 | 99 | 21.62 |
| 782 | 3.661 | 371 | 369.0136 | 96 | 34.47 |
| 783 | 3.839 | 365 | 363.0839 | 99 | 15.21 |
| 784 | 3.82 | 365 | 363.0839 | 99 | 16.52 |
| 785 | 3.855 | 365 | 363.0839 | 99 | 21.08 |
| 786 | 3.659 | 351 | 349.0682 | 99 | 21.70 |
| 787 | 3.471 | 355 | 353.0447 | 93 | 17.56 |
| 788 | 3.672 | 371 | 369.0171 | 93 | 15.05 |
| 789 | 3.855 | 405 | 402.9764 | 98 | 23.50 |
| 790 | 3.789 | 387 | 386.0745[2] | 94 | 14.96 |
| 791 | 3.784 | 387 | 386.0787[2] | 85 | 11.60 |
| 792 | 3.391 | 381 | 379.0449 | 99 | 12.15 |
| 793 | 3.437 | 367 | 365.0612 | 99 | 10.48 |
| 794 | 3.996 | 379 | 377.0984 | 99 | 7.51 |
| 795 | 4.06 | 399 | 397.0441 | 99 | 20.81 |
| 796 | 3.606 | 381[3] | 379.0795 | 86 | 10.25 |
| 797 | 3.407 | 355 | 353.0459 | 90 | 25.57 |
| 798 | 3.797 | 365 | 363.0856 | 84 | 8.45413 |
| 799 | 4.06 | 379 | 377.1007 | 99 | 13.85 |
| 800 | 3.305 | 371[4] | 371.0318 | 99 | 13.70 |
| 801 | 3.563 | 401 | 399.0235 | 86 | 19.86 |
| 802 | 3.316 | 379 | 377.0619 | 93 | 7.40 |
| 803 | 3.38 | 367[5] | 365.061 | 92 | 12.34 |

[1] See General Experimental section for description of recorded data. LC indicates the chromatographic retention time in min. HRMS indicates the observed molecular ion (M-H) by high-resolution mass spectrometry in electrospray negative mode. % Purity was determined by ELS detection.
[2] HRMS in EI mode, M+ ion.
[3] 381 (M + 1, 50), 363 (100).
[4] Electrospray negative mode, M − 1 ion; 371 (M − 1, 60), 307 (100).
[5] 367 (M + 1, 40), 349 (100).

Preparation of 5-Arylthio-2-(trifluoromethyl)-2H-chromene-3-carboxylic Acids

General Method for Preparation of 5-Arylthio-2-(trifluoromethyl)-2H-chromene-3-Carboxylic Acids by Parallel Synthesis X = H, Cl

Step 1. Preparation of ethyl 5-arylthio-2-(trifluoromethyl)-2H-chromene-3-carboxylate To 0.5 mmole of either ethyl 5-fluoro-2-(trifluoromethyl)-2H-chromene-3-carboxylate ethyl 5-fluoro-6-chloro-2-(trifluoromethyl)-2H-chromene-3-carboxylate in 1.2 mL of DMF was added 0.55 mmole of thiol (RSH) and 97 mg (0.7 mmole) of potassium carbonate. The suspension was prepared in a capped vial and placed in an aluminum heating block equipped with a magnetic stirrer. The aluminum block was heated to 110° C. for 16 hrs. After allowing the vial to cool, the mixture was treated with 5 mL of water and 2 mL of diethyl ether. The organic layer was removed and the aqueous layer extracted two times with diethyl ether. Combined organic extracts were filtered through 5 g of silica and the silica washed with 10 mL of diethyl ether. The filtrates were concentrated under a stream of $N_2$ to afford an off-white solid, which was used in the next step without further purification.

Step 2. Preparation of 5-arylthio-2-(trifluoromethyl)-2H-chromene-3-carboxylic acid To the concd product of step 1 in a suitable vial was added 200 mg of lithium hydroxide monohydrate, 1 mL of water, 2 mL of methanol and 7 mL of THF. The vial was capped, placed in an aluminum heating block and the block heated to 100° C. for 30 min. After allowing the vial to cool to rt, the mixture was treated with 5 mL of 1N HCl and 2 mL of diethyl ether. The organic layer was removed and the aqueous layer extracted two times with diethyl ether. Combined organic extracts were concd by evaporation of solvent under a stream of $N_2$ followed by conc in vacuo. Products were purified as needed by reverse phase chromatography (C18 column, 40 mm i.d.×100 mm, gradient $CH_3CN$/0.1% TFA in $H_2O$).

Preparation of 5-Arylthio-2-(trifluoromethyl)-2H-chromene-3-carboxylic Acids by a Parallel Method The following examples in Table 14 were prepared by the general method using parallel synthesis apparatus with each reaction carried out on either 1.0 or 0.5 mmole scale.

TABLE 14

Yield, Purity and Mass Spectral Data for 5-Arylthio-2-(trifluoromethyl)-2H-chromene-3-carboxylic Acids Prepared by Parallel Synthesis Methods.[1]

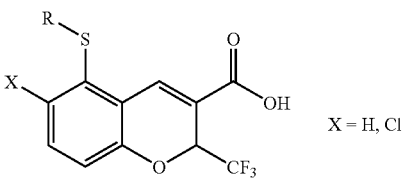

X = H, Cl

| Example # | LC (min) | MS (ES+) | HRMS | % Purity | % Yield |
|---|---|---|---|---|---|
| 804 | 3.93 | 421 | 418.9549 | 99 | 47 |
| 805 | 3.88 | 401 | 399.0099 | 99 | 30 |
| 806 | 3.72 | 417 | 415.0038 | 99 | 46 |
| 807 | 3.899 | 401 | 399.0049 | 99 | 28 |
| 808 | 3.912 | 421 | 418.953 | 99 | 27 |
| 809 | 3.723 | 387 | 385.2445 | 99 | 38 |
| 810 | 3.712 | 387 | 385.2445 | 99 | 24 |
| 811 | 3.75 | 367 | 365.0485 | 99 | 19 |
| 812 | 3.565 | 383[2] | 381.0402 | 99 | 17 |
| 813 | 3.763 | 367 | 365.0468 | 99 | 22 |
| 814 | 3.771 | 387 | 385.2445 | 99 | 26 |
| 815 | 3.563 | 353 | 351.0302 | 99 | 30 |

[1] See General Experimental section for description of recorded data. LC indicates the chromatographic retention time in min. HRMS indicates the observed molecular ion (M-H) by high-resolution mass spectrometry in electrospray negative mode. % Purity was determined by ELS detection.
[2] 383 (M + 1, 40), 365 (100).

Preparation of 5-aryloxy-6,8-dichloro-2-(trifluoromethyl)-2H-chromene-3-carboxylic acids Preparation of Ethyl 6,8-Dichloro-5-phenoxy-2-(trifluoromethyl)-2H-chromene-3-carboxylate

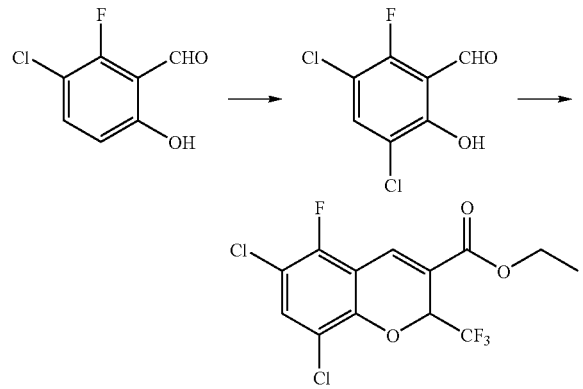

Step 1. Preparation of 3,5-dichloro-2-fluoro-6-hydroxybenzaldehyde

To 20 g (114.6 mmole) of 3-chloro-2-fluoro-6-hydroxybenzaldehyde in 250 mL of glacial acetic acid was added 27.8 g of $Cl_2$ gas over a period of 30 min. The mixture was stirred and heated to 60° C. for 2 hrs and allowed to stir at rt overnight. The reaction mixture was diluted with 1L of water and extracted four times with diethyl ether. Combined extracts were washed with water and sat. brine and concd in vacuo to afford a slurry. Addition of 250 mL of water afforded a solid which was collected by filtration and allowed to air dry for 8 hrs to afford 20.42 g (85%) of a yellow solid: mp 58-62° C.; $^1H$ NMR (CDCl$_3$/400 MHz) 7.65 (d, 1H, J=7.5 Hz), 10.26 (s, 1H), 11.88 (s, 1H); $^{13}C$ NMR (CDCl$_3$/100 MHz) 111.2 (d, J=12.0 Hz), 118.2 (d, J=4.6 Hz), 127.8, 137.6 (C—H, d, J=2.1 Hz), 156.8 (d, J=3.0 Hz), 158.3 (d, J=260.8 Hz), 191.4 (CHO, d, J=8.8 Hz); $^{19}F$ NMR (CDCl$_3$/400 MHz) -124.7 (d, 1F, J=7.7 Hz); MS (EI) 208 (M+, 100); 207 (91); HRMS (EI) m/z calcd for ($C_7H_3O_2Cl_2F$) 207.9494, found 207.9470.

Anal. Calc'd for $C_7H_3O_2Cl_2F+0.3 H_2O$: C, 39.21; H, 1.69. Found: C, 39.04; H, 1.53.

Step 2. Preparation of ethyl 6,8-dichloro-5-fluoro-2-(trifluoromethyl)-2H-chromene-3-carboxylate To 16.11 g (77 mmole) of 3,5-dichloro-2-fluoro-6-hydroxybenzaldehyde was added 23 mL (25.9 g, 154 mmole) of ethyl trifluorocrotonate followed by slow addition of 21.5 mL (15.6 g, 154 mmole) of triethylamine. The mixture was heated to reflux. After I h, the mixture was treated with an additional 23 mL of ethyl trifluorocrotonate and continued to heat for 24 hrs. The reaction mixture contained a 1:2 ratio of product and starting material as determined by $^1H$ NMR. The mixture was treated with an additional 23 mL of ethyl trifluorocrotonate heated for an additional 48 hrs. The mixture was allowed to cool, diluted with 1N HCl and extracted three times with methylene chloride. Combined extracts were filtered through a pad of silica and concd to give 19.0 g of a crude dark brown oil. The oil was treated with hexanes and the solid impurity was removed by filtration. The solids were washed with hexanes and the combined filtrates were concd to afford 15 g of crude oil. Purification by reverse phase HPLC (C18, 4.2 cm×25 cm, 10 injections) afforded 8.08 g (29.2%) of a crystalline solid: mp 72-73° C.; $^1H$ NMR (CDCl$_3$/400 MHz) 1.38 (t, 3H, J=7.1 Hz), 4.37 (m, 2H), 5.85 (q, 1H, J=6.6 Hz), 7.41 (d, 1H, J=7.5 Hz), 7.89 (s, 1H); $^{19}F$ NMR (CDCl$_3$/400 MHz) -78.9 (d, 3F, J=6.8 Hz), -120.8 (d, 1F, J=6.8 Hz); $^{13}C$ NMR (CDCl$_3$/100 MHz) 14.2, 62.1, 71.2 (q, C2, J=33.7 Hz), 110.8 (d, J=19.8 Hz), 114.7 (d, J=18.7 Hz), 117.3 (d, J=4.0 Hz), 119.1 (d, J=2.1 Hz), 122.9(q, CF$_3$, J=287.1 Hz), 128.6 (d, C—H, J=4.0 Hz), 133.0 (C—H), 147.8 (d, J=4.6 Hz), 153.5 (d, J=256.6 Hz), 162.8; MS (ES+) 359 (M+1, 100, Cl$_2$ pattern); MS(EI) 358 (M+, 26, Cl$_2$ pattern), 289 (100), 261 (54); HRMS (EI) m/z calcd for ($C_{13}H_8O_3Cl_2F_4$) 357.9787, found 357.9804.

Anal. Calc'd for $C_{13}H_8O_3Cl_2F_4$: C, 43.48; H, 2.25. Found: C, 43.47; H, 2.28.

EXAMPLE 816

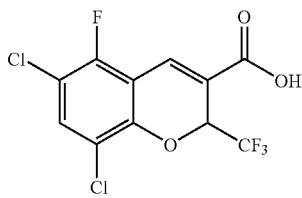

6,8-Dichloro-5-fluoro-2-(trifluoromethyl)-2H-chromene-3-carboxylic acid

To a solution of 359 mg (1.0 mmole) of ethyl 6,8-dichloro-5-fluoro-2-(trifluoromethyl)-2H-chromene-3-carboxylate in 7 mLs of THF and 2 mL of methanol was added a solution of 90 mg of lithium hydroxide monohydate in 1.0 mL of water. The mixture was heated to reflux for 60 min and allowed to cool to rt. After stirring overnight, the mixture was treated with 75 mL of 1N HCl and extracted three times with diethyl ether. The combined extracts were concd and purified by reverse phase chromatography to afford 240 mg of an impure white solid. Recrystallization from acetonitrile afforded 51 mg (15%) of a white, crystalline solid: $^1$H NMR (d$^6$-acetone/400 MHz) 6.08 (q, 1H, J=7.0 Hz), 7.74 (d, 1H, J=7.7 Hz), 7.94 (s, 1H); $^{19}$F NMR (d$^6$-acetone/400 MHz) −122.1 (d, 1F, J=7.7 Hz), −79.4 (d, 3F, J=6.8 Hz); MS (ES+) 331 (M+1, 100), 333 (M+3, 57); MS (ES−) 329 (M−1, 100), 331 (79); HRMS (ES−) m/z calcd for ($C_{11}H_4C_{12}F_4O_3$) 328.9401, found 328.9357.

General Method for Preparation of 5-Aryloxy-6,8-dichloro-2-(trifluoromethyl)-2H-chromene-3-carboxylic Acids by Parallel Synthesis

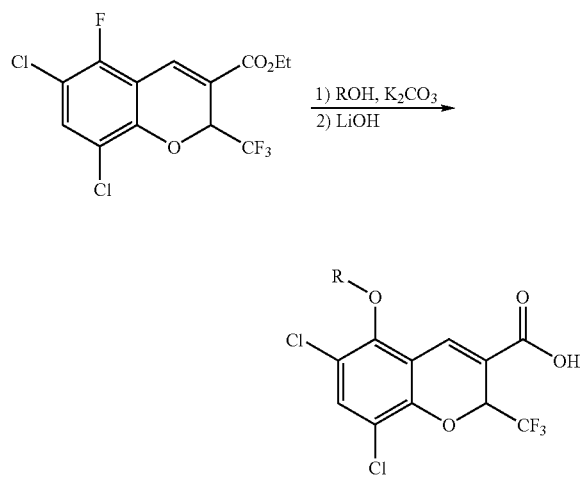

Step 1. Preparation of ethyl 5-aryloxy-6,8-dichloro-2-(trifluoromethyl)-2H-chromene-3-carboxylate To 0.5 mmole of ethyl 5-fluoro-6,8-dichloro-2-(trifluoromethyl)-2H-chromene-3-carboxylate in 1.2 mL of DMF was added 0.55 mmole of phenol (ROH) and 97 mg (0.7 mmole) of potassium carbonate. The suspension was prepared in a capped vial and placed in an aluminum heating block equipped with a magnetic stirrer. The aluminum block was heated to 55° C. for 16 hrs. After allowing the vial to cool, the mixture was treated with 5 mL of water and 2 mL of diethyl ether. The organic layer was removed and the aqueous layer was extracted two times with diethyl ether. Combined organic extracts were filtered through 5 g of silica and the silica was washed with 10 mL of diethyl ether. The filtrates were concentrated under a stream of $N_2$ to afford an off-white solid, which was used in the next step without further purification.

Step 2. Preparation of 5-aryloxy-6,8-dichloro-2-(trifluoromethyl)-2H-chromene-3-carboxylic acid To the concd product of step 1 in a suitable vial was added 400 mg of lithium hydroxide monohydrate, 1 mL of water, 2 mL of methanol and 7 mL of THF. The vial was capped, in an aluminum heating block and the block heated to 100° C. for 30 min. After allowing the vial to cool to rt, the mixture was treated with 5 mL of 1N HCl and 2 mL of diethyl ether. The organic layer was removed and the aqueous layer extracted two times with diethyl ether. Combined organic extracts were concd by evaporation of solvent under a stream of $N_2$ followed by conc in vacuo. Products were purified as needed by reverse phase chromatography (C18 column, 40 mm i.d.×100 mm, gradient $CH_3CN$/0.1% TFA in $H_2O$).

Preparation of 5-Aryloxy-6,8-dichloro-2-(trifluoromethyl)-2H-chromene-3-carboxylic Acids by a Parallel Method The following examples in Table 15 were prepared by the general method using parallel synthesis apparatus with each reaction carried out on either 1.0 or 0.5 mmole scale.

TABLE 15

Yield, Purity and Mass Spectral Data for 5-Aryloxy-6,8-dichloro-2-(trifluoromethyl)-2H-chromene-3-carboxylic Acids Prepared by Parallel Synthesis Methods.[1]

| Example # | LC (min) | MS (ES+) | HRMS | % Purity | % Yield |
|---|---|---|---|---|---|
| 817 | 4.201 | 433 | 431.0068 | 99 | 34 |
| 818 | 4.016 | 419 | 416.9919 | 99 | 37 |
| 819 | 4.269 | 453 | 450.9524 | 99 | 39 |
| 820 | 3.334 | 417[2] | 432.9852 | 99 | 35 |
| 821 | 4.141 | 453 | 450.9533 | 99 | 41 |
| 822 | 4.062 | 457 | 454.9273 | 99 | 46 |
| 823 | 4.073 | 437 | 434.9834 | 99 | 30 |
| 824 | 2.698 | 420 | 417.984 | 99 | 28 |
| 825 | 3.922 | 449 | 446.9977 | 99 | 34 |
| 826 | 4.056 | 439 | 436.9362 | 99 | 42 |
| 827 | 4.268 | 467 | 464.9675 | 99 | 33 |
| 828 | 3.741 | 440 | 437.9318 | 99 | 12 |
| 829 | 4.235 | 433 | 431.0038 | 99 | 25 |
| 830 | 3.971 | 437 | 434.9832 | 99 | 47 |
| 831 | 4.028 | 419 | 416.9911 | 99 | 44 |
| 832 | 4.049 | 439[3] | 436.9378[3] | 99 | 49 |
| 833 | 4.196 | 433 | 431.0031 | 99 | 36 |
| 834 | 4.029 | 451 | 448.9621 | 99 | 44 |
| 835 | 4.022 | 449 | 446.9977 | 99 | 30 |
| 836 | 4.041 | 419 | 416.9893 | 99 | 31 |
| 837 | 3.663 | 430 | 427.9665 | 99 | 42 |
| 838 | 3.832 | 440 | 437.9298 | 99 | 18 |
| 839 | 4.199 | 433 | 431.0028 | 99 | 23 |
| 840 | 3.995 | 469 | 466.9426 | 99 | 44 |

[1]See General Experimental section for description of recorded data. LC indicates the chromatographic retention time in min. HRMS indicates the observed molecular ion (M-H) by high-resolution mass spectrometry in electrospray negative mode. % Purity was determined by ELS detection.
[2]Observed ion is the fragment of M-18 (H2O); 417 (M + 1-18, 100).
[3]Observed ion of $Cl_3$ compound: 439 (M + 1, 80), 441 (M + 3, 100).

Preparation of 5-aryloxy-6-chloro-2-(trifluoromethyl)-2H-chromene-3-carboxylic acids

General Method for Preparation of 5-Aryloxy-6-chloro-2-(trifluoromethyl)-2H-chromene-3-carboxylic Acids by Parallel Synthesis

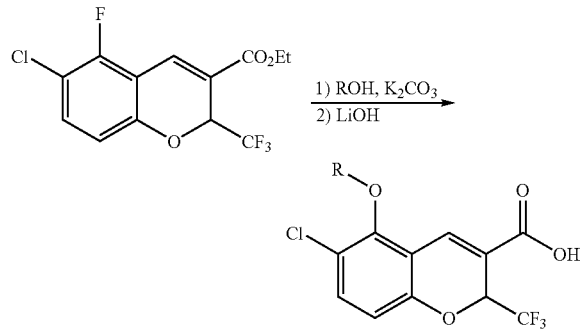

Step 1. Preparation of ethyl 5-aryloxy-6-chloro-2-(trifluoromethyl)-2H-chromene-3-carboxylate To 0.5 mmole of ethyl 5-fluoro-6-chloro-2-(trifluoromethyl)-2H-chromene-3-carboxylate in 1.2 mL of DMF was added 0.55 mmole of phenol (ROH) and 97 mg (0.7 mmole). of potassium carbonate. The suspension was prepared in a capped vial and placed in an aluminum heating block equipped with a magnetic stirrer. The aluminum block was heated to 55° C. for 16 hrs. After allowing the vial to cool, the mixture was treated with 5 mL of water and 2 mL of diethyl ether. The organic layer was removed and the aqueous layer extracted two times with diethyl ether. Combined organic extracts were filtered through 5 g of silica and the silica washed with 10 mL of diethyl ether. The filtrates were concentrated under a stream of $N_2$ to afford an off-white solid, which was used in the next step without further purification.

Step 2. Preparation of 5-aryloxy-6-chloro-2-(trifluoromethyl)-2H-chromene-3-carboxylic acid To the concd product of step 1 in a suitable vial was added 400 mg of lithium hydroxide monohydrate, 1 mL of water, 2 mL of methanol and 7 mL of THF. The vial was capped, in an aluminum heating block and the block heated to 100° C. for 30 min. After allowing the vial to cool to rt, the mixture was treated with 5 mL of 1N HCl and 2 mL of diethyl ether. The organic layer was removed and the aqueous layer was extracted two times with diethyl ether. Combined organic extracts were concd by evaporation of solvent under a stream of $N_2$ followed by conc in vacuo. Products were purified as needed by reverse phase chromatography (C18 column, 40 mm i.d.×100 mm, gradient $CH_3CN$/0.1% TFA in $H_2O$).

Preparation of 5-Aryloxy-6-chloro-2-(trifluoromethyl)-2H-chromene-3-carboxylic Acids by a Parallel Method The following examples in Table 16 were prepared by the general method using parallel synthesis apparatus with each reaction carried out on 0.5 mmole scale.

TABLE 16

Yield, Purity and Mass Spectral Data for 5-Aryloxy-6-chloro-2-(trifluoromethyl)-2H-chromene-3-carboxylic Acids Prepared by Parallel Synthesis Methods.[1]

| Example # | LC (min) | MS (ES+) | HRMS | % Purity | % Yield |
|---|---|---|---|---|---|
| 841 | 3.928 | 399 | 397.0441 | 99 | 27 |
| 842 | 3.746 | 385 | 383.0278 | 99 | 40 |
| 843 | 4.015 | 419 | 416.9879 | 99 | 40 |
| 844 | 3.08 | 383[2] | 399.0244 | 99 | 24 |
| 845 | 3.888 | 419 | 416.9903 | 99 | 31 |
| 846 | 3.822 | 423 | 420.962 | 99 | 37 |
| 847 | 3.83 | 403 | 401.0176 | 99 | 36 |
| 848 | 2.445 | 386 | 384.0266 | 99 | 24 |
| 849 | 3.65 | 415 | 413.0393 | 99 | 35 |
| 850 | 3.811 | 405 | 402.9745 | 99 | 41 |
| 851 | 4.005 | 433 | 431.0035 | 99 | 33 |
| 852 | 3.967 | 399 | 397.0433 | 99 | 35 |
| 853 | 3.72 | 403 | 401.0204 | 99 | 42 |
| 854 | 3.767 | 385 | 383.0285 | 99 | 39 |
| 855 | 3.802 | 405 | 402.9772 | 99 | 41 |
| 856 | 3.929 | 399 | 397.0417 | 99 | 34 |
| 857 | 3.778 | 417 | 415.0017 | 99 | 35 |
| 858 | 3.76 | 415 | 413.0399 | 99 | 43 |
| 859 | 3.778 | 385 | 383.0305 | 99 | 35 |
| 860 | 3.423 | 396 | 394.0072 | 99 | 22 |
| 861 | 3.54 | 406 | 403.9716 | 99 | 9 |
| 862 | 3.939 | 399 | 397.0473 | 99 | 37 |
| 863 | 3.742 | 435 | 432.9858 | 99 | 37 |

[1] See General Experimental section for description of recorded data. LC indicates the chromatographic retention time in min. HRMS indicates the observed molecular ion (M-H) by high-resolution mass spectrometry in electrospray negative mode. % Purity was determined by ELS detection.
[2] Observed ion is the fragment of M-18 (H2O); 383 (M + 1-18, 100).

Preparation of 6-Chloro-7-[(5-ethylpyrimidin-2-yl)oxy]-2-(trifluoromethyl)-2H-chromene-3-carboxylic acid

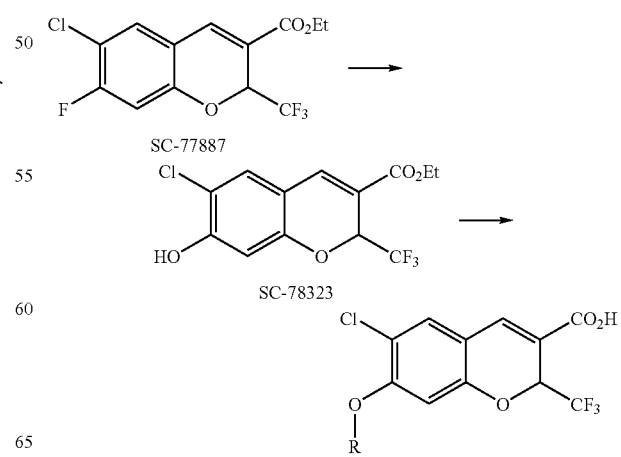

EXAMPLE 864

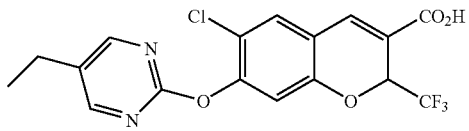

6-Chloro-7-[(5-ethylpyrimidin-2-yl)oxy]-2-(trifluoromethyl)-2H-chromene-3-carboxylic acid

Step 1. Preparation of Ethyl 6-chloro-7-hydroxyl-2-(trifluoromethyl)-2H-chromene-3-carboxylate To the mixture of ethyl 6-chloro-7-fluoro-2-(trifluoromethyl)-2H-chromene-3-carboxylate (6 g, 18.5 mmol) and 2-(methylsulfonyl)ethanol (3.45 g, 27.7 mmol) in 125 mL of anhydrous DMF at 0° C. was added sodium hydride (60%, 2.22 g, 55.5 mmol) slowly. After stirring at 0° C. for 45 min, LCMS indicated that majority of starting material was gone. The reaction was warmed to room temperature, and stirred for another 20 min. The reaction was dumped into a dilute hydrochloric acid/ice mixture with vigorously stirring. The product was then extracted with EtOAc. The resulting organic phase was washed with brine, dried over anhydrous magnesium sulfate. After removing the solvent, the residue was purified on silica gel column with 1:1 EtOAc/hexane containing 1% HOAc. The desired product was obtained as a green yellowish solid, 1.0 g (16.7%). M.P.=118.0-125.0° C. $^1$H NMR(CDCl$_3$/400 MHz) 7.61(s, 1H), 7.18(s, 1H), 6.66(s, 1H), 5.65(q, 1H, J=6.8 Hz), 4.30(m, 2H), 1.33(t, 3H, J=7.2 Hz). $^{13}$C NMR(CDCl$_3$/400 MHz) 164.1, 155.2, 153.8, 136.0, 129.3, 123.5(q, J=287.7 Hz), 115.1, 114.1, 113.6, 104.5, 71.0(q, J=33.2 Hz), 61.7, 14.4. $^{19}$F NMR(CDCl$_3$/400 MHz) −78.9(d, J=6.8 Hz). LC-MS (ES+) 323.7 (M+H, 80%), 295.2(M−27, 100%). HRMS (EI+) m/z calcd for (C$_{13}$H$_{10}$ClF$_3$O$_4$) 322.0220, found 322.0231.

Step 2. Preparation of ethyl 6-chloro-7-[(5-ethylpyrimidin-2-yl)oxy]-2-(trifluoromethyl)-2H-chromene-3-carboxylate To a mixture of ethyl 6-chloro-7-hydroxyl-2-(trifluoromethyl)-2H-chromene-3-carboxylate (0.2g, 0.62 mmol) and potassium carbonate (342 mg, 2.48 mmol) in 3 mL of dry DMF was added a reagent of 2-chloro-5-ethylpyrimidine (450 uL, 3.72 mmol). The reaction was then heated at 130° C. for 51 hours. After cooling to room temperature, to the reaction was added 150 mL of EtOAc. The resulting organic phase was washed with brine, and dried over anhydrous magnesium sulfate. After removing the solvents, the residue was purified on a short silica gel column with EtOAc/Hexane to afford 260 mg of a brown oil, which was used in the next step without further purification.

Step 3. Preparation of 6-chloro-7-[(5-ethylpyrimidin-2-vl)oxyl-2-(trifluoromethyl)-2H-chromene-3-carboxylic acid To the solution of the product of step 2 (0.26 g, 0.61 mmol) in 3 mL of THF was added a solution of lithium hydroxide hydrate (102 mg, 2.44 mmol) in 3 mL of water. To the resulting mixture was added 3 mL of ethanol. The resulting clear solution was heated to 70° C. for five hrs. LC-MS indicated that the reaction was completed. The volatiles were then removed. The residue was diluted with water. The diluted aqueous solution was acidified at 0° C. with dilute hydrochloric acid to precipitate the product. The product was extracted with EtOAc. The combined organic extracts were combined and dried over anhydrous magnesium sulfate. The volatiles were removed on rotavapor. After removing the solvents, the residue was purified on reverse phase HPLC. It gave 110 mg (45%) of a light yellow solid M.P.=96.5-98.0° C. $^1$H NMR (CDCl$_3$/300 MHz) 8.50(s, 2H), 7.72(s, 1H), 7.40(s, 1H), 6.99(s, 1H), 5.72(q, J=6.9 Hz, 1H), 2.69(q, J=7.5 Hz, 2H), 1.33(t, J=7.5 Hz, 3H). $^{13}$C NMR(CDCl$_3$/400 MHz) 167.3, 162.7, 159.3, 153.1, 152.5, 136.9, 132.6, 130.8, 123.4(q, J=287.3 Hz), 117.9, 116.7, 112.4, 70.8(d, J=33.5 Hz), 22.9, 15.2, 2.2. $^{19}$F(CDCl$_3$/400 MHz) −78.80(d, J=5.6 Hz). LC-MS (ES+) 401.3(M+1, 100). HRMS (ES+) m/z calcd for (C$_{17}$H$_{12}$ClF$_3$N$_2$O$_4$) 401.0510 (M+H), found 401.0530(M+H).

Preparation of 6-chloro-5-ethoxy-2-(trifluoromethyl)-2H-chromene-3-carboxylic acid

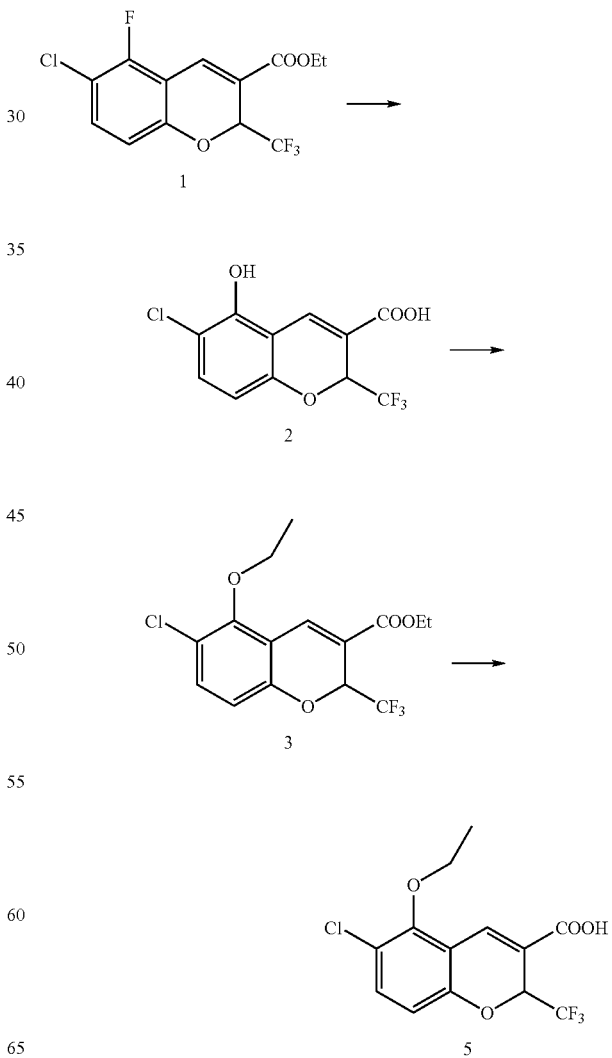

EXAMPLE 865

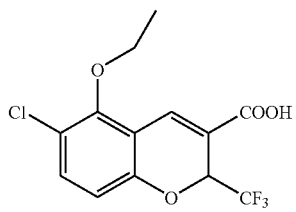

6-Chloro-5-ethoxy-2-(trifluoromethyl)-2H-chromene-3-carboxylic acid

Step 1: Preparation of 6-chloro-5-hydroxvl-2-(trifluoromethyl)-2H-chromene-3-carboxylic acid To the mixture of ethyl 6-chloro-5-fluoro-2-(trifluoromethyl)-2H-chromene-3-carboxylate (2g, 6.2 mmol) and 2-methylsulfonylethanol (2.3 g, 18.5 mmol) in 40 mL of dry DMF at 0° C. was added sodium hydride (60% mineral oil suspesion, 1.48 g, 37.2 mmol) slowly with stirring. Bubbling was observed during the process. Then the resulting black solution was stirred at room temperature for three hrs. LC-MS indicated that no any more starting material was observed. The reaction was poured into ice/aqueous ammonium chloride mixture. The product was extracted with ethyl acetate, and the resulting organic solution was washed with brine, and dried over anhydrous magnesium sulfate. After removing the volatiles, the residue was purified on silica gel column with 1:1 EtOAc/hexane+1% HOAc. The product was obtained as colorless oil, 0.8 g. Part of the product was further purified on reverse phase HPLC and gave an off-white solid. LC-MS (ES$^+$) 295.2(M+1, 100). $^1$H NMR (CD$_3$OD/300 MHz) 8.11(s, 1H), 7.30(d, J=8.7 Hz, 1H), 6.53(d, J=9.0 Hz, 1 H), 5.75(q, J=7.5 Hz, 1 H),. $^{19}$F NMR(CDCl$_3$/300 MHz) −80.31 (d, J=7.1 Hz). High resolution MS (ES−): m/e calc. For C$_{15}$H$_6$ClF$_3$O$_4$: 292.9828(M−H), found: 292.9853.

Step 2: Preparation of ethyl 6-chloro-5-ethoxy-2-(trifluoromethyl)-2H-chromene-3-carboxylate To the mixture of 6-chloro-5-hydroxyl-2-(trifluoromethyl)-2H-chromene-3-carboxylic acid (0.5g, 1.7 mmol) and cesium carbonate (800 mg, 0.94 mmol) in 10 mL of DMF was added ethyl bromide(0.80 mnL, 6.2 mmol). The mixture was stirred at room temperature overnight. To the reaction was added 150 mL of ethyl acetate, the resulting organic solution was washed with brine, and dried over anhydrous magnesium sulfate. After removing the volatiles, the residue was purified on silica gel column with EtOAc/hexane mixture. It gave 0.4 g of white solid. Part of the product was further purified on reverse phase HPLC for analytical characterization. LC-MS(ES+) 351.3(M+1, 100), $^{19}$F NMR (CDCl$_3$/400 Hz) −78.782(d, J=6.8 Hz); $^1$H NMR (CDCl$_3$/400 Hz) 7.94(s, 1H), 7.27(d, J=8.8 Hz, 1H), 6.70(d, J=8.8 Hz, 1H), 5.66(q, J=6.8 Hz, 1H), 4.32(m, 2H), 4.10(m, 2H), 1.42(t, J=7.2 Hz, 3H), 1.34(t, J=7.2 Hz, 3H); $^{13}$C NMR (CDCl$_3$/400 Hz) 163.8, 153.2, 152.6, 133.5, 132.0, 123.5(q, J=287.6 Hz), 121.2, 117.2, 115.6, 112.6, 71.4, 70.5(q, J=33.2 Hz), 61.8, 15.5, 14.4. High resolution MS(ES$^+$) m/e calc. for C$_{15}$H$_{15}$ClF$_3$O$_4$: 351.0605(M+H), 351.0641(M+H, observed).

Step 3: Preparation of 6-chloro-5-ethoxy-2-(trifluoromethyl)-2H-chromene-3-carboxylic acid To the solution of ethyl 6-chloro-5-ethoxy-2-(trifluoromethyl)-2H-chromene-3-carboxylate (300mg, 0.93 mmol) in 3 mL of THF was added a solution of lithium hydroxide hydrate (156 mg, 3.7 mmol) in 4 mL of water, followed by addition of 3 mL of ethanol. The resulting solution was heated to 80° C. for four hrs. After removing the solvent, the residue was acidified at 0° C. with ice-cold dilute hydrochloric acid. The product was extracted with EtOAc. After removing the solvents, the residue was purified on reverse phase HPLC. The product was obtained as white solid (120 mg). LC-MS (ES$^+$) 323.2(M+1, 100). $^1$H NMR (CDCl$_3$/400 MHz) 8.11(s, 1H), 7.32(d, J=8.8 Hz, 1H), 6.73(d, J=8.4 Hz, 1H), 5.65(q, J=6.8 Hz, 1H), 4.12(m, 2H), 1.44(t, J=7.2 Hz, 3H). $^{19}$F NMR(CDCl$_3$/400 MHz) −78.81(d, J=6.8 Hz). $^{13}$C NMR(CDCl$_3$/400 MHz) 169.5, 153.5, 152.8, 134.9, 134.3, 123.4(q, J=285.8 Hz), 121.3, 115.8, 115.5, 112.8, 71.6, 70.2(q, J=33.4 Hz), 15.5. HRMS (EI$^+$) m/z calc. For (C$_{13}$H$_{10}$ClF$_3$O$_4$) 322.0220 (M$^+$), found:322.0223.

Preparation of 5-aryl-6-chloro-2-(trifluoromethyl)-2H-chromene-3-carboxylic acids

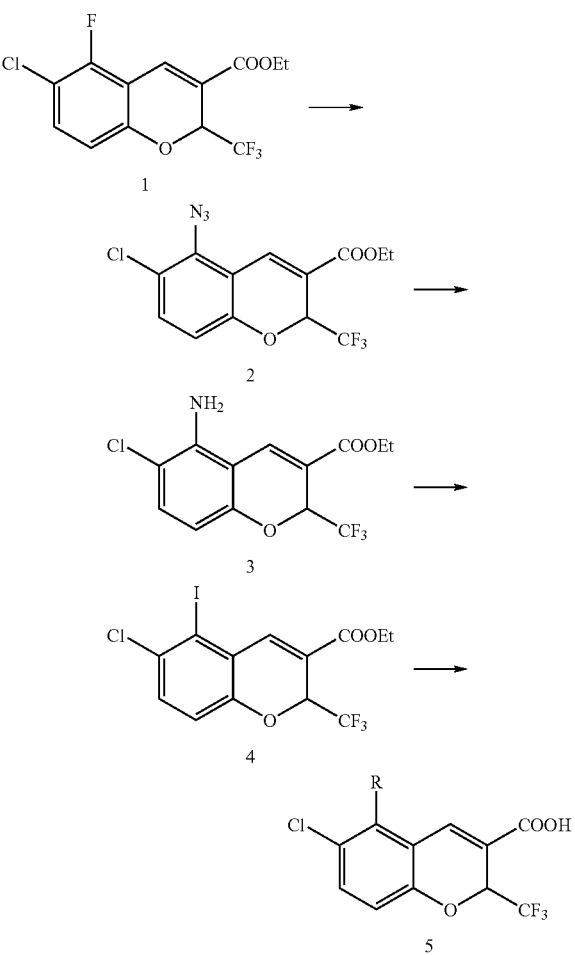

EXAMPLE 867

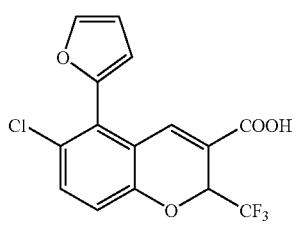

6-Chloro-5-(2-furyl)-2-(trifluoromethyl)-2H-chromene-3-carboxylic acid

Step 1. Preparation of ethyl 6-chloro-5-azido-2-(trifluoromethyl)-2H-chromene-3-carboxylate To the solution of ethyl 6-chloro-5-fluoro-2-(trifluoromethyl)-2H-chromene-3-carboxylate (1.0 g, 3.1 mmol) in 20 mL of DMSO was added a solution of sodium azide (1.0 g, 5 mmol) in minimum amount of water. The reaction was then heated to 85° C. for 15 hrs. After cooling to room temperature, to the reaction was added 200 mL of ethyl acetate. The resulting suspension was then washed with brine, and dried over anhydrous magnesium sulfate. After removing the solvents, the residue was purified on silica gel column with ethyl acetate/hexane, it gave 0.8 g of a yellow oil. Part of the product was purified on reverse phase HPLC for further analytical characterization. It gave a pink solid. LC-MS(ES+) 348.3(M+1, 70), 320.2(M−27, 100). $^1$H NMR (CDCl$_3$/400 MHz) 7.99(s, 1H), 7.24(d, J=8.8 Hz, 1H), 6.75(d, J=8.8 Hz, 1H), 5.67(q, J=6.8 Hz, 1H), 4.32(m, 2H), 1.35(t, J=7.2 Hz, 3H). $^{19}$F NMR(CDCl$_3$/400 Hz) −78.71(d, J=6.8 Hz). $^{13}$C NMR(CDCl$_3$/400 Hz) 163.7, 152.7, 134.4, 133.9, 131.9, 123.3(q, J=287.3 Hz), 122.6, 117.7, 114.6, 114.2, 70.6(q, J=33.3 Hz), 61.9, 14.4. HRSM(EI$^+$) m/e calc. for (C$_{13}$H$_9$ClF$_3$N$_3$O$_3$) 347.0285(M$^+$), found: 347.0294(M$^+$).

Step 2. Preparation of ethyl 6-chloro-5-amino-2-(trifluoromethyl)-2H-chromene-3-carboxylate To the suspension of stannous chloride hydrate (5.5 g, 24.1 mmol) in 150 mL of methanol was added at room temperature ethyl 6-chloro-5-azido-2-(trifluoromethyl)-2H-chromene-3-carboxylate (5.6 g, 16.1 mmol) in one portion. The reaction mixture gradually turned yellowish. After stirred at room temperature for about 45 min, the reaction turned a clear yellow solution. The volatiles were then removed. The residue was dissolved in EtOAc, and the resulting organic solution was washed with 5% sodium hydroxide solution (×4), brine, and dried over anhydrous magnesium sulfate. After removing the solvents, the residue was purified on silica gel column with 3:7 EtOAc/hexane, it gave 3.2 g of yellow solid. A small fraction of the product was further purified on reverse phase HPLC, it provided a yellow solid. LC-MS(ES$^+$) 322.2(M+1, 100). $^1$H NMR (CDCl$_3$/400 MHz) 7.80(s, 1H), 7.16(d, J=8.8 Hz, 1H), 6.35(d, J=8.8 Hz, 1H), 5.65(q, J=7.2 Hz, 1H), 4.31(m, 2H), 1.34(t, J=7.2 Hz, 3H). $^{19}$F NMR(CDCl$_3$/400 MHz) −78.55 (d, J=7.4 Hz). $^{13}$C NMR(CDCl$_3$/300 Mhz) 164.1, 152.8, 141.3, 133.1, 131.7, 123.7(q, J=287.7 Hz), 115.2, 113.4, 107.2, 106.6, 70.3(q, J=33.2 Hz), 61.7, 14.5. MS(ES$^+$) 322.1(M+1, 75%), HRMS(EI$^+$) m/z calc for (C$_{13}$H$_{11}$ClF$_3$NO$_3$): 321.0380 (M$^+$), found, 321.0359(M$^+$).

Step 3. Preparation of Ethyl 6-chloro-5-Iodo-2-(trifluoromethyl)-2H-chromene-3-carboxylate To a solution of 47% aqueous HI (11 mL, 59 mmol) dissolved in DMSO (11 mL) was added dropwise at 35° C. a solution of ethyl 6-chloro-5-amino-2-(trifluoromethyl)-2H-chromene-3-carboxylate (3.8 g, 11.8 mmol) in a mixture of 11 mL of DMSO and potassium nitrite (1.63 g, 23.6 mmol) with stirring. The resulted mixture was stirred at 35° C. for 15 min, and then it was transferred into 150 mL of a solution of potassium carbonate (10 g) in ice water. The product was extracted with ethyl acetate. The combined organic extracts were washed with saturated aqueous sodium carbonate, 5% aqueous sodium hydrosulfite, and brine, dried over anhydrous magnesium sulfate. After removing the solvent, the residue was purified on silica gel column with 1:9 EtOAc/hexane. The product was obtained as 2.5 g light yellow solid. A small amount of the product was further purified on reverse phase HPLC. It gave an off-white solid. m.p=117.0-119.0° C. LC-MS (ES$^+$): 433.2 (M+1, 100); $^1$H NMR(CDCl$_3$/400 MHz) 7.93(s,1H), 7.36(d, J=8.4 Hz, 1H), 6.91(d, J=8.4 Hz, 1H), 5.65(q, J=6.8 Hz, 1H), 4.33(m, 2H), 1.36(t, J=6.8 Hz, 3H). $^{19}$F NMR(CDCl$^3$/400 Hz) −78.50(d, J=6.8 Hz). $^{13}$C NMR (CDCl$_3$/400 MHz) 163.3, 152.3, 140.9, 133.6, 132.2, 124.7, 123.2(q, J=287.7 Hz), 119.4, 117.6, 104.5, 70.3(q, J=33.4 Hz), 62.0, 14.4. MS(EI$^+$) 432.0(M$^+$, 20), 363.0(M-CF$_3$, 100). High resolution MS(EI$^+$) m/z calc. for Cl$_3$H$_9$ClF$_3$IO$_3$: 431.9271 (M$^+$), found: 431.9238.

Rf. Baik, Woon Phil; Kim, Jung Min; Kim, Young Sam; Yoon, Cheol Hun; Kim, Shin Jong; Lee, Seok Woo. WO 20002053545; Application No. WO 2001-KR1586

Step 4. preparation of 6-chloro-5-(2-furyl)-2-(trifluoromethyl)-2H-chromene-3-carboxylic acid To the solution of ethyl 6-chloro-5-Iodo-2-(trifluoromethyl)-2H-chromene-3-carboxylate (300mg, 0.69 mmol), tetrakistriphenylphosphine-palladium(0) (80 mg, 0.07 mmol) and furan-2-boronic acid (112 mg, 1 mmol) in 9 mL of anhydrous dimethylacetamide was added 1.7 mL of 2.0M of aqueous sodium carbonate. The resulting mixture was heated to 95° C. and shaken for 16 hrs. After cooling to room temperature, 60 mL of EtOAc was added into the reaction flask, the resulting mixture was washed with brine (×3). After the organic phase was evaporated, to the residue was added THF (3 mL), EtOH(3 mL) and a solution of lithium hydroxide hydrate (116 mg/3 mL water). The resulting solution was heated to 80° C. for three hrs. The volatiles were then removed. The residue was diluted with water, and acidified at 0° C. with ice-cold diluted hydrochloric acid. The product was extracted with EtOAc. After removing the solvents, the residue was dissolved in acetonitrile and purified on reverse phase HPLC. It gave yellow solid. m.p.=191.0-193.0° C. (turned deep brown). LC-MS(ES+) 345.2(M+1, 100). $^1$H NMR (CDCl$_3$/400 MHz) 7.78(s, 1H), 7.63(s, 1H), 7.43(d, J=8.8 Hz, 1H), 6.98(d, J=8.8 Hz, 1H), 6.70(d, J=3.2 Hz, 1H), 6.59(m, 1H), 5.66(q, J=6.8 Hz, 1H). $^{19}$F NMR(CDCl$_3$/400 MHz) −78.59(d, J=6.8 Hz) $^{13}$C NMR (CDCl$_3$/400 MHz) 169.2, 152.7, 147.2, 144.0, 138.2, 134.3, 130.0, 127.5, 123.4(q, J=287.5 Hz), 119.9, 117.5, 116.0, 114.3, 111.5, 69.9(q, J=33.7 Hz). MS(ES$^−$): 342.9(M−H, 100), High resolution MS(ES$^−$): m/z calc.for C$_{15}$H$_7$ClF$_3$O$_4$: 342.9985(M−H), found: 343.0005.

EXAMPLE 868

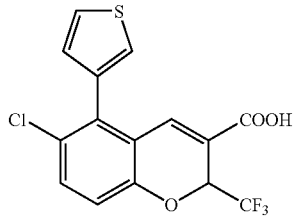

6-Chloro-5-thien-3-yl-2-(trifluoromethyl)-2H-chromene-3-carboxylic acid

This example was prepared using the same procedures as described as in the preparation of 6-chloro-5-(2-furyl)-2-(trifluoromethyl)-2H-chromene-3-carboxylic acid. Light yellow solid, m.p.=211.0-213.5° C. (turned deep brown). LC-MS(ES+) 361.2(M+1, 100), $^{19}$F NMR(CDCl$_3$/400 MHz) −78.64d, J=7.4 Hz). $^1$H NMR (CDCl$_3$/400 MHz) 7.58(s, 1H), 7.45(m, 1H), 7.42(d, J=8.8 Hz, 1H), 7.27(s, broad, 1H) 7.10(s, broad, 1H), 6.96(d, J=8.8 Hz, 1H), 5.63(q, J=6.8 Hz, 1H). $^{13}$C NMR(CDCl$_3$/400 MHz) 169.2, 152.7, 138.1, 136.1, 135.0, 133.9, 129.6, 127.5, 126.9, 126.1, 123.5(q, J=287.7 Hz), 120.0, 116.7, 115.9, 69.9(q, J=33.5 Hz). MS(ES−) 358.9(M−H,100);High resolution MS(ES−): m/z calc.for C$_{15}$H$_7$ClF$_3$O$_3$S: 358.9756(M−H), found: 358.9752

EXAMPLE 869

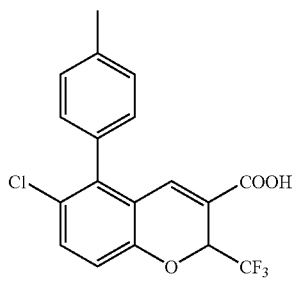

6-Chloro-5-(4-methylphenyl)-2-(trifluoromethyl)-2H-chromene-3-carboxylic acid

Preparation of 6-chloro-5-(4-methylphenyl)-2-(trifluoromethyl)-2H-chromene-3-carboxylic acid This example was prepared using the same procedures as described as in the preparation of 6-chloro-5-(2-furyl)-2-(trifluoromethyl)-2H-chromene-3-carboxylic acid. Off-white solid, m.p.=218.0-220.0° C. LC-MS(ES+): 369.2(M+1,100), $^1$H NMR (CDCl$_3$/CD$_3$OD/300 MHz) 7.45-7.43(m, 2H), 7.33-7.26(m, 3H), 7.06-7.00(m, 2H), 5.68(q, J=6.9 Hz, 1H), 2.47(s, 3H). $^{19}$F NMR(CDCl$_3$/CD$_3$OD/300 MHz) −78.61(d, J=6.9 Hz). $^{13}$C NMR(CDCl$_3$/CD$_3$OD/300 MHz) 167.0, 152.6, 140.9, 138.7, 136.9, 133.4, 132.4, 130.9, 129.9, 129.5, 129.2, 127.2, 123.7(q, J=287.6 Hz), 120.0, 116.6, 116.5, 70.2(q, J=33.3 Hz),21.6. MS(ES−) 367.0(M−H,100), High resolution MS(ES−) m/z calc.for C$_{18}$H$_{11}$ClF$_3$O$_3$: 367.0349 (M−H), found 367.0325.

EXAMPLE 870

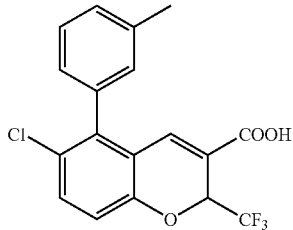

6-Chloro-5-(3-methylphenyl)-2-(trifluoromethyl)-2H-chromene-3-carboxylic acid

This example was prepared using the same procedures as described in the preparation of 6-chloro-5-(2-furyl)-2-(trifluoromethyl)-2H-chromene-3-carboxylic acid. Off-white solid, m.p.=222.5-224.0° C. LC-MS(ES+): 369.2(M+1, 100). $^1$H NMR (CD$_3$OD/300 MHz) 7.51-6.90(m, 7H), 5.79(q, J=6.9 Hz, 1H), 2.44(s, 3H). $^{19}$F NMR (CDCl$_3$/CD$_3$OD/300 MHz) −80.10(d, J=7.0 Hz). $^{13}$C NMR(CD$_3$OD/300 MHz): 165.2, 152.3, 140.7, 138.4(d, J=31.5 Hz), 135.6 (d, J=3.2 Hz),134.5(d, J=5.7 Hz), 132.8, 130.5(d, J=49.2 Hz), 29.2(d),128.3(d), 127.1, 126.7, 123.9(q, J=287.11 Hz), 119.9(d), 117.9(d), 116.3(d),70.2(q, J=32.7 Hz), 20.3. MS(ES−): 367.0(M−H,100). High resolution MS(ES−) m/z calc. for C$_{18}$H$_{11}$ClF$_3$O$_3$: 367.0349 (M−H), found 367.0325

EXAMPLE 871

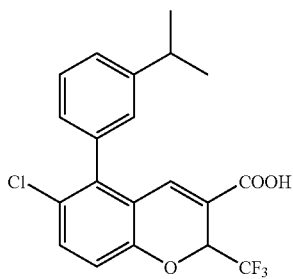

6-Chloro-5-(3-isopropylphenyl)-2-(trifluoromethyl)-2H-chromene-3-carboxylic acid This example was prepared using the same procedures as described in the preparation of 6-chloro-5-(2-furyl)-2-(trifluoromethyl)-2H-chromene-3-carboxylic acid. Off-white, m.p.=184.0-186.5° C. LC-MS(ES+) 397.3(M+1, 100). $^1$H NMR (CDCl$_3$/300 MHz) 9.53(s, broad, 1H), 7.52-7.04(m, 5H), 7.04-6.96(m, 2H), 5.68(q, J=6.6 Hz, 1H), 3.02(q, J=6.6 Hz, 1H), 1.34(m, 6H). $^{19}$F NMR(CDCl$_3$/300 MHz) −78.62. $^{13}$C NMR(CDCl$_3$/300 MHz) 169.5, 152.8, 149.3(d), 141.4, 138.3(d), 135.1, 133.9, 129.4, 128.5(d), 128.4(d), 127.5, 127.2(d), 127.1(d), 123.6(q, J=287.7 Hz), 119.8, 116.6, 115.8, 69.9(q, J=33.7 Hz), 34.3, 24.1. MS(ES−) 395.0(M−H, 100), High resoluton MS(ES−) m/z calc. for C$_{20}$H$_{15}$ClF$_3$O$_3$: 395.0662(M−H), found:395.0642.

EXAMPLE 872

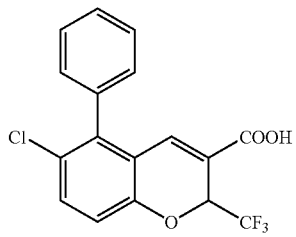

6-Chloro-5-phenyl-2-(trifluoromethyl)-2H-chromene-3-carboxylic acid

This example was prepared using the same procedures as described as in the preparation of 6-chloro-5-(2-furyl)-2-(trifluoromethyl)-2H-chromene-3-carboxylic acid. Slight yellow solid. M.P.=229.0-231.0° C. LC-MS(ES+) 355.2(M+1, 100), $^1$H NMR (CDCl$_3$/CD$_3$OD/300MHz) 7.46-7.30(m, 6H), 7.09(d, J=7.5 Hz, 1H), 6.93(d, J=9 Hz, 1H), 5.65(q, J=6.6 Hz, 1 H). $^{19}$F NMR(CDCl$_3$/CD$_3$OD/300 MHz) −78.83. $^{13}$C NMR(CDCl$_3$/CD$_3$OD/300 MHz) 169.8, 156.4, 144.5, 139.5, 139.4, 137.0, 134.8, 133.9, 132.7, 132.6, 132.3, 130.9, 127.6(q, J=287.6 Hz), 124.0, 121.5, 120.5, 74.2(q, J=33.2 Hz). MS(ES−) 353.0(M−H, 100). High resoluton MS(ES−) m/z calc. for C$_{17}$H$_9$ClF$_3$O$_3$: 353.0192(M−H), found: 353.0202.

EXAMPLE 873

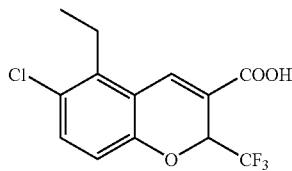

6-Chloro-5-ethyl-2-(trifluoromethyl)-2H-chromene-3-carboxylic acid

To the mixture of ethyl 6-chloro-5-iodo-2-(trifluoromethyl)-2H-chromene-3-carboxylate (0.3g, 0.7 mmol), potassium carbonate(109 mg, 2.87 mmol) and tetrakistriphenylpalladium (0) (81 mg, 0.07 mmol) in 3 mL of anhydrous DMF was added triethylboron (1.0M/THF, 1.05 mL, 1.05 mmol) under nitrogen. The resulting mixture was heated to 110° C. for five hrs. The reaction was cooled to room temperature, and diluted with 100 mL of ethyl acetate. The resulting organic phase was washed with brine. After removing the solvent, the residue was dissolved in 3 mL of THF, followed by addition of a solution of lithium hydroxide hydrate in 3 mL of water. To the resulting mixture was further added 3 mL of ethanol. The resulting solution was then heated to 80° C. for three hrs. The volatiles were then removed. The residue was diluted with water, and acidified in an ice/water bath with dilute hydrochloric acid. The product was then extracted with ethyl acetate. The organic extracts were washed with brine, and dried over anhydrous magnesium sulfate. After removing the solvent, the residue was purified on short silica gel with 3:7 EtOAc/hexane+1% HOAc to remove the polar impurities. After concentrating the collected fraction, the residue was further purified on reverse phase HPLC. It gave 75 mg slightly yellow solid. M.P.=171.5-172.5° C. $^1$H NMR (CDCl$_3$/400 Mz), 8.07(s, 1H), 7.32(d, J=8.8 Hz, 1H), 6.82(d, J=8.8 Hz, 1H), 5.65(q, J=6.8 Hz, 1H), 2.91(m, 2H), 1.18(t, J=7.6 Hz, 3H). $^{13}$C NMR(CDCl$_3$/400 MHz) 169.5, 152.8, 141.5, 136.5, 134.1, 127.7, 123.4(q, J=287.7 Hz), 118.6, 116.3, 115.5, 69.8(q, J=33.4 Hz), 23.1, 14.7. $^{19}$F NMR(CDCl$_3$/400 Mz) −78.72(d, J=6.8 Hz). MS(ES−)=305.0 (M−H, 100). High resolution MS(ES−), m/e calc. For C$_{13}$H$_{10}$ClF$_3$O$_3$: 305.0198 (M−H), found: 305.0157.

EXAMPLE 874

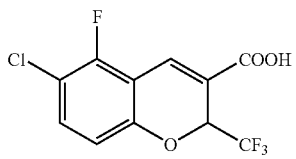

6-Chloro-5-fluoro-2-(trifluoromethyl)-2H-chromene-3-carboxylic acid

To the solution of ethyl 6-chloro-5-fluoro-2-(trifluoromethyl)-2H-chromene-3-carboxylic acid (1.1 g, 3.4 mmol) in 5 mL of THF was added a solution of lithium hydroxide hydrate (0.72 g, 17 mmol) in 5 mL of water. To the resulting mixture was added 5 mL of ethanol. The resulting solution was heated to reflux over three hrs. The reaction turned red. After cooling to room temperature, the volatiles were removed, the residue was diluted with water. The resulting solution was acidified at 0° C. with ice cold dilute hydrochloric acid. The product was then extracted with ethyl acetate. The combined organic extracts were dried over anhydrous magnesium sulfate. After removing the solvent, the residue was purified on reverse phase HPLC. It gave a yellow solid (0.3 g). LC-MS(ES+) 297.2(M+1, 100). $^1$H NMR (CDCl$_3$/CD$_3$OD/400 MHz) 7.85(s, 1H), 7.24(m, 1H), 6.69(d, J=8.8 Hz, 1H), 5.63(q, J=6.4 Hz, 1H). $^{19}$F (CDCl$_3$/CCD$_3$OD/400 MHz) −78.94(d, J=6.8 Hz), −111.92(d, J=7.5 Hz). $^{13}$C NMR(CDCl$_3$/CD$_3$OD/400 MHz) 165.4, 155.0(d, J=64.4 Hz), 152.3, 133.2, 129.4, 123.3 (q, J=287.3 Hz) 118.5 114.2(d, J=4.3 Hz), 112.6, 110.1 (d, J=4.7 Hz), 70.9(q, J=33.2 Hz). HRSM((EI+) m/z calc. for (C$_{11}$H$_5$ClF$_4$O$_3$): 295.9863(M+), found 295.9875(M+).

EXAMPLE 875

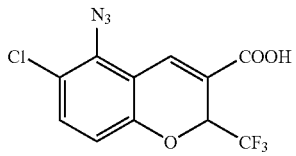

5-Azido-6-chloro-2-(trifluoromethyl)-2H-chromene-3-carboxylic acid

This example was prepared using the same procedures as described as in the preparation of 6-chloro-5-fluoro-2-(trifluoromethyl)-2H-chromene-3-carboxylic acid. LC-MS (ES+) 320.2(M+1, 45), 292.1(M−27, 100). $^1$H NMR (CDCl3/400 MHz) 8.15(s, 1H), 7.28(d, J=8.8 Hz, 1H), 6.77(d, J=8.8 Hz, 1H), 5.65(q, J=7.2 Hz, 1H). $^{19}$F NMR (CDCl$_3$/400 MHz) −78.74(d, J=6.8 Hz). $^{13}$C NMR(CDCl$_3$/400 Mhz) 169.3, 153.0, 134.8, 134.6,123.3(q, J=287.6 HZ), 122.7, 116.4, 114.4, 114.2, 106.5, 70.3(q, J=33.5 Hz). HRMS(EI$^+$) m/z calc. for (C$_{11}$H$_5$ClF$_3$N$_3$O$_3$): 318.9972 (M$^+$), found: 318.9973.

EXAMPLE 876

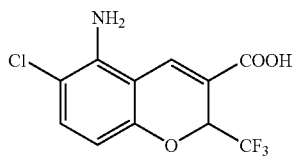

5-Amino-6-chloro-2-(trifluoromethyl)-2H-chromene-3-carboxylic acid

This example was prepared using the same procedures as described as in the preparation of 6-chloro-5-fluoro-2-(trifluoromethyl)-2H-chromene-3-carboxylic acid as a yellow solid. m.p.=208.5-210.0° C. LC-MS(ES+): 294.2(M+1, 100). $^{19}$F NMR(CD$_3$OD/300 MHz) −81.64(d, J=7.1 Hz). $^1$H NMR (CD$_3$OD/300 MHz) 8.13(s, 1H), 7.20(d, J=8.7 Hz, 1H), 6.27(d, J=8.7 Hz, 1H), 5.69(q, J=7.5 Hz, 1H), 4.91(s, broad peak). $^{13}$C NMR(CD30D/300 MHz)166.0, 152.8, 143.2, 132.7, 132.6, 124.1(q, J=287.2 Hz), 114.3, 112.4, 106.5, 104.4, 70.1 (q, J=32.8 Hz). HRMS(ES$^-$) m/z calc. for (C$_{11}$H$_6$ClF$_3$NO$_3$): 291.9988(M−H), found: 291.9966.

EXAMPLE 877

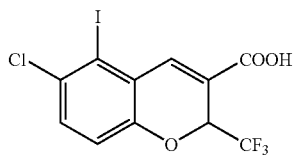

6-Chloro-5-iodo-2-(trifluoromethyl)-2H-chromene-3-carboxylic acid

This example was prepared using the same procedures as described as in the preparation of 6-chloro-5-fluoro-2-(trifluoromethyl)-2H-chromene-3-carboxylic acid. Light yellow solid. LC-MS(ES$^+$) 405.1(M+H, 100). $^1$H NMR (CDCl$_3$/CD$_3$OD/400 Hz) 8.04(s, 1H), 7.39(d, J=8.8 Hz, 1H), 6.94(d, J=8.4 Hz, 1H), 5.65(q, J=6.4 Hz, 1H). $^{13}$C NMR(CDCl$_3$/CD$_3$OD/400 Mhz) 166.5, 152.5, 142.4, 133.7, 132.6, 124.6, 123.2(q, J=287.1 Hz), 118.7, 117.7, 104.7, 70.5(q, J=33.5 Hz). $^{19}$F(CDCl$_3$/CD$_3$OD/400 Hz): −78.55(d, J=6.8 Hz). High resolution MS(ES$^-$): m/e calc. for C$_{11}$H$_4$ClF$_3$O$_3$: 402.8846 (M−H), observed: 402.8857.

Preparation of 6-Methyl-7-fluoro-2-(trifluoromethyl)-2H-chromene-3-carboxylic acid

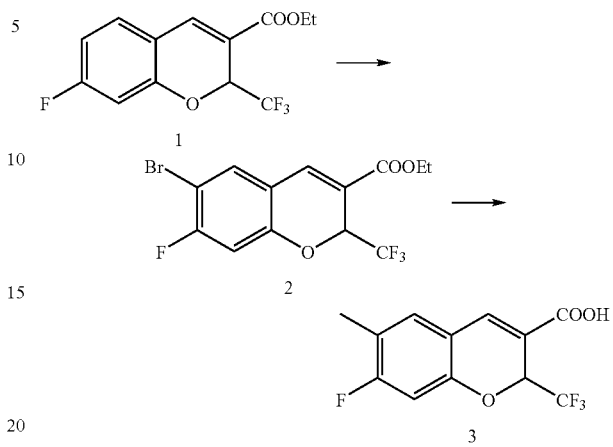

EXAMPLE 878

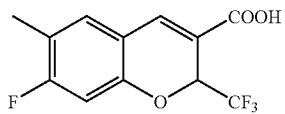

6-Methyl-7-fluoro-2-(trifluoromethyl)-2H-chromene-3-carboxylic acid

Step 1. Preparation of ethyl 6-bromo-7-fluoro-2-(trifluoromethyl)-2H-chromene-3-carboxylate To the solution of ethyl 7-fluoro-2-(trifluoromethyl)-2H chromene-3-carboxylate (5 g, 34 mmol) in 100 mL of tetrachloromethane was added dropwise at room temperature a solution of bromine(10.5 mL, 204 mmol) in 20 mL of tetrachloromethane. The resulting solution was stirred for 24 hrs. To the reaction was added 500 mL of ethyl acetate. The resulting organic phase was then washed with aqueous sodium thiosulfite to remove excess bromine, and brine, then dried over anhydrous magnesium sulfate. After removing the volatiles, the residue was purified on silica gel column with 1:9 EtOAc/hexane. It gave 5.6 g product. A small fraction of the product was further purified on reverse phase HPLC for analytica characterization. It gave a white solid. m.p.=98.5-100.0° C. $^1$H NMR(CDCl$_3$/300 MHz) 7.67(s, 1H), 7.46(d, J=7.5 Hz, 1H), 6.83(d, J=9 Hz, 1H), 5.74(q, J=6.6 Hz, 1H), 4.36(m, 2H), 1.39(t, J=7.2 Hz, 3H). $^{19}$F NMR(CDCl$_3$/300 MHz): −78.82(d, J=6.5 Hz), −98.7(t, J=7.9 Hz). $^{13}$C NMR(CDCl$_3$/300 MHz): 163.6, 163.1, 159.7,154.0(d, J=11.5 Hz), 135.1, 133.4, 123.4(q, J=287.3 Hz), 117.3, 105.6(d, J=26.7 Hz), 102.2(d, J=22.3 Hz), 71.1 (q, J=33.3 Hz), 61.9, 14.4. LC-MS(ES$^+$): 369.2(M+1, 100). HRMS (EI+): m/z calc. For C$_{13}$H$_9$BrF$_4$O$_3$: 367.9671(M$^+$), found: 367.9675.

Step 2 Preparation of 6-methyl-7-fluoro-2-(trifluoromethyl)-2H-chromene-3-carboxylic acid To the mixture of ethyl 6-bromo-7-fluoro-2-(trifluoromethyl)-2H-chromene-3-carboxylate (2.2g, 6 mmol), potassium carbonate(3.22g, 23.4mmol), and tetrakis(triphenylphosphine)palladium (0) (700 mg, 0.6 mmol) in 18 ml of anhydrous DMF was added trimethylboroxine(2.5 mL, 9 mmol). The resulting mixture was heated to 110° C. under nitrogen atmosphere for 15 hrs. After cooling to room temperature, to the reaction was added 200 mL of ethyl acetate, the resulting organic phase was washed with brine, and dried over anhydrous magnesium sulfate. After removing the solvents, the residue was purified on a short silica gel column with hexane/EtOAc mixture. The collected fraction was then evaporated to dryness. 300 mg of the purified intermediate was then dissolved in 9 mL of 1:1:1 THF/EtOH/Water, followed by addition of lithium hydroxide hydrate (102 mg). The resulting solution was heated to 80° C. for 1.5 hrs. The volatiles were then removed, the residue was diluted with water, and acidified at 0° C. with dilute hydrochloric acid. Plenty of precipitates were formed. The product was then extracted with ethyl acetate. After removing the solvents, the crude product was purified on reverse phase HPLC. Light yellow solid. $^1$H NMR (CDCl$_3$/CD$_3$OD/300 MHz) 7.76(s, 1H), 7.07(d, J=8.1 Hz, 1H), 6.68(d, J=9.9 Hz, 1H), 5.65(q, J=6.9 Hz, 1H), 2.20(s, 3H). $^{19}$F NMR (CDCl$_3$/CD$_3$OD/300 MHz) −78.93(d, J=6.9 Hz), −107.11(t, J=7.9 Hz). $^{13}$C NMR(CDCl$_3$/CD$_3$OD/300 MHz) 168.0, 165.8, 162.3, 153.2(d, J=12.8 Hz), 138.4, 132.2, 123.6(q, J=287.5 Hz), 119.8(d, J=18.5 Hz), 115.0(d, J=43.2 Hz), 104.1(d, J=27.1 hz), 70.7(q, J=33.3 Hz), 14.0(d, J=3.2 Hz). LC-MS(ES$^+$): 277.2(M+1, 100). Hight resolution mass (ES$^-$): m/z calc. For C$_{12}$H$_8$F$_4$O$_3$: 275.0337(M−H), found: 275.0341.

Preparation of 7-(4-chloro-2-methylphenoxy)-6-methyl-2-(trifluoromethyl)-2H-chromene-3-carboxylic acid

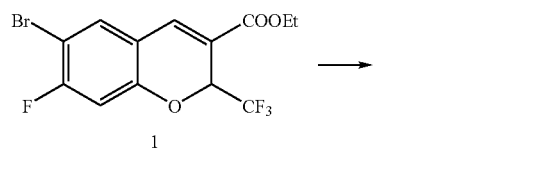

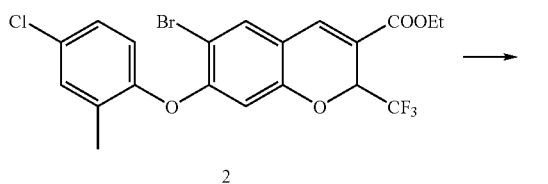

EXAMPLE 879

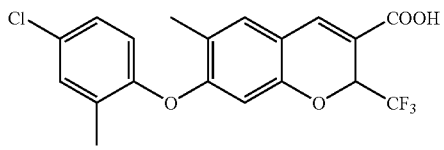

7-(4-Chloro-2-methylphenoxy)-6-methyl-2-(trifluoromethyl)-2H-chromene-3-carboxylic acid Step 1. Preparation of ethyl 7-(4-chloro-2-methylphenoxy)-6-bromo-2-(trifluoromethyl)-2H-chromene-3-carboxylate To the mixture of ethyl 6-bromo-7-fluoro-2-(trifluoromethyl)-2H-chromene-3-carboxylate (0.5 g, 1.36 mmol), potassium carbonate(560 mg, 4.06 mmol), and 5 mL of anhydrous DMF was added 4-Cl-2-methylphenol(466 mg, 3.23 mmol) and 0.32 mL of diisopropylethylamine, the resulting mixture was then heated to 90° C. for eight hrs. After cooling to room temperature, to the reactions was added 150 mL of ethyl acetate, the resulting organic solution was washed with brine, and dried over anhydrous magnesium sulfate. After removing volatiles, the residue was purified on a short silica gel column with EtOAc/hexane mixture. It gave 400 mg a yellow solid. A small amount of the product was further purified on reverse phase HPLC for analytical characterization. It provided a light yellow solid. $^1$H NMR (CDCl$_3$/300 MHz) 7.68(s, 1H), 7.52(s, 1H), 7.31 (d, J=2.7 Hz, 1H), 7.25(dd, J=2.4, 8.4 Hz, 1H), 6.95(d, J=8.7 Hz, 1H), 6.29(s, 1H), 5.65(q, J=6.6 Hz, 1H), 4.35(m, 2H), 2.21(s, 3H), 1.38(t, 6.9 Hz, 3H). $^{19}$F NMR (CDCl$_3$/300MHz) −78.84(d, J=6.5 Hz). $^{13}$C NMR(CDCl$_3$/300 MHz) 163.9, 157.9, 154.1, 151.6, 135.5, 133.8, 132.3, 131.9, 130.9, 127.8, 123.5(q, J=287.5 Hz), 121.9, 115.9, 115.5, 105.3, 104.6, 71.2(q, J=33.3 Hz), 61.8, 16.2, 14.4. LC-MS (ES+): 491.3(M+1, 70), 493.3(M+2, 100). High resolution Mass (EI+): m/z calc. For C$_{20}$H$_{15}$BrClF$_3$O$_4$: 489.9794 (M$^+$), found: 489.9765.

Step 2 Preparation of 7-(4-chloro-2-methylphenoxy)-6-methyl-2-(trifluoromethyl)-2H-chromene-3-carboxylic acid This example was prepared using the same procedures as described in the preparation of. 6-methyl-7-fluoro-2-(trifluoromethyl)-2H-chromene-3-carboxylic acid. Light yellow solid. $^1$H NMR (CDCl$_3$/CD$_3$OD/300 MHz) 7.76(s, 1H), 7.29(m, 1H), 7.20(dd, J=2.4 Hz, 8.4 Hz, 1H), 7.11(s, 1H), 6.87(d, J=8.7 Hz, 1H ), 6.20(s, 1H), 5.62(q, J=6.9 Hz, 1H), 2.28(s, 3H), 2.19(s, 3H). $^{19}$F NMR(CDCl$_3$/CD$_3$OD/300 MHz) −79.0(d, J=6.5 Hz). $^{13}$C NMR(CDCl$_3$/CD$_3$OD/300 MHz) 167.3, 159.9, 153.3, 152.2, 138.1, 132.1, 132.0, 131.7, 130.1, 127.7, 123.7(q, J=287.7 Hz), 122.2, 121.6, 113.8, 113.7, 103.2, 70.6(q, J=33.1 Hz), 16.2, 15.6. LC-MS(ES$^+$): 399.3(M+1, 100). MS(ES−):397.1(M−H, 63), 333.1(M−65, 100). High resolution Mass(ES−): m/z calc. For C$_{19}$H$_{13}$ClF$_3$O$_4$: 397.0454(M−H), found: 397.0443.

Preparation of 6-methyl-7-substituted-2-(trifluoromethyl)-2H-chromene-3-carboxylic acids

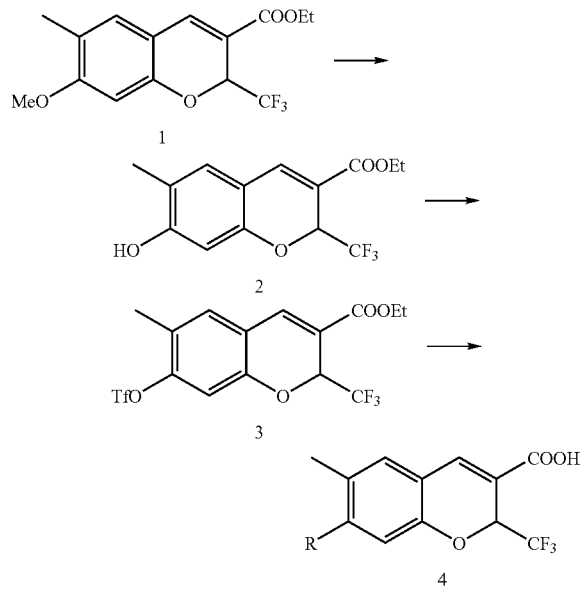

EXAMPLE 880

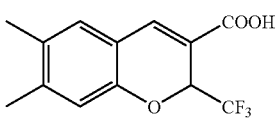

6,7-dimethyl-2-(trifluoromethyl)-2H-chromene-3-carboxylic acid

Step 1. Preparation of ethyl 7-hydroxy-6-methyl-2-(trifluoromethyl)-2H-chromene-3-carboxylate To the solution of ethyl 7-methoxyl-6-methyl-2-(trifluoromethyl)-2H-chromene-3-carboxylate (5.2 g, 16.4 mmol) in 30 mL of dry dichloromethane at −78° C. in a dry ice/acetone bath was added a solution of 1.0 M of boron tribromide (164 mL, 164 mmol) dropwise. After finishing adding, the dry ice/acetone bath was removed. The reaction was stirred at room temperature overnight. The reaction was then cooled to −78° C. in dry ice/acetone bath. 200 mL of ethanol was added dropwise. After finishing addition, the cooling bath was removed. The reaction was allowed to warm to room temperature. LC-MS indicated that the reaction was finished. The volatiles were removed on rotavapor. The residue was then purified on silica gel column with 1:9 EtOAc/hexane. The desired product was isolated as off-white solid, 3.2 g. m.p.=151.0-153.0° C. $^1$H NMR (CDCl$_3$/CD$_3$OD/300 MHZ):7.68(s, 1H), 6.97(s, 1H), 6.43(s, 1H), 5.65(q, J=7.2 Hz, 1H), 4.31(m, 2H), 2.17(s, 3H), 1.36(t, J=6.9 Hz, 3H). $^{19}$F NMR(CDCl$_3$/CD$_3$OD/300 MHz) −79.03 (d, J=7.3 Hz). $^{13}$C(CDCl$_3$/CD$_3$OD/300 Mhz) 164.8, 159.4, 153.3, 137.8, 131.8, 123.9(q, J=287.9 Hz), 119.4, 112.5, 111.8, 102.6, 70.9(q, J=32.9 Hz), 61.4, 15.3, 14.4. LC-MS (ES+): 303.1(M+1). MS(EI+): 302.0(M+, 80), 233(M−69, 100); High resolution MS: m/z calc. For C$_{14}$H$_{13}$F$_3$O$_4$: 302.0766(M+, theoretical), found: 302.0763.

Step 2. Preparation of ethyl 6-methyl-2-(trifluoromethyl)-7-I[(trifluoromethyl)sulfonyl-oxy]-2H-chromene-3-carboxylate To the mixture of ethyl 7-hydroxy-6-methyl-2-(trifluoromethyl)-2H-chromene-3-carboxylate (2.5g, 8.3 mmoL) in anhydrous DCM was added DIEA (2.79 mL, 16.6 mmol) in one portion. The resulting yellow solution was then cooled to 0° C. in an ice bath and stirred for 10 min, then (TfO)$_2$O (4.35 mL, 25 mmol) was added dropwise. After finishing addition, the ice bath was removed, the reaction was stirred at room temperature for two hrs. Then, 20 mL of 0.5 N dilute HCl solution was added, the mixture was stirred for 10 min, then to the reaction was added 50 mL of DCM, the aqueous phase was separated and extracted with DCM. The combined organic phases were washed with sat. NaHCO$_3$ and brine, after dried over anhydrous sodium sulfate, the volatiles were removed, the residue was purified on silica gel column with 1:9 EtOAc/hexane. It gave a white solid, 3.3 g. $^1$H NMR(CDCl$_3$/300 MHz):7.69(s, 1H), 7.18(s, 1H), 6.94(s, 1H), 5.74(q, J=6.6 Hz, 1H), 4.35(m, 2H), 2.32(s, 3H), 1.37(t, J=7.2 Hz, 3H). 19F NMR(CDCl$_3$/300 MHz): −74.3, −78.92 (d, J=6.5 Hz). $^{13}$C NMR(CDCl$_3$/300 MHz): 163.6, 152.3, 150.3, 135.4, 132.2, 123.4(q, J=287.3 Hz), 120.9, 119.3, 118.4, 116.7, 109.8, 71.0(q, J=33.3 Hz), 61.9, 15.7, 14.2. LC-MS(ES+): 435.0(M+1, 100). High resolution Mass (EI+): m/z calc. For C$_{15}$H$_{12}$F$_6$O$_6$S: 434.0259(M$^+$), found: 434.0257.

Step 4. Preparation of 6,7-dimethyl-2-(trifluoromethyl)-2H-chromene-3-carboxylic acid To the mixture of ethyl 6-methyl-2-(trifluoromethyl)-7-{[(trifluoromethyl) sulfonyl]-oxy}-2H-chromene-3-carboxylate (0.3 g, 0.7 mmol), potassium carbonate(0.378 g, 2.73 mmol), tetrakis(triphenylphosphine)palladium (0) (81 mg, 0.07 mmol) and 3 mL of anhydrous DMF was added trimethylboraxine(292 uL, 2.1 mmol). The resulting mixture was heated to 110° C., and stirred at 110° C. for two hrs. LC-MS indicated that the reaction was done. To the reaction was added 100 mL of EtOAc, the resulting organic solution was washed with brine, and dried over anhydrous magnesium sulfate. After removing the volatiles, the residue was purified on silica gel column with 1:9 EtOAc/hexane. It gave a white solid, about 180 mg. The purified white solid was dissolved in 3 mL of THF, to the resulting solution was added lithium hydroxide hydrate (118 mg, 2.8 mmol), 3 mL of water and 3 mL of ethanol, the resulting solution was heated to 80° C. and stirred for 45 min. After cooling to room temperature, the volatiles were removed on rotavapor, the residue was diluted with water, and acidified in ice bath with ice cold dilute hydrochloric acid. Plenty of white precipitates were formed. The solid was filtered and washed with water, and dried in vacuum. The crude product was then purified on reverse phase HPLC. It gave a white solid, 70 mg. $^1$H NMR (CDCl$_3$/CD$_3$OD/300 MHz) 7.73(s, 1H), 6.97 (s, 1H), 6.79(s, 1H), 5.65(q, J=6.6 Hz), 2.25(s, 3H), 2.19(s, 3H). $^{13}$C NMR(CDCl$_3$/ CD$_3$OD/300 MHz) 167.0, 151.8, 143.2, 138.3, 131.0, 130.4, 123.9(q, J=287.9 Hz), 117.1, 116.9, 115.2, 70.7(q, J=32.7 Hz), 20.5, 18.9. $^{19}$F NMR (CDCl$_3$/ CD$_3$OD/300 MHz) −78.97(d, J=6.5 Hz). LC-MS (ES+):273.2 (M+1, 100). High resolution Mass (ES−): m/z calc. For C$_{13}$H$_{10}$F$_3$O$_3$: 271.0582(M−H), found: 271.0563.

EXAMPLE 881

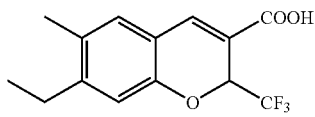

7-Ethyl-6-methyl-2-(trifluoromethyl)-2H-chromene-3-carboxylic acid

This example was prepared using the same procedures as described in the preparation of 6,7-dimethyl-2-(trifluoromethyl)-2H-chromene-3-carboxylic acid. Yellow solid. LC-MS(ES$^+$): 287.2(M+1, 100). $^1$H NMR (CD$_3$OD/300 MHz) 7.73(s, 1H), 7.06(s, 1H), 6.79(s, 1H), 5.69(q, J=7.2 Hz, 1H), 2.62(q, J=7.5 Hz, 2H), 1.21(t, J=7.8 Hz, 3H). $^{19}$F NMR (CD$_3$OD/300 MHz) −80.35(d, J=7.1 Hz). $^{13}$C NMR (CD$_3$OD/300 MHz) 166.0, 151.9, 148.5, 137.1, 130.6, 130.1, 124.1(q, J=287.4 Hz), 116.9, 115.8, 114.8, 70.7(q, J=32.5 Hz), 26.2, 17.1, 13.2. High resolution Mass (ES$^−$): m/z calc. For C$_{14}$H$_{12}$F$_3$O$_3$: 285.0739(M−H), found: 285.0708.

EXAMPLE 882

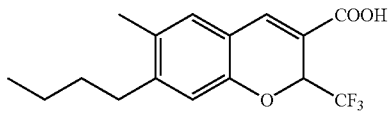

7-Butyl-6-methyl-2-(trifluoromethyl)-2H-chromene-3-carboxylic acid

This example was prepared using the same procedures as described in the preparation of 6,7-dimethyl-2-(trifluoromethyl)-2H-chromene-3-carboxylic acid. Light yellow solid. LC-MS(ES+):315.1(M+1, 100). $^1$H NMR (CDCl$_3$/300 MHz) 7.86(s, 1H), 7.04(s, 1H), 6.84(s, 1H), 5.69(q, J=6.9 Hz, 1H), 2.60(t, J=7.2 Hz, 2H), 2.27(s, 3H), 1.63-1.58(m, 2H), 1.48-1.41(m, 2H), 1.00(t, J=7.5 Hz, 3H). $^{13}$F NMR (CDCl$_3$/300 MHz) −78.90(d, J=7.1 Hz) $^{13}$C NMR(CDCl$_3$/300 MHz) 170.1, 152.2, 148.6, 140.1, 131.1, 130.6, 121.8(q, J=287.9 Hz), 116.6, 116.3, 114.2, 70.5(q, J=33.0 Hz), 33.7, 32.1, 22.9, 18.6, 14.2. High resolution MS(ES$^−$): m/z calc. For C$_{16}$H$_{16}$F$_3$O$_3$: 313.1052(M−H), found: 313.1024.

EXAMPLE 883

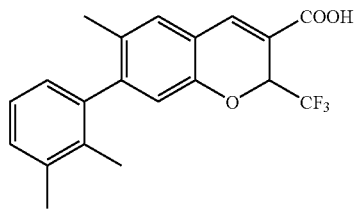

7-(2,3-Dimethylphenyl)-6-methyl-2-(trifluoromethyl)-2H-chromene-3-carboxylic acid To the mixture of ethyl 6-methyl-2-(trifluoromethyl)-7-{[(trifluoromethyl) sulfonyl]-oxy}-2H-chromene-3-carboxylate (0.3 g, 0.7 mmol), tetrakistriphenylpalladium (0)(4.5 mg, 0.035 mmol), powdered potassium phosphate (222 mg, 1.05 mmol) and 2,3-dimethylphenylboronic acid (106 mg, 0.84 mmol) was added 5 mL of anhydrous dixoane. The resulting mixture was heated to 85° C. and stirred for 6 hrs. After cooling to room temperature, to the reaction was added 100 mL of ethyl acetate. The organic phases were washed with brine, and dried over anhydrous magnesium sulfate. After removing the solvents, the residue was purified on silica gel column with 1:9 EtOAc/hexane. The collected fraction was evaporated to dryness, the residue was dissolved in 6 mL of 1:1 THF/ethanol, to the resulting solution was added lithium hydroxide hydrate (117 mg, 2.8 mmol), followed by addition of 3 mL of water. The resulting mixture was heated to 80° C. and stirred for 1.5 hr. After removing the volatiles, the residue was acidified at 0° C. with ice-cold dilute HCl. The product was then extracted with EtOAc. After removing the volatiles, the residue was purified on reverse phase HPLC. It gave 39 mg of a light yellow solid product. $^1$H NMR (CDCl$_3$/CD$_3$OD/300 MHz) 7.85(s, 1H), 7.21-7.14(m, 3H), 6.96(dd, J=6.9 Hz, 15.6 Hz, 1H), 6.79(s, 1H), 5.71(q, J=7.2 Hz, 1H), 2.35(s, 3H), 2.00(s, 6H). $^{19}$F NMR(CDCl3/300 MHz) −78.81. $^{13}$C NMR (CDCl$_3$/CD$_3$OD/300 MHz) 167.3, 151.5, 148.1, 140.6(d, J=4.8 Hz), 138.5, 137.3, 134.1(d, J=13.7 Hz), 130.7, 129.4, 126.8, 126.6, 125.6, 123.9(q, J=287.9 Hz), 118.0, 117.2, 115.9, 70.8(q, J=32.9 Hz), 20.7, 19.1, 16.6. LC-MS(ES$^+$): 363.2 (M+1, 100). High resolution MS(ES$^−$): m/z calc. For C$_{20}$H$_{16}$F$_3$O$_3$: 361.1052(M−H), found: 361.1036.

EXAMPLE 884

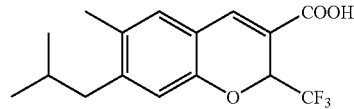

7-Isobutyl-6-methyl-2-(trifluoromethyl)-2H-chromene-3-carboxylic acid

This example was prepared using the same procedures as described in the preparation of 7-(2,3-dimethylphenyl)-6-methyl-2-(trifluoromethyl)-2H-chromene-3-carboxylic acid. White solid. $^1$H NMR (CDCl$_3$/300 MHz) 7.86(s, 1H), 7.05 (s, 1H), 6.80(s, 1H), 5.69(q, J=6.9 Hz, 1H), 2.49(m, 2H), 2.27(s, 3H), 1.92(m, 1H), 0.97(dd, J=0.9 Hz, 6.9 Hz, 6H). $^{19}$F NMR(CDCl$_3$/300 MHz) −78.89(d, J=7.3 Hz). $^{13}$C NMR (CDCl$_3$/300 MHz) 170.0, 151.9, 147.5, 140.1, 131.2, 130.9, 123.8(q, J=287.9 Hz), 117.3, 116.7, 114.3, 70.5(q, J=33.2 Hz), 43.1, 29.2, 22.9, 18.9. LC-MS(ES$^+$): 315.1(M+1, 100); High resolution MS(ES$^−$): m/z calc. For C$_{16}$H$_{16}$F$_3$O$_3$: 313.1052(M−H), found: 313.1006.

EXAMPLE 885

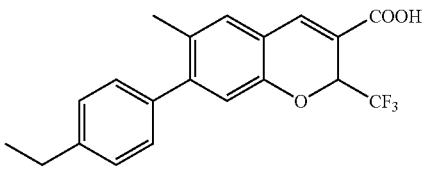

7-(4-Ethylphenyl)-6-methyl-2-(trifluoromethyl)-2H-chromene-3-carboxylic acid This example was prepared using the same procedures as described in the preparation of 7-(2,3-dimethylphenyl)-6-methyl-2-(trifluoromethyl)-2H-chromene-3-carboxylic acid. Light yellow solid. $^1$H NMR (CDCl$_3$/CD$_3$OD/400 MHz) 7.82(s, 1H), 7.23(s, 4H), 7.10(s, 1H), 6.88(s, 1H), 5.68(q, J=6.8 Hz, 1H) 2.69(q, J=7.6 Hz, 2H), 2.21(s, 3H,), 1.27(t, J=7.6 Hz, 3H). $^{19}$F NMR(CDCl$_3$/300 MHz) −78.77(d, J=6.8 Hz). $^{13}$C NMR(CDCl$_3$/300 MHz) 151.7, 147.6, 143.9, 138.8, 138.1, 131.4, 130.0, 129.0, 128.0, 125.8, 123.8(q, J=287.9 Hz), 117.9, 117.4, 115.6, 70.8(q, J=33.2 Hz), 28.8, 19.9, 15.7. LC-MS(ES+): 363.2(M+1, 100). High resolution MS(ES$^-$): m/z calc. for C$_{20}$H$_{16}$F$_3$O$_3$: 361.1052(M−H), Found: 361.1046.

EXAMPLE 886

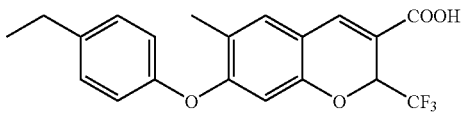

7-(4-Ethylphenoxy)-6-methyl-2-(trifluoromethyl)-2H-chromene-3-carboxylic acid To the mixture of ethyl 6-methyl-2-(trifluoromethyl)-7-{[(trifluoromethyl)-sulfonyl]-oxy}-2H-chromene-3-carboxylate (0.3 g, 0.7 mmol), powdered potassium phosphate(297 mg, 1.4 mmol), palladium acetate (15.7 mg, 0.07 mmol), and 2-(di-tert-butyl phosphino)biphenyl (31.3 mg, 0.105 mmol) and 4-ethyl- phenol (103 mg, 0.84 mmol) was added 4 mL of anhydrous toluene. The resulting mixture was heated to 110° C. and stirred at 110° C. for four hrs. LC-MS indicated that the reaction was completed. After cooling to room temperature, to the reaction was added 100 mL of EtOAc. The organic phase was then extracted with brine three times, and dried over anhydous magnesium sulfate. After removing the volatiles, the residue was purified on silica gel column with 1:18 EtOAc/hexane. The collected product was dissolved in THF(3 mL), and to the resulting solution was added ethanol (3 mL), and water (3 mL), followed by addition of lithium hydroxide hydrate (90 mg). The resulting mixture was heated to 80° C. and stirred for 1.5 hrs. LC-MS indicated that the reaction was done. The volatiles were removed, the residue was diluted with water, and acidified at 0° C. with ice-cold dilute hydrochloric acid. The product was extracted with EtOAc. After removing the solvent, the residue was purified on reverse phase HPLC. The product was isolated as light yellow solid, 100 mg. LC-MS(ES+): 379.2(M+1, 100). $^1$H NMR (CDCl$_3$/CD$_3$CD/300 MHz) 7.86 (s, 1H), 7.25(d, J=8.4 Hz, 2H), 7.14(s, 1H), 6.99(d, J=8.4 Hz, 2H), 6.40(s, 1H), 5.64(q, J=6.6 Hz, 1H), 2.70(q, J=7.5 Hz, 2H), 2.30(s, 3H), 1.30(t, J=7.5 Hz, 3H). $^{13}$C NMR (CDCl$_3$/CD$_3$OD/300 MHz) 170.0, 161.2, 153.5, 153.4, 140.9, 139.8, 132.2, 129.6, 123.7(q, J=287.9 Hz), 122.9, 120.1, 113.5, 112.7, 104.2, 70.6(q, J=33.3 Hz), 28.5, 15.9, 15.7. High resolution MS(ES−): m/z cacl. For C$_{20}$H$_{16}$F$_3$O$_4$: 377.1001(M−H), found: 377.0987.

EXAMPLE 887

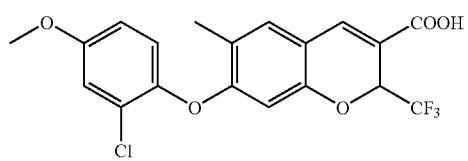

7-(2-Chloro4-methoxyphenoxy)-6-methyl-2-(trifluoromethyl)-2H-chromene-3-carboxylic acid This example was prepared using the same procedures as described in the preparation of 7-(4-ethylphenoxy)-6-methyl-2-(trifluoromethyl)-2H-chromene-3-carboxylic acid. Light yellow solid. $^1$H NMR (CDCl$_3$/300 MHz):7.85(s, 1H), 7.14(s, 1H), 7.09(d, J=8.7 Hz, 1H), 7.06(d, J=2.7 Hz, 1H), 6.90(dd, J=9 Hz, 3 Hz, 1H), 6.17(s, 1H), 5.63(q, J=6.9 Hz, 1H), 3.87(s, 3H), 2.35(s, 3H). $^{13}$C NMR(CDCl$_3$/300 MHz) 169.7, 160.9, 157.5, 153.6, 144.3, 139.7, 132.2, 127.6, 123.7(q, J=287.7 Hz),123.6, 122.0, 116.2, 114.3, 113.3, 122.6, 102.3, 70.7(q, J=33.2 Hz), 56.1, 15.7. LC-MS(ES$^+$): 415.1 (M+1, 100). High resolution MS(ES−): m/z cacl. For C$_{19}$H$_{13}$F$_3$O$_5$: 413.0404(M−H), found: 413.0374.

EXAMPLE 888

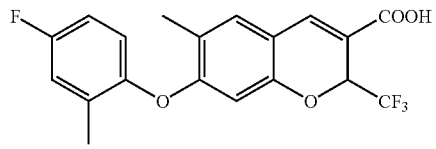

7-(4-Fluoro-2-methylphenoxy)-6-methyl-2-(trifluoromethyl)-2H-chromene-3-carboxylic acid This example was prepared using the same procedures as described in the preparation of 7-(4-ethylphenoxy)-6-methyl-2-(trifluoromethyl)-2H-chromene-3-carboxylic acid. Lihgt yellow solid. 7.77(s, 1H), 7.10(s, 1H), 7.01(d, J=8.4 Hz, 1H), 6.95-6.93(m, 2H), 6.14(s, 1H), 5.62(q, J=6.9 Hz, 1H), 2.30(s, 3H), 2.18(s, 3H). $^{19}$F NMR (CDCl$_3$/300 MHz) −79.02(d, J=6.5 Hz), −118.52(m). $^{13}$C NMR(CDCl$_3$/CD$_3$OD/300 MHz) 167.6, 160.6, 159.9(d, J=243.5 Hz), 153.4, 149.2, 138.4, 132.5(d, J=8.1 Hz), 132.0, 123.7(q, J=286.8 Hz), 122.3, 122.1, 121.8, 118.4(d, J=23.0 Hz), 114.2(d, J=23.4 Hz), 113.3(d, J=7.3 Hz), 102.4, 70.8(q, J=33.0 Hz), 16.4, 15.6. LC-MS(ES+): 383.1 (M+1). High resolution MS(ES$^-$) m/z cacd. For C$_{19}$H$_{13}$F$_4$O$_4$: 381.0750 (M−H), found: 381.0754.

467

Preparation of 8-methyl-7-substituted-2-(trifluoromethyl)-2H-chromene-3-carboxylic acids via aryl fluoride displacement Preparation of Ethyl 8-methyl-7-fluoro-2-(trifluoromethyl)-2H-chromene-3-carboxylate

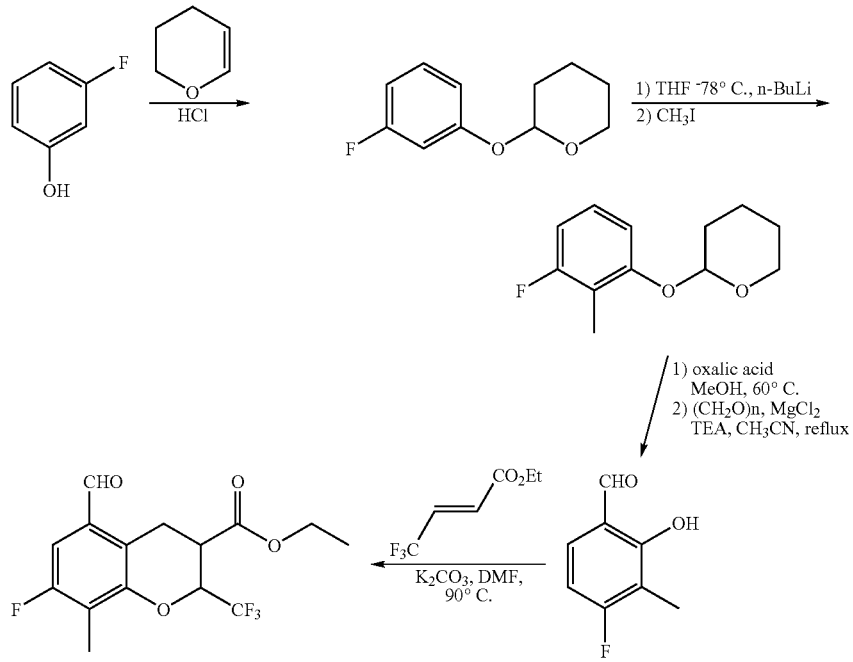

Step 1. Preparation of 2-(3-fluorophenoxy)tetrahydro-2H-pyran

To 75 g (669 mmol) of 3-fluorophenol at -35° C. was added 79 g (928 mmol) of 3,4-dihydro-2H-pyran. The ice bath was removed and added 1.0 mL of concentrated HCl. The temperature was allowed to warm to room temperature and the reaction progress was monitored by HPLC. 500 ml of diethyl ether and 500 mL of 1 M NaHCO$_3$ were added to the reaction. The organic layers were washed with NaHCO$_3$ (2×) and brine. The organic layers were dried over Na$_2$SO4, filtered, and concd to afford a yellow oil which was purified by silica gel chromatography with EtOAc/hexane (1:9). Concentration of the desired fractions afforded 102.1 g (78%) of a white solid: $^1$H NMR (CDCl$_3$/400 MHz) 1.56-2.03 (m, 6H), 3.58-3.63 (m, 1H), 3.85-3.91 (m, 1H), 5.39 (t, 1H, J=3.2 Hz), 6.65-6.70 (m, 1H), 6.78-6.84 (m, 2H), 7.21 (dd, 1H, J=8.2, 15.0 Hz); HRMS (EI+) m/z calcd for (C$_{11}$H$_{13}$FO$_2$) 196.0900, found 196.0890.

Step 2. Preparation of 2-(3-fluoro-2-methylphenoxy)tetrahydro-2H-pyran

To a chilled solution (-78° C.) of 9.33 g (47.55 mmol) of 2-(3-fluorophenoxy)-tetrahydro-2H-pyran in 150 mL of THF was added 38 mL (95.1 mmols) of n-BuLi (2.5 M soln in hexanes). The reaction mixture was stirred at -78° C. for 45 minutes and slowly added 11.9 mL (190.2 mmol) of methyl iodide via syringe. The reaction was allowed to warm to room temperature and was stirred overnight.

468

Quenched reaction with satd ammonium chloride and transferred to a round bottom flask. Removed volatiles in vacuo and partitioned mixture between EtOAc and water. Separated layers and washed organics with water (×2) and brine. Dried over Na$_2$SO$_4$, filtered, and concd to afford a 9.01 g (90%) of a yellow oil: $^1$H NMR (CDCl$_3$/400 MHz) 1.46-2.09 (m, 6H), 2.21 (d, 3H, J=2.0 Hz), 3.60-3.65 (m, 1H), 3.86-3.92 (m, 1H), 5.44 (t, 1H, J=3.2 Hz), 6.70 (t, 1H, J=8.8 Hz), 6.90 (d, 1H, J=8.4 Hz), 7.08 (dd, 1H, J=8.0, 15.2 Hz); HRMS (EI+) m/z calcd for (C$_{12}$H$_{15}$FO$_2$) 210.1056, found 210.1070.

Step 3. Preparation of 3-fluoro-2-methylphenol

The 5.0 g (23.78 mmol) of 2-(3-fluoro-2-methylphenoxy) tetrahydro-2H-pyran was dissolved in 120 mL of methanol followed by addition of 3.21 g (35.67 mmol) of oxalic acid. The mixture was heat to 60° C. for 2 hours. The volatiles were removed in vacuo while maintaining a bath temperature of <29° C. to afford an oil, which was purified by silica gel chromatography with EtOAc/hexane (1:9). Concentration of the desired fractions afforded 2.19 g (73%) of a pale yellow oil, which later solidified upon standing: $^1$H NMR (CDCl$_3$/400 MHz) 2.16 (d, 3H, J=2.0 Hz), 5.17 (s, 1H), 6.57 (d, 1H, J=8.4 Hz), 6.64 (t, 1H, J=8.8 hz), 7.00 (dd, 1H, J=8.4, 14.8 Hz); HRMS (EI+) m/z calcd for (C$_7$H$_7$FO) 126.0481, found 126.0470.

Step 4. Preparation of 4-fluoro-2-hydroxy-3-methylbenzaldehyde

To 2.19 g (17.36 mmol) of 3-fluoro-2-methylphenol in 87 mL of anhydrous acetonitrile was added 12.1 g (126.73 mmol) of MgCl$_2$ portionwise followed by addition of 9.0 mL (64.93 mmol) of TEA to afford a pinkish reaction mixture. To this mixture was added 3.8 g (126.73 mmol) of paraformaldehyde and the resulting yellow colored mixture was heated to reflux for 4 hours. After cooling to room temperature, to the mixture was added 5% HCl slowly. The reaction was extracted with EtOAc (3×), washed with satd NaCl (3×), dried over MgSO$_4$, filtered, and concd to afford an oil, which was purified by silica gel chromatography with EtOAc/hexane (1:9) to afford 2.02 g (75%) of a pale tan oil which later solidified: $^1$H NMR (CDCl$_3$/400 MHz) 2.14 (d, 3H, J=1.6 Hz), 6.68 (t, 1 H, J=8.8 Hz), 7.37 (dd, 1H, J=6.4, 8.4 Hz), 9.78 (s, 1H), 11.59 (d, 1H, J=2.0 Hz); HRMS (EI+) m/z calcd for (C$_8$H$_7$FO$_2$) 154.0430, found 154.0428.

Step 5. Preparation of ethyl 7-fluoro-8-methyl-2-(trifluoromethyl)-2H-chromene-3-carboxulate To 1.0 g (6.49 mmol) of 4-fluoro-2-hydroxy-3-methylbenzaldehyde in 1.6 mL of anhydrous DMF was added 1.79 g (12.98 mmol) of K$_2$CO$_3$ followed by addition of 1.64 g (9.74 mmol) of ethyl-4,4,4-trifluorocrotonate. The reaction mixture was heated to 70° C. overnight. The following day the reaction was monitored by LC/MS and LCMS indicated that starting material (~40%) remained. Additional 1.79 g (12.98 mmol) of K$_2$CO$_3$ and an additional 1.64 g (9.74 mmol) of ethyl-4,4,4-trifluorocrotonate were added, and the mixture was heated to 90° C. for 3 hours. After 3 hours LCMS indicated that <10% starting material remained. The crude material was purified by Gilson reverse phase chromatography (50-99% CH$_3$CN gradient) to afford 2.58 g (65%) of a pale tan solid: $^1$H NMR (CDCl$_3$/400 MHz) 1.33 (t,3H, J=7.2 Hz), 2.15 (d, 3H, J=2.0Hz),4.26-4.34 (m,2H), 5.73 (q, 1H, J=6.8 Hz), 6.68 (t, 1H, J=8.8 Hz), 7.03 (dd, 1H, J=6.4, 8.4 Hz), 7.67 (s, 1H); MS (ES+) 305.2 (M+H, 100); HRMS (EI+) m/z calcd for (C$_{14}$H$_{12}$F$_4$O$_3$) 304.0723, found 304.0720.

EXAMPLE 889

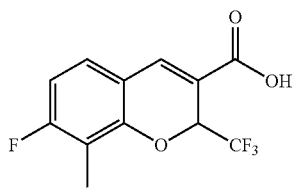

7-Fluoro-8-methyl-2-(trifluoromethyl)-2H-chromene-3-carboxylic acid

To 0.150 g (0.490 mmol) of ethyl 8-methyl-7-phenoxy-2-(trifluoromethyl)-2H-chromene-3-carboxylate in 2.5 mL THF:EtOH:H$_2$O (7:2:1) was added 0.031 g (0.735 mmol) of LiOH. The mixture was heated at 60° C. for 2 hours. Removed volatiles in vacuo and diluted with HCl (10%), CH$_3$CN, and DMF and purifed by reverse phase chromatography to afford 0.083 g (61%) of an off white solid: $^1$H NMR (CH$_3$OD/400 MHz) 2.13 (d, 3H, J=2.0 Hz), 5.81 (q, 1H, J=7.2 Hz), 6.76 (t, 1H, J=8.8 Hz), 7.20 (dd, 1H, J=6.4, 8.4 Hz), 7.75 (s, 1H); MS (ES+) 377 (M+H, 100); HRMS (ES−) m/z calcd for (C$_{12}$H$_8$F$_4$O$_3$) 275.0331, found 275.0283.

General Method for the Preparation of 8-methyl-7-substituted-2-(trifluoromethyl)-2H-chromene-3-carboxylic Acids

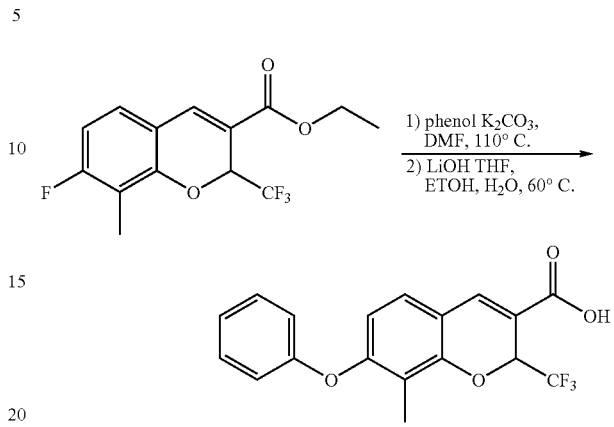

EXAMPLE 890

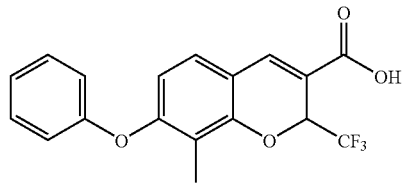

8-Methyl-7-phenoxy-2-(trifluoromethyl)-2H-chromene-3-carboxylic acid

Step 1. Preparation of ethyl 8-methyl-7-phenoxy-2-(trifluoromethyl)-2H-chromene-3-carboxylate To 0.304 g (1.00 mmol) of ethyl 7-fluoro-8-methyl-2-(trifluoromethyl)-2H-chromene-3-carboxylate in 5.0 mL of DMF was added 0.194 g of K$_2$CO$_3$ (1.40 mmol) and 0.105 mL (1.20 mmol) of phenol. The mixture was heated to 90° C. and LC/MS indicated remaining starting material. The mixture was then heated to 110° C. overnight and LC/MS still indicated starting material remaining. Added an additional 0.194 g of K$_2$CO$_3$ (1.40 mmol) and 0.105 mL (1.20 mmol) of phenol. Heated overnight and purified by Gilson reverse phase chromatography to afford 0.107 g (28%) of a pale yellow solid: $^1$H NMR (CH$_3$OD/400 MHz) 1.32 (t, 3H, J=7.2 Hz), 2.15 (s, 3H), 4.24-4.33 (m, 2H), 5.82 (q, 1H, J=7.2 Hz), 6.42 (d, 1H, J=8.4 Hz), 6.94-6.97 (m, 2H), 7.09-7.15 (m, 2H), 7.33-7.37 (m, 2H), 7.75 (s, 1H); MS (ES+) 379.3 (M+H, 100); HRMS (EI+) m/z calcd for (C$_{20}$H$_{17}$F$_3$O$_4$) 378.1079, found 378.1062.

Step 2. Preparation of 8-methyl-7-phenoxy-(trifluoromethyl)-2H-chromene-3-carboxylic acid To 0.090 g (0.24 mmol) of ethyl 8-methyl-7-phenoxy-2-(trifluoromethyl)-2H-chromene-3-carboxylate in 5 mL THF:EtOH:H$_2$O (7:2:1) was added 0.015 g (0.36 mmol) of LiOH. The mixture was heated at 60° C. for 2 hours. Removed volatiles in vacuo and diluted with HCl (10%), CH3CN, and DMF and purified by reverse phase chromatography to afford 0.046 g (55%) of a pale yellow solid: $^1$H NMR (CH$_3$OD/400 MHz) 2.15 (s, 3H), 5.79 (q, 1H, J=7.2 Hz), 6.43 (d, 1H, J=8.4 Hz), 6.94-6.96 (m, 2H), 7.09-7.14 (m, 2H), 7.33-7.37 (m, 2H), 7.74 (s, 1H); MS (ES+) 351.2 (M+H, 100); HRMS (ES−) m/z calcd for (C$_{18}$H$_{13}$F$_3$O$_4$) 349.0688, found 349.0681.

Preparation of 8-methyl-7-substituted-2-(trifluoromethyl)-2H-chromene-3-carboxylic Acids via aryl Fluoride Displacement by a Parallel Method The following examples in table 17 were prepared as previously described for 8-methyl-7-phenoxy-(trifluoromethyl)-2H-chromene-3-carboxylic acid using parallel synthesis apparatus and were purified by reverse phase chromatography.

TABLE 17

Yield, Purity and Mass Spectral Data for 8-methyl-7-substituted-2-(trifluoromethyl)-2H-chromene-3-carboxylic acids Prepared by Parallel Synthesis Methods.[1]

| Example # | LC (min) | MS (ES+) | HRMS | % Purity | % Yield[1] |
|---|---|---|---|---|---|
| 891 | 3.686 | 387 | 385.0470 | 100 | 14 |
| 892 | 3.656 | 387 | 385.0479 | 100 | 6 |
| 893 | 3.928 | 385 | 383.0298 | 100 | 7 |
| 894 | 3.934 | 385 | 383.0292 | 100 | 25 |
| 895 | 3.619 | 381 | 379.0780 | 100 | 11 |
| 896 | 4.015 | 399 | 397.0478 | 100 | 19 |
| 897 | 3.855 | 397 | 395.0584 | 100 | 22 |
| 898 | 3.870 | 365 | 363.0831 | 100 | 15 |
| 899 | 4.086 | 379 | 377.0989 | 100 | 16 |
| 900 | 3.889 | 365 | 363.0850 | 100 | 10 |
| 901 | 4.065 | 379 | 377.0958 | 100 | 10 |
| 902 | 4.222 | 393 | 391.1128 | 100 | 6 |
| 903 | 4.011 | 379 | 377.0959 | 100 | 9 |
| 904 | 4.233 | 393 | 391.1157 | 100 | 5 |
| 905 | 4.131 | 419[2] | 416.9892 | 100 | 13 |
| 906 | 3.669 | 369 | 367.0559 | 100 | 31 |
| 907 | 3.602 | 369 | 367.0591 | 100 | 11 |
| 908 | 4.279 | 393 | 391.1126 | 100 | 13 |
| 909 | 3.729 | 395 | 393.0923 | 100 | 28 |
| 910 | 3.827 | 395 | 393.0948 | 100 | 15 |
| 911 | 2.219 | 366 | 364.0815 | 100 | 32 |
| 912 | 3.912 | 403 | 401.0213 | 100 | 3 |
| 913 | 3.969 | 447[3] | 444.9734 | 100 | 4 |
| 914 | 4.154 | 413 | 411.0570 | 100 | 22 |
| 915 | 3.848 | 403 | 401.0198 | 100 | 7 |
| 916 | 3.813 | 383 | 381.0707 | 100 | 10 |
| 917 | 3.877 | 449[4] | 444.9666 | 100 | 3 |
| 918 | 4.108 | 399 | 397.0452 | 100 | 14 |
| 919 | 4.020 | 401 | 399.0805 | 100 | 23 |

[1]Overall isolated yield from 2 step reaction based on 1 mmol scale. Chromatographic retention time in min. HRMS indicates the observed molecular ion (M-H) by high-resolution mass spectrometry in electrospray negative mode. % Purity was determined by ELS detection. HPLC retention time determined with a linear gradient from 5% acetonitrile in 0.1% TFA/water at time = 0 min to 95% acetonitrile at 4.5 min.
[2]MS shows a Cl$_2$ cluster: 419 (M + 1, 100), 421 (M + 3, 61).
[3]MS shows a Br$_1$ cluster: 447 (M + 1, 100), 449 (M + 3, 93).
[4]Listed ion is M + 3 of a Br$_1$ cluster: 447 (M + 1, 87), 449 (M + 3, 100).

Preparation of 8-Benzyl-6-chloro-2-(trifluoromethyl)-2H-chromene-3-carboxylic acid

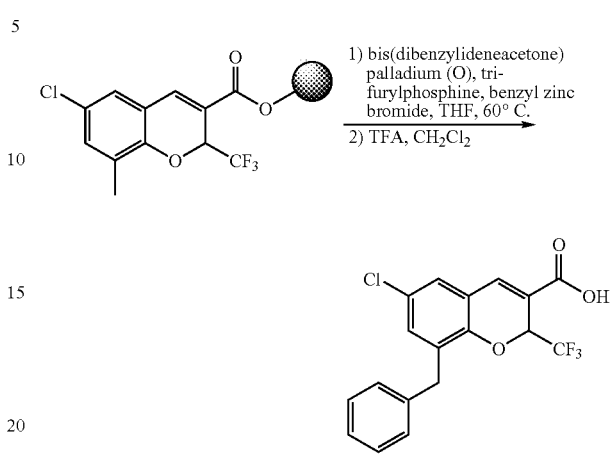

EXAMPLE 920

8-Benzyl-6-chloro-2-(trifluoromethyl)-2H-chromene-3-carboxylic acid

To a chilled solution of 0.031 g (0.054 mmole) of bis(dibenzylideneacetone) palladium (0) and 0.025 g (0.107 mmol) of tri-2-furylphosphine in 5 mL degassed THF was added 0.500 g (0.535 mmol) of Wang resin 6-chloro-8-iodo-2-(trifluoromethyl)-2H-chromene-3-carboxylate followed by addition of 3.21 mL (1.605 mmol) of a 0.5 M soln of benzylzinc bromide. The reaction mixture was heated to 60° C. overnight. The reaction mixture was transferred and washed as follows: THF (×5), aqueous NH$_4$Cl (×5), H$_2$O (×5), MeOH (×5), and CH$_2$Cl$_2$ (×5). The resin was treated with 2 mL (TFA:CH$_2$CL$_2$, 1:1) for 30 minutes. The filtrate was collected and treatment was repeated. The resin was washed with CH$_2$Cl$_2$ (×2) and all filtrates were combined and concd. The resulting oil was purified using reverse phase chromatography to afford 0.024 g (12%) of a white crystalline solid: $^1$H NMR (CDCl$_3$/400 MHz) 4.00 (s, 2H), 5.91 (q, 1H, J=7.1 Hz), 7.20 (m, 1H), 7.27 (m, 5H), 7.41 (d, 1H, J=2.5 Hz), 7.87 (s, 1H); $^{19}$F NMR (CDCl$_3$/400 MHz) −79.4 (d, 3F, J=6.8 Hz); MS (ES+) 369 (M+1, 100); HRMS (ES−) m/z calcd for (M−H: C$_{18}$H$_{11}$O$_3$ClF$_3$) 367.0343, found 367.0333.

473

Preparation of 3-Substituted-6-(trifluoromethyl)-6H-furo[2,3-]ichromene-7-carboxylic Acids and 1-Substituted-7-(trifluoromethyl)-7H-furo[3,2-]chromene-8-carboxylic Acids

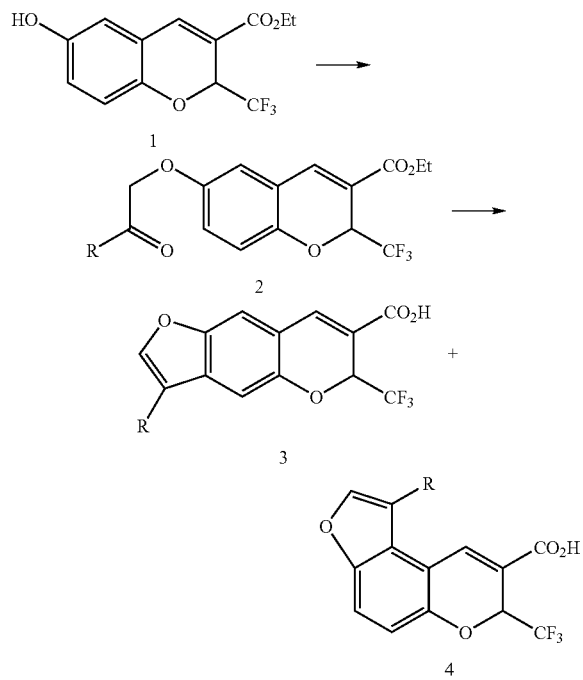

Preparation of Ethyl 6-[2-(4-bromophenyl)-2-oxoethoxy]-2-(trifluoromethyl)-2H-chromene-3-carboxylate

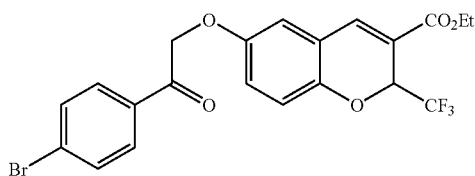

The mixture of ethyl 6-hydroxyl-2-(trifluoromethyl)-2H-chromene-3-carboxylate (1.0 g, 3.47 mmol), 2-(4-bromophenyl)-2-oxoethyl bromide (0.96g, 3.47mmol) and potassium carbonate (0.96 g, 6.94 mmol) in 4 mL of dry DMF was heated to 70° C. and shaken for two hrs, then at room temperature overnight. The solid was filtered, and washed with ethyl acetate. The combined organic phases were washed with brine, and then dried over anhydrous magnesium sulfate. After removing the volatiles, the residue was purified on silica gel column with 1:9 EtOAc/hexane. It gave 0.65 g of light yellow solid (38.6%). M.P.=130.5-131.5° C. $^1$HNMR (CDCl$_3$/400 MHz) 7.86(m, 1H), 7.83(m, 1H) 7.65(m, 1H), 7.63-7.62(m, 2H), 6.89-6.88(m, 2H), 6.77(m, 1H),5.64(q, J=6.8 Hz, 1H, ), 5.16(s, 2H), 4.33-4.26 (m, 2H), 1.33(t, J=7.2 Hz, 3H). $^{13}$C NMR (CDCl$_3$/300 MHz), 193.8, 163.9, 153.3, 148.2, 136.8, 133.3, 132.5, 129.9, 129.5, 123.6 (q, J=287.9 Hz), 119.9, 119.8, 117.8, 117.1, 115.1, 71.8, 70.8(q, J=32.8 Hz), 61.7, 14.4. $^{19}$F (CDCl$_3$/400 MHz) −78.72(d, J=6.8 Hz). LC-MS: 484.9 (M+1, 100), 486.9(M+3, 100). Purity =95%. HRMS (ES+) m/z calcd for (C$_{21}$H$_{16}$BrF$_3$O$_5$) 502.0471(M+NH$_4$), 504.0454 (M+NH$_4$+2), found 502.0484, 504.0492.

Preparation of Ethyl 6-(3,3-dimethyl-2-oxobutoxy)-2-(trifluoromethyl)-2H-chromene-3-carboxylate

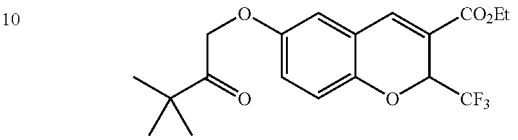

This example was prepared by using the same procedure to the preparation of ethyl 6-[2-(4-bromophenyl)-2-oxoethoxy]-2-(trifluoromethyl)-2H-chromene-3-carboxylate. It gave 3.5 g (87.2%) of off-white solid. $^1$H NMR (CDCl$_3$/300 MHz) 7.68(s, 1H), 6.91(s, 1H), 6.90(d, J=2.7 Hz, 1H), 6.77(d, J=2.4 Hz, 1H), 5.68(q, J=6.9 Hz, 1H), 4.86(s, 2H), 4.34(m, 2H), 1.38(t, J=6.9 Hz, 3H), 1.27(s, 9H). $^{19}$F(CDCl$_3$/400 MHz) −78.73(d, J=6.9 Hz). LC-MS (ES+): 387.4(M+1, 100). HRMS (ES+) m/z calcd for (C$_{19}$H$_{12}$F$_3$O$_5$) 404.1679 (M+NH$_4$), found 404.1666.

EXAMPLE 921

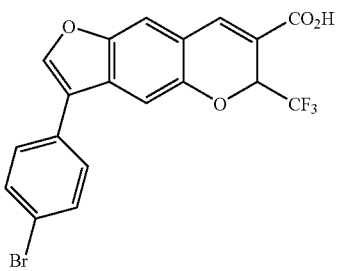

3-(4-bromophenyl)-6-(trifluoromethyl)-6H-furo[2,3-]chromene-7-carboxylic acid

Step 1: Preparation of ethyl 3-(4-bromophenyl)-6-(trifluoromethyl)-6H-ftiro[2,3-g]chromene-7-carboxylate The mixture of ethyl 6-(2-(4-bromophenyl)-2-oxoethoxy)-2-(trifluoromethyl)-2H-chromene-3-carboxylate (1.0g, 2.1 mmol), TsOH (1.0g, 5.3 mmol) and 10 mL of Xylene was heated to reflux under nitrogen. LC-MS was used to monitor the reaction until it was finished. It took about 5 hrs. After cooling to room temperature, the reaction was dumped into 100 mL of ethyl acetate. The organic phase was washed with aqueous sodium bicarbonate, brine, and dried over anhydrous magnesium sulfate. After removing the solvent, it gave a brown oil. The crude material was further purified on reverse phase HPLC. The desired intermediate was obtained as light yellow solid, 100 mg. 10%. $^1$H NMR(CDCl$_3$/300 MHz) ppm 7.87(s, 1H), 7.85(s, 1H), 7.65-7.62(m, 2H), 7.50-7.47(m, 2H), 7.42(s, 1H), 7.37(s, 1H), 5.75(q, J=6.9 Hz, 1H), 4.40-4.36(m, 2H), 1.41(t, J=7.2 Hz, 3H). $^{13}$C NMR(CDCl$_3$/300 MHz) 164.1, 151.5, 149.8, 144.6, 137.6, 132.5, 130.3, 130.2, 129.1, 123.8(q, J=288.1

Hz), 122.2, 122.1, 117.5, 117.2, 112.2, 106.7, 71.0(q, J=32.7 Hz), 61.7, 14.5. LC-MS(ES+) 466.7(M+1, 100), 468.7(M+3, 100).

Step 2: To the solution of the intermediate (100 mg, 0.21mmol) obtained in step 1 in 3 mL of THF was added a solution of lithium hydroxide hydrate (90 mg, 2.1 mmol) in 3 mL of water, followed by addition of 3 mL of ethanol. The resulting solution was heated to 80° C. for two hrs. The volatiles were removed. The residue was diluted with water, and acidified at 0° C. with dilute hydrochloric acid. The product was extracted with EtOAc. The resulting organic solution was dried over anhydrous magnesium sulfate. After removing the solvents, it gave 60 mg of the desired product as yellow solid (65.2%). M.P.>250° C. $^1$H NMR(CDCl$_3$/drops of CD$_3$OD/300 MHz) ppm 7.83(s, 1H), 7.81(s, 1H), 7.59-7.56(m, 2H) 7.46-7.42(m, 2H), 7.38(s, 1H), 7.31(s, 1H), 5.67(q, J=6.9 Hz, 1H). $^{19}$F NMR(CDCl$_3$/drops of CD$_3$OD/400 MHz) 78.51 (d, J=6.9 Hz). $^{13}$C NMR (CDCl$_3$/CD$_3$OD/400 MHz) 166.0, 151.5, 149.8, 144.6, 138.0, 132.4, 130.3, 130.2, 129.1, 123.8(q, J=287.8Hz), 122.1, 122.0, 117.4, 117.1, 112.2, 106.6, 70.9(q, J=32.7 Hz). LC-MS (ES+) 438.9(M+1, 100), 440.7(M+3, 100). HRMS (EI) m/z calcd for (C$_{19}$H$_{10}$BrF$_3$O$_4$) 437.9715, found 437.9730.

EXAMPLE 922

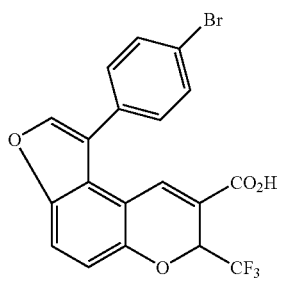

1-Para-bromophenyl-7-(trifluoromethyl)-7H-furo [3,2-]chromene-8-carboxylic acid

This example was prepared by using the same procedure to the preparation of 3-(4-bromophenyl)-6-(trifluoromethyl)-6H-furo[2,3-g]chromene-7-carboxylic acid. Yellow solid. M.P.>250° C. $^1$HNMR(CDCl$_3$/drops of CD$_3$OD/300 MHz) ppm 7.86 (s, 1H), 7.67-7.63(m, 3H), 7.50(d, J=9.0 Hz, 1H), 7.41-7.37(m, 2H), 7.02(d, J=8.7 Hz, 1H), 5.73(q, J=7.2 Hz, 1H). LC-MS(ES+): 438.7 (M+1, 100), 440.7(M+3, 100). MS(ES−) 438.9(M−1, 100); HRMS (EI+) m/z calcd for (C$_{19}$H$_{10}$BrF$_3$O$_4$) 437.9715(M$^+$), found 437.9738.

EXAMPLE 923

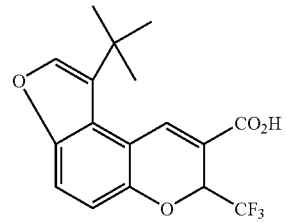

1-tert-butyl-7-(trifluoromethyl)-7H-furo [3,2-] chromene-8-carboxylic acid

This example was prepared by using the same procedure to the preparation of 3-(4-bromophenyl)-6-(trifluoromethyl)-6H-furo[2,3-g]chromene-7-carboxylic acid. Yellow solid, 60 mg (16.3%). The compound decomposed at 220° C. $^1$H NMR (CDCl$_3$/300 MHz) ppm 8.57 (s, 1H), 7.47(s, 1H), 7.41(d, J=8.7 Hz, 1H), 6.95(d, J=9 Hz, 1H), 5.68(q, J=7.2 Hz, 1H), 1.47(s, 9H). $^{19}$F NMR (CDCl$_3$/drops of CD$_3$OD/400 MHz) 78.65(d, J=7.9 Hz). LC-MS (ES$^+$) 341.1 (M+1, 100). MS(ES−) 339.1(M−1, 100); HRMS (EI$^+$) m/z calcd for (C$_{17}$H$_{15}$F$_3$O$_4$): 340.0992(M$^+$), found 340.0879.

EXAMPLE 924

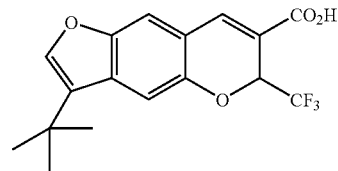

3tert-butyl-6-(trifluoromethyl)-6H-furo [2,3-]chromene-7-carboxylic acid

This example was prepared by using the same procedure to the preparation of 3-(4-bromophenyl)-6-(trifluoromethyl)-6H-furo[2,3-g]chromene-7-carboxylic acid. Yellow gtey solid. The compound decomposed at 250° C. $^1$H NMR (CDCl$_3$/300 MHz) ppm 7.86 (s, 1H), 7.40(s,1H), 7.32(s,1H), 7.30(s,1H), 5.70(q, J=6.9 Hz, 1H), 1.41(s, 9H). $^{19}$F NMR (CDCl$_3$/drops of CD$_3$OD/400 MHz) 78.55(d, J=6.9 Hz). LC-MS (ES$^+$) 341.1(M+1, 100). MS (ES−) 339.1(M−1, 100); HRMS (EI$^+$) m/z calcd for (C$_{17}$H$_{15}$F$_3$O$_4$): 340.0992, found 340.0933.

Preparation of 2-substituted-7-(trifluoromethyl)-7H-furo[32-]chromene-6-carboxylic Acids and Acyclic Analogs

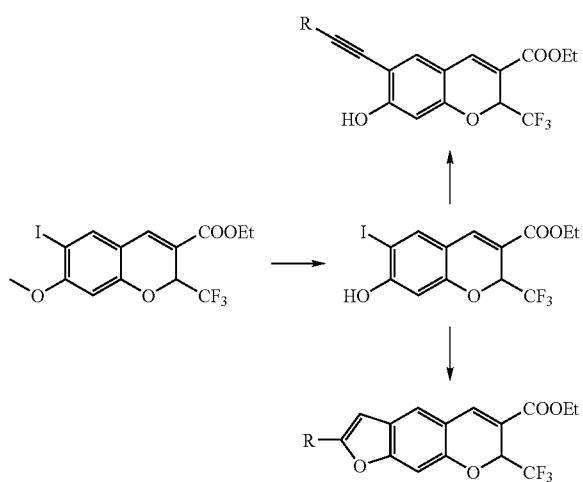

Preparation of Ethyl 6-iodo-7-hydroxyl-2-(trifluoromethyl)-2H-chromene-3-carboxylate

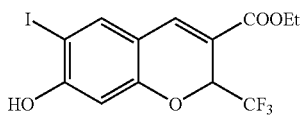

This example was prepared by using the same procedure as the preparation of ethyl 7-hydroxy-6-methyl-2-(trifluoromethyl)-2H-chromene-3-carboxylate. Yellow solid. LC-MS(ES+): 415.1(M+1, 100). $^1$H NMR (CDCl$_3$/CD$_3$OD/300 MHz): 7.62(s, 1H), 7.54(s, 1H), 6.53(s, 1H), 5.64(q, J=6.6 Hz, 1H), 4.29(m, 2H), 1.33(t, J=7.2 Hz, 1H). $^{19}$F NMR (CDCl$_3$/CD$_3$OD/300 MHz): −79.01 (d, J=7.2Hz). $^{13}$C NMR (CDCl$_3$/CD$_3$OD/300 MHz): 164.4, 160.3, 155.3, 139.4, 136.4, 123.6(q, J=287.5 Hz), 114.2, 113.7, 102.9, 76.1, 71.0(q, J=33.1 Hz), 61.1, 14.4. High resolution MS(ES−): m/e calc. for (C$_{13}$H$_{10}$F$_3$O$_4$): 412.9498(M−H), found: 412.9486.

EXAMPLE 925

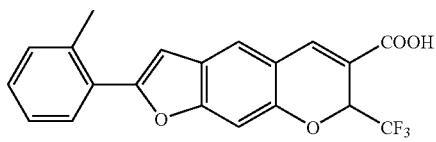

2-(2-Methylphenyl)-7-(trifluoromethyl)-7H-furo[3,2-g]chromene-6-carboxylic acid

To the solution of ethyl 6-iodo-7-hydroxyl-2-(trifluoromethyl)-2H-chromene-3-carboxylate (0.3 g, 0.72 mmol), m-tolyacetylene (420 mg, 3.6 mmol), and 10 mL of anhydrous acetonitrile was added Cu(I)I (33 mg, 0.173 mmol), 1,1′-Bis(diphenyl-phosphino)ferrocene]dichloropalladium (II) complex with dichlormethane (1:1) (25 mg, 0.043 mmol), and triethylamine (2 mL). After the triethylmine was added, the reaction was heated under nitrogen to 55° C. for 72 hrs. LC-MS indicated that the reaction was done, then the reaction was diluted with 100 mL of EtOAc. The resulting organic solution was washed with aqueous ammonium chloride, and brine, dried over anhydrous magnesium sulfate. After removing the volatiles, the residue was purified on a short silica gel column with hexane/EtOAc mixture, the collected fraction was evaporated to remove the volatiles, then to the residue was added 3 ml of THF, 3 mL of ethanol, 100 mg of lithium hydroxide hydrate and 3 mL of water. The resulting mixture was heated to 80° C. for one hrs, the organic solvents were then removed, the residue was diluted with water, and acidified at 0° C. with ice-cold dilute hydrochloric acid. The isolated product was extracted with ethyl acetate. After removing the solvents, the residue was purified on reverse phase HPLC. It gave yellow solid, 92 mg. $^1$H NMR (CDCl$_3$/CD$_3$OD/300 MHz): 7.72(s, 1H), 7.49-7.46(m, 2H), 7.28(s, 1H), 7.19(dd, J=7.5 Hz, 1H), 7.040(d, J=7.5 Hz, 1H), 7.00(s, 1H), 6.80(s, 1H), 5.58(q, J=6.9 Hz, 1H), 2.29(s, 3H). $^{19}$F NMR (CDCl$_3$/CD$_3$OD/300 MHz) −79.058(d, J=6.5 Hz). $^{13}$C NMR(CDCl$_3$/CD$_3$OD/300 MHz) 170.3, 161.5, 161.1, 155.5, 142.7, 142.1, 133.9, 133.7, 132.9, 129.4, 128.9, 127.8(q, J=287.6Hz), 126.0, 125.6, 120.0, 119.9, 104.9, 103.4, 74.9(q, J=32.7 Hz), 25.4. LC-MS (ES+):375.1(M+1, 100). High resolution MS(ES−): m/e calc. for (C$_{20}$H$_3$F$_3$O$_4$): 373.0688(M−H), found: 373.0692.

EXAMPLE 926

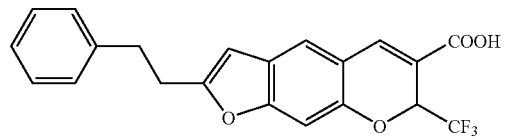

2-(2-Phenylethyl)-7-(trifluoromethyl)-7H-furo[3,2-]chromene-6-carboxylic acid

This example was prepared by using the same procedure to prepare 2-(2-methylphenyl)-7-(trifluoromethyl)-7H-furo[3,2-g]chromene-6-carboxylic acid. Light yellow solid, $^1$H NMR (CDCl$_3$/CD$_3$OD/300 MHz) 7.87(s, 1H), 7.34-7.21(m, 6H), 7.08(s, 1H), 6.30(s, 1H), 5.71(q, J=7.2 Hz, 1H), 3.06(s, 4H). $^{19}$F NMR(CDCl$_3$/CD$_3$OD /300 MHz): −78.65(d, J=7.2Hz). LC-MS(ES+): 389.1(M+1, 100). High resolution MS(ES−): m/e calc. for (C$_{21}$H$_{14}$F$_3$O$_4$): 387.0844(M−H), found:387.0811.

EXAMPLE 927

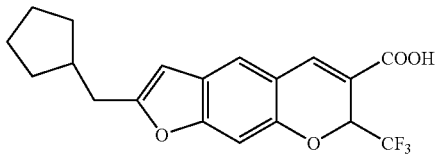

2-(Cyclopentylmethyl)-7-(trifluoromethyl)-7H-furo[3,2-g] chromene-6-carboxylic acid This example was prepared by using the same procedure to prepare 2-(2-methylphenyl)-7-(trifluoromethyl)-7H-fuiro[3,2-g]chromene-6-carboxylic acid. Yellow solid, $^1$H NMR (CDCl$_3$/CD$_3$OD/300 MHz): 7.88(s, 1H), 7.31(s, 1H), 7.05(s, 1H), 6.31(s, 1H), 5.70 (q, J=6.9 Hz, 1H), 2.73(s, 1H), 2.71(s, 1H), 2.28(m, 1H), 1.87-1.78(m, 2H), 1.69-1.55(m, 4H), 1.32-1.21(m, 2H). $^{19}$F NMR (CDCl$_3$/CD$_3$OD/300 MHz): −79.8(d, J=5.8 Hz). $^{13}$C NMR (CDCl$_3$/CD$_3$OD/300 MHz): 167.2, 160.6, 157.5, 151.0, 139.3, 124.7, 123.9(q, J=287.9 Hz), 121.2, 115.4, 115.0, 102.1, 99.4, 70.8(q, J=32.9 Hz), 38.7, 34.6, 32.7, 25.4, 25.3. LC-MS(ES+): 367.1(M+1, 100). High resolution MS(ES−): m/e calc. for (C$_{19}$H$_{16}$F$_3$O$_4$): 365.1001(M−H), found:365.1017.

EXAMPLE 928

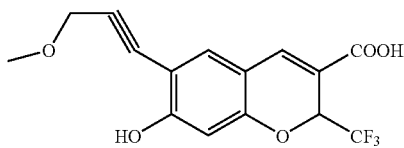

7-Hydroxy-6-(3-methoxyprop-1-ynyl)-2-(trifluoromethyl)-2H-chromene-3-carboxylic acid This example was prepared by using the same procedure to prepare 2-(2-methylphenyl)-7-(trifluoromethyl)-7H-furo[3,2-g]chromene-6-carboxylic acid. Yellow solid. $^1$H NMR (CD$_3$OD/300 MHz) 7.90(s, 1H), 7.54(s, 1H), 7.11(s, 1H), 6.76(s, 1H), 5.76(q, J=6.9 Hz, 1H), 4.54(s, 2H), 3.42(s, 3H). $^{19}$F NMR(CD$_3$OD/300 MHz): −80.06(d, J=6.5 Hz). $^{13}$C NMR (CD$_3$OD/300 MHz): 165.9, 157.8, 155.5, 151.7, 137.6, 124.0(q, J=287.2 Hz), 123.8, 122.1, 116.2, 116.1, 105.7, 88.9, 70.8(q, J=32.6 Hz), 66.2, 57.2. LC-MS(ES+): 329.0, (M+1, 35) 297.0(M−31, 100). High resolution MS(ES−): m/e calc. for (C$_{15}$H$_{10}$F$_3$O$_5$): 327.0480(M−H), found:327.0472.

Assignment of Absolute Configuration

The absolute configuration of substituted 2-(trifluoromethyl)-2H-chromene-3-carboxylic acids was determined by analysis of a pi-pi* transition observable in the CD spectra. Chiral chromene ring systems are known to exhibit a Cotton effect due to the styrene chromophore in the 275-300 nm region of the spectrum. A positive Cotton effect indicates that the twisted styrene chromophore forms a left-handed helix, corresponding to the (S)-enantiomer for the 2-trifluoromethyl-chromene-3-carboxylic acids. This correlation is confirmed by measurement of compounds in the series, which have been previously determined by x-ray crystallography.

Enantiomeric purity and absolute configuration of some of the substituted 2-(trifluoromethyl)-2H-chromene-3-carboxylic acids can be determined by $^{19}$F NMR by observation of the induced chemical shift non-equivalence in the presence of a chiral solvating agent (CSA). $^{19}$F NMR non-equivalence was observed for 6, 7 and 8-substituted chromenes and the sense of non-equivalence correlated with the previously determined assignments of absolute configuration by x-ray and CD spectroscopy. The 5-substituted chromenes, however, showed little or no non-equivalence and the $^{19}$F NMR method was not used for assignment of absolute configuration of 5-substituted examples. General Method for Assignment of Absolute Configuration of Substituted 2-(Trifluoromethyl)-2H-chromene-3-carboxylic Acids.

A carefully weighed mixture of 4 mg of the racemate and 4 mg of one of the enantiomers was prepared in a 1 dram vial to give a 1:3 mixture of enantiomers. This mixture was treated with 1.0 mL of d$^6$-benzene and 25 uL (26.5 mg, 155 umol) of (R)-(+)-1-(1-naphthyl)ethylamine. The $^{19}$F and $^1$H NMR spectra were obtained in the usual manner and analyzed for degree and sense of non-equivalence of the individual resonances. The upfield signal in the $^{19}$F NMR is assigned as the R enantiomer based on the sense of non-equivalence observed for the (R,R) diastereomeric solvates for this series.

EXAMPLE 929

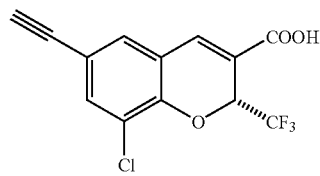

(2R)-(+)-8-Chloro-6-ethynyl-2-(trifuoromethyl)-2H-chromene-3-carboxylic acid

Resolution of 280 mg of racemic 8-Chloro-6-ethynyl-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the first eluted peak from multiple chromatographic runs afforded 100.4 mg (72%) of a yellow solid: 100% ee by analytical HPLC; NMR non-equivalence with CSA and a 2:1 mixture of the (R) and (S) enantiomers: $^{19}$F NMR (d$^6$-benzene; 3.6 eq of (R)-(+)-1-(1-naphthyl)ethylamine) −78.36 (d, 3F, J=6.8 Hz, minor peaks, S-enantiomer), −78.44 (d, 3F, J=6.8 Hz, major peak, R-enantiomer); CD (MeOH) 210 ([theta]=−7500), 250 ([theta]=−8100), 294 ([theta]=8500); [a]$^{22}_D$=+46.8 (EtOH, c=5.0); $^1$H NMR (d$^6$-acetone/400 MHz) 3.74 (s, 1H), 6.03 (q, 1H, 6.8 Hz), 7.61 (m, 2H), 7.92 (s, 1H); MS (ES+) 303 (M+1, 100).

EXAMPLE 930

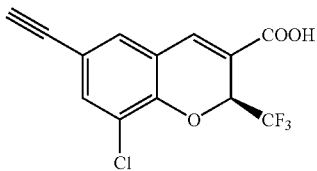

(2S)-(−)-8-Chloro-6-ethynyl-2-(trifluoromethyl)-2H-chromene-3-carboxylic acid

Resolution of 280 mg of racemic 8-Chloro-6-ethynyl-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the second eluted peak from multiple chromatographic runs afforded 100.9 mg (72%) of a yellow solid: 100% ee by analytical HPLC; $[\alpha]^{22}_D$=−46.0 (EtOH, c=5.0); $^1$H NMR (d$^6$-acetone/400 MHz) 3.74 (s, 1H), 6.03 (q, 1H, 6.8 Hz), 7.61 (m, 2H), 7.92 (s, 1H); MS (ES+) 303 (M+1, 100).

6-Chloro-7-(4-ethylphenoxy)-2-(trifluoromethyl)-2H-chromene-3-carboxylic acid

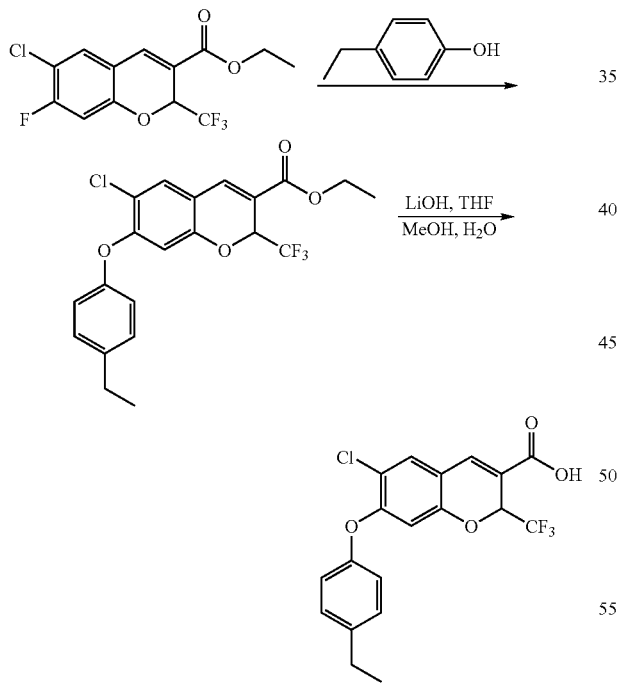

Step 1. Preparation of ethyl 6-chloro-7-(4-ethylphenoxy)-2-(trifluoromethyl)-2H-chromene-3-carboxylate To 4.05 g (12.5 mmole) of ethyl 6-chloro-7-fluoro-2-(trifluoromethyl)-2H-chromene-3-carboxylate in 30 mL of DMF was added 1.86 g (15.2 mmole) of 4-ethylphenol and 2.42 g (17.5 mmole) of potassium carbonate. The stirred mixture was heated to 100° C. for 8 h, allowed to cool and treated with 100 mL of water. The mixture was extracted three times with diethyl ether, the combined filtrates filtered through 30 g of silica and the filtrates concd in vacuo to afford a crude product. Recrystallization from methanol-water afforded 4.43 g (83%) of a yellow, crystalline solid: mp 109-110° C.; $^1$H NMR (d$^6$-acetone/400 MHz) 1.22 (t, 3H, J=7.5 Hz), 1.30 (t, 3H, J=7.1 Hz), 2.66 (q, 2H, J=7.6 Hz), 4.28 (m, 2H), 5.81 (q, 1H, J=7.0 Hz), 6.44 (s, 1H), 7.04 (d, 2H, J=8.8 Hz), 7.31 (d, 2H, J=8.6 Hz), 7.67 (s, 1H), 7.86 (s, 1H); $^{19}$F NMR (d$^6$-acetone/400 MHz) −79.5 (d, 3F, J=6.8 Hz); $^{13}$C NMR (d$^6$-acetone/100 MHz) 13.8, 15.4, 61.3, 70.8 (q, J=32.8 Hz), 105.5, 115.2, 115.9, 117.5, 119.9, 123.8 (q, J=287.1 Hz), 129.8, 131.2, 135.5, 141.5, 153.1, 153.2, 157.4, 163.4; MS (ES+) 427 (M+1, 100); HRMS (ES+) m/z calcd for ($C_{21}H_{18}O_4ClF_3$) 427.0918, found 427.0921.

Anal. Calc'd for $C_{21}H_{18}O_4ClF_3$: C, 59.09; H, 4.25. Found: C, 59.21; H, 4.24.

Step 2. Preparation of 6-chloro-7-(4-ethylphenoxy)-2-(trifluoromethyl)-2H-chromene-3-carboxylic acid To a solution of 4.43 g (10.4 mmole) of the product of step 1 in 70 mLs of THF and 20 mL of methanol was added a solution of 1.0 g of lithium hydroxide monohydate in 10 mL of water. The mixture was heated to reflux for 30 min and allowed to cool to rt. After stirring overnight, the mixture was treated with 75 mL of 1N HCl and extracted three times with diethyl ether. The combined extracts were washed with brine, dried and concd in vacuo to afford 4.02 g (97%) of a yellow solid: mp 195.5-196.5° C.; $^1$H NMR (d$^6$-acetone/400 MHz) 1.22 (t, 3H, J=7.5 Hz), 2.66 (q, 2H, J=7.6 Hz), 5.78 (q, 1H, J=7.1 Hz), 6.45 (s, 1H), 7.04 (d, 2H, J=8.4 Hz), 7.31 (d, 2H, J=8.3 Hz), 7.66 (s, 1 H), 7.87 (s, 1H); $^{19}$F NMR (d$^6$-acetone/400 MHz) −79.4 (d, 3F, J=7.7 Hz); $^{13}$C NMR (d$^6$-acetone/100 MHz) 15.4, 28.1, 70.9 (q, J=32.7 Hz), 105.6, 115.3, 116.0, 117.5, 119.9, 123.9 (q, J=286.8 Hz), 129.8, 131.1, 135.7, 141.5, 153.1, 153.3, 157.3, 164.3; MS (ES−) 397 (M−1, 100); HRMS (ES−) m/z calcd for ($C_{19}H^{13}ClF_3O_4$) 397.0449, found 397.0484.

EXAMPLE 931

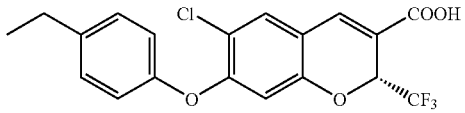

(2R)-(−)-6-chloro-7-(4-ethylphenoxy)-2-(trifluoromethyl)-2H-chromene-3-carboxylic acid Resolution of 3.3 g of racemic 6-chloro-7-(4-ethylphenoxy)-2-(trifluoromethyl)-2H-chromene-3-carboxylic acid was carried out by preparative chromatography (Chiralcel OJ) using heptane:ethanol:trifluoroacetic acid (60:40:0.1) as the mobile phase. Combination of the first eluted peak from multiple chromatographic runs afforded 1.48 g (90%) of a yellow solid (100% ee by analytical HPLC). A sample was recrystallized in hexanes-diethyl ether to give a white solid: mp 130-131° C.; $[\alpha]^{22}_D$=−28.5 (EtOH, c=1.0); $^1$H NMR (d$^6$-acetone/400 MHz) 1.22 (t, 3H, J=7.5 Hz), 2.66 (q, 2H, J=7.6 Hz), 5.78 (q, 1H, J=7.1 Hz), 6.45 (s, 1H), 7.04 (d, 2H, J=8.4 Hz), 7.31 (d, 2H, J=8.3 Hz), 7.66 (s, 1H), 7.87 (s, 1H); MS (ES+) 399 (M+1, 100); NMR non-equivalence with CSA and a 3:1 mixture of the (R) and (S) enantiomers: $^{19}$F NMR (d$^6$-benzene; 5 eq of (R)-(+)-1-(1-naphthyl)ethylamine) −77.96 (d, 3F, J=6.8 Hz, minor peaks, S-enantiomer), −78.20 (d, 3F, J=6.8 Hz, major peak, R-enantiomer); CD (MeOH) 214 ([theta]=+14700), 296 ([theta]=−10500).

EXAMPLE 939

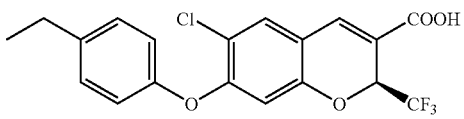

(2S)-(+)-6-chloro-7-(4-ethylphenoxy)-2-(trifluoromethyl)-2H-chromene-3-carboxylic acid Resolution of 3.3 g of racemic 6-chloro-7-(4-ethylphenoxy)-2-(trifluoromethyl)-2H-chromene-3-carboxylic acid was carried out by preparative chromatography (Chiralcel OJ) using heptane:ethanol:trifluoroacetic acid (60:40:0.1) as the mobile phase. Combination of the second eluted peak from multiple chromatographic runs afforded 1.16 g (70%) of a yellow solid (100% ee by analytical HPLC): mp 90-95° O.C; [a]$^{22}_D$=+30.5 (EtOH, c=1.0); $^1$H NMR (d$^6$-acetone/400 MHz) 1.22 (t, 3H, J=7.5Hz), 2.66 (q, 2H, J=7.6 Hz), 5.78 (q, 1H, J=7.1 Hz), 6.45(s, 1H), 7.04 (d, 2H, J=8.4Hz),7.31 (d, 2H, J=8.3 Hz), 7.66 (s, 1H), 7.87 (s, 1H); MS (ES+) 399 (M+t, 100).

EXAMPLE 940

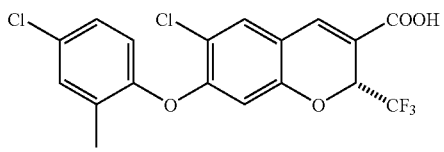

(2R)-(−)-6-chloro-7-(4-chloro-2-methylphenoxy)-2-(trifluoromethyl)-2H-chromene-3-carboxylic acid Resolution of 176.9 mg of racemic 6-chloro-7-(4-chloro-2-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 62.3 mg (70%) of a yellow solid (100% ee by analytical HPLC): [a]$^{22}_D$=−22.5 (EtOH, c=3.1); $^1$H NMR (d$^6$-acetone/400 MHz) 2.21 (s, 3H), 5.79 (q, 1H, J=7.1 Hz), 6.43 (s, 1H), 7.03 (d, 1H, J=8.6 Hz), 7.3 (dd, 1H, J=8.6 Hz, J=2.5 Hz), 7.41 (d, 1H, J=2.7 Hz), 7.69 (s, 1H), 7.86 (s, 1H); $^{19}$F NMR (d$^6$-acetone/400 MHz) −79.5 (d, 3F, J=6.8 Hz); MS (ES+) 419 (M+1, 100); NMR non-equivalence with CSA and a 1:3 mixture of the (R) and (S) enantiomers: $^{19}$F NMR (d$^6$-benzene; 10 eq of (R)-(+)-1-(1-naphthyl)ethylamine) −77.99 (d, 3F, J=7.7 Hz, major peaks, S-enantiomer), −78.19 (d, 3F, J=6.8 Hz, minor peak, R-enantiomer).

EXAMPLE 941

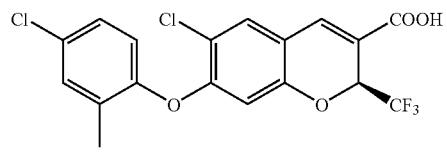

(2S)-(+)-6-chloro-7-(4-chloro-2-methylphenoxy)-2-(trifluoromethyl)-2H-chromene-3-carboxylic acid Resolution of 176.9 mg of racemic 6-chloro-7-(4-chloro-2-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 64.1 mg (72%) of a yellow solid (95.3% ee by analytical HPLC): [a]$^{22}_D$=+21.4 (EtOH, c=3.2); $^1$H NMR (d$^6$-acetone/400 MHz) 2.21 (s, 3H), 5.79 (q, 1H, J=7.1 Hz), 6.43 (s, 1H), 7.03 (d, 1H, J=8.6 Hz), 7.3 (dd, 1H, J=8.6 Hz, J=2.5 Hz), 7.41 (d, 1H, J=2.7 Hz), 7.69 (s, 1H), 7.86 (s, 1H); $^{19}$F NMR (d$^6$-acetone/400 MHz) −79.5 (d, 3F, J=6.8 Hz); MS (ES+) 419 (M+1, 100).

EXAMPLE 942

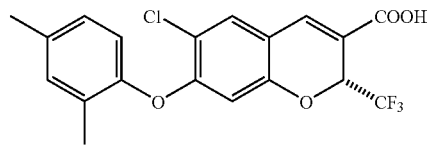

(2 R)-(−)-6-chloro-7-(2,4-dimethylphenoxy)-2-(trifluoromethyl)-2H-chromene-3-carboxylic acid Resolution of 128.3 mg of racemic 6-chloro-7-(2,4-dimethylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 32.2 mg (50%) of a yellow solid (100% ee by analytical HPLC): [a]$^{22}_D$=−40.1 (EtOH, c=1.6); $^1$H NMR (d$^6$-acetone/400 MHz) 2.12 (s, 3H), 2.32 (s, 3H), 5.76 (q, 1H, J=7.1 Hz), 6.24 (s, 1H), 6.94 (d, 1H, J=8.2 Hz), 7.11 (d, 2H, J=8.3 Hz), 7.18 (s, 1H), 7.67 (s, 1H), 7.85 (s, 1H); $^{19}$F NMR (d$^6$-acetone/400 MHz) −79.5 (d, 3F, J=6.8 Hz); MS (ES+) 399 (M+1, 100); NMR non-equivalence with CSA and a 1:3 mixture of the (R) and (S) enantiomers: $^{19}$F NMR (d$^6$-benzene; 8 eq of (R)-(+)-1-(1-naphthyl)ethylamine) −78.00 (d, 3F, J=6.8 Hz, major peaks, S-enantiomer), −78.19 (d, 3F, J=7.7 Hz, minor peak, R-enantiomer).

EXAMPLE 943

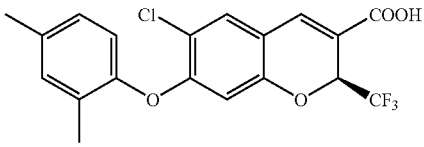

(2S)-(+)-6-chloro-7-(2,4-dimethylphenoxy)-2-(trifluoromethyl)-2H-chromene-3-carboxylic acid Resolution of 128.3 mg of racemic 6-chloro-7-(2,4-dimethylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 23.1 mg (36%) of a yellow solid (100% ee by analytical HPLC): $[a]^{22}_D$=+34.7 (EtOH, c=1.2); $^1$H NMR (d$^6$-acetone/400 MHz) 2.12 (s, 3H), 2.32 (s, 3H), 5.76 (q, 1H, J=7.1 Hz), 6.24 (s, 1H), 6.94 (d, 1H, J=8.2 Hz), 7.11 (d, 2H, J=8.3 Hz), 7.18 (s, 1H), 7.67 (s, 1H), 7.85 (s, 1H); $^{19}$F NMR (d$^6$-acetone/400 MHz) −79.5 (d, 3F, J=6.8 Hz); MS (ES+) 399 (M+1, 100).

EXAMPLE 944

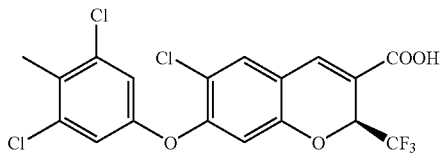

(2S)-(+)-6-chloro-7-(3,5-dichloro-4-methylphenoxy)-2-(trifluoromethyl)-2H-chromene-3-carboxylic acid Resolution of 78.4 mg of racemic 6-chloro-7-(3,5-dichloro4-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 26.1 mg (67%) of a yellow solid (100% ee by analytical HPLC): $[a]^{22}_D$=+26.1 (EtOH, c=1.3); $^1$H NMR (d$^6$-acetone/400 MHz) 2.41 (s, 3H), 5.78 (q, 1H, J=7.1 Hz), 6.18 (s, 1H), 7.45 (s, 2H), 7.71 (s, 1H), 7.86 (s, 1H); $^{19}$F NMR (d$^6$-acetone/400 MHz) −79.5 (d, 3F, J=6.8 Hz); MS (ES+) 453 (M+1, 90),455 (M+3, 100); NMR non-equivalence with CSA and a 3:1 mixture of the (R) and (S) enantiomers: $^{19}$F NMR (d$^6$-benzene; 9 eq of (R)-(+)-1-(1-naphthyl)ethylamine) −78.11 (d, 3F, J=7.7 Hz, minor peaks, S-enantiomer), −78.26 (d, 3F, J=7.7 Hz, major peak, R-enantiomer).

EXAMPLE 945

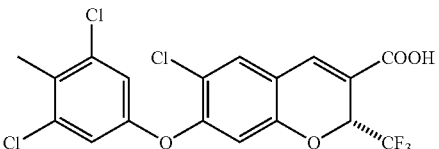

(2R)-(−)-6-chloro-7-(3,5-dichloro-4-methylphenoxy)-2-(trifluoromethyl)-2H-chromene-3-carboxylic acid Resolution of 78.4 mg of racemic 6-chloro-7-(3,5-dichloro-4-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 24.5 mg (63%) of a yellow solid (100% ee by analytical HPLC): $[a]^{22}_D$=−29.6 (EtOH, c=1.2); $^1$H NMR (d$^6$-acetone/400 MHz) 2.41 (s, 3H), 5.78 (q, 1H, J=7.1 Hz), 6.18 (s, 1H), 7.45 (s, 2H), 7.71 (s, 1H), 7.86 (s, 1H); $^{19}$F NMR (d$^6$-acetone/400 MHz) −79.5 (d, 3F, J=6.8 Hz); MS (ES+) 453 (M+1, 90), 455 (M+3, 100).

EXAMPLE 946

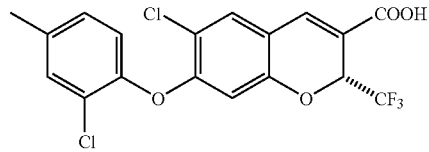

(2R)-(−)-6-chloro-7-(2-chloro-4-methylphenoxy)-2-(trifluoromethyl)-2H-chromene-3-carboxylic acid Resolution of 204.4 mg of racemic 6-chloro-7-(2-chloro-4-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 76.9 mg (75%) of a yellow solid (100% ee by analytical HPLC): $[a]^{22}_D$=−26.0 (EtOH, c=3.8); $^1$H NMR (d$^6$-acetone/400 MHz) 2.38 (s, 3H), 5.78 (q, 1H, J=7.0 Hz), 6.31 (s, 1H), 7.16 (d, 1H, J=8.3 Hz), 7.26 (dd, 1H, J=8.3 Hz, J=1.5 Hz), 7.43 (d, 1H, J=1.5 Hz), 7.69 (s, 1H), 7.87 (s, 1H); $^{19}$F NMR (d$^6$-acetone/400 MHz) −79.5 (d, 3F, J=7.7 Hz); MS (ES+) 419 (M+1, 100); NMR non-equivalence with CSA and a 1:3 mixture of the (R) and (S) enantiomers: $^{19}$F NMR (d$^6$-benzene; 9 eq of (R)-(+)-1-(1-naphthyl)ethylamine) −78.02 (d, 3F, J=7.7 Hz, major peaks, S-enantiomer), −78.21 (d, 3F, J=7.7 Hz, minor peak, R-enantiomer).

EXAMPLE 947

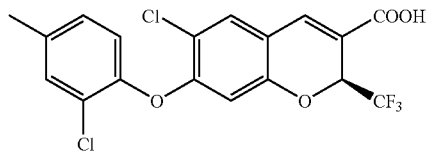

(2S)-(+)-6-chloro-7-(2-chloro-4-methylphenoxy)-2-(trifluoromethyl)-2H-chromene-3-carboxylic acid Resolution of 204.4 mg of racemic 6-chloro-7-(2-chloro-4-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 67.6 mg (66%) of a yellow solid (100% ee by analytical HPLC): $[a]^{22}_D$=+26.4 (EtOH, c=3.4); $^1$H NMR (d$^6$-acetone/400 MHz) 2.38 (s, 3H), 5.78 (q, 1H, J=7.0 Hz), 6.31 (s, 1H), 7.16 (d, 1H, J=8.3 Hz), 7.26 (dd, 1H, J=8.3 Hz, J=1.5 Hz), 7.43 (d, 1H, J=1.5 Hz), 7.69 (s, 1H), 7.87 (s, 1H); $^{19}$F NMR (d$^6$-acetone/400 MHz) −79.5 (d, 3F, J=7.7 Hz); MS (ES+) 419 (M+1, 100).

EXAMPLE 948

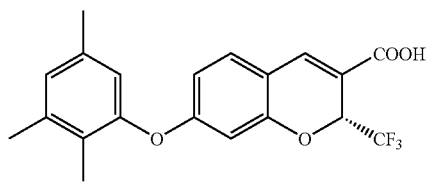

(2R)-(−)-2-(trifluoromethyl)-7-(2,3,5-trimethylphenoxy)-2H-chromene-3-carboxylic acid Resolution of 261.8 mg of racemic 2-(trifluoromethyl)-7-(2,3,5-trimethylphenoxy)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 127.8 mg (98%) of a yellow solid (100% ee by analytical HPLC): $[a]^{22}_D$=−69.6 (EtOH, c=6.4); $^1$H NMR (d$^6$-acetone/400 MHz) 2.02 (s, 3H), 2.26 (s, 3H), 2.27 (s, 3H), 2.90 (brs, 1H), 5.76 (q, 1H, J=7.2 Hz), 6.42 (d, 1H, J=2.1 Hz), 6.53 (dd, 1H, J=2.4 Hz, J=8.4 Hz), 6.72 (s, 1H), 6.92 (s, 1H), 7.40 (d, 1H, J=8.5 Hz), 7.83 (s, 1H); $^{19}$F NMR (CDCl$_3$/400 MHz) −79.6 (d, 3F, J=6.8 Hz); MS (ES+) 379 (M+1, 100); NMR non-equivalence with CSA and a 1:2 mixture of the (R) and (S) enantiomers: $^{19}$F NMR (d$^6$-benzene; 9 eq of(R)-(+)-1-(1-naphthyl)ethylamine) −78.09 (d, 3F, J=6.8 Hz, major peaks, S-enantiomer), −78.16 (d, 3F, J=6.8 Hz, minor peak, R-enantiomer).

EXAMPLE 949

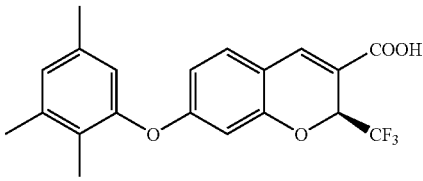

(2S)-(+)-2-(trifluoromethyl)-7-(2,3,5-trimethylphenoxy)-2H-chromene-3-carboxylic acid Resolution of 261.8 mg of racemic 2-(trifluoromethyl)-7-(2,3,5-trimethylphenoxy)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 122.4 mg (94%) of a yellow solid (99.8% ee by analytical HPLC): $[a]^{22}_D$=+71.7 (EtOH, c=6.1); $^1$H NMR (d$^6$-acetone/400 MHz) 2.02 (s, 3H), 2.26 (s, 3H), 2.27 (s, 3H), 2.90 (brs, 1H), 5.76 (q, 1H, J=7.2 Hz), 6.42 (d, 1H, J=2.1 Hz), 6.53 (dd, 1H, J=2.4 Hz, J=8.4 Hz), 6.72 (s, 1H), 6.92 (s, 1H), 7.40 (d, 1H, J=8.5 Hz), 7.83 (s, 1H); $^{19}$F NMR (CDCl$_3$/400 MHz) −79.6 (d, 3F, J=6.8 Hz); MS (ES+) 379 (M+1, 100); CD (MeOH) 214 ([theta]−16400), 250 ([theta]=−8100); 294 ([theta]=+8500).

EXAMPLE 950

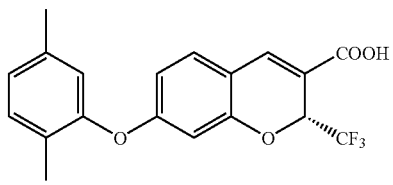

(2R)-(−)-7-(2,5-dimethylphenoxy)-2-(trifluoromethyl)-2H-chromene-3-carboxylic acid Resolution of 290.6 mg of racemic 7-(2,5-dimethylphenoxy)-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the first eluted peak from multiple chromatographic runs afforded 136.1 mg (94%) of a yellow solid (100% ee by analytical HPLC): $[a]^{22}_D$=−74.4 (EtOH, c=6.8); $^1$H NMR (d$_6$-acetone/400 MHz) 2.10 (s, 3H), 2.30 (s, 3H), 2.85 (brs, 1H), 5.77 (q, 1H, J=7.1 Hz), 6.44 (d, 1H, J=2.3 Hz), 6.55 (dd, 1H, J=2.4 Hz, J=8.5 Hz), 6.87 (s, 1H), 7.01 (d, 1H, J=8.3 Hz), 7.21 (d, 1H, J=7.8 Hz), 7.42 (d, 1H, J=8.5 Hz), 7.84 (s, 1H); $^{19}$F NMR (CDCl$_3$/400 MHz) −79.6 (d, 3F, J=6.8 Hz); MS (ES+) 365 (M+1, 100); NMR non-equivalence with CSA and a 1:2 mixture of the (R) and (S) enantiomers: $^{19}$F NMR (d$^6$-benzene; 6 eq of(R)-(+)-1-(1-naphthyl)ethylamine) −78.10 (d, 3F, J=6.8 Hz, major peaks, S-enantiomer), −78.17 (d, 3F, J=6.8 Hz, minor peak, R-enantiomer).

EXAMPLE 951

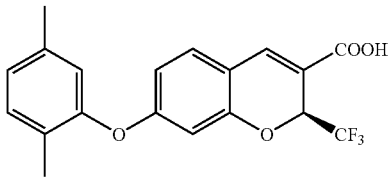

(2S)-(+)-7-(2,5-dimethylphenoxy)-2-(trifluoromethyl)-2H-chromene-3-carboxylic acid Resolution of 290.6 mg of racemic 7-(2,5-dimethylphenoxy)-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the second eluted peak from multiple chromatographic runs afforded 135.2 mg (93%) of a yellow solid (99.8% ee by analytical HPLC): $[a]^{22}D=+72.1$ (EtOH, c=6.8); $^1$H NMR ($d_6$-acetone/400 MHz) 2.10 (s, 3H), 2.30 (s, 3H), 2.85 (brs, 1H), 5.77 (q, 1H, J=7.1 Hz), 6.44 (d, 1H, J=2.3 Hz), 6.55 (dd, 1H, J=2.4 Hz, J=8.5 Hz), 6.87 (s, 1H), 7.01 (d, 1H, J=8.3 Hz), 7.21 (d, 1H, J=7.8 Hz), 7.42 (d, 1H, J=8.5 Hz), 7.84 (s, 1H); $^{19}$F NMR (CDCl$_3$/400 MHz) −79.6 (d, 3F, J=6.8 Hz); MS (ES+) 365 (M+1, 100); CD (MeOH) 212 ([theta]=−18800), 250 ([theta]=−7900); 294 ([theta]=+9000).

EXAMPLE 952

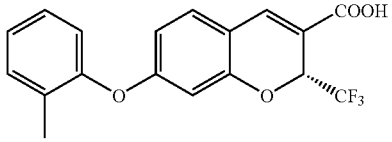

(2R)-(−)-7-(2-methylphenoxy)-2-(trifluoromethyl)-2H-chromene-3-carboxylic acid

Resolution of 314 mg of racemic 7-(2-methylphenoxy)-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the first eluted peak from multiple chromatographic runs afforded 151.6 mg (97%) of a yellow solid (100% ee by analytical HPLC): $[a]^{22}_D=-73.4$ (EtOH, c=7.6); $^1$H NMR ($d^6$-acetone/400 MHz) 2.21 (s, 3H), 5.82 (q, 1H, J=7.0 Hz), 6.50 (d, 1H, J=2.2 Hz), 6.61 (dd, 1H, J=8.5 Hz, J=2.4 Hz), 7.10 (d, 1H, J=8.0 Hz), 7.24 (t, 1H, J=6.8 Hz), 7.31-7.41 (m, 2H), 7.47 (d, 1H, J=8.5 Hz), 7.90 (s, 1H); $^{19}$F NMR (CDCl$_3$/400 MHz) −79.5 (d, 3F, J=7.2 Hz); MS (ES+) 351 (M+1, 100); NMR non-equivalence with CSA and a 2:1 mixture of the (R) and (S) enantiomers: $^{19}$F NMR ($d^6$-benzene; 6 eq of (R)-(+)-1-(1-naphthyl)ethylamine) −78.02 (d, 3F, J=7.2 Hz, minor peaks, S-enantiomer), −78.11 (d, 3F, J=7.2 Hz, major peak, R-enantiomer).

EXAMPLE 953

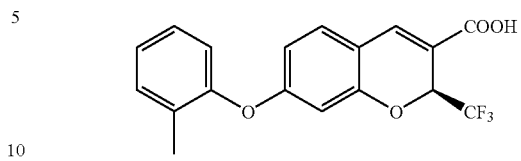

(2S)-(+)-7-(2-methylphenoxy)-2-(trifluoromethyl)-2H-chromene-3-carboxylic acid

Resolution of 314 mg of racemic 7-(2-methylphenoxy)-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the second eluted peak from multiple chromatographic runs afforded 151.5 mg (97%) of a yellow solid (100% ee by analytical HPLC): $[a]^{22}_D=+70.0$ (EtOH, c=7.6); $^1$H NMR ($d^6$-acetone/400 MHz) 2.21 (s, 3H), 5.82 (q, 1H, J=7.0 Hz), 6.50 (d, 1H, J=2.2 Hz), 6.61 (dd, 1H, J=8.5 Hz, J=2.4 Hz), 7.10 (d, 1H, J=8.0 Hz), 7.24 (t, 1H, J=6.8 Hz), 7.31-7.41 (m, 2H), 7.47 (d, 1H, J=8.5 Hz), 7.90 (s, 1H); $^{19}$F NMR (CDCl$_3$/400 MHz) −79.5 (d, 3F, J=7.2 Hz); MS (ES+) 351 (M+1, 100).

EXAMPLE 954

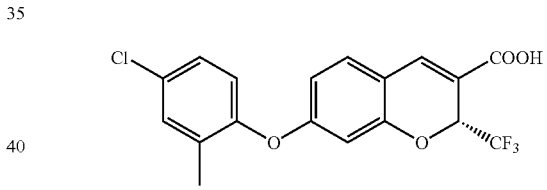

(2R)-(−)-7-(4-chloro-2-methylphenoxy)-2-(trifluoromethyl)-2H-chromene-3-carboxylic acid Resolution of 488.5 mg of racemic 7-(4-chloro-2-methylphenoxy)-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the first eluted peak from multiple chromatographic runs afforded 222.6 mg (91%) of a yellow solid (100% ee by analytical HPLC): $[a]22_D=-55.9$ (EtOH, c=11.1); $^1$H NMR ($d_6$-acetone/400 MHz) 2.23 (s, 3H), 5.83 (q, 1H, J=7.0 Hz), 6.57 (d, 1H, J=2.3 Hz), 6.64 (dd, 1H, J=8.2 Hz, J=2.4 Hz), 7.12 (d, 1H, J=8.4 Hz), 7.35 (dd, 1H, J=8.6 Hz, J=2.6 Hz), 7.44 (d, 1H, J=2.4 Hz), 7.50 (d, 1H, J=8.2 Hz), 7.91 (s, 1H); $^{19}$F NMR (CDCl$_3$/400 MHz) −79.5 (d, 3F, J=6.5 Hz); MS (ES+) 385 (M+1, 100); NMR non-equivalence with CSA and a 2:1 mixture of the (R) and (S) enantiomers: $^{19}$F NMR ($d^6$-benzene; 6 eq of(R)-(+)-1-(1-naphthyl)ethylamine) −78.02 (d, 3F, J=7.2 Hz, minor peaks, S-enantiomer), −78.09 (d, 3F, J=7.2 Hz, major peak, R-enantiomer).

EXAMPLE 955

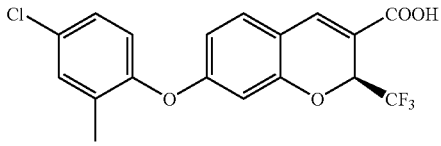

(2S)-(+)-7-(4-chloro-2-methylphenoxy)-2-(trifluoromethyl)-2H-chromene-3-carboxylic acid Resolution of 488.5 mg of racemic 7-(4-chloro-2-methylphenoxy)-2-(trifluoromethyl)-2H-chromene-3-carboxylic acid was carried out by preparative chromatography (Chiralpak AD) using heptane:2-propanol:acetic acid (97:2.5:0.5) as the mobile phase. Combination of the second eluted peak from multiple chromatographic runs afforded 220.7 mg (90%) of a yellow solid (100% ee by analytical HPLC): $[a]^{22}_D$=+56.0 (EtOH, c=11.0); $^1$H NMR ($d_6$-acetone/400 MHz) 2.23 (s, 3H), 5.83 (q, 1H, J=7.0 Hz), 6.57 (d, 1H, J=2.3 Hz), 6.64 (dd, 1H, J=8.2 Hz, J=2.4 Hz), 7.12 (d, 1H, J=8.4 Hz), 7.35 (dd, 1H, J=8.6 Hz, J=2.6 Hz), 7.44 (d, 1H, J=2.4 Hz), 7.50 (d, 1H, J=8.2 Hz), 7.91 (s, 1H); $^{19}$F NMR (CDCl$_3$/400 MHz) −79.5 (d, 3F, J=6.5 Hz); MS (ES+) 385 (M+1, 100).

EXAMPLE 956

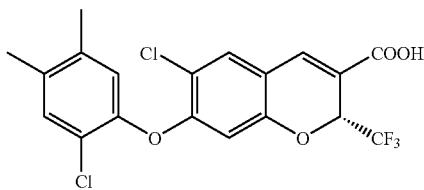

(2R)-(−)-6-chloro-7-(2-chloro-4,5-dimethylphenoxy)-2-(trifluoromethyl)-2H-chromene-3-carboxylic acid Resolution of 150.0 mg of racemic 6-chloro-7-(2-chloro-4,5-dimethylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 54.8 mg (73%) of a yellow solid (100% ee by analytical HPLC): $[a]^{22}_D$=−29.2 (EtOH, c=2.7); $^1$H NMR ($d_6$-acetone/ 400 MHz) 2.32 (s, 3H), 2.34 (s, 3H), 5.83 (q, 1H, J=6.8 Hz), 6.34 (s, 1H), 7.14 (s, 1H), 7.41 (s, 1H), 7.74 (s, 1H), 7.92 (s, 1H); $^{19}$F NMR (CDCl$_3$/400 MHz) −79.5 (d, 3F, J=6.5 Hz); MS (ES+) 433 (M+1, 100), 435 (M+3, 65); NMR non-equivalence with CSA and a 2:1 mixture of the (R) and (S) enantiomers: $^{19}$F NMR ($d^6$-benzene; 23 eq of (R)-(+)-1-(1-naphthyl)ethylamine) −77.91 (d, 3F, J=7.2 Hz, minor peaks, S-enantiomer), −78.08 (d, 3F, J=7.2 Hz, major peak, R-enantiomer).

EXAMPLE 957

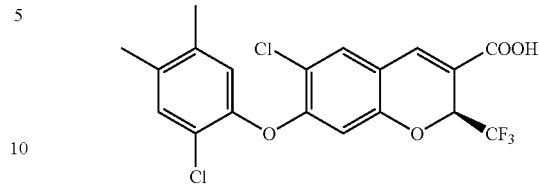

(2S)-(+)-6-chloro-7-(2-chloro4,5-dimethylphenoxy)-2-(trifluoromethyl)-2H-chromene-3-carboxylic acid Resolution of 150.0 mg of racemic 6-chloro-7-(2-chloro-4,5-dimethylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 48.6 mg (65%) of a yellow solid (100% ee by analytical HPLC): $[a]^{22}_D$=+29.2 (EtOH, c=2.4); $^1$H NMR ($d_6$-acetone/ 400 MHz) 2.32 (s, 3H), 2.34 (s, 3H), 5.83 (q, 1H, J=6.8 Hz), 6.34 (s, 1H), 7.14 (s, 1H), 7.41 (s, 1H), 7.74 (s, 1H), 7.92 (s, 1H); $^{19}$F NMR (CDCl$_3$/400 MHz) −79.5 (d, 3F, J=6.5 Hz); MS (ES+) 433 (M+1, 100), 435 (M+3, 65).

EXAMPLE 958a

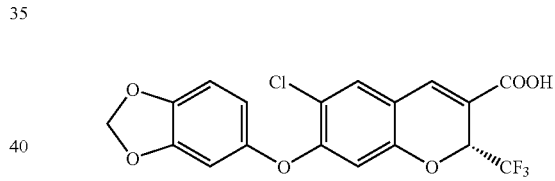

(2R)-(−)-7-(1,3-benzodioxol-5-yloxy)-6-chloro-2-(trifluoromethyl)-2H-chromene-3-carboxylic acid Resolution of 179.2 mg of racemic 7-(1,3-benzodioxol-5-yloxy)-6-chloro-2-(trifluoromethyl)-2H-chromene-3-carboxylic acid was carried out by preparative chromatography (Chiralpak AD) using heptane:2-propanol:acetic acid (85: 15:0.5) as the mobile phase. Combination of the first eluted peak from multiple chromatographic runs afforded 61.5 mg (69%) of a yellow solid (98.2% ee by analytical HPLC): $[a]^{22}_D$=−22.3 (EtOH, c=3.1); $^1$H NMR ($d_6$-acetone/400 MHz) 5.84 (q, 1H, J=6.8 Hz), 6.13 (s, 2H), 6.52 (s, 1H), 6.66 (dd, 1H, J=8.5 Hz, J=2.0 Hz), 6.80 (d, 1H, J=2.5 Hz), 6.96 (d, 1H, J=8.3 Hz), 7.69 (s, 1H), 7.90 (s, 1H); $^{19}$F NMR (CDCl$_3$/400 MHz) −79.4 (d, 3F, J=7.2 Hz); MS (ES+) 415 (M+1, 100); NMR non-equivalence with CSA and a 2:1 mixture of the (R) and (S) enantiomers: $^{19}$F NMR ($d^6$-benzene; 18 eq of (R)-(+)-1-(1-naphthyl)ethylamine) −77.84 (d, 3F, J=7.2 Hz, minor peaks, S-enantiomer), −78.03 (d, 3F, J=7.2 Hz, major peak, R-enantiomer).

EXAMPLE 958b

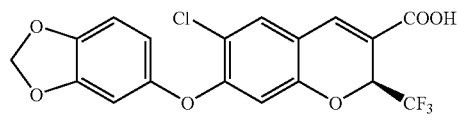

(2S)-(+)-7-(1,3-benzodioxol-5-yloxy)-6-chloro-2-(trifluoromethyl)-2H-chromene-3-carboxylic acid Resolution of 179.2 mg of racemic 7-(1,3-benzodioxol-5-yloxy)-6-chloro-2-(trifluoromethyl)-2H-chromene-3-carboxylic acid was carried out by preparative chromatography (Chiralpak AD) using heptane:2-propanol:acetic acid (85:15:0.5) as the mobile phase. Combination of the second eluted peak from multiple chromatographic runs afforded 63.5 mg (71%) of a yellow solid (97.2% ee by analytical HPLC): $[a]^{22}_D$=+20.5 (EtOH, c=3.2); $^1$H NMR ($d_6$-acetone/400 MHz) 5.84 (q, 1 H, J=6.8 Hz), 6.13 (s, 2H), 6.52 (s, 1H), 6.66 (dd, 1H, J=8.5 Hz, J=2.0 Hz), 6.80 (d, 1H, J=2.5 Hz), 6.96 (d, 1H, J=8.3 Hz), 7.69 (s, 1H), 7.90 (s, 1H); $^{19}$F NMR (CDCl$_3$/400 MHz) −79.4 (d, 3F, J=7.2 Hz); MS (ES+) 415 (M+1, 100).

EXAMPLE 959

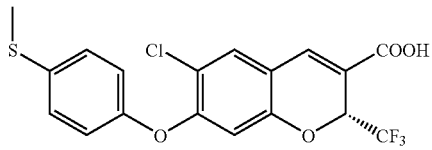

(2R)-(−)-6-chloro-7-[4-(methylthio)phenoxy]-2-(trifluoromethyl)-2H-chromene-3-carboxylic acid Resolution of 147.3 mg of racemic 6-chloro-7-[4-(methylthio)phenoxy]-2-(trifluoromethyl)-2H-chromene-3-carboxylic acid was carried out by preparative chromatography (Chiralpak OJ) using heptane:2-propanol:acetic acid (70:30:0.5) as the mobile phase. Combination of the first eluted peak from multiple chromatographic runs afforded 50.7 mg (69%) of a yellow solid (100% ee by analytical HPLC): $[a]^{22}_D$=−21.3 (EtOH, c=2.5); $^1$H NMR ($d_6$-acetone/400 MHz) 2.56 (s, 31H), 5.87 (q, 1H, J=6.6 Hz), 6.58 (s, 1H), 7.12 (d, 2H, J=8.7 Hz), 7.43 (d, 2H, J=8.9 Hz), 7.69 (s, 1H), 7.85 (s, 1H); $^{19}$F NMR (CDCl$_3$/400 MHz) −79.3 (d, 3F, J=6.5 Hz); MS (ES+) 417 (M+1, 100), 419 (M+3, 45); NMR non-equivalence with CSA and a 4:1 mixture of the (R) and (S) enantiomers: $^{19}$F NMR ($d^6$-benzene; 26 eq of (R)-(+)-1-(1-naphthyl)ethylamine) −77.80 (d, 3F, J=6.5 Hz, minor peaks, S-enantiomer), −77.96 (d, 3F, J=7.2 Hz, major peak, R-enantiomer).

EXAMPLE 960

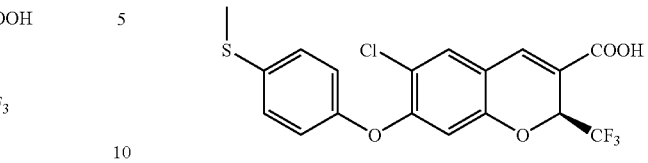

(2S)-(+)-6-chloro-7-[4-(methylthio)phenoxy]-2-(trifluoromethyl)-2H-chromene-3-carboxylic acid Resolution of 147.3 mg of racemic 6-chloro-7-[4-(methylthio)phenoxy]-2-(trifluoromethyl)-2H-chromene-3-carboxylic acid was carried out by preparative chromatography (Chiralpak OJ) using heptane:2-propanol:acetic acid (70:30:0.5) as the mobile phase. Combination of the second eluted peak from multiple chromatographic runs afforded 23.9 mg (32%) of a yellow solid (98.6% ee by analytical HPLC): $[a]^{22}_D$=+20.9 (EtOH, c=1.2); $^1$H NMR ($d_6$-acetone/400 MHz) 2.56 (s, 3H), 5.87 (q, 1H, J=6.6 Hz), 6.58 (s, 1H), 7.12 (d, 2H, J=8.7 Hz), 7.43 (d, 2H, J=8.9 Hz), 7.69 (s, 1H), 7.85 (s, 1H); $^{19}$F NMR (CDCl$_3$/400 MHz) −79.3 (d, 3F, J=6.5 Hz); MS (ES+) 417 (M+1, 100), 419 (M+3, 45).

EXAMPLE 961

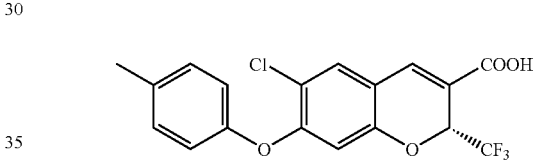

(2R)-(−)-6-chloro-7-(4-methylphenoxy)-2-(trifluoromethyl)-2H-chromene-3-carboxylic acid Resolution of 217.7 mg of racemic 6-chloro-7-(4-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 80.4 mg (74%) of a yellow solid (100% ee by analytical HPLC): $[a]^{22}_D$=−28.7 (EtOH, c=4.0); $^1$H NMR ($d_6$-acetone/400 MHz) 2.40 (s, 3H), 5.84 (q, 1H, J=7.0 Hz), 6.49 (s, 1H), 7.07 (d, 2H, J=8.5 Hz), 7.34 (d, 2H, J=8.3 Hz), 7.72 (s, 1H), 7.92 (s, 1H); $^{19}$F NMR (CDCl$_3$/400 MHz) −79.4 (d, 3F, J=7.2 Hz); MS (ES+) 385 (M+1, 100); NMR non-equivalence with CSA and a 2:1 mixture of the (R) and (S) enantiomers: $^{19}$F NMR ($d^6$-benzene; 16 eq of (R)-(+)-1-(1-naphthyl)ethylamine) −77.85 (d, 3F, J=6.5 Hz, minor peaks, S-enantiomer), −78.05 (d, 3F, J=6.5 Hz, major peak, R-enantiomer).

EXAMPLE 962

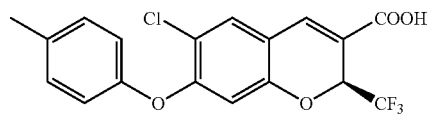

(2S)-(+)-6-chloro-7-(4-methylphenoxy)-2-(trifluoromethyl)-2H-chromene-3-carboxylic acid Resolution of 217.7 mg of racemic 6-chloro-7-(4-methylphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 70.5 mg (65%) of a yellow solid (100% ee by analytical HPLC): $[a]^{22}_D$=+29.0 (EtOH, c=3.5); $^1$H NMR (d$^6$-acetone/400 MHz) 2.40 (s, 3H), 5.84 (q, 1H, J=7.0 Hz), 6.49 (s, 1H), 7.07 (d, 2H, J=8.5 Hz), 7.34 (d, 2H, J=8.3 Hz), 7.72 (s, 1H), 7.92 (s, 1H); $^{19}$F NMR (CDCl$_3$/400 MHz) −79.4 (d, 3F, J=7.2 Hz); MS (ES+) 385 (M+1, 100).

EXAMPLE 963

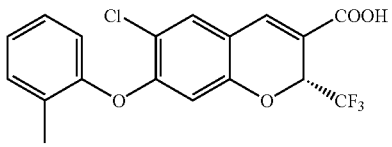

(2R)-(−)-6-chloro-7-(2-methylphenoxy)-2-(trifluoromethyl)-2H-chromene-3-carboxylic acid Resolution of 180.7 mg of racemic 6-chloro-7-(2-methylphenoxy)-2-(trifluoromethyl)-2H-chromene-3-carboxylic acid was carried out by preparative chromatography (Chiralpak AS) using heptane:2-propanol:acetic acid (90:10:0.5) as the mobile phase. Combination of the first eluted peak from multiple chromatographic runs afforded 85.3 mg (94%) of a yellow solid (100% ee by analytical HPLC): $[a]^{22}_D$=−37.0 EtOH, c=4.3); $^1$H NMR (d$^6$-acetone/400 MHz) 2.24 (s, 3H), 5.83 (q, 1H, J=7.0 Hz), 6.43 (s, 1H), 7.10 (d, 1H, J=7.0 Hz), 7.26 (t, 1H, J=7.5 Hz), 7.33-7.44 (m, 2H), 7.44 (s, 1H), 7.93 (s, 1H); $^{19}$F NMR (CDCl$_3$/400 MHz) −79.5 (d, 3F, J=7.2 Hz); MS (ES+) 385 (M+1, 100); NMR non-equivalence with CSA and a 2:1 mixture of the (R) and (S) enantiomers: $^{19}$F NMR (d$^6$-benzene; 14 eq of (R)-(+)-1-(1-naphthyl)ethylamine) −77.89 (d, 3F, J=7.2 Hz, minor peaks, S-enantiomer), −78.09 (d, 3F, J=7.2 Hz, major peak, R-enantiomer).

EXAMPLE 964

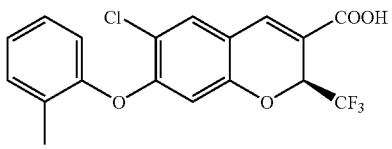

(2S)-(+)-6-chloro-7-(2-methylphenoxy)-2-(trifluoromethyl)-2H-chromene-3-carboxylic acid Resolution of 180.7 mg of racemic 6-chloro-7-(2-methylphenoxy)-2-(trifluoromethyl)-2H-chromene-3-carboxylic acid was carried out by preparative chromatography (Chiralpak AS) using heptane:2-propanol:acetic acid (90:10:0.5) as the mobile phase. Combination of the second eluted peak from multiple chromatographic runs afforded 85.3 mg (94%) of a yellow solid (100% ee by analytical HPLC): $[a]^{22}_D$=+36.5 (EtOH, c=4.3); $^1$H NMR (d$_6$-acetone/400 MHz) 2.24 (s, 3H), 5.83 (q, 1H, J=7.0 Hz), 6.43 (s, 1H), 7.10 (d, 1H, J=7.0 Hz), 7.26 (t, 1H, J=7.5 Hz), 7.33-7.44 (m, 2H), 7.44 (s, 1H), 7.93 (s, 1H); $^{19}$F NMR (CDCl$_3$/400 MHz) −79.5 (d, 3F, J=7.2 Hz); MS (ES+) 385 (M+1, 100).

EXAMPLE 965

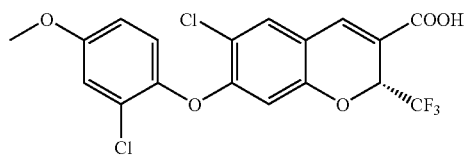

(2R)-(−)-6-chloro-7-(2-chloro4-methoxyphenoxy)-2-(trifluoromethyl)-2H-chromene-3-carboxylic acid Resolution of 223.3 mg of racemic 6-chloro-7-(2-chloro-4-methoxyphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the first eluted peak from multiple chromatographic runs afforded 95.3 mg (85%) of a yellow solid (100% ee by analytical HPLC): $[a]^{22}_D$=−24.4 (EtOH, c=4.8); $^1$H NMR (d$^6$-acetone/400 MHz) 3.93 (s, 3H), 5.83 (q, 1H, J=7.0 Hz), 6.31 (s, 1H), 7.08 (dd, 1H, J=8.9 Hz, J=2.9 Hz), 7.22 (d, 1H, J=2.8 Hz), 7.32 (d, 1H, J=8.9 Hz), 7.73 (s, 1H), 7.92 (s, 1H); $^{19}$F NMR (CDCl$_3$/400 MHz) −79.5 (d, 3F, J=7.2 Hz); MS (ES+) 435 (M+1, 100), 437 (M+3, 65); NMR non-equivalence with CSA and a 2:1 mixture of the (R) and (S) enantiomers: $^{19}$F NMR (d$^6$-benzene; 13 eq of (R)-(+)-1-(1-naphthyl_ethylamine) −77.92 (d, 3F, J=7.2 Hz, minor peaks, S-enantiomer), −78.10 (d, 3F, J=7.2 Hz, major peak, R-enantiomer).

EXAMPLE 966

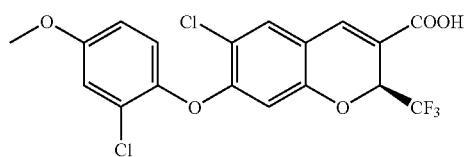

(2S)-(+)-6-chloro-7-(2-chloro4-methoxyphenoxy)-2-(trifluoromethyl)-2H-chromene-3-carboxylic acid Resolution of 223.3 mg of racemic 6-chloro-7-(2-chloro-4-methoxyphenoxy)-2-(trifluoromethyl)-2H-chromene-3-carboxylic acid was carried out by preparative chromatography (Chiralpak AD) using heptane:2-propanol:acetic acid (95:5:0.5) as the mobile phase. Combination of the second eluted peak from multiple chromatographic runs afforded 95.8 mg (86%) of a yellow solid (95.8% ee by analytical HPLC): $[a]^{22}_D$=+21.9 (EtOH, c=4.8); $^1$H NMR (d$^6$-acetone/400 MHz) 3.93 (s, 3H), 5.83 (q, 1H, J=7.0 Hz), 6.31 (s, 1H), 7.08 (dd, 1H, J=8.9 Hz, J=2.9 Hz), 7.22 (d, 1H, J=2.8 Hz), 7.32 (d, 1H, J=8.9 Hz), 7.73 (s, 1H), 7.92 (s, 1H); $^{19}$F NMR (CDCl$_3$/400 MHz) −79.5 (d, 3F, J=7.2 Hz); MS (ES+) 435 (M+1, 100), 437 (M+3, 65).

EXAMPLE 967

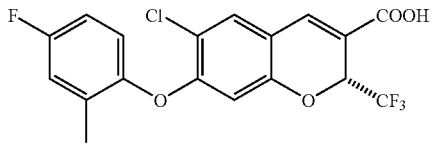

(2R)-(−)-6-chloro-7-(4-fluoro-2-methylphenoxy)-2-(trifluoromethyl)-2H-chromene-3-carboxylic acid Resolution of 216 mg of racemic 6-chloro-7-(4-fluoro-2-methylphenoxy)-2-(trifluoromethyl)-2H-chromene-3-carboxylic acid was carried out by preparative chromatography (Chiralpak OJ) using heptane:ethanol:acetic acid (75:25:0.5) as the mobile phase. Combination of the first eluted peak from multiple chromatographic runs afforded 96.5 mg (89%) of a yellow solid (100% ee by analytical HPLC): $[a]^{22}_D$=−35.6 (EtOH, c=4.8); $^1$H NMR (d$^6$-acetone/400 MHz) 2.24 (s, 3H), 5.84 (q, 1H, J=7.0 Hz), 6.36 (s, 1H), 7.11-7.24 (m, 3H), 7.72 (s, 1H), 7.89 (s, 1H); $^{19}$F NMR (CDCl$_3$/400 MHz) −79.4 (d, 3F, J=6.5 Hz), −117.9 (m, 1F); MS (ES+) 403 (M+1, 100); NMR non-equivalence with CSA and a 2:1 mixture of the (R) and (S) enantiomers: $^{19}$F NMR (d$^6$-benzene; 14 eq of (R)-(+)-1-(1-naphthyl)ethylamine) −77.87 (d, 3F, J=6.5 Hz, minor peaks, S-enantiomer), −78.04 (d, 3F, J=7.2 Hz, major peak, R-enantiomer).

EXAMPLE 968

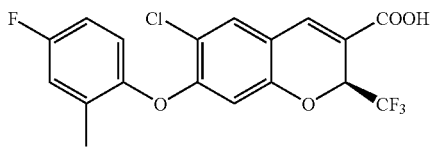

(2S)-(+)-6-chloro-7-(4-fluoro-2-methylphenoxy)-2-(trifluoromethyl)-2H-chromene-3-carboxylic acid Resolution of 216 mg of racemic 6-chloro-7-(4-fluoro-2-methylphenoxy)-2-(trifluoromethyl)-2H-chromene-3-carboxylic acid was carried out by preparative chromatography (Chiralpak OJ) using heptane:ethanol:acetic acid (75:25:0.5) as the mobile phase. Combination of the second eluted peak from multiple chromatographic runs afforded 91 mg (84%) of a yellow solid (99.3% ee by analytical HPLC): $[a]^{22}_D$=+34.3 (EtOH, c=4.6); $^1$H NMR (d$^6$-acetone/400 MHz) 2.24 (s, 3H), 5.84 (q, 1H, J=7.0 Hz), 6.36 (s, 1H), 7.11-7.24 (m, 3H), 7.72 (s, 1H), 7.89 (s, 1H); $^{19}$F NMR (CDCl$_3$/400 MHz) −79.4 (d, 3F, J=6.5 Hz), −117.9 (m, 1F); MS (ES+) 403 (M+1, 100).

EXAMPLE 969

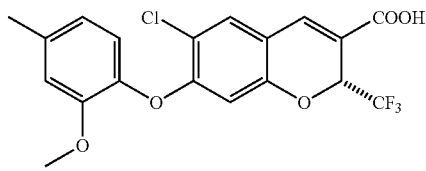

(2R)-(−)-6-chloro-7-(2-methoxy-2-methylphenoxy)-2-(trifluoromethyl)-2H-chromene-3-carboxylic acid Resolution of 267 mg of racemic 6-chloro-7-(2-methoxy-2-methylphenoxy)-2-(trifluoromethyl)-2H-chromene-3-carboxylic acid was carried out by preparative chromatography (Chiralpak AS) using heptane:ethanol:acetic acid (97:2.5:0.5) as the mobile phase. Combination of the first eluted peak from multiple chromatographic runs afforded 109 mg (82%) of a yellow solid (100% ee by analytical HPLC): $[a]^{22}_D$=−28.6 (EtOH, c=5.5); $^1$H NMR (d$^6$-acetone/400 MHz) 2.42 (s, 3H), 3.82 (s, 3H), 5.80 (q, 1H, J=7.0 Hz), 6.24 (s, 1H), 6.91 (d, 1H, J=8.0 Hz), 7.09 (m, 2H), 7.67(s, 1H), 7.90 (s, 1H); $^{19}$F NMR (CDCl$_3$/400 MHz) −79.5 (d, 3F, J=6.5 Hz); MS (ES+) 415 (M+1, 100); NMR non-equivalence with CSA and a 2:1 mixture of the (R) and (S) enantiomers: $^{19}$F NMR (d$^6$-benzene; 12 eq of (R)-(+)-1-(1-naphthyl)ethylamine) −77.90 (d, 3F, J=7.2 Hz, minor peaks, S-enantiomer), −78.09 (d, 3F, J=7.2 Hz, major peak, R-enantiomer).

EXAMPLE 970

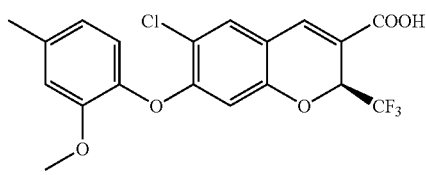

(2S)-(+)-6-chloro-7-(2-methoxy-2-methylphenoxy)-2-(trifluoromethyl)-2H-chromene-3-carboxylic acid Resolution of 267 mg of racemic 6-chloro-7-(2-methoxy-2-methylphenoxy)-2-(trifluoromethyl)-2H-chromene-3-carboxylic acid was carried out by preparative chromatography (Chiralpak AS) using heptane:ethanol:acetic acid (97:2.5:0.5) as the mobile phase. Combination of the second eluted peak from multiple chromatographic runs afforded 87.2 mg (65%) of a yellow solid (97.7% ee by analytical HPLC): $[a]^{22}_D$=+26.5 (EtOH, c=4.4); $^1$H NMR (d$^6$-acetone/400 MHz) 2.42 (s, 3H), 3.82 (s, 3H), 5.80 (q, 1H, J=7.0 Hz), 6.24 (s, 1H), 6.91 (d, 1H, J=8.0 Hz), 7.09 (m, 2H), 7.67(s, 1H), 7.90 (s, 1H); $^{19}$F NMR (CDCl$_3$/400 MHz) −79.5 (d, 3F, J=6.5 Hz); MS (ES+) 415 (M+1, 100).

EXAMPLE 971

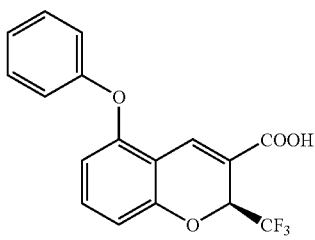

(2S)-(+)-5-phenoxy-2-(trifluoromethyl)-2H-chromene-3-carboxylic acid

Resolution of 181.1 mg of racemic 5-phenoxy-2-(trifluoromethyl)-2H-chromene-3-carboxylic acid was carried out by preparative chromatography (Chiralpak ADH) using hexane:ethanol:acetic acid (97.5:2:0.5) as the mobile phase. Combination of the second eluted peak from multiple chromatographic runs afforded 76.5 mg (84%) of a yellow solid (98.8% ee by analytical HPLC): $[a]^{22}_D$=+46.1 (EtOH, c=3.8); $^1$H NMR (d$^6$-acetone/400 MHz) 5.85 (q, 1H, J=7.2 Hz), 6.50 (d, 1H, J=8.3 Hz), 6.80 (d, 1H, J=8.3 Hz), 7.10 (d, 2H, J=7.6 Hz), 7.21 (t, 1H, J=7.4 Hz), 7.36 (t, 1H, J=8.3 Hz), 7.44 (m, 2H), 8.06 (s, 1H); $^{19}$F NMR (d$^6$-acetone/400 MHz) –79.3 (d, 3F, J=7.7 Hz); MS (ES+) 337 (M+1, 100).

EXAMPLE 972

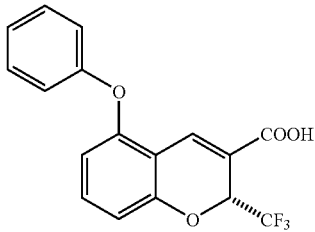

(2R)-(–)-5-phenoxy-2-(trifluoromethyl)-2H-chromene-3-carboxylic acid

Resolution of 181.1 mg of racemic 5-phenoxy-2-(trifluoromethyl)-2H-chromene-3-carboxylic acid was carried out by preparative chromatography (Chiralpak ADH) using hexane:ethanol:acetic acid (97.5:2:0.5) as the mobile phase. Combination of the first eluted peak from multiple chromatographic runs afforded 76.7 mg (84%) of a yellow solid (99.8% ee by analytical HPLC): $[a]^{22}_D$=–43.7 (EtOH, c=3.8); $^1$H NMR (d$^6$-acetone/400 MHz) 5.85 (q, 1H, J=7.2 Hz), 6.50 (d, 1H, J=8.3 Hz), 6.80 (d, 1H, J=8.3 Hz), 7.10 (d, 2H, J=7.6 Hz), 7.21 (t, 1H, J=7.4 Hz), 7.36 (t, 1H, J=8.3 Hz), 7.44 (m, 2H), 8.06 (s, 1H); $^{19}$F NMR (d$^6$-acetone/400 MHz) –79.3 (d, 3F, J=7.7 Hz); MS (ES+) 337 (M+1, 100); CD (MeOH) 214 ([theta]=+26600), 276 ([theta]=–15000).

EXAMPLE 973

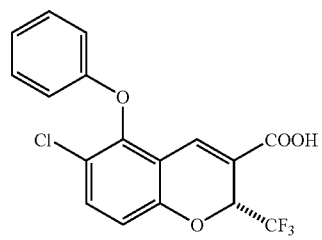

(2R)-(+)-6-chloro-5-phenoxy-2-(trifluoromethyl)-2H-chromene-3-carboxylic acid

Resolution of 215 mg of racemic 6-chloro-5-phenoxy-2-(trifluoromethyl)-2H-chromene-3-carboxylic acid was carried out by preparative chromatography (Chiralpak ADH) using hexane:2-propanol:acetic acid (97.5:2:0.5) as the mobile phase. Combination of the first eluted peak from multiple chromatographic runs afforded 98.8 mg (92%) of a yellow solid (99.8% ee by analytical HPLC): $[a]^{22}_D$=+12.6 (EtOH, c=4.9); $^1$H NMR (d$^6$-acetone/400 MHz) 5.89 (q, 1H, J=7.1 Hz), 6.87 (d, 2H, J=7.9 Hz), 7.06 (d, 1H, J=8.8 Hz), 7.09 (t, 1H, J=7.5 Hz), 7.36 (m, 2H), 7.60 (d, 1H, J=8.8 Hz), 7.75 (s, 1H); $^{19}$F NMR (d$^6$-acetone/400 MHz) –79.3 (d, 3F, J=7.7 Hz); MS (ES+) 371 (M+1, 100), 373 (M+3, 34).

EXAMPLE 974

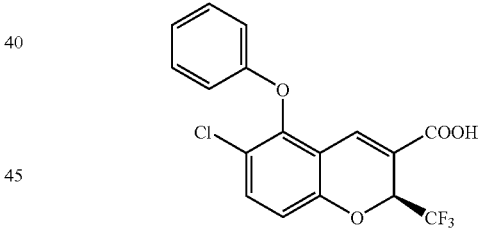

(2S)-(–)-6-chloro-5-phenoxy-2-(trifluoromethyl)-2H-chromene-3-carboxylic acid

Resolution of 215 mg of racemic 6-chloro-5-phenoxy-2-(trifluoromethyl)-2H-chromene-3-carboxylic acid was carried out by preparative chromatography (Chiralpak ADH) using hexane:2-propanol:acetic acid (97.5:2:0.5) as the mobile phase. Combination of the second eluted peak from multiple chromatographic runs afforded 98.3 mg (91%) of a yellow solid (99.0% ee by analytical HPLC): $[a]^{22}_D$=–12.6 (EtOH, c=4.9); $^1$H NMR (d$^6$-acetone/400 MHz) 5.89 (q,1 H, J=7.1 Hz), 6.87 (d, 2H, J=7.9 Hz), 7.06 (d, 1H, J=8.8 Hz), 7.09 (t, 1H, J=7.5 Hz), 7.36 (m, 2H), 7.60 (d, 1H, J=8.8 Hz), 7.75 (s, 1H); $^{19}$F NMR (d$^6$-acetone/400 MHz) –79.3 (d, 3F, J=7.7 Hz); MS (ES+) 371 (M+1, 100), 373 (M+3, 34); CD (MeOH) 218 ([theta]=–20400), 276 ([theta]=+21200).

EXAMPLE 975

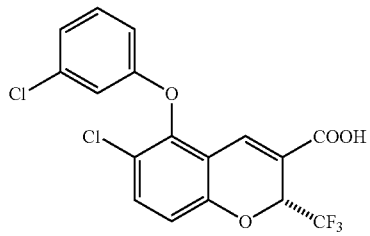

(2R)-(+)-6-chloro-5-(3-chlorophenoxy)-2-(trifluoromethyl)-2H-chromene-3-carboxylic acid Resolution of 286 mg of racemic 6-chloro-5-(3-chlorophenoxy)-2-(trifluoromethyl)-2H-chromene-3-carboxylic acid was carried out by preparative chromatography (Chiralpak ADH) using hexane:2-propanol:acetic acid (97.5:2:0.5) as the mobile phase. Combination of the first eluted peak from multiple chromatographic runs afforded 139.8 mg (98%) of a yellow solid (100% ee by analytical HPLC): $[a]^{22}_D$=+20.4 (EtOH, c=7.0); $^1$H NMR (d$^6$-acetone/400 MHz) 5.90 (q, 1H, J=7.0 Hz), 6.85 (dd, 1H, J=8.3 Hz, J=2.4 Hz), 6.94 (t, 1H, J=2.2 Hz), 7.09 (d, 1H, J=8.9 Hz), 7.14 (dt, 1H, J=8.0 Hz, J=1.0 Hz), 7.39 (t, 1H, J=8.2 Hz), 7.63 (d, 1H, J=9.0 Hz), 7.74 (s, 1H); $^{19}$F NMR (d$^6$-acetone/400 MHz) –79.3 (d, 3F, J=7.0 Hz); MS (ES+) 405 (M+1, 100), 407 (M+3, 80); CD (MeOH) 232 ([theta]=+25200), 276 ([theta]=–25000).

EXAMPLE 976

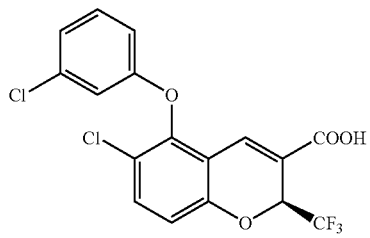

(2S)-(–)-6-chloro-5-(3-chlorophenoxy)-2-(trifluoromethyl)-2H-chromene-3-carboxylic acid Resolution of 286 mg of racemic 6-chloro-5-(3-chlorophenoxy)-2-(trifluoromethyl)-2H-chromene-3-carboxylic acid was carried out by preparative chromatography (Chiralpak ADH) using hexane:2-propanol:acetic acid (97.5:2:0.5) as the mobile phase. Combination of the second eluted peak from multiple chromatographic runs afforded 139.6 mg (98%) of a yellow solid (100% ee by analytical HPLC): $[a]^{22}_D$=–20.1 (EtOH, c=7.0); $^1$H NMR (d$^6$-acetone/400 MHz) 5.90 (q, 1H, J=7.0 Hz), 6.85 (dd, 1H, J=8.3 Hz, J=2.4 Hz), 6.94 (t, 1H, J=2.2 Hz), 7.09 (d, 1H, J=8.9 Hz), 7.14 (dt, 1H, J=8.0 Hz, J=1.0 Hz), 7.39 (t, 1H, J=8.2 Hz), 7.63 (d, 1H, J=9.0 Hz), 7.74 (s, 1 H); $^{19}$F NMR (d$^6$-acetone/400 MHz) –79.3 (d, 3F, J=7.0 Hz); MS (ES+) 405 (M+1, 100), 407 (M+3, 80); CD (MeOH) 238 ([theta]=–25200), 274 ([theta]=+25000).

EXAMPLE 977

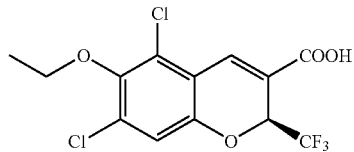

(2S)-(+)-5,7-dichloro-6-ethoxy-2-(trifluoromethyl)-2H-chromene-3-carboxylic acid Resolution of 278 mg of racemic 5,7-dichloro-6-ethoxy-2-(trifluoromethyl)-2H-chromene-3-carboxylic acid was carried out by preparative chromatography (Chiralpak AD) using heptane:2-propanol:acetic acid (94.5:5:0.5) as the mobile phase. Combination of the second peak from multiple chromatographic runs afforded 105.4 mg (75.8%) of a off-white solid. 99.8% ee by analytical HPLC; NMR non-equivalence with CSA and a 2:1 mixture of the (S) and (R) enantiomers: $^{19}$F NMR(d$^6$-benzene; 9 eq of (R)-(+)-1-(1-naphthyl)ethylamine) –78.06 (d,3F, J=6.5 Hz, major peaks, S-enantiomer), –77.89 (d, 3F, J=6.5 Hz, minor peak, R-enantiomer); CD(MeOH) 226([theta]=negative), 292 ([theta]=positive). $[a]^{22}_D$=+11.7 (EtOH, c=5.1). LC-MS (ES+): 357.0(M+1, 100). $^1$H NMR (CD$_3$OD/300 MHz): 8.02(S, 1H), 7.13(s, 1H), 5.85(q, J=6.9 Hz, 1H), 4.09(q, J=7.2 Hz, 2H), 1.46(t, J=7.2 Hz, 3H).

EXAMPLE 978

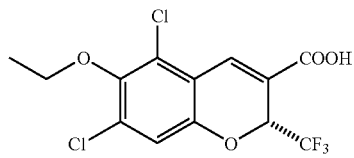

(2R)-(–)-5,7-dichloro-6-ethoxy-2-(trifluoromethyl)-2H-chromene-3-carboxylic acid Resolution of 278 mg of racemic 5,7-dichloro-6-ethoxy-2-(trifluoromethyl)-2H-chromene-3-carboxylic acid was carried out by preparative chromatography (Chiralpak AD) using heptane:2-propanol:acetic acid (94.5:5:0.5) as the mobile phase. Combination of the first peak from multiple chromatographic runs afforded 128.8 mg (92.7%) of a off-white solid. 100% ee by analytical HPLC; NMR non-equivalence with CSA and a 2:1 mixture of the (S) and (R) enantiomers: $^{19}$F NMR(d$^6$-benzene; 9 eq of (R)-(+)-1-(1-naphthyl)ethylamine) –78.06 (d, 3F, J=6.5 Hz, major peaks, S-enantiomer), –77.89 (d, 3F, J=6.5 Hz, minor peak, R-enantiomer); $[a]^{22}_D$=–11.9 (EtOH, c=6.38). LC-MS (ES+): 357.0(M+1, 100). $^1$H NMR (CD$_3$OD/300 MHz): 8.02(S, 1H), 7.13(s, 1H), 5.85(q, J=6.9 Hz, 1H), 4.09(q, J=7.2 Hz, 2H), 1.46(t, J=7.2Hz,3H).

EXAMPLE 979

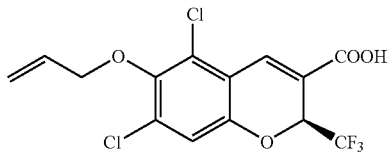

(2S)-(+)-6-(allyloxy)-5,7-dichloro-2-(trifluoromethyl)-2H-chromene-3-carboxylic acid Resolution of 270 mg of racemic 6-(allyloxy)-5,7-dichloro-2-(trifluoromethyl)-2H-chromene-3-carboxylic acid was carried out by preparative chromatography (Chiralpak AD) using heptane:2-propanol:acetic acid (94.5:5:0.5) as the mobile phase. Combination of the second eluted peak from multiple chromatographic runs afforded 129.5 mg (96%) of an off-white solid: 99.7% ee by analytical HPLC; NMR non-equivalence with CSA and a 2:1 mixture of the (S) and (R) enantiomers: $^{19}$F NMR (d$^6$-benzene; 3.6 eq of (R)-(+)-1-(1-naphthyl)ethylamine) −78.11 (d, 3F, J=6.5 Hz, major peaks, S-enantiomer), −77.93 (d, 3F, J=6.5 Hz, minor peak, R-enantiomer); CD (MeOH) 226 ([theta]=negative), 290 ([theta]=positive). $[a]^{22}_D$=+12.9 (EtOH, c=6.4); LC-MS (ES+): 369.0(M+1, 100). $^1$H NMR (CD$_3$OD/300 MHz): 7.98(s, 1H), 7.10(s, 1H), 6.22-6.09(m, 1H), 5.82(q, J=7.2 Hz, 1H), 5.44(dd, J=1.2 Hz, 17.1 Hz, 1H), 5.30(dd, J=1.2 Hz, 10.5 Hz, 1H), 4.54(d, J=6 Hz, 2H).

EXAMPLE 980

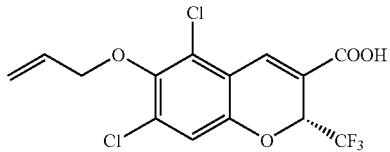

(2R)-(−)-6-(allyloxy)-5,7-dichloro-2-(trifluoromethyl)-2H-chromene-3-carboxylic acid Resolution of 270 mg of racemic 6-(allyloxy)-5,7-dichloro-2-(trifluoromethyl)-2H-chromene-3-carboxylic acid was carried out by preparative chromatography (Chiralpak AD) using heptane:2-propanol:acetic acid (94.5:5:0.5) as the mobile phase. Combination of the first eluted peak from multiple chromatographic runs afforded 122.4 mg (91%) of an off-white solid: 100% ee by analytical HPLC; NMR non-equivalence with CSA and a 2:1 mixture of the (S) and (R) enantiomers: $^{19}$F NMR (d$^6$-benzene; 3.6 eq of (R)-(+)-1-(1-naphthyl)ethylamine) −78.11 (d, 3F, J=6.5 Hz, major peaks, S-enantiomer), −77.93 (d, 3F, J=6.5 Hz, minor peak, R-enantiomer); $[a]^{22}_D$=−12.3 (EtOH, c=6.1); LC-MS (ES+): 369.0(M+1, 100). $^1$H NMR (CD$_3$OD/300 MHz): 7.98(s, 1H), 7.10(s, 1H), 6.22-6.09(m, 1H), 5.82(q, J=7.2 Hz, 1H), 5.44(dd, J=1.2 Hz, 17.1 Hz, 1H), 5.30(dd, J=1.2 Hz, 10.5 Hz, 1H), 4.54(d, J=6 Hz, 2H).

EXAMPLE 981

(2S)-(+)-5,7-dichloro-6-isopropoxy-2-(trifluoromethyl)-2H-chromene-3-carboxylic acid Resolution of 251 mg of racemic 5,7-dichloro-6-isopropoxy-2-(trifluoromethyl)-2H-chromene-3-carboxylic acid was carried out by preparative chromatography (Chiralpak AD) using heptane:acetic acid (99.5:0.5) as the mobile phase. Combination of the second eluted peak from multiple chromatographic runs afforded 37.4 mg (29.8%) of a off-white solid: 92.8% ee by analytical HPLC; NMR non-equivalence with CSA and a 2:1 mixture of the (S) and (R) enantiomers: $^{19}$F NMR (d$^6$-benzene; 6.7 eq of (R)-(+)-1-(1-naphthyl)ethylamine) −78.07 (d, 3F, J=6.5 Hz, major peaks, S-enantiomer), −77.89 (d, 3F, J=6.5 Hz, minor peak, R-enantiomer); CD (MeOH) 226 ([theta]=negative), 292 ([theta]=positive); $[a]^{22}_D$=+12.5 (EtOH, c=1.22); LC-MS (ES+): 371.0(M+1, 100). $^1$H NMR (CD$_3$OD/300 MHz): 8.03(s, 1H), 7.12(s, 1H), 5.84(q, J=7.2 Hz, 1H), 4.61(m, 1H), 1.38(d; J=6 Hz, 6H).

EXAMPLE 982

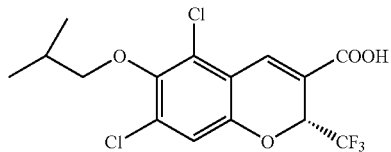

(2R)-(−)-5,7-dichloro-6-isopropoxy-2-(trifluoromethyl)-2H-chromene-3-carboxylic acid Resolution of 251 mg of racemic 5,7-dichloro-6-isopropoxy-2-(trifluoromethyl)-2H-chromene-3-carboxylic acid was carried out by preparative chromatography (Chiralpak AD) using heptane:acetic acid (99.5:0.5) as the mobile phase. Combination of the first eluted peak from multiple chromatographic runs afforded 41.5 mg (33.1%) of a off-white solid: 96.1% ee by analytical HPLC; NMR non-equivalence with CSA and a 2:1 mixture of the (S) and (R) enantiomers: $^{19}$F NMR (d$^6$-benzene; 6.7 eq of (R)-(+)-1-(1-naphthyl)ethylamine) −78.07 (d, 3F, J=6.5 Hz, major peaks, S-enantiomer), −77.89 (d, 3F, J=6.5 Hz, minor peak, R-enantiomer); $[a]^{22}_D$=−7.4 (EtOH, c=1.89); LC-MS(ES+): 371.0(M+1, 100). $^1$H NMR (CD$_3$OD/300 MHz): 8.03(s, 1H), 7.12(s, 1H), 5.84(q, J=7.2 Hz, 1H), 4.61(m, 1H), 1.38(d, J=6 Hz, 6H).

EXAMPLE 984

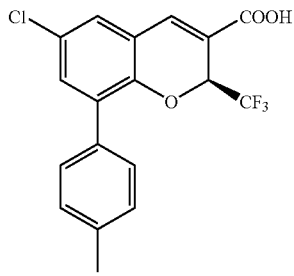

(2S)-(−)-6-Chloro-8-(methylphenyl)-2-(trifluoromethyl)-2H-chromene-3-carboxylic acid Resolution of 1.75 g of racemic 6-chloro-8-(methylphenyl)-2-(trifluoromethyl)-2H-chromene-3-carboxylic acid was carried out by preparative chromatography (Chiralpak AD) using heptane:ethanol:trifluoroacetic acid (85:15:0.1) as the mobile phase. Combination of the first eluted peak from multiple chromatographic runs afforded 0.920 g (52%) of a yellow solid: 100% ee by analytical HPLC; NMR non-equivalence with CSA and a 2:1 mixture of the (S) and (R) enantiomers: $^{19}$F NMR (d$^6$-benzene; 3.6 eq of(R)-(+)-1-(1-naphthyl)ethylamine) −77.58 (d,3F, J=8.4 Hz, major peaks, S-enantiomer), −77.72 (d, 3F, J=7.2 Hz, minor peaks, R-enantiomer); $[a]^{22}_D$=−6.51 (EtOH, c=0.049); MS (ES+) 369 (M+1, 100).

EXAMPLE 985

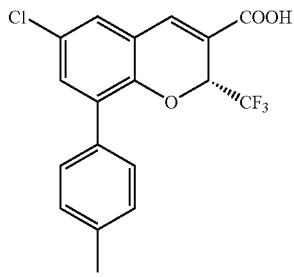

(2R)-(+)-6-Chloro-8-(methylphenyl)-2-(trifluoromethyl)-2H-chromene-3-carboxylic acid Resolution of 1.75 g of racemic 6-chloro-8-(methylphenyl)-2-(trifluoromethyl)-2H-chromene-3-carboxylic acid was carried out by preparative chromatography (Chiralpak AD) using heptane:ethanol:trifluoroacetic acid (85:15:0.1) as the mobile phase. Combination of the second eluted peak from multiple chromatographic runs afforded 0.820 g (47%) of a yellow solid: ??% ee by analytical HPLC; NMR non-equivalence with CSA and a 2:1 mixture of the (R) and (S) enantiomers: $^{19}$F NMR (d$^6$-benzene; 3.6 eq of (R)-(+)-1-(1-naphthyl)ethylamine) −77.59 (d, 3F, J=7.2 Hz, minor peaks, S-enantiomer), −77.75 (d, 3F, J=7.2 Hz, major peaks, R-enantiomer); $[a]^{22}_D$=+11.4 (EtOH, c=0.036); $^1$H NMR (CH$_3$OD/400 MHz) 2.35 (s, 3H), 5.72 (q, 1H, J=6.8 Hz), 7.20 (d, 2H, J=8.0 Hz), 7.29 (dd, 2H, J=2.8, 8.0 Hz), 7.33 (d, 2H, J=7.6 Hz), 7.75 (s, 1H); MS (ES+) 369 (M+1, 100).

EXAMPLE 986

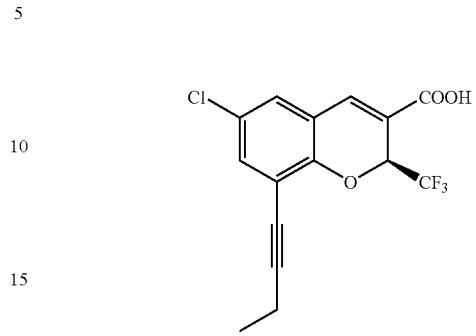

(2S)-(−)-8-But-1-ynyl-6-chloro-2-(trifluoromethyl)-2H-chromene-3-carboxylic acid Resolution of 0.331 g of racemic 8-but-1-ynyl-6-chloro-2-(trifluoromethyl)-2H-chromene-3-carboxylic acid was carried out by preparative chromatography (Chiralpak AD) using hexane:2-propanol:acetic acid (98:2:0.5) as the mobile phase. Combination of the first eluted peak from multiple chromatographic runs afforded 0.131 g (79%) of a yellow solid: 99.8% ee by analytical HPLC; NMR non-equivalence with CSA and a 2:1 mixture of the (S) and (R) enantiomers: $^{19}$F NMR (d$^6$-benzene; 3.6 eq of (R)-(+)-1-(1-naphthyl)ethylamine) −78.13 (d, 3F, J=8.4 Hz, major peaks, S-enantiomer), −78.31 (d, 3F, J=7.2 Hz, minor peaks, R-enantiomer); $[a]^{22}_D$=−67.84 (EtOH, c=0.054); MS (ES+) 331 (M+1, 100).

EXAMPLE 987

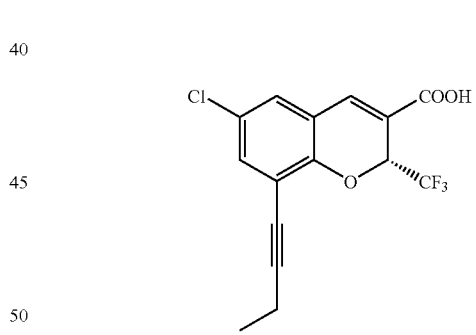

(2R)-(+)-8-But-1-ynyl-6-chloro-2-(trifluoromethyl)-2H-chromene-3-carboxylic acid Resolution of 0.331 g of racemic 8-but-1-ynyl-6-chloro-2-(trifluoromethyl)-2H-chromene-3-carboxylic acid was carried out by preparative chromatography (Chiralpak AD) using hexane:2-propanol:acetic acid (98:2:0.5) as the mobile phase. Combination of the second eluted peak from multiple chromatographic runs afforded 0.132 g (80%) of a yellow solid: 98.4% ee by analytical HPLC; CD (MeOH) 244 (+24200), 286 (−17000); $[a]^{22}_D$=+64.8 (EtOH, c=0.056); $^1$H NMR (CH$_3$OD/400 MHz) 1.22 (t, 3H, J=7.6 Hz), 2.43 (q, 2H, J=7.6 Hz), 5.82 (q, 1H, J=6.8 Hz), 7.28-7.29 (m, 2H), 7.69 (s, 1 H); MS (ES+) 331 (M+1, 100).

EXAMPLE 988

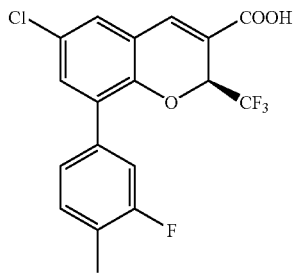

(2S)-(−)-6-Chloro-8-(3-filuoro4-methylphenyl)-2-(trifluoromethyl)-2H-chromene-3-carboxylic acid Resolution of 0.246 g of racemic 6-chloro-8-(3-fluoro-4-methylphenyl)-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the first eluted peak from multiple chromatographic runs afforded 0.125 g (102%) of a yellow solid: 99.8% ee by analytical HPLC; NMR non-equivalence with CSA and a 2:1 mixture of the (S) and (R) enantiomers: $^{19}$F NMR (d$^6$-benzene; 3.6 eq of (R)-(+)-1-(1-naphthyl)ethylamine) −77.65 (d, 3F, J=7.2 Hz, major peaks, S-enantiomer), −77.77 (d, 3F, J=6.8 Hz, minor peaks, R-enantiomer); [a]$^{22}_D$=−9.18 (EtOH, c=0.052); $^1$H NMR (CH$_3$OD/400 MHz) 2.29 (d,3H, J=1.6 Hz), 5.79 (q, 1H, J=6.8 Hz), 7.17-7.20 (m, 2H), 7.26-7.30 (m, 1H), 7.37 (dd, 2H, J=2.4, 12.8 Hz), 7.79 (s, 1H); MS (ES+) 387 (M+1, 100).

EXAMPLE 989

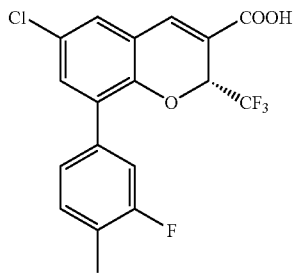

(2R)-(+)-6-Chloro-8-(3-fluoro-4-methylphenyl)-2-(trifluoromethyl)-2H-chromene-3-carboxylic acid Resolution of 0.246 g of racemic 6-chloro-8-(3-fluoro-4-methylphenyl)-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the second eluted peak from multiple chromatographic runs afforded 0.124 g (101%) of a yellow solid: 99.6% ee by analytical HPLC; [a]$^{22}_D$=+9.17 (EtOH, c=0.052); MS (ES+) 387 (M+1, 100).

EXAMPLE 990

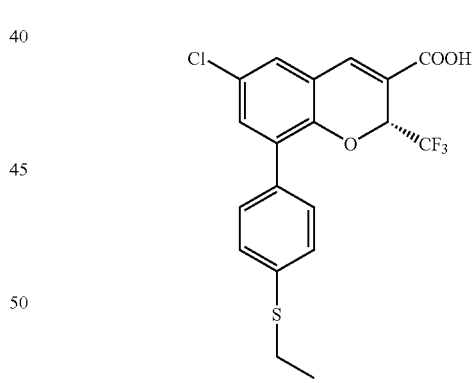

(2S)-(−)-6-Chloro-8-[4-(ethylthio)phenyl]-2-(trifluoromethyl)-2H-chromene-3-carboxylic acid Resolution of 0.137 g of racemic 6-chloro-8-[4-(ethylthio)phenyl]-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the first eluted peak from multiple chromatographic runs afforded 0.059 g (86%) of a yellow solid: 100% ee by analytical HPLC; NMR non-equivalence with CSA and a 2:1 mixture of the (S) and (R) enantiomers: $^{19}$F NMR (d$^6$-benzene; 3.6 eq of (R)-(+)-1-(1-naphthyl)ethylamine) −77.57 (d,3F, J=7.2 Hz, major peaks, S-enantiomer), −77.69 (d, 3F, J=7.2 Hz, minor peaks, R-enantiomer); [a]$^{22}_D$=−35.37 (EtOH, c=0.020); MS (ES+) 415 (M+1, 100).

EXAMPLE 991

(2R)-(+)-6-Chloro-8-[4-(ethylthio)phenyl]-2-(trifluoromethyl)-2H-chromene-3-carboxylic acid Resolution of 0.137 g of racemic 6-chloro-8-[4-(ethylthio)phenyl]-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the second eluted peak from multiple chromatographic runs afforded 0.058 g (84%) of a yellow solid: 99.8% ee by analytical HPLC; [a]$^{22}_D$=+36.43 (EtOH, c=0.020); $^1$H NMR (CH$_3$OD/400 MHz) 1.31 (t, 3H, J=7.6 Hz), 2.99 (q, 2H, J=7.6 Hz), 5.78

(q, 1H, J=6.8 Hz), 7.35-7.37 (m, 4H), 7.42 (d, 2H, J=8.4 Hz), 7.79 (s, 1H); MS (ES+) 415 (M+1, 100).

EXAMPLE 992

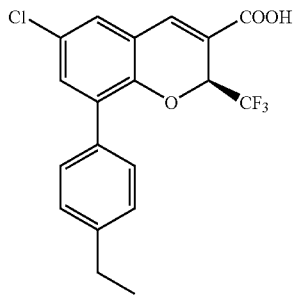

(2S)-(−)-6-Chloro-8-(4-ethylphenyl)-2-(trifluoromethyl)-2H-chromene-3-carboxylic acid Resolution of 0.134 g of racemic 6-chloro-8-(4-ethylphenyl)-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the first eluted peak from multiple chromatographic runs afforded 0.056 g (84%) of a yellow solid: 100% ee by analytical HPLC; NMR non-equivalence with CSA and a 2:1 mixture of the (S) and (R) enantiomers: $^{19}$F NMR (d$^6$-benzene; 3.6 eq of (R)-(+)-1-(1-naphthyl)ethylamine) −77.55 (d, 3F, J=8.4 Hz, major peaks, S-enantiomer), −77.68 (d, 3F, J=8.0 Hz, minor peaks, R-enantiomer); [a]$^{22}_D$=−9.64 (EtOH, c=0.0 18); $^1$H NMR (CH$_3$OD/400 MHz) 1.25 (t, 3H, J=7.6 Hz), 2.68 (q, 2H, J=7.6 Hz), 5.76 (q, 1H, J=7.2 Hz), 7.25 (d, 2H, J=8.0 Hz), 7.34 (dd, 2H, J=2.4, 11.2 Hz), 7.39 (d, 2H, J=8.0 Hz), 7.79 (s, 1H ); MS (ES+) 383 (M+1, 100).

EXAMPLE 993

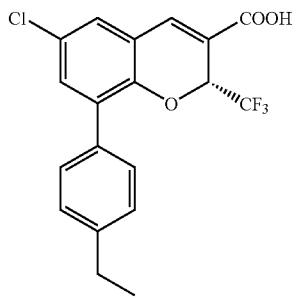

(2R)-(+)-6-Chloro-8-(4-ethylphenyl)-2-(trifluoromethyl)-2H-chromene-3-carboxylic acid Resolution of 0.134 g of racemic 6-chloro-8-(4-ethylphenyl)-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the second eluted peak from multiple chromatographic runs afforded 0.057 g (85%) of a yellow solid: 99.8% ee by analytical HPLC; [a]$^{22}_D$=+9.54 (EtOH, c=0.018); MS (ES+) 383 (M+1, 100).

EXAMPLE 994

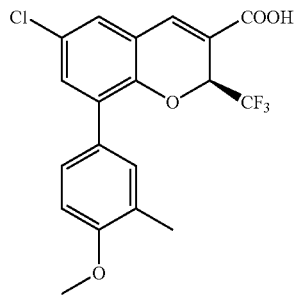

(2S)-6-Chloro-8-(4-methoxy-3-methylphenyl)-2-(trifluoromethyl)-2H-chromene-3-carboxylic acid Resolution of 0.159 g of racemic 6-chloro-8-(4-methoxy-3-methylphenyl)-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the first eluted peak from multiple chromatographic runs afforded 0.084 g (106%) of a yellow solid: 100% ee by analytical HPLC; NMR non-equivalence with CSA and a 2:1 mixture of the (S) and (R) enantiomers: $^{19}$F NMR (d$^6$-benzene; 3.6 eq of (R)-(+)-1-(1-naphthyl)ethylamine) −77.49 (d, 3F, J=8.4 Hz, major peaks, S-enantiomer), −77.63 (d, 3F, J=8.4 Hz, minor peaks, R-enantiomer); MS (ES+) 399 (M+1, 100).

EXAMPLE 995

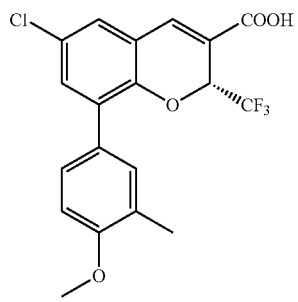

(2R)-6-chloro-8-(4-methoxy-3-methylphenyl)-2-(trifluoromethyl)-2H-chromene-3-carboxylic acid Resolution of 0.159 g of racemic 6-chloro-8-(4-methoxy-3-methylphenyl)-2-(trifluoromethyl)-2H-chromene-3-carboxylic acid was carried out by preparative chromatography (Chiralpak AD) using hexane:2-propanol:acetic acid (95:5:0.5) as the mobile phase. Combination of the second eluted peak from multiple chromatographic runs afforded 0.084 g (106%) of a yellow solid: 99.6% ee by analytical HPLC; CD (MeOH) 230 (=−32300),258 (=+11800), 286 (=−17000); $^1$H NMR (CH$_3$OD/400 MHz) 2.19 (s, 3H), 3.83 (s, 3H), 5.73 (q, 1H, J=6.8 Hz), 6.90 (d, 1H, J=8.4 Hz), 7.24-7.27 (m, 4H), 7.74 (s, 1H); MS (ES+) 399 (M+1, 100).

General Method for the Preparation of Sodium 2-(trifluoromethyl)-2H-chromene-3-carboxylates To a solution of the 2-(trifluoromethyl)-2H-chromene-3-carboxylic acid (0.1-0.3 mmole) in 2.0 mL of EtOH was added an equimolar amount of 0.1008 N NaOH. The resulting solution was stirred at rt for 15 min and the volatile solvents removed under a stream of nitrogen at 55° C. The residue was dissolved in 2.0 mL $H_2O$ and concd by lyophilization. Products were typically obtained as dry, white solids.

EXAMPLE 996

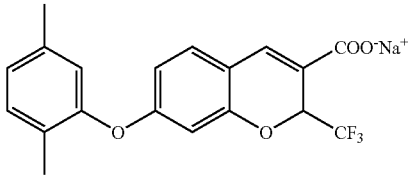

Sodium 7-(2,5-dimethylphenoxy)-2-(trifluoromethyl)-2H-chromene-3-carboxylate

To a solution of 116 mg of 7-(2,5-dimethylphenoxy)-2-(trifluoromethyl)-2H-chromene-3-carboxylic acid (0.318 mmol) in 4 mL of ethanol and 2 mL of THF was added 3.15 mL (0.318 mmol) of a 0.1008 N NaOH solution in water. The resulting solution was stirred at room temperature for 15 min. The volatiles were removed. To the solution was added 2 mL of water and the resulting suspension was cooled at −78° C. and solidified then put on high vacuum for lyophilization. The ivory solid was registered as PHA-807535A: $^1$H NMR ($CD_3OD$/400 MHz) 2.08 (s, 3H), 2.28 (s, 3H), 5.77 (q, 1H, J=7.6 Hz), 6.31 (d, 1H, J=2.0 Hz), 6.41 (dd, 1H, J=2.4 Hz, 8.4 Hz), 6.78 (s, 1H), 6.94 (d, 1H, J=8.0 Hz), 7.11-7.15 (m, 2H), 7.38 (s, 1H); MS (ES+) 365 (M+l, 100); LC-MS purity 100% at 3.575 min. (UV), 100% ELSD.

EXAMPLE 997

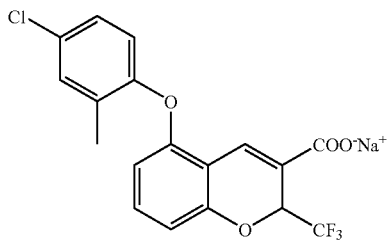

Sodium 5-(4-chloro-2-methylphenoxy)-2-(trifluoromethyl)-2H-chromene-3-carboxylate Using the general method the sodium salt was obtained as an off-white solid: MS (ES+) 385 (M+1, 100); $^1$H NMR ($CD_3OD$/400 MHz) 2.22 (s, 3H), 5.84 (q, 1H, J=7.3 Hz), 6.25 (d, 1H, J=8.2 Hz), 6.67 (d, 1H, J=8.2 Hz), 6.80 (d, 1H, J=8.7 Hz), 7.14 (m, 2H), 7.29 (d, 1H, J=2.5 Hz), 7.80 (s, 1H); $^{19}$F NMR ($CD_3OD$/400 MHz) 80.0 (d, 3F, J=6.8 Hz).

EXAMPLE 998a

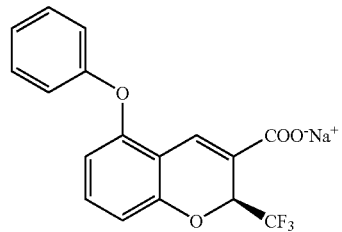

Sodium (2S)-(+)-5-phenoxy-2-(trifluoromethyl)-2H-chromene-3-carboxylate

A solution of 36.4 mg (0.108 mmole) of (2S)-(+)-5-(4-chloro-2-methylphenoxy)-2-(trifluoromethyl)-2H-chromene-3-carboxylic acid in 1.5 mL of ethanol was treated with 1.07 mL of 0.1008N NaOH. The resultant mixture was lyophilized to provide 40.8 mg (quant.) of an off-white solid: MS (ES+) 337 (M+1, 100); $^1$H NMR ($CD_3OD$/400 MHz) 5.84 (q, 1H, J=7.3 Hz), 6.43 (d, 1H, J=8.2 Hz), 6.70 (d, 1H, J=8.2 Hz), 6.99 (d, 2H, J=7.7 Hz), 7.12 (t, 1H, J=7.4 Hz), 7.17 (t, 1H, J=8.2 Hz), 7.35 (t, 2H, J=8.0 Hz), 8.55 (s, 1H); $^{19}$F NMR ($CD_3OD$/400 MHz) 80.0 (d, 3F, J=7.7 Hz).

EXAMPLE 998b

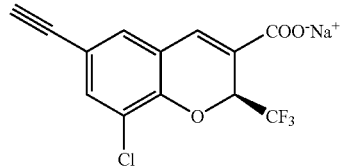

Sodium (2S)-(−)-8-Chloro-6-ethynyl-2-(trifluoromethyl)-2H-chromene-3-carboxylate A solution of 50.0 mg (0.165 mmole) of (2S)-(−)-8-chloro-6-ethynyl-2-(trifluoromethyl)-2H-chromene-3-carboxylic acid in 1.5 mL of ethanol was treated with 1.64 mL of 0.1008N NaOH. The resultant mixture was lyophilized to provide 39.0 mg (quant.) of an yellow solid: MS (ES+) 303 (M+1, 100); $^1$H NMR ($CD_3OD$/400 MHz) 5.95 (q, 1H, J=7.1 Hz), 7.29 (d, 1H, J=1.8 Hz), 7.37 (s, 1H), 7.39 (d, 1H, J=1.8 Hz); $^{19}$F NMR ($CD_3OD$/400 MHz) 80.3 (d, 3F, J=6.8 Hz).

EXAMPLE 999

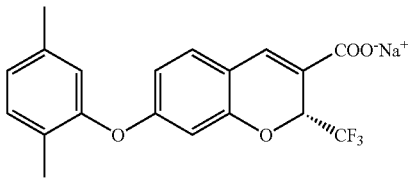

Sodium (2R)-(−)-7-(2,5-dimethylphenoxy)-2-(trifluoromethyl)-2H-chromene-3-carboxylate A solution of 53.8 mg (0.148 mmole) of (2R)-(−)-7-(2,5-dimethylphenoxy)-2-(trifluoromethyl)-2H-chromene-3-carboxylic acid in 1.5 mL of ethanol was treated with 1.47 mL of 0.1008N NaOH. The resultant mixture was lyophilized to provide 55.6 mg (97%) of an off-white solid: MS (ES+) 365 (M+1, 100); $^1$H NMR (CD$_3$OD/400 MHz) 2.09 (s, 3H), 2.28 (s, 3H), 5.77 (q, 1H, J=7.3 Hz), 6.31 (d, 1H, J=2.4 Hz), 6.41 (dd, 1H, J=8.3 Hz, J=2.3 Hz), 6.78 (s, 1H), 6.94 (d, 1H, J=7.7 Hz), 7.14 (m, 2H), 7.38 (s, 1H); $^{19}$F NMR (CD$_3$OD/400 MHz) 80.2 (d, 3F, J=7.7 Hz).

EXAMPLE 1000

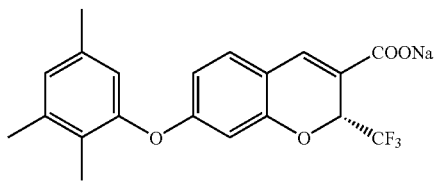

Sodium (2R)-(−)-2-(trifluoromethyl)-7-(2,3,5-trimethylphenoxy)-2H-chromene-3-carboxylate A solution of 38.1 mg (0.101 mmole) of (2R)-(−)-2-(trifluoromethyl)-7-(2,3,5-trimethylphenoxy)-2H-chromene-3-carboxylic acid in 1.5 mL of ethanol was treated with 1.00 mL of 0.1008N NaOH. The resultant mixture was lyophilized to provide 48.4 mg (quant.) of an off-white solid: MS (ES+) 379 (M+1, 100); $^1$H NMR (CD$_3$OD/400 MHz) 2.01 (s, 3H), 2.24 (s, 3H), 2.26 (s, 3H), 5.76 (q, 1H, J=7.4 Hz), 6.28 (d, 1H, J=2.4 Hz), 6.38 (dd, 1H, J=8.3 Hz, J=2.4 Hz), 6.63 (s, 1H), 6.87 (s, 1H), 7.11 (d, 1H, J=8.3 Hz), 7.38 (s, 1H); $^{19}$F NMR (CD$_3$OD/400 MHz) 80.2 (d, 3F, J=7.7 Hz).

EXAMPLE 1001

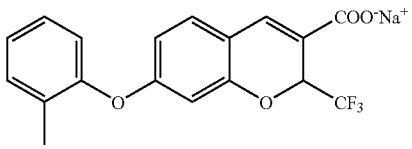

Sodium 7-(2-methylphenoxy)-2-(trifluoromethyl)-2H-chromene-3-carboxylate

Using the general method the sodium salt was obtained as an off-white solid: MS (ES+) 351 (M+1, 100); $^1$H NMR (CD$_3$OD/400 MHz) 2.17 (s, 3H), 5.79 (q, 1H, J=7.3 Hz), 6.34 (d, 1H, J=2.1 Hz), 6.44 (dd, 1H, J=8.4 Hz, J=2.3 Hz), 6.96 (d, 1H, J=8.0 Hz), 7.11-7.16 (m, 2H), 7.23 (td, 1H, J=7.8 Hz, J=1.3 Hz), 7.29 (d, 1H, J=7.5 Hz), 7.41 (s, 1H); $^{19}$F NMR (CD$_3$OD/400 MHz) 80.2 (d, 3F, J=7.7 Hz).

EXAMPLE 1002

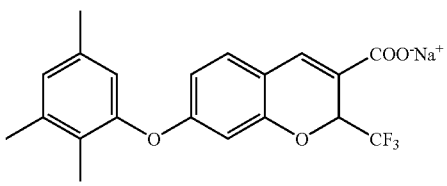

Sodium 2-(trifluoromethyl)-7-(2,3,5-trimethylphenoxy)-2H-chromene-3-carboxylate

Using the general method the sodium salt was obtained as an off-white solid: MS (ES+) 379 (M+1, 100); $^1$H NMR (CD$_3$OD/400 MHz) 2.02 (s, 3H), 2.26 (s, 3H), 2.28 (s, 3H), 5.78 (q, 1H, J=7.3 Hz), 6.30 (d, 1H, J=2.3 Hz), 6.40 (dd, 1H, J=8.3 Hz, J=2.4 Hz), 6.64 (s, 1H), 6.88 (s, 1H), 7.13 (d, 1H, J=8.4 Hz), 7.40 (s, 1H); $^{19}$F NMR (CD$_3$OD/400 MHz) 80.2 (d, 3F, J=7.7 Hz).

EXAMPLE 1003

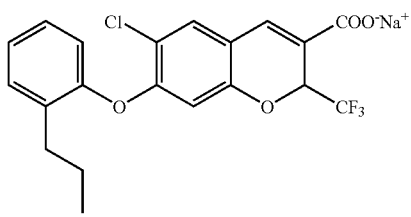

Sodium 6-chloro-7-(2-propylphenoxy)-2-(trifluoromethyl)-2H-chromene-3-carboxylate Using the general method the sodium salt was obtained as an off-white solid: MS (ES+) 413 (M+l, 100); $^1$H NMR (CD$_3$OD/400 MHz) 0.90 (t, 3H, J=7.4 Hz), 1.61 (septet, 2H, J=7.5 Hz), 2.54 (t, 2H, J=7.6 Hz), 5.77 (q, 1H, J=7.3 Hz), 6.20 (s, 1H), 6.90 (dd, 1H, J=8.0 Hz, J=1.1 Hz), 7.18 (td, 1H, J=7.4 Hz, J=1.2 Hz), 7.25 (td, 1H, J=7.8 Hz, J=1.7 Hz), 7.32 (dd, 1H, J=7.4 Hz, J=1.7 Hz), 7.37 (s, 1H), 7.38 (s, 1H); $^{19}$F NMR (CD$_3$OD/400 MHz) 80.1 (d, 3F, J=7.7 Hz).

EXAMPLE 1004

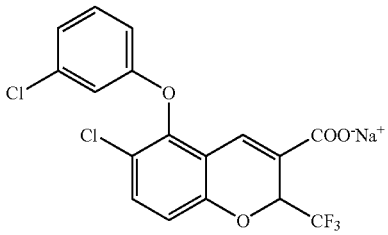

Sodium 6-Chloro-5-(3-chlorophenoxy)-2-(trifluoromethyl)-2H-chromene-3-carboxylate Using the general method the sodium salt was obtained as an off-white solid: MS (ES+) 405 (M+1, 100), 407 (M+3, 66); $^1$H NMR (CD$_3$OD/400 MHz) 5.88 (q, 1H, J=7.2 Hz), 6.72 (dd, 1H, J=8.5 Hz, J=2.3 Hz), 6.80 (t, 1H, J=2.3 Hz), 6.93 (d, 1H, J=8.9 Hz), 7.05 (m, 1H), 7.27 (t, 1H, J=8.2 Hz), 7.41 (d, 1H, J=8.7 Hz), 7.49 (s, 1H); $^9$F NMR (CD$_3$OD/400 MHz) 80.0 (d, 3F, J=7.7 Hz).

EXAMPLE 1005

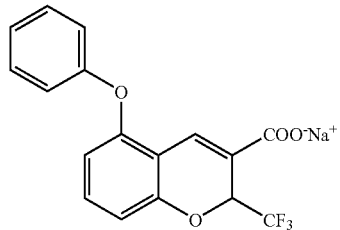

Sodium 5-phenoxy-2-(trifluoromethyl)-2H-chromene-3-carboxylate

Using the general method the sodium salt was obtained as an off-white solid: MS (ES+) 337 (M+1, 100); $^1$H NMR (CD$_3$OD/400 MHz) 5.84 (q, 1H, J=7.3 Hz), 6.43 (d, 1H, J=8.3 Hz), 6.70 (d, 1H, J=8.2Hz), 6.99 (d, 2H, J=7.7Hz), 7.12 (t, 1H, J=7.4 Hz), 7.17 (t, 1H, J=8.2 Hz), 7.35 (t, 2H, J=8.0 Hz), 8.55 (s, 1H); $^{19}$F NMR (CD$_3$OD/400 MHz) 80.0 (d, 3F, J=7.7 Hz).

EXAMPLE 1006

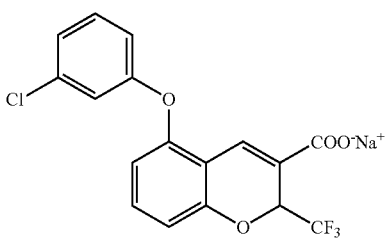

Sodium 5-(3-chlorophenoxy)-2-(trifluoromethyl)-2H-chromene-3-carboxylate

Using the general method the sodium salt was obtained as an off-white solid: MS (ES+) 371 (M+1, 100); $^1$H NMR (CD$_3$OD/400 MHz) 5.85 (q, 1H, J=7.4 Hz), 6.54 (d, 1H, J=8.3 Hz), 6.79 (d, 1H, J=8.2 Hz), 6.90 (m, 1H), 6.98 (t, 1H, J=2.1 Hz), 7.11 (m, 1H), 7.25 (t, 1H, J=8.3 Hz), 7.32 (t, 1H, J=8.1 Hz), 7.70 (s, 1H); $^{19}$F NMR (CD$_3$OD/400 MHz) 80.2 (d, 3F, J=6.8 Hz).

EXAMPLE 1007

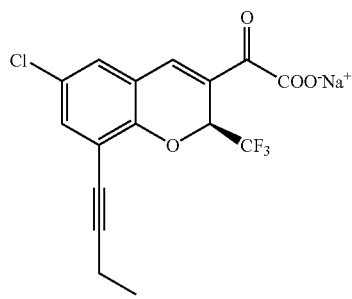

Sodium (2S)-(−)-8-but-1-ynyl-6-chloro-2-(trifluoromethyl)-2H-chromene-3-carboxylate A solution of 98.9mg (0.299 mmole) of 8-but-I-ynyl-6-chloro-2-(trifluoromethyl)-2H-chromene-3-carboxylic acid in 2.0 mL of ethanol was treated with 2.967 mL of 0.1008N NaOH. The resultant mixture was lyophilized to provide a quantitative yield of a yellow solid: $^1$H NMR (CD$_3$OD/400 MHz) 1.22 (t, 3H, J=7.6 Hz), 2.44 (q, 2H, J=7.6 Hz), 5.88 (q, 1H, J=7.2 Hz), 7.17-7.19 (m, 2H), 7.32 (s, 1H).

EXAMPLE 1008

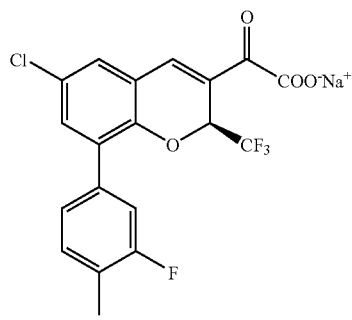

Sodium (2S)-(−)-6-chloro-8-(3-fluoro4-methylphenyl)-2-(trifluoromethyl)-2H-chromene-3-carboxylate A solution of 95.1 mg (0.246 mmole) of 6-chloro-8-(3-fluoro-4-methylphenyl)-2-(trifluoromethyl)-2H-chromene-3-carboxylic acid in 2.0 mL of ethanol was treated with 2.439 mL of0.1008N NaOH. The resultant mixture was lyophilized to provide a quantitative yield of a yellow solid: $^1$H NMR (CD$_3$OD/400 MHz) 2.29 (d, 3H, J=1.6 Hz), 5.84 (q, 1H, J=7.2 Hz), 7.17-7.20 (m, 2H), 7.24-7.29 (m, 3H), 7.40 (s, 1H).

EXAMPLE 1009

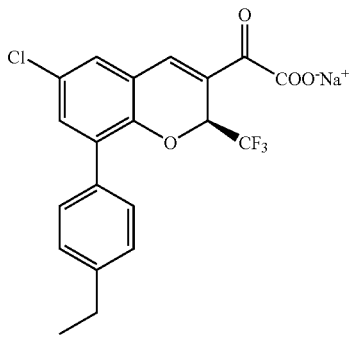

Sodium (2S)-(−)-6-chloro-8-(4-ethylphenyl)-2(trifluoromethyl)-2H-chromene-3-carboxylate A solution of 6-chloro-8-(4-ethylphenyl)-2-(trifluoromethyl)-2H-chromene-3-carboxylic acid 31.8 mg (0.083 mmole) in 2.0 mL of ethanol was treated with 0.824 mL of 0.1008N NaOH. The resultant mixture was lyophilized to provide a quantitative yield of a yellow solid: $^1$H NMR (CD$_3$OD/400 MHz) 1.25 (t,3H, J=7.6 Hz), 2.67 (q, 2H, J=7.6 Hz), 5.81 (q, 1H, J=7.2 Hz), 7.21-7.25 (m, 4H), 7.38-7.40 (m, 3H).

EXAMPLE 1010

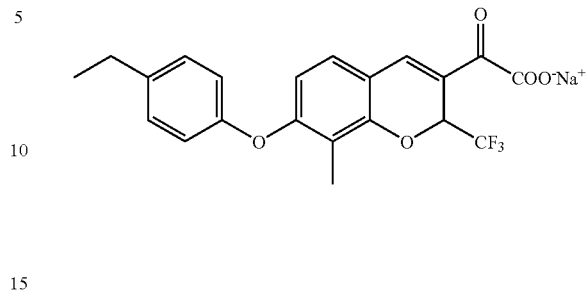

Sodium 7-(4-ethylphenoxy)-8-methyl-2-(trifluoromethyl)-2H-chromene-3-carboxylate A solution of 7-(4-ethylphenoxy)-8-methyl-2-(trifluoromethyl)-2H-chromene-3-carboxylic acid 40.3 mg (0.107 mmole) in 2.0 mL of ethanol was treated with 1.057 mL of 0.1008N NaOH. The resultant mixture was lyophilized to provide a quantitative yield of a yellow solid: $^1$H NMR (CD$_3$OD/400 MHz) 1.21 (t, 3H, J=7.6 Hz), 2.12 (s, 3H), 2.61 (q, 2H, J=7.6 Hz), 5.87 (q, 1H, J=7.2 Hz), 6.38 (d, 1H, J=8.0 Hz), 6.84 (d, 2H, J=8.0 Hz), 7.00 (d, 1H, J=8.0 Hz), 7.17 (d, 2H, J=8.0 Hz), 7.40 (s, 1H).

In light of the foregoing examples, the following compounds in Table 18 can be made by one skilled in the art.

TABLE 18

| Example No. | Structure | Compound Name |
|---|---|---|
| 1100 | 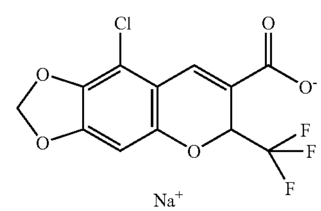 | sodium 9-chloro-6-(trifluoromethyl)-6H-[1,3]dioxolo[4,5-g]chromene-7-carboxylate |
| 1101 | 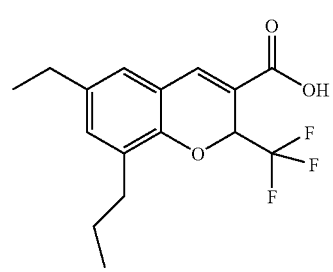 | 6-ethyl-8-propyl-2-(trifluoromethyl)-2H-chromene-3-carboxylic acid |
| 1102 | 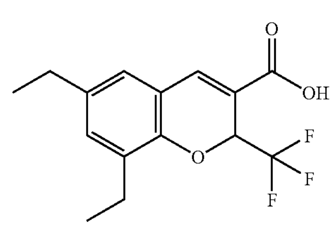 | 6,8-diethyl-2-(trifluoromethyl)-2H-chromene-3-carboxylic acid |

TABLE 18-continued

| Example No. | Structure | Compound Name |
|---|---|---|
| 1103 | 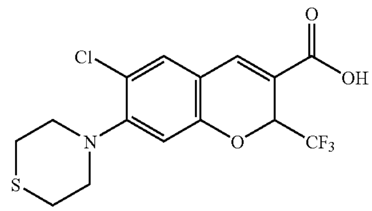 | 6-chloro-7-thiomorpholin-4-yl-2-(trifluoromethyl)-2H-chromene-3-carboxylic acid |
| 1104 | 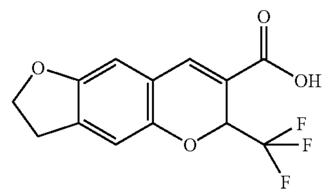 | 6-(trifluoromethyl)-3,6-dihydro-2H-furo[2,3-g]chromene-7-carboxylic acid |
| 1105 | 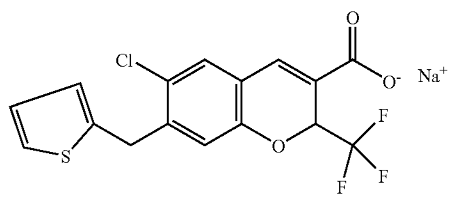 | sodium 6-chloro-7-(thien-2-ylmethyl)-2-(trifluoromethyl)-2H-chromene-3-carboxylate |
| 1106 | 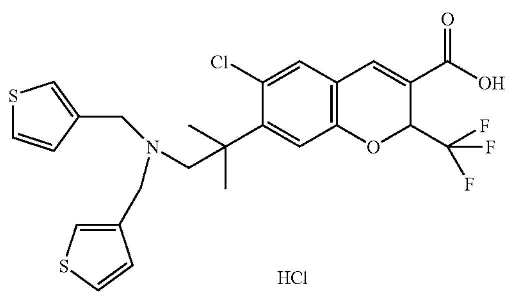 | 7-{2-[bis(thien-3-ylmethyl)amino]-1,1-dimethylethyl}-6-chloro-2-(trifluoromethyl)-2H-chromene-3-carboxylic acid hydrochloride |
| 1107 | 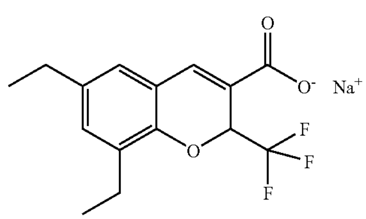 | sodium 6,8-diethyl-2-(trifluoromethyl)-2H-chromene-3-carboxylate |
| 1108 | 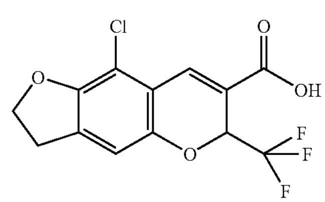 | 9-chloro-6-(trifluoromethyl)-3,6-dihydro-2H-furo[2,3-g]chromene-7-carboxylic acid |
| 1109 | 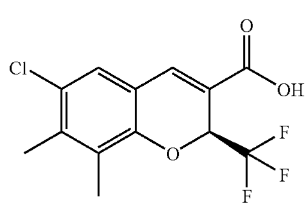 | (2R)-6-chloro-7,8-dimethyl-2-(trifluoromethyl)-2H-chromene-3-carboxylic acid |

TABLE 18-continued

| Example No. | Structure | Compound Name |
|---|---|---|
| 1110 | 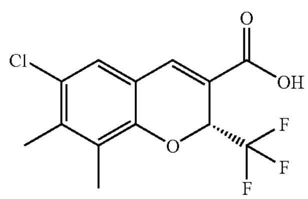 | (2S)-6-chloro-7,8-dimethyl-2-(trifluoromethyl)-2H-chromene-3-carboxylic acid |
| 1111 | 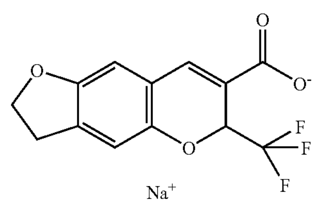 | sodium 6-(trifluoromethyl)-3,6-dihydro-2H-furo[2,3-g]chromene-7-carboxylate |
| 1112 | 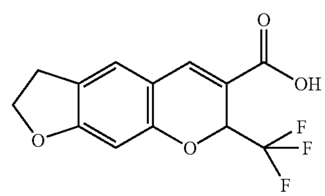 | 7-(trifluoromethyl)-2,3-dihydro-7H-furo[3,2-g]chromene-6-carboxylic acid |
| 1113 | 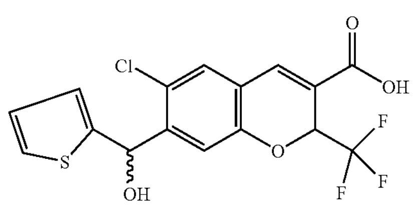 | 6-chloro-7-[hydroxy(thien-2-yl)methyl]-2-(trifluoromethyl)-2H-chromene-3-carboxylic acid |
| 1114 | 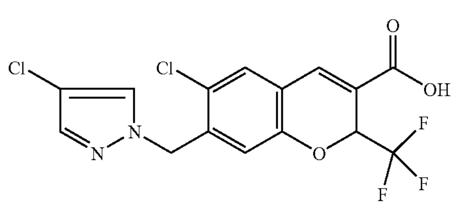 | 6-chloro-7-[(4-chloro-1H-pyrazol-1-yl)methyl]-2-(trifluoromethyl)-2H-chromene-3-carboxylic acid |
| 1115 | 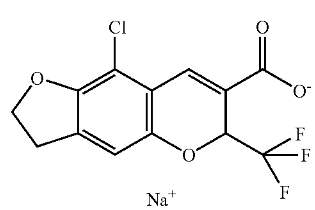 | 9-chloro-6-(trifluoromethyl)-3,6-dihydro-2H-furo[2,3-g]chromene-7-carboxylate |
| 1116 | 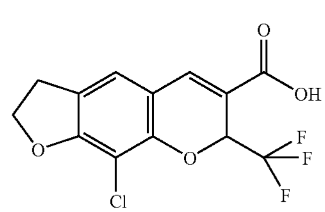 | 4-chloro-7-(trifluoromethyl)-2,3-dihydro-7H-furo[3,2-g]chromene-6-carboxylic acid |

TABLE 18-continued

| Example No. | Structure | Compound Name |
|---|---|---|
| 1117 | 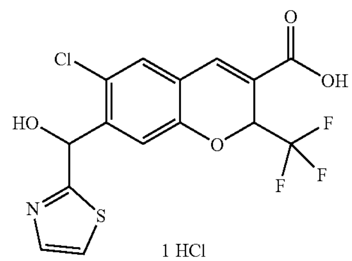 | 6-chloro-7-[hydroxy(1,3-thiazol-2-yl)methyl]-2-(trifluoromethyl)-2H-chromene-3-carboxylic acid<br><br>1 HCl |
| 1118 | 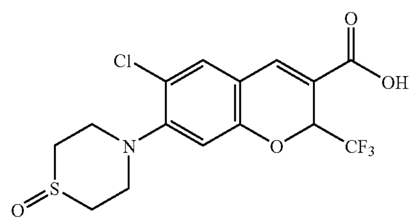 | 6-chloro-7-(1-oxidothiomorpholin-4-yl)-2-(trifluoromethyl)-2H-chromene-3-carboxylic acid |
| 1119 | 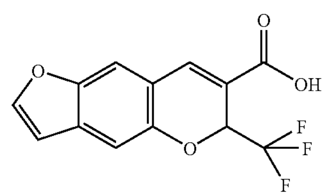 | 6-(trifluoromethyl)-6H-furo[2,3-g]chromene-7-carboxylic acid |
| 1120 | 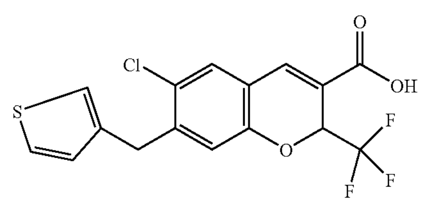 | 6-chloro-7-(thien-3-ylmethyl)-2-(trifluoromethyl)-2H-chromene-3-carboxylic acid |
| 1121 | 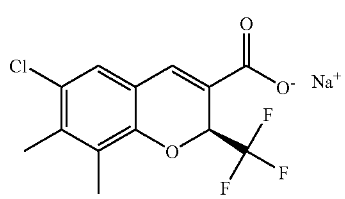 | sodium (2S)-6-chloro-7,8-dimethyl-2-(trifluoromethyl)-2H-chromene-3-carboxylate |
| 1122 | 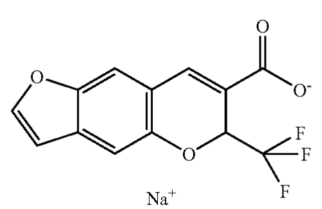 | sodium 6-(trifluoromethyl)-6H-furo[2,3-g]chromene-7-carboxylate |
| 1123 | 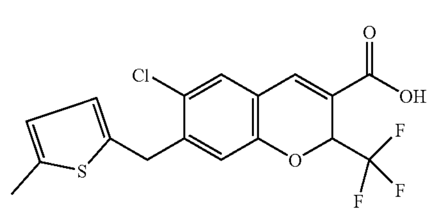 | 6-chloro-7-[(5-methylthien-2-yl)methyl]-2-(trifluoromethyl)-2H-chromene-3-carboxylic acid |

TABLE 18-continued

| Example No. | Structure | Compound Name |
|---|---|---|
| 1124 | 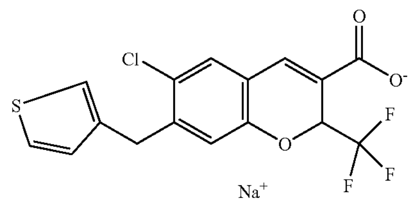 | sodium 6-chloro-7-(thien-3-ylmethyl)-2-(trifluoromethyl)-2H-chromene-3-carboxylate |
| 1125 | 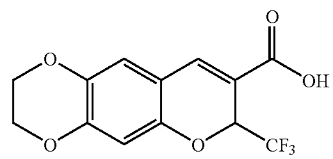 | 7-(trifluoromethyl)-2,3-dihydro-7H-[1,4]dioxino[2,3-g]chromene-8-carboxylic acid |
| 1126 | 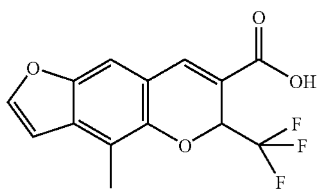 | 4-methyl-6-(trifluoromethyl)-6H-furo[2,3-g]chromene-7-carboxylic acid |
| 1127 | 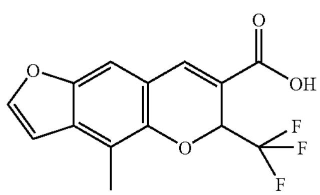 | 4-methyl-6-(trifluoromethyl)-6H-furo[2,3-g]chromene-7-carboxylic acid |
| 1128 | 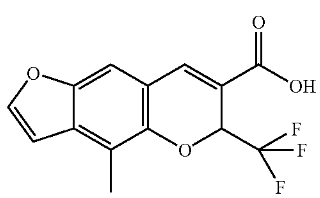 | 4-methyl-6-(trifluoromethyl)-6H-furo[2,3-g]chromene-7-carboxylic acid |
| 1129 | 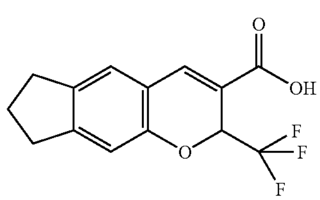 | 2-(trifluoromethyl)-2,6,7,8-tetrahydrocyclopenta[g]chromene-3-carboxylic acid |
| 1130 | 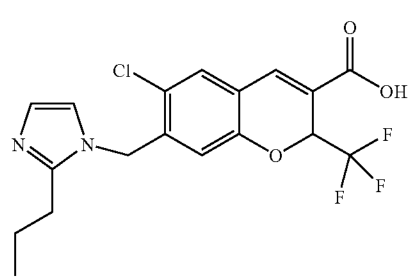 | 6-chloro-7-[(2-propyl-1H-imidazol-1-yl)methyl]-2-(trifluoromethyl)-2H-chromene-3-carboxylic acid |

TABLE 18-continued

| Example No. | Structure | Compound Name |
|---|---|---|
| 1131 | 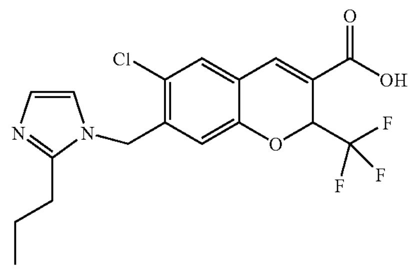 | 6-chloro-7-[(2-propyl-1H-imidazol-1-yl)methyl]-2-(trifluoromethyl)-2H-chromene-3-carboxylic acid |
| 1132 | 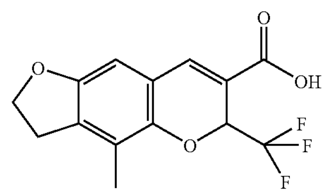 | 4-methyl-6-(trifluoromethyl)-3,6-dihydro-2H-furo[2,3-g]chromene-7-carboxylic acid |
| 1133 | 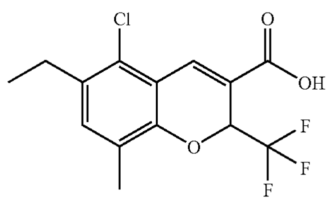 | 5-chloro-6-ethyl-8-methyl-2-(trifluoromethyl)-2H-chromene-3-carboxylic acid |
| 1134 | 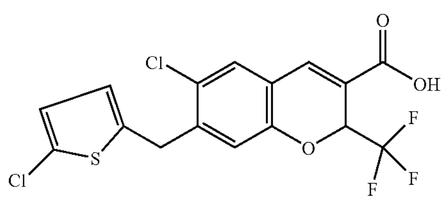 | 6-chloro-7-[(5-chlorothien-2-yl)methyl]-2-(trifluoromethyl)-2H-chromene-3-carboxylic acid |
| 1135 | 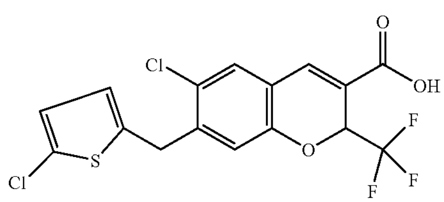 | 6-chloro-7-[(5-chlorothien-2-yl)methyl]-2-(trifluoromethyl)-2H-chromene-3-carboxylic acid |
| 1136 | 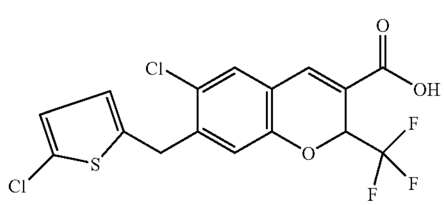 | 6-chloro-7-[(5-chlorothien-2-yl)methyl]-2-(trifluoromethyl)-2H-chromene-3-carboxylic acid |
| 1137 | 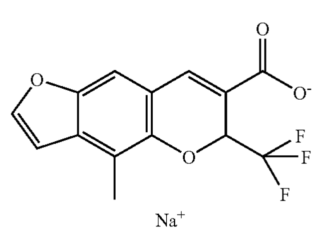 | sodium 4-methyl-6-(trifluoromethyl)-6H-furo[2,3-g]chromene-7-carboxylate |

TABLE 18-continued

| Example No. | Structure | Compound Name |
|---|---|---|
| 1138 | 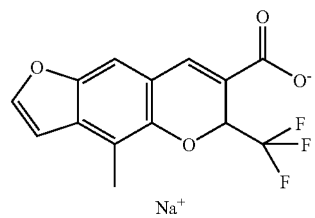 | sodium 4-methyl-6-(trifluoromethyl)-6H-furo[2,3-g]chromene-7-carboxylate |
| 1139 | 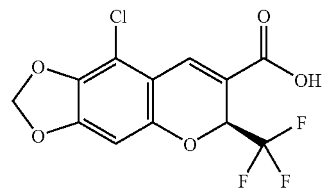 | (6S)-9-chloro-6-(trifluoromethyl)-6H-[1,3]dioxolo[4,5-g]chromene-7-carboxylic acid |
| 1140 | 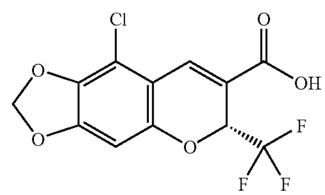 | (6R)-9-chloro-6-(trifluoromethyl)-6H-[1,3]dioxolo[4,5-g]chromene-7-carboxylic acid |
| 1141 | 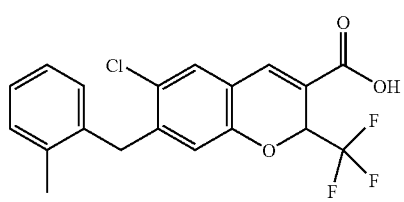 | 6-chloro-7-(2-methylbenzyl)-2-(trifluoromethyl)-2H-chromene-3-carboxylic acid |
| 1142 | 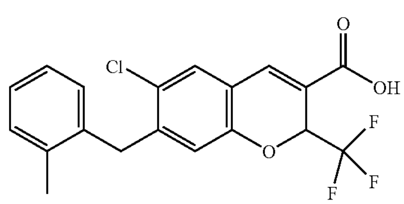 | 6-chloro-7-(2-methylbenzyl)-2-(trifluoromethyl)-2H-chromene-3-carboxylic acid |
| 1143 | 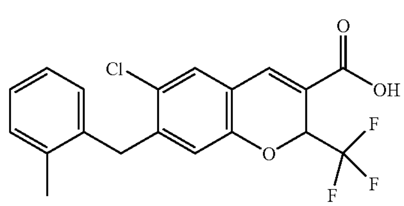 | 6-chloro-7-(2-methylbenzyl)-2-(trifluoromethyl)-2H-chromene-3-carboxylic acid |
| 1144 | 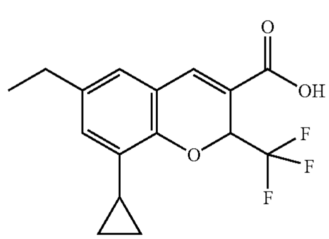 | 8-cyclopropyl-6-ethyl-2-(trifluoromethyl)-2H-chromene-3-carboxylic acid |

TABLE 18-continued

| Example No. | Structure | Compound Name |
|---|---|---|
| 1145 | 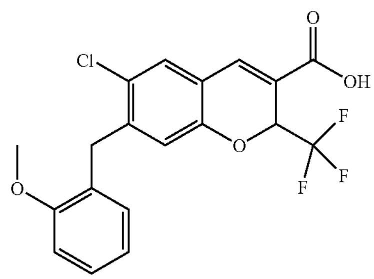 | 6-chloro-7-(2-methoxybenzyl)-2-(trifluoromethyl)-2H-chromene-3-carboxylic acid |
| 1146 | 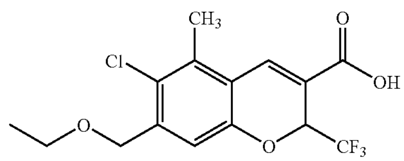 | 6-chloro-7-(ethoxymethyl)-5-methyl-2-(trifluoromethyl)-2H-chromene-3-carboxylic acid |
| 1147 | 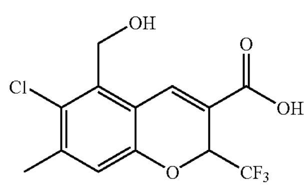 | 6-chloro-5-(hydroxymethyl)-7-methyl-2-(trifluoromethyl)-2H-chromene-3-carboxylic acid |
| 1148 | 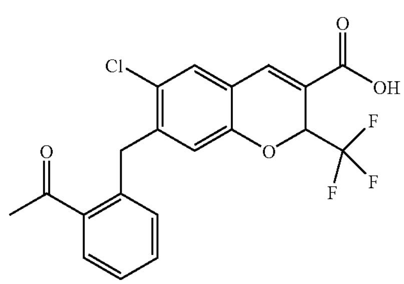 | 7-(2-acetylbenzyl)-6-chloro-2-(trifluoromethyl)-2H-chromene-3-carboxylic acid |
| 1149 | 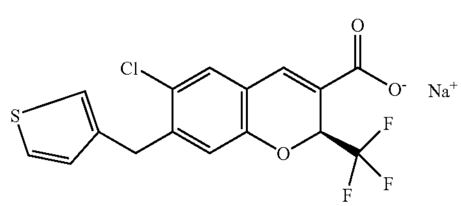 | sodium (2S)-6-chloro-7-(thien-3-ylmethyl)-2-(trifluoromethyl)-2H-chromene-3-carboxylate |
| 1150 | 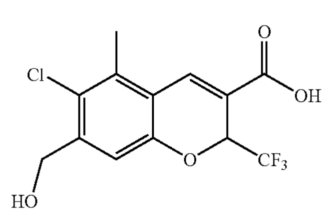 | 6-chloro-7-(hydroxymethyl)-5-methyl-2-(trifluoromethyl)-2H-chromene-3-carboxylic acid |

TABLE 18-continued

| Example No. | Structure | Compound Name |
|---|---|---|
| 1151 | 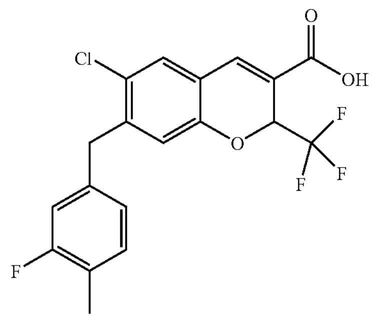 | 6-chloro-7-(3-fluoro-4-methylbenzyl)-2-(trifluoromethyl)-2H-chromene-3-carboxylic acid |
| 1152 | 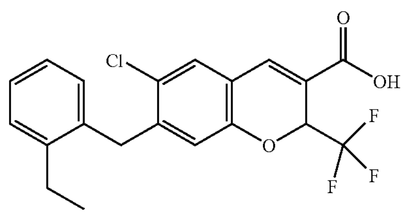 | 6-chloro-7-(2-ethylbenzyl)-2-(trifluoromethyl)-2H-chromene-3-carboxylic acid |
| 1153 | 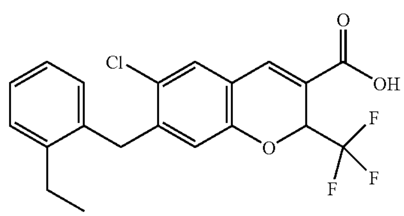 | 6-chloro-7-(2-ethylbenzyl)-2-(trifluoromethyl)-2H-chromene-3-carboxylic acid |
| 1154 | 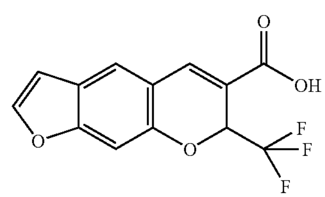 | 7-(trifluoromethyl)-7H-furo[3,2-g]chromene-6-carboxylic acid |
| 1155 | 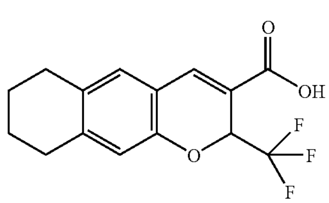 | 2-(trifluoromethyl)-6,7,8,9-tetrahydro-2H-benzo[g]chromene-3-carboxylic acid |
| 1156 | 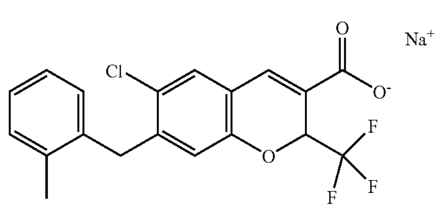 | sodium 6-chloro-7-(2-methylbenzyl)-2-(trifluoromethyl)-2H-chromene-3-carboxylate |

TABLE 18-continued

| Example No. | Structure | Compound Name |
|---|---|---|
| 1157 | 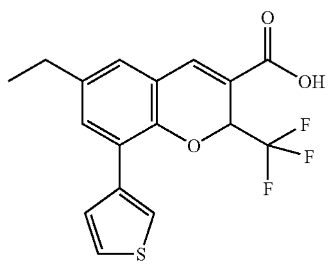 | 6-ethyl-8-thien-3-yl-2-(trifluoromethyl)-2H-chromene-3-carboxylic acid |
| 1158 | 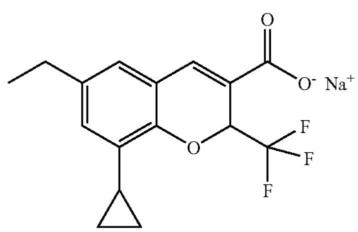 | sodium 8-cyclopropyl-6-ethyl-2-(trifluoromethyl)-2H-chromene-3-carboxylate |
| 1159 | 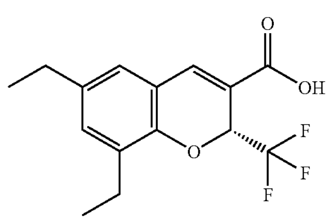 | (2R)-6,8-diethyl-2-(trifluoromethyl)-2H-chromene-3-carboxylic acid |
| 1160 | 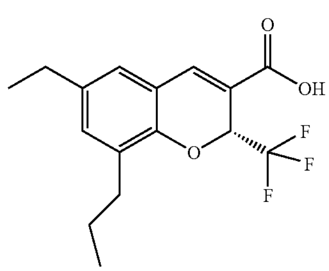 | (2R)-6-ethyl-8-propyl-2-(trifluoromethyl)-2H-chromene-3-carboxylic acid |
| 1161 | 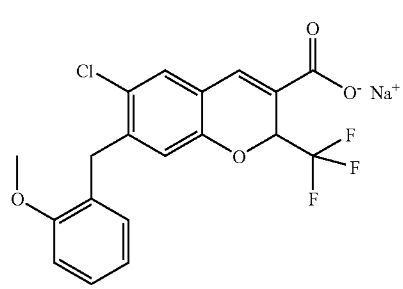 | sodium 6-chloro-7-(2-methoxybenzyl)-2-(trifluoromethyl)-2H-chromene-3-carboxylate |
| 1162 | 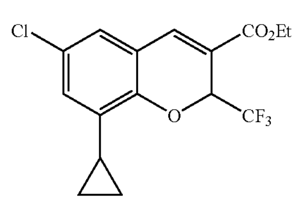 | ethyl 6-chloro-8-cyclopropyl-2-(trifluoromethyl)-2H-chromene-3-carboxylate |

TABLE 18-continued

| Example No. | Structure | Compound Name |
|---|---|---|
| 1163 | 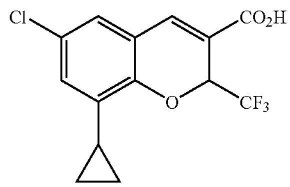 | 6-chloro-8-cyclopropyl-2-(trifluoromethyl)-2H-chromene-3-carboxylic acid |
| 1164 | 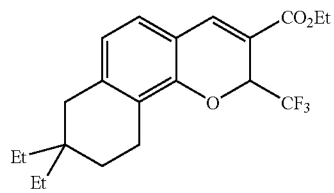 | ethyl 8,8-diethyl-2-(trifluoromethyl)-7,8,9,10-tetrahydro-2H-benzo[h]chromene-3-carboxylate |
| 1165 | 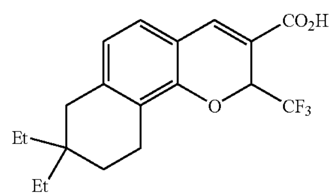 | 8,8-diethyl-2-(trifluoromethyl)-7,8,9,10-tetrahydro-2H-benzo[h]chromene-3-carboxylic acid |
| 1166 | 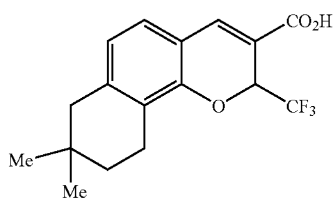 | 8,8-dimethyl-2-(trifluoromethyl)-7,8,9,10-tetrahydro-2H-benzo[h]chromene-3-carboxylic acid |
| 1167 | 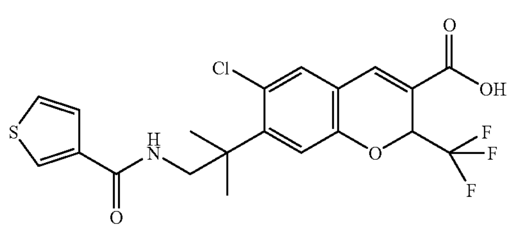 | 6-chloro-7-{1,1-dimethyl-2-[(thien-3-ylcarbonyl)amino]ethyl}-2-(trifluoromethyl)-2H-chromene-3-carboxylic acid |
| 1168 | 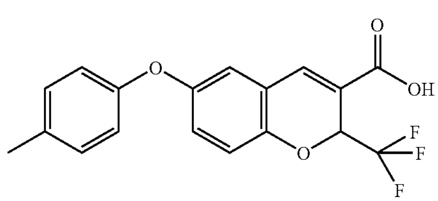 | 6-(4-methylphenoxy)-2-(trifluoromethyl)-2H-chromene-3-carboxylic acid |
| 1169 | 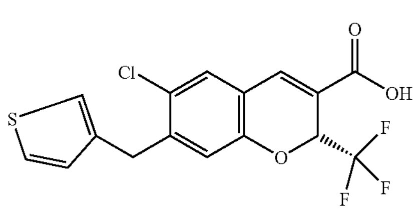 | (2R)-6-chloro-7-(thien-3-ylmethyl)-2-(trifluoromethyl)-2H-chromene-3-carboxylic acid |

TABLE 18-continued

| Example No. | Structure | Compound Name |
|---|---|---|
| 1170 | 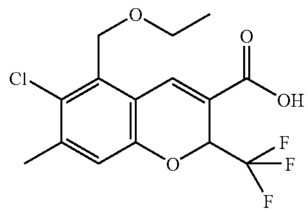 | 6-chloro-5-(ethoxymethyl)-7-methyl-2-(trifluoromethyl)-2H-chromene-3-carboxylic acid |
| 1171 | 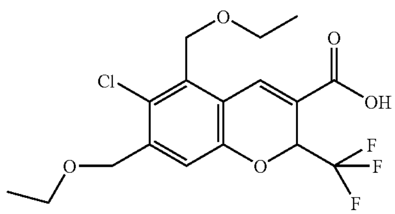 | 6-chloro-5,7-bis(ethoxymethyl)-2-(trifluoromethyl)-2H-chromene-3-carboxylic acid |
| 1172 | 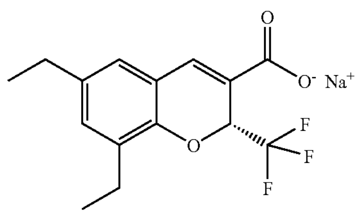 | sodium (2R)-6,8-diethyl-2-(trifluoromethyl)-2H-chromene-3-carboxylate |
| 1173 | 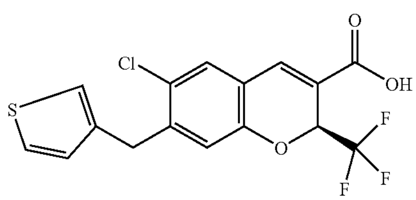 | (2S)-6-chloro-7-(thien-3-ylmethyl)-2-(trifluoromethyl)-2H-chromene-3-carboxylic acid |

Biological Evaluation

Further description of the methods for biological evaluation are found in U.S. Pat. No. 6,077,850, herein incorporated by reference. U.S. Pat. No. 6,034,256 (herein incorporated by reference) also provides description of biological evaluation methods. Additional description of methods is provided in U.S. Pat. No. 6,271,253, herein incorporated by reference.

Rat Carrageenan Foot Pad Edema Test

The carrageenan foot edema test can be performed with materials, reagents and procedures essentially as described by Winter, et al., (*Proc. Soc. Exp. Biol. Med.*, 111, 544 (1962)). Male Sprague-Dawley rats are selected in each group so that the average body weight is as close as possible. Rats are fasted with free access to water for over sixteen hours prior to the test. The rats are dosed orally (I mL) with compounds suspended in vehicle containing 0.5% methylcellulose and 0.025% surfactant, or with vehicle alone. One hour later a subplantar injection of 0.1 I mL of 1% solution of carrageenan/sterile 0.9% saline is administered and the volume of the injected foot is measured with a displacement plethysmometer connected to a pressure transducer with a digital indicator. Three hours after the injection of the carrageenan, the volume of the foot is again measured. The average foot swelling in a group of drug-treated animals is compared with that of a group of placebo-treated animals and the percentage inhibition of edema is determined (Otterness and Bliven, *Laboratory Models for Testing NSAIDs*, in Non-steroidal Anti-Inflammatory Drugs, (J. Lombardino, ed. 1985)).

Evaluation of COX-1 and COX-2 Activity in Vitro

The compounds of this invention exhibited inhibition in vitro of COX-2. The COX-2 inhibition activity of the compounds of this invention illustrated in the Examples were determined by the following methods.

a. Preparation of Recombinant COX Baculoviruses

Recombinant COX-1 and COX-2 were prepared as described by Gierse et al. [*J. Biochem.*, 305, 479-84 (1995)]. A 2.0 kb fragment containing the coding region of either human or murine COX-1 or human or murine COX-2 was cloned into a BamHI site of the baculovirus transfer vector pVL1393 (Invitrogen) to generate the baculovirus transfer vectors for COX-1 and COX-2 in a manner similar to the method of D.R. O'Reilly et al (*Baculovirus Expression Vectors: A Laboratory Manual* (1992)). Recombinant baculoviruses were isolated by transfecting 4 μg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^7$-$10^8$ pfu/mL) stocks of virus were prepared. For large scale production, SF9 insect cells were infected in 10 liter fermentors ($0.5 \times 10^6$/mL) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propane-sulfonate (CHAPS). The homogenate was centrifuged at 10,000×G for 30 minutes, and the resultant supernatant was stored at −80° C. before being assayed for COX activity.

b. Assay for COX-1 and COX-2 Activity

COX activity was assayed as PGE2 formed/lg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10-20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The PGE2 formed was measured by standard ELISA technology (Cayman Chemical). Results are shown in Table 2.

c. Modified Assay for COX-1 and COX-2 Activity

COX activity was assayed as PGE2 formed/µg protein/time using an ELISA to detect the prostaglandin released. CHAPS-solubilized insect cell membranes containing the appropriate COX enzyme were incubated in a potassium phosphate buffer (0.05 M Potassium phosphate, pH 7.5, 2 lM phenol, FM heme, 300 µM epinephrine) with the addition of 20 µl of 100 µM arachidonic acid (10 µM). Compounds were pre-incubated with the enzyme for 10 minutes at 25° C. prior to the addition of arachidonic acid. Any reaction between the arachidonic acid and the enzyme was stopped after two minutes at 37° C./room temperature by transferring 40 µof reaction mix into 160 µl ELISA buffer and 25 µM indomethacin. The PGE2 formed was measured by standard ELISA technology (Cayman Chemical). Results are shown in Table 19.

TABLE 19

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 1a | | >500 | >500 | 113 | >500 |
| 1b | | 5.73 | <0.137 | <0.137 | <0.137 |
| 1b | replicate test | 5.56 | 0.0176 | <0.137 | 0.021 |
| 1c | | 0.543 | <0.00510 | <0.137 | <0.00510 |
| 1c | replicate test | 0.143 | 0.0122 | <0.137 | 0.0076 |
| 1d | | 49.2 | 11.9 | 5.17 | 0.173 |
| 1e | | <0.137 | <0.137 | <0.137 | <0.137 |
| 1e | replicate test | <0.137 | <0.137 | <0.137 | <0.137 |
| 1e | replicate test | <0.137 | 0.0383 | <0.137 | 0.0295 |
| 1e | replicate test | 0.0024 | 0.0308 | 0.0025 | 0.0276 |
| 1f | | 16.4 | 0.894 | 4.72 | <0.137 |
| 1f | replicate test | 9.42 | 0.38 | 3.04 | 0.0336 |
| 1g | | 21 | 58.4 | 5.34 | 1.06 |
| 1h | | <0.137 | 0.224 | <0.137 | 0.0283 |
| 1h | replicate test | <0.137 | 0.229 | <0.137 | <0.137 |
| 2a | | <0.137 | 0.64 | <0.137 | 1.74 |
| 2a | replicate test | 0.347 | 1.71 | 0.122 | 0.398 |
| 2a | replicate test | 0.112 | 1.16 | 0.052 | 0.688 |
| 2b | | <0.686 | 0.205 | <0.686 | <0.137 |
| 2b | replicate test | <0.137 | 0.111 | <0.137 | 0.0573 |
| 2b | replicate test | 0.0836 | 0.139 | <0.0457 | 0.0482 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 2b | replicate test | >11.1 | 0.246 | >11.1 | 0.0496 |
| 2c | | 51.6 | 0.535 | 9.71 | 0.164 |
| 2c | replicate test | 51.6 | 0.381 | 8.31 | 0.229 |
| 2d | | 44.3 | 0.121 | 0.448 | 0.131 |
| 2e | | 68.8 | 9.17 | 4.86 | 0.564 |
| 2f | | >100 | >100 | 72.4 | 0.167 |
| 2g | | >500 | 0.886 | 203 | 0.0684 |
| 2g | replicate test | >100 | 1.09 | >100 | 0.4 |
| 2h | | >100 | >100 | >100 | 5.91 |
| 2i | | >100 | >3.70 | >500 | >100 |
| 3a | | >100 | >100 | >100 | 1.17 |
| 2i | | 187 | >500 | 78.5 | 86.6 |
| 3b | | 15.8 | <0.137 | 1.94 | <0.137 |
| 3b | replicate test | 6.7 | 0.0262 | 1.33 | 0.0224 |
| 3c | | 2.3 | 0.0181 | <0.0457 | 0.0157 |
| 3d | | <0.137 | <0.137 | <0.137 | <0.137 |
| 3e | | <0.137 | <0.137 | <0.137 | <0.137 |
| 3f | | 7.09 | <0.137 | 0.533 | <0.137 |
| 3f | replicate test | 9.55 | 0.0123 | 0.635 | 0.0077 |
| 3f | replicate test | 9.09 | 0.0176 | 0.897 | 0.0112 |
| 3g | | 74.4 | 0.167 | 5.69 | 0.185 |
| 3g | replicate test | 81.2 | 0.124 | 12.3 | 0.12 |
| 3h | | 17 | 0.2 | 3.08 | <0.137 |
| 3h | replicate test | 18.5 | 0.0275 | 3.92 | 0.0134 |
| 3h | replicate test | 18.4 | 0.0492 | 5.58 | 0.0178 |
| 3i | | >97.6 | 5.45 | >97.6 | 6.58 |
| 4a | | >500 | 237 | >500 | 131 |
| 4a | replicate test | >500 | 241 | >500 | 99.6 |
| 4a | replicate test | >100 | >100 | >100 | 33.7 |
| 4b | | >500 | 0.964 | 230 | 1.19 |
| 4b | replicate test | >500 | 3.24 | 44.4 | 1.43 |
| 5a | | >100 | >100 | 90.1 | 11.2 |
| 5a | replicate test | 264 | 137 | 23.1 | <0.137 |
| 5a | replicate test | 199 | 297 | 75.3 | 24.6 |
| 5b | | >500 | 3.45 | >500 | <0.137 |
| 5b | replicate test | >100 | 68 | >100 | 0.484 |
| 5c | | >100 | 12.1 | >100 | 4.75 |
| 5c | replicate test | 478 | 32.2 | 417 | 22.2 |
| 5d | | 31.9 | 25.2 | 15 | 6.07 |
| 5d | replicate test | 17.2 | 21.5 | 10.5 | 5.69 |
| 5e | | >100 | >100 | >100 | >100 |
| 5f | | >100 | >100 | 51 | >100 |
| 5g | | >100 | >100 | >100 | >100 |
| 6 | | >100 | 0.311 | >100 | 0.327 |
| 6 | replicate test | 188 | 0.238 | 93.5 | 0.19 |
| 6 | replicate test | 194 | 0.185 | 60.7 | 0.095 |
| 7a | | >100 | >100 | >100 | 95.8 |
| 7b | | >100 | 59 | 50.8 | 0.27 |
| 7c | | >100 | >100 | 31.1 | <0.137 |
| 7d | | 19.5 | <0.137 | 1.76 | <0.137 |
| 7d | replicate test | 19.1 | 0.0193 | 5.42 | 0.0175 |
| 7e | | >100 | >100 | 58.7 | 48.3 |
| 7f | | 70.8 | 17.9 | 23.3 | <0.137 |
| 7g | | 7.2 | <0.137 | <0.137 | <0.137 |
| 7g | replicate test | 6.35 | 0.0434 | <0.137 | 0.0348 |
| 8a | | >100 | 0.782 | 37.1 | 0.923 |
| 8a | replicate test | 57.2 | 1.43 | <0.686 | 0.164 |
| 8b | | 99 | 0.666 | 0.457 | 0.657 |
| 8b | replicate test | 189 | 1.19 | 35.2 | 0.121 |
| 8c | | >100 | 0.33 | 24.2 | 0.138 |
| 8c | replicate test | 78 | 0.208 | 15 | 0.0299 |
| 8c | replicate test | 46.8 | 0.194 | 6.75 | 0.0843 |
| 8d | | >100 | 2.88 | 33.3 | 1.71 |
| 8e | | >100 | 0.858 | 0.875 | 0.183 |
| 8e | replicate test | 130 | 0.185 | 1.68 | 0.139 |
| 8f | | >100 | 8.37 | 55.5 | 0.472 |
| 8g | | >100 | 0.696 | 47.2 | 0.514 |
| 8g | replicate test | 194 | 0.498 | 66.1 | 0.347 |
| 8h | | >100 | 80.4 | >100 | 0.425 |
| 8i | | 14.1 | 21 | 1.02 | 2.75 |
| 8j | | >100 | >100 | >100 | 1.14 |
| 8k | | >100 | >100 | >100 | 1.67 |
| 8l | | 180 | 0.294 | <0.686 | 0.149 |
| 8l | replicate test | >100 | 0.422 | 0.162 | 0.147 |
| 8l | replicate test | >33.3 | 0.429 | 0.42 | 0.181 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 8l | replicate test | >11.1 | 0.389 | 0.363 | 0.263 |
| 9a | | 9.97 | <0.0152 | 0.143 | <0.0152 |
| 9a | replicate test | 5.11 | <0.137 | <0.137 | <0.137 |
| 9a | replicate test | 9.72 | <0.686 | <0.686 | <0.686 |
| 9a | replicate test | 5.97 | <0.137 | <0.137 | <0.137 |
| 9a | replicate test | 8.31 | <0.0457 | <0.0457 | <0.0457 |
| 9a | replicate test | 9.5 | <0.0152 | <0.0152 | <0.0152 |
| 9a | replicate test | >1.20 | 0.017 | 0.0305 | 0.0058 |
| 9b | | 19 | <0.137 | 1.27 | <0.137 |
| 9b | replicate test | 17.9 | 0.0941 | 0.56 | 0.122 |
| 9c | | 3.94 | 0.0328 | <0.137 | 0.0357 |
| 9c | replicate test | 4.19 | <0.137 | <0.137 | <0.137 |
| 9c | replicate test | 2 | 0.0075 | <0.137 | <0.137 |
| 9c | replicate test | 2.2 | <0.137 | <0.137 | |
| 9d | | 4.82 | 0.0046 | 0.0552 | 0.0074 |
| 9e | | 5.76 | <0.137 | 2.27 | <0.137 |
| 9e | | >100 | 90 | >100 | 0.913 |
| 9f | | 147 | 183 | 36.6 | <0.686 |
| 9f | replicate test | >100 | >100 | 66.6 | 0.301 |
| 9g | | 24.2 | 0.437 | 0.297 | 0.187 |
| 9g | replicate test | 25.1 | 1.03 | 1.63 | 0.164 |
| 9h | | 7.94 | 13 | <0.137 | <0.137 |
| 9i | | 12.7 | 0.289 | 6.77 | <0.137 |
| 9i | replicate test | 12.5 | 0.858 | 6.25 | 0.168 |
| 9j | | 11.4 | 35.9 | 5.46 | 2.95 |
| 9j | replicate test | 14 | 34.4 | 4.43 | 1.18 |
| 9k | | 0.603 | <0.137 | <0.137 | <0.137 |
| 9k | replicate test | 2.17 | 0.0113 | <0.0457 | 0.0107 |
| 9l | | 3.05 | <0.137 | 0.15 | <0.137 |
| 9l | replicate test | 2.38 | 0.0076 | <0.137 | 0.0052 |
| 9m | | 24.1 | 0.322 | 0.453 | <0.137 |
| 9n | | 0.425 | <0.137 | <0.137 | <0.137 |
| 9o | | 9.67 | <0.137 | 4.67 | <0.137 |
| 9o | replicate test | 12.1 | 0.0098 | 5.18 | 0.0077 |
| 9p | | 1.51 | <0.137 | 0.519 | >100 |
| 9q | | 99.9 | >100 | 50.6 | 20 |
| 9r | | 80.8 | 74.3 | 33.7 | 5.4 |
| 9s | | 5.85 | 0.0137 | 0.912 | <0.137 |
| 9s | replicate test | 5.72 | <0.137 | | |
| 9t | | 5.5 | 3.03 | 1.54 | 0.388 |
| 9u | | 5.52 | 1.96 | 2.07 | 0.269 |
| 9w | | >100 | >100 | >100 | >100 |
| 9x | | 5.59 | 0.0071 | 0.476 | 0.0057 |
| 9x | replicate test | 10.3 | <0.137 | 3.34 | <0.137 |
| 9y | | 4.69 | 11.3 | 0.477 | <0.137 |
| 9z | | 27.4 | 30.5 | 8.73 | <0.137 |
| 9aa | | >100 | >100 | 51 | 46.9 |
| 9bb | | 37.4 | 35.9 | 13.1 | <0.137 |
| 10 | | <0.137 | <0.137 | <0.137 | <0.137 |
| 10 | replicate test | <0.137 | 0.0798 | <0.137 | 0.0821 |
| 11 | | >100 | >100 | 48.7 | >100 |
| 12 | | >100 | >100 | >100 | >100 |
| 13 | | 4.18 | <0.137 | <0.137 | <0.137 |
| 13 | replicate test | 2.79 | 0.132 | <0.0457 | 0.0374 |
| 14a | | <0.137 | <0.137 | <0.137 | <0.137 |
| 14b | | <0.137 | <0.137 | <0.137 | <0.137 |
| 16 | | >100 | >100 | >100 | 3.13 |
| 17a | | 0.497 | 2.66 | <0.137 | 0.996 |
| 17a | replicate test | 18.7 | 10.8 | 1.3 | >11.1 |
| 17b | | >100 | >100 | 43.6 | 0.973 |
| 17b | replicate test | 455 | >500 | 127 | 28.8 |
| 17c | | 3.58 | >100 | <0.137 | 41.5 |
| 17c | replicate test | 0.623 | 176 | 0.271 | 98.5 |
| 17d | | 0.365 | >100 | <0.137 | 44 |
| 17d | replicate test | <0.137 | 127 | <0.137 | 63.2 |
| 17e | | <0.137 | 5.44 | <0.137 | 3.58 |
| 17e | replicate test | <0.137 | 3.88 | <0.137 | 3.91 |
| 17f | | 11.1 | >100 | <0.137 | 67.6 |
| 17f | replicate test | 11.8 | 172 | <0.137 | 84 |
| 17g | | 0.5 | 5.35 | <0.137 | 2.93 |
| 17g | replicate test | 0.392 | 6.87 | 0.252 | 1.52 |
| 17h | | >100 | >100 | 62.1 | 13.1 |
| 17i | | 81.1 | 0.154 | 0.455 | 0.171 |
| 17i | replicate test | 36.4 | 0.151 | <0.686 | 0.0907 |
| 18a | | <0.137 | 1.13 | <0.137 | 0.824 |
| 18a | replicate test | <0.137 | 0.562 | <0.137 | 0.548 |
| 19 | | 82.1 | 1.04 | 0.163 | 0.76 |
| 19 | replicate test | 34.7 | 0.442 | <0.137 | 0.485 |
| 20a | | <0.137 | 0.373 | <0.137 | <0.137 |
| 20a | replicate test | <0.137 | >1.20 | <0.137 | >1.20 |
| 21a | | 10.5 | <0.137 | <0.137 | <0.137 |
| 21a | replicate test | 3.57 | 0.189 | <0.137 | <0.137 |
| 21b | | 2.46 | 0.157 | <0.137 | <0.137 |
| 21b | replicate test | 1.05 | 0.0278 | <0.137 | 0.0162 |
| 21c | | 19.2 | <0.137 | <0.137 | <0.137 |
| 21c | replicate test | 9.68 | 0.127 | <0.137 | 0.246 |
| 21d | | 0.182 | 0.694 | <0.137 | 0.5 |
| 21e | | 6.52 | <0.137 | <0.137 | <0.137 |
| 21e | replicate test | 3.06 | 0.0846 | 0.363 | 0.131 |
| 21f | | <0.137 | 1.03 | <0.137 | 0.433 |
| 21f | replicate test | 0.0312 | 0.435 | 0.0378 | 0.526 |
| 21g | | 24.4 | 0.15 | 0.257 | <0.137 |
| 21g | replicate test | 21.6 | 0.16 | 1.6 | 0.132 |
| 21g | replicate test | 9.14 | 0.0527 | 1.13 | 0.0417 |
| 21g | replicate test | 10.7 | <0.137 | <0.137 | <0.137 |
| 21h | | >100 | 0.738 | 70.5 | 0.253 |
| 21h | replicate test | 217 | 0.399 | 126 | 0.288 |
| 21i | | 20.5 | <0.137 | 5.67 | <0.137 |
| 21i | replicate test | 13.6 | 0.0723 | 8.64 | 0.0432 |
| 21j | | 40.4 | 67.5 | 17.1 | 0.206 |
| 21k | | 23.4 | <0.137 | 0.6 | <0.137 |
| 21k | replicate test | 27 | 0.0602 | 3.37 | 0.0669 |
| 21k | replicate test | 9.26 | <0.137 | 0.528 | <0.137 |
| 21k | replicate test | 11 | <0.137 | 0.484 | <0.137 |
| 21l | | >100 | 0.921 | 1.58 | 0.779 |
| 21l | replicate test | 115 | 0.756 | 6.8 | 0.656 |
| 21l | replicate test | 49.6 | 0.895 | 2.61 | 1.57 |
| 21n | | <0.137 | <0.137 | <0.137 | <0.137 |
| 21o | | 54.8 | 0.357 | 18.8 | 0.367 |
| 21o | replicate test | 68.2 | 0.435 | 22.8 | |
| 21p | | 39.2 | 6.05 | 1.67 | |
| 21q | | 5.71 | 0.208 | 0.204 | 0.327 |
| 21r | | 83.8 | 4.99 | 30.1 | 0.42 |
| 21s | | >100 | 0.236 | 42.8 | 0.159 |
| 21s | replicate test | 119 | 0.176 | 58.3 | 0.152 |
| 21t | | 32.3 | <0.137 | <0.137 | <0.137 |
| 21t | replicate test | 7.18 | <0.137 | <0.137 | <0.137 |
| 21t | replicate test | 6.42 | 0.0548 | 0.194 | 0.0412 |
| 21t | replicate test | 8.06 | <0.150 | <0.150 | <0.150 |
| 21t | replicate test | 18.4 | <0.137 | 0.226 | <0.137 |
| 21u | | >100 | 24.2 | 4.49 | 3.03 |
| 21u | replicate test | >100 | 1.1 | 0.735 | 0.854 |
| 21u | replicate test | >100 | >100 | 3.44 | >100 |
| 22 | | >1.00 | >1.00 | >1.00 | 0.477 |
| 22 | replicate test | 25.6 | 4 | 4.31 | 2.81 |
| 22 | replicate test | 12.4 | | 3.06 | |
| 23a | | >100 | >100 | >100 | 23.5 |
| 23a | replicate test | >500 | >500 | >500 | 111 |
| 23b | | 159 | 430 | 33.7 | <0.686 |
| 23b | replicate test | >100 | >100 | 40.1 | 0.273 |
| 23c | | 48.4 | >100 | 18 | <0.137 |
| 23c | replicate test | 62.6 | 181 | 14.6 | <0.686 |
| 23d | | >500 | 10.5 | 13.6 | 1.85 |
| 23d | replicate test | >100 | 42.5 | 63.4 | 1.23 |
| 23d | replicate test | >500 | 53.9 | 25.5 | 3.64 |
| 23e | | 0.471 | 0.526 | 0.123 | 0.336 |
| 23e | replicate test | <0.132 | 0.419 | <0.132 | 0.457 |
| 23f | | >100 | >100 | >100 | 16.9 |
| 23f | replicate test | >500 | >500 | 395 | 199 |
| 24a | | >500 | >100 | >500 | 2.95 |
| 24a | replicate test | >100 | 60.2 | >100 | 2.45 |
| 24b | | >100 | 6.44 | >100 | 0.39 |
| 24b | replicate test | >500 | >33.3 | >500 | 16.3 |
| 25a | | >500 | >500 | 311 | >500 |
| 25a | replicate test | >500 | >100 | 292 | >100 |
| 25a | replicate test | >100 | >33.3 | >100 | >33.3 |
| 25b | replicate test | <0.686 | 3.36 | <0.686 | 3.55 |
| 25b | replicate test | <0.137 | 3.47 | <0.137 | 2.98 |
| 25b | replicate test | 0.14 | 8.41 | 0.117 | 1.83 |
| 25d | | >100 | 14.8 | >100 | 10.7 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 25d | replicate test | >500 | >33.3 | 435 | 6.8 |
| 25d | replicate test | >500 | >33.3 | 417 | 6.39 |
| 25e | | >100 | >100 | >100 | >100 |
| 25f | | >100 | >100 | >100 | 3.05 |
| 25g | | >100 | >100 | 13.5 | <0.137 |
| 25g | replicate test | 80.7 | 139 | <0.686 | <0.686 |
| 25h | | >100 | 2.01 | 4.15 | 0.483 |
| 25h | replicate test | 72.3 | 7.43 | <0.686 | 0.263 |
| 26 | | >100 | 1.64 | 6.94 | 1.39 |
| 27 | | >100 | <0.137 | 73.8 | <0.137 |
| 27 | replicate test | 198 | 0.0864 | 58.9 | 0.0916 |
| 28a | | 43.6 | 99.8 | 49 | <0.137 |
| 28a | replicate test | 41.3 | 188 | 36.7 | <0.686 |
| 28b | | 41.7 | >100 | 28.3 | 0.34 |
| 28c | | >100 | 19.7 | 42.4 | <0.686 |
| 28d | | | | | |
| 29 | | >100 | 0.143 | 60.2 | 0.119 |
| 29 | replicate test | 217 | 0.113 | 115 | 0.228 |
| 30 | | 193 | 0.0726 | 62.2 | 0.0578 |
| 30 | replicate test | <0.137 | <0.137 | 40.5 | <0.137 |
| 31 | | >100 | 0.7 | >100 | 1.55 |
| 31 | replicate test | >500 | >33.3 | >500 | >33.3 |
| 32a | | >100 | <0.137 | | |
| 32a | replicate test | 185 | 0.336 | | |
| 32a | replicate test | 204 | 0.397 | | |
| 32a | replicate test | 165 | 0.191 | | |
| 32a | replicate test | 128 | 0.221 | | |
| 32b | | >100 | 0.289 | 2.12 | 0.265 |
| 32c | | >100 | >100 | >100 | >100 |
| 33 | | 8.28 | 0.301 | <0.137 | 0.424 |
| 33 | replicate test | 6.09 | 0.435 | <0.137 | 0.513 |
| 33 | replicate test | 43.4 | 0.213 | <0.686 | <0.137 |
| 33 | replicate test | 18.5 | 0.131 | <0.137 | 0.0993 |
| 34a | | 45.3 | <0.137 | 0.144 | 0.737 |
| 34a | replicate test | 67.1 | 0.628 | <0.137 | <0.137 |
| 34a | replicate test | 4.1 | 0.168 | 0.0406 | 0.316 |
| 34a | replicate test | 76.7 | 0.27 | 0.265 | 0.326 |
| 34a | replicate test | 23.4 | 0.536 | <0.137 | 0.407 |
| 34b | | 57.9 | 0.145 | 0.172 | <0.137 |
| 34b | replicate test | 35.5 | 0.0929 | <0.137 | 0.0913 |
| 34c | | >100 | >100 | >100 | >100 |
| 34d | | 55.4 | 0.29 | <0.137 | 1.4 |
| 34d | replicate test | >100 | 1.15 | <0.137 | <0.137 |
| 34d | replicate test | 4.42 | 0.78 | 0.125 | 0.453 |
| 34d | replicate test | 41.1 | 2.89 | <0.137 | 2.05 |
| 34d | replicate test | 87.8 | 0.56 | <0.137 | 0.736 |
| 34d | replicate test | | | <0.137 | 0.49 |
| 35 | | 2.87 | 78 | <0.137 | <0.686 |
| 36 | | 78.5 | <0.137 | <0.137 | <0.137 |
| 36 | replicate test | 52.3 | 0.231 | 0.405 | 0.133 |
| 37a | | 69.4 | 71.3 | 38.6 | 37 |
| 37b | | >100 | >100 | 66.3 | 53.1 |
| 38a | | <0.137 | <0.137 | <0.137 | <0.137 |
| 38b | | >100 | >100 | 15.2 | 0.591 |
| 38c | | <0.137 | <0.137 | <0.137 | <0.137 |
| 39b | | 3.93 | 34 | 0.408 | 18.6 |
| 41 | | 14.6 | <0.137 | 4.46 | <0.137 |
| 41 | replicate test | 12.9 | 0.0143 | 0.931 | 0.0121 |
| 42a | | 28.7 | <0.137 | 6.58 | <0.137 |
| 42a | replicate test | 25.2 | 0.0562 | 18.3 | 0.0183 |
| 42a | replicate test | 14.7 | 0.0398 | 6.76 | 0.031 |
| 42b | | >100 | >100 | 47.4 | 0.634 |
| 42c | | >100 | 12.3 | 18.5 | 6.84 |
| 42d | | 58.3 | 1.92 | 8.64 | 1.86 |
| 44 | | 0.185 | 0.314 | 0.0768 | 0.308 |
| 44 | replicate test | 0.12 | 0.11 | 0.0599 | 0.0704 |
| 44 | replicate test | <0.137 | <0.137 | <0.137 | 0.158 |
| 46 | | >100 | 2.42 | 14.7 | 1.25 |
| 47 | | >100 | 15.7 | 37.4 | 1.4 |
| 47 | replicate test | >500 | 1.54 | | |
| 48 | | 42.7 | >100 | 22.7 | >100 |
| 100 | | 30.2 | <0.137 | <0.137 | <0.137 |
| 100 | replicate test | 29.4 | 0.135 | <0.137 | 0.127 |
| 101 | | >100 | 1.17 | 10.7 | 1.21 |
| 101 | replicate test | 430 | 1.32 | 42.3 | 0.831 |
| 101 | replicate test | >100 | 2.29 | 24.4 | 2.26 |
| 101 | replicate test | >500 | 1.72 | 81 | 1.17 |
| 102 | | 42.4 | 0.0608 | 4.67 | 0.0657 |
| 102 | replicate test | 32.7 | <0.137 | 0.842 | <0.137 |
| 102 | replicate test | 28 | 0.0897 | 0.389 | 0.0589 |
| 102 | replicate test | 24.6 | <0.137 | 0.621 | <0.137 |
| 102 | replicate test | 38.2 | <0.137 | 4.37 | <0.137 |
| 102 | replicate test | 31.4 | <0.137 | 3.21 | <0.137 |
| 103 | | 33 | 0.172 | <0.137 | 0.231 |
| 103 | replicate test | 39.9 | 0.0898 | <0.137 | 0.129 |
| 104 | | 6.75 | 0.156 | <0.137 | 0.189 |
| 104 | replicate test | 12.1 | 0.125 | <0.137 | 0.201 |
| 105 | | 3.32 | 0.261 | <0.137 | <0.137 |
| 105 | replicate test | 2 | 0.177 | <0.137 | 0.129 |
| 106 | | >100 | 39.6 | 4.65 | <0.137 |
| 106 | replicate test | 93 | >100 | 18 | 0.813 |
| 107 | | 8.85 | 0.206 | <0.137 | 0.162 |
| 107 | replicate test | <0.137 | 0.479 | <0.137 | 0.142 |
| 108 | | >100 | 4.46 | 21.5 | <0.137 |
| 108 | replicate test | 169 | 4.06 | 87 | 0.349 |
| 109 | | 0.413 | <0.137 | <0.137 | <0.137 |
| 109 | replicate test | <0.137 | 7.97 | <0.137 | 1.07 |
| 110 | | 16.1 | 0.238 | 0.554 | <0.137 |
| 110 | replicate test | 13.1 | <0.137 | 0.153 | |
| 111 | | 9.16 | 0.188 | <0.137 | <0.137 |
| 111 | replicate test | 9.17 | <0.137 | <0.137 | |
| 112 | | >100 | >100 | >100 | 4.03 |
| 113 | | >100 | >100 | 50.8 | 19.4 |
| 114 | | 63.9 | 62.5 | 12.6 | 14 |
| 115 | | >100 | >100 | >100 | >100 |
| 116 | | >100 | 18.9 | 90.9 | 3.13 |
| 117 | | 77 | 26.5 | 1.45 | 12 |
| 117 | replicate test | 26.8 | 27.8 | 1.97 | 2.46 |
| 118 | | >100 | 5.48 | 5.4 | 4.05 |
| 119 | | >100 | 0.827 | >100 | 0.792 |
| 119 | replicate test | >500 | 0.902 | 365 | 0.0886 |
| 120 | | >100 | 35 | 69.5 | 42.1 |
| 121 | | >100 | >100 | >100 | >100 |
| 122 | | >100 | >100 | >100 | >100 |
| 125 | | 25.3 | <0.137 | 3.87 | <0.137 |
| 125 | replicate test | 19.3 | 0.0357 | 5.1 | 0.0201 |
| 127 | | >100 | 19.9 | >500 | 8.41 |
| 127 | replicate test | >100 | 9.52 | >500 | |
| 127 | replicate test | >500 | 40.6 | | |
| 128 | | 44.8 | >100 | 11.5 | 11.4 |
| 129 | | >100 | 17.9 | 83.6 | 20 |
| 130 | | 3.7 | 5.99 | 2.43 | 5.19 |
| 131 | | <0.137 | <0.137 | <0.137 | <0.137 |
| 131 | replicate test | 0.99 | 0.0466 | <0.137 | 0.0901 |
| 132 | | >100 | 74.3 | 89.6 | 53.1 |
| 132 | replicate test | >100 | 60.5 | >100 | 27.2 |
| 133 | | <0.137 | >100 | <0.137 | 3.4 |
| 133 | replicate test | 0.0654 | 4.7 | 0.0697 | 3.77 |
| 134 | | 4.36 | 3.35 | 0.804 | 3.11 |
| 135 | | >100 | >100 | >100 | >100 |
| 136 | | 44.4 | 0.176 | 8.04 | <0.137 |
| 136 | replicate test | 39.8 | 0.272 | 6.88 | 0.121 |
| 137 | | >100 | >100 | >100 | <0.137 |
| 137 | replicate test | >500 | >500 | >500 | 24.4 |
| 138 | | 23.8 | 0.0872 | 0.531 | 0.0692 |
| 139 | | 36.6 | 0.324 | 0.291 | 0.279 |
| 140 | | >500 | >500 | >500 | 343 |
| 140 | replicate test | >100 | >100 | >100 | 91.4 |
| 141 | | 2.96 | <0.137 | <0.137 | <0.137 |
| 141 | replicate test | 2.76 | 0.0957 | <0.137 | 0.0881 |
| 142 | | 18.6 | 5.64 | 0.226 | 0.39 |
| 143 | | 1.23 | 1.51 | <0.137 | 1.41 |
| 144 | | >100 | 0.679 | 63.7 | 0.584 |
| 144 | replicate test | 175 | 0.502 | 24.1 | 0.394 |
| 147 | | >100 | >100 | 37.5 | 4.1 |
| 148 | | <0.137 | <0.137 | <0.137 | <0.137 |
| 148 | replicate test | <0.137 | 0.13 | <0.137 | 0.108 |
| 149 | | >100 | 0.331 | >100 | <0.137 |
| 149 | replicate test | >500 | >3.70 | >500 | 1.63 |
| 149 | replicate test | >100 | 3.75 | >100 | 1.95 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 150 | | 6.21 | 0.268 | <0.137 | 0.236 |
| 150 | replicate test | 13.6 | 0.551 | <0.137 | 0.321 |
| 151 | | 18.6 | <0.137 | <0.137 | <0.137 |
| 151 | replicate test | 12.7 | 0.0464 | <0.686 | 0.0457 |
| 152 | | >100 | >100 | 71.7 | >100 |
| 153 | | 66.8 | 85.3 | 0.429 | >100 |
| 154 | | >100 | 0.262 | >100 | 0.263 |
| 154 | replicate test | 287 | 0.347 | 144 | 0.377 |
| 155 | | 9.22 | 18 | 0.178 | 3.02 |
| 156 | | <0.137 | 48.7 | 0.289 | 9.36 |
| 157 | | >100 | 3.07 | >100 | 1.95 |
| 158 | | >100 | 10.5 | >100 | 5.85 |
| 158 | replicate test | >500 | 5.71 | >500 | 4.11 |
| 159 | | >100 | >100 | >100 | 15.5 |
| 160 | | >100 | 4.31 | 39.2 | 4.93 |
| 161 | | >100 | >100 | >100 | 3.07 |
| 162-a | | >100 | 6.58 | >100 | 3.16 |
| 162-b | | >100 | >100 | >100 | >100 |
| 163a | | >100 | >100 | >100 | 69.7 |
| 163b | | >100 | 83.1 | >100 | 1.61 |
| 164 | | 43.9 | >100 | 23.6 | 11 |
| 165 | | >100 | >100 | 55.6 | 0.262 |
| 166 | | 27.9 | 5.89 | 2.45 | 3.85 |
| 167a | | 13.5 | 4.96 | 0.982 | 4.17 |
| 167b | | >100 | >100 | >100 | >100 |
| 168a | | >100 | 3.97 | >100 | 0.773 |
| 168b | | >100 | >100 | >100 | 6.68 |
| 169 | | >100 | >100 | >100 | 2.25 |
| 170 | | 7.64 | 0.0145 | 0.184 | 0.0197 |
| 170 | replicate test | 8.8 | <0.137 | 0.311 | <0.137 |
| 170 | replicate test | 4.03 | <0.137 | <0.137 | <0.137 |
| 170 | replicate test | 3.49 | 0.0069 | <0.137 | 0.006 |
| 171 | | >100 | 21.6 | >100 | 4.72 |
| 172 | | 95.6 | 0.168 | 1.52 | 0.168 |
| 172 | replicate test | 78.4 | 0.165 | 3.58 | 0.161 |
| 173 | | 5.93 | 1.42 | 0.171 | 0.616 |
| 173 | replicate test | 17.5 | 0.973 | <0.137 | |
| 174 | | 29.2 | 3.58 | 2.72 | 0.702 |
| 175 | | >100 | >100 | >100 | 38.8 |
| 201 | | | <0.137 | <0.137 | <0.137 |
| 201 | replicate test | | 0.0398 | <0.0152 | 0.0402 |
| 202 | | | 0.577 | 0.293 | 0.333 |
| 202 | replicate test | | 0.627 | 0.297 | 0.54 |
| 203 | | | 2.31 | 13.1 | 1.74 |
| 203 | replicate test | | 2.61 | 20.3 | 2.14 |
| 204 | | >100 | | 3.84 | 22.3 |
| 204 | replicate test | >100 | | 30.7 | >100 |
| 205 | | | >100 | 28.6 | 32.2 |
| 205 | replicate test | | >100 | 36.3 | 60.4 |
| 206 | | | 16.9 | 0.821 | 3.7 |
| 206 | replicate test | | 15.4 | 1.37 | 12.2 |
| 207 | | | 6.49 | 18.5 | 7.47 |
| 207 | replicate test | | 14.3 | 16.2 | 7.47 |
| 208 | | | 3.89 | 0.242 | 3.48 |
| 208 | replicate test | | 2.47 | 0.381 | 2.86 |
| 209 | | | 3.73 | 10.3 | 3.12 |
| 209 | replicate test | | 2.14 | 5.55 | 2.03 |
| 203 | | 92.8 | 2.31 | 13.1 | 1.74 |
| 203 | replicate test | >100 | 2.61 | 20.3 | 2.14 |
| 210 | | >100 | 14.4 | 9.93 | 2.8 |
| 211 | | >100 | 14.8 | >100 | 19.2 |
| 212 | | | 4.36 | 0.377 | 0.292 | 0.382 |
| 213 | | >100 | 2.3 | 3.97 | 1.76 |
| 213 | replicate test | 453 | 2.09 | 1.39 | 1.49 |
| 214 | | 17 | 3.59 | <0.137 | 0.411 |
| 214 | replicate test | 18 | 2.14 | <0.137 | 0.18 |
| 215 | | 61.4 | 3.12 | 1.92 | 1.11 |
| 215 | replicate test | 41.1 | 0.982 | 0.925 | 0.205 |
| 216 | | >100 | >100 | 9.59 | >100 |
| 217 | | 33.2 | 13 | 22.6 | 9.28 |
| 218 | | >100 | 5.47 | 4.38 | 4.9 |
| 218 | replicate test | 480 | 3.55 | 3.65 | 1.5 |
| 219 | | 3.77 | 5.45 | 2.88 | 5.99 |
| 219 | replicate test | 3.03 | >11.1 | 3.7 | >11.1 |
| 220 | | 2.18 | 3.87 | 0.823 | 2.6 |
| 220 | replicate test | 0.366 | >11.1 | 2.11 | 4.49 |
| 221 | | 51.8 | 29.7 | <0.137 | 0.998 |
| 221 | replicate test | 17 | >33.3 | <0.137 | 2.42 |
| 222 | | 32.7 | 0.64 | <0.137 | 0.608 |
| 222 | replicate test | 2.67 | 0.322 | <0.137 | 0.48 |
| 223 | | 9.67 | >100 | 3.01 | 52.9 |
| 224 | | 9.28 | 3.24 | 1.39 | 2.28 |
| 225 | | 2.43 | 2.15 | 0.266 | 2.44 |
| 226 | | 23.7 | 23 | 4.68 | 16.3 |
| 227 | | 10.9 | >100 | 4.73 | 37.3 |
| 228 | | 28.5 | 65.8 | 10.7 | 23.4 |
| 229 | | 0.626 | 2.43 | | 12.1 |
| 230 | | 4.58 | 3.1 | | 23.5 |
| 231 | | 22.4 | 7.9 | | 23.3 |
| 232 | | 27 | 7.47 | | 24.2 |
| 233 | | 17.3 | 2.53 | | 8.82 |
| 234 | | 0.213 | 3.19 | 0.21 | 2.03 |
| 235 | | 74.7 | 19.8 | 2.09 | 7.52 |
| 236 | | 2.39 | 5.15 | <0.137 | 2.15 |
| 237 | | 7.16 | 2.68 | 0.649 | 1.23 |
| 238 | | 52 | >100 | 3.2 | >100 |
| 239 | | 17 | 4.7 | 6.5 | 3.11 |
| 240 | | 4.18 | >100 | 1.82 | 31.6 |
| 241 | | 1.25 | 11.8 | 0.879 | 10.4 |
| 242 | | 3.25 | >100 | 2.51 | 21.7 |
| 243 | | 9.97 | 0.764 | 0.288 | 0.675 |
| 244 | | 1.06 | 3.19 | 0.15 | 3.69 |
| 245 | | 72.3 | 38.4 | 19.8 | 31.8 |
| 246 | | 7.19 | >100 | 0.159 | >100 |
| 247 | | >11.1 | >3.70 | >11.1 | >3.70 |
| 247 | replicate test | <0.137 | <0.137 | <0.137 | <0.137 |
| 247 | replicate test | 1.83 | 0.393 | <0.137 | 0.893 |
| 248 | | 27.4 | 73.6 | 7.18 | 3.86 |
| 248 | replicate test | 10.7 | 43.1 | 4.04 | 2.64 |
| 249 | | 5.19 | >11.1 | 1.68 | 1.24 |
| 249 | replicate test | 7.19 | 63 | 1.23 | |
| 250 | | 36.3 | 0.164 | <0.137 | 0.158 |
| 250 | replicate test | 39.4 | 0.176 | 0.146 | <0.137 |
| 251 | | 16.4 | 0.577 | 0.683 | 0.497 |
| 251 | replicate test | 17.6 | 1.74 | 0.947 | 0.927 |
| 252 | | <0.137 | 1.15 | <0.137 | 1.17 |
| 253 | | >100 | 31.5 | 10.8 | 25.9 |
| 254 | | >100 | 6.61 | 88.4 | 5.67 |
| 254 | replicate test | >500 | >11.1 | 194 | 5.03 |
| 255 | | 39.9 | 68.9 | 1.72 | 12.2 |
| 256 | | 7.57 | 0.793 | 0.19 | 0.534 |
| 256 | replicate test | 3.03 | 1.27 | 0.206 | |
| 257 | | >100 | >100 | >100 | 41.3 |
| 258 | | 0.282 | 0.38 | <0.137 | 0.476 |
| 259 | | 0.289 | 32.8 | 0.187 | 5.97 |
| 260 | | >100 | >100 | >100 | 17.2 |
| 261 | | >100 | >100 | >100 | 63.2 |
| 262 | | 26.2 | 38.2 | 1.52 | 0.178 |
| 263 | | 5.02 | 3.7 | 1.39 | 4.59 |
| 264 | | 173 | 2.32 | 2.48 | 1.84 |
| 265 | | 169 | 27.5 | 164 | 13.5 |
| 266 | | 18.2 | 30 | 58.5 | 23.2 |
| 267 | | 28.2 | 36.2 | <0.137 | 36.5 |
| 268 | | 2.9 | 2.81 | 1.21 | 1.84 |
| 269 | | 40.1 | 66.1 | 15.4 | 1.67 |
| 270 | | 7.03 | 47.4 | 3.36 | 38.5 |
| 271 | | 38.1 | >100 | 31 | >100 |
| 272 | | 5.08 | 1.17 | <0.137 | 0.813 |
| 273 | | >100 | 25.6 | >100 | 33 |
| 274 | | >100 | 1.13 | 1.71 | 0.301 |
| 274 | replicate test | 209 | 1.82 | 4.49 | 1 |
| 275 | | >500 | >100 | >500 | >100 |
| 275 | replicate test | >100 | 95.9 | 32.7 | 93.3 |
| 276 | | >100 | 0.548 | >100 | >100 |
| 276 | replicate test | >500 | >3.70 | 366 | 0.242 |
| 277 | | 51.6 | 0.178 | 13.1 | 34.9 |
| 277 | replicate test | 53.9 | 3.66 | 24.7 | 0.0623 |
| 278 | | 34.8 | 4.48 | 6.86 | 31.4 |
| 279 | | 12 | 0.723 | 9.95 | 0.586 |
| 280 | | >100 | 92.7 | 63.4 | 16.7 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 281 | | >100 | >100 | 85 | 12.6 |
| 282 | | >100 | >100 | 83.1 | >100 |
| 283 | | 30.3 | 6.95 | 5.25 | 4.04 |
| 284 | | 42.6 | 4.22 | 8.27 | 3.41 |
| 285 | | 52.2 | <0.137 | 12.5 | <0.137 |
| 285 | replicate test | 60.6 | 0.163 | 18.6 | 0.0438 |
| 286 | | 28.6 | 17.5 | 13.7 | 0.293 |
| 287 | | 26.3 | 28.3 | 12.2 | 5 |
| 288 | | >100 | 5.81 | 67.2 | 6.53 |
| 289 | | >100 | 0.858 | 19.9 | 0.964 |
| 289 | replicate test | >500 | 2.26 | 198 | 0.88 |
| 290 | | <0.137 | 0.209 | <0.137 | <0.137 |
| 290 | replicate test | 0.407 | 0.55 | 0.448 | 0.288 |
| 291 | | 168 | 0.341 | 1.78 | 0.276 |
| 291 | replicate test | >100 | 0.422 | 1.02 | 0.342 |
| 292 | | 36.8 | <0.137 | 13.4 | <0.137 |
| 292 | replicate test | 36.7 | 0.0902 | 19.4 | 0.0531 |
| 293 | | 48.8 | 0.0586 | 1.32 | 0.0488 |
| 293 | replicate test | 53.7 | <0.137 | 17.2 | <0.137 |
| 294 | | | | | |
| 295 | | | | | |
| 296 | | | | | |
| 297 | | | | | |
| 298 | | 0.737 | >100 | <0.137 | >100 |
| 299 | | 46.2 | <0.137 | 50.4 | <0.137 |
| 299 | replicate test | 42.7 | 0.392 | 36 | 0.148 |
| 300 | | 23.5 | 0.223 | 21 | <0.137 |
| 300 | replicate test | 39 | >3.70 | 20.2 | >3.70 |
| 301 | | 30.9 | >100 | 30.6 | >100 |
| 302 | | 79 | >100 | 19.9 | >100 |
| 303 | | >100 | 17.7 | 57.7 | 0.52 |
| 304 | | >100 | 29.1 | 36.8 | 2.76 |
| 305 | | >100 | 53 | 42.6 | 0.494 |
| 306 | | 4.59 | 0.16 | <0.137 | <0.137 |
| 306 | replicate test | 4.11 | 0.0658 | <0.0457 | 0.0616 |
| 307 | | 60.3 | >100 | 32.8 | 40.6 |
| 308 | | 33.8 | 0.623 | 1.43 | 0.586 |
| 308 | replicate test | | 0.271 | | 0.289 |
| 309 | | 32.1 | 0.497 | 0.513 | 0.504 |
| 309 | replicate test | | 0.254 | | 0.249 |
| 310 | | 69.1 | 94.7 | 43.9 | 30.6 |
| 310 | replicate test | 72.6 | 85.4 | 35.8 | 36.7 |
| 311 | | >100 | 3.07 | >100 | 2.33 |
| 312 | | 411 | 1.75 | 59.6 | 0.991 |
| 312 | replicate test | >100 | 1.11 | 53.2 | 0.781 |
| 313 | | 123 | 56 | 32.5 | 9.88 |
| 313 | replicate test | >100 | 57.8 | 23.6 | 8.64 |
| 314 | | | 11.3 | 40.6 | 6.15 |
| 315 | | 15 | 1.29 | 0.22 | 0.484 |
| 316 | | 40.4 | 45.6 | 15.5 | 27.9 |
| 316 | replicate test | 27 | 69.8 | 24.4 | 23.1 |
| 317 | | 1.18 | 10.3 | 0.676 | 6.05 |
| 318 | | 94.1 | 26 | 16.1 | 9.16 |
| 319 | | 88.7 | 0.292 | 20.7 | 0.21 |
| 319 | replicate test | 63 | 0.192 | 39.7 | 0.161 |
| 320 | | >100 | 71.3 | 27.7 | 5.34 |
| 321 | | 0.196 | 0.576 | 0.31 | 0.752 |
| 322 | | >100 | 4.73 | 53.9 | 3.47 |
| 323 | | 110 | 0.333 | 47.6 | 0.87 |
| 323 | replicate test | 97.9 | 0.359 | 47.4 | 0.174 |
| 324 | | >100 | >100 | 81 | 58.6 |
| 325 | | 92.7 | >100 | 64.4 | 65.9 |
| 326 | | 84.5 | 83.8 | 38 | 48.5 |
| 327 | | 39.8 | 0.943 | 29.5 | 0.307 |
| 327 | replicate test | 56.2 | 0.675 | 19.8 | 0.426 |
| 328 | | >100 | >100 | 82.1 | 4.93 |
| 329 | | >100 | 1.25 | 65.9 | 0.232 |
| 330 | | 22.7 | 39.4 | 14.6 | 8.77 |
| 331 | | 25.2 | 10.3 | 16.6 | 1.15 |
| 332 | | | >100 | 40.2 | 61 |
| 333 | | 51.4 | 0.668 | 0.224 | 0.704 |
| 333 | replicate test | 37.3 | 1.28 | 0.653 | 1.2 |
| 334 | | 17 | <0.137 | 3.94 | <0.137 |
| 334 | replicate test | 18.4 | 0.0784 | 3.07 | 0.0707 |
| 335 | | 24.8 | <0.137 | 6.02 | <0.137 |
| 335 | replicate test | 24.7 | 0.0659 | 4.89 | 0.0525 |
| 336 | | 11.4 | 1.08 | 8.62 | 1.1 |
| 337 | | >100 | 1.5 | 46.2 | 1.3 |
| 338 | | >100 | 10.6 | 56.4 | <0.137 |
| 339 | | >100 | 19.4 | 36.7 | 21.7 |
| 340 | | 2.44 | 6.38 | 0.557 | 6.32 |
| 341 | | 26.6 | >100 | 23.6 | >100 |
| 342 | | 2.91 | 3.48 | 0.755 | 3.07 |
| 343 | | >100 | 68.1 | 13.4 | 2.27 |
| 344 | | 0.423 | 2.24 | 0.281 | 0.974 |
| 345 | | >100 | 31.8 | >100 | 1.8 |
| 346 | | 73.8 | 0.269 | 55.2 | 0.144 |
| 346 | replicate test | 69.2 | 0.0481 | 33.2 | 0.0661 |
| 347 | | >100 | >100 | 91.9 | >100 |
| 348 | | >100 | >100 | >100 | >100 |
| 349 | | >100 | 96.6 | >100 | 1.38 |
| 350 | | >100 | >100 | >100 | 28.2 |
| 351 | | >100 | >100 | >100 | 23 |
| 352 | | 46 | <0.137 | 2.6 | 0.142 |
| 352 | replicate test | 31.7 | 0.0833 | 2.78 | 0.129 |
| 353 | | >100 | 11 | >100 | 11.3 |
| 354 | | >100 | >100 | >100 | 12 |
| 355 | | 13.6 | 0.164 | <0.137 | 0.19 |
| 355 | replicate test | 9.02 | <0.137 | <0.137 | 0.158 |
| 356 | | >100 | 0.526 | >100 | 0.356 |
| 356 | replicate test | 221 | 0.152 | 60 | 0.216 |
| 357 | | 26.5 | 13.4 | 21.5 | 0.606 |
| 358 | | >100 | 40.1 | 57 | 46.6 |
| 359 | | >100 | >100 | >100 | >100 |
| 360 | | >100 | 14.9 | 20.3 | 17.7 |
| 361 | | 23.6 | 24.9 | 22.4 | 11.3 |
| 362 | | >100 | >100 | >100 | 2.35 |
| 363 | | 1.39 | 1.82 | 0.498 | 1.73 |
| 364 | | 3.09 | 0.363 | 0.151 | 0.343 |
| 365 | | >100 | 1.09 | >100 | 0.809 |
| 366 | | 11.6 | 2.75 | 10.5 | 2.28 |
| 367 | | 1.84 | 0.468 | 0.229 | 0.466 |
| 368 | | >100 | 25.3 | 64.8 | 0.476 |
| 369 | | 15.9 | 6 | 5.86 | 8.89 |
| 370 | | 9.01 | 0.151 | 1.75 | <0.137 |
| 370 | replicate test | 23.4 | 3.64 | 12.2 | 0.221 |
| 371 | | 35 | 68.8 | | |
| 372 | | 2.49 | <0.0457 | <0.137 | <0.0457 |
| 373 | | 0.647 | <0.0152 | <0.137 | <0.0152 |
| 374 | | 4.17 | 0.454 | 1.21 | 0.0185 |
| 375 | | 23.7 | 9.05 | 2.71 | 0.372 |
| 376 | | 17.8 | 5.11 | 7.29 | <0.0457 |
| 377 | | 14.5 | 19.4 | 3.68 | <0.137 |
| 378 | | <0.137 | 0.055 | <0.137 | 0.0346 |
| 379 | | <0.0457 | 0.0664 | <0.0457 | 0.0456 |
| 380 | | 188 | 59.9 | 72 | 3.7 |
| 381 | | 3.46 | 2.09 | | |
| 382 | | 33.6 | 27.5 | 13 | 4.62 |
| 382 | replicate test | 20.2 | 22.5 | | |
| 383 | | 18 | 16.8 | | |
| 384 | | 14 | 0.475 | 2.27 | 0.199 |
| 385 | | 30.6 | 10.2 | | |
| 386 | | 11.2 | 6.85 | | |
| 387 | | 32.7 | 19 | | |
| 388 | | <0.137 | 0.0119 | <0.137 | <0.00510 |
| 388 | replicate test | 0.351 | 0.03 | <0.0152 | 0.0284 |
| 389 | | 28.1 | 9.88 | | |
| 390 | | 32.9 | 24.8 | 14 | 4.53 |
| 390 | replicate test | 33.4 | 32 | | |
| 391 | | 2.58 | <0.137 | <0.137 | <0.137 |
| 391 | replicate test | 1.31 | 0.0454 | <0.0457 | 0.0331 |
| 392 | | 1.22 | <0.137 | <0.137 | <0.137 |
| 392 | replicate test | 0.382 | 0.0285 | <0.0457 | 0.0122 |
| 393 | | 92.8 | 28.4 | 18 | 0.727 |
| 394 | | 11.5 | 0.17 | <0.137 | <0.137 |
| 394 | replicate test | 3.91 | 0.191 | 0.0551 | 0.108 |
| 394 | replicate test | 13.3 | 0.133 | <0.137 | 0.118 |
| 394 | replicate test | 7.07 | 0.156 | <0.137 | <0.137 |
| 395 | | 82.3 | 0.292 | 30.8 | <0.137 |
| 395 | replicate test | 63.2 | 0.103 | 26.6 | 0.0132 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 395 | replicate test | >100 | 0.673 | 23.5 | <0.137 |
| 396 | | >100 | >100 | 55.8 | 2.47 |
| 397 | | 2.84 | 1.69 | <0.137 | 1.05 |
| 398 | | 55.6 | 38.7 | 28 | 11.5 |
| 399 | | 23.8 | 3.32 | 7.46 | <0.137 |
| 400 | | 0.527 | <0.137 | <0.137 | <0.137 |
| 400 | replicate test | <0.0457 | 0.125 | <0.0457 | 0.0636 |
| 401 | | <0.137 | <0.137 | <0.137 | <0.137 |
| 401 | replicate test | <0.0457 | 0.061 | <0.0457 | 0.0668 |
| 402 | | >100 | >100 | >100 | 6.58 |
| 403 | | >100 | >100 | >100 | 13.2 |
| 404 | | 0.586 | <0.137 | <0.137 | <0.137 |
| 404 | replicate test | 0.167 | 0.0453 | <0.0457 | 0.0493 |
| 405 | | 37.2 | 73.6 | 15.3 | 61.1 |
| 406 | | 17.3 | 9.76 | 5.43 | 8.96 |
| 407 | | 20 | 17.9 | 11 | 14.4 |
| 408 | | 17.6 | 21.5 | 8.39 | 16.8 |
| 409 | | <0.137 | <0.137 | <0.137 | <0.137 |
| 410 | | 39.4 | 61.8 | 49.2 | 29 |
| 411 | | <0.137 | <0.137 | <0.137 | <0.137 |
| 411 | replicate test | <0.0457 | 0.0546 | <0.0457 | 0.0551 |
| 412 | | 12.6 | 8.7 | 3.34 | 0.169 |
| 413 | | 17.3 | 10 | 2.42 | <0.137 |
| 414 | | 8.3 | 9.25 | 3.34 | 0.632 |
| 415 | | 0.586 | <0.137 | <0.137 | <0.137 |
| 416 | | >100 | 29.5 | <0.137 | 0.353 |
| 417 | | >100 | 52.6 | 7.68 | 14.5 |
| 418 | | 59 | 13 | 4.99 | <0.137 |
| 419 | | 20.3 | 2.06 | 4.64 | 0.227 |
| 420 | | 0.326 | 0.89 | >100 | <0.137 |
| 421 | | 25 | 0.157 | >100 | <0.137 |
| 421 | replicate test | 24.5 | 0.268 | 12.1 | 0.0936 |
| 422 | | 34 | 0.146 | 18.4 | <0.137 |
| 423 | | 6.97 | 0.362 | <0.137 | 0.16 |
| 424 | | >100 | 33.6 | >100 | 1.23 |
| 425 | | >100 | 94.4 | 71.2 | 4.2 |
| 426 | | 35.7 | 19.6 | 17.8 | 1.17 |
| 427 | | 26.9 | 17.2 | 13 | 2.34 |
| 428 | | 26.3 | 4.88 | 6.8 | 0.545 |
| 428 | replicate test | 25.8 | 5.98 | 8.1 | 0.702 |
| 429 | | 44.9 | 37.1 | 47.9 | 20.2 |
| 430 | | 99.9 | 58.9 | 31.6 | 0.385 |
| 431 | | 13.6 | 49.6 | 0.245 | 14.7 |
| 432 | | 47.4 | 0.195 | 9.5 | <0.137 |
| 432 | replicate test | 53.4 | 0.338 | 14.3 | 0.0919 |
| 433 | | <0.137 | <0.137 | <0.137 | <0.137 |
| 434 | | 46.4 | 39.8 | 15 | 7.87 |
| 435 | | 38.4 | 33.6 | 17.2 | 5.57 |
| 436 | | 36.8 | 23.3 | 19.9 | 4.08 |
| 437 | | <0.137 | <0.137 | <0.137 | <0.137 |
| 438 | | 13.3 | <0.137 | 0.139 | <0.137 |
| 439 | replicate test | 18.7 | 0.0321 | 1.09 | 0.0285 |
| 439 | | >100 | 88.3 | 39.6 | 15.2 |
| 440 | | 55.1 | 16.4 | 9.98 | <0.137 |
| 441 | | 23 | <0.137 | 3.61 | <0.137 |
| 441 | replicate test | 18.6 | 0.04 | 4.41 | 0.0105 |
| 441 | replicate test | 16.2 | 0.0172 | 3.17 | 0.0081 |
| 441 | replicate test | 15.8 | <0.137 | 5.22 | <0.137 |
| 441 | replicate test | 18.6 | 0.0081 | 4.57 | 0.0054 |
| 441 | replicate test | 15.1 | <0.137 | 4.21 | <0.137 |
| 441 | replicate test | 21.1 | 0.0101 | 4.85 | 0.0091 |
| 442 | | 20.4 | 5.04 | 3.33 | <0.137 |
| 442 | replicate test | 15.3 | 10.8 | 6.16 | 0.105 |
| 443 | | 0.727 | <0.137 | <0.137 | <0.137 |
| 444 | | 26.1 | <0.137 | 7.64 | <0.137 |
| 244 | replicate test | 20.6 | 0.0403 | 3.94 | 0.0629 |
| 445 | | 7.32 | <0.137 | 1.55 | <0.137 |
| 446 | | 19.1 | 44.9 | 11.3 | 15.6 |
| 447 | | 21.8 | 4.49 | 12.3 | 0.22 |
| 448 | | >100 | >100 | 55 | >100 |
| 449 | | 2.1 | <0.137 | <0.137 | <0.137 |
| 450 | | 1.21 | <0.137 | <0.137 | <0.137 |
| 451 | | 25.3 | 8.38 | 3.37 | 0.623 |
| 452 | | 0.731 | <0.137 | <0.137 | <0.137 |
| 453 | | 0.152 | <0.137 | <0.137 | <0.137 |
| 453 | replicate test | 0.645 | <0.137 | <0.137 | <0.137 |
| 454 | | 10.1 | 0.321 | 2.5 | <0.137 |
| 454 | replicate test | 13.3 | 0.0985 | 2.95 | 0.148 |
| 455 | | 19.4 | 8.9 | 11.5 | 3.16 |
| 456 | | >100 | >100 | 12.6 | 1.64 |
| 457 | | 15.1 | 19.3 | 10.9 | 8.4 |
| 458 | | 72.3 | 3.24 | 28.7 | 0.23 |
| 459 | | 31.2 | 25.2 | 12.2 | 1.55 |
| 460 | | 46.7 | 0.588 | 1.96 | 0.576 |
| 461 | | >100 | >100 | >100 | 0.974 |
| 462 | | 16.6 | 37.6 | 20.9 | 10.1 |
| 463 | | 12.9 | 17.4 | 17.7 | 3.79 |
| 464 | | 22.2 | 3.78 | 33.8 | 0.254 |
| 465 | | >100 | 18.7 | >100 | 9.9 |
| 466 | | 3.59 | 0.0049 | 0.0857 | 0.0077 |
| 466 | replicate test | 1.72 | <0.137 | <0.137 | <0.137 |
| 467 | | >100 | >100 | >100 | 2.33 |
| 468 | | 46.6 | 0.33 | <0.686 | 0.261 |
| 468 | replicate test | 64.3 | 1.58 | 1.44 | 0.561 |
| 468 | replicate test | >500 | 1.42 | 1.67 | 0.431 |
| 469 | | 5.81 | 1.02 | 0.602 | 0.915 |
| 470 | | 8.55 | 17.8 | 1.33 | 1.11 |
| 471 | | 295 | 21.8 | 117 | 4.16 |
| 471 | replicate test | >100 | 29.1 | 85.3 | 3.48 |
| 472 | | 3.08 | 0.0124 | 0.306 | 0.0127 |
| 472 | replicate test | 5.85 | <0.137 | 1.14 | <0.137 |
| 473 | | <0.137 | <0.137 | <0.137 | <0.137 |
| 474 | | 1.24 | <0.137 | <0.137 | <0.137 |
| 474 | replicate test | 1.51 | 0.005 | 0.0263 | 0.005 |
| 475 | | 1.02 | <0.137 | <0.137 | <0.137 |
| 475 | replicate test | 1.22 | 0.0085 | <0.0152 | 0.007 |
| 475 | replicate test | 3.62 | >1.24 | <0.0152 | 0.0275 |
| 476 | | 14.9 | 27.2 | 10.8 | 6.03 |
| 477 | | 9.58 | <0.137 | 1.9 | <0.137 |
| 477 | replicate test | 7.93 | 0.0149 | 0.599 | 0.0166 |
| 478 | | 6.71 | <0.137 | 1.05 | <0.137 |
| 478 | replicate test | 9.07 | 0.0089 | 2.39 | 0.009 |
| 479 | | 25.6 | 0.106 | 8.22 | <0.0931 |
| 479 | replicate test | 19.5 | 0.207 | 4.73 | 0.0268 |
| 479 | replicate test | >22.6 | >2.52 | 7.79 | |
| 480 | | 0.652 | <0.137 | <0.137 | <0.137 |
| 481 | | 0.392 | <0.137 | <0.137 | <0.137 |
| 482 | | 10.3 | <0.137 | 1.82 | <0.137 |
| 482 | replicate test | 11.7 | 0.0955 | 2.69 | 0.0102 |
| 483 | | 89.4 | <0.137 | 19.5 | <0.137 |
| 483 | replicate test | 74.6 | 0.0854 | 33.3 | 0.0666 |
| 484 | | | 9.52 | >100 | 6.14 |
| 485 | | >100 | 8.84 | >100 | 10.1 |
| 486 | | >100 | 21 | >100 | 23.5 |
| 487 | | >100 | >100 | >100 | >100 |
| 488 | | >100 | 9 | 97.5 | 10.2 |
| 489 | | >100 | 9.4 | >100 | 9.43 |
| 490 | | >100 | 8.79 | 87.2 | 7.99 |
| 491 | | >100 | 8.83 | >100 | 8.3 |
| 492 | | >100 | >100 | >100 | 98.8 |
| 493 | | >100 | 8.22 | >100 | 6 |
| 494 | | 22.1 | 41.1 | 13 | 96.9 |
| 495 | | >100 | 23 | >100 | 18 |
| 496 | | 99 | 45.1 | >100 | 32.1 |
| 497 | | >100 | 15.3 | >100 | 12.5 |
| 498 | | >100 | 15.1 | 44 | 11.8 |
| 499 | | >100 | 9.62 | 36.8 | 7.35 |
| 500 | | >100 | >100 | >100 | >100 |
| 501 | | >100 | >100 | 79 | >100 |
| 502 | | >100 | >100 | 42.4 | >100 |
| 503 | | >100 | >100 | >100 | >100 |
| 504 | | >100 | >100 | >100 | >100 |
| 505 | | | 4.08 | 55.1 | 2.47 |
| 506 | | | 12 | 58.2 | 9.3 |
| 507 | | >100 | 13.5 | >100 | 8.2 |
| 508 | | >100 | 1.26 | >100 | 0.835 |
| 508 | replicate test | >500 | 1.25 | >500 | 1.03 |
| 509 | | >100 | 0.153 | >100 | 0.603 |
| 509 | replicate test | >500 | 1.25 | 166 | 1.48 |
| 510 | | >100 | 1.87 | >100 | 0.752 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 510 | replicate test | >500 | | >500 | |
| 511 | | >100 | 19.5 | >100 | 7.22 |
| 512 | | >100 | >100 | >100 | 11.7 |
| 513 | | >100 | 59 | >100 | 26.6 |
| 514 | | >100 | >100 | >100 | 32.3 |
| 515 | | >100 | 11.2 | 6.82 | 4.46 |
| 516 | | >100 | 18.4 | 17.9 | 20.6 |
| 516 | replicate test | 132 | 11.3 | 13.6 | 18.8 |
| 517 | | >100 | 16.3 | >100 | 12 |
| 518 | | >100 | 18.3 | >100 | 2.57 |
| 519 | | >100 | 15.1 | 54.3 | 2.76 |
| 520 | | >100 | 45.5 | >100 | 6.12 |
| 521 | | >100 | 92.3 | >100 | 22.3 |
| 522 | | >100 | >100 | >100 | 35.2 |
| 523 | | >100 | >100 | 94.3 | 0.691 |
| 524 | | >100 | 5.39 | 36.8 | 1.64 |
| 525 | | >100 | >100 | >100 | >100 |
| 526 | | >100 | >100 | >100 | 12.5 |
| 527 | | >100 | 10.6 | >100 | 5.56 |
| 527 | replicate test | >500 | 15.3 | >500 | 11.2 |
| 528 | | >100 | >100 | >100 | 56 |
| 529 | | 57.7 | 75.9 | 3.98 | 9.51 |
| 530 | | >100 | >100 | 13.8 | 5.18 |
| 531 | | >100 | >100 | 18.6 | 7.93 |
| 531 | replicate test | 76.5 | 24.2 | 18.9 | 3.23 |
| 532 | | 0.245 | <0.137 | <0.137 | <0.137 |
| 533 | | 0.696 | 0.307 | <0.137 | 0.376 |
| 534 | | 3.29 | <0.137 | <0.137 | <0.137 |
| 534 | replicate test | 1.59 | 0.492 | <0.0457 | 0.0149 |
| 535 | | 23.1 | 0.727 | 0.153 | 1.17 |
| 536 | | >100 | 0.626 | 22.1 | 0.656 |
| 536 | replicate test | 118 | 0.924 | 71.7 | 0.426 |
| 601a | | 31.6 | 7.96 | 14.7 | 0.137 |
| 601a | replicate test | 23.7 | 4.56 | 3.12 | 0.137 |
| 601b | | 17.9 | 0.335 | 5.8 | 0.176 |
| 601b | replicate test | 2.92 | 0.171 | 1.07 | 0.113 |
| 601c | | 0.137 | 0.137 | 0.137 | 0.137 |
| 601d | | 0.137 | 0.137 | 0.137 | 0.137 |
| 602a | | 100 | 100 | 49.1 | 91 |
| 602b | | 100 | 100 | 100 | 57.3 |
| 602c | | 100 | 62.2 | 100 | 15 |
| 602d | | 100 | 96 | 12.4 | 37.3 |
| 602e | | 100 | 21.3 | 51.6 | 12.3 |
| 603a | | 14.4 | 0.823 | 4.02 | 0.137 |
| 603b | | 71.7 | 0.354 | 13.3 | 0.0937 |
| 603b | replicate test | 45.9 | 0.137 | 15.1 | 0.206 |
| 604a | | 100 | 0.149 | 5.35 | 0.358 |
| 604a | replicate test | 283 | 0.203 | 25 | 0.136 |
| 604b | | 100 | 100 | 7.65 | 64.3 |
| 604c | | 100 | 83.1 | 4.89 | 1.39 |
| 604d | | 100 | 15.4 | 25.7 | 1.54 |
| 604e | | 10.8 | 0.137 | 1.86 | 0.0027 |
| 604e | replicate test | 6.21 | 0.0033 | 1.39 | 0.137 |
| 604f | | 41.4 | 12.7 | 15.4 | 0.832 |
| 604g | | 100 | 0.223 | 349 | 0.0601 |
| 604g | replicate test | 460 | 0.15 | | |
| 604h | | 100 | 2.85 | | |
| 604i | | 6.41 | 0.532 | 2.68 | 0.279 |
| 604j | | 100 | 9.83 | 84.3 | 0.276 |
| 604k | | 100 | 100 | 100 | 100 |
| 604l | | 100 | 6.53 | 100 | 0.137 |
| 604m | | 100 | 100 | 100 | 93.7 |
| 604n | | 8.21 | 16.6 | 6.98 | 4.06 |
| 604o | | 100 | 100 | 100 | 3.02 |
| 604p | | 16.1 | 9.36 | 14.1 | 0.549 |
| 604q | | 5.31 | 0.137 | 0.749 | 0.137 |
| 604q | replicate test | 6.18 | 0.0186 | 1.05 | 0.0151 |
| 605a | | 100 | 1.12 | 9.24 | 0.931 |
| 605b | | 100 | 30.5 | 100 | 16 |
| 605c | | 100 | 100 | 100 | 26.3 |
| 605d | | 84.4 | 100 | 49.5 | 40.4 |
| 605e | | 100 | 100 | 100 | 3.89 |
| 605f | | 100 | 7.03 | 100 | 3.43 |
| 605g | | 100 | 100 | 100 | 100 |
| 605h | | 100 | 100 | 100 | 69.8 |
| 605i | | 100 | 100 | 100 | 100 |
| 605j | | 100 | 100 | 72.1 | 97.4 |
| 605k | | 100 | 9.31 | 41.9 | 14.7 |
| 605l | | 100 | 100 | 100 | 100 |
| 605m | | 100 | 100 | 100 | 100 |
| 605n | | 100 | 0.72 | 75.2 | 0.137 |
| 605o | | 100 | 3.54 | 9.62 | 3.33 |
| 606a | | 100 | 100 | 80.4 | 0.284 |
| 606b | | 100 | 100 | 100 | 29.7 |
| 606b | replicate test | 100 | 100 | 100 | 43.1 |
| 606c | | 100 | 0.137 | 49.6 | 0.137 |
| 606c | replicate test | 121 | 0.0832 | 62.1 | 0.0702 |
| 607a | | 1.26 | 6.67 | 0.908 | 3.5 |
| 607b | | 0.516 | 0.526 | 0.287 | 0.448 |
| 607c | | 15.4 | 0.137 | 2.86 | 0.137 |
| 607c | replicate test | 15.2 | 0.0104 | 4.68 | 0.0076 |
| 607d | | 100 | 100 | 22.6 | 0.148 |
| 608a | | 100 | 100 | 100 | 0.333 |
| 608b | | 100 | 0.401 | 9.92 | 0.278 |
| 608b | replicate test | 99.7 | 0.27 | 24.1 | 0.349 |
| 608c | | 100 | 100 | 100 | 0.197 |
| 608d | | 100 | 1.12 | 100 | 0.387 |
| 608e | | 100 | 100 | 100 | 2.67 |
| 608f | | 54.3 | 0.356 | 14 | 0.137 |
| 608f | replicate test | 61.9 | 0.153 | 17.9 | 0.0848 |
| 608g | | 100 | 1.01 | 100 | 0.875 |
| 608h | | 100 | 1.35 | 100 | 100 |
| 608i | | 100 | 7.04 | 13.3 | 100 |
| 609a | | 55 | 0.137 | 100 | 0.137 |
| 609a | replicate test | 58.8 | 0.726 | 28.7 | 0.0207 |
| 609b | | 13.4 | 8.36 | 1.99 | 0.137 |
| 609c | | 37.2 | 6.67 | 17.6 | 0.137 |
| 609d | | 57.2 | 28.3 | 18.5 | 0.137 |
| 609e | | 100 | 10.7 | 1.95 | 0.137 |
| 609f | | 5.42 | 0.137 | 0.393 | 0.137 |
| 609f | replicate test | 3.75 | 0.008 | 0.494 | 0.0055 |
| 609g | | 20.4 | 0.137 | 4.6 | 0.137 |
| 609g | replicate test | 14.9 | 0.0683 | 2.56 | 0.0635 |
| 609g | replicate test | 6.86 | 0.137 | 0.371 | 0.137 |
| 609h | | 99.9 | 1.73 | 60.6 | 0.451 |
| 609h | replicate test | 66 | 0.743 | 28.5 | 0.525 |
| 609i | | 14.9 | 0.137 | 1.67 | 100 |
| 609i | replicate test | 25.9 | 0.0196 | 18.8 | 0.0341 |
| 609j | | 92.3 | 1.33 | 43.8 | 0.137 |
| 609k | | 1.33 | 1.07 | 0.195 | 100 |
| 609l | | 100 | 1.35 | 40.6 | 0.137 |
| 609m | | 100 | 83.2 | 20.2 | 2.88 |
| 609n | | 100 | 100 | 61 | 32.9 |
| 609o | | 40.8 | 79 | 3.39 | 0.525 |
| 609p | | 100 | 100 | 100 | 100 |
| 609r | | 0.313 | 2.74 | 0.2 | 0.357 |
| 609s | | 7.38 | 4.5 | 0.757 | 0.61 |
| 609t | | 83.1 | 24.7 | 24.1 | 2.8 |
| 609t | replicate test | 63.8 | 4.03 | 25.4 | 0.317 |
| 609u | | 3.24 | 0.575 | 0.452 | 0.241 |
| 609v | | 4.03 | 0.137 | 0.609 | 0.137 |
| 609v | replicate test | 5.84 | 0.0185 | 0.64 | 0.0134 |
| 609w | | 5.2 | 0.0122 | 0.435 | 0.0099 |
| 609w | replicate test | 5 | 0.137 | 0.692 | 0.137 |
| 609x | | 20.4 | 5.64 | 7.35 | 0.307 |
| 610 | | 0.137 | 0.137 | 0.137 | 0.137 |
| 611a | | 15.8 | 0.147 | 5.23 | 0.137 |
| 611a | replicate test | 11.6 | 0.02 | 3.19 | 0.011 |
| 611b | | 100 | 100 | 63.6 | 0.475 |
| 611c | | 73.5 | 0.438 | 0.391 | 0.394 |
| 611c | replicate test | 52.4 | 0.419 | 7.79 | 0.273 |
| 611d | | 43.7 | 4.46 | 6.66 | 4.17 |
| 611e | | 5.42 | 3.3 | 0.397 | 0.157 |
| 611f | | 3.5 | 0.137 | 0.137 | 0.137 |
| 611f | replicate test | 6.11 | 0.0324 | 0.686 | 0.0051 |
| 611g | | 45.6 | 0.137 | 29.9 | 0.137 |
| 611g | replicate test | 194 | 1.37 | 58.4 | 0.0051 |
| 611h | | 76.9 | 41.5 | 29.4 | 24.7 |
| 611i | | 39.1 | 4.14 | 13.8 | 3.52 |
| 611j | | 13.1 | 2.19 | 2.74 | 2.09 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 611k | | 17.5 | 2.74 | 2.53 | 2.71 |
| 611l | | 100 | 100 | 89.8 | 100 |
| 611m | | 100 | 100 | 80.9 | 7.21 |
| 611n | | 100 | 100 | 100 | 100 |
| 611o | | 100 | 100 | 100 | 100 |
| 611p | | 100 | 100 | 78.8 | 100 |
| 611q | | 100 | 1.36 | 100 | 0.694 |
| 611r | | 9.2 | 3.17 | 3.82 | 2.46 |
| 612a | | 100 | 100 | 100 | 9.86 |
| 612b | | 100 | 100 | 100 | 92.4 |
| 612c | | 31.3 | 100 | 18.4 | 58 |
| 613a | | 20.3 | 0.0507 | 2.22 | 0.0334 |
| 613a | replicate test | 16.2 | 0.137 | 0.137 | 0.137 |
| 613b | | 100 | 0.489 | 2.23 | 0.546 |
| 613c | | 79.3 | 0.655 | 1.23 | 0.851 |
| 614a | | 100 | 0.137 | 74.4 | 0.293 |
| 614b | | 100 | 100 | 100 | 5.67 |
| 615 | | 100 | 5.5 | 100 | 0.54 |
| 616 | | 100 | 6.84 | 24.4 | 5.89 |
| 617 | | 100 | 9.13 | 3.03 | 6.81 |
| 618 | | 72.4 | 100 | 41.1 | 80.2 |
| 619a | | 100 | 1.57 | 100 | 4.74 |
| 619a | replicate test | 472 | 3.09 | 310 | 0.0051 |
| 619b | | 100 | 100 | 100 | 28.3 |
| 620 | | 100 | 100 | 100 | 23.9 |
| 621a | | 100 | 100 | 45.9 | 100 |
| 621b | | 100 | 0.285 | 11.9 | 0.45 |
| 621b | replicate test | 500 | 0.367 | 59.5 | 0.245 |
| 621c | | 0.351 | 0.149 | 0.137 | 0.161 |
| 621d | | 62.7 | 100 | 14.6 | 100 |
| 621d | replicate test | 100 | 100 | 21.1 | 100 |
| 621e | | 2.38 | 0.137 | 0.137 | 0.137 |
| 621e | replicate test | 2.99 | 0.0142 | 0.0457 | 0.0122 |
| 621e | replicate test | 0.492 | 0.137 | 0.137 | 0.137 |
| 621f | | 100 | 16.2 | 8.99 | 6.55 |
| 621g | | 100 | 1.7 | 22.2 | 1.34 |
| 621g | replicate test | 100 | 2.71 | 32.8 | 0.848 |
| 621g | replicate test | 56.4 | 0.137 | 15.7 | 0.137 |
| 621h | | 79.3 | 0.137 | 20.9 | 0.137 |
| 621h | replicate test | 64.1 | 0.0419 | 18 | 0.038 |
| 621h | replicate test | 100 | 9.08 | 26.4 | 8.75 |
| 621j | | 18.7 | 71.7 | 2.54 | 2.84 |
| 621k | | 1.58 | 10.3 | 0.811 | 4.57 |
| 621l | | 8.05 | 49.5 | 3.5 | 2.7 |
| 621m | | 100 | 6.03 | 100 | 100 |
| 621n | | 100 | 4 | 41.9 | 5.27 |
| 621o | | 100 | 10.5 | 5.75 | 12.8 |
| 621p | | 100 | 100 | 100 | 100 |
| 621q | | 100 | 100 | 100 | 72.8 |
| 621r | | 58.2 | 90.6 | 24.7 | 46.5 |
| 621s | | 100 | 100 | 100 | 100 |
| 621t | | 100 | 15.9 | 100 | 13.9 |
| 621u | | 100 | 14.3 | 100 | 6.97 |
| 621v | | 46.1 | 0.137 | 34.2 | 0.167 |
| 621w | | 100 | 1.06 | 4.17 | 0.952 |
| 621x | | 5.09 | 0.693 | 0.324 | 0.68 |
| 621y | | 100 | 0.743 | 12.9 | 0.723 |
| 622 | | 3.5 | 0.871 | 0.478 | 0.775 |
| 623m | | 56.2 | 0.137 | 23.8 | 0.137 |
| 623n | | 100 | 0.21 | 80.1 | 0.137 |
| 700 | | 100 | 2.05 | 100 | 0.627 |
| 700 | replicate test | 500 | 3.8 | 187 | 0.799 |
| 701 | | 16.2 | 0.137 | 1.75 | 0.137 |
| 701 | replicate test | 12.3 | 0.137 | 1.22 | 0.137 |
| 702 | | 85.9 | 0.615 | 1.72 | 0.167 |
| 702 | replicate test | 123 | 1.27 | 0.686 | 0.496 |
| 703 | | 61.7 | 0.405 | 4.52 | 0.15 |
| 703 | replicate test | 93.3 | 2.09 | 0.686 | 0.495 |
| 704 | | 52.5 | 0.137 | 12.3 | 0.137 |
| 704 | replicate test | 84.5 | 0.137 | 34.6 | 0.137 |
| 705 | | 100 | 23 | 100 | 9.36 |
| 706 | | 24.8 | 0.137 | 10.4 | 0.137 |
| 706 | replicate test | 45.6 | 0.0873 | 14.9 | 0.0518 |
| 707 | | 12.3 | 0.137 | 4.96 | 0.137 |
| 707 | replicate test | 12.7 | 0.1 | 4.83 | 0.0771 |
| 708 | | 81.3 | 0.137 | 31 | 0.137 |
| 708 | replicate test | 500 | 0.45 | 401 | 0.135 |
| 709 | | 100 | 1.46 | 100 | 0.806 |
| 713 | | 23.2 | 48.7 | 9.25 | 26.8 |
| 714 | | 16.6 | 0.233 | 6.68 | 0.137 |
| 714 | replicate test | 27.8 | 0.124 | 21.7 | 0.0711 |
| 715 | | 100 | 100 | 100 | 36.4 |
| 716 | | 31.9 | 31.4 | 11.8 | 0.137 |
| 717 | | 100 | 100 | 44.5 | 0.137 |
| 718 | | 100 | 100 | 33.8 | 100 |
| 719 | | 100 | 38 | 85.2 | 0.137 |
| 720 | | 100 | 100 | 39.1 | 72.3 |
| 721 | | 22.8 | 9.04 | 5.38 | 0.137 |
| 722 | | 100 | 100 | 45.5 | 0.137 |
| 723 | | 32.9 | 7.21 | 14.3 | 0.447 |
| 724 | | 100 | 100 | 100 | 47.9 |
| 725 | | 7.67 | 0.357 | 3.51 | 0.137 |
| 725 | replicate test | 8.87 | 0.0152 | 3.34 | 0.0152 |
| 725 | replicate test | 7.97 | 0.137 | 0.99 | 0.137 |
| 725 | replicate test | 11.1 | 0.0152 | 0.639 | 0.0152 |
| 725 | replicate test | 8.77 | 0.003 | 1.44 | 0.0023 |
| 726 | | 52 | 100 | 7.45 | 3.74 |
| 727 | | 48 | 90.7 | 18.8 | 31 |
| 728 | | 18.4 | 29.6 | 8.09 | 1.81 |
| 729 | | 100 | 100 | 100 | 100 |
| 730 | | 12.9 | 2.2 | 2.64 | 0.137 |
| 732 | | 8.51 | 8.69 | 1.67 | 0.412 |
| 733 | | 38.5 | 31 | 14.8 | 10.7 |
| 734 | | 4.22 | 0.43 | 0.137 | 0.137 |
| 735 | | 26.8 | 89.1 | 9.25 | 41.2 |
| 736 | | 64.7 | 59.8 | 30.3 | 52.8 |
| 737 | | 100 | 100 | 21.3 | 5.22 |
| 739 | | 100 | 100 | 100 | 29.4 |
| 740 | | 5.21 | 7.87 | 0.427 | 0.137 |
| 741 | | 9.11 | 9.92 | 1.79 | 0.137 |
| 742 | | 100 | 84.7 | 90.7 | 19.2 |
| 743 | | 2.62 | 0.164 | 0.137 | 0.137 |
| 744 | | 40.5 | 23.6 | 20 | 22.2 |
| 745 | | 8.72 | 2.3 | 1.18 | 0.137 |
| 746 | | 21.7 | 100 | 11.3 | 62.4 |
| 747 | | 27.2 | 100 | 18.2 | 60.3 |
| 748 | | 6.59 | 0.849 | 2.25 | 0.192 |
| 749 | | 3.52 | 0.141 | 1.12 | 0.137 |
| 751 | | 9.01 | 13.6 | 1.56 | 4.82 |
| 752 | | 4.04 | 3.09 | 0.291 | 0.345 |
| 753 | | 100 | 100 | 100 | 100 |
| 754 | | 8.06 | 0.137 | 2.66 | 0.137 |
| 754 | replicate test | 7.39 | 0.0051 | 3.59 | 0.0051 |
| 755 | | 1.64 | 0.137 | 0.137 | 0.137 |
| 755 | replicate test | 1.45 | 0.0071 | 0.0586 | 0.0051 |
| 756 | | 2.32 | 0.137 | 0.34 | 0.137 |
| 756 | replicate test | 2.09 | 0.0051 | 0.5 | 0.0051 |
| 757 | | 7.43 | 0.137 | 0.137 | 0.137 |
| 757 | replicate test | 6.87 | 0.109 | 0.137 | 0.124 |
| 758 | | 100 | 100 | 13.5 | 0.137 |
| 759 | | 4.74 | 0.137 | 0.137 | 0.137 |
| 759 | replicate test | 2.98 | 0.0084 | 0.137 | 0.0074 |
| 760 | | 30.3 | 0.15 | 6.8 | 0.137 |
| 760 | replicate test | 33.2 | 0.0972 | 5.72 | 3.7 |
| 761 | | 2.54 | 2.51 | 0.137 | 0.137 |
| 762 | | 59.3 | 100 | 18.6 | 2.82 |
| 763 | | 3.93 | 0.22 | 0.585 | 0.137 |
| 764 | | 61.4 | 100 | 27.8 | 27.1 |
| 765 | | 24.7 | 12.4 | 7.17 | 4.12 |
| 766 | | 100 | 100 | 72 | 100 |
| 767 | | 100 | 100 | 64.3 | 56.1 |
| 768 | | 55.8 | 40.1 | 16.7 | 13.3 |
| 769 | | 64.7 | 79.9 | 28.8 | 41.2 |
| 770 | | 11 | 31 | 4.52 | 16.6 |
| 771 | | 15.5 | 33.6 | 8.28 | 12.8 |
| 772 | | 16.2 | 10.8 | 6.82 | 0.859 |
| 773 | | 44.4 | 50.4 | 18.8 | 8.52 |
| 774 | | 100 | 100 | 100 | 0.878 |
| 775 | | 63.9 | 3.24 | 49.3 | 3.91 |
| 775 | replicate test | 54 | 1.03 | 20.5 | 1.13 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 776 | | 57.9 | 0.316 | 23.2 | 0.236 |
| 776 | replicate test | 380 | 0.405 | 207 | 0.203 |
| 777 | | 23.2 | 0.331 | 11 | 0.456 |
| 777 | replicate test | 170 | 1.01 | 114 | 0.424 |
| 778 | | 58 | 1.17 | 39.1 | 0.575 |
| 779 | | 14.2 | 0.769 | 2.22 | 0.794 |
| 779 | replicate test | 21.2 | 0.898 | 2.27 | 0.667 |
| 780 | | 62 | 0.162 | 25 | 0.3 |
| 780 | replicate test | 335 | 1.48 | 99.5 | 1.02 |
| 780 | replicate test | 265 | 1.89 | 56.2 | 1.04 |
| 781 | | 28.1 | 0.473 | 12.5 | 1.94 |
| 782 | | 26.1 | 0.137 | 14 | 0.137 |
| 782 | replicate test | 166 | 0.497 | 59 | 0.345 |
| 782 | replicate test | 112 | 0.524 | 22.3 | 0.212 |
| 783 | | 26.4 | 0.265 | 14.6 | 0.405 |
| 783 | replicate test | 277 | 2.57 | 108 | 1.52 |
| 783 | replicate test | 158 | 4.24 | 77.2 | 2.6 |
| 784 | | 48.5 | 0.814 | 30.2 | 2.79 |
| 785 | | 6.76 | 0.317 | 3.41 | 0.287 |
| 786 | | 41.6 | 0.419 | 3.63 | 0.427 |
| 786 | replicate test | 207 | 1.48 | 50.8 | 1.03 |
| 786 | replicate test | 121 | 1.77 | 14.5 | 1.2 |
| 787 | | 344 | 1.08 | 62.9 | 0.753 |
| 787 | replicate test | 100 | 0.315 | 22 | 0.278 |
| 788 | | 126 | 0.849 | 15.9 | 0.9 |
| 788 | replicate test | 41.6 | 0.261 | 5.17 | 0.26 |
| 789 | | 10.4 | 0.163 | 0.799 | 0.17 |
| 790 | | 14.3 | 0.851 | 1.51 | 3.05 |
| 790 | replicate test | 41.6 | 2.57 | 0.569 | 0.861 |
| 791 | | 45 | 4.94 | 7.75 | 4.97 |
| 792 | | 192 | 2.28 | 36.8 | 2.88 |
| 792 | replicate test | 82.8 | 0.672 | 13.5 | 0.972 |
| 793 | | 63 | 1.05 | 3.89 | 1.32 |
| 794 | | 41.7 | 19.8 | 8.48 | 7.87 |
| 795 | | 11 | 1.79 | 1.51 | 1.99 |
| 796 | | 100 | 3.96 | 49.8 | 4.1 |
| 797 | | 500 | 1.24 | 203 | 1.06 |
| 797 | replicate test | 100 | 0.719 | 81.1 | 0.484 |
| 798 | | 100 | 11.2 | 99 | 4.91 |
| 799 | | 8.06 | 0.597 | 0.928 | 0.587 |
| 800 | | 100 | 2.49 | 100 | 1.34 |
| 801 | | 100 | 3.8 | 51.3 | 2.65 |
| 802 | | 100 | 17.8 | 100 | 7.68 |
| 803 | | 100 | 11.4 | 100 | 7.64 |
| 804 | | 100 | 3.54 | 34.8 | 2.72 |
| 805 | | 100 | 7.24 | 100 | 5.6 |
| 806 | | 100 | 100 | 100 | 95.2 |
| 807 | | 100 | 100 | 100 | 42.7 |
| 808 | | 100 | 1.06 | 65.4 | 0.742 |
| 808 | replicate test | 72.7 | 0.206 | 28.6 | 0.156 |
| 809 | | 100 | 0.786 | 66 | 0.731 |
| 809 | replicate test | 132 | 0.214 | 36.2 | 0.174 |
| 810 | | 100 | 1.06 | 8.48 | 1.04 |
| 811 | | 169 | 0.741 | 79.8 | 0.377 |
| 811 | replicate test | 100 | 0.631 | 36.5 | 0.202 |
| 812 | | 10.5 | 0.644 | 0.206 | 0.635 |
| 813 | | 40.7 | 0.473 | 2.39 | 0.426 |
| 813 | replicate test | 18.4 | 0.196 | 0.604 | 0.21 |
| 814 | | 67.9 | 1.66 | 34.5 | 0.137 |
| 815 | | 292 | 0.817 | 146 | 0.254 |
| 815 | replicate test | 100 | 0.693 | 69.7 | 0.154 |
| 816 | | 0.137 | 0.137 | 0.137 | 0.137 |
| 817 | | 56.2 | 100 | | |
| 818 | | 100 | 25 | | |
| 819 | | 100 | 100 | | |
| 820 | | 100 | 100 | | |
| 821 | | 100 | 100 | | |
| 822 | | 43.2 | 100 | | |
| 823 | | 100 | 100 | | |
| 824 | | 100 | 100 | | |
| 825 | | 100 | 100 | | |
| 826 | | 1.48 | 13.4 | | |
| 827 | | 100 | 100 | | |
| 828 | | 1.13 | 27 | | |
| 829 | | 100 | 100 | | |
| 830 | | 100 | 100 | | |
| 831 | | 18.9 | 100 | | |
| 832 | | 100 | 18.1 | | |
| 833 | | 100 | 100 | | |
| 834 | | 21.7 | 100 | | |
| 835 | | 9.35 | 100 | | |
| 836 | | 100 | 49.2 | | |
| 837 | | 14 | 100 | | |
| 838 | | 8.09 | 100 | | |
| 839 | | 7.6 | 100 | | |
| 840 | | 46.5 | 87.7 | | |
| 841 | | 100 | 69.7 | | |
| 842 | | 100 | 8.59 | | |
| 843 | | 100 | 37.8 | | |
| 844 | | 100 | 100 | | |
| 845 | | 100 | 18.9 | | |
| 846 | | 100 | 25.9 | | |
| 847 | | 100 | 29.4 | | |
| 848 | | 100 | 100 | | |
| 849 | | 100 | 100 | | |
| 850 | | 24.7 | 0.824 | | |
| 851 | | 62.1 | 5.07 | | |
| 852 | | 100 | 9.99 | | |
| 853 | | 100 | 100 | | |
| 854 | | 100 | 5.32 | | |
| 855 | | 84.5 | 0.595 | 224 | 0.879 |
| 855 | replicate test | 264 | 0.451 | | |
| 856 | | 100 | 18.1 | | |
| 857 | | 81.8 | 9.58 | | |
| 858 | | 64.3 | 100 | | |
| 859 | | 100 | 100 | | |
| 860 | | 15.9 | 6.1 | | |
| 861 | | 13.4 | 13.6 | | |
| 862 | | 77.6 | 7.54 | | |
| 863 | | 100 | 100 | | |
| 864 | | 100 | 0.951 | 100 | 0.595 |
| 864 | replicate test | 500 | 0.873 | 46.6 | 0.634 |
| 865 | | 100 | 100 | 100 | 100 |
| 867 | | 100 | 46.3 | 100 | 0.427 |
| 868 | | 100 | 100 | 80.3 | 3.82 |
| 869 | | 27.5 | 1.9 | 0.375 | 1.98 |
| 870 | | 100 | 20.2 | 100 | 9.49 |
| 871 | | 56.8 | 81.1 | 45.3 | 7.81 |
| 872 | | 100 | 100 | 68.4 | 4.64 |
| 873 | | 100 | 100 | 66.7 | 28.8 |
| 874 | | 10.1 | 0.529 | 0.628 | 0.175 |
| 875 | | 100 | 64.6 | 100 | 1.01 |
| 876 | | 100 | 100 | 100 | 1.48 |
| 877 | | 100 | 100 | 100 | 0.213 |
| 878 | | 100 | 100 | 100 | 0.273 |
| 879 | | 4.53 | 0.137 | 0.475 | 0.137 |
| 879 | replicate test | 4.27 | 0.022 | 0.419 | 0.019 |
| 880 | | 500 | 0.588 | 100 | 0.48 |
| 880 | replicate test | 100 | 0.633 | 500 | 0.344 |
| 881 | | 100 | 100 | 100 | 57.2 |
| 882 | | 22 | 0.137 | 4.17 | 0.137 |
| 883 | | 0.137 | 0.137 | 0.137 | 0.137 |
| 884 | | 100 | 2.93 | 75.9 | 0.137 |
| 885 | | 61 | 42.6 | 29.7 | 9.88 |
| 886 | | 22.2 | 5.21 | 7.18 | 0.137 |
| 887 | | 8.72 | 0.137 | 1.55 | 0.137 |
| 888 | | 4.59 | 0.137 | 0.137 | 0.137 |
| 889 | | 100 | 100 | 100 | 100 |
| 890 | | 0.137 | 0.137 | 0.137 | 0.137 |
| 891 | | 0.137 | 0.137 | 0.137 | 0.137 |
| 893 | | 0.189 | 0.137 | 0.137 | 0.137 |
| 894 | | 8.73 | 13.9 | 3.34 | 0.137 |
| 895 | | 0.668 | 0.137 | 0.137 | 0.137 |
| 896 | | 0.137 | 0.137 | 0.137 | 0.137 |
| 897 | | 0.387 | 0.137 | 0.137 | 0.137 |
| 898 | | 0.137 | 0.137 | 0.137 | 0.137 |
| 899 | | 1.33 | 0.0037 | 0.67 | 0.0028 |
| 899 | replicate test | 1.38 | 0.137 | 0.147 | 0.137 |
| 900 | | 0.137 | 0.137 | 0.137 | 0.137 |
| 901 | | 0.274 | 0.137 | 0.137 | 0.137 |

TABLE 19-continued

| Example No. | Replicate Test | hCox-1 IC50 (uM) | hCox-2 IC50 (uM) | hCox-1 Modified IC50 (uM) | hCox-2 Modified IC50 (uM) |
|---|---|---|---|---|---|
| 902 | | 3.9 | 1.29 | 53.5 | 100 |
| 903 | | 30.4 | 100 | 39.9 | 100 |
| 904 | | 27.7 | 100 | 54.9 | 100 |
| 905 | | 8.12 | 13.5 | 59.5 | 100 |
| 906 | | 0.222 | 0.137 | 0.341 | 100 |
| 907 | | 0.137 | 0.137 | 0.137 | 100 |
| 908 | | 28.6 | 30.1 | 38.4 | 51.3 |
| 909 | | 25.5 | 2.59 | 75.2 | 31.3 |
| 910 | | 32.6 | 7.85 | 40.1 | 42.5 |
| 911 | | 44.7 | 4.36 | 7.29 | 96.7 |
| 912 | | 0.137 | 0.137 | 0.137 | 100 |
| 913 | | 0.215 | 0.137 | 0.137 | 100 |
| 914 | | 11.7 | 99.2 | 11.9 | 100 |
| 915 | | 0.137 | 0.137 | 0.137 | 0.761 |
| 916 | | 31.2 | 62.1 | | |
| 917 | | 28.2 | 100 | | |
| 918 | | 8.78 | 3.51 | | |
| 919 | | 8.86 | 4.15 | | |
| 920 | | 78.8 | 100 | 23.2 | 1.49 |
| 921 | | 52.6 | 100 | 20.1 | 100 |
| 921 | replicate test | 48.7 | 100 | 10.9 | 100 |
| 922 | | 4.96 | 1.45 | 0.195 | 1.25 |
| 923 | | 100 | 100 | 100 | 1.71 |
| 924 | | 100 | 4.45 | 100 | 3 |
| 925 | | 40.3 | 100 | 18.4 | 99.9 |
| 925 | replicate test | 100 | 100 | 53.6 | 100 |
| 926 | | 43.5 | 78.1 | 32.2 | 23.8 |
| 926 | replicate test | 100 | 100 | 100 | 22.5 |
| 927 | | 87.3 | 53.6 | 56 | 17.4 |
| 927 | replicate test | 100 | 100 | 100 | 30.9 |
| 928 | | 100 | 100 | 100 | 100 |
| 928 | replicate test | 100 | 100 | 100 | 100 |
| 929 | | 100 | 100 | 100 | 100 |
| 930 | | 21.5 | 0.137 | 0.137 | 0.137 |
| 930 | replicate test | 7.62 | 0.0359 | 0.686 | 0.0265 |
| 931 | | 12.3 | 1.55 | 5.52 | 0.137 |
| 931 | replicate test | 13.2 | 0.41 | 6.71 | 0.137 |
| 931 | replicate test | 9.26 | 0.223 | 4.31 | 0.137 |
| 931 | replicate test | 11.9 | 0.0152 | 2.79 | 0.0152 |
| 931 | replicate test | 10.8 | 0.0124 | 2.14 | 0.0051 |
| 931 | replicate test | 6.72 | 0.137 | 2.77 | 0.137 |
| 931 | replicate test | 3.7 | 0.0062 | 1.91 | 0.0051 |
| 939 | | 64.2 | 100 | 49 | 100 |
| 939 | replicate test | 73.5 | 100 | 44.3 | 83.4 |
| 939 | replicate test | 47.3 | 100 | 31.3 | 35.1 |
| 940 | | 1.59 | 0.0082 | 0.0457 | 0.0086 |
| 940 | replicate test | 0.474 | 0.137 | 0.137 | 0.137 |
| 941 | | 9.91 | 3.28 | 2.15 | 0.4 |
| 942 | | 0.735 | 0.0136 | 0.0152 | 0.0128 |
| 942 | replicate test | 1.04 | 0.137 | 0.137 | 0.137 |
| 943 | | 11.6 | 3.08 | 1.95 | 0.31 |
| 944 | | 30.6 | 2.27 | 7.39 | 0.926 |
| 945 | | 13.4 | 0.2 | 1.65 | 0.162 |
| 945 | replicate test | 9.75 | 0.207 | 0.955 | 0.192 |
| 946 | | 0.123 | 0.0065 | 0.0051 | 0.0082 |
| 946 | | 0.137 | 0.137 | 0.137 | 0.137 |
| 947 | | 6.08 | 8.02 | 0.137 | 1.17 |
| 948 | | 38.1 | 0.137 | 18.2 | 0.137 |
| 948 | replicate test | 37.3 | 0.0785 | 21.5 | 0.0638 |
| 949 | | 36.9 | 0.401 | 7.23 | 0.137 |
| 949 | replicate test | 32.8 | 0.177 | 9.03 | 0.106 |
| 950 | | 3.77 | 0.137 | 2.28 | 0.137 |
| 950 | replicate test | 8.65 | 0.0567 | 7.03 | 0.027 |
| 951 | | 51.1 | 1.56 | 22.8 | 0.147 |
| 952 | | 5.05 | 0.137 | 0.137 | 0.137 |
| 952 | replicate test | 4.07 | 0.186 | 0.137 | 0.0051 |
| 953 | | 100 | 100 | 0.766 | 0.137 |
| 954 | | 8.9 | 0.137 | 3.33 | 0.137 |
| 954 | replicate test | 8.67 | 0.15 | 3.83 | 0.0051 |
| 955 | | 52.4 | 17.3 | 19.7 | 0.137 |
| 956 | | 36.9 | 46.4 | 14.8 | 3.55 |
| 957 | | 31.5 | 1.74 | 12.7 | 0.253 |
| 957 | replicate test | 11.1 | 2.26 | 11.1 | 0.211 |
| 958a | | 0.21 | 0.0358 | 0.0152 | 0.0293 |
| 958a | replicate test | 0.775 | 0.137 | 0.137 | 0.137 |
| 958b | | 41.7 | 100 | 0.587 | 21.6 |
| 959 | | 9.44 | 0.137 | 1.47 | 0.137 |
| 959 | replicate test | 7.38 | 0.0469 | 1.89 | 0.0069 |
| 960 | | 92.4 | 100 | 22.5 | 2.01 |
| 961 | | 1.67 | 0.137 | 0.137 | 0.137 |
| 961 | replicate test | 0.907 | 0.0117 | 0.137 | 0.0091 |
| 962 | | 16 | 53.4 | 0.204 | 0.706 |
| 963 | | 0.137 | 0.137 | 0.137 | 0.137 |
| 964 | | 29.3 | 62.8 | 0.137 | 0.218 |
| 965 | | 0.773 | 0.137 | 0.137 | 0.137 |
| 966 | | 9.4 | 0.266 | 0.137 | 0.137 |
| 967 | | 0.479 | 0.137 | 0.137 | 0.137 |
| 968 | | 22.1 | 10.3 | 0.137 | 0.26 |
| 969 | | 38.9 | 0.256 | 0.61 | 0.229 |
| 969 | replicate test | 40.3 | 0.216 | 1.67 | 0.152 |
| 970 | | 100 | 61.6 | 59.3 | 0.336 |
| 971 | | 220 | 0.476 | 170 | 0.17 |
| 971 | replicate test | 100 | 0.364 | 64.3 | 0.137 |
| 972 | | 100 | 72.1 | 100 | 16.5 |
| 973 | | 100 | 100 | 100 | 18 |
| 974 | | 90 | 0.466 | 67 | 0.204 |
| 974 | replicate test | 78.1 | 0.321 | 13.5 | 0.235 |
| 975 | | 100 | 33.1 | 100 | 13.9 |
| 976 | | 68.3 | 0.412 | 56.2 | 0.242 |
| 976 | replicate test | 72.9 | 0.513 | 24.4 | 0.374 |
| 977 | | 0.137 | 0.137 | 0.137 | 0.137 |
| 977 | replicate test | 0.0301 | 0.0396 | 0.0098 | 0.0417 |
| 977 | replicate test | 0.686 | 0.0392 | 0.686 | 0.0339 |
| 978 | | 71.6 | 100 | 34.8 | 100 |
| 979 | | 1.19 | 0.137 | 0.137 | 0.137 |
| 979 | replicate test | 0.669 | 0.0315 | 0.0457 | 0.0334 |
| 980 | | 77.4 | 100 | 39.4 | 0.137 |
| 981 | | 7.55 | 0.137 | 0.168 | 100 |
| 981 | replicate test | 6.22 | 0.0808 | 0.137 | 0.0982 |
| 982 | | 100 | 100 | 57.3 | 0.137 |
| 984 | | 2.61 | 0.026 | 0.0297 | 0.0349 |
| 984 | replicate test | 0.581 | 0.137 | 0.137 | 0.19 |
| 985 | | 9.58 | 3.78 | 1.9 | 6 |
| 986 | | 130 | 0.0683 | 4.19 | 0.0554 |
| 986 | replicate test | 100 | 0.137 | 6.78 | 0.137 |
| 987 | | 100 | 3.6 | 54.8 | 1.93 |
| 988 | | 12.5 | 0.0193 | 3.37 | 0.137 |
| 988 | replicate test | 14.6 | 0.137 | 4.52 | 0.0204 |
| 989 | | 100 | 1.04 | 30.8 | 1.22 |
| 990 | | 44 | 0.0427 | 26.4 | 0.137 |
| 990 | replicate test | 55.4 | 0.137 | 32.1 | 0.0431 |
| 991 | | 81.5 | 9.9 | 70.2 | 9.23 |
| 992 | | 16.3 | 0.137 | 1.68 | 0.137 |
| 992 | replicate test | 11.3 | 0.0196 | 4.04 | 0.0215 |
| 993 | | 78.9 | 1.76 | 13.3 | 1.72 |
| 994 | | 75.5 | 0.137 | 29.5 | 0.137 |
| 995 | | 100 | 36.4 | 100 | 18.6 |

What is claimed is:

1. The compound selected from the group consisting of
(2R)-6-chloro-7-isobutyl-2-(trifluoromethyl)-2H-chromene-3-carboxylic acid;

6-chloro-7-isobutyl-2-(trifluoromethyl)-2H-chromene-3-carboxylic acid;

(2R)-7-benzyl-6-chloro-2-(trifluoromethyl)-2H-chromene-3-carboxylic acid;

7-benzyl-6-chloro-2-(trifluoromethyl)-2H-chromene-3-carboxylic acid;

7-butoxy-6-chloro-8-methyl-2-(trifluoromethyl)-2H-chromene-3-carboxylic acid;

7-benzyl-6-bromo-2-(trifluoromethyl)-2H-chromene-3-carboxylic acid;

7-butyl-6-chloro-2-(trifluoromethyl)-2H-chromene-3-carboxylic acid;

6,8-dichloro-7-(2-ethylbutoxy)-2-(trifluoromethyl)-2H-chromene-3-carboxylic acid;

6-chloro-8-methyl-7-propoxy-2-(trifluoromethyl)-2H-chromene-3-carboxylic acid;

6-chloro-7-(isobutylthio)-2-(trifluoromethyl)-2H-chromene-3-carboxylic acid;

6-chloro-7-(2-ethylbutoxy)-8-methyl-2-(trifluoromethyl)-2H-chromene-3-carboxylic acid;

6-chloro-7-(isopentyloxy)-8-methyl-2-(trifluoromethyl)-2H-chromene-3-carboxylic acid;

8-methyl-6-(trifluoromethoxy)-2-(trifluoromethyl)-2H-chromene-3-carboxylic acid;

6,8-dichloro-7-isobutoxy-2-(trifluoromethyl)-2H-chromene-3-carboxylic acid;

7-benzyl-6-methyl-2-(trifluoromethyl)-2H-chromene-3-carboxylic acid;

7-(sec-butylthio)-6-chloro-2-(trifluoromethyl)-2H-chromene-3-carboxylic acid;

(2S)-6-ethyl-8-methyl-2-(trifluoromethyl)-2H-chromene-3-carboxylic acid;

6-chloro-8-(4-chloro-3-methylphenyl)-2-(trifluoromethyl)-2H-chromene-3-carboxylic acid;

8-ethyl-6-(trifluoromethoxy)-2-(trifluoromethyl)-2H-chromene-3-carboxylic acid;

(2S)-8-ethyl-6-(trifluoromethoxy)-2-(trifluoromethyl)-2H-chromene-3-carboxylic acid;

(2S)-6-chloro-5,7-dimethyl-2-(trifluoromethyl)-2H-chromene-3-carboxylic acid 6-chloro-8-(4-methylphenyl)-2-(trifluoromethyl)-2H-chromene-3-carboxylic acid;

6-chloro-8-(3-fluoro-4-methylphenyl)-2-(trifluoromethyl)-2H-chromene-3-carboxylic acid;

8-propyl-6-(trifluoromethoxy)-2-(trifluoromethyl)-2H-chromene-3-carboxylic acid;

5-bromo-6,7-dichloro-8-methoxy-2-(trifluoromethyl)-2H-chromene-3-carboxylic acid;

6-chloro-8-(4-ethylphenyl)-2-(trifluoromethyl)-2H-chromene-3-carboxylic acid; and (2S)-6,8-dimethyl-2-(trifluoromethyl)-2H-chromene-3-carboxylic acid;

or their isomer and pharmaceutically acceptable salt thereof.

* * * * *